US007851486B2

(12) United States Patent
Helgadottir et al.

(10) Patent No.: US 7,851,486 B2
(45) Date of Patent: *Dec. 14, 2010

(54) SUSCEPTIBILITY GENE FOR MYOCARDIAL INFARCTION, STROKE, AND PAOD; METHODS OF TREATMENT

(75) Inventors: Anna Helgadottir, Reykjavik (IS); Mark Gurney, East Grand Rapids, MI (US); Jeffrey R. Gulcher, Lake Barrington, IL (US); Hákon Hákonarson, Reykjavik (IS)

(73) Assignee: deCODE Genetics ehf., Reykjavik (IS)

( * ) Notice: Subject to any disclaimer, the term of this patent is extended or adjusted under 35 U.S.C. 154(b) by 706 days.

This patent is subject to a terminal disclaimer.

(21) Appl. No.: 10/830,477

(22) Filed: Apr. 22, 2004

(65) Prior Publication Data

US 2005/0113408 A1   May 26, 2005

Related U.S. Application Data

(63) Continuation-in-part of application No. 10/769,744, filed as application No. PCT/US03/32556 on Oct. 16, 2003.

(60) Provisional application No. 60/419,433, filed on Oct. 17, 2002, provisional application No. 60/449,331, filed on Feb. 21, 2003.

(51) Int. Cl.
*A61K 31/47* (2006.01)

(52) U.S. Cl. ..................................................... 514/311
(58) Field of Classification Search .................. 514/311
See application file for complete search history.

(56) References Cited

U.S. PATENT DOCUMENTS

| | | | |
|---|---|---|---|
| 4,970,215 | A | 11/1990 | Mohrs et al. |
| 5,059,609 | A | 10/1991 | Eggler et al. |
| 5,298,512 | A | 3/1994 | Eggler et al. |
| 5,306,820 | A | 4/1994 | Decker et al. |
| 5,527,827 | A | 6/1996 | Delorme et al. |
| 5,559,134 | A | 9/1996 | Buchmann et al. |
| 5,576,338 | A | 11/1996 | Friesen et al. |
| 5,641,789 | A | 6/1997 | Marfat |
| 5,939,529 | A | 8/1999 | Potempa |
| 5,981,559 | A | 11/1999 | Nagaoka et al. |
| 5,990,148 | A | 11/1999 | Isakson et al. |
| 6,040,147 | A | 3/2000 | Ridker et al. |
| 6,166,031 | A | 12/2000 | Eggler et al. |
| 6,436,924 | B2 | 8/2002 | Poppe et al. |
| 6,521,747 | B2 | 2/2003 | Anastasio et al. |
| 6,531,279 | B1 | 3/2003 | Blumenfeld et al. |
| 6,797,475 | B2 | 9/2004 | Barnes et al. |
| 2002/0107276 | A1 | 8/2002 | Isakson et al. |
| 2003/0194721 | A1 | 10/2003 | Mikita et al. |
| 2003/0225155 | A1 | 12/2003 | Fernandez-Pol et al. |
| 2004/0014759 | A1 | 1/2004 | Picard et al. |
| 2004/0053983 | A1 | 3/2004 | Barvian et al. |

FOREIGN PATENT DOCUMENTS

| | | |
|---|---|---|
| CA | 2337571 | 8/2002 |
| DE | 4118014 | 12/1992 |
| DE | 4118173 | 12/1992 |
| DE | 4127842 | 2/1993 |
| DE | 100 07203 | 8/2001 |
| EP | 0 360 246 | 3/1990 |
| EP | 0 518 819 A2 | 12/1992 |
| EP | 0 344 519 B1 | 4/1993 |
| EP | 0 509 359 B1 | 2/1996 |
| EP | 0 703 216 | 3/1996 |
| EP | 0 870 762 | 10/1998 |
| EP | 0 947 502 | 10/1999 |
| JP | 03227922 | 10/1991 |
| JP | 06072947 | 3/1994 |
| JP | 3-227922 | 12/1998 |
| JP | 00355551 | 12/2000 |
| JP | 2003238407 | 8/2003 |
| WO | WO-91/13908 | 9/1991 |
| WO | WO 94/00420 | 1/1994 |
| WO | WO-95/07249 | 3/1995 |
| WO | WO 95/18610 | 7/1995 |
| WO | WO 96/11192 | 4/1996 |
| WO | WO 96/27585 | 9/1996 |
| WO | WO 96/41625 | 12/1996 |
| WO | WO 97/29774 | 8/1997 |
| WO | WO 97/29775 | 8/1997 |

(Continued)

OTHER PUBLICATIONS

Buxton, The New England J. of Med. vol. 352(5):2638-2640, 2005.*
Jay N. Cohn, M.D., University of Minnesota Medical School, Minneapolis, Minnesota) vol. 57(8) 1998.*
Gompertz et al. Chest vol. 122, 289-294, 2002.*
Folco et al.Am. J. Respir. Crit. Care Med. vol. 161 pp. S112-S116 2000.*
Byrum et al. J. Exp. Med vol. 185(6) 1065-1075 1997.*
Rossoni et al. The J. Pharmcology and Exp. Therapeutics, vol. 276(1), 335-341, 1996.*
Am. J. Med. 1992, 93 Abstract only.*
Chemplavi Kottayam Medical college, Magazine, 1970 1-6.*
Batkai et al., "Inhibition of 4-lipoxygenase Improves Regional Myocardial Function After Repetitive Ischemia in the Rat Heart," Pluegers Archiv., Springer Verlag, 430(4):R18 (1995).
Dib et al., "A Comprehensive Genetic Map of the Human Genome Based on 5,264 Microsatellites," Nature, 380:152-154 (1996).

(Continued)

*Primary Examiner*—Michael G Hartley
*Assistant Examiner*—Shirley V Gembeh
(74) *Attorney, Agent, or Firm*—Marshall, Gerstein & Borun LLP

(57) ABSTRACT

Linkage of myocardial infarction (MI) and a locus on chromosome 13q12 is disclosed. In particular, the FLAP gene within this locus is shown by genetic association analysis to be a susceptibility gene for MI and ACS, as well as stroke and PAOD. Pathway targeting for treatment and diagnostic applications in identifying those who are at risk of developing MI, ACS, stroke or PAOD, in particular are described.

17 Claims, 131 Drawing Sheets

FOREIGN PATENT DOCUMENTS

| | | |
|---|---|---|
| WO | WO-97/34885 | 9/1997 |
| WO | WO 98/09943 | 3/1998 |
| WO | WO 98/13347 | 4/1998 |
| WO | WO 98/40354 | 9/1998 |
| WO | WO 98/40364 | 9/1998 |
| WO | WO 98/40370 | 9/1998 |
| WO | WO 98/42345 | 10/1998 |
| WO | WO 98/43954 | 10/1998 |
| WO | WO-99/52942 | 10/1999 |
| WO | WO-99/59964 | 11/1999 |
| WO | WO 00/43001 | 7/2000 |
| WO | WO 00/50577 | 8/2000 |
| WO | WO 00/59864 | 10/2000 |
| WO | WO-01/17528 | 3/2001 |
| WO | WO 01/34199 | 5/2001 |
| WO | WO 01/57025 | 8/2001 |
| WO | WO 01/96347 | 12/2001 |
| WO | WO 02/05825 | 1/2002 |
| WO | WO 02/060378 | 8/2002 |
| WO | WO 03/035670 | 5/2003 |
| WO | WO 03/037349 | 5/2003 |
| WO | WO 03/063781 | 8/2003 |
| WO | WO 03/082191 | 10/2003 |
| WO | WO 03/086282 | 10/2003 |
| WO | WO 03/103602 | 12/2003 |
| WO | WO 2004/002409 | 1/2004 |
| WO | WO 2004/012686 | 2/2004 |
| WO | WO 2004/024186 | 3/2004 |
| WO | WO-2004/028341 | 4/2004 |
| WO | WO 2004/035741 | 4/2004 |
| WO | WO-2004/035746 | 4/2004 |
| WO | WO 2004/047648 | 6/2004 |
| WO | WO 2004/052839 | 6/2004 |
| WO | WO 2004/055520 | 7/2004 |
| WO | WO-2005/027886 | 3/2005 |

OTHER PUBLICATIONS

European Search Report for EP 03 78 3063 dated Jul. 18, 2006.
Genbank Accession No. Z52271.
Genbank Accession No. Z24370.
Hatzelmann et al., Inversely-correlated Inhibition of Human 5-lipoxygenase Activity by BAY X1005 and Other Quinoline Derivatives in Intact Cells and a Cell-Free System: Implications for the Function of 5-lipoxygenase Activating Protein, Biochemical Pharmacology, 47:2259-2268 (1994).
Koshino et al., "Novel Polymorphism of the 5-lipoxygenase Activating Protein (FLAP) Promoter Gene Associated with Asthma," Molecular Cell Biology Research Communiciations, 2:32-35 (1999).
Yandava et al., "Cytogenetic and Radiation Hybrid Mapping of Human Arachidonate 5-lipoxygenase-activating Protein (ALOX5AP) to Chromosome 13q12," Genmoics, 56:131-133 (1999).
Ahmed et al., Serial Intravascular Ultrasound Assessment of the Efficacy of Intracoronary γ-Radiation Therapy for Preventing Recurrence in Very Long, Diffuse, In-Stent Restenosis Lesions, *Circ.*, 104:856-859 (2001).
Aiello et al., Leukotriene B4 Receptor Antagonism Reduces Monocytic Foam Cells In Mice, *Arterioscler. Thromb. Vasc. Biol.*, 22:443-449 (2002).
Allen et al., Enhanced Excretion of Urinary Leukotriene $E_4$ in Coronary Artery Disease and After Coronary Artery Bypass Surgery, Coronary Artery Disease, 4: 899-904 (1993).
Allen et al., Differential Leukotriene Constrictor Responses in Human Atherosclerotic Coronary Arteries, *Circulation*, 97:2406-2413 (1998).
Andresdottir et al., Fifteen Percent of Myocardial Infarctions and Coronary Revascularizations Explained by Family History Unrelated to Conventional Risk Factors, *European Heart Journal*, 23:1655-1663 (2002).

Askonas et al., Pharmacological Characterization of SC-57461A (3-[Methyl[3-[4-(Phenylmethyl)Phenoxy]Propyl]Amino]Propanoic Acid HCl), a Potent and Selective Inhibitor of Leukotriene $A_4$ Hydrolase I: In Vitro Studies, *JPET*, 300:577-582 (2002).
Bakr et al., 5-Lipoxygenase and Leukotriene $A_4$ Hydrolase Expression in Primary Nephrotic Syndrome, *Pediatr Nephrol*, 19:396-399 (2004).
Barone et al., Time-Related Changes in Myeloperoxidase Activity and Leukotriene $B_4$ Receptor Binding Reflect Leukocyte Influx in Cerebral Focal Stroke, *Mol. Chem. Neuropathol.*, 24:13-30 (1995).
Barth, J., Which Tools are in your Cardiac Workshop? Carotid Ultrasound, Endothelial Function, and Magnetic Resonance Imaging, *Am. J. Cardiol.*, 87(suppl) 8A-14A (2001).
Bermudez et al, Interrelationships Among Circulating Interleukin-6, C-Reactive Protein, and Traditional Cardiovascular Risk Factors in Women, *Arterioscler Thromb Vasc Biol.*, 22:1668-1673 (2002).
Birke at al., In Vitro and in Vivo Pharmacological Characterization of BIIL 284, a Novel and Potent Leukotriene $B_4$ Receptor Antagonist, *JPET*, 297:458-466 (2001).
Blackie et al., The Identification of Clinical Candidate SB-480848: A Potent Inhibitor of Lipoprotein-Associated Phospholipase $A_2$, *Bioorganic Med. Chem. Lett.*, 13:1067-1070 (2003).
Blake et al, C-Reactive Protein, Subclinical Atherosclerosis, and Risk of Cardiovascular Events, *Arterioscler. Thromb. Vasc Biol.*, 22:1512-1513 (2002).
Blake et al., Projected Life-Expectancy Gains With Statin Therapy for Individuals With Elevated C-Reactive Protein Levels, *JACC*, 40:49-55 (2002).
Boyd et al., N-1 Substituted Pyrimidin-4-Ones: Novel, Orally Active Inhibitors of Lipoprotein-Associated Phospholipase $A_2$, *Bioorganic Med. Chem. Lett.*, 10:2557-2561 (2000).
Brennan et al., Prognostic Value of Myeloperoxidase in Patients with Chest Pain, *N. Eng J. Med.*, 349:1595-1604 (2003).
Buffon et al., Widespread Coronary Inflammation in Unstable Angina, *N. Engl. J. Med.*, 1:5-12 (2002).
Byrum et al., Determination of the Contribution of Cysteinyl Leukotrienes and Leukotriene $B_4$ in Acute Inflammatory Responses Using 5-Lipoxygenase- and Leukotriene $A_4$ Hydrolase-Deficient Mice, *J. Immunol.*, 163:6810-6819 (1999).
Carry et al., Increased Urinary Leukotriene Excretion in Patients with Cardiac Ischemia; In vivo Evidence for 5-Lipoxygenase Activation, *Circulation*, 85: 232-236 (1992).
Caslake et al., Lipoprotein-Associated Phospholipase $A_2$ (Platelet-Activating Factor Acetylhydrolase) and Cardiovascular Disease, *Curr. Opin. Lipidol.*, 14:347-352 (2003).
Chang et al., C-Reactive Protein Binds to Both Oxidized LDL and Apoptotic Cells Through Recognition of a Common Ligand: Phosphorylcholine of Oxidized Phospholipids, *PNAS*, 99:13043-13048 (2002).
Chen et al., Leukotriene $A_4$ Hydrolase in Rat and Human Esophageal Adenocarcinomas and Inhibitory Effects of Bestatin, *J. of the Natl. Cancer Institute*, 95:1053-1060 (2003).
Collins et al., Effects of Cholesterol-Lowering with Simvastatin on Stroke and Other Major Vascular Events in 20 536 People with Cerebrovascular Disease or Other High-Risk Conditions, *Lancet*, 363:757-767 (2004).
Cyrus et al., Effect of Low-Dose Aspirin on Vascular Inflammation, Plaque Stability, and Atherogenesis in Low-Density Lipoprotein Receptor-Deficient Mice, *Circ.*, 106:1282-1287 (2002).
Dahlen et al., Inhibition of Allergen-Induced Airway Obstruction and Leukotriene Generation in Atopic Asthmatic Subjects by the Leukotriene Biosynthesis Inhibitor BAYx 10005, *Thorax*, 52: 342-347 (1997).
Danesh et al., C-Reactive Protein and Other Circulating Markers of Inflammation in the Prediction of Coronary Heart Disease, *N. Engl. J. Med.*, 350:1387-1397 (2004).
Davidson, M., Introduction: Utilization of Surrogate Markers of Atherosclerosis for the Clinical Development of Pharmaceutical Agents, *Am. J. Cardiol.*, 87(suppl): 1A-7A (2001).
De Caterina et al., Leukotriene B4 Production in Human Atherosclerotic Plaques, *Biomed. Biochim. Acta*, 47: S182-85 (1988).
Devillier et al., Leukotrienes, Leukotriene Receptor Antagonists and Leukotriene Synthesis Inhibitors in Asthma: An Update. Part II:

Clinical Studies with Leukotriene Receptor Antagonists and Leukotriene Synthesis Inhibitors in Asthma, *Pharmacol. Res.*, 40:15-29 (1999).

Doggen et al., C-Reactive Protein, Cardiovascular Risk Factors and the Association With Myocardial Infarction in Men, *J. Intern. Med.*, 248:406-414 (2000).

Drazen et al., Pharmacogenetic Association Between *ALOX5* Promoter Genotype and the Response to Anti-Asthma Treatment, *Nat. Genet.*, 22:168-170 (1999).

Dwyer et al., Arachidonate 5-Lipoxygenase Promoter Genotype, Dietary Arachidonic Acid, and Atherosclerosis, *N. Eng. J. Med.*, 350:29-37 (2004).

Eberhard et al., Leukotriene $A_4$-Hydrolase Expression and Leukotriene $B_4$ Levels in Chronic Inflammation of Bacterial Orgin; Immunohistochemistry and Reverse-Phase High-Performance Liquid Chromatography Analysis of Oral Mucosal Epithelium, *Virchows Arch*, 440:627-634 (2002).

Fauler et al., Cardiovascular Effects of Leukotrienes, *Cardiovasc. Drugs Ther.*, 3:499-505 (1989).

Feltenmark et al., Diverse Expression of Cytosolic Phospholipase $A_2$, 5-Lipoxygenase and Prostaglandin H Synthase 2 in Acute Pre-B-Lymphocytic Leukaemia Cells, *British J. of Haematology*, 90:585-594 (1995).

Fischer et al., Effect of a Novel 5-Lipoxygenase Activating Protein Inhibitor, BAYx 1005, on Asthma Induced by Cold Dry Air, *Thorax*, 52:1074-1077 (1997).

Folcik et al., Lipoxygenase Contributes to the Oxidation of Lipids in Human Atherosclerotic Plaques, J. Clin. Invest., 96:504-510 (1995).

Folco et al., Leukotrienes in Cardiovascular Diseases, *Am. J. Respir. Crit. Care Med.*, 161:S112-S116 (2000).

Frenette et al., Substituted Indoles as Potent and Orally Active 5-Lipoxygenase Activating Protein (Flap) Inhibitors, *Bioorg. Med. Chem. Lett.*, 9:2391-2396 (1999).

Friedrich et al., Mechanisms of Leukotriene $B_4$—Triggered Monocyte Adhesion, *Arterioscler. Thromb. Vasc. Biol.*, 23:1761 (2003).

Funk, C., Prostaglandins and Leukotrienes: Advances in Eicosanoid Biology, *Science*, 294:1871-1875 (2001).

Funk et al., Molecular Cloning and Amino Acid Sequence of Leukotriene $A_4$ Hydrolase, *Proc. Natl. Acad. Sci.*, 84:6677-6681 (1987).

Gompertz et al., A Randomized, Placebo-Controlled Trial of a Leukotriene Synthesis Inhibitor in Patients with COPD, *Chest.*, 122:289-94 (2002).

Hagenaars et al., Rationale and Design for the SARIS Trial; Effect of Statin on Atherosclerosis and Vascular Remodeling Assessed with Intravascular Sonography, *Cardiovasc. Drugs Ther.*, 15:339-343 (2001).

Heinzmann et al., Studies on Linkage and Association of Atopy with the Chromosomal Region 12q13-24, *Clin. Exp. Allergy*, 30:1554-1561 (2000).

Helgadottir et al., Familial Clustering of Myocardial Infarction in the Icelandic Population: Evidence for Genetic Compoents, *Am. J. of Human Gen.*, 84:A205: 1128 (1999).

Helgadottir et al., The Gene Encoding 5-Lipoxygenase Activating Protein Confers Risk of Myocardial Infarction and Stroke, *Nat. Genet.*, 36:233-239 (2004).

In et al., Naturally Occurring Mutations in the Human 5-Lipoxygenase Gene Promoter that Modify Transcription Factor Binding and Reporter Gene Transcription, *J. Clin. Invest.*, 99:1130-1137 (1997).

Ishizaka et al., Increased Leukotriene $A_4$ Hydrolase Expression in the Heart of Angiotensin II-Induced Hypertensive Rat, *FEBS Letters*, 463:155-159 (1999).

Jonsdottir et al., Incidence and Prevalence of Recognised and Unrecognised Myocardial Infarction in Women, *Eur. Heart J.*, 19:1011-1018 (1998).

Kachur et al., Pharmacological Characterization of SC-57461A (3-[Methyl[3-[4-(Phenylmethyl)Phenoxy]Propyl]Amino]Propanoic Acid HCl), a Potent and Selective Inhibitor of Leukotriene $A_4$ Hydrolase II: In Vivo Studies, *JPET*, 300:583-587 (2002).

Kaiser et al., Proteomics Applied to the Clinical Follow-up of Patients After Allogeneic Hematopoietic Stem Cell Transplantation, *Blood*, 104:340-349 (2004).

Kanayama et al., A New Prostacyclin Analog, KP-10614, Inhibits Platelet-Polymorphonuclear Leukocyte Interaction and Limits Experimental Infarct Size in Rat Heart, *J. Pharmacol. Exp. Ther.*, 266:344-349 (1993).

Keaney, Jr. et al., The Value of Inflammation for Predicting Unstable Angina, *N. Engl. J. Med.*, 347:55-57 (2002).

Kolasa et al., Synthesis of Indolylalkoxyiminoalkylcarboxylates as Leukotriene Biosynthesis Inhibitors, *Bioorg. Med. Chem.*, 5:507-514 (1997).

Kristjansson et al., Improved One-Year Survival After Acute Myocardial Infarction in Iceland Between 1986 and 1996, *Cardiology*, 91:210-214 (1999).

Kuhn et al., Amino Acids Differences in the Deduced 5-Lipoxygenase Sequence of CAST Atherosclerosis-Resistance Mice Confer Impaired Activity when Introduced Into the Human Ortholog, *Arterioscler. Thromb. Vasc. Biol.*, 23:1072-1076 (2003).

Kuribayashi et al., Inhibitory Effects of a Phosphate Diester of α-Tocopherol and Ascorbic Acid ($EPC-K_1$) on Myocardial Infarction in Rats, *Int. J. Tiss. Reac.*, 18:73-79 (1996).

Lam et al., Leukotriene $C_4$ Uses a Probenecid-Sensitive Export Carrier That Does Not Recognize Leukotriene $B_4$, *PNAS USA*, 89:11598-11602 (1992).

Lehr et al., Involvement of 5-Lipoxygenase Products in Cigarette Smoke-Induced Leukocyte/Endothelium Interaction in Hamsters, *Int. J. Microcirc.: Clin. Exp.*, 12:61-73 (1993).

Magee et al., An Integrated Pharmacokinetic/Pharmacodynamic (PK/PD) Model for SB-480848 Inhibition of Plasma Lipoprotein-Associated Phospholipase A2 (LP-PLA2) Enzyme Activity in Human, *American Society for Clinical Pharm. and Ther. Abstract* PIII-87 (2003).

Mehrabian, et al., Identification of 5-Lipoxygenase as a Major Gene Contributing to Atherosclerosis Susceptibility in Mice, *Circ. Res.*, 91:120-126 (2002).

Menegatti et al., Gene Expression of 5-Lipoxygenase and $LTA_4$ Hydrolase in Renal Tissue of Nephrotic Syndrome Patients, *Clin. Exp. Immunol*, 116:347-353 (1999).

Okano-Mitani et al. Leukotriene $A_4$ Hydrolase in Peripheral Leukocytes of Patients with Atopic Dermatitis, *Arch Dermatol Res.*, 288:168-172 (1996).

Montero et al., LTA4 Hydrolase Expression During Glomerular Inflammation: Correlation of Immunohistochemical Localization with Cytokine Regulation, *Adv. Exp. Med. Biol.*, 449-454 (1999).

Mueller et al., Leukotriene $A_4$ Hydrolase, Mutation of Tyrosine 378 Allows Conversiion of Leukotriene $A_4$ into an Isomer of Leukotriene $B_4$, *J. Biol. Chem.*, 271:24345-24348 (1996).

Muller-Peddinghaus et al., BAY X1005, A New Inhibitor of Leukotriene Synthesis: in Vivo Inflammation Pharmacology and Pharmacokinetics, *J. Pharmacol. Exp. Ther.*, 267:51-57 (1993).

Muller-Peddinghaus et al., BAY X1005, A New Selective Inhibitor of Leukotriene Synthesis: Pharmacology and Pharmacokinetics, *J. Lipid. Mediat.*, 6:245-248 (1993).

Muller-Peddinghaus, R., Potential Anti-Inflammatory Effects of 5-Lipoxygenase Inhibition—Examplified by the Leukotriene Synthesis Inhibitor BAY X 1005, *J. Phys. Pharmacol.*, 48:529-536 (1997).

Nissen, S., Coronary Angiography and Intravascular Ultrasound, *Am. J. Cardiol.*, 87(suppl):15A-20A (2001).

Oestvang et al., Role of Secretory and Cystolic Phospholipase $A_2$ Enzymes in Lysophosphatidylcholine-Stimulated Monocyte Arachidonic Acid Release, *FEBS Lett.*, 555:257-262 (2003).

Ozaki et al., Functional SNPs in the Lymphotoxin-α Gene that are Associated with Susceptibility to Myocardial Infarction, *Nat. Genet.*, Published online: Nov. 11, 2002, doi:10.1038/ng1047 , pp. 1-5 (2002).

Packard, et al., Lipoprotein-Associated Phospholipase $A_2$ s an Independent Predictor of Coronary Heart Disease, *N. Eng. J. Med.*, 343:1148-1155 (2000).

Paterniti, Jr., J., Investigational New Drug Applications: The Role of the Preclinical Dossier, *Am. J. Cardiol.*, 81(suppl):10F-12F (1998).

Penning et al., Inhibitors of Leukotriene A$_4$ (LTA$_4$) Hydrolase as Potential Anti-Inflammatory Agents, *Current Pharmaceutical Design*, 7:163-179 (2001).

Penning et al., Pyrrolidine and Piperidine Analogues of SC-57461A as Potent, Orally Active Inhibitors of Leukotriene A$_4$ Hydrolase, *Bioorg. Med. Chem. Lett.*, 12:3383-3386 (2002).

Penning et al., Structure-Activity Relationship Studies on 1-[2(4-Phenylphenoxy)Ethyl]Pyrrolidine (SC-22716), a Potent Inhibitor of Leukotriene A$_4$ (LTA$_4$) Hydrolase, *J. Med. Chem.*, 43:721-735 (2000).

Penning et al., Synthesis of Imidazopyridines and Purines as Potent Inhibitors of Leukotriene A$_4$ Hydrolase, *Bioorg. Med. Chem. Lett.*, 13:1137-1139 (2003).

Penning et al., Synthesis of Potent Leukotriene A$_4$ Hydrolase Inhibitors. Identification of 3-[Methyl[3-[4-(Phenylmethyl)Phenoxy]Propyl]Amino]Propanoic Acid, *J. Med. Chem.*, 45:3482-3490 (2002).

Pitt et al., Aggressive Lipid-Lowering Therapy Compared with Angioplasty in Stable Coronary Artery Disease, *N. Eng. J. Med.*, 341:70-76 (1999).

Potempa et al., Stimulatory Effects of the C-Reactive Protein Subunit on Monocyte Function, Including Release of IL-1, *Biol. Fluids* 34: 287-290.

Radmark, O., 5-Lipoxygenase-Derived Leukotrienes. Mediators Also of Atherosclerotic Inflammation, *Arterioscler. Thromb. Vasc. Biol.*, 23:1140-1142 (2003).

Raggi, P., Coronary Calcium on Electron Beam Tomography Imaging as a Surrogate Marker of Coronary Artery Disease, *Am. J. Cardiol.*, 87(suppl):27A-34A (2001).

Retterstol et al., C-Reactive Protein Predicts Death in Patients With Previous Premature Myocardial Infarction—A 10 Year Follow-Up Study, *Atherosclerosis*, 160:433-440 (2002).

Ridker et al, Comparison of C-Reactive Protein and Low-Density Lipoprotein Cholesterol Levels in the Prediction of First Cardiovascular Events, *N. Engl. J. Med.*, 347:1557-1565 (2002).

Ridker et al., C-Reactive Protein and Other Markers of Inflammation in the Prediction of Cardiovascular Disease in Women, *N. Engl. J. Med.*, 342:836-843 (2000).

Ridker et al., Inflammation, Pravastatin, and the Risk of Coronary Events After Myocardial Infarction in Patients with Average Cholesterol Levels, *Circulation*, 98:839-844 (1998).

Rosenfeld, M., Leukocyte Recruitment Into Developing Atherosclerotic Lesions. The Complex Interaction Between Multiple Molecules Keeps Getting More Complex, *Arterioscler. Thromb. Vasc. Biol.*, 22:361-363 (2002).

Ross, R., Atherosclerosis—An Inflammatory Disease, *N. Eng. J. Med.*; 340:115-126 (1999).

Rossoni et al., Myocardial Protection by the Leukotriene Synthesis Inhibitor BAY X1005: Importance of Transcellular Biosynthesis of Cysteinyl-Leukotrienes, *J. Pharmacol. Exp. Therapeutics*, 276:335-341 (1996).

Rybina et al., Alteration of Human Leukotriene A$_4$ Hydrolase Activity After Site-Directed Mutagenesis: Serine-415 is a Regulatory Residue, *Biochim. Biophys. ACTA*, 1438:199-203 (1999).

Sala et al., Leukotrienes: Lipid Bioeffectors of Inflammatory Reactions, *Biochemistry*, 63:84-92 (1998).

Sala et al., Monoclonal Anti-CD18 Antibody Prevents Transcellular Biosynthesis of Cysteinyl Leukotrienes in Vitro and in Vivo and Protects Against Leukotriene-Dependent Increase in Coronary Vascular Resistance and Myocardial Stiffness, *Circulation*, 101:1436-1440 (2000).

Sampson, Leukotrienes in Cardiovascular Disease, *Clinical and Experimental Allergy Review*, 1:170-174 (2001).

Shepherd, J., Economics of Lipid Lowering in Primary Prevention: Lessons from the West of Scotland Coronary Prevention Study, *Am. J. Cardiol.*, 87 (suppl):19B-22B (2001).

Showell et al., The Preclinical Pharmacological Profile of the Potent and Selective Leukotriene B$_4$ Antagonist CP-195543, *JPET*, 285:946-954 (1998).

Sigurdsson et al., Long-Term Prognosis of Different Forms of Coronary Heart Disease: The Reykjavik Study, *Int. J. Epidem.*, 24-58-68 (1995).

Sigurdsson et al., Silent ST-T Changes in an Epidemiologic Cohort Study—A Marker of Hypertension or Coronary Heart Disease, or Both: The Reykjavik Study, *J. Am. Coll. Cardiol.*, 27:1140-1147 (1996).

Smilde et al., Effect of Aggressive Versus Conventional Lipid Lowering on Atherosclerosis Progression in Familial Hypercholesterolaemia (ASAP): A Prospective, Randomised, Double-Blind Trial, *Lancet*, 357:577-581 (2001).

Spanbroek et al., Expanding Expression of the 5-Lipoxygenase Pathway within the arterial Wall During Human Atherogenesis, *PNAS USA* 100:1238-1243 (2003).

Stein E., Laboratory Surrogates for Anti-Atherosclerotic Drug Development, *Am. J. Cardio.*, 87:21A-26A (2001).

Steinhilber, D., 5-Lipoxygenase: A Target for Antiinflammatory Drugs Revisited, *Curr. Med. Chem.*, 5:71-85 (1999).

Subbarao et al., Role of Leukotriene B$_4$ Receptors in the Development of Atherosclerosis: Potential Mechanisms, *Arterioscler. Thromb. Vasc. Biol.*, 24:369 (2003).

Takase, Change of Plasma Leukotriene C4 During Myocardial Ischemia in Humans, *Clin. Cardiol.*, 19:198-204 (1996).

Taubes G., Does Inflammation Cut to the Heart of the Matter?, *Science*, 296:242-245 (2002).

Thunnissen et al., Crystal Structure of Human Leukotriene A$_4$ Hydrolase, a Bifunctional Enzyme in Inflammation, *Nat. Struct. Biol.*, 8:131-135 (2001).

Thunnissen et al., Crystal Structures of Leukotriene A$_4$ Hydrolase in Complex with Captopril and Two Competitive Tight-Binding Inhibitors, *FASEB Journal*, 16:1648-1650 (2002).

Tracy, Inflammation in Cardiovascular Disease. Cart, Horse or Both Revisited, *Arterioscler. Thromb. Vasc. Biol.*, 22:1514-1515 (2002).

Tselepis et al., Inflammation, Bioactive Lipids and Atherosclerosis: Potential Roles of a Lipoprotein-Associated Phospholipase A2, Platelet Activating Factor-Acetylhydrolase, *Artheroscler. Suppl.*, 3:57-68 (2002).

Verma et al., A Self-Fulfilling Prophecy. C-Reactive Protein Attenuates Nitric Oxide Production and Inhibits Angiogenesis, *Circulation*, 106:913-919 (2002).

Walter et al., Benefits of Immediate Initiation of Statin Therapy Following Successful Coronary Stent Implantation in Patients with Stable and Unstable Angina Pectoris and Q-Wave Acute Myocardial Infarction, *Am. J. Cardiol.*, 89:1-6 (2002).

Wang et al., Association of C-Reactive Protein With Carotid Atherosclerosis in Men and Women: The Framingham Heart Study, *Arterioscler. Thromb. Vasc. Biol.*, 22:1662-1667 (2002).

Waters et al., Effects of Atorvastatin on Stroke in Patients with Unstable Angina or Non-Q-Wave Myocardial Infarction. A Myocardial Ischemia Reduction with Aggressive Cholesterol Lowering (MIRACL) Substudy, *Circulation*, 106:1690-1695 (2002).

Wetterholm et al., Leukotriene A$_4$ Hydrolase: Abrogation of the Peptidase Activity by Mutation of Glutamic Acid-296, *Proc. Natl. Acad. Sci.*, 89:9141-9145, (1992).

Willerson et al., Protection of the Myocardium During Myocardial Infarction: Pharmacologic Protection During Thrombolytic Therapy, *Am. J. Cardio.*, 65: 35 I-41 I (1990).

Yamada et al., Prediction of the Risk of Myocardial Infarction from Polymorphisms in Candidate Genes, *N. Eng. J. Med.*, 347:1916-1923 (2002).

Yokomizo et al., cDNA Cloning, Expression, and Mutagenesis Study of Leukotriene B$_4$ 12-Hydroxydehydrogenase, *J. Biol. Chem.*, 271: 2844-2850 (1996).

Zhang et al., Association Between Myeloperoxidase Levels and Risk of Coronary Artery Disease, *JAMA*, 286:2136-2142 (2001).

Zhao et al., The 5-Lipoxygenase Pathway Promotes Pathogenesis of Hyperlipidemia-Dependent Aortic Aneurysm, *Nat. Med.*, 10:966-973 (2004).

The SNP Consortium Ltd., SNP Report for TSC0806241, Gene sequence, (rs1323898), Oct. 10, 2000.

International Search Report for PCT/US2003/32805 dated Jan. 14, 2005.

International Search Report for PCT/US2004/030582 dated Feb. 28, 2005.

Morgan et al., Nonvalidation of Reported Genetic Risk Factors for Acute Coronary Syndrome in a Large-Scale Replication Study, *J. Amer. Med. Assoc.*, 297: 1551-1561 (Apr. 11, 2007).

International Preliminary Report on Patentability for International Application No. PCT/US2004/030582 dated Dec. 8, 2005.

International Search Report for International Application No. PCT/US2004/030582 dated May 23, 2005.

Written Opinion of the International Searching Authority for International Application No. PCT/US2004/030582.

GenBank Accession No. J03459, Human leukotriene A-4 hydrolase mRNA, complete cds, Jul. 16,1988.

Jorgenson et al., Ethnicity and human genetic linkage maps. *Am. J. Hum. Genet.* 76: 276-90 (2005).

Hatlzelmann et al., Mode of action of the leukotriene synthesis (FLAP) inhibitor BAY X1005 implications for biological regulation of 5-lipoxygenase. *Adv. Prost. Thromb. Leuk. Res.* 22: 23-31 (1994).

International Search Report, European Patent Office, PCT/US2005/003312 dated Jan. 2, 2006.

International Search Report, European Patent Office, PCT/US2006/012073 dated Mar. 20, 2007.

Non-final Office Action in U.S. Appl. No. 10/829,674 mailed Jul. 21, 2006.

Final Office Action in U.S. Appl. No. 10/829,674 mailed Apr. 16, 2007.

Non-final Office Action in U.S. Appl. No. 10/829,674 mailed Jan. 4, 2008.

Non-final Office Action in U.S. Appl. No. 10/769,744 mailed Jun. 1, 2007.

Non-final Office Action in U.S. Appl. No. 10/769,744 mailed Mar. 13, 2008.

Final Office Action in U.S. Appl. No. 10/769,744 mailed Dec. 19, 2008.

Non-final Office Action in U.S. Appl. No. 11/096,191 mailed May 28, 2009.

Non-final Office Action in U.S. Appl. No. 11/270,804 mailed Apr. 3, 2009.

\* cited by examiner

Amino acid sequence of FLAP ( >alox5ap_protein translation NM_01629)
MDQETVGNVVLLAIVTLISVVQNGFFAHKVEHESRTQN
GRSFQRTGTLAFERVYTANQNCVDAYPTFLAVLWSAGL
LCSQVPAAFAGLMYLFVRQKYFVGYLGERTQSTPGYIFGK
RIILFLFLMSVAGIFNYYLIFFFGSDFENYIKTISTTISPLLLIP
(SEQ ID NO: 2)

MRNA of FLAP (NM_001629_mRNA)

Acttcccttcctgtacagggcaggttgtgcagctggaggcagagcagtcctctctggggagcctgaagcaaacatgg atcaagaaactgtaggcaatgttgtcctgttggccatcgtcaccctcatcagcgtggtccagaatggattctttgcccataa agtggagcacgaaagcaggacccagaatgggaggagcttccagaggaccggaacacttgcctttgagcgggtctaca ctgccaaccagaactgtgtagatgcgtaccccacttcctcgctgtgctctggtctgcggggctactttgcagccaagttcc tgctgcgtttgctggactgatgtacttgtttgtgaggcaaaagtactttgtcggttacctaggagagagaacgcagagcacc cctggctacatatttgggaaacgcatcatactcttcctgttcctcatgtccgttgctggcatattcaactattacctcatcttctt tttcggaagtgactttgaaaactacataaagacgatctccaccaccatctcccctctacttctcattccctaactctctgctga atatggggttggtgttctcatctaatcaatacctacaagtcatcataattcagctcttgagagcattctgctcttctttagatgg ctgtaaatctattggccatctgggcttcacagcttgagttaaccttgcttttccgggaacaaaatgatgtcatgtcagctccg cccccttgaacatgaccgtggccccaaatttgctattcccatgcattttgtttgtttcttcacttatcctgttctctgaagatgtttt gtgaccaggtttgtgttttcttaaaataaaatgcagagacatgtttt (SEQ ID NO: 3)

FIG. 4

ID CHROMOSOME 13: 28932001-29146000BP in NCBI build 34.

SQ Sequence 214000 BP SEQ ID NO: 1

| | | | | | |
|---|---|---|---|---|---|
| GACTAAGATG | AATATGCATT | CATTCACCAA | AATCTCATAT | TCCCAAAAAG | CAGGAAAGGT | 60 |
| AGTACAGTGA | GATGGATGAT | GCCTTCACAT | GACTCAGATG | TCACGTGTTT | CTCACCATTG | 120 |
| AGACCCCCAA | GGCACCCCCT | CCCAGCATTT | ACCAGAATGT | GTGTGTAACT | ATTTACAGTG | 180 |
| ATTTGTGTAA | TTATTTGATT | GTTTCTCTTG | TATCCTGTAG | CAATGAGGGT | AGAGATTATA | 240 |
| TCCCACCTAC | CACTGCAGCT | CCAGGATCCA | GCTTCACAAA | CATTTGTTGA | ATGAATGAAT | 300 |
| AAGAAAAGAG | GACACCCCCA | AAGAGGCTGC | AAGGGAAAAA | GCTACAAAGA | CAGAAGCACC | 360 |
| AGGAAAAAGT | AGGGTCATGT | AAGTCAAAGC | AGGAAAAAAG | TTCCATGGTG | GGGTGGTCAG | 420 |
| CAGTGTCTAA | TGCCACGAAG | GCACAAAGTA | GGATAAAGGT | TAAAAATCAG | CCTTTGGTTT | 480 |
| TGGCAAATAT | GAAGCTTATC | GGTAGCCTTA | GCGAGAACAA | TTCCATCAGG | GAGCAGAAGC | 540 |
| TAACTGCAGT | GGGTTGAGTC | ATCAAGCAGG | CATAAGGAAG | TAGGGATACC | CCATTATAAG | 600 |
| CTACTCTTTC | AAGAAGCTCA | AATCTGAAGG | TTAGGAGAAT | TAGGTCAGTA | GCTAGAAGGA | 660 |
| AATGTGGAGT | CGAGGGGCTG | TTTTTCCTCC | CAAGGAGTAT | AAAGGTGTAA | CGTTGCATGA | 720 |
| AACCACTTCA | GACAAAGGCC | GATATCAATA | GAGAAGTTAA | AACGCACGCC | TCAAGATTTG | 780 |
| GGAAGGCTTG | GGGTTGGGCT | TAAAGAGGTA | GGAGCATATT | TCCTATCCTA | GGACAGAGAA | 840 |
| TAAAGAAGAA | AGGATAGGTT | CCCATGGAGA | TAAATTTCTA | AGTGTTAAAG | AAGAGGCTCA | 900 |
| GAAAATTCTA | GCATGATAGG | CTCACTTTTT | TCTTTTTCCA | TGAAGGAGAT | GGCAAAGTCA | 960 |
| ACTGACATGA | GAAAGGTGAC | AATACTGATG | GGTTGAAGAG | CGATGGACAT | TTGAAATAAC | 1020 |
| TTCTTAGACC | AGTAGAGGCT | GGAGTTCATA | AATCAGAACT | GGCTACAGGT | TATATATGTT | 1080 |
| TTTTTTTTTT | TCTCCAACAG | CATAAGATAA | CAGAGCGAAG | TCTGTAGAAA | TGAAAGAAGA | 1140 |
| GTCAGATGAG | GATAGCTGGA | GCTAGTGCAA | GGAGGGAAGC | ACCACGGTGG | GAGCCAGGTA | 1200 |
| CCCCCTGGAT | TTATAATTCA | TACTGAATTC | CAACAACAGA | AGGGCTCTAA | GCAGGAGAGT | 1260 |
| GACAGATTTC | AGAAGACTGA | GACACATTTG | GTAAAAAAAA | GTAGGAGGAA | AACCTGATTC | 1320 |
| TGGAATTAGG | GCAGCCAATA | GACGGCAGTA | TTTTCAGAAA | GGAGGGAATG | GTCAACAGTG | 1380 |
| ACTTTCTAGT | CTGGAGCTCA | GGAGGAAGAG | GCAACTCTAC | CTGATGGTAT | TAAGATCATG | 1440 |
| GAGGTAGCTG | AGATCACCTA | GCTTGTGTGT | GTCAAATGAG | AAAAGAAGAA | AGAATAGGAG | 1500 |
| AAGTTCCCCA | GGAACACAGA | CATTAAGTGG | GGCTGTGGTG | ACAACACAAG | AAGAGAGGCT | 1560 |
| TGCAAAGGAG | CCTGAGCAGC | TGTCATGAGA | GAGGTAGGAT | GGTGGACTCG | GAGAAGAGGC | 1620 |
| AGAAGATGTT | CTTAAAGGAA | GGACACTGCT | GCCAAGTAGT | CAGCCAATTG | GTGACAAAGA | 1680 |
| AAGACCCTGT | TGCGAGAAAA | AAAGTCAGTG | AAGTAGTAGG | AACGATGACA | GATGACACTG | 1740 |
| GGTTGAAGAC | TGAGGAGAGA | GAAGTGTAAG | AGTGGAAGCA | GAGGGCAGAC | CACTCTTCTG | 1800 |
| AGACACTGAA | GAGGCATAGT | TAGAAATAAA | GGGGAGTCGC | CAGAAAGGAA | TTTGTGGCTA | 1860 |
| AGCAAGAGGT | TTTCTTTAAG | ACTGAAATAC | ATAAGCATGA | TTTAAATGCT | GCTGGGATGG | 1920 |
| AGTTCACAGA | CCTGGAAGAC | AGAAGACAAA | GCGGATCATC | AAGATAGTGG | AATTTACTGA | 1980 |
| AATGAGAGAG | GAAAATCCCA | TCCACAGGAA | ATGCAGACAT | GAGGGAGGGG | CCAGAAGGAC | 2040 |
| AGTGAAAACA | TCAGCAACTG | GTCCCCCAAC | TTCTGAGTGA | ATGTGGAGAT | ATAATCAGGT | 2100 |
| AAAGGACTGC | ATCATCTCCC | TGGTTAATGA | TGGAGTCAGA | GAAAAGAGTG | TCTTATACAG | 2160 |
| AAGTTGTGAT | ATACTTGGCC | GGGCGCAGTG | GCTCACGCCT | GTAATCTAAG | CACTTTGGGA | 2220 |
| GGCCAAGGCA | GCGGATCAC | CTGAGGTCAG | GAGTTCATGA | CTGGCCTGGT | CAACATGGCA | 2280 |
| AAATCCCACC | TCTACTAAAA | ACAAAAGCCT | GTAATCCCAG | CTACTAGGGA | GGCTGAGGCA | 2340 |
| GGAGAATCGC | TTGAACCCAG | GAGGCAGAGG | TTGCAGTGAG | CCAAGGTCGC | ACCACTGTAC | 2400 |
| TCCAGCCTGG | GCAACAGAGC | TAGACTCAGT | CTCAAAAAAA | AAAAAAAAAG | ATGTATTTAT | 2460 |

FIG. 6.1

```
TCTCACTGTA TAAATTTCTG TGTAAGAAAT ACTCTCTCAT ATAGAAGTAA ATTTATATAT    2520
AAAATTATAT AGAACCACTA TAAAATACTC AGGTTTATAA AATTTATATA TAAACTTGTT    2580
GACATATAAA ATTCCATGTA AATGACTATA AAGTACTCTT ATATGAAAAG TATATGAATT    2640
AAATTATATA TCAACTTACT TTTATATTAC AGTATTTTTG TTATACAGAA GTTTATATAG    2700
TGACAATAAA TATTTCTCAA GAACGATTTC ACATAATAGA AGTATAAATT ATCCATTTCC    2760
AATAGTGAAA AAGAAAAGCA GTTCCACACC AGTGACAGGG CTACGAATCT AAGAGGTACA    2820
AAGACTTCAT TCTTAGAGAC ACTGAGGTCA GGGCATGGCC AACACATCTG AAGCTGATAG    2880
AATTGGCGCT GGGTTGGTTG GAGACGGTAC GGTATTACTA TTACAATGGC AGACGCTTGG    2940
CCTTGATAAC TAGCCAATCA GGGGGAAAGA TTCTGGTTTC CTCTGTTATT ATCTGAACTA    3000
GTGTGTTCCC AAAGGGTTAA GATGGTTTAT GGAAGGCACA AGATCAGCAA ACCATAAAGG    3060
ATTAGCACTA AGAAGGAAGG AAGTAGACCA AGTGTTAATG GCGATGCCAT GTAAGAGCCA    3120
GGTCTGCGAT GTATGTTCTA CATGGTTTGG GGGGTAAAAA AAATGTCAGC CTCCAGAGCA    3180
CAGGGCTTTA AGCCTCAAGT ACTGTTAACA GTAGAGTTTA CTAGTCTACA GCAGGAATTA    3240
CAACCAGTAA TTCTAAGGCC AATTACTCAG GCAAGTTTTA CTAGAACAAG GAAGCTCTGC    3300
TTCGAGGTCA AATCGATTTC TGCATTTATA GAAGCATCTA GATGTTCTCT GTTCAAACAA    3360
TGGGGTAAAA TCCCCACACA TTTTATTTCT GACAGAGTGT TCCCTATATT GCCTGGCCAG    3420
GAGTGATAAC ATTGCTTGGC TATTATTAAT AAAACATTGC TGTGGCTGGG CGCAGTGGCT    3480
CACACCTGTA ATCCTGGCAC TTTGGGAGGC TGAGGCAGGA GGATCACTTA ACTCCAGGAG    3540
TTTGACAGCA GCCTGGGCAA CATAGCAAGA TCCCATCTCT CTAAAAAATT TTAAAATTAG    3600
CTGGGTGTGG TGGCAGACAC CTGTAGTCCC AGCTCCTCAG GAAGCTGAGG TGGGAGGATC    3660
ACTTGAGCCC AAGCAGGTTG AGGCTGCAGC GTGCTGTGAC TGTGCCACTG CACTCCAGCC    3720
TGCGCAACAC ACTGAGAGAG ACTCTGTCTC AAAAAAATAC ATCAAATAAA AATTAAAAGC    3780
CCATTTCTTT CTTTTGGTAC ATTACAGCCA TGCACTTCAA AGGCTAGCAC AATTATTTTT    3840
CTGCAGTTCT ATATTTAGAT TCTAGTTAGA AGTAACCTAG GACCTTCATG TTAGAGGTGT    3900
CTTTGGCAAA ACTGTTATGT GAGTGAAACG TTTAATCAAT TGAGGATAAA GATGCCTCAT    3960
TGCTAATGAA GATGTGGTTT AAGGATTTTA TGCACCCAGT TCATTTATTA ACAACTTGTT    4020
TAAGCTTTAT TAGCTGGGTC TCTACTTTAT AACTGTGTTC TTTAATTTAC AAGACAATAA    4080
AAATTAAAAT GGTAAATGGG AAACCTATCT TGCTTTTCAA TAAATAATTT ATTTTAATAA    4140
CTTCGTGGGC ATGGTGGCCA AAACATTTTA GCTGTGAAAA TAATTTCAAT TCATATTTTT    4200
TTGGAATCAA TATTAAAAGG TGATATATTC TCAAATGAAA AGTGGACAAA TGATCAGTTA    4260
TAGGACATGA TTAAGAAACT AACCATGAGC CACGTGCAGT GGCTCATGCC TGTAATCCCA    4320
GCACTCTGGG AGGCCGCGGT GAGCGGATTG CTTGAGCCCA GGAGTTCAAG ACCAGGCTGG    4380
GCAACATGGC AAAAACCCGG CTCTACTAAA AATGCAAAAA AAAAAAAAAA AAAAAAATT     4440
TAGCTGGGTT TTGGTGGCTT ATGCCTGCAG TCCAGCTAC TCGGGAGGCT GACTCGGGAG     4500
GCTGAGGCAC AAGAATCATT TGAACCCAGG AGGCAGAGGT TGCAATGAGC TGAGAATACA    4560
CCACTGCACT CCAGCCTGGG CAACAGAGAG AGAGAGACTC AGTCTCAAAA AACAAACAAA    4620
CAAACAAACA AACCGCTGCC CTGTGCTTGG AGAGATCTGT TTACCTTTAC CACTAAAGAC    4680
TGTTGGAAGT AAATTTTAGA AGGTTTATAA TACCTAAAAG TAATCACTTC TGTCTTATGA    4740
AAGGTTCTGC TGAGATTTTT CTATTGTGGC CACTAGTGGC AATATTCCAG AAGTCATATT    4800
TAAAGAATAT CTTTAGTGGA TTCAGCAGTT TTTCAAATAT GTACTTTTAT CTCTCCAACA    4860
TTCATGATTG CAATTTTTCA AATTAACCTC ATGATATAAA CAACTGTACT CTATGATGCC    4920
TCATAGTACA GAAACTGGAG GCAGAAAGAG AAGTTGAATG TCTAAGAATC GGTAATTCTA    4980
AAACTCAACA TAGACCATTC AGCATTAGTG GTTCTAACAA TCCCACTGCA AAATGAGTTG    5040
ATAATGTGTA ACACTTTAGT GAACTAAAGC ATAAAGAACC ATGGTCTCCT AATGCAGCAA    5100
```

FIG. 6.2

```
ATTAAAACAC ATGATAGCTA CAATTAATGA AGTACATAGT CCTGGCTGGG CACTATGGTA    5160
CGTCCTTTAC ATAGATTATC TCTTAAATTA TTAACCCCGT TTTAGAGATG AGAACATTCG    5220
GGCTCAGGAA GGTTATGTAA GTTATATAAA AATCACAAAA TAAGAGACAG AGCTAAGATT    5280
TGAATCCAAG TGTGACCAGG TTCATATCAA GCTTCCATTT TTGAATTTAT ATTAGAGGTC    5340
AATAACTCAC CTTTGTCCTT TTAAAATAAT TTTTGGCTCT GTGACCTACA CAGGCAAGCT    5400
GTTATTTACA AACAACCCAC ACATCTAGAT GGTCACTGTC TCACCGCCCA CTTTTACCAT    5460
CAGGACTCCT AGTGAGCTGT CAAGGGGAAT GCTATAATTT TGGAGGTTCT AAATCTGAGG    5520
GCTTAAGAAA GAAAGAAATT GTAAAAAGCA GGCATTACTC AGGGGCATAG ATTGTCAGGC    5580
AGATCTGTCA TGCTTATAGG TAACCTCCCA GGGCCAAAAA TATATGTGCC CAAACTGCCT    5640
AAATATTTCC TGTCACTTCA TAATACTGCC TGAAATCCTG CCAAATTAGA ACTTCATTTG    5700
TGTTGCTTGT CAATTTTTAA CGCATAAGCA AATCACCTGG AGATCTTGTT AAAATGCAAA    5760
TTCTGATTAG GTTAGGTCTG GGTCTGCATG TCTGATATGC TTCCAGAGGG CACTGATGCT    5820
GCTGGTCCAT GGACCACACT TAAAGAAGCA AAAAAGATGT CTGATATTTA CTCTCTGGCT    5880
GCCTAGGAGT GCTTCTCATT TAAGTGAGAT CTCTTTGTGC ATCATAATGG GAGGGATGAG    5940
CTGAAAAGCA GCAAATTAAG AGTGAGTTAA GTGTCTACCT CACTTCCCTA CTATCTGTAA    6000
CAAGCAGGTT TGGGCACTGT GGTCAACCAG AAAATTCTTT CCAGGACCAC AACCCTTGAG    6060
ATTATGTTGC AAAGATGCAA GGACAACTTA GAAATAATTT CCAGCACTGG TGGCACTGGA    6120
TGTCTGTCAG TGGTGCTGGT GGCAGGGTCC TATTCAGACT GTGGTTTACC TGCCTGGCCC    6180
GTTTGGTTAT GGGCCATTTT CTGAGTACCA TGGAGCATCG CCCAGCTGAC AAGGGCTTGT    6240
ACTCCACCCT TGGTGCGCAG AAGGGAAGCT TGGCTGCTAC TAAGTTTGGT GCAAAGTAAT    6300
TGTGGTTTTG CCATTAATAT TTGATACAGT GAGTCCCTAC TTTCCTCAGG TGAAACTAGA    6360
ACTTAAGGGG ACACGCTCAA GTTCTCATTA TACAGTACTA AGTTTCAAAA ATCAGCAATT    6420
TTATCAAACA CATGCTCTAC AGCAGTGGTC GGCAAACTTT TTCTGTAAGG GGCCAGAGAG    6480
TAAATGTTTT AGAGTTTCTG GGCCACATAT GGTTTCTGTT CCAGCTATAA ACTCTGCCAC    6540
TGTAGGGCAA AAGCAACCCT CCACAATACA TACATGAATA GGTGTGTTCC AAAAAAACTT    6600
TATTTGTGGA CCCTGAAATT TGAATTTCAT AAACTTTTCA TGTGTCATGA ATATTCTTT     6660
TGATTTTTTC CCAACCTTTT AAAGATGTAA CAACCATTTT TAGCCTGTAG GCCATATAGA    6720
AACAGGCAGT GGGCTGGGTT TGCTGACCCT TGCTCTGAAG CAATGATATC TCGATCCAAT    6780
TTATACCCAC AAATTTTTCT CCTTGAAACC ATGCATTTAA TTCTCATCTC TTCTTACCAT    6840
GACAATAAGA AGTTATTCTA TATAACAAAG AGATTGTACC CACCCAAGCC AGCATTTAGA    6900
TCATGTCATT TGCTTCCTCA AAATTTTGGT CTTTATAAAA ATCAATTAAA GCACCTTAAA    6960
AGGTAAGCAG TGATGAAATA TTTGAAATAA TTGGCTAATT AAACATCACC TAAATAGAAA    7020
CTGTGATAAG AACCACAAAT GCGAAAAGGA ATCATGTAGT AACTAATGTG GAGGATATCT    7080
TGGTTTAGAG ATTTGATGAA CACGAGTTTT GATTTAAAAA AATTTGTGCA ATACTCACTG    7140
CTTTGGTGGG GAGCTTGCTA TGCAAGTTGG TAGAAAAATT TATCCTAAAG TCACAGTTCT    7200
CTACCACTCT GGATTTTCTC GAGCTAACTA CCATTCCAAA CTATTTTAGG CACAGTTACT    7260
AGTTTCAAGA ATCAGGCAAA TTGCCCTGGT ATTAGCACTG TTCTTTCTGT GGTCACAAGT    7320
CAAACTACTG TGGTGAATAA AATTAGATGA TTTCTTTAGT CTTTCCTTTT TCAGCCCCTG    7380
TAGTCAATTT CCAGTGCTCC ATTCAAAGAA AAACCAAAAA TGTCCAGAAT ATAACCTTAT    7440
TTTAAAACTT GTTAACCACT GATTTCACTT GTTAACCAAA TTTTTTTTTT TTTTTTTTG    7500
AGAATGAATC TCACTCTGTC ACCAGGCTGG AGTGCAGTGG CATGATCTTG GTTCACTGCA    7560
ACCTCCGCCT CCTGGGTACT GGTTCAAGCA ATTCTCCTGC CTCAGTCTCC CGAGTAGCTG    7620
GGATTACAGG TGTGCACCCC CACACCCAGC TAATTTTTTT GTACTTTTAG TAGAGATGGG    7680
GTTTCACCAT GTTGGCCGGG CTAGTCTTAA ACTCCTGACC TCGTGATCCG CCCGCCTCGG    7740
```

FIG. 6.3

```
CCTCCCAAAG TGCTGGGATT GCAGGCATGA ACCACTGCGC CCAGCCTGTT AACCAAATTT    7800
CTAATCACAC ACACTTGAGG CCCAGTAAAT GCCTGCTGAA AAGAGGGTGC TGGTGGTGAG    7860
GCAACTGAGG GGCTAACATA CTGATAGCTG CTGAAATCTT CTACAGCTCT TTCTTGTTAG    7920
AACACTCCAT CACGGCTCCC AGGCCCACAC CACATGAAGG AACTTCTAGC TCTCTTGCTT    7980
GCTCTTTACC CAAATGTAGT TAGCAAGTCC TGGGAACTAA ACAGCATTGA CACACTTGAA    8040
GAAGACAATT AGGCAAATCC CAACTGCTGT GCTCCTGCAG CTAAAGATGA AGACTCGTCC    8100
ATTGGGCAGT TGATTAATTG TACCTAGAAA ATTAATTTCA ATGGTCCCAT GACAACATAC    8160
GGGCAGTGAA GCTCTAGTGT TCCCCCTGGG TGGAATCTTC CAGGATGTAT AGTCTCCCAT    8220
ACCAGCTCAT CCTCCCATTT TTCCAGATTC TGGTTCTTCT CTCTTACCTA GTGTGTAGTG    8280
GGCCAAATGG TGGTCCCCCA AAAAGATATG TCCATGTGTT AACCCTGGAA ACTGTGGATG    8340
TAACCTTATT TGGAAAAATG GGGCCAGGTG CAGTGGTGTG CATGTGTAGT CCCAGAACTT    8400
TGAGAAGCCA AGGTGGGAGA ATCGTTGGAG CCCAGGAGTT CAAGAACAGC CCAGGCAACA    8460
TATTGAGACC CCCGTCTCTA TAAGCAATAA AAAATTAGCT AGGTGTGGTG GCATGCACCT    8520
GAAGTTCCAG CTACTTGAGA GGCTGAGGCA GAAGGACTGC TCAAGCCCAA GGAGTTCAAG    8580
GCTGCAGTGA GCTATGATCA TGTCACCCCA CTCCAGCCTG GGTGACAGAG TCAGACTCCC    8640
TGTCTCAGGA GAAAAGAAAA AAAGGTCTTT GTAAATGTAA TAAAGAATCT TGAGATAAGA    8700
TCATCCTGAT TTAGGATGGA CCCTAAATCC AATGACATTT GTCCTTACAA AAGAAAGGTA    8760
GAGGGAACTG TGAGACAGAC ACAGAGGGGA GGGCCTTGTG AAGCAGGAAG CATAGATGCA    8820
GTTACAAGTC AAGGAATGCC AAGGACTGTC TACAACCAGA AGCCAGGAGA GATGCATGGG    8880
ATGATTTCTC CCTCACAGCC TCCAGAACTT CTGGCCTCCA GGACTGTGAA GAATCAATTT    8940
CTGTTGTTTT AAGCCACCAA GTTTGTGTGT CATTTGTTAT GGCAATGGCA GTATTAGGAC    9000
TCTAATACAC AGTATAAAAA AATAAAAATA GGGCCAGGCG TGGTGGCTCA GACCTATAAC    9060
CCCAGCACTT TGGGAGGCTA AGGCGGGGAG ATCACTTGAG GTCAGGAGTT TGAGACCAAC    9120
CAGGCCAACA TGGTGAAACC CCATCTCTAT TAAAAATAAA AATTAGTTGG GCATGGTGGT    9180
GTGCATCTGT AATCCCAGTT ACTCAGGAGG CTGAGGCAGA AGAATCGCTT GAACCCAGGA    9240
AGTGGAGGTT GTAGTGAATG CCACTGCACT CCAGCCTGGG TGACAGAGCT AGACTCCTTC    9300
ATCCTAGGAC ACAGCCAAGT CTTACGTAGC AAAAAGAAGT TGTTAAAGGT CTGTAGTTCT    9360
GCATTAAGCA ACACAGGCAT GTACCTATGA ATTATATGAT TATAAAAGTG CTCGGACAGG    9420
CCCATTTCAA ACTTGGCCTC TTTCCACCAA CTGTGTACTG TTTCTCATTC CATAACTAGA    9480
GATTATGTCT TTATATCCTG TCAAAAAAGT GAATTTTTGT GGGCTAAGAC ATTATCCCTG    9540
TGTTAAATGC ACCAGTCTTA GTGTAAACAA GCCTAGTTCC TTTTTCATTT TGGCTGTCTA    9600
GTATGCATTT GTATATGCTA GGCAGTGTAC TAGGCACCTT AAATACATTA CCTTGTTTAA    9660
CCTCTACAGG ATTCTGGGAG GTAGGCATTA TCCCCATTTT ATAGATGAGA ACACTGAGAA    9720
GACAATGTTC ATAAGTGCGT CACTTGTCTG AGATGACATA TTTACTAAGT AGCAGAACCA    9780
GGCCTCGAGC TACTCAGTCT GATTTCCAAA GCCCCTGCTC TTAATCACAT CAACTTCTTT    9840
CCTATATCAC CTTTCCCAGA GTGCGCTCTC ATGGATAAAG AGCAGAAGTA TAAGTTACTA    9900
GGCAGCAGAA AACTGTAGAG GTGGGAAGAT TAGATAAAAA ATGTAAATAA GAAGGCTTTA    9960
AGACACCAAA ATCAAATGTA AATACTTTAT AACCTGAATC AGTGCTTGTG TTCATGAGGC   10020
TAGAGGTCGT GCATTTTATC TCTAGGTCTG GTGATGCCAA TCCTGATCTA CAGCCAGCAG   10080
CAACAGTTCC CTAGCCTGCC TAGAAGTTTG TAAATGCATG GGCTTGGTA GGAGGAAGAC    10140
GAGAGAAAGC AGAACAGATT ATTACAAACC CAGTGCATTC CCCCTTGATG GGTCAACAGC   10200
GATTTCTTTG TAAGTGAAGG ACAGCACACT GGTTTTGATG ACTCACGAGA GAGTAGGAGG   10260
GAAAAAGAAG TCTGAGGCAT TGCCTGGAAG CCTCGCTCTG CTTAAACAAG TACACTAATG   10320
GCTCATGCCT GTTACTCCCA GCACTTTGGA AGGCCAAGAT GGGTGGATCA CTTGAGGCCA   10380
```

FIG. 6.4

```
GGAGTTTAAG CCCAGCCTGG TCAACATAGC GAGACCTTTT CTCTATTAAA AATAAAGAAG    10440
AAAGAAAGTA ATAATGATTC AAGTTCTCAT TCTCTACAAA ATTCACTTAT GACTTTCCAA    10500
ATGCTAGTGA AAACTTTTAG GTATTGCAAA ACTGCCTTAA TGCATAACGG GATTCTCATT    10560
TTACTTAGTC TAAGATGACT TTTTCACTTT GAACTTCTGC ATCTTTATGA TCGCTTAGCT    10620
TTCTGACAAG CAATTTCAGT AAGTGTTTAT CAATTTGCAT CCACACGCTG ACACATAGGG    10680
GTCTACTTAC ATATCCTTCA TGTAATTGAG CTTTTGTAAA TCATCTTTCT ACATGGTACA    10740
CTTCTGATTT TGTGTGCAGC TTTCTTGTTT AAGCACTGTA TTAAATGCTC TGCTTCCTAC    10800
ACCCTTAGGA ACAATGAGAA TAAAAGCGTA ATGTTGGTTA CTTCTTCATA TCAAAGGAAG    10860
TTCATCTCCT GGTTATTAAA AGCTATTATT AAATGGCCAT CTTTTTGTGC CCCTGTGTTA    10920
AGCACTCTAC CAAGATACCA TTAAATAGAT AAGGGCCACA CTCCATAGAG ATGATGGTTC    10980
TATATTCTGT ATTTTCTGGG GGAGTTCTAA TTTCATGCAA TTCCTTCTTC TTAAATAAAG    11040
GCAATTCTCT AAATATATTA CCTAATGTGC TTTCACTTTC ATATTCTTGT AAGATTTTTC    11100
ACATAAATCA ATTCTCAAAA AATAGTATCA TAGGCCTTTT AAAAATAGTC ATGTTCAAAA    11160
GTCAGGCTCA TGAATAAATG TGTGCATTCA TTACATATAT TTTCATAAAT TCAAATTTAA    11220
AAGAATAAGA GTAGCTAGAA GGTGGAAGAA AAATCTTATT CTGATTAGGA ATGCACAATC    11280
ACAAGAAAAT TTGTGATATA TATAGTCATT TTATTCTGTA TTGTTTTATT TTGATTTTGG    11340
TAAGACAAGA AACAATGTAG AAAGTTTGAC AACTTAAAAA AGTAATATGA GTGTGAGAAA    11400
GTCCTCTTCC AGGATTAGCA AAAAAATGGT TTTTTTTTTT TTTTTTTCCG AGATGGAGTC    11460
TCGCTCTCTC GCCCAGGCTG GAGTGCAGTG GCGCAATCTT GGCTCACTGC AACCTCCGCC    11520
TCCCGGGTTC AGGTGATTCT CTTGCCTCAG CCTCCCAAGT AGCTGGGACT ACAGGCATGT    11580
GCCACCATGC CCGGCTAATT TTTTTTATTT TTAGTAGAGA CGGGGTTTCA CCATGCTGGC    11640
CAGGCTGGTC TTGAACTCCT GACCTTGTGA TCTGCCCGCC TTAGCCTCCC AAAGTGCTGG    11700
GATTACAGGC GTGAGCCACC GTACCCAGCC TAAATGGCCA AGTTTTATTA TGGACAATTA    11760
AGCTGTAGAA TAAAAATCTA CTTTTAATAG CTGGCATAGT GCCTAGTGGT TTTGAAGCCA    11820
CAAGCAGGTT TACAAAAAAC ATTTAAATCC ATCTGAATCT ACAGAAAACT AAGATTACCT    11880
AAGCAGAAAA TGAAAATAGT TCAGGATTAA GGAAGATTAA CAAATGAAGA GTATATGTAT    11940
TTTAGAAGTA TTACTTTATA TTTTTATAGT ATAATAATAA TATTTACGTT CCTACACTTA    12000
TAATGAGTTT CGTATATATA TTAAAATAAT TTAATGGATT AGTATGTTTA TATTTGCTTT    12060
TAGTAAATTT GGTGTATGAT AAACTCAGTT GTCTACATTG TGAGACTACA CCTGAGGCAA    12120
TTTCTGTGTT GATATATACC TGAATAGCAG ATATTACTTG GGAGCAAATA AAATAGCTTC    12180
AGGCCTAATT TTGCAAGTTC ATGATGGGAG AGTAAGCATG ACTTCAAAGA ACTGACTTTG    12240
AGTTAAAACT TGAAGAATGA ATGTGACAAC AGCAAGTATA AAACAATGCC AGGCAGAGGT    12300
GGGACTGTTC ATGGGTATCA GGGTAAGTGT GTTGATAAAT GCTCAAAGTA GGAAATACCT    12360
TTCTTCCCCC ACACATGTCA GAAAATAACT GCAATAGAAT GCAACGACAT CTCAGAGATA    12420
AAGTGTTCAA CTTAGCTCTC AGAGACCGTT CAGTTACATT TTGTAATGAC ATTGGAATTG    12480
ATTGCATTTT GAAGGCAATT CTAAATGCAA AGTCTTCATT TTGTTGATAG AAGCTGGGTT    12540
ATTTATTATG AAATTTCAAA AATTAAGTAA AATATCTAAT TAGGATTATA CCAGCAAAGG    12600
CAAATTTAGA ATTCAAGACT TCATGATCCA TGGTAAGATT ATTTTAATGC AACTCTGCTA    12660
ATTAACTGAA ATTTCCTTTA ACTCTCACAT CTGCCTTTTA CTTCTTAAGA CATTTTTCTA    12720
GTATTTCACC AGAGCAAGAT ATCAGAAGGG TAAATCTCTT ACCAATGAAC TTTGCTAATT    12780
CTTAGTGACT CCGTTGACCC TGGTGTAAGG ATCAGGAACA AAGTGAATGA AATACATTTT    12840
AATACATTTC TGCTTTCTCT AATTCCAAAG ACCACTCTAA AGAATAAGTT ATTTGTGGGT    12900
ATTATCTGAA ACTTGGGATT AAAAGAGACC GTGATTACCC TTCAGGGATT TGGCAAAAC    12960
TTAAGCCATT TCATCTGAAG AGCAAAGCAA GCCTCCCACA CTCTTGGCTT ATTCTCACAA    13020
```

FIG. 6.5

```
TTATCTAGAT ATCTAGCAAC AAAACTCTTG AGTAGTTTGT TAACTACAGA TGCCAAGGGC    13080
TGACAGTTTC ACTTTCAGTT TTCAGAATAT CTTTTGTTTC AGTGGTGTAA GCACACCATC    13140
AGAATCTCTA CTATTTAAAA TAATTAAGTT ATAATTGTAA CTTCCATTAG ATGTAGTACT    13200
TAAAGGAATC TAGAAGACAC AACTCATTAA TTATAGGAAT TTGACTGCAA ATTCTTCTGG    13260
GGGGTCTGAA TTGCAAAGGA GGCATCTTTG TAAGTCAGAC TCAACTCATT ACTCTGTGAT    13320
GCAGGCTCCT CCAAATGGCA GCAGAAACGT ATTACTCTCT AGAAACACTA CAGTAGTGCT    13380
ACAATTTCAG GGTTCTGTAG AGATAAGGAC AAATTGACAG AAACACATTC TTAGAAGGAC    13440
AGTATCATTT AAAATAAAAA TACTGTCATA ATTGTACACC AGGATAGCTT CTCCATAATA    13500
AATTCTTTAT GATTTTCTGA TTTTTAGAAA TCAGAATTGA ACTTTTTAAT GTGAAAAAAA    13560
TGAGAGAATT GTTTCAAAAT AGGACCACAT TTCTGTGTAT AATTTTAAAA GTTTAAAAAT    13620
ATTTGATTAG TAGACTGATA AACTGAAACA TTTTTGATAA GCTTTTCATT ACATACAAAC    13680
CATATAATTT GTAAAAAATT GGAAATTATT CAAAACTTCA CATAACTAAA GTGACCAAAT    13740
AAATACTGGA GAGGAAAGAA AAGGAGTCAA ATGAATCTAG CATTTTCTTT TTTTTTTTTT    13800
TTTTGGAGAA AGGGTCTCAC TGTGCCACCC AGGTGGGAGT GCAATGGCAC GATCATGGCT    13860
CACTGCAGCC TCAACTTTAT GGGCTTAGGT GATCCTCCCA CCTCGGCCTC CCAAGTAGCA    13920
GGGACTACAG GCATGCGCCA ACACGTCCAG CTAATTTTTT TGGTATTTTT TGCAGAGACG    13980
AGGTTTCACC AGGTTGCCGT GGCTGATCTG GAACTCCTGG TCTCAAGTGA TCTACCCAAC    14040
TCAGCCTCCC AAAGTGCTGG GATTACAGGC GTGAGCCACC GCACCCGGCC TAATCTAGCA    14100
TTTTCTAAAA GGAAGGACCC AGCAGTGAAC GGCAATATCA ATAATCATGT TCAAGACTAT    14160
CAGACATGCA AGCTGGGGAT GAATGGGTGG AAGGGGAAAA TGATGAATAA ATGATGAACA    14220
CAAGTATAGA CCCAGTGGAT TTGAGATGCC CAAGATGCCA GTGAGATATT CAAAGTTTAA    14280
CTCAAAAGCC ACTTCCCATA TGAAATCCTG ACAAACACTC CTACGTCCAA CTGGAATTAA    14340
TTTCTCTTCT GGGCTCCCAC AGCACTCTGT ATTTTTCTAA TAGCATAACA CTATTTTGTT    14400
TGTAGATATT TCTCTGATAG CATTACTATC TTTCCTCTTT ATCACAACTG TTTGAAGTTC    14460
TTTTGCCTCT TGCATCCACT GTTGCCCAAT CCCACTGCTG GAAGGCTCAT CTTATTAAGT    14520
TCTGTATTCC TAGTGCTAAC ACACTGTCTA CCATAGATGA TGTTCAATAA ATGGTTGCTA    14580
AATGAATTCT CTTGTGATAA TAGCACTATG GCAACATAAT CGACGGTAAA AATTTCTTCT    14640
CAATGTTTAC TTTTAGCAGA ATGCATTCAT TTATCAACTT TCATTGAGAA TATGCTAATT    14700
TCCATGACCC TGCTAGGAAA TAGGAAAATA AAGATGAATG TAATAAGGTG CTCATTCTAC    14760
TGAAAGTCTT GACTAGTGGA GAATTATGGA TCCAACTTTT CATGAAATGC CTTCAGTGGT    14820
AAGAATTCTC ATATTTGGAA TAAAAAATGT TATGGGTTGT GCCAAGATAC CTACATACTT    14880
CATAATTTTG TAGAGGGCTG TCCTTACTGC AGAAATGTAT ACTACTATAG TCATATGTGG    14940
AAATTCTTTT TATGATGCTA ACTGCATGCT AACCAGACTT TTTAATTTAA TACTTGCATT    15000
AAATAAACCA TGCTAGGAAT CCAGGAATCT AGCTTGGTTT ATTTTCCATA CAATGTACTC    15060
TTTGTAATAT GCATATACTA CATAAAAATT CTATTAATGG CCTCGTACTA AAGATGTGTC    15120
TGTTGGGGAA TCAGTTATTC TGTATAATTT TATCTTAATT GATATATTAA AATCTACCAA    15180
AAATATAAAC TCCGAGTAAA AGTATCTGCA TGGTGTGCAT ATGTTTATTA TTTTAAGTGT    15240
CAGCGTATAC ATTTTCATGC CATAAAGTTA TAAAATGAAA AAATAGTAGC CTTTTATATT    15300
AAGTTCATGC TTATGTAGTT AGTAAAAACA AGAAAGCAAT TAACATACAA ACCATGATGG    15360
TGGTTAAACT TGCTTCAGTT TGTGTTTTTT AAAATTTGAA AGTGAGAAAT ACAGCTCGAA    15420
GTCAGCTCAT ATTTTCAGTA AGTACTGATG AGGATGTACT GGCCCTATTG ACTACGCTGA    15480
CCCCATTAAA ATATTTGTGA GTCTAAAGGT TCATATGACG CTGTTCCTTC ACTCTAGCAA    15540
CAGGCCATAC ATGTCTTACA TAGGGACTCT GTTCAATTCA TTAATACCTC CTGAAGTGCT    15600
CAACATCGTG GTTCATTTAT AGTAGATACT CAATACATAC TCCATTAACT GAATTCTAAG    15660
```

FIG. 6.6

| | |
|---|---|
| ATAAACTGTC TGTTACTGAC AGAAATTTTC ACTTAAGGGA GTCTCCGTGG CTGAAGGCAA | 15720 |
| TTTTGAAATC CTGTAAAAGA ACCCACTCCT CTCCCCAAGT AATGAAGTTT GTCAGTTTCA | 15780 |
| AGCCTGTAAT AAGGTACTGA CTTAAAATTA ATTTTCTAAT AATACAGTAC TGCTATGTAT | 15840 |
| CTAATGTGGG GTTAGTCAAT GATAGGAAAA AAACATAAGA CAGAGTCACA TTTAAAAATG | 15900 |
| TGTGCTTAGG TGCATGGTGA CACCTGCCTG TAGTCCAGCT ATTCCAGGGG CTGAGGCAGG | 15960 |
| AAGATCCCTT GAGCTCACGA GTTTGAGGCT GCAGTAAGCC ACTGCACTCA GCCTGGGCAA | 16020 |
| CAGAGTGAGA CCCTGTCTCT AAAAAAAATT CGTTTTAAGT GTGCTCAGGA CATAACAGGA | 16080 |
| GCCGCTGGTA ACATGCCATT TCCACTGTGA ATATGGTAAG GACAGAATCC CTGTCTCTAG | 16140 |
| GCCCTCTTCC ACTAGTCAAT CTCATCATCA CCATCAAGGC CAACATTGGT ATTCTCTCCT | 16200 |
| CTGAGACAAA GTCTTTGACA TTTTCTATAC TATACTATGT CTTCCTCTCC CCAAATGCAT | 16260 |
| ATACAAATAA AATTTGAATG CTTCTTTCTC CATTTAGTGT AATTTTTTTT ATAACATAGA | 16320 |
| CCCAATTTTC AAACCCCACA ATGGTGGATT TTATTTGATG TATTGTAAAA AGCGCTGGAT | 16380 |
| TGAAGTCAAA TGGCTTGGGA GACCTAAATT CTACTCCTGC CTGTACCATG AAAGAGACAA | 16440 |
| ATCCCAAGGC TTTGCAGGGC TTCAGCTTCC TTGTTTGTAG AATAAAGAAT TATAAAATCA | 16500 |
| TCTCTTTTGG TCCTACTGGG CAATAAAAAG CTATGATTCT AAGCCTGTTC CCTTTTCTCA | 16560 |
| CCTAAGAATA CAAATTTGAT ACAAAGAGGC CGCAGAATGT GTCAAACACT CCCTGTTGCC | 16620 |
| TGGAATTCTC TCTTCCTTTG GGTTCAGGGA TAAAGGTATG TTATTTCTTA AGTCTCCCTT | 16680 |
| TGCTTTCTTC TGCTTGCCTC GTAAATATTT TTCCATCTTG GCAGTCCTAC ATGTCTTCTC | 16740 |
| ACTCTACATG TTTTCCCTAG GTGATGTGAC CCAGCCTGTG GCTTCCACTG CCATCCACAC | 16800 |
| ACGTCGCTGC CTCTCTCCAC ATCAGCATCG CAACTATCTC CTGGAAGCTT TCCAAGTGCT | 16860 |
| GAACTACAGT AACCTCAACC GAACTGCTGT TCATTCACCC CACAGGCTTG CCCCTCCTCT | 16920 |
| GCATCTTTGT GAGAACCTGA GAGTCATCCT AAACTCCTCC TTCCACCTCA CTCCCCACAT | 16980 |
| CAAATCGATT ACCAACTTGT GCTGATTTTA TCTTCAAATA CTCTCCAGAA TTGTCGCTGT | 17040 |
| CATGGACTGA ATATTTGTGT TCCCCCAAAT TCATATGTCC TAATCCCTGA TGTGACTGTA | 17100 |
| TTTAGAGACG TGACCTCTAA GGAGTAATTA AGGTTCAGTG AGGTCAAAGG TGGAGCCCTG | 17160 |
| ATCTGATAGG ATCAGTGTCC TTATAAGAAG AGACTAGAGC TGGGCACAGG GGCTCACACC | 17220 |
| TGTAATCCCA GTATTTTGGG AGGCTGAGGT GGGAAGATCA CTCAAGGAGA GGAGTCTGAG | 17280 |
| ACCAGCCTGG GCAACAGAGT GAGACTCCAT CTCTACAAGA AAATAAAATA GTCAGACACA | 17340 |
| GTGGTACACA CCTGTGGTCC CAGCTCCTCA GGAGGCTGAG GCAGGAGGAT GGCTTGAGCC | 17400 |
| CAGGAATTTG AGGCTGCAGC AAGCTATGAT CACACCTCTG CACTCCAGCC TGGGTGACAG | 17460 |
| CATGAGACCC AGTCTCTTTA AAAAAAAAA AAAAAAGGC CATATATAGC CCAGAAGAGC | 17520 |
| GTCCTCACCA AAACCCAATC CTGATAGCAC CTGGAGGACT TCCAGCCTCC AGAGCTGTGA | 17580 |
| GAAAATTTCT GTTGCTTGCA CCGCCCAGTC TGTGGTATTT TGCTGTGGCA GCCCAAGCTG | 17640 |
| ACTCATCAGT GACCTTCTCT CTGTTACCGC AGAGTAGCTC ATCATCCTCT CTTCCCTAGA | 17700 |
| GTCCAGCCAC TCTCTCACAT CTACCTACCT AGCAGTATCA CTGTGGGTTA GAGTCAGATC | 17760 |
| ACTGCGGATT AAGTCCTCAT TCTGCCACTG CCTGTGTAAA TCTGAGCAAG TTACTTAATC | 17820 |
| TCTCTGTGTG TCAGTAACCT CCCTGTGAAA TGAGGCTAAT AATAGCAGGG TTGTTTCAAC | 17880 |
| AAGGCGATAC ATGCATAATG CTTACAACAC AGCTTGGCAC ATTATAAGCA TTCAACGAAA | 17940 |
| AGTGAGCTAC TATTATCTCA TCCGTTATCA GAATAAACCA CCTAAGCCAC AAGGCTGCCC | 18000 |
| ACATCATCCT CATGTTTTAA AACACTTCAG TGGGCTCCCC ACCATCAACA GGATAAAGTC | 18060 |
| CAAGCTTCCT TAGCATTTCT TAGAGGCTCC ATATGAATCC CCAAGTTCCA CTACAGGAAC | 18120 |
| ACAGGTGAAC TTTCCACTCC AACCTCAGGC TCCTTCGTGT CACTCCTCAT CCACATGGAG | 18180 |
| GTAAGCAGCA AGAGACTCCG TGCAGTTCCT GGTGGTTCCC TGACCCTCAG GCAGACTCTC | 18240 |
| CCCAGCCCTC TGCCTGCAAC GTCCTTGCCC TTTGCTTCCC TTGGCCAGCT CCCATTCATT | 18300 |

FIG. 6.7

```
CTCCTTGATT CTGCTTGGAA GTTTCCCTCT CAGGAAGGCT TTATGAACCT TAGTGTAGGT    18360
TATGAACCCA TCTTTGCTCC TTTCATACCT TTTGCAAGCC TTTATTTATT ATGACACTTA    18420
ACCATTATCA TACTGAAGTG ACCTGTTGGT GTGTCTTTGT TCCCCACTAG ACAGAAAACT    18480
CAAGATCAGA GACCAGTTCT TGTTCTTTTT TTTTTTTTTT TTTTTTTTTT TTGTATCACA    18540
GTGTTTAGCA GCCTGCTATA TGGTAAATGT CAGTAAATGT TCCACAAACT GAATGGAATT    18600
GAGCTCTGGA ATCTAGACCA TCTTTTCCAT ACCCATCACT CCTGTCTTAG TTGAAGTCCT    18660
TATTTCCCAT TTGAAGCAAT GCAAAGGATT TCCTAACTCT AATCTCTCTT TTCTTCACAC    18720
CATCCTTTAA ACAGCCGACA GAATGGTCAT CCTAAAGCAC ATATATCCTA TCTTACATAT    18780
CCTAGATTCG GAACCTCTCT GGGCTTCTCA CCATATAAGA AGAAAGTCTA ACCTCCTTAG    18840
CAAGGTGCAT AGGTCTTCAA TGGGCTCCAC CTCACTTCTC TATATATACC TATACTCTTG    18900
CTACACTAAA CTTCTTTCTT ACTGTTGCTG GAACAAGTTC AACGCTTTCA AACCTCCCTG    18960
ACTTTGCATA TGCAGTTCAT TCTGTCAGGA ATGCCCTTCT CTCTTATGCC TGGGATATTC    19020
TCATTCATTC CATATGACCT ATTTCATAAG TCACTCCTTA ATGAAGCCTT TCTTAGATAT    19080
CCACTGGGGC AATCAGCTGC TTGCTCCTGT TTCCACAGCA CATTGTTCAC ACAGATAGCA    19140
CAGGACTTAC CACAAGTTAT TATAATTTTG TCTGTCTTGC CCATTGAAT CCAAGGGCAA     19200
GGACGGAATC ATTCTCATCT TTGTATGTCC TGGGAACTAG AACTGTACCT GAGACATAAT    19260
AAACACTTGA TATGTTTGTA ATTTTTAAAT AAGTTAATGA ACGGAATGGC TAGAAAAAGT    19320
GAGAAGAAAC TCTGGCTTAC TGTATATCAT ACTGTCATAC TAAAAATATA TACTGAAGAC    19380
AGAATCACAT TATATCATCA CTTTTCACGC TATAGGCCAT GATCCATTAT GAAAAAGAGG    19440
ATAGTAAAAA AATCACAGGG CACAATTTTT GTTTCTGTCA CACACATGTG TACCTGTATA    19500
TTGGACTGGA ATGTAAAACG CATGTTCCAT TGTAGAACGT GGTTTTAAAA GAGGCTTGGA    19560
AAACACTGCA TATGGTCATT TCTTAGTTTA GTACAATTTA TTATTTTCGT AATAACCTCA    19620
GCTATAATAT AAGTCTACCA TGAAGCATTT TGGGGAGATT AAATGAGATG TGAAAAGTAA    19680
ATGTGTTAGA TAGACTGAAT TCATATCATA GCTTGCTCTG ATACTTTACA AAACATTTAA    19740
CCTTACCCAC AAGTTTTAGT TTCCTCACTA AAGTCACCCT GAGGACAGTA ATGGGATCTT    19800
CCTCACAGAG TATTGTGAGG AATACATAAG AGAACGTACG TAAATGCCTG GCACTTAGTA    19860
TTTATTCAAT AAATCTTAGC AATGATGATG ATAACAACAT GGTACCTGGC ACATAAGAGA    19920
GTTAAAAATT AGTTTCTTCA GTCAAATGTG CTTACATTGA TAGTTGATAC TAACTGGGGT    19980
TAAAAGGTCA TTGCTGGCAT CTCAGAAAGA TAGATTACAG TGAAATAAAA AATGACTACT    20040
GCTTAAAATG AATGAAGACT TATTTACAAA GTCATGTTCA TCTGGTACAA TAATGAAGTC    20100
GCTCAATTGG GAGAAAATGA CAAATAATAC AAGTGAATAT ACAATCTTAC TTAAGACGAA    20160
AGAAATAGGA CACCAGGCTA ACTATCAGTC TCCTAAACCA CAACTTTATT TCTGATACAA    20220
AGAGACAGTG AGACAATCAG GCTTCCCTC AAATAAATTA CTTAATCTCT CTTCAATTCA     20280
GTTTTGCATC TGTAAATATA AATAACTACA ATTTCACAGT ATTTCCATTT AAAAAGTTCT    20340
AGTGCAACAT CAGAAACAAG AACTTAGTAG GTGTTCAAAA AGAAATATAA GTTCTGCTTT    20400
GTTAGCCAGC AAATAGTTGC CTGTTTCTAG CCCTCACTTC TTTTCTCCTA AATCCCTATA    20460
TTGCATTTAT TTAACTTAAA GTGCTGGATG TGGCACTACG AGAAAGAAAA AGATATTTGG    20520
TAATCTTGTT AAAATCATTA GACATCCCAG GCTATCTGGA ATCACCTTGG GCTCACAGTT    20580
AGACATCAGC TATGGCTTGT TTTATTTAAA AATTCATCCA CTGATGCATG ATAATGGAAT    20640
TCACAGGAGA GCAATTTACC AAAAAAAAGA AATTTATTGA TTTATAATGT GAGATATTAA    20700
TTTAGCCACA AATATTTATT GAGCATCTCC TACATGCCAG GGAATGGACT ATATATGGCA    20760
GGAAAACAGA TACCAATCAT TTATATCAGG CATTTTTTTC TAATAGAAGG ATATTCGCAG    20820
GAGACAATGC ATAGCACCAT GCCTTGCACG TAACAGACAT TTAATAACTA TTAGTTGAAT    20880
AAAATTGGAG ACTAGAATGA TACATAAAGA GGCAAGAAAG AGCAAAGATA AGCCTTTCTG    20940
```

FIG. 6.8

```
AGAATTTCTA TCATGTTTTG CTCAATAGCT TGTCTTTATC CACTGCTTGT ATTTTTCCAT    21000
GTAGCTAATC CTCATTGGTC GTTAGAATTG AGACACCCTT TCCTTGAAAT CAGGAGCTAT    21060
AGGAGGCCAT TCTTCCTACT GGGCATTTTC TTTCTGGGAC AGGGTCTCAC TCTGTCACCT    21120
AGGCTGGAGT GCATCATAGC TCACTATAAC CTTGAAGTCC TGGGCTCAAG GAATCCTCTT    21180
GCCAAAGAGG TGGGATTACA GGCATGAGTC ACCATGCCAG CCTATTTGGC ATTTCTACTG    21240
TAGACAAAGC AGACTTACAG CAGTAGGTCT ACCTGCCTAA TACAAAAAGA AAAAAAAGAA    21300
TTTTAACAAA CAAATGAGGG AATCAGATCC AGAAAGTGAT TCTTATAACT TAGATTACTT    21360
AGAGTAGATC TATAATCTGC TCTAGATCCA CTGCATACAG TGGGCCCTTC TTATCATATT    21420
CCATAAATAG CACTTTTCTC AGCCCAGCTT TGATGATAG CTGAACAGAC TAACAGTTTG    21480
TCTAACAAAG GCTAGAGAAG GGGATAGCAA ATAATGGCCC ACAGGCTGAA TCCTGCCTGC    21540
TGCTCATTTT TGCAAAGTTT TATTAGAATA CGGTCATTTC CACTCATTTT CACACTGTCA    21600
ATGGCTGCTT TGCGCTACA GCAGCAGAGC TGGGTGGTTG GGCAGGGGT CACATGGCTA      21660
ACAAAGACTA AAATACTTAT CATCTGACCT TTTACAGAAA GTTTGCTGAT CCTTGGAGTG    21720
TACAAGTATT CTATATTGTT GATTAAGAAC AGAACCACAA GTATTAGAAG TTAGACCAGC    21780
AGGTGGTAAA GCTGATCATC TACTAATATA ATGGAAATTG GGGTTCCCAA TCAGGACTCT    21840
TGCTTTGATA GAAGGCCATC TTAACGAGGA GGGAGACACC TGCAGGCAAA GTCAGAATTT    21900
TCTGCAGGAA AAGTTTTGAG TCCATTTCCC CTTGTGAACA AGTGCTCAGC TATGCATTTC    21960
ATCTTTAGTA ACCATGCTTC TATACCTGGT TCTCCTTGGC AAAGATTTCT TCTTCAGTA     22020
AGTCTCAAGA CTTTCTGGGA AGGTAGGAG ATATGGGGGT AAAAGTGTCC CAGGACTTAC     22080
TGAAGGAAGT GTTTTATGAT TATCTGATAG AATCACTGTA TCATGGTAGA GAAGGCAAAC    22140
AGAATATAAT CTGAAAATAG AGGTGAGGGT GAACAAATGG GCACTAAAAG TGAACTCAGC    22200
ATCAGGAAGG TAGCAAAACA AGACATCAGT CAAAGATATG GGGTGATTCA GACCTAAGGA    22260
AGATTTAATG TGGGATGTTT CCGTGTGCCA GGAGCTGGAC ACTTAAGCAA GAGGAGATCC    22320
AGGAATGTTG CTAAAACCAT GGCCTCCATA CTTTATTGGA ATTAGCACAA CTTATCCTTG    22380
TTTCTTTCAT TTTGCAATCA AAATCTTTAA AAACACATTA TTTAAAAATA CATTATTTTA    22440
AAAGCTAGAA TGAAAATTAT GATATCATTT AGGTGGTTTA AAAAACATCC ACCAGCCGGG    22500
CGTGGTGGCT CATGCCTGTA ATCCCAGCAC TTTGGGAGTC CGAGGCGGGC AGATCACGAG    22560
GTCAGGAGAT TGAGACCATC CTGGCTGACA CGGTGAAACC CCGTCTCCAC TAAAAATACA    22620
AAAAATTAAC CGGGCGTGGT GGCGGGTGCC TGTGGTCCCA GCTACTCGGG AGGCTGAGGC    22680
CGGAGAATGG CATGAACCCG GGAGGTGGAG GTTGCAGTGA GCTGAGATCG TGCCACTGCA    22740
CTCCAGCCTG GGTGACAGAG CAAGACTCCA TCTAAAAAAA AAAAACAAAA ACCATCCACC    22800
AAAATGGGAA GAAGTGATGA AAAATTACAG TCCAAGAAGA AGGGCCATAG CTGTTTAAAT    22860
CAATTGGTAT ATTTGTTATC TAATATAACC CCACGTAACG ACAGGTATTT AACAAATGTT    22920
TCTGCTGAAT TTGACGATTC CATTTCCCTT ACATCCCATA TGCAATCCAT CAGCACCCCA    22980
CATCCAACCC ATCAGTACAT CCTGTCAGCA TTGGCTCCCA AATATAACCT AAATCTAACA    23040
CATATCCTAC TATCTCTGCT GCTACAACTT TAGTCTGAAA TCTCATAATC TCCCACTTGT    23100
ACTACTGTAG ATGACTCTGA ATGAGTCTTC TTGCTTCCAT TCCACACAGC ATCCATACTG    23160
ATCTATTTTT TTTTTCAATT TTTTGTAGAG ACGGGGTCTT GCCATGTTGC CCAGGCTGGT    23220
CTTGAACTCC TGGCTTCAAG GGATCCTCCC ACCTCAACCT CCCAAAGTGA TAGGATTTCA    23280
AGTATGAGCC ACTGTGCCTA ACCCTGACTG ATCTTTCTAA GCATAAATCT AATAATGCCC    23340
CTTCCTTGAT TAAACCCTTC AATGAATTCA CATTAAGCAA ACAACCTGGC CAGGTGTGAT    23400
GGTTCATGCC TGTAATCTCA GCACTTTGGG AGACCAAGAT GGGAGGATCA CTTGAGGCCA    23460
GGAGCTCAAC ATCAGCTTAG ACAACATGGT GAAACTACAT CTCTACAAAA AATACAAGAA    23520
TTAGCTGGGC ATGGTGGTGC ACCTATAGTC CCAGCTACTC GGGCGGCTGA GCTGGGAGGA    23580
```

FIG. 6.9

```
TCACTTGAGC CCTGGAGGTC AAGGCAGCAG TGAGCTGTGA TTATGCCACT ACACTTCAGC   23640
CTGGATGAAG TGAGACCTGG TCTCCAAAAA AAAAAAAAAA AAAAAAAAGA AGCAGGGCAA   23700
GGTGGCTCAC ACCTGTAATC CCATCACTTT GGGAGGCCAA GGCAGGCCTC CTGGATCATG   23760
AGGTCAAGAG ATCGAGACCA TCCTGGCCAA CATGGTGAAA CCCCATCTCT ACTAAAAATA   23820
CAAAAATTAG CTGGGCATGG TGGCATGCAC CTGTAGTCTC AGGTACTTGG GAGGCTGAGG   23880
CAGGAGAATT GCTTGAACCC GGGAGGCGAA GGTTGCAGTG AGCCAAGATT GCCTGGTGAC   23940
AGAGCGAGCG AGACTCTGTC TCAAAAAAAA AAAAAAAAAG AAAGAAAGAA AGAAAGAAAG   24000
AAAGAAGAAA TCCTTAGTCC TGTCTTAACT ACTTGAGAGG CTGAGGGAGG AGGATCACTT   24060
GAACCTAGGA ATTTGAGGCT CCAGTGAGCT ATGACAGCAC CACGGTGCTC TGGTCTGGAG   24120
AGAGTGAGAC CTTGTCTCTA AAGAAGAGAA AAGAAAAGAA TGAATGAATG AACAAAAAGA   24180
AAGAAGGAAA GGAAAAGAAG AGAGAGAGAG AGAGAGGAAG AAAGGAAGGA AGGAAACAAA   24240
ATAAAATAAA ATAATAAATA AATAAACCCA AATCCAACTT CTTTACCCTA ATCAACAAGG   24300
CTCAAATAAT CTCATGCCAA CTAAGTCTCT GAACAGCTCC TTCCATTCTA TTGCCAGATT   24360
ACTCCATCTT TCAGCCACAA GACCTTTTTA TCTTCCTTTT ACCAGCCAAA CACAATCCTA   24420
CCTCAGAACA TGTGCACTTT TTCTTTTCTC TGACTTGAAT CTCCTCCACC CATTATATAA   24480
TCTTAGCTCA AAGAGGCTTT TCTTGACAAC TTAGCGAAAG TATTTATCCC AGTCATTCTC   24540
TGCTACATTA TTCCAATTTA TTTTCTCCAT AGTACATTTC AGCACATAAA GATTTCCTTA   24600
GTATGTGCTT GTTGCCTTTC CCCAACCTCC TAAAATGTCA GCATTCCTTG AGGGCAGAGA   24660
CTGTTTCATT CCTGTATCAT CAGCACCTAA GACAGTTCCT GGAACATACC AAGTACTTAA   24720
TAAAAATTTG TTTATTGACT AGCTATGACA CATTTTACTT ATATAATTTC ATTTTCTCAG   24780
CAAAATGAAC ACTTTGAAAT GTAATTAATT ACTGATTTTT GCAGTATTTT CTAATTATTT   24840
AAATAAAATA TTTACTATTT TGGTCAACCA GAATTCTTAC ATTGTTTTAG CACCCAGATA   24900
GCTTCTAAAA ATGCTTACAA TTAACACAAT TTTATCTAGC AATATGTATT TATCACTAGA   24960
CAGAATGCAC TGAACTCTTC TTCATTAATA AAAAGCAATC CAGGCTGGGT GCAGTGGTTC   25020
ACGCCTGTAA TCCTAGCATA GTGGAAGGCC GAGGAGGGAG GATCACTTGA TACCAGGAAT   25080
TCGAGACCAG CCTGGCCAAC ATGGCAAAAC CCCATCTCTA TAAAAAACAC AAAAATTAGC   25140
TGGGTATAAT AGCAGACATC TATAGTCCCA GCTACTCAGG AGGCTGAGAG GTGGGAGGAC   25200
TGCTTGACCC CAGGAGATTG AGGTTGCAGT GAGCCGTGAT TGTGTCACTG CACTCCAGCC   25260
TGGGCTACAG AATGATACCT CATCTAAAAA AAAAAAAAAA TTAGCCAGGC ATGGTGGCAT   25320
GCACCTGTAG TCCCAGCTAC TCAGGAGGCT AAGGTGGGAG GGTCACCTGA GCCTGGAAGG   25380
TAGAGACTGC AGTGAGCCCT GGGTAGCCCG CGCCACTGCA CTCCAGCCCT GAGTGACAGA   25440
GACCCAGTTT CAAAAAAACA CAAAAAACAG AAAACAAAAC AAACAAACAA AAAAACCCAA   25500
TGCATTGCTG AAATGTTAAA TCCATTATAA AGAAAAGTAC AGGGGTGGGC ATGGTGGTTC   25560
ATGCTTGTAA TCCCAGCACT TTGGGAGGCC AAGGTGGGCA GATCACTTAA GGTCAGGAAT   25620
TCAAGAACAG CCTGGCTAAC ACAGTGAAAA ATGCAAAATA CAAAATAAGC CGGGAGTGGT   25680
GGCGCATGCC TGTAATCCCA GCTACTCGGG AGGCTGAGGG GGGAGAATCG CTTGAACCTG   25740
GGAGGTGGAG GTTGCAGTCA GCCAAGATCG AACTCCAGCC TGGGTAACAG AGACTCCATC   25800
TCAAAAAAAA AAAGTAAAAA GTATATAGTT GATTCTGCAG GGACTTAAAA AAGTATAAAT   25860
ATCTTTTTTA ACATCACAAA GCTCTGATAT CTGCAGGTTT ATGACTAACT ACTAGCTCAC   25920
TCCCATGAAT ACACGTATGT AAACAGGCTC TATACAATCT ACAATCCCAG ACTAAGGGGA   25980
AAAACTGTC CTGTCACTGT GGTCTCCAAC CCTTGGCCCA TTTCTTTCCT CTTGACCACA    26040
AAACTTCTCA GGAGTTGCTT GTTTCCTCTT GATCCACTTA TCTTTAGCCC ACTCCAATCT   26100
GGCATCGGTT CTCAGTACTC TCCACTAAAA CTGCTTTTAT GAAGGCCATC AATGACGTTC   26160
ATGCTGCCAA ATCCAGCAGA CACCTCCTGT TTTCTAATTT TTTTTATTGT TATTTTTTAA   26220
```

FIG. 6.10

```
GAGACTGGGT CTTGCTCTGT CACCCAGGCT GGAATGCAGT GATGCCATCA TAGCTCACTG    26280
CAGCCTTAAC CTCCCTGAGT TCAAGAGATC CTTCTACCTC AGCTGGGACT ACAGGCATGC    26340
ACAGCTATGC CTGGCTAATT ACTCAATCTT TAACATAGCT GATAATTCCC TCCTTGAAAC    26400
ACTCTCAACT TTTAAGAAAC CCTGTTATTT TCCTCCTACA TTTTTAGCCA GTTCTTCTAT    26460
CAGCTTCTCC TTATCTGACC TCTAAATGTT AAGAACATTA ACAAAGACTG AACCTAGTTT    26520
TTTTCTCCCC TTACTGTACT GCTCCTGGGC GATGTCAATC AGTCCCATTG CTTTAGATAC    26580
TATCTGTTGA AACACTGAAA TCACTGGTTT TTTTTGTTTT TTTTTTTTTT TTTTTTTTTT    26640
TTGAGATGGA GTTTCGCTCT GTTGCCCAGG CTGGAGTGCA GTGGTGCAAT CTCGGCTCAC    26700
TGCAAGTTCC ACCTCCTGGG CTCAAGCAAT TTTCCTGCCT CAGTCTCCCG AGTACTGGGA    26760
TTACAGGTGT GTGCCACCAT ACCCAGCTAA TTTTTCTATT TTAGTAGAGA TGGGGTTTCA    26820
CCATGTGTCC AGGCTGGTCT TAAACTCCTG ACCTCAGGTG ATCTGCCCAC CTTGGCCTCC    26880
CAAAGGTTGG GAAAAGATAT CCCAATCTTT TTCCTATGAT TTCTTAATTG ATCTACTTGA    26940
CATATCCACT TGGACTTTTA ATAGGCATCT CAAACTTAAT GTGTTCAAAA TAAACCTCGT    27000
GACTTTCCCT CCCAAACCTG TCCCTACCTC CCTCAATAAC TAATATTATC ATTCTTATAT    27060
TCATATATTG AATAAATGTT TGTTCCCCCA AGTATTTGTT GCTATAAATT TATGAAGAAT    27120
TCTTTTCTCA CTAGTTATTA TAATTAAAAT GTAATATTTA TTTTCTTTAA AAACTTTACT    27180
TTGTAGGATT ATTATTTTTT AAACAGGGAC CAACAATAAA TAACTTCTCT ACTTGATTAA    27240
AACTAGGGCT TCCTCTTGTG CTCCCTCAGG ACTATTTCTT TGTAAAAACA ATAGGCTAAA    27300
TCAGTACTGG TGTCAAAGAA ATCATAATCT CACAACTTTA TAAATACAGC ATGTGGCAAG    27360
GGATTTTCCC ATCTTATATA GTAATAAAAT TTTCAGCTGT GCCATGGCTA AAAGTTTACC    27420
ATCAAAGTTG GAATTTTAAA TTAGAGGTAG TCATCTTTCT TTCTTTTTAA AGAAATGGAG    27480
TCTCACTATG TTGCCCAGGC TGGAGTGCAG TGGCTATTTG CAGGCATGAC CACAGCACGC    27540
TACAGCATCC TGGCCTCAAG CAATTCTCCT GCCTCAGCTT GCCAAGTAGC TGGGACTACA    27600
GGTCCCTGCC ACCACACCCA GCAGAAATAT TTAGCTTTCT GAATTTCTCA AGTGTGTGTA    27660
TGAATGAGAC TAGTGGGGTC CTTAACCAAG ATTCACAGGA TTTTTAGTGA TTTATTAAAT    27720
AACTTGGATT TGTATCTACC AGCATGTTCT TTGAGGTACA GGTATGTCTT TTATATCTCC    27780
TAATATAGTT CATTACAATG CTAAATACTA AGATGTGATG CTCACACACT ACAGAATAGC    27840
CAAGCAAATG AACTACTTAT TCTCATAGGG CTATTATAAT TAACAAATTC TTGTATCACC    27900
CCATCATTAT CAACAACAAC ATGATAGGAT TTCCTTTTAT CTTGAAGAGT CTGGAAAAAG    27960
GGTAACAGAG AGATATTTCT GAGGAACAAA CTGGTAATGA GGGAGCTACT GTGTCCATTA    28020
CAATACTCCT TCTAGAAGCT CAATACATAA TGACTAATCT CTGGAAAAAA GCAAGTGTGA    28080
GAATGGAAGG CTCTTCTTCA AACTATGCAA ATGAATCAA TCAGCAGTGA ACAAATTTAT    28140
GAGCCAAACA AATTCCTACA AAAATTACCA TCATATGCTG TCATGCATGT CTGCCAGTCT    28200
ATTTATCATA TTATTTAAGA AACAAACATT TATTGAAGAT TTATCATGTG CTCAGCACTG    28260
CCAAAGAGGA AATAAAGAGC ATAATATCTA TTCTTAGAAA ATAACATTAA CACAAATAGA    28320
AAACAAGAAA CCATAATGTT AAAAATATTA CATAGTAACA CAGAAAGACA ATGTATAATT    28380
ATACATACGC ACTAAAGCAA AGATAACATA ATTTATAAAT TATGAGGTAC AGAATAGTTA    28440
GATTCTGAAA ATTAAAATAA TCAGGAAAAA CTTCATGAAG ATGAGATCTG GCTGGATCC    28500
CAAAGGATAG GCAGGTGGAT CATGTAGAAC AGGGGAAAGG AGTTCCTGAT CGGGGATACA    28560
ATATATGTAA AAACTCGGAG ACAGGACTGA GCGTGAAATG TTAATGGGAC AGTAAAGAAA    28620
TCTTCCTCTG CAGCGGGGGA AAAAACAGAA TAATGGGAAA CTGCATGGTT AAAAGGTTTG    28680
ATGTTAAGAT AGTGCTTGGA CACAAAAGAT CTTAAAGTTG AGTCAAAAGA GTACAATGAA    28740
AGCATTAGAA ATAGAAGATA AAACACAATT AGGCCGGGTG CAGCGGCTCA TGCCTGTAAT    28800
CCCAGCACTT TGGGAGGCCA AGGTGGGTAG ATCACTTGAG GTCAAGAGTT TGAGACCAGC    28860
```

FIG. 6.11

```
CTGGCCAACA TGGTGAAACC CCGTCTCTAC TAAAAATACA GAAATTAGCC GTGAATGATG   28920
GCTCGTGCCT GTAGTCCCAG CTATTTGGGA GGCTGAGGCA GGAGACTCGC TTGAATCTGG   28980
GAGGCGGAGG TTGCAGTGAG CCGACATCGC GCCACTGCAC TCCAGCCTGG GTGACAGAGC   29040
AAGCCTCTGT TTAAAAAAAA ACGGTAAAAA TAAATAACAT TTACTATTGT TTTCTGATGA   29100
TATATATGGC CTCTAATTGT AAAGCTGAAT GCCTAGTTTA CCACTTTTTT TTTTTTTTTG   29160
AGACGGAGTC TTGCTCTTGT TGCCCAGGCT GGAGGGCAAT GGCACGATCT TGGCTCACCA   29220
CAACCTCTGT CTCCCAGGTT AAGCGATTC TCCAGCCTCA GCCTCCCGAG TAGCTGGGAT   29280
TACAGGCATG TGCCATCATG CTCAGCTAAT TTTGTATTTT TAGTAGAGAT GGGGTTTCTC   29340
CATGTTGGTC AGGCTGGTCT CAAACTCCCA ACCTCAGGTG ATCCACCCGC CTCAGCCTCC   29400
CAAAGGGCTG GGATTACAGG CGTGAACCAC CGCGCCCGGC CTATCATTCT TATTTTATGC   29460
ATTAGGAAAC TAAGGCTCAA CAAGATTAAA GCTGTCTAGG GTCACAAAGA TTGTAAGTGG   29520
AGGGGCTAGA ATTCAAAATG AGACCTGCTT GACTCCTAAG CCTGTACCAT TTCTACTATA   29580
TTTAGAGTGA AGTAGATGGG TTGAAGAAAT ATTTAGGAGG TGAAATTTCA AAAGTGTACA   29640
GTCAGAAGAG AAGACATATA TGGAAACCTA AATTTTCACA CAGTAAAGTG TCAATAATAA   29700
AGGCATAATG CCAAAATGAC AGAGGCTGTG CATGGTGGCT CATGCCTGTA ATCCCAGCAC   29760
TCTGGGAGGC TGAGGCAGGA AGATCACTTG AGCCCAGGAG TTTGACACCA ACCTGGCCAA   29820
CACAGCGAAA CCCCATCTCT ACTAAAAATA CAAAAAATTA GCTGGTAATG GTGGTACACA   29880
CCTGTAATCC CAGCTACTCA GGAGGCTGAG GCATTAGAGT CACTTGAACC TGGGAGGCAG   29940
AGGTTGCCAT GAGCCAAGAT TGTGCCACTG CACTCTAGCC TGGGCAACAG AGTGAGACTC   30000
TGTCTCAAAA AAAAAAAAAG GAAGACTCGA GGGCTAGAAC CCTGAAATTG GAATGAACA   30060
GGACTGGCTG AAAATGTTTC TTGCACCTGA TAAAAATCTT GAAGAAGAAT GCTTTAAATA   30120
GATAAGAAAG GAGAGAGAGA GGTGGGCAGT GAGAGGAGAC CACCCTAAGT AATCAGAGAT   30180
TACTTACGTT GGTTACTCAG GCTGGTCTCT GAATCTGATT ATAAATGAAA TAGAGATTAC   30240
TTAAAACAAA GGGCTGTAAG GTAGCACTGT CCAGCAGCAC TTTCTATGAT GGAAATCTTC   30300
TATATCTGCA CTGTCCAATA AGGTGTAGCT GCTAGCACAT GTGGCCACTG AGTACTTAGA   30360
ATATAGCTAC GACAACCGAG AGGCTGAATT TTAAATTTAA TTTAATGAAT TCAAACAAAT   30420
TTATTTTTAA TACAGCACTT TAAATTTTAT TTTTAAATTT TAATCTATTA TTTATTTAGA   30480
GACTGGGTTA TGAGACTGGC TAATTTTTGT ATTTTTGGTA GAGACGGCGT TTCACCATGT   30540
TGCCCAAGTT AGTCTCAAAC TCCCGGGCTC AAGTGATCCA CCTGCCTTGG CCTCCCCGCA   30600
AAGTGCTGAG AATACAGGTG TGAGTCACCA CGCCCGGCCT AAACTTAAAT TTAAATAGCC   30660
ACGTGCGGGT AGTGGCTACC ATACTGCACA TGCAACTGTA AGATGTAGAA GTCAGATGTG   30720
AGCAAAGAAA TGACAAGCCG TTCAATGCTG TTAGAGAATG AAATTCAAGG TTCCAATGAT   30780
CTGAACTTGT GTCCCCTCAA ATTCGTATGT TGAAATCTTA ATCCTCAATG CAACAGTATT   30840
AAGAATTTGG GGCTTTAGGA GGTAATTTGG TTTTGAGGGT GGAGCCCTCA TGAATAGGAT   30900
GAGCACCTGA GGTAGCCTCT TTGACCCTTC CACCATGTGA GGACACACCA CGAAGGCACC   30960
ATGTTGGAAG CAGAGAGTGA GCACTCCCAA GACACTGAAT CTGCCACATC TTGATTTTGG   31020
GCTTCTCAGC CTACAGAACT GTGAGCAATA AATATCTGCT GTTTATAAAT TATCCAGTGT   31080
AAAGTATTTT GTTATAGCAG CCTGAATAGA CTAAGACAAA GGTGGACTAA GGCAGGATAA   31140
CAGGTTAGAA AAGGAGGCAG GGCCTTTTTT TTTTTTTTTT TTTTTTGAG ACAAAGCCTC   31200
ACTCTCACCC AGGCTGGAGT GCAATGGCAT GATCTTGGCT CACTGCAACC TCCACCTCCA   31260
GGGTTCAAGC AATTCTCCTG TCTCAGCCTC CCAAGTAGCT GGGATTACAG GTGTGCACCA   31320
TCACACCCAG CTAATCTTTT GTATTTTTAG TAGAGACGGG GTTTCACTAT GTTGGCCAGG   31380
CTAGTCTTGA ACTCTTGACC TTAAATGATC CACCCGCCTC GGCCTCCCAA AGTGCTGGGA   31440
TTACAGGTGT GAACCATCGC GCCTGGCCGA GGCACAGTGT TTTTACAGAG AAGCCTGTTT   31500
```

FIG. 6.12

```
AAGGTTTAAT CATATAAAAT GTATGATATC CAGTAAGTTT TGATATAAAA AAGAAACACC   31560
TGGCGATTTT ATATAATATA TTGTGCTAAG GAATTTTAAG CACTCTACAT TCTGCTCTCT   31620
AAGCTCTGTA AAGAGCACCA GGGATTTTTT TTTTTTTTTT CTTTTTGAAC AGGGTCTTGC   31680
TCTGTCAGCC AGGCTGGAGT GCAGTGGCAC AATCTTGGCT CACTGCAACC TCTGCCTCTC   31740
GGGCTCAGCG ATTCTCCCAC CTCAGCCTCC TGAGTGGTTG GGACCACAGG CGCATGCCAC   31800
TACATCTGGC TAATTTTTTG TAGAGATGGG GTTTTGCCAT GTTGCCCAGG CTGGTCTTTA   31860
ACTCCTGGGC TCAAGCGATC CTCCCACCTT GGCCTACCAC GCATGCCTGG CCACAACAGG   31920
GATTTTTAAA TGTAAGACTA CCTAGTCAAC TCTTATTCTA TATTAACAAT ATAGACAAGA   31980
AATAACCTCT AAGTAATCTC TATTTCATTT ATAATCAGAT TCAGAGGTTC TCTTATGCTT   32040
TACAATATTG TCCTACTGTG GGTAGCGCAA TAACTAAGGT AATCTGAAAG ACCAGTTATA   32100
TTATATACTA TAGTTAAATG CATTTCAACT GCATGGGAGA AAGCAACTGT GTTCTTTCCT   32160
CTCAATTTTA ACAGAAGGAA AATTGTCAAA ATTAGCTTAT TTAGAATGTC CTATCAGAGA   32220
ATTATTTTGA TTAAAATATA TTTTTAATCA ATAAAATATT TCTCTTTGGT CAATACTTGT   32280
CAATATAGAA TAATATCTAG CCACAAAATT AAAAAAAAAA CATTTTCCCC TATATTACAT   32340
TCATGGATCT TCTTGAATTT CTGTTATCTA GGTGCTTTTA AAAGTCATAT TTCTGATAAT   32400
ATGAAATCAC AGCTCCTTTT CTTTGGCATA TTTAGTTACT GTATTAAGAA AATGTACAAC   32460
ACATAATTTA GAATGGGTAA TTATTATATT CTCTTTATTC TTATATTGAA AATGACATGA   32520
AAATTACCAG TCTTCCCAGG TAATATAATT TAAGTTAAAG AACATCTACA TACTACAACC   32580
AATACCCATT CCCCTATGTT ATGTTTGGAA AAACATAGAA GTATCTTTAG TAGTACTCTT   32640
AGAAATTATC CCAGGTTCAG CATATTGGTA TTTTATTTCC AGGTTTAAGT TACAGTATTT   32700
TGGGCACCCC AAGTTTAATA AACTATTCCC TGCAGAAACC TGACAAGTGA AGTTGTGGCT   32760
GGGAATATGT TAGTCTTCAG ATAAAATGAA TTGTTTAAGA ATTTGCTAAA GATCTCAAAG   32820
CATCTTTCTT AAATCTAAAG AAAGTCAGGA ACAAAGCCAC AACCAGGACC ATAGCATCAG   32880
AAGATGGAAA GTTGCTTTGT CTTCAAACTT AAAAAACATT TTCCATTTTA AAATAATTTT   32940
ACTATTTACC TGTGATACTG TTGAAAATTA TGAAAAAACA GATAATTTAA AATTTAGTGC   33000
TTTTTTTTAA AAAAAAAAAA AAAGCGAATC CCTGGGACAC TTCATATAGT GCAAAACAAC   33060
AATTCAAGAA TTCAAGCATT GAAAGAAATA ATCTCTTATC CCCCAGTCTC TGAAAGGGAT   33120
TGCCTTTACT ACTGTTCCCA TCTTTATGTC CATATGTACC TAAGGCTTAT CTCCCACTTA   33180
CAAGTGAGAA ACTATTCAGT ATGGCTTAGT CATTTTTAAT GCAAGAGAAT AGGTAAAAAT   33240
GCCAAGCACC AGCCAGAGTT TTTTCTTTGC AGATAGATGT GACTCTTACA GGAGCAGCAG   33300
GGATTTCCCA CTTTGGGCGG AAAGCAGCAT TTAGGTATTC CCCTCCAGT GCAGTTACAG    33360
ACCACCCCCC CGTAGAAGCT GCTCCTGTCC TCTGTGGCAT GTCAGCCTCT GATTATCTTT   33420
TAATAAACAA TATGGCATAT TAAGTCTCTT TTATGCCCTT CTTTGTATTC CAGGTACCA    33480
CCTCCATGTC AGGATAACAA GAATTTGGTA ATGTTTGTTG AATAAATTTA GCAGAAGTTG   33540
AAAGAAAAAT CCTGTTTCTA CAGAAAGATA CCACTGGCTT TTGGGGAGCC CGAGTTCATG   33600
ATGAAACTAA AGAAAGCCAC AAAAGTTCAC CTCAATGCCA AGACATTTCT TGATTTTTGA   33660
AAACCCAGTT GTCGAACCAC CCATCTATAG AAACTTGAAA GACTAAAAAC TATCTTACTC   33720
TAAACATTTT CTAGGAAGTT GATTCTACAA CACATTTTGG TTTTCCAATT TGGCTTCTAA   33780
TAATTATTTC AAAGTTTCTG TGGCCTAAAT TTTGTTTTAC ATTGATCCTT TGAATGGACT   33840
ACTGTTTCCA CATTTTAGAA CATTTAAAAA GATATCTACA ACCCGAGTCT AATCATAAAA   33900
AAAATCAGAC AGATCCAAAA TGTGGAACAT TCCACTAAAA AAGGAGTGGG GAGAGGTCTT   33960
TATTCTTCCA AAAATATCAA TGCCATAAAA GACAAAGACG GCTATGGAAA TGTTACAGAT   34020
TGAAGGAGAC TAAAGTTAAA TGCAAGAAAG GAAAAAATGG CATATAGGAC AGTATTGAAT   34080
TGACTGACAA AACTGGATTA CAATAGTAGA GTATCAATGT TAAACTTGCT GAAGTTGCTA   34140
```

FIG. 6.13

```
ACTGTATTTC TTAGGAATTA TTCACCTAAG AATTTAGGCA CACAGATATG ATGTATGTAA   34200
GTTACCCTTA AATGGCTTAG AAAAAAATGT GTGTATATTC ATTTACATAC GTATCTACAC   34260
ACACGTGTAT TAGCGGAAGA GAGCAAGGCA CACATGTGCA TAAGTGATAA AGCAAATGAG   34320
ATGAAATCTT TATTTTTAAA TTTAATTTTG TAAGTTTCAG CTTTTTAAAA TTTTAGATTC   34380
CGGGGATACA CGTGCAGTTA TTACTTGGGT ATATTGTGTG AAGCTGAGGT TTGGACCTCT   34440
AATGTTCCTG TTGCCACAAC AGTGAACACA GTACCCAGCA CGCAGTTTTT CAGCCCTTGC   34500
CCCCTCCCTC CCGCTCTCCC TCCTTGCTTT TGGAGTTCCC AGTGTCTACT GTTCCCATCT   34560
TTATGTCCAT GTGTACCCAA GACTTATCTC CCACTTACAA GTGAGAGCAT GCAGTATTTA   34620
GTTTTCTTGT TCTGCGTTAG TTCCGTTAGG ATAATTGCCT CCAGTTACAT TCATGTCACT   34680
GCAAAGGATT TGATTTCATT CTTTTTAATG GCTGTGTAGT ATTCCATGTT GTATAGGTAA   34740
CACATTTTCT TTATCCACTC ATCAATTAAT GGGCACTTAC ATTGATTTCA TGTGTTTGCT   34800
ATTGTAACG GTGCTGCAAT GAACATCTGA GCGCAGGTGT CTTTCTGGCA GAATGATTTA   34860
TTTTCCTGTG GTATATACC CAGTAATGGG ATTGCTAGCT CAGATAAGTA TTTCTATTTT   34920
TAGTTGCTCT CCACAGGGGT AGAACTAATT TGCATTCCCA CCAACGGCGT GTAAGTGTTC   34980
CCTTTTCTCC ACGGCCTCGC CAACATACGT TCTTTTCTGA TTTTTAATAG TAGCCATTTT   35040
GAACTGGTAA GAGATGGTGT CTCATTGTAG TTTGGCTTTG CATCCAAATG AGACAAAATC   35100
TTAATGACAG GTGAATCTAG GTAAAAGGCA TACAGACGTT CTTTGTGTTG TTTTTTTAAC   35160
TTACATTTGA AGTTATTTTC AAATGAAAAA TAAAAGCAAG CAAAAAAAGG TCATTCTTCA   35220
TCTAGTAAAC TCTTCAAAGA TTACCACCCC CTTCAACAGT TTTTCCTGGT TCTAGTGAGT   35280
CTTCTCCCAT TTGTTTAGAT CTTTGTTGAA ATGTAGTCTC AGATAAAAAA TTGTATTTTT   35340
ATTTCTTTTA CATATTTCAA ACAATCTAAA TTCTTTTTAA ATGAAACTCA TTAAAAATAC   35400
TGCATTTGTT TCTAAATAAA ATGGTAGAGG TAATTGCAC CTTTCCAAAC AGAAGCAATA   35460
GGAGCAACCC AGATGTTCTA GCCACGATCC AAGTCAACCA CATTCAATCT AAGAAGTAAT   35520
TGAAGGCTGT AACGACTTCT GTAAGGCCTA CAAAAATGAG TTCAGACACA AGCTCTGCTC   35580
AGTAAAAATC TAGTGGCAGA TGATATATAC AATGATCTGA GAAAAAGGCA GAATCAACAA   35640
AGGTTGTATT TTTATCTATT GCTGCGTAGC ATATTTCCTT AACTTTAGTA GCTTGAAACA   35700
ATAAACATTT ATTATTTCAT AAAGTTTCTG TGGTCAGAAA TCCAGGAGCA GCTTAACTGG   35760
GTGGATCTGG CTCAGCTGTA GACAAGATGT CGGCTGGGAC GGCCATCCTT TGAGGGCTCT   35820
GAGGGCTTTG AGGGCTGCAC GATCCAATTG CAAGGTGGCT CACTCACATA CTAGGCAAGT   35880
TACTGCTGGG TGCTGGGAGG AGACCTTAGT TTCTTATCAC ATGGACCTCT CCACAGGGCT   35940
GCTGGAATGT CCTCATGACC TTCCCCATAG TGAGTATTCC AAGACAGGAA AGTGGAAGCC   36000
ACAATGTCTT TCATGACCTA GCCTCAAAAG TGACATACTG TCATTTACAC AATATTCTAC   36060
TGGCTGTACA AGTTAATCCT ATTTAGTCTG GGAGGGGACT GCATAAGGGC ATGAGTAACA   36120
AGAGGCAAGA ATCCTTGGGG GCCATCTTGG AAGCTGGCTA CACAGAAGAG AAAACACCAG   36180
GGGAGTGCGA AGAAGGTGCA ATTAAACTCA ATTCCTTGGT ATGCCAATGG TAAGAAATAT   36240
TAGGTGATCT CTGGGGTGTA ACCTTTTTAA TTTAGTTCTT CACTGAATAA TCTGGCCAGT   36300
AATTGTAATA CAAAATACGG CACTCTGACA ATATTCTCTC CCTTTATAAT CAATTACACA   36360
CCAGAATATA TATAAAGAAA GACTTACAAA GTCACAAGTA ATTGTTGGT ATTATTTTA   36420
TAATCACATA CTAGGGCCCT ACAATTAGCA TTCACAAACA TCACTCCATG TTGGCCAGAT   36480
AAGTCTGTCT TTATAGTGGT TTACCATACG CGCCTTAGCA TGAAGTTACA TGTGGTTTCC   36540
TTAGCCATCA GATGCTCCAA ATGCAAAAAA TGTCTCACCA CAGTCACAGA ATCATGGAAT   36600
CCTAAAGTTA CCTGGGGTTT CTGAAAATCT CATGGGAACA ACTCACGAGA ATTAAGGCTT   36660
AAGAAAGTGA TTTATCAAAG AACAAAACCA GCAAGACTTG AGTTTAGAAC TCGCAGCAGA   36720
GTTGTGACTA GAACCTGTTG AAATAGGCAA TGTAGAAACC CAGACTAAGG CACATTCTCT   36780
```

FIG. 6.14

```
ACAACTTTAC TATGCAAGTA TGCTTAGATA CTCCTTAGCA AACAGCAGGC CTTGAGTAAA   36840
TTCTTTCAGA ACTGAATACA CAAAGGATAC AGAACGGAAT ACACTAACAA TAGTGCATGA   36900
TGTGCTCATT TCTGTAATAG AAATGAATTA ATTCTGATCC ATCTATAATT TATTATTGCT   36960
CCATGATTAA CGGAAGGCAT AGGAAAGATG ACTGGAATAG TGTAACTAGT ACAAACAAGT   37020
ATTACACTTG ACTGAACCTC ATTACACTGC AATTGCATAT TATATAGTAT GTAGGTGAAC   37080
AAATACTGGG TTAGTCAGTG GACCTACATT TGAATACTGG TTCTGCTCCT AGACAGCTGT   37140
ATGATTTGAA TGACTTCTTT ATACTTTCAT AGTTTCTCTG TTCTTCTCTG TAAAACAAAG   37200
GCTTAGAAGA TATTATGGGT TAGATTATGC CCCTTACAAA AGATGCTGAA GTCCTAAACT   37260
ACAATACCTG TGAATGTGAC TTTATTTGGA AATAGGGTCT TTGCAAGTGA TAAAGAAGAG   37320
GTCATGGAGT GACCTAATCC AATACGACCA GTGTCCTTAT AAAAAAAAGG AAATTTGGAT   37380
ACAGATACAC ACAAACAAGG AGAATATCAA ATGAACATGA AGGCAGAGAC CGGGGCGGTA   37440
CATCTACAAG CCAAGGGACA CCAAAGATTT TCAGCAAATC ACCAGAAGTT AGGAAGAGTC   37500
ATGGGACAGG TTCTCACAGT CCTCAGAAGA AACCCACCAT GTCAATACAT CATTTTGGAC   37560
TTCTAGTCTT CAGAACCGTA AGAAAATAAA TTTTTGTTGT TCAAGCTACC CAATTTGTGG   37620
TACTTTGTTA CAGCAGTCCT AGCAAACTAA TACAAATGAG CTCTTAACAC TGGTCTAAAA   37680
TAGGATAATC CTATGAAATG CTACAAATGT TTGGGAAGAT TTCTCATACT CAACTGTTTA   37740
CAGTATACCA CAAGCCTGTC AGTTGAAGAT ACAAACAGAC CCTCTATAAT CCTCTATACT   37800
TATATGCAAG GAACAGCACA CTTTTTCTGC AAAAGGTCAG ATAGTAAACA TTTTAGGCTT   37860
TGTGGGCCAA ACAAGGTTTC TGTTACATTT TTTTTTTATA ACTCCTTAAA AATGTAAAAA   37920
TCACCCTCAT CCCAACGGAC TACAGGAACA GACCTCAGGT CACATTTGAC TCATAGCCTG   37980
ACCCCTGGTG TGTAGGGTTA ACAAGCCTCC TTTCCCTGGG CTCCTTTTTC TTTCAGCATT   38040
CCAAGCCAAA GGAAACTATC TTTTTCAAAT CATTTTCTCT CCTAGGTGGG ACATCTTACA   38100
CCAGCCCAGG CATGCTTCCG ATAGCCTTAG AGTAGCTGTC CCTTCCTCAG AATTACTGTC   38160
TAATTGGCTA GAAGTTAGCA ACTTTTTACA TTTTTCCTTC AATTCCTTTC CATTAAGAAG   38220
AAGGCATGCA CCGGCAAATT ACTTGTGACT ATCAATGACA TACTCTCAGA AGCACCAGTA   38280
CCCCTGTGTT GTTTCTAAAC CCATTCTAAT AGACACATAC CCCAAGGTTA TGCTGTTTGT   38340
CATCTCACAA AATGACTTAC ATCTAGAGAT TTAAATAATT AATGTACTTT TCATAACTAC   38400
CAGGTACAGT AGATCTGATA ATGGCAGAGC TAAGCACATA TACAGAAAGT AGGGCAAGGG   38460
CCAGAGACTC ATTTTAAAGC AATGTTACAA GATCGTCACT GTTGCTTTTC ATTTTTCTAA   38520
ATGTGGCCAC TGCTGTTTTC TCACTAAAGG AAATGTTTTA TGTAAAGTGA ATAACAGTAC   38580
CTGGCATAAA ATAAGTGCTC AATAAATGTT AAGGCCTTCT CTCCCTCTTC AACTGGCCTC   38640
CTCATTTTTC ACAAAGTGAA ATAGAAAAAC AACATGGAAG ATAATCCTGT TGCTTAGGAA   38700
AAATAACTAA AGCTTGCTAG ACAAAATACA CCTGAAAATA TAGGAAGTGA GCTATAGCTG   38760
GCCTATATGC ATGTATGTTG GAACAGGACA AGATAGTGTA GGGTGGGGTG AAGAGGACAG   38820
AGAAATGGAA GGAAAGGGGC TACAGCCTTG GTGGCAAAAT AAAGGATAAG ACGACTCTTT   38880
TAAAATGGTC TATTTCAAAT GCTGGGTTGT GAAACTTAAT TTGATTACTT CATGAGAAAC   38940
AGCATCTATA ATCCATCCCT GATTTTTCTA CAACAAAAAT TTATTATTTA TTTTATGTTT   39000
GTGTGTAGAT CTTTTATATA TATACATGTA CACACGTATA TGTATATATT ATATATGCAT   39060
ATGCATATAT ATGTGTATAT ACATATATAA TATATTGTGT GTGTATGTGT GTGTATATAT   39120
AATTTTTTTA AAGGAATGGG GTCTCACTAT GTTGCCCAGG CTGGACTTGA ACTCCTGGGC   39180
TCAAGCAATC CTCCACCTCA GCCTCCCAAG TAGCAACCAA CAGTTTTAGT TTTGAAAAAA   39240
TAACAAATAT TAAACACCCA TGTGTAAGGG TTGGTACTGG GCCCTGTGTT AGTTTGCATG   39300
GGCTGTCGTA ACGTAACACT ACAGGCCGGG CACAACGGCT CACGCCTGTA ATCCCAGTAC   39360
TTTATGAGGC CAAGGTGGGC GGATCACCTG AGGTCAGGAG TTTGAGACCA GTCTGACCAA   39420
```

FIG. 6.15

```
CATGGAGAAA CCCCGTCTCT ACTAAAAATA CAAAATTAGC CATGTGTGGT GGCTCATGCC  39480
TGTAATCCCA GCTACTTGGG AGACTGAGGC AGGAGAATCG CTTGAACCTG GGAGGCGGAG  39540
GTTGTGATGA GCTGAGATCA GGCCATTGTA CTCCAGCCTG GGCAACAAGA GCAAAACTCT  39600
GTCTCAAAAA CAAAAAAACA AAAACAAAAA AACCCTGATA ACACTACAGA CTGGGTAGCT  39660
GGACCAACAG AAATTTATTT TCTCACAGTT CTGGAGGCTG GAAATCTAAG ATAAAGTTGT  39720
TGGCTGGTTT GGTTTCTGAG GCCTCTCTCC TTAACTTGCA GATGGCTGCT TTCTTGAAAT  39780
GTCCTCACAT AGCTGTCCCT CTGTCTGTTT CTGGTGTCTC CCCACGTATC CAAATTTCCT  39840
CTTCTTATAA AGATACTAGT CATATTGGAT TAGGGTCCAC CATAAAGACC TCATTTAAAC  39900
TTAATCACCT TTTTACGGCC CTGTGTCCAA ATACAGTCAC ATTCCGAGTT CCAGGGGATT  39960
AGGGCTTCAA CCTATGAATT GGGGGTGGGG CACAATTCAG CCCGTAACAG GCCTAGACCT  40020
TAATTTGTCA ACACTACAGT TAGATTTATA GTATAGTAAC TGCATCTGTG CTCATCTAAA  40080
TGTCATACCC AAATGAAATA ATATAGCATG ATGATCTGAA TTTATTAAAG GCAATTTTTC  40140
CTATAGAAAC CCAAATCTAT AAATTATATA CAAACTGTGG TAAGTTACTC GATACCTTGC  40200
CAGGACTCAT CTATGGTGGT AGATAGACCA CAAAGAGTAC CACTGAAAGA TCCCTTTCCT  40260
AATCACAGTT TCCTCACTGG CTTGCCACAA AACCTAAAAT TCTTCTATTC TTTCATTGGC  40320
AATTTATTTC CCCTGAAAAT GTAAATAATC TCTGGCAGAG CAATCTATTA AGTGATCATC  40380
AGCCACTAAC ACCTTAGGGT AGAACAGCTC AGATCACAGT CTTAAAATAA ATTCCATCAG  40440
TATGAAATTT TCTTTATTAC TGCTCCGCTA CTGGAATGTT AGATCACTGT CTGCTTTAAT  40500
AATAATTCTG GTGTAGGTCA TTCAAATTTT GTTTAAGATA ATAAGACAAA TAGCAGGTAT  40560
AAAAACATTC CGTCATCTAA TAAAGCAACC CGAGAACAGT AAGAAGAACG TGATGAAATT  40620
AACATTTTTG AGTACCTGCT AGGAATCAAG TATTCTGCTA GATATTTTAG AAATCATCTC  40680
AATTCAATCC TAAAAATTAT TCTGTATAAT AGTATAGGTT GAGTATTCCT AATCCAAAAA  40740
TCTGAAGCTT TTTTTTTCCT GAGACGGAGT TTTGCTCTTG TTGACCAGGC TGGAGTGCAA  40800
TGGCGCAATC CTGACTCACT GCAACCTCCG CCTCCTGGGT TCAAGTGATT AGGGATACTC  40860
AACTGGCTAA ATATAATGCA AATATTTCAA AATCTGAAAA AACCCAAATC TGAAACACTT  40920
CTGGTCCCAA ACATTTCAGG CAAGGGACAC TCAAGTTGTA TTAATCCCAT TTTACAGAAG  40980
AAGAAACAGG CTCAGATAAA TGAACATCTC AGAGCTTGTT GATAGCAAAG GAGAGATTGA  41040
AACTGTCAGG CCTCTGATCC CAAGCCAAGC CATCACTTCC CCTGTGACTT GCATGTATAC  41100
ATCCAGATGG CCTGAAGTAA CTGAAGATCC ACAAAAGAAG TAAAAATAAC CTTAACTAAT  41160
GACATTCTAC CACTGTGATT TGTTTCTGCC CCACCCTCAC TGATCAATGT ACTTTGTAAT  41220
CTCCGCCACC CTTAAGAAGG TTCTTTATAA TTTCCCCCAC CCTTAAGAAG GTTCTTTGTA  41280
ATTCTCCCCA CCCTTGAGAA TGTAATTTGT GAGATCCACC GCTGCCCGCA AAACATTGCT  41340
CTTAACTTCA CCACCTATCC CAAAACCTAT AAGAAGTAAT GATAATCCAC CACCCTTTGC  41400
TGACTCTCTT TTCTGACTCA GCCCGCCTGC ACCCAGGTGA ATAAATAGC CATGTTGCTC  41460
ACACAAAGCC TGTTTGGTGT CTCTTCACAT GGACACGCAT GAAAGAAACC CTACCTGGTT  41520
CTGTGTCTTA CCTGTTGGGG GCCTGTGGTC AAACTACTAG TACGGAGTTT TAGTGTCCTC  41580
ACTTTAAAAA TGAGGGTTGT GGCCGGGCGC GGTGGCTCAC GCCTGTAATC CCAGCACTTT  41640
GGGAGGCCGA GGCGGGCGGA TCACGAGGTC AAGAGATCGA GACCATCCCG GCTAAAACGG  41700
TGAAACCCCG TCTCTACTAA AAATACAAAA AAATTAGCCG GGCGTAGTGG CGGGCGCCTG  41760
TAGTCCCAGC TACTTGGGAG GCTGAGGCAG GAGAATGGCG TGAACCCGGG AGGCGGAGCT  41820
TGCAGTGAGC CGAGATCCCG CCACTGCACT CCAGCCTGGG CGACAGAGCG AGACTCCGTC  41880
TCAAAAAAAA AAAAAAAAAA AAAAAAAAAA AAAAAAAAAA AAAATGAGG GTTGTAAGGT  41940
AACTACCTAC TTTTTATAGC ATTGTAGTGA AGTTGAAATG AATTAATCCA CATATATTAT  42000
AGTGTGGTAG AATGCAGCAG AACTGATGAT GTATGACTTC TAAGACTAGT CCTTAAGAGA  42060
```

FIG. 6.16

```
CCTGCAGTTT TTGCTTTTGC CCTCTTGGAA CACTCCTGTT GCCATGTTAA GAAAAACTCT    42120
GGGGAGACTA TGAAGGAAGA GAGCATACTC GGGGCAGGGG GGTGAACAGG ACGTGCACAT    42180
GTACGAGCGT ACAAGCCAGG TGACACCAGT ACCACAGCCT CAGACATGTC ACCGGGGATA    42240
CCAGCACCAC AGCCTCAGAC ATGTCACCGG GGACACCAGC ACCACAGCCT CAGACATGTC    42300
ACCGGGGACA CCAGCACCAC GGCCTCAGAC ATGTCACCCA GGGACACCAG CACCAGCACC    42360
ACAGCCTCAG ACATGTCATC GGGGACACCA GCCCCATGGT CTCAGACATG TCCCTGAGGC    42420
CCACTTAGAC CCTTCAACCC CAGCCCAGCT GCTAACTGAC TACAGCCACA TGAACAGAAC    42480
CAGGTGAGAC CAGAGGAAAC TTCCAGTCAC CTACCAGATC ATGACAAATA ATAAACGATG    42540
TTTTTTAAAC CACAAAGATT TGGAGCAGCA TTTGTTACAC AAAATTAGAC AACTATTACA    42600
GTTCGACTAA AAACATGTTC ATTTACAATA CTAAATTAGA AGTGTAAGAA TGGGAGAAAA    42660
ACTTCATACT TTAAAAGTCA TTTTTTCCTC CAAAAACTTC CAACTTTGAA AAACTGATTT    42720
TTATAATGCA TAAAAATTAA AATAACCTTA GAATTTATAT GAGTAGCATA GCCAGCTGGC    42780
TTTATTATCT GTTGTACTCA ACACTTCAAT AATCACTGAT GTTTTAGAAC TCTTCAGATT    42840
TAGAACTCTT GCCCTTGCTT TAGTCTGGTT TAAGCTAAAT AATTGTTCTT CCTCAAGAAC    42900
AAATGACCTT ACCTCGTTTT GTTTTCCTTG TCTGAGAGAA ACACATTAGC AGTCTCCCAT    42960
CTTGTTTTTC CTTTTCCTGT CACCCAGGAC AGAGGGCAGT GGTGTGATCA CAGCTCTGCA    43020
GCACGACTTC CCCAGGTTCA GGTGATCCTC CCACCTCAGC CTCCCAAGGA GCTGGGACCA    43080
CAGGCACATG CCACCACGTC CAGCTTAATT TTGTATTTTT TTGGTAGAGA TCAGGTTTTG    43140
CCTTATTGCC CCAAGCTGAT CTTGAATTCC TGGGCTGAAG CAATCTGCCT GCCCTGGCCT    43200
CTCCAAGTGT TAGGATTACA GGTATAAGCC ACCGTGCAGC CTTATATTTT GTTTTAAATT    43260
TTCCTCTGTA TTTTTCTCTC TGGCAAATTG TTTAGGGAGT TTCTTTAGTT TATCAGACTA    43320
AATTTCAAGG CTTTCCTTCC AATTTTGACA TGTAAACAGT CCCTCATTTC TGCTTATCTA    43380
GTGATTATTC CCAAATCTGT GTTTACAGTC TAGCTGTCTC TCCTGAGATT AAGACTTGTT    43440
TCTCTAACTA CCTGACGGCA GAATCCCTC TTGGAAGTAT CAAGGAGGCA GTTCAAAACT    43500
GAACTGGGCA TTGGCTCCAC TCCTTCTCCT TCTCTTTACT ATTAATACCC TTTCTCTCCT    43560
TCTATATGAC CACACTAAGT CTTATTTAGG CATCGTTTCT TCTGGGAGAC CTTTGTAGAA    43620
TCTCTGAGGT TATGTTAACA TGCTAAGGTT TTCTTGACAT TCTCAGATTG GGTTAGGTGA    43680
ACTTTTAGCA ACTTATCTTT TTACTAAAAA GTCATCCCTC AGTATCTGTG GGGAATTGGT    43740
TCTAGGACTC CCTAAGGATA TCAAAATCTG CATGAGCAGC CCAGGTGAGA CCAGCAGAAG    43800
CACTTTACAG TCACCTACAG GATCATGACA AATAATAAAT CATGTTTAAG CCACAAAGTC    43860
CTTTACATAA AATGGTATAG TATTTGCATA TAACCTACAC ATCTTCCTGT ATCCTTTAAA    43920
TCATCTCTAG TTTATAATAC CTCATACGAT GAAAATACTA CGTAAATAGT TGTTATACTG    43980
TATTGTTTAG GGAATAATGA CAAGGAAAAA AGTCCACGCG TGTTCAGAAT AGATGCTTTT    44040
TTTTCTCGTC TAATATTATG GATCCACAGT TGGTTGAATC CACAGATGTG GAATCCATGG    44100
ATACCAAGGA ACGACTGTAT GCATTTTGAC AATTATACTT CTCATCTTAC CATGCATTCA    44160
ACAAACAGAA CATGTAAAGC GGTGATAATG CTGTGATGAA AAATAAAGCA GGGGAAGAGG    44220
CTGCATCCAT CTAGTGGAAA CGATGCCCTT TTCAATCTGC ACAAAGAGAA AAAGCTGCTC    44280
TCCAAGTTGG GGGTGGGTG GGTCAGGTAT GTAAATTGGT CAGGAAGGGA TCTGTAGGCA    44340
CTTACAGATT TGACGCTAAT GAGATGGGAA GCCACAGGAA GGTTGTGAAG AAAAGACAAG    44400
ACATGATCTG ATTCATGTTT TGATCTGATA CACTGGTTGC TAGATGGAGA ATAAGCTGCA    44460
TGGCGGTGAG AGGAAGCAGA AACAATAGGA GGGTAATGCT ATAATCCAGT GGTCCATAAT    44520
CCAATATCCC CCCAAGGAAC AGTTCGGCAA TGTCTGGTGA CATTTCTGGC TGTCACAACT    44580
GTTGGGGCGG AGTGCTACTT GCATCTAGCA GGTAGAAGCT AGGGATGCTA CTAAACATCC    44640
TACAATGCAC AAGACAGCCC TTCCCCCAAC ATTGCTGGCC CAAAACGTTG ATAGTACCAA    44700
```

FIG. 6.17

GGCTGAGAAA CTCTGTTATA ATCTGTCCTA GAATGTAGCT TGGATTGAGA TGGCAGTGGT 44760
AAGAGCTGGA GAAGTGCTTA GCTTCCCAAT GTTTTTTTGT TTGTTTGTTT TTGAGACGGA 44820
GTCTCGCTCT GTCGCCCGGG CTGGAGTGCA GTGGCGTGAT CTCGGCTCAC TGCAAGCTCT 44880
GCCTCCTGGG TTCACGCCAT TCTCCCACCT CAGCCTCCCG AGTAGCTGGG ACTACGGGCG 44940
CGTGCCACCA CACCCAGCTA ATTTTTTTGT ATTTTTAGTA CAGACAGGGT TTCACCATGT 45000
TAGCCAGGAT GGTCTCCATC TCCTGATCCC GTGATCCACC CACCTCGGCC TCCCAAAGTG 45060
CTGGGATTGC AGGCGTGAGC CACCGCGCCC GGCCTGAATG TTTTTAAAGT ACTGGTGACC 45120
ATATTCGCTG AGGGATTAAA TGTAAGGTAT GAGGGGAAAA TAGGAATCAG ACACCAGGGT 45180
TTACTGCCTG AGCAATGAGA AGAACGACGT TCCTCATACG GAGATGAGGA AGAATGTGGA 45240
ATAGCAGGTA AATAGCATGT GCTTGCTTTG TTTGGGGCTG TGCAGAAGAG ACTGATGGGA 45300
CCAACGTGCT CAGTTCTGGA TATATTAAAC TTGGAATGCC TATTTGGCAC CAAGTGAATG 45360
TATCAGGTAG GCAGATGGAT AAATGAGTCT GAAGTTCAGG GGAGAGGCTG GGGTGGCAAT 45420
ATGAACTTGG GAGTCTCCAC ATCTGAATAG TATTTAAAGC TATACAACAG GATAAGGTGA 45480
TTTAGGAACT AAACACAAAT TGAGACGAGA TCCGAGCCCA GAGGCACTCC GATGTTTAAA 45540
AAAGAGGAGG AACCATCAAA AGATACTAAG GAGAAGCCAA GAAGTAGGAG AACTGAGAGT 45600
CTGAGAGAAT CATTATACTC ATTTGATCGA CTGCAACAAA TGCTGCTTAG AGGTCAAGCA 45660
AAATGAGGAC TAAGCAAGGA CCACCAGGTC TGGCAACATG GAGGCCAATG CCGACGTGGA 45720
AATGAGAGTT TTGGTGGGAA GACAGGAATA AAAGTCTCAC AGGTCTGAAT TCAAGAGAGA 45780
GAACAGCAGA AGAAGGGTAG AGGTGGTAGC CATAAACAAT GATACATTCT CTTGAGGCCT 45840
TTTCTTGCAA AGCTCAGTGA AGAAACATGG TTCCAGAGAG GGATTTTTTT TTCTCTCATT 45900
TTACATATGC AAACATATAA AAAAGCTGAA AGAATTGTTT GACAACCACC CTTATTCTTA 45960
CCACAGATTC AACATTTAAT GCCATATGTT TTCCCTGTAT GTACTGTGTA TTGTTTGAGG 46020
ATAACTTCCC CTCTAAATAT ACCTCGGATG TATCTCCTAA AATAAGTCCA TTCTCCTACA 46080
TAGCCATAGT AACCATGAAC ACACCTAGGA AAATTAAAAA TATATTCTCA AATATATTAT 46140
ATAGCTGGGT ATATTACAAT TTCCCCAATA TGTGATTTGC AAACCAGGAT CAAGTCAAAG 46200
TCCATGCACA GCATTTGGTT GTCATGTGTC TTTGGTCTCT ATTAATAATG ATGACTGTTT 46260
GAAAAGACCT GTCCTATAGA ATAAATTTGA CTGATTATGT CATGCCATTG AACTTGTTTT 46320
TCTATTCTAG AAGGATAGTT TTTTAGGGTA GTGAATACAT TTATTACTCT TGGCACAATA 46380
GTCTAACATT TCCCAATTTC CTTATATCTC TGCCCTTTCA TTTTCAGAAA ATCAATTATT 46440
CCAAGATTTG TTTTTCATTT ATCATCACTT ATTAGCTCTG AAGACTCAAC TGAGCAACTT 46500
TCAGGGTTTA TATACCCTAT ATTCAGAAAA AAACTACTAC CATCTCTCAT TTACCCTAAG 46560
AATTCATAGG AGAGCATGTC TTAAAGCTGA TCAATAACCA AACCAAACAT TTTATTGATC 46620
ATATTACATT TGGAAAGCAA AATGAATTTC CTAAAATTTC TTCCCTGATT AGCAAAATAG 46680
TGCCTCCGAA CACTTGAGGG TGAAAGTTGT TGTCAAATAT GCCTACATGA CTGGAAATTA 46740
TGACATCCAA ATGAGTTCAC TGGGTCTGAT AATAATATGC TCTACATGCT TATGTCTATG 46800
TAATAAACAG CTTACATCTG GATGAGAAAA TTGATTATAC AAATATTTGG GCTTCTACAA 46860
CTGGTCACTC ATCTGTAAGT ACTTAAAGCA ACTTAAAATG CAAACTGACC TAACAATGCT 46920
TATGGTTAGA ATTCCAAAGA ATGTTTAGGC ATTGTCAGGT TATGTTAAAA CATCTTCTGC 46980
CACAATCTTC AAGTGATTTA TCTTTTCTGT TGTGTTGAAT AGCTATAGAA GACAAATGAA 47040
TTCTGCACTC CTGAATTCAA TGAACATTTC AAGTTCCTC ACTTACACTG TAAGATTACG 47100
TAGCATATTT TAAGAAATAA ATTATAATCA TTTTATTTCA CTTATTGAAC TTCTTTTAAG 47160
CTTTGGCATT AGAATTTTAA TCAAAGCACT GCCACTTGCT TACAGTGATG GTTTTTAGGC 47220
TCTTTGGGCC TATGGACTAT TTCAATGACC TTCACTAGCC ATCTAGTCCA CCTTATCCTA 47280
ATTATTACCA CTGCAAAAGA AACCCTCACT TGAATAAATC AGTAGATGGG CATGAGGCAC 47340

FIG. 6.18

```
CTCCCAGGAG ACTATAATTA TTAACTCATA CTAAAATCAA AATTGTAGCT ATTATCACTC   47400
ATATGGTTTG GCTCTGTGTC TCCACCCAAA TCTCATCTTG AATTGTAATC CCCACGTGTC   47460
AAAGGAGAAG CCTGGTGCGA AAGGACTGGA TCATGGGGGC GGCCTTCCCC CTTGCTGTTC   47520
TTGTGAAAGA GTTCTCCGAT GGTTTAAACG CATGGGACTT CCTCCTACTT GCTCGCTCTC   47580
TTCTGCCACC ATGTAAGATG TGCCTTGCTT CCCCTTTGCC TTCTGCCATG ATTTTAAGTT   47640
TCCTGAGGCC TCCCCAGCCA TGCAGAAATG TGAGTCAATT AAACCTCTTT TCTTTGTAAA   47700
TTACCCAGTC TCAGGTAGTT CTTTACAGCA GTGTGAAAAT AGACTAATAC AATCACCTTA   47760
TGGTAAGTCT GTCTATAAAT CACCTGAACT TTCACAGACT ATCTAGAAGA ACATGTAACC   47820
AGAGTAGTTC TTGATCATGC TATATAAATT ACTGATACAG AAATAGAGCT AGACAGGAAG   47880
GGGCTGGTAG TAGAGAATCA TCCTCTGGAC ATATTCTCAC AGCCTAATCT CTAGCTAGCA   47940
AATTTTATAA TATATATAAA AATACAATTA TTTCACAAAA TTACCATGAA ACGATTTTAT   48000
TGGGATATTA GACATTACTG AATTACTTGT TCTGTGAGGT ATACAGTGAA ATTAACATGT   48060
TATAAAATTG TGGTAGCCGG CCCCCAAGAT GGCCTCCAAT GAATCCTTCA CCTCTTGGTA   48120
TTCATACCTT TGTGTAGGTA GGTCTGTGTA ACCCATAGAA TACAGCACAG TGACAGTAGG   48180
TCACTTCCGA GGTTAGGTTG TGAAAGACAC TGTGGTTTCT GCCTCTCTCT CAGATCACGT   48240
GCTCTGGGGG AAAAGCCAGG TGTCATTTTG TGAAGACACT CAAGCAGCCT TTAGATGACT   48300
GCAACCACAT AAGAGGCTCC GAACTGGAGC CACTCAGCTA AACCACTCCC AGATTCCTGA   48360
CCATGTATCA TTTCATACAC AATGTATGAA ATGACAAATG TCTGTTGTTT TAAGCTGTTT   48420
GGGGAATAAT TTGTTACATA ACAAAATATA ACTAATACAA TAATACATAC TGATTTAACT   48480
GAAGTTGTAA CTTCATAACT TATTTAGGTA CTAAAAATCA CAGCAACCCG ATGCAAAGTA   48540
CTAAAAAAAA AATCCATTAA TACCTATTGA GTACTGTTGA GGGCATGAGG AAAGCTCTTT   48600
CATACTCCAC ATAAAACTTC CTTACCGTAA TATTCATGGC TGACCTCTAC TCTTAACTCC   48660
TTTCTAGGAT AGGAGGGGCT AACTGATCTG ACAGCAAGTT TGGGAGAAAA AATTCTGAGG   48720
CTCGGCCAAC TTCCTCTCTT CTTTCCATTT GGGATTTGGC TGACTGAAGA GGGTCATTTG   48780
TTTTGGCCTG CTCTCTTACA CAGTAAATGT AGTGGGACAA GCTCTATTCT TGTTGATAGA   48840
AAAACTCGAA TTTTAAATCT GCCTAGTTCT TTGCAGCTCG TTGTTGCTCC AAATCTCAGC   48900
TACCTTTTGA AACAACTTTT TTCAGTAAAC TTAATTTCAA TCTTCATGTG ATTTAACTGG   48960
ATCCAAACAC AGGCAGATAA AAAAGGTGGG GCATTACTTA TCAACCTCTA AACTAAGTTT   49020
AATTTTGTGC CCTCATGGAG TTTATAGTAT ATTTGAGGTT TAAACTAAAA CACCTGGTTT   49080
TAAACAGAAA CTATAAAAAA CACGATTAAT AGGTGAGGCC GGGCGCGGCG GCTCACGCCT   49140
GTAATCCCAG CACTTGGGGA GGCCAAGGCG GTGGATCAC GAGGTCAGGA GATCAAGACC   49200
ATCCTGGCTA ACACGGTGTG AAACCCCGTC TCTACTAAAA ATACAAAAAA TTAGCCCGGC   49260
GTAGTGGTGG GAGCCTGTAG TCCCAGCTAC TCAGGACGCT GAGGCAGGAG AATGGCGTGA   49320
ACCCGGAAGG CGGAGCTTGC AGTGAGCCAT TGCGCCACTG CACTCCAGCC TGGGTGACAG   49380
AGCCAGACTC CGTCTCAAAA AAACAAACAA ACAAAAAACA AATAGGTGAA AGGCCGTGAT   49440
CATTGGTAAG CGTAAGAAAA TCTGAGGGAG AAAAAAATAT AGATGCCCAG GCCCCATGCC   49500
AAACTCATGG AATCATGCAT GAAACCCAAG CAGCTGCAGT TTTAACAAGT TCCCAATATA   49560
TAGTTGACCC CTGAACAATG CAGGTTTGAA CTGCCTGGGT CCACTTATAA AATGGATTTG   49620
ATTTTTTTCA ATAAAAGTTA CACCGAGTGT GCCTGCCTCT CCTCCCTCCC TCCCTACATG   49680
CTCCTGCTCT TAAGCCTCTG CCATGAGGCT TAAGACAGCA AGAACAACCC GTCCTGTTTA   49740
TTTCAATAGT TTTGGGGGGT GCAGGTGGTT TTTGGTTACA TGGATAAGTT CTTTAGTGGT   49800
GATTTCTGAG ATTTTAGTGC AACTGTCACC TGAGCAGTGT ACACTGTATC CAACATGTAG   49860
TCTTTTAACC CCCATCCAAC CTTCTTCCCC AACCCGAATC CCCAAAGTCC ACTGTATGAT   49920
TCTTATGCCT CTGTGTTTTT ATAGCTTAGC TCCCACTTTT AAGTGAGAAC ATACCATTTT   49980
```

FIG. 6.19

```
TGGTTTCCCA TTCCTGAGCT ACTTCACTTA GAATACTGGC CTCCAGCTCC ATCCAAATTG   50040
CTGCAAAAGA TATTATTTCG TTCCTTTGTA TGGATGAATA GTATTCCACG ATGTACATAA   50100
ACATTTTCTT TATCCACTCA GCTCCTCTTC AGTCTACTCA ATGTGAAGGT GACAAGGACG   50160
AAGATCTTTA TGATGATCCA TTTCCACTTA ATGATTAGTA AATATACTTA CTTTTCCTTA   50220
TGATTTTCTT AGTAACTTTT TTTCTCTAAC TTACTTTATT GTAAGAATAC AGTATATAAC   50280
ACATATGACA TACAAAATAC GTTAGTCAAC AATATATGCT ATCAGTAAAC TTCCAGTCAT   50340
CAGTGGGCTA TTAGCAGCTA CGTTTTTTGG GCAGTCAAAA GCATGGGGAA GGAGAGGGTG   50400
GTCCCTAACC CCTGTGTTGC TCAAGGGTCA ATTGTAATAA TACCCATTTA AGAATCCATG   50460
GTATATATGG TAAGTGCAAC AACTCTAGAA GAGAGTGCTA GGAGTTGGAA AAGGAAAGAG   50520
AAAACAGAAT TTAAAGCAAT CTGTAAAGGA CATGCAGGGT TTAGATGAGG TGGAAGGGTG   50580
AGGGAAAACC AACATCTGCT GTGAGGGCAT ATTAACTGCC AGACATTGTT CTATGTCTTA   50640
CCTCATTTAA GAGAATTTCA TTTCACACAT GGAAAAACTG AAGCCCAGAG AGGTTAAATA   50700
ATTTGCCTGA GGCCAAAATT AGTTAAATAA CAGAAGTGGG ATTAGTAGAT GTTTTCATTT   50760
TATCAGTGAA ACTGAGCCTC AGGGAGGTTA AATATTTTGT ATGAAGTAAC AAAACTGAGA   50820
TTAATATATG GCCAAGTTTA AATGAGATCT GTAAATCTAA TGCCTACACT AAAACAAAAA   50880
AAAAAAAGTG GGAAGAAAAG GTCTATATTG CTTAGCAAAA CAGAGGTAGG GAAGCAAAAA   50940
TAAACTTACA AAATCAGATT AGACCACCAA AAAACAGTCC CCATTTTAAC TTATGTGGTG   51000
AGAACCATAT ATTAAAGACC ACCAGTGGCT AAAAAATCTT TTTAAAAAAT GAATCTGTTT   51060
TCATTATTCA TTAGTTTTTA TCTAATGAAT AATGTATCTT AACTGATACA TTTACTAAAC   51120
AATTACCAGC TCCAATTAGC ACTCAGTTAC AATTCAATCA TTAAACTGAC CCTCAATTTA   51180
GCTGTCAACC TAGTCAAAAC AGTTAAGTGA TTTTACGGTC ATCCTCAGTT GCAGAAGTAT   51240
AATGTTTATG GCTGGAGTCA TTTTATTTTT AACTAACATT TTTTAAAAAG ATTGCTTTGT   51300
AACAATGTGT TATGAGTCCT TTGTGGTAAA TACTGCTTTT TTTTTGAGAC GCAGTCTCGC   51360
TTTATTGCCC AGGCTGGAGT GCAGTGGTGC GATCTTGGAT CTGAGGCTCC TGCCTCAGCC   51420
TCCTGAGTAG CTGGGACTAC AGGCATGCGC CAACGTGCCC AGCTAATTTT TTGTTTTTTT   51480
AGTAGAGATG GGGTTTCACC ATGCTGGCCA GGCTGGTCTC GAACTCCTGA CCTCGTGATC   51540
TGCCCACCTC GGCCTTCCAA AGTGCTGGGA TTACAGCTAT TTTAAGGACT TTTTAAAAAG   51600
TGAAGCTAAA CATTTATTCA TCCCTATTCC TCATCTATAG GGACTTGTGC TCTATTTTTC   51660
TTTGAAGACT GAAGTAAAAA TTCACCTTTG TGAGGGTCTT CCTATAATTA AAATTAATCA   51720
TTTTTTCCTC CATAGCTTCT ACAAAACATT GCCTGTACAA CTCTATTTAG CACTTATTTC   51780
ATCCCGCCTT GTATGAAAAC TATTTGTTTA CAAACGTTTC TACTTCTCTT TAGGAATAAG   51840
GACTATGCAT TATTCACTGT TGTATTCTCC CTGCATTTAT GGCAGTCCTT TGCACATTAA   51900
ATACAAGCTT TTTGGCTCTG TGCATCTCTT CATCTGGCTG TTCATCTGTA CCCTTTAAAA   51960
CATCCTTTAT TAAAAAAACA GTAAATGTAA AAAAAAAAAA AAGCCATTGA TGAAAAAGTT   52020
AATAGCTTTC TCAATAAGAA AAGAGTATCA ATTATGCATA CGTCTGAACT AACAAACATG   52080
AATGAAATAG GCTATTTAAT ACATTCTGTT TTAAAAGTAG GTTGGTCAG CCATGTAAAT    52140
TGAAAATTGG GAGCCACCAA GATAACTCAT CAACAAATAT GCACTATGTA CTAGGCACTA   52200
TATAGATGAT GGTGAACCAA ACAGATGTAA TCCTTGCTCT TACAGATCTC ACAACCTACT   52260
ATGGGCCAA AAATATATGT GTATGTGTGT GTGTTATACA TATATACACA CACATACATG     52320
TATATATACA TATACACATA CACATATATA CATACGCACA CATACACATA TATACACACA   52380
CATACATATG CTATGAGGAA AACAAACAGG TGGTGAGAAA GAATTAGAGT AGGGGTAGAG   52440
GACAGAGGGC TCCTCAAATA GGGTGGACAG CTTGACACAA GACACTCGAG CTAAGACTCC   52500
AAGGATGAGA AGACAGTTAT GTAAAGAAAA GGGGACTAGC ATTGTCAGCA GGTAGCTAAG   52560
GCCTTAAAGC AGACAGTCAT GTGCTGCAAT GCCAGCTTCA AGCGAATACA GTTACTAAAG   52620
```

FIG. 6.20

```
CATATCTAAC CTTCTATGTG AATGTAGTTA CTAAAGCATA TCCTCCAACT TTCCATTTTT   52680
CTTTTGCTAT TGTTTCTACC ACTTCTCCTT TTCTGTTGAC AATTATTTTA AATTTCCTGG   52740
CTAAATTAAA TGATGGCATG AACTCTGGGG AAAGTAAGAC TACCTATGTC CAAATAATCC   52800
TAAATTCCTT CTAGTCCTTA TGACTGATCA ATTCACCCTG AAGTGACAAC TATGTCCCAA   52860
TTAGGAAAGA GTGTTTCTTT ATCTGCACTT AATTTTTTGA TTTGGAGGCT TCCTGATTGC   52920
TAATCAACAT GTTGTGTGAT TACTTCAACA AGTACTTATA GAACGTTATT TTGTCACTGG   52980
AAAAACGTTC TGCTGCTTTC TGAACTTTAG GTTGCTCTAG AGTCTAGGAA GAGTGACTGT   53040
ACCTAAAGCA GTTCCTAATT ACTGGACATT CTCAGATCTG CTAGAGCTAC ATGTCCAATT   53100
ACGAGAATAT ACTGGAAAAA GCCCTGGATT AGAAATGAGA GGATGTAGGT TTTAGTACCA   53160
GGTCAGCCAC CTTGTTAATG CAAATTTGAG TAAATTGTTA CTTCTTTTAG GCCTTGTTTT   53220
TGCTGTTTTG TTTTTCTGAC AGTATGGTCT CTGTGGTCCA GGCTGGAGTG CAGAGGCACA   53280
ATATCAGGTC CCTGCAGTCT CTACCTCCCA GGATCAAGCC ATTTTCATGC CTCATCCTCC   53340
TGAGTAGCTG GGATTACAGG CATGTGCCAC CACACCCTCG AACTCCTGAC CTCAAGTGAT   53400
CTGCTTGCCT CAGCCTCCCA AAGTGCTGGG ATTAGAGGTG TGAGCCACTG TGCCTAGCCT   53460
TACACATTGT TTTCTTACTG GTAAAGTGGG AATATCTAGA AGTTGCATGC TACATAAATT   53520
CAACCATATA TTATTGGCAA AAAATTTTAA AGAAAAACAT CAGCTTAAGA GTACTAATTG   53580
AGTACATGCC TTGGAATGAG CATGAGCTGG AAAGAACAAA CCTGTTGTTA CATCACTCAT   53640
TGCTGTTTTC ATATGCTGCT CATTGTAAAT CTTGCTCAGT GGCATGATTT TAGTGTTTAA   53700
AGATTTATTT GTTTGTTTGT TTAGGACAAA GTCTCTACAC ATAATCTACT TGCTTCATAT   53760
ATACATACTT ATGCATATTA TGTATGTACA TACATGCTCT CAGGGCTCAC ATGAAAAAAC   53820
AGCCATTCAG GTGATGTGAT TTATCTCATA TGCTTACTTT AGAGTCAACA GGGTGTTGAC   53880
TCCACTATAC AATACTGGCA TGGAGAACAC ATAAGTCAAA GTAGACAGGA CCCAGCCGTA   53940
CCATTGGCTA GGGCACAAAT ATATTCACAT ATGTGGAGAA TGATGTACGT AGAAAGGTCT   54000
TCATTGCACA ATGCTCTTTA ATAAAGATCT GGAAAAAAAA AACACCTAAA TGTTCAAAAG   54060
GATAGGGTAG ATGAAATAAT GGTACATTAT AAAATGGAAG ATTATGCAGC CATAAAAATA   54120
AGGAAATACC TTAAATAATA ACAGAACAAC TTTTAAGGTA AGTGAACAAA TAAGGTACAT   54180
AATCACTATG CATAGTATGT ACCATTTACA TAGAAAAAGG GAAGAAAAAT AAAATATATA   54240
TAGTAATTTA TTTGTTCTTA CATGTGTAAA ATTTTTCTGA AAAATATACC AGAAACTGGT   54300
AGCACTGGTT GCTTCCTAGG CAGAAAATGA CTGAGTATCC TTTTGTACCT TTTGAATTTT   54360
GAACCACGTG AATGAATGTG TTACCTATGA ACAAAATGAC AAGTTTAGAT CAGCAAGACA   54420
GCAGTTTGAG ATGAAATGGG ATTACACCCT TAGTAGGAAA AACTTTTTAA AGCAGGTGGT   54480
ACTTCTAAGA GCAAATACCT GCACATGGAA TGTTGAAACT ATAAGGAACT CTCCTTAAGA   54540
GATCCATCTA TTCCAAACTT CTCATTTTAT AGATCTGTAA ACTGAGACCT TAAAAATTCA   54600
GTGACTTGCA TAAGGTCACA CAGCAGAAGA GATGGGATTA GATGCTAGAT ATTCCAATAT   54660
CAAGTTTAGA CTATTAAAAA TTCAGTGACT TGTGTAAGGT CACACAGCAG AAGAGATGGG   54720
ATTAGATGTC AGATATTCCA GTATCAACTT TAGACTATTA TCACACCATC TTCTCATTTT   54780
CTGGGGGCAA AACAGAACCA AGTAAGTTTG GGCTACATTA CGAGTTGTCA TGTTTTTGTT   54840
TTTGTTTTTT TGAGATGGAG TCTTGCTCTG TCGCTCAGGC TGGAGTGCAG TGGTGTAATC   54900
TCAGCTCATT GCAATCTCTG ACCCCCGGGG TTCAAGCAAT TCTCCCTGCC TTAGCCTCCC   54960
GAGTAGCTGG GTTTACAGGC GCCTCCCACC GCGCCCGGTT AATTTTTGTA TTTTTTTTTT   55020
TTTTTTTTAG TAGAGACGGG GTTTCACCAT CTTGGCCAGG CTGGTCTTGA ACTCCTGACC   55080
TCGTGATCCA CCCACCTCAG CCTCCCAAAG TGCTGGGATT ACAGGTGTGA GCCACCACGC   55140
CCGGCCGAGT TGTCATGTTT TATCTAAATT TTAGAGTCTA ATGTATAAAT TAACCTTAAG   55200
CCCTGAAACT ACTAATTTCT TGTTTGGATC ACTATACGGC TACACTTAAA AATATGCTGT   55260
```

FIG. 6.21

```
GCATACCTCT ATCATTGCAT GTATACAATA TGATAGATGC ATGATATGAC AGACACACAA   55320
TATGATACAC GTATTTTTTT CTATCCTAAC ACATCTGAAT TTACTGAAAT AACTAAAATG   55380
TCTTAAGTTA CTTTTTTAAA TATACACATG CATAGCACAA GCGTGTTGCC AAAAATATGA   55440
ATACAGGTTT ACAATTCCTT AACTAAAACC CAAGGGTTGG ATGTGTTTTA GAAATAAGAA   55500
TTTCATACAA TTTTTAAGTG TTACAGGGTA TATAAACCAT TATATAACAC ATACCAGGGG   55560
CCAAGGGCAG CACCCCATAA TCAAACATAT TAATATAGTT TCAGCAAAAC ACATGGGATA   55620
AAGACTATAT ACAGCTTCTC AATAGTTCAG GTCATATTTT GCTACCAAAT GAATTTTGTT   55680
GCCAAGCTTA AGAAGTTTTT GGTTTTCACC GCTTTCTGAA TGTTAGATTG AGATGTGGGA   55740
TTACAGACTG TACTCATAGA GTGCTTCTAG AAAGCAGTCA GTCACTTCAA CTCTCATTTT   55800
TTTTTTATGA GACTAAAAAA GAAATCATAG CAAGTAGCTT TTATATCCCA GGTTTGGGCC   55860
AAAGACTTGT ATTGTGGTTA AGGAATCTAA CTTAGTAGAA GGTGCACGAG CTGACATCGT   55920
GAGTGGCTAA AATGAGAGAA AAAAAGAGAA AATCCTAATC ATACAGAAGC ACTGAACTAC   55980
TGCAGCTGTT CGTTAGTTAT TAATTTAATA AAAGCTTCCT CCCTTTAAAT CATGTGAGTT   56040
TATAACTGGA AATAGGTCAA TAAAATTTCT GTCCCACACT GCTGACAAGC GATGGACGCA   56100
ATTAGCTTTA ATCCCACTGG AAGGTACTGC ACTCTCTCTG GACCAGGAT ATGTAGAAAA    56160
AAGCATTTCA AATATATAGG AATAACCAGA AATGTATACA GTATTCTCAA CTTGGGACCG   56220
TTACTCTATA ATATAAACGA AAGGGGTTTT CTAGTCAATC TCTGCTGATC TCCTGTACCA   56280
AAGTTCTTCC CTTTATAAGT CTTGTACTAC CTTTTACAAG AGGAAAAAGC TCTAGAGCGA   56340
AAACACAGAA CACACTAAAA TCCCTTCCTT TCTCTTTACA ACTCAAGCCC CGCCTCCATT   56400
TTGTTTCTGT TACTAATTTT TCTTCTGAAA AAATACCAAA TTTACACTGA AAGACTAAAA   56460
TTCAACTTTG CAGACAACGT TTTAAAAAAT ACAATTCAGT TTGGTGATGT TGTTTTGCAG   56520
TCTTACAATT TTAGCTACAT TTTAACTGAA CCAATTGTTT TGTTCAATTT ATGAGTTAAT   56580
ACTCAGCAAG TTTGTTTTTT ACAAATAGTG TATTCCATTC TAAAAATGGA AGTAGCAGTG   56640
GTGAACAAGA AAACAACCCT CTGAGTTTTG TCTATTTCAG GAGGAAGTAC TACTTTCTCC   56700
AATTTTAATC ACAATTCATA AAAAAGAAAA ACCTAACTAG CTAGATCTTA AATATACAAA   56760
TACATTAACA ATCTAGTAAA GCAACAGAAA AAGGTAAACA AACTAACCAG CCTATTTTTG   56820
TCTGGAGAAA CCCCAACAAA CTGCTGGATT CCTTGGCCAT TTGCATTCAG AAGTACCAAA   56880
AACTAAAATC CTTTTTACTA AATAATTTCT TCTACACGAG ACTTGTTTCC TCCACACCAC   56940
CCTATCCAAA TTGTCAGCAT TATTCCAGAA TATAATCATT TAGTTTGAGA CCACTAAAAA   57000
ACCCCGCAGT CCAAAATACC AATTGTGGTT TTTCTGTAAA GAAATGGTCA GAAACTACAA   57060
ATTGTTATCC TAGGACACAG AACCAATCGA CCAAAGGAC TTCTGGAATA TGCTGCCCCC    57120
AAGATTTAGA ATGCACAGGC AGAAATAGCA TACGCGGTCA CGATGTCCCT TAAGCCACAT   57180
GACCTTCCTA CGAAAGCAAA GGCTTAAACT TATCAAATGA GAACTCCCCC TTTCTCTGAA   57240
GTTAAAACAA GGCAGGGCAG CTGGAATTAG AGCAGCAGGG ACAGATCGGC TGTTGACTAG   57300
TCAGAACGGG TCGTGGAATG CAAAGTCCCT GCGCTTTCGC TGCTCCCCTT ACCGTGAGAA   57360
GATCTGGGAG GGAGGAAAGG AGGAGAAACA CCCCAGAATC CTGGTAGAAA AGCCCCTGGC   57420
CTCGAAGATG GGCTCTAGGG AGACAGGGAG GGGCAGCTCC GTGTGTGATG ACCCTTTGTG   57480
AACATGCACT CTGTGGCAGC TTCAGCTCCA CCGAGGCTTT GGGAGAGCGG ACTACGGATG   57540
CCCGGCGCGG CCCAGCTGTG AAGGCCGCGC CGGCGGAGAG GGTCCATGGC ACCCCCGCCG   57600
GCTTCGGAAG CCCTTCCCTC TCCCACCTCC GCGGGTCACC CCAGGAACCA GCGGCTCCCG   57660
ACCACGCTCG CGCGGACCAC GGAACAGCGA CGCGCAAGCA GGTCTCTTTC GTCAGCGTAA   57720
TCCCTCCGCA GAAAGCCGCG CACTAGTTTT AATCACGCCC CACCCCCTGG CCGCTGGCGC   57780
CACCTCCGCC ACTCGGGCGC TTTCCAGCAG CTTCCAGAAA CGTCGCCTCC CCAAACCCAG   57840
CCACTCACAC ATGGCGGGCT CAGCAGCCAC CGGCCCCGCC CCTCCTCGTC GCCGCAGTCG   57900
```

FIG. 6.22

```
CAACTGCGTC TGCGGCCACA GGGCGGACAG CCACGCCTCT GCGGAGGGCG ACCGGAAGTG    57960
CTCACGTCTT CACCTTCCCC GCCACGCCAC CGTCCTTTCA GGCCCAGCGT GCAGCAGGAA    58020
GGAGGACTCT TTTGCCGCGG ACTCAAGCCG GAAGCCGCCT TCCTAGTGGA GACGCGAGTG   58080
GGGGAGGAGC AGTCCGAGGG GAACGTGGGT TGAACGTTGC AACTAGGGTG GAGATCAAGC   58140
TGGAACAGGA GTTCCGATCG ACCCGGTACC AAGAAGGGGA GTGCCCGCGG CAGGTAAGGG   58200
AGAAGAGGGA GGGGTTTCTT TCCGCTCTCG AAATTGGGAA AAGAGACAGA GCTGGGATGA   58260
CCTATGGGGT AGTCGGCGCG CTGAAAGGAT GGGCTGGGCT GGGACGGGGT TCAAGTGGGA   58320
AAGGTTGATG ATTAAGGTAT AGAGTTGGAC TTACAGATCC GTTGGGCGC AGAGAGGTGA    58380
ACGCTGAAGA GAAACCAGAG TTTGTTTTCG TTTTCCAAGG AGCGTGGAGA TGGGCAGGGT   58440
TAACGGACCC TGCGCCTCCT TCGGCTTCTT AGTTTGGGTG TTGAAACTCA CCTCCTTTGG   58500
TCCTGTTCGT CTCTGATTCA AGACAGTTGG GTTTGGTACC TGACAGGGCT GGGTGCAGAA   58560
AGCTGACCCT GTTCCTCGGC TTCCAGGTCG GTTGTGGCCT CGCTTTTGAC AGTTCACGTG   58620
CCGAGCCTAC TCGCTCTCGG AGGGCGAGCT CAAATGGGTG GGTTTAAGGC CCCCTCTTCG   58680
AACAGCTGTT TCCCTGGGTT TCTCCATTTT GCACACAGGA GTGTGAATTA AGTTTAATTG   58740
AATACTTTTT GCGATTCCCA GGGCCACCTT GACACGTTCA TTGTGCTATC TAACTGGGTT   58800
CATGCTGGGC TAATAATTCA CATTAAGGCT TCTGGAGTAT AAGTGGTTCA CAGAAGTATG   58860
AAAAGGGGAT GTTAGAAGAA AGATGCTGGG GGTGAAGTAG AGTTGAGGAA GACAGAACTG   58920
GAAAGCTAGG TTGGTTTCAC AGTACAATGA GCTTTAGGTC ATAATACTAC CTTTAGGTTA   58980
TATTGGGCTG TTTGGACGGA GTTTGCTGTA ATCAGGCTAG AGTAAATAGA GAATTTTAAA   59040
CTAAGCATTG ACAGGCTCAG ACTTGTAGAG GCATCATTTT GACAGTGATA TGGAAGGGAA   59100
AGAGGTAGAG ATTTGAGACC TTTCCAAAGA ACTGTCCACA GAATTTGGTG ACTTACTGTG   59160
CGAAGAGGGA AATAAAGAAT AGGGAACAAC TCAAGACTTT CTAGTCTGTG TGTTTGGAAG   59220
GATGGAGACG CCCACATTTA AGTGAGATAT GGGAAGGAGG AGCAGATTGT TTTTGAAGGG   59280
AGGAAGAGCA GTTACTTAGG GTCAAATTAA GTTGTAAAAT CCCCCCCGGG ATTTTGTATG   59340
TAAGTCAAAG TGAATTGTAT TTGGAAGAAG AACTGGGGAG CCCACCTCTG GTATTTTTTT   59400
TATGTCCCTC ATATGGACAA ATAAACCTCT GGTATTAAAT GAATTTTCTT TTGGGGGATT   59460
CTATATATTC GGGATTTCAA CCACCAACCT ATCTGGTTTT TCCCGCTGAA ATGTTGGGTG   59520
ATGGAATCAG GAGAGCAGAT TTGGAGACTC TTTATATTTT ATAATTGAGA GAGACAAAGA   59580
GAAAACCGTT TGATTTGAAA AAGTTTTCTA GGTTCCCTCA GGTAGATGGA AATTTTCATC   59640
AAAAACAGTT TATTCAAGGT ACATAGCCTA CTAGTTTCCC ATTTGAGAGT ACCGCAGAAT   59700
GATACGACGT GTACTGCTTC TCTACGCAGA ATGAAGTATA AAATTAGCAC CAAATAGTAA   59760
CTTTAATTTG TCAGGTGCTA AACTTTTTAC ATGCTTTATC TCATTTAATT CTTAGAAGAA   59820
ACTAATTTTA CAAGTAAGTG TCTGGACCAA CATCTGCAGG TACAAAGCCT GAAAAGCGTA   59880
AGTTTGACTC CTACATAGTT CTCTTTTGTA AGTAGATTAT AAATAGAACC AGCCAAAGGT   59940
AATAAGTTGT CTGTGCCTAA AAAGAAAGAA AAAAGTTAGC ATCAGTAGTT CTCACCAGAA   60000
GGGGTGATTT TGCTTACCAG GGGACATTTG GCAAGTCAGG AAACTTTTGG CTGTTGGATC   60060
TAGAGGGTAA AGGTCAGTGA CGCTGCTAAA CATCGTCAGT GCATAGAACA GCCTTCACAA   60120
ACAATTATTT GGTCAAAGAT ATTTGTAGTG CTGCAGTTGA GAAATTTCTG TCTTATGGTT   60180
ATTTCTTCAG GAATAGGAAA TTAAGATTCG CCGATACTTT CTTTAAAAAG CAGTTTTATT   60240
TTTGAAATTA TTCCTTGGCT TGAAAGGTTT GTGAAGTTTA TATAGCCGAA CCAGAATAGC   60300
GTAATTAGAT TTTAAAGTGA ATTGTGAGCC ATCGATTCCC AGGAGATGGG TGTCATAGAA   60360
TCATGGATTC TTGGATTTGG GAAAGACTTA TGCCTAGAAT TATTTTACAA CATTTCTGCT   60420
AAGTGGTAAT TCTCCTCTGC CCTAAAGGTC TCCTGTATTT GATTTTCCTA TCATTGTGAA   60480
CCCACAATTA AAATGCTCTT AATTATTTTT TGCTTACACT GAGCTCCGGT CTCTTGTAAT   60540
```

FIG. 6.23

```
TTTTACTCTG TTAAATGTGG TTCTGCACCA TAGGACTGCA CTCAAAACAA GCTTGCCACA    60600
TATGTAATTT GTACTAGGAC AGTGTTTATA TTTTTGTTCA GATAACAAAA TAAGTTAAAT    60660
GTGGTGTAAA TTAGATCATT TACAAATAAT AATTTGTTAG CAGCTTTTAA TAAGTAGTAT    60720
TTTTCCCAAC TGGTGAAGTA TTAATGTTGG TAGTTGAAAA CAATAGGAAT GTATGGAATA    60780
TATGGTTCAC TGGTTCTTTT GTTCCTGTCA AATAGTGGCA CAATGGATCT GGGGTTTTTC    60840
TCAGTATAAT GCTGGCATAT TTGTTTCAAA TTGTACATAG ACTCTAAAAA GTTAGGCTTT    60900
CAAATTCTGG TCAATATAGT TTGCTTTAAA TAGTAGCTGC CTCTACTACA AGTTTTATTT    60960
AATTTGTTGA CAAATGAGTC TGCTATGAAA ACCGGTCCTG TTGCCAGTCA CTACCCTCTG    61020
TTCACAAATT TGCTGGGTTT ATAAATATAG GTATCATTTT CACTTCAAGA TTATAATTTT    61080
AGAATATGTT TATTCTAGGA CATATAGCCC TCAAAATCTG CTTACTATAT ACGTCTTATA    61140
AAATAGCATG GTTCTTTTTT ATAGTAAATA GAATTTTTAT TTAATTGTCT ATTGACTTTT    61200
TTTTCCAGG GTTCATTGAA AAAATCCTTA GTGATATTGA CATGTCTCAA GTGACATAAA    61260
TTAGCCAATG ACTCGGAATG ATGGATTCTC CGAAGATTGG AAATGGTTTG CCAGTGATTG    61320
GACCAGGGAC TGATATAGGG ATATCTTCAC TCCACATGGT GGGGTATTTG GGAAAAGTTA    61380
GTGAACTTAT TTTTTGCCTG AGTGCAAAGT TTTTTTTTTT TCTCTATTTT TGAGACTTAA    61440
ATTCAATTTT GATGTTACCA GTTAACTTCT AAAAAATTGT GTCTTCCACG AAATCTTAC    61500
AGTAATGGCG AAAGATTGTT TTAATGTGTT TACCTTTCTG TGTTTTATTG ATACATGAAA    61560
GTGGAAATAA AACATAGACC TTATGATTTA CTGTTCTTTG AAAATATGG ACATAAATTC    61620
TCCCGGGTAA TTGATGTTAC TTTTTTCCTT GCAAATAAAA TTGATACTAT TCTTAACACA    61680
TAAAATTTAA TATTTAAAAC TATAACATAA TTCTTTTTGG AATAATAGCT GTATTTAAAG    61740
GCTTATATGC ATTTCTTTTG TTTGCCATGT TTAAAATACC TTGTCAGGAT ACTTGTAATT    61800
GAAAATTATA ATTTTTTCTG GTTACCTTTC CATTTAACTT TTAATATTTT GATATATTCT    61860
AGGAATGTCT ATATTTTAAT TTGCTTTATT TCTCTTTTAG AATTTTGATT CAGCTAAAGT    61920
TCCATCAGAT GAGTATTGCC CTGCTTGTAG AGAGAAGGGA AAGTTAAAAG CCTTAAAGAC    61980
TTACCGAATT AGTTTTCAAG AATCTATCTT TTTGTGTGAG GATCTGCAGG TAAAGTATTA    62040
ATCTTATATA GTATATATAA GATTTTTCTT TTTTCTTTTG CTTTTTATT AATTGTTTTA    62100
AAAGTTTACT CATTTTTTGT TTTTTAGACT AGATTTTTAA TATGTAATCT CAGTTTGTAA    62160
GTCTGTCTGG TATACAATGT TATTTTTCCA CCTACCTTTA CTTGGTTGCG TAAAGATGTT    62220
CGTTTTTATT GCCATTTGAT TTGCGAGAGG AGAAAATACA TTTCAAGGTT TTTTTCTTTT    62280
TTTTTAACCT TTTGGAGGTC CTTGTTAGCT ATTAGCATAT AGTAGTTACT CTCTCATCTC    62340
TTTGGTTTAT CTTTGCAACT GATGGGAAAA GTTATGAATT TCTAATGTAC CTGGAAGAGT    62400
ATTTTGGAAA TTGGTTAGTC CAAAACCAGT ATATATACTC TGAACTAAAG AGAGTATAGA    62460
ATCTTGTAAA TTCTAAAAGA TCCTTTTAGA AGCTCTAAAT CGCTTTTAGA ATTATAGTAA    62520
TTTGTACCGA CTGGTACGGC TTTTATATAG CAGCTCATTA AATTCTGTAA TACTCCACAT    62580
TTTATTGTAT TTGACAGTTT ATGAGACTGT CTCATACACT TTTAATTCTC AGAACTTTGC    62640
AAGATTTGTA TTCCTATTTC ATGAATAAGA AAATAAATTG ATTTCAGAGG GTTTGGGAAC    62700
ATAAGATCCT GATACAGTGG CAGAGCTGTG GTTGGAATAC AGACTTCTAA TTTCAGATCT    62760
GTTTATTCCA GCAAAAAATT AGCAGTTCAT CAGAATTACC TGGAGTGCTT TTAATAAATT    62820
TCTGAGTATC ACCCCCAGAT GCTGATTCAA TAGAGTTGGC CCAGAATTCT GTGGTTTTGT    62880
AACATTTGAG GATGAGTCTG ATCATCATCA GCCAGGTTTG GAAAATACTA GACTAAATCA    62940
CATGGTTGTT AATAGATACT TATGCTGGGT ATAATTTGAA GTAAAGTAAT CCCAGGCGTG    63000
TCTACAAATA TAAATTTCTT TATGTTTATA TTCAGTAATT TTTTTTATGA GTGTCACTGT    63060
TTGGCACTGT TGCAGATACA ATGTTAGGAT ACAATAATAA AACAAAAATT TCTTGCCCTT    63120
AAGGAAGTTA TGTCATAGAG TGGGAAAGAC AGTGAACAAG TATGTGTTTT TCTGTCAGGT    63180
```

FIG. 6.24

```
GATAAAAAGT GCTGTGGAGA AAAATAAGGC AGTAGGGACT GGAATGCCAA AGTAGGGGGA    63240
GTTTGCAATT TTAAATAGGA TGGTGAGGGG AACGCTTCAA TGAAAAGTGC AATTCGAGCA    63300
AAAGCCTGAA AGAGGTGAAG AGCAGTGAGC TTTCTAGGCA GGGGAAGCAA GTTCCAGGAA    63360
GGCCCTGAGA GAATGGAGGC TGCCTGTCAT GTTTGTGCTA CTGCAATGAA AGCAGCAGAG    63420
CGATAGAAGG TGGATCAGAA AAATAATGGG GGAGCTGGAC CAAGTAGGGT CTTATAAGCC    63480
ATTGTAAGCT TTCTGGCTTT TACTATGGGT GAAACCAGGA ACCATGGCAG AGATGTTGGC    63540
AGAGGAGTGA CATAAGTTGA CTTCAGTGTT AAAAGCATTA CTGTGGCTGC ACTGTTGAAA    63600
ATATATGTAA TGGGCAAGAC CTGAAGCAGG GAGATTAGTT ATAGTATAAT ATGAATTATA    63660
TTTGGTCCTT GTCTATGGTT TCCGTTACAG AGCTAAAAGT CTTGGAATTT CCTGAATGAT    63720
AAGAGTGTCC TGTTATTCAG AATGAGCCTG TTTGCTAACA CCGGGGTTCA TACTATTGTG    63780
GTGACTTAGG ATGGAGCCGT AGATAGCCTC AGATGGGGCA AGTAGCTGGA AAGACCACAT    63840
GATTAGAGAA TTAACGGGTT AGAACTTTTA GCCCCACGTA CAGGCCTCCA GGAAAGGAGT    63900
GGAGGGGCTG GAGATCAAGC TGTATAAAAA TATCAAGATT TGGATTTAAT GAGTGGGTTG    63960
CTGGGGGCTG GTGCCGTGTA GGAGGTGGTA TGCTTAGAGG AAGTGGAAGC TTCATACCTC    64020
TTCTGTCCCA TACCTTGCCC TACTCATTTC TTCATCTATA CCCTTTATAA TATCCTTTAG    64080
GATAAACCAA TAAACATAAG TAAGTGTTTG TTTGAGTTCT GCGAGCTGTC CTTGCAAACT    64140
AGTTATGCCC AAGAAGGGGG AGTGGGAACC TTTGTAGCCA GTCAGTCAGA TGTACTGGTG    64200
GCCTGGATGT GGGATTGGCA TCTGAAGTGG AGGGAGTCAT GGGACTGAGC CCTCAACCTG    64260
TAGGATCTGA CATGGTCTCT AGGTAGATAA CATCCAAATG GAATTGGATT ATAGGATACC    64320
CATTTGGTGT CCTCTGGAGA ATTGCTTGGT GTGGGAAAA AGCCCCCACA CATCTGGTCA    64380
CAAAAGTGTG CTGGGAGGAT AGAATATGTG AAAATTGTCA TAATCAAAAT GGAGTCACTT    64440
GTGTTAAAAA AGAAAAAAAA ATCCTGACTG GCCAGGCACA GTGGCTGACA ACTGTAATCC    64500
CAACACTTTG GGAGGCTGAG GCAGGAGGAT TGCTTGATCC CAGGAATTGG AGACCAGCCC    64560
ATGCAACATA GTGTGGCCTT GTCTCTACAA AAAAAAAAAT TTAAATTAGC TGGGCATGGT    64620
GGTGTGAGTC TGTAGCCCCA GCTACCCGGG AGGGGGACTA CGGGTGCACG GCACCATGCC    64680
CAGGAGGTCC AGGCTGCAGT GAGCTGTGAT TGTGCCACTG CATTCCAGTC AGGATGACAG    64740
AGTGTGAGAC CCTGTCTCTA TTAAAAGAAA AAAAAAAGAC AAATAGATCC AGGAAAGGCT    64800
ATGAAGAGAG AGCTTTCATG CATAAATACC AAAATATCTC AAAAGACTCT GCAAAAACCA    64860
CACCCTTGCA CAAAGGCCAT CATGAAATAC TTCTGAAATA CACAGAAAAT ACATCATGAA    64920
ATAAATACAC AGAAAATACT TCTGCAAGGA CATCTGCCCA GCAACTGCCT GGTCCATCTG    64980
TGGACGGGTG TCATCCTTGT TATTGATCCT TGTAGCCAAG GGTAATTATC TCAAAACAAG    65040
TATGTGATCC TCCTTATTTT CCTTTAAAAA CCTTTGTCT TCCCTTACCT CCCTGAACAC    65100
ACACAGTTTA CTATGGCATG TGTATTCCCA TTGGAATACT TTATTCCTGA ATAAATGTCA    65160
CTTTCTTTTT AGAAGCTTCT CTTTTCTTTT TATTTAGATT GATAAGTAGA AAGGAAAAAA    65220
AGCTTTTTTC CCTTTGGACT AGTTGAAGGC AGTTGCAGTA TTCTGGGGGA GAGGGTGGTG    65280
GCAGAGGTGT TGAGGCATGG TTGGAGTTTA TTTATACTTT GAAGGTAAAG CCAACAGGAT    65340
TTGCTGAAAG ATTGGGATAT GGGGTTGGAA AGAGGAATCA AGGATAGTTC CAAGATTTTT    65400
GGCTTGAAAA ATTAGAAGAA TGGAATCGTG AATTACTGAG CTGGGAAGAC TTGGAAGAGC    65460
AAGGTTTTGG GGAGAAGATC AGGACTGTAA GAATAGAGAA GTCCTTGTCC CCAGGAGTTA    65520
GGTTTTTGGC TATTAAAGTT AGATGTACTA CATAGATTTT TAGTTGGTTT TTTGTTTTTT    65580
GTTTTTTTTT TTTTTTTTTT TGAGACGGAG TCTCGCTCTG TCACGAGGCT GGAGTGCAGT    65640
GGTGCGATCT CGGCTCACCG CAACCTCCGA CTCCCTGGTT CAAGGGATTC TCCTGCCTCA    65700
GCCTCCTCAG TAGGTGAGAT TACAGGCATG TGCCACCCAG CCCAGCTAAT TTTTGTATTT    65760
TTAGTAGAGA CGGGGTTTCA CTATGGCCAG GATGGGCTTG ATTTCCTGAC CTCAGGTGAT    65820
```

FIG. 6.25

```
CCACCCACCT CGGCCTCCCA AAATGCTGGG GTTACAGGTG TGAGCCACCA CGCCCAGCCC   65880
GGAGTTTTGG TTTTTGAAGC ATTCTTTTTC AAGTGATAAA GCAAAAAATA TATAATCAAG   65940
AATTTTAAGT ATATACTTTG GAAATGTTAA AAAGGAACAT GAGTAATTTA TTATTATTTT   66000
TTTAATTTCT AGTCAGCAAT GAGAGCCCAG TGTACTTTAT GAAGTAGATT GGTTTACACC   66060
AGGAGTGAGC AGACATTTTG TATGATGCAC AAACAAGGAA TGATTTTTTT GTTTTTTAAA   66120
TGGTTAGGAA AATATCAAAA TAAAAAATGC CAGAAAAAAT CAAAAGAAGG GCCAGGTGCA   66180
GTGTTTCACA CCTGTAATCC CAGCACTTTG GGAGGCCAAG GTGGGTGGAT TCTCTTGAGG   66240
TCAGGAGTTC GAGACCAGCC TGGCCAACAT GGTGAAAACC TGTCTCTACT AAAAATACAA   66300
AATAGCCGGG TGTGGTGGCA TATGCCTGTA ATCCCAGCTA CTTGGGAGGC TGAGGCAGGA   66360
GAGTCGCTTG AAGCCAGTGG CAGAAGTTGC AGTGAGCCAA GATTTGAGCC ACTGCACTCC   66420
AGCCTGGGCG ACAGAGGAGA CTCTATCTCA AAATAAATAA ATAAATAAAT AAATAAATAA   66480
ATAAATCAAA AGAAGAATAC CCTTTCATAA TATGTGAAAA TTAAATGAAA TTCAAATTTC   66540
AGTGTTCATA AATAAAGTTT TACCGGAACA TAGCCATGCT CAATCATTTA TGTATTGTTC   66600
ATGGCTTCTT TTGCATACAA CAACAGAGTT GGGTAGTTGT GACAGACTAT GTAGCTCATA   66660
AAATCTAAAT ATTTATTATC TAGCCCTTTA TCAGTAAACT TGCTGATCC CTGTATAAGT   66720
CCTCTGAATC AAATTATTTC CAAAGAGTTC CGTTATAAAA TTTGGAGTTT ACTCTGCTGT   66780
AAATTGCAAA GAACCATTTG GAAAACCTCT TTTAGTCAGG TATTTACATT AAAATGTTCC   66840
TTGATTTGTA AACACTAATA TTCAAGACTG GTCCAAAATT ATACCAAATT GAAACTCTCA   66900
AGTGTTTTA AACAGTAGGA AGTTTTAACT TTTTTTTTTT CGTGGAGTAG TCTATCATTC   66960
AGCGTTTACT TTGGAACATT TAATTAGTCT TTTTTAAAAA CCCATGAAAT TTATAATAAA   67020
AATTTTAAAT CATTAATGTT GAGTAATCAA AGAAAACTTT TTTTGTTTTC TCCATTTGTA   67080
AAATGAGTAC ATTATTATTA TAATTTGTCT TTGGCCATAC CTTGTTGATA ATTACTTATA   67140
CAAGTATAAG AAGACATGGT ATGTTTTCCT TTTTCCTATT TCACAAGAAT AAGTACAGGA   67200
ATTTACTTAA GCTGCTCCAA AACTCAGTGA AAGAGACAGG ATTAGGTTTT TTTCAGCATT   67260
GGATTTTAAA TGATACTAGA TGGTTGCGCT GGGCTAAAAT ACTAATGCTT TGTGTATATT   67320
TTTATGACTT TTTTGAAGAC AGCTTAAAAG CTTTATTCTA GTTATAAAAA TGATACATGT   67380
TCACTGTAAA TAGAAACAAG TCAGGTATAC AGAGATACAA ATATTTAGAA CATGTGGAAA   67440
GAGGCAACAA AATTTTATAA AAAGAAAAAA GATAAAAATC TGAAATCATT AATTTATAAG   67500
GGAAAAATCA GGGCAAGGAC AAATTATATT ACAGATTGGC CTATGGTGGG AGCACAGATT   67560
ATATAGAGAA AAGTCAGTGA AGACACTTGC GAAGAGTGTG GGTGGAAATC ACTAAGTTTT   67620
GCAGTCCCGG GGCCTCTTAT GGTTATTAC TGTTTTGTTC TTTTTTTTTT TTTAATATGC   67680
ATTCCTTTGG AACCAAGGGT TTATTATGTT TTGAATAAAG TAGAGGTGTA AGTAGGATGC   67740
ATATACCATG ATCTTGACTA CTTGAGATTC ACAAAGGGTT TTCGTCTCAG GATTTTTTTT   67800
TCTCTTAAAA AAATTTGTAT TAATTTTTAA ATTGTAAAAA AATTCATCAA CTTAACCATT   67860
TTTATGTATA GAGTTCAGGA GTATTAGGTA TATTCACTTG TGCAGCAGAT CTCTAGAACT   67920
TTTTTCATCT TGCAAAACTG AAACTCTGTA CCCATTAAAC AACCACTTCC CATTTTCCTC   67980
TCCCCCAGCT TCTGGCAACC ATTCTAGTTT CTGTTTCTTT TCTTTTTTTT TCTTTTGAGA   68040
TGGAGTCTCT GTCGCCCAGG CTGGAGTGTA GTGGCATGAT CTCGGCTCGC TGCAACTTCT   68100
GCCTGCGGGT TCAAGCAGTT CTCCTCCCTC AGCCTCCTGA GTAGCTGGGA CTACAGGGGT   68160
GCACCACCAT GCCTGGCTAA TTTTTTTTTT TTTTTTTTTT TTTGTATTTT TAGTAGAGAC   68220
GGGGGTTTCA CCATGTTGGC CAGGCTGGTC TCGAACTCCT GACCTCAGGT GTTCTGCCTG   68280
CCTCAGCCTC CCAAAGTGCT GGGATTACAG GCTTGAGCCA CTGTACCCGG CCTCTAGTTT   68340
ATGTTTCTAT GAATCAGACT CAGTACCTCA TATAAACGGA ATCATACAGT ATTTGCCTTT   68400
TTTGTGACTG GCTTATTTCA CTTGGCATAA TGGCCTCAAG ATTCATCCAT GTTGTAGCAT   68460
```

FIG. 6.26

```
GGATGAATAT ACAGTTAGGA GTTCCTTTTC TTTTTTAAGT CTTAATCTCC AGTTTATTTC   68520
TGTTTATTTA TTTATTTTAT TATACTTTAA GTTCTGGGAT ACATGTGCAG AACGTGCAGG   68580
CTTGTTACAT AGGTATACAC GTGCCATGGT GGTTTGTTGC ACCTGTCAGC CTGTCATCTA   68640
CGTTAGGTAT TTCTCCTAAT GCTATCCCTC CCCTAGCCCC CTACCCGCCG ACAGGCCCCG   68700
GTGTGTGATG TTCCCCTCTC TGTGTCCGTG TGTTCTCATT GTTCAGCTCC CACTTACGAG   68760
TGAGAACATG CGGTGTTTGG TTTTCTGTTC CTGTGTTAGT TTGCTGAGAA TGATGGTTTC   68820
CAGCTTCATC CATGTCTCTG CAAAGGACAT GAGGAGTTTC TTACTTTTAA GGTTGAGTAA   68880
TATTCCACAT TATGTGTATG CCACATTTTC TTTATCCATT CACCTATCTG CAGATGTTTG   68940
AGTTGCTTTC ACTTTTTGGG AATTGTGAAT AATGCTGCAG TGAATGTGGG TGTGCAGGTA   69000
CCTTTTCAAG ATTCTGCTTT TGAGTTTTTT TTGGATACGT ACCTTTTTAT GATGCTTTAA   69060
ATACATATAT GCTATTTTTA AAGGATTCTC AGTTTTCTGA CATATGATAG GACTTAGGAA   69120
GTAATCTCAA AGCATCATGT TGACAGGTTG TTAGTTGATG GTGACTGCAG CTAGTTGGAA   69180
AGTCAGAAGA ATCTAGAACT TGTCCATTTA TACTAAAGAA TTTCATAGTA AGTGCAGTAT   69240
TATGAGTGTA ATGTTCAATT GGTAGAAGAG GCTATCTGAG GGGATTTAGT GCATTTCAGT   69300
TATCTGTTGG TGTGAAACGA ATCACCTTGA AACTTAGTCG CTCAAAAATT TTAATGGTGG   69360
CTGGGCATGG TGGCTCACAT CTGGAACTCC AGCACTTTGG GAGGCCGAGG CAGGCAGATT   69420
GCTTGAACCC AGGAGTTTGA GAGCAGCCTG GGCAACGTGG TGAAACCTTG TCTCTACAGA   69480
AAATACCGTG GCAGGCGCCT TTAGCACCAG CTACTTGGGA GGCTAAGGTT GTAGGATCTC   69540
TTGATCCCAG GAGGCAGAGG TTGCAGTGAG CTGGGATCGT GCCACTATAC TCCAGCCTGG   69600
ATAACAGAGC CAGACCCTGT CTCAAAAAAA AATTTTAATG GCTCCATTTA TTATTTCACA   69660
TGATTATGTG AGTTGACTAG GGAATTCTTA CACATCACAC CATGTCAGCT GGGACAGCTG   69720
AAATGTCCAC ATGGCTGGCA GTTGGTACTA GCTGCTAGCT GGAAGTTGAG TTCAAATAGT   69780
CAGCCAGGGG TCTCAGTTAT TTTCCATGAG GTTCTCTCCA TGAGGCCAGC TGGGCTCTTC   69840
ACAGTGTGAT AGCTGGGACT AAGAAGGAGT GTTCCAGAAG AAGGGCTTGT CCTCTTGAGC   69900
CAGTGCTTAT CAGGCCTCTA TGTATATCAT GTGTGCTAAT GTTCCATCAA AGCTAGTCAC   69960
AGGGCCAAGC CAACTCTGTA CAGTGTAGGG ACTGGCTGCA GGAGGGCATG AATTACCAGG   70020
AGGTGTAGTT CTCTAGTTCA TAGGGAGGGC CATCAAGATA GTAGTCTACC ATACTTGTGT   70080
AAAAGAAGGC ATTAATTAAC TATTATTATT ATTATTATTA TTATTTTAGA GACAGGGTCT   70140
TGCTCTGTTG CCCAGGCTGG AGCAGTAGAG TGGGCAATC ATAGCTCATT GCAGCCTCCA   70200
ACTCCTGGGC TTAAGCAATC CTCCCATCTC AGCCTCCCAA GTAGCTGGGA ATACGGGAGT   70260
GTACTGCCAT GCCCACCTGA AAAAGAAGGC ATATTTTAAA AGCAGACCTT TAGTGTAGAG   70320
GGTTCTTGAA TTTGTTATTT AAAATATTCT GGTAGTTTTT AAACTTAGGA AAGACCCACT   70380
GATTCTTTTA GTGATATGTT TACATTGTTG TTATTTGGCA TAAATTGTGT TAATGCACAG   70440
TAAGATTTCA TGAAGTCATT AAAATTCAGC CACTTGGACT CTAAACCCAA TAAAGATGTA   70500
AAACAGCAGT GCTATGAGAT GCATATTCAG TTTCAAAATA TAGGAAACAC AGAAATTACT   70560
CTGTGCACTT TTAATTTGAA AATACTTTTA AAATGTGTAG TATAATGTAG TGTCTGTCCC   70620
AAAAGAGTAA CATTCATTAT AGTGTTTCTT TACGTTGTTG AAAATTTTAA ATTCACTTAA   70680
CATTAGATTT TTATTAAAGC AAAAATATGT TTTCCTTATT AGCTTACCCT TTTGTAACTC   70740
AGATTAAACC CTTGATTGTT CAAATTAACC TGAAAAAAAT TATTCTTTTG GAGGCCAAAC   70800
TTTTGATTAA GTAGTTGTTT GTCTCTAATT TTTTCAAATT TATGTGTATA AATATAACCT   70860
GTCATCAAAT CAATGCTAAC ATTCTATACA TGTTTTTCAT GATATGAAAA CTATAAAACA   70920
TGAAGTTATT TGAATTTGTG TAGTTTTTAT CATTTTATTT TTACTTTCCA GTGCATCTAT   70980
CCTTTGGGCT CTAAATCACT TAATAACCTA ATTTCTCCTG ATTTGGAAGA ATGTCACACT   71040
CCACATAAGC CTCAGAAAAG GAAGAGCTTA GAAAGCAGCT ATAAGGATTC ACTTCTTTTA   71100
```

FIG. 6.27

```
GCAAATTCCA AAAAGACTAG AAATTATATT GCTATTGACG GTGGAAAAGT TTTGAACAGC    71160
AAACATAATG GAGAAGTATA TGACGAAACC TCGTCAAACT TACCTGATAG TAGTGGTCAA    71220
CAGAATCCAA TTAGGACAGC TGATTCCTTG GAGCGGAATG AGATTTTGGA AGCTGATACT    71280
GTTGACATGG CTACTACAAA AGATCCTGCT ACAGTTGATG TCTCTGGAAC TGGCAGACCT    71340
TCCCCTCAAA ATGAAGGATG TACATCTAAA CTGGAAATGC CACTGGAGAG CAAATGTACA    71400
TCATTTCCCC AGGCTTTATG TGTCCAGTGG AAAAATGCTT ATGCTCTCTG TTGGTTAGAC    71460
TGTATCCTGT CAGCTTTGGT GCACTCGGAA GAGTTAAAGA ACACCGTGAC TGGACTGTGC    71520
TCGAAGGAGG AATCTATATT CTGGCGGTTG CTTACAAAAT ATAATCAAGC AAATACACTT    71580
CTATATACCA GTCAATTGAG TGGTGTTAAA GGTTGGTACT AATATTTTAT TTTTATTTAC    71640
TTATTTATTC ATCTGGAGTC AGGGTCTCAT TCTGTCACCC AGGCTGGAGT GCAGTGGCAT    71700
GATCATGTCT CCTTGCAGCC TTGACTTCCC TGGCTCAGGT GGGCCTCCCA CCTCAGTCTC    71760
CCAAGTAGCT GGAACTACAG TCGTGCACCA CCATAGCCAG CTAAGATAGT GAGATGGTGG    71820
CCCCACTGTC TTGCCCAGGC TGGACTCGAT TTCCTGGGTG CAAGCACCCT TCCCGCCTCA    71880
GCCTCCCAAA GTGCTGGGAT TACAGGCATG AGTCACCATT CCAGCCTACT TGTCTTTAAT    71940
TCTTAAAAAT ATTAATGTTG AGTTTTGTCT CCCAGCATGT GGGAAAGATG TCATCCATTG    72000
CTTCTGTTTC CTGGAGGCCT GGGAGCAAGG AGCCCAGGAA CAGTATCACG AAGCTTGAGA    72060
TAATACCAGT TACATTATCC TGACTGCCCA AAAGGCAGTT TTTTTGTTTT TTTTTTTTAT    72120
ACTTTAAGTT CTGGGGTACA TGTGCAGAAC GTGCAGTTTT GTTACATAGG TATACGTGTG    72180
CCATGGTGGT TTGTTGCACC CATCAACCCG TCACCTATAT TAGGTATTTC TCCTAATGCT    72240
GTCCTTCCCC AACCCCTCCA TTCCCCATCA GGCCCCAGTG TGTGATGTTC CCCTCCCTGT    72300
GTCCATGTGT TCTCATTGTT CAACTGTCAC TTATGAGTGA GAATATATGG TGTTTGGTTT    72360
TTTGTTCTTG TGTTAGTTTG CTGAGAATGA TGGTTTCCAG CTTTATCCAT GTCCCTGCAA    72420
AGGACATGAA CTCATCCTTT TTTATGGCTG CATAGTATTC TATGGTGTAT ATGTGCCACA    72480
TTTTCTTTAT CCAGTCTATC ATTGATGGGC ATTTGGGTTG GTTCCAAGTC TTTGCTATTG    72540
TGATTTTTTT TTTTTTTTTT TTTTTTTAA GACAGAGCCT CACTCTGTTG CCCAGGCTGG    72600
AGTGCGATGG CATGATCTCA GCTCACTGCA ACCTCCGCCT CTCAGGTTCA AGCAATTCTT    72660
CTGCCTCAGC CTCCCAAGTA GCTGGGACTA CAGGCGCCCA CCACCAGGCC CAGCTAATTT    72720
TTGTATTTTT AGTAGAGACA GGGTTTCACC ATGTTGGTCA GGCTGGTCTT GAACTCCAGA    72780
CCTCATGATC TGCCTGCCTT GGCCTCCCAA AGTGCTGAAA TTACAGGTGT GAGCCACCAT    72840
ACCTGGCCTA GGCAGTCTTT TTCAAAACTC TAAGACTGTG CTTGTGTCTC AGGGTGTCAG    72900
GATAATAGTG GTTAGTTTTA AGTGTTTAAA CTACTGAAAA GCAGAATGAA GAAGTGAGTA    72960
AAAATCACCC ATAATCACAC AACCTCCTAA GATCTCTTGG CACAATAAGG GATATGTTTT    73020
TCATTTTATT CTCTGTAAAA TAGGATACTT ATGAACCCAC CTCCCAACAC AGGAAGAATT    73080
AAAACATTCC CAATAACTTA CATTTACCTA TGCGTTTCCT CCCATCCCAT TCTCTACCTC    73140
CCCCCCATAA GTAATCATTA TCTGAAATGT GTTTCATCAT TCCATCTTTT CTTAGTTTTT    73200
CTTACATGTG TTTATCTAAA CAGTATACAG TAGTCTCCCC TTATTGTAGT TGTACTTTTC    73260
TTGGTTTCAT TTAACCCGAG GTCTGAAAGT AGATGAGTAT AGTACAGTAA TATATTTTGA    73320
GAGAGAGGGA GACCACATTC ACATAACTTT CATTACAGCA TATTGTTATA ATTGTTGTAT    73380
TTTATTATTA GTTTTAATCT TACTATGCCT AATTATAAAA CTTGATCATA GGTATGTAGT    73440
TATAGGAAAA AGCATAATAT ATAAAATGTT TAGTTACTAT CCAAGGTTTT AGGCATCCAC    73500
TGGGGTCTTG GAAGGTATCC CTCTCAGATA ATGGGGGATG GATGGTACTG AACCCTGTAT    73560
ATACAATGTT TTTCCCTATA CATACATAAT TATGATCAAG TTTAATTAAG AGTAAATTAA    73620
ATGTGGGCCA GGTGCAGTGG CTCACATCTG TAATCCCAGC ACTTTAGGAA GCTGAAGCGG    73680
GCAGATCTCA TGAGGTCAAG AGTTCGAGAC CAGCCTGGCC AACATGGTGA AACCCCATCT    73740
```

FIG. 6.28

CTACTAAAAA ATACAAAAAT TGGCTGGCTA TGGTGGCACA CGCCTGTAGT CACAGCTACT    73800
CTGGGAGGTT GAGGCAGGAG AATTGCTTGA ACCCAGGAGG TGGAAGTTGA ACAATCACTT    73860
GAACCTGGGA TCACGCCACT GCACTCCAAC CTGCCTGGGT GATAGAATGA GACTCTGTCT    73920
CAAAAAAAAA AAAAAAAAAA AAAAAGTAAA GTAAATGTGG CTCAACATGT TGCTGTCAGT    73980
TGGAACATTT GTTTCTGATC GTGTCTTCCA CCCACAAATT GAATGCTTTT TCCATCTTAA    74040
CACTTATCAG GCACTGTGGC CATAACTTGA GCAGTTGAGA TGCAACAGCA AAATTAGCAC    74100
AAATTTCTTT TTCTTTCTTC GCAGTTTCAT GGATAAGAGA TTTGTTCTTA GATCTCAGCA    74160
ACCTCAGCAT ATGATTTTTT TCTTTAAGTT GAGAACTTTG ACCTTTTTAC TTAGAGAAGC    74220
ATTTTACAGC TTCTCTTTGG CATATCTGAA TTGCCAGCAT TACTATGCTC GTGCTTTGGG    74280
GCCATTATTA AGTCAAATAA GGGTTGCTTG AACACAAGCA CTGCAATACC ATGGCAATAG    74340
ATCGCATCAC CAAGATGGCT GCTAAGTGAA CCACAGGCAG GAGTGTAGAC AGCATGGACA    74400
CATTAGACGA AGGGAAGATT CACGTTGCCA GTGGAACACA GCAGGACAGC AAGAGAGTTC    74460
ATGATGCTAC TCAGAATGGC ATGAAATTTA AAGCTTATAA ATTGTTTCTG GAATTTTCCG    74520
CTTAATATTT TCAGACCACG GTTGAGTTCA GGTAACTGAA ACCATAGGAA GCAAAACACG    74580
GATGAAGAGG GACCACTTCG TATTGCCTAA TTTAGTTTGT TTTGATCTTC TGGGACCTTT    74640
TTTTCTTGTT GTAAAAATTT ATGGGGCTGT TTATAGTTGT GGCTCATTGA TTTTTCATTG    74700
CTACATAATA CTTCCATTTT GTAAATATAA CAGAATATTC ATCTACCTGT CAGTGGACAG    74760
TGGGGTTTTT TTGCCATTAT AAATGCTGCT GCTGTGACCA TTTGGGGGGC AAGTCTCCTG    74820
GGGCACAGTA TGAGTTTCCC TTCTGTATAA CAAAGGAATG GAAAATTATA GACTTTCGTG    74880
TCCAAATTTA CAAGATAATG ACAATTGTTT TCCAAAGTGG TTGTACCAAG CAATTCTCCC    74940
ATTAATAGTG TATATAAGAG GTCTTCCTGA TCCATATATT CTTCTTGGTT TATTTTCACA    75000
CTTTTGAGAT TTTTGCTATT TGAGTGGTAT AAAATGGTCT GTGATCTTGA TTTGCCGTTT    75060
CCACATTTTG AAGAGGTTGT CGGCTCTATG TGTATATATT GCTCATATTT GTTCCCTCTT    75120
CTGTGAAATG CCTTTTGTAT CTTATCCCTA TTTGTTCTGT TCTGTTGATT GTCACGTTTT    75180
AATTGATTTG TATGAGTTTG TTCCTTGTAT CATTGTTGCT AGAGTTACAT CAGATGTGTT    75240
GCTGAATCTG CTCCCAGTTT GCAGCTTGTG TTTTTACTTT TTAAAAACTG TCTTGATTTA    75300
TAGGGAAGTC TTTATCTTTT CATTTGGAGC TAGTAATGTT TGTGGCTTTT TAAAGAAATT    75360
ATTACTATTC CCAAGGTCAG AAAATCATTC ACCTATATTT TAACTGAAAA GTTATAAAGT    75420
TTTGCTTTTG ACATTGAAAT TTCTCATTCA GTTGGAATTC ATATTGATGT GTGGTATGAG    75480
GTAAGGATCC ATTTTTTTCC CATTTGCATA GCCAGTTTTT GTAGCTCCAC TTTATTTTCT    75540
CACTTGATCT GCCATGCCAC CTCTAGCATG TATCAACATA TCATGTATGT GTGCAGCTGT    75600
TCCTTAACTC TCAATTTTAT TCTCTTGGTT ACTTTGTCTA ACCCAGCACT CATACTTTTT    75660
AAATTATTAT GGCTACCTTG TAGGGCAAGA ATCCTCACTT TTATTCAACT TCTTTTGAAG    75720
TGTCTTGATG CATATTTTTT CTGATCTTAC TTGGCCATAT ATATTTTGGG GACAGATGTG    75780
ACATCATACC AAGCTTTCTT TGCTTGACAT TGTAGATATT TTCTTATTCA TTAATGTGCT    75840
AAAAATTTTG AGTTTGGTCA TACAGTCTTT TATATGGATC TTATACATCG TTTCCCTCTT    75900
GTTAACCATT CAGGCTGTTA CTAGTTTTTG CTGTTGTGAA TTAACACCAG GACAAATATC    75960
CATATATCTT TTGAATTAAT TACTGACTAG TTTCCTAGGA AAGATATTAG AATATGAATA    76020
TTAAAGGTCT TGCTGAATAC AGTTTCAGA ATGGTTGTAC CAATATATAA TTCCATTTTC     76080
ATTATGTAGA AAAAATACCT CAGTGTTTTC TAACCACCTT TGGTTAGAAC ATTCAAGACG    76140
TTATGGTTTT GTTAGGTAAG AAATATTTTG TTTCAGTGTA GGTTTTCTTT GAGACTGAAC    76200
TTTTTTGTGT GTGTCAGTCA TTTACAGTTT TTTGCAATTT TTAAAATTCA GTTTCTCACA    76260
AGCATTTTGC CTTTGACTTT TCTTCTATTT CTGCTTTCTC TAATTACAGA AACCCCAGTG    76320
TTAAGTAGGT GACAGTTCAG TTGTTTGCTG CAGAAGAGCA GCAGTTCAAT ATTGGAATTA    76380

FIG. 6.29

ACTTTAATTT TATGTTTTTA ATCTGTTACT AATTTTTTAC AGAATAATTG TAGTTTTTAT 76440
AATCTGGTTA ATTATATGTT TGAGCTGCAT TACTTTGCAA TGTAAGTTTT TTTTTTTGGC 76500
ATGGTCAAAT AACAAAAATT CTGGTTAATG CTTATTTCAT ATTACAGGAG AATCCAGATA 76560
TTTCATTAGG GAAACATATA AGCAGAGTGT GATCAGGCTG TATGAATTAT TTATAAGAGA 76620
TGTGAGTGAA AAGATCTATT TGTAGCTTAA GAGTAAGTAG AGTCAGATGC ATGTAGAGTC 76680
TTTTATTCAA AATAATTTTC TTATTAATCT TGGATAGTTT CTTGTCACAG TAATTCCATT 76740
TTGAAGATAA TAAATATTAC CATAAAGAAG TGATCAAAAA CATAGATATG TGTGCCCAAA 76800
GGTATTTATC ACAATAGTAT TTATAATAGT GAAAAAAGAA ACAACTAAAA TGTCTGGCAA 76860
TAGGAGAATG ATTAATAAAG CGATGTTTCA GCTGAATATA GTGGCATGCG CCTGTAAGCC 76920
CAGCTACTCA GGAGGTTGAG GCTGCAAGAT GGCTTGAGCC CAGGAGTTAA TGACCAGCCC 76980
AGGCAACATA GCAAGACCCT GTCTCCAAAC ACACAAACAC ACACACAAGT GCTATGTTTC 77040
AGTCACTGTA TAATAACTAG CCAGATTTTT TGTTGTTGTT GTTTTGTTTT TGTTTTTGTT 77100
TTTTGAGAGA GCATCTCACT TGCCCAGGCT GGAGTGCAGT AGTACAATCA CAGCTCACTG 77160
CAGCTTGTAG AACCCTAACC CTCCTGGGCT CAAATGATCC TCCCACCTCA GCCTCCTGAG 77220
TAGCTGGGAC TACGGGTGGG TACCACCATA CCCAGCTTTT TTTCTAAGAG ATAGGGGTTT 77280
CACTATGTTG CCCAGGCTGG TCAGTTTTTA ATGAAGCACA TTTGTGTAGA CAAAGCAGGA 77340
TGTGGAACCG GATAAACACT ATGTTGCCAC TGAAGACCCC TTCAAACCCC TCAAAAATGA 77400
CATAGAAGGG AAATATGAGA TATTAGTTTG GAAATAATT GTAACTTTAT TAAGACTCCT 77460
TATAAATTTA TCTGTTCCTA TGACCTGGCT AAGTTCAATA AAAGTTACAC AGAGTGGAAT 77520
AAATGGTTAG ACATCATTTG TAGTATAAGT AATTGCACAT AAGGAGGTAA CTTTAGCTGT 77580
TTTAGAGATA GACATAGTAT CTGAAAGGTT AGTTATTTTA CTAGACCTGT GATTATTTGG 77640
GTGAGAAAGG CTTTCACTGA GATTTTACCC ATTCAGTAAG TACTAATGAT ATTGTGCTGA 77700
TAGCATATAT TAAGGGAATA TATGGTATAC CACAGAGAAA GAATTAAGGA AATTTTGTGT 77760
TTTGCTTTTT GTCTGTTTGC AAAACTTACT GACTCAGCTT TCATTCTTGG GAATGTGTCA 77820
GTTTTCTGTG GAAGATATA CATTGATGAG GAATTGATAA TGTTCTCTGT ATTTTCTTAG 77880
ATGGAGATTG TAAAAAACTT ACCTCAGAAA TATTTGCAGA GATAGAGACC TGTCTGAATG 77940
AAGTTAGAGA TGAAATTTTT ATTAGCCTTC AGCCCCAGCT TAGATGCACA TTAGGTAAGT 78000
AATTGGTAAA ACTTACTTGT ATTATACTCA TCTACCATAT AGAAATATGT ACCTCATAAG 78060
GAAATATAAT ACTGTTTGAT TACCTTGGAT GATCATATTC TTGGGAGAGA GAATCTGAGT 78120
AGTTTGACTT AGGAATCTAC CACTGGGTAA GTTATTGTAG GGCAGAGCTG TTCCATATAA 78180
ATATGTAGGC TGGTGTTCCA CCTCTTGAGA GTGGGTGCAG TTCTCAGAAC CAGGAGAATT 78240
TTAGGGGGCA TATCATTAGT TGCTTCTCTA GTACGTTTCC TAGTAGACAG ATCTAGCATT 78300
TTTAACCTCA ATTGTGCATT AAAAAGCACC GAGGGAATTT AAAAGTAAAT GCCAATGCTG 78360
GGGCATTTGA ATTAGGATCT CAGGGATGGG GCTCAGGAAA TCAGTAATTT TTAGAAACCC 78420
CACATGATTG TTATATGTAC CCAGGGTTTA GAATCTCATC TAAACCAACC ATAGTAATTC 78480
TACTTCCCTA CCAGTGATTG GTTTAGGAAT GTCCTTGTGG TAGAGTTTTG GCCAGTGGAT 78540
ATTAAGAGAA ATATGCTGAT GGCCTTTTGG GAAAGCTTCC TCGCCTTTAG AAAGGGCACA 78600
AGGATGGGAC CTCTTTGTTC TCTGTGACTT GGTTTTTGGC CTGTGGGAGT GGCGTGCAGC 78660
AAGTGAGCTA GAGAGTCTGT CCAAACCTTT CTAAATTTTT TTAGTATTGC GAAAGGAGC 78720
TGCGGGGTTT TTTTGTTTGT TTTTGTTTTG AAAGGGCTTT TGTTTTATT TTTCTTGTAT 78780
CCTTGTATTA ACTCTTCTAT TAATGTTATA GTAGCAGAAT ATGATACTCC CTATTAGTAA 78840
TAACCCATAT TATGTAAAAT ATCAGTGCCT TCTAGTTTTT CTCTCAATGA GTGACATTTA 78900
ACTTATATTA AAAAATGATA TTTATATTTT ATAATAAAAT CAGTTGTTGC TACTGATTTG 78960
TCTAGCATGT ACAAAAGACA CCATGCTTCC AGATCATTAT AAAATATGAT ATTTTATAAT 79020

FIG. 6.30

```
ATATTTACAA TATATTTATA ACATATTTAT ATACTTAGAA TATATTTTAT AAGGCTGGGC   79080
TTGGTGGCTC ATGCTTGTAA TCCCAGCACT TTGGGAGGCC AAGGCAGGCG TATCACAAGG   79140
TCAAGAGATT GAGACCATCC TGGCCAACAT GGTGAAACCC TGTCTCTACT AAAAATACAA   79200
AAATTAGCCG GGCGTGGTAG TGTGTGCCTG TAGTTCCAGC TACTCGGGAG GCTGAGGCAG   79260
GAGAATCGCT TGAACTTGGG AGACAGAGGT TGCAGTGAGC TGAGATCACG CCATTGCATT   79320
CCAGCCTGGG GACAGAGCGA GACTCCGTCT CAAAAAATGT ATATATATAT ATATATATAT   79380
ATGTGTGTAT GTGTGTGTAT GTGCGTGTGT ATATATATAT ATCGGGAAGC ATGGCATCTT   79440
TTGTACATGC TGGACAGCTT TTGACGTACT TCTTTGACTC ATGCTTCTGC CCCCTAATTT   79500
TCACTTTTTT TCCTACATTT TATTAAAATT AATATATAAT AGTTGTATAT CTGCTTTATT   79560
TTTCATGGAC TTATACATAC ATATTTATTC TGTTCTTATA AAAGTCTGAT TTTTCGTATG   79620
CCAAATTTCT GACATTTCCT CCTCTAGGCC TGAAGAACTG TTGTAATTTA TGCATCAGAT   79680
AGGCCCTCAG ATGGAATGAA TATTCTTTTT TCTTTATATC AAGGTGTAAT TTACATATAG   79740
TAAGACCGTT TTTAAGTGTG TACAGCTCTG TAACCCTCAC TACAATCAAG ATATAGGACT   79800
CTGTCACTCT AAAACTTCTC ACCAGGTTCA TCACCCCAG CCACTGATCT GTTGAGCGAA   79860
TACTCATTTC AAAGGAGCTT TTTCCGTAAG ATCCCTAGAG TTTAGATGGA AGGGCTTTCG   79920
TGGTGCATTT AGCAGATACC ATTTCCCTTC TAGACTCCCT ACTTCAGTTC CCAGTTGAAT   79980
TAAAGAATGG TTTCTCCCCC AGCCTGAGTC ACTACCCTTC TTATCCCTGA TAATTATTTT   80040
TGGAACAAAG TTACATCTTT TGCTCCACCT CCGCCATGGG CCTGGTTTTC TATGTAACAG   80100
AAGGAATTTT TAAATTATTG TTTTGTGTAA TCATAATAAT TGGGCAAGCA TACAGCTCTT   80160
TTCAGTGCAG GAGGATTCCT CTCTTGTTTT ACTGCCCATT CAAGGATAGG TGCTATATTT   80220
TAGCTGAAGA TCTTACTAAT GAAATGCTCT GTAATCATAT AACTTATTTA AAGATGTGTT   80280
TTGAGCTCTT TCATAATATT TTAATTCATG GAGAACTTTA TGTATTTTAG ACCTGAAGAT   80340
TTTATATTGT CATTATGAAA TGTAAATTGT TTGCTTTTTC AGTTAATATA TAGTTACAAT   80400
AGAATACGGA TTTAAAGGCT GATAATGAAT TACAAAATTG TGCTATATGA CATACTGTTT   80460
ATGCATACAG TGTTGCATAT TTTCATTTCT AGGATATTGA TTTGTATTTC TACTTACAAA   80520
AAAACTTTTT AAAACTTATT TTATGGCTGG GCCCGGTGGC TCACACCTGT AATCCCAGCA   80580
CTTTGGGAGG CCGAGGCGGG TGGATCACCT GAGGTCAGGA GTTCAAGATC AGCCTGGCCA   80640
ACATGGTGAA ACCCTGTCTC TACTAAAAAT ACAAAAAATT AGCCGGACGT GGTGTAGGTG   80700
CCTGTAATCC CAGCTACTCG GGAGGCTGAG GCAGGAAAAT TGCTTGAAAC CAGGAGGCAG   80760
TGGTTGCAGC GAGCAGAGAT TGCGCCATTG CACTCCAACC TGAGCAACAA GTGCGAAACT   80820
CCTTCTCAAA AAGAAACAAA AAAACTTTTT TTAATGTTTT TGTTCAAAAG TAGCAGTGAG   80880
ACTATCCCGC AAAGGTGACT ACTAAAATAG CCTTTGTAAC TACTGATATT TATAGAATAT-  80940
GCTTAGGGTT AGGGTATAAC TCGCTTGTAT TATACTCATC TACCATGTAG AAATATGTAC   81000
ATCATAAGGA AATATAATAC TGTTTGATTA CCTTGGATGA TCATATTCTT GGGAGAGAGA   81060
ATCTGAGTAG TTTGACTTAG GAATCTACCA CTGGGTAAGT TATTGTAGGG CAGAGCTGTT   81120
CCATATAAAT ATGTAGGCTG GTGTTCCACC TCTTGAGAGT GGGTGCAGTT CTCAGAACCG   81180
GGAGAATATT TAGGGGACAT ATTGTTAGTT GCTTCTCTAG TACTTTTCCC AGTAGACAGA   81240
TCTAGCATTT TTAACCTCAA TTGTGCATTA AAAAGCACCG AGGGAATTTA AAAGTAAATA   81300
CCAATCATAG GGACATTTGA ATTAGGATCT CAGGGAAGGG GCTCAGGAAA TCAGTAATTT   81360
TTAGAAACCC CACATGATTG TTATTGCTTA GGTAATAACA CCTACTGTCT ACCTTGTGGT   81420
CCTGCCAAGG TGACTGTTCC TGGCCATGTT CCAGGCAACT GTAGTTCCAG GCTAGGGGA   81480
GAACTGGACC ATGGAAGTGA GGCTCTGTCC AGGGTAGGGG AAGGGATGGA AGGTGACTGT   81540
TCCTGGCCAT GTTCCAGGCA ACTGTAGTTC CAGGCTAGGG GGAGAACTGG ACCATGGAAG   81600
TGAGGCTCTG TGCAGGGTAG GGGAAGGGAT GGAAGGACTC AGTCTCTTGG GCCAAATCGG   81660
```

FIG. 6.31

```
TAAGGCAGCA TCTAAGCTCC TCTGAGAATA GGAAGGAGAG CAACCAATTG GAAAAAGAAT    81720
GGGAAACATG TAGATTCTCC TGCTTACCTT ACTTTCCAGT CTCAAAGCTG GAAGCCAGCA    81780
TTCACTGTTC AGTTATTTTC AATGACAACA AGATTCAAAT CTTCAGTTGT AAAGTTGTTA    81840
AAGGAAAGGA TTAGACTGAA AAGTTAAGAA GAACGGTAGA TGAAGAGTCC AAAGAGTTGA    81900
GGCTGGTCAT TTAACCATTG TGTGGCCACG CCCTCTCCAC AGGTGGAACA AGATGATCAG    81960
AATAGAAATG GCCAATTCTG ATGTGTTTCT ACAGTGTTTC ACTGATTACA TTTTTTAACA    82020
TCTGTAGCAA ACCATTTCCA TAATTTTTTT TTTTTTTTTT AGAGACGAGG TCTCGCTCTG    82080
TCACCCAGGC TGGTATGCAG CGGCATGATC ATAGCTCACT GCAGCCTCAA ATTCCTGGGC    82140
TCAAATGAGC CTCCTGCCTT AGCCTCCTAA GTAGCTTGGA CTACAGGTGT GTAGCACCAC    82200
TCTCAGCTAA TTTATTTCAT TTTATTTTTT GTAGAGATAA TGCCTCGCTA TATTGGCCAG    82260
GATGGTCTCA AACGTTCATA GAAACTGGTT TTAGGTTCCT AGAGGCTGGC AGCAATTCTC    82320
AGAGGTAACG CAAGCAGTCT TCCTGCCTTG GCCTCCCAGT GTGCTGGGAT TACAAGGTGT    82380
GAGCCACCAC ACCTCATCAA TTTTTGTTTT AATATACTCT AAGGCTTATC ATAGTTCCGA    82440
GATCTTTTTT TTTTTCCTGA GAAATCTAGA AAGATGGAAG ACAGTATGGG TCTTTTGTGG    82500
ATTTTTTGTC CTAAGAAATT TTCATAAATG TCTGCCAAGG AAAAGGAAAG AGATCAAAGT    82560
GGTAATTAAA TCTTTAGGAT GGACATTTTT AGAAAAATGC TTTATAAACT TCCCCTCTCC    82620
CAACTCTGAG TGACTTATTG TGTCATACTG TATTAACACA TATTCATGCT GTAAATATAG    82680
TAAGAAAAGA CAATAGTTCA CAATTTTGGT TTAGTTTTTG CCATTATTGA TTATGAGCAG    82740
TAATTCTTCC TTTTCTTTTT GAAGGTGATA TGGAAAGCCC TGTGTTTGCA TTTCCCCTGC    82800
TCTTAAAACT AGAAACCCAC ATTGAAAAGC TCTTCCTATA TTCTTTTTCT TGGGACTTTG    82860
AATGTTCGCA GTGTGGACAC CAATATCAAA ACAGGTTAGT TTCTTTTGTT TTTTAAAATG    82920
GGTTCTTCTA GTTTCTCCAC CACTAAGGTT AAGAGAACAA TTTGAGCACC AGACACTACA    82980
GTTTGCTTGC TTCTTTAAAC TGGAAGGGTC AAAACCTCAT CGTTTGATAG ACTGCTAGTA    83040
GGATATTTCC TAAGGAGTTC TTCAGTGGGA AATAGGGACG ATGAGAGGAA TAATACACCT    83100
CCCTTCTCCA GAGTCCTTGC TGAGTAGAAT ACCTCTCAGA ATGCCATGAA ACTGTAGGCA    83160
TTTTTGTTTA TTCCTCTATT AGAAATGAGG GGTTTTGCTT GTTTACTTTA GGTTTCTAAC    83220
ATTATAGACA CTAGTTTTAG GCTCTTGGAG GCTAGCAGCA ATTCTCAGAG GTAATGCAAG    83280
CTTCCCCATT TCTTCCCGTA GTCCTGTGAA AGACCAGCCA CCTCCAGAAG CCTACACATG    83340
AGTCTTCTCA GCCATACTTT CTGCTTTTCC TAATGCCTCT CAGCAGCGTA TTAGAAAGGC    83400
CATGATCGAT GTACCTGTTA CCTTCAGGCT TTGCATAAGG TGTATATGAA ACATAATGAA    83460
TTTCGTGTTT AGGCTCAGGT CCCATCCCCA GGTTACCTCT TTATCTTGGA GACACTTCTG    83520
GTCCCATACA TTTCAGATAA GAGATATTCA ACCTGTACCC ACCACGTAAG GAGAGGAATA    83580
GGTTTTAGAA GAGGAGTCAG GGAGGCAAGG TATTCCCAGA GGGATATTCT CACTTGGTCC    83640
ATACCTGAGA AAGTTGCTGG CTGGCAGTTA GGAAGATGAC CAGACTGGCT CAATTGTTCG    83700
TGTATTCAAA TTATTACAAT AGAAATAACT CTTTCCACCC CCCCCCGCCC TTTTTTTTTT    83760
TTTGAGTTGG AGTCTCGCTC CCGTCACACA GGCTGGAGTG CAGCAGCGTG ATCCCGGCTC    83820
ACTGCAGCCT CCACCTCCTG GGTTAAAGCG ATTCTCCTTC CTCAGCTTCC TGAGTAGCTG    83880
GGATTACAGG TGTGTGCCAC CACGCCCGGC TGATTTTTGT ATTTTTAGTA GAGACAGGGT    83940
TTTGCCATGT TGGCCAGGCT GGTCTTGAAC TCCTGACCTC AGGTGATCCA GCCACCTGAG    84000
CCTCCCACAG TGCTGGGATT ACAGGTGTGA GCCACCATGC CTAGCCACAC TTTTCTTTAG    84060
CTTAAGTGCT TAAGTTAGAA AACTTGAAGT CTCTCTAAGT TACTCAAGTA AAATGTGAGA    84120
TAAAAATATT ACTTTGAAAG GCCGGGCACA GTGGCTCACA TCTGTAATCC CAGCACTTTG    84180
GTAGGCCGAG GCGGGTGGAT CACGAGGTCA GGAGTTTGAG ACCAGCCTGG CCAACATGGT    84240
GAAACGCTGT CTCTACTGAA AATACAAAAA TTAGCCGGGC ATGATGGCGG ACACCTGTAG    84300
```

FIG. 6.32

```
TCCCAGCTAC TCGGGAGGCT GAGGCAGGAG AATAACTTGA AACCCGAAGG TGGAGGTTGC    84360
AGTGAGCTGA GATTGCACCA CTGCACTCCA GCCTGGTCAA CAAGAATGAC ACTCCGTCTC    84420
AAAAAAAATT AAAAAAAATT ACTTAGATAT TCATTATCTA AATATGAAAT CCTTTTTAGG    84480
TATTTAAGGA GTAGTCAAGG AGAGTTCAGT CTGGGAGGAT GCTCCAGGGA ATGCAGGCAA    84540
CAAAGGTTTT GTTTTTTTTT TAACTGGTTA ACTCAGATCT ACTAGAACAG GGTAAGGGAG    84600
GCCACAGAGT AGACACCATG AGCAAAGCTA ACCTCCTGA GTTGAAAAAA TTATGGACGA    84660
GAAGTTATCA TTGAAATTAA CTGTTGGCAG ACATATCCAA AGAATATCGC AAGGATTTGG    84720
TCCCTTTATG CATCCTGAGA CAGATGAATG TGTGGAATGG CAGCTGGTGG GCAACAGAGC    84780
GATATTGGCA TGGTGGTGAT ACAGGGAAAT AGTTTCATCG TGTTAAAAGC CATGGAACAA    84840
AGATACATAA TGGCTGCTCT GCAGAAAAAT CCACGTCCCC TCTCCAAAGG GCCTGTTTTA    84900
CTCTGATGTA AAAATTGGGT CAGATAAATT TTCATATTAA GCTTTTTGTT GAGTAAACTT    84960
TTGTAATAGT CCCCAAAACT CCCACTAGAA CAGGGTGAGA ATTAACGTTT TATTCATACC    85020
TAGGACTTAA ATAATTTAGT GTAAGCAAGT GAGTATGAGA ACACATCTGT TTCCAGTCTT    85080
CTATCATTGC TTTATATAAA TTCTCTGGTT TTCTCCTCAC AGTAACTCAG TGAGGAAGAT    85140
CCTAGTGTCC TCATTTGGCA CGTATGGATA TGACAGCTTG AAAGGGGTTA GATTGATTCC    85200
CAAGATGACA CACTGTAAGT GGCAGAGTCA GGAGACACAC TTAGGCTCTT CTGGCCTCTA    85260
AGACTTTCTT GCTCACTGTG GTATACTCCT TAATCACTAC CTGGGTTTTA AATAATATAA    85320
ATAACCTTGC TGATTAAAAT CAGCTTAATT GTAGCTTCTC TGGAATCCAT ATCTTAGTTG    85380
TTTGACAGTT TTCGGTTGAG TGTCTTCTGT GTGTTAGGAA CTCAGGCACT GGAAATAGTG    85440
TATCTTTGCC AAATTTACTA ATTAGGTAGA GAGATAATAC ACGAACACAT AATAGAGGTC    85500
CAGTGACTTC GTAATTAATC TGATCTTTGG GCTGCTTAAC GTTAGCTTTG AATGCAAGAT    85560
GTTAAATGCG TTTTAGAGAT ATATAGCACA AACTGTGAGA GCTCAAGGGA GGGAAGCCAC    85620
TAGCCGCTTT TGTTTGCTTT TTTGTTTTTT AAAAATAATC TTACTTTGTT CTAAAAATAA    85680
AAGTAGTTAT AGAGGGAAAG CTAAAATGAA GTGACGTTTT CTTAAATATG TTTTAATATG    85740
TCATAACTTA AAACTTATTT CCACTTAATC TGAAGGAGAA CTGTCCAGCA AATTCCTTTG    85800
TTTTTGTGAA GCTGTTTTTA GTGCCAGCAT AAGGGCTTTT TACTCAACTT GGAAAGTGTA    85860
ACCCAGAGTC AGTTAAAAAC ATAGTCTTCA GAGGCAGATC TCAGGTCTGT TATTTATCAC    85920
TGTACTCTAT GTGTCACTTT CCCCATCTGT AAAATGGGGA TAAGAATAGC ACCTGCCTCT    85980
GAGAGTTGTT TGGAAGATGA GTGTCCAGTG CCATGCCCTT TGCACATAGT TTAAGTGTTC    86040
AGAAATGTCA GATGTCATGT GGAGAATTAA CACTTACTTG CTGAGACAGT CTCCTTTTTA    86100
TAAACTAAAC AGTAGGAGCC TTTACATAAC AATTATCTTT GAAAATTTAA GAATTTAGCA    86160
GAAATCAGTG CATTTGTTGA TATCTTTATG TTGCTTTGCT TTTAAAATGT TAACCTCCCT    86220
GACTACTGAT GTTTTTAACA GACAGTGCTT CCTCACAAGA TTTATAAGTA TTTGCTATTG    86280
TTTAGAAAGG AAGCTTGTAT CTCTTAAGTA GCTGCTCTTT AAATTACAAA TATTTTTATT    86340
AAAGTGGATG CAGTTGAGGT TTAGTGTACA TCTTTAAAGG TCATCTTTTT AGATGGCGTT    86400
GCTCTCAAGT ATTCAGACTA AAGTGCAAAT TTAGAACTTG TGTAACCTGT GAAAACAAAA    86460
TTTGTTCACA ATTAATGCTG TGTGTGTGTG TGTTTTTTTT TTAAGGATTA AAAAAAGTTA    86520
AGTTGTATGT ATTCCTGATT TTATGTTTGG AAACATCCCC TTTTCATTTT TGGTTGTCTG    86580
TAATGGCTAG CCAGTTTGAG TTATTTGAGT AAGGGGTGAG CTCTTAATAA ATTTGACAAC    86640
CTTAGAACAG TGGTTCTTCA CTAAGGGCTA TTTTTTCCCC CTTGGGACAT TTGGCAACAT    86700
CTACAGACAA CTGGATGCCG TTACTGGCAT CTGGTGAGGA GAGGCCAGGG ATGATGCTTA    86760
ACATCCTACA GTGCACAGGA CAGTGCTTCA CAGCAAAGAC TCTCTGGTGA AAAATGCAGT    86820
GATACCATTG AGGAACCCTG TCTTTTTTTC TTGCTTCATC TCATAGTTGA AAGATATGGG    86880
AAATTAACAT GGAGCATCTT CACAGAGCTT CTTTACTAGA GGTAGGGAGG AACATTGCCA    86940
```

FIG. 6.33

```
TATTAACATG ATTTGGGGAA ATAAGAAAGT ATGAATCACG AAAAAGGGGA GGAATACTTT    87000
TAGACATTGG TTTAAATTAA TGTAAATGCA TTTAACGTTA ATGAATTTGT TATGTCATTT    87060
TTTTATAGGC ATATGAAGAG TCTGGTCACC TTTACAAATG TCATCCCTGA GTGGCACCCA    87120
CTTAATGCTG CCCATTTTGG TCCATGTAAC AATTGCAACA GTAAATCACA AATAAGAAAA    87180
ATGGTATTAG AAAAGTGAGT TAAAATTGTC TTATAATTTT TAGTACAAAA TGAAGGTGGA    87240
TTTACATTTT TCTTAATGTG TAGGATTGAA AATGGTGACA ACAACTTACC TTTCTGAAAT    87300
TTGAGTTAAC ATATATTTCT GGGTTGCCAG CTGCCTCGCT CTATCTGGCC AGTGAGCCCA    87360
CTGTCACGGT GAAGCCACTG AAAAGCCAAC TTAGGCTGAC TCTCTGGCCC CACTCTCCTA    87420
GTGTCTTTCC TTCTTTTTGC CTTTTTTCTC CCTTTAAGGA TATCAAGCTT CAGTTTTTCT    87480
CTCCTCTGCC AAGTGTATGG AGTTTCTAGA ATTCTGGGAT TTCCTTAATC AGATTTCAAG    87540
AACTAAGATG ATTCAAAGAT AAGCCACAGG CTCATCTCTC TGAATTTCCA TCTTCTCCTA    87600
GATCTCAGCA TGCTAATTCC TCATCATCTT GAAAGCTATC TAGTGGCCTT GAGCAGATAT    87660
ATTTTCATTG TATTTTGCCA GCTTTCTGT TTGTCCTCAG TTGGGGAGGT TGGTCAGCAT    87720
TACCTTTTCC AGTATTACCA GAGAACCATC TGTTTAAACT CACAGGTCAG TTCCATCTCA    87780
GGCCGTTTCC CTCTGTCTCA TTAATGCACT CACACATGTA CACAACCTCT CTACTCTTCA    87840
TTTTCAGTCT AATCGTACAT TAAGGAAATG TTTTGAGGTC TAATTTGATG TAATAAAGAA    87900
CCGGGAACAT TAACCTTTAT GCCCTTGAAT GTGCCAGAAA CCCTTCAGAA TCTTTCCTAA    87960
AGGTTTATTC TCATTGAAGT AATAAATCCT CAGTTTATCA GTGCTTACAG GCTCAAAAGG    88020
GAAAAGGGC AGTAGTCCCC TGTTCCCTCC TCCAGGTATC TACTTTAAAC CTTCAAATTA    88080
AGGTAGTATT TACTTTTACT TTTCAAATTG ATGTGCCTAT TCTACCGTAA TGCAGTCTGT    88140
TCTCCTTTTA TAGTAATTGA GACTAGGGTT CTCACACCAA CACCTGGGCC CCATCTCTGT    88200
TTAGCCTTTC CCTGTCCTTT CAATGCAATT GCGTATTTGG CTAACTCAGT ACTCGGTGTT    88260
TGCATTGTTA TTAATATACA TGTGTTATTC CCTCTTCAGC CAAGCAGTAT ATATAGTTAG    88320
GTTTCACTTT TACAATTCTT ATTTTTCCGG GAATTGTTAT TTGCCTTGTT TTCATTTGTT    88380
TTATTATGTA CTGTGAGTTT TTGCCAAATA CTTTAAAGAC TTATTAATAA ATTTTCAATA    88440
CTCAGATGCT TCACAGTTTT TTACTCTGTT CCTCTCCCCT TTTTTTCCTG GAACTCTTTC    88500
CTGCCACCTT TCACTCTTTG CTGCAGTCTG CGCTGGTTCC TCTCTGGGCC TGCAGCATAG    88560
GGTGCTCTTT ATTATGTACA CACTTCCAGT CACTATCGTA GTTTTTAGCC CAAGGCCTCA    88620
TCCCCACATT CTATCACATC TGTTGCCCAT AAATATCCAG TCCTTTAGGG GTTCTCTGGG    88680
AAAAATAAGC TCTTCTTTGT CATCAACATA TGCACTCCGT AGTACTCATG TCTTCACTTT    88740
GCCCGTTCTG CTGGGTAAGG TGCCACTTCT CTGTTTGCTT TCTGTCCTCT AAATATTTGA    88800
CTTCTTATTT GCTTATTTTC CTTTCTTTGT CCTTTTGGAC TCATATCTTT TTTGCCCCTC    88860
ACTATTATTT GATAGCATTT GTGTAGGAGG GCGAAGTGGG AAGGAAGAGG AGGTGTCTGT    88920
ATCTGTCTGA AGATTACAGA AGTCTGTAAT CTGTCTTGGC TGCCAGGTGT CAGTTTTGAG    88980
ATGTAAATGT TGATGATGAG GTGAGGAGAA GAGCAGCAGA GCATGGGGTC TGCCATCCTG    89040
CCTTGGACCA TGGCCTGCTT TAGGCTGCTT GGTGTATATG ATTTCATCTA GCTGTTCATA    89100
CCTGCTTTTT CCTGTGCCCC AGCACTGAAC ATAGACTCGT ACCATTGTTT TGTGTAATCT    89160
GTTAATTGGT TGCACTGCAG CATATATATT TTTTAACTAT ACAAATAAGT TGCTTCCCTT    89220
AAAGATTCAT GCTCTGATCT GGAAATGGAT TCATTAGGTA AAAGTCTTTT AATGGAAAAT    89280
GTGTTTTGAG TTCCAGTGGG CCAATTTATG AGCAGAATTT ATAATGTGGG CATTTCCTGT    89340
TTTCTTCAAA AGTAAATTGA ACTAGTGTAT GAAGTTTCAC TTAAATTTTA AATGCCAAGG    89400
TCTTTATATA AGTCCTTTGT GTTTTTTTAA TTTTGAAATT TGTATAACTT GATTTGTTTG    89460
TGTCTAATGG AATTTAGAAA TAAATTTAAT ATAGTTTTTA GGGCTAACCT AAAAGTAATT    89520
GGGTTCATCA TGGTGTCATA TGTAATTAAA ACATATAGAA TCCTAAAAAC TAATTAAGTT    89580
```

FIG. 6.34

```
CCTTGGACAC CTTATCTCAC ATAACCCACA TCTCTAATGT CTCCCCATTG GGAAAAGAGT    89640
CCATTGATAA ATCAGGTGAA TTATGCCTAG CGGGCCCAAA TCTGCTACTT TTCTTTAAGT    89700
TGTTTAGGAG TTACATTCAG ACCATGGTGA CATGGAGCAC CAAGAACTTA GAATCAGATT    89760
TCATTTTACT TGACAAACTC TTGAAAGGTC ACTGCCACAG TCTCTCTTGA GTGCAAGGCT    89820
ATGGCTATGC TTTGTAGCAC AGGGACGCGA TATTTCTCTG CTATCTTTGG GTAGCAGAGG    89880
TTAACACAGC TCCCTTGTGC TTTCTTTCTC TCTTTTCTAT TTTCTTTTCT TTTCCTAAGG    89940
ATAGATCTTT AAATAGGAGG AGTTTAACCC CATGTTAGGT GAATTCAAAT GGATCTTAGC    90000
CTGATGTCTC TTGTTCTCTT TTGGTTCCAG TTTGGTTAAT TCCTTTCATC CAATTTTCCA    90060
GTGGTTGAGG GAGAACCTAA CTTGCTCTCC TCGACTCTGA GCATCATCCT TCACTGACAG    90120
TTCAGGCATT GTGGGTAGGA AGAAGTCTGA GAACAAAACC TAGGGATAAA GTTTAGTAGA    90180
GATGGGGTTT CACCATGTTG GCCAGGTTGG TCTCGAACTC CCGACCTCAG GTAATCCACC    90240
TGCCTTGGCC TCCCAAAGTG AGGCTGGAAA TAAGACATGC TGGAATTGTA AGTAGGACAC    90300
TAGAGTCTAG GGGAATCAAA GAGGAAAATG AACAGAAAAG GGAAGGGGAA GGATATTATT    90360
TGATTGACTC CAAGATGCTA CTGTTTGTAA GTTTTACCAT TTTAAAAATA TGCCATTAAG    90420
AAAGAAATGC TGGCCGGGCA TGGTGGCTTA TGCCTGTAGT CCCAGCACTT TGGGAGGCTG    90480
AAGCGGACAG ATCACCTGAG ACTAGGAATT TGAGACCATC CTGGCCAACG TGGTGAAACC    90540
GCATCTCTAC TAAAAATACA AAAATCAGCT GGATATGGTG GCACATGCCT ATTGTCCCAG    90600
CTACTCAGGA GGCTGAGACA TTAGTACTGC TTGAACTGGG GAGGCAAAGG TTTCAGTGAG    90660
CAGAGATTGT GCCACTGCAC TCCAGCCTGG GCAACAGAGT GAGACTGTCT CAAAAAAAAA    90720
AAAAAAAAGA AAGAAATGCT GCTTATTTAA CTGTGTTCTG TCAATGTTAA GGTGTATCCC    90780
GACTTCAGAG ATGTTAACAA ATGGGAAAAA ATTTGGAATT CATTAGGCAT TTGGAACTTA    90840
CAAAGTTTCG GCCGGGCATA GTGGCTCATG CCTGTAATCA CTTGGGAGG CCAAGGCGGG     90900
TGGATTACCT AAGGTCAGGA GTTCGAGACC AATCTGGCCA ACATGGTGAA ACCCCATCTC    90960
TACTAAAAAT ACAAAAATTA GCTGGGTGTG GTGGCATGCG CCTGTAGTCC CAGCTACTCA    91020
GGAGGCTAAG GCAGGAGAAT CGCTTGAACC CAGGGGGCGG AGGTTGCAGA GAGCTGAGAT    91080
CGTGCCCTGC ACTCCAACTT GGACAACAGA GTGAGACGCC ATCTCAAAAA CAAACAAACC    91140
AAAAAAAAAA AAAAAATTTC ATAGTTACAG AAAGTAGTAT GGAGGCCATA CCGAGATTTT    91200
CGACATGGTA GTAAAACTCT GCATTATGGC TCTGTTCTGC ATCATCTCTG TTCTGCATCG    91260
TTTCACTCCA CATCAGACCC TGGATAGCTT TGGTGTACTG GTCGATCTTG TGGCAGTAAG    91320
GCTAGTGTAA TTAAGAGGAT ATTTTAAAAC TTAACATATA ATTGCTCTAG TTGTTGTCTC    91380
TTTTTTGCTG GTTAAGAAAA TCAAATTTCT ATCCTATCTG AATCTCATAG CAGACTTTGG    91440
AGATTTCTGA CAAGTCATTT CTTACTACCT AGGGGAATGT ACTTGTACTC AGCTAGAGTC    91500
TGAGTATCTT CTACATCCAG GGAATTGGGC TGAGTGTGGA TTTTGGTCTT GGCAGTTTTT    91560
ACTTTTATTA ATTTGCAAAA GAATAGAAGA CTTGGAATGT ACAAGAAGCA TAAAAATGTG    91620
TCAGGTGGTT TTACATGCGT TATTTATCAC GTTAATATGT CTTAAGATAT TTTCCACGTG    91680
TAAACTTATG TAAAGGCAGG AAACTAGTGA GATTTCATAT TCTAGGGATC AAGAGATTGT    91740
TTTAGTAACT AGCCTCAGAA AGTATCTTGA AAGGTATTAT ATAAGGTCAA GGAACTAAAT    91800
ATTAGTAAAG AGTCAGGCCA GGCGTGGTGG CTTATGCCTG TAATCCCAGC ACTTTGGGAG    91860
GCCAAGGCAG GCAGATCACT TGAAGTCAGC AGTTCGAGAC CAGCCTGGCC AACATGGTGA    91920
AACCCTGTCT TTACTAAAAA TAGTAGTGTG TGGTATGGTG GCGCATGCCT GTAATCCAGC    91980
TCCTCAGGAG GCTGTGGTGG GAGAATCACT TGAGCCCAGG AGGCGGAGAT TGCAGTAAGC    92040
TGAGATTGCA CCACTGCACT CCAACCTGGG TGACAGAGCT AGTGTCTGTC TCAAAAAAAG    92100
AAAAAAAAAA AGGTCAGATA GGTGCCTAAA GCCTGTGTGT CTCGCTATGA GAATACATCT    92160
CAAGTTTTAC TGTGGTTCAT TGATTCAGAC ATGTAGTTCA CATTTTAACC TGTCTGAAAT    92220
```

FIG. 6.35

| | |
|---|---|
| GGTAATATGT GAAATTGATG TCATGATATA GTTTAATTGG CAGCATGTTT TCATAGTGGT | 92280 |
| ACATTTTATA ATTAGTGAAA TCTTAGATTT GATGAAATAG ATATGATTTT TTAAAGTGGG | 92340 |
| AAAGTTTAGT GTTATAGACA GTTTGCAGGA CTTTTTATTT TGTAGGTACT TAAATTTTGA | 92400 |
| GGACTTAATT ATTCTCTAAT AAAGTGATTG ACAAGGATTA ATGTATAAAT TATACCTTGT | 92460 |
| CAGTCTGAAC AATCTGCAGT TTGGACATTG ATTCAAATTC ATTTAGGCTG AATAAATTTT | 92520 |
| GATAAACTAA GTAAGTTTTG ACAGCTATTT AAATATTGGG AAAGGGGATA TTCAACATTT | 92580 |
| TTCTTACATC CTGAGAGCTT TGTTAAATTT AGTTATTTGA GACCCATTGG GTTCTATTTT | 92640 |
| CTGGTTCAGC ATGTTGCTGT AATGGTAAAA TACAATTTTG AAATTATAGT TGTCTTGAAG | 92700 |
| TTAATAATAA ATTGACCAAT ATGTTGTATT TTTTTCTCTA CTTAGTTACA AATTGAACTT | 92760 |
| TTCCTAAGTA GAACTTTTAA TTTGACAGGC CCCCTTTGCT TCCTGAGGTA ACTGAAATAG | 92820 |
| GCCAAATTAA TGCTTTTTTG AATATCTTAG GTTTGTTGCT TTCTTTCACA TGTTACCTAC | 92880 |
| CCCACTTAAC AAAAGCAATT AATCTCAGCA CTTGATGCCA AGAAAATTC TAAAAGGTCT | 92940 |
| GGATTTTTTC CTTGGATTTT ACAAAGTAGC TACAATGGGA CTTTTAAGAC AAAGCTGCAT | 93000 |
| TGCTGCTTAC AGAGCAATTT TTGTTTAATG GTCTGTGTTA GAGTCATACT GCATGATGAC | 93060 |
| TTCCAACTGT CTGGGATACC ATTCTGAAAA GGGTTTAGTG TTACATACTT CTTAGAGAGA | 93120 |
| GTTCTCCATT TCTAATTAAG GCACACATCT GGAGGTGCTC AAGAAAAATT AGTGCAGTTA | 93180 |
| GCCTTGGAAG TGTTATGTGT GACTAGTTCA CTTCAGACAT CTTTTGTATA ATCAGACACA | 93240 |
| TGGCATTAAA TTTATTTAAC TTCTCTTGCT TTTCTCTCCC ACAGAGTATC TCCCATATTC | 93300 |
| ATGTTGCACT TTGTAGAAGG CTTACCACAG AATGACTTGC AGCACTATGC ATTTCATTTT | 93360 |
| GAAGGCTGTC TTTATCAGAT AACTTCTGTA ATTCAGTATC GAGCAAATAA TCATTTTATA | 93420 |
| ACATGGATTT TAGATGCTGA TGGTAAGTGT TTAGAGGTTT TCTTTTAAGA TAATTGGCAT | 93480 |
| AGAAACTAAA TTCTAGCATG TGGGGACTTT TTGGTTTTTG TTTTATAAAA AAAGACAAAC | 93540 |
| TTTGTCCTGA CTCTTTCTCT CTCCATTCTC GCCTTTGCCT TCTGCCCCTC CTCGCATCTA | 93600 |
| TTAAAAGTGA TGGTTTTAGT ATCCTGTCTC ATTTTTTCCT TTCCTTACAT CATGTATTAT | 93660 |
| AGGTAAACAC ATGCGCATGT GTGTATTTCT CTTTTAGACA AAGGATGAGA TTACTACTGT | 93720 |
| TAGCTCAGTT TTTTTTTCCC TACTTAACAT CTTTGCTTTT ATTTTTTAGA CATATTTCTA | 93780 |
| AGACTATTAA ACATTAGACT TACGTAGCCC TTCTGTCATT GTGAAATACA TAGTTTACTA | 93840 |
| ACAGCTACCA TCAAGATAAA GCCTTTATTT AAATAATTAA ACTTCTTAGT GGAAAGCTAA | 93900 |
| GTAAGCACAG TTTATGGATT TTGGGAATTT TTGCCTTGCA TTTGTCTGAT ATGGTAAAAT | 93960 |
| ATTGAGTTTG TTTTTCTCAT AATGTTCACT TTGTCTTAGA CAAGATAACT CAATCCCCTT | 94020 |
| AAAGGGTTGT ATCAAGCCAT TGATAAGGGC TCACTTTGAT ATAACCATTT TCTGTTATTT | 94080 |
| AGACACTCTT TCACACTTCC TATTTTCCTC CTGGGGATGG TTTGAATGGA TGACACAATA | 94140 |
| CCATATTATA AAAGCACTTT ACAAACTGTA ACTTATGTTA TAAATGTAAT TATTACCTTA | 94200 |
| AGGTTTTACC CTGTTTCAGA TTTGAGTGGA AGTAGTTCTT TACAATACAA AACAACTTAT | 94260 |
| TTTAACTTTT TTTGCATTTC AAAGAATGAT CAATCCACTT CAGGTGCAGC ATGGTTTCCA | 94320 |
| ACCCTGACAG CATGGAAGAA TCATTTATTT AGCTTCTAAA AATGTGCAGG CTGTACCCTA | 94380 |
| GACCAGCCTT GGGGATTAGG CCCAAATATC AATGTTGGGT GTTTTTGGTA TTGGTTTTTG | 94440 |
| GCCCGCCTAC CCGCCCTTCC TTCCTTCGTT CCTCTCTCTC ATTCTCTCTC TCTCTCTCTT | 94500 |
| TCTCTCTCTC CTTCTTTGCT CCTTCATTCC TTCTCTCTCT CTCTTTTTTT TTTGAGACAG | 94560 |
| CATCTCACTA TATTGCCCAG GCTGTTCTCA AACTCCTGGG CTCAAGTGAT CCTCCTGCCT | 94620 |
| CAGCTTCCTG AGTAGCTAGG ACTACAGGCA CATGCTATGG CAATACTGTT TTAAACATTG | 94680 |
| TTTTCAAGGC TCCCCAGGTG ATTCCAGTGT GGGTCATGTG GTAGAGAACC ACTGACACAG | 94740 |
| GCAAACAAAG GATACATAAA GTTGTCTATT TAATGGGTAG GTGCAGGTAG TAGATAAGAG | 94800 |
| TGTAGCCACA TAAACCACAT GCTTAGTGAA CGGTTTTGTT TTGTGTGTAT GTGAGGGATT | 94860 |

FIG. 6.36

```
AGCATCTCTG AGTATATTTT GTTTTCCCTT TTGAAACTTA TCAGAGAATT CATATGTCTG   94920
TTATGTGACT AATGCTCACA TTAAAAAAAG TTATGTGACT TTTTTTAATT CATATGTCTT   94980
TTTAATTCAT TTATTCATTC ATATGTCTGT TATGTGACTA ATGCTCTCAT AAAAAAAGTA   95040
ATGCTCAGTT TACTTTTTTT ATATCAGATC ATATATATAT GTTTTTTTTT TTGAGATGGA   95100
GTTTTGCTCT TGTTGCCCAG GCTGGAGTGT ATTGGCGCAG TCTTGTCTCA CCACCACGTC   95160
TGCCTCCCGG GTTCAAGTGA TTCTCCTGCC TCATCCTCCT GAGTAGCCGG AATACACGCA   95220
GGCGCTACCA TGCCCGGCTA ATTTTGTATT TTTAGTAGAG ACAGGGTTTC TCCATGTTGG   95280
TCAGGTTGGT CTTGAACTCC CAACCTCAGG TGACCCACCC GCCTCGGCCT CCCGAAGTGC   95340
TGGGATTACA GGCATGAGCC ACCGCACCCG GCCATATCTT ATATTTTAAT AAATATTTTA   95400
ATTTGGTCTG TAAATTTTTC TTTTTGGGGA ATGTGTTTTA AGTCTGTGTT GAGTCCTAGA   95460
CATTTGTTGT TCTCAGATAG TCACTAGTGA TACCTTAACA TTAACCAGCC TGTTGGCAAC   95520
TAAATTGGCC TGAAGTGACA ACTAAGGAAA GGTCTCTTTC TCCTTTCTTA ATCTTTGCAT   95580
TCCTTAAGAT TAGTTCTTTG TAGGAAGGCT TTGAAGTCTG GTGGCAAGTA CCCTTTATCC   95640
CTCACAATCT TAAGATAAGG TCTTTCTGAG CATTAAAAAG TGACTGTGGG AGATATGTCA   95700
AATGAGTTTT CTGTGTGTGC TCTGAGAAAT CTTTTTTTCA AAAAAGGATA GATGTACTTG   95760
TATAAGGAAA AGAGAAACTG AGCGCACTTT CAATATTTAA GTAAGTGTCT CTAACATGTT   95820
TTGCAACATA AAATGATGAC CACTGTGTTG GTCATTACTT CTCTACTGCT AAAACAATGT   95880
TTTCTAAAAT AATATACTCC TTAGAAAAAA ATATAGTGCT TGGGTGTGC ACTGTTGTAA   95940
TCCAAGGAAT AGGAAATGTT TTGTAGTAAG TGCGATGGTG TTTGACATCG TGATTTATTA   96000
ATTTATCACA TTTGGTTTCA TAGAAATAGA GTAAGCTACG TATTTGCTGT GCCGCAATTA   96060
CCATGACATT ACACTTGTAT CTATTTCTGT TTCATAGATG TGTAGATATT GATATATACA   96120
GTGGAAGTAT GGATTGTTTT GATAAGTTTC TAATGAAAGT ACAGATATTT GTTGATTATT   96180
TATTAAGAAA GGTTGTTACT CATCCAAGCC CGTGGTTAGC TTTTCCCAAA TTATCATGTG   96240
GTAGTAAGTA AAATGTAAAG AAATATACCC TCCCTTAACC CCACACCACC TGTTAGCACC   96300
TAGCCACCTT CCTTTACTTC TCAGCCGTAC TTTTTGTATT TTTTTGTTGT AGTGGTAAAA   96360
TATAAATAAC ATAAAATTTA CCATTTTAAC ATTTGTAAGT GTACAATTCA TTGGCATTGA   96420
ATACATTGTG TGCAACCACC ATCACCATCA GGACTTTTTC ATCAACCCAA ACAGAAACTA   96480
CTCATTAAAC AATAACTCCG CATCCTTCCA CCCCAAAGCC CTGGTAACCA CTATTCTACT   96540
TTCTGTCTCT GTGAATCTGT CTATTCTAGA TACCTCATAG AAGTGGAATC GTACATTATT   96600
TGTCCTTTTG TGTCTGGCTT ATTTTACTCA GCATATTTTC AAGATTCATT TGTGTTGTGG   96660
GATGTAGCAG AATGTCATTC CTTTCTAAGG CTGAGTAGCA TTGTATGTAT TATCCATTTA   96720
TCTGTTACGG ACATTTGACT ATTGTGAATA ATGCTGTTGT GAACATTGGT GGACAAGGAA   96780
CTGAAAGTCC CTGCTTTTCA TTCTTTTTGG CATAAACCTA CAAGAGGAAT TGCTGGGTCT   96840
TAACGGTAAT TCTGTGTTTA ATTTTTGGAC GAACTGCCAG ACTGTTTCCA CAGCAGTTGT   96900
ACTATTTTAC ATCCCCACCA GCGTTACACA AGGATTCCAA TTTCTCTACA TCCTTGCCAA   96960
CATTTGCTAT TTTCTATTTT TTTTTAATAA TATCCATCCT AATGGGTGTC TTTTTTTTTT   97020
TTTAAAGGAA TGGTTTAAAC AGGTTACCTT CTTACTCCTC ATTCATGCTT TAGTTGACTA   97080
CATAAGGACC CCTCTCCCTA TTGGCACCAT TGAAATTGTT CAGGCAAAAA TAACTGCCAG   97140
CGACACACTG CTTTAAGTAA TGGACTTTTC CCAAGTTTTG TATTAATATT TCAGTATTTG   97200
GTAGTGCATC CTACTGCTAG TTTTTAAACT CTTCCCTTGT CATCTATCAT CTCATTCTCT   97260
CTTGACAAAT GTGAAAATGG AAGCTCAGAA ATAAAACAAG AATTAAAACG AATAGTGATC   97320
CTTCAGGTAA CAAGCTTCAT TTATCATGAA AACATATATG TATGAAACAT TCTGTTTTCT   97380
GATGTTATTG GATAAATTAG GTGATAACCA AATTCTAAGT TCCAAAAATT AAATATACTC   97440
TATCTAAGGA CTTTAACATG GCAGACAATG GTGACAAGGT CAAGAACATG TTTTAGAGTC   97500
```

FIG. 6.37

```
TTCTCCTTTG GTCGGTATTC AATGATACAA CAGTTGAAAA GGCCAGAAGA AAGTTAACCT    97560
AGGATGGTGG TTTTTGAATA TCTAACTTTC ACTTCTTTCC CATCTTCCAG GAAGTTGGCT    97620
GGAATGTGAT GACTTAAAAG GCCCATGTTC TGAAAGGCAC AAGAAATTTG AAGTTCCTGC    97680
TTCAGAGATA CATATTGTTA TTTGGGAAAG AAAAATATCC CAAGTGACAG ATAAAGAAGC    97740
TGCCTGCCTT CCACTTAAAA AGACTAATGA CCAACACGCT CTCAGTAATG AGAAACCAGT    97800
ATCTTTAACA TCGTGTTCTG TGGGTGATGC TGCCTCAGCT GAAACAGCCT CAGTAACTCA    97860
CCCTAAAGAT ATATCAGTTG CCCCTCGTAC TCTTTCACAG GACACAGCTG TAACTCATGG    97920
AGATCATTTA CTTTCAGGTC CAAAAGGTTT GGTTGACAAT ATTTTACCTC TGACACTTGA    97980
AGAAACTATC CAGAAAACAG CCTCAGTTTC ACAGTTAAAT CTGAAGCTT TCCTGTTAGA    98040
AAATAAACCT GTAGCAGAAA ATACAGGAAT TCTCAAAACC AATACTTTGC TATCACAAGA    98100
ATCACTAATG GCTTCTTCAG TATCAGCTCC ATGTAATGAA AAGCTTATTC AAGACCAATT    98160
TGTGGACATA AGTTTTCCAT CCCAAGTTGT AAATACAAAC ATGCAGTCAG TACAGCTGAA    98220
TACAGAAGAT ACTGTAAATA CTAAATCTGT GAATAATACT GATGCTACTG GTCTTATACA    98280
GGGAGTGAAG TCAGTAGAAA TTGAGAAGGA CGCTCAGTTA AAACAATTCC TTACACCAAA    98340
AACTGAACAA TTAAAACCAG AACGTGTCAC ATCTCAGGTA TCTAATTTGA AGAAAAAAGA    98400
AACTACAGCA GATTCTCAAA CCACAACATC TAAGTCATTA CAGAATCAGT CTCTGAAAGA    98460
AAATCAGAAG AAGCCATTTG TGGGAAGTTG GGTTAAAGGC TTAATAAGCA GGGGTGCTTC    98520
TTTTATGCCA CTCTGTGTTT CAGCTCATAA TAGAAACACT ATAACTGATT TACAACCTTC    98580
AGTTAAAGGG GTAAATAATT TTGGTGGCTT TAAAACTAAA GGTATAAACC AGAAGGCCAG    98640
CCACGTATCC AAGAAAGCTC GTAAGAGTGC AAGTAAGCCT CCTCCCATCA GTAAGCCACC    98700
AGCAGGCCCT CCATCGTCTA ATGGCACAGC TGCCCACCCA CATGCTCATG CTGCTTCAGA    98760
AGTTTTGGAA AAGTCTGGAA GCACCTCATG TGGAGCTCAA CTCAACCACA GTTCTTATGG    98820
GAATGGTATT TCTTCAGCAA ACCATGAAGA CTTGGTGGAA GGTCAGATTC ATAAACTTCG    98880
TCTAAAACTT CGTAAAAAGC TAAAGGCAGA AAAGAAGAAA TTAGCTGCTC TTATGTCTTC    98940
CCCGCAAAGC AGAACAGTTC GAAGTGAAAA TCTAGAACAG GTGCCCCAGG ATGGGTCTCC    99000
AAATGATTGT GAATCAATAG AGGACTTGTT AAATGAGCTA CCATATCCAA TTGATATTGC    99060
CAGTGAGTCT GCATGCACCA CTGTTCCTGG TGTTTCCCTG TACAGTAGTC AAACTCATGA    99120
AGAAATTTTA GCGGAATTAT TGTCTCCTAC ACCTGTTTCA ACAGAGCTGT CAGAAAATGG    99180
GGAAGGTGAC TTTAGGTATT TGGGAATGGG AGATAGTCAT ATCCCACCAC CAGTACCAAG    99240
TGAATTCAAT GATGTTTCCC AGAACACACA TCTGAGACAG GACCATAATT ATTGTAGCCC    99300
CACCAAGAAA AATCCATGTG AAGTTCAGCC AGACTCTCTG ACAAATAATG CCTGCGTTAG    99360
AACATTAAAC TTGGAGAGTC CGATGAAGAC TGATATTTTC GATGAGTTTT TTTCCTCCTC    99420
AGCATTAAAT GCTTTAGCAA ATGACACATT AGACCTACCT CATTTCGATG AATATCTGTT    99480
TGAGAATTAT TGAATTAATG CTTGTTAACT TTTTTCATAT AATATTTATT ATTATTAGAA    99540
GAACTTACAA TGTGTTCAGG TAGTGTTTAT ACACTGGACT TGTGTAATTA CTTGTGTAAT    99600
AACCATGAAC AAAATGCAAG GTTTAACCTT TGGTTCTGCC CATGAAGCAT GTAATCTTTC    99660
TTACACATTA AAATCACTGA ATGTGTTCTC CTTTTTGGTT TCATTTTGTT CTTGTGAGAG    99720
TATGAGGATT TCAAAATGTT AAAGATGAAA AGTGGCGTCT AGTTTCTGAC AGTTTGTACA    99780
GTTGGATGCA TTACATTTTT AGATTTGAAG TTTTGGTTAT GTTAGTGTTA TGAGTGATCT    99840
TTGTGGTGGT TTTCTTCCCC TGGAAACCTG TTGCTCGTGG CGCTTTGCCC ACGGTGCCCG    99900
AGTTCTTGTC CTGTGTCCAG ATATGCAGAC AAATGAAGGG TGAAGAAGAA GAAGAGGAGC    99960
TTTATTTAGT GTTAGAACAG CTCAGAAGGA GACCCACAGT GAGCAGCTCC CCTGTGTCGG   100020
CGGGCAGGTC GTCCCTCAAG TGTTCAGCTC TCAGCAGAGA AAAGGCCCTG GAGAGGGTGA   100080
CTCCTCTCAG CTCTCAGCAG AGAAGCAGCC CTGGAGAAGG TAGCTTCTGT TCGCAGGCAG   100140
```

FIG. 6.38

ATTGTCCAGA GGTCCTGCTG CTCTCAGACG GGGCCCTGGA GAGGATAGCT TCTATCCATA  100200
GGCAGGTTGT TCTGCCGTCT CTACAGGTCT CTGAAGCTCT TAGCAGAGAG GGTAGCTCCT  100260
CCCTGTTGCT GGTCGTCCCA CCCTCTGCTC AGTTCTGGCT GAGCCTGGGG CATTTTACGG  100320
GCCTCGGGGG AGGAAGTGCA TACTTACTGG CCTGGAAAAG GCACCAGTTC CCACTCCTAC  100380
AGGTGGGACT GGCAGCCTGG CCCTCAGCCT TCAGGCCCTC CCTGTTCATG GCTTCCAGGC  100440
TTACCCCCCT GCTTTGATCT GAGAGCTGGT GCCAATAGCA GGGAGAAGCC AAGCTGCAGA  100500
GGCAAGCACT TCCGAGCCTG CAAAAGCAGG CCCCCAAAAG TGCAGGGATG CCTGAGTCTG  100560
CACCCGCACC CAGGAGGGTG GAGATCTTGC CTGCTCCAAG GCTGCAGCCG AATGATAGC  100620
AGGCTGACTG GAGCACCTGC CACCATCATT AGTTCAAGAG TTTATGCAGA TTTAAGTTGT  100680
ATACGGTATA TGAATGTGTG ACAGTTTTCC TTATGGTTGT GTGGCCTTCT GTAAGAGCCT  100740
ACGCCTGTTT GTTACACCGG TAGAGTGCTG TGGAATGTAA ACTTTCCCTA TGTCACTTAT  100800
CTCCTTTATC TCTCCATACA GAGGAGGGCA AGAAACCTTG TTACTTGAAC TTTAGTAATG  100860
TTAAGTGATC AATAAATCTA TAAATAAATG ATAGCAGAAA AAAGTTACCT GTTTTTGTGA  100920
TGATGTACAA ACTTTACATG TTATCACAAA TACCATCTTT CTTCCCAAGA CATTTACTTC  100980
TGTAACCAAA GTGGGACACC ATCTAACAGT TCTGTTTTGG GAGAGAGTAA TAACCAGTGC  101040
TTGTGAGGCT TGTTAGATGT TGGTTGTGAT ATATGAGATA GATGTTATTT CATTTAGACC  101100
TCAACATTCC TGTGCGTGAG ATACTTTTAT CACATCTTAC AGATAAGGAG ACTGTACTCA  101160
TTCAGTTGTG GAGCTGAGAT TGAGTAGAGT GGCTATTACA GCAGTTGAGT GCTGAGCTTA  101220
TCAATATATG TTCCACTCCT CAGGCTTCAT TTAAAGTAGG ATGCCCAAAC AGCACCACTG  101280
CCGTAGAGAT TTGAGTTAAC AGCAGTACTT ACTGAGGTTT AAGGCTGGCA GCCAGTGTCC  101340
TTGCAGTAAA ATTATTTGCT AGGGACTCAG TACTTCATAA TCTATTTGTC AGATTTACTC  101400
CTAAGCTTCT GTGTTGTTTT ATTTTTTTTC TGACAAAAGT AGTGCATATT GTCAAGGAAA  101460
AACTAGGAAA ATACCAAAAA AAAAGATTTT TGACCATGCA TTTTAATACT TAGTGACTAC  101520
AAACATTTTC CTATTTTATG CATATAGATT TTAAATAAAC GTGAGATCCT ATTGTATCTG  101580
TTTTAATGGA TAAACATTGT TTCACTGTTT TAAGATTCTG AGGTGATTTA TACTGTCTTG  101640
CCATTGTTAA TTGCAGCAGT TAGCCTTGTT GATAAATTTT TGCATGGATC CAAGTTTTGT  101700
TTTCCAGGAG TGGAGTTGCT TGGTCAAAGG AAATGCACAT TTAAGGTTTT TTGGTGATTG  101760
CATGACTGAC TTCCCTGGGC CCTCGCCAAC ACTAGGTAGT AGTATTGGGA GGAAGGGGGG  101820
AACCAATCCT GGGTGCTCCA AGATTACTAG TGAGCCTGAA CATTTTCTAT AACTATTGTC  101880
CACTTGAGTT GTTGTTTTGT TTTTTTTTTG GTGGAGGCGG GGGTGGGTTT AAGAATTGCT  101940
TATCCTTTGC TTGTACTAAT TATCTTTTCA ACAAATATTT CTAGATTACT GCTAAGGACC  102000
AAGCACTGTT ATCAGCCTGA GATAAGGCAG CACACTAGAA GGAAATCCTT GCTCCTTTTG  102060
AGTTTGCCTT CCAAACATGG AGATCAATAT ATAATGTTAG GTAGTAATAG GAGATACATG  102120
CAGTTGATTC ATGTCATTTG TAGTAGTTAT GGTCAATAAA GTTGCCTTGA ACACTGAATT  102180
AGTATAAACT GAAATACTGT TCCTAGGGGA AATAGGTTCC TGCTAGCCTG TGGTCATGAG  102240
ATTTTTGTCA AACAATCACT ATATAACCTT TTCTGTTTCT GTTTAAAGAC ATGTTATTTG  102300
ATCTATATGG TTGATTCTTT ACATTAACAT GGCCAACAGC ACTGTAACTC AGCCTGAACG  102360
AAGCTTATCT GACACATGGT GTTCTCCATA AGGCACATCA TAGCTTTCTG TGCTTAGGAA  102420
CACTAGACGG CACTTCAGCA CTGCACTTGA GGACGTTTTA AACAGTGAAA TCAACAAAAA  102480
GCACAAAAAA ATGCAACAAT AGGCTGGGCA AGGTGGCTCA CGCCTGTAAT CCCATCACTT  102540
AGGGAGGCCG AGGCGGGCGG ATCACGAGGT CAGGAGATCA AGACCATCCT GGCTAACACG  102600
GTGAAACCCC GTCTCTACTA AAAATACAAA GAATTAGCCG GGCGAGGTGG CAGGCGCCTG  102660
TAGTCCCAGC TACTCGGGAG GCTGAGGCAA GAGAATGGTG TGAACCTGGG AGGCGGAGCT  102720
TGAAGTGAGC CGAGATTGCG CCACTGCACT CCAGCCTGGG CGACAGAGCG AGACTGCGTC  102780

FIG. 6.39

| | |
|---|---|
| TCAAAAAAAA AAAAAAAGGA ACAATAACAA AGACACTAGT CCCCCAAAAA TACACTTGTT | 102840 |
| TACAGTGTGA ACTGAAAGAG GAAGGTGGAG TATTGACTTG TTTGACCTCA GCTGGAAATG | 102900 |
| TGCACGTCCT GTGACTCAAA TTTTTCTCTG TTCTGTGCAT GCATGTCCAC GAATAACCAC | 102960 |
| AAGAAGCACT GAAAGCATTG ATTTTTAGGG TTACAAATTA ATTTTAGCAA GTAAATGAAT | 103020 |
| TCACAAATAC GGAATCTGTG AGTAATGAGG ACTGATTCTT TTTTTTTTTG GAGATGGAGT | 103080 |
| TTCACTCTTG TAGCCTAGGC TGGAGTGCAA TGGCATGATC TCGGCTCACT GCAACCTCCG | 103140 |
| CCTCCCGGGT TCAGCCTCCA CCTCCCGGGT TCAAGCGATT CTCCTGCCTC AGCCTCCCGA | 103200 |
| ATAGCTGGGA TTACAGGCTT GCACCACCAT GCCCGGCTAA TTTTTGTATT TTTAGTACAG | 103260 |
| ACGGGGTTTC ACCATGTTGG CCAGGCTAGC CTCGAACTCC TGACCTCAGG CAATCCACCC | 103320 |
| ACCTCAGCCT CTCAAAGTGC TGGGATTACA GGCGTGAGCC ACCGCGCCCG GCCGAGGACT | 103380 |
| GATTCTTATG TCAGATGGCA CTAAATGCTA TGGAGAAGAG GAGTGGATGA GAGGGAGAAG | 103440 |
| TATTTTAGAC CAGGTAGACT TGGAAGGTTT CTTGGAGGTG GGTGATGTTT GAGAAGAGGC | 103500 |
| TTCAATAAAG TTAGGGAGCT CGCCATGTGA TTGCAGGAAG AGCGTTCCAG GAGAACAAAA | 103560 |
| GTCATGAAGA GTGAGTGCTA GGCATGTGTC TGGTCTGTTT GGGCTGCTAT AACAAAATAC | 103620 |
| CTTAGACTGG GTAAAATGTA TAAATAATAG AAGTGTATTG CTTATAGTTC TAGAAGCTGG | 103680 |
| GAAGTCCAAG ATCAAGGTAT CAGCACATTC TGGTGAAAGC TGCTCTGCTT CATGGCTGGT | 103740 |
| TCTCTCACTG TCCTCACATG GCATAAGAGG GGCACAGAGC CCTCAACCGT CTCTCCAGTG | 103800 |
| GCCCCATCTC TTAGTACTGT TGGATTGGGG ATTTAGACTT CACTAATTTT GGGGGGACAC | 103860 |
| AAACATTGAG ACCACAGCAG CATGACTGAG GATAAGCAAG AGGCCAGTGT GGTTGAGCAG | 103920 |
| AGTGATCAGT GAAGGAGAGT TAGGACATGA GTAAAGAGGC TAGCAGACAC CAGATCTCAT | 103980 |
| ATGGCTTTGT AGGCCATAGT GAGGACTTTG TTTAAGCTGA GAATAATAGA TAACCTCAGG | 104040 |
| AAAGTTTCAG GCAAGAGGGT AACATGATCT GATCTGGGTT TTAAAAGGAT CACTGAAGTG | 104100 |
| GGGAGACTGT CTACAGATGG TCTGAATAGG AGTCCTAGTC TATTACAATC TCCTTGGAGT | 104160 |
| TTAGGGTGGT AACTGGAGGT GTTCAAGAGT AGTTGGATTA CTGTTGGATT TCAAAAGTAG | 104220 |
| AGCCAACACG ATATGTGCAT TGGCTGTGAG GTAGAAGAGG AGTCAAAATG AACTCCAGGT | 104280 |
| TTTATTGACT GAGCAATTGT GCCATTTCCT GAGATGGGTC AGATTTGGGA AGGAAAGAAT | 104340 |
| TTAAAGGGGA TAAGATAATC CCATTAGGAG TGTGTTAAGT GTGAGATTCC TATTAGACTT | 104400 |
| TCGAGTGGAG ATGATTTAAT AGGAAGATAG ATCTGCAACA CTGGAGCTCA GCGGAGAGGG | 104460 |
| ACACCCTGGA GATAGCCGTT TGGGAATTAG GAATGTGTGG ATCATGTTAT AGGATGGGGT | 104520 |
| CATTTAGGGA CTTAAAACAG CTCTGAAGAA CAAAAATGGT GCCTTGATCT TGGACTTCCT | 104580 |
| GGTTTATAGA ACTGTGAGCA ATATATATAT ATTTTTTTCA AGACAGAGTC TTGCTCCGTC | 104640 |
| ATCCAGGCTG GAGTGCAGTC GCACCATCTC GGCTCACTGC AACCTCCACT TCCTGGTTCA | 104700 |
| AGCAATTCTG GTGCCTAAGC CTCCCAAGTG GTTGGGACTA TAGGTGTATG ACACCATGCC | 104760 |
| CGACTAATTT TTGTATTTTT TTGTAGAGAC AGGGTTTTGC CATGTTGGCC AGGCTGGTCT | 104820 |
| CAAACTCCTG ACCTCAAGTG ATCTGCCTGC CTTGGCCTCC CAAAGTGCTT GGATTATAGG | 104880 |
| CGTGAGCCAC CATGCCCAGA CTAAATTTCT AACATTTATA AATTATCCAG TCTAAGATAT | 104940 |
| TTTGTGATAG CAGCCCAAGC AGACCAAGGC AAAGGCCAAG CACACTTGCT CCTCCTGACT | 105000 |
| TTTGCTCTTC CTGGAATGTT CTTCCTTTAG TCACATGGTT GCCTGCCTAG CTTCATTCAA | 105060 |
| TAGGAGTGTG GTGCCCTGAA AATACAAGGA AGAATGCTTT TCTTTTTTTT AAAAGGAAGG | 105120 |
| GATGATTATC TGTCAGATGC TGCTGAAAAA GAGTAATAGA GTAATTGGCC ACTGGCTCTG | 105180 |
| GCAATAGGGA AGTTAGCTCT GCTAACTCCA CATGAACAGT TTCACATGAA CAAGTGTGAG | 105240 |
| TGGGCTCAAG AGAAGGGATG GTGAGAAAGT GGAGCTATGG ACTCACTCTT GAAACATTTT | 105300 |
| CTGGTGCCTC GTAGGGCAAT GTGAGGTCAA GGTTTTTGTT ACTGTTCTGA AGATGGGAGA | 105360 |
| GGCTGACACA TGGATGTTGT AGGTGAGAGA AGGGGCGCTT GCGGGGGCAA ACTTCTCCAG | 105420 |

FIG. 6.40

```
GGATGGGATT CCAGTGTCTA AGAGGAGGCG GTGTGACCCT AAGAGCTAGA AAAATTATTT  105480
TATTAATAGG AAAGACAAAG TACTTAGGCT CAGATGCTAA GAGATTTGCT GATAAAAGAA  105540
TGAGAACGGT CTCTTCTGAT TATTTTCTTG GGGAAATAAA TAGATCATCA GCTGAGGGTG  105600
TGAGGGGAGA AGGAGTTGAA CATGGAGGAA GACAGGTGTG AAATATTGGT CTCAGAATGG  105660
AGAGCGAATT GAATAGGGAC ATGCAGTGGG CTTGCTAAGC TGTGCGGAGA GCCCGTGGGA  105720
AGTTTATGGT CATCAATTTA ATGGCGACCA GCCAAGATGG TGGTTTATTT TTCTCCAGTT  105780
GTATTTAACT GCTCAGGTGC AGGACAGAGA GACTAAGTGT GAAGTTAATT TCAGCCAACG  105840
TAGAGGAATT GTCAGGCAGA TGGGACAAGG AGATAGAGGA GAAAAGGAAT AAGGCTTCCT  105900
GCAAGGGTAA TGATTGTAGG GATGGATAAG TAAGGAACAC AGGAAGTGGC TGTCTGCTGA  105960
GTGGTGGCAG AGCTCAGTGG GTCAGAGCAA GGTTCAAAGA ATGGCAGAGA GGCACTTGTG  106020
GAGGAAGTAA GCTGGCTAGA AAGTAGTGTG CTTGAAATTA AGCTTCTGGA GATAGCAAGG  106080
TTACAGGTGA TGACAAAGTC TGAGTATGAC AAGGAAACTG CAGGGCCAGA GTTGGCAAGA  106140
ATTCATGAAA AATGAGGAGA AAGAGGCACC AAGAGGCTGG GATAGCACAT GGATTGTCTC  106200
TGTGTGAGGC AAAGTCATCT AAATGGCAGC AGTGGCCCTA GCAGAAAGAA ATATACAGTG  106260
AGCCGGAGCA AAAATCCTCA AGGACAGGCA GAACGCCATG AAAACGGCAG ATGACAGCCA  106320
AAGGAGCAGG GGCAGGGGCT CAGTCCAAAG TGTTTCAGAG TCACTGGAGG GTTGAGTGGG  106380
AAGGGGAGGG AGTGGCTGAA ATGGCAACAA GGAAGAACCT CTCTCATCTC CAGGCCCAAA  106440
AGTATGTGGA ATGCGGGAGA TAAGACAGCC ACCACTGGCC AGGGCTGTAA AGGGACATTC  106500
AGCGAATATT CAGGTTCCAT TTAGCACGAC AGCAGGGAAG GGACTGTTGG CAGAAAAAAA  106560
CTGGGGCAGT GGGATTAAAG ACAGACCACA CATTCCAAAA GGCACCGTGG GAGGGTCAGG  106620
GGGCGAGGTT AGGTCTAGGC TTCAGTGTCC TGGGAGACTC AGTCTTCACA GGGTGACAGC  106680
GATCAAGAGT GCAGCTTAGG CTGGGTGCAG TGGCTCATGC CTGTAGTCCC AGCACTTTGG  106740
GAGGCCGAGA CGGGAGGATT GCTTGAAGCC AGGAGTTTGA GACCAGTCTG ACCAACATGG  106800
CAAAACCCCA TCTCTACTAA AAATACAAAA ATCAACTGGG CATGGTGGCG TGTGCCTGTA  106860
GTCCCAGCTA CTTGAGAGGC TGAGGCAAGA GAATCACTTG AACCTGGGAA GCAGAGGTTG  106920
CAGTGAGCTG AGATCGTGCC ACTGCACTCC AACCTGGGCA ACAGAGTGAG ACCCTGTCTC  106980
AAAAACAACA ACAACAAAAA AGAAAAGAGT ACAACTTATG AAGGGGTCTC CTGGGGAGAG  107040
GGTTTTTGGG ATTCTCCTGC CTCTCAAAGT GCTGGGATTA TGGGCGTGAG CCACCACACC  107100
CAGCCGAGGG AGGCTGAGTT CTAATTGTTG TATCTCTCTT GGGATTGGCC TCCTGGGCAG  107160
TTTAAAAGAC AAGGCAAGGA ATCTTTTGGA GAAAGAGACT GGGGGCAAGG TGTGTCTGAA  107220
CAAGAAGTGT GAGAAGCTCT GTGGGCTCCC TTCAGACTTC CAGTCGTTGA ATTGGGATCT  107280
CATTTATATC AGCTCTAGGT GTAACGATAT TAAATCTTCT CTGTCATTTG CAATTTTGG   107340
TTTATGCTTG ATCATCATTT TTAATGTTTC GACATGTAGA AGTTTAACAT TATTTTACAT  107400
TCTTTTCCTT CTGGCATCAT GTTTTAGCAA GATTGTTTCC ACCAAAAGAA TATATATATC  107460
TTCTAATGAA ACTACGTTTC TTTTTTTTTT TTCCTTTGCT TTCTCTTTTG GTATATGAAT  107520
CTTTGATTAT TTGTAATGTA TTTTGATGTG TAACACTGAA GTTTCTATTT TGTACTATTT  107580
TTTTCCCCAA ACAGTAAACT TATTGTTCAA ATACTTATTG AACAACCTTC ACTATTCTTT  107640
AACCATTTAG AATACGCCAT TCACATATCT TTCATACTAC ATTTAATAAC ATTTTTTAAT  107700
TAAAAAATAT TCTACTGATT TGTTTATTTT GAGACCAGGT TATGAAACTG GCTAATTTTT  107760
GTATTTTTGT TAAATACCGA AATTCACTGT GTTGCCAAGG CTGGTCTCGA ACTCCTGGGC  107820
TCAAGCAATC TGCCCACCTT GGCGTCTCAA AGTGCTGGGA TTACAGGTGT GAGCCGCTAC  107880
ACCCGGCCAC ACCCGGCCAA CACATATTAT TTGTTATTAC ATTTAATTCC CACAGTACAT  107940
TGAAATTATC AGGGAAAAGT TTCAGTGAAA ACATTATTGA ACGCCACATT AAAAGTGTAA  108000
ATTACAAAGA TTTAATGCCA ATTTTTCAGA AGAAAAAAGA CCAGGAGGAA GGTCTATGAA  108060
```

FIG. 6.41

```
GTTTTAGCCA GTCTCTCATC CACCTACCAT TTCACGATCA TGCACTGTGT AAGTCAGGAA  108120
AAGAGTAAGA AAAGTGAAAG ATACAATTGA TTAGAGAGTT TTGCTGGATA CTATAGATGA  108180
AAAGAACACA AAATGGAACA GCCTCTTCAA GCTTAGAGTC AACGGCTGTA GTCCCAAAGA  108240
CTGTAGTCAG AGGCGGTAGG GCCAAAAGAC ATGACTTATG GCATTGGAGG AAGAGGATGC  108300
TTTGGGAGTT CATGGTAGAA GAGGCGGAAA AAATCTGGTG GATTAAAGAA AGCATCCCAA  108360
AGTGACATTA AACTAATGAC TAAATTCTGA GCTGTTTTCA GGGGCAAAGC CTGTTTGGGC  108420
ACCCCTGCCA CACTTAAAGA GTCACCTAGG TATGGTTCGT GGGCTCTGAA CAGGCCTGCT  108480
CAGTGAACAT ATTTGTGACT GTTTCTCCGG CCCTTTTAGC TGTATTGAGT AAAATTTAAA  108540
GAGACCATTG TTTTGGCCTA AGCTCCTGCC CTAGGCCCAA AGAACAGACC AAACCTGAAT  108600
GGCTTCACTT GTCCTAGGTG CTGTGTACTC AAACTGAACT TTGAAACAGG TCGGTTTTTC  108660
AAAAAAAGCA AAAGATTCAC AGCAACCAAT TAGAAGAGGC CCGGTCAACC TGAGCCAGCA  108720
TGATGAGGCT CTTCTGCTTT AATCCTACAA GGAAAGAAAC TTTGAAATGA CCAATCTGCT  108780
TTCATTCTTG GTTTCTGCTT TCTTTGGTCT ATTTCTGCCT GTAAACCTA TCTCCTCTGC  108840
TCAGCTCATT GAAGTACCCT TCTATTTATA GATGGGATGC TGCCCGACTC ATGTATCGCT  108900
AGTAAAAGCC AATTAAATTA TTACACTCGA TTTGTTGGAA TTTTGCTATT TTGACAGCTT  108960
TTCAAAAACA CCAGTAGGTT CACATCCCTA ATTCCCCAGC CAGTGTTCCC TCAAGGAACC  109020
ATGGAAGAAG CAAAGGTGGC TGAAAGGCGC CTCAGGATGC TTCTAAGCAC GGCACATCCA  109080
TGAAAAGGCA CTTACTAATA TTTGCAGGAT AGCAAAGCAC TGCAGTGACG ATAAATCTAG  109140
TATTGGAGAA GTTCAAAATA ATCAGTAGAT TAACACAGAA GCCAGAGCTT ATAGGGAGAA  109200
AAGGAACCCT ATGAAATACT TCAAATCCGA AAACGAACAT GCATTTCCTG TTTAGTTAGT  109260
GCAGGTACGT AAAAGCTTGG TAAAGTACCC TTCTTGCCAG CTTTCTCTTT CTTACAAGCC  109320
TTTTCACTGG GCTGGGAGGC TGATATTATC TAAATATGCT GAGGAGGTTC AAGTATCTCC  109380
ACAACTCACC TCAGAGTGAA TGCTCCCCTC GGCCTTAAGG CAATATAAAC CAGCCCTGTT  109440
TAGCAGGATA GCAAAATGTT TGCGGTTGTA AACTGGTGTC CCATTGGCTG TGGCGCTTGT  109500
GGTGTAAAGA ATCCCTGTGC TTGGTAATTA ATAGAGAAAT TCTATATTTT AAACTTCAGT  109560
TGTATATTGG CTCTTATCCA TGGCAGATTT TCACGTATGT GTTATTTTTT TATTTATTCA  109620
GAGCCGGAGT CTCGCTTTGT CGCCCAGGCT GGAGTGCAGT GGCGCGATCT TGGCTCATTG  109680
CAGCCTCTGC CTCTTGGGCT CAAGCAATTC TTCTGCCTCA GCCTCCCTAG TAGCTGGGAC  109740
TACAGGTGCA TGCCACCACG CCCGGCTAAT TTTTTGTATT TTAGTAGAGA TGGGGTTTCA  109800
CCGTGTTGCT CAGGCTGGTC TTGAATTTCT GAGCTCAGGC AATCCGCCCG CCTCGGCCTC  109860
CCAAAGTGCT GGGATTATAG GTGTGAGCCA TCATGCTCGG CCCTATGTGA TATTTATTAC  109920
AATGAATTCC AATGATCAGA CCTATACTCA AGTATAAGTG AATATATCAT TCAATGAAGT  109980
ATAAATGATC ATTATGTTCA TATTCACACA TACAATAATG TACTCAAGTT TATTGCTAAG  110040
GTAATTCAGA ATCTCCTTAT TTTGAAGTGT GCATTTGATA TACCTGTTTG GGAATAACTA  110100
GTTTCTTATC TTTGACAGAA AATAATTTTG TTGTTTTGTT TTTACTAAAA AAGCATGGTG  110160
AAAAATGGCT CCATTTCTAA GAGAGGTAAC TAAAATATCG CAATTTGCTG GGTGTCATTA  110220
AAGTAACTCA CAAGGGAAAA AATGCAAATT GGTATCTGCT GATGGAGTAA ATCTCCGCAG  110280
AAGTGATGAC CCTGAAAGGA TCAATATATT AAAGCCCCTC CCAGCTGGTC ATTCCAGATT  110340
GCAACAATAA AGCATTAAGT GTTAAAACCT CAAGGCAGCT TTTTTTTTTT TTTTTTGTCT  110400
CAAGTCCTTT ATTATTAATT TTATAGACCT ACTTAATTAC TAAGCCAAAA AAAATCAAAC  110460
TTGTTTCTCT TTGTGACTTG TCAATAGTAT TAAACTATTC TGGTTTTTTA TTTTTGTGTT  110520
ACCTTAAAGT CTCCAGTTTA GTAATTTTTC TGTACCTAAA CACTTCGGAT TTGACATGCT  110580
TTGTGGCCTT TATCAGTAGT TAGAATGTAA ATCCAATAAA TAAAGTAAAA GCCAGGTCTT  110640
CAAAACCTGG GGGCCAAGAA CTCTGTTTTA GAGGGCCTGT GACTCTCTTG GACACTGGAC  110700
```

FIG. 6.42

AAAATCTCAT CTCTAAATAT GGATATTTTA GGGAGAGGGT CTTTAGGCTG TCATTTGGAT 110760
TTTCACAGGG CTCCATGTAT CCATAAGGTA GTCTCTTGGG AAGTTTGACT TCAATAAATG 110820
AAGTTTAACT TAAACCTAAA ATGAAATTTA ACTGAAAAAC AAAATCCAAT GAAAGATGCT 110880
TTCTTATGCA AAAACAAACA AACAAAAAAA AAACAAAAAA ACCCCAAAAA ACCCAAAGCC 110940
AAAGATTGTT TCTGAAATTA GGTTCTAGGT TCCAGAGCAA CTCCATGGTG GGGAATCAGC 111000
CACATGTAAA GTAAGCTAAG AGTTTGGACA ATTTGTAATA TTTATTCCTA GGTTTCTTTA 111060
AGACCCTTTC AGATTTTGAA TTCCTATTAG TAGCATCAGC CAGGTTCTAA ATGTAGGCAT 111120
CACCATAGAC ACTTCCCCAC TGCTGCAGTC CCCAACACTT GCCCAATTTT CCCTTGAATT 111180
GCACCCATGC TGCCTTCTCC AGGCCTATTT GAACCCAGAA CCTCGTTGTG CCTCGTTTGA 111240
AATATAATTT CCTCCTAACT AGTCTCTGAT CTACTATTTC CCTACATTG CTGCCACACT 111300
AATCACCTAA AATAGATTTC ATTCTACCCT GAAACAGAAA TCTCTAATAA GTTACTCCCT 111360
TCCCTTACGG GGTAAAGTTA GCCACATCCT AGGTATTCAA GGACCTTCCA GGAGCTAAGA 111420
ACATTTCCCC TGCACCTTCT TGAAGTACAC TTGTCCTATG TACTGGTTAT GTTCATTTCT 111480
TACCCTCGCT CTCGTTTTGT CTGGAATTTT CCTTGGCCTT AAATGCCTCT CACCTGCCTG 111540
CCCACATCTC TCAGGGTTGT TTCAAATCCT CAATGAAGGC TCACAGCCCC AGTCTATGTT 111600
GGCCACTTAC TTCGTGGCCT GGGAACATTT TTCTTTGGCT GACTTGCTGA CACTCCATCA 111660
GATGCATTTT TATCTGGTTG TCCATCTGTG AACCATACCC TGAGAAGGCA GAGAGTGCCT 111720
CTGCACTGAA CATGTGCTAG GGACAGGTC TGTGCTAGAG GGGCAAGCAC TGGGAATGAA 111780
GAACTGGTCC CTACTCCCAA GGAGTTCATA TCTCAGTGGA GGTGACAAGC AACTCACTGT 111840
TTCCGGGGGT TGTGGTGACT GCTGGGAGAA GGGGTGTCTA TATTAGATCG AAGCAGCATC 111900
AGGGGAGGTT CCCTGAGAAG GTGATGCCTC AGCGGATGTC TCCCAGCTAA GTGGGGTGGA 111960
GGTGGAGAAG GGCAGAGCAG GGAGAGGATC TAGGTGGGGC GTGTAAGTCT GCATGGGTAA 112020
CTCAGGGAAC CCTTGGTAAC TGCATGTAAC TGTGTGAAGC TTTCATGAAG GAACATGGTA 112080
GGAGACTAGG GTATGGACTA TAGAAGCCCT TTTGCTAAGC TCAAGAATTT GAGGCCGGGA 112140
GCGGTGGCTC ACGCCTGAAA TCCCAGCACT TTGGGAGGCC AAGGCGGGCG GATCACGAGG 112200
TCAGGAGATC GAGACCATCC TGGCTAACAT GGTGAAACCC CGTCTCTACT AAAAAAAAAG 112260
TACAAAAAAT TAGCGGGGCG TGGTGGCGGG CGCCCGTAGT CCCAGCTACT CAGGGAGCTG 112320
AGGCAGGAGA ATGGCATGAA CCCGGGAGGC GGAGCTTGCA GTGGGCGGAG ACTGTGCCAC 112380
TGCACTCCAG CCTGGGCAAC AGTGCAAGAC TCCATCTGAA ACAACAACA ACAACAAAAA 112440
ATTTGAAGTG TATCTTGAAG GAAATCCCTT GGAGCCTAAA ATGATCATT GATAACAGAA 112500
AATGATCTCT GCTCTCGCCT AGGGTAATAT ATTCAGCTTC AAAGTGGAAG GGCATGTTTT 112560
CCAAGGGCAT GTTTTCTAAG TCCCTGTAAT TGTAGTGATA GCAAATATAT GCCCTGCATC 112620
TTGAAATGTA AGACTAGGTT TGAACAGTAT ATAAATTATC TTATGATCTA ATTTCCCCTC 112680
ATTTTGTGGT TTCTACTATA AGCTACCCAG AAGTGTAGAC AGGACGTTTG GAATTTGATG 112740
GGCATCGGAA AGATTCCTAC CTAAGAACAT TTTTTTTTTT TTTTTTTTTT CTGAGAAGGA 112800
GCCTTGCTCT GTCACCCAGG CTGGAGTGCA GTGGCACGAT CTCAGCTTAC TGCAACCTCC 112860
ACCTCTCAGG TTCAAGTGAT TCTCCTGCCT CAGCCTCCTG AGTAGCTGGG ACTACAGGTG 112920
TGCACCATCA TGCCTAGTTA ATTTTTATAT TTTTAATAAA GGCAGGATTT CACTATGTTA 112980
GCCAGGCTGG TCTTGAACTC CTGACCCCAT GATCTGCCCA CCTTGGCCTC CCAAAGTGCT 113040
GGGATTACAG GTGTGAGCCA CTGCGCCCGG CCTCTAAGAA AATTTTTGAG AGCTACTTGT 113100
TCTGTTGCCT GGAATTCCAC CGTAAGTACG ACGTTGTGTC TCCTTCTCCA GGGCTACTAA 113160
CTAAACAACA GAGGGTATTG TGTTATCGAC AATTATTTGA TTGATAACTA TCAGCAAACA 113220
TTTGCCAAGG CATTCCTTTA AAGATAGCCT AGTGACTCTA TTAACTACTC CTTCTTCCAG 113280
GCTTCTAAGT TCTGTTGGAG GTAAGTAGAT CCCAGAGATA AAGCACCTAC CATAGGACCT 113340

FIG. 6.43

```
GAATCTTGGT AGAAATAAAT TATATCATCA TGTTATCATA TTATCATGTG TTTTTCTATC    113400
TTTAAAGTCT TATGTGAATA TTCTGCTTGA AAAATATGTG TCCTCTGTTA GACCAGAGTT    113460
GAAAATATGT TATTCAAGAA CTTGTAACAG GAACCCGCAC AATTTCTGCT GGAGTTTAAT    113520
TTCAGGGTTA ATTCTGTCAG CAATCTAAGG TAAACATTAA CATTTTTCCC TAGATTCAAG    113580
TCCGTTGTCC AAAAGCTGTA ACAGAACTTA ACTGAATAAA TAGTTTCTTA AGATGGTAAG    113640
CTTCCATATG CTTATAATGA CTCCTCTACA CGTTTTCATC TGGAAGGCTG CTCATGCTTT    113700
TGGAAGCAAA GAAGACAATC TTAAATAACT ACATTTGCTT TTTGGTGGTG CCAGATTTTT    113760
CTGAGAAACA CCAATGGAAT TTATAAATTC ACCAGTCAAT GGGCAATTGA GTTGCTGTTT    113820
TGCTATTACC ACTGCCGTTT GTGAGCATTG TTGGGAAGGT GTCTTGAAGC ACACGTGCAA    113880
GTTTCCCTTG GATAAGTAGT AGGAATAGAA TTGCCAAACC ATGGCTTCCA GTGCAGACAC    113940
AGTCTCTCCC TTGGGCCCAG CCACTAGGCA CCACACATTA AGAGGATATT GTCTGTCCAT    114000
GTCCTAGAAA CGTTGTAGCA TCATGCTCCT ATTCGATTAA AAATCTCATT ATTAAAATGA    114060
ACCATCGGGT AAATGTTGTC TCGGGAAAAG AAGCACTGAC CGTCCCTGGG TGGGCTCGAA    114120
CCACCAACCT TTCGGTTAAC AGCCGAACGC GCTAACCGAT TGCGCCACAG AGACCCAGTT    114180
ACTCAGGCCG CGCTGCGGTG TGTACAGATT CCGCGGCGC CGGCAGCCGC TCTAGCCACC     114240
CTGGGCGTCG CCACCCCAGG CGTTGCCACC CCAGGCACGG GCTGAGAAGT CGCGGGGCGC    114300
GCCGAGGAGG CAGCGGAAGC GGCCGAGGTG CCCAGCGGCC GCCGCGGGGG GAGAGGCTGT    114360
GCCCCGGCGC GCGGGAGGGG GCGGGCGAGG CCGCGTGACT CCGGGCTTCT CTGGGGACGA    114420
AGCGCGCCCC TCGTGGCGGC AGCGGCCAGT GGTCCGCAGT CGGCCCGGAC TCGGGGTAGG    114480
AAAGATCCTC TCAGCAATGG CTGCGCGCCA TGCGTGCTCT GCGGCGGGGA CCGTGCCGGC    114540
CGGGCGCGCC ACCAGTAACC AGGGACCCAG GGGAGAACCT GCCAAGGGGA ATAGGTCGCA    114600
CGGAGAGAAT ACGACACGCT TGGAGGGAAG AACCACGTGC TGTACAGGTT TAAAGGATGG    114660
AGAGTCACGT GCGCTTAGGT CCCAAACTTA AGGGACCTAA CCCTTTTTCT GGGTTGCCGC    114720
TATTGCCCCT TCTCCTTAGA CAGTTTTTCA TCTCATCACC TCTCACCCCG TAAAATGCAA    114780
CGAACATAGA TAGGCTGTGT ATCAATGTAG ACTGTATGTA TATCTGTGCT TCGTACATAA    114840
AAAGAATATG ATTTTTGCCA CCTTCTAAGA ACCAATTTGC ACCCCATTTT GAGGCATATG    114900
GCCTCTGTTG AGATTGCATA GTTTAGGGGA CATCAAAAAA GCCTTATAGA GGGACTGGCA    114960
ATTAAGATAG CCTTTCAGTT TGAAATGGCC ATTGAAGGCT TCTCCCTTTC CTGACTTCT     115020
GAATTTTTTT TTTTTTTTT TTTTTTTTTT TTTGAGATGG AGTCTTGCCC TGTTGCTGGA    115080
GTGCAATGGC GCGATCTCGG CTCACTGCAA CCTCCGCCTC CCGGGTTCAA GCGATTCCTG    115140
CCTCAGCCTC CCGAGTAGCT GGGAATACAG GCGCCTGCCA CCACGCCCAG CTAACTTTTG    115200
TATTTTTAGT AGAGGCGGGG TTTCGCCATG CTGGCCAGGC TGGTCTGGTA CTCCTGACCT    115260
CGTGATCCGC CCGCCTCCGC CTCCCAAAGT GCTGGGATGA CATTACAGGC GTGAGCCACC    115320
GTGCCCGGCC AATTTTTTTA GGCGCACTGT TCAGTGGCAC TAAGTACATT CACATTGTTA    115380
TGCAACTATC ACCGCCATCC ATTTCCAGAA CCTTTTCATC TTCCGAAACA GAAGCTCCCT    115440
ACCCATTACA CGGTAACTCA CGATTCCCCT CCTCTAGTCG GAACAATCAC CATTCTACTT    115500
TCTGTCCCTT TGAATTTGAC TACTCTTAGA GACCTCATGT AAATGGAGTC ATACGGTGTT    115560
TGCCTGTGGC TGGCTTATTT CACTTACCAT ATGTCTTCAA GGTCCATCCA CGTTGTAGCC    115620
TGTGTCAGGA TTTCCTTCCT GGATAAGGCT GAATAAGCTG CACTGTATGC AGGTATCGCA    115680
TTTTGCTTTT CCATTCATCT CTCCGTGAAC ATTAGGGTTG CTTCCACCTG CAGCTATGAA    115740
CATGGGTCTA CAAATAACTG ATTCCCTGCT TTCAATTCTT TTGGGAATAT ACCCAGAGAT    115800
GGAGTAGCTG GATCACATGG TTTGCTATTG GCTGTACCAT TTTACATTCG CACCAACAGT    115860
GTACAAGAGT CCCTATTTCT CCTCATCTAT TTTTTTTTTA AATAATGGGC ATCCTAATGG    115920
GTATGAAGTA TCATCTCATT GTGGTTTTGC TCTGCATTTC TCTAACGATT AGTGGTGTTG    115980
```

FIG. 6.44

```
GGCATCTTTT CCAGACACCA CCAATCTGAA TTCTATGGCC CTTCGTTTAC TCACTTCCTC  116040
CCAGCAAGAG CCATTTCTGC TTCAGCAAGG AGGAAGCTGC GACTGATAGA GGGAAAGGGC  116100
CCAGGGGGCT TGCAGAGTGG GGCCTGTGCC ATGCAAGGAG AGGAGAAGAA GGTGGATCTT  116160
TGAGTAGGAC TATCTGGAGA TCCTGCTTTC ACAAGGTCCT TGCTTGTGTG CTGGGCAGCT  116220
TTTGGAGCTA GTTATCTTTA TTTTAGCCCT TGAGGGATAT TTAGGCATGT GGTGCTTGTG  116280
AGCAGCCAAT CCATGAAGAA GGAACTGATG GTCTCCACCT TGGAAATATT GGAAGAGATA  116340
ATGCCGTCCA AATTGCAGTT TTAGAAGTTA ACTTAAAATT ATGCTATTTT AATGGAATTT  116400
TGGGTGCATT TCCATTTTCT TCTTAAGAAT TGCTGGAATT TCTTAAGTGT TTAGGTGATG  116460
ATCTCTTTTT GTGATTCCTT TTTTAAAAAA CAACAACAAA ATCTTTCAAA TACATAAGAA  116520
ATAGGCCGGG CACGGTGGCG TAATCCCACC ACTTTGGGAG GCCGAGGAGG GCGGATCATG  116580
AGGTCAGGAG ATCAAGACCA TCCCGGCTAA CACGGTGAAA CCCCGTCTCT ACTAAAAAAT  116640
ACAAAAAATT AGCCGGGCGT GGTGGCGGGC GCCTGTAGTC CCAGCTACTC GGGAGGCTGA  116700
GGCAGGAGAA TGGCATGAAC CCGGGAGGCG AAGCTTGCAG TGAGCCTAGA TCGCACCACT  116760
GTACTTTAGC CTGGGCGATG GAGCAAGACT GTCTCAAAAA AAAAAAAAAG AAAAAAAAAG  116820
AAAGAAATAG ACCTTTATTT TTCTGTAACT CCACAAAATT TCTATTTTGA TTCCCTATTA  116880
TTTTGCTATT GTCAACACAG TCTCAGTCAA TTCAAGATCC TGTTTGTGCC TTTCCCTGGA  116940
GTCATTTCCA AGTGCTAAGG CTTTGGTCCA TGAGTCGCAT GTGCACACTC ATGGCTGTAG  117000
AGGGAGTTTT GCTCCCGGTG AAGGTCTTGG TGGCTCTTCT ATACCTTGAT TGAGGGAAAG  117060
GAATCTTATG TGAAGTTAGC TTTGTTGTAT CAGATATTCC ATAAAGCCAT TTCTGGGACA  117120
GTCCCCTCTG TTTATCGGAC CACAAGCTTC TCTGTCCTCA TCAAGCCCAC CTTTATACTT  117180
CATTTCTCCA GACTTCATGT CCAGACTGTG GGATGAACAA GTGGTTATAA GGTTTTAGAG  117240
GCTCCTGTAG GACTAGATGG AAGGCAAAAA AAGGAAATAA CCTTTAAGCA TGCTCTCGAT  117300
TCCTTAAATC CCATCTGAAA GTCTTAAGGA TGTCTTCTCA GTCATACTTA TTTGACAATA  117360
TTACCTAATT TTCTCCATTA GCCCAAGCTC AGGGGTCTTT CTTCTTCCAT ATTCACATGG  117420
GTGCAATGGT TTTCTGAAAG GAAAACAGCA TTACTAGGGC AGTAACATTT AATTAATCAC  117480
AGGTACTTAT CAAACTACAA AACAGGCATT CCAGGAACTG GGTGTTTCTG TTTGTAAAAT  117540
TACACTCTCG TGTACATGCT CCCACTAAAA TGTAAGTTCG CTGAGGATGG AGGTTTTGGT  117600
CTCTTTGCTC TGTGCTGTAA CCCCAACACT GCAGCAGGGC CTGGCACATA GCAGGCATGC  117660
AGGGACTATG CACTGAATCA ATGAGGAAAT GAAAACCAGG ACCATGAAGT AAACTGGACA  117720
AAATAAAATG TGATAGAAAA TCTAAATTCC TAATACATAA GGAGCACTTA TCAATTGATA  117780
TTTACAAAAT CTTTTTACAA TTCAATTAAA GACAACATAA ACAAATAAG AATGGGGACA   117840
GGAACAGAAA ATTCCCCCAA AGAAAAAAAT ATATATACAT GGTACAGCCA TTGTGGAAAG  117900
CAGTATGGAG TTCTCAAAAA TATTAAAATA GAACTATCAT ATAATCCAGC AATCCCATCC  117960
CTGGGTATAT ATCTAAAGGA AATGAAATCA GTACCCCAAA GAGGTGTCTG CACTCCCATG  118020
TTTATTGCAG CATTAGTTAC AACAGCCAAG ATATGGAATC AACCCATCAG CAGATGAAAG  118080
GATAAAGGAC ATGTGATACA TATACACAAT GGAGTAGTAT TCAGCCTTAA AAAAGAAGAA  118140
AATCCTGTCA TTTGCAACAA CATGGATGAG CCTAGAGAAC ATACTAAATG AAATAAGCCA  118200
GGCATAGAAA GACAAATGCT GCATAGTCTC ACTTAGGTGT GGAATCTAAA AAAGTCAAAT  118260
TAAAAAAAAA TGTCAAGCAG AGAATAGAAT GGTAGTTGCC AGGGACTCTG GAAGTAGCA   118320
GGGGTGGGGG TGGAGGGGAG GGGATGGGCA GAAGTTGGTC AAAAGGTACA AAGTTTCAGG  118380
TAGACAGGTG TAAGTTCTGG GGATCTATTG TACAGCGTGG TGACTGTAGT TAATACTGTA  118440
TTGTGTACTT AAAAATTGCT CACCAAAAAT GTTCTCACCA AAAAAATGAT GTTTGGATAT  118500
GTTAAACAGT TTGATTTAAT CATTTTGACG TGTGTGTGTG TGTGTGTGTG TGTGTGTGTG  118560
TGTATACATC AAAACATCAC ATTATATACC ATATACAATT AATATATACA ATTTTTGTCA  118620
```

FIG. 6.45

```
AAGAAAAAAT GCACATGACC AATATGATAA AAGTTTAGTC TCACTAGTAA TAAAAATCAA  118680
AATTAAATGA AATAAAAATT TCTTTCCCCA AATCGCAAAA GAGAAAGAAA GGTAATACTA  118740
AAACACAGTC ACGGTGTAGT GAGAGGGCTG CTCTCACACA GGACTGATGA GAATAAAATT  118800
GGAGAGCAGT GTGGTAATAT ACATATTAAA CAATGTATAT ACCCTCTCAT TTTAGAAATT  118860
CTATATTAGA AATCCATCCT AAGAAAATAA CCAGGGATGT GATCAAAATT TTGAATGCAG  118920
CAGCACAGTA TTATTTATAA TAGTTATAAA TAAGAAACAA CCTGAATGTC CAGCAACAGG  118980
CAAAAATGAT AAATAAATTG TGGCATATTT AAGCTGGTGG CTCATGCCTG TAATCCCAGC  119040
ACTTTGGGAG GCTGAGGCAG GAGGATCTCT TGAGGCCAGG AGTTTGAAAC CTGTCTGGGC  119100
AACATAACGA GACCCAGTCT CTACAACATA TTTTTTAAAA TTAGGTGGGG CATGGTAACT  119160
CATGCCTGTA ATCCCAGCAC TTTGGGAGGC TGAGGTGAGC AGATCACCTG AGGTGAGGAG  119220
TTTGAAACTA GCCTGGCCAA CATGGTGTAA CACCATCTCT ACAAAAAATA CAAAAATTAG  119280
CCAGGGTGGG GTGCGTTCCT GTAGTCCCAG CTACTCGGCA GACTGAGGTA GGAGAATCAC  119340
TTGAACCCGG GATTCGGAGG TTGCATTGAG CTGATATCAT GCCACTGCAC TCCAGCCTGG  119400
GTGAGACCCT GTCTCAAAAA AAAAAAAAAA AGAAAAAGAA AAAATTAGCT GGGCGTGGTG  119460
CTGTACGCCT GTAGTCCCAG CTATTCCGGA AGCTGAAGCG GGGGATTGC TTGAGCCCAG  119520
GAATTTAAGG CTGCAGTGAG CTATGATTGT GCCACTCCGC TCCAGCCTGA GTGAGAAAGC  119580
AAGACTCTGT CTCTTAAAAA AAAAAAGTG ATATATTTTT AAAATAGAGT ATATTACTTA   119640
TATAGACATC AAAAACAATA TTTTCAAGGG ATATTTAAAA ACATAGGATC ATGACAAAAT  119700
GTAAAGTTCA AAGGTAAGAT GGAGAATGGA GAACTGTGGG GAACTGTATA ATCTGACAAT  119760
TCGTAGTTGC ATACATCTTT CTGTGTGCTG GTGCTGTTAG AACACTTTGT ACGCATCACC   119820
TCATTTAAGT TCAGCATCCC TAGGTGGCAG ATACTATTAT TATATTCCAG TTTTGTTTCA   119880
CGTTGTATAT GCGGTGTGAG CCCCAATATG GGATGTGTGT GTGCACATGT GCAGTATTTG   119940
GAAAGTTCTA TGAAATATTA TTAGTGGTTA TCTCTGGGAG GTGATTTTTA TTCCTTTTCC   120000
AGTATGTTCT CAAGCATTTG CTGCAAGCAG TCTTTTGCGG GGCCAGGGTT GAGAGGCAGC   120060
AGCAGTTTCC CTAAATTACA GATAGAGGGA GGTAGGTGGT TATGCTTGGC CAGATCTCTG   120120
TCTAGGGGTA GAGGAGTGCC TGTGTGTGGG TAGGGACACC GGCGGGGGGC TTTGCCAAAC   120180
ACAGTGGAAC TGTCACGCTG GTCTCTCTTC TCAACTCTTT CACTCACCTG AGAAAAGGGT   120240
GTCTATGGAC CATGCACACT TCTGTGGGGA ATTTTACAAG ATGTGAATCA TCAGTGATGA  120300
AGATGCTTTC ATTTAAAAAG AATTGGAGTA CCTGAGATTA GAGATAACTT CTACCCTTTT   120360
AAAATATTTT TAAAAATTTC TTTGCACTGA TTTTTTTTCT TCGTTTTTAT GAGTTGTTTT   120420
CATTTGGGTG GGATAACTCA ATCTACAGGA GAATATTAAG ACTTTTTAAA TTTTAAAAAA   120480
TATACTTTCA AATACTTAAT ACATTTGTG TTAAATGACA GCCAGCAGAT ATTGACTGAA    120540
TTGGGCTAGA TGCTTCAGGG ATCTCCCTTC CATTTAAGAC TCTCCGAGAG GCCATTCCTG   120600
ACTGCAGGTC ACTGTATTAT TTTTAATTTT AAAATTTTTA CTTACTTATT TTATTTAATT   120660
TTATTTTTTG AGACAGAGTC TCACTCTGTC GCCCAGGTTG GAGTGCAGTG GCACAATCTC   120720
AGCTCACTGC AACCTCCACC TCCCGGGCTC AAGCGATTCT CCTGCCTCAG CCTCCTGACT   120780
AGCTGGGGTT ACAGGTGCAG GCCACCACAC CCCGTTAATT TTTGTATATT TAGTGGAGTC   120840
AGGGATTCGC CATGTTGGCC AGGCTAGTCT CAAACTCCTG ACCTCAAGCG ATCCTTCCAC   120900
CTCAGCCTCC CAAAATGCTG GGATTACAGG CCTGAGCCAC CCCACTCGGC CTACTTTATT   120960
AATCCACTTG CAGAAACAGG ATATACACAA AAACGTTTCA AGGCTGTAAG TGCCACTGCA   121020
TGGCACCAAT GGTAAACGTT TTACAAATTT GAGTCAGGAA CAATCATTAG TGTCACTAGC   121080
AACAAAAATC AAAATTAAAT GAAATAAAAA ATTTCTTTCC CCAAATGGCA AAGGAGAAAG   121140
AAAGGTAATA CTAACACGCA GTCAGGGTGT AGTGAGAGGG CCGCTCTCAC ACAGGACTGG   121200
TAAGTACAGA GCCATGGAGT AAGCAGGTCT TGAGCTGACA CTGGAGAGGA TCCTTTTTTT   121260
```

FIG. 6.46

TTTTTATTTT TATTTTTTTA GAGTCAGGGT CTTGCTTTTT TACCCAGGCT GGAGTACAGT 121320
GGTGCCATCA TAGCTCACTG CAGCTTCAAA CTCCTGGGCT CAAGAGATCC TCCTGCCTCA 121380
GCATCCCCAG TAGCAGGGAC CACAAGTGAG AGGATCCTTT AGTGTTGTCA AGGAGAAGGA 121440
ACAGAGGTGT GGATGGGTGG GCACAGACAC AGGAGCACAG CTGAAGCAGA GGATTACAAA 121500
GGGTGGAGCC TGATGTAAAG AAACCTAATA GGTGACAGAG CATGGAGGCT CTTGAATACC 121560
AGGCTGGAAA CTGCATTAGG AACGGTGCTC ATAATTGCAG AAAATTTTAC ATGGCCTAGA 121620
TAGTCATCAA AGGATGATGT ACAAACAACT ATGGCATATT TATACAATGT GCCGACAGGA 121680
TGCACTGAAC ATTTTGAACA ACAAAGAGAC TTGATAATGG CGAGGTTTTG AGGAGGTGAA 121740
TCAGGATGCA AAAAAAGCAA ACAACTAATA AAGTTGATTG ATGACAAACA CTATCAAAAG 121800
GCAGCCAGGA GAAAAGCTAC TGGTTACCTC CAGGGAGCTG GTGAGGGAGG CTGGGTGGGA 121860
GGATCTACCC TTCTGAATTC TGAGGGCACC TCCAGTGTGG CCCTCAGAAA GCAGGAGCTT 121920
CCAGGCTAGA ATCAGATCCC GACATCCCTG TTAATTCCAC GGATTCCACA CCGAGTCAGA 121980
TTTATGATTT ACTATAGGGT TTTAAAAACC AAATTGCAGG GATGCTAGCC TATCACAGCT 122040
TATCTCAGAC ATTGTCCACT AAGGTATACA GAGTGCTGCC TGTTCCTTTG GTACCCTAAT 122100
CAGGAAACCC CATCAGATCT GCTCCTTCCT ATGGGGTAGT GAGTAACACG AAGGCTTACC 122160
ATCTCACACA GATAACTGGT CATAGGTCCA GCAGAAGTTT AAAACAGAAA ATGAGGAAAG 122220
CCATGTGATT AACTGCTGCC AGACTGTTTG TGTTACAAAC AGCAGTTCCT TAGGCATTGC 122280
CTGGGACATG CAATAATTTC TGTTACACAA TCTGTGGTAG TTAAAATGCT GCACGATGAA 122340
AGCTATCTGA TTTGGATTCA TTATTAGGTG AGCCATCTCG TCTGCAATTT GGTTCCACCA 122400
TTTTCATTTA ACAAATGTAA AAAAGTTTAT TAAGCTCTTA CAAAGTTATG CTGGGCAAAT 122460
ATGCAAAAGT CCAGATCACC TACCGCAGGA ACTAATCTAG CCTCCTCTCT GGGCACCCTG 122520
TTGTTTGGGG CTGGGCAGTT CTTTCCTGTG TAGAACCATC TAGGGCTGAA TAGGTCATTC 122580
TGACACCTGG GCACCTCTGC CTGCTCGTAA ATGGGACAAT CAGAAAGGGC CCTTATGTTT 122640
CCAAACTTTC TTTAAAGTAG CTGTTCTGAA AACATGGTCC AGGGACCCCT GATTGTCCCT 122700
GAGACCTTTG AGGGGATCTT CAAGGTTAAA ATTAATGTCA TAATAATACT AATATGTTAT 122760
CTGTCTTTTT TCACTCTCAC TTTCTCACAC GTGAACAGTG GCATTTTCCA GGTGACAGAG 122820
TGTGTGATAA TGAACCTAAC TGAATGCAGA AGCAAACATG AGAACCTAGT TTTTTCAATC 122880
AAACCAGACG TGAAAGAGAT TTGCAAAAAT GAAAAAACAA TGCTATCCTC CTCACAATAT 122940
TTTTGTTTTA GAAAATAAAG TTATTTTTCC TAGAAATGTT TTTGAGTTTA TCAGTCATAG 123000
GTTTATTATT ATAATTAAAA AATGAAATAT ACATACACAG ACATATTTTT TAAAGTTCTC 123060
AGTTTTAATC TCTTTTTTTT TTTTTTTTTT TTTGAGACGG AGTCTCGCTC TGTCGCCCAG 123120
GTTGGAGTGC AGTGGTGCGA TCTCAGCTCA CTGCAAGCTC CGCCTCCCTG GTTCGCGCCA 123180
TTCTCCTGCC TCAGCCTCCC GAGTAGCTGG GACTACAGGC ACCCGCCACC GCGCCCGGCT 123240
AATTTTTTGT ATTTTTAGTA GAGACGGTGT TCACCATGT TAGCCAGGAT GGTCTCGATC 123300
TCCTGACCTC GTGATCTGCC CACCTCGGCC TCCCAAAGTG CTGGGATTAC AGGCGTGAAC 123360
CACCACGCCC GGTCTCAGTT TTAATTTCTA ATACAGTAAG TATTGATCAG TGTGCCCCAC 123420
ATTAGTAAAA GCTCTTGGGG TCCTCAGTAC TTCTTTTTAA GAGTTGTCAA GGAGTCCTGT 123480
GACCAAAAAT AGGAGAGCCA CTGCCCTAGA AGGACAGCCC CAGCCCGGGT CAGGAACAAC 123540
TGGGACAGAA CCTACTGCTC CTAGTGGATT GTAATATGAT AGGATTTAAC CTTCAAGGTT 123600
TCAACTCTTG GCAAGAGTCC ATGAGGGGCC ATGGTTTGTC CTGAGCATTG CTTACTGTTA 123660
ACAGGAGCAA GTTCCTTAGG CTGGTGAGCC AAGCCAGCCT GACGCTGGCC ATGGACATCT 123720
TAGTGGGCTG CTTGTTCTAG TGTGGGTTTT CATTTTATGG GAAATGTCAT CTGCTCTAAG 123780
GCTCTTCTCA TTTGGGGAAA TCACAAGTTC TCAGAATGTT TGTCTCTCTT GGTTGGGGCC 123840
TCTATAATTA AATTATAAAA CAGAGGTAAT GGTTAAGTAA TGCAAGATTT GACAGAAACC 123900

FIG. 6.47

| | |
|---|---|
| ACAGAGGATT TAGGGTTTAA TTTGAGTGAG GCAAAGGGGG GATGAAGATG AGCGGTCCTG | 123960 |
| GAGACAAGAA AAAGATTGGA TGAAGCTGGG CACGGTGGCT CACGCCTGTA ATCCCAGTAC | 124020 |
| TTTGGGAGGC CAAGGTGGGC AGATCACTTG AGGCCAGGAG TTTGAGACCA GCCTGGCTAA | 124080 |
| CATAATGCAA CCCCGTCTCT ACTAAAAATA CAAAAATTAG CCAGGCGTGT TGGTGTGTGC | 124140 |
| CTGTAGTCAC AGCTACTTGG GAGGCTGAGG CATGAGAATC GCTTGAATCC GGGAGGCAGA | 124200 |
| GGTTGCAGTG AGCAGAGATC ATGCCACTGC ACTCCAGCCT AGGCAACAGG GTGAGACTCT | 124260 |
| GTCTTCTTTT TTTTGAGAC GGAGTCTGTC GCCCAGGCTG GAGTGCAGTG GCATGATCTC | 124320 |
| TGCTCACTGC AAGCTCCGCC TCCCAGCTTC AAGCGAGTCT CCTGCCTCAG CCTCCCGAGT | 124380 |
| AGCTGGGATT ACAGGCATGT GCCACCACAC CCAGCTAATT TTTATATTTT TAGTAGAGAC | 124440 |
| GGGGTTTCAC CATGTTGGTC AGGCTGGTCT CAAACTCCTG ACCTCGTGAT CTGCCCGCCG | 124500 |
| CGGCCTCCCA AAGTGCTGGG ATTACAGGTG TGAGCCACCA TACCTGGCTG AGACTCTGTC | 124560 |
| TTTAAAAAAA AAAGAGAGAG AGGGAGAGAA AGATTGGATG AAACAACAGA GTGGGGAGGA | 124620 |
| CCTGTGAGCT TGGTAGCTTG GTGAAGGCAG GGCTTTATTG GGGGCCTTAG AGGGGATCCA | 124680 |
| ATAAAGGTTC CCAGTCATGG TAGTGACCTA AAGAAAATAG CATTTTAACA TCTTTCATTT | 124740 |
| CATAATAGAC AGTCACAGTT TACAAGACCC TTTCCATACA TTCCTTATGA CATCCATACT | 124800 |
| ACAGCCCAGA GGCAAGTTGT GCACTCTCTC CTCTCACAAA TACAAAAACT CAGCCTCTAG | 124860 |
| AGGCCAGCGA CCTGCTCAGG GTGATGTGCA ATTCAGGGAT GACAGAGTCG AGGCTCCCAG | 124920 |
| CCCAGTGGTT ATCCCTCACA GGCACGTTGC CTGTCAGTGT GCAGTATAAA ACTTTGTACA | 124980 |
| AGAAATCAAG TTGCATTAGT CAGTCGGATT CCCCAAATGA TCACATTGTA GATGGTGTAT | 125040 |
| GCTGTGGGCA GAGCAAGGGC TGCTGTTTCT TGGGCAAAAC AATCAGTCCC CCTCCCCCCC | 125100 |
| AAAATAAATG AATGCCAATG GTGTGACTTT ATTTTATTTA TTTTATTTTT ATTATTATTT | 125160 |
| GTGAGACAGA GTCTCACTCT TTCACCCAGG CTGGAGTGCA ATGGCATGGT CTCGGCTCAC | 125220 |
| TGCAACCTCT GCCTCCTGGG TTCAAGCGAT TCTCCCGCCT CACCCTCCCG AGTAGCTGGG | 125280 |
| ACTACAAGTG CATGCCACTG CACCCGGCTA ATTTTTGTAT TTTTTTTAAG TAGAGACAGG | 125340 |
| GTTTCACTAT GTTGGTCAGG CTGGTCTTGA ACTCCTGACC TCATGATCCA CCTGCCTCAG | 125400 |
| CCTCCCAAAG TGCTGGGATT ACAGGCATGA GCCACCGCGC CCAGCAATGT GACTTTATAA | 125460 |
| TTACAGAATG TAGGACTCAG CTCCCACTAT TGTTATGACT CAATATTCTC TTAGATAATG | 125520 |
| TTTGGGGCAC TAGCTTACAG GCAGCATTGC CCGGTGGTTA ATGTTGTAGC TTTGCAGGCA | 125580 |
| GACTGACCAT ATTAAAATTC GATCACACCA TTTGCTAAGC CTGTGGACTC GGGCACGCTT | 125640 |
| CTTTCTCTGC GTTAGTTTCC TCCTCTGTAA AACACGGATG ATGCTATAAA CACACCCAAG | 125700 |
| TCCTAGAATT GTTATATGAG TTAGAAAAGA TAGGCAAATA CAACTCTCAC AAGACAGCCT | 125760 |
| GGCCTCCAGT AAGTGCCACT GAGTGTTTGC TCTTATTGTA CAGTGGCTCC AAGTGCTTCT | 125820 |
| GTCTTGGATT ATTTCTGACC AGGTGGCTAT GTCTCCTAGT AACTTACCAA TCCTGTTGAG | 125880 |
| TCTTAATAAG CACGTCTTTG ATGCCTACAG TGCGACTGAA TTTCCAGGCC TCATTACTGG | 125940 |
| AGACACAATC ATCCTATATG CTTTTTTCCA TTTGTTTTTA ATAAAGTGGT ACATGTGTAT | 126000 |
| GGCACCAGAT CAAACAGTAC AGAACAAGTT ACAATGGAAG AGAATGGCCT CCCAGCTTTC | 126060 |
| CTGAAATCCT CAACTCAGAG ACAACTTTTT TTTTTCTGAC GGTTCTTTA TACAGCCCTT | 126120 |
| TTTGTGGTTA CCTTCCTAAC TCTAGAAAAA CTATTCTTAC CTCTGTTTAT TTACTTAGAA | 126180 |
| ACATTAGACG TTACCTTTCA ACTCCTCAGT ATGAAGCTTT AGTTTTCAGC ACCCCAGGCC | 126240 |
| ACCACCCTCT TTCCAGGACT TACTACTTAT ACTGGTGGTA GGTGGAATTT TAAAATTCAT | 126300 |
| CAGCATTCTT TTGTGATTCT CTGTGTGTTC CAGTTTTACA GCAACCCGTA CTTGTTGCAT | 126360 |
| GAGTACAGTA GAACTGGGAG GCTCATAACT TAGCCTGCAG GACTTTTCAC TTAAAGCCTG | 126420 |
| GCCCTCAGGG TGATGTCACC CACCTCATTG TGCCTGGCTC AGGAGTTTAG TCCCTCAGTT | 126480 |
| GCCTGGTTGT ATAGTTTGGA TGTTCAGCAC CTCCAAATCT CACATTGAAA TGTGATCTCC | 126540 |

FIG. 6.48

```
AATGTTGGAT GTGGGGCCTG GTGGGAGGTG TCTGGGTCAT CAGGTGGGTC CCTCTTGAAT   126600
GGCTTGGTGC CTTCCCCATC GTAACGAGTG AGTTCTTGCT CTGGCAGTTC ACACAAGAGC   126660
TGGCTTTTTA AAGGAGCCTG GCACCTTCCG CTCTTTCTCT TGCTCTTCCT CTTCCCTTCC   126720
TTTGTCACTA AAAGCTTCCT GAGCCCTCAC CAGAAGCGGT GCAGATGCTG GTGCCATGCT   126780
TGGACCTCCT GTAGAACTGT GAGCCAAATA AACTCTTTCC TATAAATTAC CCAGTTTCAG   126840
GTATTCCTTT ATACAATGCA AAACAGACTC ACACATCTGG TAAACCCCAG TTGTTTGCTT   126900
CTAGGTAAGA CGGGAGGAGT GGGGAGCTGG TGAGGGTTTC CACTGCATTG TCTATTTTCA   126960
GGCAAGGTGT CTCCACTGAG TAGGCTTCAC ATTCAGAGCT CTGGGTAAGG TGGGCAGGAA   127020
GAGGGTTGCA GGCTGCCCAA AGGAGGGAGA GAAGAAGGCT GAATCCTTCA GTGACAACCT   127080
GTGAACCAGA GTCTTAGCTC TCTTTGAATA TTTTGTTCAG TATCTTTGGG TTTTGTTTTA   127140
TTTTGCCTAG GGGTAAATGC TGACTGCCTG TTCTCTGGAC AGGAATGGAG AAGATGGTGC   127200
TAGCAGGGTT GCTGTTCATA TGTAGACATT CATGCAGTCA CTCTCTTTTC AGCACACTTC   127260
TTACTTCTGC CCTGGGTTCA GTTGCTGACT CTGAGCCCAG AAACCTTCTA GGGTTCTGTT   127320
AGGTAGATTG GCTTCCACCG TCTTTGCGAC AACCACAGAA AATTCTAGAC TGTTTTCTCT   127380
TCGGGCTTCA TTAGTCAACT TGCTTCAGTC TGTCTTGCAT CTTCTAAATA TTTATAGATC   127440
TCTCTCTTTT GTTGGAGTGG CAGAAAATGC TAGTTGACCA CCCAATATTC AAATTATCCT   127500
GCCTCCTTAA TAACAGAATA TCATTGGATG TGGTGGGTAA ATAATATACC CTAACTTTCC   127560
TTGCAGAGAG GGGTGGCCAA TGAGATGGAA ATGAAAGTCA TTGGGAAAGA CTCCCAAGAC   127620
ATCTCTTTAA ACAAGACAGA CTGAAGCAAG TTGACTAATG AAGCCCAAAG CTAGCAGTTG   127680
TTTTTGTTTA TCTTTGCCTC TTTCTTCTTC TTCCTGTGGG GACAAAGGGC AGTGATATCT   127740
GGAGCTGCAG CAGCCATTTT GGCATAATGT TGGAAAAGCC AAGAGACTCT CAGAGACCGC   127800
AGCTCCAGCA GTTTTTTATT TTTTCCAAAT ATTTGCTCCA CTGCAGGAGG ATGAGATATT   127860
CGTGTTTGTT GCCTTGTGAC TGTAGGAGGA CTGCACTTCC CTGCCTTGTT GTCAAGTTTC   127920
CCCATGTGGT CTGCTTTGGC CAGTAAAACA TGAGTGGGAG AAGCTTGGTG AACCATTGCA   127980
TGTCTACCAG CTTTTTTGCT CTCTTCCCTT TGGCATTAGA AAGGCATGTC CAGGATGGAG   128040
TTGTTCCTTC AGCCTAGATT GGGTTATGAG AAGCTAGCTG GGGGAGTCCA GTAACATATA   128100
AAGCGAGTTA GAAATAAAAC TTTGTTGTTG TAAGCTATAT ATATATATAT ATATATATAT   128160
ATATATATAT ATATATATAT AATATGTATG TAATATATAA ATACATATTA TACTTTAAGT   128220
TCTAGGGTAC ATTTGCACAA TGTGCAGGTT TATTACATAG GTATACATGT GCCATGTTGG   128280
TTTGCTGCAC CCATCAACTG CTCATTTACA TTAGGTATTT CTCCTAATGC TATCCCTCCC   128340
CAGCCCCCCA CCCCTCAACA AGCCCTAGTG TGTGATGTTC CCCTTCCTGT GTCCAAGTGT   128400
TCTCATTGTT CAATTCCCAC CTATGAGTGA GAACATGTGG TGTTTGGTTT TCTGTCCTTG   128460
TGATAGTTTG CTGAGAATAA TGGTTTCCAG CTTCATTCGT GTCCCTGCAA AGGACATGAA   128520
CTCATCCTTT TTTATGGCTG CATGGTATTC CATGGTGTAT ATGTGCCACA TTTTCTTAAT   128580
CTAGTCTATC ATTGATGGAC ATTTGGGTTG GTTCCAAGTA TTTGCTATTG TGAATAGTGC   128640
CGCAATAAAC ATATGTGTGC ATGTGTCTTT ATAGTAGCAT GATTTATAAT TCTTTGGATA   128700
TATACCCAGT AATGGGATCA CTGGGTTAAG TGGTATTTCA AGTTCTAGAT CCTTGAGGAG   128760
TCGCCACACT GTCTTCCACA GTGGTTGAAC TAATTTACAC TCCCACCATC AGTGTAAAAG   128820
CATTCCTATT CCTATGTCTC CACATCCTCT CCAGAATCTG TTGTTTCCTG ACTTTTTAAT   128880
GATTGCCATT CTAATTGGCC TGAGATGGTA CCTCATTATG GTTTTGATTT GCATTTCTCT   128940
GATGACCAGT GATGATGAGC ATTTTTTCAT GTGTCTGTTG GCTGCATAAA TGTCTTCTTT   129000
TGAGTAGTGT CTGTTCATAT TGTTTGCCCA TTTTTTGATG GGGTTGTTTG TTTTTTTTCT   129060
TGTAAATTTG TTTCAGTTCT TTGTAGATTC TGGATATTAG CCCTTTGTCA GATGGGTAGG   129120
TTGCAAAAAT TATCTCCCAT TCTGTAGGTT GCCTGTTCAC TCTGATGATA GTTTCTTTTG   129180
```

FIG. 6.49

```
CTGTGCAGAA GCTCTTTAGT TTAATTAGAT CCCATTTATC TATTTTGGCT TTTGTTGCCA   129240
TTGCTTTTGG TGTTTTAGAC ATGAAGTCCT TGCCCATACC TATGTCCTGA ATGGTATCGC   129300
CTAGGTTTTC TTCTAGGGTT TTTATGGTTT TTAGGTCTAA CATTTAAGTC TTTAATCCAT   129360
CTTGAATTAA TTTTTGTATA AGGTGTAAGG ATGGTTTCCA GTTTCAGCTT TCTACATATG   129420
GCTGGCCAGT TTTCCCAGCA CCATTTATTA AATAGGGAAT CGTTCCCCA TTTCTTGAGC   129480
TACAGATATT TTGAGTTTGG TTACCACAGT ATTATCTAGT GGAAGTTGAC TTATACAGTA   129540
TGTAATAGGA TAAATATAGG TGTGTAACAG AATATTAAGT GTTCGTGTTT CAAAGCTGAG   129600
GGGAAAATGT TAAAAGTGTT CACACACTCT AAAAAGAGAT TAGCTAAAAC TGCTTCATTA   129660
ACCACACTTT GGGGAAACCA GTTCTGAGAT TCTTCTCCAT TACTCTGACA GGTTGGACCC   129720
TCTGGGGAGC AGATCTCAAG ATCAAGTTAT GAGTGCAAGA GGTGTGTTGG AAGCGATGG    129780
TTGTAAAAGA ATCCTGCAGT AGCACCAGGC ACAAGTCTGT CCAGGGAGAG GAGGACTTCT   129840
ACTCTCTACC AGCATCTCTC CTAAGTCCCC TTAGGGGACG GGGGCAAGGA AGTGCTGGGA   129900
AGGGCAGGGC ATGGTTCCTG GCTAGGACTC CACCCCCCTG GGGCCTGTAC CACGGACCT    129960
AGGTGAAGAC AGGCACTCCT GCCTTCTCGC CAACGGTTG CGTTTCCCAA GATCATCCTG    130020
GCCTGCCACG CCCCCATCTA CCTATTAAAC TCCCCCACCT TCCCCAAACC CTAGCAGGCA   130080
GACACACATC GGTGGAAGAA GACAGGAGCG GCTGGACATT GAAAGGACGT CGAGAGGAGC   130140
ACACCTGCAC ACCATCGACC AGCGGAACGA GGCAGAGTGT GGCTGGAGCA GTCGGAGGGA   130200
AGCCTGGGCC GCTGACTCCA GGGGAAAACC ATCTCCTTTC TGGCTCCCCC CTCTGCTGGG   130260
AGATACTTTC ACTGAATAAA ACCTTGCACT CATTCTCCAA GCCCACCTGT GATCCGATTC   130320
TTCCTGTACA CCAAGGCAAG AACCTGGGAT ACAGAAAGCC CTCTGTCCTT GTGATAAGGT   130380
AGAGGGTCTA ACTGAGCTGG TTAACACAAG CTGCCTATAG ACAGCGAAAC TGAAAGAGCA   130440
CACAATAGCA CACACTCATT GGGGCTTCAG GAGCTGTAAA TATCCACCCC TAGACGCTGC   130500
CATGGGGCGG GAGCCCCACA GCCTGCCCGT CTAGAGGTTT GAGCAGCGGG ACACTGAAGA   130560
AGAGAGCCAC ACCCTCATCG CACGTCCTGC GAGGGAGACA AGGGAACTTT TCCGGTTTCA   130620
CTTCTGCTTG GCTTGAGCTG GCACTGAAGC ACCCTTTTCC CTCCTCACTG AGGGAGCAGA   130680
GGGGAAAAGC GGTAGAACTA ACAGGCTAAC AATGCTCCTC CGAAAATATA TCGTATTTTT   130740
GGATCCCTAG AGATAGGTGA TCACGGCAGC CGCGGAGTGC ATTTGGGTCT CCTTTCAAGA   130800
AAGAACTTGC TGCTCAGCGT TGAAGAATGC AGTTGGCCAA CAGCCTCCAG CTGCTCTGTC   130860
TTCAGCATCT GCCATGGCAT CTGAGCTGAG GTCATGTTCT TCCTGGGAGG TCCCCAGCAG   130920
AAGGATCACG TGGAAGCTCC ACAAGCTCCA CAGATGTTCC AGGAGAGGAA TAGGCAGCAT   130980
TTGGAAGACA TATCCTGCCA TAACAGAGGG CATTTGCTAG TAGAGACAAC AAACAGCAAC   131040
AGCCAAGTAA ACAAACACAC AAGCACAAAG CACTTTCTCC CATTTCCCCT CATTGATCCT   131100
GTCCGGGTAG AAGCTGGGGA GGAAGTAGAA TAGGGTGAGG CGGGGTGGGG CTGGGGGGCC   131160
TACACCTTCT TCCTTCCCCC GCAGGTCCTG TCCCTGGGCC AGGCTTGAAC TAGGGGAATG   131220
GGAAAAGCTG TGAAGTGAAT GAGAATTAGG AGTTTTTATT TAGACTGGAC TTGAATTTTT   131280
TTTTTTTTTT TTTTTTTTTT GAGACAGAGC CTCGCTCTGT CACCCAGGCT GGAGTCCCGT   131340
GGCGCCATCT TGGCTCACTA CAGCCTCTGC CTCCCGGGTT CAAGCGATCC TCCCACCACA   131400
GTCTCCTGAG TAGCCGGGAT TACAGGTGCC TGCCACCATG CCCAGCTATT TTTTTTTTTT   131460
TTTGTATTTT TAGTAGAGAC AGGGCGTCAC CGTGTTGGCC AGGCTGGTCT CGAACTCCTG   131520
GCCTCAAGTG ATCTGTCCGC CTCGGCCTCC CCAAGTGCTA GGATTATAGG AGTGAGCCAC   131580
CACGCCTGGC CTGGACTTGA ATTTTTAATT CCTAAAAATG AACTACCAGT TAAAATTTAA   131640
AAATGACCAA AAAAGCTATG GATATGCTG ATGTTTTGCT TTGGGGATAA GGAAAAGATA    131700
TCTGGTTGAG CGGCATTGAA AACAGTGTAG GGAGAGAAAA ACTCATTCCT GGCTCACCCT   131760
TTTGAGTCCC ACTATCTCAA TAATCTGATG TTATATGACA CACACACACA CACACGGAGG   131820
```

FIG. 6.50

```
AATCCTGGAA GACTCCATAT CAAGGTGGTG ATGAAGGTGA CCAGTGGGTG ATAGGATTAT   131880
AGGTGTGTGT TTATTTATTT ATTTTAATTA CCTTTTTTTA GAGACAGGGT CTCTGTCATC   131940
CAGGCTGCAG TGCAGTGGTG TGATCATGGC TCACTGCAGT CTTGCACTCC AGGGCTCAAT   132000
CCTCCTGCCT CAGTCTCCTG AGTAGCTGGA GCTGCAGTCA TGCACCAACG TGCCCAACTA   132060
ATTTACTTTA TTTTATTTTT TATTTTTTGT TAAGATGGAA TCTCACTTTA TTGCCTAGGC   132120
TGGTCTTAAA CTCCTGGTTT CAAGCATTCC TCCTACCTCA GCCTCTCAAA GTGCTGGAAT   132180
TACTGCACTT GGCCCTATTA TATTTTTAAA AAATTTCAAT AGTTTTAGGG GTAAAAGTGG   132240
CTTTGGTTAC ATAGATGAAT TGTATAGTGA TGAAGTCTGG ATTTTTAGTG TACCCATCAC   132300
CCAAATAGTG TACATTGTAC CCAATGAGTA GTTTTTCATT CCTCACCCCC ACACTGTCCC   132360
CACTTCTGAG TCTCCTGATG TCCATTATAG CACCCTGCTT TGCGCACTT AGAGCTTACC    132420
TCCCACTTAG AAGTGAGAAC ATGTGGTAGT TGGTTTTCCC TTCCTGAGTT ACTTCACTTA   132480
GGTCAGTGGC CTCCAATTTC ATCTGAGTTG CTGCACATAA CATGATTTCA TTCTTTTTTT   132540
GACTGAGTAG TAGTCCATCT CTCTCTCTCA CACACACACA TACACACACA CACACACACA   132600
CACACACACA CACATTTATC CACTCATCCA TTGATGGGCA CTTAGGTTGC TTCTATATCT   132660
TTGCAATTGT GAATTGTGCT CCAATAAACA TACATGTGCA AGTGCTGTTT TTTCTCCCTT   132720
TTATCCTTCT TTTCTTCCCT ATGCTTCCAT AGGTACTGAG AAAGAGTCTT TTTTATATAA   132780
TTATTTCTTT TCCTTTGGGA AGATACCCAG TAGTGGGATG GCTTGATCCA ATGGTAGATC   132840
TGTTTTTAGT TCTTTGAGAA ATCTCCATAT TATCTCCATA TTGTTTTCCA TAGAGATTGT   132900
ACTAATTTAC ATTCCCACCA ACAATGTATG TGTTCCATTT TCACTGCATC GGCACCAACA   132960
ACGGTTGTTT TTTGACTTTT TAATAATGGC CATTCTGGCT GGGGTAAGGT GGTATCTCAC   133020
TGTGGTTTTA ACTTGTATTT CCCTGATAAT TAGTGATGTT GAGCATTTAA GAAATATATT   133080
TGTTGGCCAT TTGTATATCT TCTTTTAAGA AATATCTCTT GAAGTTGTTT GCCCACTTTT   133140
TAATGTGATT ATTTGTTTTT TTTTCTTGCT GATTTGTTTG AGTTCCTTGT AGCTTCTGAA   133200
TATTAGTCCT TTGTCAGAGG TATAGTTTGC AAATACTTTC TCCCATTCTG TAGGTTGTCT   133260
CTTTACTCTG TTGGTTATTT CTTTTGCTAT GCAGAAGCTT TTTAGAATAA TTAGGTCCCA   133320
TTTACTTATT TCTGTTATTT TGTTGCATTT GTTTTGGGG TGTTAGTCAC AAATTCTTTG    133380
CCTAGACCAA TGTCCAGAAG AGTTTTTCCT AGGTTTTCTT CTAGAATTTT TATGGTTTCA   133440
GGTCTTAGAT TTATGTCTTT AATCCATCTT GAATTAATTT TTGTATATGG TGAGAGATAG   133500
GAACCCGGTT TCATTCTTTT ACACTACATG TGGCTATCCA ATTTTCCCAG CACTGTTTAT   133560
TGAATAGGAT TTCCTTTCCC CAGTGTATGT TTTTGTTTGT TTGGCTGAAG ATCAGTTGGT   133620
TGTAGGTATT TGGTTTTATT TCTGGGTTCT CTATGCTATT CTACTTTTAT ACCGGTTCCA   133680
TGCTGTTTTG ATTACAATAG CCTCGTAGTA TAATTTGAAG TTGGGTAATG TGATGCCTCC   133740
AGATTTGCTC TTTTTTTGCT TAGGATTGCT TTGGCTATTT GGACCCCTCT TTGGTCTCAT   133800
ATAAATTTTA GGATTGGTTT TTCTAATTCT GTGAAAAATG ACATTGGTAT TTTGATAAGG   133860
GTTGCACTGA ATCTGTGGAT TGCTTTGGGT AGTATAGTCA TTTTTACAAT ATTGATTCTT   133920
CTAATCCATA AGCATGGTAT GTTTCTCCAT TTGCTTGTGT CATCTATTAT TTCTTTCATT   133980
AGTGTTTTGT AATTCTCCTT GTAGGGGTCT TTCACCTCCT TGGTTAAGTA TATTCCTATG   134040
TATTTTATTT TTATTTTTTG CAGCTATTGT AAATGGGATT GAGTTCTTGA TTTGATTTTG   134100
AGCTTGGCCA TCATTGGTGT ATAGCAGTGC TAGTGATTTG TGTACATTGA TTTTGTAACC   134160
TAACACTACT AAATTCACTT ATCAAATCTG GGAGATTTTT GAGGATTCCT TAGGATTTTC   134220
TAGGTATGAG ATCATATCAT TGGTAGAGGT AGTTTGAGTT TCTCTTTTCC AGTTTGGATG   134280
CCCTTTATTT CTTTCTCTTG CCTGATTGCT CTGACTAGGG CTTCTAGTAC TATGTTGAAT   134340
AGAAATGGTG AAAAGTGGGC ATCCTTGTCT CATTCTAATT TTTAGGGGGA AATGCTTTCA   134400
ACTTTTCCCC ATTCATTTTG ATGTTGGCTG TGAGTTTGTC ATAGATGATT CTTACTATTT   134460
```

```
TGAGATATAT TCATTTGATG CCTAGTTTGT TGAGGGATTT TATCATAAAA GGAGGCTGGA    134520
TTTTATTGAA TGCTTTTTCT GCATCTATTA AAATGATTAC GTTTTTCATT TTTAATTCTG    134580
TTTATGTCAT GAATCACATT TATTGACTTA TGTTTATTTG TTGCTTACAT CTACTTTCTA    134640
ATTTTACTAT AATAAACATG TATAATTTTG TTATCAGAAA AGTAAATGTA AAAGTGAGTT    134700
TTAATTTTAA AACTTGGGCC TAAGTCTTCC TGCCTCCCAA GCCCATTCCC TTCCTGATAT    134760
CTGGGGCTTC CCTCCTCAAG CCTGCTCTGC AGGATAAGGG GATACAGTCC ACATGCCTGC    134820
TGCTGGTTTG GCCCATGATA ACCTCCATGG GCAATGTCTG AGCCTCTGCT GTTGAGTTTT    134880
GCTTTACACA CTCCTGGCAA GGAAAGGATG GCCAACATGG CTTGGACATG GGTTGCTGAT    134940
AATTGGTGAT GTCTCATGAC TGGTTCTGCC TGGAGGGCTT GCTGTAAGTC CCTGATAGGA    135000
GGAACATGGA CCTGCACAAG AGCAGAACTT ATCTGACACT GAAGAGGACA CTTCAAGAAC    135060
AGATTATCAA AGTCTAGCTC AGGGAGAAAT ATACTTTAGA GCAGAATGAG GAATGGCGAG    135120
GCAGCTGAGC TTAGACACAA GCAGAAGGAA ATCCATGGTG AGGGCACAGG CAAGGAAAGG    135180
GGCTGAGAGA GCATTAGTGG GGGCAGTCAG GGGCAGTGGT CAGGATGCTC GGATGCCAGC    135240
GTGAACAATC GCATCAAGAT TAAACACCAT GAGGATCGTT AGACTTCCTG TCATATGTCT    135300
CCAGGTGGTG CTCCAAATAT CCTAAACCAG ATGACAGCAC CCCTCCACCC TCTGCTGTAT    135360
AAGCACATCT GCTCTCCTAT AATCATTCCC ACATAGCAAT TTATCATTTT TATTGATTTT    135420
TCTTCATTTA ATACACGTAT AAGTGTGTCT TTTATTTTTA AAAATTTGCA TTCCTTTAAT    135480
TGCTTTGGAG ATTGTGCATT TTTCTCTCTG TTGATTTACT CTGCCAATAA ACATGTAATC    135540
CTACCATAAG CATGTTTTAC TTGTGTAATC AACCAAAATA AAAAATTTAA AAAGGAATCA    135600
CTGACTATGA ATTAGACATG TGGATAGGCA CCAGGGTTGC AGACATGGCC CACGTTCTTG    135660
CATTAACTTG CACTGTGGCT GGGGCATTGG ATGGGTACAT TAAAAGGATT AAAGTAATAT    135720
AAGGCAGTAT TTATTAAGTG TTGAGTGAGC ACTACAGAAC CCAAGTGCTG AGGGAGTTTC    135780
ATGCAGGAAG AGATCAAGAG TAACACAGAG AAGAAGAATA GATCAATTTA GCGCATTCAT    135840
TTAAAAATTC ACCTTTTGCA TAAGGGGATG TGTCTTTTGT GGGGAGGAGG GGAGTTCCGA    135900
TTGGCAGTTT GTTCTCAGGG AGCTTGAAGA AGAGATCTTG GAGAGGAGAC GCAGAGAAAA    135960
CAAATGAAGA AAATGTCAAA ATGGAAGGGG TTGGCCCGGC TATGCATACC TTAGTTAGCT    136020
TAGGTAGAGT CTAAACTTTT ACAAGTGGTT TCAATAGGTG TGTTTGGTCT GGGTTCTTTG    136080
GGAGGTATCA TAGGAGAATG AAGGCAGGGA GGACGCTTCC AGCACCAAAA TTCAAAGGGA    136140
AATGTATTTT ACATGCATAG CATTGTTTTA CTCTCTTTCC ATTTGGAGCA TATCTTAAAA    136200
ATTCCATTTG GAGCATATCT TAAAAAACCC ATTTCTCTGA CAATGGTTCT AAAAGGGGGA    136260
AACATCCTTT GCAACAGAAT CATTCATTCT CTCATTCATC AACCACTGAT TGTGTACTAA    136320
GTGTCAGACC TGATCTCCAT CCTGCCTGGT ATGGCACTAG CTTCTGTCTT GAGACAAGCA    136380
TTGTGATAAA CCATGACCAA AAAAAGGGCA GTTTTATAAA CACAAGTCTG CCAGGCTTTC    136440
AGCAATTCTA AATTTCCTTT TGCAAGTCAG GCTGGAGTTA ATGGCTCTTT CCTGCAGCGG    136500
CGGAGATGAC AGGGCTCTCC CACAGTGCTG AGCAGGCAGT TTGAAAGCCC CACTTCCTGT    136560
CTCTGCATGG GCGAGTGTCC ACTGGAAGCC ACTGAGAGGA AGGAGGGAAA CCTCAGAAAC    136620
CGGCCCCTGC CTGGCTGCTT CACCCTAGAA AGCCCAGGCA GAGGAGGGAA AGGTGAAGTG    136680
CTGAAAAAGA ATAAAAAAGG GGGAACATGA AAAAGAGCAA GAGCAGGAAG GAGGCAGGGA    136740
CGGGAAAGGA GGGGAAGCAC GGAAACAGCC AATGTCAAGG AGAAGAAAAG ATGGCTGGTG    136800
GAAAGGAGCT TCCAGGAATT GGGACACAGC CCTGTCTTAT TGCAAAAGAT GGAAACCCTG    136860
AAGGAGAACA GGAAGGAAAA AGAAAACAAG TCCGTCTGAG CTGGCAGGGT CCACTTTCTC    136920
ATTCTACAGA TGAGGAAACA GAGGCACAGA GAGGAAGTGG CTTGCCCAAG GGGGCAGATT    136980
CTTGAAAGGA TCATCTGCAC TCTCTCTCCC TTAATGCATT CTTACCTCTT CTTTACTCGT    137040
GAGTCAGTCC TGAAGGACAA GCTGCCTGAA GTCCCACACA GATGGGCCTG GGGCAAGCAT    137100
```

FIG. 6.52

```
CAAACATCCT GGGGGCCCTG GGTGAGGTTT GCTTTTAAAT TCCAGGTCAG GGAAAGGAAG   137160
GTCTTTAAGT TGTCTGCTCT AAGCTTAGTA ATCCCCCTCA GAGTTATGGG TGCGGTGTCT   137220
GGGGTAGCCG TTGCGTCTCT GGGCAAATAC CCTGGAGAAT GCAGTGTTGG TTGTCTGAGC   137280
TGGGGACAGA GTGACAGCAT AGTTGCATGC AGAGCTGGAG GCTCCTGCAG CTGTACAGGT   137340
AAGGTGCTGA AATTCTCCAC CAACCCTTCC TCTTTGCCCC CAGCACCACG AAGATAACCC   137400
TCTTTGAATA TGTGGAAGTC TGTTCTCCAA ACTTTCTAAC ATTCTCATGT CAGTCTTAAT   137460
AGATTCAGCT CAGTTACTGC CTCCTCCAGG AAGTCCTCCT TGTCTGCAAA TCGGCTGCCC   137520
ACCATGCCGG CTCACTCATA GTTTTAACTC TGTATCTTTC TAATATGCCT TAGCCCACTC   137580
TGTCAGGATT CCAGTCAGCT TCCTTCTCCT AGACTAGGAG TTGCCTCAGG CCAGGAGGAC   137640
CAGCCTTGTT CATATCTGTA CCCTGCAAAC CTGTCAATGC CCAAACCTGC TCAGTGCTTT   137700
GGAGTATGGA ACCAGCCGTC AATGCAGGAA TGTTACACTC TAAGAGTTCC CAAAGGTAGA   137760
GAGATGAGGG ATTGGTGCTG GAAGTGGGAG GTTATTCTAA GGATGGGTAT GGCAGGAAAC   137820
ACAATTATAG TTCAGGGAGT GGAGTGTCCA GGAGTGGGAG GAGAGGAACT GGGAGAAAGA   137880
GCAGAGAGTG AAAGTGAGAG CGGGCACAAA GAAAGGGAAA AAGAGTCAGG GATCAACCAA   137940
AGTGCATGCT TCCTTTTCAG CCCTGCCAGG ATGTGCAGGG CGGCTGCTGT GGACGCGTCA   138000
AGGCTCAGCC TCAAACATGT CTTCTTCCTT GACTTTTGTC TATCATTCTA AAGCTAGGTC   138060
ATTTAAAAAG TTCTTTTGTT TTCTTTCCAC CGATACTCTG ATTTCTGACA TTCGCCAAAA   138120
AGAGGTCAAG ACCCTGGCAT ACCGCCCTAC TAAGATTAAA ATAAATATTA TCCATTGAAA   138180
CTGTTATTTT TTCCTTAACT GTTATTTGTA GAGTTAAAGA TTCCCATGAT CGCGCTGGCT   138240
CTAACATCAT TTTTGGCTCT TTTGAGATCA AATTTGCAAT TGATGCAAA ATAGCTGTG   138300
ACGCATATGT GTCTGTATGT GTGTGGTTAG GAGATTTTTT ATCATTACAT CTTCTTTTGC   138360
CCTGCCTTTC TGCCTTTCTG TCCTTTTAAT TTGCGGGCTT TTGGCAACCA CAGCACGGGT   138420
CTGGTTTCCT AGGAGTTTCT TTTGTAGGAT CAAACCGCTA GTTGGCTCTT GGCCCTGTGA   138480
TAGGGCCCTG GGCTAACTTA TTGGGAAAAT GTTGCTGTAA CCCCTGCCCA GAGGTGCCTG   138540
TGACATGGGC CGCCATCTTC TCCTCTTCCC TTGGCTTCAG CCCCACCTAG AAACCTGAAC   138600
AAACATTTTC CTTGACATTT CATAAAGTGT CAGTGGCTCC TCATTTAGCA AAATACATCC   138660
CAGGGAAGTT CAAAAGTGAA AAAAGGCCGT AACTTCTTCT TCTTCTCAGG GACCTACAGA   138720
AAATATGTGG CACCTCGGCA GCCTGGCCTG CAGCACTCCC CTCCCCATCG GTGAGTCCTG   138780
CTACAGTGGG TCCAGGTGTC TGGACGCCCG GCACGCACGG CTCTCTGCAG ACCTCTGGAC   138840
AGTACCATGG GAGCCGCACA GTCCCTGCCT GTTCTGTCCG GCAGTTCTTG TTTCCCAGCA   138900
CCCTGTCTCA GGTGAGAGGT TCCCTCTTCT GCTGGGCTTC TCCTCCCTGC TGTGAACCCC   138960
AAATATCTGA GGCAGGTCAA TTTAGGAACC TTATTTTGCC AAAGTTGAGG ATGTACCCAT   139020
GACACGGCCT CAGGAGGTCC TGAAGACAAG TGCCCGAGGT GATCGCGGCA CAGCTTGGTT   139080
TTATACATTT ATACAGACAT CAGTCAATAT ATGTAAGATA AACATTGGTT CGGTCCCGAA   139140
AGGCCGGACA ACTCCAAGTG GAGAGGGGGC TTCCAGTTCA CAGGTAGATA AGAGACAAAA   139200
TGTTGCATTC TTTTGAGTTT CTGATTAGCT TTTCCAAAGG AGGCAATCAG ATATGCATTT   139260
ATCTCAGTGA GCAGAGGGGT GACTTGGAAT GGAATGGAAG GCAGTTCTCA GTTTAAATTT   139320
TCCCTTTAGC TTAGTGATTT TGGGGTCCCA AGATTTATTT TCCATTCACT CTGCAGACAG   139380
GGGCTTCTGT GCATCCAGGG AGCCCCTCCT CACAGAAGGA AGCAGGCCAT TAATGAGACC   139440
CAATCCAGCT TCAACCACCT GGTAACAATT AGGACATCAC TTCTCTGAGC AAGAGCTCCT   139500
GCCTGTCCAT GAGTTATCAA GACATTCCAA TTGTTCCTCC ACATCTTTGA CATGAAGACT   139560
TGAGGGGGTC AGATTTTCCA GGGGGCTTGA TGGCATGTTC TCTTCACTGT TCCCTGCCCT   139620
GGTCATCCAA GTGACCCTTG GCAGGGAAGA GGCCCCGAGT TGCAGAATCT CTGTTCTCAC   139680
AAGCCATTGC CAACCCGGAG AGTGGCTTTG CCACTATTCC TAGCATGTTG TTGGCTATTT   139740
```

FIG. 6.53

```
CAGGAATGGG AGTATTTGAC TTTTCCCTTT GCAGTGATTG CTGCAAGGAG AGGAATTGAG  139800
AGACTCAAGT CCCTGAGATA AATATTTATC AACTATTACT GAAAGGGAGT ATGTCAAAGA  139860
AAAAATGTGG AGAAACTTCA GCTTGAACAC ATAGTTTAAA TCCAGCTTGG GTGTACTCCA  139920
GTGGGCATGG ATGTATTACT GTTTTGCAGT GCATTCTTCT ATGATCAATA CACAGAAGCA  139980
AACAGGCCAC GTGGGTAAAC AGTAATTTTC ATTTACCAGG GTGAATATGG AAGTCCTCTT  140040
GTTTCCATGT CATGATGAAG GAAAGCAAGG ACCATCTTTT GCCAAGGAAC AGTGGCTGTG  140100
GGGGAACTGA GGAGATGGAA GGACAAGGCA GTCAAAAGCT TTGGAACAAC TCTTTTTTTG  140160
AGATGGAGTT TTGCTCTTGT TGTCCAGGCT GGAGTGCAAT GGCACGACCT CGGCTCACCA  140220
CAACCGCTGC CTCCCAGGTT CAAGTGATTC TCCTGCCTCA GCCTCCCGAG TAGCTGGGAT  140280
TGCAGGTATG CTCCACCATG CCTGGCTAAT TTTGTATTTT TAATAGAGAC GGGATTTCTC  140340
CACGTTGGTC AGCTGGTCTT GAACTCCCGA CCTCAGGTGA TCCACCTGCC TCGGCCTCCC  140400
AAAGTGCTGG GATTACAGGC ATGAGCCACC ATACCCGGCC CTTTTTGGA ATAATTTTAT   140460
AGGTTTTCAA ACTATTACAC TTACCTTTTT ATATAAGAGA CAGGACATAG TCACTGAACA  140520
ATCACTCCAG ATTTTAAGTA AGTCCAGGAT GGGATGACAA TGGAACAACC ATGAAATGAA  140580
AGGAAGAATG TGTCACTGGT ATGTCCACAC GTCTCCAAAT CTCTCACCTC TGTCAGCTGC  140640
AAACAGAGCC TGAAATAAAT GTTTCCTCTG TGCACAGCCT CCACAACTTC CTCCCTCCAC  140700
GTTTCTCACT CACTCCTCTC CAGCACTTCT CTCCGGGTTC TGCTTACAAA CTTGAAACCG  140760
GCTATGCAAA AATTATAACT GTGGAAATTA TGACAGTGAA AGAGATCAGA CCTAACCGAC  140820
TCCATCTTGC TTCTAACCTT TAAGCTGTCC TTGTTCATTT TTGGGCTGAA CTAACTTTGG  140880
GAAGGAATTC AGTTCATGGT AGAACTCTGA AACAAAATTG ATAATAGCCC TTTCCTGAAA  140940
AGACCCCCTT CTTGCCTGGG ACAAGTCTG CCATTGTAGG ACTAACAAAT TAACTACAAG   141000
ATTAGAAATT AAGGTTTAGG GTTCATGCAG CCTCCAGTTC CAAGAGTCTA AACCTCCCCA  141060
AATTGCTCCT GGGGATAACA TCACTGTTGT AAAAGCTAAG ACCAGTGCTT GAGATATTTT  141120
GTAGACCCTG CTCTGGATGG ATCAGCTGAC ACCATCCAGA CTGGTAATTT GGCTCAACCA  141180
GCTCTGCCAT CCCACCCAGG AACAGAAAAA TACTCACTTC ATCACCCCAT GAGTCCATCT  141240
CTAACCTGAC CAATCAGCAC TCCCTACTTC CCAGGCCCCT ACTCGCCAAA TCTGCCTTTG  141300
GAGGCAGATA ACAACTTATC TTTAAAAACT CTGATCCCTG AATGCTCAGG AGACTGATTT  141360
GAGTAATAAT AAAACTCCGG CTCTGCATGA ATTACTCCTT TTCCATTGCA ATTCTCTTGT  141420
CTTGATAAAT TGGTTCTGTC TAGGCAGCCA GCAAGGCGAA CCCTTTGGGC GGTTACAAAC  141480
TCATCCTCTG TGGAAGAGTA GGAGTTCATG GAGAAATTGG TTGCAAATTA CAAAATTTTA  141540
TTGTAAGGTC AACTTGTCCC AGTGTCCGTC TGTGCAGCGA AGGGCCCCTG CATGGTTTAG  141600
TGATTGCAAG TTGAGCCTCT AGGGTCAGGT TGTCTAGGTT TCCATCCCAG CTCATTCACT  141660
TATTATCTGT GTGTTCTTGA GCAAGCTCCT TAATCAATTG AGGCTTTGTC CTTCTGTTTG  141720
TATAATGATG AGAATAATAA CCTCCACAAT AACCTCATCA TAAGGTTGTT GTGAAGATGG  141780
ATCAGATAAT ATATATGTAG AGTGCTTATA ACAGTGCCTG GCACATAAAA AATGCTCAAA  141840
AATCTTAAGT GTTATTAATA ATAAACTGAC ATATATTTCT TGAGCAGGGT GGTGGTAAAT  141900
GGGTGTTCTT TTTATTAAGC TTTAAAGTGT GCATAGATCA TATTAATTCT TTTTATGCAT  141960
ATGATATATT GCACATGCAT GAAAATACAT GCATTAAAAA TAAATGAGCA TTTATGAGAT  142020
TTAGTTTAGC AGTCACATGT CCCAGGATTA CAAGCCAGCA ATAATGGGTT GGAAAACATT  142080
CCAACCCATT CCAACCATTG GAAAACATTC CAACCCATCA CTGGACCCAT GTGCCAAACA  142140
ATGGAACCGC CCACAGGTTC TCATTCTTGG TTAAAAAAAT ATGATTATTA CGGGAATAAT  142200
ACTGATTCCC TAAGAATTAA TATCTGAGCA AGTTTCTTTT TTTTCCTGTC TTCTTGGAAG  142260
ATCAGCAGGT TCTAGATTCA ATGGAGTCAC TAGGATTGAG CCACCAGTAT ACGCCAGTCC  142320
TCTCCAGAAC GGCCACCTGG TGGTGGGCAC TAAGGCAGTC TCAGATGAGG ACTGATTGAC  142380
```

FIG. 6.54

```
TTTTGTGTGA ACTCAAACTG CCAAAGTCCC TCCCTCACCT TGCAAACTTC AAAGCACAAC  142440
TTTCAAAGCA CTACTTTCTT TCTTGGCTCT CAATTCTCTG CCTAGAAAAA GGGAGGTGTT  142500
GGCAAGGATG TTTGTTTAGT TCTGGGCATC AGTCAATGGT ACCCAGATCT TGCTGAACAG  142560
AAAAGACACA GATTTGTTTC TCTGAGGCAG TTGGTAGTGC TTATTGCTTA TTGCTCTCAG  142620
GGGCTTCTGC AGCAGTAGAA GGGCCCTCTT CCCCTGCCAT GCCACACTGA GAGGAGCATC  142680
CTTGGAGTCA TGGTTGGAAT CTGTTTTTGT TATGCTAGTC CTCTTCCGCA TGCTAGCTGT  142740
TGCATTGCAG GGATATGTGT ACCTGTTTAT CTTCTCCACT AGGCTCTAAG AAGCCAGGTT  142800
TCTTAAAGGA AGGAAGCTGA TCTTGTTTAT CTTGAAGTCC TCACAGTGAC ATTGCTCAGT  142860
CAATGTTGAG TGTATGAATG AATAAACGGG AACCATCACG AAAAAGCCGA AAATACAGTG  142920
GAAAGACTGG ATCATAAAAT CTTCTAAGCA AATTTTTTTT CCTCTTACAC TCCATTTCCA  142980
AATAGATAAA GTATTTTTTA AAATCCTATC AGAATATTCT AACACACTGA GTTGACAGAA  143040
TAGAGATTTT TAAATGCAGT GTCATTTGGC CAGCCATTTG TGAGAATTTA TAAATGTTTC  143100
AGTAGGTTGA AAACACTATA AAAGCAAGGA CTATGTTCAT ACCCAACAGC TGGCACTTAG  143160
TATGAATGCT AAATGAAACA TTCTCTTCTC TTTCAAGAGT CAGTCCAACC AGTGACCCTG  143220
ACAAGAAGGA AGGCACATTT AACTCAATTT AATGAACTCT TATAGAGCAT CTCCTTCTCC  143280
AAGTGCTTTG CTAAGGATGG GGTAAAAACA TGAATAAGTC TTGGATTCTG TCCTTCAGGA  143340
ATTTTCAGTC TTTGGAGGCA GATACATTTG CACCCAACTA TTATCCTAGG CAGAGTGTGA  143400
TAAGTACGAT AATAGCAGTA AAAGCTCTAA GTTAGGCAGG AGAGGAGGAG CTCGTTAAAG  143460
CTTATGGGGC CTGGGAGGCT TTCGGCGGAG TAAACTCCAG GGGACAGCT AGGCATCTGG  143520
CTGCTGGAAT TGGGAGGAGG ATCATTTTAA GTGGCTACAA CTCTGGGTGC ACAGGACTAG  143580
AGGGTGAGGG CCAAGATGGG AAATTGTGGC AGCCATCTTC CACACTGGGC GCCCGCCGAC  143640
CCTTGCTTCC TGGTATTCAT ATTATTGTGT AGTGTCCCCC AACATTGTAT CAGGGTTGGC  143700
CTGTGTGACC AATTGCATAT GGTGGGAATG ATGGTGTGTG ACTTCTAAGA CCAGTTCATA  143760
GAAGATGTGG CCAATTCCCT TACTGTCTTT TTTTTTGGCA GGGGAGTGCC GAGTTTCACC  143820
CTTGTCGCCC AGGCTGGAGT GCAATGGTGC GATCTCTGCT CACTGCAACC TCTGCCTCCC  143880
AGGTTCAAGT GATTCTCCTG CCTCAGCCTC CCAACTAGCT GTGATTACAG GTATGCGCCA  143940
CCATGCCTGG CTAATTTTGT ATTTTTAGTA GAGACGGGGT GAGATCAATG AGGCAGTCAA  144000
TTGGCCAGCC TGGTTTTGAA CTCCTGACCT CAGGTGATCC ACCCGCCTCG GCCTCCCAAA  144060
GTGCTGGGAT TACAGGCATG CGCCAACCGC GCCTGGCCCT TACTGTCCTT TGGATCAGCT  144120
GCTCTGGGGC TAGGTCAATC CTTCATGTGA CTGCAGCCCC AGCCAACATC TGGACTGAAA  144180
CCCATGAGAC ACCCTGAGCC AAAAAAGCCC AGCTAAGACT TCCTGCATTT CTGACCCACA  144240
GAAACTGAGA AAAGAAATGT TTTGTTGTTG CTTTAAGCCA CTGACTTCTG GGGTCATTTG  144300
TTTTGCAGAA ATAGATAGCA GATACAGAAA AGCAGGCTGG TGGAACAGTG TGGGAAACAC  144360
CTTGATTTTC AGGGAGTTGC ACTTTGTTTA TGTGCAATGG TGCACTGTTT TTAGAAAGAC  144420
ACAAAGATGA TAATACTGGT GATGGGCATA ATACGGGTTG TCAAGAGGAG TGACTGAGGC  144480
GGGGATAATT TAAGAGGCCA CAGCAGTAGT GTGGCAAGAG GTAATGAGGG AATTGAACTT  144540
GGTGGGAATG GGTGAGATCA ACGAGGCAGT CAATATGGGC AGTGAGTGTG AAGGAGCTGC  144600
GAAGGATGAT TCTTTGGTTT TGAGCTTAGG AACATGAGAG AACCAAGATC TCATTTATCC  144660
AAAGAGGAAA CACAGAAGTG AGCCCTGTT TGGGGCAGG GCTGGGTAGG AGGAAAAGAG  144720
TGGAGACGTC TATCTCCCCA GGAAGAGAGC CCCTGCTTC CAGATCCCAG TGGATGGCAG  144780
GGCACTCGGC TCATTCACAG ACTGGGCTCG TTGAGAAACC TTTCCCTGGA GGGCAGGGCT  144840
GCTCTGTTTC ACAGCCCATA TCCCTCATGG CCAAGTGTTC CTCGAGTGAC AGTCTCTGCC  144900
ATCAATATTT TTAGCATGTG GTCTTTCAGA GACTAAAGAG TGGCATCCAT CTCCTGAAAC  144960
TCCTTCCCCA GCTGACAGCT GGTGACCCGT GGAGGAGGGA GCTTCAGGGA GCCTGATGGG  145020
```

FIG. 6.55

```
CGAGAGTCTG TTCCAATGCC AATCCATTGG AAGAGATGAA GTCAGACCCG AGTTTGATAG   145080
AAAGCCTACT TCCTCCCTTG TATCCAGCTG TGGAGACCTA CCAACATCAA TGCAAACCAG   145140
AAGCTAACAC CCAGTTCATA TATCCCAAGT GGAAGGAAGC TTCTCGTGGA ATTGTCTTAC   145200
ATGACAGTAA CATAAATCCT GAAGGTAATA CTTGGCCAGG TAATGTTAGA AAAGAACCCG   145260
AACATAGGCA TTGCTATTAT AGATCCTAGG ATAGGCCTGA GCAAAAACTG TCTGGGATTC   145320
ATAACATGCT TCGTTGCAAT CTGATAGAGG GAGTGAGATC CACTCCAAAT GGAGTCTGAT   145380
TTGGGGCAAA GCAAAGAGTA TGGAAGGAAA CTTGAGAAAG GGGGACAGCT TCTCAAATGG   145440
AGTCTGGCCA CAGCTGGGGC TGGAAAAGAG ACATGACTGC GCTTGCAGAG TGGTGAGAAT   145500
TTGCTGCTAG AATTTTTAAG TTGTGTGTTT TCATTTTTAT GATAATGTAA ACTGAGATAA   145560
GCATATTCTC TGCTATCCCA ATGAGCCCCT CCTCTAGGAG GACTACCTTG CCACCTTATC   145620
CATAAATGTG TTTATAAATT ATTTTGATGC CAGCTGGTAT TTTTTAAAAA GTGGTTTTGG   145680
ACTCACAAAA AAACCATGA TGGATTTAAT ACATAACAAA GCATTTGTGT CAAGTGAAGG   145740
CCAAGTAACA TCTTAGCGTC CTGTGTGAGC GAAGGTGTCG TGGCAGTTCA AACAAGAATG   145800
CCGATGAAGC TGCCCAGGAT GGCCAAGGCC ACCTTGGTGT GTTTGAGGGG AATTAGAGTT   145860
TAGAAAAAAA AAAAAAGGCA CCTGACACTC TGAACTAATG TGGTTACCTG GAATTTTGGG   145920
GTTTTGAAGC TTTGCATTTA ATTTGCAGCT TATGGCCTGA AGGAAAAGAC AGGTGAAATG   145980
CATATCCTGG GATGAGTCAC CTGGAGGAGA GGGCTGGGAA GGGGCTGAGC TGCACATGCT   146040
CAGATCTTCT CCCAGGCTTA TCGACCCAGT GAGTCAAGTC TTCTTCCAAC GGGATAGAGT   146100
GTGAGAGAGA GCAGGGAACA GAAGCCAGAG TCTCTGTTAA ATTTCTCGGT ACATTTCTGT   146160
TAGAGAATGG AAGTTTCTCT ATCGTAGGAG ACCTTGAGAG CCTGGGATAG AAATTACCCC   146220
TTTGTCATGT ATTTTCCTCC CAGAAATAGC ATGGCCACTG TCACTGCTAA GCTGGAGTAT   146280
CATGAGCACA ATTTCTCTCA CTTTCTATAC CCATGCCTTT CTAGGAGATT GGTGGCTCCA   146340
TCAAAAAGGA GTTAAAAAGA AGCAGCACTA TTTTGTGGAA TACAATCATC ACCATTATCA   146400
CCATCAGCAC CACCAACCAG CACCACCATT ATCAAAAGCA TTCACCTGGT GTCTGCCTTA   146460
CAAACTGCAA ACTGCAGTAG GTATTTGTAA TAGAATGTTT CCTTTCCCCC TTGGGATCTG   146520
CAGAAAAGCT GGAGAATGTT TTGGTATCAA CACACTAGGT TGCATTGCTA ATCATGTGAT   146580
GGCCCCATGA CAGTCTCTGT TGGCTGGTGT AGTTCAGGTG GACGACTGCA GGATTTTGTT   146640
CTTGGAGCCT CAGTTCTGAC TGGGCTTGGG GTGTAAAAGG TTTGGGAGCC AGATGACAAG   146700
AGTATTTGAT GGGTAGAATA ATGGGTTCAT CCAAAAGATC ACCAGAATGG TTATTAAATA   146760
GTACAAAGGA GGAATTTACT GGTAATACCA GTTTGCAAAC AGAGAAGAGA GTCTCCAATG   146820
TGGACTGAAA GTGCTCTCTC TTTGAAGAGG GGAAGGACAG ATTGGGTTTT ATGCCTCACA   146880
GGACTGGTAC CATACATATT CAGCAGGTTT TTGGGGAAAA TCTATACATA TTTATAAGGT   146940
GAGCTGATGC CTGCATAATA GATAAACATA TATGTAACAT ACTTTTCATA TTCATTTTGG   147000
GACTGGGTTT TGGCACTAAA ATTTGTGGAA TTTGGCTCTT TATGTTAAAA GGTGAACTAG   147060
AGGACACAAA GACGGTTTGT GTGCACCCTC TATAAACTGG CTGAAACTGG CTTAAGGTCT   147120
GCAACTGCTT ATCCAAAAAG AATGTTTGTA AGGCCAGGCC TCTGTCCAGT CAGAGTTGTA   147180
GTGGTCCAGG TTGTAAATCA AAGTTTATAG CTCTTTTTGT TAGAGAGTTC AGCTGTAGGA   147240
ATTTAGAAAT TTGCCATGCC TGCCAGGCCC TGAACCTTTG ACCCATAGGT AACTTTATTT   147300
CCTTAACCTT AGGGTCAGTC TTAGTTGATA TGGGGCATCT ATTCTGGTAT CTCAGATCCT   147360
ATGGTCAAGA GAAAAGATCC TCCACAAGAG GGTCCTATGT GGCTGCAAAA ACTGCTCTGA   147420
GCTAAATCCA CTCAAAATCA CTGCAGGATG TCACTACTAG AAAATAGGGC AGGGATAGGG   147480
ATCCCCTTCC CATGCTGCCA GAAAATGCCT GATAGCTTAC CTCCCCGGC CCTTGAGGCT   147540
CCCTTGGAAT AGGCACATGC AATCCCATCT CCACCCAATA GAGCTTGTCC TAGAGCTCAG   147600
TTTTTTCCCA TAGTTTTCCC ACCCACTTGC ACCAGAAAAT CTAATAAAGT CATGTGATTA   147660
```

FIG. 6.56

ATACAATTCA TTTTATCACG CTTCTGAAGA TTTAAGAGAG AGCGGTCACA TTGGATTCCA 147720
CAGTACCGAC CTTCTGACGA TTCTTCATTT CACCTTTATC TATTTTTATT TTTATTTTAT 147780
TTTTTTTTCG AGACGGGGTC TCACTCTGTC ACCCAGGCTG GAGTGCAGTG GGGCAATTAC 147840
GGCTCACTGC AACCTCTGCC TTCTGTGCTC AAGCAATCCT CCCACCTCAG CCTCCCAAGT 147900
AGCTGGGATC ATAGGTGCAC ATCACCAAGC CTGGCTAATT TTTTGTATTT TTGGTAGAGA 147960
TGGGGTTTCA CCATGTTGCC CAGGCTGGTC TTGAACTTCT GAGCTCAAGT GATCTGCCCA 148020
CCATAGCCTC CCAAAGTGCT GGGATTACTC ACGTGAGCCA CCTCGCCTGG TCCCTTTCAC 148080
CTTTATTATC TTTGCCTTTA ACTCTAGTGC TTCCTCCCTG AATCAGTTAA GGATTGCATT 148140
TGGCTGCATT AACAGAAACC TGACTGCAGA AGCTTAACCA AATAGGGTAG TTTTTAAAGA 148200
GAGATTGCTT ACATCACGCA AATTGCACAA ATTTAAGTG CATAGTTCAA TGAGTTTTGA 148260
CAAATGTAGA ATAACATAGC TATATAAAAC CATTCCATCA AAAAAATTTT ATCACCATAG 148320
GAAATTGTGT CCTGTCCCTT TCTTGTCAAT CCCAACTCCT CCCCACAAGG CAACCTTCAT 148380
TCTCATTTCT CTCACCATAG CTTAGTTTTA CATGTTTCTA TAATACAGCA TCATATAAAT 148440
GGAATAATAC AGAATGCAAT CTTTTGTATG AAGCTTCCTT TGGCTCAATG TAATGTTTAT 148500
GAGATTCATC CATGTTATTG AATGTATCAG TAGTGTTTTC ATTTATATTT CCTAGTGTTC 148560
TATTGAATAA ATATACTACA ATTTGTTTAT CCACTTATTT GTTGATGAAC ATTTGGACCG 148620
TTGGCAATTT TTGCCTATTA TGCATAAAGC TGTTAAAAAA CATTCTTGTA CAAGTCTTTC 148680
ATTTCATATG TTTTTCTTTT TCTGAGGTAA ATAACTACAA GTAGAATTGT TGGGTAATAA 148740
ATAGGCATCC ATCTAATATT ATAAGCAACT GCACAACAGT TTTTCAACGT GGCTGTACTA 148800
TTTCACTCTC CAATAGCAA CGTATGTGTT TTCCAGCTAC TCCACATGCT CACTGGCATT 148860
TCCTGTTGCC AGTTTAAACA TTTCAGCCAT TCCAGTGGAT ATGAAATCTC TCTGGCTATA 148920
ATAATTGTAT TTCTCTGATG ACTAATTATG TCAAGCCCCT TTTCAAATGC TTATCAGCCA 148980
CTTCTATACT GTCCTCTGTG ACATGTCCGT TCAATCTTTT TGCTCATTCT TTAAAAACAT 149040
TGGGTTGTTT GTCTTTTTCT TAGTTTGTCT TTTGCTTTTC ATTTATAGGA GTACATATCT 149100
TCGGAATACA AGTCCTTTGT CAGATAAATG TATTGTGAAT AATTTTCTCC TAGTTTGTGG 149160
TTTGCCTTTT CACATTCTTA ATATCTTTTG ATGAGTGGAA ACTAACTTTC AAATTATGTT 149220
CAGTAGATTA ACTTGTTTTT GTTTTGTTTT GTTTTGTTTT TTGTTTTTAA CACTGGGTCT 149280
CACTTGTTGC CCAGGCTGGA GTGTAGTGGT GCCATCATGG CTCACTGCAA CCTCTGCCTC 149340
CTGGACTCAA GGGATCCTCC TGCCTCAGCC TCCCAAGTAG CTGGGACCAC AAGCACGCAC 149400
CACTACACTT GGCTACTTTT TTATATTTTT GGTAGACACA GGATTTCGCC ATGTTGCTCA 149460
GGCTGGTCTG GAGCTCCTGA GCTCAAGCGA TTCACCCACC TCAGCCTACC AAAGTGCTGG 149520
GATTACAGGC GTGAGCCACC ACGCCCAGTC GAGTAGATCA AGTTTTAATT TTATGGCCAG 149580
TAGAGATCTA TTTCAAGGCT CTCTATTTTG TTCTGTTGCT CTATTTATCT ACCTTTATGC 149640
CAATTTTCTT CTCTTTTGAT TCAGATAGGG TTATAATAAT AATTATTTTT TCCAGGGATT 149700
AGATGGACCA GGGCTGGTGA AGTTGTTCAA GGGAGTGATC AAGAGCCTGG CTCCTTTCAT 149760
CCTTCTGTTC CATCTCCTTT GGCTCATGGA TTTTGTTTTC CAAGTGGCAA GATGGCGCCT 149820
CCACCTTTGG TATCCTATTT TAGTTCCTGG CAGAAAGAAA GGAACAGGCT AATGGCCCTG 149880
ATGAGTCTAC CCCCTTTTAA CAGGAGAAAA TTTAAAAAAC AAAAACCATG AAACCCTTTC 149940
CCAGAGGCAA CAACCAGAAT TCCATTTATC TTTCATTGAC CAGAACAGAC CACATGGTCA 150000
CTGGTGGTGG CAATGGAGAC TGGGGAGATG AATATTTTTA AGGTGGCATA TTCCAGAAGA 150060
ACACTGTGCA CTGATTGCAT TAATGAACCC ATTAATGTGC CAAGGGGAGG TTTACCTATG 150120
AGCATGGGCA AATTAGAACC CACTCTTGGA GCTGCAGGTG AGCCAATCCC ACCTAAACAG 150180
TGTGGATGCT ACAAGATGGG GAAGTAAATT GATTCTATTC CATACCCTAA CCTCTCTCCA 150240
AGATGTATTC TTAAAATAGA AGAGGGAAGA CAGAAGAAAA CATCCAGAAT ATATTTTTAT 150300

FIG. 6.57

```
TGTCTTTTAC TTCTTCAGTG CATTTTAGAT CAGTGCTTCT CAATCTGGCA AGGGGCATGC  150360
AGGAGGATGT GAGTTTTATC AGGAAAACTA CACAACCCCC CAACCACAAT GCTACCCCCA  150420
CTCCTGTGGA CCTTCTTTAA GAGAGACTCA CTATTATAGA TGGAGTTGAT ACGATTTTAA  150480
GAGAGGCCAT ATATTATTTG CTTTCTGTCT TGAAAAACTT GTGATTTTTC TGTATTGTGC  150540
TACTGCCAAA GAGAATAGAA ACCTGACTGA GGTGTCAATG TTTATGTAAC TGATTTCATG  150600
TACTTTCTGT AGTTCTACCA TTTCTGATGG TTAAAAATTT CTTGTGTGTG TGCAGTTGGG  150660
GAGTGTGTCC TCCTCCTTCT GCTCTTATAC CACACATTAG CACATCAAAA TGCTCTAATC  150720
TTTGTATGAT TATGTGGCAT GTGGTGATGC AGCCTCACAG TGGAAAAACT TCTCTTGGGC  150780
CATTGCAAAT GTAACATTTC TTTCAATCAG ATAGTGCCAT TAAGGATTTC ATTATGGCCG  150840
TCACATCCTG TGACATCTCT AAACATGCAG CATTAGGGCC TAAGTGCAGC CCTGCAGGTA  150900
GAGTTGCCAG GTTTAACAAA TAAAAATTAC ACGCTGGCCA GGCGGGGTGG CTCATGCCTG  150960
TAATCCCAGC ACTTTGGGAG GCTGAGGCAG GTGGATCATT TGAGGTCAGG AGTTCGAAAC  151020
CAGCCTGGCC AACATGGTGA AACCCCATCT CTACTAAAAA TACAAAAATT AGCTGGGCAT  151080
GGTGGCAAAT GCCTGTAATC CTAGCTACTT GCGAGGCTGA GGCAGGAGAA TCACTTGAGC  151140
CCTGGAGGCG GGGGTTGCAG TGAGCAGAGA TCACACCATT GCACTCCAGC CTGGGTGGCA  151200
GAGCGAGATT CTGTCTAAAA AACAACACCG TATTTGGGGC ATGCTGATAC TAAAAAATTA  151260
TTCATTGTTT GTCTGAAATT AAAATTTAAA TTGGGGGCCC TGTATTTTAC TGGGCAACCC  151320
ATTTGCAATA TCAGCAACAA TCTCTTATTC AGACCACTGA TTAAGTGTGC AAAATTTGAA  151380
TCTCTGAACA GTACCTATGT CCTTGATATC TTAAATTAAT GAGTGTCTTA GACACTCAAA  151440
GCAGGAGGAA GCATTATGGC AGATGTTTGA GCCCCAGAGA TGTCCATGAG CACAGCATAG  151500
AGCTCAGAGC CTTCTTTATT ATTTGCTTCA CGACAGAGCA AAGGACTGCA GCAGGTTGAC  151560
TGATATAAAA GTTTTACCAT GTCTCACAGC AGGCCTTTGC TCAAGTTTCC AGTAAGGATA  151620
TTGTATCATT TCTTGCCTGC AGTACTTGTA AATCCACTTA CACTGCCTGC TGTTGAGTCA  151680
TTTGTTTCGT CTTGAGTAGC ATGTCATCCT TGTTCCTAGA AGATAGTGAG TTTAGAGACA  151740
GTAGCCAAGC AACAGCAGAG CAGCCTCAAC CAAAACGATT TTCCATTTTG GTGGGATGAA  151800
TTGAAACACA AGCATCTTCT ATCCAGGGGA GATTTGGGGA TCATAAAGAA TCAATCTGAG  151860
CTGGTACCAC CATATTGGCT GCTGCATTTT CTAGAGTTGC CGTAACTAGT CTCACAAGCT  151920
GGGAGGCTTT ACACAACAGA CATGTATTGT CTCATAGTTC TGGATGCTAG AAATCTGGAA  151980
TCAAGGCTCC AGGGGAGAAG CTGCTCCATG GTTTTCTCTT AGCTTCTGGT GTTGCCAGCA  152040
ATCCCTGGTG TTCCTTGGCC CGCAGGCGGA TCACTCCCAT CTCTGCCTCC ATTGTCACAC  152100
GGCATTTTCC CAGTGTGCCT GACTCTGTGT TTCTTCTCAT AAGAACATCG GTCATATTGG  152160
ATTACAGGCC CGTGCTACTC CATTATGACC TCATCTTAAC TTAAACAATT ACATCTGCAG  152220
TGATCCTGTT TGCAAATAAG GTCACATTCT GAGGTTCCAG GAATTAGAAC ATAGACATAT  152280
CTTTTGGGAA CAAAATTCCA GTGATAACAG TTTCGGAGAC AGACTAGTCC TGGAGTTTGT  152340
AAGGTGAGCC AGGACCAAGG TGCCAGGATT CTCATTTTGT AAGGTCCAGG AACAAAGTGA  152400
TGTTAATAGA AAGAACATGT TTTTGTTTGT TTATTTGTTT TTGAGACAGT CTCACTCCAT  152460
CACCCAGGCT GGAATGCAGT GGTACAATCT CGGCTCACTG CCGCTGCCAT CTCCCAGGTT  152520
CAAGCGATTC TCCTGCCTCA GCCTCCTAAG TAGCTGGAAT TACAGGTGTG TCCCACCATG  152580
CCCAGCTAAT TTTTGTATAT TTGTGTGTGT GTGTGTGTGT ATATATATAC ACACACACAT  152640
ACATACATAT ATATACATAC ATATATATAT ACACACACAC ACATATATAT ATATATAAAA  152700
TATATATTTC TTTTAGTAGA GACTGGGTTT CACCATGTTG CCCAGGCTGG TCTCGAACTC  152760
CTGCGCTCAA GTGATCCACC TGTCTTGGAC TCCCTAAGTG GTGGGACTAC AGGCACAAAC  152820
CACCACGCCC AGACAGAAGG AATATGTTTC CTTCCAGTCT CACTTGACTG GCTGCTTCCC  152880
TAGATAACAA CAGAGGATGT CTGTTGCAGT TCTCATTGCT GGGGAGTCTA AACTGGAATA  152940
```

FIG. 6.58

```
AAACACCCAC TATCTCCATC AGGCTTGCAC TAGAGCCCAG CTCTAGCTGG AGAGAAAGAA  153000
GCTAACCCGC ACAGACACAG GACTGTAGGC AGGGAGCATC CGGGGGTATT TGGGTCCTGG  153060
CTCTGATGTG CCTAAGGCCA ACTTCTCTCT GGCCATGCTG GCGTGCATGA GCTCACTAAT  153120
CTTCCTTTTT GCCTTCCATT TTCTCCAATC CTGACTTAGC AAAGGTTGGG CAAAAGAGAC  153180
TCTGTGTGAG TTCGAGCAAA GCCTGAGATG CTGGATTTTC CAAGATACGA GAAGGGGCTG  153240
GGGGCTGGGT GAACTGGTGG TGGAGGAGGG AAGGATTAAT TTCCCAAGGA GGGGAAGGGG  153300
CCAGGACATC AGGCCCCGGG GACTTTGAAG AGAGGGTCGT GGGTAGGAGG TAGATCAAGT  153360
GGAGTGACAC AAAGGTCAGG AAAGAGGAAG TGTCCACACT GTCCTTCGAC AGACTTGAGT  153420
CTATGGGACT TCCTCCCTGC ACGGTACAAG GAAATGAGTA AGTGAGATAA TGTTGTAACT  153480
TCTGGCCCTC TGACATTGCA CTGCCCCGAT GTCACAGTTG GAAACTGTAC CTGCCCCCAT  153540
CCTTGTCTGG GGTGTGTTTG GTCTGGGGAG GGCTGGTGAA GCAAGAGGTA CTCAGAAAAA  153600
GGACAGAAAT TGCTTCCTAT TATCTGGGCA TTTGGAGGTG AAGGGGTCAC AGCTCTGGCA  153660
AAGATGGGGT TGAAAGGGCC CGGACTCCAG GGAGGGGCAG CTCTGCATGG CCTGATTCCT  153720
GCACCCCACC TTTGCCCCCT CACACCTCCT CTCATCTCCC GTTTTTGAAG AGGAGGACCC  153780
TGTCACATCT GGACAATTCT GCAAGAACTC TGTAGAACTG ACTTCACTGT GAACCAGGCT  153840
CCAGAAGTCA ACAGAAACAA AAATGCTCAC ATTTAATCAC GATGCTCCCT GGCATACACA  153900
GAAGACTCTG AAAACTTCTG AATTTGGGAA ATCCTTTGGC ACCTTGGGGC ACATTGGGAA  153960
CATAAGCCAT CAGTGCTGGT GTGTGTGTGT GTGCGCGCAC ACGCGCATGT GTGTGCATCT  154020
TCTACCATGC CTCCTACAAA TTTGACCTGG GCCCAGGGCC ATGTTCGGTG GTTTTTAAGA  154080
ACCGAGGCTC CCAGAAGCAG TATTGGGCAG CTAGAGTGGC CCCAGGATCT ATATCAAACT  154140
CTACCTGTTT CTGAACCAAA TTTCTTCTAG AATTTTATTC CATAAATCTG AATTATGGTG  154200
TCAGACTCCT AGCATACACT AAAGGAACTC TCTGCCTTGC ATTAAATAAC AGGAGTTACC  154260
CCTGGAGGTA ACTCCTAGCC CTGGCTCTTT AGAGAACAGA TGCCGAATAG GCATTAGGGG  154320
ATGTGATGGA TGTGCTAACT TTCAAAAAAA AAAAAAAAAA AAGGCCTGAG CTGAGTGCTC  154380
AGAGATTCAC AAAAAGCTGA CAGCATCTCT CTGTTCCATT GGAAGCTGGG TGATCCTTTC  154440
TACTCTTTCC TGAGAAAGGC AGTTGGGCAG GAAAAAGCTG TATCTCTGTC CTCACTGAGA  154500
GGGTTTCCCA GTCTGAGGGT GAAGGATCAG GAGAGGGAGA CCTGACGGGT CGATGTGGGG  154560
CATCATCCAC TTGAGTGAGA ACCAGAGGGA TCCCGTCATT GCCCAGGGCA GATGCTCCAT  154620
TTTGGGGGGC ATCATTCATT CTTTCCTGTT CTCCCTGCAT TCCTCTGGCT CCTGCCCAGG  154680
AGAGGTGGCC GCTGGCAAGA GAGCTTGGTG GAGGTGGGAG GTGGGAGGTG GGGGGTGGGG  154740
GGTGGGGAGT TCTTGAGCCA GGACCTAGCG CATAGTCTCC AGCCTGCTGA TGGCTGTCTT  154800
GGATGCTTCA AAGGGGAGAA GATCCTAGAT GTGGGAAACA TTGGTGGGCG TTCTGCTGGG  154860
GCATCTGTAG CCTCTGAGAA GGCTACCAGT CTCTCCTAAG CTTACGCCGT CACACCCTGG  154920
GCACTTGTTG AATGACTTTA CTTAGCTTAC AGCCTCTGGT TCCTGTTGGG AAACTTAGGG  154980
CTTGCCACAG TGTTCATTTT CCTTTGCGGG CAACTCCGTT CCTGGCACTT ATCATATTAC  155040
CCACTGTACT CCCCGCTTAG AGCTGTGTCA AGGTTCTGAG AATCTATCCC TTGGCTTGGA  155100
AGGGGTCATC TCTCTGGCCA GATCATTTCC TGATAGGTCC TGAGGCACCA CAACACATAG  155160
GAGGCTTGTC CTCTCTCTGG GGTTCACTGC CTTGCTCCTT CTCCAGGTCA ATATGTGACC  155220
TTGGACCGGT TGCTTGAGTC CCCTGGTCAT TCAGAAACAA TTGGGTTTCC CTGGCTTTGG  155280
AGCCTGGCAG CCTGGCTTTG AGAACCGGGC TTTAACTTGT CACATGACTA TGGCCAAGTT  155340
CCTGGGGCTC TCCAAGCTTC ACTTCCTCTG TAAAAAGGGC AATAATATAA TACCTGTCTT  155400
ATTGGGTTTT GTCCATGTTA GATGAGACAT TGGGTACAAA GCACTTGGTC CCGTGCCTGG  155460
CACATTTACT GCACTTAATG TATGATAGTT TTCTTATTAT TCTAATAAAC AATATGGCTT  155520
TGGGAGTATA GTTCTGCCAC ATTGCAGTGG CCAGAGTGAA GGTGGTGAGT GCCTTCTGGG  155580
```

FIG. 6.59

```
GCCCTGGGAG TCAAGGTTAT CCGCATGCCC TTTCTTGCTT GCTCCTCAGT GTGGCTGCCT    155640
CTATGTCCAC ACCATGCAGA TGCAACAGGT AGTTTGAACC TCTGAGGCCC ACAGTGGGAT    155700
GGGGAGGCAG GGACATCACT TATGGGGTGG GAAGTCACCC ATTCCCCAGG AAATGGCCCC    155760
AGCTGCCTTT TCCATGACTC CTCTTGAAAC CCTGTGGAGG CCACATTCGT GTTGGGGCGG    155820
TCTTTCCCAT GAGGATATGT TCAGATGCCG AGGCATTTTG AAAAGCCCTC CATAGAGTTT    155880
CCTTTCATAA CACATGATCA TCCCCTTGGG CTTCTGGTTT TTTTTCTTTC AGGACCTTAT    155940
TTTCAGGCAA GTGGCCTTTG ACCTCTAAGG CTGTCCTTTC CTAGCTACCG AATCCAGCAT    156000
TCAAAGTGAT GGAAATATGT ATATATAGTA ATAGTAAAAT ATCAGCACTT AATGGCCTGA    156060
TAAGAATGTC ACTGCAATGC TGAGTTTGGA CCAACATTTG CCTGCTCCTG CCATTGAGCC    156120
CGGGCTCCCC TCCAGAGCTG AGCTGCTGCA AGGGATCTGA GTAACTAGGG CTGTGTCAGA    156180
GTGGCGATGA CAGCCACCAC ATGCTAAGGA AGAGATCCCC AAGGACAAGG AGAATCCCAC    156240
GTGGAGCTAC TTGCTTCTTT GTCAGTCTTG TTTTTCTTAT TCACAACCT TCTAAAACAC     156300
AATCTCTCAA CCTCTATTGT TAGCTTGCAT TTTTCAATCA TGAGCACAGC TTTACCTGGC    156360
TCCATGCTTT GATTGACTCT ACCTGCCAAC ACTGCAACAA CAGGGAAAGG GACACCGGCC    156420
TCATACCATT AGATGGTGTG TAGCCTGGGC ATGAGGATAA TTAAAAACTC CAAGGGGAT     156480
TTTAACATGT AACACAGTTT GGAAACCATT GATGTAAGAT CTTCTTACTC AACATGTGCT    156540
CCAAGGAGCT GTTGTATCAG CTTATCAGAA ATGTAGATCA GGCCGCACTT GGACCTGTAG    156600
AATCAGAATC TGCATTTTAT CAGATTCCGA CATTATTTGT ATGAACATTA GCTTTTGAGA    156660
AGTGTTGCTT TAAGAGACTA AGGGGGTCAA TCTACCTCAC TTTGCAGCTC TGTGTTCCTT    156720
AGTCATTGGC TAAAATATCA GCCCCCCTGC AATGAGCCAT CCTCCCTTGT ATAGTCAGTG    156780
ATGGCCTGTG AACCTTTAGC CAACTGGAAG TGGGAGGGGA CACAGTCCAC AAAACACTAT    156840
CCTGACTTTT GACACCAACT ACAAGTCAAG GGGTTCCCCA AACCACCCTG AGTTGTGATA    156900
ATTCGCTGGG AGATCTGACA GAACTCACTG AAGGTTGTTA TACTCATGGT TGTGATCTCT    156960
TATAGGGAGG GAATACAGAT TAAAATCAGC CAAAGGAAGA AGCACACAGC ACAGAGTCCA    157020
GGACAGTGCC TGACATGGAG CCCCTACGGT CCTCTCCCGT GGAGTCACGG ACAGCGCCAC    157080
TCTCCTGGCA TTGATGTGTG ACAACACACA GGGAGTGTTC CCCACCAGGG AAGCCTTGGT    157140
GTCCAGGGTC TTTACTGTGG CTCTGTCACA TGAGCACAGC TGACTGCCCA TGCGGCCGAT    157200
CTGTTCCCAG ACTCTCCACC GCTACACATC ACTCACAGTC CTGCTCTAA ATCACACACC     157260
ATGACCCAAT GTCCCCGGGC AAATGAAAAC ACCTCTAGCA GGCAGGACGT TCCAAAGCCT    157320
TAGAGATCAC CTCTCAGAAG CTGAGGGCAG AAGCCAGACC TCTTTTTGGG CAGGGTTAAA    157380
TTCTTTATTA CTGTTTTTGA AAAAACTCCC AAATTGAGTT TTTCCTCTTC ACTTACAGCA    157440
GCATAACAAC AATCATCAAT GCAGAAGACT TCTGCGAGCA AAGGTGTGGG GGAAAACCCC    157500
AAGCAGTGGA CACTAGCTGG TGTCCTCCAA TTTGATTCTG ATGCTGTCTA CTGGGAGATA    157560
GTGTCAGATC CTCAAGCCTA AACCCTCCTT CTCCCAGTCA GAGGGCTGGC CTTTGGAACT    157620
TCTGACCAAT CCACTTCAAG TTGAGGTTCC AACCACTCCG CTCTTTGGGT TGGTTGATT    157680
TGCTAGAGTG GCTCACAGAA CTCAGGGAAA CACAGCTACC AGTTTATTGC GAAGGACATT    157740
TTAAAGGATA AAAGTAGGCA GATAAAGAGA TGCATAGGGC GAGGTGTGGA AAGGTCCCTA    157800
GTGCAGGAGC TTCTGTCCAT GTGGAGCGGG GGTGCACCAC CCTCTCAGTA CATGAATGAG    157860
TTCTCCTTCA CCTGCCTATC AGCCTCTACA TGTTCAGCTC CCCAACCCAG TCCTCTTGGG    157920
TTTTTATGGA AGCTTCAAGA CACCCACATT CTTTCCCCAG AGTATAGGGC AAGACCTTCT    157980
CTGGGGAGGG TTTTAAGACC CACAGTCAGA AAGGTGGGGT GGGGTCAAGA TTAGAGTCCT    158040
GCCTTGACGG GCAGGTGAAA GGGGTAGGGG GAGTAGGTGA GAAAAATTCT GTTTATTTTT    158100
TCTTTTTTTT TTGAGACGG AGTTTCACTC TTGTTGCCCA GGGTGGAGTG CAATGGCACA     158160
ATCTCAGCTC ACTGCAACCT CCGCCTCCCA GGTTTAAGCG ATTCTCCTGC CTCAGCCTCC    158220
```

FIG. 6.60

```
CGAGTAGCTG GGATTACAGG CGTGTGCCAC CATGCCTGGC TAATTTTGTA TTTTTAATAG  158280
AGACAGGGTT CTCCATGTT GGTCAGGCTG GTCTCAAACT CCTGACCTCA GGTGATCCAC   158340
TTGCCTCAGC CTCCCAAAGT GCTGGGATCA CAGGTGTGAG CCACTGCATC TGGCCAAAAG  158400
ATTCTGTTTT TGAGGCCTGC CTCTGAGGTC TAACACACTC AACATTATAA CAAGACTGTA  158460
GTAAGGGCTA TGGGAGTTAT GAGCCAGGAA CTGTGGATGA AAACCTATCA CAGATATGCA  158520
TATATATATA TATATATATA TATGCATATC TATAATAACT CCACAACTAC ACACTGCCTT  158580
ATTGCTCAGT TCTTCTCTCC ATGTCTCTGA CCCACCCTTG CCCCCTTCCT CCATCCTTTT  158640
CTCCATTGCA TACCCATCCA CTGTGCCCTT TGGAATGCTC ACACCATGAA CTGCAAACTC  158700
TCGTGTGGCT TCAGCCTCTT CTCTGAAAGT TCCTCTCACC TATTACTTTC TCTGGAACCT  158760
GCCATCCCTG CCACCTTCTC AAAAAAGGCC TTTTATTCTC TTCATTCCAC AAAGCTCAGT  158820
GTCAAAACAT GGGGTTTACA CTGGAAGCTG AGGTCACATC AGTAGCCGGG ATCAGGGTCG  158880
CCCTAGCTGC CCAATGCAGC TCCCAGGCCT CCTGTAAAAC CTTGACCTTT GAGGTCATGA  158940
CAGCCCTCTC CTGCTATGCT CATAGCTGAC CACTGAACTC CTGGACACTC CCTCCCCCAA  159000
GTTCACAGAG AATGTGGGCA CATGCCTTAC AGTCTTCCCT TGATCCAAAC TACTGCCTTC  159060
ATCTTGAGTG ACAGCAGCAT CTTTTGGATG TCTTGGCCTG TCTAGCTTTA TTTTTTTGTG  159120
TTCTGCCATC AAGTTGCTAC TTCTGTTGCC ATCGTGCCTG TCAGCGCAGT GCAGGCTGTG  159180
GTGAAATCCC ACGAACTCAG GCATCACACT GACCGGGTCT GAGTCCTGTC TCAGTTGTCA  159240
GCTAGTTGTG CAATGAAGGG AAAGGGACCT ACACTTTCCA AGCCTCAATT CACTCATCTA  159300
TGGCATGGTG ACAATAATGG AGGTTGATTT AAAGTCCTTT GTAAGAATTA AGAGTTATAA  159360
TAGACATAAA GTGCTGTATC TGGTATACCT AGAAAACATT CCATAAAAGT TAGTAATTGT  159420
TGGTCATGTA ATGATGACTC TCTAGGCTAG GATTTCAGCT TCATTGCATG CACATGGTGC  159480
ACTCACAGGG CGTGACCTCT CTCTGTCTCA GTAACCTCAT CTGAGGACCG GGATAATCAT  159540
ACCGCTTCAA AGGGATGTCA TAAAGATTAA ATAATATGTG TAAGGCTGCT TGCATTTAGC  159600
TGCATTCAAC AAATATTTCT GTATCTTTCT CCTCATTTCT CCTTACTTTC TTGCTTATTA  159660
TCTGCTCTAG GTATAGATTT CAGAGAACTA AGCTTGTTAC AATCCTTCAT AAAATAACCA  159720
GGTTGGTTAG GGCATTTCCA AGAGTCAATA CTGTTTAGTG ACTATTCTCT GTTTAATCTA  159780
TTTTGATTGT CCAGGGTCAT CTTTTGCTAT GTCATAGGTT GTTGGCTTCT TCTAGAGAAG  159840
TGAGACGATG GACAAGTTCC AAGTGAGTGA GGCGACTGGT CAGGATATTC CGCTGAAAAA  159900
CTCATGTCAG TTCTAATTCG TGATTGTAAT TCAATCACAG CCTGAGAACA GTAGGACTGT  159960
AGTTCAAATG CTCTGTTCCC TTTTTTTTTT CCCAGAGGAT AATTTTTTT TTTCTTTGAG  160020
ATGGAGTCTT GCTCTGTCAC TAGGCTGGAG TGCAGTGGCG TGATCTCGGC TCACTGCAAC  160080
CTCCGCCTCC TGGGTTCAAG CAATTCTCCT GCCTCAGCCT CCCAAGTAGC TGGGACTACA  160140
GGCACATGCC ACCACGCCCA GATAATTTTC GTATTTTTAG TAGAGACGGG GTTTCCCCTT  160200
GTTGGCCAGG GTGGTCTTGA TCTCTTGACC TCATGATCCG CCCACCTCGG CCTCCCAAAG  160260
TGCTGGGATT ACAGGCGTGA GCCACCGCGC CCGGCCTCTA GAGGATAATT TTTAAATGTG  160320
CTTTTGCATT TGGAAAATGT GATTGGCATT TTTTTCTAAT TTTCTAATAT GATACGCTGT  160380
CGGATGCTAT GGATTACTTA AACCCTCTGG CTACCTAGAA AGATCTTTAA GTGGTTCTCA  160440
ACAAGCTTCA TACGCAATGT AAATTGTATT ATCTCTCAGG ATGTGTGAGA ACATCTGTTT  160500
TTCTTCTAAT GCAGTAAACA TATAAGGGTC TCTTGGGATA TCTTTTAAAT AGACTTAATA  160560
CAACATTCAG GAATGATAAC AAAATATAAT CACAGTTGTA AGGGAATGTG AGCATTTCAT  160620
ATTAATAACA TTGGAACCTT ATGTTTAATA CAGTGTTAAA AGTTGACAAA CATGTAGGAG  160680
TCAGAAAATT CAATTAAAAT TATCACAGTA ATATGAATTT AGCCACATCC TGTGTTAGTT  160740
ATGAAATCCA TTTAACACCA CAAACAGTAA TATTTTTAGC CAGTTTATTC AAAAGGAAAA  160800
CAGGAACTAA ACCACTTTCA TGCAATATAT ACTCTGTTAA TGTGGTCAGG CTAATTTTGC  160860
```

FIG. 6.61

| | |
|---|---|
| TGGGGGAAGG AACTTAACTT TTGAATATTT GAATGCCCAG TCATTTAATC TGAATATCCT | 160920 |
| ATTTCCTTGC ATGTTGCAAA ATTTTTGTCA ATAAAAGGCA GAAAAGAAA TCTCTTCTCC | 160980 |
| ATGCTCATCC CTAAGAGAAT GGGTTGTCTG TACCCTGAGA GCATTTTATG GAGGGGACAA | 161040 |
| CCACTTTTCT AATTTTCCTT CCCACTTCTC TGTGGGCACA AATGCTCTTT GGTTGAAAGA | 161100 |
| GTTGTAATTC AGTCCCAAGA TGAGGTGTGG TTACTGCATC CCTAACCTAT ATCTGGGGAC | 161160 |
| CCCACAGCCA CACACATGGG GGAAATGGAG CTTGTCATTC AGTTCTCCAG CCATTGCACA | 161220 |
| GGGTTCATGG ACTCTTCGTT GATCCCACCC CACGCTTCTT CTCTCTGCTA GCCGAACACA | 161280 |
| CTTCTCTCTT CTTTATCAGG AGGCCATAGG AGAAGGGCAT TCATTTTTAA TACACATACA | 161340 |
| TCTGCATCAA GTCTAATTTT GCCATGTCTC AATCCAACTG TCAAATGGGT TGTTTGGGGG | 161400 |
| CTATGGTGCT TATCAAACAT TTACTCAAGA ATAGCCAAAA TTAGCCAAGC AAGGAGAACT | 161460 |
| TCAGCAACGT TCCCAAATGG CCCCAACCAA GTACTGTAAG ACTGAGGATA GCTAAAGGGT | 161520 |
| CTTGAGAGGG ACTTCTCAGG CAGTGGCCCC GACATTTATC TGTTTTTTTA AGTGAGAAAT | 161580 |
| CTGAGTACCA TTCTTGACTC CTCTTCCTTA CCCCCAACCC CTCACTAAGC CTTGTGCTAC | 161640 |
| TATTTAGTAA ACAGACCCTC AATGCACAAA CTTCTGTCTA AGGCCATGGC CACCACCCTA | 161700 |
| GTCTAATCCA CCATCTCTTC TCTGGAACAG ACCCCAGCTG CTCTCCCTGT CTCTGTGCTG | 161760 |
| GTCTCTCAAT CCATGCTCCA CACTGCAGCC AGAGTGCTCT ACAATGCAAA TCCATTTGTG | 161820 |
| AGACTCCTCC TCTTAAAATC CTCAAGTGGC TTCTCTTTGC CCCCAGGATC ATTTTGAAAC | 161880 |
| TCCTTAATGG AAGAGGCATG GCCCTTTGGG ATGTGGTTCC CCAACCCCTC CCACATCATC | 161940 |
| TTTTCAATCA GATTTCCCAC TAAATGGAAA TTTTTTCAGG TCCTCAACTT TATGGTGACT | 162000 |
| TTCTCTTGCT CAGGATCTTT GAACATACTG TTTCTTCTTT CCTTTTGTAT TTGCCAAGAC | 162060 |
| AACACTTCCT CTGGTAAGAT TTTCCTGACA TCCTCTATAA AAAAAGATTG AGATAGTTGA | 162120 |
| CTACCCAAAA TGTTTCCCAT TCATTCCAAG CTCTATTCAA GGCAGTAAAG TGCCCGGCTG | 162180 |
| ACAGATTGCA TTCCTCATCT TTTCTGAAGC TAGCAATGGC CATGCAACAG CATTCTGGCC | 162240 |
| AATAAGATAG AAGTCGAAGT TGAAGGGTGG GATTTCCAAG AAAGCTCGTT GAAGACATAA | 162300 |
| TTCCTCATTT CACTTCTTAC TCTTTCTCTT CCTGCTTCC TAAAATGCGG TGCAGATGGC | 162360 |
| AGACACTTCA AAGCTGTCTC AGGCAATCAG GTGATGTTAA GGCAGAAACC AGCTTTATGA | 162420 |
| TGGGTAGAAC AGGAAGAAAG AAGGCACCTA TGTTCTTGTT CACCTTGAAC CACACCAGCA | 162480 |
| CTGCCTTGCC TACCCCTGGA ATTCCTTTAA TGAGAGGCAA ATGAGAGCTT ACGTGTTTAA | 162540 |
| GCCATTGCTA TTTTATTTTT TTTTGTTTAT ATGCAAAAGA ACTTAATCCT AACTGATATT | 162600 |
| AACACTAACT GGGTCTATTG CTTGGTACCA AGCCAATGCA TGACACATGG TATATATGCT | 162660 |
| CAGTAAGTAT TTGTTGAATG AGTGAGGCAA TGAAAGAACA TAGAGGATAT ATATAACAGT | 162720 |
| CCTCCTGCCC AGATGTCATC TGATCCTCTT TAGGATCTGG GCCCATAAAA CTGTATCTGA | 162780 |
| TATAGTTTGA ATATTTGTTC CCTACAAATC TCATGTTGAC ATTTATCCC TAATATTGGA | 162840 |
| GGCAGGGCCT AGTAGGAGGT GTTTTGGTCA TAGTGATAAA TGGCTTGGTG CCGTTCTCAC | 162900 |
| AGTAACGAGT GAGTTTTTAT TCTAGTGGTT CCTGCAAGAA CTGATTGTTA AAAGAGCTTG | 162960 |
| GATCCTTCCA CCCCTCTCTC ACTCTTGCTT CCTCTCTCTC ACCTTGTAAT CTCTACAAGC | 163020 |
| TCTTCACCTC CCCTTCTCCT TTTGCCATAA GTGGAAGATT TCTGAGGCCT CACCAGAAGC | 163080 |
| AGATGTTGGT TCCATGCTTC TTGTACAGCC TGCAGAACCA TGAGCCAAAT CAACTTCTTT | 163140 |
| TCTTTATAAT TATCCAGTCT CAGGTATTCC TTTATAGCAA CACAAATGGA CTAAGACAGT | 163200 |
| TTCTAATGCT ATGGTTCCTT TAGTAGGTCA GTGTAAAACC CTGGATCACT CCTGTAACAA | 163260 |
| ATTACTTGGA ACTCTTCTCA CCATACATAT TTAAAAATAG TTGCCATGTT GAAAATCCTA | 163320 |
| TAAGATCATA TTTTATTTCA AATCCAACAA CTCATTGCTA AGGAGATACA AGAAGCAGAA | 163380 |
| AATACAGAGA GACTAATGTG TTGATGATTT TTGTGAGGGA CATAAGGTCT GTGTCTAGAT | 163440 |
| TCATTTTTT GCATGTGGAT GTCCAGTTGT TCCAGCACCA TTTGTTGAAA AGACTATCTT | 163500 |

FIG. 6.62

TGCTCCACTG TATTGCTTTT TCTCCTTTGT CATAGATATC TGGTCACCTT ACCTTAGAGT 163560
CACAGATGAA TGGTCCTATT ACTTAACTAC TGAAAATACA GGCCAAAGCA AACAGAGGAA 163620
TAAGGGATAT ATAATAAAGT ATTTGTGTAC TTGACTTGGC TCTAAAGGAA GCATTGCGTG 163680
TCTGTGTAAA AAGAATGGGT GAGAGTTTTC CACCATTCAA TATTTCTAAT CTTTCTGAAA 163740
TACAAAGCCA GGACATCCTC TAATCCATAC ATTCCATAGT TTGGTTAATA TAAATTCCTT 163800
TATTAAATCC TTATTAAATA AAGTTATTTA TGTTTCTATG AAACTCATTT TAACTCCTAA 163860
GTGAAAAATA CTACTGAGCT AACTAAACAT CAAACATTTT TAATTTTTTA AATTTTTTTA 163920
GAGACAGGGT CTTGCTATGT TGCCCAGGCT GGCTTTGAAC TCCTGTGCTC AAGCGATCCT 163980
CCAAACTCAG CCTCCCGAGT AGCTGGGACT ACAGGTGCAT GCCACTGTGC TCAGCTAAAC 164040
ATTTTTTTGA AATGCTCTTT TAAAATCAAT TTTATTGAAG TATAAGTTAC ATACCATAAA 164100
AGTACTCATT TTGAGTGTAC AGATTGACAA GTTCTGACAA ATGTGAACAA CCATGTAACC 164160
ATCACCAAAA ATAAAGATAT GAGACATTTC CATTACCCCA AAAGTTCCC GTGTCCCTCT 164220
CCAGTCAATA TCCAGCCCTA GCCCAGCTC CAGGCAACCA CCAATCTGCT TTCTGTTGCT 164280
ATAAATTGTA CTTATCTTTT CTAGTGTTTC ATACAAATGG AATCATACAG CATTTACTCT 164340
TTTGTGTCTG TCTTCTTCTG CTCAGTGTAA TGTTTTTGAG ATTCATCTAT GTTCTGTGCC 164400
TCAGTAGTTT GTTCTTTTTA TTACTGGATA ATTCCATTAT AAGAATATAC CACAATTTGT 164460
TTATCCATTT ACTGCCTGAT GGGCATTTGG TTGTTTCCAG CTTTGAACTA TTTTGAATCC 164520
TAAAAGACTG CCAGTTTTGA ATGAGACCCC AGAACAATGA ATGTAGGCTC TGTATACAAG 164580
TTCAGGCTGC TGGGCAACTT AGGCCTTAAG ACACAACTCT GCCACTTAGG CCTTAAGACA 164640
CAACTGACAT GATGGTGCTT AAAGTGGCTG TGATGGAAAA GGAGGCTGTT TGGAGCCTTT 164700
GGAGTGCCTT TATAGGTGAA CCCCAGCATA GCACCTAATG ATTTGGAGCA AAGCTGTGTC 164760
ATTCCCCAAA GATAACTATT CGCCTTTTGA GAAACATCTT CTAGCTACTA TCAATAATAA 164820
ACACAGAATG CATCACCATG GGCCACCGTG TTGTCTTTTG ACCTGAGTTT CCATTGTGAA 164880
CAAGAGTCAT TTGATCCAAG GCAGAAAGTT GGGTGCACAC AGCAGTGTTC CATCATCAAA 164940
TGGAATATGA GATTGGGCCC AAGTAGGTCC TGCAGACACA AATAAGTTGC AAGAGCAAGT 165000
AGTACAGGCG CTTGGCCTGG CCAGTACTGT TGCCAAGTTG ACTGCTTCCC CTCAGTCTGC 165060
ATCTGTGGCT TCATGGGGAG TTTCCTATGA CCACTTGATG GAGGAAAAAA CAAATTGGAG 165120
CATAGTTTAT AGTGCTGGTA CTACCCAAAG TGGCTAGCTG AGGCACTACA TCTCCACTCT 165180
GGGGTGCCCG TGAAGGACAG TGCCAAAGGA AAACCCCCTC AGTGAGCAGA ACTTGGAGCA 165240
ATACAAGTGG GTGTTCATTT TACCTAGAAG AGAAGATGTC CGTGAGTTAC AGATCTACAC 165300
AAAATCACAG AGAGTGGTTA ATCGTTTAGT CTGATGGTCA GGGACTTCCA AGAGACATGA 165360
TTAGAAAACT GGTGACAAGG AGTCCTGGGG AAGAGGCATA TGGATACCTC TGAACACACA 165420
CAAAACATGA GAATATGTAT CCCATATGAA TGTTAACCAA AGAGCAGCCA CAACAGAAGA 165480
GGATTTTAAA ATCAGCTGAA TAAGATGATT CATTCTGACA GCATCAGCTA GTCTCTTTCC 165540
CCAGCCACTG TTGCCCAGTG GGCTTACATA TATCATGGCC ATGGGGGCAG GGCTATGTAT 165600
GGACACAGCA ACATGAATTT CCACTCATCA AGGCCAATTT GGCTCCAGCC ATTGCTGAGT 165660
GCTCAGCCTG CCAAGATAGA AATCTACGCC AATATGGCAC CATTCCCTGG CTAGAAAAC 165720
CAACTGGTGG AAGGTTGATT ACATTGGACC ATTTCCATCA TGGAAGGGGC AGTGCTTTGT 165780
CTTCCCTGGA ATAGACATTT ACTCTGGATA TGGATGTGCC TTCCCTGACT ACTACAATGC 165840
TCTGCCAAAC CTACCATCCA TGGGCTTAAT TTTATTTGTT ATAAAATTTC AACCACCATT 165900
GCTTCTGACC AAGGAAGTAA TCTTACAGCA AAGGAAGTAC AGATATGAGC TTCTGATCAT 165960
GGGCTTCACT GGCCTCACAG TGAAGCAGGT GGCCAGATTA GAACAGTGGA ATGGATTTTA 166020
AAGGCTCAGT TACAGCACCA GCTGGGTAGC AACACCCTGC TGGCCTGGGG TTATGTCCTG 166080
CAGGATGCTT TAAGTCAGTG ACCAATATAT GATGCTATTT CTCCCATTGT CAGGATTCAT 166140

FIG. 6.63

```
GGGTCCAAGA ATCATGGGGT CAAAATGGGA GTGGCTTTTC TCACTATCAC CCTGGTGTTC  166200
GGGTAGTAAT TTTTCCTTCC CATTCCTGTA ACTTTGGGCT CTGCTATTGC AGAAATCTTA  166260
GCTCCTGTGG GGGGAATGCT TCCATCAGGG AATACAATGG TGGTTCCACT AAACTGACAG  166320
CTGAGTTTGC CATCTCCTCG TGCCAGTGAA TACACAAGCA AGGAAGGGGG TTCCTTTCTC  166380
ACCTAGGGTG ACTGATCCTA ATTACCAAGG AGAAATTGGA CTGCCACTTC ACAATGAGGG  166440
TGAGGAGTAT GTACTCTATG TGTCTGTGAT TAATGTCAAT AGAAAGTGAC ACCAACCTAG  166500
TACACAGAGG ACTGATCATG GTCCAGGCCC TTCAGGAATG AAGATTTGAG TCACCAGGCA  166560
AGGAACTTGG ACTCACTGAG GAGGGCATAT CCAAGGAGA ATATTTATC TATGTCCATC  166620
TATGTCCATC TATATTCCAT CTGTGTTCCC CTTGGAATTC CTATTCATGA ACATGGGGAA  166680
TTCCAAGGGG AATATAGAAT GAGTAGTGGA AGGTAGTTAT AAATGTAAGT CAAAAACCAC  166740
ACAACCAATT TGAGAAATGA GGAAGGTAAT AGTGTTGAAT ATGTCTTCTT TATCTTGATA  166800
TAAATGTATT TGTGCATATA TTAACCAGTT TATTTATTTA TTATTATTTT TTGAGATGAG  166860
CTCTCGCCAT GTTGCCCAGG CTGGTCTTGA ACTCCTGGGC TCAACTGATT CTACCATTTA  166920
GTCCTCCGAG TAGCTGGGAC TACAGGCATG CACCACCATA CCCAGCTGAC CAGTTTTTTC  166980
CTATTCCTCT ACTTAATTTC TCTACTATAC AACATAATAT GTGTTAATGG TAGTTAACTT  167040
TATATCTCAG TATTAAGTCA CAAGATATCA AAAAGGGAAT GCGACTTAGT TACAAGCAGA  167100
ATGAATATCA CTCAAAGATG AATAAAGAGA AGAGGGTTAG TGCATTTTCT GTTGGATGAG  167160
AGAAAGTTTC ATTGTTAGGC AGAAGCATGA TTTTGCCTTT TTTTTTTTTT TCCAAGGTCT  167220
CACTCTGTGG CCCAGGCTGC AGTGCAGTGG TGCGATCTTG GCTCACTACA ACCTCTGCCT  167280
CCCGGGTTCA AGTGATTCTC CAGCCTCAGC CTCCAGAGTA GCTGGGATTA TAGGTGCGCC  167340
AGGTTAATTT TTGTATTTTT AGTAGAGAAG GTGTTTCTCC ATGTTGGCCA GGCTGGTCTT  167400
GAACTCCTGG CCTCAAGTGA CCCACCTGCT TGACCTCCC AAAGTGCTAG GATTACAGGT  167460
GTGAGCCACT GTGCACAGTC ACCACGGTCT TTTTGGGAGG CAACTTTAGC ATGGTTAAGA  167520
GGTGCGAATG GATGTTAAGC TAACACCAGG TAAGCCCTGG TAGATGTGTA TTGTGTCAGT  167580
GGGCCTACGC TGGAGCCATG TTTCCCCAAA TTCACTTTTC CTATGTACCT CTGGATTAGT  167640
GTGGGCCACT GGAGACATTT CACATGAGAT GAGGAAGGTG GGAGTGAAGG AGCAGCATCT  167700
TTTTACACTA AGCAGGTCGG GGAGGGCATG TGGCTCTGTC TCACATTGTT GGGAATCTGT  167760
CCATCATCTG GTTGGCTTAG GTCAGTGGGT GAGTTCACAG CTGTTCCAGC TTCTGCTGGA  167820
AACTCCTTCG GTTTCTCTGA CTGCTCCGTG ATGAGGGCAT CAGATTCTCC TGCAGAAAGC  167880
CCCAGTGTTG AAGTTGGGGC TTCATGTTGG TGAGTGATAG TTACGGGTTC TAGCCCAACC  167940
TGTGGTTTCT TGCAAATTTC AGTGTCAGCT CAGTCTTGCG GGTTTTGGGT TGTCCTTGCT  168000
TCCCACACTT CATGCCTTTC TTTCCCTCCT GACAGTCTGC CCTTTAGATT TTAGGATTCA  168060
GCACCAGCCA CAGAAACAGC AACCTCACTG TTAAGGGTTG AATTGTATCT CCCCAAAAGG  168120
TAGGTTGAGG CCCTACCTGC CAGGACTTCA GAATGTAACC TCATCTGGGA ATAGCATCAT  168180
TGCAAATATA ATTAATTAAG ATGAGGGCAT ACTGGCTCAG GATGGGCTCC TAATTCAATA  168240
CAACTAATGT CCTTCTATGA CAGCCACAGG AAGACAGAAA CGCCAAGGGA GAACACCATA  168300
TGCTGATGGA GGCAGTGGCA GCTGCCAGCC AAGGATTATA ACCAGAAGTC AGGAAAAAGC  168360
AAGAAGGAAT CCTCCCTTAG TGATTTTACA GGGAGCATAG CCCTGCTGAC ACCTTGATTT  168420
TGGACTTTTA TTCCCCAAAA CTGTAAAACA ATACACTTCT GTTGTTTTAA GCCACTCAGT  168480
TTGTGCTACT TTGTTATGGC AACTCCAGAA AACAAAAATA CACTCAGACT GTTTAATCAA  168540
CCTCCATAAT TGCATAAGGT CTAATCCCTA TAATAAATCC CTTAAAAATG TCTGTGTATA  168600
TATATTTAAA AATATAAAAT ATCTTCTAGT GGTTCTGCAT CTCTGGTCAA TCCCTGACTG  168660
ATACAGAATA TGTATTTTCA TTTCTAATGA TGAAATACCT GAATGAAATT CTAGGACAT  168720
ATGGTAAGTG TATGTTTAGC TTTTAAGAAA CTGCCAACTT GGGGGAATTG CTTGAGGCCA  168780
```

FIG. 6.64

```
GGAGTTCAAA CAGCCTGGGT AACAGTGATA CCCTGTCTGT ACAAAATAAA AAATATTAGC  168840
AGCGTGTGGT GGTGTGTGTC TGTAGTCCCA GCTACTCAGG AGGCTGAGGT GGGAGATTCA  168900
CCTGAGCCCA GATCTTTGAA GTTATAGTGA GCTATGATCA CGCCACTGCA CTCTAGCCTG  168960
GGTGACAGAG TGAGAAAGCT GGTCTCTAAA AAACAAACAA ACAAAAAAGA AACTGTCAAA  169020
CTCTTCCCAA CATGTTGCCA TTTTTACATT TACCATTTTA CATTCTTACC AGCAATGATT  169080
GATAGTTCCA GTTGCTCCAT ACCCTTGCTG ACCATTCCAA TAGATGTATT GTGTTATCTC  169140
ATTGTAGTTC TAATTTGTAT TTCCCTAGTG ATTAATGATG TTTAACATCT TTTCATGCAC  169200
CTATTGGCTA TATGTATATC TTCTTTAGCA AAATATATGT TGTTATTTGA AGAGCGGAAG  169260
TTTTACATTT TGATGAAGTC TAATTTATTG ATTTTTTTTT TCTTAGATGG CTCATGCTTT  169320
TTGTGTTATC TAAAAAAAAT TTGCCTTCTT CATGGTCACA AAGACTTTCT CCTATGTTTT  169380
CTTTTGGAAG CTTTATATTT TTAGTTTTTA TGTTTATGTT TAAGACCCAT TTCTAGTTAC  169440
AATTTGTGTG ATTTTTTGGA AGGGTCAAGG TTCATTTTCT TTTCCATAAG AATGTACAGT  169500
TGTTCTAGCA CCCTTGTTAA AAAGACTTTC CTTTCCCCAT TGAACTACTT TGTCAAAAAT  169560
CAACTGAGCA TATATGGGCA TCATGAATTT TAATCCTGTT AGAACTGAAT GTTCCCAAGG  169620
CAGGCCATGC CCATGACTGA CCTCCTTTCC TTGGATTGCC TACAAAACAG ATAAAGCTAA  169680
GTCTGGAGCA AAGAAATCCA TGTCTAACCT GTATTTTTTT TTTTTTTTTT TTAGATGGGG  169740
TCTCGCTCTG TCACCCAGGC TGGAGTGCAG TGGCGTGATC CCAGCTCACT GCAATCTCTG  169800
CCTCCTGGGT TCAAGTGATT CTCCTGCCTC AGCCTCCCGA GGGGCTGGGA TTGTAGGCGT  169860
GCACCACTAT GCCCATCTAA TTTTTGTATT TTTAGTAGAG ATAGGGTTTT GCCATTTTGG  169920
CCAGACTGTC TTGAACTCCT GACCTCAGGT GATCTGCCTG CCTCGGCCTC CCACAGTTTT  169980
GTGATTATAG GCATGAGCCA CCGTGCCCGG CCTTAACCTT TGTTTTCTTA CACAACACAC  170040
TACGTGATGT TTTCCACATG CATGGGTCAT TTGCTTCATT TACGTACAAA TGCATAAGCA  170100
ATATACTGTG TGGTGTGAGT TTGTGATGGG AAAAGGAAGA AGTTTTGCGG ATACTACACT  170160
GGCTTCCTGC TATCTGTCTG TGTGAATGGC TATGGACTTT GTCTTCTATT TGTTCGCTTA  170220
GCGCAGATAT GATCAGCTTA CAACTTAAGA TTCTAGAGAA AGAGGGTCAT ATCTGTAAAG  170280
CACTCTGAGC ATGTGTGAAG TTTAATCAAT AGCATATGAG GTTACAGCAA ATTCACTATC  170340
TTTGTTTCTT CAGCTATAGA ATGGCATGAG GATTCATCTC AATTTAGTTC AATTCTGTTC  170400
AGAACCATGA GCTAGCTGTT CATGGAAGGA AAGCCCACCT GATTGTGGCC AGGGAAGGAG  170460
AAACAACACT TAACCAGGT TGATTTGGTT CTCACAGACA CCATTGGCAT GTGACATCTG  170520
GAACAGACCA TGCCTGGTCT CTGTTCGTAT CACTTACTAT TCAGCTCAAT ATTGGTCTGA  170580
ATATTCTTTA GACTGACTGA AATGAAAAGG AACTGTTGTG TAACCATCCA TAATTCCAGC  170640
CTGTAGACCT GGGCTGTATC TCTATGCCCT GCCTGGCACA GACCCCACCT CCTGCTCCTT  170700
CTCCCTCACC ACCAGTCAAT CCTTGTCCTA ATGAACAGGG AGGGCAACCC TGAATGGGGA  170760
GTGGAGGGAA GAGATGTCAT GAGATGGCAA CGTGCACCCT GAAGTGAGGA TGAAGGCTAT  170820
GTGAATGTTG TAGGCTGACA GCCGGGCATA GTGGCCCCGT TGCCATGGCG ATGGAGGCAT  170880
GTTGATGCGA AGTGTCTGCA CAGCTCCTAG GATTTTTAAC AGCAGCTGGG CAGAGCCTCG  170940
GCGTCCCTGA ATTGTTGCCC CCCTGAGTCA CTGCTTGGCC CCAGCTGTCC TGATCTCTGT  171000
TGACAAATGG TTGTCCTTCA CAGTCAAACT ACTAACAGTA CTCTAATTAA TGAATGTGCT  171060
AATTATTCTT GCCTACTCCC AGCATATTTG TCTAACTAAC CTGTCACACA CAGATCAGTG  171120
CAGCATATGC ATAATTACGG AGAGCGCTGG GAGCAGGGGA TGGGTGGGAG AGGGGTGGGC  171180
TCGCAGCCCT GTCGCTGTGG GATATTTCTT GTAAAGTTAC CTTTGCTAAC GGTCAGATGT  171240
CGTGGGGATA TGTTATTTCC CGTGAAGTGT ATATGTCTTC CTTTCTTTCC TTTCTAAGAA  171300
TCTCTCTTCA GGGCTGAGGG GCCATTGCTC AGTGCTTTAG CCTGTGAGGG GATTGCCAGG  171360
TACAAATGCA GAAGGACCAG GGAGCCCAGG TTCTGAAGAC GATTCCGGTA GCAGCACGTA  171420
```

FIG. 6.65

```
GGGTGATTAA AACTCCAGAC TTTAAAGCCA GACCGGCCTG GGCTTGAACC CTTGTTCTGC   171480
TCCTTGCTAT GTGGGTCTTT GCCTTGACCA CATTTTTTTT TTTTTTTTAA GACAGGATCT   171540
CCCTCTCTTG CCCAGGCTGT AATGCAGTGT TGCGATCACA GCTCACTGAA GCCTCCATCT   171600
CTACAGCCTC AAGCGATCCT CCTGCCTCAG CCCCGAGTAG CTGGGACTAC AGGTCTGTGC   171660
CACCACGTCC AGCTAATTTA CTTTTGTAGA GTTGGGGGTC TTGCTATGTT GCCCAGGCTG   171720
TTCTCCAACT CCTGGACTCA AGCCATCCTC TAGCCTCGGC CTTCCAAAGT GCTGGGACTA   171780
TAGGCGTGAG CCACGGTGCC AGGCCCTTGA CCACATTTTT AACCCCTCTG AACCTCAGTT   171840
TCACTTTCTG GGCAATGGGA GGGGGGTAAT TTGTCCCTCA GAGGGTTGCA CTGAGGGCA    171900
AATGTGAGGC TCTGGGTACA ATGCCCAGTA CAGACTAGGT CCCCACGACA CAGCCGCTCA   171960
GCGGCTCCGG ATTCTGGGCT GCTCTGGACT GCGGCCAGGC GGTCTTCTGC GGGAATCCGG   172020
GCAGGCAGGG CGGGCTGCGC TCCCCTCCCC GGCTCTCCCG GTGCCCCTTG TCTTTTTGTT   172080
CTGTCTCAGC AGCTCTCTAT TAAGATGAAT GGCATTTCCA AAGGCTTCAC CTCTGATAAG   172140
TGTTCCTCTG CAGCTGCAGC CAGAATCTTA ATGTGCGCGC TGTAATTTAA TGGCCGTCTC   172200
GGCTATTAAC ACGCTCTTCT CGGGTGAAGT GGACTCCCTC CATCCCCGGG CCTCTGCACG   172260
TGCTCTGCGC GCTGGCTGGG GGTGACTCCA AGGAGCTCAG AGCGGGGTGC CCGGCACCTC   172320
TCGCCAGGCG CCTTTCGACC TTCTAAAGCG CGAATGGCTG GACTTTTCTC CCATGTGTGG   172380
GGCCCCAGAA GGTGTGGGGC CCCAGAAGGT GTGGGGTCCC TGCGTTCCAC GGAGCCCGGA   172440
AGGTTTCCAG TGATGGTGGG GGCTGACCAC GTTGGTCCCC GTGGGTGCTG TTTTCATGTG   172500
CCGGCAGATT GGGATGAGTT TAAAAGACAG AAGCGTGTAG GATAGAGAAA CTTCTTTAAA   172560
AACTGGAAAT TTTAATCTGG GGATTATAAC TATTGGACAG TCAAGTGCAA GAGTGAATAC   172620
ACTTCTCACT CCCTCCTCCC AATTTTTATT GCGGGATTA GTCAGTCCCC CTCTGCCACA    172680
TGATAATTGT GAGAACTACC AGGGTCTTCA TTCTCCTGCC ATCTGGTTGA CCTCTCCAAG   172740
AATGGACACC CGGGCAGCCT GGGCCAATGA GGCTGTCCTA AGAGTTTAGA TGAGAGAAGT   172800
CAGTCTTTGA CAGGTGATGG AAGCTGTAAA ATGTAAAACT CCACAGTTGG TGAAGATGTC   172860
TCCAGGAAAC AGGTCTGCAG AGAGAATACG TTTGACATGC TAAGAGAAGC TGAGAGAGAG   172920
CGAGAGGAGA GATTGGAAGA AAGACAGAGA CAGAGGTAGA GAGAAGGGAA AGAGAGAGAG   172980
AAAGGGACAG AAGAGAGAGA AAAAAGAGGG GGCCGGGCGC GGTGGCTCAC GCCTGTAATC   173040
TCAGCACTTT GGGAGGCCGA GGCGGGCAGA TCACGAGGTC AGGAGATCGA GACCATCCCG   173100
GCTAACACGG TGAAACCCCC GTCTCTACTA AAAAATATAA AAAAATTAG CCAGGCGTGG    173160
TGGTGGGTGC CTGTAGTCCC AGCTACTGAG GAGGCTGAGA CAGGAGAATG GCGTGAACCC   173220
GGGAGGCAGA GCTTGCAGTG AGCTGAGATC GCGCCACTGC ACTCCAGCCT GGGCAACAGA   173280
GCAAGACTCC GTCTCAAAAA AAAAAAAAAA AAAGAGAGGA AGGGCGGGAG AGAGAGAGAG   173340
AGAAAGCTCT CTAGCTCCAA GGCCTAACCA CATCTCTGTT CTTTTCAACT TCAGCTGTCA   173400
GATTTTTAGA CTCTTTGAGT GAATAAATTC TCCTTTTTGC TTAAACTAGT TTGAGCTAAG   173460
TTTCTATTGC TTGCAACTGG AATACTTTGT AAGAGGACTG GCCTTCATTT CTGATGCATT   173520
GTCACTAAGA TGTAAGTGTT AGAAGAGCTA ACGCTTTATG GGGTTCAAAC TCCTTGGCTA   173580
CCAAAACCTA AACATCCCCT GAAACTTACC AAACTGCAGG TATGAATTGG ATCTCACTAA   173640
GGTGAATATA CAAATCTTGC AAGTGCTGAG CCCTAACCAA TCTTGTAATA ACTCTGTGGT   173700
AGTTAATTTT ATGTCAAATT GATTGAGCTA AAAAATGCCC AGGTAGCTGG TAAAATGTTT   173760
TTTTCTGGGT GTGTTAGGGA GGGTGTTTCT GAAAGAGATC AGCACTGGAA TCAGCGGACT   173820
AAGTAAAGAA TTCCCACCCT CACCAATATG GTGGGTGTCA TCAATCCACT GAGGGCCTGA   173880
ATAGAACAAA AAGCGGGCAG AAGGGCAAAT TCCCTCTTCT TCTTGAGCTG GCCATCCAT    173940
CTTCTCCTGC CCTTGGACAC TGGAGCCCCT TGTTCTCCAG CTTTTGGATT CAGACTGGGT   174000
CTTGCACCAT TGCCCTCCAT CTTCTCCTGC CCTTGGACAC TGGAGCCCCT TGTTCTCCAG   174060
```

FIG. 6.66

CTTTTGGATT CAGACTGGGT CTTGCACCAT TGCCCTCCTT GATGCTCAGG CCTTTGAATG 174120
CAGACTGGTC TCCACCAGCA GCTTTTCTGA GTCTCCAGCT TGCAGATGGC AAACCATGAA 174180
ACTTCATGGT GTCCATGAGC ATGTGAACCA ATTTCTATTA TAAATCTGCA ATATATATAT 174240
ATGAGGAGAC TTATTTATAT ATTGGTTCAG TTTCTCTGGA GAGCCTTGGC TAATATAAAG 174300
TCTATACTCT ACAAAGTGCC CTAGGTACTC AGGGAGTACC CAAGTGTGTC ATGACCAGCC 174360
CGACAGCCCT GGCTGCTGGC TTCCCCGCAC ACAACTCTGC ACGCTGCCTT CATCAGCCTT 174420
TCTCTCTCAG CTGAACCGAG GGCATTGAAG CGGGCCTCTG GCACTGTACC TATGAGGGAG 174480
CAATATCTTC CCCTACACTG ACCTCTTCCG TGCCGAGATG CAGCCCTCCC TGCTGCCACT 174540
AGTTACAGTG GTCCATGTTC CCTTTCAAAG TGAAGTTTTG ATAAAAGCAC CTCTTAACCA 174600
ATGCCAAATA GCTAAGTCTG GGACAAAGAT TGCAGGTATT TTGCATTTTC CATGTAACCT 174660
CAGAGGGATT GCCATTCACA CTGATCTGAG CTGCAGAATA CCAGGCAGCC ACCTCACCCA 174720
CCCAGCAGGT CCACTCTTAT ACTTCTCAG AAAGCACAGC CACTCTACTC TTATTCAGTT 174780
GAAAAGAATT TCCAGGAAGG TGTTTCTGCG ATTGCCTCAG AAAAGTCAGT TCCCTTTGGG 174840
AATTTCCCTT AGGGATCATC TGTAACTCCA TTTCTGCCTT TTACCTGAAT TCTTTGGTTT 174900
GGTTTGAATT CTTTGGTTTA ATTTATGAAT TCCCTTTATT ACTTTTCTCT GAAGAAATGG 174960
AGATATCAGC TGTCCCTCCC CACTGCCATT TATTCCTTCC TTCATTCAAA CCTTATGTGG 175020
CTGCTACTTA CCGTGTGTTA AGTGTTCACT TTTTTTCTTG GAATTCAAAA AAAGAAGGAC 175080
AGTATTTGGG GCACAGATCT TTTGGTGTTC TATACATTTT TTTAAAGTTT CATTTTACAT 175140
TTGTGTGTGC GTGTGTGTGT GTGTGTGAGA CAGTCTTGCT CTGTTGCCCA GGCTGGAGTG 175200
CAGTGGCATA ATCATTGGCT CACTGTAGCC TCAAAGTCCT GGGCCCAAGC AATCTTCCCA 175260
CCTCAGCCAC CCAAAATGCT GGGGTTACAG GTTTATGCCA CTCTGTCTGA CCTGAAAGTT 175320
TTGGGTTTAC TTTCCCTTCT TTCTCTTTGC TGAAGTCAGA GATGATGGCA GCTTCCAGAT 175380
TCTCTGGTGC CTGTGCTGGG CTCGTGCTGG TCATGGTCTT GGGTCCAGGA TTCATTCTGG 175440
AGACTCTCAG GGAAGTTTCC CATGACAAGG AAATGTAGGA GAGTGTGCTG GCTTGCGTG 175500
CTCCTCTGCC AAGCCCTGCT TCTCCTGGTG GGACACACTG AACCACAGCC AGGGCATTTT 175560
GGTGGTTAGT TAAAAAAAAA AAAAAAAAAA AAAAAAGGAA GAAGAAGGCA CTGTGTAATT 175620
GTGCCGGGGA TCTTCAGAAA TTGTAATGAT GAAAGAGTGC AAGCTCTCAC TTCCCCTTCC 175680
TGTACAGGGC AGGTTGTGCA GCTGGAGGCA GAGCAGTCCT CTCTGGGGAG CCTGAAGCAA 175740
ACATGGATCA AGAAACTGTA GGCAATGTTG TCCTGTTGGC CATCGTCACC CTCATCAGCG 175800
TGGTCCAGAA TGGTAAGGAA AGCCCTTCAC TCAGGGAAGA ACAGAAGGGG AGATTTTCTT 175860
TGATGGTTGT TTGGAAGTCA GGCTTAAACA ATTGTGTCTG TGTGTGCGCA TGCACAAACA 175920
CTTTTACCTT ATCTTTATTT TCTTCTTTTT ATTTGAATGT ATAGGGTTGT GTGTATTTCT 175980
GTGTAAATTT GGGGTTTTCC TCCTCTTAGT CTTTCACTTT TGTGGTGATT ACCAGTCCCA 176040
TTTTTAGAGC CAGGGCTGCA ACTTGAAGGT TTTGCTAAAA CCCTCACCGA AGTGTCTATG 176100
ATCAGCATTT TAACTATTAA TTAATGTGGC CAGGCAAGGG GTGGAAGGTG AGAAGACTAG 176160
AAAGGGAACA TGATATACAC ATTTACTCAG ATACTGGGCT TTTCTAACAT CTGCAGTGCA 176220
ATTGAAGTTA CCAGTCATCT GCAGTCTAAA AAGAAAGTGA TTTTGGGAGG TGCGTAGAAA 176280
AAATCATCTT ATTATTTTTC CTCTATATTA CTTTTTTCTT TTTTTCTCCT GAAGAAACTT 176340
TTTTTTTTGG TGATACCTTC TTTTTCTCTA GCACGTATAA TTTTGGAAGC ATTTTTCATA 176400
TGCAGTGTAT ACTTCAGAAA GAGAGAGAGA GAGAGGAAAA TTGTCCTGTT CAGCGTTTGC 176460
ATTTCCATTA TTCCTGCTAT TAGTTAAAAA CAACAACAAC AACAAAAAAC AAGCAGGATA 176520
CCTAGATCTG GAAAAGGGAG AATTGTGTAG AGCTGTCTTC CTAAAGTTCT GAGTTAGGGC 176580
TGCCTCAGAC CACTTTCATA ACTATCTCCA GTGGCTTTGT GTTTTATATT TATTAAGATA 176640
GAGAAAAAAA GAGTAATTAC TAAGGGCAGC TGCTGTAGCT TTATGGTGAT TACTGAACAT 176700

FIG. 6.67

```
TGACATGCTG TCACGTTTTT GGAACTTTGA GTATTTAATC ACTTTGGGAT ATTCTATTTT  176760
CCCCCATCTT GAGTGTGGAC AGATGCTGGT GATGTAGCCT TCTGGGCACA GAGCAAGCCT  176820
CCCCCTCAGC CTCTGCACCA GAAAGGCTCA GCTTCACACA CTCCAAGTAT GTTTTCTACA  176880
AGAACTACAC TTTGTGGCTT TCTGACCCAA ACATTTTTAT ACTAAATTAC ACACAACAAA  176940
GTTGTAGCTC AGAGAGGGAA CAAATGGCTT ATTTAGGCCA CCATTTTCTT GAGCCATTAT  177000
GATTTCACAC AGGGCTCCCT TGGCCCTGTA AATTGGCAAG GATTCCATTA TTCAACCCGC  177060
ATACATGTAC AGAGACCCTG CTCTGGCCCA GATAGTATTC TGGGTACAGG CGGATAGAGC  177120
AGGAAACAAA ACAGCTACAG TGATGGACAG GTCAGCCTGC AGCAATGCCT GCAGTCTCTG  177180
CAAAGGTAGC TGTATGGGTG GGCAGGTGGC TAGCACTTAT TCAGCTCTGG AAGGATCTCC  177240
CCTCTGGCCT CTCCCCTGAC ACCCATCAAT AAAACTGAGG AGCATCGGTG GACAGGGGAC  177300
CTTGTGCCCC CTCCCTGCCT GTGCAGTTGG GGCTGAACCC AGCTACGAAG TTTGAGCTCA  177360
CTCTCTCCAG CTCCCTCTCA ATTCAGAGCT GAACTGTGGG AAGCTTCAGA GCTCTCTGTT  177420
TCAAGGACAG GTTCTCCTCA CCTCTCCTAA TGGAGGTGCA CCAGGGAACT GGCCCTGCTC  177480
TGCCCAGGGC TTTCTCCTGG ACTTTGCCAT CATGGTCTAG CAAACCCTGT TCAGATTGAG  177540
GTGAGTGGTG AGATTTCGAA TTCTTTTTGA CAGATAGGAT TAAGTCTTCT TCTGTGGGAC  177600
AAGTGGGAGG TAGAGGTAAG ATTAAAGATG GCCAAATGTC TGAGTCCTGA CAGCCACAAT  177660
ATGGAGATCT AGACTTTTTA CAGACCACAG GGCACAGGGG CCTCACTAAC AGAGTTCCCG  177720
GAAGTGATGA GTGTGCTGGG GGCTTCCTGG TTGAAGAGAC ACTAGAATGG ACCAGCTGGG  177780
AGCTAATTTT TTGGGCTGGA GTGTGATGGC CTGCACATCA CTGCCTCTGT CCCTCCATTG  177840
TCACAGCTGC CCCTTAGGAG CCAGCTGAGG CAATTTGTGG TCAGAGTGAC TTTGCACAGT  177900
TGTCCTGCCT GTGTTCAGGA AGGGAGTTTC TGTGGTCCCT TTGAAACCAC AGAAGAGCCC  177960
CTCGTATAGC TCTCAATGGA GGGGGCAAAA CATTCAAATA ACTCAGGAGA TAACACAACT  178020
ATTTGTTTTT AACTGTGAGT TTTTAGGCAA TCACAAAGAT CCAGATGTAT GTCCAAGCCT  178080
CTCTTTGCAA TTCTAATTAA CCTCAATGTT GCAACCATAG ACCTACCTTA CAGAGTTCAA  178140
AAAAATATGC AAAAACCCTG CCTTTCTTCT TCCTCATACC CCAAAATGCC ATTCTGAACA  178200
TTTCCTGTTA GTTAAAAAAA GATTTCCATG GTGTTACCAG GCACTGTACA CAGTCTGTGT  178260
CCCAAGACAA GGAGGTACAG TTCCACATGC GCCCATGACT GGGTTGGGCT CTGCACTCTC  178320
TCTATACTTT GAGAGCCTGA TTTTCTGTGA TTGGGCAGAG CTGGCCCACC TGGTGCAATG  178380
TCCTCCTCTG CCTTTCAAAC ATGTTTTAGT CATCAAGATC TTCAAATTTG TAACCCTTTC  178440
CAGCTTGATC CAGCAGAATG CAGATTTGGA AAAACAGAAC GAGTTTAAAA TACATGATTC  178500
TAAGAAACCT GGACCAGAAC TATCAAAACT TGGTTTCCCA GAGAATATAG CAAATGGGCT  178560
CATTGGCCAA TACTATGACA TTGGCTTTTG AGAAAAGAAA GGCTTTATTG CAAGGCTGGC  178620
CAGCAAGGAG ACAGGAGTTG GGCTCAAATC TGTCTCCCCA GTTTGGGGCT TAGGGCAAGT  178680
TTTAATTACA CAGACGCATT TCTTATGAGT AGCAGGCAGA GAGCCTCCAA CTTCTTCTGC  178740
CTAGGTACCA GCAGCTTAGA CATGATGCAA ACCTGGGAAG CACATACTGT ATTTGGAGAA  178800
AGTGATTGGG AAGAAATGTG AGCTGAGGGG AGGGGCTCAG TGCCCCTGAG CTACACTTAG  178860
TGATGGCAGA GGAAGGATGT CCTCCCGCAG GAGGCTGTTC CACATCTGCT CTGGTTGTAG  178920
GGGGAGCTGG CAGGCATTAG CAGCGGCCTC TTTCCCCCAA GAGAGGCAGC CTCCTCCAAG  178980
TTTTGGCGAC ATTATGGCCC TGCAATCATA AGGGTTTGTG AGCATAGTGC TAAGGAGGGA  179040
AATGGAGCTG CTGTTACTAG TTCCACCCCA ACACACACAC ACACACTCAC AAGAAACCTC  179100
ACAAGCACCG TATTGGAAGA CTTTGCCATC CAACCTGGGA TTTGACAGGC TCTAGAAGCA  179160
GAATCATAGA CTCATGAAGT TCCCCCAAAG CAGGAATCTT CCTTACAGTA ACCCCCAACC  179220
ACCCCCCTCC ACCGCCTCCA CCGGCTGCTT CTTCCTGAAC ACTGCAGTGT TTGGAAAACT  179280
CACAAACTTC CAAGCTTGCC TTTCCTATTG TTGCATGGAT TGAAAGCTTG CGTTGTGTGA  179340
```

FIG. 6.68

AGAATGGCGC TTCCTGCTGT GCTTAGTTTT ATCTCATATA ATCTTTGCAC CATTTAATCC 179400
TTGCACTCAC CCACTCATGC AACTGCCTTT GCAGAGACTG GAGGGGCCGC TGTAGGCTGA 179460
CCTTTCCTTC ACTGTACCTA TTTTGTTCCC TGCTTTATTC CCCTGCACCC AGGACACTGC 179520
CTGGCACAAA GACAGGTCTT TATAAGTGTA TGCAAGTGAA TAAAGATATA TATATTATTA 179580
TTGTTATTTT TGAGACAGTT TCACTCTGTC ACCCAGGCTG GAGTGCAGTA GCGCAATCTC 179640
AGCTGACTGC AACCTCTGCC TCCCAGGCTC AAGTGATTCT CATGTCTCAG CCTCCTGAGT 179700
AGCTAGGACT ACAAGCATGT GCCACCACGC CCAGCTAATT TTTGTATTTT TAGTAAGGAC 179760
AGGGTTTCAC CATGTTGGCC AGGTTGGCCT CCAACTCCTG ACCTCAAGTC ATCCTCCTGC 179820
CTCGACCTCC CAAAGTGCTG GGATTACAGG CATGAAACCA GCCTAGAAAT ACATACTATT 179880
ATTTATTCTT GTTTTACAGA TAAGCAAAGT GAGTCATGGA GAATTTGGTT GAAAGTCCCA 179940
AGGTCAGGAG TCGTGAAGCT GGGATTAAAA CCTAATCATC TGACTTTAGA GAGTAGACAC 180000
TTGCTCCATG CATATTGCCT CCAATTCATT CATTCAAGCA CTCCTGCTC AAGAAGTTCT 180060
TTCTTATGTT GAGCTGAAAT CTGCAGCCCT ATGCGTTTTA CCCAGCAGTC CTGGTGCTGT 180120
TCCCTAAAAT CACTTAGACT GTGCCTGCTC TTTCTGTGTT TACAGTGTCA GCTGTAATAT 180180
CCCCCTCTTC GGCCTAACGT TTCTGAAGTC CCTTGCCACT GGGTCTCCTC TCCTCTTCCT 180240
GTGTTCTTTC TAAGAACACC TATGCAGATA GGTGTCTTCT GTACAGGGAA GCTGTTCCTG 180300
AGATCCGGGC ATCGACTCTG TTAGAATAAT CTACGTATGA GTTATTTTTT TGAGAACTAT 180360
GTGTCATTGC TGACTCATAT TAACTCTGTG GTTAACTAAA ATCTCAAGAT CTCTTTATGT 180420
TTGTTGAGAA ACTTATTTAA CTTCTCTGGC CCTCCGTTTC CTTCACTGAG CAGTGGAGTG 180480
ATTGATAACC TCCACCTGTG GTTGCTGAAG GTCTTGCACA AGATGATATA GTTAAAGTAG 180540
CTAGCAGTGC CCACGTACGG CGGATGCCTC ACAACGGTTT GCAGCCATCT CTCTATCTGT 180600
GTCTTTGTCT CTCTCTCACA CTGGTTTTGG CTTACTGTTA GCAGCTAGCC GAGATAAGTG 180660
TGTTTATGGT CTTTGCATGT ATTGTTTCTG TAGCATACTG GAGGATTACA AGAGGTTGGG 180720
GAGTGAGGGG GCGGTGAGGA GTAGACAAAG GCAGCCAACT CTTCCAAGTT TAGCTTAGAA 180780
GGAAGGAGCG GTAAACCCTA GTTGAATGTT GGACTGAAGC AGGTTTGTTT TTGTTTTGTT 180840
TAAAGGATAG GGAAGATCTG TGCGTGTTTC CAGGATAAAG AAAAGGAGAG AATATGATAT 180900
TAAAGATTCT GGAAGTGGGA GAAGGAGCAA TGAAATACAG ACTTGAAGTC AGTGGCATGG 180960
ACAGGGTCAA GATCACAGTT AGAGGATGCA GCCTTAGAGA AAAGGAAGGG GCTCGGTTCT 181020
CTGAGCAAGG AGGGAAAGAA GAGAGGCAGA TGCAGAGAAG TACGGCACAT CGTGCTGCTG 181080
GTTGTAGAAA TAACCTCTGA CTTTTAATAA AGTCATCCCT CGGTATCCCT GGGGGATTAG 181140
TTCTATGACC TCCCTCGGAT GCCAAAATTC GTGGATGCTC AAGTCCCTGA TATAAAATGG 181200
CATAGTATTT GCATTTAACC TACACACATC CTCCATATCC TTTTTTTTTT TTTTTTTTTT 181260
TTTTTTTTTT TTTTGTGAG ATGGAGTCTT GCTCTGTCGC CCTGGCTGGA GTACAGTGGC 181320
TCGATCTTGG CTCACTGCAA GCTCCGCCTC CCGGGTTCAT GCCATTCTCC TGCCTCAGCC 181380
TACAGGTGCC TGCCACCACG CCCAGCTAAT TTTTTTTTTG TATTTTTTAG TAGAGACAGG 181440
GTTTCACCAT GTTAGCCAGG ATGGTCTCGA CACATCCTCC ATATACTTTA AGTAACCTCT 181500
AGATAATCTC TAGATTACTT GTTTTGTCTT TTTTTTTTTT TTTTCTTTTT GAGATGGAGT 181560
TTCACTCTTG TCACCCAGGC TGGAGTGCAA TGGTGCAATC TCAGTTCACT GCAACCTCCG 181620
CCTCCTGGGT TCAAGCAATT CTCCTGTCTC AGCCTCCTGT GTAGCTAGGA TTACAGGCCC 181680
CTCCCCACCC CCACCCCCCA ACAACTGGCT AATTTTTGTA TTTTTAGTAG AGATGGGGTG 181740
TCACCACGTT GGCCTGGCTG GTCTTGAACT CCTGACCTCA GGTGATCTAC CCGCTTCAGC 181800
CTCCCAAAGT GATGGGATTA TAGGCATGAG CCACTGTGTG TGGCCTAGAT TACTTATAAT 181860
ACCTGATAGA ATGTAAATGC TATGTAAACA GTTGTTATAC TGTATTGTTA AAAGACAGTA 181920
ACAAGAAAAA AAATCTGTAC ATGTTCAGTC CAGACAAATG GTTTTCTGTT TTTTTTTTTT 181980

FIG. 6.69

```
TTTTTTAATA TTTTTGGTCA GTGGTTGGTT GACTCCAGGA ATGCAGAACC CGCAGATATA   182040
GAAGGTTGAT TATGCGTTCA GAGGCAGGGA ATACCATCTT GGGTTCCAGA AAGAAAATGA   182100
TCAGCATTTT CTGTCATACT CTGGTAAAAA CAGATCTTTT GAATGGACAG GTGTATTAAA   182160
CCCTGTGGAG CTGGCTGGGC CTGGCGGCTC ACGCCTGTAA TCCCAGCACT TTGGGAGGCT   182220
GAGGCAGGTG GATCACGAGG TCAGGAGTTC GAGACCAGCC TGGCCAATAT GGTGAAACCC   182280
CAACTCTACT AAAAATACAA AAATTAGCCG GGCGTGATGA CGCATGCCTG TAGTCCCAGC   182340
TACTCGGGAG GCTGAGGCAG AAGAATCGCT TGAACCCTGG AGGTGGAGGT TGCAGTGAGC   182400
CGAGATCACG CCACTGCACT CCAGCCTGGG CAACAGAGTG AGACTCCGTA TCTAAAAAAA   182460
AAAAACAAAA ACCTGTGGAG CTGATGAAAT CCTGCAGGGA GCTTCACGGT GACAGCAAGA   182520
GGAGAAACAC ATCCCCATAT GCCCCGCAGA GTTTGAAGTC CCGGCTGCAC CTCTCCCCAG   182580
CAGCAGGTTG ACTCTGGAAA GTTGCAGCGT TCTTACCTAC AGAGTGGGAA CAGTACTACC   182640
CATTGCACAG AGTGGGTGCA AAGCTCTGTG ACGGAATACA TGGCAAGTGC CCACCACATT   182700
GCCTGGGATG AGGTGGGCCC TTCCTTTACG TAAGAGAGCC CTACAGATAC ACTCAAAGTG   182760
GGCACATTCC TACAGAAGGA GTGTTATTTG TGTAGAAAAG AAAAACATGA AAGGCTTTTA   182820
TTCCTATACA CAATAAAGCA CCCCTTTAAT GTCTTTTTGA GGAGGATAAT ATGAAATTGA   182880
TGAAAAGGAA CCCTGTGGTT GGATCCCTGA CAATCACATG TATCCCTTTT TTCACTCTTG   182940
AAAAAAGGAGT AAAGGAATAA AATAGAAGGG GAGAGGGGGC AGAGAGACCT TCACCGCCCC   183000
CCCCCCACCC CCCATCATCC AATCTATAGT CAAACCCTCC AGACTGTGTC TCCTTGGCAT   183060
CTCTGACACC CCCACCGCCA CCACCCCAGT CAATTCCTAT CTTATCCCCC TATCCTGGAT   183120
CTGATTCTGC TAAGTTCCTG CCACACTAAA GACAGGGTGG CTTTCTGATG ACAACATTCC   183180
TCTGCTTAAA CCTGTCAGTA ATTCCTTGTT GCTCTCAGAC GGAACTAAGT TCTGAATTTC   183240
TTCACACGGC TCTCAGCAAG GTCACAGTCA CCCTGCTAGG CCCCAGGGGC AAATCTCAAT   183300
GGTCATCTTC TTGAAGACCT GGCTCAGTTA TTTCTTTCTC ATTGAGGCTC ACGACCCCAC   183360
CTTCTTGCAT GCCTCAAACG GCCCCTTACC ATGCTCTTCT TTCGCCCATA GCTCAGCACA   183420
CCATATCATT TTAATTTATG TATTTTGCTT AATGTGGATG ATCTGTCTCC TCCTCTGCTG   183480
TCCTCACCAG AGCATCAGTT CCTCAAACCA AGGCTCTTTG TTTTGTTCTT GGATGCAAGC   183540
TAAATGTCTG GCATGTGGCA AATGGTCATA GATACATGTC ATTGAAAGAA TGATTCATCA   183600
CCTCCCTCTT TGGCCTTGTC TGTGGTTCTA CCAAATCCCA TTCCCTCCCC AGTGCCCTCC   183660
ATTCCCCCTC CTTGGCTGAA CATTCTGAAC CACAGACAGT TCTTTACCCT GAACCTTTGC   183720
ATATTTTGTT CTCTTAGCTT AGAGCGGCCC CTCTCCCTCC GTCTGCTTGG CTAATTTCTA   183780
CTTGTTCTTC AGATTTTATC TTAGATGTCA TTCCCTCAAG GAATCCTTCT GTGACTCAAC   183840
ATGGAATTAA GTTGCCTCCT TTGACCCTGA AAGCACCATG TACTCAATCT CATCTTGGCA   183900
TGACTCACTT TGCTGTGTGG AATGTCTGCT TTCCTTGTTT GTCTATTCCT TTAGACTGTA   183960
AGATCCTAGA AAGTGGGGGC CGTGCCTTGC TCATGACTGT GTTTCTAACA CCAAACACAG   184020
TGTTCAGTAG AGAGCAGCTG CTGAGTACGT TTCTGCTAAA TGACAGTTGA TGGAGGACAT   184080
TTAGGGTTGC TTGGAGGTCA AGTCAAGGAG GCATTTAACA TTCTAGTAAA ACAAGGAAGT   184140
AACAGGCTCC TGAACATGCC CACAATGAAC CAGATGCAAA CCTTTTCCCT TGGCAGGATT   184200
CTTTGCCCAT AAAGTGGAGC ACGAAAGCAG GACCCAGAAT GGGAGGAGCT TCCAGAGGAC   184260
CGGAACACTT GCCTTTGAGC GGGTCTACAC TGCCAAGTGA GTCCTAACCC TGATGTTGCT   184320
AATAAGTGGG GGCATGGGCA GGGGGGCCTC CTTCTAGGAG TGATGACCAC CCTTAATACC   184380
ACATGTCTGT CTGAGCCAAG TTTCTGAGCG CCAGGGAGGT GAGGAAGGTT GGACTTCACC   184440
AGAGAGGCTT TGTGGACACC CTTTATCATC TTAGTGAGTG CTAGTGTCAA AACAAAGGGA   184500
GTGGGGATAT GGGGCACATT GGTGGAGGGA GGTGTGATCT CTGCAGCTTC AGAAAGATCT   184560
GAAAGAGTCA TTTGGTTAGA GAAGTTGACC TATTTCCTGT GGGGTTAGAC CAGGGTTGCT   184620
```

FIG. 6.70

```
ACTGTGAACA CCAGCCATGA CTCACCAGTC ACCTTCAGAA GCCACAGGCA GGACATGCTG   184680
ACGACAGCCT TCAACTCACC CACCCCTTGC TCCCCTGCGG GTGGAAGTCT GGAGGTGACA   184740
CCACTGCATT TTCTAACACG GGGGCTCCTT GAGCAACTAG AACAAGAACA GAAAGAATGG   184800
GGACATTAGC AGGTGCTTTC CCCCTCTCTC ATTCTTTTCT TTGAATAAAA AGGTTGTTTG   184860
AAAACACCTG AGCGGCTCCT AAAGATGGGT GCAATCTATT CGGGATGCAA ATCCGAATGA   184920
ATGTTATTCA AATGCTCCTC TCTTCTTTAT GCAGAGTGTA TTTCAAGGCT CAGCCAGTGG   184980
CAGGCATGCT GGGGACTATG GACTACGGAC TAGGGGCCTG TCACAGAGGA AGGCCTCATG   185040
CTAGAGAGCT AAGGGAGGAG CTGGCCTTCA GTTCCATCCC AGGAGCAACT TTGATGTTCC   185100
CAGAGATCCT TCCAAAGGGG GAGTCATGGT CACCCAAGAA AAATGTATTC AGAATGCCAA   185160
GAATGGTGCA AACTCAGGAC AAAGATTCAC ACTGCAGGGT GGAGTCCCT GGGCTTGCTG    185220
CTGGCACCAT GGGAGGGAGG GTCCCCTTCA GGGGTACCGT TGGTTTCCTG TGAATTAAAC   185280
TGGCTTCAAG GGATCTCGAC TGAACAGGCC TATATCACAC TCACTGATAT ACTCTCTCTT   185340
CAGTCCTTCT CCTCATCTAG GTATTTTTAA TTGTTTCAGT GAGGTGTAGG CATGAGGGGA   185400
TTGGAGGGGG CATCTCCTCC ATTGCAGTTT TTCATTGGCT GCTTTGCTCC CTCAGCTCCG   185460
AAATCGCTGG GCCACTCTCG AACGCATTAG TACGGTAGTC ACAGGTTGAT TGCCTGGCCC   185520
CTTGCCCTCT GTGGGCATTT TCCCTTTCAG ACAGCCCCTG AGTACTCACA GTGCTGCTAC   185580
AGTGGGCCAC CTAGATCTCC CTCTTTCTCC ATGCTCCCAC GTGCTCTGGG CTCCACTCCC   185640
TTCTCCCAAG CACTTCTGTC CAGGGCTATT CCAGCAGTCT GACCTCAAGG AAATCCTTTG   185700
CTAAACTGAT TATAGAGAGG TTTCTATTTT AACATTTAGG TCTTCCATGT ATTAATTCTC   185760
AGAATCAATT TAAGATGTTT AAAGGTGTGA TTTAAGACAT TTTAAAACCA TTTGGAGGAG   185820
AGTACAGAAA TTATGTCACT TGCTGTCAGC CTCTTTGCAC CATCTGCAGA GAAAGATACT   185880
AGAGTCCCGC CTTGGACACA TCCACATGCA AGAGGTGCAA AGAAGGTGTC TTTGATGAGG   185940
CAAGGTCAAA ACTTCTCCCC AGACGAAATC CAAAGAAAGC ATTCCTACTA TGCTATATCA   186000
GTTTGGAAAG AAAAACTTCT GCCAGGTGAC TGCATTCTCA CTGGTCACAT TGTGTTCCTA   186060
TGGACTCCTC AGCTCAACCA ATTTGGAGAA GTTATGGTGC AATTTCACCA TATCTGGTTA   186120
GAAGTTAAGT TTCCAATTTG CTGGCAATGA AGAAGAAATG GAGCAGGCCA GGCTGTGTAG   186180
TTTCTGCCAC GTGCCCCCGG GAGTGAACAG CTCTGTTTGT AAGAAGCCAT GGTGCTTAGA   186240
CCTGGGCTCG CTAGTTGCCA GCCTCCAAAT TGCAGAAGTG CCCTTTGGTT GGTGGCTATG   186300
CTGTGTCACT TGGGAAGGTC GTTTGGAAGT TCCACAGTCG TTGTGGGGTG CCAGAGATTA   186360
AAAAGCGTAA GAGGAGAGTG GAAAGTGATT GTTGCTGCTT GGGCATCCCC ACCGTGTGGG   186420
TGCTGCAGCC CAGCTCTCAA AACCCATGGG TCTGTACACT CAACCTCCAT GAGAGGGAAG   186480
GAGAAGGATG AGGGAGGGGA GAGATAGCCA TGGAAAGGTA GGAACTAAGC AGGCAGGGTG   186540
GAGAGTTTTC TGTAAGACAA AAACTGTCTG GACACTGCTG CGGTTCTGTT ACAAAGACCA   186600
CTTCCTCCCT GGGCCAGCAA CATATCTGTG TGCCTGTCTG GGTTGTAAAA AGGGTCAAAG   186660
ATCAATGCAG CAGGCAGCTA CATGCTGGCA AAAGCCAGAG GCAGCTGGTC TGTTTGCCTG   186720
TGCCAGGAAA CCACTGGGAA TGGGGTTGTG TGTTATTCTA GGAGAAAGTC GTCCCAGCAG   186780
CAGCTTCTCC AGGGGCATCC AAGAGCACTG AAAAGGGTTG CAAGATGACC CATGAGGCTG   186840
CAGGAAGAAA AGAACATGCA TTTAATCTTG CTATCTGAAA AGTAAGACAT GAAGCTTTCC   186900
TCATTTTTAA TATACACATG GACAGTAGTA TGTGTATATA GTTTATATGC AAATATACTT   186960
GTTATAAGGT TGCATGCTCA AAATTTTTGG TTCATGGGGT GTGGGATCAT AAATGTTTAG   187020
GGACCATGGC TATCAAGGAA AAACAGCATG AAGGATAAAT GATACTGGTG GATTAAAAAG   187080
ACAGATGCAT GTATTTTTAG CATAAAACAC AACTGCTGAC TGATACAGAT AGCTCAAGAT   187140
TCTGGGGCAG CTGCTGAACA GATACACTAG CCAGTGTGGC TCATCGGCTC AGACTTGGCC   187200
TTAATTAATG GGCTGTCCCT CCACCCATCT CCCATGAGGG CAGAGCTGAG CCAGGGTTTG   187260
```

FIG. 6.71

```
AGAGCTAAAA GGAATTGGAC CTGGACTCTG TTCACGTGTA TATTTTAATT CTAATTAATT  187320
CATTCTTTTG AAAGACAGAG TCACACTCTG TTGCCTAGGC TGGAGTGCAG TGGCACGATC  187380
TTGGCTCACT GCAACCTCGG CCTCCCAGGT TCAAGTTATT CTCCTGCTTC AGCCTCCTGA  187440
GTAGCTGGGA TTATAGGCAC ATGCCCCCAT GCCTGACTAA TTTTTGTATT TTTAGTAGAG  187500
ACGGGGTTTC ACCATGTCAG GCTGGTCTTG AACTCCTGAC CTCAGGTTAT CCACCCGCCT  187560
TGGCCCCTCA AAGTGTTGGA ATTACAGGTG TGAGCCACCG TGCCTGGCCT GTTCACATGT  187620
ATAAAACACA GTTTAATGTC CTATTCCCAG CCAATGAGCA TGGCTAGAGC AGCCTTGGTC  187680
AAAGTTTGGT TTTTGGAGAA AAATCCTTGT TAGCTGACCT AAGATTCCTC TTTGTGAGTG  187740
TAAGTAAGCA CAGGTTGCAG AGAGGAGAAG GGTCTCTGGA GAGGTGTAAT TTTCTAAATG  187800
GATTACAAGT TCATGGACTT TTAACAGGTG TTACAGGGGA TAACAAGTTC TTTATAGACA  187860
GACTTTTGAG GACGTTTAAG GGTATTCTGA TTCTTGGTTT TCTAAGAGGG GAATGTATTA  187920
TTTAACTACA GACACCCCTA CCGCCCACTT TTGCAGAGT GTATCAAAAC ATGTTTTTGG  187980
AATACCACCC TCATGTCGCT TCTCCCTGCA TCTCTTATCT CTTGGTGTCC ATTCTAGACT  188040
CACTTTCTTT CTGTTTTTTA TTTTTATTTT TTTTGAGAT GGAGCTTCAC TCTGTCACCA  188100
GGCTGGAGTG CAGTGGTGCA ATCTTGGCTG ACTGCAACCT CTGCCTTCCG GGCTTAAGCA  188160
ATTTTTGTGC CTCAGCCTCC TGAGTAGCTG GGATTACAGC ATGCACCACC ATGTCCGGCT  188220
AATTTTTGTA TCTTTAGTAG AGACAGGGTT TCACTATGCT GGCCAGCCTG GTCTCAAACT  188280
CCTTACCTCA GGTGATCTGC CCGCCTCGGC CTCCCAGAGT GCTCAGATTA CAGACGTGAG  188340
CCACTGGTGC CTGGCCTAGA CTCACTTTCA AGTGGCATAG ACTTGTAAAA TTATTTAAAG  188400
GTGATAGGTC TACAATGATC CTGTCAATTA GTATTGACAC TATTATTAAT AAACTGTTAT  188460
TAATTATATT TACTTACTTT AAATTAATCC AAACTAATTA ACGGAACACT AAAGAGTTTC  188520
TATGTTTTAT TCCAGAGGT GGAGAAAAAT GAAAGGGAAT ATAGCAACGA ATTCTTTTCT  188580
CCATAAAAAC ATGAATAGTG CAGCACATCA AGTTGAACAT ACCACAGCAA ATTGTTGCAA  188640
GATCTGCTGA GTAGCTCCTA TTTAGACCTC AAGGAATGAG ACTCAAAATG GGTTCATCAG  188700
TTCTGTTTTG CAGAAAAAAT AGCGCAAAAT TTCTCAAAAG AAAATCCAGA ATAATAATAA  188760
TTTGTCAATA GGAAAGACAT TTCCACTGGG GGTTAAGAAG GAAGACATTG AACAATGAT  188820
AGCCACCACT TATTGAATGC TTACTGTGAG CCAGGTGGCA CTTCACCTTG TTTCATTCTC  188880
ACAACAGTCT AGGGAAGTAA TTACTAATGT CTCCATCCAC CTCTTGTAGA TGAGCAAACT  188940
GAGGCTCATT GAGGCTAGGA AATGCACCCA CACTCACATA GCCCATAAGA GGCAGCCATG  189000
GCATTGGGCC CAGACCATGT GAACTTCAAA GACTACACGA GCAGCCACTG GGCAGCTGTC  189060
ATGGCTAAAG CCACTTGAAT TCAGCCCAGC AGCAACCCCC TCTCCAGGAG GGCACATAA  189120
GCTTGCAGCT TTGGGTAGAA GCTGCACTTG AAGTCCTGGA TGGCGAGAGG GACTGGCTTG  189180
AGCCAGAGCC AGGAACAAGG CTCTGAGAAT ATTCTGGAAA TCCACAGGAG GAACCCATTT  189240
TCTTACAGCT GGGAGAATTT CATTCAACTC CAGGCTGACC ATGTTTTATT AGGAACGAAG  189300
GTGACTTGAA CTAATAGTCA GGAATGGTTG AATACGGACC CAATGTCAAA TCACTAGGCA  189360
GTTCACATTT CTAATGAGCA AATCCCTTAG ACAATTAAGA ATTTTTTTCC TTTTGCATAA  189420
CCCAGACAAA ATCGCTACTT AAAAACAAAC CAAAGACCCG AAACATGAGA AAGAGAAGGA  189480
AGCAGGGGAA ATCTTTGGTA CTAATAAGTT TTTAAACAAT AAGAGCACCA GATATTTTAC  189540
CCCATCAGAC ACAGAATGTT ATTCGAATAA CCAAAAAAGG AATTTTTTCT CTAAGTTTCT  189600
TGAACTGGAA AATGAATCAT ATTTTCTCAG TCCTGAGGCT GCAATTTTGT GCCTCTAGTA  189660
ACATATAAGA ATAGATGTGA TGCCAGTGCC CAGTAGCTGC TGCAATTGTT ACTTGGGGAC  189720
CTGTTTATTC ACTAAGCACT TCACCCCAGT GATAAATTTG TAGGGGCCTC CTGCCCTTTG  189780
GAGCTCCTAC CGTGTCCATT AGATCAGTGG AAATTCTGGG ATTCAGAGCA CTTTGCAAGG  189840
TCAGCAGGGG TCTGCTCTTT CTGTCCTGTT CCTGGTTTTT GGTTGTGCCT GGATTCCAGG  189900
```

FIG. 6.72

```
GTAGGTTTCT CATCTGTTAC CTTCATAGAC TTCTCCAGAA AAGGATCTTT TGACCATCAG   189960
AGGACCACGA AGATTCCATT GGTGAGGCGC AGATAACCTG ATCTCTCTGG GTTCTCTGCA   190020
GGGCACAGAT GAAGGGCTGG CCATTCCCAA GTTCTCAGTG GTACCACTGA GGCATGAGAC   190080
CCTAATGGTT TGCATGAGCA GTTTGAAAAT TGCATCTTTG TTTTTACCTA TATAATCACA   190140
TGAAACCCGT GGTTCTCAAA CGTCAGCAGG CATCAGCATC ACATGGAGGG CTTGTTAAAA   190200
CAGATTTCTG GCCCCAACA CAGAGTTTTA AATTCTGAAG GCCTGAGGTG GGTGTGAACA    190260
TTTGCATTTC TAACATGTTC TCGATGCTGC TGCCGCCTCT GGTCCCGAGA GCATGCCTGG   190320
AGAACTGCCA CCTTCGACCA TGGACTGTGA GAATTCACAT GGACCTCAGA ATTATAATCA   190380
GTCTCTCAGT TTTACAGATA AGGAAACTAA ATCCAGAGAG ATTGTTTTGC CAATGGTGAA   190440
CAGCTGGTTA AAGTCAGGAT GGAGACTTTA ATCCTAGTCA AGTGACCTTT CCTCTGTATT   190500
TATTTCCCTC CCTTTTTATG CCTCTCAAGT CTAGTTACAC TGTTTTTCAT GGATGGGCAT   190560
ATTTATTGTC CTGATCTGGA CTGCAGACTT CTCAGGAGGA CACCTATGAT TTAATTTAGT   190620
ATAGTTGAAG AGTTAACAGA CATGGCTTTG GAGACAGACT GATTATGGTG TGAATCCCGG   190680
CTTTGCCACT CCCTAGCTGG ATGACCCTGA GCAAGTTATT CAGCTTCTCC AAGCCTGAGT   190740
TCCTTATTGG AAACATGAGA GCAATTGTGA TAGGCAGAAT AATGGCCCCC TCACCAATCA   190800
TGCCCACATC CTAATCCTAG GAACCTGTGA ATATGTTATG TTACATGGCA AGGGGAAATT   190860
CAGGCAGCTA GCCAGTTGGC CTTAAAATAA AGAGATTATC CTGGATGATC TGGGTAGGAC   190920
CTGATGTAAC CACAAGGGTC TTTTTAATGT GGAAGAAGGA GGCATAAGAG TAGATGTCAG   190980
AGTCATTCAA AATAAGAAAG ATTTGATGGG CCATCCCTGA CTTTCAGGTT GGAAGGAGGT   191040
TCTGAGTCAA GGAATACAGG TGACCTCTAG AAGCTGGAGA AGGCAAGGAA ATGGTTTCTC   191100
CCCTAGAAGT TCCAGAAGGA TTGCAGCCCT GCTAATATCT TGACTTTATA GCCCTTTGAG   191160
ATTTATTTTG GATTTCTGAC ATCCTGAACC ATAGTAAAAG GGTGTTTTTT GTTTTTTTGA   191220
GACAGAGTCT TGCTCTGTTG CCTGGGCTGG AGTGCAGTGG TGTGATCTTG GCTCGCTGCA   191280
ACCTCCGCCT CCCAGGTTCA AGTGATTCTC CTGCCTCAGC CTCCTGAGTA GCTGGGATTA   191340
CAGGTGCTTG CCACCACACC TGGCTATTTT TTGTGTTTTT AGTAGAGACA GGGTTTCACC   191400
ATGTTGGCCA GGCTGGTCTT GAACTCCTGA CCTTGTGATC TGCCTGCCTC AGCCTCCCAA   191460
ATTGCTGGGA TTACAAGGCG TGTTGTTTTA AGCCACTCAG TTTGTGGCCA CTTGTTACAG   191520
CAGCAAGAGG AAACTCATAC AGTTATCATG TGAACTCACA GGAATATGGT GAGTTAAAAA   191580
GAGAGGAAGG GTGCAAAACA TCCACGGTAG AGTGAGAACT CTCCAGGGAG TGAGGACTGT   191640
GCCCAGCATA CAGTGATCAC CCTCTTAGTA AGCTAAGTTT CTGAGCACCA GCTTTTTTGA   191700
GTTGACTTTG TTGTCTTTAA CATTTGAAGA TCACCCTTCT TTGCTCAGCC TGGCTTGCAG   191760
ACCTGGGCTG ATTTGTGGAT CTGATAGAAA AGTTTCCTTA GTTGGGCTCT TCTCCCCGAC   191820
CACCCCCATG CCAGTGTGGC CACATCCTCT GTCTGCATTG CTCACTCTTC AATTCCAAGA   191880
AGCGCAGGGG CACCGCCAGG AACAGGAACC CTGCCAGAGG AATACATCAA GAAACCAAGT   191940
CTCCCTTACG CATCACCGTA GGAACAGAGT TAATGGATTA TGAACATGTG TTTGCTTTAT   192000
ACCATTGTTT GTTTCCCAGG TGGCAGCTGG CTGCCCCATC TTATTGGGTA GATGTAAGTG   192060
GAATTACGAA TGGGATTTAT GTTTCATGCA CGATGGTGAT TATTAACTTC AACTTTCAGG   192120
TAATTTTCAG ACCACATTGC ACTAACTTGG TCTCTGATTG TTTTTCTCCT TGTTTGTTTA   192180
TTCTGCAGCC AGAACTGTGT AGATGCGTAC CCCACTTTCC TCGCTGTGCT CTGGTCTGCG   192240
GGGCTACTTT GCAGCCAAGG TAACTCAGAC TTCCCTTTGT TCATTCTCCT TCTATAAAGT   192300
GCATCTCAAG GAGGTTCAAA GGGCAGGCTT TTTGTTGAAA GGACTTTGCC TGACCTCTGG   192360
CTCCCATCTG TGAAGCCCTG GAGAGGTGAG AGCCCTCGGG AGGCCGTGTT CAGGCATGC   192420
TCTGCACCCG TGCAGAGCGC GTGTGATAAT GCATTGCTAA TGCTTGCTCC CTGGTGGCTG   192480
GCTGAGAGCT GCTGTGCTGA CAAGGGTGGT TTAAGGCTAA ATGTGACTCA GAATCCTTAA   192540
```

FIG. 6.73

```
GCAGTGTTAG TTCAGATACA AGGGCATTAT AAATGAGAGT GCCTGAGGGA TCTATTTTGG  192600
GACCGCTGTC ACTTGGCTCT TCTGCTAATA AGCTTCCAGT GTGGTGGCCC TCCTTCAGGC  192660
ATGTTTCCAC TGAGCCACGG GCTGGATGCC ACATCCCCGG CCTTCCCACA GTTATCAGCA  192720
GCCCACAGGC TTGACTTGAG CAAGTTGGAA AGACAAATCA ACTTCCAGAG TTGATTTAAC  192780
ATTGAGTGGA AATCAGTCAT ACTTTTGGTC CCCTTTCGGG GCCACGCCTG GCACTGTGCC  192840
TGGTGGCAGA TCGGCATGAA CTGGCCAGCT TCTGTGGCCC TGGAGGGCAC AGGCAGAAAG  192900
GCCACACTCA GTCCATGAT GAACTGTTTA AGACTTATTG TTGTCTCCCC GCTCTGTAAA   192960
GTAGATAGAG TGGATTTTAT GTCCCTTATT ACCTTTCAGG ATACTTTGAC TCAGGGAGAT  193020
AAAGTAACTT GGGTACAGCT ACTCAGCTGG TGAAGAACAC AGGCAGAATG AGTGCCTGGG  193080
TCTTTTGACT TAAAATTCTG GATTTTTCAC AAAGATCCTC TTACTTTATT CATTTACATA  193140
ATAAATATAT ATTGAAGAGC TACTCTGTGC CAAGCCCTGT GCCTAGATAT ACAGTGATAA  193200
ATAAAGAGTA GCTTCTAGAG GTCACCTGGC GGTGAGGCAC AGGCCAGCTG GCAAGATGGA  193260
CCACAGAAGT CAGTGAATGA AGACAATGAC AAGGGTGGGA AGCGCCATAT GGGAAGAGAA  193320
CCAAGTTCAG TGATAGAGAG CAGAGGTGAG GCGGCAGCAG AAACCACTTA AGGGACACCA  193380
CGTGGCACTC CTTCTGTGCT GAGAAGGCTG TCAGTAAGCT CACCATTTAT TTCCTATTTT  193440
CTCTCCTGAG TTAAATAGGA AACATGTCTC GCATTACTTG AAAAATCAAG TCAAACTATG  193500
CTCTTACTAG GAGTTATGGT TCTTTTTATG TCTTAGATGA TGCTTGATCT AGATGAATGC  193560
GGACTTGCTG TAGCTAGATA AATACAATGG GAGTTTGAAG GTGTTTCGTA GCCCTGGAAA  193620
TAGGTATTTC CTGTCAAAAC AAGCTTGTC ATTGCCAGCA GACAAAAGCA TCAGTAACCT   193680
TGGTTGATAA TCGTCATTTC TTAGGAATAA AGTAGACTGT AGAATTTTTT TTAGCAGAAA  193740
GGAAACCCAA AGATAATTCT AGTGCAAATC CCTCACTTTA TAGAGCAGAA GCTCAAGTCC  193800
CAGAGGAACA AGTGGCTTGA ACGAACATCA GAATTTTAGG GGCTGGATTT GTACCCTCCT  193860
GGTGCCAGCA GCCCACTTCC CTGCAGGAGG CACTCACCTT CCTTGCACAG GGGTATGAGT  193920
GTGGCCATTT TCCACCCATA ATCTCTGTTA GCTCATGTTC AATTGGGTTC CCATTGAAAG  193980
AAAAATGGAC CAGTAAGTTG GAGCAGAATC ATTCAGATGG TATAACATAA GGAAAAACTT  194040
TGCCCAAGGC AAATCGTGAT TGTGACAGCT TTGTGATTTT TAGAGAATAG CATGGGCCAG  194100
GCACAGTGGC TCATGCCTGT AATCCCAGCA CTTTGGGAGG CCGAGGCAGG CAGGTCACTT  194160
GAGGTTGGGA GTTCGACAAC AGCCTGACCA ACATGGAGAA ACCCTGTCTC TACTAAAAAT  194220
ACAAAATTAG CTGGGCGTGG TGGTGCATGC CTGTAATGCC AGCTACTCGG GAGGCTGAGG  194280
CAGGAGAATC ACTTAAACCT GGGAGGCGGA GGTTGCGGTG AACCAAGATA GCACCATTGC  194340
ACTCCAGCCT GGGCAACAAG AGTGAAACTC CGTCTCAAAA AGAGTTCACA GTTTCTCTTT  194400
TGCTTTGATT TTCTTATCTG CCGGATAACA ATAGTATTTT GGAAGGCAGG AGGAATTGTG  194460
GAAAGAAATG GGTTTTGGGG AGTGGCTGAT TGGAGGCAAA TCCAAGGACA CTCATTGCTG  194520
GTGTGTGACT CCAGGCAGTT ACTCAGCTTT TCCAAGCCTC AGTTTCCTTA TTGTAAAACA  194580
GGACCATGGT CTAGCTAGTA GCATTCCTAT GGTGAGTGAA ATAATATGTA TAAAGCTCCT  194640
GACACAGTGC TTGGCATATA TCAGATTGAG CCATGTAAAA CTGCCAATAT CTGGCTATTT  194700
ATGACCTACA AAAATAGCAT TCATATGAT TCCACCTAAC ATCTGAAGCG CAATAAATGT   194760
TATTATTGAT AATGCAGGTG GTGGTGATAA AGTTTTGAAA TCAGAAAGAC CTGGCTTCAA  194820
ATTCCACGCC TTCACTGGCC TGACTTATTT TCATTCATTT GACAAATATT ATTTTGAACA  194880
CCCCTATGTG CCAGGCACTA TGCCAGGCTC AGAGATGATC TAGGAAAAAG ACAGATGTCC  194940
TCATCTGTCT TAGGCTCTTG TGGCCTAAGC CTAAATTTCC TCGTCTGTCA AATGGTGACA  195000
GTAACACACT CCTTACCAGA GAGCTGGGAG GATTGGAGAC TCAAGTTCCC AAAACGCCAG  195060
GAGCACTGCG GCAGGTGAAA AGTATTCCCT CAATGGCGGA AGTGTTTAAA TTGCTTTTAT  195120
ATCTGTAGCT CTAGATAACA CTAGTTCCAG CTTAGTTAAC TCCCAGCTCC AAGCCTTCAG  195180
```

FIG. 6.74

```
GACTTCATAG AGTTATTGGG GTGCTGCTCT TGGCAGTTTC CCAAAAAGCT AGAATGCAGA   195240
GGGAATCTCC TTCCCAAAAA GCTAGAATGC AGAGGGAATC TCCTTCCCAA AAGGCTAGAA   195300
CGCAGAGGGA ATCTCCTTCC CAAAAGGCTA GAACGCAGAG GGAATCTCCT TCCCAAAAGG   195360
CTAGAATGCA GAGGGAATGT CCTTCTCTTC TAAATGGTAG CTGTTAGTTC AAGAAAGGTT   195420
AAACATTGTG CTGTGGGGAG GCTCAGGGGT GAAGGGTGTA CTTTTAAGAG AACCAGTTTC   195480
AGAGCTGGGT TTGGGGTTTA AGCCCTACCC TCTGCCCCCT TTTACGAGCT GACAGCCTTA   195540
TGCAAGCCTG GTTGACCACC TGAACCCACG TTTCCACATC TGGAAATAGA AATGTGGGTA   195600
CTAGTTATGT TGAAAGGACT CAGGTTAGAT GATAGATATG CAAATACCTT GGAAACCAGG   195660
AGTGTCCAGT CTTTTGGGTT CCCTGAGCCA CACTGGAAGA AGAGTTGTCT TGGGCCACAC   195720
ATAGAATACA CTAACCCTAT CAATAGCTGA TGAGCTAAAG AAAAAACGTT GCAAAAAAAA   195780
TCTCATATTT TTAAGAAAGT TTATGAATTT GTGTTGGGCT GTATTCAAAG CCATCCTGGG   195840
CCACGTGCGA CCCGCAGGCT CCGGGTTGGA CAAGTTTGTT GTAAACAATG CCATGATGCC   195900
GGCATAAGGT CGTTACCAGT ATTAGGAAGG TTCTCAGGTT TCCTCTAGCC CTTGGGCTCT   195960
TTTCCTGAAG TGCGTGTGTC TTCTGCTAGA TTTTGTGACC AATGTTGATT GCCTAATTGG   196020
GCTAACAGCA TGTTTTGGTG GCTACGAAAC TGACACAGGT GTTTTCATTT CTCCACTTAG   196080
TTCCTGCTGC GTTTGCTGGA CTGATGTACT TGTTTGTGAG GCAAAAGTAC TTTGTCGGTT   196140
ACCTAGGAGA GAGAACGCAG AGGTAGGTAA CTGGGACTAC TAAAGAACTG TGGAGCGATT   196200
CCTGATTTTT GAGCAGGAAG AGTGACAATT CAAAACAGTA TTTGACTAGA TTCACGGCTC   196260
CGTAGCATCC CCTTGGGTGG GAGGGGGAAG GCTGACTAGG ACCTCTGATT CTTCTTTCCC   196320
TGAGCTTTGA AGGCTCTGAA AATACAGCTG GGGGGACTTG CCCAGTTTTC TTATTAAGCA   196380
ATTCCTCCGC ATGGTGCTGG CTTTCAAAGG GTGCTTCAGT GCTGTTTGCT GCACGTGCCT   196440
TGCAGCCCCA CACCCTGCAC TCCCGCCCTG CAGAGTCTGG CGCTGGAATG ACATTTTAGG   196500
TCTGGGTTCC CAGGCCTCCT GAGAGTGAAA TGTTTCATTG TTTGTCTAGA GAAATGAGAA   196560
CTAAAGCTTG CACCTTGTGA TAAGTTGTCC TGAGGAACAT ATCTTTCAGG GACCAGAAGA   196620
AAGAATGTTG GGAAAATAAG ATGCAGTAAG ATGCAGACAT GACAGCAGGG TGCAGCGGCT   196680
CACGCCTATA ATCCCAGCAC TTTGGGAGGC TGAGGTGGGT GGATCACCTG AGGTCAGGAG   196740
TTTGAGACCA GCCTGGCCAA CATGGTGAAA CCCCGTCTCT ACTAAAAAAT ATACAAAACA   196800
TTAGCCAGGC ATGGTGGTGG GCGCCTGTAA TCCCAGCTAC TCCATAGGCT GAGGCTGGAG   196860
AATCGCTTGA ACCCAGGAGG CAGAGGTTGC AGTGAGCCGA GATTGCGCCA CTGCACTCCA   196920
GCCTGGGCAA CAAAAGCAAA ACTCCATCTC AAAAAAAAAA AAAAAAAAAA AAAAAAAGAT   196980
GCAGACACGA GACTGTGAAA CTGACTAGCA TCACCATTGC ATTGTTTATA GATGTTGCCA   197040
GACAGAAAGC CCCAAAGCAG CACAGTACCT TCCTGACATC TGGACTAGGA AATCTAGATT   197100
TTAGTAAAAT ACATGCTAAT ACTTACAGAA GAAATGTCGG CGTTAGAGTA TGCCGTCAGT   197160
TCCTTAGAGA TTGCAATTCC TAATGCACTA GTATGGTTTC AGGTGCCAGG AACACGTTCT   197220
GTGAGGCTGC TGCCCCAGGT GCTGACCCCA GCCTTCCACA CCATTTTCCT TCCTTGTGTT   197280
CACAGCCGCT CTGTCTTTTA CAATAGCACC CCTCTCTAGT GGCTAATGGG CTCTATGATT   197340
AGATAGCATC CTTCAGTAGT GATAAAGGCA GTGACATCCT AGGGAGGTCA GCGGGTGAAA   197400
GCGCTATATC TGGAAAACCT GAGAGCCTGT GAAGCTCAAG GACTTGACGG GGTTAGACCG   197460
TGAGCCGGGC TGCAGCTGGA AAAAGAATGA CTGTTCTTTC AGCAGATCCT TCCCTGTGCC   197520
ATCTCTTTCT TCATTCCTCT CTAGTGGCAT TCTTATTTAT CCTCTAAAAC CACAATTCCA   197580
TTATCTCTCC TATTCTTATC AACACTGCCC TAAATGATAT TCTTTATTCT CTTTTGCCCT   197640
GGAAAACCTC TATCATGCCT TTTCCCATGT GATTACCTCG TTAAGAGTGG GGGTGGAATG   197700
TCTAGCAATG AAATAAGAGG GTCTTCTCTT TTGCCTGGCT CCCTATGCAG CCCTATCTTA   197760
CCCCCTGCAA AGTCCCAGGG ATGTGGCTCA GTCACTGCTC CTCTCTTCAT CTGTCACCAC   197820
```

FIG. 6.75

```
TTGCTTGAGA TCCTACAGCT GCTTTAATTC CGAGACCATC TGCAGAACAT GACAAAATTT   197880
GTCCACCTAC CCACATGTCC TTTTAACTTT AAAGGCTTTA CTAACTGATT CCTATTAGGG   197940
AATGAACAGA GGTGGCAAAA ATAAACAATA GGAGATTGAT TTACAAGAAA TCTTTAAAAT   198000
AGTAGATTTC TTCGGACCTC ATTGAAATAT AAATGGCCTG CCTTCTTGTG TCCCTCCCTG   198060
GTCTCCCTCT TTAGGTGATA AGAAGAAGAT CCTGCCAGCC CCATAACCCG CCATCTGCGC   198120
GGGTTCTAGA CCCCCTTCTC CTCCCCTCTG GCCGTGGTAG GCATTACTGA TGAATCATGG   198180
TGCTCTTTCT TCCAGAGACC AAACCTGGCC TCGGAATCCT TCTTAACACA GATACTGCTT   198240
AACACAACCA CTCTGAGCAG CTGTCATAAG TAGAAGTAAT AGATACTAGA AGAAATGTCT   198300
AAGCCTAATC TAGACCAAAA TACGGCCTGA TATAGATGCA AGCCAGAGGG GCTTTATGGT   198360
TAAATGCAAG GAGATTTTCA ACCCTGCCGT CTAGAAGCTA CTTGCTGAGA TCTTCTTCAG   198420
TTGGGCCCAT CTCCTCCCCA GGCCTCTCTT CTGTTCCTGG GCTATGTCAC ACTTGGACTC   198480
TGCAGACACC TAATGCTCTT GGGACCTGCT TTAGTTCTTG ACCTCACCAA CCGAGGAGGA   198540
ATTGCTAGAT GAGATCCTTC CCCCGGAATT TCTCTCTTGA ACCCCAGATG GTCCGTTGCC   198600
CCTTTCCAGA AGTTGCTCCA GCCCTGTCCG CTTAGGAAGT TCAGTGTCAT CCTTGATCCA   198660
GTGGGTAGGG AAGACATTCC ATAATGAATG CCCCAGTCTG AGCTTCTTCC TTCAGGCTTC   198720
AGGCTGCCCT GCGAGGATTT TGCAGCTCCC TTTTTAATGC CCTCTAGAAG TTTCTGGCTC   198780
TTATTTTCAG CCCTTCATCC TACTCTCTCT GACCCCTTCC TCTATCCTGT TTAGTTCACC   198840
TGTAGCAGTT ACTACCCAGC AGTGAAGGAT GAATCTTGGT TTCGTTTCTT TTCTCTTCTT   198900
TTCTTTTTTC TCTTCTCTTT TCCCCTTCCC TTCCCTTCCC TCCCTTCACA TCACCTCATC   198960
TCACCTCACC TTACATAGTC TTGCTCTGTC ACCCAAACTG GAGTGCAGTG GCCTGATCTT   199020
GGCTCACTGC AACCTCCACC TCTTCCCAGG TTCAAGTGAT TCTTATACCT CAGCCTCTTG   199080
AGTAGCTGAG ACTACAGGTG TGCACTACCA CACCCAGCTA ATTTTTTGTA TTTTTAGTAG   199140
AGATAGGGTT TAGCTATGTT GGCCAGGCTG GTCTCGAACT GCTGAACTCA AGCAATCTGC   199200
CATCCCCGGC CTCCCAAAGT ACTGGGAGTA TAGGCATAAG CCACCCATGA TGCCCAGCCT   199260
GAATCTTGGT TTCTTCCCCA TTCATTTAAG CTATTACCTG GCCCTGAACT CAATGGCACC   199320
TGGCACCAAC TGGCAACTGA CTCTTGGTCT TTTATTACCT ACCTTCCCTA GCAGGCACTG   199380
GGTTGCTCCC TCTTCCTATC CCATGGAGTC CTGTCCTCTG TTGGGGCTCC TACTGATCCT   199440
CTTGGCAATA TGAAGTTCTC AGCTCAATGG TGGGTGGGCA ATGACTGCCA ACTCTTGAGG   199500
CCAATGAACT CAGGTTACCC CACTCCTCCT CCTCCTGAGT TGCTCACTCA CTCCTCATTC   199560
ACTCAACATT GATTCAGTAG ATATTTGCTA CCTGCTCTGT GCCAGGTACC AGGTCAGTTG   199620
CTGAAGGAGT AACAGTGAAC ATGACGGAGT CTTTGTCCCC AAGGAGACCC AAGGTGTCTC   199680
CTAGAGCCAG GGGCACATTG CAAGACCAAA TATATTCAAC TTACCAAAAT AATCATAGAC   199740
CTAGTTCTCA AAAAGCAAGA AGACTGATTC CTCGTTGTCA TTTCTCCTCC TCAGCATCAA   199800
TGTTTTAGAG TCTGTGGGCC CCTCCAAGTG TGGAGTATGG TGTTACTTCA CCAGAGTTTG   199860
AGGAGAAACA TTCTTCTTTT GGAAGGCCGG GGAGCATAGA TGGATATCAA GGCTGCTGTT   199920
TCTAAAAGCG AAACCCACCA AACAACAGTA TTAGAATCAT CTGTGGTGCT TATTAAAGAT   199980
ACAGATTCCT GGGCCCCATC CCAGACTTAT GAATCAGAAT CTCTGCCAGA GGAAGCCTGA   200040
GAATTTGCAT TCTCAGATGA TTCTGCATTC TCAGATAACA CATTCTTTAG GTGATTCTTA   200100
CACACACTGG AGTTTGGGAA TCGCTGAAGG CTGTTCACTT CTCTTTTCTG AGAAATGATT   200160
CATTCATTTC AGAAATATTT GCAGAGGTCC TTATTTATTG GAGATTTGTG GGTGGGCAGA   200220
GGAGAAATAT CTTGTCCTCA CAGAGCTTAC AATTTTTATT TTCTTTAGAG GTCACCAGGC   200280
TTAAAATGAC ACTTCCCTAA ATTCTGAAAA GAACAGATTT TTAAAACAAG AAGGGACTGT   200340
AATGTTTTCT GTTCCTACCT CGTATTTTGT TCACATTAAG AACCTGGGGT GGGAAGTGGA   200400
GGAGGGGGGG TGACTGGCGG GGGGCCACAG AGAGCTGAGC TGGGGTGGTC TCGAACTCCT   200460
```

FIG. 6.76

```
GAACTCAAGC AATCTGCCAG CCTCAGTCTC CCAAAGTGCT GGGATTATAG GCATGAGCCA   200520
CCCACGATGC CTGGGTGGAA CTCAGGGCTC TGGATGCCTG GGCGCCCCCA TCTCCCACAC   200580
TACGGCGCCT CATCCTAGAA GTGGTTAGCA CCTTTGAGAT GGGAATTATT TAGCAGGATG   200640
CTTTTGTGTT TTCATGTAAG TTTTATGCTG CCTGTGGAGG GCACAGCTGT TTCAAAACTA   200700
ATAACCAAAT CCTGGTCTCC GAAGTCTGAA GGCATCCTTT GCCCTGCAGT GCAAAGCACG   200760
GGATTCTGGC CTCACACAGG CAGGTCTGAA CTCCTGTGTT GCCTCTTGCT GGCTGTGGGA   200820
CCTGAGGCAA ATCATGCAAC CTCTCTTTTC TGTTTGCCTA GATGGAAAAT AGGTTTACAA   200880
TACGCCCCCA TAGGATGGCT GTGAGAATTA AAGGAAGTCA TGGGTGTACA ATACCTGGCC   200940
CCGAAAGATG CTTAATAATT TAATTCTGAC CTTCCTCACT CATTTAGGAT TATGTACCAA   201000
CTTTTAGAAA CAATGAAAGA TTAGTGAGTC TTCTGTGGTT GGTATAAAAA AAAAATAGAA   201060
ACATGAAAGA GATGTCCTCC TTGTTCAAGG GCTAATGACC CTGGTGTGCG CTGTCTAGGC   201120
CCCCAAGGTC TTCCTTCCCT GCTCACAGCA TTTCAGGTTC TCCGCAGCTT TGCTGAGCCT   201180
GGGTCAGGTT CGGTATCTGC CCACCATGCT CACTTGCCAC AGCTGTGGCC CCATTTCCAA   201240
ACTTCAGAGA CTTAAAGGTG CAGCTAATGA TGTGCCCGGC CTGGGGTCAC ATTCCCTGAG   201300
CCCTGCAGAC AAGGGAGCAG GAGGCTGAGC TCTTATCTTC CACACCCTGT GCACAGCCTG   201360
GGAAGAGTTA AAGCACCCTA GTCCTATGCT GCGAGGGCCA CATGCCCTGA GACCTTGGAA   201420
AAAATCCTAC CTGAATTGAA GAGCATCACT ATTTCATCAG GAGGCGCTGC CATTTCATTT   201480
TTCACTTCGG TTTTATCTTG AGTGTAAAAC AGCTTCGCAA ATCACTTTTT CTTGTTTCTG   201540
TAATGAGCAT ATGGTGGCCT CATTCGTGTG ATAAATCTGA GCCACCACGA TATTTGACTT   201600
TTCACAATTT AATTTATCTG AACCCTCTAT TCTCTGGCTA AAAAATATCC CTTACTTGGA   201660
CTTCTTTATT TTATTTTCAA TTCCCTTACC AGCACTAGCA GGGGACTCTG TACTCATCTG   201720
CTGGCGCTGC CATAACAAAG CACTGCAGCC TGGGGGGCTC AAACCACAGA ATTTATTCTC   201780
TCACAGTCCT AGAGGCTAGA AGTCCAAGAT CAAAGTGTGG GCAGGGTCGG TTTCTCCTGC   201840
AGCCTCTCTC CTTGGCTTAT AGAGTGCCAC CTTCTACCTG TGTCTTCACA TCATCACCTC   201900
ACTGAGCATG TCTGTGTCCA AATCTCCCCT TCTTATAAGA CCCCAGTCAT ACTGGATGAG   201960
GATCCACCCA TATGAGTTCA TTTTACCTTA ATTATCTCTT TAAACACCCT GTCTCCAAAT   202020
ACAGTCCCAT TCTGAGGAAC TGAGAGTAAA GATTCAACAT ATGAATTTTG GAAGGGACCT   202080
AATTCAGCCC ACAACACCCT CTTTTGGGAT GTTTATTTTC CCCCTTAAGG AGCTAGTTAG   202140
GATGTCTTAT CTCATGAACA TGACTGTGAA CAGGAAAACA GGGAGAGAAT GAAGCTGGCC   202200
AAGGAACAGG GCTGGTGTCA GCTAGCAGTG CTTTTCTGAT GTGAGTGGGT CCCACAGGGA   202260
GCTTGTTAAA ATGCAGATTC TGATTCATTA GGTTCCAGAG GGACCTGAGA TTTCCCATTT   202320
CTGACAAGTT TCCAGTGTGG GGGCTGATGC TGCTGGTCCA CGGACCATAC TTTGAGTAGC   202380
AAGGAGCTTG ATACATAATG GCTGAGTGAC TTTCAGACTC CTGCTGTAGA AAAATTATGA   202440
GTTGGCTGGG CGTGGTGGCT CACGCCTGTA ATCCCAGCAC TTTGGGAGGC CGAGGTGGGC   202500
AGATCACCTG AGGTCAGGAG TTCGAGACCA GCCTGGCCAA CATGGTGAAA CACCATCTCT   202560
ACCAAAAATA CAAAAATTAG CCAGGTGTGG TGGCAGGTGC CTGTAATCCC AGCTACTCAG   202620
GAGGCTGAGG CAGGAGAATC GCTTGAACCC GGGAGGCAGA GGTTGCAGTG ATCTGAGATC   202680
GTGCCACTGC ACTCCAGCTG GGCAATAGAG CTTGACTCAG TCTCAAAAAA AAAAAAAGAA   202740
AAGAAAAAGA AAAATTATGA GTTATATTAT CAGCATATGG GGTGCCTTTC AAATTGATAA   202800
AATTTCTAAT ATTAAACCTG TGGATGCCAA ATGCTGCTCT CTGATTATGG CAGGAAACGG   202860
CACTTGGCAG TACGAAGTTA GCTGTTGGGC TGAGCTGGCT CATCTTGTTG TGCGGTCCTG   202920
ATTGCCTAAA GATGCCTTCC CAGGATCTTT ACTAACAATC CTCCTGAGTC ATTTGGACTT   202980
TCCCAACCTG TTATCACCTC TCAGATGGGC CAGCCATGGA GGCAGTCAGA GGAGGGCTCT   203040
GCAGAGGGAG GGCAGAAACA GGGTGGCCTC TGCATGCCAT TAGGAGGTCA CATCTCACTG   203100
```

FIG. 6.77

| | |
|---|---|
| GGGGATGCAG TTTAGGATTT AGTGCCTTGG AGAGAAGGAT AGAGTATATT AAAACATGTC | 203160 |
| TCCGCTAGGC ATGGTGGTTT ACGCCTATAA TCCCAGCACT TTGGGAGGCC GAGGTGAGTG | 203220 |
| GATTGCCTGA GCTCAGGAGT TCAAGACCAG CCTGGCTAAC ATGACGAAAC CTCATCTCTA | 203280 |
| CTAAAATACA AAAAGTTAGC TGGGAGTGGT GGCGTGCGCC TGTAGTTGCA GCTACTTGGG | 203340 |
| AGGCTGAGGC ATGAGAATCA CTTAAGCCCA GAAGACTGAG GTTGCAGTGA GCCGAGATTG | 203400 |
| CACCACTGCA CTCCAGCTTG GGCTACAGAG TGAGACTCTA TCTCAAAAAC AAAGAAACAA | 203460 |
| ACAACAACAA TAACAACAAA AACCAAGTCT CTCCCTCCAC TCAAAAATGC AAGGGCCTGT | 203520 |
| CTCCCATTGC TGGGTGCCCA GGTCTCATGA ATGTAGATAT GAATTATTCC AGTCAGCCTC | 203580 |
| AGGAGAATAG AATGAGCCCT CAGATGCCGA AGCACCTTTC AGATTCCACC GGTTTTATCG | 203640 |
| GCTCATTTAA ACTTCACTTC TAACACAGTC CTGCATTACA CACGTGTCTG TCGTTATGGG | 203700 |
| CAGCTGCAGA GAGGGTCTTA ATGGTCCTAA TGCTCAGTGA GGATGCCCAA TGGTCAACAG | 203760 |
| AACCTGCCAT CTTCAGGCCA TCAAGGAGCT CTGGAGTTAA GGAAATCATG AGAGCACAGA | 203820 |
| GGGGCGGGTA CAGCAGAGCC CTCGTGGTAA TGGGTTTTGA GGTCTAGGCT CTCTTCACTT | 203880 |
| GGGTTTGAAA TAAGTTCAAT GACTAGTAAT AGCTGAGACA CTTCTACCCT TCAAATGAAG | 203940 |
| TAAATGGGAA AATGGAGCAT TGTTGAGTCC AGGGAGCTAT AATTTAAACC CCATATATCT | 204000 |
| AAAAGGGGTA ACATTTTTGT GTGTGTGAAA TTGGTGTCAT TCGCACTGCA TCTACAGTTT | 204060 |
| TCTTTTTCCT TCTCTTCCAG CACCCCTGGC TACATATTTG GGAAACGCAT CATACTCTTC | 204120 |
| CTGTTCCTCA TGTCCGTTGC TGGCATATTC AACTATTACC TCATCTTCTT TTTCGGAAGT | 204180 |
| GACTTTGAAA ACTACATAAA GACGATCTCC ACCACCATCT CCCTCTACT TCTCATTCCC | 204240 |
| TAACTCTCTG CTGAATATGG GGTTGGTGTT CTCATCTAAT CAATACCTAC AAGTCATCAT | 204300 |
| AATTCAGCTC TTGAGAGCAT TCTGCTCTTC TTTAGATGGC TGTAAATCTA TTGGCCATCT | 204360 |
| GGGCTTCACA GCTTGAGTTA ACCTTGCTTT TCCGGGAACA AAATGATGTC ATGTCAGCTC | 204420 |
| CGCCCCTTGA ACATGACCGT GGCCCCAAAT TTGCTATTCC CATGCATTTT GTTTGTTTCT | 204480 |
| TCACTTATCC TGTTCTCTGA AGATGTTTTG TGACCAGGTT TGTGTTTTCT TAAAATAAAA | 204540 |
| TGCAGAGACA TGTTTTAAGC TGATAGTTGA GGGGTTTTGT TAATGGCTTT TGGGGGATTT | 204600 |
| ATCTCTATAC CCACAAACGA CTAGTTTGTT TTCCTCAAAC TAAATGATAA TATTAAAAAT | 204660 |
| ACACATCCTG GCCAGGTGTG GTGGCTCATA CCTGTAATCC CAGCACTTTG GGAGGCCGAG | 204720 |
| GCAGGTGGAT CACTTGAGGT CAGGAATTAA GACCAGCCTG GCCAATATGG TGAAAGCCTG | 204780 |
| TCTGTACTAA AAATACAAAA ATTAGCCAGG TATGCTGGTG GATGCTTATA ATCCCAGCTA | 204840 |
| CTTGGGAGGT TGAGGCAGGA GAATTGCTTG AACCCGGGAG GTAGAGGTTG CAGTGAGCCA | 204900 |
| AGATCATGCC ACTGCACTCC AGCTTGGGCA ACAGAGTGAG ACTCCATCTC AAATTAAAAA | 204960 |
| AAATACACAT CTGGCTTCTG GAAAAATTAC TTGAAGATCT TTTATGACAT CCATCCCTCT | 205020 |
| TCACACAGCC ATGTGAATTA GGTTGGTATC TTCATATACT AGCATCGTGC CCAGCACTTC | 205080 |
| CATGTTATAC AGTTTAAAAT GTTCTGTAAT TCCCTGTGGG AACCTAAGAT AATGCGAGGA | 205140 |
| CCGTCATACG TGCCCCCAAA TATTGGCAAA CCAATGAATA AATGAATGAA TGAGTTTATG | 205200 |
| AATCGCTAAC TGGCTGTATT TAATGAAGTA TGTGTGTTGA GCCATTTCCC ACAGTGTGGA | 205260 |
| CAGATTTGTC CCACAATATG GGCCTCTTCC CAAAGGCCCT ACCACCTAAT GCCATCACAC | 205320 |
| TGGGGATTTG ATTTCAACAT GTGAATTTGG GGAGAGTGCA AACACTCAGA CCATAGCACC | 205380 |
| ATCTCAGTAA ATGTCCCACT GGTCACTCAG TTCATAGTGA CAGTGATCCA GCCACTGTCA | 205440 |
| TGACAGGTGC CACTTGGCAG AAACAGCACA GCTTGGAAGA TGGCGGGGTG TAGTCAAGAT | 205500 |
| TCCAGGATCC CCAACAGAGA AGCCAGCTCT TATAGGGGAG CCATTCATCA GGATTGAACT | 205560 |
| CTCAATCGAG CTGGACAGTA ATAGGTGGGT CTGTGTTATT CCCCAGATGA GTATCATGAC | 205620 |
| AGTCACAATC CTAGGAAGGA TGTGAAGCCT CCCCCAGCTC TCCTCCAGTT GCCTGCTTGG | 205680 |
| GCAGCAGAGA TGATGGAATG TGGAGTCTGG CGTGGTCTGA GGCCTGAATC CATGTGCCTC | 205740 |

FIG. 6.78

ATGTATGATG CTCAGGCAAG AGGATCTCTC AATTCAAGGG AGAGGGCCTG AATGAGCCTT 205800
GCTTTCCAGG CCTGTCTGAT GGTCCAGGCT GAAGCCCCTC CTGGCTTGCA CTGCCAGACC 205860
TCATCCAGCA GGAGCTCCTT GGCATTGACT GCTTCAGGAT AGTTGCTTCT GCTCTGAGTG 205920
CTCTCTAAAG AGCAGTGCTC TACCATCCAA GCTGGGCTTT TCTTTTCTTC TTGCTGATAG 205980
GGAAGGCATG GGACATTGCA GGATGGAAGT GGCCCCCAGG CCTTCTCATG CCTGGGCTTG 206040
GTTTGGAAGG TGGTCAGGTG ATCAATAATC CTGATTGGCC TGGCATTGAG GAGTTTTCCT 206100
GGGATGTGGT CCTTTCGGTT TTTTAAAAAT TATTTTTATT GATACACATA TTTGTAGGTA 206160
TTTGTGGGGT GCATGTGATA CTTTATTATG TGTGTGGATT GTGTAATGAT GAAGTCAGGG 206220
CATTTAGGGT CTTCATCACC TTGATTATCA TTTCTATGTG TTGAGAACAT TTCAAGTTCT 206280
CAGTTCCAGC TATTTTGAAA TAGACAGTCC ATTTTGTTAG CTACAGTCAC CCAACCCGGC 206340
TGTCAGACAT TGGAACTTAC TCCTATTGAA CTGTGTATTT GTACCCATTC ACCAAACTCT 206400
CTTTGGGCTT TCAGTTTTAC AACTGGGATG ATCCTGGGAA AACTAAAGTA AATCAGACAC 206460
CCGACGTGTG AGCTAGGTTA TAATATGCCC AGTGGACCCT GGGGACATCT TAGCTTTCAG 206520
AGGTCATGCT GTCCAAGCTG ACTGTGGGGC TTCCAGAAGG TGGGGAGAGG AAATGATGCA 206580
ATGGCCCATC AGAGGCACTA CTTGGGGCCT GGGGCCAGAG TGCATGTCTA AGGCATTAAG 206640
GGGAGGGGAG AGCAGCCTTC ATAATTATGA AGAGGAGTCT CAGGTGCACA GCTTCTGATG 206700
AGGGACAGCT TCTAATTGAA GACAGCATTG TGTAATGCTC AAACTCCCTG TCTTCAGAGT 206760
GCCTGCTGTA TCCCACCATC AGTTCTGTGA CTTCTCCCTA AGCCTCAATT TTGCATGTGT 206820
TACATTGGGA TAATAATAGT GCCAAACTCA TGGGGTTGTG AGGAATAATG AGGTAAAGCA 206880
ATTGAAAAGG TTTAGCACAA TATAAGTGCT CAATAAAAGC CATTATTATT ATTTTATTAC 206940
ACTAGTTTTC AATTCCTGCA TAGCAAATTC TTGCAAATGT AGGGACTCAA AACAATATAA 207000
ATTTATTATC TGACAGTTTT TCTGGGTCAG AGGTCTTACT AGGCTGTAAT CAGAGGGCAA 207060
CCAAAGCTGT GATCTCAGCT GAAGCTCAGG ATTCTCTTCC AAGCTCACTG GTTGTTGGCA 207120
GAATTCAGTT CTTTCCAGTT GGAAGACTAA AGCCTACAGT CTTCAGTCTC TAGAAGCCTT 207180
TTCTCTGGCA CAGGTTTCTC TACAACATGG CCATTTATGT CTTTAAGGCC AATAGGAGAA 207240
CATGATTAGC ATATTTTTTT TAAGTGAACT TTAGACCCTT TTTTAAAGGC CTATCTGATT 207300
AGGCCAGGCC CAAGTGAGCT TTAAGTCAAC TGATTAGAGA TCTTAATTAC ATCTGCAAAG 207360
TCCCTTCATG TTTACCGTAT AACATAACTT AGTGAAAGGA GTGAAATTGC AACCAGGTTC 207420
TGCCTGCACT CCACGGAAGG GGATTCTGCA GAAGTGTGGG TCACGGGGGG GTTATTTTGG 207480
GATTCTGCCT ACGTCACTGA GTCAAAAGAA GCTGAATGGT TGTGATGCTG AGGTTTTTGG 207540
GCAGCAGCAG TGTGTGTGTG TGAGTGAATT CATACGTATG ACCACCTGGG AAGAAAGGAG 207600
GCTGTGGTTT CCTCCACCTC CTGGCAGACA GAGAAATTTC TTTTTTTTTT TGAGACAGGG 207660
TCTGGCTCTG TTACCCAGGC TGGAGTGCAG TGGCTTGATC TCTGCTCACT GGCTCACTGC 207720
AGCCTCTGCC TCCCAGGTTC AAGTAATTCT TGTGCCTCAA CTCCAAGTAG CTGGGATTAC 207780
AGACACACAC TGCCACGCCT GGCTAATTTT TGTATTTTTA GTAGAGACGA GGTTTTGCCA 207840
TGTTGGCCAG GCTGGTCTTG AACTCCTGAC CTCAAGTGAT CCGCCCACCT CAGCCTCCCA 207900
AAGTGCTGGG ATTACAGACG TGAGCCACCA TTAACCATTT TTCTATCTCC TGTGGGAAAG 207960
GGCACAGTGA AGAACAGAT GAAGCTGAGA CATACAAGTG AACTCCTCCC TCCTCTCCAT 208020
TTAGACTAAA ATAGGATTAT TCATACTGAG ATTCTCCCTG GTTGCAAAGA GATAATCTGT 208080
GCAACTGGGT TTTTACAATT ATCCCTACCC TATGCTTTCC TCATCTGTCT TCCTCGTAGT 208140
CAGCTCAGGC TGCTATAACA AAACACCATA ACTGGGGGCT TTTGAACAAC AAAACTTTAC 208200
TTCTCACAGT TCTAGAGGCT GGAAATCCAA GATCAAGTTT CTGGCAGATT CGGTGTCTAA 208260
TGAGGTCCTG CTTTCCAGTT TATAGACAGT GCCTTATCGC TACCGCCTTA CACAGTGGAA 208320
GGAGAGGACG AGAAGCTCCT TGGGCTTTTT TTTGTTTCTT TCTTTCTCTC TCTCTCTCTT 208380

FIG. 6.79

TTTTTTTTTT TTAATAAGGT CACTATCTTA GTCCATTTTG TGTTGCTAAA AGGAACATCT 208440
GAGGTTGAGT AATTTATTTT ATTTTAAAAA GTGGCCAGGC ATGGAGGCTT ATCCTGTAAC 208500
CCTAATCCTT TAGGAGGCCA AAACAGCAGG ATTGTTTGAG GCCAGGAGTT CAAGACCAGC 208560
CTAGGCAAGA TAGTGAGACC CCATCTACCC CATCTCTACT AAAATTTTAA AAAATTAGCT 208620
GTGTGTTGTA AAGTGTGCTT GTAGTCCCGG CCACTTGAGA GGCTGAGGTG GGTGGAGTTC 208680
AAGGCTGCAG TGAGTTATGA TTGAGCCACT GCACTCCAAC CCGGGTAACG GGCAAGACC 208740
TTGTCTCTAT TTAAAAAAAA AAAATCTTTA TGTGGCTCAC TATTCTGGGT GGCTGGAAAG 208800
TTCAAGATTG GGCATCTGCA TCTGGTGACA GCCTCATGTC GCTTCCAGTC ATGGGGAAG 208860
ACGAAGGAGA GCTGGCACGT GCAGATATCA CGTGTTGAGG GCAGAAGCGA GAGAGAGAGG 208920
GGAGAGATGC CAGGCTCTTT TTAACAACCA GCACTGGGGA AACTAATAGA GTGAGAGCTC 208980
ACTGACTCCT GAGGGAGGAC ATTAATCTAT TGATGAGCGA CCTGCCTCCA TGACCCAAAC 209040
ACCTCCAACG ATACCCCACC TCCAACACTG CCACACTAGG GATTAACTTT CAACTTGAGA 209100
TTTAGAGGGG GGAAACTTAC AAACTATCGC AGGCACTAAT ACCACTCATG AGGGCTCCAC 209160
CTTCATGACC TAATCACTTC CTAAAGGCCT TACCTCTTAA TCTCATCACA TTGAGGATTC 209220
GATTTCAACT TGAATTTTGG GGGGACACCA ACATTCAGGC CATAGCATCA TCTCAATAAC 209280
TGTCCCATTG GTGGTCACTC AGGCCCCAAA CAAAGGAACC TTCCTCCATT CCTTTCCGCC 209340
CTCCCACCCA CAGTCAATCA TCCCCAAGCT CCATCAGCTC CACCTTTAAC GGCCAACCCA 209400
CCTCTGCCAC ATCTCACCAT CTCCACTGCT ATCCCTGTCA CCTGGGCCCA CCATTCTCTC 209460
TCCTGGACAG TCTCCATAGC CACCTCTGTC AGATTTATTT TATTTTTTTA TTTTTTTTTT 209520
TGAGACAGGT TCCTGCTCTG TTGCCCAGAC TGGAGTGCCA TGGCATGATC ACATCTCACT 209580
GCGGCCTCCA TCACCTGGGC TCAAGCAATC CTCCCATCTC AGCCTCCCAA GTAGCTGGGA 209640
CTACTGGCAC CACCATACCT GGCTAATTTT TTGTTGTTGT TGTTTAATTT TTAATACAGA 209700
TGAAGCCTCA CTATGTTGCC CAGGCTGCTC TTGAACTCCT GGGCTCAAGT GATCCTCCGG 209760
CCTTGGCCTC CCAAAGTGCT GGGATTACAG GCATGAGCCA CCGTGCCCAG CCCATCAGAT 209820
GTTAATGCTA CACGCACTTG CTTAAAATCC CCCAGATAAT TCTCGCTGCT CTTGGAATAA 209880
TTCCCACACA CCTTGGCGTG GCCATGCAGG CTCTGTGCCA TCGGATATGT CCCTGCCCCC 209940
TCTCCCAACT CCTCCTTTCG CTTGCTCGTT CACTCAGTTC CAGCCACATT GCCCTGGGAG 210000
CTGCTCCCAC CATGGGGCTT CCTAATGCAC TGGTCTCTCT CATGCAGTGG GGCCTCTCCC 210060
TCCTTTTACT CAGTGTCTCC CAGCACCCAC CTCCTCCAGA GCCTTCCCTG ACCACCACAC 210120
CTACACCTAG GCCCTTCCTC CTCCACGCTC CCTCCTCCAC CCCGGCCTCC TACCCACGTG 210180
TCACTTCTTT ATACTCGCTG CCACCTGAAA TTAGATCATT TATTTACCCC TTTATTTGTT 210240
CAGTTTGCCT TGTCCGTTAG AATATAAGCT TCCAAAGGGC AGGAGCTTTG CCTATATTGT 210300
TAGGCCGGGC ATACAATGAG CACTCAAAAA AATATTTGAT GAGTGTATGA AAGAACAGAC 210360
TGGGTTATGT AATTGTGCCT ACTTACCTAT ATGACCGTGT GGTGGGGTTT ATGGTGGGTG 210420
TGGTGGTGAT GGCTATAGGG CTATAAGCAA ATTTGGGACA GGGAGTCTAA GAAATGTTCT 210480
TAAATTTTAG TAAGCAAAGC ATCCTCTACA GAACCTGTCT TAAAACATGA AAGTTCCTTA 210540
GTGCTACCCC CAGAGGTATG ATTTGGTAGG TCAAGGATAG GGCCTGGAAA TTCACATTCT 210600
TGTTAAGATG TTCTTCATCC GGGGTTTGTT GACCACCTTT TCAGAAGATT TTTGCTCTGT 210660
AGCTGTACTA CCCAATGCAG TAGTTCGTAG TCAGTGTGGC TCCTGAGCCC TTGAAGTGTA 210720
GCTCCTCTGA ACTGAGACGT GCTGTAAATG TAAATTGCAC ACCGGAGTTT GAAGAGTTAA 210780
TACAAAGAAA AAGGAATGCA AAACATCTCA TTAATAATGC TTTACACTGA TTACATATTG 210840
AAATGGTAAT CTTGTAGATA TAGTGCGTTA AATAAAATAT ACTGTTAGGC TTAATTTCAC 210900
GTCTTTATAC TTTTAATGTG GCTACTAGAA AAATTTAAAT AACATATTCA GCTCACATTA 210960
TACTCCTATT GAACAGAGCT GATCTATAAG TTCCATGGAA GATGGCAAGT CTTCGCAGCT 211020

FIG. 6.80

```
GAAATAAAGG CTGGATCCCA TTCTACGGGC TCATCTTTAG CAATGATTTC TTGCAGACGA    211080
TATTGAAAAA TGTGGCAATG AAAGTTACCA CAAGCATCAA ACCAGTCCTG CCTAAATCTG    211140
GAAAATAGTT ATCTGAGGCT GTTAGCATAT GATCATGAGA GCGTTTCACC ATGGATTTCT    211200
GATCACAGAT GTGGCACATT ATTAAAATAT CACTTTTACA GTCACCCTAG AGGCTAGGGT    211260
TATCTGAATA TGGAGAAAGA AACAGCTTGT GGAGCTGTTG TATAAATGAA ATTACTAGAA    211320
AGTAATGCAC TCAATTGCAT ATTGGCTCGG GGGGTTATTC TTATTAAAAT GTTTAGAGAG    211380
GACTTTCTGT TCATTTCTGC AGAATTGCTC TTCAAATTAA GAATTTGCTT GACACGCTAA    211440
TAGACCACAG TCCCAAGAGA AGTTTATCCT TTTTTCTTCT TATCCTTGCT AAGCACTTAG    211500
ATGCTCTGCT GATAGGTAGC ATATATTGTC TATATGAAGC TTTTGTGTTA ACATTGACTA    211560
GTCCTGCAAG TTGGCACACT CTTACTTGGC CTAAAAGAAA TCAGCACCAG GCTTTAAGAA    211620
AATCAGATGA TCTACCTAAA GGAACACAAC TCTGTCTCTC TTTTGACAAT TGTTGTAAAC    211680
AAATTTTAAT GGAAATTTGC CTTAATTGTG AAGAAGTTGC TGCTAAAATG GACTTGCCAT    211740
TAATGGACTG GAACCCATTG CATAAGCAGA ATGAAATATA AGCCTTCTCA GGATTCACAC    211800
TTATAAAAAA CCATTCAGCC AATCAACAAG AGGGCAAAAG AACAAACATT TGATGTGTAA    211860
TTACTTAATT TAGTGCATAT GCATTTGGGT CCTCAATGTC AGCACTATGG CAACCAGAAC    211920
ATGGCCACAA TAACTGTCTG GAAATGTCTA TTCTTACCTG GACCCAGCAG GCCATGCCCC    211980
ACTGATTATA TAATCTCCCT CTCTCCTTGT TACGGTCTGA ATGCTTGCAT CCCTCAAAAA    212040
TTCATGTGTT GAAATCCTAA CCCCCAAGGT GATGATATTA GGAGGTCGGC CTTTTGAGAG    212100
GTAATTAGGT CATGAAGACA GCATCCTCAT GAATGGGATT AGTGTCCTTA TAAAATAGGC    212160
CCAAGGGAGC TCATTCACTT TGTCCACCAT GTGAGAACAC AGCGAGAGGG CACCATTTAT    212220
GCACCAGGAA ATGGGCCTTT TCCAGACAAT CTGTCGGTGC CTGGATCTTG GACTTCACAG    212280
CCTCTAGAAC TGTGAGAAAT TAATTTGTTT TTTATAAGCC ACCAAATCTA TGGTTTTTTT    212340
TATAGAAACC GTAATGGACT AAAACACTCC CTAATTATAT TTAAACTTAT CAGTGCACTG    212400
GGCAGTGACA TATTAAAAGA ATGCTGGCCA ACGTAATTGA CACCATAAGG CTGGATGATT    212460
CTTGTAATTT TCAGCCTCAG AAAAAGGCTG GGGAGAGGAG TCAGGGGAAA GGAGGTGGTG    212520
TGTGTGTGTG TGTGTGTGTG TGTGTGTGTG TGTGTGGTAC GGTGGATGCC TGCTGAGAGA    212580
GAAAGAGCTA TAATAACATT CTGTGGTTCA GCTGACACAT CCTTTCTGCA TCCCCTCCAA    212640
TCACCTGGGT TAATGGGGAC CTCGCTAATG TCTGAACCTC ATCTCATTTT AACCTTTTGT    212700
TTCAAAGCCT CTCTTTTCAT GACTTCCCCG CCTTCATTTT TCCCATATGG TGGGGTTATT    212760
ATTAAGACAT TAAATGAGAG TGGACAGGTA GGCAAAGGAG GTGGGTTGCA GGGGAGTTGA    212820
GGGTTGCCTG TGTACTTTTC TAGACTGTTC CACTTCACAT CAGTGAAATA TTCCCAATTG    212880
ATACTATCAT GAAACAAAGC AAATGAAATG CTGAGCACGG AGCTTCGTCT TGATGAAATG    212940
CTGAAAGAAA AGAAAGGAAA AATAAAGTAG CCATTATTTT TGCCCTTCCT CCCACCCCCA    213000
TGTTTACTAC TCTTATTTCT CTTTTGTATT GTTGTGTTGG AAGCACAGCA TCAGAAAAAC    213060
TCCCAGTTTT GAGAGATAAC TCAGTGTTTA GTTCACTTAA ACCTGAGAAA GGAGAAGAGG    213120
ATGCCACCGT GAGGTCCAGG ACGTAAAGAG GAAAAAACA GACAAAAAAA TCCATATGAA    213180
ATGAAAATGT GAAAGAGGCG CTTTCGAGCA GATGAGTGTT GTAGATTACA GTGTTGAGAG    213240
CTGTTTGTGT CCAGAGCTGC TTGCTGCACC TGGCGGGATA AACACTGGTC TAACAGAGGA    213300
TCCTTGTTTC AAGGAGGCTG CCTTTTATTT GGGGGACAA AATTGTTCTT GAAAGCTGCT    213360
CAGTGGTTCA AGCTACAGCA TGGTGGACTA GCAGAATGGA CTCCAGGGCC TCCGAGGAGA    213420
CAGTGACTGC TGCCAGAAAT AGTCAAGGAT AGAAAGGAAG GACTTCACTG AGGCCTGGGA    213480
GAAGATTATG GAATGGGACT GACAGCAGTG ACGGGGAGTA AAAGGGGGTG TCTGGGGGAA    213540
TTGTGCCCCA TGGTGAGAGC TAGAGGGTTC ACAAAGACTT AACCCGACGC ATCTCTCTCA    213600
CCCTGGAGAT TGGGCCCGTT CAATCTAACT GGATGGCTAT AATTTAAAAG GTTTAGGTAT    213660
```

FIG. 6.81

```
TATGACAAAC ATGGATATAT TAGGTGATAG CAATGCAAAA TGCATATGGC TTCTTGATAT    213720
AAAACACAAG ACTTGAAAGC AGCATCTTTG GCTGGGTACT ACAGCCACCC TCCTCTGTCA    213780
CTAAGGGAGG CTTTGGTGGA AAGGGCTGAG AGCCTCTAGA CTGTGAACAA AAGTAGGCAC    213840
AGAAGAACAG TTGGAGATAA TAAGTAAACC ATCTTGACAG GAATGAAGAA TTTCCTGAAA    213900
GGAAGGTCCC TGAGTTAGGT TGTTGGATGC TTTCAGTAGT GAGTTATTGA AAGTGTTTGG    213960
GGGGTGTGTG TGTGTGTGTG TATGTGCAGT ATGTGTGTGT                          214000
//
```

FIG. 6.82

Figure 7
7.1
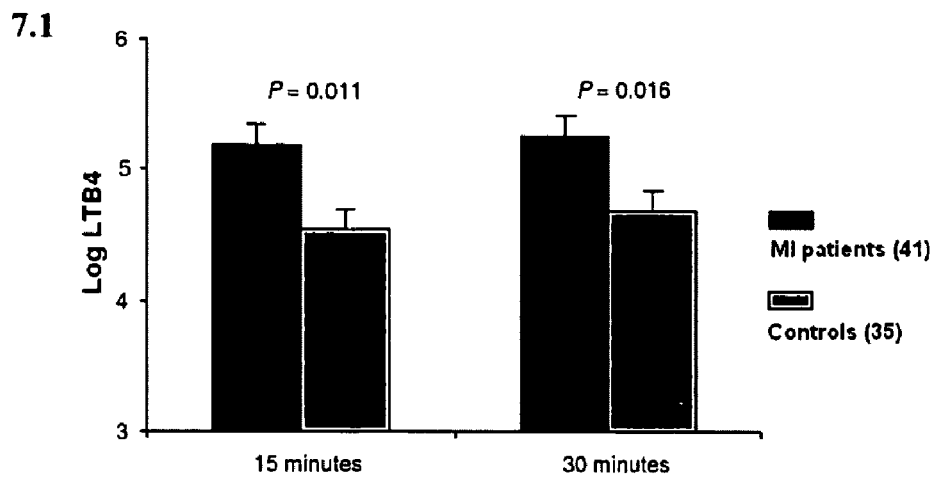
7.2
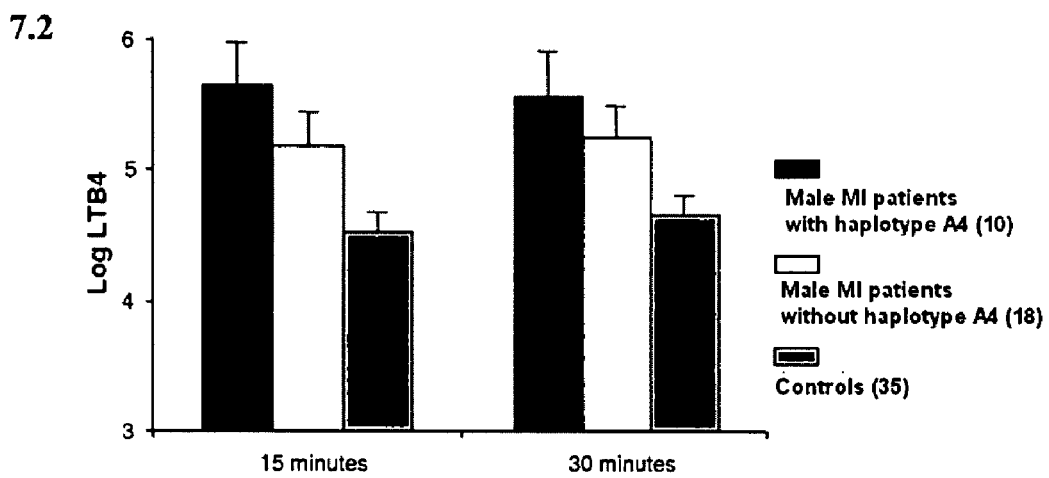
7.3
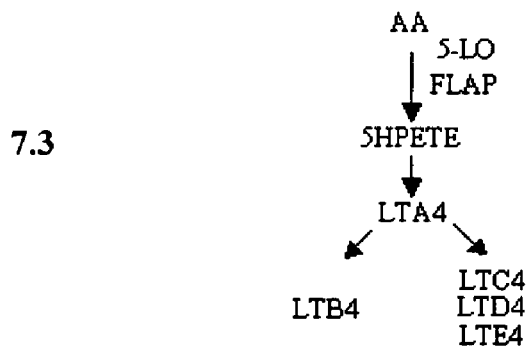

SNP name    SNP amplimers

SG13S421
GATTATATCCCACCTACCACTGCAGCTCCAGGATCCAGCTTCACAA
ACATTTGTTGAATGAATGAATAAGAAAAGAGGACACCCCCAAAGAGGCT
GCAAGGGAAAAAGCTACAAAGACAGAAGCACCAGGAAAAAGTAGGGTC
ATGTAAGTCAAAGCAGGAAAAAGTTCCATGGTGGGGTGGTCAGCAGTGT
CTAAT[A/G]CCACGAAGGCACAAAGTAGGATAAAGGTTAAAAATCAGCCT
TTGGTTTTGGCAAATATGAAGCTTATCGGTAGCCTTAGCGAGAACAATTCC
ATCAGGGAGCAGAAGCTAACTGCAGTGGGTTGAGTCATCAAGCAGGCAT
AAGGAAGTAGGGATACCCCATTATAAGCTACTCTTTCAAGAAGCTCAAAT
CTGAAG

SG13S417
ACAAAAATTACCATCATATGCTGTCATGCATGTCTGCCAGTCTATTT
ATCATATTATTTAAGAAACAAACATTTATTGAAGATTTATCATGTGCTCAG
CACTGCCAAAGAGGAAATAAAGAGCATAATATCTATTCTTAGAAAATAAC
ATTAACACAAATAGAAAACAAGAAACCATAATGTTAAAAATATTACATAG
[C/T]AACACAGAAAGACAATGTATAATTATACATACGCACTAAAGCAAAG
ATAACATAATTTATAAATTATGAGGTACAGAATAGTTAGATTCTGAAAAT
TAAAATAATCAGGAAAAACTTCATGAAGATGAGATCTGGGCTGGATCCCA
AAGGATAGGCAGGTGGATCATGTAGAACAGGGGAAAGGAGTTCCTGATC
GG

SG13S418
AACTAAAGAAAGCCACAAAAGTTCACCTCAATGCCAAGACATTTCT
TGATTTTTGAAAACCCAGTTGTCGAACCACCCATCTATAGAAACTTGAAA
GACTAAAAACTATCTTACTCTAAACATTTTCTAGGAAGTTGATTCTACAAC
ACATTTTGGTTTTCCAATTTGGCTTCTAATAATTATTTCAAAGTTTCTGTG[
A/G]CCTAAATTTTGTTTTACATTGATCCTTTGAATGGACTACTGTTTCCACA
TTTTAGAACATTTAAAAAGATATCTACAACCCGAGTCTAATCATAAAAAA
AATCAGACAGATCCAAAATGTGGAACATTCCACTAAAAAAGGAGTGGGG
AGAGGTCTTTATTCTTCCAAAAATATCAATGCCATAAAAGACAAAGACG

SG13S44
ACCCTTCAACCCCAGCCCAGCTGCTAACTGACTACAGCCACATGAA
CAGAACCAGGTGAGACCAGAGGAAACTTCCAGTCACCTACCAGATCATGA
CAAATAATAAACGATGTTTTTAAACCACAAAGATTTGGAGCAGCATTTG
TTACACAAAATTAGACAACTATTACAGTTCGACTAAAAACATGTTCATTTA
C[A/G]ATACTAAATTAGAAGTGTAAGAATGGGAGAAAAACTTCATACTTTA
AAAGTCATTTTTTCCTCCAAAAACTTCCAACTTTGAAAAACTGATTTTTAT
AATGCATAAAAATTAAAATAACCTTAGAATTTATATGAGTAGCATAGCCA
GCTGGCTTTATTATCTGTTGTACTCAACACTTCAATAATCACTGATGTTT

SG13S45
ATGACCTTACCTCGTTTTGTTTTCCTTGTCTGAGAGAAACACATTAG
CAGTCTCCCATCTTGTTTTTCCTTTTCCTGTCACCCAGGACAGAGGGCAGT
GGTGTGATCACAGCTCTGCAGCACGACTTCCCCAGGTTCAGGTGATCCTCC
CACCTCAGCCTCCCAAGGAGCTGGGACCACAGGCACATGCCACCACGTC[
C/G]AGCTTAATTTTGTATTTTTTGGTAGAGATCAGGTTTTGCCTTATTGCC
CCAAGCTGATCTTGAATTCCTGGGCTGAAGCAATCTGCCTGCCCTGGCCTC
TCCAAGTGTTAGGATTACAGGTATAAGCCACCGTGCAGCCTTATATTTTGT
TTTAAATTTTCCTCTGTATTTTCTCTCTGGCAAATTGTTTAGGGA

FIG. 8.1

SG13S46
TTTTTTGGTAGAGATCAGGTTTTGCCTTATTGCCCCAAGCTGATCTT
GAATTCCTGGGCTGAAGCAATCTGCCTGCCCTGGCCTCTCCAAGTGTTAGG
ATTACAGGTATAAGCCACCGTGCAGCCTTATATTTTGTTTTAAATTTTCCTC
TGTATTTTCTCTCTGGCAAATTGTTTAGGGAGTTTCTTTAGTTTATC[A/G]
GACTAAATTTCAAGGCTTTCCTTCCAATTTTGACATGTAAACAGTCCCTCA
TTTCTGCTTATCTAGTGATTATTCCCAAATCTGTGTTTACAGTCTAGCTGTC
TCTCCTGAGATTAAGACTTGTTTCTCTAACTACCTGACGGCAGAATCTCCT
CTTGGAAGTATCAAGGAGGCAGTTCAAAACTGAACTGGGCATT
SG13S50
GCTGATCTTGAATTCCTGGGCTGAAGCAATCTGCCTGCCCTGGCCT
CTCCAAGTGTTAGGATTACAGGTATAAGCCACCGTGCAGCCTTATATTTTG
TTTTAAATTTTCCTCTGTATTTTCTCTCTGGCAAATTGTTTAGGGAGTTTC
TTTAGTTTATCAGACTAAATTTCAAGGCTTTCCTTCCAATTTTGACATG[C/T
]AAACAGTCCCTCATTTCTGCTTATCTAGTGATTATTCCCAAATCTGTGTTT
ACAGTCTAGCTGTCTCTCCTGAGATTAAGACTTGTTTCTCTAACTACCTGA
CGGCAGAATCTCCTCTTGGAAGTATCAAGGAGGCAGTTCAAAACTGAACT
GGGCATTGGCTCCACTCCTTCTCCTTCTCTTTACTATTAATACCC
SG13S52
TAAGTCTTATTTAGGCATCGTTTCTTCTGGGAGACCTTTGTAGAATC
TCTGAGGTTATGTTAACATGCTAAGGTTTTCTTGACATTCTCAGATTGGGT
TAGGTGAACTTTTAGCAACTTATCTTTTTACTAAAAAGTCATCCCTCAGTA
TCTGTGGGGAATTGGTTCTAGGACTCCCTAAGGATATCAAAATCTGCAT[A/
G]AGCAGCCCAGGTGAGACCAGCAGAAGCACTTTACAGTCACCTACAGGA
TCATGACAAATAATAAATCATGTTTAAGCCACAAAGTCCTTTACATAAAA
TGGTATAGTATTTGCATATAACCTACACATCTTCCTGTATCCTTTAAATCAT
CTCTAGTTTATAATACCTCATACGATGAAAATACTACGTAAATAGTT
SG13S53
AAGCAGTTCCTAATTACTGGACATTCTCAGATCTGCTAGAGCTACA
TGTCCAATTACGAGAATATACTGGAAAAAGCCCTGGATTAGAAATGAGAG
GATGTAGGTTTTAGTACCAGGTCAGCCACCTTGTTAATGCAAATTTGAGTA
AATTGTTACTTCTTTTAGGCCTTGTTTTGCTGTTTTGTTTTTCTGACAGT[A/
C]TGGTCTCTGTGGTCCAGGCTGGAGTGCAGAGGCACAATATCAGGTCCCT
GCAGTCTCTACCTCCCAGGATCAAGCCATTTTCATGCCTCATCCTCCTGAG
TAGCTGGGATTACAGGCATGTGCCACCACACCCTCGAACTCCTGACCTCA
AGTGATCTGCTTGCCTCAGCCTCCCAAAGTGCTGGGATTAGAGGTGT
SG13S55
GAATATACTGGAAAAAGCCCTGGATTAGAAATGAGAGGATGTAGG
TTTTAGTACCAGGTCAGCCACCTTGTTAATGCAAATTTGAGTAAATTGTTA
CTTCTTTTAGGCCTTGTTTTGCTGTTTTGTTTTTCTGACAGTATGGTCTCTG
TGGTCCAGGCTGGAGTGCAGAGGCACAATATCAGGTCCCTGCAGTCTCT[A
/G]CCTCCCAGGATCAAGCCATTTTCATGCCTCATCCTCCTGAGTAGCTGGG
ATTACAGGCATGTGCCACCACACCCTCGAACTCCTGACCTCAAGTGATCT
GCTTGCCTCAGCCTCCCAAAGTGCTGGGATTAGAGGTGTGAGCCACTGTG
CCTAGCCTTACACATTGTTTCTTACTGGTAAAGTGGGAATATCTAGA
SG13S56
GTTTGTTTTTCTGACAGTATGGTCTCTGTGGTCCAGGCTGGAGTGC
AGAGGCACAATATCAGGTCCCTGCAGTCTCTACCTCCCAGGATCAAGCCA
TTTTCATGCCTCATCCTCCTGAGTAGCTGGGATTACAGGCATGTGCCACCA
CACCCTCGAACTCCTGACCTCAAGTGATCTGCTTGCCTCAGCCTCCCAAA[

FIG. 8.2

G/T]TGCTGGGATTAGAGGTGTGAGCCACTGTGCCTAGCCTTACACATTGTT
TTCTTACTGGTAAAGTGGGAATATCTAGAAGTTGCATGCTACATAAATTCA
ACCATATATTATTGGCAAAAAATTTTAAAGAAAAACATCAGCTTAAGAGT
ACTAATTGAGTACATGCCTTGGAATGAGCATGAGCTGGAAAGAACAAA
SG13S57
  GGCAAAAAATTTTAAAGAAAAACATCAGCTTAAGAGTACTAATTG
AGTACATGCCTTGGAATGAGCATGAGCTGGAAAGAACAAACCTGTTGTTA
CATCACTCATTGCTGTTTTCATATGCTGCTCATTGTAAATCTTGCTCAGTGG
CATGATTTTAGTGTTTAAAGATTTATTTGTTTGTTTGTTTAGGACAAAGTC[
C/T]CTACACATAATCTACTTGCTTCATATATACATACTTATGCATATTATGT
ATGTACATACATGCTCTCAGGGCTCACATGAAAAAACAGCCATTCAGGTG
ATGTGATTTATCTCATATGCTTACTTTAGAGTCAACAGGGTGTTGACTCCA
CTATACAATACTGGCATGGAGAACACATAAGTCAAAGTAGACAGGAC
SG13S58
  TTTATTTGTTTGTTTGTTTAGGACAAAGTCTCTACACATAATCTACT
TGCTTCATATATACATACTTATGCATATTATGTATGTACATACATGCTCTC
AGGGCTCACATGAAAAAACAGCCATTCAGGTGATGTGATTTATCTCATAT
GCTTACTTTAGAGTCAACAGGGTGTTGACTCCACTATACAATACTGGCAT[
A/G]GAGAACACATAAGTCAAAGTAGACAGGACCCAGCCGTACCATTGGCT
AGGGCACAAATATATTCACATATGTGGAGAATGATGTACGTAGAAAGGTC
TTCATTGCACAATGCTCTTTAATAAAGATCTGGAAAAAAAAAACACCTAA
ATGTTCAAAAGGATAGGGTAGATGAAATAATGGTACATTATAAAATGGAA
SG13S59
  TCTGTCACCCAGGCTGGAGTGCAGTGGCATGATCATGTCTCCTTGC
AGCCTTGACTTCCCTGGCTCAGGTGGGCCTCCCACCTCAGTCTCCCAAGTA
GCTGGAACTACAGTCGTGCACCACCATAGCCAGCTAAGATAGTGAGATGG
TGGCCCCACTGTCTTGCCCAGGCTGGACTCGATTTCCTGGGTGCAAGCACC
[C/G]TTCCCGCCTCAGCCTCCCAAAGTGCTGGGATTACAGGCATGAGTCAC
CATTCCAGCCTACTTGTCTTTAATTCTTAAAAATATTAATGTTGAGTTTTGT
CTCCCAGCATGTGGGAAAGATGTCATCCATTGCTTCTGTTTCCTGGAGGCC
TGGGAGCAAGGAGCCCAGGAACAGTATCACGAAGCTTGAGATAATAC
SG13S60
  ATCATTGATGGGCATTTGGGTTGGTTCCAAGTCTTTGCTATTGTGAT
TTTTTTTTTTTTTTTTTTTTAAGACAGAGCCTCACTCTGTTGCCCAGGC
TGGAGTGCGATGGCATGATCTCAGCTCACTGCAACCTCCGCCTCTCAGGTT
CAAGCAATTCTTCTGCCTCAGCCTCCCAAGTAGCTGGGACTACAGGC[A/G]
CCCACCACCAGGCCCAGCTAATTTTTGTATTTTTAGTAGAGACAGGGTTTC
ACCATGTTGGTCAGGCTGGTCTTGAACTCCAGACCTCATGATCTGCCTGCC
TTGGCCTCCCAAAGTGCTGAAATTACAGGTGTGAGCCACCATACCTGGCC
TAGGCAGTCTTTTTCAAAACTCTAAGACTGTGCTTGTGTCTCAGG
SG13S419
  TGGTATGAGGTAAGGATCCATTTTTTTCCCATTTGCATAGCCAGTTT
TTGTAGCTCCACTTTATTTCTCACTTGATCTGCCATGCCACCTCTAGCATG
TATCAACATATCATGTATGTGTGCAGCTGTTCCTTAACTCTCAATTTTATTC
TCTTGGTTACTTTGTCTAACCCAGCACTCATACTTTTTAAATTATTA[C/T]G
GCTACCTTGTAGGGCAAGAATCCTCACTTTTATTCAACTTCTTTTGAAGTG
TCTTGATGCATATTTTTCTGATCTTACTTGGCCATATATATTTGGGGACA
GATGTGACATCATACCAAGCTTTCTTTGCTTGACATTGTAGATATTTTCTTA
TTCATTAATGTGCTAAAAATTTTGAGTTTGGTCATACAGTC

GTTTCTAACATTATAGACACTAGTTTTAGGCTCTTGGAGGCTAGCA
GCAATTCTCAGAGGTAATGCAAGCTTCCCCATTTCTTCCCGTAGTCCTGTG
AAAGACCAGCCACCTCCAGAAGCCTACACATGAGTCTTCTCAGCCATACT
TTCTGCTTTTCCTAATGCCTCTCAGCAGCGTATTAGAAAGGCCATGATCGA
[C/T]GTACCTGTTACCTTCAGGCTTTGCATAAGGTGTATATGAAACATAAT
GAATTTCGTGTTTAGGCTCAGGTCCCATCCCCAGGTTACCTCTTTATCTTG
GAGACACTTCTGGTCCCATACATTTCAGATAAGAGATATTCAACCTGTACC
CACCACGTAAGGAGAGGAATAGGTTTTAGAAGAGGAGTCAGGGAGGCA

SG13S62

GCATCTATTAAAAGTGATGGTTTTAGTATCCTGTCTCATTTTTTCCT
TTCCTTACATCATGTATTATAGGTAAACACATGCGCATGTGTGTATTTCTC
TTTTAGACAAAGGATGAGATTACTACTGTTAGCTCAGTTTTTTTTCCCTAC
TTAACATCTTTGCTTTTATTTTTAGACATATTTCTAAGACTATTAAA[C/T]A
TTAGACTTACGTAGCCCTTCTGTCATTGTGAAATACATAGTTTACTAACAG
CTACCATCAAGATAAAGCCTTTATTTAAATAATTAAACTTCTTAGTGGAAA
GCTAAGTAAGCACAGTTTATGGATTTTGGGAATTTTTGCCTTGCATTTGTC
TGATATGGTAAAATATTGAGTTTGTTTTCTCATAATGTTCAC

SG13S63

GATAACTCAATCCCCTTAAAGGGTTGTATCAAGCCATTGATAAGGG
CTCACTTTGATATAACCATTTTCTGTTATTTAGACACTCTTTCACACTTCCT
ATTTTCCTCCTGGGGATGGTTTGAATGGATGACACAATACCATATTATAAA
AGCACTTTACAAACTGTAACTTATGTTATAAATGTAATTATTACCTTAA[A/
G]GTTTTACCCTGTTTCAGATTTGAGTGGAAGTAGTTCTTTACAATACAAA
ACAACTTATTTTAACTTTTTTGCATTTCAAAGAATGATCAATCCACTTCA
GGTGCAGCATGGTTTCCAACCCTGACAGCATGGAAGAATCATTTATTTAG
CTTCTAAAAATGTGCAGGCTGTACCCTAGACCAGCCTTGGGGATTAG

SG13S64

TCCTCTCTCTCATTCTCTCTCTCTCTCTCTTTCTCTCTCTCCTTCTTTG
CTCCTTCATTCCTTCTCTCTCTCTTTTTTTTTGAGACAGCATCTCACTAT
ATTGCCCAGGCTGTTCTCAAACTCCTGGGCTCAAGTGATCCTCCTGCCTCA
GCTTCCTGAGTAGCTAGGACTACAGGCACATGCTATGGCAATACT[A/G]TT
TTAAACATTGTTTTCAAGGCTCCCCAGGTGATTCCAGTGTGGGTCATGTGG
TAGAGAACCACTGACACAGGCAAACAAAGGATACATAAAGTTGTCTATTT
AATGGGTAGGTGCAGGTAGTAGATAAGAGTGTAGCCACATAAACCACAT
GCTTAGTGAACGGTTTTGTTTTGTGTATGTGAGGGATTAGCAT

SG13S65

TTCAGGTTCCATTTAGCACGACAGCAGGGAAGGGACTGTTGGCAG
AAAAAAACTGGGGCAGTGGGATTAAAGACAGACCACACATTCCAAAAGG
CACCGTGGGAGGGTCAGGGGGCGAGGTTAGGTCTAGGCTTCAGTGTCCTG
GGAGACTCAGTCTTCACAGGGTGACAGCGATCAAGAGTGCAGCTTAGGCT
GGGT[A/G]CAGTGGCTCATGCCTGTAGTCCCAGCACTTTGGGAGGCCGAGA
CGGGAGGATTGCTTGAAGCCAGGAGTTTGAGACCAGTCTGACCAACATGG
CAAAACCCCATCTCTACTAAAAATACAAAAATCAACTGGGCATGGTGGCG
TGTGCCTGTAGTCCCAGCTACTTGAGAGGCTGAGGCAAGAGAATCACTTG
AACC

SG13S420

TAAATGATCATTATGTTCATATTCACACATACAATAATGTACTCAA
GTTTATTGCTAAGGTAATTCAGAATCTCCTTATTTTGAAGTGTGCATTTGA
TATACCTGTTTGGGAATAACTAGTTTCTTATCTTTGACAGAAAATAATTTT

FIG. 8.4

GTTGTTTTGTTTTTACTAAAAAAGCATGGTGAAAAATGGCTCCATTTCTA[A
/T]GAGAGGTAACTAAAATATCGCAATTTGCTGGGTGTCATTAAAGTAACT
CACAAGGGAAAAAATGCAAATTGGTATCTGCTGATGGAGTAAATCTCCGC
AGAAGTGATGACCCTGAAAGGATCAATATATTAAAGCCCCTCCCAGCTGG
TCATTCCAGATTGCAACAATAAAGCATTAAGTGTTAAAACCTCAAGGCA

SG13S66

CTCATCAAGCCCACCTTTATACTTCATTTCTCCAGACTTCATGTCCA
GACTGTGGGATGAACAAGTGGTTATAAGGTTTTAGAGGCTCCTGTAGGAC
TAGATGGAAGGCAAAAAAGGAAATAACCTTTAAGCATGCTCTCGATTCC
TTAAATCCCATCTGAAAGTCTTAAGGATGTCTTCTCAGTCATACTTATTTG[
A/G]CAATATTACCTAATTTTCTCCATTAGCCCAAGCTCAGGGGTCTTTCTT
CTTCCATATTCACATGGGTGCAATGGTTTTCTGAAAGGAAAACAGCATTA
CTAGGGCAGTAACATTTAATTAATCACAGGTACTTATCAAACTACAAAAC
AGGCATTCCAGGAACTGGGTGTTTCTGTTTGTAAAATTACACTCTCGTG

SG13S67

TAGGACTAGATGGAAGGCAAAAAAGGAAATAACCTTTAAGCATG
CTCTCGATTCCTTAAATCCCATCTGAAAGTCTTAAGGATGTCTTCTCAGTC
ATACTTATTTGACAATATTACCTAATTTTCTCCATTAGCCCAAGCTCAGGG
GTCTTTCTTCTTCCATATTCACATGGGTGCAATGGTTTTCTGAAAGGAAAA[
C/T]AGCATTACTAGGGCAGTAACATTTAATTAATCACAGGTACTTATCAAA
CTACAAAACAGGCATTCCAGGAACTGGGTGTTTCTGTTTGTAAAATTACA
CTCTCGTGTACATGCTCCCACTAAAATGTAAGTTCGCTGAGGATGGAGTT
TTGGTCTCTTTGCTCTGTGCTGTAACCCCAACACTGCAGCAGGGCCTG

SG13S69

GCTGCATAGTCTCACTTAGGTGTGGAATCTAAAAAAGTCAAATTAA
AAAAAAATGTCAAGCAGAGAATAGAATGGTAGTTGCCAGGGACTCTGGG
AAGTAGCAGGGGTGGGGGTGGAGGGGAGGGGATGGGCAGAAGTTGGTCA
AAAGGTACAAAGTTTCAGGTAGACAGGTGTAAGTTCTGGGGATCTATTGT
ACAG[A/C]GTGGTGACTGTAGTTAATACTGTATTGTGTACTTAAAAATTGC
TCACCAAAAATGTTCTCACCAAAAAAATGATGTTTGGATATGTTAAACAG
TTTGATTTAATCATTTTGACGTGTGTGTGTGTGTGTGTGTGTGTGTGTGTGT
GTATACATCAAAACATCACATTATATACCATATACAATTAATATATACAAT
T

SG13S70

GGGGTAAATGCTGACTGCCTGTTCTCTGGACAGGAATGGAGAAGA
TGGTGCTAGCAGGGTTGCTGTTCATATGTAGACATTCATGCAGTCACTCTC
TTTTCAGCACACTTCTTACTTCTGCCCTGGGTTCAGTTGCTGACTCTGAGCC
CAGAAACCTTCTAGGGTTCTGTTAGGTAGATTGGCTTCCACCGTCTTTGC[
A/G]ACAACCACAGAAAATTCTAGACTGTTTTCTCTTCGGGCTTCATTAGTC
AACTTGCTTCAGTCTGTCTTGCATCTTCTAAATATTTATAGATCTCTCTCTT
TTGTTGGAGTGGCAGAAAATGCTAGTTGACCACCCAATATTCAAATTATC
CTGCCTCCTTAATAACAGAATATCATTGGATGTGGTGGGTAAATAAT

SG13S71

ATGGAGAAGATGGTGCTAGCAGGGTTGCTGTTCATATGTAGACATT
CATGCAGTCACTCTCTTTTCAGCACACTTCTTACTTCTGCCCTGGGTTCAGT
TGCTGACTCTGAGCCCAGAAACCTTCTAGGGTTCTGTTAGGTAGATTGGCT
TCCACCGTCTTTGCGACAACCACAGAAAATTCTAGACTGTTTTCTCTTC[A/
G]GGCTTCATTAGTCAACTTGCTTCAGTCTGTCTTGCATCTTCTAAATATTT
ATAGATCTCTCTCTTTTGTTGGAGTGGCAGAAAATGCTAGTTGACCACCCA

FIG. 8.5

ATATTCAAATTATCCTGCCTCCTTAATAACAGAATATCATTGGATGTGGTG
GGTAAATAATATACCCTAACTTTCCTTGCAGAGAGGGGTGGCCAA

SG13S72

CAGGGTTGCTGTTCATATGTAGACATTCATGCAGTCACTCTCTTTTC
AGCACACTTCTTACTTCTGCCCTGGGTTCAGTTGCTGACTCTGAGCCCAGA
AACCTTCTAGGGTTCTGTTAGGTAGATTGGCTTCCACCGTCTTTGCGACAA
CCACAGAAAATTCTAGACTGTTTTCTCTTCGGGCTTCATTAGTCAACTT[G/
T]CTTCAGTCTGTCTTGCATCTTCTAAATATTTATAGATCTCTCTCTTTTGTT
GGAGTGGCAGAAAATGCTAGTTGACCACCCAATATTCAAATTATCCTGCC
TCCTTAATAACAGAATATCATTGGATGTGGTGGGTAAATAATATACCCTA
ACTTTCCTTGCAGAGAGGGGTGGCCAATGAGATGGAAATGAAAGTC

SG13S73

TGGGATTGAGTTCTTGATTTGATTTTGAGCTTGGCCATCATTGGTGT
ATAGCAGTGCTAGTGATTTGTGTACATTGATTTGTAACCTAACACTACTA
AATTCACTTATCAAATCTGGGAGATTTTGAGGATTCCTTAGGATTTCTA
GGTATGAGATCATATCATTGGTAGAGGTAGTTTGAGTTTCTCTTTTCCA[A/
G]TTTGGATGCCCTTTATTTCTTTCTCTTGCCTGATTGCTCTGACTAGGGCTT
CTAGTACTATGTTGAATAGAAATGGTGAAAAGTGGGCATCCTTGTCTCATT
CTAATTTTTAGGGGGAAATGCTTTCAACTTTTCCCCATTCATTTTGATGTTG
GCTGTGAGTTTGTCATAGATGATTCTTACTATTTTGAGATATA

SG13S99

TCTTTTGCCCTGCCTTTCTGCCTTTCTGTCCTTTTAATTTGCGGGCTT
TTGGCAACCACAGCACGGGTCTGGTTTCCTAGGAGTTTCTTTTGTAGGATC
AAACCGCTAGTTGGCTCTTGGCCCTGTGATAGGGCCCTGGGCTAACTTATT
GGGAAAATGTTGCTGTAACCCCTGCCCAGAGGTGCCTGTGACATGGGC[C/
T]GCCATCTTCTCCTCTTCCCTTGGCTTCAGCCCCACCTAGAAACCTGAACA
AACATTTTCCTTGACATTTCATAAAGTGTCAGTGGCTCCTCATTTAGCAAA
ATACATCCCAGGGAAGTTCAAAAGTGAAAAAGGCCGTAACTTCTTCTTC
TTCTCAGGGACCTACAGAAAATATGTGGCACCTCGGCAGCCTGGCC

SG13S382

CATGGATTTTGTTTTCCAAGTGGCAAGATGGCGCCTCCACCTTTGGT
ATCCTATTTTAGTTCCTGGCAGAAAGAAAGGAACAGGCTAATGGCCCTGA
TGAGTCTACCCCCTTTTAACAGGAGAAAATTTAAAAAACAAAAACCATGA
AACCCTTTCCCAGAGGCAACAACCAGAATTCCATTTATCTTTCATTGACCA
[A/G]AACAGACCACATGGTCACTGGTGGTGGCAATGGAGACTGGGGAGAT
GAATATTTTAAGGTGGCATATTCCAGAAGAACACTGTGCACTGATTGCAT
TAATGAACCCATTAATGTGCCAAGGGGAGGTTTACCTATGAGCATGGGCA
AATTAGAACCCACTCTTGGAGCTGCAGGTGAGCCAATCCCACCTAAACAG

SG13S383

TGGTGGTGGCAATGGAGACTGGGGAGATGAATATTTTAAGGTGGC
ATATTCCAGAAGAACACTGTGCACTGATTGCATTAATGAACCCATTAATG
TGCCAAGGGGAGGTTTACCTATGAGCATGGGCAAATTAGAACCCACTCTT
GGAGCTGCAGGTGAGCCAATCCCACCTAAACAGTGTGGATGCTACAAGAT
GG[A/G]GAAGTAAATTGATTCTATTCCATACCCTAACCTCTCTCCAAGATG
TATTCTTAAAATAGAAGAGGGAAGACAGAAGAAAACATCCAGAATATATT
TTTATTGTCTTTTACTTCTTCAGTGCATTTTAGATCAGTGCTTCTCAATCTG
GCAAGGGGCATGCAGGAGGATGTGAGTTTTATCAGGAAAACTACACAAC
C

SG13S384

TGAGCCAATCCCACCTAAACAGTGTGGATGCTACAAGATGGGGAA

FIG. 8.6

GTAAATTGATTCTATTCCATACCCTAACCTCTCTCCAAGATGTATTCTTAA
AATAGAAGAGGGAAGACAGAAGAAAACATCCAGAATATATTTTTATTGTC
TTTTACTTCTTCAGTGCATTTAGATCAGTGCTTCTCAATCTGGCAAGGGG
C[A/G]TGCAGGAGGATGTGAGTTTTATCAGGAAAACTACACAACCCCCCA
ACCACAATGCTACCCCCACTCCTGTGGACCTTCTTTAAGAGAGACTCACTA
TTATAGATGGAGTTGATACGATTTTAAGAGAGGCCATATATTATTTGCTTT
CTGTCTTGAAAAACTTGTGATTTTTCTGTATTGTGCTACTGCCAAAGAGA
SG13S381
  GGGTTGCAGTGAGCAGAGATCACACCATTGCACTCCAGCCTGGGTG
GCAGAGCGAGATTCTGTCTAAAAAACAACACCGTATTTGGGGCATGCTGA
TACTAAAAAATTATTCATTGTTTGTCTGAAATTAAAATTTAAATTGGGGGC
CCTGTATTTTACTGGGCAACCCATTTGCAATATCAGCAACAATCTCTTATT[
C/G]AGACCACTGATTAAGTGTGCAAAATTTGAATCTCTGAACAGTACCTA
TGTCCTTGATATCTTAAATTAATGAGTGTCTTAGACACTCAAAGCAGGAGG
AAGCATTATGGCAGATGTTTGAGCCCCAGAGATGTCCATGAGCACAGCAT
AGAGCTCAGAGCCTTCTTTATTATTTGCTTCACGACAGAGCAAAGGACT
SG13S366
  CATTTGCAATATCAGCAACAATCTCTTATTCAGACCACTGATTAAG
TGTGCAAAATTTGAATCTCTGAACAGTACCTATGTCCTTGATATCTTAAAT
TAATGAGTGTCTTAGACACTCAAAGCAGGAGGAAGCATTATGGCAGATGT
TTGAGCCCCAGAGATGTCCATGAGCACAGCATAGAGCTCAGAGCCTTCTT
T[A/G]TTATTTGCTTCACGACAGAGCAAAGGACTGCAGCAGGTTGACTGAT
ATAAAAGTTTTACCATGTCTCACAGCAGGCCTTTGCTCAAGTTCCAGTAA
GGATATTGTATCATTTCTTGCCTGCAGTACTTGTAAATCCACTTACACTGC
CTGCTGTTGAGTCATTTGTTTCGTCTTGAGTAGCATGTCATCCTTGTTC
SG13S385
  TTGCAGTTCTCATTGCTGGGGAGTCTAAACTGGAATAAAACACCCA
CTATCTCCATCAGGCTTGCACTAGAGCCCAGCTCTAGCTGGAGAGAAAGA
AGCTAACCCGCACAGACACAGGACTGTAGGCAGGGAGCATCCGGGGGTA
TTTGGGTCCTGGCTCTGATGTGCCTAAGGCCAACTTCTCTCTGGCCATGCT
GG[C/T]GTGCATGAGCTCACTAATCTTCCTTTTGCCTTCCATTTTCTCCAA
TCCTGACTTAGCAAAGGTTGGGCAAAAGAGACTCTGTGTGAGTTCGAGCA
AAGCCTGAGATGCTGGATTTTCCAAGATACGAGAAGGGGCTGGGGGCTGG
GTGAACTGGTGGTGGAGGAGGGAAGGATTAATTTCCCAAGGAGGGGAAG
GG
SG13S386
  GAGAAAGAAGCTAACCCGCACAGACACAGGACTGTAGGCAGGGA
GCATCCGGGGGTATTTGGGTCCTGGCTCTGATGTGCCTAAGGCCAACTTCT
CTCTGGCCATGCTGGCGTGCATGAGCTCACTAATCTTCCTTTTGCCTTCC
ATTTTCTCCAATCCTGACTTAGCAAAGGTTGGGCAAAAGAGACTCTGTGT
GA[A/G]TTCGAGCAAAGCCTGAGATGCTGGATTTTCCAAGATACGAGAAG
GGGCTGGGGGCTGGGTGAACTGGTGGTGGAGGAGGGAAGGATTAATTTCC
CAAGGAGGGGAAGGGGCCAGGACATCAGGCCCCGGGGACTTTGAAGAGA
GGGTCGTGGGTAGGAGGTAGATCAAGTGGAGTGACACAAAGGTCAGGAA
AGAGG
SG13S1
  CATGCCTCCTACAAATTTGACCTGGGCCCAGGGCCATGTTCGGTGG
TTTTTAAGAACCGAGGCTCCCAGAAGCAGTATTGGGCAGCTAGAGTGGCC
CCAGGATCTATATCAAACTCTACCTGTTTCTGAACCAAATTTCTTCTAGAA
TTTTATTCCATAAATCTGAATTATGGTGTCAGACTCCTAGCATACACTAAA[

FIG. 8.7

G/T]GAACTCTCTGCCTTGCATTAAATAACAGGAGTTACCCCTGGAGGTAA
CTCCTAGCCCTGGCTCTTTAGAGAACAGATGCCGAATAGGCATTAGGGGA
TGTGATGGATGTGCTAACTTTCAAAAAAAAAAAAAAAAAAAGGCCTGAG
CTGAGTGCTCAGAGATTCACAAAAAGCTGACAGCATCTCTCTGTTCCATTG
SG13S2

CTTTGGAGCCTGGCAGCCTGGCTTTGAGAACCGGGCTTTAACTTGT
CACATGACTATGGCCAAGTTCCTGGGGCTCTCCAAGCTTCACTTCCTCTGT
AAAAAGGGCAATAATATAATACCTGTCTTATTGGGTTTTGTCCATGTTAGA
TGAGACATTGGGTACAAAGCACTTGGTCCCGTGCCTGGCACATTTACTGC[
A/G]CTTAATGTATGATAGTTTTCTTATTATTCTAATAAACAATATGGCTTTG
GGAGTATAGTTCTGCCACATTGCAGTGGCCAGAGTGAAGGTGGTGAGTGC
CTTCTGGGGCCCTGGGAGTCAAGGTTATCCGCATGCCCTTTCTTGCTTGCT
CCTCAGTGTGGCTGCCTCTATGTCCACACCATGCAGATGCAACAGGT
SG13S367

ACATGATCATCCCCTTGGGCTTCTGGTTTTTTTCTTTCAGGACCTT
ATTTTCAGGCAAGTGGCCTTTGACCTCTAAGGCTGTCCTTTCCTAGCTACC
GAATCCAGCATTCAAAGTGATGGAAATATGTATATATAGTAATAGTAAAA
TATCAGCACTTAATGGCCTGATAAGAATGTCACTGCAATGCTGAGTTTGG[
A/G]CCAACATTTGCCTGCTCCTGCCATTGAGCCCGGGCTCCCTCCAGAGC
TGAGCTGCTGCAAGGGATCTGAGTAACTAGGGCTGTGTCAGAGTGGCGAT
GACAGCCACCACATGCTAAGGAAGAGATCCCCAAGGACAAGGAGAATCC
CACGTGGAGCTACTTGCTTCTTTGTCAGTCTTGTTTTCTTATTTCACAA
SG13S388

CCGAATCCAGCATTCAAAGTGATGGAAATATGTATATATAGTAATA
GTAAAATATCAGCACTTAATGGCCTGATAAGAATGTCACTGCAATGCTGA
GTTTGGACCAACATTTGCCTGCTCCTGCCATTGAGCCCGGGCTCCCTCCA
GAGCTGAGCTGCTGCAAGGGATCTGAGTAACTAGGGCTGTGTCAGAGTGG
C[A/G]ATGACAGCCACCACATGCTAAGGAAGAGATCCCCAAGGACAAGGA
GAATCCCACGTGGAGCTACTTGCTTCTTTGTCAGTCTTGTTTTCTTATTC
ACAACCTTCTAAAACACAATCTCTCAACCTCTATTGTTAGCTTGCATTTTT
CAATCATGAGCACAGCTTTACCTGGCTCCATGCTTTGATTGACTCTACC
SG13S10

TCTTATTTCACAACCTTCTAAAACACAATCTCTCAACCTCTATTGTT
AGCTTGCATTTTTCAATCATGAGCACAGCTTTACCTGGCTCCATGCTTTGA
TTGACTCTACCTGCCAACACTGCAACAACAGGGAAAGGGACACCGGCCTC
ATACCATTAGATGGTGTGTAGCCTGGGCATGAGGATAATTAAAAACTCCC[
A/T]AGGGGATTTTAACATGTAACACAGTTTGGAAACCATTGATGTAAGAT
CTTCTTACTCAACATGTGCTCCAAGGAGCTGTTGTATCAGCTTATCAGAAA
TGTAGATCAGGCCGCACTTGGACCTGTAGAATCAGAATCTGCATTTTATCA
GATTCCGACATTATTTGTATGAACATTAGCTTTTGAGAAGTGTTGCTT
SG13S3

CTTTTGACACCAACTACAAGTCAAGGGGTTCCCCAAACCACCCTGA
GTTGTGATAATTCGCTGGGAGATCTGACAGAACTCACTGAAGGTTGTTAT
ACTCATGGTTGTGATCTCTTATAGGGAGGGAATACAGATTAAAATCAGCC
AAAGGAAGAAGCACACAGCACAGAGTCCAGGACAGTGCCTGACATGGAG
CCC[C/T]TACGGTCCTCTCCCGTGGAGTCACGGACAGCGCCACTCTCCTGG
CATTGATGTGTGACAACACACAGGGAGTGTTCCCCACCAGGGAAGCCTTG
GTGTCCAGGGTCTTTACTGTGGCTCTGTCACATGAGCACAGCTGACTGCCC
ATGCGGCCGATCTGTTCCCAGACTCTCCACCGCTACACATCACTCACAGTC
C

GTGGCTCACAGAACTCAGGGAAACACAGCTACCAGTTTATTGCGA
AGGACATTTTAAAGGATAAAAGTAGGCAGATAAAGAGATGCATAGGGCG
AGGTGTGGAAAGGTCCCTAGTGCAGGAGCTTCTGTCCATGTGGAGCGGGG
GTGCACCACCCTCTCAGTACATGAATGAGTTCTCCTTCACCTGCCTATCAG
CCT[C/T]TACATGTTCAGCTCCCCAACCCAGTCCTCTTGGGTTTTTATGGAA
GCTTCAAGACACCCACATTCTTTCCCCAGAGTATAGGGCAAGACCTTCTCT
GGGGAGGGTTTTAAGACCCACAGTCAGAAAGGTGGGGTGGGGTCAAGAT
TAGAGTCCTGCCTTGACGGGCAGGTGAAAGGGGTAGGGGGAGTAGGTGA
GAA

SG13S369

CGGGGGTGCACCACCCTCTCAGTACATGAATGAGTTCTCCTTCACC
TGCCTATCAGCCTCTACATGTTCAGCTCCCCAACCCAGTCCTCTTGGGTTT
TTATGGAAGCTTCAAGACACCCACATTCTTTCCCCAGAGTATAGGGCAAG
ACCTTCTCTGGGGAGGGTTTTAAGACCCACAGTCAGAAAGGTGGGGTGGG
G[G/T]CAAGATTAGAGTCCTGCCTTGACGGGCAGGTGAAAGGGGTAGGGG
GAGTAGGTGAGAAAAATTCTGTTTATTTTTCTTTTTTTTTTGAGACGGAG
TTTCACTCTTGTTGCCCAGGGTGGAGTGCAATGGCACAATCTCAGCTCACT
GCAACCTCCGCCTCCCAGGTTTAAGCGATTCTCCTGCCTCAGCCTCCCG

SG13S370

ATGAGTTCTCCTTCACCTGCCTATCAGCCTCTACATGTTCAGCTCCC
CAACCCAGTCCTCTTGGGTTTTTATGGAAGCTTCAAGACACCCACATTCTT
TCCCCAGAGTATAGGGCAAGACCTTCTCTGGGGAGGGTTTTAAGACCCAC
AGTCAGAAAGGTGGGGTGGGGTCAAGATTAGAGTCCTGCCTTGACGGGCA
[A/G]GTGAAAGGGGTAGGGGGAGTAGGTGAGAAAAATTCTGTTTATTTTT
CTTTTTTTTTTGAGACGGAGTTTCACTCTTGTTGCCCAGGGTGGAGTGCA
ATGGCACAATCTCAGCTCACTGCAACCTCCGCCTCCCAGGTTTAAGCGATT
CTCCTGCCTCAGCCTCCCGAGTAGCTGGGATTACAGGCGTGTGCCACC

SG13S4

TCTTCATTCCACAAAGCTCAGTGTCAAAACATGGGGTTTACACTGG
AAGCTGAGGTCACATCAGTAGCCGGGATCAGGGTCGCCCTAGCTGCCCAA
TGCAGCTCCCAGGCCTCCTGTAAAACCTTGACCTTTGAGGTCATGACAGCC
CTCTCCTGCTATGCTCATAGCTGACCACTGAACTCCTGGACACTCCCTCCC[
G/C]CAAGTTCACAGAGAATGTGGGCACATGCCTTACAGTCTTCCCTTGATC
CAAACTACTGCCTTCATCTTGAGTGACAGCAGCATCTTTTGGATGTCTTGG
CCTGTCTAGCTTTATTTTTTTGTGTTCTGCCATCAAGTTGCTACTTCTGTTG
CCATCGTGCCTGTCAGCGCAGTGCAGGCTGTGGTGAAATCCCACGA

SG13S5

TATTTTTTTGTGTTCTGCCATCAAGTTGCTACTTCTGTTGCCATCGTG
CCTGTCAGCGCAGTGCAGGCTGTGGTGAAATCCCACGAACTCAGGCATCA
CACTGACCGGGTCTGAGTCCTGTCTCAGTTGTCAGCTAGTTGTGCAATGAA
GGGAAAGGGACCTACACTTTCCAAGCCTCAATTCACTCATCTATGGCAT[G
/T]GTGACAATAATGGAGGTTGATTTAAAGTCCTTTGTAAGAATTAAGAGTT
ATAATAGACATAAAGTGCTGTATCTGGTATACCTAGAAAACATTCCATAA
AAGTTAGTAATTGTTGGTCATGTAATGATGACTCTCTAGGCTAGGATTTCA
GCTTCATTGCATGCACATGGTGCACTCACAGGGCGTGACCTCTCTCT

SG13S389

GGTATACCTAGAAAACATTCCATAAAAGTTAGTAATTGTTGGTCAT
GTAATGATGACTCTCTAGGCTAGGATTTCAGCTTCATTGCATGCACATGGT
GCACTCACAGGGCGTGACCTCTCTCTGTCTCAGTAACCTCATCTGAGGACC

FIG. 8.9

GGGATAATCATACCGCTTCAAAGGGATGTCATAAAGATTAAATAATATGT[
A/G]TAAGGCTGCTTGCATTTAGCTGCATTCAACAAATATTTCTGTATCTTT
CTCCTCATTTCTCCTTACTTTCTTGCTTATTATCTGCTCTAGGTATAGATTTC
AGAGAACTAAGCTTGTTACAATCCTTCATAAAATAACCAGGTTGGTTAGG
GCATTTCCAAGAGTCAATACTGTTTAGTGACTATTCTCTGTTTAAT
SG13S90

AAGGCTGCTTGCATTTAGCTGCATTCAACAAATATTTCTGTATCTTT
CTCCTCATTTCTCCTTACTTTCTTGCTTATTATCTGCTCTAGGTATAGATTTC
AGAGAACTAAGCTTGTTACAATCCTTCATAAAATAACCAGGTTGGTTAGG
GCATTTCCAAGAGTCAATACTGTTTAGTGACTATTCTCTGTTTAATCT[A/C]
TTTTGATTGTCCAGGGTCATCTTTTGCTATGTCATAGGTTGTTGGCTTCTTC
TAGAGAAGTGAGACGATGGACAAGTTCCAAGTGAGTGAGGCGACTGGTC
AGGATATTCCGCTGAAAAACTCATGTCAGTTCTAATTCGTGATTGTAATTC
AATCACAGCCTGAGAACAGTAGGACTGTAGTTCAAATGCTCTGTT
SG13S390

CCTGGGTTCAAGCAATTCTCCTGCCTCAGCCTCCCAAGTAGCTGGG
ACTACAGGCACATGCCACCACGCCCAGATAATTTTCGTATTTTAGTAGAG
ACGGGGTTTCCCCTTGTTGGCCAGGGTGGTCTTGATCTCTTGACCTCATGA
TCCGCCCACCTCGGCCTCCCAAAGTGCTGGGATTACAGGCGTGAGCCACC[
A/G]CGCCCGGCCTCTAGAGGATAATTTTTAAATGTGCTTTTGCATTTGGAA
AATGTGATTGGCATTTTTTTCTAATTTTCTAATATGATACGCTGTCGGATGC
TATGGATTACTTAAACCCTCTGGCTACCTAGAAAGATCTTTAAGTGGTTCT
CAACAAGCTTCATACGCAATGTAAATTGTATTATCTCTCAGGATGT
SG13S6

TGTGATTGGCATTTTTTTCTAATTTTCTAATATGATACGCTGTCGGA
TGCTATGGATTACTTAAACCCTCTGGCTACCTAGAAAGATCTTTAAGTGGT
TCTCAACAAGCTTCATACGCAATGTAAATTGTATTATCTCTCAGGATGTGT
GAGAACATCTGTTTTCTTCTAATGCAGTAAACATATAAGGGTCTCTTG[A/
G]GATATCTTTTAAATAGACTTAATACAACATTCAGGAATGATAACAAAAT
ATAATCACAGTTGTAAGGGAATGTGAGCATTTCATATTAATAACATTGGA
ACCTTATGTTTAATACAGTGTTAAAAGTTGACAAACATGTAGGAGTCAGA
AAATTCAATTAAAATTATCACAGTAATATGAATTTAGCCACATCCTGT
SG13S391

ACTTAAACCCTCTGGCTACCTAGAAAGATCTTTAAGTGGTTCTCAA
CAAGCTTCATACGCAATGTAAATTGTATTATCTCTCAGGATGTGTGAGAAC
ATCTGTTTTCTTCTAATGCAGTAAACATATAAGGGTCTCTTGGGATATCT
TTTAAATAGACTTAATACAACATTCAGGAATGATAACAAAATATAATCAC[
A/G]GTTGTAAGGGAATGTGAGCATTTCATATTAATAACATTGGAACCTTAT
GTTTAATACAGTGTTAAAAGTTGACAAACATGTAGGAGTCAGAAAATTCA
ATTAAAATTATCACAGTAATATGAATTTAGCCACATCCTGTGTTAGTTATG
AAATCCATTTAACACCACAAACAGTAATATTTTAGCCAGTTTATTCA
SG13S392

CATTTAACACCACAAACAGTAATATTTTAGCCAGTTTATTCAAAA
GGAAAACAGGAACTAAACCACTTTCATGCAATATATACTCTGTTAATGTG
GTCAGGCTAATTTTGCTGGGGGAAGGAACTTAACTTTTGAATATTTGAATG
CCCAGTCATTTAATCTGAATATCCTATTTCCTTGCATGTTGCAAAATTTTT[
G/T]TCAATAAAAGGCAGAAAAGAAATCTCTTCTCCATGCTCATCCCTAA
GAGAATGGGTTGTCTGTACCCTGAGAGCATTTTATGGAGGGGACAACCAC
TTTTCTAATTTTCCTTCCCACTTCTCTGTGGGCACAAATGCTCTTTGGTTGA
AAGAGTTGTAATTCAGTCCCAAGATGAGGTGTGGTTACTGCATCCCTA

FIG. 8.10

SG13S371
TCAATCCATGCTCCACACTGCAGCCAGAGTGCTCTACAATGCAAAT
CCATTTGTGAGACTCCTCCTCTTAAAATCCTCAAGTGGCTTCTCTTTGCCCC
CAGGATCATTTTGAAACTCCTTAATGGAAGAGGCATGGCCCTTTGGGATG
TGGTTCCCCAACCCCTCCCACATCATCTTTTCAATCAGATTTCCCACTAA[A
/G]TGGAAATTTTTTCAGGTCCTCAACTTTATGGTGACTTTCTCTTGCTCAGG
ATCTTTGAACATACTGTTTCTTCTTTCCTTTTGTATTTGCCAAGACAACACT
TCCTCTGGTAAGATTTTCCTGACATCCTCTATAAAAAAGATTGAGATAGT
TGACTACCCAAAATGTTTCCCATTCATTCCAAGCTCTATTCAAG
SG13S372
AACACTTCCTCTGGTAAGATTTTCCTGACATCCTCTATAAAAAAG
ATTGAGATAGTTGACTACCCAAAATGTTTCCCATTCATTCCAAGCTCTATT
CAAGGCAGTAAAGTGCCCGGCTGACAGATTGCATTCCTCATCTTTCTGAA
GCTAGCAATGGCCATGCAACAGCATTCTGGCCAATAAGATAGAAGTCGAA
[A/G]TTGAAGGGTGGGATTTCCAAGAAAGCTCGTTGAAGACATAATTCCTC
ATTTCACTTCTTACTCTTTCTCTTTCCTGCTTCCTAAAATGCGGTGCAGATG
GCAGACACTTCAAAGCTGTCTCAGGCAATCAGGTGATGTTAAGGCAGAAA
CCAGCTTTATGATGGGTAGAACAGGAAGAAAGAAGGCACCTATGTTCT
SG13S393
CCTACAAATCTCATGTTGACATTTTATCCCTAATATTGGAGGCAGG
GCCTAGTAGGAGGTGTTTTGGTCATAGTGATAAATGGCTTGGTGCCGTTCT
CACAGTAACGAGTGAGTTTTTATTCTAGTGGTTCCTGCAAGAACTGATTGT
TAAAAGAGCTTGGATCCTTCCACCCCTCTCTCACTCTTGCTTCCTCTCTC[A/
T]CACCTTGTAATCTCTACAAGCTCTTCACCTCCCCTTCTCCTTTTGCCATA
AGTGGAAGATTTCTGAGGCCTCACCAGAAGCAGATGTTGGTTCCATGCTT
CTTGTACAGCCTGCAGAACCATGAGCCAAATCAACTTCTTTTCTTTATAAT
TATCCAGTCTCAGGTATTCCTTTATAGCAACACAAATGGACTAAGA
SG13S373
GTTGTTTCCAGCTTTGAACTATTTTGAATCCTAAAAGACTGCCAGTT
TTGAATGAGACCCCAGAACAATGAATGTAGGCTCTGTATACAAGTTCAGG
CTGCTGGGCAACTTAGGCCTTAAGACACAACTCTGCCACTTAGGCCTTAA
GACACAACTGACATGATGGTGCTTAAAGTGGCTGTGATGGAAAAGGAGG
CT[A/G]TTTGGAGCCTTTGGAGTGCCTTTATAGGTGAACCCCAGCATAGCA
CCTAATGATTTGGAGCAAAGCTGTGTCATTCCCCAAAGATAACTATTCGCC
TTTTGAGAAACATCTTCTAGCTACTATCAATAATAAACACAGAATGCATC
ACCATGGGCCACCGTGTTGTCTTTTGACCTGAGTTTCCATTGTGAACAAGA
SG13S374
AACTCTGCCACTTAGGCCTTAAGACACAACTGACATGATGGTGCTT
AAAGTGGCTGTGATGGAAAAGGAGGCTGTTTGGAGCCTTTGGAGTGCCTT
TATAGGTGAACCCCAGCATAGCACCTAATGATTTGGAGCAAAGCTGTGTC
ATTCCCCAAAGATAACTATTCGCCTTTTGAGAAACATCTTCTAGCTACTAT
C[A/G]ATAATAAACACAGAATGCATCACCATGGGCCACCGTGTTGTCTTTT
GACCTGAGTTTCCATTGTGAACAAGAGTCATTTGATCCAAGGCAGAAAGT
TGGGTGCACACAGCAGTGTTCCATCATCAAATGGAATATGAGATTGGGCC
CAAGTAGGTCCTGCAGACACAAATAAGTTGCAAGAGCAAGTAGTACAGG
CG
SG13S375
GAAAAGGAGGCTGTTTGGAGCCTTTGGAGTGCCTTTATAGGTGAAC
CCCAGCATAGCACCTAATGATTTGGAGCAAAGCTGTGTCATTCCCCAAAG
ATAACTATTCGCCTTTTGAGAAACATCTTCTAGCTACTATCAATAATAAAC

FIG. 8.11

ACAGAATGCATCACCATGGGCCACCGTGTTGTCTTTTGACCTGAGTTTCCA
[C/T]TGTGAACAAGAGTCATTTGATCCAAGGCAGAAAGTTGGGTGCACAC
AGCAGTGTTCCATCATCAAATGGAATATGAGATTGGGCCCAAGTAGGTCC
TGCAGACACAAATAAGTTGCAAGAGCAAGTAGTACAGGCGCTTGGCCTGG
CCAGTACTGTTGCCAAGTTGACTGCTTCCCCTCAGTCTGCATCTGTGGCTT

SG13S376

CCCCAAAGATAACTATTCGCCTTTTGAGAAACATCTTCTAGCTACT
ATCAATAATAAACACAGAATGCATCACCATGGGCCACCGTGTTGTCTTTT
GACCTGAGTTTCCATTGTGAACAAGAGTCATTTGATCCAAGGCAGAAAGT
TGGGTGCACACAGCAGTGTTCCATCATCAAATGGAATATGAGATTGGGCC
CA[A/G]GTAGGTCCTGCAGACACAAATAAGTTGCAAGAGCAAGTAGTACA
GGCGCTTGGCCTGGCCAGTACTGTTGCCAAGTTGACTGCTTCCCCTCAGTC
TGCATCTGTGGCTTCATGGGGAGTTTCCTATGACCACTTGATGGAGGAAA
AAACAAATTGGAGCATAGTTTATAGTGCTGGTACTACCCAAAGTGGCTAG
CT

SG13S394

GTCCGTGAGTTACAGATCTACACAAAATCACAGAGAGTGGTTAATC
GTTTAGTCTGATGGTCAGGGACTTCCAAGAGACATGATTAGAAAACTGGT
GACAAGGAGTCCTGGGGAAGAGGCATATGGATACCTCTGAACACACACA
AAACATGAGAATATGTATCCCATATGAATGTTAACCAAAGAGCAGCCACA
ACA[C/G]AAGAGGATTTTAAAATCAGCTGAATAAGATGATTCATTCTGACA
GCATCAGCTAGTCTCTTTCCCCAGCCACTGTTGCCCAGTGGGCTTACATAT
ATCATGGCCATGGGGGCAGGGCTATGTATGGACACAGCAACATGAATTTC
CACTCATCAAGGCCAATTTGGCTCCAGCCATTGCTGAGTGCTCAGCCTGCC
A

SG13S25

ACATGATTAGAAAACTGGTGACAAGGAGTCCTGGGGAAGAGGCAT
ATGGATACCTCTGAACACACACAAAACATGAGAATATGTATCCCATATGA
ATGTTAACCAAAGAGCAGCCACAACAGAAGAGGATTTTAAAATCAGCTG
AATAAGATGATTCATTCTGACAGCATCAGCTAGTCTCTTTCCCCAGCCACT
GTT[A/G]CCCAGTGGGCTTACATATATCATGGCCATGGGGGCAGGGCTATG
TATGGACACAGCAACATGAATTTCCACTCATCAAGGCCAATTTGGCTCCA
GCCATTGCTGAGTGCTCAGCCTGCCAAGATAGAAATCTACGCCAATATGG
CACCATTCCCTGGGCTAGAAAACCAACTGGTGGAAGGTTGATTACATTGG
ACC

SG13S395

GGGAATACAATGGTGGTTCCACTAAACTGACAGCTGAGTTTGCCAT
CTCCTCGTGCCAGTGAATACACAAGCAAGGAAGGGGGTTCCTTTCTCACC
TAGGGTGACTGATCCTAATTACCAAGGAGAAATTGGACTGCCACTTCACA
ATGAGGGTGAGGAGTATGTACTCTATGTGTCTGTGATTAATGTCAATAGA
AA[A/G]TGACACCAACCTAGTACACAGAGGACTGATCATGGTCCAGGCCC
TTCAGGAATGAAGATTTGAGTCACCAGGCAAGGAACTTGGACTCACTGAG
GAGGGCATATTCCAAGGAGAATATTTTATCTATGTCCATCTATGTCCATCT
ATATTCCATCTGTGTTCCCCTTGGAATTCCATTCATGAACATGGGGAATT
C

SG13S396

TATAGAATGAGTAGTGGAAGGTAGTTATAAATGTAAGTCAAAAAC
CACACAACCAATTTGAGAAATGAGGAAGGTAATAGTGTTGAATATGTCTT
CTTTATCTTGATATAAATGTATTTGTGCATATATTAACCAGTTTATTTATTT
ATTATTATTTTTTGAGATGAGCTCTCGCCATGTTGCCCAGGCTGGTCTTGA[

FIG. 8.12

A/C]CTCCTGGGCTCAACTGATTCTACCATTTAGTCCTCCGAGTAGCTGGGA
CTACAGGCATGCACCACCATACCCAGCTGACCAGTTTTTCCTATTCCTCT
ACTTAATTTCTCTACTATACAACATAATATGTGTTAATGGTAGTTAACTTT
ATATCTCAGTATTAAGTCACAAGATATCAAAAAGGGAATGCGACTTA
SG13S397

ATGTCTTCTTTATCTTGATATAAATGTATTTGTGCATATATTAACCA
GTTTATTTATTTATTATTTTTTGAGATGAGCTCTCGCCATGTTGCCCAG
GCTGGTCTTGAACTCCTGGGCTCAACTGATTCTACCATTTAGTCCTCCGAG
TAGCTGGGACTACAGGCATGCACCACCATACCCAGCTGACCAGTTTTT[C/T
]CCTATTCCTCTACTTAATTTCTCTACTATACAACATAATATGTGTTAATGG
TAGTTAACTTTATATCTCAGTATTAAGTCACAAGATATCAAAAAGGGAAT
GCGACTTAGTTACAAGCAGAATGAATATCACTCAAAGATGAATAAAGAG
AAGAGGGTTAGTGCATTTCTGTTGGATGAGAGAAAGTTTCATTGTT
SG13S377

GCAGTGGCGTGATCCCAGCTCACTGCAATCTCTGCCTCCTGGGTTC
AAGTGATTCTCCTGCCTCAGCCTCCCGAGGGGCTGGGATTGTAGGCGTGC
ACCACTATGCCCATCTAATTTTTGTATTTTTAGTAGAGATAGGGTTTTGCC
ATTTTGGCCAGACTGTCTTGAACTCCTGACCTCAGGTGATCTGCCTGCCTC[
A/G]GCCTCCCACAGTTTTGTGATTATAGGCATGAGCCACCGTGCCCGGCCT
TAACCTTTGTTTTCTTACACAACACACTACGTGATGTTTTCCACATGCATG
GGTCATTTGCTTCATTTACGTACAAATGCATAAGCAATATACTGTGTGGTG
TGAGTTTGTGATGGGAAAAGGAAGAAGTTTTGCGGATACTACACTGG
SG13S189

GCCCAGGCTGTTCTCCAACTCCTGGACTCAAGCCATCCTCTAGCCT
CGGCCTTCCAAAGTGCTGGGACTATAGGCGTGAGCCACGGTGCCAGGCCC
TTGACCACATTTTTAACCCCTCTGAACCTCAGTTTCACTTTCTGGGCAATG
GGAGGGGGGTAATTTGTCCCTCAGAGGGTTGCACTGAGGGCAAATGTGA
G[C/G]CTCTGGGTACAATGCCCAGTACAGACTAGGTCCCCACGACACAGCC
GCTCAGCGGCTCCGGATTCTGGGCTGCTCTGGACTGCGGCCAGGCGGTCT
TCTGCGGGAATCCGGGCAGGCAGGGCGGGCTGCGCTCCCCTCCCCGGCTC
TCCCGGTGCCCCTTGTCTTTTGTTCTGTCTCAGCAGCTCTCTATTAAGAT
SG13S100

TTTTTGTTCTGTCTCAGCAGCTCTCTATTAAGATGAATGGCATTTCC
AAAGGCTTCACCTCTGATAAGTGTTCCTCTGCAGCTGCAGCCAGAATCTTA
ATGTGCGCGCTGTAATTTAATGGCCGTCTCGGCTATTAACACGCTCTTCTC
GGGTGAAGTGGACTCCCTCCATCCCCGGGCCTCTGCACGTGCTCTGCGC[A/
G]CTGGCTGGGGGTGACTCCAAGGAGCTCAGAGCGGGGTGCCCGGCACCT
CTCGCCAGGCGCCTTTCGACCTTCTAAAGCGCGAATGGCTGGACTTTTCTC
CCATGTGTGGGGCCCCAGAAGGTGTGGGGCCCCAGAAGGTGTGGGGTCCC
TGCGTTCCACGGAGCCCGGAAGGTTTCCAGTGATGGTGGGGCTGACC
SG13S398

GGAGCCCGGAAGGTTTCCAGTGATGGTGGGGCTGACCACGTTGG
TCCCCGTGGGTGCTGTTTTCATGTGCCGGCAGATTGGGATGAGTTTAAAAG
ACAGAAGCGTGTAGGATAGAGAAACTTCTTTAAAAACTGGAAATTTTAAT
CTGGGGATTATAACTATTGGACAGTCAAGTGCAAGAGTGAATACACTTCT
CA[C/G]TCCCTCCTCCCAATTTTTATTTGCGGGATTAGTCAGTCCCCCTCTG
CCACATGATAATTGTGAGAACTACCAGGGTCTTCATTCTCCTGCCATCTGG
TTGACCTCTCCAAGAATGGACACCCGGGCAGCCTGGGCCAATGAGGCTGT
CCTAAGAGTTTAGATGAGAGAAGTCAGTCTTTGACAGGTGATGGAAGCTG

CAGTGATGGTGGGGGCTGACCACGTTGGTCCCCGTGGGTGCTGTTT
TCATGTGCCGGCAGATTGGGATGAGTTTAAAAGACAGAAGCGTGTAGGAT
AGAGAAACTTCTTTAAAAACTGGAAATTTTAATCTGGGGATTATAACTATT
GGACAGTCAAGTGCAAGAGTGAATACACTTCTCACTCCCTCCTCCCAATTT
[C/T]TATTTGCGGGATTAGTCAGTCCCCCTCTGCCACATGATAATTGTGAG
AACTACCAGGGTCTTCATTCTCCTGCCATCTGGTTGACCTCTCCAAGAATG
GACACCCGGGCAGCCTGGGCCAATGAGGCTGTCCTAAGAGTTTAGATGAG
AGAAGTCAGTCTTTGACAGGTGATGGAAGCTGTAAATGTAAAACTCCA

SG13S101

TAAGAGAAGCTGAGAGAGAGCGAGAGGAGAGATTGGAAGAAAGA
CAGAGACAGAGGTAGAGAGAAGGGAAAGAGAGAGAGAAAGGGACAGAA
GAGAGAGAAAAAGAGGGGGCCGGGCGCGGTGGCTCACGCCTGTAATCT
CAGCACTTTGGGAGGCCGAGGCGGGCAGATCACGAGGTCAGGAGATCGA
GACCATCC[C/T]GGCTAACACGGTGAAACCCCGTCTCTACTAAAAATAT
AAAAAAAATTAGCCAGGCGTGGTGGTGGGTGCCTGTAGTCCCAGCTACTG
AGGAGGCTGAGACAGGAGAATGGCGTGAACCCGGGAGGCAGAGCTTGCA
GTGAGCTGAGATCGCGCCACTGCACTCCAGCCTGGGCAACAGAGCAAGAC
TCCGTCTCA

SG13S95

TCCACCAGCAGCTTTTCTGAGTCTCCAGCTTGCAGATGGCAAACCA
TGAAACTTCATGGTGTCCATGAGCATGTGAACCAATTTCTATTATAAATCT
GCAATATATATATGAGGAGACTTATTTATATATTGGTTCAGTTTCTCTG
GAGAGCCTTGGCTAATATAAAGTCTATACTCTACAAAGTGCCCTAGGTAC[
G/T]CAGGGAGTACCCAAGTGTGTCATGACCAGCCCGACAGCCCTGGCTGC
TGGCTTCCCCGCACACAACTCTGCACGCTGCCTTCATCAGCCTTTCTCTCT
CAGCTGAACCGAGGGCATTGAAGCGGGCCTCTGGCACTGTACCTATGAGG
GAGCAATATCTTCCCCTACACTGACCTCTTCCGTGCCGAGATGCAGCCC

SG13S102

GCCTCTGGCACTGTACCTATGAGGGAGCAATATCTTCCCCTACACT
GACCTCTTCCGTGCCGAGATGCAGCCCTCCCTGCTGCCACTAGTTACAGTG
GTCCATGTTCCCTTTCAAAGTGAAGTTTTGATAAAAGCACCTCTTAACCAA
TGCCAAATAGCTAAGTCTGGGACAAAGATTGCAGGTATTTGCATTTTCC[
A/T]TGTAACCTCAGAGGGATTGCCATTCACACTGATCTGAGCTGCAGAAT
ACCAGGCAGCCACCTCACCCACCCAGCAGGTCCACTCTTATACTTTCTCAG
AAAGCACAGCCACTCTACTCTTATTCAGTTGAAAAGAATTTCCAGGAAGG
TGTTTCTGCGATTGCCTCAGAAAAGTCAGTTCCCTTTGGGAATTTCCCT

SG13S103

TACTTTTCTCTGAAGAAATGGAGATATCAGCTGTCCCTCCCCACTG
CCATTTATTCCTTCCTTCATTCAAACCTTATGTGGCTGCTACTTACCGTGTG
TTAAGTGTTCACTTTTTTTCTTGGAATTCAAAAAAGAAGGACAGTATTTG
GGGCACAGATCTTTTGGTGTTCTATACATTTTTTAAAGTTTCATTTTA[C/T]
ATTTGTGTGTGCGTGTGTGTGTGTGTGAGACAGTCTTGCTCTGTTGCCC
AGGCTGGAGTGCAGTGGCATAATCATTGGCTCACTGTAGCCTCAAAGTCC
TGGGCCCAAGCAATCTTCCCACCTCAGCCACCCAAAATGCTGGGGTTACA
GGTTTATGCCACTCTGTCTGACCTGAAAGTTTGGGTTTACTTTCC

SG13S104

GCATAATCATTGGCTCACTGTAGCCTCAAAGTCCTGGGCCCAAGCA
ATCTTCCCACCTCAGCCACCCAAAATGCTGGGGTTACAGGTTTATGCCACT
CTGTCTGACCTGAAAGTTTGGGTTTACTTTCCCTTCTTTCTCTTTGCTGAA

FIG. 8.14

GTCAGAGATGATGGCAGCTTCCAGATTCTCTGGTGCCTGTGCTGGGCTC[A/
G]TGCTGGTCATGGTCTTGGGTCCAGGATTCATTCTGGAGACTCTCAGGGA
AGTTTCCCATGACAAGGAAATGTAGGAGAGTGTGCTGGCTTTGCGTGCTC
CTCTGCCAAGCCCTGCTTCTCCTGGTGGGACACACTGAACCACAGCCAGG
GCATTTGGTGGTTAGTTAAAAAAAAAAAAAAAAAAAAAAAAAGGAAG
SG13S191

CTTCAGAAATTGTAATGATGAAAGAGTGCAAGCTCTCACTTCCCCT
TCCTGTACAGGGCAGGTTGTGCAGCTGGAGGCAGAGCAGTCCTCTCTGGG
GAGCCTGAAGCAAACATGGATCAAGAAACTGTAGGCAATGTTGTCCTGTT
GGCCATCGTCACCCTCATCAGCGTGGTCCAGAATGGTAAGGAAAGCCCTT
CA[A/C]TCAGGGAAGAACAGAAGGGGAGATTTTCTTTGATGGTTGTTTGGA
AGTCAGGCTTAAACAATTGTGTCTGTGTGTGCGCATGCACAAACACTTTTA
CCTTATCTTTATTTTCTTCTTTTTATTTGAATGTATAGGGTTGTGTGTATTTC
TGTGTAAATTTGGGGTTTTCCTCCTCTTAGTCTTTCACTTTTGTGGTG
SG13S105

TTTTCTAACATCTGCAGTGCAATTGAAGTTACCAGTCATCTGCAGTC
TAAAAAGAAAGTGATTTTGGGAGGTGCGTAGAAAAAATCATCTTATTATT
TTTCCTCTATATTACTTTTTTCTTTTTTTCTCCTGAAGAAACTTTTTTTTTTG
GTGATACCTTCTTTTTCTCTAGCACGTATAATTTTGGAAGCATTTTTC[A/G]
TATGCAGTGTATACTTCAGAAAGAGAGAGAGAGAGGAAAATTGTCCTG
TTCAGCGTTTGCATTTCCATTATTCCTGCTATTAGTTAAAAACAACAACAA
CAACAAAAAACAAGCAGGATACCTAGATCTGGAAAAGGGAGAATTGTGT
AGAGCTGTCTTCCTAAAGTTCTGAGTTAGGGCTGCCTCAGACCACTT
SG13S106

TTTGGAAGCATTTTTCATATGCAGTGTATACTTCAGAAAGAGAGA
GAGAGAGGAAAATTGTCCTGTTCAGCGTTTGCATTTCCATTATTCCTGC
TATTAGTTAAAAACAACAACAACAACAAAAAACAAGCAGGATACCTAGA
TCTGGAAAAGGGAGAATTGTGTAGAGCTGTCTTCCTAAAGTTCTGAGTTA
GG[A/G]CTGCCTCAGACCACTTTCATAACTATCTCCAGTGGCTTTGTGTTTT
ATATTTATTAAGATAGAGAAAAAAGAGTAATTACTAAGGGCAGCTGCTG
TAGCTTTATGGTGATTACTGAACATTGACATGCTGTCACGTTTTGGAACT
TTGAGTATTTAATCACTTTGGGATATTCTATTTTCCCCATCTTGAGTGT
SG13S107

GGAACTTTGAGTATTTAATCACTTTGGGATATTCTATTTTCCCCCAT
CTTGAGTGTGGACAGATGCTGGTGATGTAGCCTTCTGGGCACAGAGCAAG
CCTCCCCCTCAGCCTCTGCACCAGAAAGGCTCAGCTTCACACACTCCAAGT
ATGTTTTCTACAAGAACTACACTTTGTGGCTTTCTGACCCAAACATTTTT[A/
G]TACTAAATTACACACAACAAAGTTGTAGCTCAGAGAGGGAACAAATGG
CTTATTTAGGCCACCATTTTCTTGAGCCATTATGATTTCACACAGGGCTCC
CTTGGCCCTGTAAATTGGCAAGGATTCCATTATTCAACCCGCATACATGTA
CAGAGACCCTGCTCTGGCCCAGATAGTATTCTGGGTACAGGCGGATA
SG13S108

TGTGGACAGATGCTGGTGATGTAGCCTTCTGGGCACAGAGCAAGCC
TCCCCCTCAGCCTCTGCACCAGAAAGGCTCAGCTTCACACACTCCAAGTAT
GTTTTCTACAAGAACTACACTTTGTGGCTTTCTGACCCAAACATTTTTATA
CTAAATTACACACAACAAAGTTGTAGCTCAGAGAGGGAACAAATGGCTTA
[C/T]TTAGGCCACCATTTTCTTGAGCCATTATGATTTCACACAGGGCTCCCT
TGGCCCTGTAAATTGGCAAGGATTCCATTATTCAACCCGCATACATGTACA
GAGACCCTGCTCTGGCCCAGATAGTATTCTGGGTACAGGCGGATAGAGCA
GGAAACAAAACAGCTACAGTGATGGACAGGTCAGCCTGCAGCAATGCC

FIG. 8.15

SG13S109
TTTTTATACTAAATTACACACAACAAAGTTGTAGCTCAGAGAGGGA
ACAAATGGCTTATTTAGGCCACCATTTTCTTGAGCCATTATGATTTCACAC
AGGGCTCCCTTGGCCCTGTAAATTGGCAAGGATTCCATTATTCAACCCGCA
TACATGTACAGAGACCCTGCTCTGGCCCAGATAGTATTCTGGGTACAGGC[
A/G]GATAGAGCAGGAAACAAAACAGCTACAGTGATGGACAGGTCAGCCT
GCAGCAATGCCTGCAGTCTCTGCAAAGGTAGCTGTATGGGTGGGCAGGTG
GCTAGCACTTATTCAGCTCTGGAAGGATCTCCCCTCTGGCCTCTCCCCTGA
CACCCATCAATAAAACTGAGGAGCATCGGTGGACAGGGGACCTTGTGCCC
SG13S110
TTTTCTTGAGCCATTATGATTTCACACAGGGCTCCCTTGGCCCTGTA
AATTGGCAAGGATTCCATTATTCAACCCGCATACATGTACAGAGACCCTG
CTCTGGCCCAGATAGTATTCTGGGTACAGGCGGATAGAGCAGGAAACAAA
ACAGCTACAGTGATGGACAGGTCAGCCTGCAGCAATGCCTGCAGTCTCTG
C[A/G]AAGGTAGCTGTATGGGTGGGCAGGTGGCTAGCACTTATTCAGCTCT
GGAAGGATCTCCCCTCTGGCCTCTCCCCTGACACCCATCAATAAAACTGA
GGAGCATCGGTGGACAGGGGACCTTGTGCCCCCTCCCTGCCTGTGCAGTT
GGGGCTGAACCCAGCTACGAAGTTTGAGCTCACTCTCTCCAGCTCCCTCTC
SG13S111
GACAGGTCAGCCTGCAGCAATGCCTGCAGTCTCTGCAAAGGTAGCT
GTATGGGTGGGCAGGTGGCTAGCACTTATTCAGCTCTGGAAGGATCTCCC
CTCTGGCCTCTCCCCTGACACCCATCAATAAAACTGAGGAGCATCGGTGG
ACAGGGGACCTTGTGCCCCCTCCCTGCCTGTGCAGTTGGGGCTGAACCCA
GC[C/T]ACGAAGTTTGAGCTCACTCTCTCCAGCTCCCTCTCAATTCAGAGCT
GAACTGTGGGAAGCTTCAGAGCTCTCTGTTTCAAGGACAGGTTCTCCTCAC
CTCTCCTAATGGAGGTGCACCAGGGAACTGGCCCTGCTCTGCCCAGGGCT
TTCTCCTGGACTTTGCCATCATGGTCTAGCAAACCCTGTTCAGATTGAGG
SG13S112
CACTCTCTCCAGCTCCCTCTCAATTCAGAGCTGAACTGTGGGAAGC
TTCAGAGCTCTCTGTTTCAAGGACAGGTTCTCCTCACCTCTCCTAATGGAG
GTGCACCAGGGAACTGGCCCTGCTCTGCCCAGGGCTTTCTCCTGGACTTTG
CCATCATGGTCTAGCAAACCCTGTTCAGATTGAGGTGAGTGGTGAGATTT[
C/T]GAATTCTTTTTGACAGATAGGATTAAGTCTTCTTCTGTGGGACAAGTG
GGAGGTAGAGGTAAGATTAAAGATGGCCAAATGTCTGAGTCCTGACAGCC
ACAATATGGAGATCTAGACTTTTTACAGACCACAGGGCACAGGGGCCTCA
CTAACAGAGTTCCCGGAAGTGATGAGTGTGCTGGGGGCTTCCTGGTTGA
SG13S113
TAGGATTAAGTCTTCTTCTGTGGGACAAGTGGGAGGTAGAGGTAAG
ATTAAAGATGGCCAAATGTCTGAGTCCTGACAGCCACAATATGGAGATCT
AGACTTTTTACAGACCACAGGGCACAGGGGCCTCACTAACAGAGTTCCCG
GAAGTGATGAGTGTGCTGGGGGCTTCCTGGTTGAAGAGACACTAGAATGG
AC[C/G]AGCTGGGAGCTAATTTTTGGGCTGGAGTGTGATGGCCTGCACAT
CACTGCCTCTGTCCCTCCATTGTCACAGCTGCCCCTTAGGAGCCAGCTGAG
GCAATTTGTGGTCAGAGTGACTTTGCACAGTTGTCCTGCCTGTGTTCAGGA
AGGGAGTTTCTGTGGTCCCTTTGAAACCACAGAAGAGCCCCTCGTATAGC
SG13S114
AGTTGTCCTGCCTGTGTTCAGGAAGGGAGTTTCTGTGGTCCCTTTGA
AACCACAGAAGAGCCCCTCGTATAGCTCTCAATGGAGGGGGCAAAACATT
CAAATAACTCAGGAGATAACACAACTATTTGTTTTTAACTGTGAGTTTTA
GGCAATCACAAAGATCCAGATGTATGTCCAAGCCTCTCTTTGCAATTCTA[

FIG. 8.16

A/T]TTAACCTCAATGTTGCAACCATAGACCTACCTTACAGAGTTCAAAAA
AATATGCAAAAACCCTGCCTTTCTTCTTCCTCATACCCCAAAATGCCATTC
TGAACATTTCCTGTTAGTTAAAAAAAGATTTCCATGGTGTTACCAGGCACT
GTACACAGTCTGTGTCCCAAGACAAGGAGGTACAGTTCCACATGCGCC

SG13S115

AGGGGGCAAAACATTCAAATAACTCAGGAGATAACACAACTATTT
GTTTTTAACTGTGAGTTTTAGGCAATCACAAAGATCCAGATGTATGTCCA
AGCCTCTCTTTGCAATTCTAATTAACCTCAATGTTGCAACCATAGACCTAC
CTTACAGAGTTCAAAAAAATATGCAAAAACCCTGCCTTTCTTCTTCCTCAT
[A/T]CCCCAAAATGCCATTCTGAACATTTCCTGTTAGTTAAAAAAAGATTT
CCATGGTGTTACCAGGCACTGTACACAGTCTGTGTCCCAAGACAAGGAGG
TACAGTTCCACATGCGCCCATGACTGGGTTGGGCTCTGCACTCTCTATA
CTTTGAGAGCCTGATTTTCTGTGATTGGGCAGAGCTGGCCCACCTGGTG

SG13S116

TCTGCACTCTCTCTATACTTTGAGAGCCTGATTTTCTGTGATTGGGC
AGAGCTGGCCCACCTGGTGCAATGTCCTCCTCTGCCTTTCAAACATGTTTT
AGTCATCAAGATCTTCAAATTTGTAACCCTTTCCAGCTTGATCCAGCAGAA
TGCAGATTTGGAAAAACAGAACGAGTTTAAAATACATGATTCTAAGAAA[
C/T]CTGGACCAGAACTATCAAAACTTGGTTTCCCAGAGAATATAGCAAAT
GGGCTCATTGGCCAATACTATGACATTGGCTTTTGAGAAAGAAAGGCTT
TATTGCAAGGCTGGCCAGCAAGGAGACAGGAGTTGGGCTCAAATCTGTCT
CCCCAGTTTGGGGCTTAGGGCAAGTTTTAATTACACAGACGCATTTCTTA

SG13S117

AACCCTTTCCAGCTTGATCCAGCAGAATGCAGATTTGGAAAAACAG
AACGAGTTTAAAATACATGATTCTAAGAAACCTGGACCAGAACTATCAAA
ACTTGGTTTCCCAGAGAATATAGCAAATGGGCTCATTGGCCAATACTATG
ACATTGGCTTTTGAGAAAGAAAGGCTTTATTGCAAGGCTGGCCAGCAAG
GA[A/G]ACAGGAGTTGGGCTCAAATCTGTCTCCCCAGTTTGGGGCTTAGGG
CAAGTTTTAATTACACAGACGCATTTCTTATGAGTAGCAGGCAGAGAGCC
TCCAACTTCTTCTGCCTAGGTACCAGCAGCTTAGACATGATGCAAACCTGG
GAAGCACATACTGTATTTGGAGAAAGTGATTGGGAAGAAATGTGAGCTGA
G

SG13S118

TACATGATTCTAAGAAACCTGGACCAGAACTATCAAAACTTGGTTT
CCCAGAGAATATAGCAAATGGGCTCATTGGCCAATACTATGACATTGGCT
TTTGAGAAAGAAAGGCTTTATTGCAAGGCTGGCCAGCAAGGAGACAGG
AGTTGGGCTCAAATCTGTCTCCCCAGTTTGGGGCTTAGGGCAAGTTTTAAT
TA[C/T]ACAGACGCATTTCTTATGAGTAGCAGGCAGAGAGCCTCCAACTTC
TTCTGCCTAGGTACCAGCAGCTTAGACATGATGCAAACCTGGGAAGCACA
TACTGTATTTGGAGAAAGTGATTGGGAAGAAATGTGAGCTGAGGGGAGG
GGCTCAGTGCCCCTGAGCTACACTTAGTGATGGCAGAGGAAGGATGTCCT
CCC

SG13S119

TGGGGCTTAGGGCAAGTTTTAATTACACAGACGCATTTCTTATGAG
TAGCAGGCAGAGAGCCTCCAACTTCTTCTGCCTAGGTACCAGCAGCTTAG
ACATGATGCAAACCTGGGAAGCACATACTGTATTTGGAGAAAGTGATTGG
GAAGAAATGTGAGCTGAGGGGAGGGGCTCAGTGCCCCTGAGCTACACTTA
GT[A/G]ATGGCAGAGGAAGGATGTCCTCCCGCAGGAGGCTGTTCCACATCT
GCTCTGGTTGTAGGGGAGCTGGCAGGCATTAGCAGCGGCCTCTTTCCCC
CAAGAGAGGCAGCCTCCTCCAAGTTTGGCGACATTATGGCCCTGCAATC

FIG. 8.17

ATAAGGGTTTGTGAGCATAGTGCTAAGGAGGGAAATGGAGCTGCTGTTAC
TA

SG13S120

CCTCCTGAGTAGCTAGGACTACAAGCATGTGCCACCACGCCCAGCT
AATTTTTGTATTTTTAGTAAGGACAGGGTTTCACCATGTTGGCCAGGTTGG
CCTCCAACTCCTGACCTCAAGTCATCCTCCTGCCTCGACCTCCCAAAGTGC
TGGGATTACAGGCATGAAACCAGCCTAGAAATACATACTATTATTTATTC[
C/T]TGTTTTACAGATAAGCAAAGTGAGTCATGGAGAATTTGGTTGAAAGT
CCCAAGGTCAGGAGTCGTGAAGCTGGGATTAAAACCTAATCATCTGACTT
TAGAGAGTAGACACTTGCTCCATGCATATTGCCTCCAATTCATTCATTCAA
GCACTCCTGCTCAAGAAGTTCTTTCTTATGTTGAGCTGAAATCTGCAG

SG13S121

TCATCTGACTTTAGAGAGTAGACACTTGCTCCATGCATATTGCCTCC
AATTCATTCATTCAAGCACTCCCTGCTCAAGAAGTTCTTTCTTATGTTGAG
CTGAAATCTGCAGCCCTATGCGTTTTACCCAGCAGTCCTGGTGCTGTTCCC
TAAAATCACTTAGACTGTGCCTGCTCTTTCTGTGTTTACAGTGTCAGCT[A/
G]TAATATCCCCCTCTTCGGCCTAACGTTTCTGAAGTCCCTTGCCACTGGGT
CTCCTCTCCTCTTCCTGTGTTCTTTCTAAGAACACCTATGCAGATAGGTGTC
TTCTGTACAGGGAAGCTGTTCCTGAGATCCGGGCATCGACTCTGTTAGAAT
AATCTACGTATGAGTTATTTTTTGAGAACTATGTGTCATTGCT

SG13S122

ATGTTGAGCTGAAATCTGCAGCCCTATGCGTTTTACCCAGCAGTCC
TGGTGCTGTTCCCTAAAATCACTTAGACTGTGCCTGCTCTTTCTGTGTTTAC
AGTGTCAGCTGTAATATCCCCCTCTTCGGCCTAACGTTTCTGAAGTCCCTT
GCCACTGGGTCTCCTCTCCTCTTCCTGTGTTCTTTCTAAGAACACCTAT[A/G
]CAGATAGGTGTCTTCTGTACAGGGAAGCTGTTCCTGAGATCCGGGCATCG
ACTCTGTTAGAATAATCTACGTATGAGTTATTTTTTGAGAACTATGTGTC
ATTGCTGACTCATATTAACTCTGTGGTTAACTAAAATCTCAAGATCTCTTT
ATGTTTGTTGAGAAACTTATTTAACTTCTCTGGCCCTCCGTTTCC

SG13S123

GTCCTGGTGCTGTTCCCTAAAATCACTTAGACTGTGCCTGCTCTTTC
TGTGTTTACAGTGTCAGCTGTAATATCCCCCTCTTCGGCCTAACGTTTCTG
AAGTCCCTTGCCACTGGGTCTCCTCTCCTCTTCCTGTGTTCTTTCTAAGAAC
ACCTATGCAGATAGGTGTCTTCTGTACAGGGAAGCTGTTCCTGAGATC[C/T
]GGGCATCGACTCTGTTAGAATAATCTACGTATGAGTTATTTTTTGAGAA
CTATGTGTCATTGCTGACTCATATTAACTCTGTGGTTAACTAAAATCTCAA
GATCTCTTTATGTTTGTTGAGAAACTTATTTAACTTCTCTGGCCCTCCGTTT
CCTTCACTGAGCAGTGGAGTGATTGATAACCTCCACCTGTGGTT

SG13S43

CACCTATGCAGATAGGTGTCTTCTGTACAGGGAAGCTGTTCCTGAG
ATCCGGGCATCGACTCTGTTAGAATAATCTACGTATGAGTTATTTTTTGA
GAACTATGTGTCATTGCTGACTCATATTAACTCTGTGGTTAACTAAAATCT
CAAGATCTCTTTATGTTTGTTGAGAAACTTATTTAACTTCTCTGGCCCTC[A/
C]GTTTCCTTCACTGAGCAGTGGAGTGATTGATAACCTCCACCTGTGGTTG
CTGAAGGTCTTGCACAAGATGATATAGTTAAAGTAGCTAGCAGTGCCCAC
GTACGGCGGATGCCTCACAACGGTTTGCAGCCATCTCTCTATCTGTGTCTT
TGTCTCTCTCTCACACTGGTTTTGGCTTACTGTTAGCAGCTAGCCGA

SG13S399

TCTGTGGTTAACTAAAATCTCAAGATCTCTTTATGTTTGTTGAGAAA
CTTATTTAACTTCTCTGGCCCTCCGTTTCCTTCACTGAGCAGTGGAGTGATT

FIG. 8.18

GATAACCTCCACCTGTGGTTGCTGAAGGTCTTGCACAAGATGATATAGTT
AAAGTAGCTAGCAGTGCCCACGTACGGCGGATGCCTCACAACGGTTTGC[
A/C]GCCATCTCTCTATCTGTGTCTTTGTCTCTCTCTCACACTGGTTTTGGCT
TACTGTTAGCAGCTAGCCGAGATAAGTGTGTTTATGGTCTTTGCATGTATT
GTTTCTGTAGCATACTGGAGGATTACAAGAGGTTGGGGAGTGAGGGGGCG
GTGAGGAGTAGACAAAGGCAGCCAACTCTTCCAAGTTTAGCTTAGAA

SG13S124

TTGATAACCTCCACCTGTGGTTGCTGAAGGTCTTGCACAAGATGAT
ATAGTTAAAGTAGCTAGCAGTGCCCACGTACGGCGGATGCCTCACAACGG
TTTGCAGCCATCTCTCTATCTGTGTCTTTGTCTCTCTCTCACACTGGTTTTG
GCTTACTGTTAGCAGCTAGCCGAGATAAGTGTGTTTATGGTCTTTGCATG[
C/T]ATTGTTTCTGTAGCATACTGGAGGATTACAAGAGGTTGGGGAGTGAG
GGGGCGGTGAGGAGTAGACAAAGGCAGCCAACTCTTCCAAGTTTAGCTTA
GAAGGAAGGAGCGGTAAACCCTAGTTGAATGTTGGACTGAAGCAGGTTTG
TTTTTGTTTTGTTTAAAGGATAGGGAAGATCTGTGCGTGTTTCCAGGATA

SG13S125

ACTTGAAGTCAGTGGCATGGACAGGGTCAAGATCACAGTTAGAGG
ATGCAGCCTTAGAGAAAAGGAAGGGGCTCGGTTCTCTGAGCAAGGAGGG
AAAGAAGAGAGGCAGATGCAGAGAAGTACGGCACATCGTGCTGCTGGTT
GTAGAAATAACCTCTGACTTTTAATAAAGTCATCCCTCGGTATCCCTGGGG
GATT[A/G]GTTCTATGACCTCCCTCGGATGCCAAAATTCGTGGATGCTCAA
GTCCCTGATATAAATGGCATAGTATTTGCATTTAACCTACACACATCCTC
CATATCCTTTTTTTTTTTTTTTTTTTTTTTTTTTTTTTTGTGAGATGGAGT
CTTGCTCTGTCGCCCTGGCTGGAGTACAGTGGCTCGATCTTGGCTCACT

SG13S400

AATACCTGATAGAATGTAAATGCTATGTAAACAGTTGTTATACTGT
ATTGTTAAAAGACAGTAACAAGAAAAAAATCTGTACATGTTCAGTCCAG
ACAAATGGTTTTCTGTTTTTTTTTTTTTTTTTAATATTTTTGGTCAGTGGTT
GGTTGACTCCAGGAATGCAGAACCCGCAGATATAGAAGGTTGATTATGC[
A/G]TTCAGAGGCAGGGAATACCATCTTGGGTTCCAGAAAGAAAATGATCA
GCATTTTCTGTCATACTCTGGTAAAAACAGATCTTTTGAATGGACAGGTGT
ATTAAACCCTGTGGAGCTGGCTGGGCCTGGCGGCTCACGCCTGTAATCCC
AGCACTTTGGGAGGCTGAGGCAGGTGGATCACGAGGTCAGGAGTTCGAG

SG13S126

TGCCCCGCAGAGTTTGAAGTCCCGGCTGCACCTCTCCCCAGCAGCA
GGTTGACTCTGGAAAGTTGCAGCGTTCTTACCTACAGAGTGGGAACAGTA
CTACCCATTGCACAGAGTGGGTGCAAAGCTCTGTGACGGAATACATGGCA
AGTGCCCACCACATTGCCTGGGATGAGGTGGGCCCTTCCTTTACGTAAGA
GA[A/G]CCCTACAGATACACTCAAAGTGGGCACATTCCTACAGAAGGAGT
GTTATTTGTGTAGAAAGAAAAACATGAAAGGCTTTTATTCCTATACACA
ATAAAGCACCCCTTTAATGTCTTTTTGAGGAGGATAATATGAAATTGATGA
AAAGGAACCCTGTGGTTGGATCCCTGACAATCACATGTATCCCTTTTTTCA
C

SG13S127

TACAGATACACTCAAAGTGGGCACATTCCTACAGAAGGAGTGTTAT
TTGTGTAGAAAAGAAAAACATGAAAGGCTTTTATTCCTATACACAATAAA
GCACCCCTTTAATGTCTTTTTGAGGAGGATAATATGAAATTGATGAAAAG
GAACCCTGTGGTTGGATCCCTGACAATCACATGTATCCCTTTTTTCACTCT
T[A/G]AAAAAGGAGTAAAGGAATAAAATAGAANNNNNNNNNNNNNNNNN
NNNNNNNNNNNNNNNNNNNNNNNNNNNNNNNNNNNNNNNN

FIG. 8.19

NNNNNNNNNNNNNNNNNNNNNNNNNNNNNNNNNNNNNNNATGTTTCAGTCA
CTGTATAATAACTAGCCAGATTTTTGTTGTTGTTGTTTTGTTTTGTTTTG
TTTTT
SG13S128
      ACATTCTGAACCACAGACAGTTCTTTACCCTGAACCTTTGCATATTT
TGTTCTCTTAGCTTAGAGCGGCCCCTCTCCCTCCGTCTGCTTGGCTAATTTC
TACTTGTTCTTCAGATTTTATCTTAGATGTCATTCCCTCAAGGAATCCTTCT
GTGACTCAACATGGAATTAAGTTGCCTCCTTTGACCCTGAAAGCACC[A/G]
TGTACTCAATCTCATCTTGGCATGACTCACTTTGCTGTGTGGAATGTCTGC
TTTCCTTGTTTGTCTATTCCTTTAGACTGTAAGATCCTAGAAAGTGGGGGC
CGTGCCTTGCTCATGACTGTGTTTCTAACACCAAACACAGTGTTCAGTAGA
GAGCAGCTGCTGAGTACGTTTCTGCTAAATGACAGTTGATGGAG
SG13S129
      AATCCTTCTGTGACTCAACATGGAATTAAGTTGCCTCCTTTGACCCT
GAAAGCACCATGTACTCAATCTCATCTTGGCATGACTCACTTTGCTGTGTG
GAATGTCTGCTTTCCTTGTTTGTCTATTCCTTTAGACTGTAAGATCCTAGAA
AGTGGGGGCCGTGCCTTGCTCATGACTGTGTTTCTAACACCAAACACA[A/
G]TGTTCAGTAGAGAGCAGCTGCTGAGTACGTTTCTGCTAAATGACAGTTG
ATGGAGGACATTTAGGGTTGCTTGGAGGTCAAGTCAAGGAGGCATTTAAC
ATTCTAGTAAAACAAGGAAGTAACAGGCTCCTGAACATGCCCACAATGAA
CCAGATGCAAACCTTTTCCCTTGGCAGGATTCTTTGCCCATAAAGTGG
SG13S130
      AAAGCACCATGTACTCAATCTCATCTTGGCATGACTCACTTTGCTGT
GTGGAATGTCTGCTTTCCTTGTTTGTCTATTCCTTTAGACTGTAAGATCCTA
GAAAGTGGGGGCCGTGCCTTGCTCATGACTGTGTTTCTAACACCAAACAC
AGTGTTCAGTAGAGAGCAGCTGCTGAGTACGTTTCTGCTAAATGACAGT[G
/T]GATGGAGGACATTTAGGGTTGCTTGGAGGTCAAGTCAAGGAGGCATTT
AACATTCTAGTAAAACAAGGAAGTAACAGGCTCCTGAACATGCCCACAAT
GAACCAGATGCAAACCTTTTCCCTTGGCAGGATTCTTTGCCCATAAAGTGG
AGCACGAAAGCAGGACCCAGAATGGGAGGAGCTTCCAGAGGACCGGAA
SG13S190
      TTCTGCTAAATGACAGTTGATGGAGGACATTTAGGGTTGCTTGGAG
GTCAAGTCAAGGAGGCATTTAACATTCTAGTAAAACAAGGAAGTAACAG
GCTCCTGAACATGCCCACAATGAACCAGATGCAAACCTTTTCCCTTGGCA
GGATTCTTTGCCCATAAAGTGGAGCACGAAAGCAGGACCCAGAATGGGA
GGAG[C/T]TTCCAGAGGACCGGAACACTTGCCTTTGAGCGGGTCTACACTG
CCAAGTGAGTCCTAACCCTGATGTTGCTAATAAGTGGGGGCATGGGCAGG
GGGGCCTCCTTCTAGGAGTGATGACCACCCTTAATACCACATGTCTGTCTG
AGCCAAGTTTCTGAGCGCCAGGGAGGTGAGGAAGGTTGGACTTCACCAGA
GAG
SG13S192
      GGCATTTAACATTCTAGTAAAACAAGGAAGTAACAGGCTCCTGAA
CATGCCCACAATGAACCAGATGCAAACCTTTTCCCTTGGCAGGATTCTTTG
CCCATAAAGTGGAGCACGAAAGCAGGACCCAGAATGGGAGGAGCTTCCA
GAGGACCGGAACACTTGCCTTTGAGCGGGTCTACACTGCCAAGTGAGTCC
TAA[A/C]CCTGATGTTGCTAATAAGTGGGGGCATGGGCAGGGGGGCCTCCT
TCTAGGAGTGATGACCACCCTTAATACCACATGTCTGTCTGAGCCAAGTTT
CTGAGCGCCAGGGAGGTGAGGAAGGTTGGACTTCACCAGAGAGGCTTTGT
GGACACCCTTTATCATCTTAGTGAGTGCTAGTGTCAAAACAAAGGGAGTG
GG

GCTCCTGAACATGCCCACAATGAACCAGATGCAAACCTTTTCCCTT
GGCAGGATTCTTTGCCCATAAAGTGGAGCACGAAAGCAGGACCCAGAAT
GGGAGGAGCTTCCAGAGGACCGGAACACTTGCCTTTGAGCGGGTCTACAC
TGCCAAGTGAGTCCTAACCCTGATGTTGCTAATAAGTGGGGGCATGGGCA
GGG[A/G]GGCCTCCTTCTAGGAGTGATGACCACCCTTAATACCACATGTCT
GTCTGAGCCAAGTTTCTGAGCGCCAGGGAGGTGAGGAAGGTTGGACTTCA
CCAGAGAGGCTTTGTGGACACCCTTTATCATCTTAGTGAGTGCTAGTGTCA
AAACAAAGGGAGTGGGGATATGGGGCACATTGGTGGAGGGAGGTGTGATCTC

SG13S88

TTGCCCATAAAGTGGAGCACGAAAGCAGGACCCAGAATGGGAGGA
GCTTCCAGAGGACCGGAACACTTGCCTTTGAGCGGGTCTACACTGCCAAG
TGAGTCCTAACCCTGATGTTGCTAATAAGTGGGGGCATGGGCAGGGGGGC
CTCCTTCTAGGAGTGATGACCACCCTTAATACCACATGTCTGTCTGAGCCA
AG[C/T]TTCTGAGCGCCAGGGAGGTGAGGAAGGTTGGACTTCACCAGAGA
GGCTTTGTGGACACCCTTTATCATCTTAGTGAGTGCTAGTGTCAAAACAAA
GGGAGTGGGGATATGGGGCACATTGGTGGAGGGAGGTGTGATCTCTGCAG
CTTCAGAAAGATCTGAAAGAGTCATTTGGTTAGAGAAGTTGACCTATTTCCT

SG13S131

AAACAAAGGGAGTGGGGATATGGGGCACATTGGTGGAGGGAGGTG
TGATCTCTGCAGCTTCAGAAAGATCTGAAAGAGTCATTTGGTTAGAGAAG
TTGACCTATTTCCTGTGGGGTTAGACCAGGGTTGCTACTGTGAACACCAGC
CATGACTCACCAGTCACCTTCAGAAGCCACAGGCAGGACATGCTGACGAC
AG[C/T]CTTCAACTCACCCACCCCTTGCTCCCCTGCGGGTGGAAGTCTGGA
GGTGACACCACTGCATTTCTAACACGGGGCTCCTTGAGCAACTAGAAC
AAGAACAGAAAGAATGGGGACATTAGCAGGTGCTTTCCCCCTCTCTCATT
CTTTTCTTTGAATAAAAGGTTGTTTGAAAACACCTGAGCGGCTCCTAAAGA

SG13S132

CTCCTCTCTTCTTTATGCAGAGTGTATTTCAAGGCTCAGCCAGTGGC
AGGCATGCTGGGGACTATGGACTACGGACTAGGGGCCTGTCACAGAGGA
AGGCCTCATGCTAGAGAGCTAAGGGAGGAGCTGGCCTTCAGTTCCATCCC
AGGAGCAACTTTGATGTTCCCAGAGATCCTTCCAAAGGGGGAGTCATGGT
CA[A/C]CCAAGAAAATGTATTCAGAATGCCAAGAATGGTGCAAACTCAG
GACAAAGATTCACACTGCAGGGTTGGAGTCCCTGGGCTTGCTGCTGGCAC
CATGGGAGGGAGGGTCCCCTTCAGGGGTACCGTTGGTTTCCTGTGAATTA
AACTGGCTTCAAGGGATCTCGACTGAACAGGCCTATATCACACTCACTGATAT

SG13S133

TCTCCTCATCTAGGTATTTTTAATTGTTTCAGTGAGGTGTAGGCATG
AGGGGATTGGAGGGGGCATCTCCTCCATTGCAGTTTTTCATTGGCTGCTTT
GCTCCCTCAGCTCCGAAATCGCTGGGCCACTCTCGAACGCATTAGTACGG
TAGTCACAGGTTGATTGCCTGGCCCCTTGCCCTCTGTGGGCATTTTCCCT[C/T]TCAGACAGCCCCTGAGTACTCACAGTGCTGCTACAGTGGGCCACCTAG
ATCTCCCTCTTTCTCCATGCTCCCACGTGCTCTGGGCTCCACTCCCTTCTCC
CAAGCACTTCTGTCCAGGGCTATTCCAGCAGTCTGACCTCAAGGAAATCC
TTTGCTAAACTGATTATAGAGAGGTTTCTATTTTAACATTTAGGTCT

FIG. 8.21

SG13S38
ATCTAGGTATTTTTAATTGTTTCAGTGAGGTGTAGGCATGAGGGGA
TTGGAGGGGGCATCTCCTCCATTGCAGTTTTTCATTGGCTGCTTTGCTCCCT
CAGCTCCGAAATCGCTGGGCCACTCTCGAACGCATTAGTACGGTAGTCAC
AGGTTGATTGCCTGGCCCCTTGCCCTCTGTGGGCATTTTCCCTTTCAGAC[A
/T]GCCCCTGAGTACTCACAGTGCTGCTACAGTGGGCCACCTAGATCTCCCT
CTTTCTCCATGCTCCCACGTGCTCTGGGCTCCACTCCCTTCTCCCAAGCACT
TCTGTCCAGGGCTATTCCAGCAGTCTGACCTCAAGGAAATCCTTTGCTAAA
CTGATTATAGAGAGGTTTCTATTTTAACATTTAGGTCTTCCATGT
SG13S134
AGGTGTAGGCATGAGGGGATTGGAGGGGGCATCTCCTCCATTGCA
GTTTTTCATTGGCTGCTTTGCTCCCTCAGCTCCGAAATCGCTGGGCCACTC
TCGAACGCATTAGTACGGTAGTCACAGGTTGATTGCCTGGCCCCTTGCCCT
CTGTGGGCATTTTCCCTTTCAGACAGCCCCTGAGTACTCACAGTGCTGCTA
[C/T]AGTGGGCCACCTAGATCTCCCTCTTTCTCCATGCTCCCACGTGCTCTG
GGCTCCACTCCCTTCTCCCAAGCACTTCTGTCCAGGGCTATTCCAGCAGTC
TGACCTCAAGGAAATCCTTTGCTAAACTGATTATAGAGAGGTTTCTATTTT
AACATTTAGGTCTTCCATGTATTAATTCTCAGAATCAATTTAAGATG
SG13S135
CCTTTCAGACAGCCCCTGAGTACTCACAGTGCTGCTACAGTGGGCC
ACCTAGATCTCCCTCTTTCTCCATGCTCCCACGTGCTCTGGGCTCCACTCCC
TTCTCCCAAGCACTTCTGTCCAGGGCTATTCCAGCAGTCTGACCTCAAGGA
AATCCTTTGCTAAACTGATTATAGAGAGGTTTCTATTTTAACATTTAGG[C/
T]CTTCCATGTATTAATTCTCAGAATCAATTTAAGATGTTTAAAGGTGTGAT
TTAAGACATTTTAAAACCATTTGGAGGAGAGTACAGAAATTATGTCACTT
GCTGTCAGCCTCTTTGCACCATCTGCAGAGAAAGATACTAGAGTCCCGCC
TTGGACACATCCACATGCAAGAGGTGCAAAGAAGGTGTCTTTGATGA
SG13S136
TTCTCAGAATCAATTTAAGATGTTTAAAGGTGTGATTTAAGACATTT
TAAAACCATTTGGAGGAGAGTACAGAAATTATGTCACTTGCTGTCAGCCT
CTTTGCACCATCTGCAGAGAAAGATACTAGAGTCCCGCCTTGGACACATC
CACATGCAAGAGGTGCAAAGAAGGTGTCTTTGATGAGGCAAGGTCAAAA
CT[C/T]CTCCCCAGACGAAATCCAAAGAAAGCATTCCTACTATGCTATATC
AGTTTGGAAAGAAAAACTTCTGCCAGGTGACTGCATTCTCACTGGTCACA
TTGTGTTCCTATGGACTCCTCAGCTCAACCAATTTGGAGAAGTTATGGTGC
AATTTCACCATATCTGGTTAGAAGTTAAGTTTCCAATTTGCTGGCAATGAA
SG13S137
AAGAAGGTGTCTTTGATGAGGCAAGGTCAAAACTTCTCCCCAGACG
AAATCCAAAGAAAGCATTCCTACTATGCTATATCAGTTTGGAAAGAAAAA
CTTCTGCCAGGTGACTGCATTCTCACTGGTCACATTGTGTTCCTATGGACT
CCTCAGCTCAACCAATTTGGAGAAGTTATGGTGCAATTTCACCATATCTGG
[C/T]TAGAAGTTAAGTTTCCAATTTGCTGGCAATGAAGAAGAAATGGAGCA
GGCCAGGCTGTGTAGTTTCTGCCACGTGCCCCCGGGAGTGAACAGCTCTG
TTTGTAAGAAGCCATGGTGCTTAGACCTGGGCTCGCTAGTTGCCAGCCTCC
AAAATTGCAGAAGTGCCCTTTGGTTGGTGGCTATGCTGTGTCACTTGGGA
SG13S86
GCAACATATCTGTGTGCCTGTCTGGGTTGTAAAAGGGTCAAAGAT
CAATGCAGCAGGCAGCTACATGCTGGCAAAAGCCAGAGGCAGCTGGTCT
GTTTGCCTGTGCCAGGAAACCACTGGGAATGGGGTTGTGTGTTATTCTAGG
AGAAAGTCGTCCCAGCAGCAGCTTCTCCAGGGGCATCCAAGAGCACTGAA

FIG. 8.22

AA[A/G]GGTTGCAAGATGACCCATGAGGCTGCAGGAAGAAAAGAACATGC
ATTTAATCTTGCTATCTGAAAAGTAAGACATGAAGCTTTCCTCATTTTTAA
TATACACATGGACAGTAGTATGTGTATATAGTTTATATGCAAATATACTTG
TTATAAGGTTGCATGCTCAAAATTTTTGGTTCATGGGGTGTGGGATCATAA

SG13S87

CAGCTACATGCTGGCAAAAGCCAGAGGCAGCTGGTCTGTTTGCCTG
TGCCAGGAAACCACTGGGAATGGGGTTGTGTGTTATTCTAGGAGAAAGTC
GTCCCAGCAGCAGCTTCCAGGGGCATCCAAGAGCACTGAAAAGGGTTG
CAAGATGACCCATGAGGCTGCAGGAAGAAAAGAACATGCATTTAATCTTG
CT[A/G]TCTGAAAAGTAAGACATGAAGCTTTCCTCATTTTTAATATACACA
TGGACAGTAGTATGTGTATATAGTTTATATGCAAATATACTTGTTATAAGG
TTGCATGCTCAAAATTTTTGGTTCATGGGGTGTGGGATCATAAATGTTTAG
GGACCATGGCTATCAAGGAAAAACAGCATGAAGGATAAATGATACTGGT
G

SG13S138

CTATCTGAAAAGTAAGACATGAAGCTTTCCTCATTTTTAATATACA
CATGGACAGTAGTATGTGTATATAGTTTATATGCAAATATACTTGTTATAA
GGTTGCATGCTCAAAATTTTTGGTTCATGGGGTGTGGGATCATAAATGTTT
AGGGACCATGGCTATCAAGGAAAAACAGCATGAAGGATAAATGATACTG
G[C/T]GGATTAAAAAGACAGATGCATGTATTTTAGCATAAAACACAACTG
CTGACTGATACAGATAGCTCAAGATTCTGGGGCAGCTGCTGAACAGATAC
ACTAGCCAGTGTGGCTCATCGGCTCAGACTTGGCCTTAATTAATGGGCTGT
CCCTCCACCCATCTCCCATGAGGGCAGAGCTGAGCCAGGGTTTGAGAGCT

SG13S139

AGTTTATATGCAAATATACTTGTTATAAGGTTGCATGCTCAAAATTT
TTGGTTCATGGGGTGTGGGATCATAAATGTTTAGGGACCATGGCTATCAA
GGAAAAACAGCATGAAGGATAAATGATACTGGTGGATTAAAAAGACAGA
TGCATGTATTTTAGCATAAAACACAACTGCTGACTGATACAGATAGCTC
AA[C/G]ATTCTGGGGCAGCTGCTGAACAGATACACTAGCCAGTGTGGCTCA
TCGGCTCAGACTTGGCCTTAATTAATGGGCTGTCCCTCCACCCATCTCCCA
TGAGGGCAGAGCTGAGCCAGGGTTTGAGAGCTAAAAGGAATTGGACCTG
GACTCTGTTCACGTGTATATTTTAATTCTAATTAATTCATTCTTTTGAAAGA

SG13S140

GTATTTTAGCATAAAACACAACTGCTGACTGATACAGATAGCTCA
AGATTCTGGGGCAGCTGCTGAACAGATACACTAGCCAGTGTGGCTCATCG
GCTCAGACTTGGCCTTAATTAATGGGCTGTCCCTCCACCCATCTCCCATGA
GGGCAGAGCTGAGCCAGGGTTTGAGAGCTAAAAGGAATTGGACCTGGAC
TC[A/G/T]GTTCACGTGTATATTTTAATTCTAATTAATTCATTCTTTTGAAAG
ACAGAGTCACACTCTGTTGCCTAGGCTGGAGTGCAGTGGCACGATCTTGG
CTCACTGCAACCTCGGCCTCCCAGGTTCAAGTTATTCCTGCTTCAGCCT
CCTGAGTAGCTGGGATTATAGGCACATGCCCCATGCCTGACTAATTTT

SG13S141

GCTAAAAGGAATTGGACCTGGACTCTGTTCACGTGTATATTTTAAT
TCTAATTAATTCATTCTTTTGAAAGACAGAGTCACACTCTGTTGCCTAGGC
TGGAGTGCAGTGGCACGATCTTGGCTCACTGCAACCTCGGCCTCCCAGGT
TCAAGTTATTCCTGCTTCAGCCTCCTGAGTAGCTGGGATTATAGGCACA
[C/T]GCCCCATGCCTGACTAATTTTGTATTTTAGTAGAGACGGGGTTTC
ACCATGTCAGGCTGGTCTTGAACTCCTGACCTCAGGTTATCCACCCGCCTT
GGCCCCTCAAAGTGTTGGAATTACAGGTGTGAGCCACCGTGCCTGGCCTG
TTCACATGTATAAAACACAGTTTAATGTCCTATTCCCAGCCAATGAGC

FIG. 8.23

SG13S39
TCAGGTTATCCACCCGCCTTGGCCCCTCAAAGTGTTGGAATTACAG
GTGTGAGCCACCGTGCCTGGCCTGTTCACATGTATAAAACACAGTTTAAT
GTCCTATTCCCAGCCAATGAGCATGGCTAGAGCAGCCTTGGTCAAAGTTT
GGTTTTTGGAGAAAAATCCTTGTTAGCTGACCTAAGATTCCTCTTTGTGAG
T[G/T]TAAGTAAGCACAGGTTGCAGAGAGGAGAAGGGTCTCTGGAGAGGT
GTAATTTTCTAAATGGATTACAAGTTCATGGACTTTTAACAGGTGTTACAG
GGGATAACAAGTTCTTTATAGACAGACTTTTGAGGACGTTTAAGGGTATTC
TGATTCTTGGTTTTCTAAGAGGGGAATGTATTATTTAACTACAGACACCC

SG13S142
AAAATCCAGAATAATAATAATTTGTCAATAGGAAAGACATTTCCAC
TGGGGGTTAAGAAGGAAGACATTGGAACAATGATAGCCACCACTTATTGA
ATGCTTACTGTGAGCCAGGTGGCACTTCACCTTGTTTCATTCTCACAACAG
TCTAGGGAAGTAATTACTAATGTCTCCATCCACCTCTTGTAGATGAGCAAA
[C/T]TGAGGCTCATTGAGGCTAGGAAATGCACCCACACTCACATAGCCCAT
AAGAGGCAGCCATGGCATTGGGCCCAGACCATGTGAACTTCAAAGACTAC
ACGAGCAGCCACTGGGCAGCTGTCATGGCTAAAGCCACTTGAATTCAGCC
CAGCAGCAACCCCCTCTCCAGGAGGGGCACATAAGCTTGCAGCTTTGGGT

SG13S143
ATAATAATAATTTGTCAATAGGAAAGACATTTCCACTGGGGGTTAA
GAAGGAAGACATTGGAACAATGATAGCCACCACTTATTGAATGCTTACTG
TGAGCCAGGTGGCACTTCACCTTGTTTCATTCTCACAACAGTCTAGGGAAG
TAATTACTAATGTCTCCATCCACCTCTTGTAGATGAGCAAACTGAGGCTCA
[C/T]TGAGGCTAGGAAATGCACCCACACTCACATAGCCCATAAGAGGCAG
CCATGGCATTGGGCCCAGACCATGTGAACTTCAAAGACTACACGAGCAGC
CACTGGGCAGCTGTCATGGCTAAAGCCACTTGAATTCAGCCCAGCAGCAA
CCCCCTCTCCAGGAGGGGCACATAAGCTTGCAGCTTTGGGTAGAAGCTGC
A

SG13S144
GCACTTGAAGTCCTGGATGGCGAGAGGGACTGGCTTGAGCCAGAG
CCAGGAACAAGGCTCTGAGAATATTCTGGAAATCCACAGGAGGAACCCAT
TTTCTTACAGCTGGGAGAATTTCATTCAACTCCAGGCTGACCATGTTTTAT
TAGGAACGAAGGTGACTTGAACTAATAGTCAGGAATGGTTGAATACGGAC
CC[A/G]ATGTCAAATCACTAGGCAGTTCACATTTCTAATGAGCAAATCCCT
TAGACAATTAAGAATTTTTTCCTTTTGCATAACCCAGACAAAATCGCTAC
TTAAAAACAAACCAAAGACCCGAAACATGAGAAAGAGAAGGAAGCAGG
GGAAATCTTTGGTACTAATAAGTTTTAAACAATAAGAGCACCAGATATTT
TA

SG13S145
ATGAGCAAATCCCTTAGACAATTAAGAATTTTTTCCTTTTGCATAA
CCCAGACAAAATCGCTACTTAAAAACAAACCAAAGACCCGAAACATGAG
AAAGAGAAGGAAGCAGGGGAAATCTTTGGTACTAATAAGTTTTAAACAA
TAAGAGCACCAGATATTTTACCCCATCAGACACAGAATGTTATTCGAATA
AC[C/G]AAAAAAGGAATTTTTTCTCTAAGTTTCTTGAACTGGAAAATGAAT
CATATTTTCTCAGTCCTGAGGCTGCAATTTGTGCCTCTAGTAACATATAA
GAATAGATGTGATGCCAGTGCCCAGTAGCTGCTGCAATTGTTACTTGGGG
ACCTGTTTATTCACTAAGCACTTCACCCCAGTGATAAATTTGTAGGGGCCT

SG13S146
CCGTGTCCATTAGATCAGTGGAAATTCTGGGATTCAGAGCACTTTG
CAAGGTCAGCAGGGGTCTGCTCTTTCTGTCCTGTTCCTGGTTTTTGGTTGTG

FIG. 8.24

CCTGGATTCCAGGGTAGGTTTCTCATCTGTTACCTTCATAGACTTCTCCAG
AAAAGGATCTTTTGACCATCAGAGGACCACGAAGATTCCATTGGTGAGG[
C/T]GCAGATAACCTGATCTCTCTGGGTTCTCTGCAGGGCACAGATGAAGG
GCTGGCCATTCCCAAGTTCTCAGTGGTACCACTGAGGCATGAGACCCTAA
TGGTTTGCATGAGCAGTTTGAAAATTGCATCTTTGTTTTTACCTATATAATC
ACATGAAACCCGTGGTTCTCAAACGTCAGCAGGCATCAGCATCACATG
SG13S26

TCAGTGGTACCACTGAGGCATGAGACCCTAATGGTTTGCATGAGCA
GTTTGAAAATTGCATCTTTGTTTTTACCTATATAATCACATGAAACCCGTG
GTTCTCAAACGTCAGCAGGCATCAGCATCACATGGAGGGCTTGTTAAAAC
AGATTTCTGGGCCCCAACACAGAGTTTTAAATTCTGAAGGCCTGAGGTGG
G[C/T]GTGAACATTTGCATTTCTAACATGTTCTCGATGCTGCTGCCGCCTCT
GGTCCCGAGAGCATGCCTGGAGAACTGCCACCTTCGACCATGGACTGTGA
GAATTCACATGGACCTCAGAATTATAATCAGTCTCTCAGTTTTACAGATAA
GGAAACTAAATCCAGAGAGATTGTTTTGCCAATGGTGAACAGCTGGTTA
SG13S27

ATGGTTTGCATGAGCAGTTTGAAAATTGCATCTTTGTTTTTACCTAT
ATAATCACATGAAACCCGTGGTTCTCAAACGTCAGCAGGCATCAGCATCA
CATGGAGGGCTTGTTAAAACAGATTTCTGGGCCCCAACACAGAGTTTTAA
ATTCTGAAGGCCTGAGGTGGGTGTGAACATTTGCATTTCTAACATGTTCTC
[A/G]ATGCTGCTGCCGCCTCTGGTCCCGAGAGCATGCCTGGAGAACTGCCA
CCTTCGACCATGGACTGTGAGAATTCACATGGACCTCAGAATTATAATCA
GTCTCTCAGTTTTACAGATAAGGAAACTAAATCCAGAGAGATTGTTTTGCC
AATGGTGAACAGCTGGTTAAAGTCAGGATGGAGACTTTAATCCTAGTCA
SG13S147

GAGCAGTTTGAAAATTGCATCTTTGTTTTTACCTATATAATCACATG
AAACCCGTGGTTCTCAAACGTCAGCAGGCATCAGCATCACATGGAGGGCT
TGTTAAAACAGATTTCTGGGCCCCAACACAGAGTTTTAAATTCTGAAGGC
CTGAGGTGGGTGTGAACATTTGCATTTCTAACATGTTCTCGATGCTGCTGC[
C/T]GCCTCTGGTCCCGAGAGCATGCCTGGAGAACTGCCACCTTCGACCAT
GGACTGTGAGAATTCACATGGACCTCAGAATTATAATCAGTCTCTCAGTTT
TACAGATAAGGAAACTAAATCCAGAGAGATTGTTTTGCCAATGGTGAACA
GCTGGTTAAAGTCAGGATGGAGACTTTAATCCTAGTCAAGTGACCTTTC
SG13S28

AGTTTGAAAATTGCATCTTTGTTTTTACCTATATAATCACATGAAAC
CCGTGGTTCTCAAACGTCAGCAGGCATCAGCATCACATGGAGGGCTTGTT
AAAACAGATTTCTGGGCCCCAACACAGAGTTTTAAATTCTGAAGGCCTGA
GGTGGGTGTGAACATTTGCATTTCTAACATGTTCTCGATGCTGCTGCCGCC
[G/T]CTGGTCCCGAGAGCATGCCTGGAGAACTGCCACCTTCGACCATGGAC
TGTGAGAATTCACATGGACCTCAGAATTATAATCAGTCTCTCAGTTTTACA
GATAAGGAAACTAAATCCAGAGAGATTGTTTTGCCAATGGTGAACAGCTG
GTTAAAGTCAGGATGGAGACTTTAATCCTAGTCAAGTGACCTTTCCTCT
SG13S148

CATCTTTGTTTTTACCTATATAATCACATGAAACCCGTGGTTCTCAA
ACGTCAGCAGGCATCAGCATCACATGGAGGGCTTGTTAAAACAGATTTCT
GGGCCCCAACACAGAGTTTTAAATTCTGAAGGCCTGAGGTGGGTGTGAAC
ATTTGCATTTCTAACATGTTCTCGATGCTGCTGCCGCCTCTGGTCCCGAGA[
G/T]CATGCCTGGAGAACTGCCACCTTCGACCATGGACTGTGAGAATTCAC
ATGGACCTCAGAATTATAATCAGTCTCTCAGTTTTACAGATAAGGAAACT

FIG. 8.25

AAATCCAGAGAGATTGTTTTGCCAATGGTGAACAGCTGGTTAAAGTCAGG
ATGGAGACTTTAATCCTAGTCAAGTGACCTTTCCTCTGTATTTATTTCCC
SG13S98
ATTTCTGACATCCTGAACCATAGTAAAAGGGTGTTTTTTGTTTTTTT
GAGACAGAGTCTTGCTCTGTTGCCTGGGCTGGAGTGCAGTGGTGTGATCTT
GGCTCGCTGCAACCTCCGCCTCCCAGGTTCAAGTGATTCTCCTGCCTCAGC
CTCCTGAGTAGCTGGGATTACAGGTGCTTGCCACCACACCTGGCTATTT[G/
T]TTGTGTTTTTAGTAGAGACAGGGTTTCACCATGTTGGCCAGGCTGGTCTT
GAACTCCTGACCTTGTGATCTGCCTGCCTCAGCCTCCCAAATTGCTGGGAT
TACAAGGCGTGTTGTTTTAAGCCACTCAGTTTGTGGCCACTTGTTACAGCA
GCAAGAGGAAACTCATACAGTTATCATGTGAACTCACAGGAATAT
SG13S149
GATCTGCCTGCCTCAGCCTCCCAAATTGCTGGGATTACAAGGCGTG
TTGTTTTAAGCCACTCAGTTTGTGGCCACTTGTTACAGCAGCAAGAGGAA
ACTCATACAGTTATCATGTGAACTCACAGGAATATGGTGAGTTAAAAAGA
GAGGAAGGGTGCAAAACATCCACGGTAGAGTGAGAACTCTCCAGGGAGT
GAG[A/G]ACTGTGCCCAGCATACAGTGATCACCCTCTTAGTAAGCTAAGTT
TCTGAGCACCAGCTTTTTGAGTTGACTTTGTTGTCTTTAACATTTGAAGAT
CACCCTTCTTTGCTCAGCCTGGCTTGCAGACCTGGGCTGATTTGTGGATCT
GATAGAAAAGTTTCCTTAGTTGGGCTCTTCTCCCCGACCACCCCCATGCC
SG13S29
TGCCTCAGCCTCCCAAATTGCTGGGATTACAAGGCGTGTTGTTTTA
AGCCACTCAGTTTGTGGCCACTTGTTACAGCAGCAAGAGGAAACTCATAC
AGTTATCATGTGAACTCACAGGAATATGGTGAGTTAAAAAGAGAGGAAG
GGTGCAAAACATCCACGGTAGAGTGAGAACTCTCCAGGGAGTGAGGACT
GTGC[A/C]CAGCATACAGTGATCACCCTCTTAGTAAGCTAAGTTTCTGAGC
ACCAGCTTTTTGAGTTGACTTTGTTGTCTTTAACATTTGAAGATCACCCTT
CTTTGCTCAGCCTGGCTTGCAGACCTGGGCTGATTTGTGGATCTGATAGAA
AAGTTTCCTTAGTTGGGCTCTTCTCCCCGACCACCCCCATGCCAGTGTGGC
SG13S89
GCTACTTTGCAGCCAAGGTAACTCAGACTTCCCTTTGTTCATTCTCC
TTCTATAAAGTGCATCTCAAGGAGGTTCAAAGGGCAGGCTTTTTGTTGAA
AGGACTTTGCCTGACCTCTGGCTCCCATCTGTGAAGCCCTGGAGAGGTGA
GAGCCCTCGGGAGGCCGTGTTTCAGGCATGCTCTGCACCCGTGCAGAGCG
C[A/G]TGTGATAATGCATTGCTAATGCTTGCTCCCTGGTGGCTGGCTGAGA
GCTGCTGTGCTGACAAGGGTGGTTTAAGGCTAAATGTGACTCAGAATCCT
TAAGCAGTGTTAGTTCAGATACAAGGGCATTATAAATGAGAGTGCCTGAG
GGATCTATTTTGGGACCGCTGTCACTTGGCTCTTCTGCTAATAAGCTTCCA
SG13S96
ACAGTTATCAGCAGCCCACAGGCTTGACTTGAGCAAGTTGGAAAG
ACAAATCAACTTCCAGAGTTGATTTAACATTGAGTGGAAATCAGTCATAC
TTTTGGTCCCCTTTCGGGGCCACGCCTGGCACTGTGCCTGGTGGCAGATCG
GCATGAACTGGCCAGCTTCTGTGGCCCTGGAGGGCACAGGCAGAAAGGCC
AC[A/G]CTCAGTCCCATGATGAACTGTTTAAGACTTATTGTTGTCTCCCCGC
TCTGTAAAGTAGATAGAGTGGATTTTATGTCCCTTATTACCTTTCAGGATA
CTTTGACTCAGGGAGATAAAGTAACTTGGGTACAGCTACTCAGCTGGTGA
AGAACACAGGCAGAATGAGTGCCTGGGTCTTTTGACTTAAAATTCTGGAT
SG13S150
CTGTGCCTGGTGGCAGATCGGCATGAACTGGCCAGCTTCTGTGGCC
CTGGAGGGCACAGGCAGAAAGGCCACACTCAGTCCCATGATGAACTGTTT

FIG. 8.26

AAGACTTATTGTTGTCTCCCCGCTCTGTAAAGTAGATAGAGTGGATTTTAT
GTCCCTTATTACCTTTCAGGATACTTTGACTCAGGGAGATAAAGTAACTTG
[C/G]GTACAGCTACTCAGCTGGTGAAGAACACAGGCAGAATGAGTGCCTG
GGTCTTTTGACTTAAAATTCTGGATTTTTCACAAAGATCCTCTTACTTTATT
CATTTACATAATAAATATATATTGAAGAGCTACTCTGTGCCAAGCCCTGTG
CCTAGATATACAGTGATAAATAAAGAGTAGCTTCTAGAGGTCACCTGG
SG13S401
      AAGTTCAGTGATAGAGAGCAGAGGTGAGGCGGCAGCAGAAACCAC
TTAAGGGACACCACGTGGCACTCCTTCTGTGCTGAGAAGGCTGTCAGTAA
GCTCACCATTTATTTCCTATTTTCTCTCCTGAGTTAAATAGGAAACATGTCT
CGCATTACTTGAAAAATCAAGTCAAACTATGCTCTTACTAGGAGTTATGGT
[C/T]CTTTTTATGTCTTAGATGATGCTTGATCTAGATGAATGCGGACTTGCT
GTAGCTAGATAAATACAATGGGAGTTTGAAGGTGTTTCGTAGCCCTGGAA
ATAGGTATTTCCTGTCAAAACAAGCTTTGTCATTGCCAGCAGACAAAAGC
ATCAGTAACCTTGGTTGATAATCGTCATTTCTTAGGAATAAAGTAGACT
SG13S151
      GTATTTCCTGTCAAAACAAGCTTTGTCATTGCCAGCAGACAAAAGC
ATCAGTAACCTTGGTTGATAATCGTCATTTCTTAGGAATAAAGTAGACTGT
AGAATTTTTTTAGCAGAAAGGAAACCCAAAGATAATTCTAGTGCAAATC
CCTCACTTTATAGAGCAGAAGCTCAAGTCCCAGAGGAACAAGTGGCTTGA
A[C/T]GAACATCAGAATTTTAGGGGCTGGATTTGTACCCTCCTGGTGCCAG
CAGCCCACTTCCCTGCAGGAGGCACTCACCTTCCTTGCACAGGGGTATGA
GTGTGGCCATTTTCCACCCATAATCTCTGTTAGCTCATGTTCAATTGGGTT
CCCATTGAAAGAAAAATGGACCAGTAAGTTGGAGCAGAATCATTCAGATG
SG13S30
      AGCTTTGTCATTGCCAGCAGACAAAAGCATCAGTAACCTTGGTTGA
TAATCGTCATTTCTTAGGAATAAAGTAGACTGTAGAATTTTTTTAGCAGA
AAGGAAACCCAAAGATAATTCTAGTGCAAATCCCTCACTTTATAGAGCAG
AAGCTCAAGTCCCAGAGGAACAAGTGGCTTGAACGAACATCAGAATTTTA
G[G/T]GGCTGGATTTGTACCCTCCTGGTGCCAGCAGCCCACTTCCCTGCAG
GAGGCACTCACCTTCCTTGCACAGGGGTATGAGTGTGGCCATTTTCCACCC
ATAATCTCTGTTAGCTCATGTTCAATTGGGTTCCCATTGAAAGAAAAATGG
ACCAGTAAGTTGGAGCAGAATCATTCAGATGGTATAACATAAGGAAAAA
SG13S31
      TGTTTAAATTGCTTTTATATCTGTAGCTCTAGATAACACTAGTTCCA
GCTTAGTTAACTCCCAGCTCCAAGCCTTCAGGACTTCATAGAGTTATTGGG
GTGCTGCTCTTGGCAGTTTCCCAAAAAGCTAGAATGCAGAGGGAATCTCC
TTCCCAAAAAGCTAGAATGCAGAGGGAATCTCCTTCCCAAAAGGCTAGAA
[C/T]GCAGAGGGAATCTCCTTCCCAAAAAGCTAGAATGCAGAGGGAATCT
CCTTCCCAAAAGGCTAGAACGCAGAGGGAATCTCCTTCCCAAAAGGCTAG
AACGCAGAGGGAATCTCCTTCCCAAAAGGCTAGAATGCAGAGGGAATGT
CCTTCTCTTCTAAATGGTAGCTGTTAGTTCAAGAAAGGTTAAACATTGTGC
T
SG13S152
      GCTGCGTTTGCTGGACTGATGTACTTGTTTGTGAGGCAAAAGTACT
TTGTCGGTTACCTAGGAGAGAACGCAGAGGTAGGTAACTGGGACTACT
AAAGAACTGTGGAGCGATTCCTGATTTTTGAGCAGGAAGAGTGACAATTC
AAAACAGTATTTGACTAGATTCACGGCTCCGTAGCATCCCCTTGGGTGGG
AG[C/G]GGGAAGGCTGACTAGGACCTCTGATTCTTCTTTCCCTGAGCTTTG
AAGGCTCTGAAAATACAGCTGGGGGGACTTGCCCAGTTTTCTTATTAAGC

FIG. 8.27

AATTCCTCCGCATGGTGCTGGCTTTCAAAGGGTGCTTCAGTGCTGTTTGCT
GCACGTGCCTTGCAGCCCCACACCCTGCACTCCCGCCCTGCAGAGTCTGG
C
SG13S402
GAGGCAAAAGTACTTTGTCGGTTACCTAGGAGAGAGAACGCAGAG
GTAGGTAACTGGGACTACTAAAGAACTGTGGAGCGATTCCTGATTTTTGA
GCAGGAAGAGTGACAATTCAAAACAGTATTTGACTAGATTCACGGCTCCG
TAGCATCCCCTTGGGTGGGAGGGGGAAGGCTGACTAGGACCTCTGATTCT
TCT[C/T]TCCCTGAGCTTTGAAGGCTCTGAAAATACAGCTGGGGGGACTTG
CCCAGTTTTCTTATTAAGCAATTCCTCCGCATGGTGCTGGCTTTCAAAGGG
TGCTTCAGTGCTGTTTGCTGCACGTGCCTTGCAGCCCCACACCCTGCACTC
CCGCCCTGCAGAGTCTGGCGCTGGAATGACATTTTAGGTCTGGGTTCCCA
G
SG13S403
TATCTTTCAGGGACCAGAAGAAAGAATGTTGGGAAAATAAGATGC
AGTAAGATGCAGACATGACAGCAGGGTGCAGCGGCTCACGCCTATAATCC
CAGCACTTTGGGAGGCTGAGGTGGGTGGATCACCTGAGGTCAGGAGTTTG
AGACCAGCCTGGCCAACATGGTGAAACCCCGTCTCTACTAAAAAATATAC
AAA[A/G]CATTAGCCAGGCATGGTGGTGGGCGCCTGTAATCCCAGCTACTC
CATAGGCTGAGGCTGGAGAATCGCTTGAACCCAGGAGGCAGAGGTTGCA
GTGAGCCGAGATTGCGCCACTGCACTCCAGCCTGGGCAACAAAAGCAAA
ACTCCATCTCAAAAAAAAAAAAAAAAAAAAAAAAAAAAGATGCAGACACG
AGACTG
SG13S153
TGGGCGCCTGTAATCCCAGCTACTCCATAGGCTGAGGCTGGAGAAT
CGCTTGAACCCAGGAGGCAGAGGTTGCAGTGAGCCGAGATTGCGCCACTG
CACTCCAGCCTGGGCAACAAAAGCAAAACTCCATCTCAAAAAAAAAAAA
AAAAAAAAAAAAAGATGCAGACACGAGACTGTGAAACTGACTAGCAT
CACC[A/T]TTGCATTGTTTATAGATGTTGCCAGACAGAAAGCCCCAAAGCA
GCACAGTACCTTCCTGACATCTGGACTAGGAAATCTAGATTTTAGTAAAA
TACATGCTAATACTTACAGAAGAAATGTCGGCGTTAGAGTATGCCGTCAG
TTCCTTAGAGATTGCAATTCCTAATGCACTAGTATGGTTTCAGGTGCCAGG
AAC
SG13S97
ACTCCATCTCAAAAAAAAAAAAAAAAAAAAAAAAAAAAGATGCAG
ACACGAGACTGTGAAACTGACTAGCATCACCATTGCATTGTTTATAGATG
TTGCCAGACAGAAAGCCCCAAAGCAGCACAGTACCTTCCTGACATCTGGA
CTAGGAAATCTAGATTTTAGTAAAATACATGCTAATACTTACAGAAGAAA
TGTC[A/G]GCGTTAGAGTATGCCGTCAGTTCCTTAGAGATTGCAATTCCTA
ATGCACTAGTATGGTTTCAGGTGCCAGGAACACGTTCTGTGAGGCTGCTG
CCCCAGGTGCTGACCCCAGCCTTCCACACCATTTTCCTTCCTTGTGTTCAC
AGCCGCTCTGTCTTTTACAATAGCACCCCTCTCTAGTGGCTAATGGGCTCT
AT
SG13S154
AAAAAAAAAAAAAAAAAAAAAAGATGCAGACACGAGACTGTGAA
ACTGACTAGCATCACCATTGCATTGTTTATAGATGTTGCCAGACAGAAAG
CCCCAAAGCAGCACAGTACCTTCCTGACATCTGGACTAGGAAATCTAGAT
TTTAGTAAAATACATGCTAATACTTACAGAAGAAATGTCGGCGTTAGAGT
ATGC[C/T]GTCAGTTCCTTAGAGATTGCAATTCCTAATGCACTAGTATGGTT
TCAGGTGCCAGGAACACGTTCTGTGAGGCTGCTGCCCCAGGTGCTGACCC

FIG. 8.28

CAGCCTTCCACACCATTTTCCTTCCTTGTGTTCACAGCCGCTCTGTCTTTTA
CAATAGCACCCCTCTCTAGTGGCTAATGGGCTCTATGATTAGATAGCATCC
SG13S40
       TTTCAGGTGCCAGGAACACGTTCTGTGAGGCTGCTGCCCCAGGTGC
TGACCCCAGCCTTCCACACCATTTTCCTTCCTTGTGTTCACAGCCGCTCTGT
CTTTTACAATAGCACCCCTCTCTAGTGGCTAATGGGCTCTATGATTAGATA
GCATCCTTCAGTAGTGATAAAGGCAGTGACATCCTAGGGAGGTCAGCGG[
G/T]TGAAAGCGCTATATCTGGAAAACCTGAGAGCCTGTGAAGCTCAAGGA
CTTGACGGGGTTAGACCGTGAGCCGGGCTGCAGCTGGAAAAAGAATGACT
GTTCTTTCAGCAGATCCTTCCCTGTGCCATCTCTTTCTTCATTCCTCTCTAG
TGGCATTCTTATTTATCCTCTAAAACCACAATTCCATTATCTCTCCTA
SG13S155
       GAGGGTCTTCTCTTTTGCCTGGCTCCCTATGCAGCCCTATCTTACCC
CCTGCAAAGTCCCAGGGATGTGGCTCAGTCACTGCTCCTCTCTTCATCTGT
CACCACTTGCTTGAGATCCTACAGCTGCTTTAATTCCGAGACCATCTGCAG
AACATGACAAATTTGTCCACCTACCCACATGTCCTTTTAACTTTAAAG[A/
G]CTTTACTAACTGATTCCTATTAGGGAATGAACAGAGGTGGCAAAAATAA
ACAATAGGAGATTGATTTACAAGAAATCTTTAAAATAGTAGATTTCTTCG
GACCTCATTGAAATATAAATGGCCTGCCTTCTTGTGTCCCTCCCTGGTCTC
CCTCTTTAGGTGATAAGAAGAAGATCCTGCCAGCCCCATAACCCGCC
SG13S156
       TTAAAATAGTAGATTTCTTCGGACCTCATTGAAATATAAATGGCCT
GCCTTCTTGTGTCCCTCCCTGGTCTCCCTCTTTAGGTGATAAGAAGAAGAT
CCTGCCAGCCCCATAACCCGCCATCTGCGCGGGTTCTAGACCCCCTTCTCC
TCCCCTCTGGCCGTGGTAGGCATTACTGATGAATCATGGTGCTCTTTCTT[A
/C]CAGAGACCAAACCTGGCCTCGGAATCCTTCTTAACACAGATACTGCTT
AACACAACCACTCTGAGCAGCTGTCATAAGTAGAAGTAATAGATACTAGA
AGAAATGTCTAAGCCTAATCTAGACCAAAATACGGCCTGATATAGATGCA
AGCCAGAGGGGCTTTATGGTTAAATGCAAGGAGATTTTCAACCCTGCCG
SG13S157
       CTGGTCTCCCTCTTTAGGTGATAAGAAGAAGATCCTGCCAGCCCCA
TAACCCGCCATCTGCGCGGGTTCTAGACCCCCTTCTCCTCCCCTCTGGCCG
TGGTAGGCATTACTGATGAATCATGGTGCTCTTTCTTCCAGAGACCAAACC
TGGCCTCGGAATCCTTCTTAACACAGATACTGCTTAACACAACCACTCTG[
A/G]GCAGCTGTCATAAGTAGAAGTAATAGATACTAGAAGAAATGTCTAAG
CCTAATCTAGACCAAAATACGGCCTGATATAGATGCAAGCCAGAGGGGCT
TTATGGTTAAATGCAAGGAGATTTTCAACCCTGCCGTCTAGAAGCTACTTG
CTGAGATCTTCTTCAGTTGGGCCCATCTCCTCCCCAGGCCTCTCTTCTG
SG13S158
       CCATAACCCGCCATCTGCGCGGGTTCTAGACCCCCTTCTCCTCCCCT
CTGGCCGTGGTAGGCATTACTGATGAATCATGGTGCTCTTTCTTCCAGAGA
CCAAACCTGGCCTCGGAATCCTTCTTAACACAGATACTGCTTAACACAAC
CACTCTGAGCAGCTGTCATAAGTAGAAGTAATAGATACTAGAAGAAATGT
[A/C]TAAGCCTAATCTAGACCAAAATACGGCCTGATATAGATGCAAGCCA
GAGGGGCTTTATGGTTAAATGCAAGGAGATTTTCAACCCTGCCGTCTAGA
AGCTACTTGCTGAGATCTTCTTCAGTTGGGCCCATCTCCTCCCCAGGCCTC
TCTTCTGTTCCTGGGCTATGTCACACTTGGACTCTGCAGACACCTAATGC
SG13S159
       TGGTAGGCATTACTGATGAATCATGGTGCTCTTTCTTCCAGAGACC
AAACCTGGCCTCGGAATCCTTCTTAACACAGATACTGCTTAACACAACCA

FIG. 8.29

CTCTGAGCAGCTGTCATAAGTAGAAGTAATAGATACTAGAAGAAATGTCT
AAGCCTAATCTAGACCAAAATACGGCCTGATATAGATGCAAGCCAGAGG
GGC[G/T]TTATGGTTAAATGCAAGGAGATTTTCAACCCTGCCGTCTAGAAG
CTACTTGCTGAGATCTTCTTCAGTTGGGCCCATCTCCTCCCCAGGCCTCTCT
TCTGTTCCTGGGCTATGTCACACTTGGACTCTGCAGACACCTAATGCTCTT
GGGACCTGCTTTAGTTCTTGACCTCACCAACCGAGGAGGAATTGCTAGAT
SG13S160
    CAGAGACCAAACCTGGCCTCGGAATCCTTCTTAACACAGATACTGC
TTAACACAACCACTCTGAGCAGCTGTCATAAGTAGAAGTAATAGATACTA
GAAGAAATGTCTAAGCCTAATCTAGACCAAAATACGGCCTGATATAGATG
CAAGCCAGAGGGGCTTTATGGTTAAATGCAAGGAGATTTTCAACCCTGCC
GT[C/T]TAGAAGCTACTTGCTGAGATCTTCTTCAGTTGGGCCCATCTCCTCC
CCAGGCCTCTCTTCTGTTCCTGGGCTATGTCACACTTGGACTCTGCAGACA
CCTAATGCTCTTGGGACCTGCTTTAGTTCTTGACCTCACCAACCGAGGAGG
AATTGCTAGATGAGATCCTTCCCCGGAATTTCTCTCTTGAACCCCAGA
SG13S32
    GGGCTTTATGGTTAAATGCAAGGAGATTTTCAACCCTGCCGTCTAG
AAGCTACTTGCTGAGATCTTCTTCAGTTGGGCCCATCTCCTCCCCAGGCCT
CTCTTCTGTTCCTGGGCTATGTCACACTTGGACTCTGCAGACACCTAATGC
TCTTGGGACCTGCTTTAGTTCTTGACCTCACCAACCGAGGAGGAATTGCT[
A/C]GATGAGATCCTTCCCCGGAATTTCTCTCTTGAACCCCAGATGGTCCG
TTGCCCCTTTCCAGAAGTTGCTCCAGCCCTGTCCGCTTAGGAAGTTCAGTG
TCATCCTTGATCCAGTGGGTAGGGAAGACATTCCATAATGAATGCCCCAG
TCTGAGCTTCTTCCTTCAGGCTTCAGGCTGCCCTGCGAGGATTTTGCA
SG13S161
    GTAGCTGAGACTACAGGTGTGCACTACCACACCCAGCTAATTTTTT
GTATTTTTAGTAGAGATAGGGTTTAGCTATGTTGGCCAGGCTGGTCTCGAA
CTGCTGAACTCAAGCAATCTGCCATCCCCGGCCTCCCAAAGTACTGGGAG
TATAGGCATAAGCCACCCATGATGCCCAGCCTGAATCTTGGTTTCTTCCCC
[A/G]TTCATTTAAGCTATTACCTGGGCCTGAACTCAATGGCACCTGGCACC
AACTGGCAACTGACTCTTGGTCTTTTATTACCTACCTTCCCTAGCAGGCAC
TGGGTTGCTCCCTCTTCCTATCCCATGGAGTCCTGTCCTCTGTTGGGGCTCC
TACTGATCCTCTTGGCAATATGAAGTTCTCAGCTCAATGGTGGGTGG
SG13S162
    CCCGGCCTCCCAAAGTACTGGGAGTATAGGCATAAGCCACCCATG
ATGCCCAGCCTGAATCTTGGTTTCTTCCCCATTCATTTAAGCTATTACCTG
GGCCTGAACTCAATGGCACCTGGCACCAACTGGCAACTGACTCTTGGTCT
TTTATTACCTACCTTCCCTAGCAGGCACTGGGTTGCTCCCTCTTCCTATCCC
[A/G]TGGAGTCCTGTCCTCTGTTGGGGCTCCTACTGATCCTCTTGGCAATAT
GAAGTTCTCAGCTCAATGGTGGGTGGGCAATGACTGCCAACTCTTGAGGC
CAATGAACTCAGGTTACCCCACTCCTCCTCCTCCTGAGTTGCTCACTCACT
CCTCATTCACTCAACATTGATTCAGTAGATATTTGCTACCTGCTCTGT
SG13S163
    CCGGCCTCCCAAAGTACTGGGAGTATAGGCATAAGCCACCCATGAT
GCCCAGCCTGAATCTTGGTTTCTTCCCCATTCATTTAAGCTATTACCTGGG
CCTGAACTCAATGGCACCTGGCACCAACTGGCAACTGACTCTTGGTCTTTT
ATTACCTACCTTCCCTAGCAGGCACTGGGTTGCTCCCTCTTCCTATCCCA[C
/T]GGAGTCCTGTCCTCTGTTGGGGCTCCTACTGATCCTCTTGGCAATATGA
AGTTCTCAGCTCAATGGTGGGTGGGCAATGACTGCCAACTCTTGAGGCCA

FIG. 8.30

ATGAACTCAGGTTACCCCACTCCTCCTCCTCCTGAGTTGCTCACTCACTCC
TCATTCACTCAACATTGATTCAGTAGATATTTGCTACCTGCTCTGTG

SG13S164

GGCATAAGCCACCCATGATGCCCAGCCTGAATCTTGGTTTCTTCCC
CATTCATTTAAGCTATTACCTGGGCCTGAACTCAATGGCACCTGGCACCAA
CTGGCAACTGACTCTTGGTCTTTTATTACCTACCTTCCCTAGCAGGCACTG
GGTTGCTCCCTCTTCCTATCCCATGGAGTCCTGTCCTCTGTTGGGGCTCC[C/
T]ACTGATCCTCTTGGCAATATGAAGTTCTCAGCTCAATGGTGGGTGGGCA
ATGACTGCCAACTCTTGAGGCCAATGAACTCAGGTTACCCCACTCCTCCTC
CTCCTGAGTTGCTCACTCACTCCTCATTCACTCAACATTGATTCAGTAGAT
ATTTGCTACCTGCTCTGTGCCAGGTACCAGGTCAGTTGCTGAAGGA

SG13S165

CCTGGCACCAACTGGCAACTGACTCTTGGTCTTTTATTACCTACCTT
CCCTAGCAGGCACTGGGTTGCTCCCTCTTCCTATCCCATGGAGTCCTGTCC
TCTGTTGGGGCTCCTACTGATCCTCTTGGCAATATGAAGTTCTCAGCTCAA
TGGTGGGTGGGCAATGACTGCCAACTCTTGAGGCCAATGAACTCAGGTT[A
/T]CCCCACTCCTCCTCCTCCTGAGTTGCTCACTCACTCCTCATTCACTCAAC
ATTGATTCAGTAGATATTTGCTACCTGCTCTGTGCCAGGTACCAGGTCAGT
TGCTGAAGGAGTAACAGTGAACATGACGGAGTCTTTGTCCCCAAGGAGAC
CCAAGGTGTCTCCTAGAGCCAGGGGCACATTGCAAGACCAAATATA

SG13S166

CTGGCAACTGACTCTTGGTCTTTTATTACCTACCTTCCCTAGCAGGC
ACTGGGTTGCTCCCTCTTCCTATCCCATGGAGTCCTGTCCTCTGTTGGGGC
TCCTACTGATCCTCTTGGCAATATGAAGTTCTCAGCTCAATGGTGGGTGGG
CAATGACTGCCAACTCTTGAGGCCAATGAACTCAGGTTACCCCACTCCT[C/
T]CTCCTCCTGAGTTGCTCACTCACTCCTCATTCACTCAACATTGATTCAGT
AGATATTTGCTACCTGCTCTGTGCCAGGTACCAGGTCAGTTGCTGAAGGA
GTAACAGTGAACATGACGGAGTCTTTGTCCCCAAGGAGACCCAAGGTGTC
TCCTAGAGCCAGGGGCACATTGCAAGACCAAATATATTCAACTTACC

SG13S167

CCATGGAGTCCTGTCCTCTGTTGGGGCTCCTACTGATCCTCTTGGCA
ATATGAAGTTCTCAGCTCAATGGTGGGTGGGCAATGACTGCCAACTCTTG
AGGCCAATGAACTCAGGTTACCCCACTCCTCCTCCTCCTGAGTTGCTCACT
CACTCCTCATTCACTCAACATTGATTCAGTAGATATTTGCTACCTGCTCT[A
/G]TGCCAGGTACCAGGTCAGTTGCTGAAGGAGTAACAGTGAACATGACGG
AGTCTTTGTCCCCAAGGAGACCCAAGGTGTCTCCTAGAGCCAGGGGCACA
TTGCAAGACCAAATATATTCAACTTACCAAAATAATCATAGACCTAGTTCT
CAAAAAGCAAGAAGACTGATTCCTCGTTGTCATTTCTCCTCCTCAGCA

SG13S168

TTAGAGTCTGTGGGCCCCTCCAAGTGTGGAGTATGGTGTTACTTCA
CCAGAGTTTGAGGAGAAACATTCTTCTTTTGGAAGGCCGGGGAGCATAGA
TGGATATCAAGGCTGCTGTTTCTAAAAGCGAAACCCACCAAACAACAGTA
TTAGAATCATCTGTGGTGCTTATTAAAGATACAGATTCCTGGGCCCCATCC
C[A/C]GACTTATGAATCAGAATCTCTGCCAGAGGAAGCCTGAGAATTTGCA
TTCTCAGATGATTCTGCATTCTCAGATAACACATTCTTTAGGTGATTCTTAC
ACACACTGGAGTTTGGGAATCGCTGAAGGCTGTTCACTTCTCTTTTCTGAG
AAATGATTCATTCATTTCAGAAATATTTGCAGAGGTCCTTATTTATTG

SG13S33

TGGCCTCATTCGTGTGATAAATCTGAGCCACCACGATATTTGACTTT
TCACAATTTAATTTATCTGAACCCTCTATTCTCTGGCTAAAAAATATCCCT

FIG. 8.31

TACTTGGACTTCTTTATTTTATTTTCAATTCCCTTACCAGCACTAGCAGGGG
ACTCTGTACTCATCTGCTGGCGCTGCCATAACAAAGCACTGCAGCCTG[G/T
]GGGGCTCAAACCACAGAATTTATTCTCTCACAGTCCTAGAGGCTAGAAGT
CCAAGATCAAAGTGTGGGCAGGGTCGGTTTCTCCTGCAGCCTCTCTCCTTG
GCTTATAGAGTGCCACCTTCTACCTGTGTCTTCACATCATCACCTCACTGA
GCATGTCTGTGTCCAAATCTCCCCTTCTTATAAGACCCCAGTCAT
SG13S41

TCTCCTTGGCTTATAGAGTGCCACCTTCTACCTGTGTCTTCACATCA
TCACCTCACTGAGCATGTCTGTGTCCAAATCTCCCCTTCTTATAAGACCCC
AGTCATACTGGATGAGGATCCACCCATATGAGTTCATTTTACCTTAATTAT
CTCTTTAAACACCCTGTCTCCAAATACAGTCCCATTCTGAGGAACTGAG[A/
G]GTAAAGATTCAACATATGAATTTTGGAAGGGACCTAATTCAGCCCACA
ACACCCTCTTTGGGATGTTTATTTTCCCCCTTAAGGAGCTAGTTAGGATG
TCTTATCTCATGAACATGACTGTGAACAGGAAAACAGGGAGAGAATGAA
GCTGGCCAAGGAACAGGGCTGGTGTCAGCTAGCAGTGCTTTTCTGATGT
SG13S169

CATTTTACCTTAATTATCTCTTTAAACACCCTGTCTCCAAATACAGT
CCCATTCTGAGGAACTGAGAGTAAAGATTCAACATATGAATTTTGGAAGG
GACCTAATTCAGCCCACAACACCCTCTTTGGGATGTTTATTTTCCCCCTT
AAGGAGCTAGTTAGGATGTCTTATCTCATGAACATGACTGTGAACAGGAA[
A/G]ACAGGGAGAGAATGAAGCTGGCCAAGGAACAGGGCTGGTGTCAGCT
AGCAGTGCTTTTCTGATGTGAGTGGGTCCCACAGGGAGCTTGTTAAAATG
CAGATTCTGATTCATTAGGTTCCAGAGGGACCTGAGATTTCCCATTTCTGA
CAAGTTTCCAGTGTGGGGGCTGATGCTGCTGGTCCACGGACCATACTTTG
SG13S404

GGGAGAGAATGAAGCTGGCCAAGGAACAGGGCTGGTGTCAGCTAG
CAGTGCTTTTCTGATGTGAGTGGGTCCCACAGGGAGCTTGTTAAAATGCA
GATTCTGATTCATTAGGTTCCAGAGGGACCTGAGATTTCCCATTTCTGACA
AGTTTCCAGTGTGGGGGCTGATGCTGCTGGTCCACGGACCATACTTTGAGT
A[G/T]CAAGGAGCTTGATACATAATGGCTGAGTGACTTTCAGACTCCTGCT
GTAGAAAAATTATGAGTTGGCTGGGCGTGGTGGCTCACGCCTGTAATCCC
AGCACTTTGGGAGGCCGAGGTGGGCAGATCACCTGAGGTCAGGAGTTCGA
GACCAGCCTGGCCAACATGGTGAAACACCATCTCTACCAAAAATACAAAA
A
SG13S170

ACTTAAGCCCAGAAGACTGAGGTTGCAGTGAGCCGAGATTGCACC
ACTGCACTCCAGCTTGGGCTACAGAGTGAGACTCTATCTCAAAAACAAAG
AAACAAACAACAACAATAACAACAAAAACCAAGTCTCTCCCTCCACTCAA
AAATGCAAGGGCCTGTCTCCCATTGCTGGGTGCCCAGGTCTCATGAATGT
AGA[C/T]ATGAATTATTCCAGTCAGCCTCAGGAGAATAGAATGAGCCCTCA
GATGCCGAAGCACCTTTCAGATTCCACCGGTTTTATCGGCTCATTTAAACT
TCACTTCTAACACAGTCCTGCATTACACACGTGTCTGTCGTTATGGGCAGC
TGCAGAGGGTCTTAATGGTCCTAATGCTCAGTGAGGATGCCCAATGGT
C
SG13S171

CTCAAAAACAAAGAAACAAACAACAACAATAACAACAAAAACCA
AGTCTCTCCCTCCACTCAAAAATGCAAGGGCCTGTCTCCCATTGCTGGGTG
CCCAGGTCTCATGAATGTAGATATGAATTATTCCAGTCAGCCTCAGGAGA
ATAGAATGAGCCCTCAGATGCCGAAGCACCTTTCAGATTCCACCGGTTTT
ATC[A/G]GCTCATTTAAACTTCACTTCTAACACAGTCCTGCATTACACACGT

FIG. 8.32

GTCTGTCGTTATGGGCAGCTGCAGAGAGGGTCTTAATGGTCCTAATGCTC
AGTGAGGATGCCCAATGGTCAACAGAACCTGCCATCTTCAGGCCATCAAG
GAGCTCTGGAGTTAAGGAAATCATGAGAGCACAGAGGGGCGGGTACAGC
AGA

SG13S172

TGTAGATATGAATTATTCCAGTCAGCCTCAGGAGAATAGAATGAGC
CCTCAGATGCCGAAGCACCTTTCAGATTCCACCGGTTTTATCGGCTCATTT
AAACTTCACTTCTAACACAGTCCTGCATTACACACGTGTCTGTCGTTATGG
GCAGCTGCAGAGAGGGTCTTAATGGTCCTAATGCTCAGTGAGGATGCCCA
[A/G]TGGTCAACAGAACCTGCCATCTTCAGGCCATCAAGGAGCTCTGGAGT
TAAGGAAATCATGAGAGCACAGAGGGGCGGGTACAGCAGAGCCCTCGTG
GTAATGGGTTTTGAGGTCTAGGCTCTCTTCACTTGGGTTTGAAATAAGTTC
AATGACTAGTAATAGCTGAGACACTTCTACCCTTCAAATGAAGTAAATGG

SG13S173

AGCACCTTTCAGATTCCACCGGTTTTATCGGCTCATTTAAACTTCAC
TTCTAACACAGTCCTGCATTACACACGTGTCTGTCGTTATGGGCAGCTGCA
GAGAGGGTCTTAATGGTCCTAATGCTCAGTGAGGATGCCCAATGGTCAAC
AGAACCTGCCATCTTCAGGCCATCAAGGAGCTCTGGAGTTAAGGAAATCA
[A/T]GAGAGCACAGAGGGGCGGGTACAGCAGAGCCCTCGTGGTAATGGGT
TTTGAGGTCTAGGCTCTCTTCACTTGGGTTTGAAATAAGTTCAATGACTAG
TAATAGCTGAGACACTTCTACCCTTCAAATGAAGTAAATGGGAAAATGGA
GCATTGTTGAGTCCAGGGAGCTATAATTTAAACCCCATATATCTAAAAGG

SG13S42

CACACGTGTCTGTCGTTATGGGCAGCTGCAGAGAGGGTCTTAATGG
TCCTAATGCTCAGTGAGGATGCCCAATGGTCAACAGAACCTGCCATCTTC
AGGCCATCAAGGAGCTCTGGAGTTAAGGAAATCATGAGAGCACAGAGGG
GCGGGTACAGCAGAGCCCTCGTGGTAATGGGTTTTGAGGTCTAGGCTCTC
TTC[A/G]CTTGGGTTTGAAATAAGTTCAATGACTAGTAATAGCTGAGACAC
TTCTACCCTTCAAATGAAGTAAATGGGAAAATGGAGCATTGTTGAGTCCA
GGGAGCTATAATTTAAACCCCATATATCTAAAAGGGGTAACATTTTGTGT
GTGTGAAATTGGTGTCATTCGCACTGCATCTACAGTTTTCTTTTTCCTTCTC

SG13S194

ACATATTTGGGAAACGCATCATACTCTTCCTGTTCCTCATGTCCGTT
GCTGGCATATTCAACTATTACCTCATCTTCTTTTTCGGAAGTGACTTTGAA
AACTACATAAAGACGATCTCCACCACCATCTCCCCTCTACTTCTCATTCCC
TAACTCTCTGCTGAATATGGGGTTGGTGTTCTCATCTAATCAATACCTA[C/
T]AAGTCATCATAATTCAGCTCTTGAGAGCATTCTGCTCTTCTTTAGATGGC
TGTAAATCTATTGGCCATCTGGGCTTCACAGCTTGAGTTAACCTTGCTTTT
CCGGGAACAAAATGATGTCATGTCAGCTCCGCCCCTTGAACATGACCGTG
GCCCCAAATTTGCTATTCCCATGCATTTGTTTGTTTCTTCACTTA

SG13S195

TGGTGTTCTCATCTAATCAATACCTACAAGTCATCATAATTCAGCTC
TTGAGAGCATTCTGCTCTTCTTTAGATGGCTGTAAATCTATTGGCCATCTG
GGCTTCACAGCTTGAGTTAACCTTGCTTTTCCGGGAACAAAATGATGTCAT
GTCAGCTCCGCCCCTTGAACATGACCGTGGCCCCAAATTTGCTATTCCC[A/
G]TGCATTTGTTTGTTTCTTCACTTATCCTGTTCTCTGAAGATGTTTTGTGA
CCAGGTTTGTGTTTTCTTAAAATAAAATGCAGAGACATGTTTTAAGCTGAT
AGTTGAGGGGTTTTGTTAATGGCTTTTGGGGGATTTATCTCTATACCCACA
AACGACTAGTTTGTTTTCCTCAAACTAAATGATAATATTAAAAA

TTATCTCTATACCCACAAACGACTAGTTTGTTTTCCTCAAACTAAAT
GATAATATTAAAAATACACATCCTGGCCAGGTGTGGTGGCTCATACCTGT
AATCCCAGCACTTTGGGAGGCCGAGGCAGGTGGATCACTTGAGGTCAGGA
ATTAAGACCAGCCTGGCCAATATGGTGAAAGCCTGTCTGTACTAAAAATA
C[A/G]AAAATTAGCCAGGTATGCTGGTGGATGCTTATAATCCCAGCTACTT
GGGAGGTTGAGGCAGGAGAATTGCTTGAACCCGGGAGGTAGAGGTTGCA
GTGAGCCAAGATCATGCCACTGCACTCCAGCTTGGGCAACAGAGTGAGAC
TCCATCTCAAATTAAAAAAAATACACATCTGGCTTCTGGAAAAATTACTT
GA

SG13S34

GATCATGCCACTGCACTCCAGCTTGGGCAACAGAGTGAGACTCCAT
CTCAAATTAAAAAAAATACACATCTGGCTTCTGGAAAAATTACTTGAAGA
TCTTTTATGACATCCATCCCTCTTCACACAGCCATGTGAATTAGGTTGGTA
TCTTCATATACTAGCATCGTGCCCAGCACTTCCATGTTATACAGTTTAAAA[
G/T]GTTCTGTAATTCCCTGTGGGAACCTAAGATAATGCGAGGACCGTCAT
ACGTGCCCCCAAATATTGGCAAACCAATGAATAAATGAATGAATGAGTTT
ATGAATCGCTAACTGGCTGTATTTAATGAAGTATGTGTGTTGAGCCATTTC
CCACAGTGTGGACAGATTTGTCCCACAATATGGGCCTCTTCCCAAAGGC

SG13S175

AATTAAAAAAAATACACATCTGGCTTCTGGAAAAATTACTTGAAGA
TCTTTTATGACATCCATCCCTCTTCACACAGCCATGTGAATTAGGTTGGTA
TCTTCATATACTAGCATCGTGCCCAGCACTTCCATGTTATACAGTTTAAAA
TGTTCTGTAATTCCCTGTGGGAACCTAAGATAATGCGAGGACCGTCATAC[
A/G]TGCCCCCAAATATTGGCAAACCAATGAATAAATGAATGAATGAGTTT
ATGAATCGCTAACTGGCTGTATTTAATGAAGTATGTGTGTTGAGCCATTTC
CCACAGTGTGGACAGATTTGTCCCACAATATGGGCCTCTTCCCAAAGGCC
CTACCACCTAATGCCATCACACTGGGGATTTGATTTCAACATGTGAATT

SG13S176

AGTTCATAGTGACAGTGATCCAGCCACTGTCATGACAGGTGCCACT
TGGCAGAAACAGCACAGCTTGGAAGATGGCGGGGTGTAGTCAAGATTCC
AGGATCCCCAACAGAGAAGCCAGCTCTTATAGGGGAGCCATTCATCAGGA
TTGAACTCTCAATCGAGCTGGACAGTAATAGGTGGGTCTGTGTTATTCCCC
AG[A/G]TGAGTATCATGACAGTCACAATCCTAGGAAGGATGTGAAGCCTC
CCCCAGCTCTCCTCCAGTTGCCTGCTTGGGCAGCAGAGATGATGGAATGT
GGAGTCTGGCGTGGTCTGAGGCCTGAATCCATGTGCCTCATGTATGATGCT
CAGGCAAGAGGATCTCTCAATTCAAGGGAGAGGGCCTGAATGAGCCTTGC
TT

SG13S177

CTTGGCAGAAACAGCACAGCTTGGAAGATGGCGGGGTGTAGTCAA
GATTCCAGGATCCCCAACAGAGAAGCCAGCTCTTATAGGGGAGCCATTCA
TCAGGATTGAACTCTCAATCGAGCTGGACAGTAATAGGTGGGTCTGTGTT
ATTCCCCAGATGAGTATCATGACAGTCACAATCCTAGGAAGGATGTGAAG
CCT[C/T]CCCCAGCTCTCCTCCAGTTGCCTGCTTGGGCAGCAGAGATGATG
GAATGTGGAGTCTGGCGTGGTCTGAGGCCTGAATCCATGTGCCTCATGTA
TGATGCTCAGGCAAGAGGATCTCTCAATTCAAGGGAGAGGGCCTGAATGA
GCCTTGCTTTCCAGGCCTGTCTGATGGTCCAGGCTGAAGCCCCTCCTGGCT
TG

SG13S178

CTGGCGTGGTCTGAGGCCTGAATCCATGTGCCTCATGTATGATGCT

FIG. 8.34

CAGGCAAGAGGATCTCTCAATTCAAGGGAGAGGGCCTGAATGAGCCTTGC
TTTCCAGGCCTGTCTGATGGTCCAGGCTGAAGCCCCTCCTGGCTTGCACTG
CCAGACCTCATCCAGCAGGAGCTCCTTGGCATTGACTGCTTCAGGATAGTT
[C/G]CTTCTGCTCTGAGTGCTCTCTAAAGAGCAGTGCTCTACCATCCAAGC
TGGGCTTTTCTTTTCTTCTTGCTGATAGGGAAGGCATGGGACATTGCAGGA
TGGAAGTGGCCCCCAGGCCTTCTCATGCCTGGGCTTGGTTTGGAAGGTGG
TCAGGTGATCAATAATCCTGATTGGCCTGGCATTGAGGAGTTTTCCTGG
SG13S35
TGCTCTCTAAAGAGCAGTGCTCTACCATCCAAGCTGGGCTTTTCTTT
TCTTCTTGCTGATAGGGAAGGCATGGGACATTGCAGGATGGAAGTGGCCC
CCAGGCCTTCTCATGCCTGGGCTTGGTTTGGAAGGTGGTCAGGTGATCAAT
AATCCTGATTGGCCTGGCATTGAGGAGTTTTCCTGGGATGTGGTCCTTTC[A
/G]GTTTTTAAAAATTATTTTTATTGATACACATATTTGTAGGTATTTGTGG
GGTGCATGTGATACTTTATTATGTGTGTGGATTGTGTAATGATGAAGTCAG
GGCATTTAGGGTCTTCATCACCTTGATTATCATTTCTATGTGTTGAGAACA
TTTCAAGTTCTCAGTTCCAGCTATTTTGAAATAGACAGTCCATTT
SG13S179
GATACTTTATTATGTGTGTGGATTGTGTAATGATGAAGTCAGGGCA
TTTAGGGTCTTCATCACCTTGATTATCATTTCTATGTGTTGAGAACATTTCA
AGTTCTCAGTTCCAGCTATTTTGAAATAGACAGTCCATTTTGTTAGCTACA
GTCACCCAACCCGGCTGTCAGACATTGGAACTTACTCCTATTGAACTGT[A/
G]TATTTGTACCCATTCACCAAACTCTCTTTGGGCTTTCAGTTTTACAACTG
GGATGATCCTGGGAAAACTAAAGTAAATCAGACACCCGACGTGTGAGCTA
GGTTATAATATGCCCAGTGGACCCTGGGGACATCTTAGCTTTCAGAGGTC
ATGCTGTCCAAGCTGACTGTGGGGCTTCCAGAAGGTGGGGAGAGGAA
SG13S180
TATGTGTGTGGATTGTGTAATGATGAAGTCAGGGCATTTAGGGTCT
TCATCACCTTGATTATCATTTCTATGTGTTGAGAACATTTCAAGTTCTCAGT
TCCAGCTATTTTGAAATAGACAGTCCATTTTGTTAGCTACAGTCACCCAAC
CCGGCTGTCAGACATTGGAACTTACTCCTATTGAACTGTGTATTTGTAC[C/
T]CATTCACCAAACTCTCTTTGGGCTTTCAGTTTTACAACTGGGATGATCCT
GGGAAAACTAAAGTAAATCAGACACCCGACGTGTGAGCTAGGTTATAATA
TGCCCAGTGGACCCTGGGGACATCTTAGCTTTCAGAGGTCATGCTGTCCA
AGCTGACTGTGGGGCTTCCAGAAGGTGGGGAGAGGAAATGATGCAAT
SG13S181
TGGGAAAACTAAAGTAAATCAGACACCCGACGTGTGAGCTAGGTT
ATAATATGCCCAGTGGACCCTGGGGACATCTTAGCTTTCAGAGGTCATGC
TGTCCAAGCTGACTGTGGGGCTTCCAGAAGGTGGGGAGAGGAAATGATGC
AATGGCCCATCAGAGGCACTACTTGGGGCCTGGGGCCAGAGTGCATGTCT
AAG[C/G]CATTAAGGGGAGGGGAGAGCAGCCTTCATAATTATGAAGAGGA
GTCTCAGGTGCACAGCTTCTGATGAGGGACAGCTTCTAATTGAAGACAGC
ATTGTGTAATGCTCAAACTCCCTGTCTTCAGAGTGCCTGCTGTATCCCACC
ATCAGTTCTGTGACTTCTCCCTAAGCCTCAATTTTGCATGTGTTACATTGG
GA
SG13S182
CCTGCATAGCAAATTCTTGCAAATGTAGGGACTCAAAACAATATAA
ATTATTATCTGACAGTTTTCTGGGTCAGAGGTCTTACTAGGCTGTAATC
AGAGGGCAACCAAAGCTGTGATCTCAGCTGAAGCTCAGGATTCTCTTCCA
AGCTCACTGGTTGTTGGCAGAATTCAGTTCTTTCCAGTTGGAAGACTAAAG
[C/T]CTACAGTCTTCAGTCTCTAGAAGCCTTTTCTCTGGCACAGGTTTCTCT

FIG. 8.35

ACAACATGGCCATTTATGTCTTTAAGGCCAATAGGAGAACATGATTAGCA
TATTTTTTTAAGTGAACTTTAGACCCTTTTTAAAGGCCTATCTGATTAGG
CCAGGCCCAAGTGAGCTTTAAGTCAACTGATTAGAGATCTTAATTAC

SG13S183

CTGAAGCTCAGGATTCTCTTCCAAGCTCACTGGTTGTTGGCAGAAT
TCAGTTCTTTCCAGTTGGAAGACTAAAGCCTACAGTCTTCAGTCTCTAGAA
GCCTTTTCTCTGGCACAGGTTTCTCTACAACATGGCCATTTATGTCTTTAA
GGCCAATAGGAGAACATGATTAGCATATTTTTTTAAGTGAACTTTAGAC[
C/T]CTTTTTAAAGGCCTATCTGATTAGGCCAGGCCCAAGTGAGCTTTAAG
TCAACTGATTAGAGATCTTAATTACATCTGCAAAGTCCCTTCATGTTTACC
GTATAACATAACTTAGTGAAAGGAGTGAAATTGCAACCAGGTTCTGCCTG
CACTCCACGGAAGGGGATTCTGCAGAAGTGTGGGTCACGGGGGGGTTA

SG13S184

AGAACATGATTAGCATATTTTTTTAAGTGAACTTTAGACCCTTTTT
TAAAGGCCTATCTGATTAGGCCAGGCCCAAGTGAGCTTTAAGTCAACTGA
TTAGAGATCTTAATTACATCTGCAAAGTCCCTTCATGTTTACCGTATAACA
TAACTTAGTGAAAGGAGTGAAATTGCAACCAGGTTCTGCCTGCACTCCAC[
A/G]GAAGGGGATTCTGCAGAAGTGTGGGTCACGGGGGGGTTATTTTGGGA
TTCTGCCTACGTCACTGAGTCAAAAGAAGCTGAATGGTTGTGATGCTGAG
GTTTTTGGGCAGCAGCAGTGTGTGTGTGAGTGAATTCATACGTATGACC
ACCTGGGAAGAAAGGAGGCTGTGGTTTCCTCCACCTCCTGGCAGACAGA

SG13S185

GGGATTACAGACACACACTGCCACGCCTGGCTAATTTTTGTATTTTT
AGTAGAGACGAGGTTTTGCCATGTTGGCCAGGCTGGTCTTGAACTCCTGA
CCTCAAGTGATCCGCCCACCTCAGCCTCCCAAAGTGCTGGGATTACAGAC
GTGAGCCACCATTAACCATTTTTCTATCTCCTGTGGGAAAGGGCACAGTG
A[A/G]AGAACAGATGAAGCTGAGACATACAAGTGAACTCCTCCCTCCTCTC
CATTTAGACTAAAATAGGATTATTCATACTGAGATTCTCCCTGGTTGCAAA
GAGATAATCTGTGCAACTGGGTTTTACAATTATCCCTACCCTATGCTTTC
CTCATCTGTCTTCCTCGTAGTCAGCTCAGGCTGCTATAACAAAACACCA

SG13S405

GGCAGATTCGGTGTCTAATGAGGTCCTGCTTTCCAGTTTATAGACA
GTGCCTTATCGCTACCGCCTTACACAGTGGAAGGAGAGGACGAGAAGCTC
CTTGGGCTTTTTTTGTTTCTTTCTTTCTCTCTCTCTCTTTTTTTTTTTTT
AATAAGGTCACTATCTTAGTCCATTTGTGTTGCTAAAAGGAACATCT[A/G
]AGGTTGAGTAATTTATTTTATTTTAAAAAGTGGCCAGGCATGGAGGCTTA
TCCTGTAACCCTAATCCTTTAGGAGGCCAAAACAGCAGGATTGTTTGAGG
CCAGGAGTTCAAGACCAGCCTAGGCAAGATAGTGAGACCCCATCTACCCC
ATCTCTACTAAAATTTTAAAAAATTAGCTGTGTGTTGTAAAGTGTGC

SG13S91

AATTTATTTTATTTTAAAAAGTGGCCAGGCATGGAGGCTTATCCTGT
AACCCTAATCCTTTAGGAGGCCAAAACAGCAGGATTGTTTGAGGCCAGGA
GTTCAAGACCAGCCTAGGCAAGATAGTGAGACCCCATCTACCCCATCTCT
ACTAAAATTTTAAAAAATTAGCTGTGTGTTGTAAAGTGTGCTTGTAGTCCC
[A/G]GCCACTTGAGAGGCTGAGGTGGGTGGAGTTCAAGGCTGCAGTGAGT
TATGATTGAGCCACTGCACTCCAACCCGGGTAACGGGGCAAGACCTTGTC
TCTATTTAAAAAAAAAAAATCTTTATGTGGCTCACTATTCTGGGTGGCTGG
AAAGTTCAAGATTGGGCATCTGCATCTGGTGACAGCCTCATGTCGCTTCC

SG13S186

TAACCCTAATCCTTTAGGAGGCCAAAACAGCAGGATTGTTTGAGGC

FIG. 8.36

CAGGAGTTCAAGACCAGCCTAGGCAAGATAGTGAGACCCCATCTACCCCA
TCTCTACTAAAATTTTAAAAAATTAGCTGTGTGTTGTAAAGTGTGCTTGTA
GTCCCGGCCACTTGAGAGGCTGAGGTGGGTGGAGTTCAAGGCTGCAGTGA
G[A/T]TATGATTGAGCCACTGCACTCCAACCCGGGTAACGGGGCAAGACCT
TGTCTCTATTTAAAAAAAAAAAATCTTTATGTGGCTCACTATTCTGGGTGG
CTGGAAAGTTCAAGATTGGGCATCTGCATCTGGTGACAGCCTCATGTCGC
TTCCAGTCATGGGGGAAGACGAAGGAGAGCTGGCACGTGCAGATATCAC
G

SG13S187

ATCCTTTAGGAGGCCAAAACAGCAGGATTGTTTGAGGCCAGGAGTT
CAAGACCAGCCTAGGCAAGATAGTGAGACCCCATCTACCCCATCTCTACT
AAAATTTTAAAAAATTAGCTGTGTGTTGTAAAGTGTGCTTGTAGTCCCGGC
CACTTGAGAGGCTGAGGTGGGTGGAGTTCAAGGCTGCAGTGAGTTATGAT
T[A/G]AGCCACTGCACTCCAACCCGGGTAACGGGGCAAGACCTTGTCTCTA
TTTAAAAAAAAAAAATCTTTATGTGGCTCACTATTCTGGGTGGCTGGAAA
GTTCAAGATTGGGCATCTGCATCTGGTGACAGCCTCATGTCGCTTCCAGTC
ATGGGGGAAGACGAAGGAGAGCTGGCACGTGCAGATATCACGTGTTGAG
G

SG13S188

TTAAAAAATTAGCTGTGTGTTGTAAAGTGTGCTTGTAGTCCCGGCC
ACTTGAGAGGCTGAGGTGGGTGGAGTTCAAGGCTGCAGTGAGTTATGATT
GAGCCACTGCACTCCAACCCGGGTAACGGGGCAAGACCTTGTCTCTATTT
AAAAAAAAAAAATCTTTATGTGGCTCACTATTCTGGGTGGCTGGAAAGTT
CA[A/G]GATTGGGCATCTGCATCTGGTGACAGCCTCATGTCGCTTCCAGTC
ATGGGGGAAGACGAAGGAGAGCTGGCACGTGCAGATATCACGTGTTGAG
GGCAGAAGCGAGAGAGAGAGGGGAGAGATGCCAGGCTCTTTTTAACAAC
CAGCACTGGGGAAACTAATAGAGTGAGAGCTCACTGACTCCTGAGGGAG
GACAT

SG13S406

ATGGGGGAAGACGAAGGAGAGCTGGCACGTGCAGATATCACGTGT
TGAGGGCAGAAGCGAGAGAGAGAGGGGAGAGATGCCAGGCTCTTTTTAA
CAACCAGCACTGGGGAAACTAATAGAGTGAGAGCTCACTGACTCCTGAGG
GAGGACATTAATCTATTGATGAGCGACCTGCCTCCATGACCCAAACACCT
CCAA[C/T]GATACCCCACCTCCAACACTGCCACACTAGGGATTAACTTTCA
ACTTGAGATTTAGAGGGGGGAAACTTACAAACTATCGCAGGCACTAATAC
CACTCATGAGGGCTCCACCTTCATGACCTAATCACTTCCTAAAGGCCTTAC
CTCTTAATCTCATCACATTGAGGATTCGATTTCAACTTGAATTTTGGGGGG
AC

SG13S92

CTCGCTGCCACCTGAAATTAGATCATTTATTTACCCCTTTATTTGTT
CAGTTTGCCTTGTCCGTTAGAATATAAGCTTCCAAAGGGCAGGAGCTTTGC
CTATATTGTAGGCCGGGCATACAATGAGCACTCAAAAAAATATTTGATG
AGTGTATGAAAGAACAGACTGGGTTATGTAATTGTGCCTACTTACCTATA[
C/T]GACCGTGTGGTGGGGTTTATGGTGGGTGTGGTGGTGATGGCTATAGG
GCTATAAGCAAATTTGGGACAGGGAGTCTAAGAAATGTTCTTAAATTTTA
GTAAGCAAAGCATCCTCTACAGAACCTGTCTTAAAACATGAAAGTTCCTT
AGTGCTACCCCCAGAGGTATGATTTGGTAGGTCAAGGATAGGGCCTGGAA

SG13S93

TGCCACCTGAAATTAGATCATTTATTTACCCCTTTATTTGTTCAGTT
TGCCTTGTCCGTTAGAATATAAGCTTCCAAAGGGCAGGAGCTTTGCCTATA

FIG. 8.37

TTGTTAGGCCGGGCATACAATGAGCACTCAAAAAAATATTTGATGAGTGT
ATGAAAGAACAGACTGGGTTATGTAATTGTGCCTACTTACCTATATGACC[
A/G]TGTGGTGGGGTTTATGGTGGGTGTGGTGGTGATGGCTATAGGGCTAT
AAGCAAATTTGGGACAGGGAGTCTAAGAAATGTTCTTAAATTTTAGTAAG
CAAAGCATCCTCTACAGAACCTGTCTTAAAACATGAAAGTTCCTTAGTGCT
ACCCCCAGAGGTATGATTTGGTAGGTCAAGGATAGGGCCTGGAAATTCA

SG13S36

CCTGTCTTAAAACATGAAAGTTCCTTAGTGCTACCCCCAGAGGTAT
GATTTGGTAGGTCAAGGATAGGGCCTGGAAATTCACATTCTTGTTAAGAT
GTTCTTCATCCGGGGTTTGTTGACCACCTTTTCAGAAGATTTTGCTCTGTA
GCTGTACTACCCAATGCAGTAGTTCGTAGTCAGTGTGGCTCCTGAGCCCT[
C/T]GAAGTGTAGCTCCTCTGAACTGAGACGTGCTGTAAATGTAAATTGCA
CACCGGAGTTTGAAGAGTTAATACAAAGAAAAAGGAATGCAAAACATCT
CATTAATAATGCTTTACACTGATTACATATTGAAATGGTAATCTTGTAGAT
ATAGTGCGTTAAATAAAATATACTGTTAGGCTTAATTTCACGTCTTTATA

SG13S407

TCAGCCAATCAACAAGAGGGCAAAAGAACAAACATTTGATGTGTA
ATTACTTAATTTAGTGCATATGCATTTGGGTCCTCAATGTCAGCACTATGG
CAACCAGAACATGGCCACAATAACTGTCTGGAAATGTCTATTCTTACCTG
GACCCAGCAGGCCATGCCCCACTGATTATATAATCTCCCTCTCTCCTTGTT
A[C/T]GGTCTGAATGCTTGCATCCCTCAAAAATTCATGTGTTGAAATCCTA
ACCCCCAAGGTGATGATATTAGGAGGTCGGCCTTTTGAGAGGTAATTAGG
TCATGAAGACAGCATCCTCATGAATGGGATTAGTGTCCTTATAAAATAGG
CCCAAGGGAGCTCATTCACTTTGTCCACCATGTGAGAACACAGCGAGAGG
G

SG13S408

CCTTGTTACGGTCTGAATGCTTGCATCCCTCAAAAATTCATGTGTTG
AAATCCTAACCCCCAAGGTGATGATATTAGGAGGTCGGCCTTTTGAGAGG
TAATTAGGTCATGAAGACAGCATCCTCATGAATGGGATTAGTGTCCTTATA
AAATAGGCCCAAGGGAGCTCATTCACTTTGTCCACCATGTGAGAACACAG
[C/T]GAGAGGGCACCATTTATGCACCAGGAAATGGGCCTTTTCCAGACAAT
CTGTCGGTGCCTGGATCTTGGACTTCACAGCCTCTAGAACTGTGAGAAATT
AATTTGTTTTTTATAAGCCACCAAATCTATGGTTTTTTTATAGAAACCGTA
ATGGACTAAAACACTCCCTAATTATATTTAAACTTATCAGTGCACTG

SG13S7

CTAACCCCCAAGGTGATGATATTAGGAGGTCGGCCTTTTGAGAGGT
AATTAGGTCATGAAGACAGCATCCTCATGAATGGGATTAGTGTCCTTATA
AAATAGGCCCAAGGGAGCTCATTCACTTTGTCCACCATGTGAGAACACAG
CGAGAGGGCACCATTTATGCACCAGGAAATGGGCCTTTTCCAGACAATCT
GT[C/T]GGTGCCTGGATCTTGGACTTCACAGCCTCTAGAACTGTGAGAAAT
TAATTTGTTTTTTATAAGCCACCAAATCTATGGTTTTTTTATAGAAACCGT
AATGGACTAAAACACTCCCTAATTATATTTAAACTTATCAGTGCACTGGGC
AGTGACATATTAAAAGAATGCTGGCCAACGTAATTGACACCATAAGGCT

SG13S37

TCATCTCATTTTAACCTTTTGTTTCAAAGCCTCTCTTTTCATGACTTC
CCCGCCTTCATTTTTCCCATATGGTGGGGTTATTATTAAGACATTAAATGA
GAGTGGACAGGTAGGCAAAGGAGGTGGGTTGCAGGGGAGTTGAGGGTTG
CCTGTGTACTTTTCTAGACTGTTCCACTTCACATCAGTGAAATATTCCCA[A
/G]TTGATACTATCATGAAACAAAGCAAATGAAATGCTGAGCACGGAGCTT
CGTCTTGATGAAATGCTGAAAGAAAAGAAAGGAAAAATAAAGTAGCCAT

FIG. 8.38

TATTTTTGCCCTTCCTCCCACCCCCATGTTTACTACTCTTATTTCTCTTTTGT
ATTGTTGTGTTGGAAGCACAGCATCAGAAAAACTCCCAGTTTTGAGA

SG13S409

ACAGGTAGGCAAAGGAGGTGGGTTGCAGGGGAGTTGAGGGTTGCC
TGTGTACTTTTCTAGACTGTTCCACTTCACATCAGTGAAATATTCCCAATT
GATACTATCATGAAACAAAGCAAATGAAATGCTGAGCACGGAGCTTCGTC
TTGATGAAATGCTGAAAGAAAAGAAAGGAAAAATAAAGTAGCCATTATTT
TT[A/G]CCCTTCCTCCCACCCCCATGTTTACTACTCTTATTTCTCTTTTGTAT
TGTTGTGTTGGAAGCACAGCATCAGAAAAACTCCCAGTTTTGAGAGATAA
CTCAGTGTTTAGTTCACTTAAACCTGAGAAGGAGAAGAGGATGCCACCG
TGAGGTCCAGGACGTAAAGAGGAAAAAAACAGACAAAAAATCCATATG
A

SG13S8

CAGGTAGGCAAAGGAGGTGGGTTGCAGGGGAGTTGAGGGTTGCCT
GTGTACTTTTCTAGACTGTTCCACTTCACATCAGTGAAATATTCCCAATTG
ATACTATCATGAAACAAAGCAAATGAAATGCTGAGCACGGAGCTTCGTCT
TGATGAAATGCTGAAAGAAAAGAAAGGAAAAATAAAGTAGCCATTATTTT
TG[A/C]CCTTCCTCCCACCCCCATGTTTACTACTCTTATTTCTCTTTTGTATT
GTTGTGTTGGAAGCACAGCATCAGAAAAACTCCCAGTTTTGAGAGATAAC
TCAGTGTTTAGTTCACTTAAACCTGAGAAGGAGAAGAGGATGCCACCGT
GAGGTCCAGGACGTAAAGAGGAAAAAAACAGACAAAAAATCCATATGA
A

SG13S410

TTCGTCTTGATGAAATGCTGAAAGAAAAGAAAGGAAAAATAAAGT
AGCCATTATTTTTGCCCTTCCTCCCACCCCCATGTTTACTACTCTTATTTCT
CTTTTGTATTGTTGTGTTGGAAGCACAGCATCAGAAAAACTCCCAGTTTTG
AGAGATAACTCAGTGTTTAGTTCACTTAAACCTGAGAAGGAGAAGAGGA
[C/T]GCCACCGTGAGGTCCAGGACGTAAAGAGGAAAAAAACAGACAAAA
AAATCCATATGAAATGAAAATGTGAAAGAGGCGCTTTCGAGCAGATGAGT
GTTGTAGATTACAGTGTTGAGAGCTGTTTGTGTCCAGAGCTGCTTGCTGCA
CCTGGCGGGATAAACACTGGTCTAACAGAGGATCCTTGTTTCAAGGAGGC
T

SG13S411

AAGAAAAGAAAGGAAAAATAAAGTAGCCATTATTTTTGCCCTTCCT
CCCACCCCCATGTTTACTACTCTTATTTCTCTTTTGTATTGTTGTGTTGGAA
GCACAGCATCAGAAAAACTCCCAGTTTTGAGAGATAACTCAGTGTTTAGT
TCACTTAAACCTGAGAAGGAGAAGAGGATGCCACCGTGAGGTCCAGGA
C[A/G]TAAAGAGGAAAAAAACAGACAAAAAATCCATATGAAATGAAAA
TGTGAAAGAGGCGCTTTCGAGCAGATGAGTGTTGTAGATTACAGTGTTGA
GAGCTGTTTGTGTCCAGAGCTGCTTGCTGCACCTGGCGGGATAAACACTG
GTCTAACAGAGGATCCTTGTTTCAAGGAGGCTGCCTTTTATTTGGGGGGAC
AA

SG13S9

ATTATTTTTGCCCTTCCTCCCACCCCCATGTTTACTACTCTTATTTCT
CTTTTGTATTGTTGTGTTGGAAGCACAGCATCAGAAAAACTCCCAGTTTTG
AGAGATAACTCAGTGTTTAGTTCACTTAAACCTGAGAAGGAGAAGAGGA
TGCCACCGTGAGGTCCAGGACGTAAAGAGGAAAAAAACAGACAAAAAA
[C/T]CCATATGAAATGAAAATGTGAAAGAGGCGCTTTCGAGCAGATGAGT
GTTGTAGATTACAGTGTTGAGAGCTGTTTGTGTCCAGAGCTGCTTGCTGCA

FIG. 8.39

CCTGGCGGGATAAACACTGGTCTAACAGAGGATCCTTGTTTCAAGGAGGC
TGCCTTTTATTTGGGGGGACAAAATTGTTCTTGAAAGCTGCTCAGTGGTT

SG13S412

TTTGTATTGTTGTGTTGGAAGCACAGCATCAGAAAAACTCCCAGTT
TTGAGAGATAACTCAGTGTTTAGTTCACTTAAACCTGAGAAAGGAGAAGA
GGATGCCACCGTGAGGTCCAGGACGTAAAGAGGAAAAAAACAGACAAAA
AAATCCATATGAAATGAAAATGTGAAAGAGGCGCTTTCGAGCAGATGAGT
GTT[A/G]TAGATTACAGTGTTGAGAGCTGTTTGTGTCCAGAGCTGCTTGCT
GCACCTGGCGGGATAAACACTGGTCTAACAGAGGATCCTTGTTTCAAGGA
GGCTGCCTTTTATTTGGGGGGACAAAATTGTTCTTGAAAGCTGCTCAGTGG
TTCAAGCTACAGCATGGTGGACTAGCAGAATGGACTCCAGGGCCTCCGAG
GA

SG13S413

TTTTGAGAGATAACTCAGTGTTTAGTTCACTTAAACCTGAGAAAGG
AGAAGAGGATGCCACCGTGAGGTCCAGGACGTAAAGAGGAAAAAAACAG
ACAAAAAAATCCATATGAAATGAAAATGTGAAAGAGGCGCTTTCGAGCA
GATGAGTGTTGTAGATTACAGTGTTGAGAGCTGTTTGTGTCCAGAGCTGCT
TGC[C/T]GCACCTGGCGGGATAAACACTGGTCTAACAGAGGATCCTTGTTT
CAAGGAGGCTGCCTTTTATTTGGGGGGACAAAATTGTTCTTGAAAGCTGCT
CAGTGGTTCAAGCTACAGCATGGTGGACTAGCAGAATGGACTCCAGGGCC
TCCGAGGAGACAGTGACTGCTGCCAGAAATAGTCAAGGATAGAAAGGAA
GGA

FIG. 8.40

SUSCEPTIBILITY GENE FOR MYOCARDIAL INFARCTION, STROKE, AND PAOD; METHODS OF TREATMENT

RELATED APPLICATIONS

This application is a continuation-in-part of U.S. patent application Ser. No. 10/769,744, filed on Jan. 30, 2004, which is a continuation-in-part of International Application No. PCT/US03/32556, which designated the United States and was filed on Oct. 16, 2003, published in English, which claims the benefit of U.S. Provisional Application No. 60/419,433, filed on Oct. 17, 2002 and U.S. Provisional Application No. 60/449,331, filed on Feb. 21, 2003. The entire teachings of the above applications are incorporated herein by reference.

BACKGROUND OF THE INVENTION

Myocardial infarction (MI) and Acute Coronary Syndrome (ACS), e.g., unstable angina, non-ST-elevation myocardial infarction (NSTEMI) or ST-elevation myocardial infarction (STEMI), are the leading causes of hospital admissions in industrialized countries. Cardiovascular disease continues to be the principle cause of death in the United States, Europe and Japan. The costs of the disease are high both in terms of morbidity and mortality, as well as in terms of the financial burden on health care systems.

Myocardial infarction generally occurs when there is an abrupt decrease in coronary blood flow following a thrombotic occlusion of a coronary artery previously damaged by atherosclerosis. In most cases, infarction occurs when an atherosclerotic plaque fissures, ruptures or ulcerates and when conditions favor thrombogenesis. In rare cases, infarction may be due to coronary artery occlusion caused by coronary emboli, congenital abnormalities, coronary spasm, and a wide variety of systemic, particularly inflammatory diseases. Medical risk factors for MI include cigarette smoking, diabetes, hypertension and serum total cholesterol levels >200 mg/dL, elevated serum LDL cholesterol, and low serum HDL cholesterol. Event rates in individuals without a prior history of cardiovascular disease are about 1%. In individuals who have had a first MI or ACS, the risk of a repeat MI within the next year is 10-14%, despite maximal medical management including angioplasty and stent placement.

Atherosclerosis can affect vascular beds in many large and medium arteries. Myocardial infarction and unstable angina (acute coronary syndrome (ACS)) stem from coronary artery atherosclerosis, while ischemic stroke most frequently is a consequence of carotid or cerebral artery atherosclerosis. Limb ischemia caused by peripheral arterial occlusive disease (PAOD) may occur as a consequence of iliac, femoral and popliteal artery atherosclerosis. The atherosclerotic diseases remain common despite the wide-spread use of medications that inhibit thrombosis (aspirin) or treat medical risk factors such as elevated cholesterol levels in blood (statins), diabetes, or hypertension (diuretics and anti-hypertensives).

Atherosclerotic disease is initiated by the accumulation of lipids within the artery wall, and in particular, the accumulation of low-density lipoprotein (LDL) cholesterol. The trapped LDL becomes oxidized and internalized by macrophages. This causes the formation of atherosclerotic lesions containing accumulations of cholesterol-engorged macrophages, referred to as "foam cells". As disease progresses, smooth muscle cells proliferate and grow into the artery wall forming a "fibrous cap" of extracellular matrix enclosing a lipid-rich, necrotic core. Present in the arterial walls of most people throughout their lifetimes, fibrous atherosclerotic plaques are relatively stable. Such fibrous lesions cause extensive remodeling of the arterial wall, outwardly displacing the external, elastic membrane, without reduction in luminal diameter or serious impact on delivery of oxygen to the heart. Accordingly, patients can develop large, fibrous atherosclerotic lesions without luminal narrowing until late in the disease process. However, the coronary arterial lumen can become gradually narrowed over time and in some cases compromise blood flow to the heart, especially under high demand states such as exercise. This can result in reversible ischemia causing chest pain relieved by rest called stable angina.

In contrast to the relative stability of fibrous atherosclerotic lesions, the culprit lesions associated with myocardial infarction and unstable angina (each of which are part of the acute coronary syndrome) are characterized by a thin fibrous cap, a large lipid core, and infiltration of inflammatory cells such as T-lymphocytes and monocyte/macrophages. Non-invasive imaging techniques have shown that most MI's occur at sites with low- or intermediate-grade stenoses, indicating that coronary artery occlusion is due most frequently to rupture of culprit lesions with consequent formation of a thrombus or blood clot and not solely due to luminal narrowing by stenosis. Plaque rupture may be due to erosion or uneven thinning of the fibrous cap, usually at the margins of the lesion where macrophages enter, accumulate, and become activated by a local inflammatory process. Thinning of the fibrous cap may result from degradation of the extracellular matrix by proteases released from activated macrophages. These changes producing plaque instability and risk of MI may be augmented by production of tissue-factor procoagulant and other factors increasing the likelihood of thrombosis.

In acute coronary syndrome, the culprit lesion showing rupture or erosion with local thrombosis typically is treated by angioplasty or by balloon dilation and placement of a stent to maintain luminal patency. Patients experiencing ACS are at high risk for a second coronary event due to the multi-vessel nature of coronary artery disease with event rates approaching 10-14% within 12 months after the first incident.

The emerging view of MI is as an inflammatory disease of the arterial vessel wall on preexisting chronic atherosclerotic lesions, sometimes triggering rupture of culprit lesions and leading to local thrombosis and subsequent myocardial infarction. The process that triggers and sustains arterial wall inflammation leading to plaque instability is unknown, however, it results in the release into the circulation of tumor necrosis factor alpha and interleukin-6. These and other cytokines or biological mediators released from the damaged vessel wall stimulate an inflammatory response in the liver causing elevation in several non-specific general inflammatory markers including C-reactive protein. Although not specific to atherosclerosis, elevated C-reactive protein (CRP) and serum amyloid A appear to predict risk for MI, perhaps as surrogates for vessel wall inflammation.

Although classical risk factors such as smoking, hyperlipidemia, hypertension, and diabetes are associated with many cases of coronary heart disease (CHD) and MI, many patients do not have involvement of these risk factors. In fact, many patients who exhibit one or more of these risk factors do not develop MI. Family history has long been recognized as one of the major risk factors. Although some of the familial clustering of MI reflects the genetic contribution to the other conventional risk factors, a large number of studies have suggested that there are significant genetic susceptibility factors, beyond those of the known risk factors (Friedlander Y, et al., *Br. Heart J.* 1985; 53:382-7, Shea S. et al., *J. Am. Coll.*

Cardiol. 1984; 4:793-801, and Hopkins P. N., et al., *Am. J. Cardiol.* 1988; 62:703-7). Major genetic susceptibility factors have only been identified for the rare Mendelian forms of hyperlipidemia such as a familial hypercholesterolemia.

Genetic risk is conferred by subtle differences in genes among individuals in a population. Genes differ between individuals most frequently due to single nucleotide polymorphisms (SNP), although other variations are also important. SNP are located on average every 1000 base pairs in the human genome. Accordingly, a typical human gene containing 250,000 base pairs may contain 250 different SNP. Only a minor number of SNP are located in exons and alter the amino acid sequence of the protein encoded by the gene. Most SNP have no effect on gene function, while others may alter transcription, splicing, translation, or stability of the mRNA encoded by the gene. Additional genetic polymorphism in the human genome is caused by insertion, deletion, translocation, or inversion of either short or long stretches of DNA. Genetic polymorphisms conferring disease risk may therefore directly alter the amino acid sequence of proteins, may increase the amount of protein produced from the gene, or may decrease the amount of protein produced by the gene.

As genetic polymorphisms conferring risk of disease are uncovered, genetic testing for such risk factors is becoming important for clinical medicine. Examples are apolipoprotein E testing to identify genetic carriers of the apoE4 polymorphism in dementia patients for the differential diagnosis of Alzheimer's disease, and of Factor V Leiden testing for predisposition to deep venous thrombosis. More importantly, in the treatment of cancer, diagnosis of genetic variants in tumor cells is used for the selection of the most appropriate treatment regime for the individual patient. In breast cancer, genetic variation in estrogen receptor expression or heregulin type 2 (Her2) receptor tyrosine kinase expression determine if anti-estrogenic drugs (tamoxifen) or anti-Her2 antibody (Herceptin) will be incorporated into the treatment plan. In chronic myeloid leukemia (CML) diagnosis of the Philadelphia chromosome genetic translocation fusing the genes encoding the Bcr and Abl receptor tyrosine kinases indicates that Gleevec (STI571), a specific inhibitor of the Bcr-Abl kinase should be used for treatment of the cancer. For CML patients with such a genetic alteration, inhibition of the Bcr-Abl kinase leads to rapid elimination of the tumor cells and remission from leukemia.

Many general inflammatory markers predict risk of coronary heart disease, although these markers are not specific to atherosclerosis. For example, Stein (Stein, S., *Am J Cardiol*, 87 (suppl):21A-26A (2001)) discusses the use of any one of the following serum inflammatory markers as surrogates for predicting risk of coronary heart disease including C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, and matrix metalloprotease type-9. Elevation in one more of these serum inflammatory markers is not specific to coronary heart disease but also occurs with age or in association with cerebrovascular disease, peripheral vascular disease, non-insulin dependent diabetes, osteoarthritis, bacterial infection, and sepsis.

Serum C-reactive protein (CRP) is viewed as a convenient and sensitive marker of systemic inflammation. Generally CRP is measured in serum samples using commercially available enzyme-linked immunosorbent assays (EIA). Consistent across multiple published studies is the finding of a correlation between increased risk for coronary artery disease with increased serum CRP. For example, in the Women's Health Study, CRP was measured in 27,939 apparently healthy American women. The cut-off points for quintiles of serum CRP in women were: less than or equal to 0.49, more than 0.49 to 1.08, more than 1.08 to 2.09, more than 2.09 to 4.19, and more than 4.19 mg CRP per liter, see Ridker, P. M. et al., *New England. J. Med.*, 347: 1557-1565 (2001). In comparison to the lowest quintile, and even when adjusting for age, every quintile more than 0.49 mg CRP per liter was associated with increased risk for coronary heart disease with the highest relative risk of 4.5 seen for those women in the highest quintile of serum CRP (more than 4.19 mg CRP per liter). A similar correlation between increased serum CRP and increased risk for coronary heart disease in women has been reported (Ridker, P. M et al., *New Engld. J. Med.*, 342:836-843 (2000) and Bermudez, E. A. et. al., *Arterioscler. Thromb. Vasc. Biol.*, 22: 1668-1673 (2002)). Men also show a correlation between increased serum inflammatory markers such as CR and increased risk for coronary heart disease has been reported (Doggen, C. J. M. et al., *J. Internal Med.*, 248:406-414 (2000) and Ridker, P. M. et al., *New England. J. Med.*, 336: 973-979 (1997)). Quintiles for serum CRP as reported by Doggen et al., were less than 0.65, more than 0.65 to 1.18, more than 1.18 to 2.07, more than 2.07 to 4.23, and more than 4.23 mg CRP per liter. Unlike women, elevated serum CRP correlates with increased relative risk for coronary heart disease only in the $4^{th}$ and $5^{th}$ quintiles of CRP (relative risk of 1.7× and 1.9×, respectively).

Serum CRP in women also has been measured in conjunction with lipid markers such as levels of serum low density lipoprotein-cholesterol (LDL-C). In the study by Ridker, P. M. et al. (2002), serum CRP and LDL-C are minimally correlated, screening for both serum markers provided better prognostic indication than either alone. Thus, women with serum CRP above median values (more than 1.52 mg CRP per liter) and also serum LDL-C above median values (more than 123.7 mg LDL-C per deciliter) were at highest risk for coronary heart disease.

Elevated CRP or other serum inflammatory markers is also prognostic for increased risk of a second myocardial infarct in patients with a previous myocardial infarct (Retterstol, L. et al., *Atheroscler.*, 160: 433-440 (2002)).

Since CRP is produced in the liver, there is no a priori mechanistic explanation for why elevation in CRP and other serum inflammatory markers should be prognostic for coronary artery disease. As discussed by Doggen, C. J. M., et al., one or more of the following factors were speculated to account for the correlation observed: (1) intrinsic inflammation and tissue damage within arterial lesions, (2) prior infection by *Helicobacter pylori* or by *Chlamydia pneumoniae*, (3) release of peptide cytokines including interleukin-6, or (4) activation of the complement system.

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. LTC4, LTD4, and LTE4, are known to induce vasoconstriction. Allen et al., *Circulation*, 97:2406-2413 (1998) described a novel mechanism in which atherosclerosis is associated with the appearance of a leukotriene receptor(s) capable of inducing hyperactivity of human epicardial coronary arteries in response to LTC4 and LTD4. LTB4, on the other hand, is a strong proinflammatory agent. Increased production of these end products, of the leukotriene pathway, could therefore serve as a risk factor for MI and atherosclerosis, whereas both inflammation and vasoconstriction/vasospasm have a well established role in the pathogenesis of MI and atherosclerosis. It has also been shown that a heterozygous deficiency of the 5-LO enzyme in a knockout mouse model decreases atherosclerotic lesion size in LDLR−/− mice by about 95%. (Mehrabian et al., *Circulation Research*. 91:120 (2002)). However, such genetic evidence for leukotriene involvement in MI or atherosclerosis in humans has not been reported. Mehrabian et al. did report a very small genetic association study looking for correlation between promoter polymorphisms of 5-LO and carotid intimal thickening in normal individuals. However, their data paradoxically suggest that a lower amount of leukotriene production correlates with carotid atherosclerosis.

SUMMARY OF THE INVENTION

As described herein, a gene on chromosome 13q12-13 has been identified as playing a major role in myocardial infarction (MI). This gene, herein after referred to as the MI gene, comprises nucleic acid that encodes 5-lipoxygenase activating protein (ALOX5AP or FLAP,) herein after referred to as FLAP. The gene has also been shown to play a role in stroke and PAOD.

The invention pertains to methods of treatment (prophylactic and/or therapeutic) for certain diseases and conditions (e.g., MI, ACS, atherosclerosis, stroke, PAOD) associated with FLAP or with other members of the leukotriene pathway (e.g., biosynthetic enzymes or proteins such as FLAP, arachidonate 4-lipoxygenase (5-LO), leukotriene C4 synthase (LTC4S), leukotriene A4 hydrolase (LTA4H), leukotriene B4 12-hydroxydehydrogenase (LTB4DH)); receptors and/or binding agents of the enzymes; and receptors for the leukotrienes LTA4, LTB4, LTC4, LTD4, LTE4, Cys LT1, Cys LT2, including leukotriene B4 receptor 1 (BLT1), leukotriene B4 receptor 2 (BLT2), cysteinyl leukotriene receptor 1 (CysLTR1), cysteinyl leukotriene receptor 2 (CysLTR2). The methods include the following: methods of treatment for myocardial infarction or susceptibility to myocardial infarction; methods of treatment for transient ischemic attack, transient monocular blindness or stroke, or susceptibility to stroke; methods of treatment for claudication, PAOD or susceptibility to PAOD; methods of treatment for acute coronary syndrome (e.g., unstable angina, non-ST-elevation myocardial infarction (NSTEMI) or ST-elevation myocardial infarction (STEMI)); methods for reducing risk of MI, stroke or PAOD in persons with asymptomatic ankle/brachial index less than 0.9; methods for decreasing risk of a second myocardial infarction or stroke; methods of treatment for atherosclerosis, such as for patients requiring treatment (e.g., angioplasty, stents, revascularization procedure) to restore blood flow in arteries (e.g., coronary, carotid, and/or femoral arteries); methods of treatment for asymptomatic ankle/brachial index of less than 0.9; and/or methods for decreasing leukotriene synthesis (e.g., for treatment of myocardial infarction, stroke or PAOD).

In the methods of the invention, a leukotriene synthesis inhibitor is administered to an individual in a therapeutically effective amount. The leukotriene synthesis inhibitor can be an agent that inhibits or antagonizes a member of the leukotriene synthesis pathway (e.g., FLAP, 5-LO, LTC4S, LTA4H, and LTB4DH). For example, the leukotriene synthesis inhibitor can be an agent that inhibits or antagonizes FLAP polypeptide activity (e.g., a FLAP inhibitor) and/or FLAP nucleic acid expression, as described herein (e.g., a FLAP nucleic acid antagonist). In another embodiment, the leukotriene synthesis inhibitor is an agent that inhibits or antagonizes polypeptide activity and/or nucleic acid expression of another member of the leukotriene biosynthetic pathway (e.g., LTC4S, LTA4H) or that increases breakdown of leukotrienes (e.g., LTB4DH). In preferred embodiments, the agent alters activity and/or nucleic acid expression of FLAP or of 5-LO. Preferred agents include those set forth in the Agent Table herein. In another embodiment, preferred agents can be: 1-((4-chlorophenyl)methyl)-3-((1,1-dimethylethyl)thio)-alpha,alpha-dimethyl-5-(2-quinolinylmethoxy)-1H-Indole-2-propanoic acid otherwise known as MK-0591, (R)-(+)-alpha-cyclopentyl-4-(2-quinolinylmethoxy)-Benzeneacetic acid otherwise known as BAY-x-1005, 3-(3-(1,1-dimethyl-ethylthio-5-(quinoline-2-ylmethoxy)-1-(4-chloromethylphenyl)indole-2-yl)-2,2-dimethylpropionaldehyde oxime-0-2-acetic acid otherwise known as A-81834, optically pure enantiomers, salts, chemical derivatives, and analogues; or can be zileuton, atreleuton, 6-((3-fluoro-5-(tetrahydro-4-methoxy-2H-pyran-4yl)phenoxy)methyl)-1-methyl-2(1H)-quinlolinone otherwise known as ZD-2138, 1-((4-chlorophenyl)methyl)-3-((1,1dimethylethyl)thio)-alpha,alpha-dimethyl-5-(2-quinolinylmethoxy)-1H-Indole-2-propanoic acid otherwise known as MK-886, 4-(3-(4-(2-Methyl-imidazol-1-yl)-phenylsulfanyl)-phenyl)-tetrahydro-pyran-4-carboxylic acid amide otherwise known as CJ-13610, their optically pure enantiomers, salts, chemical derivatives, and analogues. In another embodiment, the agent alters metabolism or activity of a leukotriene (e.g., LTA4, LTB4, LTC4, LTD4, LTE4, Cys LT1, Cys LT2), such as leukotriene antagonists or antibodies to leukotrienes, as well as agents which alter activity of a leukotriene receptor (e.g., BLT1, BLT2, CysLTR1, and CysLTR2).

In certain embodiments of the invention, the individual is an individual who has at least one risk factor, such as an at-risk haplotype for myocardial infarction, stroke or PAOD; an at-risk haplotype in the FLAP gene; a polymorphism in a FLAP nucleic acid; an at-risk polymorphism in the 5-LO gene promoter, diabetes; hypertension; hypercholesterolemia; elevated triglycerides; elevated lp(a); obesity; ankle/brachial index (ABI) less than 0.9; a past or current smoker; transient ischemic attack; transient monocular blindness; carotid endarterectomy; asymptomatic carotid stenosis; claudicatioin; limb ischemia leading to gangrene, ulceration or amputation; a vascular or peripheral artery revascularization graft; an elevated inflammatory marker (e.g., a marker such as C-reactive protein (CRP), serum amyloid A, fibrinogen, a leukotriene, a leukotriene metabolite, interleukin-6, tissue necrosis factor-alpha, a soluble vascular cell adhesion molecule (sVCAM), a soluble intervascular adhesion molecule (sICAM), E-selectin, matrix metalloprotease type-1, matrix metalloprotease type-2, matrix metalloprotease type-3, matrix metalloprotease type-9, myeloperoxidase (MPO), and N-tyrosine); increased LDL cholesterol and/or decreased HDL cholesterol; increased leukotriene synthesis; and/or at least one previous myocardial infarction, ACS, stable angina, previous transient ischemic attack, transient monocular blindness, or stroke, asymptomatic carotid stenosis or carotid endarterectomy, atherosclerosis, requires treatment for restoration of coronary artery blood flow (e.g., angioplasty, stent, revascularization procedure).

The invention additionally pertains to methods of assessing an individual for an increased risk of MI, ACS, atherosclerosis, stroke, or PAOD, by assessing a level of a leukotriene metabolite (e.g., LTE4, LTD4, LTB3) in the individual (e.g., in a sample of blood, serum, plasma or urine). An increased level of leukotriene metabolite is indicative of an increased risk. The invention also encompasses methods of assessing an individual for an increased risk of MI, ACS, atherosclerosis, stroke, transient ischemic attack, transient monocular blindness, asymptomatic carotid stenosis, PAOD, claudication, or limb ischemia, by stimulating production of a leukotriene or a leukotriene metabolite in a test sample from the individual (e.g., a sample comprising neutrophils), using a calcium ionophore, and comparing the level of the leukotriene or leukotriene metabolite with a control level. A level of production of the leukotriene or leukotriene metabolite that is significantly greater than the control level, is indicative of increased risk.

The invention further pertains to methods of assessing response to treatment with a leukotriene synthesis inhibitor, by assessing a level of a leukotriene or leukotriene metabolite in the individual before treatment, and comparing the level to a level of the leukotriene or leukotriene metabolite assessed during or after treatment. A level that is significantly lower during or after treatment, than before treatment, is indicative of efficacy of the treatment with the leukotriene synthesis inhibitor. The invention additionally pertains to methods of assessing response to treatment with a leukotriene synthesis inhibitor, by stimulating production of a leukotriene or a leukotriene metabolite in a first test sample from the individual (e.g., a sample comprising neutrophils) before treatment, using a calcium ionophore, and comparing the level of the leukotriene or leukotriene metabolite with a level of production of the leukotriene or leukotriene metabolite in a second test sample from the individual, during or after treatment. A level of production of the leukotriene or leukotriene metabolite in the second test sample that is significantly lower than the level in the first test sample, is indicative of efficacy of the treatment. Similarly, the invention encompasses methods of assessing response to treatment with a leukotriene synthesis inhibitor, by assessing a level of an inflammatory marker in the individual before treatment, and during or after treatment. A level of the inflammatory marker during or after treatment, that is significantly lower than the level of inflammatory marker before treatment, is indicative of efficacy of the treatment.

The invention also pertains to use of leukotriene synthesis inhibitors for the manufacture of a medicament for the treatment of MI, ACS, stroke, PAOD, and/or atherosclerosis, as described herein, as well as for the manufacture of a medicament for the reduction of leukotriene synthesis.

BRIEF DESCRIPTION OF THE DRAWINGS

The foregoing and other objects, features and advantages of the invention will be apparent from the following more particular description of preferred embodiments of the invention.

FIG. 4 shows the amino acid sequence of FLAP (SEQ ID NO:2) and the mRNA of FLAP (SEQ ID NO: 3).

FIGS. 6.1-6.82 show the genomic sequence of the FLAP gene (SEQ ID NO: 1).

FIG. 7 depicts LTB4 production of ionomycin stimulated neutrophils from MI patients (n=41) and controls (n=35). The log-transformed (mean+SD) values measured at 15 and 30 minutes of stimulated cells are shown. (7.1) LTB4 production in MI patients and controls. The difference in the mean values between patients and the controls is tested using a two-sample t-test of the log-transformed values. (7.2) LTB4 production in MI male carriers and non-carriers of haplotype A4. Mean values of controls are included for comparison. Of note, males with the haplotype A4 produce the highest amounts of LTB4 (p<0.005 compared to controls). (7.3). Schematic representation of the 5-LO pathway with leukotriene bioactive products.

FIGS. 8.1-8.40 show the sequences of the FLAP nucleic acid flanking the SNPs that were identified by sequencing samples from patients (SEQ ID NOs: 506-717).

DETAILED DESCRIPTION OF THE INVENTION

Figure 1:
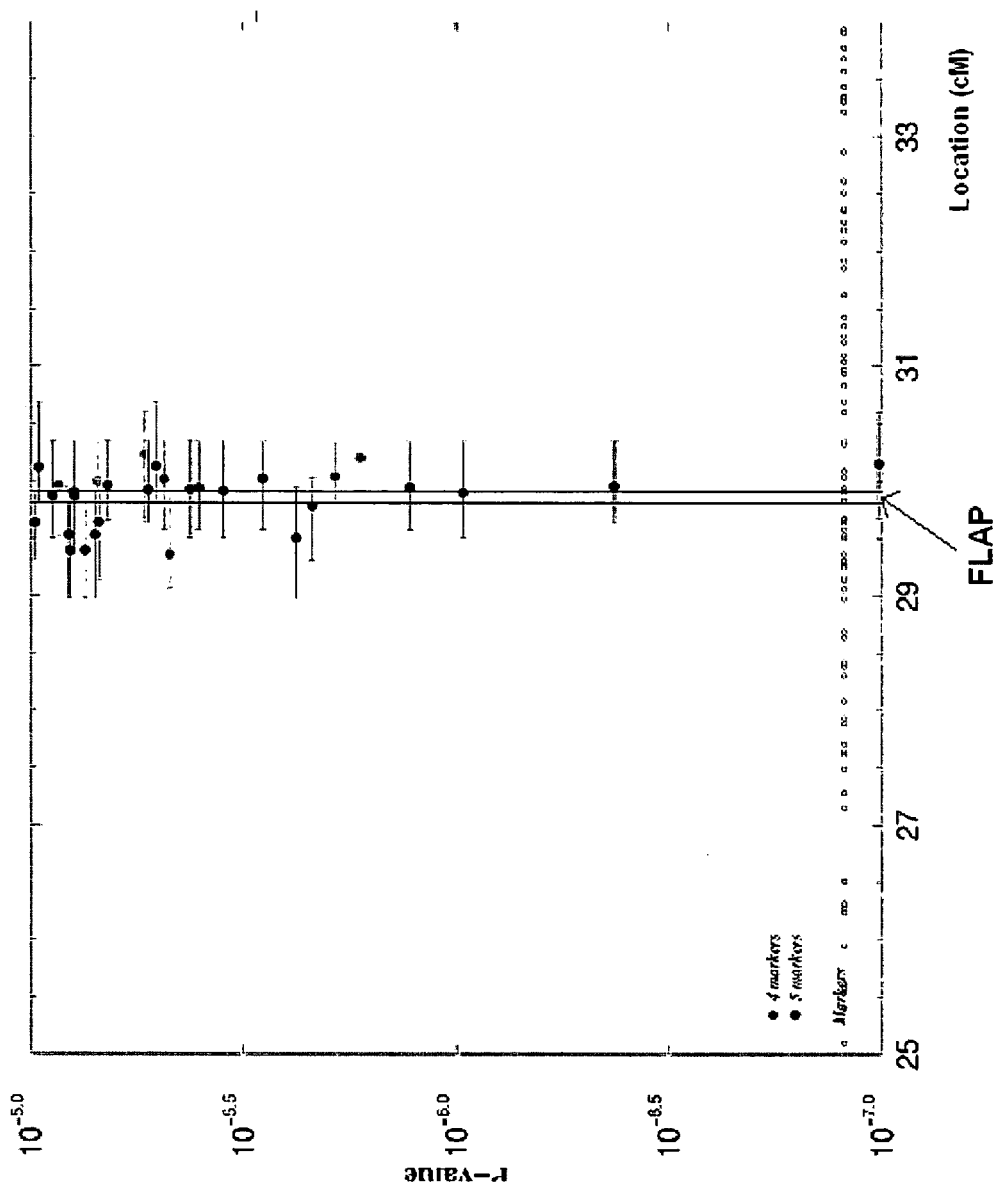
FIG. 1 shows the results from a haplotype association case-control analysis of 437 female MI patients versus 721 controls using combinations 4 and 5 microsatellite markers to define the test haplotypes. The p-value of the association is plotted on the y-axis and position of markers on the x-axis. Only haplotypes that show association with a p-value<$10^{-5}$ are shown in the figure. The most significant microsatellite marker haplotype association is found using markers DG13S1103, DG13S166, DG13S1287, DG13S1061 and DG13S301, with alleles 4, 0, 2, 14 and 3, respectively (p-value of $1.02\times10^{-7}$). Carrier frequency of the haplotype is 7.3% in female MI patients and 0.3% in controls. The segment that is common to all the haplotypes shown in the figure includes only one gene, FLAP.

Extensive genealogical information has been combined with powerful gene sharing methods to map a gene on chromosome 13q12-13 that is associated with myocardial infarction. A genome wide search for susceptibility genes for MI, using a framework map of 1000 microsatellite markers, revealed a locus suggestive of linkage on 13q12-13. Sixty families with 159 female MI patients that clustered within and including 6 meiotic events were used in linkage analysis. At first, only female MI patients were used in the linkage analysis in an effort to enrich for patients with stronger genetic factors contributing to their risk for MI. The epidemiological study of a population-based sample of Icelandic MI patients had previously suggested that the genetic factors for MI might be stronger for females than males, as the relative risk for siblings of female MI patients was significantly higher than the relative risk for siblings of male probands (1.59 (CI 1.47-1.73) vs. 1.35 (CI 1.28-1.42)) (unpublished data). The highest LOD score (2.5) was found at marker D13S289. The LOD score results for the families remained the same after adding 14 microsatellite markers to the candidate region. The inclusion of the additional markers increased the information on sharing by descent from 0.7 to 0.8, around the markers that gave the highest LOD scores. This linkage analysis mapped a gene contributing to MI to chromosome 13q12-13.

The candidate MI locus on chromosome 13q12-13 was then finely mapped with microsatellite markers. Patients with myocardial infarction and controls were initially genotyped with microsatellite markers with an average spacing between markers of less than 100 kb over the 12 Mb candidate region. Initial haplotype association analysis that included all genotyped microsatellite markers across the MI candidate locus, resulted in several extended haplotypes composed of 4 and 5 microsatellite markers that were significantly associated with female MI (see, e.g., Tables 14 and 15 below). A region common to all these extended haplotypes, is defined by markers DG13S166 and D13S1238. This region includes only one gene, the FLAP nucleic acid sequence. The two marker haplotype involving alleles 0 and –2 for markers DG13S166 and D13S1238, respectively, was found in excess in patients. Specific variants of the gene were then sought that were associated with MI.

In order to screen for SNPs in the FLAP gene, the whole gene was sequenced, both exons and introns. Initially, 9 SNPs identified within the gene were genotyped in patients and controls. Additional microsatellite markers close to or within the FLAP gene were also genotyped in all patients and controls. Five publicly known SNPs that are located within a 200 kb distance 5' to the FLAP gene were also genotyped in patients and controls. Haplotype association analysis in this case-control study including these additional markers showed several different variants of the same haplotype that were all significantly associated with female MI (see, e.g., Table 8). Table 9 shows two haplotypes that are representative of these female MI risk haplotypes which are referred to herein as the female MI "at risk" haplotypes. The relative risk for male MI patients that had the female MI-"at risk" haplotype was increased (see, e.g., Table 9), indicating that the female MI-"at risk" haplotype also increased the risk of having an MI in males. These results further strengthened the hypothesis that the FLAP gene was an MI susceptibility gene.

SNP Haplotype Association to MI, and Subsequently to Stroke and PAOD

In an effort to identify haplotypes involving only SNP markers that associate with MI, additional SNPs were identified by sequencing the FLAP gene and the region flanking the gene. Currently, a total of 45 SNPs in 1343 patients and 624 unrelated controls have been genotyped. Two correlated series of SNP haplotypes have been observed in excess in patients, denoted as A and B in Table 7. The length of the haplotypes varies between 33 and 69 kb, and the haplotypes cover one or two blocks of linkage disequilibrium. Both series of haplotypes contain the common allele G of the SNP SG13S25. All haplotypes in the A series contain the SNP SG13S114, while all haplotypes in the B series contain the SNP SG13S106. In the B series, the haplotypes B4, B5, and B6 have a relative risk (RR) greater than 2 and with allelic frequencies above 10%. The haplotypes in the A series have slightly lower RR and lower p-values, but higher frequency (15-16%). The haplotypes in series B and A are strongly correlated, i.e., the haplotypes in B define a subset of the haplotypes in A. Hence, haplotypes in series B are more specific than A. However, haplotypes in series A are more sensitive, i.e., they capture more individuals with the putative mutation, as is observed in the population attributable risk which is less for B than for A. Furthermore, these haplotypes show similar risk ratios and allelic frequencies for early-onset patients (defined as onset of first MI before the age of 55) and for both genders. In addition, analyzing various groups of patients with known risk factors, such as hypertension, high cholesterol, smoking and diabetes, does not reveal any significant correlation with these haplotypes, suggesting that the haplotypes in the FLAP gene represent an independent genetic susceptibility factor for MI.

Because stroke and PAOD are diseases that are closely related to MI (all occur on the basis of atherosclerosis), the SNP haplotype in the FLAP gene that confers risk to MI was assessed to determine whether it also conferred risk of stroke and/or PAOD. Table 20 shows that haplotype A4 increases the risk of having a stroke to a similar extent as it increases the risk of having an MI. Although not as significantly, haplotype A4 also confers risk of developing PAOD.

The FLAP nucleic acid encodes a 5-lipoxygenase activating protein, which, in combination with 5-lipoxygenase (5-LO), is required for leukotriene synthesis. FLAP acts coordinately with 5-LO to catalyze the first step in the synthesis of leukotrienes from arachidonic acid. It catalyzes the conversion of arachidonic acid to 5(S)-hydroperoxy-6-trans-8,11, 14-cis-eicosatetraenoic acid (5-HPETE), and further to the allylic epoxide 5 (S)-trans-7,9 trans 11,14-cis-eicosatetraenoic acid (leukotriene A4, LTA4).

The leukotrienes are a family of highly potent biological mediators of inflammatory processes produced primarily by bone marrow derived leukocytes such as monocytes, macrophages, and neurophils. Both FLAP and 5-LO are detected within atherosclerosis lesions (Proc Natl Acad Sci USA. 2003 Feb. 4;100(3):1238-43.), indicating that the vessel itself can be a source of leukotrienes. It was found at first that the MI-risk FLAP haplotype was associated with higher serum leukotriene levels. Increased production of leukotriene in individuals with pre-existing atherosclerosis lesions may lead to plaque instability or friability of the fibrous cap leading to local thrombotic events. If this occurs in coronary artery arteries it leads to MI or unstable angina. If it occurs in the cerebrovasculature it leads to stroke or transient ischemic attack. If it occurs in large arteries to the limbs, it causes or exacerbates limb ischemia in persons with peripheral arterial occlusive disease (PAOD). Therefore, those with genetically influenced predisposition to produce higher leukotriene levels have higher risk for events due to pre-existing atherosclerosis such as MI.

Inhibitors of FLAP function impede translocation of 5-LO from the cytoplasm to the cell membrane and inhibit activation of 5-LO and thereby decrease leukotriene synthesis.

As a result of these discoveries, methods are now available for the treatment of myocardial infarction (MI) and acute coronary syndrome (ACS), as well as stroke and PAOD, through the use of leukotriene inhibitors, such as agents that inhibit leukotriene biosynthesis or antagonize signaling through leukotriene receptors. The term, "treatment" as used herein, refers not only to ameliorating symptoms associated with the disease or condition, but also preventing or delaying the onset of the disease or condition; preventing or delaying the occurrence of a second episode of the disease or condition; and/or also lessening the severity or frequency of symptoms of the disease or condition. In the case of atherosclerosis, "treatment" also refers to a minimization or reversal of the development of plaques. Methods are additionally available for assessing an individual's risk for MI, ACS, stroke or PAOD. In a preferred embodiment, the individual to be treated is an individual who is susceptible (at increased risk) for MI, ACS, stroke or PAOD, such as an individual who is in one of the representative target populations described herein.

Representative Target Populations

In one embodiment of the invention, an individual who is at risk for MI, ACS, stroke or PAOD is an individual who has an at-risk haplotype in FLAP, as described herein. In one embodiment, a haplotype associated with a susceptibility to myocardial infarction, ACS, stroke or PAOD comprises markers SG13S99, SG13S25, SG13S377, SG13S106, SG13S32 and SG13S35 at the 13q12-13 locus. In another embodiment, a haplotype associated with a susceptibility to myocardial infarction, ACS, stroke or PAOD comprises markers SG13S99, SG13S25, SG13S106, SG13S30 and SG13S42 at the 13q12 locus. In a third embodiment, a haplotype associated with a susceptibility to myocardial infarction, ACS, stroke or PAOD comprises markers SG13S25, SG13S106, SG13S30 and SG13S42 at the 13q12-13 locus. In a fourth embodiment, a haplotype associated with a susceptibility to myocardial infarction, ACS, stroke or PAOD comprises markers SG13S99, SG13S25, SG13S114, SG13S89 and SG13S32 at the 13q12-13 locus. In a fifth embodiment, a haplotype associated with a susceptibility to myocardial infarction, ACS, stroke or PAOD comprises markers SG13S25, SG13S114, SG13S89 and SG13S32 at the 13q12-13 locus. Additional haplotypes associated with a susceptibility to myocardial infarction, ACS, stroke or PAOD include the haplotypes shown in Tables 4, 8, 9, 14, 15, 17 and 19, as well as haplotypes comprising markers shown in Table 13.

Increased risk for MI, ACS, stroke or PAOD in individuals with a FLAP at-risk haplotype is logically conferred by increased production of leukotrienes in the arterial vessel wall or in bone-marrow derived inflammatory cells within the blood and/or arterial vessel wall. It is shown herein that FLAP at-risk haplotypes are associated with higher production of LTB4 ex vivo. It is further shown herein that serum leukotriene levels (specifically, leukotriene E4) correlate with serum CRP levels in myocardial infarction patients. FLAP genetic variation may drive high leukotriene levels (within the blood vessel and/or systemically), which in turn may drive higher CRP levels which has been shown as a risk factor for MI. Accordingly, individuals with a FLAP at-risk haplotype are likely to have elevated serum CRP as well as other serum inflammatory markers. The level of serum CRP or other serum inflammatory markers can be used as a surrogate for the level of arterial wall inflammation initiated by lipid deposition and atherogenesis conferred by the presence of the at-risk FLAP haplotype.

In another embodiment of the invention, an individual who is at risk for MI, ACS, stroke or PAOD is an individual who has a polymorphism in a FLAP gene, in which the presence of the polymorphism is indicative of a susceptibility to MI, ACS, stroke or PAOD. The term "gene," as used herein, refers to not only the sequence of nucleic acids encoding a polypeptide, but also the promoter regions, transcription enhancement elements, splice donor/acceptor sites, and other non-transcribed nucleic acid elements. Representative polymorphisms include those presented in Table 13, below.

In a further embodiment of the invention, an individual who is at risk for MI, ACS, stroke or PAOD is an individual who has an at-risk polymorphism in the 5-LO gene in the promoter region, as described herein.

In a fourth embodiment, an individual who is at risk for MI, ACS, stroke or PAOD is an individual who has an elevated inflammatory marker. An "elevated inflammatory marker," as used herein, is the presence of an amount of an inflammatory marker that is greater, by an amount that is statistically significant, than the amount that is typically found in control individual(s) or by comparison of disease risk in a population associated with the lowest band of measurement (e.g., below the mean or median, the lowest quartile or the lowest quintile) compared to higher bands of measurement (e.g., above the mean or median, the second, third or fourth quartile; the second, third, fourth or fifth quintile). An "inflammatory marker" refers to a molecule that is indicative of the presence of inflammation in an individual, for example, C-reactive protein (CRP), serum amyloid A, fibrinogen, leukotriene levels (e.g., leukotriene B4, leukotriene C4), leukotriene metabolites (e.g., leukotriene E4), interleukin-6, tissue necrosis factor-alpha, soluble vasculare cell adhesion molecules (sVCAM), soluble intervascular adhesion molecules (sI-CAM), E-selectin, matrix metalloprotease type-1, matrix metalloprotease type-2, matrix metalloprotease type-3, matrix metalloprotease type-9, myeloperoxidase (MPO), N-tyrosine) or other markers (see, e.g., Doggen, C. J. M. et al., *J. Internal Med.*, 248:406-414 (2000); Ridker, P. M. et al., *New Englnd. J. Med.* 1997: 336: 973-979, Rettersol, L. et al., 2002: 160:433-440; Ridker, P. M. et. al., *New England. J. Med.*, 2002: 347: 1557-1565; Bermudez, E. A. et. al., *Arterioscler. Thromb. Vasc. Biol.*, 2002: 22:1668-1673). In certain embodiments, the presence of such inflammatory markers can be measured in serum or urine.

In a fifth embodiment, an individual who is at risk for MI, ACS, stroke or PAOD is an individual who has increased LDL cholesterol and/or decreased HDL cholesterol levels. For example, the American Heart Association indicates that an LDL cholesterol level of less than 100 mg/dL is optimal; from 100-129 mg/dL is near/above optimal; from 130-159 mg/dL is borderline high; from 160-189 is high; and from 190 and up is very high. Therefore, an individual who is at risk for MI, ACS, stroke or PAOD because of an increased LDL cholesterol level is, for example, an individual who has more than 100 mg/dL cholesterol, such as an individual who has a near/above optimal level, a borderline high level, a high level or a very high level. Similarly, the American Heart Association indicates that an HDL cholesterol level of less than 40 mg/dL is a major risk factor for heart disease; and an HDL cholesterol level of 60 mg/dL or more is protective against heart disease. Thus, an individual who is at risk for MI, ACS, stroke or PAOD because of a decreased HDL cholesterol level is, for example, an individual who has less than 60 mg/dL HDL cholesterol, such as an individual who has less than 40 mg/dL HDL cholesterol.

In a sixth embodiment, an individual who is at risk for MI, ACS, stroke or PAOD is an individual who has increased leukotriene synthesis. "Increased leukotriene synthesis," as used herein, indicates an amount of production of leukotrienes that is greater, by an amount that is statistically significant, than the amount of production of leukotrienes that is typically found in control individual(s) or by comparison of leukotriene production in a population associated with the lowest band of measurement (e.g., below the mean or median, the lowest quartile or the lowest quintile) compared to higher bands of measurement (e.g., above the mean or median, the second, third or fourth quartile; the second, third, fourth or fifth quintile). For example, the FLAP at-risk haplotypes correlate with increased serum leukotriene synthesis levels, and with increased production of leukotrienes ex vivo. An individual can be assessed for the presence of increased leukotriene synthesis by a variety of methods. For example, an individual can be assessed for an increased risk of MI, ACS, stroke, PAOD or atherosclerosis, by assessing the level of a leukotriene metabolite (e.g., LTE4) in a sample (e.g., serum, plasma or urine) from the individual. Samples containing blood, cells, or tissue can also be obtained from an individual and used to assess leukotriene or leukotriene metabolite production ex vivo under appropriate assay conditions. An increased level of leukotriene metabolites, and/or an increased level of leukotriene production ex vivo, is indicative of increased production of leukotrienes in the individual, and of an increased risk of MI, ACS, stroke, PAOD or atherosclerosis.

In a further embodiment, an individual who is at risk for MI, ACS, or stroke is an individual who has already experienced at least one MI, ACS event or stroke, or who has stable angina, and is therefore at risk for a second MI, ACS event or stroke. In another embodiment, an individual who is at risk for MI, ACS, stroke or PAOD is an individual who has atherosclerosis or who requires treatment (e.g., angioplasty, stents, revascularization procedure) to restore blood flow in arteries.

In further embodiments, an individual who is at risk for MI, stroke or PAOD is an individual having asymptomatic ankle/brachial index of less than 0.9; an individual who is at risk for stroke, is an individual who has had one or more transient ischemic attacks; who has had transient monocular blindness; has had a carotid endarterectomy; or has asymptomatic carotid stenosis; an individual who is at risk for PAOD, is an individual who has (or had) claudication, limb ischemia leading to gangrene, ulceration or amputation, or has had a revascularization procedure.

In additional embodiments, an individual who is at risk for MI, ACS, stroke or PAOD is an individual who has diabetes; hypertension; hypercholesterolemia; elevated triglycerides (e.g., >200 mg/dl); elevated lp(a); obesity; ankle/brachial index (ABI) less than 0.9; and/or is a past or current smoker.

Individuals at risk for MI, ACS, stroke or PAOD may fall into more than one of these representative target populations. For example, an individual may have experienced at least one MI, ACS event, transient ischemic attack, transient monocular blindness, or stroke, and may also have an increased level of an inflammatory marker. As used therein, the term "individual in a target population" refers to an individual who is at risk for MI, ACS, stroke or PAOD who falls into at least one of the representative target populations described above.

Assessment for at-Risk Haplotypes

A "haplotype," as described herein, refers to a combination of genetic markers ("alleles"), such as those set forth in Table 13. In a certain embodiment, the haplotype can comprise one or more alleles (e.g., a haplotype containing a single SNP), two or more alleles, three or more alleles, four or more alleles, or five or more alleles. The genetic markers are particular "alleles" at "polymorphic sites" associated with FLAP. A nucleotide position at which more than one sequence is possible in a population (either a natural population or a synthetic population, e.g., a library of synthetic molecules), is referred to herein as a "polymorphic site". Where a polymorphic site is a single nucleotide in length, the site is referred to as a single nucleotide polymorphism ("SNP"). For example, if at a particular chromosomal location, one member of a population has an adenine and another member of the population has a thymine at the same position, then this position is a polymorphic site, and, more specifically, the polymorphic site is a SNP. Polymorphic sites can allow for differences in sequences based on substitutions, insertions or deletions. Each version of the sequence with respect to the polymorphic site is referred to herein as an "allele" of the polymorphic site. Thus, in the previous example, the SNP allows for both an adenine allele and a thymine allele.

Typically, a reference sequence is referred to for a particular sequence. Alleles that differ from the reference are referred to as "variant" alleles. For example, the reference FLAP sequence is described herein by SEQ ID NO: 1. The term, "variant FLAP", as used herein, refers to a sequence that differs from SEQ ID NO: 1, but is otherwise substantially similar. The genetic markers that make up the haplotypes described herein are FLAP variants.

Additional variants can include changes that affect a polypeptide, e.g., the FLAP polypeptide. These sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence, as described in detail above. Such sequence changes alter the polypeptide encoded by a FLAP nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a susceptibility to MI, ACS, stroke or PAOD can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of the polypeptide. The polypeptide encoded by the reference nucleotide sequence is the "reference" polypeptide with a particular reference amino acid sequence, and polypeptides encoded by variant alleles are referred to as "variant" polypeptides with variant amino acid sequences.

Haplotypes are a combination of genetic markers, e.g., particular alleles at polymorphic sites. The haplotypes described herein, e.g., having markers such as those shown in Table 13, are found more frequently in individuals with MI, ACS, stroke or PAOD than in individuals without MI, ACS, stroke or PAOD. Therefore, these haplotypes have predictive value for detecting a susceptibility to MI, ACS, stroke or PAOD in an individual. The haplotypes described herein are in some cases a combination of various genetic markers, e.g., SNPs and microsatellites. Therefore, detecting haplotypes can be accomplished by methods known in the art for detecting sequences at polymorphic sites, such as the methods described above.

In certain methods described herein, an individual who is at risk for MI, ACS, stroke or PAOD is an individual in whom an at-risk haplotype is identified. In one embodiment, the at-risk haplotype is one that confers a significant risk of MI, ACS, stroke or PAOD. In one embodiment, significance associated with a haplotype is measured by an odds ratio. In a further embodiment, the significance is measured by a percentage. In one embodiment, a significant risk is measured as an odds ratio of at least about 1.2, including by not limited to: 1.2, 1.3, 1.4, 1.5, 1.6, 1.7, 1.8, and 1.9. In a further embodiment, an odds ratio of at least 1.2 is significant. In a further embodiment, an odds ratio of at least about 1.5 is significant. In a further embodiment, a significant increase in risk is at least about 1.7 is significant. In a further embodiment, a significant increase in risk is at least about 20%, including but not limited to about 25%, 30%, 35%, 40%, 45%, 50%, 55%, 60%, 65%, 70%, 75%, 80%, 85%, 90%, 95%, and 98%. In a further embodiment, a significant increase in risk is at least about 50%. In yet another embodiment, an at-risk haplotype has a p value<0.05. It is understood however, that identifying whether a risk is medically significant may also depend on a variety of factors, including the specific disease, the haplotype, and often, environmental factors.

An at-risk haplotype in, or comprising portions of, the FLAP gene, in one where the haplotype is more frequently present in an individual at risk for MI, ACS, stroke or PAOD (affected), compared to the frequency of its presence in a healthy individual (control), and wherein the presence of the haplotype is indicative of susceptibility to MI, ACS, stroke or PAOD. As an example of a simple test for correlation would be a Fisher-exact test on a two by two table. Given a cohort of chromosomes the two by two table is constructed out of the number of chromosomes that include both of the haplotypes, one of the haplotype but not the other and neither of the haplotypes.

In certain embodiments, an at-risk haplotype is an at-risk haplotype within or near FLAP that significantly correlates with a haplotype such as a halotype shown in Table 14; a haplotype shown in Table 15; a haplotype shown in Table 19; haplotype B4; haplotype B5; haplotype B6; haplotype A4; haplotype A5; or haplotype HapB. In other embodiments, an at-risk haplotype comprises an at-risk haplotype within or near FLAP that significantly correlates with susceptibility to myocardial infarction or stroke. In a particular embodiment, a haplotype associated with a susceptibility to myocardial infarction, ACS, stroke or PAOD comprises markers SG13S99, SG13S25, SG13S377, SG13S106, SG13S32 and SG13S35 at the 13q12-13 locus. In another embodiment, a haplotype associated with a susceptibility to myocardial infarction, ACS, stroke or PAOD comprises markers SG13S99, SG13S25, SG13S106, SG13S30 and SG13S42 at the 13q12-13 locus. In a third embodiment, a haplotype associated with a susceptibility to myocardial infarction, ACS, stroke or PAOD comprises markers SG13S25, SG13S106, SG13S30 and SG13S42 at the 13q12-13 locus. In a fourth embodiment, a haplotype associated with a susceptibility to myocardial infarction, ACS, stroke or PAOD comprises markers SG13S99, SG13S25, SG13S114, SG13S89 and SG13S32 at the 13q12-13 locus. In other embodiments, the at-risk haplotype is selected from the group consisting of: haplotype B4, B5, B6, A4 and A5. The at-risk haplotype can also comprise a combination of the markers in the haplotypes B4, B5, B6, A4 and/or A5. In further embodiments, the at-risk haplotype can be haplotype HapB. In other embodiments, the at-risk haplotype comprises a polymorphism shown in Table 13.

Standard techniques for genotyping for the presence of SNPs and/or microsatellite markers can be used, such as fluorescent based techniques (Chen, et al., *Genome Res.* 9, 492 (1999)), PCR, LCR, Nested PCR and other techniques for nucleic acid amplification. In a preferred embodiment, the method comprises assessing in an individual the presence or frequency of SNPs and/or microsatellites in, comprising portions of, the FLAP gene, wherein an excess or higher frequency of the SNPs and/or microsatellites compared to a healthy control individual is indicative that the individual is susceptible to MI, ACS, stroke or PAOD. See, for example, Table 13 (below) for SNPs and markers that can form haplotypes that can be used as screening tools. These markers and SNPs can be identified in at-risk haploptypes. For example, an at-risk haplotype can include microsatellite markers and/or SNPs such as those set forth in Table 13. The presence of the haplotype is indicative of a susceptibility to MI, ACS, stroke or PAOD, and therefore is indicative of an individual who falls within a target population for the treatment methods described herein.

Haplotype analysis involves defining a candidate susceptibility locus using LOD scores. The defined regions are then ultra-fine mapped with microsatellite markers with an average spacing between markers of less than 100 kb. All usable microsatellite markers that are found in public databases and mapped within that region can be used. In addition, microsatellite markers identified within the deCODE genetics sequence assembly of the human genome can be used. The frequencies of haplotypes in the patient and the control groups can be estimated using an expectation-maximization algorithm (Dempster A. et al., 1977. *J. R. Stat. Soc. B*, 39:1-389). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistic significance.

To look for at-risk-haplotypes in the 1-lod drop, for example, association of all possible combinations of genotyped markers is studied, provided those markers span a practical region. The combined patient and control groups can be randomly divided into two sets, equal in size to the original group of patients and controls. The haplotype analysis is then repeated and the most significant p-value registered is determined. This randomization scheme can be repeated, for example, over 100 times to construct an empirical distribution of p-values. In a preferred embodiment, a p-value of <0.05 is indicative of an at-risk haplotype.

A detailed discussion of haplotype analysis follows.

Haplotype Analysis

Our general approach to haplotype analysis involves using likelihood-based inference applied to NEsted MOdels. The method is implemented in our program NEMO, which allows for many polymorphic markers, SNPs and microsatellites. The method and software are specifically designed for case-control studies where the purpose is to identify haplotype groups that confer different risks. It is also a tool for studying LD structures.

When investigating haplotypes constructed from many markers, apart from looking at each haplotype individually, meaningful summaries often require putting haplotypes into groups. A particular partition of the haplotype space is a model that assumes haplotypes within a group have the same risk, while haplotypes in different groups can have different risks. Two models/partitions are nested when one, the alternative model, is a finer partition compared to the other, the null model, i.e, the alternative model allows some haplotypes assumed to have the same risk in the null model to have different risks. The models are nested in the classical sense that the null model is a special case of the alternative model. Hence traditional generalized likelihood ratio tests can be used to test the null model against the alternative model. Note that, with a multiplicative model, if haplotypes $h_i$ and $h_j$ are assumed to have the same risk, it corresponds to assuming that $f_i/p_i = f_j/p_j$ where f and p denote haplotype frequencies in the affected population and the control population respectively.

One common way to handle uncertainty in phase and missing genotypes is a two-step method of first estimating haplotype counts and then treating the estimated counts as the exact counts, a method that can sometimes be problematic (e.g., see the information measure section below) and may require randomization to properly evaluate statistical significance. In NEMO, maximum likelihood estimates, likelihood ratios and p-values are calculated directly, with the aid of the EM algorithm, for the observed data treating it as a missing-data problem.

NEMO allows complete flexibility for partitions. For example, the first haplotype problem described in the Methods section on Statistical analysis considers testing whether $h_1$ has the same risk as the other haplotypes $h_2, \ldots, h_k$. Here the alternative grouping is $[h_1], [h_2, \ldots, h_k]$ and the null grouping is $[h_1, \ldots, h_k]$. The second haplotype problem in the same section involves three haplotypes $h_1$=G0, $h_2$=GX and $h_3$=AX, and the focus is on comparing $h_1$ and $h_2$. The alternative grouping is $[h_1], [h_2], [h_3]$ and the null grouping is $[h_1, h_2], [h_3]$. If composite alleles exist, one could collapse these alleles into one at the data processing stage, and performed the test as described. This is a perfectly valid approach, and indeed, whether we collapse or not makes no difference if there were no missing information regarding phase. But, with the actual data, if each of the alleles making up a composite correlates differently with the SNP alleles, this will provide some partial information on phase. Collapsing at the data processing stage will unnecessarily increase the amount of missing information. A nested-models/partition framework can be used in this scenario. Let $h_2$ be split into $h_{2a}, h_{2b}, \ldots, h_{2e}$, and $h_3$ be split into $h_{3a}, h_{3b}, \ldots, h_{3e}$. Then the alternative grouping is $[h_1], [h_{2a}, h_{2b}, \ldots, h_{2e}], [h_{3a}, h_{3b}, \ldots, h_{3e}]$ and the null grouping is $[h_1, h_{2a}, h_{2b}, \ldots, h_{2e}], [h_{3a}, h_{3b}, \ldots, h_{3e}]$. The same method can be used to handle composite where collapsing at the data processing stage is not even an option since $L_C$ represents multiple haplotypes constructed from multiple SNPs. Alternatively, a 3-way test with the alternative grouping of $[h_1], [h_{2a}, h_{2b}, \ldots, h_{2e}], [h_{3a}, h_{3b}, \ldots, h_{3e}]$ versus the null grouping of $[h_1, h_{2a}, h_{2b}, \ldots, h_{2e}, h_{3a}, h_{3b}, \ldots, h_{3e}]$ could also be performed. Note that the generalized likelihood ratio test-statistic would have two degrees of freedom instead of one.

Measuring Information

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. Interestingly, one can measure information loss by considering a two-step procedure to evaluating statistical significance that appears natural but happens to be systematically anti-conservative. Suppose we calculate the maximum likelihood estimates for the population haplotype frequencies calculated under the alternative hypothesis that there are differences between the affected population and control population, and use these frequency estimates as estimates of the observed frequencies of haplotype counts in the affected sample and in the control sample. Suppose we then perform a likelihood ratio test treating these estimated haplotype counts as though they are the actual counts. We could also perform a Fisher's exact test, but we would then need to round off these estimated counts since they are in general non-integers. This test will in general be anti-conservative because treating the estimated counts as if they were exact counts ignores the uncertainty with the counts, overestimates the effective sample size and underestimates the sampling variation. It means that the chi-square likelihood-ratio test statistic calculated this way, denoted by $\Lambda^*$, will in general be bigger than $\Lambda$, the likelihood-ratio test-statistic calculated directly from the observed data as described in methods. But $\Lambda^*$ is useful because the ratio $\Lambda/\Lambda^*$ happens to be a good measure of information, or $1-(\Lambda/\Lambda^*)$ is a measure of the fraction of information lost due to missing information. This information measure for haplotype analysis is described in Nicolae and Kong, Technical Report 537, Department of Statistics, University of Statistics, University of Chicago, Revised for *Biometrics* (2003) as a natural extension of information measures defined for linkage analysis, and is implemented in NEMO.

Statistical analysis.

For single marker association to the disease, the Fisher exact test can be used to calculate two-sided p-values for each individual allele. All p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure (e.g., as described in Risch, N. & Teng, J., "The relative power of family-based and case-control designs for linkage disequilibrium studies of complex human diseases I. DNA pooling," *Genome Res.* 8:1278-1288 (1998)) for sibships so that it can be applied to general familial relationships, and present both adjusted and unadjusted p-values for comparison. The differences are in general very small as expected. To assess the significance of single-marker association corrected for multiple testing we carried out a randomisation test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model), (Terwilliger, J. D. & Ott, J., *Hum Hered,* 42, 337-46 (1992) and Falk, C. T. & Rubinstein, P, *Ann Hum Genet* 51 (Pt 3), 227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes $h_i$ and $h_j$, $\text{risk}(h_i)/\text{risk}(h_j) = (f_i/p_i)/(f_j/p_j)$, where f and p denote respectively frequencies in the affected population and in the control population. While there is some power loss if the true model is not multiplicative, the loss tends to be mild except for extreme cases. Most importantly, p-values are always valid since they are computed with respect to null hypothesis.

In general, haplotype frequencies are estimated by maximum likelihood and tests of differences between cases and controls are performed using a generalized likelihood ratio test (Rice, J. A. *Mathematical Statistics and Data Analysis*, 602 (International Thomson Publishing, (1995)). deCODE's haplotype analysis program called NEMO, which stands for NEsted MOdels, can be used to calculate all the haplotype results. To handle uncertainties with phase and missing genotypes, it is emphasized that we do not use a common two-step approach to association tests, where haplotype counts are first estimated, possibly with the use of the EM algorithm, Dempster, (A. P., Laird, N. M. & Rubin, D. B., *Journal of the Royal Statistical Society B*, 39, 1-38 (1971)) and then tests are performed treating the estimated counts as though they are true counts, a method that can sometimes be problematic and may require randomisation to properly evaluate statistical significance. Instead, with NEMO, maximum likelihood estimates, likelihood ratios and p-values are computed with the aid of the EM-algorithm directly for the observed data, and hence the loss of information due to uncertainty with phase and missing genotypes is automatically captured by the likelihood ratios. Even so, it is of interest to know how much information is retained, or lost, due to incomplete information. Described herein is such a measure that is natural under the likelihood framework. For a fixed set of markers, the simplest tests performed compare one selected haplotype against all the others. Call the selected haplotype $h_1$, and the others $h_2, \ldots, h_k$. Let $p_1, \ldots, p_k$ denote the population frequencies of the haplotypes in the controls, and $f_1, \ldots, f_k$ denote the population frequencies of the haplotypes in the affecteds. Under the null hypothesis, $f_i = p_i$ for all i. The alternative model we use for the test assumes $h_2, \ldots, h_k$ to have the same risk while $h_1$ is allowed to have a different risk. This implies that while $p_1$ can be different from $f_1$, $f_i/(f_2+\ldots+f_k)=p_i/(p_2+\ldots+p_k)=\beta_i$ for $i=2,\ldots,k$. Denoting $f_1/p_1$ by r, and noting that $\beta_2+\ldots\beta_k=1$, the test statistic based on generalized likelihood ratios is $$\Lambda = 2[l(\hat{r}, \hat{p}_1, \hat{\beta}_2, \ldots, \hat{\beta}_{k-1}) - l(1, \tilde{p}_1, \tilde{\beta}_2, \ldots, \tilde{\beta}_{k-1})]$$

where l denotes $\log_e$ likelihood and and ^ denote maximum likelihood estimates under the null hypothesis and alternative hypothesis respectively. $\Lambda$ has asymptotically a chi-square distribution with 1-df, under the null hypothesis. Slightly more complicated null and alternative hypotheses can also be used. For example, let $h_1$ be G0, $h_2$ be GX and $h_3$ be AX. When comparing G0 against GX, i.e., this is the test which gives estimated RR of 1.46 and p-value=0.0002, the null assumes G0 and GX have the same risk but AX is allowed to have a different risk. The alternative hypothesis allows, for example, three haplotype groups to have different risks. This implies that, under the null hypothesis, there is a constraint that $f_1/p_1=f_2/p_2$, or $w=[f_1/p_1]/[f_2/p_2]=1$. The test statistic based on generalized likelihood ratios is $$\Lambda = 2[l(\hat{p}_1, f_1, \hat{p}_2, \hat{w}) - l(\tilde{p}_1, f_1, \tilde{p}_2, 1)]$$

that again has asymptotically a chi-square distribution with 1-df under the null hypothesis. If there are composite haplotypes (for example, $h_2$ and $h_3$), that is handled in a natural manner under the nested models framework.

LD between pairs of SNPs can be calculated using the standard definition of D' and $R^2$ (Lewontin, R., Genetics 49, 49-67 (1964) and Hill, W. G. & Robertson, A. Theor. Appl. Genet. 22, 226-231 (1968)). Using NEMO, frequencies of the two marker allele combinations are estimated by maximum likelihood and deviation from linkage equilibrium is evaluated by a likelihood ratio test. The definitions of D' and $R^2$ are extended to include microsatellites by averaging over the values for all possible allele combination of the two markers weighted by the marginal allele probabilities. When plotting all marker combination to elucidate the LD structure in a particular region, we plot D' in the upper left corner and the p-value in the lower right corner. In the LD plots the markers can be plotted equidistant rather than according to their physical location, if desired.

Statistical Methods for Linkage Analysis

Multipoint, affected-only allele-sharing methods can be used in the analyses to assess evidence for linkage. Results, both the LOD-score and the non-parametric linkage (NPL) score, can be obtained using the program Allegro (Gudbjartsson et al., *Nat. Genet.* 25:12-3, 2000). Our baseline linkage analysis uses the Spairs scoring function (Whittemore, A. S., Halpern, J. (1994), *Biometrics* 50:118-27; Kruglyak L, et al. (1996), *Am J Hum Genet* 58:1347-63), the exponential allele-sharing model (Kong, A. and Cox, N. J. (1997), *Am J Hum Genet* 61:1179-88) and a family weighting scheme that is halfway, on the log-scale, between weighting each affected pair equally and weighting each family equally. The information measure we use is part of the Allegro program output and the information value equals zero if the marker genotypes are completely uninformative and equals one if the genotypes determine the exact amount of allele sharing by decent among the affected relatives (Gretarsdottir et al., *Am. J. Hom. Genet*, 70:593-603, (2002)). We computed the P-values two different ways and here report the less significant result. The first P-value can be computed on the basis of large sample theory; the distribution of $Z_{lr}=\sqrt{(2[\log_e(10)\text{LOD}])}$ approximates a standard normal variable under the null hypothesis of no linkage (Kong, A. and Cox, N. J. (1997), *Am J Hum Genet* 61:1179-88). The second P-value can be calculated by comparing the observed LOD-score with its complete data sampling distribution under the null hypothesis (e.g., Gudbjartsson et al., *Nat. Genet.* 25:12-3, 2000). When the data consist of more than a few families, these two P-values tend to be very similar.

Methods of Treatment

The present invention encompasses methods of treatment (prophylactic and/or therapeutic, as described above) for MI, ACS, stroke or PAOD in individuals, such as individuals in the target populations described above, as well as for other diseases and conditions associated with FLAP or with other members of the leukotriene pathway (e.g., for atherosclerosis). Members of the "leukotriene pathway," as used herein, include polypeptides (e.g., enzymes, receptors) and other molecules that are associated with production of leukotrienes: for example, proteins or enzymes such as FLAP, 5-LO, other leukotriene biosynthetic enzymes (e.g., leukotriene C4 synthase, leukotriene A4 hydrolase); receptors or binding agents of the enzymes; leukotrienes such as LTA4, LTB4, LTC4, LTD4, LTE4; and receptors of leukotrienes (e.g., leukotriene B4 receptor 1 (BLT1), leukotriene B4 receptor 2 (BLT2), cysteinyl leukotriene receptor 1 (CysLTR1), cysteinyl leukotriene receptor 2 (CysLTR2)).

In particular, the invention relates to methods of treatment for myocardial infarction or susceptibility to myocardial infarction (for example, for individuals in an at-risk population such as those described above); as well as methods of treatment for acute coronary syndrome (e.g., unstable angina, non-ST-elevation myocardial infarction (NSTEMI) or ST-elevation myocardial infarction (STEMI)); methods for reducing risk of MI, stroke or PAOD in persons with asymptomatic ankle/brachial index less than 0.9; for decreasing risk of a second myocardial infarction; for stroke or susceptibility to stroke; for transient ischemic attack; for transient monocular blindness; for decreasing risk of a second stroke; for PAOD or susceptibility to PAOD; for ABI less than 0.9; for claudication or limb ischemia; for atherosclerosis, such as for patients requiring treatment (e.g., angioplasty, stents, revascularization procedure) to restore blood flow in arteries (e.g., coronary, carotid, and/or femoral arteries); for treatment of asymptomatic ankle/brachial index of less than 0.9; and/or for decreasing leukotriene synthesis (e.g., for treatment of MI, ACS, stroke or PAOD). The invention additionally pertains to use of one or more leukotriene synthesis inhibitors, as described herein, for the manufacture of a medicament for the treatment of MI, ACS, stroke, PAOD and/or atherosclerosis, e.g., using the methods described herein.

In the methods of the invention, a "leukotriene synthesis inhibitor" is used. In one embodiment, a "leukotriene synthesis inhibitor" is an agent that inhibits FLAP polypeptide activity and/or FLAP nucleic acid expression, as described herein (e.g., a nucleic acid antagonist). In another embodiment, a leukotriene synthesis inhibitor is an agent that inhibits polypeptide activity and/or nucleic acid expression of another member of the leukotriene biosynthetic pathway (e.g., 5-LO; LTC4S; LTA4H; LTB4DH). In still another embodiment, a leukotriene synthesis inhibitor is an agent that alters activity or metabolism of a leukotriene (e.g., an antagonist of a leukotriene; an antagonist of a leukotriene receptor). In preferred embodiments, the leukotriene synthesis inhibitor alters activity and/or nucleic acid expression of FLAP or of 5-LO, or alters interaction between FLAP and 5-LO.

Leukotriene synthesis inhibitors can alter polypeptide activity or nucleic acid expression of a member of the leukotriene pathway by a variety of means, such as, for example, by catalytically degrading, downregulating or interfering with the expression, transcription or translation of a nucleic acid encoding the member of the leukotriene pathway; by altering posttranslational processing of the polypeptide; by altering transcription of splicing variants; or by interfering with polypeptide activity (e.g., by binding to the polypeptide, or by binding to another polypeptide that interacts with that member of the leukotriene pathway, such as a FLAP binding agent as described herein or some other binding agent of a member of the leukotriene pathway; by altering interaction among two or more members of the leukotriene pathway (e.g., interaction between FLAP and 5-LO); or by antagonizing activity of a member of the leukotriene pathway.

Representative leukotriene synthesis inhibitors include the following:

agents that inhibit activity of a member of the leukotriene biosynthetic pathway (e.g., FLAP, 5-LO), LTC4S, LTA4H, such as the agents presented in the Agent Table below; agents that inhibit activity of receptors of members of the leukotriene pathway, such as FLAP receptors, LTA4 receptors, LTB4 receptors, LTC4 receptors, LTD4 receptors, LTE4 receptors, Cys LT1 receptors, Cys LT2 receptors, 5-LO receptors; BLT1; BLT2; CysLTR1; CysLTR2; agents that bind to the members of the leukotriene pathway, such as FLAP binding agents (e.g., 5-LO) or agents that bind to receptors of members of the leukotriene pathway (e.g., leukotriene receptor antagonists); agents that bind to a leukotriene (e.g., to LTA4, LTB4, LTC4, LTD4, LTE4, Cys LT1, Cys LT2); agents that increase breakdown of leukotrienes (e.g., LTB4DH); or other agents that otherwise affect (e.g., increase or decrease) activity of the leukotriene;

antibodies to leukotrienes;

antisense nucleic acids or small double-stranded interfering RNA, to nucleic acids encoding FLAP, 5-LO, or a leukotriene synthetase or other member of the leukotriene pathway, or fragments or derivatives thereof, including antisense nucleic acids to nucleic acids encoding the FLAP, 5-LO or leukotriene synthetase polypeptides, and vectors comprising such antisense nucleic acids (e.g., nucleic acid, cDNA, and/or mRNA, double-stranded interfering RNA, or a nucleic acid encoding an active fragment or derivative thereof, or an oligonucleotide; for example, the complement of one of SEQ ID Nos. 1 or 3, or a nucleic acid complementary to the nucleic acid encoding SEQ ID NO: 2, or fragments or derivatives thereof);

peptidomimetics; fusion proteins or prodrugs thereof; ribozymes; other small molecules; and other agents that alter (e.g., inhibit or antagonize) expression of a member of the leukotriene pathway, such as FLAP or 5-LO nucleic acid expression or polypeptide activity, or that regulate transcription of FLAP splicing variants or 5-LO splicing variants (e.g., agents that affect which splicing variants are expressed, or that affect the amount of each splicing variant that is expressed).

More than one leukotriene synthesis inhibitor can be used concurrently, if desired.

The therapy is designed to alter activity of a FLAP polypeptide, a 5-LO polypeptide, or another member of the leukotriene pathway in an individual, such as by inhibiting or antagonizing activity. For example, a leukotriene synthesis inhibitor can be administered in order to decrease synthesis of leukotrienes within the individual, or to downregulate or decrease the expression or availability of the FLAP nucleic acid or specific splicing variants of the FLAP nucleic acid. Downregulation or decreasing expression or availability of a native FLAP nucleic acid or of a particular splicing variant could minimize the expression or activity of a defective nucleic acid or the particular splicing variant and thereby minimize the impact of the defective nucleic acid or the particular splicing variant. Similarly, for example, a leukotriene synthesis inhibitor can be administered in order to downregulate or decrease the expression or availability of the nucleic acid encoding 5-LO or specific splicing variants of the nucleic acid encoding 5-LO.

The leukotriene synthesis inhibitor(s) are administered in a therapeutically effective amount (i.e., an amount that is sufficient to treat the disease or condition, such as by ameliorating symptoms associated with the disease or condition, preventing or delaying the onset of the disease or condition, and/or also lessening the severity or frequency of symptoms of the disease or condition). The amount which will be therapeutically effective in the treatment of a particular individual's disease or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

In preferred embodiments of the invention, the leukotriene synthesis inhibitor agent is an agent that inhibits activity of FLAP and/or of 5-LO. Preferred agents include the following, as set forth in the Agent Table:

| Company | Product_Name (Code) | Structure | Chemical Name | Patent Ref | Date Patent Issued/Application Published | MOA |
|---|---|---|---|---|---|---|
| Abbott | atreleuton (ABT-761) | | (R)-(+)-N-[3-[5-[(4-fluorophenyl)methyl]-2thienyl]-1methyl-2-propynyl]-N-hydroxyurea | U.S. Pat. No. 5,288,751, U.S. Pat. No. 5,288,743, U.S. Pat. No. 5,616,596 | Feb. 22, 1994 Apr. 1, 1997 | 5-LPO inhibitor |
| Abbott | A-81834 | | 3-(3-(1,1-dimethylethylthio-5-(quinoline-2-ylmethoxy)-1-(4-chloromethylphenyl)indole-2-yl)-2,2-dimethylpropionaldehyde oxime-0-2-acetic acid | WO9203132, U.S. Pat. No. 5,459,150 | Mar. 5, 1992, Oct. 17, 1995 | FLAP inhibitor |
| Abbott | A-86886 | | 3-(3-(1,1-dimethylethylthio-5-(pyridin-2-ylmethoxy)-1-(4-chloromethylphenyl)indole-2-yl)-2,2-dimethylpropionaldehyde oxime-0-2-acetic acid | WO9203132, U.S. Pat. No. 5,459,150 | Mar. 5, 1992, Oct. 17, 1995 | 5-LPO inhibitor |

-continued
| Company | Product_Name (Code) | Structure | Chemical Name | Patent Ref | Date Patent Issued/Application Published | MOA |
|---|---|---|---|---|---|---|
| Abbott | A-93178 | 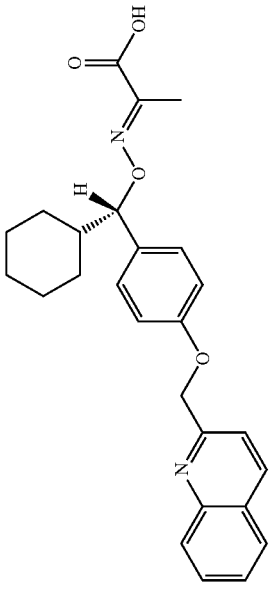 | | | | FLAP inhibitor |
| AstraZeneca | AZD-4407 | 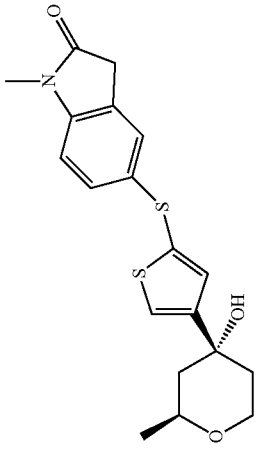 | | EP 623614 | Sep. 11, 1994 | 5-LPO inhibitor |
| AstraZeneca | ZD-2138 | 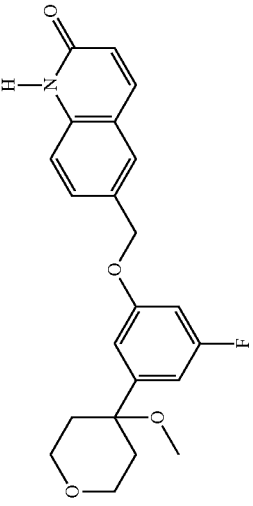 | 6-((3-fluoro-5-(tetrahydro-4-methoxy-2H-pyran-4yl)phenoxy)methyl)-1-methyl-2(1H)-quinlolinone (alternatively NH can be N-methyl) | EP 466452 | | 5-LPO inhibitor |

-continued

| Company | Product_Name (Code) | Structure | Chemical Name | Patent Ref | Date Patent Issued/Application Published | MOA |
|---|---|---|---|---|---|---|
| Bayer | BAY-X-1005 | 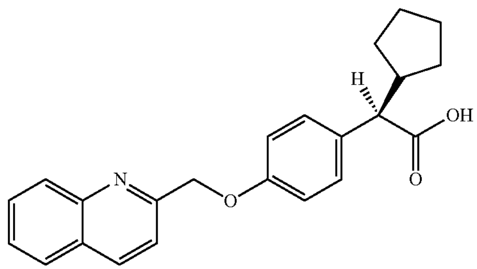 | (R)-(+)-alpha-cyclopentyl-4-(2-quinolinylmethoxy)-Benzeneacetic acid | U.S. Pat. No. 4,970,215 EP 344519, DE 198531 | | FLAP inhibitor |
| Merck | MK-0591 | | 1-((4-chlorophenyl)methyl)-3-((1,1-dimethylethyl)thio)-alpha, alpha-dimethoxy-5-(2-quinolinylmethoxy)-1H-Indole-2-propanoic acid | EP 419049, U.S. Pat. No. 1,989,0822 | | FLAP inhibitor |
| Merck | MK-866 | | (3[3-(4-chlorobenzyl)-3-t-butyl-thio-5-isopropylindol-2yl[2,2-dimethyl-proanoic acid | | | 5-LPO inhibitor |

-continued

| Company | Product_Name (Code) | Structure | Chemical Name | Patent Ref | Date Patent Issued/Application Published | MOA |
|---|---|---|---|---|---|---|
| Merck | MK-886 | 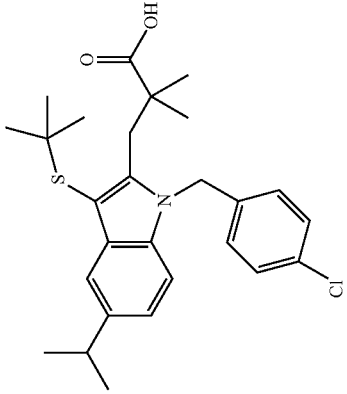 | 1-((4-chlorophenyl)methyl)-3-((1,1dimethylethyl)thio)-alpha,alpha-dimethyl-5-(2-quinolinylmethoxy)-1H-Indole-2-propanoic acid | EP 419049, U.S. Pat. No. 1,989,0822 | | 5-LPO inhibitor |
| Pfizer | CJ-13610 | | 4-(3-(4-(2-Methyl-imidazol-1-yl)-phenylsulfanyl)-phenyl)-tetrahydro-pyran-4-carboxylic acid amide | | | 5-LPO inhibitor |

In preferred methods of the invention, the agents set forth in the Agent Table can be used for prophylactic and/or therapeutic treatment for diseases and conditions associated with FLAP or with other members of the leukotriene pathway, or with increased leukotriene synthesis. In particular, they can be used for treatment for myocardial infarction or susceptibility to myocardial infarction, such as for individuals in an at-risk population as described above, (e.g., based on identified risk factors such as elevated cholesterol, elevated C-reactive protein, and/or genotype); for individuals suffering from acute coronary syndrome, such as unstable angina, non-ST-elevation myocardial infarction (NSTEMI) or ST-elevation myocardial infarction (STEMI); methods for reducing risk of MI, stroke or PAOD in persons with asymptomatic ankle/brachial index less than 0.9; for decreasing risk of a subsequent myocardial infarction, such as in individuals who have already had one or more myocardial infarctions; for stroke or susceptibility to stroke; for decreasing risk of a second stroke; for PAOD or susceptibility to PAOD; for treatment of atherosclerosis, such as in patients requiring treatment (e.g., angioplasty, stents, revascularization procedure) to restore blood flow in arteries (e.g., coronary, carotid, and/or femoral arteries); for treatment of asymptomatic ankle/brachial index of less than 0.9; and/or for decreasing leukotriene synthesis (e.g., for treatment of myocardial infarction, ACS, stroke or PAOD.

In one preferred embodiment of the invention, the leukotriene synthesis inhibitor is an inhibitor of FLAP such as 1-((4-chlorophenyl)methyl)-3-((1,1-dimethylethyl)thio)-alpha,alpha-dimethyl-5-(2-quinolinylmethoxy)-1H-Indole-2-propanoic acid otherwise known as MK-0591, (R)-(+)-alpha-cyclopentyl-4-(2-quinolinylmethoxy)-Benzeneacetic acid otherwise known as BAY-x-1005, 3-(3-(1,1-dimethylethylthio-5-(quinoline-2-ylmethoxy)-1-(4-chloromethylphenyl)indole-2-yl)-2,2-dimethylpropionaldehyde oxime-0-2-acetic acid otherwise known as A-81834, their optically pure enantiomers, salts, chemical derivatives, analogues, or other compounds inhibiting FLAP that effectively decrease leukotriene biosynthesis when administered to humans.

In another preferred embodiment of the invention, the leukotriene synthesis inhibitor is an inhibitor of 5LO such as zileuton, atreleuton, 6-((3-fluoro-5-(tetrahydro-4-methoxy-2H-pyran-4yl)phenoxy)methyl)-1-methyl-2(1H)-quinolinone otherwise known as ZD-2138, 1-((4-chlorophenyl)methyl)-3-((1,1 dimethylethyl)thio)-alpha,alpha-dimethyl-5-(2-quinolinylmethoxy)-1H-Indole-2-propanoic acid otherwise known as MK-886, 4-(3-(4-(2-Methyl-imidazol-1-yl)-phenylsulfanyl)-phenyl)-tetrahydro-pyran-4-carboxylic acid amide otherwise known as CJ-13610, their optically pure enantiomers, salts, chemical derivatives, analogues or other compounds inhibiting 5-LO that effectively decrease leukotriene biosynthesis when administered to humans.

The compound can be represented by the following formula:

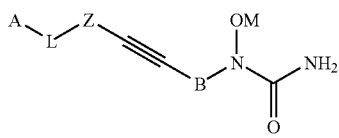

or a pharmaceutically acceptable salt thereof, wherein M is selected from the group consisting of hydrogen, a pharmaceutically acceptable cation, and a pharmaceutically acceptable metabolically cleavable group; B is a straight or branched divalent alkylene group of from one to twelve carbon atoms; Z is thiazolyl, optionally substituted with alkyl of from one to six carbon atoms or haloalkyl of from one to six carbon atoms; L is selected from the group consisting of (a) alkylene of from 1-6 carbon atoms, (b) alkenylene of from 2-6 carbon atoms, (c) alkynylene of from 2-6 carbon atoms, (d) hydroxyalkyl of 1-6 carbon atoms, (e) >C=O, (f)>C=N—OR$_1$, where R$_1$ is hydrogen or C$_1$-C$_6$ alkyl, (g) —(CHR1)$_n$(CO)(CHR$_2$)$_m$, where n and m are independently selected from an integer from one to six and R$_1$ and R$_2$ are independently selected from hydrogen and C$_1$-C$_6$-alkyl, (h) —(CHR1)$_n$C=NOR$_2$, where R$_1$, R$_2$ and n are as defined above; (i) —(CHR1)$_n$ON=CR$_2$, where R$_1$, R$_2$ and n are as: defined above; (j) —(CHR$_1$)$_n$—O—(CHR$_2$)$_m$—, where R$_1$, R$_2$, n and m are as defined above, (k) —(CHR$_1$)$_n$—NR$_2$(CHR$_3$)$_m$—, where R$_1$, R$_2$, n and m are as defined above and R$_3$ is selected from hydrogen and C$_1$-C$_6$-alkyl; (l) —(CHR$_1$)$_n$—S—CHR$_2$)$_m$—, where R$_1$, R$_2$, n and m are as defined above; and (m) —(CHR$_1$)$_n$—(SO$_2$)—(CHR$_2$)$_m$—, where R$_1$, R$_2$, n and m are as defined above; A is carbocyclic aryl optionally substituted with alkyl of from one to six carbon atoms, haloalkyl of from one to six carbon atoms, hydroxyalkyl of from one to six carbon atoms, alkoxy of from one to twelve carbon atoms, alkoxyalkoxyl in which the two alkoxy portions may each independently contain from one to six carbon atoms, alkylthio of from one to six carbon atoms, hydroxy, halogen, cyano, amino, alkylamino of from one to six carbon atoms, dialkylamino in which the two alkyl groups may independently contain from one to six carbon atoms, alkanoylamino of from two to eight carbon atoms, N-alkanoyl-N-alkylamino in which the alkanoyl is of from two to eight carbon atoms and the alkyl group is of from one to six carbon atoms, alkylaminocarbonyl of from two to eight carbon atoms, dialkylaminocarbonyl in which the two alkyl groups are independently of from one to six carbon atoms, carboxyl, alkoxycarbonyl or from two to eight carbon atoms, phenyl, optionally substituted with alkyl of from one to six carbon atoms, haloalkyl of from one to six carbon atoms, alkoxy of from one to six carbon atoms, hydroxy or halogen, phenoxy, optionally substituted with alkyl of from one to six carbon atoms, haloalkyl of from one to six carbon atoms, alkoxy of from one to six carbon atoms, hydroxy or halogen, and phenylthio, optionally substituted with alkyl of from one to six carbon atoms, haloalkyl of from one to six carbon atoms, alkoxy of from one to six carbon atoms, hydroxy or halogen. Preferably, the compound is a compound or pharmaceutically acceptable salt thereof having the name (R)-N-{3-[-5-(4-fluorophenylmethyl)thiazo-2-yl]-1methyl-2-propynyl}-N-hydroxyurea. See U.S. Pat. No. 4,615,596, incorporated herein by reference.

The compound is represented by the following formula:

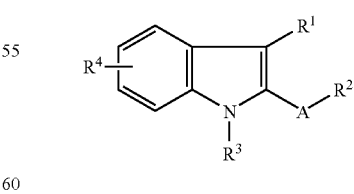

or a pharmaceutically acceptable salt thereof, wherein A is selected from the group consisting of straight or branched divalent alkylene of from one to twelve carbon atoms and divalent cycloalkylene of from three to eight carbon atoms; R$_1$ is selected from the group consisting of hydrogen, alkylthio of from one to six carbon atoms, phenylthio, optionally substituted with alkyl of from one to six carbon atoms, alkoxy of from one to six carbon atoms, or halogen, phenylalkylthio in which the alkyl portion contains from one to six carbon atoms, and the phenyl group is optionally substituted with alkyl of from one to six carbon atoms, alkoxy of from one to six carbon atoms, or halogen, $R_2$ is selected from the group consisting of —COOB wherein B is selected from hydrogen, a pharmaceutically acceptable cation, or a metabolically cleavable group, —COOalkyl where the alkyl portion contains from one to six carbon atoms, —COOalkylcarbocyclicaryl where the alkyl portion contains from one to six carbon atoms and the aryl portion is optionally substituted with alkyl of from one to six carbon atoms, alkoxy of from one to six carbon atoms, or halogen, —CONR$_5$R$_6$ wherein $R_5$ is selected from the group consisting of hydrogen, hydroxyl, alkyl of from one to six carbon atoms, and alkoxy of from one to six carbon atoms, and $R_6$ is selected from the group consisting of hydrogen and alkyl of from one to six carbon atoms, —COR$_6$, and —OH; $R_3$ is selected from the group consisting of phenylalkyl in which the alkyl portion contains from one to six carbon atoms, and the phenyl group is optionally substituted with alkyl of from one to six carbon atoms, alkoxy of from one to six carbon atoms, or halogen, $R_4$ is selected from the group consisting of thiazolylalkyloxy in which the alkyl portion contains from one to six carbon atoms, and the heteroaryl portion is optionally substituted with alkyl of from one to six carbon atoms, alkoxy of from one to six carbon atoms, or halogen, and thiazolyloxy optionally substituted with alkyl of from one to six carbon atoms, alkoxy of from one to six carbon atoms, or halogen. See U.S. Pat. No. 5,288,743, incorporated herein by reference.

The compound can be represented by the formula:

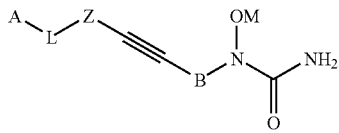

or a pharmaceutically acceptable salt thereof, wherein M is selected from the group consisting of hydrogen, and a pharmaceutically acceptable cation;

B is a straight or branched divalent alkylene group of from one to twelve carbon atoms; Z is selected from the group consisting of: (a) furyl, optionally substituted with alkyl of from one to six carbon atoms, or haloalkyl of from one to six carbon atoms, and (b) thienyl, optionally substituted with alkyl of from one to six carbon atoms, or haloalkyl of from one to six carbon atoms; and L is alkylene of from 1-6 carbon atoms; A is phenyl optionally substituted with alkyl of from one to six carbon atoms, haloalkyl of from one to six carbon atoms, hydroxyalkyl of from one to six carbon atoms, alkoxy of from one to twelve carbon atoms, alkoxyalkoxyl in which the two alkoxy portions may each independently contain from one to six carbon atoms, alkylthio of from one to six carbon atoms, hydroxy, halogen, cyano, amino, alkylamino of from one to six carbon atoms, dialkylamino in which the two alkyl groups may independently contain from one to six carbon atoms, alkanoylamino of from two to eight carbon atoms, N-alkanoyl-N-alkylamino in which the alkanoyl is of from two to eight carbon atoms and the alkyl group is of from one to six carbon atoms, alkylaminocarbonyl of from two to eight carbon atoms, dialkylaminocarbonyl in which the two alkyl groups are independently of from one to six carbon atoms, carboxyl, alkoxycarbonyl of from two to eight carbon atoms, phenyl, optionally substituted with alkyl of from one to six carbon atoms, haloalkyl of from one to six carbon atoms, alkoxy of from one to six carbon atoms, hydroxy or halogen, phenoxy, optionally substituted with alkyl of from one to six carbon atoms, haloalkyl of from one to six carbon atoms, alkoxy of from one to six carbon atoms, hydroxy or halogen, or phenylthio, optionally substituted with alkyl of from one to six carbon atoms, haloalkyl of from one to six carbon atoms, alkoxy of from one to six carbon atoms, hydroxy or halogen. Preferably, the compound is a compound or a pharmaceutically acceptable salt thereof selected from the group consisting of: N-{3-(5-(4-fluorophenylmethyl)fur-2-yl)-3-butyn-2-yl}-N-hydroxyurea; N-{3-(5-(4-fluorophenylmethyl)-2-thienyl)-1-methyl-2-propynyl}-N-hydroxyurea; (R)-N-{3-(5-(4-fluorophenylmethyl)-2-thienyl)-1-methyl-2-propynyl}-N-hydroxyurea; and (R)-N-{3-(5-(4-chlorophenylmethyl)-2-thienyl)-1-methyl-2-propynyl}-N-hydroxyurea; (S)-N-{3-[5-(4-fluorophenylmethyl)-2-thienyl]-1-methyl-2-propynyl}-N-hydroxyurea. See U.S. Pat. No. 5,288,751, incorporated by reference herein.

The compound can be represented by the formula:

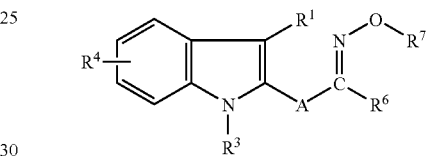

or a pharmaceutically acceptable salt thereof, wherein A is selected from the group consisting of straight or branched divalent alkylene of one to twelve carbon atoms, straight or branched divalent alkenylene of two to twelve carbon atoms, and divalent cycloalkylene of three to eight carbon atoms; $R^1$ is alkylthio of one to six carbon atoms; $R^6$ is selected from the group consisting of hydrogen and alkyl of one to six carbon atoms; $R^7$ is selected from the group consisting of (carboxyl)alkyl in which the alkyl portion is of one to six carbon atoms, (alkoxycarbonyl)alkyl in which the alkoxycarbonyl portion is of two to six carbon atoms and the alkyl portion is of one to six carbon atoms, (aminocarbonyl)alkyl in which the alkyl portion is of one to six carbon atoms, ((alkylamino)carbonyl)alkyl in which each alkyl portion independently is of one to six carbon atoms, and ((dialkylamino)carbonyl)alkyl in which each alkyl portion independently is of one to six carbon atoms; $R^3$ is phenylalkyl in which the alkyl portion is of one to six carbon atoms; $R^4$ is 2-, 3- or 6-quinolylmethoxy, optionally substituted with alkyl of one to six carbon atoms, haloalkyl of one to six carbon atoms, alkoxy of one to twelve carbon atoms, halogen, or hydroxy. Preferably, the compound is selected from the group consisting of: 3-(3-1,1-dimethylethylthio)-5-(quinolin-2-ylmethoxy-1-(4-chlorophenylmethyl)-indol-2-yl)-2,2-dimethylpropionaldehyde oxime-O-2 acetic acid; 3-(3-(1,1-dimethylethylthio)-5-(quinolin-2-ylmethoxy)-1-(4-chlorophenylmethyl) indol-2-yl)-2,2-dimethylpropionaldehyde oxime-O-2-(3-methyl)butyric acid; 3-(3-(1,1-dimethylethylthio)-5-(6,7-dichloroquinolin-2-ylmethoxy)-1-(4-chlorophenylmethyl)indol-2-yl)-2,2-dimethylpropionaldehyde oxime-O-2-acetic acid; and 3-(3-(1,1-dimethylethylthio)-5-(6-fluoroquinolin-2-ylmethoxy)-1-(4chlorophenylmethyl)indol-2-yl)-2,2-dimethylpropionaldehyde oxime-O-2-propionic acid; or a pharmaceutically acceptable salt or ester thereof. See U.S. Pat. No. 5,459,150, incorporated by reference herein.

The compound can be represented by the formula:

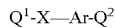

or pharmaceutically acceptable salts thereof, wherein Q is a 9-, 10- or 11-membered bicyclic heterocyclic moiety containing one or two nitrogen heteroatoms and optionally containing a further heteroatom selected from nitrogen, oxygen and sulphur, and Q may optionally bear up to four substituents selected from halogeno, hydroxy, cyano, formyl, oxo, thioxo, (1-4C)alkyl, (3-4C)alkenyl, (3-4C)alkynyl, (1-4C)alkoxy, fluoro-(1-4C)alkyl, hydroxy-(1-4C)alkyl, (2-5C)alkanoyl, phenyl, benzoyl and benzyl, and wherein said phenyl, benzoyl and benzyl substituents may optionally bear one or two substituents selected from halogeno, (1-4C)alkyl and (1-4C)alkoxy;

X is oxy, thio, sulphinyl or sulphonyl; Ar is phenylene, pyridinediyl, pyrimidinediyl, thiophenediyl, furandiyl, thiazolediyl, oxazolediyl, thiadiazolediyl or oxadiazolediyl which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino; and Q is selected from the groups of the formulae II and III:

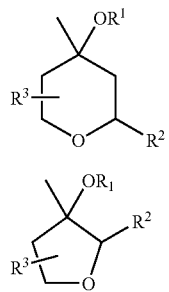

wherein R is hydrogen, (2-5C)alkanoyl or benzoyl, and wherein said benzoyl group may optionally bear one or two substituents selected from halogeno, (1-4C)alkyl and (1-4C)alkoxy; R is (1-4C)alkyl; and R is hydrogen or (1-4C)alkyl; or R and R are linked to form a methylene, vinylene, ethylene or trimethylene group. Preferably, the compound is selected from the group consisting of: (2S,4R)-4-[5-fluoro-3-(1-methyl-2-oxo-1,2,3,4-tetrahydroquinolin-6-ylthio)phenyl]-4-hydroxy-2-ethyltetrahydropyran, (2S,4R)-4-[5-fluoro-3-(1-methyl-2-oxo-1,2,3,4-tetrahydroquinolin-6-ylsulphonyl)phenyl]-4-hydroxy-2-methyltetrahydropyran, (2S,4R)-4-hydroxy-2-methyl-4-[2-(1-methyl-2-oxo-1,2,3,4-tetrahydroquinolin-6-ylthio)thiazol-5-yl]tetrahydropyran, (2S,4R)-4-hydroxy-2-methyl-4-[2-(1-methyl-2-oxo-1,2,3,4-tetrahydroquinolin-6-ylsulphonyl)thiazol-5-yl]tetrahydropyran, (2S,4R)-4-[2-(7-fluoro-1-methyl-2-oxo-1,2,3,4-tetrahydroquinolin-6-ylthio)thiazol-5-yl]-4-hydroxy-2-methyltetrahydropyran, (2S,4R)-4-hydroxy-2-methyl-4-[2-(1-methyl-2-oxoindolin-5-ylthio)thiazol-5-yl]tetrahydropyran, (2S,4R)-4-hydroxy-2-methyl-4-[2-(1-methyl-2-oxo-1,2,3,4-tetrahydroquinolin-6-ylthio)thien-4-yl]tetrahydropyran, (2S,4R)-4-hydroxy-2-methyl-4-[2-(1-methyl-2-oxo-1,2,3,4-tetrahydroquinolin-6-ylsulphonyl)thien-4-yl]tetrahydropyran, (2S,4R)-4-hydroxy-2-methyl-4-[2-(1-methyl-2-oxo-1,2,3,4-tetrahydroquinolin-6-ylthio)thien-5-yl]tetrahydropyran, (2S,4R)-4-hydroxy-2-methyl-4-[2-(1-methyl-2-oxo-1,2-dihydroquinolin-6-ylthio)thien-4-yl]tetrahydropyran, (2S,4R)-4-hydroxy-2-methyl-4-[2-(1,8-dimethyl-2-oxo-1,2,3,4-tetrahydroquinolin-6-ylthio)thien-4-yl]tetrahydropyran, 4-[2-(8-fluoro-1-methyl-2-oxo-1,2,3,4-tetrahydroquinolin-6-ylthio)thien-4-yl]-4-hydroxy-2-methyltetrahydropyran, 4-[2-(7-fluoro-1-methyl-2-oxo-1,2,3,4-tetrahydroquinolin-6-ylthio)thien-4-yl]-4-hydroxy-2-methyltetrahydropyran, (2S,4R)-4-hydroxy-2-methyl-4-[2-(1-methyl-2-oxoindolin-5-ylthio)thien-4-yl]tetrahydropyran, (2S,4R)-4-hydroxy-2-methyl-4-[3-(1-methyl-2-oxo-1,2,3,4-tetrahydroquinolin-6-ylthio)phenyl]tetrahydropyran, (2S,4R)-4-hydroxy-2-methyl-4-[3-(1-methyl-2-oxo-1,2,3,4-tetrahydroquinolin-6-ylsulphonyl)phenyl]tetrahydropyran, (2S,4R)-4-[3-(1-ethyl-2-oxo-1,2,3,4-tetrahydroquinolin-6-ylthio)phenyl]-4-hydroxy-2-methyltetrahydropyran, (2S,4R)-4-[3-(7-fluoro-1-methyl-2-oxo-1,2,3,4-tetrahydroquinolin-6-ylthio)phenyl]-4-hydroxy-2-methyltetrahydropyran, (2S,4R)-4-hydroxy-2-methyl-4-[3-(1-methyl-2-oxo-1,2-dihydroquinolin-6-ylthio)phenyl]tetrahydropyran, (2S,4R)-4-[3-(8-chloro-1-methyl-2-oxo-1,2,3,4-tetrahydroquinolin-6-ylthio)phenyl]-4-hydroxy-2-methyltetrahydropyran and (2S,4R)-4-hydroxy-2-methyl-4-[3-(1-methyl-2-oxoindolin-5-ylthio)phenyl]tetrahydropyran. See EP 623614 B1, incorporated herein by reference.

The compound can be represented by the formula:

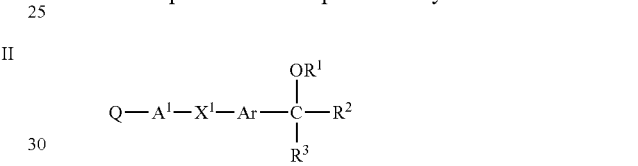

wherein Q is a 10-membered bicyclic heterocyclic moiety containing one or two nitrogen heteroatoms which bears one or two thioxo substituents, and which heterocyclic moiety may optionally bear one, two or three further substituents selected from halogeno, hydroxy, cyano, amino, (1-4C)alkyl, (1-4C)alkoxy, fluoro-(1-4C)alkyl, (1-4C)alkylamino, di-[(1-4C)alkyl]amino, amino-(1-4C)alkyl, (1-4C)alkylamino-(1-4C)alkyl, di-[(1-4C)alkyl]amino-(1-4C)alkyl, phenyl and phenyl-(1-4C)alkyl, and wherein said phenyl or phenyl-(1-4C)alkyl substituent may optionally bear a substituent selected from halogeno, (1-4C)alkyl and (1-4C)alkoxy; wherein A is a direct link to X or is (1-3C)alkylene; wherein X is oxy, thio, sulphinyl, sulphonyl or imino; wherein Ar is phenylene which may optionally bear one or two substituents selected from halogeno, hydroxy, amino, nitro, cyano, carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino; or Ar is pyridylene; wherein R is (1-4C)alkyl, (3-4C)alkenyl or (3-4C)alkynyl; and wherein R and R together form a group of the formula -A-X-A- which, together with the carbon atom to which A and A are attached, defines a ring having 5 to 7 ring atoms, wherein A and A, which may be the same or different, each is (1-3C)alkylene and X is oxy, thio, sulphinyl or sulphonyl, and which ring may bear one, two or three substituents, which may be the same or different, selected from hydroxy, (1-4C)alkyl and (1-4C)alkoxy; or wherein R and R together form a group of the formula -A-X-A- which, together with the oxygen atom to which A is attached and with the carbon atom to which A is attached, defines a ring having 5 to 7 ring atoms, wherein A and A, which may be the same or different, each is (1-3C)alkylene and X is oxy, thio, sulphinyl or sulphonyl, and which ring may bear one, two or three (1-4C)alkyl substituents, and wherein R is (1-4C)alkyl, (2-4C)alkenyl or (2-4C)alkynyl; or a pharmaceutically-acceptable salt thereof. Preferably, the compound is selected from the group consisting of: 4-(5-fluoro-3-(1-methyl-2-thioxo-1,2-dihydroquinolin-6-yl-methoxy)phenyl]-4-ethoxytetrahydropyran and 4-(5-fluoro-3-(1-methyl-2-thioxo-1,2,3,4-tetrahydroquinolin-6-1methoxy)phenyl]-4-methoxytetrahydropyran, 4-(5-fluoro-3-(1-methyl-2-thioxo-1,2,3,4-tetrahydroquinolin-6-ylthio)phenyl]-4-methoxytetrahydropyran and pharmaceutically-acceptable salt thereof. See EP 466452 B 1, incorporated herein by reference.

The compound can be a substituted 4-(quinolin-2-61-methoxy)phenylacetic acid derivative represented by the following formula:

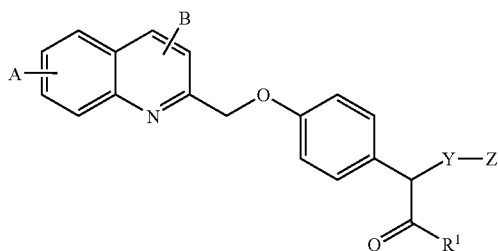

or pharmaceutically acceptable salt thereof, wherein $R^1$ represents a group of the formula:

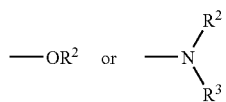

$R^2$ and $R^3$ are identical or different and represent hydrogen, lower alkyl, phenyl, benzyl or a group of the formula:

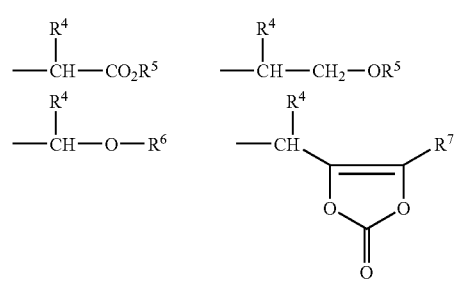

$R^4$ represents hydrogen, lower alkyl, phenyl or benzyl, which can optionally be substituted by hydroxyl, carboxyl, lower alkoxycarbonyl, lower alkylthio, heteroaryl or carbamoyl, $R^5$ represents hydrogen, lower alkyl, phenyl or benzyl, $R^6$ represents a group of the formula —$COR^5$ or —$CO^2R^5$, $R^7$ represents hydrogen, lower alkyl or phenyl, Y represents a group of the formula:

wherein $R^8$ represents hydrogen, lower alkyl or phenyl and n denotes a number of 0 to 5, Z represents norbornyl, or represents a group of the formula:

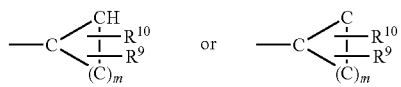

wherein $R^9$ and $R^{10}$ are identical or different and denote hydrogen, lower alkyl or phenyl, or $R^9$ and $R^{10}$ can together form a saturated carbocyclic ring having up to 6 carbon atoms and m denotes a number from 1 to 6, and A and B are identical or different and denote hydrogen, lower alkyl or halogen, or a pharmaceutically acceptable salt thereof. Preferably the compounds are selected from the group consisting of: 2-[4-(quinolin-2-yl-methoxy)phenyl]-2-cyclopentylacetic acid, 2-[4-(quinolin-2-yl-methoxy)phenyl]-2-cyclohexylacetic acid, and 2-[4-(quinolin-2-yl-methoxy)phenyl]-2-cycloheptylacetic acid, (+)-enantiomer of 2-[4-(quinolin-2-yl-methoxy)phenyl]-2-cyclopentylacetic acid, (−)-enantiomer of 2-[4-(quinolin-2-yl-methoxy)phenyl]-2-cyclopentylacetic acid and pharmaceutically acceptable salts thereof. See U.S. Pat. No. 4,970,215, incorporated herein by reference.

The compound can be represented by the formula:

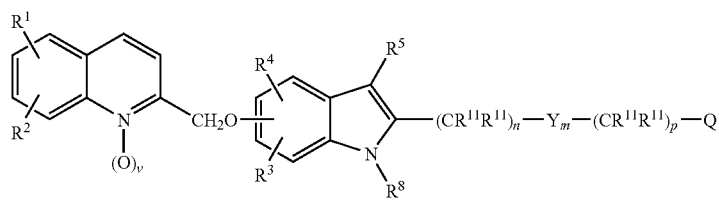

wherein R, R, R, R and R are independently hydrogen, halogen, lower alkyl, lower alkenyl, lower alkynyl, —CF3, —CN, —NO2, —N3, —C(OH)RR, —CO2R, —SR, —S(O)R, —S(O)2R, —S(O)2NRR, —OR, —NRR, —C(O)R or —(CH2)tR; R is hydrogen, —CH3, —CF3, —C(O)H, X—R or X—R; R and R are independently: alkyl, —(CH2)uPh(R)2 or —(CH2)uTh(R)2; R is —CF3 or R; R is hydrogen or X—R; each R is independently hydrogen or lower alkyl, or two R's on same carbon atom are joined to form a cycloalkyl ring of 3 to 6 carbon atoms; R is hydrogen, lower alkyl or —CH2R;

R is lower alkyl or —(CH2)rR; R is —CF3 or R; R is hydrogen, —C(O)R, R, or two R's on the same nitrogen may be joined to form a monocyclic heterocyclic ring of 4 to 6 atoms containing up to 2 heteroatoms chosen from O, S or N; R is hydrogen, —CF3, lower alkyl, lower alkenyl, lower alkynyl or —(CH2)rR; R is —(CH2)s—C(RR)—(CH2)s—R or —CH2C(O)NRR; R is hydrogen or lower alkyl; R is a) a monocyclic or bicyclic heterocyclic ring containing from 3 to 9 nuclear carbon atoms and 1 or 2 nuclear hetero-atoms selected from N, S or O and with each ring in the heterocyclic radical being formed of 5 or 6 atoms, or b) the radical W-R; R is alkyl or C(O)R; R is phenyl substituted with 1 or 2 R groups; R is hydrogen, halogen, lower alxyl, lower alkoxy, lower alkylthio, lower alkylsulfonyl, lower alkylcarbonyl, —CF3, —CN, —NO2 or —N3; R is alkyl, cycloalkyl, monocyclic monoheterocyclic ring; R is the residual structure of a standard amino acid, or R and R attached to the same N can cyclize to form a proline residue; m is 0 to 1; n is 0 to 3; p is 1 to 3 when m is 1; p is 0 to 3 when m is 0; r is 0 to 2; s is 0 to 3; t is 0 to 2; u is 0 to 3; v is 0 or 1; W is 0, S or NR; X is 0, or NR; X is C(O), CRR, S, S(O) or S(O)2; X is C(O), CRR, S(O)2 or a bond; Y is X or X; Q is —CO2R, —C(O)NHS(O)2R, —NHS(O)2R, —S(O)2NHR—C(O)NRR, —CO2R, —C(O)NRR, —CH2OH, or 1H- or 2H-tetrazol-5-yl; and the pharmaceutically acceptable salts thereof. Preferred embodiments of the compounds are selected from the following and pharmaceutically acceptable salts thereof:

- 3-[N-(p-chlorobenzyl)-3-(t-butylthio)-5-(quinolin-2-ylmethoxy)indol-2-yl]-2,2-dimethylpropanoic acid;
- 3-[N-(p-chlorobenzyl)-3-methyl-5-(quinolin-2-ylmethoxy)indol-2-yl]-2,2-dimethylpropanoic acid;
- 3-[N-(p-t-butylthiobenzyl)-3-(t-butylthio)-5-(quinolin-2-ylmethoxy)indol-2-yl]-2,2-dimethylpropanoic acid;
- 3-[N-(p-chlorobenzyl)-3-(phenylthio)-5-(quinolin-2-ylmethoxy)indol-2-yl]-2,2-dimethylpropanoic acid;
- 3-[N-(p-chlorobenzyl)-3-(phenylsulfonyl)-5-(quinolin-2-ylmethoxy)indol-2-yl]-2,2-dimethyl propanoic acid, N-oxide;
- 3-[N-(p-chlorobenzyl)-3-(phenylsulfonyl)-5-(quinolin-2-ylmethoxy)indol-2-yl]-2,2-dimethylpropanoic acid;
- 3-[N-(p-chlorobenzyl)-3-(phenylsulfinyl)-5-(quinolin-2-ylmethoxy)indol-2-yl]-2,2-dimethylpropanoic acid;
- 3-[N-(p-chlorobenzyl)-5-(quinolin-2-ylmethoxy)indol-2-yl]-2,2-dimethylpropanoic acid;
- 3-[N-(p-chlorobenzyl)-3-benzoyl-5-(quinolin-2-ylmethoxy)indol-2-yl]-2,2-dimethylpropanoic acid;
- 3-[N-(p-chlorobenzyl)-3-benzyl-5-(quinolin-2-ylmethoxy)indol-2-yl]-2,2-dimethylpropanoic acid;
- 3-[N-(p-chlorobenzyl)-3-(3,3-dimethyl-1-oxo-1-butyl)-5-(quinolin-2-ylmethoxy)indol-2-yl]-2,2-dimethylpropanoic acid;
- 2-[N-(p-chlorobenzyl)-3-(t-butylthio)-5-(quinolin-2-ylmethoxy)indol-2-yl]ethoxyethanoic acid;
- 3-[N-(p-chlorobenzyl)-3-(3,3-dimethyl-1-butyl)-5-(quinolin-2-ylmethoxy)indol-2-yl]-2,2-dimethylpropanoic acid;
- 3-[N-(p-chlorobenzyl)-3-(t-butylthio)-5-(quinolin-2-ylmethoxy)indol-2-yl]-2-methylpropanoic acid;
- 3-[N-(p-chlorobenzyl)-3-methyl-5-(6,7-dichloroquinolin-2-ylmethoxy)indol-2-yl]-2,2-dimethylpropanoic acid;
- 3-[N-(p-chlorobenzyl)-3-methyl-5-(7-chloroquinolin-2-ylmethoxy)indol-2-yl]-2,2-dimethylpropanoic acid;
- 3-[N-(p-chlorobenzyl)-4-allyl-5-(quinolin-2-ylmethoxy)-3-(t-butylthio)indol-2-yl]-2,2-dimethylpropanoic acid;
- 3-[N-(p-chlorobenzyl)-4-allyl-5-(quinolin-2-ylmethoxy)indol-2-yl]-2,2-dimethylpropanoic acid;
- 3-[N-(p-chlorobenzyl)-6-(quinolin-2-ylmethoxy)-3-(t-butylthio)indol-2-yl]-2,2-dimethylpropanoic acid;
- 3-[N-(p-chlorobenzyl)-4-(quinolin-2-ylmethoxy)-3-(t-butylthio)indol-2-yl]-2,2-dimethylpropanoic acid;
- 3-[N-(p-chlorobenzyl)-7-(quinolin-2-ylmethoxy)-3-(t-butylthio)indol-2-yl]-2,2-dimethylpropanoic acid;
- 2-[2-[N-(p-chlorobenzyl)-3-(t-butylthio)-5-(quinolin-2-ylmethoxy)indol-2-yl]ethoxy]propanoic acid;
- 3-[N-(p-chlorobenzyl)-4-(quinolin-2-ylmethoxy)indol-2-yl]-2,2-dimethylpropanoic acid;
- 3-[N-methyl-3-(p-chlorobenzoyl)-6-(quinolin-2-ylmethoxy)indol-2-yl]-2,2-dimethylpropanoic acid,
- 3-[N-methyl-3-(p-chlorobenzyl)-6-(quinolin-2-ylmethoxy)indol-2-yl]-2,2-dimethylpropanoic acid,
- 3-[N-(4-chlorobenzyl)-3-1-propoxy-5-(quinolin-2-ylmethoxy)indol-2-yl]-2,2-dimethylpropanoic acid,
- 3-[N-(4-chlorobenzyl)-3-(t-butylthio)-5-(quinolin-2-yl-methoxy)indol-2-yl]-2-ethylpropanoic acid,
- 3-[N-(4-chlorobenzyl)-3-trifluoroacetyl-5-(quinolin-2-ylmethoxy)indol-2-yl]-2,2-dimethylpropanoic acid,
- 3-[N-(4-chlorobenzyl)-3-(3,3-dimethyl-1-oxo-1-butyl)-5-(quinolin-2-ylmethoxy)indol-2-yl]-2-methylpropanoic acid,
- 3-[3-(3,3-dimethyl-1-oxo-1-butyl-5-(quinolin-2-ylmethoxy)indol-2-yl]-2,2-dimethylpropanoic acid,
- 3-[N-(4-triflouromethylbenzyl)-3-(3,3-dimethyl-1-oxo-1-butyl)-5-(quinolin-2-yl-methoxy)indol-2-yl]-2,2-dimethylpropanoic acid,
- 3-[N-benzyl-3-(3,3-dimethyl-1-oxo-1-butyl)-5-(quinolin-2-ylmethoxy)indol-2-yl]-2,2-dimethylpropanoic acid,
- 3-[N-(3-methoxybenzyl)-3-(3,3-dimethyl-1-oxo-1-butyl)-5-(quinolin-2-ylmethoxy)indol-2-yl]-2,2-dimethylpropanoic acid,
- 3-[N-allyl-3-(3,3-dimethyl-1-oxo-1-butyl)-5-(quinolin-2-ylmethoxy)indol-2-yl]-2,2-dimethylpropanoic acid,
- 3-[N-(4-methoxybenzyl)-3-(3,3-dimethyl-1-oxo-1-butyl)-5-(quinolin-2-ylmethoxy)indol-2-yl]-2,2-dimethylpropanoic acid,
- 3-[N-methyl-3-(3,3-dimethyl-1-oxo-3-butyl)-5-(quinolin-2-ylmethoxy)indol-2-yl]-2,2-dimethylpropanoic acid,
- 3-[3-(4-chlorobenzyl)-6-(quinolin-2-ylmethoxy)indol-2-yl]-2,2-dimethylpropanoic acid.
- 3-[N-(phenylsulfonyl)-3-(4-chlorobenzyl)-6-(quinolin-2-ylmethoxy)indol-2-yl]-2,2-dimethylpropanoic acid,
- 3-[N-benzyl-3-(4-chlorobenzyl)-6-(quinolin-2-ylmethoxy)indol-2-yl]-2,2-dimethylpropanoic acid,
- 3-[N-(4-chlorobenzyl)-3-(t-butylsulfonyl)-5-(quinolin-2-ylmethoxy)indol-2-yl]-2,2-dimethylpropanoic acid,
- 3-[N-(4-chlorobenzyl)-3-(t-butylsulfinyl)-5-(quinolin-2-ylmethoxy)indol-2-yl]-2,2-dimethylpropanoic acid,
- 3-[N-allyl-3-(4-chlorobenzyl)-6-(quinolin-2-ylmethoxy)indol-2-yl]-2,2-dimethylpropanoic acid,
- 3-[N-(n-propyl)-3-(4-chlorobenzyl)-6-(quinoline-2-ylmethoxy)indol-2-yl]-2,2-dimethylpropanoic acid,
- 3-[N-ethyl-3-(4-chlorobenzyl)-6-(quinolin-2-ylmethoxy)indol-2-yl]-2,2-dimethylpropanoic acid,
- 3-[N-(4-chlorobenzyl)-3-(4-t-butylbenzoyl)-5-(quinolin-2-yl-methoxy)indol-2-yl]-2,2-dimethylpropanoic acid, 3-[N-(4-chlorobenzyl)-3-(4-chlorobenzoyl)-5-(quinolin-2-ylmethoxy)indol-2-yl]-2,2-dimethylpropanoic acid,
3-[N-(4-chlorobenzyl)-3-(1,1-dimethylethyl)-5-(quinolin-2-ylmethoxy)indol-2-yl]-2,2-dimethylpropanoic acid,
3-[N-(4-chlorobenzyl)-3-acetyl-5-(quinolin-2-ylmethoxy)indol-2-yl]-2,2-dimethylpropanoic acid
3-[N-(4-chlorobenzyl)-3-cyclopropanecarbonyl-5-(quinolin-2-ylmethoxy)indol-2-yl]-2,2-dimethylpropanoic acid,
3-[N-(4-chlorobenzyl)-3-(3-cyclopentylpropanoyl)-5-(quinolin-2-ylmethoxy)indol-2-yl]-2,2-dimethylpropanoic acid,
3-[N-(4-chlorobenzyl)-3-(3-methylbutanoyl)-5-(quinolin-2-yl-methoxy)indol-2-yl]-2,2-dimethylpropanoic acid,
3-[N-(4-chlorobenzyl)-3-propanoyl-5-(quinolin-2-yl-methoxy)indol-2-yl]-2,2-dimethylpropanoic acid,
3-[N-(4-chlorobenzyl)-3-(2-methylpropanoyl)-5-(quinolin-2-ylmethoxy)indol-2-yl]-2,2-dimethylpropanoic acid,
3-[N-(4-chlorobenzyl)-3-trimethylacetyl-5-(quinolin-2-ylmethoxy)indol-2-yl]-2,2-dimethylpropanoic acid,
3-[N-(4-chlorobenzyl)-3-phenylacetyl-5-(quinolin-2-ylmethoxy)indol-2-yl]-2,2-dimethylpropanoic acid,
3-[N-(4-fluorobenzyl)-3-(3,3-dimethyl-1-oxo-1-butyl)-5-(quinolin-2-ylmethoxy)indol-2-yl]-2,2-dimethylpropanoic acid,
3-[N-(4-bromobenzyl)-3-(3,3-dimethyl-1-oxo-1-butyl)-5-(quinolin-2-ylmethoxy)indol-2-yl]-2,2-dimethylpropanoic acid,
3-[N-(4-iodobenzyl)-3-(3,3-dimethyl-1-oxo-1-butyl)-5-(quinolin-2-ylmethoxy)indol-2-yl]-2,2-dimethylpropanoic acid,
3-[N-(4-chlorobenzyl)-3-(1,1-dimethylbutyl)-5-(quinolin-2-ylmethoxy)indol-2-yl]-2,2-dimethylpropanoic acid,
3-[N-(4-chlorobenzyl)-3-(1,1-dimethylpropyl)-5-(quinolin-2-ylmethoxy)indol-2-yl]-2,2-dimethylpropanoic acid,
3-[N-(3-fluorobenzyl)-3-(1,1-dimethylethyl)-5-(quinolin-2-ylmethoxy)indol-2-yl]-2,2-dimethylpropanoic acid,
3-[N-(4-chlorobenzyl)-3-(3-methylethyl)-5-(quinolin-2-ylmethoxy)indol-2-yl]-2,2-dimethylpropanoic acid,
3-[N-(4-chlorobenzyl)-3-cyclopropyl-5-(quinolin-2-ylmethoxy)indol-2-yl]-2,2-dimethylpropanoic acid,
3-[N-(4-chlorobenzyl)-3-(1-methyl-1-cyclopropyl)-5-(quinolin-2-ylmethoxy)indol-2-yl]-2,2-dimethylpropanoic acid,
3-[N-(4-chlorobenzyl)-3-cyclopentyl-5-(quinolin-2-ylmethoxy)indol-2-yl]-2,2-dimethylpropanoic acid,
3-[N-(4-chlorobenzyl)-3-cyclohexyl-5-(quinolin-2-ylmethoxy)indol-2-yl]-2,2-dimethylpropanoic acid,
3-[N-(4-chlorobenzyl)-3-(alpha, alpha-dimethylbenzyl)-5-(quinolin-2-ylmethoxy)indol-2-yl]-2,2-dimethylpropanoic acid,
3-[N-(4-chlorobenzyl)-3-(2-{4-chloro-alpha, alpha-dimethylbenzyl}-5-(quinolin-2-ylmethoxy)indol-2-yl]-2,2-dimethylpropanoic acid,
3-[N-(4-chlorobenzyl)-3-(1-adamantyl)-5-(quinolin-2-ylmethoxy)indol-2-yl]-2,2-dimethylpropanoic acid,
3-[N-(4-chlorobenzyl)-3-((1-adamantyl)methyl)-5-(quinolin-2-ylmethoxy)indol-2-yl]-2,2-dimethylpropanoic acid,
3-[N-(1,1-dimethylethyl)-3-(4-chlorobenzyl)-6-(quinolin-2-ylmethoxy)indol-2-yl]-2,2-dimethylpropanoic acid,
3-[N-(1,1-dimethylpropyl)-3-(4-chlorobenzyl)-6-(quinoline-2-ylmethoxy)indol-2-yl]-2,2-dimethylpropanoic acid,
3-[N-(4-chlorobenzyl)-3-(3,3-dimethyl-1-oxo-1-butyl)-5-(quinolin-2-ylmethoxy)indol-2-yl]-2,2-diethylpropanoic acid,
methyl 3-[N-(4-chlorobenzyl)-3,6-bis(acetyl)-5-(quinolin-2-ylmethoxy)indol-2-yl]-2,2 dimethyl propanoate or
methyl 3-[N-(4-chlorobenzyl)-3,6-bis(cyclopropanecarbonyl)-5-(quinolin-2-ylmethoxy)indol-2-yl]-2,2-dimethyl propanoate. See EP 419049 B 1, incorporated herein by reference.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like. The term "hydroxyalkyl" represents an alkyl group, as defined above, substituted by one to three hydroxyl groups with the proviso that no more than one hydroxy group may be attached to a single carbon atom of the alkyl group. The term "alkylamino" refers to a group having the structure —NHR' wherein R' is alkyl, as previously defined, examples of alkylamino include methylamino, ethylamino, iso-propylamino and the like. The term "alkylaminocarbonyl" refers to an alkylamino group, as previously defined, attached to the parent molecular moiety through a carbonyl group. Examples of alkylaminocarbonyl include methylamino-carbonyl, ethylaminocarbonyl, iso-propylaminocarbonyl and the like. The term "alkylthio" refers to an alkyl group, as defined above, attached to the parent molecular moiety through a sulfur atom and includes such examples as methylthio, ethylthio, propylthio, n-, sec- and tert-butylthio and the like. The term "alkanoyl" represents an alkyl group, as defined above, attached to the parent molecular moiety through a carbonyl group. Alkanoyl groups are exemplified by formyl, acetyl, propionyl, butanoyl and the like. The term "alkanoylamino" refers to an alkanoyl group, as previously defined, attached to the parent molecular moiety through a nitrogen atom. Examples of alkanoylamino include formamido, acetamido, and the like. The term "N-alkanoyl-N-alkylamino" refers to an alkanoyl group, as previously defined, attached to the parent molecular moiety through an aminoalkyl group. Examples of N-alkanoyl-N-alkylamino include N-methylformamido, N-methyl-acetamido, and the like. The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like. The term "alkoxyalkoxyl" refers to an alkyl group, as defined above, attached through an oxygen to an alkyl group, as defined above, attached in turn through an oxygen to the parent molecular moiety. Examples of alkoxyalkoxyl include methoxymethoxyl, methoxyethyoxyl, ethoxyethoxyl and the like. The term "alkoxyalkyl" refers to an alkoxy group, as defined above, attached through an alkylene group to the parent molecular moiety. The term "alkoxycarbonyl" represents an ester group; i.e., an alkoxy group, attached to the parent molecular moiety through a carbonyl group such as methoxycarbonyl, ethoxycarbonyl, and the like. The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like. The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like. The term "alkenylene" denotes a divalent group derived from a straight or branched chain hydrocarbon containing at least one carbon-carbon double bond. Examples of alkenylene include —CH=CH—, —CH$_2$ CH=CH—, —C(CH$_3$)=CH—, —CH$_2$CH=CHCH$_2$—, and the like. The term "cycloalkylene" refers to a divalent group derived from a saturated carbocyclic hydrocarbon by the removal of two hydrogen atoms, for example cyclopentylene, cyclohexylene, and the like. The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl. The term "alkynylene" refers to a divalent group derived by the removal of two hydrogen atoms from a straight or branched chain acyclic hydrocarbon group containing a carbon-carbon triple bond. Examples of alkynylene include —CH≡CH—, —CH≡CH—CH$_2$—, —CH≡CH—CH(CH$_3$)—, and the like. The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl, fluorenyl, and the like. The term "(carbocyclic aryl)alkyl" refers to a carbocyclic aryl ring group as defined above, attached to the parent molecular moiety through an alkylene group. Representative (carbocyclic aryl)alkyl groups include phenylmethyl, phenylethyl, phenylpropyl, 1-naphthylmethyl, and the like. The term "carbocyclicarylalkoxy" refers to a carbocyclicaryl alkyl group, as defined above, attached to the parent molecular moiety through an oxygen atom. The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like. The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like. "Carbocyclic arylthioalkyl" represents a carbocyclic aryl group as defined above, attached to the parent molecular moiety through a sulfur atom and thence through an alklyene group and are typified by phenylthiomethyl, 1- and 2-naphthylthioethyl and the like. The term "dialkylamino" refers to a group having the structure —NR'R" wherein R' and R" are independently selected from alkyl, as previously defined. Additionally, R' and R" taken together may optionally be —(CH$_2$)$_{kk}$—where kk is an integer of from 2 to 6. Examples of dialkylamino include, dimethylamino, diethylaminocarbonyl, methylethylamino, piperidino, and the like. The term "halo or halogen" denotes fluorine, chlorine, bromine or iodine. The term "haloalkyl" denotes an alkyl group, as defined above, having one, two, or three halogen atoms attached thereto and is exemplified by such groups as chloromethyl, bromoethyl, trifluoromethyl, and the like. The term "hydroxyalkyl" represents an alkyl group, as defined above, substituted by one to three hydroxyl groups with the proviso that no more than one hydroxy group may be attached to a single carbon atom of the alkyl group. The term "phenoxy" refers to a phenyl group attached to the parent molecular moiety through an oxygen atom. The term "phenylthio" refers to a phenyl group attached to the parent molecular moiety through a sulfur atom. The term "pyridyloxy" refers to a pyridyl group attached to the parent molecular moiety through an oxygen atom. The terms "heteroaryl" or "heterocyclic aryl" as used herein refers to substituted or unsubstituted 5- or 6-membered ring aromatic groups containing one oxygen atom, one, two, three, or four nitrogen atoms, one nitrogen and one sulfur atom, or one nitrogen and one oxygen atom. The term heteroaryl also includes bi- or tricyclic groups in which the aromatic heterocyclic ring is fused to one or two benzene rings. Representative heteroaryl groups are pyridyl, thienyl, indolyl, pyrazinyl, isoquinolyl, pyrrolyl, pyrimidyl, benzothienyl, furyl, benzo[b]furyl, imidazolyl, thiazolyl, carbazolyl, and the like. The term "heteroarylalkyl" denotes a heteroaryl group, as defined above, attached to the parent molecular moiety through an alkylene group. The term "heteroaryloxy" denotes a heteroaryl group, as defined above, attached to the parent molecular moiety through an oxygen atom. The term "heteroarylalkoxy" denotes a heteroarylalkyl group, as defined above, attached to the parent molecular moiety through an oxygen atom.

Nucleic Acid Therapeutic Agents

In another embodiment, a nucleic acid of the invention; a nucleic acid complementary to a nucleic acid of the invention; or a portion of such a nucleic acid (e.g., an oligonucleotide as described below); or a nucleic acid encoding a member of the leukotriene pathway (e.g., 5-LO), can be used in "antisense" therapy, in which a nucleic acid (e.g., an oligonucleotide) which specifically hybridizes to the mRNA and/or genomic DNA of a nucleic acid is administered or generated in situ. The antisense nucleic acid that specifically hybridizes to the mRNA and/or DNA inhibits expression of the polypeptide encoded by that mRNA and/or DNA, e.g., by inhibiting translation and/or transcription. Binding of the antisense nucleic acid can be by conventional base pair complementarity, or, for example, in the case of binding to DNA duplexes, through specific interaction in the major groove of the double helix.

An antisense construct can be delivered, for example, as an expression plasmid as described above. When the plasmid is transcribed in the cell, it produces RNA that is complementary to a portion of the mRNA and/or DNA that encodes the polypeptide for the member of the leukotriene pathway (e.g., FLAP or 5-LO). Alternatively, the antisense construct can be an oligonucleotide probe that is generated ex vivo and introduced into cells; it then inhibits expression by hybridizing with the mRNA and/or genomic DNA of the polypeptide. In one embodiment, the oligonucleotide probes are modified oligonucleotides that are resistant to endogenous nucleases, e.g., exonucleases and/or endonucleases, thereby rendering them stable in vivo. Exemplary nucleic acid molecules for use as antisense oligonucleotides are phosphoramidate, phosphothioate and methylphosphonate analogs of DNA (see also U.S. Pat. Nos. 5,176,996, 5,264,564 and 5,256,775). Additionally, general approaches to constructing oligomers useful in antisense therapy are also described, for example, by Van der Krol et al. (*Biotechniques* 6:958-976 (1988)); and Stein et al. (*Cancer Res.* 48:2659-2668 (1988)). With respect to antisense DNA, oligodeoxyribonucleotides derived from the translation initiation site are preferred.

To perform antisense therapy, oligonucleotides (mRNA, cDNA or DNA) are designed that are complementary to mRNA encoding the polypeptide. The antisense oligonucleotides bind to mRNA transcripts and prevent translation. Absolute complementarity, although preferred, is not required. A sequence "complementary" to a portion of an RNA, as referred to herein, indicates that a sequence has sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid, as described in detail above. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures.

The oligonucleotides used in antisense therapy can be DNA, RNA, or chimeric mixtures or derivatives or modified versions thereof, single-stranded or double-stranded. The oligonucleotides can be modified at the base moiety, sugar moiety, or phosphate backbone, for example, to improve stability of the molecule, hybridization, etc. The oligonucleotides can include other appended groups such as peptides (e.g. for targeting host cell receptors in vivo), or agents facilitating transport across the cell membrane (see, e.g., Letsinger et al., *Proc. Natl. Acad. Sci. USA* 86:6553-6556 (1989); Lemaitre et al., *Proc. Natl. Acad. Sci. USA* 84:648-652 (1987); PCT International Publication No. WO 88/09810) or the blood-brain barrier (see, e.g., PCT International Publication No. WO 89/10134), or hybridization-triggered cleavage agents (see, e.g., Krol et al., *BioTechniques* 6:958-976 (1988)) or intercalating agents. (See, e.g., Zon, Pharm. Res. 5: 539-549 (1988)). To this end, the oligonucleotide may be conjugated to another molecule (e.g., a peptide, hybridization triggered cross-linking agent, transport agent, hybridization-triggered cleavage agent).

The antisense molecules are delivered to cells that express the member of the leukotriene pathway in vivo. A number of methods can be used for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. Alternatively, in a preferred embodiment, a recombinant DNA construct is utilized in which the antisense oligonucleotide is placed under the control of a strong promoter (e.g., pol III or pol II). The use of such a construct to transfect target cells in the patient results in the transcription of sufficient amounts of single stranded RNAs that will form complementary base pairs with the endogenous transcripts and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art and described above. For example, a plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systemically).

In another embodiment of the invention, small double-stranded interfering RNA (RNA interference (RNAi)) can be used. RNAi is a post-transcription process, in which double-stranded RNA is introduced, and sequence-specific gene silencing results, though catalytic degradation of the targeted mRNA. See, e.g., Elbashir, S. M. et al., *Nature* 411:494-498 (2001); Lee, N. S., *Nature Biotech.* 19:500-505 (2002); Lee, S-K. et al., *Nature Medicine* 8(7):681-686 (2002); the entire teachings of these references are incorporated herein by reference. RNAi is used routinely to investigate gene function in a high throughput fashion or to modulate gene expression in human diseases (Chi et al., *PNAS*, 100 (11):6343-6346 (2003)). Introduction of long double standed RNA leads to sequence-specific degradation of homologous gene transcripts. The long double stranded RNA is metabolized to small 21-23 nucleotide siRNA (small interfering RNA). The siRNA then binds to protein complex RISC (RNA-induced silencing complex) with dual function helicase. The helicase has RNAas activity and is able to unwind the RNA. The unwound si RNA allows an antisense strand to bind to a target. This results in sequence dependent degradation of cognate mRNA. Aside from endogenous RNAi, exogenous RNAi, chemically synthesized or recombinantly produced can also be used. Using non-intronic portions of the FLAP gene, such as corresponding mRNA portions of SEQ ID NO.1, or portions of SEQ ID NO: 3, target regions of the FLAP gene that are accessible for RNAi are targeted and silenced. With this technique it is possible to conduct a RNAi gene walk of the nucleic acids of the FLAP gene and determine the amount of inhibition of the protein product. Thus it is possible to design gene-specific therapeutics by directly targeting the mRNAs of the gene.

Endogenous expression of a member of the leukotriene pathway (e.g., FLAP, 5-LO) can also be reduced by inactivating or "knocking out" the gene or its promoter using targeted homologous recombination (e.g., see Smithies et al., *Nature* 317:230-234 (1985); Thomas & Capecchi, *Cell* 51:503-512 (1987); Thompson et al., *Cell* 5:313-321 (1989)). For example, an altered, non-functional gene of a member of the leukotriene pathway (or a completely unrelated DNA sequence) flanked by DNA homologous to the endogenous gene (either the coding regions or regulatory regions of the gene) can be used, with or without a selectable marker and/or a negative selectable marker, to transfect cells that express the gene in vivo. Insertion of the DNA construct, via targeted homologous recombination, results in inactivation of the gene. The recombinant DNA constructs can be directly administered or targeted to the required site in vivo using appropriate vectors, as described above. Alternatively, expression of non-altered genes can be increased using a similar method: targeted homologous recombination can be used to insert a DNA construct comprising a non-altered functional gene, or the complement thereof, or a portion thereof, in place of an gene in the cell, as described above. In another embodiment, targeted homologous recombination can be used to insert a DNA construct comprising a nucleic acid that encodes a polypeptide variant that differs from that present in the cell.

Alternatively, endogenous expression of a member of the leukotriene pathway can be reduced by targeting deoxyribonucleotide sequences complementary to the regulatory region of the member of the leukotriene pathway (i.e., the promoter and/or enhancers) to form triple helical structures that prevent transcription of the gene in target cells in the body. (See generally, Helene, C., *Anticancer Drug Des.*, 6(6):569-84 (1991); Helene, C. et al., *Ann. N.Y. Acad. Sci.* 660:27-36 (1992); and Maher, L. J., *Bioassays* 14(12):807-15 (1992)). Likewise, the antisense constructs described herein, by antagonizing the normal biological activity of one of the members of the leukotriene pathway, can be used in the manipulation of tissue, e.g., tissue differentiation, both in vivo and for ex vivo tissue cultures. Furthermore, the antisense techniques (e.g., microinjection of antisense molecules, or transfection with plasmids whose transcripts are anti-sense with regard to a nucleic acid RNA or nucleic acid sequence) can be used to investigate the role of one or more members of the leukotriene pathway in the development of disease-related conditions. Such techniques can be utilized in cell culture, but can also be used in the creation of transgenic animals.

The therapeutic agents as described herein can be delivered in a composition, as described above, or by themselves. They can be administered systemically, or can be targeted to a particular tissue. The therapeutic agents can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein. In addition, a combination of any of the above methods of treatment (e.g., administration of non-altered polypeptide in conjunction with antisense therapy targeting altered mRNA for a member of the leukotriene pathway; administration of a first splicing variant in conjunction with antisense therapy targeting a second splicing variant) can also be used.

The invention additionally pertains to use of such therapeutic agents, as described herein, for the manufacture of a medicament for the treatment of MI, ACS, stroke, PAOD and/or atherosclerosis, e.g., using the methods described herein.

Monitoring Progress of Treatment

The current invention also pertains to methods of monitoring the response of an individual, such as an individual in one of the target populations described above, to treatment with a leukotriene synthesis inhibitor.

Because the level of inflammatory markers can be elevated in individuals who are in the target populations described above, an assessment of the level of inflammatory markers of the individual both before, and during, treatment with the leukotriene synthesis inhibitor will indicate whether the treatment has successfully decreased production of leukotrienes in the arterial vessel wall or in bone-marrow derived inflammatory cells. For example, in one embodiment of the invention, an individual who is a member of a target population as described above (e.g., an individual at risk for MI, ACS, stroke or PAOD, such as an individual who is at-risk due to a FLAP haplotype) can be assessed for response to treatment with a leukotriene synthesis inhibitor, by examining leukotriene levels or leukotriene metabolite levels in the individual. Blood, serum, plasma or urinary leukotrienes (e.g., leukotriene E4, cysteinyl leukotriene 1), or ex vivo production of leukotrienes (e.g., in blood samples stimulated with a calcium ionophore to produce leukotrienes), or leukotriene metabolites, can be measured before, and during or after treatment with the leukotriene synthesis inhibitor. The leukotriene or leukotriene metabolite level before treatment is compared with the leukotriene or leukotriene metabolite level during or after treatment. The efficacy of treatment is indicated by a decrease in leukotriene production: a level of leukotriene or leukotriene metabolite during or after treatment that is significantly lower than the level of leukotriene or leukotriene metabolite before treatment, is indicative of efficacy. A level that is lower during or after treatment can be shown, for example, by decreased serum or urinary leukotrienes, or decreased ex vivo production of leukotrienes, or decreased leukotriene metabolites. A level that is "significantly lower", as used herein, is a level that is less than the amount that is typically found in control individual(s), or is less in a comparison of disease risk in a population associated with the other bands of measurement (e.g., the mean or median, the highest quartile or the highest quintile) compared to lower bands of measurement (e.g., the mean or median, the other quartiles; the other quintiles).

For example, in one embodiment of the invention, the level of a leukotriene or leukotriene metabolite is assessed in an individual before treatment with a leukotriene synthesis inhibitor; and during or after treatment with the leukotriene synthesis inhibitor, and the levels are compared. A level of the leukotriene or leukotriene metabolite during or after treatment that is significantly lower than the level of the leukotriene or leukotriene metabolite before treatment, is indicative of efficacy of treatment with the leukotriene synthesis inhibitor. In another embodiment, production of a leukotriene or a leukotriene metabolite is stimulated in a first test sample from the individual, using a calcium ionophore, before treatment with a leukotriene synthesis inhibitor, and is also stimulated in a second test sample from the individual, using a calcium ionophore, during or after treatment with the leukotriene synthesis inhibitor, and the level of production in the first test sample is compared with with the level of production of the leukotriene or leukotriene metabolite in the second test sample. A level of the leukotriene or leukotriene metabolite in the second test sample that is significantly lower than the level of the leukotriene or leukotriene metabolite in the first test sample, is indicative of efficacy of treatment with the leukotriene synthesis inhibitor.

In another embodiment of the invention, an individual who is a member of a target population of individuals at risk for MI, ACS, stroke or PAOD (e.g., an individual in a target population described above, such as an individual at-risk due to elevated C-reactive protein) can be assessed for response to treatment with a leukotriene synthesis inhibitor, by examining levels of inflammatory markers in the individual. For example, levels of an inflammatory marker in an appropriate test sample (e.g., serum, plasma or urine) can be measured before, and during or after treatment with the leukotriene synthesis inhibitor. The level of the inflammatory marker before treatment is compared with the level of the inflammatory marker during or after treatment. The efficacy of treatment is indicated by a decrease in the level of the inflammatory marker, that is, a level of the inflammatory marker during or after treatment that is significantly lower (e.g., significantly lower), than the level of inflammatory marker before treatment, is indicative of efficacy. Representative inflammatory markers include: C-reactive protein (CRP), serum amyloid A, fibrinogen, a leukotriene (e.g., LTB4, LTC4, LTD4, LTE4), a leukotriene metabolite, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, myeloperoxidase (MPO), and N-tyrosine. In a preferred embodiment, the marker is CRP or MPO.

Assessment of Increased Risk

The present invention additionally pertains to methods for assessing an individual (e.g., an individual who is in a target population as described herein, such as an individual who is at risk for MI, ACS, stroke or PAOD), for an increased risk of MI, ACS, atherosclerosis, stroke, transient ischemic attack, transient monocular blindness, asymptomatic carotid stenosis, PAOD, claudication, or limb ischemia. The methods comprise assessing the level of a leukotriene metabolite (e.g., LTE4, LTD4, LTB4) in the individual, wherein an increased level of leukotriene metabolite is indicative of an increased risk. The level can be measured in any appropriate tissue or fluid sample, such as blood, serum, plasma, or urine. In one particular embodiment, the sample comprises neutrophils. The level of the leukotriene metabolite can be measured by standard methods, such as the methods described herein. For example, in one embodiment, production of a leukotriene metabolite is stimulated in a first test sample from the individual, using a calcium ionophore. The level of production is compared with a control level. The control level is a level that is typically found in control individual(s), such as individual who are not at risk for MI, ACS, stroke or PAOD; alternatively, a control level is the level that is found by comparison of disease risk in a population associated with the lowest band of measurement (e.g., below the mean or median, the lowest quartile or the lowest quintile) compared to higher bands of measurement (e.g., above the mean or median, the second, third or fourth quartile; the second, third, fourth or fifth quintile). A level of production of the leukotriene metabolite that is significantly greater than the control level, is indicative of an increased risk. Individuals at increased risk are candidates for treatments described herein.

Pharmaceutical Compositions

The present invention also pertains to pharmaceutical compositions comprising agents described herein, for example, an agent that is a leukotriene synthesis inhibitor as described herein. For instance, a leukotriene synthesis inhibitor can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devices ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The agents are administered in a therapeutically effective amount. The amount of agents which will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

Nucleic Acids of the Invention

FLAP Nucleic Acids, Portions and Variants

In addition, the invention pertains to isolated nucleic acid molecules comprising a human FLAP nucleic acid. The term, "FLAP nucleic acid," as used herein, refers to an isolated nucleic acid molecule encoding FLAP polypeptide. The FLAP nucleic acid molecules of the present invention can be RNA, for example, mRNA, or DNA, such as cDNA and genomic DNA. DNA molecules can be double-stranded or single-stranded; single stranded RNA or DNA can be either the coding, or sense strand or the non-coding, or antisense strand. The nucleic acid molecule can include all or a portion of the coding sequence of the gene or nucleic acid and can further comprise additional non-coding sequences such as introns and non-coding 3' and 5' sequences (including regulatory sequences, for example, as well as promoters, transcription enhancement elements, splice donor/acceptor sites, etc.).

For example, a FLAP nucleic acid can consist of SEQ ID NOs: 1 or 3 or the complement thereof, or to a portion or fragment of such an isolated nucleic acid molecule (e.g., cDNA or the nucleic acid) that encodes FLAP polypeptide (e.g., a polypeptide such as SEQ ID NO: 2). In a preferred embodiment, the isolated nucleic acid molecule comprises a nucleic acid molecule selected from the group consisting of SEQ ID NOs: 1 or 3, or their complement thereof.

Additionally, the nucleic acid molecules of the invention can be fused to a marker sequence, for example, a sequence that encodes a polypeptide to assist in isolation or purification of the polypeptide. Such sequences include, but are not limited to, those that encode a glutathione-S-transferase (GST) fusion protein and those that encode a hemagglutinin A (HA) polypeptide marker from influenza.

An "isolated" nucleic acid molecule, as used herein, is one that is separated from nucleic acids that normally flank the gene or nucleic acid sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as HPLC. In certain embodiments, an isolated nucleic acid molecule comprises at least about 50, 80 or 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 5 kb, including but not limited to 4 kb, 3 kb, 2 kb, 1 kb, 0.5 kb or 0.1 kb of nucleotides which flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleic acid sequence can include a nucleic acid molecule or nucleic acid sequence that is synthesized chemically or by recombinant means. Therefore, recombinant DNA contained in a vector is included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species), for gene mapping (e.g., by in situ hybridization with chromosomes), or for detecting expression of the nucleic acid in tissue (e.g., human tissue), such as by Northern blot analysis.

The present invention also pertains to nucleic acid molecules which are not necessarily found in nature but which encode a FLAP polypeptide (e.g., a polypeptide having an amino acid sequence comprising an amino acid sequence of SEQ ID NOs: 2), or another splicing variant of a FLAP polypeptide or polymorphic variant thereof. Thus, for example, DNA molecules that comprise a sequence that is different from the naturally occurring nucleic acid sequence but which, due to the degeneracy of the genetic code, encode a FLAP polypeptide of the present invention are also the subjects of this invention. The invention also encompasses nucleotide sequences encoding portions (fragments), or encoding variant polypeptides such as analogues or derivatives of a FLAP polypeptide. Such variants can be naturally occurring, such as in the case of allelic variation or single nucleotide polymorphisms, or non-naturally-occurring, such as those induced by various mutagens and mutagenic processes. Intended variations include, but are not limited to, addition, deletion and substitution of one or more nucleotides that can result in conservative or non-conservative amino acid changes, including additions and deletions. Preferably the nucleotide (and/or resultant amino acid) changes are silent or conserved; that is, they do not alter the characteristics or activity of a FLAP polypeptide. In one preferred embodiment, the nucleotide sequences are fragments that comprise one or more polymorphic microsatellite markers. In another preferred embodiment, the nucleotide sequences are fragments that comprise one or more single nucleotide polymorphisms in a FLAP nucleic acid (e.g., the single nucleotide polymorphisms set forth in Table 13, below).

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

The invention also pertains to nucleic acid molecules that hybridize under high stringency hybridization conditions, such as for selective hybridization, to a nucleic acid sequence described herein (e.g., nucleic acid molecules which specifically hybridize to a nucleic acid sequence encoding polypeptides described herein, and, optionally, have an activity of the polypeptide). In one embodiment, the invention includes variants described herein which hybridize under high stringency hybridization conditions (e.g., for selective hybridization) to a nucleic acid sequence comprising a nucleic acid sequence selected from the group consisting of SEQ ID NOs: 1 or 3 or the complement thereof. In another embodiment, the invention includes variants described herein which hybridize under high stringency hybridization conditions (e.g., for selective hybridization) to a nucleic acid sequence encoding an amino acid sequence of SEQ ID NO: 2 or a polymorphic variant thereof. In a preferred embodiment, the variant that hybridizes under high stringency hybridizations has an activity of a FLAP.

Such nucleic acid molecules can be detected and/or isolated by specific hybridization (e.g., under high stringency conditions). "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity that is less than perfect (e.g., 70%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology* 200: 546-556 (1991), and in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of −17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 minutes at room temperature; a moderate stringency wash can comprise washing in a prewarmed solution (42° C.) solution containing 0.2×SSC/0.1% SDS for 15 minutes at 42° C.; and a high stringency wash can comprise washing in prewarmed (68° C.) solution containing 0.1×SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

The percent homology or identity of two nucleotide or amino acid sequences can be determined by aligning the sequences for optimal comparison purposes (e.g., gaps can be introduced in the sequence of a first sequence for optimal alignment). The nucleotides or amino acids at corresponding positions are then compared, and the percent identity between the two sequences is a function of the number of identical positions shared by the sequences (i.e., % identity=# of identical positions/total # of positions×100). When a position in one sequence is occupied by the same nucleotide or amino acid residue as the corresponding position in the other sequence, then the molecules are homologous at that position. As used herein, nucleic acid or amino acid "homology" is equivalent to nucleic acid or amino acid "identity". In certain embodiments, the length of a sequence aligned for comparison purposes is at least 30%, for example, at least 40%, in certain embodiments at least 60%, and in other embodiments at least 70%, 80%, 90% or 95% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA* 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

Another preferred, non-limiting example of a mathematical algorithm utilized for the comparison of sequences is the algorithm of Myers and Miller, *CABIOS* 4(1): 11-17 (1988).

Such an algorithm is incorporated into the ALIGN program (version 2.0) which is part of the GCG sequence alignment software package (Accelrys, Cambridge, UK). When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, *Comput. Appl. Biosci.* 10:3-5 (1994); and FASTA described in Pearson and Lipman, *Proc. Natl. Acad. Sci. USA* 85:2444-8 (1988).

In another embodiment, the percent identity between two amino acid sequences can be accomplished using the GAP program in the GCG software package using either a BLOSUM63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package using a gap weight of 50 and a length weight of 3.

The present invention also provides isolated nucleic acid molecules that contain a fragment or portion that hybridizes under highly stringent conditions to a nucleic acid sequence comprising SEQ ID NO: 1 or 3 or the complement of SEQ ID NO: 1 or 3, and also provides isolated nucleic acid molecules that contain a fragment or portion that hybridizes under highly stringent conditions to a nucleic acid sequence encoding an amino acid sequence of the invention or polymorphic variant thereof. The nucleic acid fragments of the invention are at least about 15, for example, at least about 18, 20, 23 or 25 nucleotides, and can be 30, 40, 50, 100, 200 or more nucleotides in length. Longer fragments, for example, 30 or more nucleotides in length, encoding antigenic polypeptides described herein are particularly useful, such as for the generation of antibodies as described below.

Probes and Primers

In a related aspect, the nucleic acid fragments of the invention are used as probes or primers in assays such as those described herein. "Probes" or "primers" are oligonucleotides that hybridize in a base-specific manner to a complementary strand of nucleic acid molecules. Such probes and primers include polypeptide nucleic acids, as described in Nielsen et al., (*Science* 254:1497-1500 (1991)).

A probe or primer comprises a region of nucleic acid that hybridizes to at least about 15, for example about 20-25, and in certain embodiments about 40, 50 or 75, consecutive nucleotides of a nucleic acid of the invention, such as a nucleic acid comprising a contiguous nucleic acid sequence of SEQ ID NOs: 1 or 3 or the complement of SEQ ID Nos: 1 or 3, or a nucleic acid sequence encoding an amino acid sequence of SEQ ID NO: 2 or polymorphic variant thereof. In preferred embodiments, a probe or primer comprises 100 or fewer nucleotides, in certain embodiments, from 6 to 50 nucleotides, for example, from 12 to 30 nucleotides. In other embodiments, the probe or primer is at least 70% identical to the contiguous nucleic acid sequence or to the complement of the contiguous nucleotide sequence, for example, at least 80% identical, in certain embodiments at least 90% identical, and in other embodiments at least 95% identical, or even capable of selectively hybridizing to the contiguous nucleic acid sequence or to the complement of the contiguous nucleotide sequence. Often, the probe or primer further comprises a label, e.g., radioisotope, fluorescent compound, enzyme, or enzyme co-factor.

The nucleic acid molecules of the invention such as those described above can be identified and isolated using standard molecular biology techniques and the sequence information provided herein. For example, nucleic acid molecules can be amplified and isolated using the polymerase chain reaction and synthetic oligonucleotide primers based on one or more of SEQ ID NOs: 1 or 3, or the complement thereof, or designed based on nucleotides based on sequences encoding one or more of the amino acid sequences provided herein. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis et al., Academic Press, San Diego, Calif., 1990); Mattila et al., *Nucl. Acids Res.* 19:4967 (1991); Eckert et al., *PCR Methods and Applications* 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), and self-sustained sequence replication (Guatelli et al., *Proc. Nat. Acad. Sci. USA* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be labeled, for example, radiolabeled, and used as a probe for screening a cDNA library derived from human cells, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a polypeptide of the appropriate molecular weight. For example, the direct analysis of the nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the polypeptide and the DNA encoding the polypeptide can be isolated, sequenced and further characterized.

Antisense nucleic acid molecules of the invention can be designed using the nucleotide sequences of SEQ ID NOs: 1 or 3 and/or the complement of one or more of SEQ ID NOs: 1 or 3 and/or a portion of one or more of SEQ ID NOs: 1 or 3 or the complement of one or more of SEQ ID NOs: 1 or 3 and/or a sequence encoding the amino acid sequences of SEQ ID NOs: 2 or encoding a portion of one or more of SEQ ID NOs: 1 or 3 or their complement. They can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

The nucleic acid sequences can also be used to compare with endogenous DNA sequences in patients to identify one or more of the disorders related to FLAP, and as probes, such as to hybridize and discover related DNA sequences or to subtract out known sequences from a sample. The nucleic acid sequences can further be used to derive primers for genetic fingerprinting, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways as polynucleotide reagents. For example, these sequences can be used to: (i) map their respective genes on a chromosome; and, thus, locate gene regions or nucleic acid regions associated with genetic disease; (ii) identify an individual from a minute biological sample (tissue typing); and (iii) aid in forensic identification of a biological sample. Additionally, the nucleotide sequences of the invention can be used to identify and express recombinant polypeptides for analysis, characterization or therapeutic use, or as markers for tissues in which the corresponding polypeptide is expressed, either constitutively, during tissue differentiation, or in diseased states. The nucleic acid sequences can additionally be used as reagents in the screening and/or diagnostic assays described herein, and can also be included as components of kits (e.g., reagent kits) for use in the screening and/or diagnostic assays described herein.

Vectors

Another aspect of the invention pertains to nucleic acid constructs containing a nucleic acid molecule of SEQ ID NOs: 1 or 3 or the complement thereof (or a portion thereof). Yet another aspect of the invention pertains to nucleic acid constructs containing a nucleic acid molecule encoding an amino acid of SEQ ID NO: 2 or polymorphic variant thereof. The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, such as expression vectors, are capable of directing the expression of genes or nucleic acids to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" or "operatively linked" is intended to mean that the nucleic acid sequence of interest is linked to the regulatory sequence(s) in a manner which allows for expression of the nucleic acid sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, "Gene Expression Technology", *Methods in Enzymology* 185, Academic Press, San Diego, Calif. (1990). Regulatory sequences include those which direct constitutive expression of a nucleic acid sequence in many types of host cell and those which direct expression of the nucleic acid sequence only in certain host cells (e.g., tissue-specific regulatory sequences). It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells such as E. coli, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., E. coli), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene or nucleic acid that encodes a selectable marker (e.g., for resistance to antibiotics) is generally introduced into the host cells along with the gene or nucleic acid of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene or nucleic acid will survive, while the other cells die).

A host cell of the invention, such as a prokaryotic host cell or eukaryotic host cell in culture can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid molecule of the invention has been introduced (e.g., an exogenous FLAP nucleic acid, or an exogenous nucleic acid encoding a FLAP polypeptide). Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleic acid sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens and amphibians. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Methods for constructing homologous recombination vectors and homologous recombinant animals are described further in Bradley, *Current Opinion in BioTechnology* 2:823-829 (1991) and in PCT Publication Nos. WO 90/11354, WO 91/01140, WO 92/0968, and WO 93/04169. Clones of the non-human transgenic animals described herein can also be produced according to the methods described in Wilmut et al., *Nature* 385: 810-813 (1997) and PCT Publication Nos. WO 97/07668 and WO 97/07669.

Polypeptides of the Invention

The present invention also pertains to isolated polypeptides encoded by FLAP nucleic acids ("FLAP polypeptides"), and fragments and variants thereof, as well as polypeptides encoded by nucleotide sequences described herein (e.g., other splicing variants). The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell (e.g., in a "fusion protein") and still be "isolated" or "purified."

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide of the invention comprises an amino acid sequence encoded by a nucleic acid molecule comprising a nucleic acid sequence selected from the group consisting of SEQ ID NO: 1 or 3, or the complement of SEQ ID NO: 1 or 3, or portions thereof, or a portion or polymorphic variant thereof. However, the polypeptides of the invention also encompass fragment and sequence variants. Variants include a substantially homologous polypeptide encoded by the same genetic locus in an organism, i.e., an allelic variant, as well as other splicing variants. Variants also encompass polypeptides derived from other genetic loci in an organism, but having substantial homology to a polypeptide encoded by a nucleic acid molecule comprising a nucleic acid sequence selected from the group consisting of SEQ ID NOs: 1 or 3 or their complement, or portions thereof, or having substantial homology to a polypeptide encoded by a nucleic acid molecule comprising a nucleic acid sequence selected from the group consisting of nucleotide sequences encoding SEQ ID NO: 2 or polymorphic variants thereof. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 45-55%, in certain embodiments at least about 70-75%, and in other embodiments at least about 80-85%, and in others greater than about 90% or more homologous or identical. A substantially homologous amino acid sequence, according to the present invention, will be encoded by a nucleic acid molecule hybridizing to SEQ ID NO: 1 or 3 or portion thereof, under stringent conditions as more particularly described above, or will be encoded by a nucleic acid molecule hybridizing to a nucleic acid sequence encoding SEQ ID NO: 2 or a portion thereof or polymorphic variant thereof, under stringent conditions as more particularly described thereof.

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., *Science* 247:1306-1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., *J. Mol. Biol.* 224:899-904 (1992); de Vos et al., *Science* 255:306-312 (1992)).

The invention also includes fragments of the polypeptides of the invention. Fragments can be derived from a polypeptide encoded by a nucleic acid molecule comprising SEQ ID NO: 1 or 3, or the complement of SEQ ID NO: 1 or 3 (or other variants). However, the invention also encompasses fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide-specific antibodies.

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment the fusion polypeptide does not affect function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example beta-galactosidase fusions, yeast two-hybrid GAL fusions, poly-His fusions and Ig fusions. Such fusion polypeptides, particularly poly-His fusions, can facilitate the purification of recombinant polypeptide. In certain host cells (e.g., mammalian host cells), expression and/or secretion of a polypeptide can be increased using a heterologous signal sequence. Therefore, in another embodiment, the fusion polypeptide contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., *Journal of Molecular Recognition*, 8:52-58 (1995) and Johanson et al., *The Journal of Biological Chemistry*, 270, 16:9459-9471 (1995). Thus, this invention also encompasses soluble fusion polypeptides containing a polypeptide of the invention and various portions of the constant regions of heavy or light chains of immunoglobulins of various subclasses (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., *Current Protocols in Molecular Biology*, 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The isolated polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

The polypeptides of the present invention can be used to raise antibodies or to elicit an immune response. The polypeptides can also be used as a reagent, e.g., a labeled reagent, in assays to quantitatively determine levels of the polypeptide or a molecule to which it binds (e.g., a ligand) in biological fluids. The polypeptides can also be used as markers for cells or tissues in which the corresponding polypeptide is preferentially expressed, either constitutively, during tissue differentiation, or in diseased states. The polypeptides can be used to isolate a corresponding binding agent, e.g., ligand, such as, for example, in an interaction trap assay, and to screen for peptide or small molecule antagonists or agonists of the binding interaction. For example, because members of the leukotriene pathway including FLAP bind to receptors, the leukotriene pathway polypeptides can be used to isolate such receptors.

Antibodies of the Invention

Polyclonal and/or monoclonal antibodies that specifically bind one form of the polypeptide or nucleic acid product (e.g., a polypeptide encoded by a nucleic acid having a SNP as set forth in Table 13), but not to another form of the polypeptide or nucleic acid product, are also provided. Antibodies are also provided which bind a portion of either polypeptide encoded by nucleic acids of the invention (e.g., SEQ ID NO: 1 or SEQ ID NO: 3, or the complement of SEQ ID NO: 1 or SEQ ID NO: 3), or to a polypeptide encoded by nucleic acids of the invention that contain a polymorphic site or sites. The invention also provides antibodies to the polypeptides and polypeptide fragments of the invention, or a portion thereof, or having an amino acid sequence encoded by a nucleic acid molecule comprising all or a portion of SEQ ID NOs: 1 or 3, or the complement thereof, or another variant or portion thereof.

The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4:72 (1983)); the EBV-hybridoma technique (Cole et al., *Monoclonal Antibodies and Cancer Therapy*, Alan R. Liss, 1985, Inc., pp. 77-96); or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin and aequorin, and examples of suitable radioactive material include $^{125}$I, $^{131}$I, $^{35}$S or $^{3}$H.

As described above, antibodies to leukotrienes can be used in the methods of the invention. The methods described herein can be used to generate such antibodies for use in the methods.

Diagnostic Assays

The nucleic acids, probes, primers, polypeptides and antibodies described herein can be used in methods of diagnosis of a susceptibility to MI, ACS, stroke or PAOD, or to another disease or condition associated with an MI gene, such as FLAP, as well as in kits useful for diagnosis of a susceptibility to MI, ACS, stroke or PAOD, or to another disease or condition associated with FLAP. In one embodiment, the kit useful for diagnosis of susceptibility to MI, ACS, stroke or PAOD, or to another disease or condition associated with FLAP comprises primers as described herein, wherein the primers contain one or more of the SNPs identified in Table 13.

In one embodiment of the invention, diagnosis of susceptibility to MI, ACS, stroke or PAOD (or diagnosis of susceptibility to another disease or condition associated with FLAP), is made by detecting a polymorphism in a FLAP nucleic acid as described herein. The polymorphism can be an alteration in a FLAP nucleic acid, such as the insertion or deletion of a single nucleotide, or of more than one nucleotide, resulting in a frame shift alteration; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene or nucleic acid; duplication of all or a part of the gene or nucleic acid; transposition of all or a part of the gene or nucleic acid; or rearrangement of all or a part of the gene or nucleic acid. More than one such alteration may be present in a single gene or nucleic acid. Such sequence changes cause an alteration in the polypeptide encoded by a FLAP nucleic acid. For example, if the alteration is a frame shift alteration, the frame shift can result in a change in the encoded amino acids, and/or can result in the generation of a premature stop codon, causing generation of a truncated polypeptide. Alternatively, a polymorphism associated with a disease or condition associated with a FLAP nucleic acid or a susceptibility to a disease or condition associated with a FLAP nucleic acid can be a synonymous alteration in one or more nucleotides (i.e., an alteration that does not result in a change in the polypeptide encoded by a FLAP nucleic acid). Such a polymorphism may alter splicing sites, affect the stability or transport of mRNA, or otherwise affect the transcription or translation of the nucleic acid. A FLAP nucleic acid that has any of the alteration described above is referred to herein as an "altered nucleic acid."

In a first method of diagnosing a susceptibility to MI, ACS, stroke or PAOD, hybridization methods, such as Southern analysis, Northern analysis, or in situ hybridizations, can be used (see *Current Protocols in Molecular Biology*, Ausubel, F. et al., eds., John Wiley & Sons, including all supplements through 1999). For example, a biological sample from a test subject (a "test sample") of genomic DNA, RNA, or cDNA, is obtained from an individual suspected of having, being susceptible to or predisposed for, or carrying a defect for, a susceptibility to a disease or condition associated with a FLAP nucleic acid (the "test individual"). The individual can be an adult, child, or fetus. The test sample can be from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a polymorphism in an MI nucleic acid is present, and/or to determine which splicing variant(s) encoded by the FLAP is present. The presence of the polymorphism or splicing variant(s) can be indicated by hybridization of the nucleic acid in the genomic DNA, RNA, or cDNA to a nucleic acid probe. A "nucleic acid probe," as used herein, can be a DNA probe or an RNA probe; the nucleic acid probe can contain at least one polymorphism in a FLAP nucleic acid or contains a nucleic acid encoding a particular splicing variant of a FLAP nucleic acid. The probe can be any of the nucleic acid molecules described above (e.g., the nucleic acid, a fragment, a vector comprising the nucleic acid, a probe or primer, etc.).

To diagnose a susceptibility to MI, ACS, stroke or PAOD (or another disease or condition associated with FLAP), the test sample containing a FLAP nucleic acid is contacted with at least one nucleic acid probe to form a hybridization sample. A preferred probe for detecting mRNA or genomic DNA is a labeled nucleic acid probe capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of one of SEQ ID NOs: 1 and 3, or the complement thereof or a portion thereof; or can be a nucleic acid encoding all or a portion of one of SEQ ID NO: 2. Other suitable probes for use in the diagnostic assays of the invention are described above (see e.g., probes and primers discussed under the heading, "Nucleic Acids of the Invention").

The hybridization sample is maintained under conditions that are sufficient to allow specific hybridization of the nucleic acid probe to a FLAP nucleic acid. "Specific hybridization," as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and FLAP nucleic acid in the test sample, then the FLAP has the polymorphism, or is the splicing variant, that is present in the nucleic acid probe. More than one nucleic acid probe can also be used concurrently in this method. Specific hybridization of any one of the nucleic acid probes is indicative of a polymorphism in the FLAP nucleic acid, or of the presence of a particular splicing variant encoding the FLAP nucleic acid, and is therefore diagnostic for a susceptibility to a disease or condition associated with FLAP (e.g., MI, ACS, stroke or PAOD).

In Northern analysis (see *Current Protocols in Molecular Biology*, Ausubel, F. et al., eds., John Wiley & Sons, supra) the hybridization methods described above are used to identify the presence of a polymorphism or a particular splicing variant, associated with a susceptibility to a disease or condition associated with FLAP (e.g., MI, ACS, stroke or PAOD). For Northern analysis, a test sample of RNA is obtained from the individual by appropriate means. Specific hybridization of a nucleic acid probe, as described above, to RNA from the individual is indicative of a polymorphism in a FLAP nucleic acid, or of the presence of a particular splicing variant encoded by a FLAP nucleic acid, and is therefore diagnostic for susceptibility to a disease or condition associated with FLAP (e.g., MI, ACS, stroke or PAOD).

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry* 5, American Chemical Society, p. 1 (1994). The PNA probe can be designed to specifically hybridize to a nucleic acid having a polymorphism with a susceptibility to a disease or condition associated with FLAP (e.g., MI). Hybridization of the PNA probe to a FLAP nucleic acid as described herein is diagnostic for the susceptibility to the disease or condition.

In another method of the invention, mutation analysis by restriction digestion can be used to detect an altered nucleic acid, or nucleic acids containing a polymorphism(s), if the mutation or polymorphism in the nucleic acid results in the creation or elimination of a restriction site. A test sample containing genomic DNA is obtained from the individual. Polymerase chain reaction (PCR) can be used to amplify a FLAP nucleic acid (and, if necessary, the flanking sequences) in the test sample of genomic DNA from the test individual. RFLP analysis is conducted as described (see *Current Protocols in Molecular Biology*, supra). The digestion pattern of the relevant DNA fragment indicates the presence or absence of the alteration or polymorphism in the FLAP nucleic acid, and therefore indicates the presence or absence of the susceptibility to a disease or condition associated with FLAP (e.g., MI, ACS, stroke or PAOD).

Sequence analysis can also be used to detect specific polymorphisms in the FLAP nucleic acid. A test sample of DNA or RNA is obtained from the test individual. PCR or other appropriate methods can be used to amplify the nucleic acid, and/or its flanking sequences, if desired. The sequence of a FLAP nucleic acid, or a fragment of the nucleic acid, or cDNA, or fragment of the cDNA, or mRNA, or fragment of the mRNA, is determined, using standard methods. The sequence of the nucleic acid, nucleic acid fragment, cDNA, cDNA fragment, mRNA, or mRNA fragment is compared with the known nucleic acid sequence of the nucleic acid, cDNA (e.g., one or more of SEQ ID NOs: 1 or 3, and/or the complement of SEQ ID NO: 1 or 3), or a nucleic acid sequence encoding SEQ ID NO: 2 or a fragment thereof) or mRNA, as appropriate. The presence of a polymorphism in the FLAP indicates that the individual has a susceptibility to a disease associated with FLAP (e.g., MI, ACS, stroke or PAOD).

Allele-specific oligonucleotides can also be used to detect the presence of polymorphism(s) in the FLAP nucleic acid, through the use of dot-blot hybridization of amplified oligonucleotides with allele-specific oligonucleotide (ASO) probes (see, for example, Saiki, R. et al., *Nature* 324:163-166 (1986)). An "allele-specific oligonucleotide" (also referred to herein as an "allele-specific oligonucleotide probe") is an oligonucleotide of approximately 10-50 base pairs, for example, approximately 15-30 base pairs, that specifically hybridizes to a FLAP nucleic acid, and that contains a polymorphism associated with a susceptibility to a disease or condition associated with FLAP (e.g., MI, ACS, stroke or PAOD). An allele-specific oligonucleotide probe that is specific for particular polymorphisms in a FLAP nucleic acid can be prepared, using standard methods (see *Current Protocols in Molecular Biology*, supra). To identify polymorphisms in the nucleic acid associated with susceptibility to disease, a test sample of DNA is obtained from the individual. PCR can be used to amplify all or a fragment of a FLAP nucleic acid, and its flanking sequences. The DNA containing the amplified FLAP nucleic acid (or fragment of the nucleic acid) is dot-blotted, using standard methods (see *Current Protocols in Molecular Biology*, supra), and the blot is contacted with the oligonucleotide probe. The presence of specific hybridization of the probe to the amplified FLAP is then detected. Specific hybridization of an allele-specific oligonucleotide probe to DNA from the individual is indicative of a polymorphism in the FLAP, and is therefore indicative of a susceptibility to a disease or condition associated with FLAP (e.g., MI, ACS, stroke or PAOD).

An allele-specific primer hybridizes to a site on target DNA overlapping a polymorphism and only primes amplification of an allelic form to which the primer exhibits perfect complementarity. See Gibbs, *Nucleic Acid Res.* 17, 2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

With the addition of such analogs as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures of 64° C. and 74° C. when in complex with complementary DNA or RNA, respectively, as oposed to 28° C. for both DNA and RNA for the corresponding DNA nonamer. Substantial increases in $T_m$ are also obtained when LNA monomers are used in combination with standard DNA or RNA monomers. For primers and probes, depending on where the LNA monomers are included (e.g., the 3' end, the 5' end, or in the middle), the $T_m$ could be increased considerably.

In another embodiment, arrays of oligonucleotide probes that are complementary to target nucleic acid sequence segments from an individual, can be used to identify polymorphisms in a FLAP nucleic acid. For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and WO 92/10092. These arrays can generally be produced using mechanical synthesis methods or light directed synthesis methods that incorporate a combination of photolithographic methods and solid phase oligonucleotide synthesis methods. See Fodor et al., *Science* 251:767-777 (1991); Pirrung et al., U.S. Pat. No. 5,143,854; (see also PCT Application WO 90/15070); Fodor et al., PCT Publication WO 92/10092; and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein. In another example, linear arrays can be utilized.

Once an oligonucleotide array is prepared, a nucleic acid of interest is hybridized with the array and scanned for polymorphisms. Hybridization and scanning are generally carried out by methods described herein and also in, e.g., published PCT Application Nos. WO 92/10092 and WO 95/11995, and U.S. Pat. No. 5,424,186, the entire teachings of which are incorporated by reference herein. In brief, a target nucleic acid sequence that includes one or more previously identified polymorphic markers is amplified using well-known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array. In a reverse method, a probe, containing a polymorphism, can be coupled to a solid surface and PCR amplicons are then added to hybridize to these probes.

Although primarily described in terms of a single detection block, e.g., detection of a single polymorphism arrays can include multiple detection blocks, and thus be capable of analyzing multiple, specific polymorphisms. It will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional uses of oligonucleotide arrays for detection of polymorphisms can be found, for example, in U.S. Pat. Nos. 5,858,659 and 5,837,832, the entire teachings of which are incorporated by reference herein. Other methods of nucleic acid analysis can be used to detect polymorphisms in a nucleic acid described herein, or variants encoded by a nucleic acid described herein. Representative methods include direct manual sequencing (Church and Gilbert, *Proc. Natl. Acad. Sci. USA* 81:1991-1995 (1988); Sanger, F. et al., *Proc. Natl. Acad. Sci., USA* 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al., *Proc. Natl. Acad. Sci. USA* 86:232-236 (1989)), mobility shift analysis (Orita, M. et al., *Proc. Natl. Acad. Sci. USA* 86:2766-2770 (1989)), restriction enzyme analysis (Flavell et al., *Cell* 15:25 (1978); Geever, et al., *Proc. Natl. Acad. Sci. USA* 78:5081 (1981)); heteroduplex analysis; chemical mismatch cleavage (CMC) (Cotton et al., *Proc. Natl. Acad. Sci. USA* 85:4397-4401 (1985)); RNase protection assays (Myers, R. M. et al., *Science* 230:1242 (1985)); use of polypeptides which recognize nucleotide mismatches, such as *E. coli* mutS protein; allele-specific PCR, for example.

In one embodiment of the invention, diagnosis of a susceptibility to a disease or condition associated with FLAP (e.g., MI, ACS, stroke or PAOD) can also be made by expression analysis by quantitative PCR (kinetic thermal cycling). This technique utilizing TaqMan® can be used to allow the identification of polymorphisms and whether a patient is homozygous or heterozygous. The technique can assess the presence of an alteration in the expression or composition of the polypeptide encoded by a FLAP nucleic acid or splicing variants encoded by a FLAP nucleic acid. Further, the expression of the variants can be quantified as physically or functionally different.

In another embodiment of the invention, diagnosis of a susceptibility to MI, ACS, stroke or PAOD (or of another disease or condition associated with FLAP) can also be made by examining expression and/or composition of a FLAP polypeptide, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by a FLAP nucleic acid, or for the presence of a particular variant encoded by a FLAP nucleic acid. An alteration in expression of a polypeptide encoded by a FLAP nucleic acid can be, for example, an alteration in the quantitative polypeptide expression (i.e., the amount of polypeptide produced); an alteration in the composition of a polypeptide encoded by a FLAP nucleic acid is an alteration in the qualitative polypeptide expression (e.g., expression of an altered FLAP polypeptide or of a different splicing variant). In a preferred embodiment, diagnosis of a susceptibility to a disease or condition associated with FLAP is made by detecting a particular splicing variant encoded by that FLAP variant, or a particular pattern of splicing variants.

Both such alterations (quantitative and qualitative) can also be present. An "alteration" in the polypeptide expression or composition, refers to an alteration in expression or composition in a test sample, as compared with the expression or composition of polypeptide by a FLAP nucleic acid in a control sample. A control sample is a sample that corresponds to the test sample (e.g., is from the same type of cells), and is from an individual who is not affected by the disease or a susceptibility to a disease or condition associated with a FLAP nucleic acid. An alteration in the expression or composition of the polypeptide in the test sample, as compared with the control sample, is indicative of a susceptibility to a disease or condition associated with FLAP (e.g., MI, ACS, stroke or PAOD). Similarly, the presence of one or more different splicing variants in the test sample, or the presence of significantly different amounts of different splicing variants in the test sample, as compared with the control sample, is indicative of a susceptibility to a disease or condition associated with a FLAP nucleic acid. Various means of examining expression or composition of the polypeptide encoded by a FLAP nucleic acid can be used, including: spectroscopy, colorimetry, electrophoresis, isoelectric focusing and immunoassays (e.g., David et al., U.S. Pat. No. 4,376,110) such as immunoblotting (see also *Current Protocols in Molecular Biology*, particularly Chapter 10). For example, in one embodiment, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Western blotting analysis, using an antibody as described above that specifically binds to a polypeptide encoded by an altered FLAP (e.g., by a FLAP having a SNP as shown in Table 13), or an antibody that specifically binds to a polypeptide encoded by a non-altered nucleic acid, or an antibody that specifically binds to a particular splicing variant encoded by a nucleic acid, can be used to identify the presence in a test sample of a particular splicing variant or of a polypeptide encoded by a polymorphic or altered FLAP, or the absence in a test sample of a particular splicing variant or of a polypeptide encoded by a non-polymorphic or non-altered nucleic acid. The presence of a polypeptide encoded by a polymorphic or altered nucleic acid, or the absence of a polypeptide encoded by a non-polymorphic or non-altered nucleic acid, is diagnostic for a susceptibility to a disease or condition associated with FLAP, as is the presence (or absence) of particular splicing variants encoded by the FLAP nucleic acid.

In one embodiment of this method, the level or amount of polypeptide encoded by a FLAP nucleic acid in a test sample is compared with the level or amount of the polypeptide encoded by the FLAP in a control sample. A level or amount of the polypeptide in the test sample that is higher or lower than the level or amount of the polypeptide in the control sample, such that the difference is statistically significant, is indicative of an alteration in the expression of the polypeptide encoded by the FLAP, and is diagnostic for a susceptibility to a disease or condition associated with that FLAP. Alternatively, the composition of the polypeptide encoded by a FLAP nucleic acid in a test sample is compared with the composition of the polypeptide encoded by the FLAP in a control sample (e.g., the presence of different splicing variants). A difference in the composition of the polypeptide in the test sample, as compared with the composition of the polypeptide in the control sample, is diagnostic for a susceptibility to a disease or condition associated with that FLAP. In another embodiment, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of a susceptibility to a disease or condition associated with FLAP (e.g., MI).

The invention further pertains to a method for the diagnosis and identification of susceptibility to myocardial infarction, ACS, stroke or PAOD in an individual, by identifying an at-risk haplotype in FLAP. In one embodiment, the at-risk haplotype is one which confers a significant risk of MI, ACS, stroke or PAOD. In one embodiment, significance associated with a haplotype is measured by an odds ratio. In a further embodiment, the significance is measured by a percentage. In one embodiment, a significant risk is measured as an odds ratio of at least about 1.2, including by not limited to: 1.2, 1.3, 1.4, 1.5, 1.6, 1.7, 1.8, and 1.9. In a further embodiment, an odds ratio of at least 1.2 is significant. In a further embodiment, an odds ratio of at least about 1.5 is significant. In a further embodiment, a significant increase in risk is at least about 1.7 is significant. In a further embodiment, a significant increase in risk is at least about 20%, including but not limited to about 25%, 30%, 35%, 40%, 45%, 50%, 55%, 60%, 65%, 70%, 75%, 80%, 85%, 90%, 95, and 98%. In a further embodiment, a significant increase in risk is at least about 50%. In yet another embodiment, an at-risk haplotype has a p value<0.05. It is understood however, that identifying whether a risk is medically significant may also depend on a variety of factors, including the specific disease, the haplotype, and often, environmental factors.

The invention also pertains to methods of diagnosing a susceptibility to myocardial infarction, ACS, stroke or PAOD in an individual, comprising screening for an at-risk haplotype in the FLAP nucleic acid that is more frequently present in an individual susceptible to myocardial infarction (affected), compared to the frequency of its presence in a healthy individual (control), wherein the presence of the haplotype is indicative of susceptibility to myocardial infarction. Standard techniques for genotyping for the presence of SNPs and/or microsatellite markers that are associated with myocardial infarction, ACS, stroke or PAOD can be used, such as fluorescent based techniques (Chen, et al., *Genome Res.* 9, 492 (1999), PCR, LCR, Nested PCR and other techniques for nucleic acid amplification. In a preferred embodiment, the method comprises assessing in an individual the presence or frequency of SNPs and/or microsatellites in the FLAP nucleic acid that are associated with myocardial infarction, ACS, stroke or PAOD, wherein an excess or higher frequency of the SNPs and/or microsatellites compared to a healthy control individual is indicative that the individual is susceptible to myocardial infarction, ACS, stroke or PAOD. See Table 7 for SNPs that comprise haplotypes that can be used as screening tools. See also Table 13 that sets forth SNPs and markers for use as screening tools.

In one embodiment, the at-risk haplotype is characterized by the presence of polymorphism(s) represented in Table 13. For example, SG13S99, where the SNP can be a "C" or a "T"; SG13S25, where the SNP can be a "G" or an "A"; SG13S377, where the SNP can be a "G" or an "A"; SG13S106, where the SNP can be a "G" or an "A"; SG13S114, where the SNP can be a "T" or an "A"; SG13S89, where the SNP can be a "G" or an "A"; SG13S30, where the SNP can be a "G" or a "T"; SG13S32, where the SNP can be a "C" or an "A"; SG13S42, where the SNP can be a "G" or an "A"; and SG13S35, where the SNP can be a "G" or an "A".

Kits (e.g., reagent kits) useful in the methods of diagnosis comprise components useful in any of the methods described herein, including for example, hybridization probes or primers as described herein (e.g., labeled probes or primers), reagents for detection of labeled molecules, restriction enzymes (e.g., for RFLP analysis), allele-specific oligonucleotides, antibodies which bind to altered or to non-altered (native) FLAP polypeptide, means for amplification of nucleic acids comprising a FLAP, or means for analyzing the nucleic acid sequence of a nucleic acid described herein, or for analyzing the amino acid sequence of a polypeptide as described herein, etc. In one embodiment, a kit for diagnosing susceptibility to MI, ACS, stroke or PAOD can comprise primers for nucleic acid amplification of a region in the FLAP nucleic acid comprising an at-risk haplotype that is more frequently present in an individual having MI, ACS, stroke or PAOD or susceptible to MI, ACS, stroke or PAOD. The primers can be designed using portions of the nucleic acids flanking SNPs that are indicative of MI. In a particularly preferred embodiment, the primers are designed to amplify regions of the FLAP nucleic acid associated with an at-risk haplotype for MI, ACS, stroke or PAOD, as shown in Table 7, or more particularly the haplotype defined by the following SNP markers: In one embodiment, a haplotype associated with a susceptibility to myocardial infarction, ACS, stroke or PAOD comprises markers SG13S99, SG13S25, SG13S377, SG13S106, SG13S32 and SG13S35 at the 13q12-13 locus. In one particular embodiment, the presence of the alleles T, G, G, G, A and G at SG13S99, SG13S25, SG13S377, SG13S106, SG13S32 and SG13S35, respectively (the B6 haplotype), is diagnostic of susceptibility to myocardial infarction, ACS, stroke or PAOD. In another embodiment, a haplotype associated with a susceptibility to myocardial infarction, ACS, stroke or PAOD comprises markers SG13S99, SG13S25, SG13S106, SG13S30 and SG13S42 at the 13q12-13 locus. In one particular embodiment, the presence of the alleles T, G, G, G and A at SG13S99, SG13S25, SG13S106, SG13S30 and SG13S42, respectively (the B5 haplotype), is diagnostic of susceptibility to myocardial infarction, ACS, stroke or PAOD. In a third embodiment, a haplotype associated with a susceptibility to myocardial infarction, ACS, stroke or PAOD comprises markers SG13S25, SG13S106, SG13S30 and SG13S42 at the 13q12-13 locus. In one particular embodiment, the presence of the alleles G, G, G and A at SG13S25, SG13S106, SG13S30 and SG13S42, respectively (the B4 haplotype), is diagnostic of susceptibility to myocardial infarction, ACS, stroke or PAOD. In a fourth embodiment, a haplotype associated with a susceptibility to myocardial infarction, ACS, stroke or PAOD comprises markers SG13S99, SG13S25, SG13S114, SG13S89 and SG13S32 at the 13q12-13 locus. In one particular embodiment, the presence of the alleles T, G, T, G and A at SG13S99, SG13S25, SG13S114, SG13S89 and SG13S32, respectively (the A5 haplotype), is diagnostic of susceptibility to myocardial infarction, ACS, stroke or PAOD. In a fifth embodiment, a haplotype associated with a susceptibility to myocardial infarction, ACS, stroke or PAOD comprises markers SG13S25, SG13S114, SG13S89 and SG13S32 at the 13q12-12 locus. In one particular embodiment, the presence of the alleles G, T, G and A at SG13S25, SG13S114, SG13S89 and SG13S32, respectively (the A4 haplotype), is diagnostic of susceptibility to myocardial infarction, ACS, stroke or PAOD.

Screening Assays and Agents Identified Thereby

The invention provides methods (also referred to herein as "screening assays") for identifying the presence of a nucleotide that hybridizes to a nucleic acid of the invention, as well as for identifying the presence of a polypeptide encoded by a nucleic acid of the invention. In one embodiment, the presence (or absence) of a nucleic acid molecule of interest (e.g., a nucleic acid that has significant homology with a nucleic acid of the invention) in a sample can be assessed by contacting the sample with a nucleic acid comprising a nucleic acid of the invention (e.g., a nucleic acid having the sequence of one of SEQ ID NOs: 1 or 3 or the complement thereof, or a nucleic acid encoding an amino acid having the sequence of SEQ ID NO: 2, or a fragment or variant of such nucleic acids), under stringent conditions as described above, and then assessing the sample for the presence (or absence) of hybridization. In a preferred embodiment, high stringency conditions are conditions appropriate for selective hybridization. In another embodiment, a sample containing a nucleic acid molecule of interest is contacted with a nucleic acid containing a contiguous nucleic acid sequence (e.g., a primer or a probe as described above) that is at least partially complementary to a part of the nucleic acid molecule of interest (e.g., a FLAP nucleic acid), and the contacted sample is assessed for the presence or absence of hybridization. In a preferred embodiment, the nucleic acid containing a contiguous nucleic acid sequence is completely complementary to a part of the nucleic acid molecule of interest.

In any of these embodiments, all or a portion of the nucleic acid of interest can be subjected to amplification prior to performing the hybridization.

In another embodiment, the presence (or absence) of a polypeptide of interest, such as a polypeptide of the invention or a fragment or variant thereof, in a sample can be assessed by contacting the sample with an antibody that specifically hybridizes to the polypeptide of interest (e.g., an antibody such as those described above), and then assessing the sample for the presence (or absence) of binding of the antibody to the polypeptide of interest.

In another embodiment, the invention provides methods for identifying agents (e.g., fusion proteins, polypeptides, peptidomimetics, prodrugs, receptors, binding agents, antibodies, small molecules or other drugs, or ribozymes which alter (e.g., increase or decrease) the activity of the polypeptides described herein, or which otherwise interact with the polypeptides herein. For example, such agents can be agents which bind to polypeptides described herein (e.g., binding agent for members of the leukotriene pathway, such as FLAP binding agents); which have a stimulatory or inhibitory effect on, for example, activity of polypeptides of the invention; or which change (e.g., enhance or inhibit) the ability of the polypeptides of the invention to interact with members of the leukotriene pathway binding agents (e.g., receptors or other binding agents); or which alter posttranslational processing of the leukotriene pathway member polypeptide, such as a FLAP polypeptide (e.g., agents that alter proteolytic processing to direct the polypeptide from where it is normally synthesized to another location in the cell, such as the cell surface; agents that alter proteolytic processing such that more polypeptide is released from the cell, etc.)

In one embodiment, the invention provides assays for screening candidate or test agents that bind to or modulate the activity of polypeptides described herein (or biologically active portion(s) thereof), as well as agents identifiable by the assays. Test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, K. S., *Anticancer Drug Des.* 12:145 (1997)).

In one embodiment, to identify agents which alter the activity of a FLAP polypeptide, a cell, cell lysate, or solution containing or expressing a FLAP polypeptide (e.g., SEQ ID NO: 2 or another splicing variant encoded by a FLAP nucleic acid, such as a nucleic acid comprising a SNP as shown in Table 13), or a fragment or derivative thereof (as described above), can be contacted with an agent to be tested; alternatively, the polypeptide can be contacted directly with the agent to be tested. The level (amount) of FLAP activity is assessed (e.g., the level (amount) of FLAP activity is measured, either directly or indirectly), and is compared with the level of activity in a control (i.e., the level of activity of the FLAP polypeptide or active fragment or derivative thereof in the absence of the agent to be tested). If the level of the activity in the presence of the agent differs, by an amount that is statistically significant, from the level of the activity in the absence of the agent, then the agent is an agent that alters the activity of a FLAP polypeptide. An increase in the level of FLAP activity in the presence of the agent relative to the activity in the absence of the agent, indicates that the agent is an agent that enhances FLAP activity. Similarly, a decrease in the level of FLAP activity in the presence of the agent, relative to the activity in the absence of the agent, indicates that the agent is an agent that inhibits FLAP activity. In another embodiment, the level of activity of a FLAP polypeptide or derivative or fragment thereof in the presence of the agent to be tested, is compared with a control level that has previously been established. A statistically significant difference in the level of the activity in the presence of the agent from the control level indicates that the agent alters FLAP activity.

The present invention also relates to an assay for identifying agents which alter the expression of a FLAP nucleic acid (e.g., antisense nucleic acids, fusion proteins, polypeptides, peptidomimetics, prodrugs, receptors, binding agents, antibodies, small molecules or other drugs, or ribozymes; which alter (e.g., increase or decrease) expression (e.g., transcription or translation) of the nucleic acid or which otherwise interact with the nucleic acids described herein, as well as agents identifiable by the assays. For example, a solution containing a nucleic acid encoding a FLAP polypeptide (e.g., a FLAP nucleic acid) can be contacted with an agent to be tested. The solution can comprise, for example, cells containing the nucleic acid or cell lysate containing the nucleic acid; alternatively, the solution can be another solution that comprises elements necessary for transcription/translation of the nucleic acid. Cells not suspended in solution can also be employed, if desired. The level and/or pattern of FLAP expression (e.g., the level and/or pattern of mRNA or of protein expressed, such as the level and/or pattern of different splicing variants) is assessed, and is compared with the level and/or pattern of expression in a control (i.e., the level and/or pattern of the FLAP expression in the absence of the agent to be tested). If the level and/or pattern in the presence of the agent differ, by an amount or in a manner that is statistically significant, from the level and/or pattern in the absence of the agent, then the agent is an agent that alters the expression of the FLAP nucleic acid. Enhancement of FLAP expression indicates that the agent is an activator of FLAP activity. Similarly, inhibition of FLAP expression indicates that the agent is a repressor of FLAP activity.

In another embodiment, the level and/or pattern of FLAP polypeptide(s) (e.g., different splicing variants) in the presence of the agent to be tested, is compared with a control level and/or pattern that have previously been established. A level and/or pattern in the presence of the agent that differs from the control level and/or pattern by an amount or in a manner that is statistically significant indicates that the agent alters FLAP expression.

In another embodiment of the invention, agents which alter the expression of a FLAP nucleic acid or which otherwise interact with the nucleic acids described herein, can be identified using a cell, cell lysate, or solution containing a nucleic acid encoding the promoter region of the FLAP nucleic acid operably linked to a reporter gene. After contact with an agent to be tested, the level of expression of the reporter gene (e.g., the level of mRNA or of protein expressed) is assessed, and is compared with the level of expression in a control (i.e., the level of the expression of the reporter gene in the absence of the agent to be tested). If the level in the presence of the agent differs, by an amount or in a manner that is statistically significant, from the level in the absence of the agent, then the agent is an agent that alters the expression of the FLAP nucleic acid, as indicated by its ability to alter expression of a nucleic acid that is operably linked to the FLAP nucleic acid promoter.

Enhancement of the expression of the reporter indicates that the agent is an activator of FLAPexpression. Similarly, inhibition of the expression of the reporter indicates that the agent is a repressor of FLAPexpression. In another embodiment, the level of expression of the reporter in the presence of the test agent, is compared with a control level that has previously been established. A level in the presence of the agent that differs from the control level by an amount or in a manner that is statistically significant indicates that the agent alters expression.

Agents which alter the amounts of different splicing variants encoded by a FLAP nucleic acid (e.g., an agent which enhances expression of a first splicing variant, and which inhibits expression of a second splicing variant), as well as agents which stimulate activity of a first splicing variant and inhibit activity of a second splicing variant, can easily be identified using these methods described above.

In other embodiments of the invention, assays can be used to assess the impact of a test agent on the activity of a polypeptide relative to a FLAP binding agent. For example, a cell that expresses a compound that interacts with a FLAP nucleic acid (herein referred to as a "FLAP binding agent", which can be a polypeptide or other molecule that interacts with a FLAP nucleic acid, such as a receptor, or another molecule, such as 5-LO) is contacted with a FLAP in the presence of a test agent, and the ability of the test agent to alter the interaction between the FLAP and the FLAP binding agent is determined. Alternatively, a cell lysate or a solution containing the FLAP binding agent, can be used. An agent which binds to the FLAP or the FLAP binding agent can alter the interaction by interfering with, or enhancing the ability of the FLAP to bind to, associate with, or otherwise interact with the FLAP binding agent. Determining the ability of the test agent to bind to a FLAP nucleic acid or a FLAP nucleic acid binding agent can be accomplished, for example, by coupling the test agent with a radioisotope or enzymatic label such that binding of the test agent to the polypeptide can be determined by detecting the labeled with $^{125}$I, $^{35}$S, $^{14}$C or $^{3}$H, either directly or indirectly, and the radioisotope detected by direct counting of radioemmission or by scintillation counting. Alternatively, test agents can be enzymatically labeled with, for example, horseradish peroxidase, alkaline phosphatase, or luciferase, and the enzymatic label detected by determination of conversion of an appropriate substrate to product. It is also within the scope of this invention to determine the ability of a test agent to interact with the polypeptide without the labeling of any of the interactants. For example, a microphysiometer can be used to detect the interaction of a test agent with a FLAP or a FLAP binding agent without the labeling of either the test agent, FLAP, or the FLAP binding agent. McConnell, H. M. et al., *Science* 257:1906-1912 (1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

Thus, these receptors can be used to screen for compounds that are agonists for use in treating a disease or condition associated with FLAP or a susceptibility to a disease or condition associated with FLAP, or antagonists for studying a susceptibility to a disease or condition associated with FLAP (e.g., MI, ACS, stroke or PAOD). Drugs can be designed to regulate FLAP activation, that in turn can be used to regulate signaling pathways and transcription events of genes downstream or of proteins or polypeptides interacting with FLAP (e.g., 5-LO).

In another embodiment of the invention, assays can be used to identify polypeptides that interact with one or more FLAP polypeptides, as described herein. For example, a yeast two-hybrid system such as that described by Fields and Song (Fields, S. and Song, O., *Nature* 340:245-246 (1989)) can be used to identify polypeptides that interact with one or more FLAP polypeptides. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used which includes a nucleic acid encoding a DNA binding domain and also a FLAP polypeptide, splicing variant, or fragment or derivative thereof, and a second vector is used which includes a nucleic acid encoding a transcription activation domain and also a nucleic acid encoding a polypeptide which potentially may interact with the FLAP polypeptide, splicing variant, or fragment or derivative thereof (e.g., a FLAP polypeptide binding agent or receptor). Incubation of yeast containing the first vector and the second vector under appropriate conditions (e.g., mating conditions such as used in the Matchmaker™ system from Clontech (Palo Alto, Calif., USA)) allows identification of colonies that express the markers of interest. These colonies can be examined to identify the polypeptide(s) that interact with the FLAP polypeptide or fragment or derivative thereof. Such polypeptides may be useful as agents that alter the activity of expression of a FLAP polypeptide, as described above.

In more than one embodiment of the above assay methods of the present invention, it may be desirable to immobilize either the FLAP, the FLAP binding agent, or other components of the assay on a solid support, in order to facilitate separation of complexed from uncomplexed forms of one or both of the polypeptides, as well as to accommodate automation of the assay. Binding of a test agent to the polypeptide, or interaction of the polypeptide with a binding agent in the presence and absence of a test agent, can be accomplished in any vessel suitable for containing the reactants. Examples of such vessels include microtitre plates, test tubes, and microcentrifuge tubes. In one embodiment, a fusion protein (e.g., a glutathione-S-transferase fusion protein) can be provided which adds a domain that allows a FLAP nucleic acid or a FLAP binding agent to be bound to a matrix or other solid support.

In another embodiment, modulators of expression of nucleic acid molecules of the invention are identified in a method wherein a cell, cell lysate, or solution containing a nucleic acid encoding a FLAP nucleic acid is contacted with a test agent and the expression of appropriate mRNA or polypeptide (e.g., splicing variant(s)) in the cell, cell lysate, or solution, is determined. The level of expression of appropriate mRNA or polypeptide(s) in the presence of the test agent is compared to the level of expression of mRNA or polypeptide(s) in the absence of the test agent. The test agent can then be identified as a modulator of expression based on this comparison. For example, when expression of mRNA or polypeptide is greater (statistically significantly greater) in the presence of the test agent than in its absence, the test agent is identified as a stimulator or enhancer of the mRNA or polypeptide expression. Alternatively, when expression of the mRNA or polypeptide is less (statistically significantly less) in the presence of the test agent than in its absence, the test agent is identified as an inhibitor of the mRNA or polypeptide expression. The level of mRNA or polypeptide expression in the cells can be determined by methods described herein for detecting mRNA or polypeptide.

In yet another embodiment, the invention provides methods for identifying agents (e.g., fusion proteins, polypeptides, peptidomimetics, prodrugs, receptors, binding agents, antibodies, small molecules or other drugs, or ribozymes) which alter (e.g., increase or decrease) the activity of a member of leukotriene pathway binding agent, such as a FLAP binding agent (e.g., 5-LO), as described herein. For example, such agents can be agents which have a stimulatory or inhibitory effect on, for example, the activity of a member of leukotriene pathway binding agent, such as a FLAP binding agent; which change (e.g., enhance or inhibit) the ability a member of leukotriene pathway binding agents, (e.g., receptors or other binding agents) to interact with the polypeptides of the invention; or which alter posttranslational processing of the member of leukotriene pathway binding agent, (e.g., agents that alter proteolytic processing to direct the member of the leukotriene pathway binding agent from where it is normally synthesized to another location in the cell, such as the cell surface; agents that alter proteolytic processing such that more active binding agent is released from the cell, etc.).

For example, the invention provides assays for screening candidate or test agents that bind to or modulate the activity of a member of the leukotriene pathway (or enzymatically active portion(s) thereof), as well as agents identifiable by the assays. As described above, test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, K. S. *Anticancer Drug Des.,* 12:145 (1997)).

In one embodiment, to identify agents which alter the activity of a member of the leukotriene pathway (such as a FLAP binding agent, or an agent which binds to a member of the leukotriene pathway (a "binding agent")), a cell, cell lysate, or solution containing or expressing a binding agent (e.g., 5-LO, or a leukotriene pathway member receptor, or other binding agent), or a fragment (e.g., an enzymatically active fragment) or derivative thereof, can be contacted with an agent to be tested; alternatively, the binding agent (or fragment or derivative thereof) can be contacted directly with the agent to be tested. The level (amount) of binding agent activity is assessed (either directly or indirectly), and is compared with the level of activity in a control (i.e., the level of activity in the absence of the agent to be tested). If the level of the activity in the presence of the agent differs, by an amount that is statistically significant, from the level of the activity in the absence of the agent, then the agent is an agent that alters the activity of the member of the leukotriene pathway. An increase in the level of the activity relative to a control, indicates that the agent is an agent that enhances (is an agonist of) the activity. Similarly, a decrease in the level of activity relative to a control, indicates that the agent is an agent that inhibits (is an antagonist of) the activity. In another embodiment, the level of activity in the presence of the agent to be tested, is compared with a control level that has previously been established. A level of the activity in the presence of the agent that differs from the control level by an amount that is statistically significant indicates that the agent alters the activity.

This invention further pertains to novel agents identified by the above-described screening assays. Accordingly, it is within the scope of this invention to further use an agent identified as described herein in an appropriate animal model. For example, an agent identified as described herein (e.g., a test agent that is a modulating agent, an antisense nucleic acid molecule, a specific antibody, or a polypeptide-binding agent) can be used in an animal model to determine the efficacy, toxicity, or side effects of treatment with such an agent. Alternatively, an agent identified as described herein can be used in an animal model to determine the mechanism of action of such an agent.

Furthermore, this invention pertains to uses of novel agents identified by the above-described screening assays for treatments as described herein. In addition, an agent identified as described herein can be used to alter activity of a polypeptide encoded by a FLAP nucleic acid, or to alter expression of a FLAP nucleic acid, by contacting the polypeptide or the nucleic acid (or contacting a cell comprising the polypeptide or the nucleic acid) with the agent identified as described herein.

The present invention is now illustrated by the following Examples, which are not intended to be limiting in any way. The teachings of all references cited are incorporated herein in their entirety.

EXAMPLE 1

Identification of Gene and Haplotypes Associated with MI

A genome wide scan of 296 multiplex Icelandic families with 713 MI patients was performed. Through the suggestive linkage to a locus on chromosome 13q12-13 for female MI patients and early onset MI patients, and haplotype association analysis, the gene encoding the 5-lipoxygenase activating protein (FLAP) was identified, and a 4-SNP haplotype within the gene was determined to confer a near 2-fold risk of MI. Male patients showed strongest association to the at-risk haplotype. Independent confirmation of FLAP association to MI was obtained in a British cohort of patients with sporadic MI. These findings support FLAP as the first specific gene isolated that confers substantial risk of the complex trait of MI.

Methods

Study Population

Patients entering the study were recruited from a registry that includes all MIs that occurred before the age of 75 (over 8,000 patients) in Iceland from 1981 to 2000. This registry is a part of the World Health Organization MONICA Project (The World Health Organization MONICA Project, WHO MONICA Project Principal Investigators, *J Clin Epidemiol* 41, 105-14 (1988)). Diagnoses of all patients in the registry followed strict diagnostic rules based on signs, symptoms, electrocardiograms, cardiac enzymes, and necropsy findings.

Genotypes from 713 MI patients and 1741 of their first-degree relatives were used in the linkage analysis. For the microsatellite association study of the MI locus, 802 unrelated MI patients (n=233 females, n=624 males and n=302 early onset) and 837 population-based controls were used. For the SNP association study in and around the FLAP gene 779 unrelated MI patients were genotyped (n=293 females, n=486 males and n=358 early onset). The control group for the SNP association study was population based and comprised of 628 unrelated males and females in the age range of 30-85 years whose medical history was unknown.

The study was approved by the Data Protection Commission of Iceland and the National Bioethics Committee of Iceland. Informed consent was obtained from all study participants. Personal identifiers associated with medical information and blood samples were encrypted with a third party encryption system as previously described (Gulcher, J. R., Kristjansson, K., Gudbjartsson, H. & Stefansson, K.,. *Eur J Hum Genet* 8, 739-42 (2000)).

Statistical Analysis

A genome-wide scan was performed as previously described (Gretarsdottir, S. et al. *Am J Hum Genet* 70, 593-603 (2002)), using a set of approximately 1000 microsatellite markers. Multipoint, affected-only allele-sharing methods (Kong, A. & Cox, N. J., *Am J Hum Genet* 61, 1179-88 (1997)) were used to assess the evidence for linkage. All results were obtained using the program Allegro (Gudbjartsson, D. F., Jonasson, K., Frigge, M. L. & Kong, A. Allegro, *Nat Genet* 25, 12-3 (2000)) and the deCODE genetic map (Kong, A. et al., *Nat Genet* 31, 241-7 (2002)). The $S_{pairs}$ scoring function (Whittemore, A. S. & Halpern, J., *Biometrics* 50, 118-27 (1994); Kruglyak, L., Daly, M. J., Reeve-Daly, M. P. & Lander, E. S., *Am J Hum Genet* 58, 1347-63 (1996)) was used, as was the exponential allele-sharing model (Kong, A. & Cox, N. J. *Am J Hum Genet* 61, 1179-88 (1997)) to generate the relevant 1-df (degree of freedom) statistics. When combining the family scores to obtain an overall score, a weighting scheme was used that is halfway on a log scale between weighting each affected pair equally and weighting each family equally. In the analysis, all genotyped individuals who are not affected are treated as "unknown". Because of concern with small sample behaviour, corresponding P values were usually computede in two different ways for comparison, and the less significant one was reported. The first P value is computed based on large sample theory; $Z_{lr}=\sqrt{(2 \log_e(10) \text{LOD})}$ and is distributed approximately as a standard normal distribution under the null hypothesis of no linkage (Kong, A. & Cox, N. J. *Am J Hum Genet* 61, 1179-88 (1997)). A second P value is computed by comparing the observed LOD score to its complete data sampling distribution under the null hypothesis (Gudbjartsson, D. F., Jonasson, K., Frigge, M. L. &

Kong, A. Allegro, *Nat Genet* 25, 12-3 (2000)). When a data set consists of more than a handful of families, these two P values tend to be very similar. The information measure that was used (Nicolae, D. University of Chicago (1999)), and is implemented in Allegro, is closely related to a classical measure of information (Dempster, A., Laird, N M, Rubin, D B., *J R Stat Soc B* 39, 1-38 (1977) and has a property that is between 0, if the marker genotypes are completely uninformative, and 1, if the genotypes determine the exact amount of allele sharing by descent among the affected relatives.

For single-marker association studies, Fisher's exact test was used to calculate two-sided P values for each allele. All P values were unadjusted for multiple comparisons unless specifically indicated. Allelic rather than carrier frequencies were presented for microsatellites, SNPs and haplotypes. To minimize any bias due to the relatedness of the patients that were recruited as families for the linkage analysis first and second-degree relatives were eliminated from the patient list. For the haplotype analysis, the program NEMO was used (Gretarsdottir, S. et al., *Nat Genet* 35, 131-8 (2003)), which handles missing genotypes and uncertainty with phase through a likelihood procedure, using the expectation-maximization algorithm as a computational tool to estimate haplotype frequencies. Under the null hypothesis, the affected individuals and controls are assumed to have identical haplotype frequencies. Under the alternative hypotheses, the candidate at-risk haplotype is allowed to have a higher frequency in the affected individuals than in controls, while the ratios of frequencies of all other haplotypes are assumed to be the same in both groups. Likelihoods are maximized separately under both hypotheses, and a corresponding 1-df likelihood ratio statistic used to evaluate statistical significance (id). Even though searches were only performed for haplotypes that increase the risk, all reported P values are two-sided unless otherwise stated. To assess the significance of the haplotype association corrected for multiple testing, a randomisation test was carried out using the same genotype data. The cohorts of affected individuals and controls were randomized, and the analysis was repeated. This procedure was repeated up to 1.000 times and the P value presented is the fraction of replications that produced a P value for a haplotype tested that is lower than or equal to the P value observed using the original patient and control cohorts.

For both single-marker and haplotype analysis, relative risk (RR) and population attributable risk was calculated assuming a multiplicative model (Terwilliger, J. D. & Ott, J. A., *Hum Hered* 42, 337-46 (1992); Falk, C. T. & Rubinstein, P., *Ann Hum Genet* 51 (Pt 3), 227-33 (1987)) in which the risk of the two alleles of haplotypes a person carries multiply. LD was calculated between pairs of SNPs using the standard definition of D' (Lewontin, R. C., *Genetics* 50, 757-82 (1964)) and $R^2$ (Hill, W. G. & Robertson, A., *Genetics* 60, 615-28 (1968)). Using NEMO, frequencies of the two marker allele combinations are estimated by maximum likelihood, and deviation from linkage equilibrium is evaluated by a likelihood ratio test. When plotting all SNP combinations to elucidate the LD structure in a particular region, D' was plotted in the upper left corner and the P value in the lower right corner. In the LD plots presented, the markers are plotted equidistantly rather than according to their physical positions.

Identification of DNA polymorphisms.

New polymorphic repeats (e.g., dinucleotide or trinucleotide repeats) were identified with the Sputnik program. For microsatellite alleles: the CEPH sample 1347-02 (Centre d'Etudes du Polymorphisme Humain, genomics repository) is used as a reference. The lower allele of each microsatellite in this sample is set at 0 and all other alleles in other samples are numbered according in relation to this reference. Thus allele1 is 1 bp longer than the lower allele in the CEPH sample, allele 2 is 2 bp longer than the lower allele in the CEPH sample, allele 3 is 3 bp longer than the lower allele in the CEPH sample, allele 4 is 4 bp longer than the lower allele in the CEPH sample, allele-1 is 1 bp shorter than the lower allele in the CEPH sample, allele-2 is 2 bp shorter than the lower allele in the CEPH sample, and so on. Single nucleotide polymorphisms in the gene were detected by PCR sequencing exonic and intronic regions from patients and controls. Public single nucleotide polymorphisms were obtained from the NCBI SNP database. SNPs were genotyped using a method for detecting SNPs with fluorescent polarization template-directed dye-terminator incorporation (SNP-FP-TDI assay) (Chen, X., Zehnbauer, B., Gnirke, A. & Kwok, P. Y., *Proc Natl Acad Sci USA* 94, 10756-61. (1997)) and TaqMan assays (Applied Biosystems).

Results

Linkage Analysis

A genome wide scan was performed in search of MI susceptibility genes using a framework set of around 1000 microsatellite markers. The initial linkage analysis included 713 MI patients who fulfilled the WHO MONICA research criteria (The World Health Organization MONICA Project, WHO MONICA Project Principal Investigators, *J Clin Epidemiol* 41, 105-14 (1988)) and were clustered in 296 extended families. The linkage analysis was also repeated for early onset, male and female patients separately. Description of the number of patients and families in each analysis are provided in Table 1.

TABLE 1

Number of patients that cluster into families and the corresponding number of families used in the linkage analysis

| Phenotype | Number of patients | Number of families | Number of pairs | Genotyped relatives[a] |
|---|---|---|---|---|
| All MI patients | 713 | 296 | 863 | 1741 |
| Males | 575 | 248 | 724 | 1385 |
| Females | 140 | 56 | 108 | 366 |
| Early onset | 194 | 93 | 156 | 739 |

Figure 9:
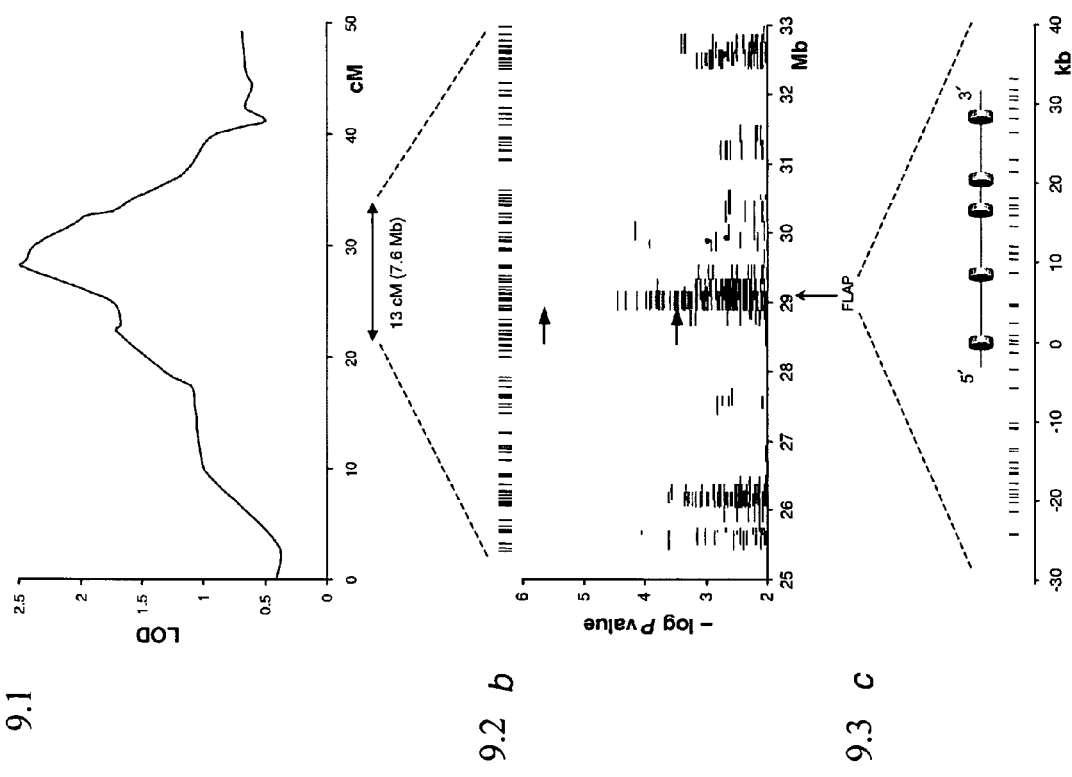
FIG. 9 shows a schematic view of the chromosome 13 linkage region showing the FLAP gene. (9.1) The linkage scan for female MI patients and the one LOD drop region that includes the FLAP gene; (9.2) Microsatellite association for all MI patients: single marker association and two, three, four and five marker haplotype association. The arrows indicate the location of the most significant haplotype association across the FLAP gene in males and females. (9.3) The FLAP gene structure, with exons shown as cylinders, and the location of all the SNPs typed in the region (vertical lines). The vertical lines indicate the position of the microsatellites (shown in 9.2) and SNPs (shown in 9.3) used in the analysis.

[a]Genotyped relatives were used to increase the information on IBD sharing among the patients in the linkage analysis None of these analyses yielded a locus of genome-wide significance. However, the most promising LOD score (LOD=2.86) was observed on chromosome 13q12-13 for female MI patients at the peak marker D13S289 (data not shown). This locus also had the most promising LOD score (LOD=2.03) for patients with early onset MI. After increasing the information on identity-by-descent sharing to over 90% by typing 14 additional microsatellite markers in a 30 centiMorgan (cM) region around D13S289, the LOD score from the female analysis dropped to 2.48 (P value=0.00036), while the highest LOD score remained at D13S289 (FIG. 9.1).

Microsatellite Association Study

The 7.6 Mb region that corresponds to a drop of one in LOD score in the female MI linkage analysis, contains 40 known genes (Table 2).

TABLE 2

Genes residing within the one LOD drop region of the chromosome 13q12-13 linkage peak.

| LL_Symbol | LL_gene_name |
|---|---|
| USP12L1 | ubiquitin specific protease 12 like 1 |
| RPL21 | ribosomal protein L21 |
| GTF3A | general transcription factor IIIA |

TABLE 2-continued

Genes residing within the one LOD drop region of the chromosome 13q12-13 linkage peak.

| LL_Symbol | LL_gene_name |
|---|---|
| MTIF3 | mitochondrial translational initiation factor 3 |
| PDZRN1 | PDZ domain containing ring finger 1 |
| MGC9850 | hypothetical protein MGC9850 |
| POLR1D | polymerase (RNA) I polypeptide D, 16 kDa |
| GSH1 | GS homeobox 1 |
| IPF1 | insulin promoter factor 1, homeodomain transcription factor |
| CDX2 | caudal type homeo box transcription factor 2 |
| FLT3 | fms-related tyrosine kinase 3 |
| LOC255967 | hypothetical protein LOC255967 |
| FLT1 | fms-related tyrosine kinase 1 (vascular endothelial growth factor/vascular permeability factor receptor) |
| C13orf12 | chromosome 13 open reading frame 12 |
| LOC283537 | hypothetical protein LOC283537 |
| KIAA0774 | KIAA0774 protein |
| SLC7A1 | solute carrier family 7 (cationic amino acid transporter, y+ system), member 1 |
| UBL3 | ubiquitin-like 3 |
| MGC2599 | hypothetical protein MGC2599 similar to katanin p60 subunit A 1 2599 |
| HMGB1 | high-mobility group box 1 |
| D13S106E | highly charged protein |
| ALOX5AP | arachidonate 5-lipoxygenase-activating protein |
| FLJ14834 | hypothetical protein FLJ14834 |
| MGC40178 | hypothetical protein MGC40178 |
| HSPH1 | heat shock 105 kDa/110 kDa protein 1 |
| B3GTL | beta 3-glycosyltransferase-like |
| GREAT | similar to G protein coupled receptor affecting testicular descent (*H. sapiens*) |
| LOC196549 | similar to hypothetical protein FLJ20897 |
| 13CDNA73 | hypothetical protein CG003 |
| BRCA2 | breast cancer 2, early onset |
| CG018 | hypothetical gene CG018 |
| PRO0297 | PRO0297 protein |
| LOC88523 | CG016 |
| CG012 | hypothetical gene CG012 |
| CG030 | hypothetical gene CG030 |
| CG005 | hypothetical protein from BCRA2 region |
| APRIN | androgen-induced proliferation inhibitor |
| KL | Klotho |
| STARD13 | START domain containing 13 |
| RFC3 | replication factor C (activator 1) 3, 38 kDa |

To determine which gene in this region most likely contributes to MI, 120 microsatellite markers positioned within this region were typed, and a case-control association study was performed using 802 unrelated MI patients and 837 population-based controls. The association study was also repeated for each of the three phenotypes that were used in the linkage study, i.e. early onset, male and female MI patients.

Figure 2:
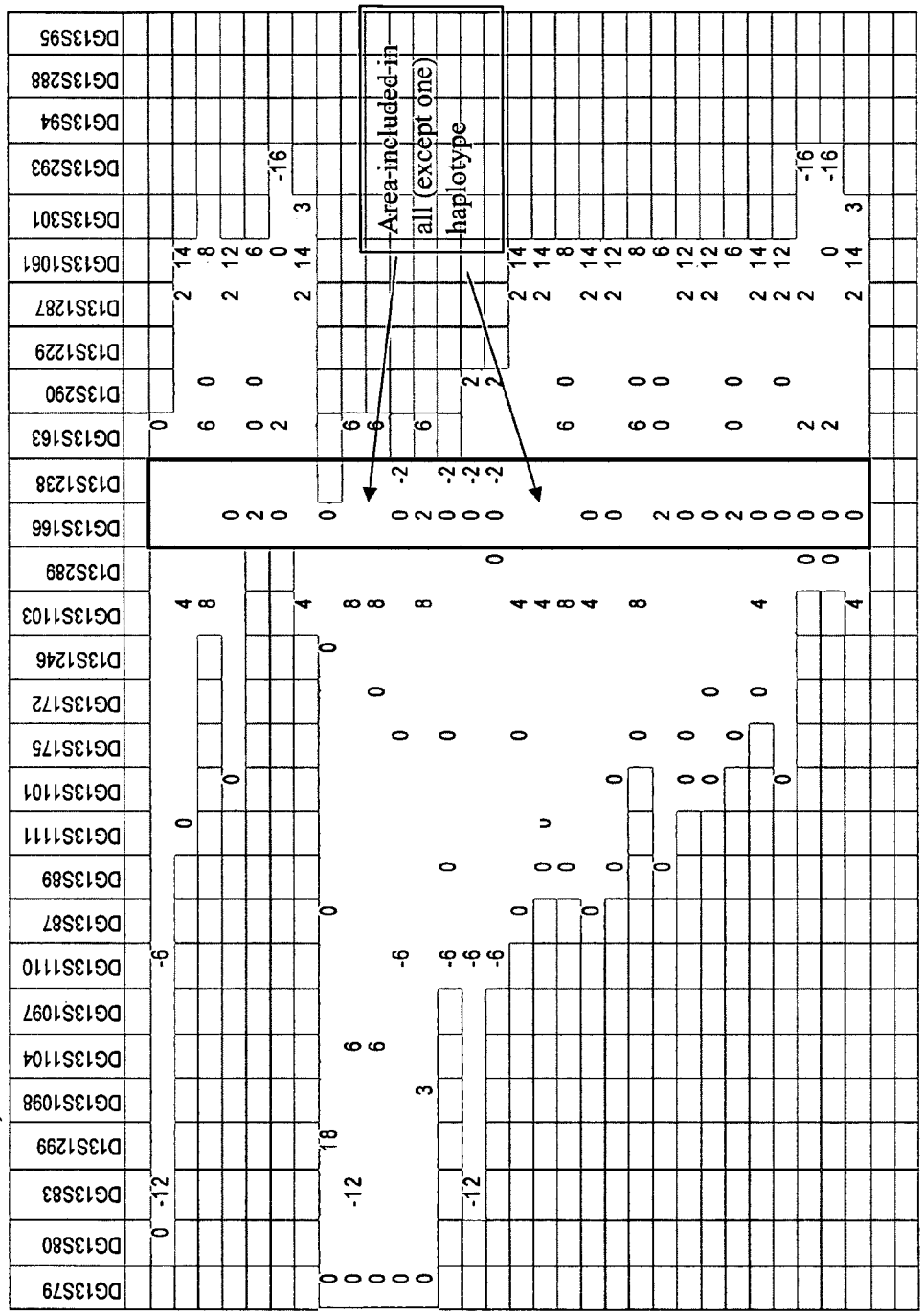
FIG. 2 shows the alleles of the markers defining the most significant microsatellite marker haplotypes. The segment defined with a black square is common to all the of most significantly associated haplotypes. The FLAP nucleic acid is located between makers DG13S166 and D13S1238. Two marker haplotype involving alleles 0 and −2 for markers DG13S166 and D13S1238, respectively, is found in excess in patients. Carrier frequency of this haploype is 27% in patients and 15.4% in controls (p-value $1\times10^{-3}$). Therefore, association analysis confirms that the most tightly MI-associated gene within the linkage peak is FLAP.
Figure 3:
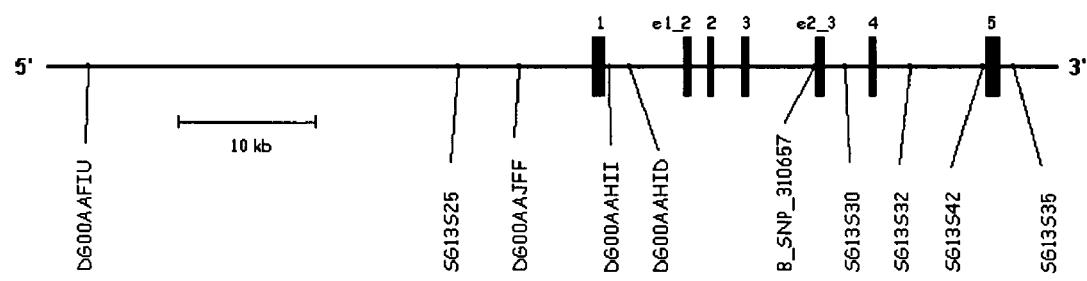
FIG. 3 shows the relative location of key SNPs and exons of the ALOX5AP/FLAP gene (exons shown in vertical rectangles). Haplotype length varies between 33 to 68 kb.

The initial association analysis was performed when the average spacing between microsatellite markers was approximately 100 kb. This analysis revealed several extended haplotypes composed of 4 and 5 microsatellite markers that were significantly associated with female MI (see FIGS. 1 and 2, and Tables 13 and 14). A region common to all these extended haplotypes, is defined by markers DG 13 S166 and D13S1238. This region included only one gene, the FLAP nucleic acid sequence. The two marker haplotype involving alleles 0 and −2 for markers DG13S166 and D13S1238, respectively, was found in excess in patients.

This was the first evidence that the FLAP gene might be involved in the pathogenesis of myocardial infarction.

Subsequent haplotype analysis that included more microsatellite markers (n=120) in the candidate region on chromosome 13q12-13, now with a marker density of 1 microsatellite marker per 60 kb, showed decreased significance of the original haplotype association. However, the haplotype association analysis using increased density of markers again pointed towards the FLAP gene. This analysis strongly suggested that a 300 kb region was involved in the susceptibility of myocardial infarction. As shown in FIG. 7.2, the haplotype that showed association to all MI with the lowest P value (0.00009) covered a region that contains 2 known genes, including the gene encoding arachidonate 5-lipoxygenase-activating protein (FLAP) and a gene with an unknown function called highly charged protein. However, the haplotype association to female MI in this region was less significant (P value=0.005) than for all MI patients and to our surprise, the most significant haplotype association was observed for male MI patients (P value=0.000002). This male MI haplotype was the only haplotype that remained significant after adjusting for all haplotypes tested.

In view of the association results described above, FLAP was an attractive candidate and therefore efforts were focused on this gene.

Screening for Polymorphisms in FLAP and Linkage Disequilibrium Mapping

To determine whether variations within the FLAP gene significantly associate with MI and to search for causal variations, the FLAP gene was sequenced in 93 patients and 93 controls. The sequenced region covers 60 kb containing the FLAP gene, including the 5 known exons and introns and the 26 kb region 5' to the first exon and 7 kb region 3' to the fifth exon. In all, 144 SNPs were identified, of those 96 were excluded from further analysis either because of low minor allele frequency or they were completely correlated with other SNPs and thus redundant. FIG. 9 shows the distribution of the 48 SNPs, used for genotyping, relative to exons, introns and the 5' and 3' flanking regions of the FLAP gene. Only one SNP was identified within a coding sequence (exon 2). This SNP did not lead to amino acid substitution. The locations of these SNPs in the NCBI human genome assembly, build 34, are listed in Table 3.

TABLE 3

Locations of all genotyped SNPs in NCBI build 34 of the human genome assembly

| SNP name | Build34 start |
|---|---|
| SG13S381 | 29083350 |
| SG13S366 | 29083518 |
| SG13S1 | 29086224 |
| SG13S2 | 29087473 |
| SG13S367 | 29088090 |
| SG13S10 | 29088473 |
| SG13S3 | 29089044 |
| SG13S368 | 29089886 |
| SG13S4 | 29090997 |
| SG13S5 | 29091307 |
| SG13S90 | 29091780 |
| SG13S6 | 29092536 |
| SG13S371 | 29093964 |
| SG13S372 | 29094259 |
| SG13S373 | 29096688 |
| SG13S375 | 29096874 |
| SG13S376 | 29096962 |
| SG13S25 | 29097553 |
| SG13S377 | 29101965 |
| SG13S100 | 29104271 |
| SG13S95 | 29106329 |
| SG13S191 | 29107830 |
| SG13S106 | 29108579 |
| SG13S114 | 29110096 |
| SG13S121 | 29112174 |
| SG13S122 | 29112264 |
| SG13S43 | 29112455 |
| SG13S192 | 29116308 |
| SG13S88 | 29116401 |
| SG13S137 | 29118118 |
| SG13S86 | 29118815 |
| SG13S87 | 29118873 |
| SG13S39 | 29119740 |

TABLE 3-continued

Locations of all genotyped SNPs in NCBI build 34 of the human genome assembly

| SNP name | Build34 start |
|---|---|
| SG13S26 | 29122253 |
| SG13S27 | 29122283 |
| SG13S29 | 29123643 |
| SG13S89 | 29124441 |
| SG13S96 | 29124906 |
| SG13S30 | 29125840 |
| SG13S97 | 29129139 |
| SG13S32 | 29130547 |
| SG13S41 | 29134045 |
| SG13S42 | 29135877 |
| SG13S34 | 29137100 |
| SG13S35 | 29138117 |
| SG13S181 | 29138633 |
| SG13S184 | 29139435 |
| SG13S188 | 29140805 |

In addition to the SNPs, a polymorphism consisting of a monopolymer A repeat that has been described in the FLAP promoter region was typed (Koshino, T. et al., *Mol Cell Biol Res Commun* 2, 32-5 (1999)).

Figure 11:
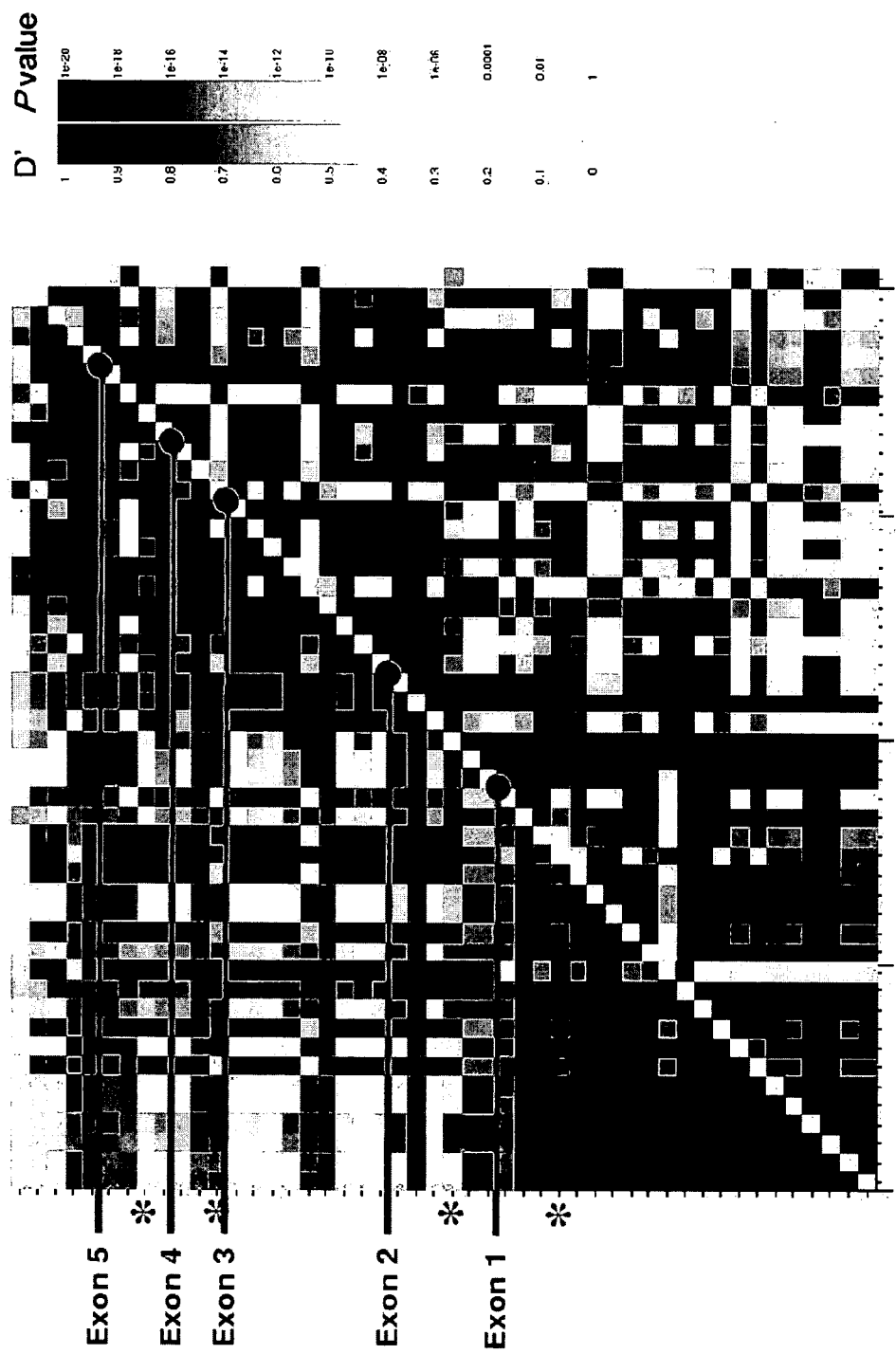
FIG. 11 shows a pairwise linkage disequilibrium (LD) between SNPs in a 60 kb region encompassing FLAP. The markers are plotted equidistantly. Two measures of LD are shown: D' in the upper left triangle and P values in the lower right triangle. Shaded lines indicate the positions of the exons of FLAP and the stars indicate the location of the markers of the at-risk haplotype A4. Scales for the LD strength are provided for both measures to the right.

The linkage disequilibrium (LD) block structure defined by the 48 SNPs that were selected for further genotyping is shown in FIG. 11. A strong LD was detected across the FLAP region, although it appears that at least one recombination may have occurred dividing the region into two strongly correlated LD blocks.

Haplotype Association to MI

To perform a case-control association study the 48 selected SNPs and the monopolymer A repeat marker were genotyped in a set of 779 unrelated MI patients and 628 population-based controls. Each of the 49 markers were tested individually for association to the disease. Three SNPs, one located 3 kb upstream of the first exon and the other two 1 and 3 kb downstream of the first exon, showed nominally significant association to MI (Table 4).

TABLE 4

SNP allelic association in the MI cohort

| Phenotype | Marker | Allele | P value | RR | # Pat. | % Pat. | # Ctrl | % Ctrl |
|---|---|---|---|---|---|---|---|---|
| All patients | SG13S106 | G | 0.0044 | 1.29 | 681 | 72.0 | 530 | 66.6 |
|  | SG13S100 | A | 0.020 | 1.29 | 388 | 69.6 | 377 | 63.9 |
|  | SG13S114 | T | 0.021 | 1.21 | 764 | 70.0 | 602 | 65.8 |
| Males | SG13S106 | G | 0.0037 | 1.35 | 422 | 72.9 | 530 | 66.6 |
|  | SG13S100 | A | 0.0099 | 1.36 | 292 | 70.7 | 377 | 63.9 |
|  | SG13S114 | T | 0.026 | 1.24 | 477 | 70.4 | 602 | 65.8 |
| Early onset | SG13S100 | A | 0.0440 | 1.43 | 99 | 71.7 | 377 | 63.9 |

Nominally significant SNP association with corresponding number of patients (# Pat.) and controls (#Ctrl). RR refers to relative risk.

However, after adjusting for the number of markers tested, these results were not significant. A search was then conducted for haplotypes that show association to the disease using the same cohorts. For computational reasons, the search was limited to haplotype combinations constructed out of two, three or four SNPs and only haplotypes that were in excess in the patients were tested. The resulting P values were adjusted for all the haplotypes tested by randomizing the patients and controls (see Methods).

Several haplotypes were found that were significantly associated to the disease with an adjusted P value less that 0.05 (Table 5).

TABLE 5

SNP haplotypes that significantly associate with Icelandic MI patients

| SG13S4 | SG13S6 | SG13S372 | SG13S25 | SG13S377 | SG13S100 | SG13S95 | SG13S114 | SG13S192 | SG13S137 | SG13S86 | SG13S87 | SG13S39 |
|---|---|---|---|---|---|---|---|---|---|---|---|---|
|  |  | G |  |  |  |  | T |  |  |  |  |  |
|  |  | G |  |  |  |  | T |  |  |  | A |  |
|  |  | G |  |  |  |  | T |  |  |  |  |  |
|  |  | G |  |  | A |  |  |  |  |  | A |  |
|  |  | G |  |  |  | T | T |  |  |  |  |  |
|  |  | G |  |  |  |  | T |  |  | G |  |  |
|  |  | G |  | A |  |  |  |  |  |  |  |  |
|  |  | G |  | A |  |  |  |  |  |  |  |  |
|  |  | G |  |  |  |  | T |  |  |  |  |  |
|  |  | G |  |  |  |  | T |  |  |  |  |  |
|  | G |  |  |  |  | T | T |  |  |  |  |  |
|  |  | G |  |  | A |  |  |  |  | G |  |  |
|  |  | G |  |  |  |  | T | A |  |  |  |  |
|  |  | G |  |  |  |  | T |  |  |  |  |  |

TABLE 5-continued

SNP haplotypes that significantly associate with Icelandic MI patients

| | | | | | | | |
|---|---|---|---|---|---|---|---|
| | | G | | | | T | |
| | G | G | | | | T | |
| | | G | | A | | | |
| | | | G | A | | | |
| | | G | | A | | | A |
| | | | G | A | | | |
| | | G | | A | | T | A |
| | | | G | A | | A | |
| | | | G | | | T | G |
| | | G | | A | | | |
| | | G | | | | T | |
| | | | G | A | | | |
| | | G | | | | T | |
| | | G | | G | A | | |
| | | | G | A | A | | |
| | | | G | | T | A | |
| | | | G | A | A | | |
| | | | G | | T | | C |
| | | | G | | T | | |
| | | | G | | T | | C |
| | | | G | G | A | | |
| | | G | | | | T | |
| | | G | | | | T | G |
| | | G | | A | | | |
| | | | G | A | | | G |
| C | | G | | A | | | |
| | | G | | | T | A | |
| | | G | | A | | | |
| | | G | | | | T | |
| | | | G | | | T | |
| | G | | G | A | | | |
| | G | | G | A | | | A |

| SG13S27 | SG13S89 | SG13S96 | SG13S32 | SG13S41 | SG13S42 | SG13S34 | SG13S188 | P value[a] | P value[b] | Pat.frq | Ctrl.frq | RR | D'[c] |
|---|---|---|---|---|---|---|---|---|---|---|---|---|---|
| | G | | A | | | | | 0.0000023 | 0.005 | 0.158 | 0.095 | 1.80 | 1.00 |
| | | | A | | | | | 0.0000030 | 0.006 | 0.158 | 0.095 | 1.78 | 1.00 |
| | | | A | | | T | | 0.0000032 | 0.007 | 0.157 | 0.094 | 1.79 | 1.00 |
| | | | A | | | | | 0.0000046 | 0.012 | 0.158 | 0.083 | 2.07 | 0.89 |
| | | | A | | | | | 0.0000047 | 0.012 | 0.154 | 0.093 | 1.78 | 1.00 |
| | | | A | | | | | 0.0000055 | 0.015 | 0.147 | 0.087 | 1.81 | 1.00 |
| | | | A | | | T | | 0.0000061 | 0.017 | 0.157 | 0.083 | 2.07 | 0.89 |
| | G | | A | | | | | 0.0000063 | 0.017 | 0.157 | 0.084 | 2.04 | 0.89 |
| | | | A | | | | | 0.0000070 | 0.021 | 0.157 | 0.096 | 1.76 | 1.00 |
| | | A | A | | | | | 0.0000075 | 0.022 | 0.149 | 0.089 | 1.78 | 1.00 |
| | | | A | | | | | 0.0000083 | 0.024 | 0.208 | 0.139 | 1.62 | 0.99 |
| | | | A | | | | | 0.0000084 | 0.026 | 0.145 | 0.074 | 2.14 | 0.88 |
| | | | A | | | | | 0.0000084 | 0.026 | 0.139 | 0.082 | 1.82 | 1.00 |
| G | | | A | | | | | 0.0000091 | 0.028 | 0.156 | 0.096 | 1.75 | 1.00 |
| | | | A | | | T | | 0.0000094 | 0.028 | 0.210 | 0.141 | 1.61 | 0.99 |
| | | | A | | | | | 0.0000100 | 0.028 | 0.156 | 0.096 | 1.74 | 1.00 |
| | | | A | | | | A | 0.0000101 | 0.028 | 0.215 | 0.133 | 1.80 | 0.81 |
| | | | A | | | | | 0.0000105 | 0.028 | 0.157 | 0.084 | 2.03 | 0.89 |
| | | | A | | | | | 0.0000108 | 0.029 | 0.214 | 0.133 | 1.78 | 0.81 |
| | | A | A | | | | | 0.0000110 | 0.030 | 0.146 | 0.075 | 2.10 | 0.88 |
| | | | A | | | | | 0.0000112 | 0.030 | 0.212 | 0.144 | 1.60 | 1.00 |
| | | | | | | T | | 0.0000113 | 0.030 | 0.151 | 0.081 | 2.03 | 0.78 |
| | | | A | | | | | 0.0000118 | 0.031 | 0.156 | 0.096 | 1.73 | 1.00 |
| | | | A | | | T | | 0.0000126 | 0.034 | 0.212 | 0.131 | 1.79 | 0.79 |
| | G | | A | | | | | 0.0000129 | 0.035 | 0.211 | 0.144 | 1.59 | 1.00 |
| G | | | A | | | | | 0.0000134 | 0.035 | 0.156 | 0.084 | 2.01 | 0.89 |
| | | | A | | | | | 0.0000136 | 0.036 | 0.211 | 0.143 | 1.60 | 1.00 |
| | | | A | | | | | 0.0000137 | 0.036 | 0.156 | 0.085 | 2.00 | 0.89 |
| | | A | | | | | | 0.0000148 | 0.037 | 0.151 | 0.081 | 2.01 | 0.78 |
| | | | | | | T | | 0.0000150 | 0.037 | 0.160 | 0.099 | 1.73 | 0.87 |
| | | | A | | | | | 0.0000150 | 0.037 | 0.130 | 0.066 | 2.13 | 0.90 |
| | | | | | | T | | 0.0000154 | 0.039 | 0.152 | 0.094 | 1.73 | 0.93 |
| | | | A | | A | | | 0.0000154 | 0.040 | 0.155 | 0.097 | 1.70 | 1.00 |
| | | | A | | | | | 0.0000157 | 0.040 | 0.141 | 0.085 | 1.76 | 1.00 |
| | | | A | | | | | 0.0000158 | 0.040 | 0.152 | 0.084 | 1.94 | 0.90 |
| G | | | A | | | | | 0.0000163 | 0.040 | 0.210 | 0.143 | 1.59 | 0.99 |
| | | | A | | | | | 0.0000166 | 0.041 | 0.200 | 0.134 | 1.61 | 0.92 |
| | G | | A | | | | | 0.0000168 | 0.042 | 0.213 | 0.133 | 1.76 | 0.81 |
| | | | A | | | | | 0.0000168 | 0.042 | 0.156 | 0.084 | 2.00 | 0.89 |
| | | | A | | | | | 0.0000171 | 0.042 | 0.211 | 0.136 | 1.70 | 0.81 |
| | | | A | | | | | 0.0000183 | 0.043 | 0.192 | 0.128 | 1.62 | 0.85 |
| | | | A | | | | | 0.0000184 | 0.043 | 0.212 | 0.132 | 1.77 | 0.81 |

TABLE 5-continued

SNP haplotypes that significantly associate with Icelandic MI patients

|   |   | A |   | T | 0.0000193 | 0.046 | 0.328 | 0.251 | 1.46 | 0.99 |
|---|---|---|---|---|-----------|-------|-------|-------|------|------|
| G |   |   |   | T | 0.0000194 | 0.046 | 0.175 | 0.115 | 1.64 | 0.98 |
|   |   |   | A |   | 0.0000202 | 0.048 | 0.210 | 0.136 | 1.70 | 0.81 |
|   |   |   |   |   | 0.0000209 | 0.049 | 0.151 | 0.082 | 2.00 | 0.76 |

[a]Single test P values.
[b]P values adjusted for all the SNP haplotypes tested.
[c]Measure of correlation with Haplotype A4.

The most significant association was observed for a four SNP haplotype spanning 33 kb, including the first four exons of the gene (FIG. 9.3), with a nominal P value of 0.0000023 and an adjusted P value of 0.005. This haplotype, labelled A4, has haplotype frequency of 15.8% (carrier frequency 30.3%) in patients versus 9.5% (carrier frequency 17.9%) in controls (Table 6).

TABLE 6

Association of the A4 haplotype to MI, Stroke and PAOD

| Phenotype (n) | Frq. Pat. | RR | PAR | P-value | P-value[a] |
|---|---|---|---|---|---|
| MI (779) | 0.158 | 1.80 | 0.135 | 0.0000023 | 0.005 |
| Males (486) | 0.169 | 1.95 | 0.158 | 0.00000091 | ND[b] |
| Females (293) | 0.138 | 1.53 | 0.094 | 0.0098 | ND |
| Early onset (358) | 0.138 | 1.53 | 0.094 | 0.0058 | ND |
| Stroke (702)[c] | 0.149 | 1.67 | 0.116 | 0.000095 | ND |
| Males (373) | 0.156 | 1.76 | 0.131 | 0.00018 | ND |
| Females (329) | 0.141 | 1.55 | 0.098 | 0.0074 | ND |
| PAOD (577)[c] | 0.122 | 1.31 | 0.056 | 0.061 | ND |
| Males (356) | 0.126 | 1.36 | 0.065 | 0.057 | ND |
| Females (221) | 0.114 | 1.22 | 0.041 | 0.31 | ND |

[a]P value adjusted for the number of haplotypes tested.
[b]Not done.
[c]Excluding known cases of MI. Shown is the FLAP A4 haplotype and corresponding number of patients (n), haplotype frequency in patients (Frq. pat.), relative risk (RR), population attributed risk (PAR) and P values. The A4 haplotype is defined by the following SNPs: SG13S25, SG13S114, SG13S89 and SG13S32 (Table 5). The same controls (n = 628) are used for the association analysis in MI, stroke and PAOD as well as for the male, female and early onset analysis. The A4 haplotype frequency in the control cohort is 0.095.

The relative risk conferred by The A4 haplotype compared to other haplotypes constructed out of the same SNPs, assuming a multiplicative model, was 1.8 and the corresponding population attributable risk (PAR) was 13.5%. As shown in Table 6, the A4 haplotype was observed in higher frequency in male patients (carrier frequency 30.9%) than in female patients (carrier frequency 25.7%). All the other haplotypes that were significantly associated with an adjusted P value less than 0.05, were highly correlated with the A4 haplotype and should be considered variants of that haplotype (Table 5).

Table 6 shows the results of the haplotype A4 association study using 779 MI patients, 702 stroke patients, 577 PAOD patients and 628 controls. First and second degree relatives were excluded from the patient cohorts. All known cases of MI were removed from the stroke and PAOD cohorts before testing for association. A significant association of the A4 haplotype to stroke was observed, with a relative risk of 1.67 (P value=0.000095). In addition, it was determined whether the A4 haplotype was primarily associated with a particular sub-phenotype of stroke, and found that both ischemic and hemorrhagic stroke were significantly associated with the A4 haplotype (Table 22, below).

More Variants of Haplotype A4

Two correlated series of SNP haplotypes were observed in excess in patients, denoted as A and B in Table 7. The length of the haplotypes varies between 33 and 69 Kb, and the haplotypes cover one or two blocks of linkage disequilibrium. Both series of haplotypes contain the common allele G of the SNP SG13S25. All haplotypes in the A series contain the SNP SG13S114, while all haplotypes in the B series contain the SNP SG13S106. In the B series, the haplotypes B4, B5, and B6 have a relative risk (RR) greater than 2 and with allelic frequencies above 10%. The haplotypes in A series have slightly lower RR and lower p-values, but higher frequency (15-16%). The haplotypes in series B and A are strongly correlated, i.e. the haplotypes in B define a subset of the haplotypes in A. Hence, haplotypes B are more specific than A. Haplotypes A are however more sensitive, i.e. they capture more individuals with the putative mutation, as is observed in the population attributable risk which is less for B than for A. Furthermore, these haplotypes show similar risk ratios and allelic frequency for early-onset patients (defined as onset of first MI before the age of 55) and for both gender. In addition, analyzing various groups of patients with known risk factors, such as hypertension, high cholesterol, smoking and diabetes, did not reveal any significant correlation with these haplotypes, indicating that the haplotypes in the FLAP gene represent an independent genetic susceptibility factor for MI.

TABLE 7

The selected SNP haplotypes and the corresponding p-values

|    | p-val    | RR   | #aff | aff.frq | carr.frq | #con | con.frq | PAR  | SG13S99 | SG13S25 |
|----|----------|------|------|---------|----------|------|---------|------|---------|---------|
| B4 | 4.80E−05 | 2.08 | 903  | 0.106   | 0.2      | 619  | 0.054   | 0.11 |         | G       |
| B5 | 2.40E−05 | 2.2  | 910  | 0.101   | 0.19     | 623  | 0.049   | 0.11 | T       | G       |
| B6 | 1.80E−06 | 2.22 | 913  | 0.131   | 0.24     | 623  | 0.063   | 0.14 | T       | G       |
| A4 | 5.10E−06 | 1.81 | 919  | 0.159   | 0.29     | 623  | 0.095   | 0.14 |         | G       |
| A5 | 2.60E−06 | 1.91 | 920  | 0.15    | 0.28     | 624  | 0.085   | 0.14 | T       | G       |

|    | SG13S377 | SG13S106 | SG13S114 | SG13S89 | SG13S30 | SG13S32 | SG13S42 | SG13S35 |
|----|----------|----------|----------|---------|---------|---------|---------|---------|
| B4 |          | G        |          |         | G       |         | A       |         |
| B5 |          | G        |          |         | G       |         | A       |         |
| B6 | G        | G        |          |         |         | A       |         | G       |

TABLE 7-continued

The selected SNP haplotypes and the corresponding p-values

| A4 | T | G | A |
|---|---|---|---|
| A5 | T | G | A |

Relative risk (RR),
number of patients (#aff),
allelic frequency in patients (aff.frq.),
carrier frequency in patients (carr.frq.),
number of controls (#con),
allelic frequency in controls (con.frq.),
population attributable risk (PAR).
The patients used for this analysis were all unrelated within 4 meioses.

Haplotype Association to Female MI

Before we had typed all the SNPs that eventually lead to the identification of A4 haplotype we performed a haplotype association analysis that included 437 female MI patients, 1049 male MI patients, and 811 controls that had been genotyped with several SNPs and 3 microsatellite markers. These markers were all located within 300 kb region encompassing the FLAP gene. In a case-control study of the MI patients using these data, several haplotypes were found, that were significantly over-represented in the female MI patients compared to controls (see Table 8). All these haplotypes were highly correlated with each other.

TABLE 8 haplotypes in the FLAP region (FLAP and flanking nucleotide sequences) that were associated with female MI.

| SG13S421 | SG13S418 | SG13S419 | SG13S420 | SG13S166 | SG13S106 | SG13S114 | SG13S121 | SG13S122 | SG13S88 | SG13S181 | SG13S184 | D13S1238 | DG13S2605 | p-val | N_aff | aff.frq | N_ctrl | ctrl.frq | rol_risk | PAR | info |
|---|---|---|---|---|---|---|---|---|---|---|---|---|---|---|---|---|---|---|---|---|---|
|  |  |  | C |  | T | 0 |  |  |  |  |  | -2 |  | 1.30E-05 | 455 | 0.108 | 811 | 0.048 | 2.4 | 0.122 | 0.615 |
|  |  |  | C |  | T | 0 | T |  | A | T |  | -2 |  | 7.61E-06 | 455 | 0.065 | 812 | 0.02 | 3.45 | 0.091 | 0.615 |
|  |  |  | C |  | T | 0 | T |  |  | T |  | -2 | 0 | 8.82E-06 | 455 | 0.065 | 812 | 0.02 | 3.47 | 0.092 | 0.602 |
|  |  |  | C |  | T | 0 | T | G |  | T |  | -2 | 0 | 9.31E-06 | 455 | 0.065 | 812 | 0.02 | 3.39 | 0.089 | 0.611 |
|  |  |  | C |  | T | 0 | T |  |  | T | G | -2 | 0 | 6.91E-06 | 455 | 0.063 | 812 | 0.019 | 3.54 | 0.09 | 0.624 |
|  |  |  | C | A | T | 0 | T |  |  | T |  | -2 | 0 | 9.76E-06 | 455 | 0.063 | 812 | 0.019 | 3.51 | 0.089 | 0.606 |
|  |  |  | C |  | T | 0 | T |  | A | T | G | -2 |  | 1.09E-05 | 455 | 0.063 | 811 | 0.019 | 3.41 | 0.086 | 0.618 |
|  |  |  | C |  | T | 0 | T |  |  | T |  | -2 | 0 | 1.10E-05 | 455 | 0.063 | 812 | 0.019 | 3.44 | 0.087 | 0.611 |
|  |  |  | C |  | T | 0 |  |  |  | T | G | -2 | 0 | 1.11E-05 | 455 | 0.063 | 812 | 0.018 | 3.56 | 0.086 | 0.589 |
|  |  |  | C |  | T | 0 |  | G |  | T | G | -2 |  | 1.22E-05 | 455 | 0.063 | 811 | 0.018 | 3.6 | 0.087 | 0.577 |
|  |  |  | C |  | T | 0 |  | G |  | T | G | -2 | 0 | 1.26E-05 | 455 | 0.063 | 812 | 0.02 | 3.35 | 0.088 | 0.629 |
|  |  |  | C |  | T | 0 | G |  |  | T | G | -2 | 0 | 8.59E-06 | 455 | 0.062 | 812 | 0.018 | 3.53 | 0.085 | 0.62 |
|  |  |  | C |  | T | 0 |  |  | A | T | G | -2 |  | 1.20E-05 | 455 | 0.062 | 811 | 0.019 | 3.42 | 0.086 | 0.617 |
|  |  |  | C |  | T | 0 |  |  | A | T | G | -2 |  | 1.21E-05 | 455 | 0.062 | 811 | 0.019 | 3.43 | 0.086 | 0.619 |
|  |  |  | C |  | T | 0 |  | G | A | T | G | -2 |  | 7.93E-06 | 455 | 0.061 | 811 | 0.016 | 3.95 | 0.088 | 0.562 |
| A |  |  | C |  | T | 0 |  | G |  | T | G | -2 |  | 1.09E-05 | 455 | 0.061 | 811 | 0.017 | 3.85 | 0.09 | 0.56 |
| A |  |  | C |  | T | 0 |  |  |  | T | G | -2 |  | 5.00E-06 | 455 | 0.06 | 811 | 0.015 | 4.11 | 0.087 | 0.576 |
| A |  |  | C |  | T | 0 | T |  |  | T | G | -2 |  | 1.31E-05 | 455 | 0.06 | 811 | 0.017 | 3.66 | 0.085 | 0.586 |
|  |  |  | C | A | T | 0 |  | G |  | T | G | -2 |  | 8.53E-06 | 455 | 0.059 | 811 | 0.016 | 3.85 | 0.085 | 0.593 |
| A |  |  | C |  | T | 0 |  |  | A | T | G | -2 |  | 9.63E-06 | 455 | 0.058 | 811 | 0.015 | 4.03 | 0.085 | 0.565 |
| A |  | A |  | C | A | T | 0 |  |  |  | T | G | -2 |  |  |  |  |  |  |  |  |

Table 9 shows two haplotypes that are representative of these female MI risk haplotypes. The relative risk of these haplotypes were 2.4 and 4, and they were carried by 23% and 13% of female MI patients, respectively.

TABLE 9

Two representative variants of the female MI "at risk" haplotypes

| | SG13S418 | SG13S420 | DG13S166 | SG13S114 | SG13S88 | SG13S184 | D13S1238 |
|---|---|---|---|---|---|---|---|
| Female | C | T | 0 | T | T | G | −2 |
| MI | C | T | 0 | | | G | −2 |

| | p-val | N_aff | aff.frq | N_ctrl | ctrl.frq | rel_risk | PAR | info |
|---|---|---|---|---|---|---|---|---|
| Female | 6.38E−06 | 454 | 0.059 | 809 | 0.015 | 4.05 | 0.086 | 0.577 |
| MI | 2.74E−05 | 447 | 0.106 | 809 | 0.048 | 2.33 | 0.116 | 0.623 |

P-val: p-value for the association.
N_aff: Number of patients used in the analysis.
Aff.frq: haplotype frequency in patients.
N_ctrl: number of controls used in the analysis.
Ctrl.frq: Haplotype frequency in controls.
Rel_risk: Relative risk of the haplotype.
PAR: population attributable risk.
Info: information content.

Table 10 shows that these same haplotypes were also over-represented in male MI patients compared to controls, although with lower relative risk. It should be noted that after typing and analysing more SNPs in the FLAP region these female MI "at risk" haplotypes could no longer be considered significant after adjusting for multiple testing.

TABLE 10

The frequencies of the female MI "at risk" haplotypes in male patients vs controls.

| | SG13S418 | SG13S420 | DG13S166 | SG13S114 | SG13S88 | SG13S184 | D13S1238 |
|---|---|---|---|---|---|---|---|
| Male | C | T | 0 | T | T | G | −2 |
| MI | C | T | 0 | | | G | −2 |

| | p-val | N_aff | aff.frq | N_ctrl | ctrl.frq | rel_risk | PAR | info |
|---|---|---|---|---|---|---|---|---|
| Male | 3.37E−01 | 1087 | 0.027 | 809 | 0.021 | 1.32 | 0.013 | 0.577 |
| MI | 5.39E−01 | 1087 | 0.056 | 809 | 0.05 | 1.13 | 0.013 | 0.568 |

P-val: p-value for the association.
N_aff: Number of patients used in the analysis.
Aff.frq: haplotype frequency in patients.
N_ctrl: number of controls used in the analysis.
Ctrl.frq: Haplotype frequency in controls.
Rel_risk: Relative risk of the haplotype.
PAR: population attributable risk.
Info: information content.

TABLE 11

The marker map for chromosome 13 used in the linkage analysis.

| Location (cM) | Marker |
|---|---|
| 6 | D13S175 |
| 9.8 | D13S1243 |
| 13.5 | D13S1304 |
| 17.2 | D13S217 |
| 21.5 | D13S289 |
| 25.1 | D13S171 |
| 28.9 | D13S219 |
| 32.9 | D13S218 |
| 38.3 | D13S263 |
| 42.8 | D13S326 |
| 45.6 | D13S153 |
| 49.4 | D13S1320 |
| 52.6 | D13S1296 |
| 55.9 | D13S156 |
| 59.8 | D13S1306 |
| 63.9 | D13S170 |
| 68.7 | D13S265 |
| 73 | D13S167 |

TABLE 11-continued

The marker map for chromosome 13 used in the linkage analysis.

| Location (cM) | Marker |
|---|---|
| 76.3 | D13S1241 |
| 79.5 | D13S1298 |
| 81.6 | D13S1267 |
| 84.7 | D13S1256 |
| 85.1 | D13S158 |
| 87 | D13S274 |
| 93.5 | D13S173 |
| 96.7 | D13S778 |
| 102.7 | D13S1315 |
| 110.6 | D13S285 |
| 115 | D13S293 |

TABLE 12

Marker Map for the second step of Linkage Analysis

| Location (cM) | Marker |
|---|---|
| 1.758 | D13S175 |
| 9.235 | D13S787 |
| 11.565 | D13S1243 |
| 16.898 | D13S221 |
| 17.454 | D13S1304 |
| 18.011 | D13S1254 |
| 18.59 | D13S625 |
| 19.308 | D13S1244 |
| 19.768 | D13S243 |
| 22.234 | D13S1250 |
| 22.642 | D13S1242 |
| 22.879 | D13S217 |
| 25.013 | D13S1299 |
| 28.136 | D13S289 |
| 28.678 | D13S290 |
| 29.134 | D13S1287 |
| 30.073 | D13S260 |
| 31.98 | D13S171 |
| 32.859 | D13S267 |
| 33.069 | D13S1293 |
| 33.07 | D13S620 |
| 34.131 | D13S220 |
| 36.427 | D13S219 |
| 39.458 | D13S1808 |
| 40.441 | D13S218 |
| 41.113 | D13S1288 |
| 41.996 | D13S1253 |
| 42.585 | D13S1248 |
| 44.288 | D13S1233 |
| 44.377 | D13S263 |
| 45.535 | D13S325 |
| 45.536 | D13S1270 |
| 45.537 | D13S1276 |
| 49.149 | D13S326 |
| 49.532 | D13S1272 |
| 52.421 | D13S168 |
| 52.674 | D13S287 |
| 60.536 | D13S1320 |
| 64.272 | D13S1296 |
| 71.287 | D13S156 |
| 76.828 | D13S1306 |
| 77.86 | D13S170 |
| 82.828 | D13S265 |
| 91.199 | D13S1241 |
| 93.863 | D13S1298 |
| 97.735 | D13S779 |
| 100.547 | D13S1256 |
| 102.277 | D13S274 |
| 111.885 | D13S173 |
| 112.198 | D13S796 |
| 115.619 | D13S778 |
| 119.036 | D13S1315 |
| 126.898 | D13S285 |
| 131.962 | D13S293 |

Table 13 shows the exons with positions that encode the FLAP protein, markers, polymorphisma and SNPs identified within the genomic sequence by the methods described herein.

| NCBI build34; start on chr. 13 (bp) | NCBI build34; stop on chr. 13 (bp) | SNP/marker/ exon name | alias1 | alias2 | public SNP | Variation |
|---|---|---|---|---|---|---|
| 28932432 | 28932432 | SG13S421 | | DG00AAFQR | rs1556428 | A/G |
| 28960356 | 28960356 | SG13S417 | | SNP13B_R1028729 | rs1028729 | C/T |
| 28965803 | 28965803 | SG13S418 | | SNP13B_Y1323898 | rs1323898 | A/G |
| 28974627 | 28974627 | SG13S44 | | | | A/G |
| 28975101 | 28975101 | SG13S45 | | | | C/G |
| 28975315 | 28975315 | SG13S46 | | | | A/G |
| 28975353 | 28975353 | SG13S50 | | | | C/T |
| 28975774 | 28975774 | SG13S52 | | | | A/G |
| 28985244 | 28985244 | SG13S53 | | | rs1408167 | A/C |
| 28985303 | 28985303 | SG13S55 | | | rs1408169 | A/G |
| 28985423 | 28985423 | SG13S56 | | | | G/T |
| 28985734 | 28985734 | SG13S57 | | | rs6490471 | C/T |
| 28985902 | 28985902 | SG13S58 | | | rs6490472 | A/G |
| 29003869 | 29003869 | SG13S59 | | | | C/G |
| 29004696 | 29004696 | SG13S60 | | | | A/G |
| 29007670 | 29007670 | SG13S419 | | SNP13B_K912392 | rs912392 | C/T |
| 29015410 | 29015410 | SG13S61 | | | | C/T |
| 29025792 | 29025792 | SG13S62 | | | | C/T |
| 29026202 | 29026202 | SG13S63 | | | rs7997114 | A/G |
| 29026668 | 29026668 | SG13S64 | | | | A/G |
| 29038707 | 29038707 | SG13S65 | | | | A/G |

-continued

| | | | | | | |
|---|---|---|---|---|---|---|
| 29042180 | 29042180 | SG13S420 | | DG00AAFIV | rs2248564 | A/T |
| 29049355 | 29049355 | SG13S66 | | | | A/G |
| 29049446 | 29049446 | SG13S67 | | | | C/T |
| 29050416 | 29050416 | SG13S69 | | | | A/C |
| 29059348 | 29059348 | SG13S70 | | | | A/G |
| 29059383 | 29059383 | SG13S71 | | | | A/G |
| 29059402 | 29059402 | SG13S72 | | | | G/T |
| 29063702 | 29063949 | D13S289 | | | | |
| 29064359 | 29064753 | DG13S166 | | | | |
| 29066272 | 29066272 | SG13S73 | | | | A/G |
| 29070551 | 29070551 | SG13S99 | SNP_13_Y1323892 | DG00AAFIU | rs1323892 | C/T |
| 29081983 | 29081983 | SG13S382 | FLA267479 | | | A/G |
| 29082200 | 29082200 | SG13S383 | FLA267696 | | | A/G |
| 29082357 | 29082357 | SG13S384 | FLA267853 | | | A/G |
| 29083350 | 29083350 | SG13S381 | FLA268846 | DG00AAJER | | C/G |
| 29083518 | 29083518 | SG13S366 | FLA269014 | DG00AAJES | rs4312166 | A/G |
| 29085102 | 29085102 | SG13S385 | FLA270742 | | | C/T |
| 29085190 | 29085190 | SG13S386 | FLA270830 | | | A/G |
| 29086224 | 29086224 | SG13S1 | FLA271864 | | | G/T |
| 29087473 | 29087473 | SG13S2 | FLA273371 | | | A/G |
| 29088090 | 29088090 | SG13S367 | FLA273988 | DG00AAJEU | rs4474551 | A/G |
| 29088186 | 29088186 | SG13S388 | FLA274084 | | | A/G |
| 29088473 | 29088473 | SG13S10 | FLA274371 | | | A/T |
| 29089044 | 29089044 | SG13S3 | FLA274942 | | | C/T |
| 29089886 | 29089886 | SG13S368 | FLA275784 | DG00AAJEV | | C/T |
| 29090025 | 29090025 | SG13S369 | FLA275923 | DG00AAJEW | | G/T |
| 29090054 | 29090054 | SG13S370 | FLA275952 | DG00AAJEX | | A/G |
| 29090997 | 29090997 | SG13S4 | FLA276895 | | | G/C |
| 29091307 | 29091307 | SG13S5 | FLA277205 | | rs4238133 | G/T |
| 29091580 | 29091580 | SG13S389 | FLA277478 | | | A/G |
| 29091780 | 29091780 | SG13S90 | FLA277678 | | | A/C |
| 29092287 | 29092287 | SG13S390 | FLA278185 | | rs5004913 | A/G |
| 29092536 | 29092536 | SG13S6 | FLA278434 | | | A/G |
| 29092594 | 29092594 | SG13S391 | FLA278492 | | | A/G |
| 29092947 | 29092947 | SG13S392 | FLA278845 | | | G/T |
| 29093964 | 29093964 | SG13S371 | FLA279888 | DG00AAJEY | rs4409939 | A/G |
| 29094259 | 29094259 | SG13S372 | FLA280183 | DG00AAJEZ | | A/G |
| 29094999 | 29094999 | SG13S393 | FLA280923 | | | A/T |
| 29096688 | 29096688 | SG13S373 | FLA282612 | DG00AAJFA | | A/G |
| 29096813 | 29096813 | SG13S374 | FLA282737 | DG00AAJFB | | A/G |
| 29096874 | 29096874 | SG13S375 | FLA282798 | DG00AAJFC | | C/T |
| 29096962 | 29096962 | SG13S376 | FLA282886 | DG00AAJFD | | A/G |
| 29097476 | 29097476 | SC13S394 | FLA283400 | | | C/G |
| 29097553 | 29097553 | SC13S25 | FLA283477 | | | A/G |
| 29098486 | 29098486 | SG13S395 | FLA284410 | | | A/G |
| 29098891 | 29098891 | SG13S396 | FLA284815 | | | A/C |
| 29098979 | 29098979 | SG13S397 | FLA284903 | | | C/T |
| 29101965 | 29101965 | SG13S377 | FLA287889 | DG00AAJFF | | A/G |
| 29103909 | 29103909 | SG13S189 | FLA289833 | | | C/G |
| 29104271 | 29104271 | SG13S100 | FLA290195 | DG00AAHIK | rs4073259 | A/G |
| 29104629 | 29104629 | SG13S398 | FLA290553 | | | C/G |
| 29104646 | 29104646 | SG13S94 | FLA290570 | | rs4073261 | C/T |
| 29105099 | 29105099 | SG13S101 | FLA291023 | | rs4075474 | C/T |
| 29106329 | 29106329 | SG13S95 | FLA292253 | | | G/T |
| 29106652 | 29106652 | SG13S102 | FLA292576 | | | A/T |
| 29107138 | 29107138 | SG13S103 | FLA293062 | | | C/T |
| 29107404 | 29107404 | SG13S104 | FLA293328 | | | A/G |
| 29107668 | 29107812 | EXON1 | | | | |
| 29107830 | 29107830 | SG13S191 | FLA293754 | DG00AAFJT | rs4769055 | A/C |
| 29108398 | 29108398 | SG13S105 | FLA294322 | | | A/G |
| 29108579 | 29108579 | SG13S106 | FLA294503 | DG00AAHII | | A/G |
| 29108919 | 29108919 | SG13S107 | FLA294843 | | rs4075131 | A/G |
| 29108972 | 29108972 | SG13S108 | FLA294896 | | rs4075132 | C/T |
| 29109112 | 29109112 | SG13S109 | FLA295036 | | | A/G |
| 29109182 | 29109182 | SG13S110 | FLA295106 | | | A/G |
| 29109344 | 29109344 | SG13S111 | FLA295268 | | rs4597169 | C/T |
| 29109557 | 29109557 | SG13S112 | FLA295481 | | | C/T |
| 29109773 | 29109773 | SG13S113 | FLA295697 | | rs4293222 | C/G |
| 29110096 | 29110096 | SG13S114 | FLA296020 | DG00AAHID | | |
| 29110178 | 29110178 | SG13S115 | FLA296102 | | | A/T |
| 29110508 | 29110508 | SG13S116 | FLA296432 | | rs4769871 | C/T |
| 29110630 | 29110630 | SG13S117 | FLA296554 | | rs4769872 | A/G |
| 29110689 | 29110689 | SG13S118 | FLA296613 | | rs4769873 | C/T |
| 29110862 | 29110862 | SG13S119 | FLA296786 | | | A/G |
| 29111889 | 29111889 | SG13S120 | FLA297813 | | | C/T |

-continued

| | | | | | | |
|---|---|---|---|---|---|---|
| 29112174 | 29112174 | SG13S121 | FLA298098 | DG00AAHIJ | rs4503649 | A/G |
| 29112264 | 29112264 | SG13S122 | FLA298188 | DG00AAHIH | | A/G |
| 29112306 | 29112306 | SG13S123 | FLA298230 | | | C/T |
| 29112455 | 29112455 | SG13S43 | FLA298379 | | rs3885907 | A/C |
| 29112583 | 29112583 | SG13S399 | FLA298507 | | | A/C |
| 29112680 | 29112680 | SG13S124 | FLA298604 | | rs3922435 | C/T |
| 29113139 | 29113139 | SG13S125 | FLA299063 | | | A/G |
| 29114056 | 29114056 | SG13S400 | FLA299980 | | | A/G |
| 29114738 | 29114738 | SG13S126 | FLA300662 | | | A/G |
| 29114940 | 29114940 | SG13S127 | FLA300864 | | | A/G |
| 29115878 | 29115878 | SG13S128 | FLA302094 | | rs4254165 | A/G |
| 29116020 | 29116020 | SG13S129 | FLA302236 | | rs4360791 | A/G |
| 29116068 | 29116068 | SG13S130 | FLA302284 | | | G/T |
| 29116196 | 29116296 | EXON2 | | | | |
| 29116249 | 29116249 | SG13S190 | FLA302465 | | | C/T |
| 29116308 | 29116308 | SG13S192 | FLA302524 | B_SNP_302524 | rs3803277 | A/C |
| 29116344 | 29116344 | SG13S193 | FLA302560 | | | A/G |
| 29116401 | 29116401 | SG13S88 | FLA302617 | B_SNP_302617 | rs3803278 | C/T |
| 29116688 | 29116688 | SG13S131 | FLA302904 | | | C/T |
| 29117133 | 29117133 | SG13S132 | FLA303349 | | | A/C |
| 29117546 | 29117546 | SG13S133 | FLA303762 | | rs4356336 | C/T |
| 29117553 | 29117553 | SG13S38 | FLA303769 | | rs4584668 | A/T |
| 29117580 | 29117580 | SG13S134 | FLA303796 | | | C/T |
| 29117741 | 29117741 | SG13S135 | FLA303957 | | rs4238137 | C/T |
| 29117954 | 29117954 | SG13S136 | FLA304170 | | rs4147063 | C/T |
| 29118118 | 29118118 | SG13S137 | FLA304334 | DG00AAHIG | rs4147064 | C/T |
| 29118815 | 29118815 | SG13S86 | FLA305031 | | | A/G |
| 29118873 | 29118873 | SG13S87 | FLA305089 | DG00AAHOJ | | A/G |
| 29119069 | 29119069 | SG13S138 | FLA305285 | | | C/T |
| 29119138 | 29119138 | SG13S139 | FLA305354 | | | C/G |
| 29119289 | 29119289 | SG13S140 | FLA305505 | | | A/G/T |
| 29119462 | 29119462 | SG13S141 | FLA305678 | | | C/T |
| 29119740 | 29119740 | SG13S39 | FLA305956 | | | G/T |
| 29120939 | 29120939 | SG13S142 | FLA307155 | | rs4387455 | C/T |
| 29120949 | 29120949 | SG13S143 | FLA307165 | | rs4254166 | C/T |
| 29121342 | 29121342 | SG13S144 | FLA307558 | | rs4075692 | A/G |
| 29121572 | 29121572 | SG13S145 | FLA307788 | | | C/G |
| 29121988 | 29121988 | SG13S146 | FLA308204 | | | C/T |
| 29122253 | 29122253 | SG13S26 | FLA308469 | | | C/T |
| 29122283 | 29122283 | SG13S27 | FLA308499 | | | A/G |
| 29122294 | 29122294 | SG13S147 | FLA308510 | | | C/T |
| 29122298 | 29122298 | SG13S28 | FLA308514 | | | G/T |
| 29122311 | 29122311 | SG13S148 | FLA308527 | | | G/T |
| 29123370 | 29123370 | SG13S98 | FLA309586 | | | G/T |
| 29123635 | 29123635 | SG13S149 | FLA309851 | | | A/G |
| 29123643 | 29123643 | SG13S29 | FLA309859 | | | A/C |
| 29124188 | 29124259 | EXON3 | | | | |
| 29124441 | 29124441 | SG13S89 | FLA310657 | B_SNP_310657 | rs4769874 | A/G |
| 29124906 | 29124906 | SG13S96 | FLA311122 | | rs4072653 | A/G |
| 29125032 | 29125032 | SG13S150 | FLA311248 | | | C/G |
| 29125521 | 29125521 | SG13S401 | FLA311737 | | | C/T |
| 29125822 | 29125822 | SG13S151 | FLA312038 | | | C/T |
| 29125840 | 29125840 | SG13S30 | FLA312056 | | | G/T |
| 29127301 | 29127301 | SG13S31 | FLA313550 | | | C/T |
| 29128080 | 29128162 | EXON4 | | | | |
| 29128284 | 29128284 | SG13S152 | FLA314500 | | | C/G |
| 29128316 | 29128316 | SG13S402 | FLA314532 | | rs4468448 | C/T |
| 29128798 | 29128798 | SG13S403 | FLA315014 | | rs4399410 | A/G |
| 29129016 | 29129016 | SG13S153 | FLA315232 | | | A/T |
| 29129139 | 29129139 | SG13S97 | FLA315355 | | | A/G |
| 29129154 | 29129154 | SG13S154 | FLA315370 | | | C/T |
| 29129395 | 29129395 | SG13S40 | FLA315611 | | | G/T |
| 29129915 | 29129915 | SG13S155 | FLA316131 | | rs4769875 | A/G |
| 29130192 | 29130192 | SG13S156 | FLA316408 | | | A/C |
| 29130256 | 29130256 | SG13S157 | FLA316472 | | | A/G |
| 29130299 | 29130299 | SG13S158 | FLA316515 | | | A/C |
| 29130353 | 29130353 | SG13S159 | FLA316569 | | | G/T |
| 29130391 | 29130391 | SG13S160 | FLA316607 | | | C/T |
| 29130547 | 29130547 | SG13S32 | FLA316763 | | | A/C |
| 29131280 | 29131280 | SG13S161 | FLA317496 | | | A/G |
| 29131403 | 29131403 | SG13S162 | FLA317619 | | | A/G |
| 29131404 | 29131404 | SG13S163 | FLA317620 | | | C/T |
| 29131431 | 29131431 | SG13S164 | FLA317647 | | rs4769058 | C/T |
| 29131517 | 29131517 | SG13S165 | FLA317733 | | | A/T |
| 29131528 | 29131528 | SG13S166 | FLA317744 | | rs4769059 | C/T |
| 29131599 | 29131599 | SG13S167 | FLA317815 | | rs4769876 | A/G |
| 29132003 | 29132003 | SG13S168 | FLA318219 | | | A/C |
| 29133753 | 29133753 | SG13S33 | FLA319969 | | | G/T |
| 29134045 | 29134045 | SG13S41 | FLA320261 | | | A/G |

-continued

| | | | | | | |
|---|---|---|---|---|---|---|
| 29134177 | 29134177 | SG13S169 | FLA320393 | | | A/G |
| 29134379 | 29134379 | SG13S404 | FLA320595 | | rs4427651 | G/T |
| 29135558 | 29135558 | SG13S170 | FLA321774 | | rs3935645 | C/T |
| 29135640 | 29135640 | SG13S171 | FLA321856 | | rs3935644 | A/G |
| 29135750 | 29135750 | SG13S172 | FLA321966 | | | A/G |
| 29135809 | 29135809 | SG13S173 | FLA322025 | | | A/T |
| 29135877 | 29135877 | SG13S42 | FLA322093 | | rs4769060 | A/G |
| 29136080 | 29136556 | EXON5 | | | | |
| 29136290 | 29136290 | SG13S194 | FLA322506 | | | C/T |
| 29136462 | 29136462 | SG13S195 | FLA322678 | | rs1132340 | A/G |
| 29136797 | 29136797 | SG13S174 | FLA323013 | | | A/G |
| 29137100 | 29137100 | SG13S34 | FLA323316 | | | G/T |
| 29137150 | 29137150 | SG13S175 | FLA323366 | | | A/G |
| 29137607 | 29137607 | SG13S176 | FLA323823 | | | A/G |
| 29137651 | 29137651 | SG13S177 | FLA323867 | | | C/T |
| 29137905 | 29137905 | SG13S178 | FLA324121 | | | C/G |
| 29138117 | 29138117 | SG13S35 | FLA324333 | | | A/G |
| 29138375 | 29138375 | SG13S179 | FLA324591 | | | A/G |
| 29138385 | 29138385 | SG13S180 | FLA324601 | | | C/T |
| 29138633 | 29138633 | SG13S181 | FLA324849 | DG00AAHIF | rs4420371 | C/G |
| 29139153 | 29139153 | SG13S182 | FLA325369 | | | C/T |
| 29139277 | 29139277 | SG13S183 | FLA325493 | | rs4466940 | C/T |
| 29139435 | 29139435 | SG13S184 | FLA325651 | DG00AAHOI | rs4445746 | A/G |
| 29139971 | 29139971 | SG13S185 | FLA326187 | | | A/G |
| 29140441 | 29140441 | SG13S405 | FLA326657 | | | A/G |
| 29140649 | 29140649 | SG13S91 | FLA326865 | | | A/G |
| 29140695 | 29140695 | SG13S186 | FLA326911 | | rs4769877 | A/T |
| 29140703 | 29140703 | SG13S187 | FLA326919 | | | A/G |
| 29140805 | 29140805 | SG13S188 | FLA327021 | DG00AAJFE | | A/G |
| 29141049 | 29141049 | SG13S406 | FLA327265 | | | C/T |
| 29142392 | 29142392 | SG13S92 | FLA328644 | | rs4429158 | C/T |
| 29142397 | 29142397 | SG13S93 | FLA328649 | | | A/G |
| 29142712 | 29142712 | SG13S36 | FLA328964 | | | C/T |
| 29144013 | 29144013 | SG13S407 | FLA330265 | | | C/T |
| 29144203 | 29144203 | SG13S408 | FLA330455 | | | C/T |
| 29144234 | 29144589 | D13S1238 | | | | |
| 29144255 | 29144255 | SG13S7 | FLA330507 | | | C/T |
| 29144877 | 29144877 | SG13S37 | FLA331129 | | | A/G |
| 29144982 | 29144982 | SG13S409 | FLA331234 | | | A/G |
| 29144983 | 29144983 | SG13S8 | FLA331235 | | rs4491352 | A/C |
| 29145122 | 29145122 | SG13S410 | FLA331374 | | rs4319601 | C/T |
| 29145143 | 29145143 | SG13S411 | FLA331395 | | | A/G |
| 29145171 | 29145171 | SG13S9 | FLA331423 | | | C/T |
| 29145221 | 29145221 | SG13S412 | FLA331473 | | rs4769062 | A/G |
| 29145265 | 29145265 | SG13S413 | FLA331517 | | rs4238138 | C/T |

| minor allele | minor allele frequency (%) | start position in SEQ ID NO: 1 | end position in SEQ ID NO: 1 |
|---|---|---|---|
| G | 10.32 | 432 | 432 |
| G | 30.46 | 28356 | 28356 |
| T | 37.38 | 33803 | 33803 |
| G | 0.545 | 42627 | 42627 |
| G | 1.111 | 43101 | 43101 |
| G | 0.328 | 43315 | 43315 |
| C | 0.495 | 43353 | 43353 |
| A | 6.993 | 43774 | 43774 |
| C | 30.876 | 53244 | 53244 |
| G | 6.731 | 53303 | 53303 |
| T | 0.353 | 53423 | 53423 |
| C | 31.356 | 53734 | 53734 |
| A | 30.935 | 53902 | 53902 |
| G | 5.492 | 71869 | 71869 |
| A | 1.812 | 72696 | 72696 |
| G | 35.00 | 75670 | 75670 |
| C | 1.314 | 83410 | 83410 |
| T | 3.521 | 93792 | 93792 |
| A | 30.031 | 94202 | 94202 |
| A | 1.724 | 94668 | 94668 |
| A | 0.369 | 106707 | 106707 |
| A | 13.66 | 110180 | 110180 |
| A | 20.779 | 117355 | 117355 |
| T | 5.965 | 117446 | 117446 |
| A | 16.923 | 118416 | 118416 |
| A | 34.364 | 127348 | 127348 |

-continued

| | | | |
|---|---|---|---|
| A | 8.537 | 127383 | 127383 |
| T | 25.536 | 127402 | 127402 |
| | | 131702 | 131949 |
| | | 132359 | 132753 |
| A | 37.302 | 134272 | 134272 |
| C | 6.25 | 138551 | 138551 |
| A | 0.49 | 149983 | 149983 |
| A | 14.08 | 150200 | 150200 |
| G | 0.62 | 150357 | 150357 |
| G | 14.01 | 151350 | 151350 |
| T | 0.58 | 151518 | 151518 |
| C | 30.21 | 153102 | 153102 |
| A | 10.95 | 153190 | 153190 |
| G | 30.00 | 154224 | 154224 |
| A | 27.95 | 155473 | 155473 |
| G | 2.41 | 156090 | 156090 |
| A | 0.39 | 156186 | 156186 |
| T | 10.23 | 156473 | 156473 |
| T | 15.17 | 157044 | 157044 |
| T | 13.60 | 157886 | 157886 |
| G | 12.44 | 158025 | 158025 |
| A | 13.45 | 158054 | 158054 |
| G | 14.59 | 158997 | 158997 |
| T | 26.84 | 159307 | 159307 |
| A | 12.73 | 159580 | 159580 |
| C | 43.67 | 159780 | 159780 |
| A | 12.18 | 160287 | 160287 |
| A | 8.38 | 160536 | 160536 |
| G | 0.62 | 160594 | 160594 |
| T | 12.34 | 160947 | 160947 |
| G | 25.34 | 161964 | 161964 |
| C | 0.24 | 162259 | 162259 |
| T | 25.66 | 162999 | 162999 |
| A | 14.84 | 164688 | 164688 |
| G | 12.37 | 164813 | 164813 |
| C | 14.55 | 164874 | 164874 |
| G | 11.99 | 164962 | 164962 |
| C | 14.66 | 165476 | 165476 |
| A | 12.21 | 165553 | 165553 |
| A | 0.79 | 166486 | 166486 |
| C | 10.15 | 166891 | 166891 |
| C | 3.53 | 166979 | 166979 |
| A | 12.45 | 169965 | 169965 |
| C | 0.62 | 171909 | 171909 |
| G | 31.55 | 172271 | 172271 |
| G | 4.94 | 172629 | 172629 |
| C | 15.51 | 172646 | 172646 |
| T | 27.91 | 173099 | 173099 |
| G | 14.74 | 174329 | 174329 |
| T | 1.17 | 174652 | 174652 |
| T | 1.28 | 175138 | 175138 |
| A | 2.17 | 175404 | 175404 |
| | | 175668 | 175812 |
| A | 30.11 | 175830 | 175830 |
| G | 0.66 | 176398 | 176398 |
| A | 28.31 | 176579 | 176579 |
| G | 14.85 | 176919 | 176919 |
| C | 1.21 | 176972 | 176972 |
| A | 1.04 | 177112 | 177112 |
| G | 0.88 | 177182 | 177182 |
| C | 1.14 | 177344 | 177344 |
| T | 7.10 | 177557 | 177557 |
| C | 22.52 | 177773 | 177773 |
| A | 20.86 | 178096 | 178096 |
| T | 13.83 | 178178 | 178178 |
| T | 4.05 | 178508 | 178508 |
| A | 4.07 | 178630 | 178630 |
| T | 4.07 | 178689 | 178689 |
| A | 1.06 | 178862 | 178862 |
| C | 16.00 | 179889 | 179889 |
| G | 49.36 | 180174 | 180174 |
| A | 29.75 | 180264 | 180264 |
| T | 5.06 | 180306 | 180306 |
| C | 46.23 | 180455 | 180455 |
| C | 1.59 | 180583 | 180583 |
| T | 1.45 | 180680 | 180680 |
| G | 11.32 | 181139 | 181139 |
| A | 3.25 | 182056 | 182056 |
| A | 34.12 | 182738 | 182738 |

-continued

| | | | |
|---|---|---|---|
| G | 29.63 | 182940 | 182940 |
| A | 45.68 | 183878 | 183878 |
| G | 36.65 | 184020 | 184020 |
| G | 8.07 | 184068 | 184068 |
| | | 184196 | 184296 |
| T | 1.02 | 184249 | 184249 |
| A | 49.57 | 184308 | 184308 |
| A | 0.58 | 184344 | 184344 |
| C | 24.71 | 184401 | 184401 |
| T | 7.19 | 184688 | 184688 |
| A | 1.10 | 185133 | 185133 |
| T | 37.65 | 185546 | 185546 |
| A | 45.50 | 185553 | 185553 |
| T | 1.22 | 185580 | 185580 |
| T | 0.89 | 185741 | 185741 |
| T | 36.69 | 185954 | 185954 |
| T | 29.11 | 186118 | 186118 |
| A | 30.19 | 186815 | 186815 |
| G | 3.29 | 186873 | 186873 |
| T | 36.96 | 187069 | 187069 |
| G | 36.63 | 187138 | 187138 |
| T | 37.34 | 187289 | 187289 |
| C | 1.15 | 187462 | 187462 |
| T | 9.91 | 187740 | 187740 |
| C | 3.36 | 188939 | 188939 |
| T | 36.24 | 188949 | 188949 |
| A | 31.58 | 189342 | 189342 |
| G | 0.45 | 189572 | 189572 |
| T | 1.14 | 189988 | 189988 |
| T | 46.57 | 190253 | 190253 |
| A | 10.34 | 190283 | 190283 |
| T | 8.00 | 190294 | 190294 |
| T | 33.71 | 190298 | 190298 |
| T | 2.29 | 190311 | 190311 |
| G | 1.19 | 191370 | 191370 |
| A | 1.01 | 191635 | 191635 |
| A | 47.88 | 191643 | 191643 |
| | | 192188 | 192259 |
| A | 4.68 | 192441 | 192441 |
| G | 29.72 | 192906 | 192906 |
| C | 8.22 | 193032 | 193032 |
| C | 21.10 | 193521 | 193521 |
| T | 8.57 | 193822 | 193822 |
| T | 23.23 | 193840 | 193840 |
| T | 24.20 | 195301 | 195301 |
| | | 196080 | 196162 |
| C | 23.89 | 196284 | 196284 |
| T | 19.33 | 196316 | 196316 |
| G | 11.50 | 196798 | 196798 |
| T | 3.08 | 197016 | 197016 |
| A | 9.72 | 197139 | 197139 |
| T | 0.98 | 197154 | 197154 |
| T | 2.24 | 197395 | 197395 |
| A | 1.43 | 197915 | 197915 |
| A | 1.80 | 198192 | 198192 |
| G | 2.38 | 198256 | 198256 |
| A | 0.61 | 198299 | 198299 |
| G | 2.55 | 198353 | 198353 |
| T | 0.83 | 198391 | 198391 |
| C | 48.50 | 198547 | 198547 |
| G | 2.44 | 199280 | 199280 |
| G | 2.45 | 199403 | 199403 |
| C | 2.45 | 199404 | 199404 |
| C | 2.55 | 199431 | 199431 |
| T | 20.00 | 199517 | 199517 |
| T | 2.46 | 199528 | 199528 |
| A | 3.50 | 199599 | 199599 |
| C | 8.39 | 200003 | 200003 |
| T | 8.99 | 201753 | 201753 |
| G | 5.41 | 202045 | 202045 |
| G | 4.12 | 202177 | 202177 |
| G | 38.33 | 202379 | 202379 |
| C | 32.77 | 203558 | 203558 |
| G | 48.03 | 203640 | 203640 |
| G | 1.67 | 203750 | 203750 |

-continued

| | | | |
|---|---|---|---|
| A | 0.68 | 203809 | 203809 |
| G | 42.44 | 203877 | 203877 |
| | | 204080 | 204556 |
| T | 0.30 | 204290 | 204290 |
| G | 2.46 | 204462 | 204462 |
| G | 0.56 | 204797 | 204797 |
| G | 30.23 | 205100 | 205100 |
| A | 2.40 | 205150 | 205150 |
| A | 2.24 | 205607 | 205607 |
| T | 1.64 | 205651 | 205651 |
| C | 1.40 | 205905 | 205905 |
| A | 9.52 | 206117 | 206117 |
| A | 48.14 | 206375 | 206375 |
| T | 2.50 | 206385 | 206385 |
| C | 49.41 | 206633 | 206633 |
| T | 2.36 | 207153 | 207153 |
| T | 12.07 | 207277 | 207277 |
| A | 16.67 | 207435 | 207435 |
| G | 7.66 | 207971 | 207971 |
| A | 9.66 | 208441 | 208441 |
| A | 7.78 | 208649 | 208649 |
| A | 25.71 | 208695 | 208695 |
| A | 1.43 | 208703 | 208703 |
| G | 4.71 | 208805 | 208805 |
| T | 0.56 | 209049 | 209049 |
| T | 8.33 | 210392 | 210392 |
| A | 7.23 | 210397 | 210397 |
| C | 15.88 | 210712 | 210712 |
| T | 3.29 | 212013 | 212013 |
| T | 0.30 | 212203 | 212203 |
| | | 212234 | 212589 |
| T | 16.28 | 212255 | 212255 |
| G | 16.70 | 212877 | 212877 |
| A | 1.93 | 212982 | 212982 |
| C | 30.64 | 212983 | 212983 |
| T | 20.57 | 213122 | 213122 |
| A | 1.54 | 213143 | 213143 |
| C | 16.37 | 213171 | 213171 |
| A | 7.42 | 213221 | 213221 |
| T | 1.91 | 213265 | 213265 |

TABLE 14

Extended 4 microsatellite marker haplotypes 4 markers : pos.rr.frqgt1perc

| Length | p-val | RR | N_af | P_al | P_ca | N_ct | P_al | P_ca | Alleles | | | | Markers |
|---|---|---|---|---|---|---|---|---|---|---|---|---|---|
| 0.88 | 4.71E−06 | 6.23 | 428 | 0.065 | 0.125 | 721 | 0.011 | 0.022 | 0 | −12 | −6 | 0 | DG13S80 DG13S83 DG13S1110 DG13S163 |
| 0.82 | 8.60E−06 | INF | 438 | 0.032 | 0.062 | 720 | 0 | 0 | 0 | 4 | 2 | 14 | DG13S111 1 DG13S1103 D13S1287 DG13S1061 |
| 0.67 | 6.98E−06 | 19.91 | 435 | 0.03 | 0.059 | 721 | 0.002 | 0.003 | 8 | 6 | 0 | 8 | DG13S1103 DG13S163 D13S290 DG13S1061 |
| 0.767 | 4.85E−06 | 26.72 | 436 | 0.048 | 0.094 | 721 | 0.002 | 0.004 | 0 | 0 | 2 | 12 | DG13S1101 DG13S166 D13S1287 DG13S1061 |
| 0.515 | 1.93E−06 | INF | 422 | 0.048 | 0.094 | 721 | 0 | 0 | 2 | 0 | 0 | 6 | DG13S166 DG13S163 D13S290 DG13S1061 |
| 0.864 | 1.68E−06 | INF | 424 | 0.024 | 0.048 | 717 | 0 | 0 | 0 | 2 | 0 | −16 | DG13S166 DG13S163 DG13S1061 DG13S293 |

TABLE 14-continued

Extended 4 microsatellite marker haplotypes 4 markers : pos.rr.frqgt1perc

| Length | p-val | RR | N_af | P_al | P_ca | N_ct | P_al | P_ca | Alleles | | | | Markers |
|---|---|---|---|---|---|---|---|---|---|---|---|---|---|
| 0.927 | 5.38E−06 | INF | 435 | 0.034 | 0.067 | 720 | 0 | 0 | 4 | 2 | 14 | 3 | DG13S1103 D13S1287 DG13S1061 DG13S301 |

Alleles #'s: For SNP alleles A = 0, C = 1, G = 2, T = 3; for microsatellite alleles: the CEPH sample (Centre d'Etudes du Polymorphisme Humain, genomics repository) is used as a reference, as described above.
Length = length of haplotype in Mb.
P-val = p-value.
RR = Relative risk.
N af = Number of patients.
P al = allelic frequency of haplotype.
P ca = carrier frequency of haplotype.
N ct = number of controls.
Alleles = alleles in the haplotype.
Markers = markers in the haplotype.

TABLE 15

Extended 5 microsatellite marker haplotypes

5markers : pos.rr.frqgt1perc

| Length | p-val | RR | N_af | P_al | P_ca | N_ct | P_al | P_ca | Alleles | | | | | Markers |
|---|---|---|---|---|---|---|---|---|---|---|---|---|---|---|
| 0.851 | 7.45E−06 | 15.43 | 413 | 0.034 | 0.067 | 715 | 0.002 | 0.005 | 0 | 18 | 0 | 0 | 0 | DG13S79 D13S1299 DG13S87 D13S1246 DG13S166 |
| 0.964 | 8.07E−06 | INF | 437 | 0.023 | 0.045 | 721 | 0 | 0 | 0 | −12 | 6 | 8 | 6 | DG13S79 DG13S83 DG13S1104 DG13S1103 DG13S163 |
| 0.964 | 2.38E−06 | INF | 437 | 0.026 | 0.052 | 720 | 0 | 0 | 0 | 6 | 0 | 8 | 6 | DG13S79 DG13S1104 DG13S172 DG13S1103 DG13S163 |
| 0.931 | 7.05E−06 | 5.8 | 429 | 0.068 | 0.131 | 721 | 0.012 | 0.025 | 0 | −6 | 0 | 0 | −2 | DG13S79 DG13S1110 DG13S175 DG13S166 D13S1238 |
| 0.964 | 8.13E−06 | INF | 434 | 0.021 | 0.041 | 721 | 0 | 0 | 0 | 3 | 8 | 2 | 6 | DG13S79 DG13S1098 DG13S1103 DG13S166 DG13S163 |
| 0.597 | 9.78E−06 | 4.58 | 428 | 0.074 | 0.143 | 717 | 0.017 | 0.034 | −6 | 0 | 0 | 0 | −2 | DG13S1110 DG13S89 DG13S175 DG13S166 D13S1238 |
| 0.896 | 6.92E−06 | INF | 428 | 0.026 | 0.051 | 721 | 0 | 0 | −12 | −6 | 0 | −2 | 2 | DG13S83 DG13S1110 DG13S166 D13S1238 D13S290 |
| 0.722 | 2.18E−06 | INF | 453 | 0.026 | 0.051 | 738 | 0 | 0 | −6 | 0 | 0 | −2 | 2 | DG13S1110 D13S289 DG13S166 D13S1238 D13S290 |
| 0.982 | 7.88E−06 | INF | 437 | 0.028 | 0.055 | 721 | 0 | 0 | 0 | 0 | 4 | 2 | 14 | DG13S87 DG13S175 DG13S1103 D13S1287 DG13S1061 |

TABLE 15-continued

Extended 5 microsatellite marker haplotypes

5markers : pos.rr.frqgt1perc

| Length | p-val | RR | N_af | P_al | P_ca | N_ct | P_al | P_ca | Alleles | | | | | Markers |
|---|---|---|---|---|---|---|---|---|---|---|---|---|---|---|
| 0.841 | 8.88E−06 | INF | 438 | 0.032 | 0.062 | 720 | 0 | 0 | 0 | 0 | 4 | 2 | 14 | DG13S89 DG13S1111 DG13S1103 D13S1287 DG13S1061 |
| 0.841 | 9.67E−07 | INF | 435 | 0.029 | 0.057 | 721 | 0 | 0 | 0 | 8 | 6 | 0 | 8 | DG13S89 DG13S1103 DG13S163 D13S290 DG13S1061 |
| 0.982 | 7.90E−06 | 18.63 | 437 | 0.026 | 0.052 | 721 | 0.001 | 0.003 | 0 | 4 | 0 | 2 | 14 | DG13S87 DG13S1103 DG13S166 D13S1287 DG13S1061 |
| 0.841 | 3.52E−06 | 28.52 | 436 | 0.048 | 0.094 | 721 | 0.002 | 0.004 | 0 | 0 | 0 | 2 | 12 | DG13S89 DG13S1101 DG13S166 D13S1287 DG13S1061 |
| 0.705 | 5.28E−06 | INF | 435 | 0.027 | 0.053 | 721 | 0 | 0 | 0 | 8 | 6 | 0 | 8 | DG13S175 DG13S1103 DG13S163 D13S290 DG13S1061 |
| 0.841 | 4.21E−06 | INF | 422 | 0.048 | 0.093 | 721 | 0 | 0 | 0 | 2 | 0 | 0 | 6 | DG13S89 DG13S166 DG13S163 D13S290 DG13S1061 |
| 0.767 | 4.02E−0 | 28.11 | 436 | 0.049 | 0.095 | 721 | 0.002 | 0.004 | 0 | 0 | 0 | 2 | 12 | DG13S1101 DG13S175 DG13S166 D13S1287 DG13S1061 |
| 0.767 | 1.29E−06 | 31.07 | 436 | 0.047 | 0.092 | 721 | 0.002 | 0.003 | 0 | 0 | 0 | 2 | 12 | DG13S1101 DG13S172 DG13S166 D13S1287 DG13S1061 |
| 0.705 | 4.25E−07 | INF | 422 | 0.048 | 0.093 | 721 | 0 | 0 | 0 | 2 | 0 | 0 | 6 | DG13S175 DG13S166 DG13S163 D13S290 DG13S1061 |
| 0.683 | 6.58E−06 | INF | 437 | 0.029 | 0.056 | 721 | 0 | 0 | 0 | 4 | 0 | 2 | 14 | DG13S172 DG13S1103 DG13S166 D13S1287 DG13S1061 |
| 0.767 | 2.85E−06 | 32.43 | 436 | 0.044 | 0.087 | 721 | 0.001 | 0.003 | 0 | 0 | 0 | 2 | 12 | DG13S1101 DG13S166 D13S290 D13S1287 DG13S1061 |
| 0.865 | 9.58E−06 | 18.39 | 451 | 0.023 | 0.045 | 739 | 0.001 | 0.003 | 0 | 0 | 2 | 2 | −16 | D13S289 DG13S166 DG13S163 D13S1287 DG13S293 |
| 0.865 | 5.08E−06 | INF | 453 | 0.019 | 0.038 | 739 | 0 | 0 | 0 | 0 | 2 | 0 | −16 | D13S289 DG13S166 DG13S163 DG13S1061 DG13S293 |

TABLE 15-continued

Extended 5 microsatellite marker haplotypes

5markers : pos.rr.frqgt1perc

| Length | p-val | RR | N_af | P_al | P_ca | N_ct | P_al | P_ca | Alleles | | | | | Markers |
|---|---|---|---|---|---|---|---|---|---|---|---|---|---|---|
| 0.927 | 1.02E−07 | 27.65 | 437 | 0.037 | 0.073 | 721 | 0.001 | 0.003 | 4 | 0 | 2 | 14 | 3 | DG13S1103 |
| | | | | | | | | | | | | | | DG13S166 |
| | | | | | | | | | | | | | | D13S1287 |
| | | | | | | | | | | | | | | DG13S1061 |
| | | | | | | | | | | | | | | DG13S301 |

Length = length of haplotype in Mb.
P-val = p-value.
RR = Relative risk.
N af = Number of patients.
P al = allelic frequency of haplotype.
P ca = carrier frequency of haplotype.
N ct = number of controls.
Alleles = alleles in the haplotype.
Markers = markers in the haplotype

EXAMPLE 2

Relationship Between Polymorphism in the 5-Lipoxygenase Promoter and MI

A family of mutations in the G-C rich transcription factor binding region of the 5-LO gene has previously been identified. These mutations consist of deletion of one, deletion of two, or addition of one zinc finger (Sp1/Egr-1) binding sites in the region 176 to 147 bp upstream from the ATG translation start site where there are normally 5 Sp1 binding motifs in tandem. These naturally occurring mutations in the human 5-LO gene promoter have been shown to modify transcription factor binding and reporter gene transcription. The capacity of the mutant forms of DNA to promote transcription of CAT reporter constructs have been shown to be significantly less than that of the wild type DNA (*J. Clin. Invest.* Volume 99, Number 5, March 1997, 1130-1137). To test whether 5-LO is associated with the atherosclerotic diseases, particularly myocardial infarction (MI) in the human population, this promoter polymorphism, consisting of variable number of tandem Sp1/Egr-1 binding sites, was genotyped in 1112 MI patients, 748 patients with PAOD, and 541 stroke patients.

The results, shown in Table 16, demonstrate that the wild type allele (which represents the allele with the most active promoter and thus with the highest expression of the 5-LO mRNA; *J. Clin. Invest.* Volume 99, Number 5, March 1997, 1130-1137) is significantly associated with MI (RR=1.2, p<0.05). The results are consistent with a disease hypothesis that increased expression of the 5-LO plays a role in the pathogenesis of MI.

TABLE 16

| | N_aff | Frq_aff | N_ctrl | Frq_ctrl | Risk Ratio | P-value |
|---|---|---|---|---|---|---|
| MI patients | 1112 | 0.8701 | 734 | 0.8501 | 1.1803 | 0.048 |
| Independent | 969 | 0.8720 | 734 | 0.8501 | 1.2013 | 0.037 |
| Males | 646 | 0.8740 | 734 | 0.8501 | 1.2232 | 0.039 |
| Females | 465 | 0.8645 | 734 | 0.8501 | 1.1249 | 0.180 |
| Age of onset < 60 | 522 | 0.8745 | 734 | 0.8501 | 1.2286 | 0.046 |
| Males | 353 | 0.8768 | 734 | 0.8501 | 1.2542 | 0.053 |
| Females | 169 | 0.8698 | 734 | 0.8501 | 1.1779 | 0.202 |
| PAOD patients | 748 | 0.8763 | 734 | 0.8501 | 1.2492 | 0.022 |
| Independent | 703 | 0.8755 | 734 | 0.8501 | 1.2400 | 0.027 |
| Males | 473 | 0.8774 | 734 | 0.8501 | 1.2613 | 0.033 |
| Females | 275 | 0.8745 | 734 | 0.8501 | 1.2289 | 0.092 |
| Stroke patients | 541 | 0.8743 | 734 | 0.8501 | 1.2262 | 0.046 |
| Males | 326 | 0.8758 | 734 | 0.8501 | 1.2427 | 0.067 |

TABLE 16-continued

| | N_aff | Frq_aff | N_ctrl | Frq_ctrl | Risk Ratio | P-value |
|---|---|---|---|---|---|---|
| Females | 215 | 0.8721 | 734 | 0.8501 | 1.2019 | 0.144 |
| Cardio/Large V | 202 | 0.8861 | 734 | 0.8501 | 1.3719 | 0.038 |
| Cardioembolic | 114 | 0.8772 | 734 | 0.8501 | 1.2592 | 0.165 |
| Large Vessel | 88 | 0.8977 | 734 | 0.8501 | 1.5474 | 0.053 |
| Small Vessel | 77 | 0.8831 | 734 | 0.8501 | 1.2791 | 0.163 |
| Hemorrhagic | 27 | 0.9259 | 734 | 0.8501 | 2.2035 | 0.081 | single sided p-values: Fisher exact test.
N_aff = number of affected individuals;
Frq_aff = frequency of the wild type allele of the promoter polymorphism in the affected group;
N_ctrl = number of controls;
Frq_ctrl = frequency of the wild type allele of the promoter polymorphism in the control group;

EXAMPLE 3

Elevated LTE4 Biosynthesis in Individuals with the Flap MI-Risk Haplotype

Based on the known function of the end products of the leukotriene pathway and based on our 5-LO association data, the association of the FLAP haplotype with MI is best explained by increased expression and/or increased function of the FLAP gene. In other words, those individuals that have a "at risk" FLAP haplotype have either, or both, increased amount of FLAP, or more active FLAP. This would lead to increased production of leukotrienes in these individuals.

To demonstrate this theory, LTE4, a downstream leukotriene metabolite, was measured in patient serum samples. A quantitative determination of LTE4 in human serum was performed by liquid chromatography coupled with tandem mass spectrometry. The protocol was performed as follows:

Analytical Method

TABLE P1

| (Protocol 1): List of Abbreviations | |
|---|---|
| CAN | Acetonitrile |
| IS | Internal standard |
| LC-MS/MS | Liquid chromatography tandem mass spectrometry |
| LOQ | Limit of quantification |
| QCs | Quality controls |
| $R^2$ | Coefficient of determination |
| SS | Spiking solution |

Apparatus and Conditions

TABLE P2
Analytical apparatus and conditions

| Instruments/Conditions | Details |
|---|---|
| Analytical column | Zorbax extend $C_{18}$, 3.5 μm (50 × 2.1 mm) |
| Column temperature | Ambient |
| Pump and flow | Hewlett Packard Series 1100 Binary pump delivering 0.3 ml/min |
| Mobile phase | A: Buffer: Acetonitrile:$H_2O$ (5:95% v/v). (Containing 10 mM Ammonium Acetate and 0.1% Acetic acid at pH 4.6). B: Buffer: Acetonitrile:$H_2O$ (95:5% v/v). (Containing 10 mM Ammonium Acetate and 0.1% Acetic acid at pH 4.6). |
| Gradient | Time / % A / % B / Flow rate |
| | 0.00 / 30 / 70 / 0.3 ml/min |
| | 1.00 / 30 / 70 / 0.3 ml/min |
| | 1.50 / 90 / 10 / 0.3 ml/min |
| | 6.00 / 90 / 10 / 0.3 ml/min |
| | 6.50 / 30 / 70 / 0.3 ml/min |
| | 10.00 / 30 / 70 / 0.3 ml/min |
| Sample injection | HTC PAL autosampler 10 μl onto the HPLC column |
| Mass Spectrometric system | Quattro Ultima ™ Tandem MS/MS, Micromass. England. |
| Recording and integration | Mass Lynx, version 3.5. All chromatograms and reports are printed out in hardcopy and stored in electronic form on the workstation hard disk drive. Recording time was 10 min. |
| Retentions times | $LTE_4$~3.05 min. $LTE_4$-$d_3$~3.05 min. |
| Ionization mode | Electrospray atmospheric pressure in negative ion mode |
| Scan mode | Multiple reaction monitoring (MRM) |
| | Compound / Parent ion / Daughter ion |
| | $LTE_4$ / 438.2 / 333.2 |
| | $LTE_4$-$d_3$ / 441.2 / 336.2 |

Other Instruments

TABLE P3
The apparatus used for sample treatment and measurements

| Apparatus | Brand | Type |
|---|---|---|
| Pipette | Eppendorf | Edos 5221 |
| Pipette | Labsystems | Finnpipette 200 μl |
| Centrifuge | Eppendorf | 5417C |
| Evaporation unit | Porvair | Ultravap |
| Vibrofix | Ika-Werk | VF-1 |
| | Thermolyne | Maxi-mix III ™, 65800 |
| Balance | Sartorius | LA 120 S |
| Ultra sonic bath | Cole Parmer | 8891 |

Materials

TABLE P4
Reagents for sample treatment and measurements

| Reagent | Manufacturer | Quality | Art no. |
|---|---|---|---|
| Acetonitrile (ACN) | Rathburn | HPLC grade | RH 1016 |
| Methanol | Rathburn | HPLC grade | RH 1019 |
| Ammonium acetate | Merck | Pro analysis | 1116 |

TABLE P5
Reference substances

| | Details | Reference |
|---|---|---|
| Reference standards | Leukotrine $E_4$ from Cayman Chemical, MI, USA | 20410 |
| Internal standards | Leukotriene $E_4$-20, 20,20-$d_3$ from Biomol, PA, USA | S10120 |

Stock Solutions

A stock solution of $LTE_4$ was prepared by the supplier at a concentration of 100 μg/ml in methanol. The stock solution was diluted to a concentration of 20 μg/ml in methanol and this working solution (WS-1) was kept refrigerated at 2-8° C.

An internal standard stock solution ($LTE_4$-$d_3$) was prepared by the supplier at concentration of 49.5 μg/ml. The stock solution was diluted to a concentration of 1 μg/ml in methanol and this working solution was kept refrigerated at 2-8° C.

Preparation of Spiking Solutions, Calibration Standards and Quality Control Samples Spiking solutions (SS) in the concentration range of 1 ng/ml to 10000 ng/ml were prepared by dilution of the working Solution.

The following spiking solutions were prepared:

TABLE P6

Spiking solutions for calibration standards

| SS | Concentration (ng/ml) | Preparation |
|---|---|---|
| 1 | 10000 | 500 µl of WS-1 (20 µg/ml) diluted to 1.0 ml with 70% MeOH/water |
| 2 | 1000 | 100 µl of SS-1 was diluted to 1.0 ml with 70% MeOH/water |
| 3 | 100 | 100 µl of SS-2 was diluted to 1.0 ml with 70% MeOH/water |
| 4 | 30 | 300 µl of SS-3 was diluted to 1.0 ml with 70% MeOH/water |
| 5 | 20 | 200 µl of SS-3 was diluted to 1.0 ml with 70% MeOH/water |
| 6 | 16 | 160 µl of SS-3 was diluted to 1.0 ml with 70% MeOH/water |
| 7 | 12 | 120 µl of SS-3 was diluted to 1.0 ml with 70% MeOH/water |
| 8 | 8.0 | 400 µl of SS-5 diluted to 1.0 ml with 70% MeOH/water |
| 9 | 4.0 | 200 µl of SS-5 diluted to 1.0 ml with 70% MeOH/water |
| 10 | 2.0 | 100 µl of SS-5 diluted to 1.0 ml with 70% MeOH/water |
| 11 | 1.4 | 175 µl of SS-8 was diluted to 1.0 ml with 70% MeOH/water |
| 12 | 1.0 | 125 µl of SS-8 was diluted to 1.0 ml with 70% MeOH/water |

TABLE P7

Spiking solutions for quality controls

| SS | Concentration (ng/ml) | Preparation |
|---|---|---|
| 13 | 14 | 140 µl of SS-3 was diluted to 1.0 ml with 70% MeOH/water |
| 14 | 6.0 | 300 µl of SS-5 was diluted to 1.0 ml with 70% MeOH/water |
| 15 | 2.4 | 120 µl of SS-5 was diluted to 1.0 ml with 70% MeOH/water |

After preparation, spiking solutions for calibration standards and quality controls were kept refrigerated at 2-8° C.

Preparation of Calibration Standards and Quality Controls

Fresh calibration standards and quality controls (QCs) were prepared each day by spiking blank plasma as described in Tables P8 and P9, respectively.

TABLE P8

Preparation of calibration standards

| Concentration (ng/ml) | SS (µl) | Blank Plasma |
|---|---|---|
| 1500 | 20 µl of the SS-4 (30 ng/ml) | 380 µl |
| 1000 | 20 µl of the SS-5 (20 ng/ml) | 380 µl |
| 800 | 20 µl of the SS-6 (16 ng/ml) | 380 µl |
| 600 | 20 µl of the SS-7 (12 ng/ml) | 380 µl |
| 400 | 20 µl of the SS-8 (8 ng/ml) | 380 µl |
| 200 | 20 µl of the SS-9 (4.0 ng/ml) | 380 µl |
| 100 | 20 µl of the SS-10 (2.0 ng/ml) | 380 µl |
| 70 | 20 µl of the SS-11 (1.4 ng/ml) | 380 µl |
| 50 | 20 µl of the SS-12 (1.0 ng/ml) | 380 µl |

TABLE P9

Preparation of quality controls

| Concentration (ng/ml) | SS (µl) | Blank Plasma |
|---|---|---|
| 800 | 20 µl of the SS-13 (14 ng/ml) | 380 µl |
| 40 | 20 µl of the SS-14 (6.0 ng/ml) | 380 µl |
| 8.0 | 20 µl of the SS-15 (2.4 ng/ml) | 380 µl |

Sample Preparation

Aliquots of 400 µl of each study sample, calibration standards, QC samples and control blank are pipetted into an eppendorf vial. All samples apart from blank are then spiked with 20 µl of internal standard working solution and the samples are then vortex-mixed for few seconds. The pH of the plasma samples is adjusted to pH 4.5 using 60 µl of 10% acetic acid and centrifuged for 10 min. at 4100 rpm immediately before the extraction. The solid phase extraction 96-well plate is conditioned with 1 ml methanol and 1 ml water. Then 400 µl of the plasma samples are loaded on the plate. Vacuum is applied, followed by drying the disk for 1 min. After being washed with 2 ml water and 1 ml 30% methanol in 2% acetic acid. Next the plate is eluted with 0.6 ml methanol. The plate is then dried for few minutes. The methanol eluate is evaporated almost to dryness under a stream of nitrogen at 45° C. The residue is reconstituted in 30 µl mobile phase and vortex-mixed for few min. Subsequently, the solutions are centrifuged for 10 min at 10.000 rpm. and 10 µl are injected by the autosampler into the LC-MS/MS system for quantification.

Performance of Measurements

The samples will be prepared and measured in batches and a typical batch will consist of:

One set of calibration standards, one extra lowest calibration standard and one blank. Samples collected from a 16 individuals and one set of control samples ($C_L$, $C_M$, $C_H$) Samples collected from a 17 individuals and one set of control samples ($C_L$, $C_M$, $C_H$)

Quantitative Determination of Analyte in Plasma Samples

The standard curve is calculated from the peak area ratios ANALYTE/INTERNAL STANDARD of the calibration standards and their nominal ANALYTE concentrations. The unknown samples for $LTE_4$ were calculated from a quadratic regression equation where a weighted curve, $1/X^2$, is used. The measured peak area of the samples was converted into pictogram of ANALYTE per milliliter (pg/ml) of plasma according to the calculated equation for the standard curve.

The calculation of the regression for the standard curve and the calculations of the concentration of the unknown samples and the control samples are performed with MassLynx Software.

Acceptance Criteria

Calibration Standards

The coefficient of determination ($R^2$) for the calibration curve must exceed 0.98.

The calibration curve included the concentration range from 50 pg/ml-1500 pg/ml.

Concentration of the calibration standards must be within ±25% of their nominal value when recalculated from the regression equation. Calibration standards that fail these criteria (at most 3 in each run) are rejected and the calibration performed again with the remaining standards. If the standard curve is not accepted, the samples must be reanalyzed.

Control Samples

At least two thirds of the analysed quality controls must be within ±25% of their nominal value when calculated from regression equation. If more than a third of the controls fail, the samples must be reanalyzed.

Results

Table 17 (below) shows that the female MI "at risk" haplotype was more associated with female MI patients who have high LTE4 levels (top 50th percentile), than with female MI patients who have low levels of LTE4 (bottom 50th percentile).

In addition, haplotype analysis, comparing female MI patients with high levels of LTE4 with female patients with low levels, showed that those with high levels had increased prevalence of the "at risk" haplotype by 1.6 fold (see Table 18). Although the association did not rise to the level of statistical significance, the results show clearly that the "at risk" haplotypes are enriched in the MI patient group that has high levels of LTE4. The carrier frequency of the "at risk" haplotypes are 12% and 20%, respectively, in the whole female MI group, but go up to 15% and 24%, respectively, in the female MI group that has high levels of LTE4. Correspondingly, the carrier frequency of the "at risk" haplotypes decrease to 8% and 18%, respectively, in the group of female MI that has low levels of LTE4 (Note carrier frequencies are twice the disease allele frequency times 1 minus the disease allele frequency plus the square of the disease allele frequency).

Note that LTE4 may simply reflect the leukotriene synthesis rate of the leukotriene synthetic pathway upstream of the key leukotriene metabolite involved in MI risk. For example, leukotriene B4 is probably more likely than leukotriene E4 to be involved in the inflammatory aspects of MI plaques but since B4 has a short half life, it is difficult to measure reliably in serum samples, while E4 has long term stability.

TABLE 17

Association of the at risk haplotypes for female MI, with female MI who also have high levels of LTE4 (>50 pg/ml (roughly the upper 50th percentile).

| | SG13S418 | SG13S420 | DG13S166 | SG13S114 | SG13S88 | SG13S184 | D13S1238 |
|---|---|---|---|---|---|---|---|
| High LTE4 | C | T | 0 | T | T | G | −2 |
| | C | T | 0 | | | G | −2 |
| Low LTE4 | C | T | 0 | T | T | G | −2 |
| | C | T | 0 | | | G | −2 |

| | p_val | N_aff | aff.frq | N_ctrl | ctrl.frq | rel_risk | PAR | info |
|---|---|---|---|---|---|---|---|---|
| High LTE4 | 3.72E−06 | 221 | 0.075 | 809 | 0.014 | 5.51 | 0.115 | 0.565 |
| | 2.30E−05 | 220 | 0.122 | 809 | 0.046 | 2.89 | 0.154 | 0.608 |
| Low LTE4 | 4.65E−02 | 185 | 0.040 | 809 | 0.015 | 2.67 | 0.048 | 0.511 |
| | 2.88E−02 | 182 | 0.087 | 809 | 0.048 | 1.89 | 0.08 | 0.622 |

P-val: p-value for the association.
N_aff: Number of patients used in the analysis.
Aff.frq: haplotype frequency in patients.
N_ctrl: number of controls used in the analysis.
Ctrl.frq: Haplotype frequency in controls.
Rel_risk: Relative risk of the haplotype.
PAR: population attributable risk.
Info: information content.
Less association was found between the at risk haplotype for female MI, with female MI who also have low levels of LTE4 (<50 pg/ml).

TABLE 18

Association between haplotypes that were most significantly associated with female MI, and serum LTE4 levels.

| | SG13S418 | SG13S420 | DG13S166 | SG13S114 | SG13S88 | SG13S184 | D13S1238 |
|---|---|---|---|---|---|---|---|
| High vs low LTE4 | C | T | 0 | T | T | G | −2 |
| | C | T | 0 | | | G | −2 |

| | p_val | N_aff | aff.frq | N_ctrl | ctrl.frq | rel_risk | PAR | info |
|---|---|---|---|---|---|---|---|---|
| High vs low LTE4 | 1.61E−01 | 221 | 0.084 | 185 | 0.054 | 1.61 | 0.063 | 0.689 |
| | 1.20E−01 | 220 | 0.13 | 182 | 0.088 | 1.54 | 0.089 | 0.686 |

P-val: p-value for the association.
N_aff: Number of patients used in the analysis.
Aff.frq: haplotype frequency in patients.
N_ctrl: number of controls used in the analysis.
Ctrl.frq: Haplotype frequency in controls.
Rel_risk: Relative risk of the haplotype.
PAR: population attributable risk.
Info: information content.
Here, the group of affected individuals were defined as female MI patients with high serum LTE4 (higher than 50 pg/ml) and the control group is defined as female MI patients with low serum LTE4 (below 50 pg/ml).

EXAMPLE 4

Elevated LTE4 Correlated with Elevated C-Reactive Protein (CRP)

Figure 5:
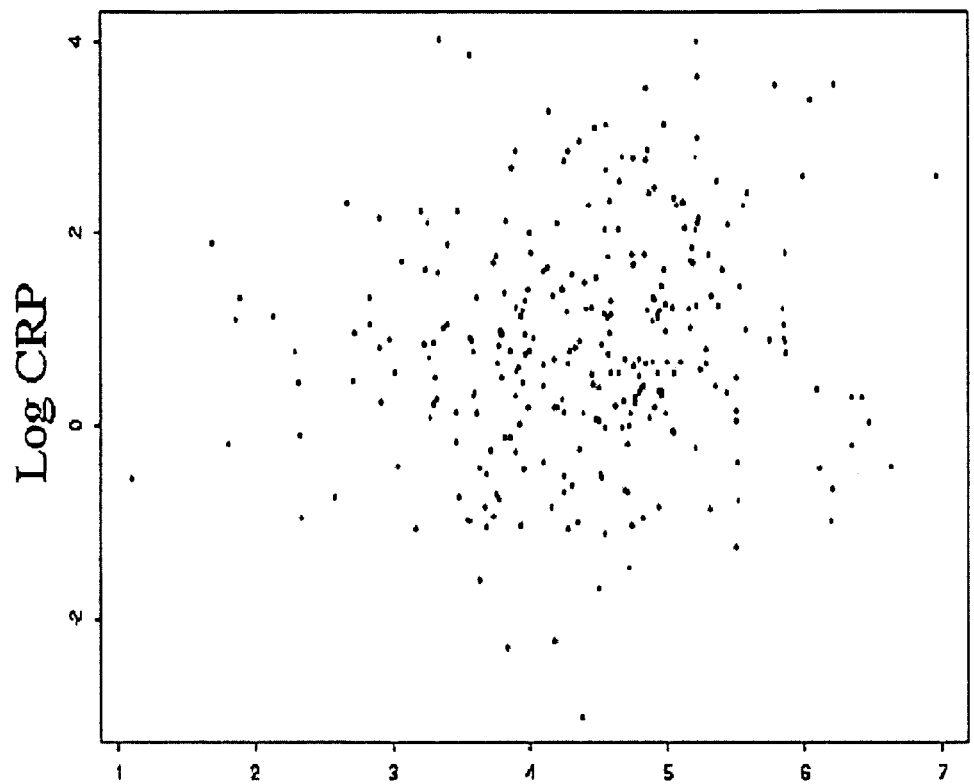
FIG. 5 shows a significant positive correlation between serum LTE4 levels and serum CRP levels.

The relationship between the increased production of leukotrienes and the inflammatory marker CRP, a well established risk factor for MI, was then explored. As shown in FIG. 5, a significant positive correlation was found between serum LTE4 levels and serum CRP levels.

EXAMPLE 5

Assessment of Level of CRP in Patients with At-Risk Haplotype

The level of CRP in female patients with female MI at-risk haplotypes was assessed, in order to assess whether there was a presence of a raised level of inflammatory marker in the presence of the female MI at-risk haplotype. Results are shown in Table 19. Although the association did not rise to the level of statistical significance, it was demonstrated that the average CRP was elevated in those patients with the at-risk haplotype versus those without it.

TABLE 19

| All female patients | | | | |
|---|---|---|---|---|
| | | no | Mean CRP | SE CRP |
| affecteds: | With haplotype. | 155 | 4.91 | 8.7 |
| | Not with haplotype. | 218 | 4.35 | 6.13 |

EXAMPLE 6

Elevated Serum LTE4 Levels in MI Patients Versus Controls

The end products of the leukotriene pathway are potent inflammatory lipid mediators that can potentially contribute to development of atherosclerosis and destabilization of atherosclerotic plaques through lipid oxidation and/or proinflammatory effects. Examples one through five show that: 1) MI correlates with genetic variation at FLAP; 2) MI correlates with high expression promoter polymorphism at 5-LO; 3) C-reactive protein levels correlate with serum leukotriene E4; and 4) Patients with MI-risk FLAP haplotypes have higher levels of serum leukotriene E4 and CRP. Based on these data, it was hypothesized that serum leukotriene E4 levels correlate with MI risk.

To test this hypothesis, LTE4, a downstream leukotriene metabolite, was measured in 488 female MI patient and 164 control serum samples. The LTE4 levels for the patients were higher than that for the controls using a one-sided Wilcoxon rank-sum test. The p-value of the difference was 0.0092, thus confirming our hypothesis. Therefore, elevated leukotriene E4 represents a risk factor for MI. Serum or plasma LTE4 levels may be used to profile the MI risk for individuals to aid in deciding which treatment and lifestyle management plan is best for primary or secondary MI prevention. In the same way other leukotriene metabolites may be used to risk profile for MI.

EXAMPLE 7

Increased LTB4 Production in Activated Neutrophils from MI Patients

A principal bioactive product of one of the two branches of the 5-LO pathway is LTB4. To determine whether the patients with past history of MI have increased activity of the 5-LO pathway compared to controls, the LTB4 production in isolated blood neutrophils was measured before and after stimulation in vitro with the calcium ionophore, ionomycin. No difference was detected between the LTB4 production in resting neutrophils from MI patients or controls (results not shown). In contrast, the LTB4 generation by neutrophils from MI patients stimulated with the ionophore was significantly greater than by neutrophils from controls at 15 and 30 minutes, respectively (FIG. 7.1). Moreover, as shown in FIG. 7.2, the observed increase in the LTB4 release was largely accounted for by male carriers of haplotype A4, whose cells produced significantly more LTB4 than cells from controls (P value=0.0042) (Table 20). As shown in Table 20, there was also a heightened LTB4 response in males who do not carry HapA but of borderline significance. This could be explained by additional variants in the FLAP gene that have not been uncovered, or alternatively in other genes belonging to the 5-LO pathway, that may account for upregulation in the LTB4 response in some of the patients without the FLAP at-risk haplotype. As shown in Table 20, differences in LTB4 response were not detected in females. However, due to a small sample size this cannot be considered conclusive. Taken together, the elevated levels of LTB4 production of stimulated neutrophils from male carriers of the at-risk haplotype suggest that the disease associated variants in the FLAP gene increase FLAP's response to factors that stimulate inflammatory cells, resulting in increased leukotriene production and increased risk for MI.

Methods

Isolation and Activation of Peripheral Blood Neutrophils 50 ml of blood were drawn into EDTA containing vacutainers from 43 MI patients and 35 age and sex matched controls. All blood was drawn at the same time in the early morning after 12 hours of fasting. The neutrophils were isolated using Ficoll-Paque PLUS (Amersham Biosciences).

Briefly, the red cell pellets from the Ficoll gradient were harvested and red blood cells subsequently lysed in 0.165 M $NH_4CL$ for 10 minutes on ice. After washing with PBS, neutrophils were counted and plated at $2\times10^6$ cells/ml in 4 ml cultures of 15% Fetal calf serum (FCS) (GIBCO BRL) in RPMI-1640 (GIBCO BRL). The cells were then stimulated with maximum effective concentration of ionomycin (1 µM). At 0, 15, 30, 60 minutes post ionomycin addition 600 µl of culture medium was aspirated and stored at −80 C for the measurement of LTB4 release as described below. The cells were maintained at 37° C. in a humidified atmosphere of 5% $CO_2$/95% air. All samples were treated with indomethasine (1 µM) to block the cyclooxygenase enzyme.

Ionomycin-induced Release of LTB4 in Neutrophils

LTB4 Immunoassay (R&D systems) was used to quantitate LTB4 concentration in supernatant from cultured ionomycin stimulated neutrophils. The assay used is based on the competitive binding technique in which LTB4 present in the testing samples (200 µl) competes with a fixed amount of alkaline phosphatase-labelled LTB4 for sites on a rabbit polyclonal antibody. During the incubation, the polyclonal Ab becomes bound to a goat anti-rabbit Ab coated onto the microplates. Following a wash to remove excess conjugate and unbound sample, a substrate solution is added to the wells to determine the bound enzyme activity. The color development is stopped and the absorbance is read at 405 nm. The intensity of the color is inversely proportional to the concentration of LTB4 in the sample. Each LTB4 measurement using the LTB4 Immunoassay, was done in duplicate.

TABLE 20

LTB4 levels after ionomycin stimulation of isolated neutrophils[a]

| Phenotype (n) | After 15 Minutes | | After 30 Minutes | |
|---|---|---|---|---|
| | Mean (SD) | P value | Mean (SD) | P value |
| Controls (35) | 4.53 (1.00) | | 4.67 (0.88) | |
| Males (18) | 4.61 (1.10) | | 4.68 (1.07) | |
| Females (17) | 4.51 (0.88) | | 4.67 (0.62) | |
| MI (41) | 5.18 (1.09) | 0.011 | 5.24 (1.06) | 0.016 |
| Carriers(16) | 5.26 (1.09) | 0.027 | 5.27 (1.09) | 0.051 |
| Non-carriers (24) | 5.12 (1.08) | 0.040 | 5.22 (1.03) | 0.035 |
| MI males (28) | 5.37 (1.10) | 0.0033 | 5.38 (1.09) | 0.0076 |
| Carriers(10) | 5.66 (1.04) | 0.0042 | 5.58 (1.12) | 0.013 |
| Non-carriers (18) | 5.20 (1.09) | 0.039 | 5.26 (1.05) | 0.041 |
| MI females (13) | 4.78 (0.95) | 0.46 | 4.95 (0.92) | 0.36 |
| Carriers(6) | 4.59 (0.80) | 0.90 | 4.75 (0.82) | 0.85 |
| Non-carriers (7) | 4.94 (1.04) | 0.34 | 5.12 (0.96) | 0.25 |

[a]Mean ± SD of log-transformed values of LTB4 levels of ionomycin-stimulated neutrophils from MI patients and controls. Results are shown for two time points: 15 and 30 minutes. The results for males and females and for MI male and female carriers and non-carriers of the at-risk haplotype HapA are shown separately. Two-sided p values corresponding to a standard two-sample test of the difference in the mean values between the MI patients, their various sub-cohorts and the controls are shown.

EXAMPLE 8

Haplotypes Associated with MI Also Confer Risk of Stroke and PAOD

Because stroke and PAOD are diseases that are closely related to MI (all occur on the basis of atherosclerosis), it was examined whether the SNP haplotype in the FLAP gene that confers risk to MI also conferred risk of stroke and/or PAOD. The 'at risk' haplotype (A4 haplotype) can be defined by the following 4 SNPs: SG13S25 with allele G, SG13S114 with allele T, SG13S89 with allele G, and SG13S32 with allele A.

Table 21 shows that the haplotype A4 increases the risk of having a stroke to a similar extent as it increases the risk of having an MI. The 'at risk' haplotype is carried by 28% of stroke patients and 17% of controls, meaning that the relative risk of having stroke for the carriers of this haplotype is 1.7 (p-value=5.8 $10^{-06}$). Although not as significant, the 'at risk' haplotype also confers risk of having PAOD.

TABLE 21

| | p-val | r | #aff | aff.frq. | #con | con.frq. | Info | SG13S25 |
|---|---|---|---|---|---|---|---|---|
| MI haplotypes | | | | | | | | |
| All MI patients | | | | | | | | |
| A4 | 5.3E−07 | 1.80 | 1407 | 0.16 | 614 | 0.09 | 0.82 | G |
| B4 | 1.0E−04 | 1.87 | 1388 | 0.10 | 612 | 0.06 | 0.67 | G |
| Males MI | | | | | | | | |
| A4 | 2.5E−08 | 2.00 | 864 | 0.17 | 614 | 0.09 | 0.82 | G |
| B4 | 1.1E−05 | 2.12 | 852 | 0.11 | 612 | 0.06 | 0.67 | G |
| Females MI | | | | | | | | |
| A4 | 1.9E−02 | 1.44 | 543 | 0.13 | 614 | 0.09 | 0.73 | G |
| B4 | 7.9E−02 | 1.45 | 536 | 0.08 | 612 | 0.06 | 0.60 | G |
| Replication in stroke | | | | | | | | |
| All stroke patients | | | | | | | | |
| A4 | 5.8E−06 | 1.73 | 1238 | 0.15 | 614 | 0.09 | 0.80 | G |
| B4 | 2.3E−04 | 1.83 | 1000 | 0.10 | 612 | 0.06 | 0.71 | G |
| Males stroke | | | | | | | | |
| A4 | 1.1E−06 | 1.91 | 710 | 0.17 | 614 | 0.09 | 0.79 | G |
| B4 | 3.1E−05 | 2.11 | 574 | 0.11 | 612 | 0.06 | 0.72 | G |
| Females stroke | | | | | | | | |
| A4 | 9.9E−03 | 1.49 | 528 | 0.13 | 614 | 0.10 | 0.74 | G |
| B4 | 6.3E−02 | 1.47 | 426 | 0.08 | 612 | 0.06 | 0.70 | G |
| All stroke excluding MI | 8.4E−05 | 1.65 | 1054 | 0.15 | 614 | 0.09 | 0.78 | G |
| Males stroke excluding MI | 6.4E−05 | 1.78 | 573 | 0.16 | 614 | 0.09 | 0.75 | G |
| Females stroke excluding MI | 1.2E−02 | 1.49 | 481 | 0.14 | 614 | 0.10 | 0.72 | G |
| Cardioembolic stroke | 6.6E−04 | 1.87 | 248 | 0.16 | 614 | 0.10 | 0.74 | G |
| Cardioembolic stroke excluding MI | 3.8E−02 | 1.56 | 191 | 0.14 | 614 | 0.10 | 0.70 | G |
| Large vessel stroke | 8.0E−02 | 1.47 | 150 | 0.13 | 614 | 0.09 | 0.83 | G |
| Large vessel stroke excluding MI | 2.9E−01 | 1.31 | 114 | 0.12 | 614 | 0.09 | 0.80 | G |
| Small vessel stroke | 7.2E−04 | 2.05 | 166 | 0.18 | 614 | 0.09 | 0.71 | G |
| Small vessel stroke excluding MI | 1.0E−04 | 2.31 | 152 | 0.20 | 614 | 0.10 | 0.71 | G |
| Hemorrhagic stroke | 4.4E−02 | 1.73 | 97 | 0.15 | 614 | 0.09 | 0.72 | G |
| Hemorrhagic stroke excluding MI | 3.9E−02 | 1.78 | 92 | 0.16 | 614 | 0.09 | 0.71 | G |
| Unknown cause stroke | 1.3E−04 | 1.88 | 335 | 0.16 | 614 | 0.09 | 0.75 | G |
| Unknown cause stroke excluding MI | 6.5E−04 | 1.82 | 297 | 0.16 | 614 | 0.09 | 0.72 | G |
| MI and stroke together | | | | | | | | |
| All patients | | | | | | | | |
| Best haplo A4 | 4.1E−07 | 1.75 | 2659 | 0.15 | 614 | 0.09 | 0.82 | G |
| B4 | 4.1E−05 | 1.85 | 2205 | 0.10 | 612 | 0.06 | 0.70 | G |

TABLE 21-continued

| | | | | | | | | |
|---|---|---|---|---|---|---|---|---|
| Males | | | | | | | | |
| A4 | 1.4E−08 | 1.93 | 1437 | 0.17 | 614 | 0.09 | 0.82 | G |
| B4 | 2.0E−06 | 2.11 | 1290 | 0.11 | 612 | 0.06 | 0.70 | G |
| Females | | | | | | | | |
| A4 | 3.6E−03 | 1.47 | 1024 | 0.13 | 614 | 0.09 | 0.77 | G |
| B4 | 2.8E−02 | 1.48 | 915 | 0.08 | 612 | 0.06 | 0.66 | G |
| Patients with both MI and stroke | | | | | | | | |
| A4 | 6.1E−05 | 2.10 | 184 | 0.18 | 614 | 0.09 | 0.86 | G |
| Replication in PAOD | | | | | | | | |
| All PAOD patients | 3.6E−02 | 1.31 | 920 | 0.12 | 614 | 0.10 | 0.84 | G |
| Males PAOD | 1.8E−02 | 1.40 | 580 | 0.13 | 614 | 0.10 | 0.84 | G |
| Females PAOD | 3.7E−01 | 1.17 | 340 | 0.11 | 614 | 0.10 | 0.83 | G |
| All PAOD excluding MI | 1.1E−01 | 1.24 | 750 | 0.12 | 614 | 0.10 | 0.83 | G |
| Males PAOD excluding MI | 8.3E−02 | 1.30 | 461 | 0.12 | 614 | 0.10 | 0.83 | G |
| Males PAOD excluding MI and stroke | 8.7E−02 | 1.32 | 388 | 0.12 | 614 | 0.10 | 0.83 | G |

| | SG13S106 | SG13S114 | SG13S89 | SG13S30 | SG13S32 | SG13S42 |
|---|---|---|---|---|---|---|
| MI haplotypes All MI patients | | | | | | |
| A4 | | T | G | | A | |
| B4 | G | | | G | | A |
| Males MI | | | | | | |
| A4 | | T | G | | A | |
| B4 | G | | | G | | A |
| Females MI | | | | | | |
| A4 | | T | G | | A | |
| B4 | G | | | G | | A |
| Replication in stroke All stroke patients | | | | | | |
| A4 | | T | G | | A | |
| B4 | G | | | G | | A |
| Males stroke | | | | | | |
| A4 | | T | G | | A | |
| B4 | G | | | G | | A |
| Females stroke | | | | | | |
| A4 | | T | G | | A | |
| B4 | G | | | G | | A |
| All stroke excluding MI | | T | G | | A | |
| Males stroke excluding MI | | T | G | | A | |
| Females stroke excluding MI | | T | G | | A | |
| Cardioembolic stroke | | T | G | | A | |
| Cardioembolic stroke excluding MI | | T | G | | A | |
| Large vessel stroke | | T | G | | A | |
| Large vessel stroke excluding MI | | T | G | | A | |
| Small vessel stroke | | T | G | | A | |
| Small vessel stroke excluding MI | | T | G | | A | |
| Hemorrhagic stroke | | T | G | | A | |
| Hemorrhagic stroke excluding MI | | T | G | | A | |
| Unknown cause stroke | | T | G | | A | |
| Unknown cause stroke excluding MI | | T | G | | A | |
| MI and stroke together All patients | | | | | | |
| Best haplo A4 | | T | G | | A | |
| B4 | G | | | G | | A |
| Males | | | | | | |
| A4 | | T | G | | A | |
| B4 | G | | | G | | A |
| Females | | | | | | |
| A4 | | T | G | | A | |
| B4 | G | | | G | | A |

TABLE 21-continued

| Patients with both MI and stroke | | | |
|---|---|---|---|
| A4 | T | G | A |
| Replication in PAOD | | | |
| All PAOD patients | T | G | A |
| Males PAOD | T | G | A |
| Females PAOD | T | G | A |
| All PAOD excluding MI | T | G | A |
| Males PAOD excluding MI | T | G | A |
| Males PAOD excluding MI and stroke | T | G | A |

The patient cohorts used in the association analysis shown in Table 21 may include first and second degree relatives.

Table 21, discussed above, shows the results of the haplotype A4 association study using 779 MI patients, 702 stroke patients, 577 PAOD patients and 628 controls. First and second degree relatives were excluded from the patient cohorts. All known cases of MI were removed from the stroke and PAOD cohorts before testing for association. A significant association of the A4 haplotype to stroke was observed, with a relative risk of 1.67 (P value=0.000095). In addition, it was determined whether the A4 haplotype was primarily associated with a particular sub-phenotype of stroke, and found that both ischemic and hemorrhagic stroke were significantly associated with the A4 haplotype (Table 22).

TABLE 22

Association of the A4 haplotype to subgroups of stroke

| Phenotype (n) | Pat. Frq. | RR | PAR | P-value |
|---|---|---|---|---|
| Stroke[a] (702) | 0.149 | 1.67 | 0.116 | 0.000095 |
| Ischemic (484) | 0.148 | 1.65 | 0.113 | 0.00053 |
| TIA (148) | 0.137 | 1.51 | 0.090 | 0.058 |
| Hemorrhagic (68) | 0.167 | 1.91 | 0.153 | 0.024 |

[a]Excluding known cases of MI.

Finally, the A4 haplotype was less significantly associated with PAOD (Table 21). It should be noted that similar to the stronger association of the A4 haplotype to male MI compared to female MI, it also shows stronger association to male stroke and PAOD (Table 21).

Study Population

The stroke and PAOD cohorts used in this study have previously been described (Gretarsdottir, S. et al. *Nat Genet* 35, 131-8 (2003); Gretarsdottir, S. et al., *Am J Hum Genet* 70, 593-603 (2002); Gudmundsson, G. et al., *Am J Hum Genet* 70, 586-92 (2002)). For the stroke linkage analysis, genotypes from 342 male patients with ischemic stroke or TIA that were linked to at least one other male patient within and including 6 meioses in 164 families were used. For the association studies 702 patients with all forms of stroke (n=329 females and n=373 males) and 577 PAOD patients (n=221 females and n=356 males) were analysed. Patients with stroke or PAOD that also had MI were excluded. Controls used for the stroke and PAOD association studies were the same as used in the MI SNP association study (n=628).

The study was approved by the Data Protection Commission of Iceland and the National Bioethics Committee of Iceland. Informed consent was obtained from all study participants. Personal identifiers associated with medical information and blood samples were encrypted with a third party encryption system as previously described (Gulcher, J. R., Kristjansson, K., Gudbjartsson, H. & Stefansson, K., *Eur J Hum Genet* 8, 739-42 (2000)).

Figure 10:
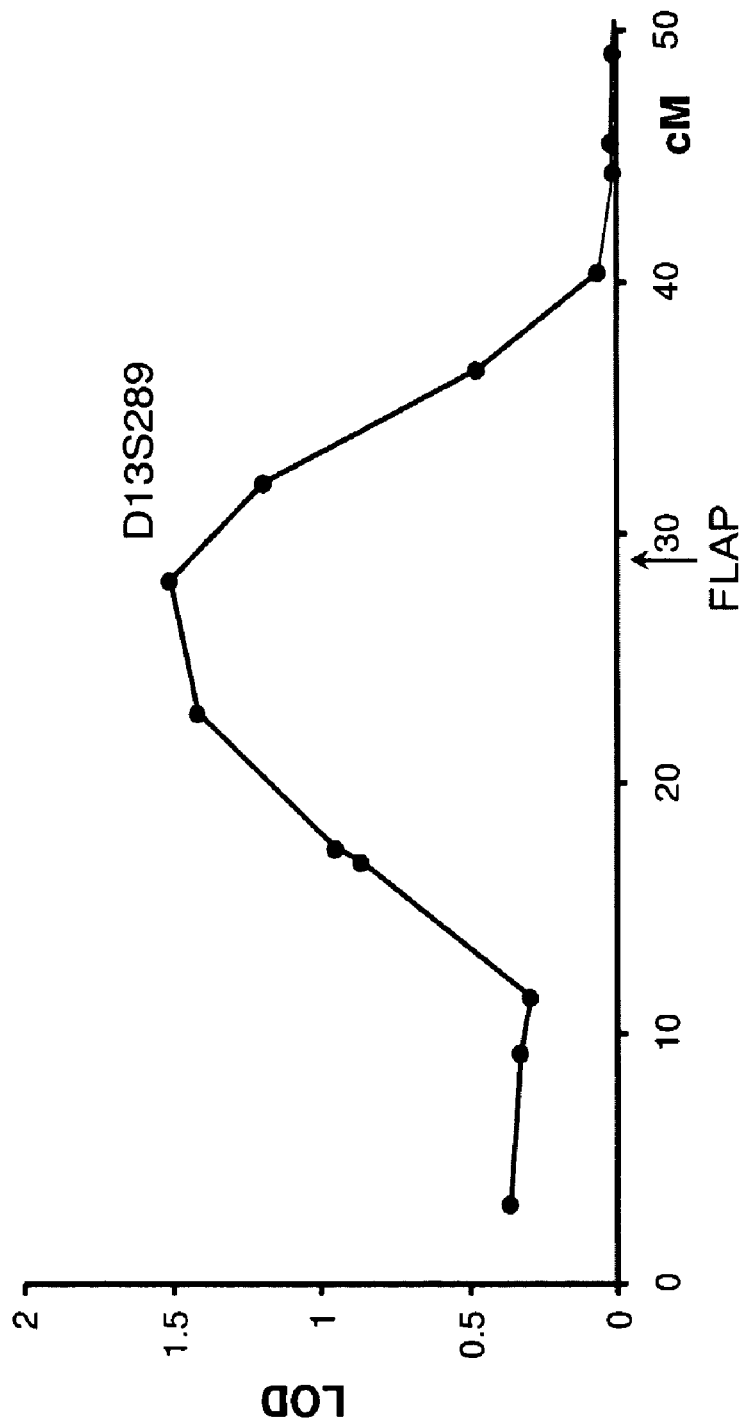
FIG. 10 shows a linkage scan using framework microsatellite markers on chromosome 13 for male patients with ischemic stroke or TIA (n=342 in 164 families at 6 meiosis). The LOD score is expressed on the y axis and the distance from the pter in Kosambi cM on the x axis.

In addition, in an independent linkage study of male patients with ischemic stroke or transient ischemic attack, linkage to the same locus was observed with a LOD score of 1.51 at the same peak marker (FIG. 10), further suggested that a cardiovascular susceptibility factor might reside at this locus.

EXAMPLE 9

Haplotype Association to Flap in a British Cohort

In an independent study, it was determined whether variants in the FLAP gene also have impact on risk of MI in a population outside Iceland. The four SNPs, defining the A4 haplotype, were typed in a cohort of 750 patients from the United Kingdom who had sporadic MI, and in 728 British population controls. The patients and controls come from 3 separate study cohorts recruited in Leicester and Sheffield. No significant differences were found in the frequency of the haplotype between patients and controls (16.9% versus 15.3%, respectively). However, when an additional 9 SNPs, distributed across the FLAP gene, were typed in the British cohort and searched for other haplotypes that might be associated with MI, two SNPs showed association to MI with a nominally significant P value (data not shown). Moreover, three and four SNP haplotype combinations increased the risk of MI in the British cohort further and the most significant association was observed for a four SNP haplotype with a nominal P value=0.00037 (Table 23).

TABLE 23

Association of the HapB haplotype to British MI patients

| Phenotype (n) | Frq. Pat. | RR | PAR | P-value | P-value[a] |
|---|---|---|---|---|---|
| MI (750) | 0.075 | 1.95 | 0.072 | 0.00037 | 0.046 |
| Males (546) | 0.075 | 1.97 | 0.072 | 0.00093 | ND |
| Females (204) | 0.073 | 1.90 | 0.068 | 0.021 | ND |

[a]P value adjusted for the number of haplotypes tested using 1,000 randomization tests.
Shown are the results for HapB that shows the strongest association in British MI cohort. HapB is defined by the following SNPs: SG13S377, SG13S114, SG13S41 and SG13S35 (that have the following alleles A, A, A and G, respectively. In all three phenotypes shown the same set of n = 728 British controls is used and the frequency of HapB in the control cohort is 0.040.
Number of patients (n), haplotype frequency in patients (Frq. pat.), relative risk (RR) and population attributed risk (PAR).

This was called haplotype HapB. The haplotype frequency of HapB is 7.5% in the MI patient cohort (carrier frequency 14.4%), compared to 4.0% (carrier frequency 7.8%) in controls, conferring a relative risk of 1.95 (Table 23). This haplotype remained significant after adjusting for all haplotypes tested, using 1000 randomisation steps, with an adjusted P value=0.046. No other SNP haplotype had an adjusted P value less than 0.05. The two at-risk haplotypes A4 and HapB appear to be mutually exclusive with no instance where the same chromosome carries both haplotypes.

British Study Population

The method of recruitment of 3 separate cohorts of British subjects has been described previously (Steeds, R., Adams, M., Smith, P., Channer, K. & Samani, N. J., *Thromb Haemost* 79, 980-4 (1998); Brouilette, S., Singh, R. K., Thompson, J. R., Goodall, A. H. & Samani, N. J., *Arterioscler Thromb Vasc Biol* 23, 842-6 (2003)). In brief, in the first two cohorts a total of 547 patients included those who were admitted to the coronary care units (CCU) of the Leicester Royal Infirmary, Leicester (July 1993-April 1994) and the Royal Hallamshire Hospital, Sheffield (November 1995-March 1997) and satisfied the World Health Organisation criteria for acute MI in terms of symptoms, elevations in cardiac enzymes or electrocardiographic changes (Nomenclature and criteria for diagnosis of ischemic heart disease. Report of the Joint International Society and Federation of Cardiology/World Health Organization task force on standardization of clinical nomenclature. *Circulation* 59, 607-9 (1979)). A total of 530 control subjects were recruited in each hospital from adult visitors to patients with non-cardiovascular disease on general medical, surgical, orthopaedic and obstetric wards to provide subjects likely to be representative of the source population from which the subjects originated. Subjects who reported a history of coronary heart disease were excluded.

In the third cohort, 203 subjects were recruited retrospectively from the registries of 3 coronary care units in Leicester. All had suffered an MI according to WHO criteria before the age of 50 years. At the time of participation, patients were at least 3 months from the acute event. The control cohort comprised 180 subjects with no personal or family history of premature coronary heart disease, matched for age, sex, and current smoking status with the cases. Control subjects were recruited from 3 primary care practices located within the same geographical area. In all cohorts subjects were white of Northern European origin.

Discussion

These results show that variants of the gene encoding FLAP associate with increased risk of MI and stroke. In the Icelandic cohort, a haplotype that spans the FLAP gene is carried by 30% of all MI patients and almost doubles the risk of MI. These findings were subsequently replicated in an independent cohort of stroke patients. In addition, another haplotype that spans the FLAP gene is associated with MI in a British cohort. Suggestive linkage to chromosome 13q12-13 was observed with several different phenotypes, including female MI, early onset MI of both sexes, and ischemic stroke or TIA in males. However, surprisingly, the strongest haplotype association was observed to males with MI or stroke. Therefore, there may be other variants or haplotypes within the FLAP gene, or in other genes within the linkage region, that also may confer risk to these cardiovascular phenotypes.

These data also show that the at-risk haplotype of the FLAP gene has increased frequency in all subgroups of stroke, including ischemic, TIA, and hemorrhagic stroke. Of interest is that the A4 haplotype confers significantly higher risk of MI and stroke than it does of PAOD. This could be explained by differences in the pathogenesis of these diseases. Unlike PAOD patients who have ischemic legs because of atherosclerotic lesions that are responsible for gradually diminishing blood flow to the legs, the MI and stroke patients have suffered acute events, with disruption of the vessel wall suddenly decreasing blood flow to regions of the heart and the brain.

Association was not found between the A4 haplotype and MI in a British cohort. However, significant association to MI was found with a different variant spanning the FLAP gene. The fact that different haplotypes of the gene are found conferring risk to MI in a second population is not surprising. A common disease like MI associates with many different mutations or sequence variations, and the frequencies of these disease associated variants may differ between populations. Furthermore, the same mutations may be seen arising on different haplotypic backgrounds.

Summary

In summary, it has been found that: MI correlates with genetic variation at FLAP; MI correlates with high expression promoter polymorphism at 5-LO; patients with female MI at-risk FLAP haplotypes have higher levels of serum LTE4; LTE4 levels correlate with CRP levels in serum; and patients with MI at-risk FLAP haplotypes have elevated CRP. In addition, we have shown that isolated neutrophils from MI patients, produce more LTB4 when stimulated with ionomycin compared to controls. Taken together, these results show that increased leukotriene synthesis is a risk factor for MI, and that this risk is driven in part by variants in FLAP and 5-LO genes and are captured in part by measurement of levels of serum LTE4 and CRP. Furthermore, the SNP haplotype in the FLAP gene that confers risk to MI also confers risk of stroke and/or PAOD.

Markers Utilized Herein

TABLE 24

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S2393 | CCTTTGCTTTGTTCCTATTTCTTT (SEQ ID NO. 4) | TCCCATTGCCCAGAGTTAAT (SEQ ID NO. 5) | 22831401 | 22831787 |
| DG13S2070 | TCCTCATGTCTTCACCTAGAAGC (SEQ ID NO. 6) | CCACTCATGAGGGAGCTGTT (SEQ ID NO. 7) | 23020439 | 23020651 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S2071 | TGTCACAGGCACACACTCTCT (SEQ ID NO. 8) | GAGTATGGCTGCTGCTCCTC (SEQ ID NO. 9) | 23066973 | 23067076 |
| DG13S2072 | ATGGCTCACACTGGCCTAAA (SEQ ID NO. 10) | TGAACAGACCAATAATAGTGCAG (SEQ ID NO. 11) | 23136964 | 23137114 |
| DG13S2078 | AAGCCACCCTTTAAACAGCA (SEQ ID NO. 12) | GCTGAGGAAGCAACTCCACT (SEQ ID NO. 13) | 23591927 | 23592081 |
| DG13S2079 | GCTCTGAATTCCCTGGCATA (SEQ ID NO. 14) | TTAGCCCTAGTCCCACTCTCC (SEQ ID NO. 15) | 23646974 | 23647183 |
| DG13S2082 | CAAGAGGCCTGCATAAGGAA (SEQ ID NO. 16) | AGATTGCCGGTGGCTTAAAT (SEQ ID NO. 17) | 23807898 | 23808174 |
| DG13S2083 | TGTCTGTTCCCGTCTGTCTG (SEQ ID NO. 18) | TTCATCCTCTGCCAAATTCC (SEQ ID NO. 19) | 23882291 | 23882532 |
| DG13S2086 | GGCATGTATTCACTGCCTGA (SEQ ID NO. 20) | AAACCCATTCTTCTTCCTCTTAC (SEQ ID NO. 21) | 24069346 | 24069771 |
| DG13S2089 | TATGTGTTCAGCCCAGACCTC (SEQ ID NO. 22) | CCCTGCCATGTGCATTTAC (SEQ ID NO. 23) | 24274920 | 24275129 |
| DG13S44 | CATTTCGGAAGGCAAAGAAA (SEQ ID NO. 24) | TTGCAATGAGGAATGAAGCA (SEQ ID NO. 25) | 24413148 | 24413382 |
| DG13S2095 | TCCATTATCCATCTGTTCATTCA (SEQ ID NO. 26) | GAAGAATTAATTGTAGGAGGCAAGA (SEQ ID NO. 27) | 24621830 | 24622121 |
| DG13S46 | CTGACATCACCACATTGATCG (SEQ ID NO. 28) | CATACACAGCCATGTGGAATTA (SEQ ID NO. 29) | 24652046 | 24652291 |
| DG13S2101 | ACGGTGATGACGCCTACATT (SEQ ID NO. 30) | TCACATGGACCAATTACCTAGAA (SEQ ID NO. 31) | 24863557 | 24863744 |
| D13S1254 | AAAATTACTTCATCTTGACGATAACA (SEQ ID NO. 32) | CTATTGGGGACTGCAGAGAG (SEQ ID NO. 33) | 25316434 | 25316657 |
| DG13S55 | AGCCAGTGTCCACAAGGAAG (SEQ ID NO. 34) | GAGGGTGAGACACATCTCTGG (SEQ ID NO. 35) | 25337471 | 25337753 |
| DG13S54 | AATCGTGCCTCAGTTCCATC (SEQ ID NO. 36) | CCACCAGGAACAACACACAC (SEQ ID NO. 37) | 25377308 | 25377463 |
| D13S625 | TTGCTCTCCAGCCTGGGC (SEQ ID NO. 38) | TTCCTCTGGCTGCCTGCG (SEQ ID NO. 39) | 25391207 | 25391395 |
| DG13S2695 | TCCTGCATGAGAAGGAACTG (SEQ ID NO. 40) | CGACATTCACTGTGGCTCTT (SEQ ID NO. 41) | 25415551 | 25415807 |
| DG13S1479 | TTTGATTCCGTGGTCCATTA (SEQ ID NO. 42) | TTATTTGGTCGGTGCACCTTT (SEQ ID NO. 43) | 25459039 | 25459368 |
| DG13S2696 | GGTGCACCGACCAAATAAGT (SEQ ID NO. 44) | CCAGCTTATTCTCTCTGCCTTC (SEQ ID NO. 45) | 25459351 | 25459478 |
| DG13S1440 | GGTAGGTTGAAATGGGCTAACA (SEQ ID NO. 46) | TCATGACAAGGTGTTGGATTT (SEQ ID NO. 47) | 25520858 | 25520987 |
| DG13S1890 | CCTCCTCTGCCATGAAGCTA (SEQ ID NO. 48) | CTATTTGGTCTGCGGGTTGT (SEQ ID NO. 49) | 25672727 | 25673140 |
| DG13S1540 | TACTGGGTTATCGCCTGACC (SEQ ID NO. 50) | CCAATGGACCTCTTGGACAT (SEQ ID NO. 51) | 25704358 | 25704504 |
| DG13S59 | TTTCGGCACAGTCCTCAATA (SEQ ID NO. 52) | CAGCTGGGTGTGGTGACAT (SEQ ID NO. 53) | 25720194 | 25720421 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S1545 | CAGAGAGGAACAGGCAGAGG (SEQ ID NO. 54) | AGTGGCTGGGAAGCCTTATT (SEQ ID NO. 55) | 25760018 | 25760404 |
| DG13S1524 | AGGTGAGAGAACAAACCTGTCTT (SEQ ID NO. 56) | GCCTTCCTTCTAAGGCCAAC (SEQ ID NO. 57) | 25843657 | 25843768 |
| DG13S1529 | CTGTAGACTTTATCCCTGACTTACTG (SEQ ID NO. 58) | CAATGAATGATGAAGATTCCACTC (SEQ ID NO. 59) | 26098943 | 26099063 |
| DG13S1908 | TGACACCATGTCTTACTGTTTGC (SEQ ID NO. 60) | GAGGATACAATGAGAACCAAATCTC (SEQ ID NO. 61) | 26110282 | 26110493 |
| DG13S2525 | CAGGATCATCAGCCAGGTTT (SEQ ID NO. 62) | GCTGCATGTCACTAGGCATT (SEQ ID NO. 63) | 26123233 | 26123381 |
| DG13S1546 | CCACAGAATGCTCCAAAGGT (SEQ ID NO. 64) | GAGTTCAAGTGATGGATGACGA (SEQ ID NO. 65) | 26159644 | 26159995 |
| DG13S1444 | CAGATAGATGAATAGGTGGATGGA (SEQ ID NO. 66) | CACTGTTCCAAGTGCTTTGC (SEQ ID NO. 67) | 26207544 | 26207727 |
| DG13S66 | TATGCGTTGTGTGTGCTGTG (SEQ ID NO. 68) | GGGCCTTAGATTCTTGTAGTGG (SEQ ID NO. 69) | 26279746 | 26279962 |
| DG13S1907 | TGTCCAGACTGCCTCCTACA (SEQ ID NO. 70) | TGCAACACCTGGTTCACAAT (SEQ ID NO. 71) | 26378401 | 26378521 |
| DG13S68 | TTTGCGAGTCCTTGTGGAGT (SEQ ID NO. 72) | ACAGTCCGCTCCCTCCTAAT (SEQ ID NO. 73) | 26511587 | 26511825 |
| DG13S69 | ATGCTTGGCCCTCAGTTT (SEQ ID NO. 74) | TTGGCAACCCAAGCTAATATG (SEQ ID NO. 75) | 26518188 | 26518483 |
| D13S1250 | CTCCACAGTGACAGTGAGG (SEQ ID NO. 76) | GAGAGGTTCCCAATCCC (SEQ ID NO. 77) | 26721525 | 26721686 |
| DG13S574 | CAGCTCCTGGCCATATTTCT (SEQ ID NO. 78) | GAGCCATTTCTCTGGGTCTG (SEQ ID NO. 79) | 26853541 | 26853693 |
| DG13S73 | GGTCCGTGTCAACCCTTAGA (SEQ ID NO. 80) | CAGGTTGATGGGAGGGAAA (SEQ ID NO. 81) | 26878938 | 26879133 |
| DG13S1532 | CGGGAAATGACAGTGAGACC (SEQ ID NO. 82) | TGCCTAGATTCTCCCGTAAG (SEQ ID NO. 83) | 26899505 | 26899652 |
| D13S1242 | GTGCCCAGCCAGATTC (SEQ ID NO. 84) | GCCCCAGTCAGGTTT (SEQ ID NO. 85) | 26943073 | 26943316 |
| DG13S576 | TTTCTCTCTCCACGGAATGAA (SEQ ID NO. 86) | AACCCATTCTCACAGGGTGTA (SEQ ID NO. 87) | 27121599 | 27121797 |
| DG13S1917 | AGGAGTGTGGCAGCTTTGAG (SEQ ID NO. 88) | TGGATTCCCGTGAGTACCAG (SEQ ID NO. 89) | 27135092 | 27135232 |
| D13S217 | ATGCTGGGATCACAGGC (SEQ ID NO. 90) | AACCTGGTGGACTTTTGCT (SEQ ID NO. 91) | 27169880 | 27170051 |
| DG13S581 | AGCATTTCCAATGGTGCTTT (SEQ ID NO. 92) | CATGTTGATATGCCTGAAGGA (SEQ ID NO. 93) | 27318359 | 27318725 |
| DG13S1471 | CACTGTCTGCTGCCACTCAT (SEQ ID NO. 94) | AGAGATTATGTGATGTACCCTCTCTAT (SEQ ID NO. 95) | 27403303 | 27403544 |
| DG13S2505 | TGATGAAGATCTGGGCGTTA (SEQ ID NO. 96) | TGCCTGTGCTCACTCACTCT (SEQ ID NO. 97) | 27493479 | 27493626 |
| D13S120 | ATGACCTAGAAATGATACTGGC (SEQ ID NO. 98) | CAGACACCACAACACACATT (SEQ ID NO. 99) | 27540983 | 27541093 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| D13S1486 | TGGTTTAAAAACCTCATGCC (SEQ ID NO. 100) | ATCCCAAACTCTGTACTTATGTAGG (SEQ ID NO. 101) | 27623349 | 27623496 |
| DG13S1495 | CCTTGGCTGTTGTGACTGGT (SEQ ID NO. 102) | CACTCAGGTGGGAGGATCAC (SEQ ID NO. 103) | 27668199 | 27668471 |
| DG13S1845 | CACTTTGCCAGTAGCCTTGA (SEQ ID NO. 104) | TTGGGAAAGTTAACCCAGAGA (SEQ ID NO. 105) | 27788787 | 27789056 |
| DG13S1030 | TTTGGGAAGAGCCATGAGAC (SEQ ID NO. 106) | CTCTGGGCATTGGAGGATTA (SEQ ID NO. 107) | 27872811 | 27873164 |
| DG13S584 | GGGAGACAAGTCAGGTGAGG (SEQ ID NO. 108) | CTGAGTATGGAGTCTTCATCATTATC (SEQ ID NO. 109) | 27924334 | 27924484 |
| DG13S79 | TGCTACTAGATTTGACCAACCA (SEQ ID NO. 110) | GACTTGTAAAGGATTTAGTGATTTCG (SEQ ID NO. 111) | 28213368 | 28213495 |
| DG13S80 | GTGGAAGGCCTCTCTCTGTG (SEQ ID NO. 112) | TGCTTCTTGAGGGAAAGCAT (SEQ ID NO. 113) | 28297121 | 28297353 |
| DG13S1934 | CCTTCAGAGGATTTCCCTTTC (SEQ ID NO. 114) | CTGGTTTGACTCCAGCTTCA (SEQ ID NO. 115) | 28461787 | 28462194 |
| DG13S1104 | CCTGGCACGGAATAGACACT (SEQ ID NO. 116) | GGCCTCCTTTGCTCTGAAG (SEQ ID NO. 117) | 28497694 | 28498071 |
| DG13S1097 | CATCCCTGTGGCTGATTAAGA (SEQ ID NO. 118) | AACAGTTCCAGCCCGTTCTA (SEQ ID NO. 119) | 28532382 | 28532543 |
| DG13S1110 | TTTCAAAGGAATATCCAAGTGC (SEQ ID NO. 120) | TGGCGTACCATATAAACAGTTCTC (SEQ ID NO. 121) | 28547636 | 28547900 |
| DG13S87 | TTCAATGAAGGTGCCGAAGT (SEQ ID NO. 122) | TGTCTATCCCAAAGCTGCAA (SEQ ID NO. 123) | 28597688 | 28597905 |
| DG13S2400 | GCTCAGTCCAAGTTCATGCTC (SEQ ID NO. 124) | TGGGATTGGGTTCTGGATAC (SEQ ID NO. 125) | 28671947 | 28672231 |
| DG13S3114 | CCTACTTTCCATCTCCTCCTTG (SEQ ID NO. 126) | TGGAGTAAGTTGGAGAATTGTTGA (SEQ ID NO. 127) | 28678081 | 28678248 |
| DG13S1111 | GCAAGACTCTGTTGAAGAAGAAGA (SEQ ID NO. 128) | TCCCTCTGTTTGAGTTTCTCG (SEQ ID NO. 129) | 28760422 | 28760531 |
| DG13S3122 | CCTTGGGCAGTCAGAGAAAC (SEQ ID NO. 130) | CCCGTGAAGTCTGAGAGGTG (SEQ ID NO. 131) | 28778662 | 28778906 |
| DG13S1101 | AGGCACAGTCGCTCATGTC (SEQ ID NO. 132) | AAACTTTAGCTAATGGTGGTCAAA (SEQ ID NO. 133) | 28812542 | 28812874 |
| D13S1246 | GAGCATGTGTGACTTTCATATTCAG (SEQ ID NO. 134) | AGTGGCTATTCATTGCTACAGG (SEQ ID NO. 135) | 28903534 | 28903738 |
| DG13S1103 | TTGCTGGATGCTGGTTTCTA (SEQ ID NO. 136) | AAAGAGAGAGAGAAAGAGAAAGAAGA (SEQ ID NO. 137) | 28910502 | 28910765 |
| DG13S3147 | AAAGTGGATGCAGTTGAGGTTT (SEQ ID NO. 138) | GCTAGCCATTACAGACAACCAA (SEQ ID NO. 139) | 29018341 | 29018591 |
| DG13S3150 | CAGGGCTCCATGTATCCATAA (SEQ ID NO. 140) | CAATCTTTGGCTTTGGGTTT (SEQ ID NO. 141) | 29042766 | 29042948 |
| D13S289 | CTGGTTGAGCGGCATT (SEQ ID NO. 142) | TGCAGCCTGGATGACA (SEQ ID NO. 143) | 29063702 | 29063949 |
| DG13S166 | CCTATGGAAGCATAGGGAAGAA (SEQ ID NO. 144) | CCCACTTCTGAGTCTCCTGAT (SEQ ID NO. 145) | 29064359 | 29064753 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S3156 | GGGAAATGGAGCTGCTGTTA (SEQ ID NO. 146) | GAGTGGGTGAGTGCAAGGAT (SEQ ID NO. 147) | 29111037 | 29111416 |
| D13S1238 | CTCTCAGCAGGCATCCA (SEQ ID NO. 148) | GCCAACGTAATTGACACCA (SEQ ID NO. 149) | 29144427 | 29144579 |
| DG13S2605 | TGAAAGGAAGGTCCCTGAGTT (SEQ ID NO. 150) | CCCTGCTTTGCACAAGTTATC (SEQ ID NO.151) | 29145896 | 29146055 |
| DG13S163 | CACATGAGGCTGTATGTGGA (SEQ ID NO. 152) | TGTGCAGGAATGAGAAGTCG (SEQ ID NO. 153) | 29177152 | 29177313 |
| D13S290 | CCTTAGGCCCCATAATCT (SEQ ID NO. 154) | CAAATTCCTCAATTGCAAAAT (SEQ ID NO. 155) | 29227323 | 29227512 |
| D13S1229 | GGTCATTCAGGGAGCCATTC (SEQ ID NO. 156) | CCATTATATTTCACCAAGAGGCTGC (SEQ ID NO. 157) | 29282262 | 29282396 |
| DG13S2358 | AGTCAAGGCTGACAGGGAAG (SEQ ID NO. 158) | GCTCTCAGCCCTCAATGTGT (SEQ ID NO. 159) | 29342275 | 29342399 |
| DG13S2658 | ATTTGGGTTCCTCTCCCAAT (SEQ ID NO. 160) | ACAAACTCTTGCTGCTGGTG (SEQ ID NO. 161) | 29348162 | 29348426 |
| DG13S1460 | TGCCTGGTCATCTACCCATT (SEQ ID NO. 162) | TCTACTGCAGCGCTGATCTT (SEQ ID NO. 163) | 29389048 | 29389297 |
| DG13S2434 | TCCTTCCAGAAGGTTTGCAT (SEQ ID NO. 164) | TGCAAAGTTGTTCAAGAGAGACA (SEQ ID NO. 165) | 29485254 | 29485392 |
| DG13S1448 | CAGCAGGAAGATGGACAGGT (SEQ ID NO. 166) | CACACTGCATCACACATACCC (SEQ ID NO. 167) | 29499404 | 29499531 |
| D13S1287 | TATGCCAGTATGCCTGCT (SEQ ID NO. 168) | GTCACATCAGTCCATTTGC (SEQ ID NO. 169) | 29513830 | 29514063 |
| DG13S2665 | GGTTTATGTCTGTGTGTGTGC (SEQ ID NO. 170) | TGAGGGATGTCAGAGAAATATGC (SEQ ID NO. 171) | 29747845 | 29747984 |
| DG13S1904 | TGATGAAATTGCCTAGTGATGC (SEQ ID NO. 172) | GGATCCAATCGTACGCTACC (SEQ ID NO. 173) | 29767797 | 29767922 |
| DG13S1490 | ACCTAAACACCACGGACTGG (SEQ ID NO. 174) | CAGGTATCGACATTCTTCCAAA (SEQ ID NO. 175) | 29908555 | 29908958 |
| DG13S2637 | GGTGATCTAGGGAATTATTTGTCTTC (SEQ ID NO. 176) | TTGGCCACTAAGGTCCAGAT (SEQ ID NO. 177) | 29941956 | 29942120 |
| DG13S96 | CCTTTGAGGCTGGATCTGTT (SEQ ID NO. 178) | TTTCCTTATCATTCATTCCCTCA (SEQ ID NO. 179) | 30166433 | 30166650 |
| D13S260 | AGATATTGTCTCCGTTCCATGA (SEQ ID NO. 180) | CCCAGATATAAGGACCTGGCTA (SEQ ID NO. 181) | 30234833 | 30234997 |
| DG13S17 | TTTAAGCCCTGTGGAATGTATTT (SEQ ID NO. 182) | GACATTGCAGGTCAAGTAGGG (SEQ ID NO. 183) | 30288392 | 30288544 |
| DG13S306 | TGCATAAGGCTGGAGACAGA (SEQ ID NO. 184) | CACAGCAGATGGGAGCAAA (SEQ ID NO. 185) | 30404049 | 30404203 |
| DG13S2486 | AGCCAGTTGTCTTTCATCCTG (SEQ ID NO. 186) | TGCCTGTGCTTGTATATTCTGTG (SEQ ID NO. 187) | 30411508 | 30411755 |
| DG13S18 | GTGCATGTGCATACCAGACC (SEQ ID NO. 188) | GGCAAGATGACCTCTGGAAA (SEQ ID NO. 189) | 30456875 | 30457193 |
| DG13S1062 | TTTGTGTTCCAGGTGAGAATTG (SEQ ID NO. 190) | GAACCATATCCCAAGGCACT (SEQ ID NO. 191) | 30551596 | 30551715 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S1093 | TTGTTCCCACATTCATTCTACA (SEQ ID NO. 192) | TTAAACTCGTGGCAAAGACG (SEQ ID NO. 193) | 30625918 | 30626190 |
| DG13S1059 | CACCATGCCTGGCTCTTT (SEQ ID NO. 194) | AACTTCTCCAGTTGTGTGGTTG (SEQ ID NO. 195) | 30822917 | 30823246 |
| D13S171 | CCTACCATTGACACTCTCAG (SEQ ID NO. 196) | TAGGGCCATCCATTCT (SEQ ID NO. 197) | 31051937 | 31052167 |
| DG13S2359 | TCTGTGTGTATTGTGTACTCCTCTG (SEQ ID NO. 198) | TCACACAATTTGAACCAATCCT (SEQ ID NO. 199) | 31073673 | 31073849 |
| DG13S1092 | ACCAAGATATGAAGGCCAAA (SEQ ID NO. 200) | CCTCCAGCTAGAACAATGTGAA (SEQ ID NO. 201) | 31113759 | 31113934 |
| DG13S2629 | TGATCATGTCAGCAGCAGAAG (SEQ ID NO. 202) | AGTAACAGGTGAGGGCATGG (SEQ ID NO. 203) | 31179791 | 31179953 |
| DG13S1449 | TGTCCATAGCTGTAGCCCTGT (SEQ ID NO. 204) | CTCAATGGGCATCTTTAGGC (SEQ ID NO. 205) | 31199228 | 31199498 |
| DG13S312 | CAAACAAACAAACAAGCAAACC (SEQ ID NO. 206) | TGGACGTTTCTTTCAGTGAGG (SEQ ID NO. 207) | 31280202 | 31280550 |
| DG13S1511 | TGATAACTTACCAGCATGTGAGC (SEQ ID NO. 208) | TCACCTCACCTAAGGATCTGC (SEQ ID NO. 209) | 31321562 | 31321854 |
| DG13S2454 | GCTAGCAAATCTCTCAACTTCCA (SEQ ID NO. 210) | TCTTCTCCATGCTGCTTCCT (SEQ ID NO. 211) | 31352662 | 31352803 |
| DG13S314 | CATGCAATTGCCCAATAGAG (SEQ ID NO. 212) | TTGGGCTTGTCTACCTAGTTCA (SEQ ID NO. 213) | 31379760 | 31380086 |
| DG13S1071 | GCTGCACGTATTTGTTGGTG (SEQ ID NO. 214) | AAACAGCAGAAATGGGAACC (SEQ ID NO. 215) | 31447431 | 31447669 |
| DG13S1068 | CCGTGGGCTATCAATTTCTG (SEQ ID NO. 216) | AAGATGCAATCTGGTTTCCAA (SEQ ID NO. 217) | 31553333 | 31553570 |
| DG13S1077 | CCCAAGACTGAGGAGGTCAA (SEQ ID NO. 218) | GCTGACGGAGAGGAAAGAGA (SEQ ID NO. 219) | 31569360 | 31569733 |
| DG13S2343 | TCACAAAGCAAGCAATCACA (SEQ ID NO. 220) | TGATGGATGCACCATGTTTA (SEQ ID NO. 221) | 31653489 | 31653608 |
| DG13S316 | TGAGAAGCCTGGGCATTAAG (SEQ ID NO. 222) | ACAAGCTCATCCAGGGAAAG (SEQ ID NO. 223) | 31708002 | 31708244 |
| DG13S1558 | AGAGCTGATCTGGCCGAAG (SEQ ID NO. 224) | GGTGGACACAGAATCCACACT (SEQ ID NO. 225) | 31986248 | 31986627 |
| D13S267 | GGCCTGAAAGGTATCCTC (SEQ ID NO. 226) | TCCCACCATAAGCACAAG (SEQ ID NO. 227) | 32062233 | 32062380 |
| DG13S1478 | TCAACCTAGGATTGGCATTACA (SEQ ID NO. 228) | TCTAGGATTTGTGCCTTTCCA (SEQ ID NO. 229) | 32157761 | 32158137 |
| DG13S1551 | ATTCGTGCAGCTGTTTCTGC (SEQ ID NO. 230) | GCATGACATTGTAAATGGAGGA (SEQ ID NO. 231) | 32364898 | 32365153 |
| DG13S1884 | GGTGGGAATGTGTGACTGAA (SEQ ID NO. 232) | CCAGGTACAACATTCTCCTGAT (SEQ ID NO. 233) | 32451203 | 32451315 |
| D13S1293 | TGCAGGTGGGAGTCAA (SEQ ID NO. 234) | AAATAACAAGAAGTGACCTTCCTA (SEQ ID NO. 235) | 32536337 | 32536467 |
| DG13S1518 | AAAGGATGCATTCGGTTAGAG (SEQ ID NO. 236) | ACTGTCCTGTGCCTGTGCTT (SEQ ID NO. 237) | 32588965 | 32589321 |

TABLE 24-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| D13S620 | GTCCACCTAATGGCTCATTC (SEQ ID NO. 238) | CAAGAAGCACTCATGTTTGTG (SEQ ID NO. 239) | 32627749 | 32627947 |
| DG13S1866 | AGCCTGTGATTGGCTGAGA (SEQ ID NO. 240) | GGCTTACAGCTGCCTCCTTT (SEQ ID NO. 241) | 32633306 | 32633709 |
| DG13S1927 | CCCACAGAGCACTTTGTTAGA (SEQ ID NO. 242) | GCCTCCCTTAAGCTGTTATGC (SEQ ID NO. 243) | 32691932 | 32692304 |
| DG13S1503 | CACTCTTTACTGCCAATCACTCC (SEQ ID NO. 244) | GCCGTGTGGGTGTATGAAT (SEQ ID NO. 245) | 32699827 | 32700058 |
| DG13S332 | TTGTACCAGGAACCAAAGACAA (SEQ ID NO. 246) | CACAGACAGAGGCACATTGA (SEQ ID NO. 247) | 32764576 | 32764751 |
| DG13S333 | GCTCTGGTCACTCCTGCTGT (SEQ ID NO. 248) | CATGCCTGGCTGATTGTTT (SEQ ID NO. 249) | 32872275 | 32872720 |
| D13S220 | CCAACATCGGGAACTG (SEQ ID NO. 250) | TGCATTCTTTAAGTCCATGTC (SEQ ID NO. 251) | 32967602 | 32967793 |
| DG13S1919 | CAGCAACTGACAACTCATCCA (SEQ ID NO. 252) | CCTCAATCCTCAGCTCCAAC (SEQ ID NO. 253) | 33014255 | 33014477 |
| DG13S2383 | TGATTGGTTCTGTTGTTGCTG (SEQ ID NO. 254) | AGCCCAAGGCTCTTGTGAG (SEQ ID NO. 255) | 33053369 | 33053553 |
| DG13S1439 | TCCTTCACAGCTTCAAACTCA (SEQ ID NO. 256) | AGTGAGAAGCTTCCATACTGGT (SEQ ID NO. 257) | 33070030 | 33070264 |
| DG13S335 | GCCAACCGTTAGACAAATGA (SEQ ID NO. 258) | CTACATGTGCACCACAACACC (SEQ ID NO. 259) | 33102278 | 33102478 |
| DG13S340 | AGTTTATTGCCGCCGAGAG (SEQ ID NO. 260) | ACCCACCACATTCACAAGC (SEQ ID NO. 261) | 33124866 | 33125238 |
| DG13S1496 | CGATTGCCATGTCTCTTTGA (SEQ ID NO. 262) | GAGATCTGGCCTGGATTTGT (SEQ ID NO. 263) | 33215915 | 33216066 |
| DG13S347 | TCATTGTCAGCACAGAATGAACT (SEQ ID NO. 264) | GGAGGGAGGGAAGAAAGAGA (SEQ ID NO. 265) | 33280351 | 33280688 |
| DG13S339 | GGGAAGAGGAGATTGACTTGTT (SEQ ID NO. 266) | GGAACACCATCATTCCAACC (SEQ ID NO. 267) | 33352425 | 33352656 |
| DG13S1926 | TACAAGCTCCACCGTCCTTC (SEQ ID NO. 268) | TGAGTTGCTGCCTCTTCAAA (SEQ ID NO. 269) | 33388692 | 33388919 |
| DG13S1469 | TGCTAATGGGCCAAGGAATA (SEQ ID NO. 270) | GCTAAATGTCCTCATGAATAGCC (SEQ ID NO. 271) | 33416571 | 33416940 |
| DG13S351 | TGTCCTGCAGACAGATGGTC (SEQ ID NO. 272) | CCTCCGGAGTAGCTGGATTA (SEQ ID NO. 273) | 33497762 | 33498055 |
| DG13S26 | GAGACTGGCCCTCATTCTTG (SEQ ID NO. 274) | AAGAAGCCAGAGACAAAGAAATACA (SEQ ID NO. 275) | 33584096 | 33584425 |
| DG13S30 | CATCTATCTTTGGATTCAGTGGTG (SEQ ID NO. 276) | TGCTCCCAACATCTTACCAG (SEQ ID NO. 277) | 33731684 | 33732071 |
| DG13S1435 | TGTCCTCTGGTCATTTCTATGGT (SEQ ID NO. 278) | CATGAATGAGAAGTGATGAATGG (SEQ ID NO. 279) | 33762069 | 33762285 |
| DG13S356 | CAGACACTGTAAACTGGCTTCG (SEQ ID NO. 280) | GCCACATTGCTATCAGCGTA (SEQ ID NO. 281) | 33908746 | 33908957 |
| DG13S2316 | ATGTGCTGTGGTCCAGATTT (SEQ ID NO. 282) | CCTACTACTGCAATTACTCCCTACC (SEQ ID NO. 283) | 33913787 | 33913954 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S357 | TGTCATAGGCTTGCGGTATTT (SEQ ID NO. 284) | TTGGTAGGGTCCTTTCCTTT (SEQ ID NO. 285) | 33935177 | 33935378 |
| DG13S1032 | GCCTGCTCACTGTTGTTTGA (SEQ ID NO. 286) | CGGTTATCAGAGACTGGTGGT (SEQ ID NO. 287) | 33967059 | 33967269 |
| DG13S1557 | GGCTTATTTCATGTACGGCTA (SEQ ID NO. 288) | GGTTAAACTCTACTTAGTCCTGATGC (SEQ ID NO. 289) | 33996100 | 33996249 |
| DG13S1925 | GAACTCTGCAGGCACCTCTT (SEQ ID NO. 290) | CCTGAAGCGCTTGTACTGAA (SEQ ID NO. 291) | 34079148 | 34079570 |
| DG13S360 | TTGGCTTCTCGCTCTTTCTT (SEQ ID NO. 292) | AGCCATCAGTCACATGCAAA (SEQ ID NO. 293) | 34138872 | 34139221 |
| DG13S1522 | AGATCTCCAGGGCAGAGGAC (SEQ ID NO. 294) | CCTTCCTCCCTCCTTCTCTC (SEQ ID NO. 295) | 34195314 | 34195659 |
| DG13S2324 | CAGTCAAATGTCTCAACCTTCC (SEQ ID NO. 296) | CTAGCAACATGGCCAAGAAA (SEQ ID NO. 297) | 34224040 | 34224206 |
| DG13S1517 | CGTCATTGATCCCAATCATCT (SEQ ID NO. 298) | GGCTGATAGCCTCCCTTGTA (SEQ ID NO. 299) | 34271358 | 34271587 |
| DG13S364 | ACCTTTCAAGCTTCCGGTTT (SEQ ID NO. 300) | TTCCATCCGTCCATCTATCC (SEQ ID NO. 301) | 34323307 | 34323478 |
| DG13S1036 | TTAAAGTCACTTGTCTGTGGTCA (SEQ ID NO. 302) | TTTGTAGGAATCAAGTCAAATAATGTA (SEQ ID NO. 303) | 34525065 | 34525280 |
| DG13S1037 | CTTTCGGAAGCTTGAGCCTA (SEQ ID NO. 304) | CCCAAGACCACTGCCATATT (SEQ ID NO. 305) | 34616658 | 34616926 |
| DG13S1854 | TGACAGGTTTGGGTATATTGGA (SEQ ID NO. 306) | TGCTTAATGTAGTGGCAGCA (SEQ ID NO. 307) | 34622055 | 34622151 |
| DG13S1038 | TCCTGCCTTTGTGAATTCCT (SEQ ID NO. 308) | GTTGAATGAGGTGGGCATTA (SEQ ID NO. 309) | 34702405 | 34702738 |
| DG13S2366 | TTGGGAATAAATCAGGTGTTGA (SEQ ID NO. 310) | GCAGCAGCTCAGCATTTCTC (SEQ ID NO. 311) | 34735455 | 34735583 |
| DG13S1039 | CCATTTAATCCTCCAGCCATT (SEQ ID NO. 312) | GCTCCACCTTGTTACCCTGA (SEQ ID NO. 313) | 34743651 | 34743817 |
| DG13S1840 | ACAACCCTGGAATCTGGACT (SEQ ID NO. 314) | GAAGGAAAGGAAAGGAAAGAAA (SEQ ID NO. 315) | 34805466 | 34805682 |
| DG13S369 | TGACAAGACTGAAACTTCATCAG (SEQ ID NO. 316) | GATGCTTGCTTTGGGAGGTA (SEQ ID NO. 317) | 34815499 | 34815755 |
| DG13S2481 | CAGGTTAGAGCCCATCCAAG (SEQ ID NO. 318) | AGGCTCAGCTTCATCCACAT (SEQ ID NO. 319) | 34867728 | 34867872 |
| D13S219 | AAGCAAATATGCAAAATTGC (SEQ ID NO. 320) | TCCTTCTGTTTCTTGACTTAACA (SEQ ID NO. 321) | 34956581 | 34956707 |
| DG13S2351 | GGGAACAGGTCACAGGTCAT (SEQ ID NO. 322) | GGAAGACTGGGTGGTCACAG (SEQ ID NO. 323) | 35099146 | 35099320 |
| DG13S384 | TTCCTTCTGCTTGTGAGCTG (SEQ ID NO. 324) | TACCCTCACCTTCCTCATGC (SEQ ID NO. 325) | 35499548 | 35499763 |
| DG13S1507 | GAAGACATTGGCAGGTCTGG (SEQ ID NO. 326) | GAGCCCTCATGTTGGGATAA (SEQ ID NO. 327) | 35557977 | 35558206 |
| DG13S1512 | TTGTTGATTCTCCCATTCTGTG (SEQ ID NO. 328) | TCACCTACCTCATCTCATACTCAAA (SEQ ID NO. 329) | 35668964 | 35669201 |

TABLE 24-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S1556 | TCTTCCGGACAAGTTTCCAA (SEQ ID NO. 330) | TGGGTCATTCTGGACATTCA (SEQ ID NO. 331) | 35791215 | 35791467 |
| DG13S388 | GCAAATGAGGCTGGTAAGGT (SEQ ID NO. 332) | TGCACTGTGGTAGAGGGAAA (SEQ ID NO. 333) | 35817061 | 35817320 |
| DG13S1442 | CAACATACTCCTATGCCTAGAAAGAAA (SEQ ID NO. 334) | CTCACCAGGCAGAAACAGGT (SEQ ID NO. 335) | 35842967 | 35843335 |
| DG13S1045 | CCCAATGGCATGCTTCACT (SEQ ID NO. 336) | GGTTCTCCCAGCATTGGTT (SEQ ID NO. 337) | 35928180 | 35928324 |
| DG13S2452 | AAGGCCTCTGGGTAGGTAGG (SEQ ID NO. 338) | AAGCAATCCTTATGGGCTCT (SEQ ID NO. 339) | 35948528 | 35948826 |
| DG13S2350 | CCAGGTAATCAGAAGCCTCA (SEQ ID NO. 340) | TTCCGTTAAATCCAGCCATC (SEQ ID NO. 341) | 36011840 | 36011961 |
| DG13S2483 | CAGGGACTGCAGTGTCTCAA (SEQ ID NO. 342) | ATGCCACATTTGCCTCTCTC (SEQ ID NO. 343) | 36027396 | 36027703 |
| DG13S1100 | CCACCTTCCACTTAATACAAACTTC (SEQ ID NO. 344) | GAAGCAATCCATTCCAAGAAA (SEQ ID NO. 345) | 36056838 | 36057115 |
| DG13S1501 | GTCCTGAGGGTGTCCAGGTA (SEQ ID NO. 346) | GCTGGAGAACTCCTATTCTGCT (SEQ ID NO. 347) | 36215761 | 36215909 |
| DG13S1868 | TGGAGCTATTGCGGTTCTCT (SEQ ID NO. 348) | TCAAATCTCTCTTTCCTCCTCCT (SEQ ID NO. 349) | 36313203 | 36313417 |
| DG13S395 | CAGTTCCAGCTACGGGAGAA (SEQ ID NO. 350) | CCGCATTTAGGCAAGTCTCA (SEQ ID NO. 351) | 36317151 | 36317507 |
| D13S1491 | AAGCACACACAGATGCTAGG (SEQ ID NO. 352) | CCTCAGCCTCCATAATCTCA (SEQ ID NO. 353) | 36361442 | 36361571 |
| DG13S400 | GTACAGAGCCCACCTTCTGG (SEQ ID NO. 354) | TCACTATGCTGCAAGGCAAG (SEQ ID NO. 355) | 36369862 | 36370134 |
| D13S894 | GGTGCTTGCTGTAAATATAATTG (SEQ ID NO. 356) | CACTACAGCAGATTGCACCA (SEQ ID NO. 357) | 36536509 | 36536706 |
| D13S218 | GATTTGAAAATGAGCAGTCC (SEQ ID NO. 358) | GTCGGGCACTACGTTTATCT (SEQ ID NO. 359) | 36830331 | 36830519 |
| DG13S1553 | TGGGTGAAGATGCTACCTGA (SEQ ID NO. 360) | CCCTTCTTCCTTTCCCTCTC (SEQ ID NO. 361) | 36898814 | 36899040 |
| DG13S411 | TGCCAGGTCTGAGTTGTAAGC (SEQ ID NO. 362) | CAGCATGAGACCCTGTCAAA (SEQ ID NO. 363) | 36908058 | 36908265 |
| DG13S1870 | GAAAGAAAGAAAGAAAGAAGAAAGAAA (SEQ ID NO. 364) | AATCACCAAACCTGGAAGCA (SEQ ID NO. 365) | 36927423 | 36927632 |
| DG13S1870 | GAAAGAAAGAAAGAAAGAAGAAAGAAA (SEQ ID NO. 366) | AATCACCAAACCTGGAAGCA (SEQ ID NO. 367) | 36927485 | 36927632 |
| DG13S39 | TCTGAGTTAAACACTTGAGTTGCTG (SEQ ID NO. 368) | CCAGTAAATGGCAGTGTGGTT (SEQ ID NO. 369) | 36957292 | 36957640 |
| DG13S2415 | TGTCATGGATATTTCTACATAAACCAA (SEQ ID NO. 370) | TGAAGATGGTTATTGCTTCCTTC (SEQ ID NO. 371) | 36984719 | 36984955 |
| DG13S412 | CGCTTTGTTTGGTTTGGTTT (SEQ ID NO. 372) | ATGCAGTTGTCCCACATGCT (SEQ ID NO. 373) | 37036929 | 37037137 |
| DG13S414 | TCCTGCACTCCAAAGGAAAC (SEQ ID NO. 374) | AACTCTGCTTTAATTCAGCTTTGTC (SEQ ID NO. 375) | 37047489 | 37047713 |

TABLE 24-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S1872 | TTCTTGAGGGCATAAAGCTGA (SEQ ID NO. 376) | CACACTCACCAGGCACTCTG (SEQ ID NO. 377) | 37119505 | 37119608 |
| DG13S416 | CAGGTTTGATGAAGGAAATATGC (SEQ ID NO. 378) | GGGATCCTCTGCATTTCTCTAA (SEQ ID NO. 379) | 37125983 | 37126184 |
| DG13S2607 | TTTGCCAAATCAACCTTCAG (SEQ ID NO. 380) | CCTGCTTCACACCTCTGACC (SEQ ID NO. 381) | 37317455 | 37317831 |
| DG13S1898 | ACTCACACACAACCACCACA (SEQ ID NO. 382) | GCTACTGGTGGGTCGTAAGC (SEQ ID NO. 383) | 37318932 | 37319055 |
| D13S1288 | TTCAGAGACCATCACGGC (SEQ ID NO. 384) | CTGGAAAAATCAGTTGAATCCTAGC (SEQ ID NO. 385) | 37321295 | 37321486 |
| DG13S2567 | AGGAAAGCCGAGAAAGCATA (SEQ ID NO. 386) | CATGTATCCACATGCCCAGA (SEQ ID NO. 387) | 37416093 | 37416462 |
| DG13S418 | CCTTCAGCGCAGCTACATCT (SEQ ID NO. 388) | AGAACTGCGAGGTCCAAGTG (SEQ ID NO. 389) | 37473016 | 37473380 |
| DG13S419 | GGGAGAAAGAGAGGTAGGAAGG (SEQ ID NO. 390) | TTCCCAAGTTAGCAGCATCC (SEQ ID NO. 391) | 37532947 | 37533123 |
| DG13S1051 | TTCTAGAGGAGTCTATTTCTTTACTGG (SEQ ID NO. 392) | GGAGCTGTCACTTGAGCTTTG (SEQ ID NO. 393) | 37694432 | 37694579 |
| DG13S1841 | CCGTGACCTACAGGGAACAT (SEQ ID NO. 394) | GGCATCGGGTGTTTCTATTC (SEQ ID NO. 395) | 37715601 | 37715829 |
| DG13S1052 | AGACCTGCCTGTGTTCTGGT (SEQ ID NO. 396) | GGAGTGAAATAAGTGGAACTGGA (SEQ ID NO. 397) | 37831275 | 37831438 |
| DG13S1053 | CATTAAATGAGTCATAAAGGTCATGG (SEQ ID NO. 398) | AACATTGTTGCTTTGCTGGA (SEQ ID NO. 399) | 37935190 | 37935311 |
| DG13S423 | GGCCTTAGCTCAGTTTCTGG (SEQ ID NO. 400) | TGCAAAGACATTTGCGGATA (SEQ ID NO. 401) | 37941221 | 37941411 |
| D13S1253 | CCTGCATTTGTGTACGTGT (SEQ ID NO. 402) | CAGAGCCGTGGTAGTATATTTTT (SEQ ID NO. 403) | 37944396 | 37944533 |
| DG13S2539 | GGAACCAGTCATTTGGGTGT (SEQ ID NO. 404) | TTATTGCTCCCTCGTCCAAG (SEQ ID NO. 405) | 38050898 | 38051253 |
| DG13S2509 | TGCCTTAAGGTCTATTATTTCCTTTC (SEQ ID NO. 406) | ACCAATGCAGGAAGACTCAA (SEQ ID NO. 407) | 38067039 | 38067186 |
| DG13S1863 | CTGATGAAAGGACACACATGC (SEQ ID NO. 408) | TGCATTAACTATGCAGCTTGAAA (SEQ ID NO. 409) | 38092085 | 38092353 |
| DG13S2510 | GTCGTGCAATCCCGAGAG (SEQ ID NO. 410) | GGATTCCTGCTGGCTCTTCT (SEQ ID NO. 411) | 38197807 | 38198059 |
| DG13S1909 | CTGGTGTGGTCAGGAAATGA (SEQ ID NO. 412) | GTGCTAAACACATGTGAGTGAGAG (SEQ ID NO. 413) | 38309328 | 38309442 |
| DG13S428 | TTTGACCATGCTTTCTCTTTGA (SEQ ID NO. 414) | GCTTGATGACTCCCTGCTGT (SEQ ID NO. 415) | 38346716 | 38347069 |
| DG13S1858 | AAGCCATTGAAAGGCAGGTA (SEQ ID NO. 416) | GGGACTTTCCGGCTTCTATT (SEQ ID NO. 417) | 38371574 | 38371742 |
| DG13S1911 | GGTTTGGGAACCATTCTCCT (SEQ ID NO. 418) | GCAGAGAAGGGATTTACTCCAG (SEQ ID NO. 419) | 38475656 | 38475877 |
| DG13S433 | ACTTGACATGGAGCAAGCTG (SEQ ID NO. 420) | AGCTCATCATGCTGTAAGGAG (SEQ ID NO. 421) | 38516056 | 38516191 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S2421 | CACAGGCTCTCACATTCTCG (SEQ ID NO. 422) | TGACACTCATCCCTCTGCTG (SEQ ID NO. 423) | 38534972 | 38535357 |
| DG13S2375 | TGAGTTTCATAAGTTTACTACCTGCTG (SEQ ID NO. 424) | GGCAGGGAGAAAGGACAAAT (SEQ ID NO. 425) | 38548257 | 38548440 |
| D13S1248 | TCCCTTATGTGGGATTAGTTGA (SEQ ID NO. 426) | CAGACATGGAACTGAGATTTTTT (SEQ ID NO. 427) | 38558005 | 38558267 |
| DG13S1856 | TGTTCCATCTCTCTACCCATGT (SEQ ID NO. 428) | TCAATGTTCTTATTGAGTGGGAAA (SEQ ID NO. 429) | 38577323 | 38577506 |
| DG13S435 | ATATCCACCCACCCACACAT (SEQ ID NO. 430) | TAGCTCTGAGGGCAGAGACC (SEQ ID NO. 431) | 38591043 | 38591261 |
| DG13S2459 | CCGTCCTTCCTCCACTGAT (SEQ ID NO. 432) | AGAGCACTGAGGGAGCAAAT (SEQ ID NO. 433) | 38596056 | 38596299 |
| DG13S438 | AGCTACAGCACGAGGCAGTT (SEQ ID NO. 434) | TTTGAATTGAGTTGCTGTTCG (SEQ ID NO. 435) | 38676957 | 38677248 |
| DG13S1865 | TGTACACCACCAACCATTCTG (SEQ ID NO. 436) | GGGAAGAAAGGCAAATAGCA (SEQ ID NO. 437) | 38684800 | 38684904 |
| DG13S2354 | GGATTGGCAATTAGCAGGTC (SEQ ID NO. 438) | GCCTGGTCAAAGATAACAGACG (SEQ ID NO. 439) | 38773862 | 38774026 |
| DG13S2534 | CCTGATTAAGCTGGCCTTTG (SEQ ID NO. 440) | ATCCTTCTGGGACCCTCATC (SEQ ID NO. 441) | 38801698 | 38801951 |
| DG13S1903 | GCTTTGCTTCCTTCTTGGTG (SEQ ID NO. 442) | CAACATTACGGCCAGTCTCA (SEQ ID NO. 443) | 38802843 | 38803052 |
| DG13S1896 | GGTGCATCTGATAAGCCAAA (SEQ ID NO. 444) | GCTGTCTTGGACACAGTGGA (SEQ ID NO. 445) | 38815291 | 38815405 |
| DG13S443 | CACCATCATCATCTGGTTGG (SEQ ID NO. 446) | GAGCTCATTGAAAGGCAGGA (SEQ ID NO. 447) | 38838839 | 38839093 |
| DG13S445 | CCATCCATCTATCCATTTATCTCTG (SEQ ID NO. 448) | GGATTTATCCTTGCCCTGCT (SEQ ID NO. 449) | 38840399 | 38840584 |
| DG13S447 | CTATCATCCATCCATCCTATTTG (SEQ ID NO. 450) | TTAGGGCAGCTACCTGGAAA (SEQ ID NO. 451) | 38840751 | 38840928 |
| D13S1233 | AGGACTANAGATGAATGCTC (SEQ ID NO. 452) | GACATGACTCCATGTTTGGT (SEQ ID NO. 453) | 38875108 | 38875292 |
| DG13S2320 | CCTCACCTTGCAATTTCCTG (SEQ ID NO. 454) | CTGACTTGCCTGTTGGCATA (SEQ ID NO. 455) | 38957405 | 38957570 |
| DG13S451 | TTTGGGATCTTGAAGACCTTT (SEQ ID NO. 456) | TTGTGGCATGTCCTTGGTT (SEQ ID NO. 457) | 39032835 | 39033191 |
| DG13S180 | TGTACACTGCAAACATTGCTAAA (SEQ ID NO. 458) | TTGTCCTTTCATTATGACGTGTCT (SEQ ID NO. 459) | 39233968 | 39234350 |
| DG13S458 | AAGCCTGAAAGGATACACACAAA (SEQ ID NO. 460) | CAGGATCCCAGACTTTCCAG (SEQ ID NO. 461) | 39475899 | 39476187 |
| DG13S2547 | GGTGAATCCCACCCTCATAC (SEQ ID NO. 462) | TTGGTATGTTTCCTATTGTTGCAT (SEQ ID NO. 463) | 39612492 | 39612849 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| D13S244 | GAACCAGTGAGTTTTTATTAC (SEQ ID NO. 464) | AGACACAGCATATAATACATG (SEQ ID NO. 465) | 39665226 | 39665353 |
| DG13S2435 | TGAAGCTTTGTGGCTTGTTG (SEQ ID NO. 466) | GACTGAGTCCACAGCCCATT (SEQ ID NO. 467) | 39863067 | 39863301 |
| D13S263 | CCTGGCCTGTTAGTTTTTATTGTTA (SEQ ID NO. 468) | CCCAGTCTTGGGTATGTTTTTA (SEQ ID NO. 469) | 39878976 | 39879126 |
| DG13S188 | CCACCATGCAAGAACAGATG (SEQ ID NO. 470) | GCTTTGCACTTGGCTGTCTT (SEQ ID NO. 471) | 39935769 | 39936103 |
| DG13S189 | TTGCATGAAGTAAAGTATCCCTGT (SEQ ID NO. 472) | CACAAACCACAAGATGATTGG (SEQ ID NO. 473) | 39968676 | 39969030 |
| DG13S190 | GGGCATCATGTCTACAACTCA (SEQ ID NO. 474) | ACCAAGGGCACTTGCTGATA (SEQ ID NO. 475) | 40027542 | 40027801 |
| DG13S2370 | AGGATGAAGAGGGAGGAAGG (SEQ ID NO. 476) | CCAGACTGATCTTCCTTAATTAGTTG (SEQ ID NO. 477) | 40159684 | 40159812 |
| DG13S196 | CCTCCTCTTTCTGCTGCTGT (SEQ ID NO. 478) | AGCCAAAGAACCCAAAGAAAC (SEQ ID NO. 479) | 40251445 | 40251793 |
| DG13S2457 | GCCCTACTTTGCCTCAGAAA (SEQ ID NO. 480) | GCAACTCATGCCAGCCTCTA (SEQ ID NO. 481) | 40376042 | 40376447 |
| DG13S2445 | AACTGTGTTAATGATGGGCAAA (SEQ ID NO. 482) | AACGAGCGCATGAAACCTAT (SEQ ID NO. 483) | 40422793 | 40423200 |
| DG13S211 | CCTGGTCAATTGAACCCAAA (SEQ ID NO. 484) | TGAAGGAAGATAAAGCAGGGTAA (SEQ ID NO. 485) | 40434073 | 40434172 |
| DG13S472 | CTCTCTCTGGCCCTCTCTTG (SEQ ID NO. 486) | GGTAACTTGCCATTCTTCTACCA (SEQ ID NO. 487) | 40476985 | 40477395 |
| DG13S207 | ACTCCACCTGAAGGGAGAAA (SEQ ID NO. 488) | TGGAAGCCACTAATTGGAGAA (SEQ ID NO. 489) | 40545942 | 40546202 |
| DG13S200 | AATGGATGGATACCTCCTTATCA (SEQ ID NO. 490) | CTCATTGTGGCTTTCTGTGC (SEQ ID NO. 491) | 40737337 | 40737570 |
| DG13S198 | GTACCCACACCTCACCAAGC (SEQ ID NO. 492) | CGTAGCTCACATTCCCAACA (SEQ ID NO. 493) | 40811813 | 40812059 |
| DG13S215 | GGCGAGTGAAAGAGAGGACA (SEQ ID NO. 494) | GGGTGGTAATTCCCAGATGA (SEQ ID NO. 495) | 40871695 | 40871992 |
| DG13S221 | TCTGCAACAGCCAGAATCAA (SEQ ID NO. 496) | TGTCTGTTGGCAACTTTCTGTC (SEQ ID NO. 497) | 41107773 | 41108117 |
| DG13S219 | AGGTGAACCCAGTCCAGCTA (SEQ ID NO. 498) | TCTTAGGCAAAGGAGCCAGT (SEQ ID NO. 499) | 41127591 | 41127734 |
| D13S1270 | ACATGAGCACTGGTGACTG (SEQ ID NO. 500) | GGCCTCAAATGTTTTAAGCA (SEQ ID NO. 501) | 41161654 | 41161831 |
| DG13S225 | TTCTGGGTGTTCGCTATTCC (SEQ ID NO. 502) | TTTCCTGTCCAGTCCTGACC (SEQ ID NO. 503) | 41212951 | 41213310 |

TABLE 24-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| D13S1276 | GTTTTGCAGGTCTAGGTCACAC (SEQ ID NO. 504) | AGGATAGCTTGAGCCCG (SEQ ID NO. 505) | 41213917 | 41214090 |

All references cited herein are incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of treating a human subject to reduce risk of myocardial infarction (MI) comprising:
   screening nucleic acid of a human subject to determine whether the nucleic acid comprises a 5-lipoxygenase activating protein (FLAP) (SEQ ID NO: 1) genotype or haplotype that correlates with an increased risk for MI, wherein the FLAP genotype or haplotype comprises at least one polymorphism selected from the group consisting of the polymorphisms set out in Table 5 or 7,
   selecting a human subject comprising the FLAP genotype or haplotype that correlates with an increased risk for MI, and
   administering to the human subject a composition comprising a therapeutically effective amount of an MI therapeutic agent that inhibits leukotriene synthesis in vivo,
   wherein the MI therapeutic agent is a compound represented by the formula:

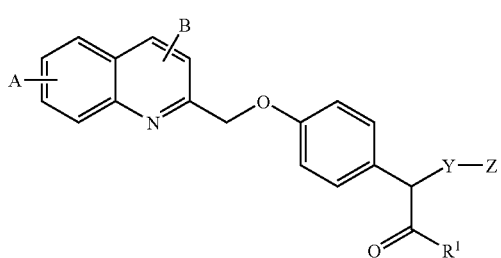

or pharmaceutically acceptable salt thereof, wherein $R^1$ represents a group of the formula:

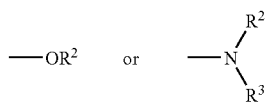

$R^2$ and $R^3$ are identical or different and represent hydrogen, lower alkyl, phenyl, benzyl or a group of the formula:

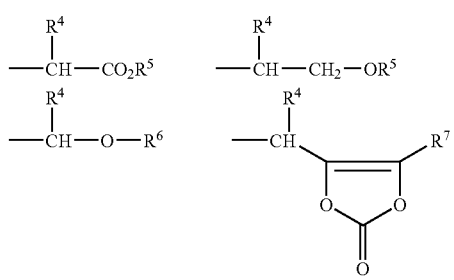

$R^4$ represents hydrogen, lower alkyl, phenyl or benzyl, which can optionally be substituted by hydroxyl, carboxyl, lower alkoxycarbonyl, lower alkylthio, heteroaryl or carbamoyl, $R^5$ represents hydrogen, lower alkyl, phenyl or benzyl, $R^6$ represents a group of the formula —$COR^5$ or —$CO^2 R^5$, $R^7$ represents hydrogen, lower alkyl or phenyl, Y represents a group of the formula:

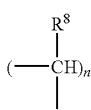

wherein R$^8$ represents hydrogen, lower alkyl or phenyl and n denotes a number of 0 to 5, Z represents norbornyl, or represents a group of the formula:

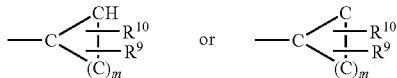

wherein R$^9$ and R$^{10}$ are identical or different and denote hydrogen, lower alkyl or phenyl, or R$^9$ and R$^{10}$ can together form a saturated carbocyclic ring having up to 6 carbon atoms and m denotes a number from 1 to 6, and A and B are identical or different and denote hydrogen, lower alkyl or halogen, or a pharmaceutically acceptable salt thereof.

2. A method according to claim 1, wherein the composition is administered in an amount effective to inhibit FLAP polypeptide activity in the human subject.

3. A method according to claim 2, wherein the composition further comprises a physiologically acceptable carrier or excipient.

4. A method according to claim 3, wherein the selecting step comprises selecting a human subject susceptible to primary myocardial infarction.

5. A method according to claim 1, wherein the MI therapeutic agent is BAY-X-1005.

6. A method according to claim 1, wherein the MI therapeutic agent is BAY-X-1005 or a physiologically acceptable salt or formulation thereof.

7. A method according to claim 6, wherein the composition is administered orally.

8. A method according to claim 1, further comprising monitoring at least one inflammatory marker in the human subject before and during the therapy with either C-reactive protein (CRP) or myeloperoxidase (MPO) wherein the MI therapeutic agent is administered to reduce the level of said inflammatory marker in the human subject.

9. A method according to claim 8, wherein the at least one inflammatory marker comprises C-reactive protein (CRP).

10. A method according to claim 8 or 9, wherein the at least one inflammatory marker comprises myeloperoxidase (MPO).

11. A method according to claim 1, further comprising monitoring a leukotriene level in the subject before and during the therapy, wherein the MI therapeutic agent is administered in an amount effective to reduce the leukotriene level in the subject.

12. A method according to claim 11, wherein the monitoring comprises monitoring a leukotriene level in serum, plasma, or urine from the subject.

13. A method according to claim 11, wherein the monitoring comprises measuring leukotriene production ex vivo in a blood sample from the human subject.

14. A method according to claim 13, wherein the blood sample is stimulated with a calcium ionophore prior to measuring leukotriene production.

15. A method according to claim 11, wherein the MI therapeutic agent is administered in an amount effective to reduce the leukotriene level in the subject lower than a median level of leukotrienes in human subjects.

16. A method according to claim 1, wherein the selecting further comprises selecting a human subject at risk for myocardial infarction.

17. A method of treatment to reduce the risk of a subsequent myocardial infarction in a human subject who has had at least one myocardial infarction (MI), comprising screening nucleic acid of a human subject to determine whether the nucleic acid comprises a 5-lipoxygenase activating protein (FLAP) (SEQ ID NO: 1) genotype or haplotype that correlates with an increased risk for MI, wherein the FLAP genotype or haplotype comprises at least one polymorphism selected from the group consisting of the polymorphism set out in Table 5 or 7, selecting a human subject who has had at least one MI and who has the FLAP genotype or haplotype that correlates with an increased risk for MI, and administering to the human subject a leukotriene synthesis inhibitor, in an amount effective to inhibit leukotriene synthesis in the individual, wherein the MI therapeutic agent is a compound represented by the formula:

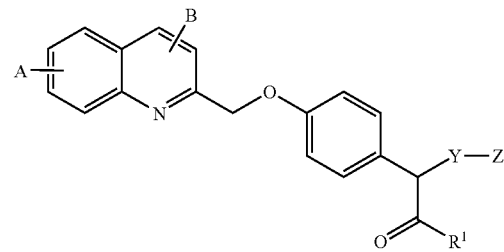

or pharmaceutically acceptable salt thereof,
wherein R$^1$ represents a group of the formula:

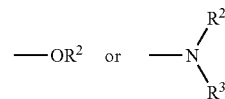

R$^2$ and R$^3$ are identical or different and represent hydrogen, lower alkyl, phenyl, benzyl or a group of the formula:

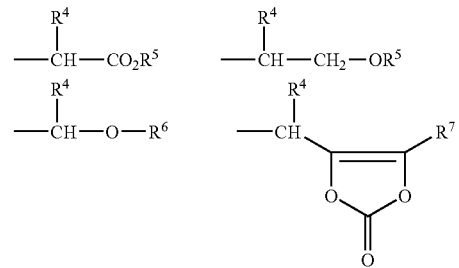

R$^4$ represents hydrogen, lower alkyl, phenyl or benzyl, which can optionally be substituted by hydroxyl, carboxyl, lower alkoxycarbonyl, lower alkylthio, heteroaryl or carbamoyl, R$^5$ represents hydrogen, lower alkyl, phenyl or benzyl, R$^6$ represents a group of the formula —COR$^5$ or —CO$^2$R$^5$, R$^7$ represents hydrogen, lower alkyl or phenyl, Y represents a group of the formula:

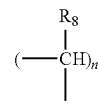

wherein $R^8$ represents hydrogen, lower alkyl or phenyl and n denotes a number of 0 to 5, Z represents norbornyl, or represents a group of the formula:

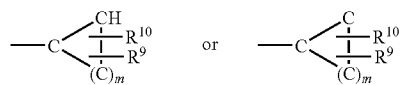

wherein $R^9$ and $R^{10}$ are identical or different and denote hydrogen, lower alkyl or phenyl, or $R^9$ and $R^{10}$ can together form a saturated carbocyclic ring having up to 6 carbon atoms and m denotes a number from 1 to 6, and A and B are identical or different and denote hydrogen, lower alkyl or halogen, or a pharmaceutically acceptable salt thereof.

* * * * *

SEQUENCE LISTING

<160> NUMBER OF SEQ ID NOS: 717

<210> SEQ ID NO 1
<211> LENGTH: 214000
<212> TYPE: DNA
<213> ORGANISM: Homo sapiens

<400> SEQUENCE: 1

```
gactaagatg aatatgcatt cattcaccaa aatctcatat tcccaaaaag caggaaaggt      60
agtacagtga gatggatgat gccttcacat gactcagatg tcacgtgttt ctcaccattg     120
agaccccccaa ggcacccccct cccagcattt accagaatgt gtgtgtaact atttacagtg    180
atttgtgtaa ttatttgatt gtttctcttg tatcctgtag caatgagggt agagattata     240
tcccacctac cactgcagct ccaggatcca gcttcacaaa catttgttga atgaatgaat     300
aagaaaagag gacaccccca aagaggctgc aagggaaaaa gctacaaaga cagaagcacc     360
aggaaaaagt agggtcatgt aagtcaaagc aggaaaaaag ttccatggtg gggtggtcag     420
cagtgtctaa tgccacgaag gcacaaagta ggataaaggt taaaaatcag cctttggttt     480
tggcaaatat gaagcttatc ggtagcctta gcgagaacaa ttccatcagg gagcagaagc     540
taactgcagt gggttgagtc atcaagcagg cataaggaag tagggatacc ccattataag     600
ctactctttc aagaagctca aatctgaagg ttaggagaat taggtcagta gctagaagga     660
aatgtggagt cgaggggctg tttttcctcc caaggagtat aaaggtgtaa cgttgcatga     720
aaccacttca gacaaaggcc gatatcaata gagaagttaa aacgcacgcc tcaagatttg     780
ggaaggcttg gggttgggct taaagaggta ggagcatatt tcctatccta ggacagagaa     840
taagaagaa aggataggtt cccatggaga taaatttcta agtgttaaag aagaggctca     900
gaaaattcta gcatgatagg ctcacttttt tctttttcca tgaaggagat ggcaaagtca     960
actgacatga gaaaggtgac aatactgatg ggttgaagag cgatggacat ttgaaataac    1020
ttcttagacc agtagaggct ggagttcata aatcagaact ggctacaggt tatatatgtt    1080
tttttttttt tctccaacag cataagataa cagagcgaag tctgtagaaa tgaaagaaga    1140
gtcagatgag gatagctgga gctagtgcaa ggagggaagc accacggtgg gagccaggta    1200
cccctggat ttataattca tactgaattc caacaacaga agggctctaa gcaggagagt    1260
gacagatttc agaagactga gacacatttg gtaaaaaaaa gtaggaggaa aacctgattc    1320
```

```
tggaattagg gcagccaata gacggcagta ttttcagaaa ggagggaatg gtcaacagtg      1380
actttctagt ctggagctca ggaggaagag gcaactctac ctgatggtat taagatcatg      1440
gaggtagctg agatcaccta gcttgtgtgt gtcaaatgag aaaagaagaa agaataggag      1500
aagttcccca ggaacacaga cattaagtgg ggctgtggtg acaacacaag aagagaggct      1560
tgcaaaggag cctgagcagc tgtcatgaga gaggtaggat ggtggactcg gagaagaggc      1620
agaagatgtt cttaaaggaa ggacactgct gccaagtagt cagccaattg gtgacaaaga      1680
aagaccctgt tgcgagaaaa aaagtcagtg aagtagtagg aacgatgaca gatgacactg      1740
ggttgaagac tgaggagaga gaagtgtaag agtggaagca gagggcagac cactcttctg      1800
agacactgaa gaggcatagt tagaaataaa ggggagtcgc cagaaaggaa tttgtggcta      1860
agcaagaggt tttctttaag actgaaatac ataagcatga tttaaatgct gctgggatgg      1920
agttcacaga cctggaagac agaagacaaa gcggatcatc aagatagtgg aatttactga      1980
aatgagagag gaaaatccca tccacaggaa atgcagacat gagggagggg ccagaaggac      2040
agtgaaaaca tcagcaactg gtcccccaac ttctgagtga atgtggagat ataatcaggt      2100
aaaggactgc atcatctccc tggttaatga tggagtcaga gaaagagtg tcttatacag       2160 aagttgtgat atacttggcc gggcgcagtg gctcacgcct gtaatctaag cactttggga      2220
ggccaaggca gcggatcac ctgaggtcag gagttcatga ctggcctggt caacatggca       2280
aaatcccacc tctactaaaa acaaaagcct gtaatcccag ctactaggga ggctgaggca      2340
ggagaatcgc ttgaacccag gaggcagagg ttgcagtgag ccaaggtcgc accactgtac      2400
tccagcctgg gcaacagagc tagactcagt ctcaaaaaaa aaaaaaaaag atgtatttat      2460
tctcactgta taaatttctg tgtaagaaat actctctcat atagaagtaa atttatatat      2520
aaaattatat agaaccacta taaaatactc aggtttataa aatttatata taaacttgtt      2580
gacatataaa attccatgta aatgactata aagtactctt atatgaaaag tatatgaatt      2640
aaattatata tcaacttact tttatattac agtatttttg ttatacagaa gtttatatag      2700
tgacaataaa tatttctcaa gaacgatttc acataataga agtataaatt atccatttcc      2760
aatagtgaaa aagaaaagca gttccacacc agtgacaggg ctacgaatct aagaggtaca      2820
aagacttcat tcttagagac actgaggtca gggcatggcc aacacatctg aagctgatag      2880
aattggcgct gggttggttg gagacggtac ggtattacta ttacaatggc agacgcttgg      2940
ccttgataac tagccaatca gggggaaaga ttctggtttc ctctgttatt atctgaacta      3000
gtgtgttccc aaagggttaa gatggtttat ggaaggcaca agatcagcaa accataaagg      3060
attagcacta agaaggaagg aagtagacca agtgttaatg gcgatgccat gtaagagcca      3120
ggtctgcgat gtatgttcta catggtttgg ggggtaaaaa aaatgtcagc ctccagagca      3180
cagggcttta agcctcaagt actgttaaca gtagagttta ctagtctaca gcaggaatta      3240
caaccagtaa ttctaaggcc aattactcag gcaagtttta ctagaacaag gaagctctgc      3300
ttcgaggtca aatcgatttc tgcatttata gaagcatcta gatgttctct gttcaaacaa      3360
tggggtaaaa tccccacaca ttttatttct gacagagtgt tccctatatt gcctggccag      3420
gagtgataac attgcttggc tattattaat aaaacattgc tgtggctggg cgcagtggct      3480
cacacctgta atcctggcac tttgggaggc tgaggcagga ggatcactta actccaggag      3540
tttgacagca gcctgggcaa catagcaaga tcccatctct ctaaaaaatt ttaaaattag      3600
ctgggtgtgg tggcagacac ctgtagtccc agctcctcag gaagctgagg tgggaggatc      3660
acttgagccc aagcaggttg aggctgcagc gtgctgtgac tgtgccactg cactccagcc      3720
```

```
tgcgcaacac actgagagag actctgtctc aaaaaaatac atcaaataaa aattaaaagc    3780
ccatttcttt cttttggtac attacagcca tgcacttcaa aggctagcac aattattttt    3840
ctgcagttct atatttagat tctagttaga agtaacctag gaccttcatg ttagaggtgt    3900
ctttggcaaa actgttatgt gagtgaaacg tttaatcaat tgaggataaa gatgcctcat    3960
tgctaatgaa gatgtggttt aaggatttta tgcacccagt tcatttatta acaacttgtt    4020
taagctttat tagctgggtc tctactttat aactgtgttc tttaatttac aagacaataa    4080
aaattaaaat ggtaaatggg aaacctatct tgcttttcaa taaataattt attttaataa    4140
cttcgtgggc atggtggcca aaacatttta gctgtgaaaa taatttcaat tcatatttt     4200 ttggaatcaa tattaaaagg tgatatattc tcaaatgaaa agtggacaaa tgatcagtta    4260
taggacatga ttaagaaact aaccatgagc cacgtgcagt ggctcatgcc tgtaatccca    4320
gcactctggg aggccgcggt gagcggattg cttgagccca ggagttcaag accaggctgg    4380
gcaacatggc aaaaacccgg ctctactaaa aatgcaaaaa aaaaaaaaa aaaaaaatt      4440 tagctgggtt ttggtggctt atgcctgcag tcccagctac tcgggaggct gactcgggag    4500
gctgaggcac aagaatcatt tgaacccagg aggcagaggt tgcaatgagc tgagaataca    4560
ccactgcact ccagcctggg caacagagag agagagactc agtctcaaaa aacaaacaaa    4620
caaacaaaca aaccgctgcc ctgtgcttgg agagatctgt ttacctttac cactaaagac    4680
tgttggaagt aaattttaga aggtttataa tacctaaaag taatcacttc tgtcttatga    4740
aaggttctgc tgagattttt ctattgtggc cactagtggc aatattccag aagtcatatt    4800
taaagaatat ctttagtgga ttcagcagtt tttcaaatat gtacttttat ctctccaaca    4860
ttcatgattg caattttca aattaacctc atgatataaa caactgtact ctatgatgcc     4920
tcatagtaca gaaactggag gcagaaagag aagttgaatg tctaagaatc ggtaattcta    4980
aaactcaaca tagaccattc agcattagtg gttctaacaa tcccactgca aaatgagttg    5040
ataatgtgta acactttagt gaactaaagc ataagaacc atggtctcct aatgcagcaa     5100
attaaaacac atgatagcta caattaatga agtacatagt cctggctggg cactatggta    5160
cgtcctttac atagattatc tcttaaatta ttaaccccgt tttagagatg agaacattcg    5220
ggctcaggaa ggttatgtaa gttatataaa aatcacaaaa taagagacag agctaagatt    5280
tgaatccaag tgtgaccagg ttcatatcaa gcttccattt ttgaatttat attagaggtc    5340 ataactcac ctttgtcctt ttaaaataat ttttggctct gtgacctaca caggcaagct     5400
gttatttaca aacaacccac acatctagat ggtcactgtc tcaccgccca cttttaccat    5460
caggactcct agtgagctgt caaggggaat gctataattt tggaggttct aaatctgagg    5520
gcttaagaaa gaaagaaatt gtaaaaagca ggcattactc aggggcatag attgtcaggc    5580
agatctgtca tgcttatagg taacctccca gggccaaaaa tatatgtgcc caaactgcct    5640
aaatatttcc tgtcacttca taatactgcc tgaaatcctg ccaaattaga acttcatttg    5700
tgttgcttgt caattttaa cgcataagca aatcacctgg agatcttgtt aaaatgcaaa     5760
ttctgattag gttaggtctg ggtctgcatg tctgatatgc ttccagaggg cactgatgct    5820
gctggtccat ggaccacact taaagaagca aaaagatgt ctgatattta ctctctggct     5880
gcctaggagt gcttctcatt taagtgagat ctctttgtgc atcataatgg gagggatgag    5940
ctgaaaagca gcaaattaag agtgagttaa gtgtctacct cacttcccta ctatctgtaa    6000
caagcaggtt tgggcactgt ggtcaaccag aaaattcttt ccaggaccac aacccttgag    6060
attatgttgc aaagatgcaa ggacaactta gaaataattt ccagcactgg tggcactgga    6120
```

```
tgtctgtcag tggtgctggt ggcagggtcc tattcagact gtggtttacc tgcctggccc    6180
gtttggttat gggccatttt ctgagtacca tggagcatcg cccagctgac aagggcttgt    6240
actccaccct tggtgcgcag aagggaagct tggctgctac taagtttggt gcaaagtaat    6300
tgtggttttg ccattaatat tgatacagt  gagtccctac tttcctcagg tgaaactaga    6360
acttaagggg acacgctcaa gttctcatta tacagtacta agtttcaaaa atcagcaatt    6420
ttatcaaaca catgctctac agcagtggtc ggcaaacttt ttctgtaagg ggccagagag    6480
taaatgtttt agagtttctg ggccacatat ggtttctgtt ccagctataa actctgccac    6540
tgtagggcaa aagcaaccct ccacaataca tacatgaata ggtgtgttcc aaaaaaactt    6600
tatttgtgga ccctgaaatt tgaatttcat aaacttttca tgtgtcatga aatattcttt    6660
tgattttttc ccaaccttttt aaagatgtaa caaccatttt tagcctgtag gccatataga    6720
aacaggcagt gggctgggtt tgctgaccct tgctctgaag caatgatatc tcgatccaat    6780
ttatacccac aaattttttct ccttgaaacc atgcatttaa ttctcatctc ttcttaccat    6840
gacaataaga agttattcta tataacaaag agattgtacc cacccaagcc agcatttaga    6900
tcatgtcatt tgcttcctca aaattttggt ctttataaaa atcaattaaa gcaccttaaa    6960
aggtaagcag tgatgaaata tttgaaataa ttggctaatt aaacatcacc taaatagaaa    7020
ctgtgataag aaccacaaat gcgaaaagga atcatgtagt aactaatgtg gaggatatct    7080
tggtttagag atttgatgaa cacgagtttt gatttaaaaa aatttgtgca atactcactg    7140
ctttggtggg gagcttgcta tgcaagttgg tagaaaaatt tatcctaaag tcacagttct    7200
ctaccactct ggattttctc gagctaacta ccattccaaa ctattttagg cacagttact    7260
agtttcaaga atcaggcaaa ttgccctggt attagcactg ttctttctgt ggtcacaagt    7320
caaactactg tggtgaataa aattagatga tttctttagt cttttcctttt tcagcccctg    7380
tagtcaattt ccagtgctcc attcaaagaa aaaccaaaaa tgtccagaat ataaccttat    7440
tttaaaactt gttaaccact gatttcactt gttaaccaaa tttttttttt tttttttttg    7500
agaatgaatc tcactctgtc accaggctgg agtgcagtgg catgatcttg gttcactgca    7560
acctccgcct cctgggtact ggttcaagca attctcctgc ctcagtctcc cgagtagctg    7620
ggattacagg tgtgcacccc cacacccagc taattttttt gtactttttag tagagatggg    7680
gtttcaccat gttggccggg ctagtcttaa actcctgacc tcgtgatccg cccgcctcgg    7740
cctcccaaag tgctgggatt gcaggcatga accactgcgc ccagcctgtt aaccaaattt    7800
ctaatcacac acacttgagg cccagtaaat gcctgctgaa aagagggtgc tggtggtgag    7860
gcaactgagg ggctaacata ctgatagctg ctgaaatctt ctacagctct ttcttgttag    7920
aacactccat cacggctccc aggcccacac cacatgaagg aacttctagc tctcttgctt    7980
gctctttacc caaatgtagt tagcaagtcc tgggaactaa acagcattga cacacttgaa    8040
gaagacaatt aggcaaatcc caactgctgt gctcctgcag ctaaagatga agactcgtcc    8100
attgggcagt tgattaattg tacctagaaa attaatttca atggtcccat gacaacatac    8160
gggcagtgaa gctctagtgt tcccctgggt tggaatcttc caggatgtat agtctcccat    8220
accagctcat cctcccattt ttccagattc tggttcttct ctcttaccta gtgtgtagtg    8280
ggccaaatgg tggtccccca aaaagatatg tccatgtgtt aaccctggaa actgtggatg    8340
taaccttatt tggaaaaatg gggccaggtg cagtggtgtg catgtgtagt cccagaactt    8400
tgagaagcca aggtgggaga atcgttggag cccaggagtt caagaacagc ccaggcaaca    8460
```

```
tattgagacc cccgtctcta taagcaataa aaaattagct aggtgtggtg gcatgcacct   8520
gaagttccag ctacttgaga ggctgaggca gaaggactgc tcaagcccaa ggagttcaag   8580
gctgcagtga gctatgatca tgtcacccca ctccagcctg ggtgacagag tcagactccc   8640
tgtctcagga gaaagaaaaa aaggtctttt gtaaatgtaa taaagaatct tgagataaga   8700
tcatcctgat ttaggatgga ccctaaatcc aatgacattt gtccttacaa aagaaaggta   8760
gagggaactg tgagacagac acagagggga gggccttgtg aagcaggaag catagatgca   8820
gttacaagtc aaggaatgcc aaggactgtc tacaaccaga agccaggaga gatgcatggg   8880
atgatttctc cctcacagcc tccagaactt ctggcctcca ggactgtgaa gaatcaattt   8940
ctgttgtttt aagccaccaa gtttgtgtgt catttgttat ggcaatggca gtattaggac   9000
tctaatacac agtataaaaa aataaaaata gggccaggcg tggtggctca gacctataac   9060
cccagcactt tgggaggcta aggcgggag atcacttgag gtcaggagtt tgagaccaac   9120
caggccaaca tggtgaaacc ccatctctat taaaaataaa aattagttgg gcatggtggt   9180
gtgcatctgt aatcccagtt actcaggagg ctgaggcaga agaatcgctt gaacccagga   9240
agtggaggtt gtagtgaatg ccactgcact ccagcctggg tgacagagct agactccttc   9300
atcctaggac acagccaagt cttacgtagc aaaaagaagt tgttaaaggt ctgtagttct   9360
gcattaagca acacaggcat gtacctatga attatatgat tataaaagtg ctcggacagg   9420
cccatttcaa acttggcctc tttccaccaa ctgtgtactg tttctcattc cataactaga   9480
gattatgtct ttatatcctg tcaaaaaagt gaattttttgt gggctaagac attatccctg   9540
tgttaaatgc accagtctta gtgtaaacaa gcctagttcc tttttcattt tggctgtcta   9600
gtatgcattt gtatatgcta ggcagtgtac taggcaccttt aaatacatta ccttgtttaa   9660
cctctacagg attctgggag gtaggcatta tccccatttt atagatgaga acactgagaa   9720
gacaatgttc ataagtgcgt cacttgtctg agatgacata tttactaagt agcagaacca   9780
ggcctcgagc tactcagtct gatttccaaa gcccctgctc ttaatcacat caacttcttt   9840
cctatatcac ctttcccaga gtgcgctctc atggataaag agcagaagta taagttacta   9900
ggcagcagaa aactgtagag gtgggaagat tagataaaaa atgtaaataa gaaggcttta   9960
agacaccaaa atcaaatgta aatactttat aacctgaatc agtgcttgtg ttcatgaggc  10020
tagaggtcgt gcattttatc tctaggtctg gtgatgccaa tcctgatcta cagccagcag  10080
caacagttcc ctagcctgcc tagaagtttg taaatgcatg ggctttggta ggaggaagac  10140
gagagaaagc agaacagatt attacaaacc cagtgcattc cccttgatg ggtcaacagc  10200
gatttctttg taagtgaagg acagcacact ggttttgatg actcacgaga gagtaggagg  10260
gaaaaagaag tctgaggcat tgcctggaag cctcgctctg cttaaacaag tacactaatg  10320
gctcatgcct gttactccca gcactttgga aggccaagat gggtggatca cttgaggcca  10380
ggagtttaag cccagcctgg tcaacatagc gagacctttt ctctattaaa aataaagaag  10440
aaagaaagta ataatgattc aagttctcat tctctacaaa attcacttat gactttccaa  10500
atgctagtga aaacttttag gtattgcaaa actgccttaa tgcataacgg gattctcatt  10560
ttacttagtc taagatgact ttttcacttt gaacttctgc atctttatga tcgcttagct  10620
ttctgacaag caatttcagt aagtgtttat caatttgcat ccacacgctg acacataggg  10680
gtctacttac atatccttca tgtaattgag cttttgtaaa tcatctttct acatggtaca  10740
cttctgattt tgtgtgcagc tttcttgttt aagcactgta ttaaatgctc tgcttcctac  10800
acccttagga acaatgagaa taaaagcgta atgttggtta cttcttcata tcaaaggaag  10860
```

```
ttcatctcct ggttattaaa agctattatt aaatggccat cttttttgtgc ccctgtgtta    10920 agcactctac caagatacca ttaaatagat aagggccaca ctccatagag atgatggttc    10980
tatattctgt attttctggg ggagttctaa tttcatgcaa ttccttcttc ttaaataaag    11040
gcaattctct aaatatatta cctaatgtgc tttcactttc atattcttgt aagattttc     11100 acataaatca attctcaaaa aatagtatca taggccttt aaaaatagtc atgttcaaaa     11160
gtcaggctca tgaataaatg tgtgcattca ttacatatat tttcataaat tcaaatttaa    11220
aagaataaga gtagctagaa ggtggaagaa aaatcttatt ctgattagga atgcacaatc    11280
acaagaaaat ttgtgatata tatagtcatt ttattctgta ttgttttatt ttgattttgg    11340
taagacaaga aacaatgtag aaagtttgac aacttaaaaa agtaatatga gtgtgagaaa    11400
gtcctcttcc aggattagca aaaaaatggt ttttttttt ttttttccg agatggagtc      11460 tcgctctctc gcccaggctg gagtgcagtg gcgcaatctt ggctcactgc aacctccgcc    11520
tcccgggttc aagtgattct cttgcctcag cctcccaagt agctgggact acaggcatgt    11580
gccaccatgc ccggctaatt ttttttattt ttagtagaga cggggtttca ccatgctggc    11640
caggctggtc ttgaactcct gaccttgtga tctgcccgcc ttagcctccc aaagtgctgg    11700
gattacaggc gtgagccacc gtacccagcc taaatggcca agttttatta tggacaatta    11760
agctgtagaa taaaaatcta cttttaatag ctggcatagt gcctagtggt tttgaagcca    11820
caagcaggtt tacaaaaaac atttaaatcc atctgaatct acagaaaact aagattacct    11880
aagcagaaaa tgaaaatagt tcaggattaa ggaagattaa caaatgaaga gtatatgtat    11940
tttagaagta ttactttata tttttatagt ataataataa tatttacgtt cctacactta    12000
taatgagttt cgtatatata ttaaaataat ttaatggatt agtatgttta tatttgcttt    12060
tagtaaattt ggtgtatgat aaactcagtt gtctacattg tgagactaca cctgaggcaa    12120
tttctgtgtt gatatatacc tgaatagcag atattacttg ggagcaaata aaatagcttc    12180
aggcctaatt ttgcaagttc atgatgggag agtaagcatg acttcaaaga actgactttg    12240
agttaaaact tgaagaatga atgtgacaac agcaagtata aaacaatgcc aggcagaggt    12300
gggactgttc atgggtatca gggtaagtgt gttgataaat gctcaaagta ggaaatacct    12360
ttcttccccc acacatgtca gaaataact gcaatagaat gcaacgacat ctcagagata    12420
aagtgttcaa cttagctctc agagaccgtt cagttacatt ttgtaatgac attggaattg    12480
attgcatttt gaaggcaatt ctaaatgcaa agtcttcatt ttgttgatag aagctggtt     12540 atttattatg aaatttcaaa aattaagtaa aatatctaat taggattata ccagcaaagg    12600
caaatttaga attcaagact tcatgatcca tggtaagatt attttaatgc aactctgcta    12660
attaactgaa atttcctta actctcacat ctgcctttta cttcttaaga cattttcta      12720 gtatttcacc agagcaagat atcagaaggg taaatctctt accaatgaac tttgctaatt    12780
cttagtgact ccgttgaccc tggtgtaagg atcaggaaca aagtgaatga aatacatttt    12840
aatacatttc tgctttctct aattccaaag accactctaa agaataagtt atttgtgggt    12900
attatctgaa acttgggatt aaaagagacc gtgattaccc ttcagggatt ttggcaaaac    12960
ttaagccatt tcatctgaag agcaaagcaa ggcctcccaca ctcttggctt attctcacaa    13020
ttatctagat atctagcaac aaaactcttg agtagtttgt taactacaga tgccaagggc    13080
tgacagtttc actttcagtt ttcagaatat cttttgtttc agtggtgtaa gcacaccatc    13140
agaatctcta ctatttaaaa taattaagtt ataattgtaa cttccattag atgtagtact    13200
```

```
taaaggaatc tagaagacac aactcattaa ttataggaat ttgactgcaa attcttctgg   13260
ggggtctgaa ttgcaaagga ggcatctttg taagtcagac tcaactcatt actctgtgat   13320
gcaggctcct ccaaatggca gcagaaacgt attactctct agaaacacta cagtagtgct   13380
acaatttcag ggttctgtag agataaggac aaattgacag aaacacattc ttagaaggac   13440
agtatcattt aaaataaaaa tactgtcata attgtacacc aggatagctt ctccataata   13500
aattctttat gattttctga tttttagaaa tcagaattga acttttaat gtgaaaaaaa   13560 tgagagaatt gtttcaaaat aggaccacat ttctgtgtat aatttaaaa gtttaaaaat   13620 atttgattag tagactgata aactgaaaca tttttgataa gcttttcatt acatacaaac   13680
catataattt gtaaaaaatt ggaaattatt caaaacttca cataactaaa gtgaccaaat   13740
aaatactgga gaggaaagaa aaggagtcaa atgaatctag cattttcttt tttttttttt   13800
ttttggagaa agggtctcac tgtgccaccc aggtgggagt gcaatggcac gatcatggct   13860
cactgcagcc tcaactttat gggcttaggt gatcctccca cctcggcctc ccaagtagca   13920
gggactacag gcatgcgcca acacgtccag ctaatttttt tggtattttt tgcagagacg   13980
aggtttcacc aggttgccgt ggctgatctg gaactcctgg tctcaagtga tctacccaac   14040
tcagcctccc aaagtgctgg gattacaggc gtgagccacc gcaccggcc taatctagca   14100 ttttctaaaa ggaaggaccc agcagtgaac ggcaatatca ataatcatgt tcaagactat   14160
cagacatgca agctggggat gaatgggtgg aaggggaaaa tgatgaataa atgatgaaca   14220
caagtataga cccagtggat ttgagatgcc caagatgcca gtgagatatt caaagtttaa   14280
ctcaaaagcc acttcccata tgaaatcctg acaaacactc ctacgtccaa ctggaattaa   14340
tttctcttct gggctcccac agcactctgt attttctaa tagcataaca ctattttgtt   14400
tgtagatatt tctctgatag cattactatc tttcctcttt atcacaactg tttgaagttc   14460
ttttgcctct tgcatccact gttgcccaat cccactgctg gaaggctcat cttattaagt   14520
tctgtattcc tagtgctaac acactgtcta ccatagatga tgttcaataa atggttgcta   14580
aatgaattct cttgtgataa tagcactatg gcaacataat cgacggtaaa aatttcttct   14640
caatgtttac ttttagcaga atgcattcat ttatcaactt tcattgagaa tatgctaatt   14700
tccatgaccc tgctaggaaa taggaaaata aagatgaatg taataaggtg ctcattctac   14760
tgaaagtctt gactagtgga gaattatgga tccaactttt catgaaatgc cttcagtggt   14820
aagaattctc atatttggaa taaaaaatgt tatgggttgt gccaagatac ctacatactt   14880
cataattttg tagagggctg tccttactgc agaaatgtat actactatag tcatatgtgg   14940
aaattctttt tatgatgcta actgcatgct aaccagactt tttaatttaa tacttgcatt   15000
aaataaacca tgctaggaat ccaggaatct agcttggttt attttccata caatgtactc   15060
tttgtaatat gcatatacta cataaaaatt ctattaatgg cctcgtacta aagatgtgtc   15120
tgttggggaa tcagttattc tgtataattt tatcttaatt gatatattaa aatctaccaa   15180
aaatataaac tccgagtaaa agtatctgca tggtgtgcat atgttttatta ttttaagtgt   15240 cagcgtatac atttcatgc cataaagtta taaaatgaaa aaatagtagc cttttatatt   15300
aagttcatgc ttatgtagtt agtaaaaaca agaaagcaat taacatacaa accatgatgg   15360 tggttaaaact tgcttcagtt tgtgtttttt aaaatttgaa agtgagaaat acagctcgaa   15420
gtcagctcat attttcagta agtactgatg aggatgtact ggcccttattg actacgctga   15480 ccccattaaa atatttgtga gtctaaaggt tcatatgacg ctgttccttc actctagcaa   15540
caggccatac atgtcttaca tagggactct gttcaattca ttaataccct ctgaagtgct   15600
```

```
caacatcgtg gttcatttat agtagatact caatacatac tccattaact gaattctaag    15660
ataaactgtc tgttactgac agaaattttc acttaaggga gtctccgtgg ctgaaggcaa    15720
ttttgaaatc ctgtaaaaga acccactcct ctccccaagt aatgaagttt gtcagtttca    15780
agcctgtaat aaggtactga cttaaaatta attttctaat aatacagtac tgctatgtat    15840
ctaatgtggg gttagtcaat gataggaaaa aaacataaga cagagtcaca tttaaaaatg    15900
tgtgcttagg tgcatggtga cacctgcctg tagtccagct attccagggg ctgaggcagg    15960
aagatccctt gagctcacga gtttgaggct gcagtaagcc actgcactca gcctgggcaa    16020
cagagtgaga ccctgtctct aaaaaaaatt cgttttaagt gtgctcagga cataacagga    16080
gccgctggta acatgccatt tccactgtga atatggtaag dacagaatcc ctgtctctag    16140
gccctcttcc actagtcaat ctcatcatca ccatcaaggc caacattggt attctctcct    16200
ctgagacaaa gtctttgaca ttttctatac tatactatgt cttcctctcc ccaaatgcat    16260
atacaaataa aatttgaatg cttctttctc catttagtgt aattttttt ataacataga    16320 cccaattttc aaaccccaca atggtggatt ttatttgatg tattgtaaaa agcgctggat    16380
tgaagtcaaa tggcttggga gacctaaatt ctactcctgc ctgtaccatg aaagagacaa    16440
atcccaaggc tttgcagggc ttcagcttcc ttgtttgtag aataaagaat tataaaatca    16500
tctcttttgg tcctactggg caataaaaag ctatgattct aagcctgttc cctttctca    16560 cctaagaata caaatttgat acaaagaggc cgcagaatgt gtcaaacact ccctgttgcc    16620
tggaattctc tcttcctttg ggttcaggga taaaggtatg ttatttctta agtctccctt    16680
tgctttcttc tgcttgcctc gtaaatattt ttccatcttg gcagtcctac atgtcttctc    16740
actctacatg ttttccctag gtgatgtgac ccagcctgtg gcttccactg ccatccacac    16800
acgtcgctgc ctctctccac atcagcatcg caactatctc ctggaagctt ccaagtgct    16860 gaactacagt aacctcaacc gaactgctgt tcattcaccc cacaggcttg ccctcctct    16920 gcatctttgt gagaacctga gagtcatcct aaaactcctcc ttccacctca ctccccacat    16980
caaatcgatt accaacttgt gctgatttta tcttcaaata ctctccagaa ttgtcgctgt    17040
catggactga atattttgtgt tcccccaaat tcatatgtcc taatccctga tgtgactgta    17100
tttagagacg tgacctctaa ggagtaatta aggttcagtg aggtcaaagg tggagccctg    17160
atctgatagg atcagtgtcc ttataagaag agactagagc tgggcacagg ggctcacacc    17220
tgtaatccca gtattttggg aggctgaggt gggaagatca ctcaaggaga ggagtctgag    17280
accagcctgg gcaacagagt gagactccat ctctacaaga aaataaaata gtcagacaca    17340
gtggtacaca cctgtggtcc cagctcctca ggaggctgag gcaggaggat ggcttgagcc    17400
caggaatttg aggctgcagc aagctatgat cacacctctg cactccagcc tgggtgacag    17460
catgagaccc agtctcttta aaaaaaaaa aaaaaaggc catatatagc ccagaagagc    17520
gtcctcacca aaacccaatc ctgatagcac ctggaggact tccagcctcc agagctgtga    17580
gaaaatttct gttgcttgca ccgcccagtc tgtggtattt tgctgtggca gcccaagctg    17640
actcatcagt gaccttctct ctgttaccgc agagtagctc atcatcctct cttccctaga    17700
gtccagccac tctctcacat ctacctacct agcagtatca ctgtgggtta gagtcagatc    17760
actgcggatt aagtcctcat tctgccactg cctgtgtaaa tctgagcaag ttacttaatc    17820
tctctgtgtg tcagtaacct ccctgtgaaa tgaggctaat aatagcaggg ttgtttcaac    17880
aaggcgatac atgcataatg cttacaacac agcttggcac attataagca ttcaacgaaa    17940
```

```
agtgagctac tattatctca tccgttatca gaataaacca cctaagccac aaggctgccc   18000
acatcatcct catgttttaa aacacttcag tgggctcccc accatcaaca ggataaagtc   18060
caagcttcct tagcatttct tagaggctcc atatgaatcc ccaagttcca ctacaggaac   18120
acaggtgaac tttccactcc aacctcaggc tccttcgtgt cactcctcat ccacatggag   18180
gtaagcagca agagactccg tgcagttcct ggtggttccc tgaccctcag gcagactctc   18240
cccagccctc tgcctgcaac gtccttgccc tttgcttccc ttggccagct cccattcatt   18300
ctccttgatt ctgcttggaa gtttccctct caggaaggct ttatgaacct tagtgtaggt   18360
tatgaaccca tctttgctcc tttcatacct tttgcaagcc tttatttatt atgacactta   18420
accattatca tactgaagtg acctgttggt gtgtctttgt tccccactag acagaaaact   18480
caagatcaga gaccagttct tgttcttttt tttttttttt tttttttttt ttgtatcaca   18540
gtgtttagca gcctgctata tggtaaatgt cagtaaatgt tccacaaact gaatggaatt   18600
gagctctgga atctagacca tcttttccat acccatcact cctgtcttag ttgaagtcct   18660
tatttcccat ttgaagcaat gcaaaggatt tcctaactct aatctctctt ttcttcacac   18720 catccttaa acagccgaca gaatggtcat cctaaagcac atatatccta tcttacatat   18780
cctagattcg gaacctctct gggcttctca ccatataaga agaaagtcta acctccttag   18840
caaggtgcat aggtcttcaa tgggctccac ctcacttctc tatatatacc tatactcttg   18900
ctacactaaa cttcttcctt actgttgctg gaacaagttc aacgcttca aacctccctg   18960 actttgcata tgcagttcat tctgtcagga atgcccttct ctcttatgcc tgggatattc   19020
tcattcattc catatgacct atttcataag tcactcctta atgaagcctt tcttagatat   19080
ccactggggc aatcagctgc ttgctcctgt ttccacagca cattgttcac acagatagca   19140
caggacttac cacaagttat tataattttg tctgtcttgc ccatttgaat ccaagggcaa   19200
ggacggaatc attctcatct ttgtatgtcc tgggaactag aactgtacct gagacataat   19260
aaacacttga tatgtttgta atttttaaat aagttaatga acggaatggc tagaaaaagt   19320
gagaagaaac tctggcttac tgtatatcat actgtcatac taaaaatata tactgaagac   19380
agaatcacat tatatcatca cttttcacgc tataggccat gatccattat gaaaagagg   19440 atagtaaaaa aatcacaggg cacaattttt gtttctgtca cacacatgtg tacctgtata   19500
ttggactgga atgtaaaacg catgttccat tgtagaacgt ggttttaaaa gaggcttgga   19560
aaacactgca tatggtcatt tcttagttta gtacaattta ttatttttcgt aataacctca   19620 gctataatat aagtctacca tgaagcattt tggggagatt aaatgagatg tgaaaagtaa   19680
atgtgttaga tagactgaat tcatatcata gcttgctctg atactttaca aaacatttaa   19740
ccttacccac aagttttagt ttcctcacta aagtcaccct gaggacagta atgggatctt   19800
cctcacagag tattgtgagg aatacataag agaacgtacg taaatgcctg gcacttagta   19860
tttattcaat aaatcttagc aatgatgatg ataacaacat ggtacctggc acataagaga   19920
gttaaaaatt agtttcttca gtcaaatgtg cttacattga tagttgatac taactggggt   19980 taaaggtca ttgctggcat ctcagaaaga tagattacag tgaaataaaa aatgactact   20040
gcttaaaatg aatgaagact tatttacaaa gtcatgttca tctggtacaa taatgaagtc   20100
gctcaattgg gagaaaatga caaataatac aagtgaatat acaatcttac ttaagacgaa   20160
```

```
agaaatagga caccaggcta actatcagtc tcctaaacca caactttatt tctgatacaa    20220
agagacagtg agacaatcag ggcttccctc aaataaatta cttaatctct cttcaattca    20280
gttttgcatc tgtaaatata aataactaca atttcacagt atttccattt aaaaagttct    20340
agtgcaacat cagaaacaag aacttagtag gtgttcaaaa agaaatataa gttctgcttt    20400
gttagccagc aaatagttgc ctgttctag ccctcacttc ttttctccta aatccctata    20460
ttgcatttat ttaacttaaa gtgctggatg tggcactacg agaaagaaaa agatatttgg    20520
taatcttgtt aaaatcatta gacatcccag gctatctgga atcaccttgg gctcacagtt    20580
agacatcagc tatggcttgt tttatttaaa aattcatcca ctgatgcatg ataatggaat    20640
tcacaggaga gcaatttacc aaaaaaaaga aatttattga tttataatgt gagatattaa    20700
tttagccaca aatatttatt gagcatctcc tacatgccag ggaatggact atatatggca    20760
ggaaaacaga taccaatcat ttatatcagg cattttttc taatagaagg atattcgcag    20820
gagacaatgc atagcaccat gccttgcacg taacagacat ttaataacta ttagttgaat    20880
aaaattggag actagaatga tacataaaga ggcaagaaag agcaaagata agcctttctg    20940
agaatttcta tcatgttttg ctcaatagct tgtctttatc cactgcttgt atttttccat    21000
gtagctaatc ctcattggtc gttagaattg agacacccct tccttgaaat caggagctat    21060
aggaggccat tcttcctact gggcatttc tttctgggac agggtctcac tctgtcacct    21120
aggctggagt gcatcatagc tcactataac cttgaagtcc tgggctcaag gaatcctctt    21180
gccaaagagg tgggattaca ggcatgagtc accatgccag cctatttggc atttctactg    21240
tagacaaagc agacttacag cagtaggtct acctgcctaa tacaaaaaga aaaaaaagaa    21300
ttttaacaaa caaatgaggg aatcagatcc agaaagtgat tcttataact tagattactt    21360
agagtagatc tataatctgc tctagatcca ctgcatacag tgggcccttc ttatcatatt    21420 ccataaaatag cacttttctc agcccagctt ttgatgatag ctgaacagac taacagtttg    21480
tctaacaaag gctagagaag gggatagcaa ataatggccc acaggctgaa tcctgcctgc    21540
tgctcatttt tgcaaagttt tattagaata cggtcatttc cactcatttt cacactgtca    21600
atggctgctt ttgcgctaca gcagcagagc tgggtggttg gggcaggggt cacatggcta    21660
acaaagacta aaatacttat catctgacct tttacagaaa gtttgctgat ccttggagtg    21720
tacaagtatt ctatattgtt gattaagaac agaaccacaa gtattagaag ttagaccagc    21780
aggtggtaaa gctgatcatc tactaatata atggaaattg gggttcccaa tcaggactct    21840
tgctttgata gaaggccatc ttaacgagga gggagacacc tgcaggcaaa gtcagaattt    21900
tctgcaggaa aagttttgag tccatttccc cttgtgaaca agtgctcagc tatgcatttc    21960
atctttagta accatgcttc tatacctggt tctccttggc aaagatttct ttcttcagta    22020
agtctcaaga ctttctggga aggtaggag atatgggggt aaaagtgtcc caggacttac    22080
tgaaggaagt gttttatgat tatctgatag aatcactgta tcatggtaga aaggcaaac    22140 agaatataat ctgaaaatag aggtgagggt gaacaaatgg gcactaaaag tgaactcagc    22200
atcaggaagg tagcaaaaca agacatcagt caaagatatg gggtgattca gacctaagga    22260
agatttaatg tgggatgttt ccgtgtgcca ggagctggac acttaagcaa gaggagatcc    22320
aggaatgttg ctaaaaccat ggcctccata ctttattgga attagcacaa cttatccttg    22380
tttctttcat tttgcaatca aaatcttttaa aaacacatta tttaaaaata cattatttta    22440
aaagctagaa tgaaaattat gatatcattt aggtggttta aaaaacatcc accagccggg    22500
```

```
cgtggtggct catgcctgta atcccagcac tttgggagtc cgaggcgggc agatcacgag   22560
gtcaggagat tgagaccatc ctggctgaca cggtgaaacc ccgtctccac taaaaataca   22620
aaaaattaac cgggcgtggt ggcgggtgcc tgtggtccca gctactcggg aggctgaggc   22680
cggagaatgg catgaacccg ggaggtggag gttgcagtga gctgagatcg tgccactgca   22740
ctccagcctg ggtgacagag caagactcca tctaaaaaaa aaaaacaaaa accatccacc   22800
aaaatgggaa gaagtgatga aaaattacag tccaagaaga agggccatag ctgtttaaat   22860
caattggtat atttgttatc taatataacc ccacgtaacg acaggtattt aacaaatgtt   22920
tctgctgaat ttgacgattc catttccctt acatcccata tgcaatccat cagcacccca   22980
catccaaccc atcagtacat cctgtcagca ttggctccca aatataacct aaatctaaca   23040
catatcctac tatctctgct gctacaactt tagtctgaaa tctcataatc tcccacttgt   23100
actactgtag atgactctga atgagtcttc ttgcttccat tccacacagc atccatactg   23160
atctattttt tttttcaatt ttttgtagag acggggtctt gccatgttgc ccaggctggt   23220
cttgaactcc tggcttcaag ggatcctccc acctcaacct cccaaagtga taggatttca   23280
agtatgagcc actgtgccta accctgactg atctttctaa gcataaatct aataatgccc   23340
cttccttgat taaacccttc aatgaattca cattaagcaa acaacctggc caggtgtgat   23400
ggttcatgcc tgtaatctca gcactttggg agaccaagat gggaggatca cttgaggcca   23460
ggagctcaac atcagcttag acaacatggt gaaactacat ctctacaaaa aatacaagaa   23520
ttagctgggg atggtggtgc acctatagtc ccagctactc gggcggctga gctggggaga   23580
tcacttgagc cctggaggtc aaggcagcag tgagctgtga ttatgccact acacttcagc   23640
ctggatgaag tgagacctgg tctccaaaaa aaaaaaaaa aaaaaaaga agcagggcaa   23700
ggtggctcac acctgtaatc ccatcacttt gggaggccaa ggcaggcctc ctggatcatg   23760
aggtcaagag atcgagacca tcctggccaa catggtgaaa ccccatctct actaaaaata   23820
caaaaattag ctgggcatgg tggcatgcac ctgtagtctc aggtacttgg gaggctgagg   23880
caggagaatt gcttgaaccc gggaggcgaa ggttgcagtg agccaagatt gcctggtgac   23940
agagcgagcg agactctgtc tcaaaaaaaa aaaaaaaag aaagaaagaa agaaagaaag   24000
aaagaagaaa tccttagtcc tgtcttaact acttgagagg ctgagggagg aggatcactt   24060
gaacctagga atttgaggct ccagtgagct atgacagcac cacggtgctc tggtctggag   24120
agagtgagac cttgtctcta aagaagagaa aagaaaagaa tgaatgaatg aacaaaaaga   24180
aagaaggaaa ggaaaagaag agagagagag agagaggaag aaaggaagga aggaaacaaa   24240
ataaaataaa ataataaata aataaaccca aatccaactt ctttacccta atcaacaagg   24300
ctcaaataat ctcatgccaa ctaagtctct gaacagctcc ttccattcta ttgccagatt   24360
actccatctt tcagccacaa gacctttta tcttcctttt accagccaaa cacaatccta   24420
cctcagaaca tgtgcacttt ttcttttctc tgacttgaat ctcctccacc cattatataa   24480
tcttagctca aagaggcttt tcttgacaac ttagcgaaag tatttatccc agtcattctc   24540
tgctacatta ttccaattta ttttctccat agtacatttc agcacataaa gatttcctta   24600
gtatgtgctt gttgcctttc cccaacctcc taaaatgtca gcattccttg agggcagaga   24660
ctgtttcatt cctgtatcat cagcacctaa gacagttcct ggaacatacc aagtacttaa   24720
taaaaatttg tttattgact agctatgaca catttttactt atataatttc attttctcag   24780
caaaatgaac acttttgaaat gtaattaatt actgattttt gcagtatttt ctaattattt   24840
aaataaaata tttactattt tggtcaacca gaattcttac attgttttag cacccagata   24900
```

```
gcttctaaaa atgcttacaa ttaacacaat tttatctagc aatatgtatt tatcactaga   24960
cagaatgcac tgaactcttc ttcattaata aaaagcaatc caggctgggt gcagtggttc   25020
acgcctgtaa tcctagcata gtggaaggcc gaggagggag gatcacttga taccaggaat   25080
tcgagaccag cctggccaac atggcaaaac cccatctcta aaaaaacac aaaaattagc    25140
tgggtataat agcagacatc tatagtccca gctactcagg aggctgagag gtgggaggac   25200
tgcttgaccc caggagattg aggttgcagt gagccgtgat tgtgtcactg cactccagcc   25260
tgggctacaa aatgatacct catctaaaaa aaaaaaaaaa ttagccaggc atggtggcat   25320
gcacctgtag tcccagctac tcaggaggct aaggtgggag ggtcacctga gcctggaagg   25380
tagagactgc agtgagccct gggtagcccg cgccactgca ctccagccct gagtgacaga   25440
gacccagttt caaaaaaaca caaaaaacag aaaacaaaac aaacaaacaa aaaaacccaa   25500
tgcattgctg aaatgttaaa tccattataa agaaaagtac aggggtgggc atggtggttc   25560
atgcttgtaa tcccagcact ttgggaggcc aaggtgggca gatcacttaa ggtcaggaat   25620
tcaagaacag cctggctaac acagtgaaaa atgcaaaata caaataagc cgggagtggt    25680
ggcgcatgcc tgtaatccca gctactcggg aggctgaggg gggagaatcg cttgaacctg   25740
ggaggtggag gttgcagtca gccaagatcg aactccagcc tgggtaacag agactccatc   25800
tcaaaaaaaa aaagtaaaaa gtatatagtt gattctgcag ggacttaaaa aagtataaat   25860
atcttttta acatcacaaa gctctgatat ctgcaggttt atgactaact actagctcac    25920
tcccatgaat acacgtatgt aaacaggctc tatacaatct acaatcccag actaagggga   25980
aaaaactgtc ctgtcactgt ggtctccaac ccttggccca tttctttcct cttgaccaca   26040
aaacttctca ggagttgctt gtttcctctt gatccactta tctttagccc actccaatct   26100
ggcatcggtt ctcagtactc tccactaaaa ctgcttttat gaaggccatc aatgacgttc   26160
atgctgccaa atccagcaga cacctcctgt tttctaattt tttttattgt tatttttaa    26220
gagactgggt cttgctctgt cacccaggct ggaatgcagt gatgccatca tagctcactg   26280
cagccttaac ctccctgagt tcaagagatc cttctacctc agctgggact acaggcatgc   26340
acagctatgc ctggctaatt actcaatctt taacatagct gataattccc tccttgaaac   26400
actctcaact tttaagaaac cctgttattt tcctcctaca tttttagcca gttcttctat   26460
cagcttctcc ttatctgacc tctaaatgtt aagaacatta acaaagactg aacctagttt   26520
tttttctcccc ttactgtact gctcctgggc gatgtcaatc agtcccattg ctttagatac   26580
tatctgttga aacactgaaa tcactggttt tttttgtttt tttttttttt tttttttttt   26640
ttgagatgga gtttcgctct gttgcccagg ctggagtgca gtggtgcaat ctcggctcac   26700
tgcaagttcc acctcctggg ctcaagcaat tttcctgcct cagtctcccg agtactggga   26760
ttacaggtgt gtgccaccat acccagctaa ttttttctatt ttagtagaga tggggtttca   26820
ccatgtgtcc aggctggtct taaactcctg acctcaggtg atctgccac cttggcctcc     26880
caaaggttgg gaaaagatat cccaatcttt ttcctatgat ttcttaattg atctacttga   26940
catatccact tggactttta ataggcatct caaacttaat gtgttcaaaa taaacctcgt   27000
gactttccct cccaaacctg tccctacctc cctcaataac taatattatc attcttatat   27060
tcatatattg aataaatgtt tgttcccccca agtatttgtt gctataaatt tatgaagaat   27120
tcttttctca ctagttatta taattaaaat gtaatattta ttttctttaa aaactttact   27180
ttgtaggatt attattttttt aaacagggac caacaataaa taacttctct acttgattaa   27240
```

```
aactagggct tcctcttgtg ctccctcagg actatttctt tgtaaaaaca ataggctaaa   27300
tcagtactgg tgtcaaagaa atcataatct cacaacttta taaatacagc atgtggcaag   27360
ggattttccc atcttatata gtaataaaat tttcagctgt gccatggcta aaagtttacc   27420
atcaaagttg gaattttaaa ttagaggtag tcatctttct ttcttttaa agaaatggag    27480 tctcactatg ttgcccaggc tggagtgcag tggctatttg caggcatgac cacagcacgc   27540
tacagcatcc tggcctcaag caattctcct gcctcagctt gccaagtagc tgggactaca   27600
ggtccctgcc accacaccca gcagaaatat ttagctttct gaatttctca agtgtgtgta   27660
tgaatgagac tagtggggtc cttaaccaag attcacagga tttttagtga tttattaaat   27720
aacttggatt tgtatctacc agcatgttct ttgaggtaca ggtatgtctt ttatatctcc   27780
taatatagtt cattacaatg ctaaatacta agatgtgatg ctcacacact acagaatagc   27840
caagcaaatg aactacttat tctcataggg ctattataat taacaaattc ttgtatcacc   27900
ccatcattat caacaacaac atgataggat ttccttttat cttgaagagt ctggaaaaag   27960
ggtaacagag agatatttct gaggaacaaa ctggtaatga gggagctact gtgtccatta   28020
caatactcct tctagaagct caatacataa tgactaatct ctggaaaaaa gcaagtgtga   28080
gaatggaagg ctcttcttca aactatgcaa aatgaatcaa tcagcagtga acaaatttat   28140
gagccaaaca aattcctaca aaaattacca tcatatgctg tcatgcatgt ctgccagtct   28200
atttatcata ttatttaaga aacaaacatt tattgaagat ttatcatgtg ctcagcactg   28260
ccaaagagga aataaagagc ataatatcta ttcttagaaa ataacattaa cacaaataga   28320
aaacaagaaa ccataatgtt aaaaatatta catagtaaca cagaaagaca atgtataatt   28380
atacatacgc actaaagcaa agataacata atttataaat tatgaggtac agaatagtta   28440
gattctgaaa attaaaataa tcaggaaaaa cttcatgaag atgagatctg gctggatcc    28500 caaaggatag gcaggtggat catgtagaac agggggaaagg agttcctgat cggggataca   28560
atatatgtaa aaactcggag acaggactga gcgtgaaatg ttaatgggac agtaaagaaa   28620
tcttcctctg cagcggggga aaaaacagaa taatgggaaa ctgcatggtt aaaaggtttg   28680
atgttaagat agtgcttgga cacaaaagat cttaaagttg agtcaaaaga gtacaatgaa   28740
agcattagaa atagaagata aaacacaatt aggccgggtg cagcggctca tgcctgtaat   28800
cccagcactt tgggaggcca aggtgggtag atcacttgag gtcaagagtt tgagaccagc   28860
ctggccaaca tggtgaaacc ccgtctctac taaaaataca gaaattagcc gtgaatgatg   28920
gctcgtgcct gtagtcccag ctatttggga ggctgaggca ggagactcgc ttgaatctgg   28980
gaggcggagg ttgcagtgag ccgacatcgc gccactgcac tccagcctgg gtgacagagc   29040
aagcctctgt ttaaaaaaaa acggtaaaaa taaataacat ttactattgt tttctgatga   29100
tatatatggc ctctaattgt aaagctgaat gcctagttta ccactttttt tttttttttg   29160
agacggagtc ttgctcttgt tgcccaggct ggagggcaat ggcacgatct tggctcacca   29220
caacctctgt ctcccaggtt aagcgattc tccagcctca gcctcccgag tagctgggat    29280
tacaggcatg tgccatcatg ctcagctaat tttgtatttt tagtagagat ggggtttctc   29340
catgttggtc aggctggtct caaactccca acctcaggtg atccacccgc ctcagcctcc   29400
caaagggctg ggattacagg cgtgaaccac cgcgcccggc ctatcattct tatttatgc    29460 attaggaaac taaggctcaa caagattaaa gctgtctagg gtcacaaaga ttgtaagtgg   29520 agggctaga attcaaaatg agacctgctt gactcctaag cctgtaccat ttctactata    29580
tttagagtga agtagatggg ttgaagaaat atttaggagg tgaaatttca aaagtgtaca   29640
```

```
gtcagaagag aagacatata tggaaaccta aattttcaca cagtaaagtg tcaataataa   29700
aggcataatg ccaaaatgac agaggctgtg catggtggct catgcctgta atcccagcac   29760
tctgggaggc tgaggcagga agatcacttg agcccaggag tttgacacca acctggccaa   29820
cacagcgaaa ccccatctct actaaaaata caaaaaatta gctggtaatg gtggtacaca   29880
cctgtaatcc cagctactca ggaggctgag gcattagagt cacttgaacc tgggaggcag   29940
aggttgccat gagccaagat tgtgccactg cactctagcc tgggcaacag agtgagactc   30000
tgtctcaaaa aaaaaaaaag gaagactcga gggctagaac cctgaaattg gaatgaaca    30060
ggactggctg aaaatgtttc ttgcacctga taaaaatctt gaagaagaat gctttaaata   30120
gataagaaag agagagagaga ggtgggcagt gagaggagac caccctaagt aatcagagat   30180
tacttacgtt ggttactcag gctggtctct gaatctgatt ataaatgaaa tagagattac   30240
ttaaaacaaa gggctgtaag gtagcactgt ccagcagcac tttctatgat ggaaatcttc   30300
tatatctgca ctgtccaata aggtgtagct gctagcacat gtggccactg agtacttaga   30360
atatagctac gacaaccgag aggctgaatt ttaaatttaa tttaatgaat tcaaacaaat   30420
ttatttttaa tacagcactt taaatttttat ttttaaattt taatctatta tttatttaga   30480
gactgggtta tgagactggc taattttttgt attttttggta gagacggcgt ttcaccatgt   30540
tgcccaagtt agtctcaaac tcccgggctc aagtgatcca cctgccttgg cctccccgca   30600
aagtgctgag aatacaggtg tgagtcacca cgcccggcct aaacttaaat ttaaatagcc   30660
acgtgcgggt agtggctacc atactgcaca tgcaactgta agatgtagaa gtcagatgtg   30720
agcaaagaaa tgacaagccg ttcaatgctg ttagagaatg aaattcaagg ttccaatgat   30780
ctgaacttgt gtcccctcaa attcgtatgt tgaaatctta atcctcaatg caacagtatt   30840
aagaatttgg ggctttagga ggtaatttgg ttttgagggt ggagccctca tgaataggat   30900
gagcacctga ggtagcctct ttgaccccttc caccatgtga ggacacacca cgaaggcacc   30960
atgttggaag cagagagtga gcactcccaa gacactgaat ctgccacatc ttgattttgg   31020
gcttctcagc ctacagaact gtgagcaata aatatctgct gtttataaat tatccagtgt   31080
aaagtatttt gttatagcag cctgaataga ctaagacaaa ggtggactaa ggcaggataa   31140
caggttagaa aaggaggcag ggcctttttt tttttttttt ttttttttgag acaaagcctc   31200
actctcaccc aggctggagt gcaatggcat gatcttggct cactgcaacc tccacctcca   31260
gggttcaagc aattctcctg tctcagcctc ccaagtagct gggattacag gtgtgcacca   31320
tcacacccag ctaatctttt gtattttttag tagagacggg gtttcactat gttggccagg   31380
ctagtcttga actcttgacc ttaaatgatc caccccgcctc ggcctcccaa agtgctggga   31440
ttacaggtgt gaaccatcgc gcctggccga ggcacagtgt ttttacagag aagcctgttt   31500
aaggtttaat catataaaat gtatgatatc cagtaagttt tgatataaaa aagaaacacc   31560
tggcgatttt atataatata ttgtgctaag gaattttaag cactctacat tctgctctct   31620
aagctctgta aagagcacca gggattttttt tttttttttt cttttttgaac agggtcttgc   31680
tctgtcagcc aggctggagt gcagtggcac aatcttggct cactgcaacc tctgcctctc   31740
gggctcagcg attctcccac ctcagcctcc tgagtggttg gaccacagg cgcatgccac   31800
tacatctggc taatttttttg tagagatggg gttttgccat gttgcccagg ctggtcttta   31860
actcctgggc tcaagcgatc ctcccacctt ggcctaccac gcatgcctgg ccacaacagg   31920
gattttttaaa tgtaagacta cctagtcaac tcttattcta tattaacaat atagacaaga   31980
```

-continued

```
aataacctct aagtaatctc tatttcattt ataatcagat tcagaggttc tcttatgctt    32040
tacaatattg tcctactgtg ggtagcgcaa taactaaggt aatctgaaag accagttata    32100
ttatatacta tagttaaatg catttcaact gcatgggaga aagcaactgt gttctttcct    32160
ctcaatttta acagaaggaa aattgtcaaa attagcttat ttagaatgtc ctatcagaga    32220
attattttga ttaaaatata ttttaatca ataaaatatt tctctttggt caatacttgt     32280
caatatagaa taatatctag ccacaaaatt aaaaaaaaaa cattttcccc tatattacat    32340
tcatggatct tcttgaattt ctgttatcta ggtgctttta aaagtcatat ttctgataat    32400
atgaaatcac agctccttt ctttggcata tttagttact gtattaagaa aatgtacaac     32460
acataattta gaatgggtaa ttattatatt ctctttattc ttatattgaa aatgacatga    32520
aaattaccag tcttcccagg taatataatt taagttaaag aacatctaca tactacaacc    32580
aatacccatt cccctatgtt atgtttggaa aaacatagaa gtatctttag tagtactctt    32640
agaaattatc ccaggttcag catattggta ttttatttcc aggtttaagt tacagtattt    32700
tgggcacccc aagtttaata aactattccc tgcagaaacc tgacaagtga agttgtggct    32760
gggaatatgt tagtcttcag ataaaatgaa ttgtttaaga atttgctaaa gatctcaaag    32820
catctttctt aaatctaaag aaagtcagga acaaagccac aaccaggacc atagcatcag    32880
aagatggaaa gttgctttgt cttcaaactt aaaaaacatt ttccatttta aaataatttt    32940
actatttacc tgtgatactg ttgaaaatta tgaaaaaaca gataatttaa aatttagtgc    33000
ttttttttaa aaaaaaaaa aaagcgaatc cctgggacac ttcatatagt gcaaaacaac    33060
aattcaagaa ttcaagcatt gaaagaaata atctcttatc ccccagtctc tgaaagggat    33120
tgcctttact actgttccca tctttatgtc catatgtacc taaggcttat ctcccactta    33180
caagtgagaa actattcagt atggcttagt cattttaat gcaagagaat aggtaaaaat     33240
gccaagcacc agccagagtt ttttctttgc agatagatgt gactcttaca ggagcagcag    33300
ggatttccca ctttgggcgg aaagcagcat ttaggtattc cccctccagt gcagttacag    33360
accaccccc cgtagaagct gctcctgtcc tctgtggcat gtcagcctct gattatcttt     33420
taataaacaa tatggcatat taagtctctt ttatgcccct ctttgtattc ccaggtacca    33480
cctccatgtc aggataacaa gaatttggta atgtttgttg aataaattta gcagaagttg    33540
aaagaaaaat cctgtttcta cagaaagata ccactggctt tggggagcc cgagttcatg     33600
atgaaactaa agaaagccac aaaagttcac ctcaatgcca agacatttct tgattttga    33660
aacccagtt gtcgaaccac ccatctatag aaacttgaaa gactaaaaac tatcttactc     33720
taaacatttt ctaggaagtt gattctacaa cacattttgg ttttccaatt tggcttctaa    33780
taattatttc aaagtttctg tggcctaaat tttgttttac attgatcctt tgaatggact    33840
actgttccca cattttagaa catttaaaaa gatatctaca acccgagtct aatcataaaa    33900
aaaatcagac agatccaaaa tgtggaacat tccactaaaa aaggagtggg gagaggtctt    33960
tattcttcca aaaatatcaa tgccataaaa gacaagacg gctatggaaa tgttacagat     34020
tgaaggagac taaagttaaa tgcaagaaag gaaaaaatgg catataggac agtattgaat    34080
tgactgacaa aactggatta caatagtaga gtatcaatgt taaacttgct gaagttgcta    34140
actgtatttc ttaggaatta ttcacctaag aatttaggca cacagatatg atgtatgtaa    34200
gttacccctta aatggcttag aaaaaaatgt gtgtatattc atttacatac gtatctacac   34260
acacgtgtat tagcggaaga gagcaaggca cacatgtgca taagtgataa agcaaatgag   34320
atgaaatctt tattttaaa tttaattttg taagtttcag ctttttaaaa ttttagattc    34380
```

-continued

```
cggggataca cgtgcagtta ttacttgggt atattgtgtg aagctgaggt ttggacctct    34440
aatgttcctg ttgccacaac agtgaacaca gtacccagca cgcagttttt cagcccttgc    34500
cccctccctc ccgctctccc tccttgcttt tggagttccc agtgtctact gttcccatct    34560
ttatgtccat gtgtacccaa gacttatctc ccacttacaa gtgagagcat gcagtattta    34620
gttttcttgt tctgcgttag ttccgttagg ataattgcct ccagttacat tcatgtcact    34680
gcaaaggatt tgatttcatt cttttttaatg gctgtgtagt attccatgtt gtataggtaa    34740
cacattttct ttatccactc atcaattaat gggcacttac attgatttca tgtgtttgct    34800
attgtgaacg gtgctgcaat gaacatctga gcgcaggtgt ctttctggca gaatgattta    34860
ttttcctgtg ggtatatacc cagtaatggg attgctagct cagataagta tttctatttt    34920
tagttgctct ccacaggggt agaactaatt tgcattccca ccaacggcgt gtaagtgttc    34980
ccttttctcc acggcctcgc caacatacgt tcttttctga tttttaatag tagccatttt    35040
gaactggtaa gagatggtgt ctcattgtag tttggctttg catccaaatg agacaaaatc    35100
ttaatgacag gtgaatctag gtaaaaggca tacagacgtt ctttgtgttg ttttttttaac   35160 ttacatttga agttattttc aaatgaaaaa taaaagcaag caaaaaaagg tcattcttca    35220
tctagtaaac tcttcaaaga ttaccacccc cttcaacagt ttttcctggt tctagtgagt    35280
cttctcccat ttgtttagat ctttgttgaa atgtagtctc agataaaaaa ttgtattttt    35340 atttcttttta catatttcaa acaatctaaa ttctttttaa atgaaactca ttaaaaatac    35400
tgcatttgtt tctaaataaa atggtagagg taatttgcac ctttcaaac agaagcaata    35460 ggagcaaccc agatgttcta gccacgatcc aagtcaacca cattcaatct aagaagtaat    35520
tgaaggctgt aacgacttct gtaaggccta caaaaatgag ttcagacaca agctctgctc    35580
agtaaaaatc tagtggcaga tgatatatac aatgatctga gaaaaggca gaatcaacaa    35640 aggttgtatt tttatctatt gctgcgtagc atatttcctt aactttagta gcttgaaaca    35700
ataaacattt attatttcat aaagtttctg tggtcagaaa tccaggagca gcttaactgg    35760
gtggatctgg ctcagctgta gacaagatgt cggctgggac ggccatcctt tgagggctct    35820
gagggctttg agggctgcac gatccaattg caaggtggct cactcacata ctaggcaagt    35880
tactgctggg tgctgggagg agaccttagt ttccttatcac atggacctct ccacagggct    35940
gctggaatgt cctcatgacc ttccccatag tgagtattcc aagacaggaa agtggaagcc    36000
acaatgtctt tcatgaccta gcctcaaaag tgacatactg tcatttacac aatattctac    36060
tggctgtaca agttaatcct atttagtctg ggaggggact gcataagggc atgagtaaca    36120
agaggcaaga atccttgggg gccatcttgg aagctggcta cacagaagag aaaacaccag    36180
gggagtgcga agaaggtgca attaaactca attccttggt atgccaatgg taagaaatat    36240
taggtgatct ctgggggtgta accttttttaa tttagttctt cactgaataa tctgaccagt   36300
aattgtaata caaaatacgg cactctgaca atattctctc cctttataat caattacaca    36360
ccagaatata tataaagaaa gacttacaaa gtcacaagta attgtttggt attattttta    36420
taatcacata ctagggcccct acaattagca ttcacaaaca tcactccatg ttggccagat   36480
aagtctgtct ttatagtggt ttaccatacg cgccttagca tgaagttaca tgtggtttcc    36540
ttagccatca gatgctccaa atgcaaaaaa tgtctcacca cagtcacaga atcatggaat    36600
cctaaagtta cctgggggttt ctgaaaatct catgggaaca actcacgaga attaaggctt   36660
aagaaagtga tttatcaaag aacaaaacca gcaagacttg agtttagaac tcgcagcaga    36720
```

```
gttgtgacta gaacctgttg aaataggcaa tgtagaaacc cagactaagg cacattctct   36780
acaactttac tatgcaagta tgcttagata ctccttagca aacagcaggc cttgagtaaa   36840
ttctttcaga actgaataca caaaggatac agaacggaat acactaacaa tagtgcatga   36900
tgtgctcatt tctgtaatag aaatgaatta attctgatcc atctataatt tattattgct   36960
ccatgattaa cggaaggcat aggaaagatg actggaatag tgtaactagt acaaacaagt   37020
attacacttg actgaacctc attacactgc aattgcatat tatatagtat gtaggtgaac   37080
aaatactggg ttagtcagtg gacctacatt tgaatactgg ttctgctcct agacagctgt   37140
atgatttgaa tgacttcttt atactttcat agtttctctg ttcttctctg taaaacaaag   37200
gcttagaaga tattatgggt tagattatgc cccttacaaa agatgctgaa gtcctaaact   37260
acaatacctg tgaatgtgac tttatttgga aatagggtct ttgcaagtga taagaagag   37320 gtcatggagt gacctaatcc aatacgacca gtgtccttat aaaaaaaagg aaatttggat   37380
acagatacac acaaacaagg agaatatcaa atgaacatga aggcagagac cggggcggta   37440
catctacaag ccaagggaca ccaaagattt tcagcaaatc accagaagtt aggaagagtc   37500
atgggacagg ttctcacagt cctcagaaga aacccaccat gtcaatacat cattttggac   37560
ttctagtctt cagaaccgta agaaaataaa ttttgttgt tcaagctacc caatttgtgg   37620
tactttgtta cagcagtcct agcaaactaa tacaaatgag ctcttaacac tggtctaaaa   37680
taggataatc ctatgaaatg ctacaaatgt ttgggaagat ttctcatact caactgttta   37740
cagtatacca caagcctgtc agttgaagat acaaacagac cctctataat cctctatact   37800
tatatgcaag gaacagcaca cttttctgc aaaaggtcag atagtaaaca ttttaggctt   37860
tgtgggccaa acaaggtttc tgttacattt tttttttata actccttaaa aatgtaaaaa   37920
tcaccctcat cccaacggac tacaggaaca gacctcaggt cacatttgac tcatagcctg   37980 accctggtg tgtagggtta acaagcctcc tttccctggg ctccttttc tttcagcatt   38040 ccaagccaaa ggaaactatc tttttcaaat cattttctct cctaggtggg acatcttaca   38100
ccagcccagg catgcttccg atagccttag agtagctgtc ccttcctcag aattactgtc   38160
taattggcta gaagttagca actttttaca tttttccttc aattcctttc cattaagaag   38220
aaggcatgca ccggcaaatt acttgtgact atcaatgaca tactctcaga agcaccagta   38280
cccctgtgtt gtttctaaac ccattctaat agacacatac cccaaggtta tgctgtttgt   38340
catctcacaa aatgacttac atctagagat ttaaataatt aatgtacttt tcataactac   38400
caggtacagt agatctgata atggcagagc taagcacata tacagaaagt agggcaaggg   38460
ccagagactc attttaaagc aatgttacaa gatcgtcact gttgcttttc attttctaa   38520 atgtggccac tgctgttttc tcactaaagg aaatgtttta tgtaaagtga ataacagtac   38580
ctggcataaa ataagtgctc aataaatgtt aaggccttct ctccctcttc aactggcctc   38640 ctcattttc acaaagtgaa atagaaaaac aacatggaag ataatcctgt tgcttaggaa   38700
aaataactaa agcttgctag acaaaataca cctgaaaata taggaagtga gctatagctg   38760
gcctatatgc atgtatgttg gaacaggaca agatagtgta gggtggggtg aagaggacag   38820
agaaatggaa ggaaagggc tacagccttg gtggcaaaat aaaggataag acgactcttt   38880
taaaatggtc tatttcaaat gctgggttgt gaaacttaat ttgattactt catgagaaac   38940
agcatctata atccatccct gattttctca caacaaaaat ttattattta ttttatgttt   39000
gtgtgtagat cttttatata tatacatgta cacacgtata tgtatatatt atatatgcat   39060
atgcatatat atgtgtatat acatatataa tatattgtgt gtgtatgtgt gtgtatatat   39120
```

```
aattttttta aaggaatggg gtctcactat gttgcccagg ctggacttga actcctgggc   39180
tcaagcaatc ctccacctca gcctcccaag tagcaaccaa cagttttagt tttgaaaaaa   39240
taacaaatat taaacaccca tgtgtaaggg ttggtactgg gccctgtgtt agtttgcatg   39300
ggctgtcgta acgtaacact acaggccggg cacaacggct cacgcctgta atcccagtac   39360
tttatgaggc caaggtgggc ggatcacctg aggtcaggag tttgagacca gtctgaccaa   39420
catggagaaa ccccgtctct actaaaaata caaaattagc catgtgtggt ggctcatgcc   39480
tgtaatccca gctacttggg agactgaggc aggagaatcg cttgaacctg ggaggcggag   39540
gttgtgatga gctgagatca ggccattgta ctccagcctg gcaacaaga gcaaaactct    39600 gtctcaaaaa caaaaaaaca aaaacaaaaa aaccctgata acactacaga ctgggtagct   39660
ggaccaacag aaatttattt tctcacagtt ctggaggctg gaaatctaag ataaagttgt   39720
tggctggttt ggtttctgag gcctctctcc ttaacttgca gatggctgct ttcttgaaat   39780
gtcctcacat agctgtccct ctgtctgttt ctggtgtctc cccacgtatc caaatttcct   39840
cttcttataa agatactagt catattggat tagggtccac cataaagacc tcatttaaac   39900
ttaatcacct ttttacggcc ctgtgtccaa atacagtcac attccgagtt ccaggggatt   39960
agggcttcaa cctatgaatt gggggtgggg cacaattcag cccgtaacag gcctagacct   40020
taatttgtca acactacagt tagatttata gtatagtaac tgcatctgtg ctcatctaaa   40080
tgtcataccc aaatgaaata atatagcatg atgatctgaa tttattaaag gcaatttttc   40140
ctatagaaac ccaaatctat aaattatata caaactgtgg taagttactc gataccttgc   40200
caggactcat ctatggtggt agatagacca caaagagtac cactgaaaga tcccttttcct  40260 aatcacagtt tcctcactgg cttgccacaa aacctaaaat tcttctattc tttcattggc   40320
aatttatttc ccctgaaaat gtaaataatc tctggcagag caatctatta agtgatcatc   40380
agccactaac accttagggt agaacagctc agatcacagt cttaaaataa attccatcag   40440
tatgaaattt tctttattac tgctccgcta ctggaatgtt agatcactgt ctgctttaat   40500
aataattctg gtgtaggtca ttcaaatttt gtttaagata ataagacaaa tagcaggtat   40560
aaaaacattc cgtcatctaa taaagcaacc cgagaacagt aagaagaacg tgatgaaatt   40620 aacattttg agtacctgct aggaatcaag tattctgcta gatattttag aaatcatctc    40680
aattcaatcc taaaaattat tctgtataat agtataggtt gagtattcct aatccaaaaa   40740
tctgaagctt ttttttttcct gagacggagt tttgctcttg ttgaccaggc tggagtgcaa   40800
tggcgcaatc ctgactcact gcaacctccg cctcctgggt tcaagtgatt agggatactc   40860
aactggctaa atataatgca aatatttcaa aatctgaaaa aacccaaatc tgaaacactt   40920
ctggtcccaa acatttcagg caagggacac tcaagttgta ttaatcccat tttacagaag   40980
aagaaacagg ctcagataaa tgaacatctc agagcttgtt gatagcaaag gagagattga   41040
aactgtcagg cctctgatcc caagccaagc catcacttcc cctgtgactt gcatgtatac   41100
atccagatgg cctgaagtaa ctgaagatcc acaaaagaag taaaaataac cttaactaat   41160
gacattctac cactgtgatt tgtttctgcc ccaccctcac tgatcaatgt actttgtaat   41220
ctccgccacc cttaagaagg ttcttttataa tttcccccac ccttaagaag gttcttgta    41280 attctcccca cccttgagaa tgtaatttgt gagatccacc gctgcccgca aaacattgct   41340
cttaacttca ccacctatcc caaaacctat aagaagtaat gataatccac cacccttgc    41400 tgactctctt ttctgactca gcccgcctgc acccaggtga aataaatagc catgttgctc   41460
```

```
acacaaagcc tgtttggtgt ctcttcacat ggacacgcat gaaagaaacc ctacctggtt  41520
ctgtgtctta cctgttgggg gcctgtggtc aaactactag tacggagttt tagtgtcctc  41580
actttaaaaa tgagggttgt ggccgggcgc ggtggctcac gcctgtaatc ccagcacttt  41640
gggaggccga ggcgggcgga tcacgaggtc aagagatcga gaccatcccg gctaaaacgg  41700
tgaaaccccg tctctactaa aaatacaaaa aaattagccg ggcgtagtgg cgggcgcctg  41760
tagtcccagc tacttgggag gctgaggcag gagaatggcg tgaacccggg aggcggagct  41820
tgcagtgagc cgagatcccg ccactgcact ccagcctggg cgacagagcg agactccgtc  41880
tcaaaaaaaa aaaaaaaaaa aaaaaaaaaa aaaaaaaaaa aaaaatgagg gttgtaaggt  41940
aactacctac ttttatagc attgtagtga agttgaaatg aattaatcca catatattat  42000
agtgtggtag aatgcagcag aactgatgat gtatgacttc taagactagt ccttaagaga  42060
cctgcagttt ttgcttttgc cctcttggaa cactcctgtt gccatgttaa gaaaaactct  42120
ggggagacta tgaaggaaga gagcatactc ggggcagggg ggtgaacagg acgtgcacat  42180
gtacgagcgt acaagccagg tgacaccagt accacagcct cagacatgtc accggggata  42240
ccagcaccac agcctcagac atgtcaccgg ggacaccagc accacagcct cagacatgtc  42300
accggggaca ccagcaccac ggcctcagac atgtcaccca gggacaccag caccagcacc  42360
acagcctcag acatgtcatc ggggacacca gccccatggt ctcagacatg tccctgaggc  42420
ccacttagac ccttcaaccc cagcccagct gctaactgac tacagccaca tgaacagaac  42480
caggtgagac cagaggaaac ttccagtcac ctaccagatc atgacaaata ataaacgatg  42540
tttttaaac cacaaagatt tggagcagca tttgttacac aaaattagac aactattaca  42600
gttcgactaa aaacatgttc atttacaata ctaaattaga agtgtaagaa tgggagaaaa  42660
acttcatact ttaaaagtca ttttttcctc caaaaacttc caactttgaa aaactgattt  42720
ttataatgca taaaaattaa aataaccta gaatttatat gagtagcata gccagctggc  42780
tttattatct gttgtactca acacttcaat aatcactgat gttttagaac tcttcagatt  42840
tagaactctt gcccttgctt tagtctggtt taagctaaat aattgttctt cctcaagaac  42900
aaatgacctt acctcgtttt gttttccttg tctgagagaa acacattagc agtctcccat  42960
cttgttttc cttttcctgt cacccaggac agagggcagt ggtgtgatca cagctctgca  43020
gcacgacttc cccaggttca ggtgatcctc ccacctcagc ctcccaagga gctgggacca  43080
caggcacatg ccaccacgtc cagcttaatt ttgtattttt ttggtagaga tcaggttttg  43140
ccttattgcc ccaagctgat cttgaattcc tgggctgaag caatctgcct gccctggcct  43200
ctccaagtgt taggattaca ggtataagcc accgtgcagc cttatatttt gttttaaatt  43260
ttcctctgta tttttctctc tggcaaattg tttagggagt ttctttagtt tatcagacta  43320
aatttcaagg ctttccttcc aattttgaca tgtaaacagt ccctcatttc tgcttatcta  43380
gtgattattc ccaaatctgt gtttacagtc tagctgtctc tcctgagatt aagacttgtt  43440
tctctaacta cctgacggca gaatctcctc ttggaagtat caaggaggca gttcaaaact  43500
gaactgggca ttggctccac tccttctcct tctctttact attaataccc tttctctcct  43560
tctatatgac cacactaagt cttatttagg catcgtttct tctgggagac ctttgtagaa  43620
tctctgaggt tatgttaaca tgctaaggtt ttccttgacat tctcagattg ggttaggtga  43680
acttttagca acttatcttt ttactaaaaa gtcatccctc agtatctgtg gggaattggt  43740
tctaggactc cctaaggata tcaaaatctg catgagcagc ccaggtgaga ccagcagaag  43800
cactttacag tcacctacag gatcatgaca aataataaat catgtttaag ccacaaagtc  43860
```

```
ctttacataa aatggtatag tatttgcata taacctacac atcttcctgt atcctttaaa    43920
tcatctctag tttataatac ctcatacgat gaaaatacta cgtaaatagt tgttatactg    43980
tattgtttag ggaataatga caaggaaaaa agtccacgcg tgttcagaat agatgctttt    44040
ttttctcgtc taatattatg gatccacagt tggttgaatc cacagatgtg gaatccatgg    44100
ataccaagga acgactgtat gcattttgac aattatactt ctcatcttac catgcattca    44160
acaaacagaa catgtaaagc ggtgataatg ctgtgatgaa aaataaagca ggggaagagg    44220
ctgcatccat ctagtggaaa cgatgcccct ttcaatctgc acaaagagaa aaagctgctc    44280
tccaagttgg ggggtgggtg ggtcaggtat gtaaattggt caggaaggga tctgtaggca    44340
cttacagatt tgacgctaat gagatgggaa gccacaggaa ggttgtgaag aaaagacaag    44400
acatgatctg attcatgttt tgatctgata cactggttgc tagatggaga ataagctgca    44460
tggcggtgag aggaagcaga aacaatagga gggtaatgct ataatccagt ggtccataat    44520
ccaatatccc cccaaggaac agttcggcaa tgtctggtga catttctggc tgtcacaact    44580
gttggggcgg agtgctactt gcatctagca ggtagaagct agggatgcta ctaaacatcc    44640
tacaatgcac aagacagccc ttcccccaac attgctggcc caaaacgttg atagtaccaa    44700
ggctgagaaa ctctgttata atctgtccta gaatgtagct tggattgaga tggcagtggt    44760
aagagctgga gaagtgctta gcttcccaat gttttttgt ttgtttgttt ttgagacgga    44820
gtctcgctct gtcgcccggg ctggagtgca gtggcgtgat ctcggctcac tgcaagctct    44880
gcctcctggg ttcacgccat tctcccacct cagcctcccg agtagctggg actacgggcg    44940
cgtgccacca cacccagcta atttttttgt attttttagta cagacagggt ttcaccatgt    45000
tagccaggat ggtctccatc tcctgatccc gtgatccacc cacctcggcc tcccaaagtg    45060
ctgggattgc aggcgtgagc caccgcgccc ggcctgaatg ttttttaaagt actggtgacc    45120 atattcgctg agggattaaa tgtaaggtat gaggggaaaa taggaatcag acaccagggt    45180
ttactgcctg agcaatgaga agaacgacgt tcctcatacg gagatgagga agaatgtgga    45240
atagcaggta aatagcatgt gcttgctttg tttggggctg tgcagaagag actgatggga    45300
ccaacgtgct cagttctgga tatattaaac ttggaatgcc tatttggcac caagtgaatg    45360
tatcaggtag gcagatggat aaatgagtct gaagttcagg ggagaggctg gggtggcaat    45420
atgaacttgg gagtctccac atctgaatag tatttaaagc tatacaacag gataaggtga    45480
tttaggaact aaacacaaat tgagacgaga tccgagccca gaggcactcc gatgttttaaa    45540 aaagaggagg aaccatcaaa agatactaag gagaagccaa gaagtaggag aactgagagt    45600
ctgagagaat cattatactc atttgatcga ctgcaacaaa tgctgcttag aggtcaagca    45660
aaatgaggac taagcaagga ccaccaggtc tggcaacatg gaggccaatg ccgacgtgga    45720
aatgagagtt ttggtgggaa gacaggaata aaagtctcac aggtctgaat tcaagagaga    45780
gaacagcaga agaagggtag aggtggtagc cataaacaat gatacattct cttgaggcct    45840
tttcttgcaa agctcagtga agaaacatgg ttccagagag ggattttttt ttctctcatt    45900
ttacatatgc aaacatataa aaaagctgaa agaattgttt gacaaccacc cttattctta    45960
ccacagattc aacatttaat gccatatgtt ttccctgtat gtactgtgta ttgtttgagg    46020
ataacttccc ctctaaatat acctcggatg tatctcctaa aataagtcca ttctcctaca    46080
tagccatagt aaccatgaac acacctagga aaattaaaaa tatattctca aatatattat    46140
atagctgggt atattacaat ttccccaata tgtgatttgc aaaccaggat caagtcaaag    46200
```

```
tccatgcaca gcatttggtt gtcatgtgtc tttggtctct attaataatg atgactgttt    46260
gaaaagacct gtcctataga ataaatttga ctgattatgt catgccattg aacttgtttt    46320
tctattctag aaggatagtt ttttagggta gtgaatacat ttattactct tggcacaata    46380
gtctaacatt tcccaatttc cttatatctc tgcccttttca ttttcagaaa atcaattatt    46440
ccaagatttg ttttttcattt atcatcactt attagctctg aagactcaac tgagcaactt    46500
tcagggttta tatacccctat attcagaaaa aaactactac catctctcat ttaccctaag    46560
aattcatagg agagcatgtc ttaaagctga tcaataacca aaccaaacat tttattgatc    46620
atattacatt tggaaagcaa aatgaatttc ctaaaatttc ttccctgatt agcaaaatag    46680
tgcctccgaa cacttgaggg tgaaagttgt tgtcaaatat gcctacatga ctggaaatta    46740
tgacatccaa atgagttcac tgggtctgat aataatatgc tctacatgct tatgtctatg    46800
taataaacag cttacatctg gatgagaaaa ttgattatac aaatatttgg gcttctacaa    46860
ctggtcactc atctgtaagt acttaaagca acttaaaatg caaactgacc taacaatgct    46920
tatggttaga attccaaaga atgtttaggc attgtcaggt tatgttaaaa catcttctgc    46980
cacaatcttc aagtgattta tcttttctgt tgtgttgaat agctatagaa gacaaatgaa    47040
ttctgcactc ctgaattcaa tgaacatttc aagtttcctc acttacactg taagattacg    47100
tagcatattt taagaaataa attataatca ttttatttca cttattgaac ttcttttaag    47160
ctttggcatt agaattttaa tcaaagcact gccacttgct tacagtgatg ttttttaggc    47220
tctttgggcc tatggactat ttcaatgacc ttcactagcc atctagtcca ccttatccta    47280
attattacca ctgcaaaaga aaccctcact tgaataaatc agtagatggg catgaggcac    47340
ctcccaggag actataatta ttaactcata ctaaaatcaa aattgtagct attatcactc    47400
atatggtttg gctctgtgtc tccacccaaa tctcatcttg aattgtaatc cccacgtgtc    47460
aaaggagaag cctggtgcga aaggactgga tcatgggggc ggccttcccc cttgctgttc    47520
ttgtgaaaga gttctccgat ggtttaaacg catgggactt cctcctactt gctcgctctc    47580
ttctgccacc atgtaagatg tgccttgctt cccctttgcc ttctgccatg attttaagtt    47640
tcctgaggcc tccccagcca tgcagaaatg tgagtcaatt aaacctcttt tctttgtaaa    47700
ttacccagtc tcaggtagtt ctttacagca gtgtgaaaat agactaatac aatcacctta    47760
tggtaagtct gtctataaat cacctgaact ttcacagact atctagaaga acatgtaacc    47820
agagtagttc ttgatcatgc tatataaatt actgatacag aaatagagct agacaggaag    47880
gggctggtag tagagaatca tcctctggac atattctcac agcctaatct ctagctagca    47940 aatttttataa tatatataaa aatacaatta tttcacaaaa ttaccatgaa acgattttat    48000
tgggatatta gacattactg aattacttgt tctgtgaggt atacagtgaa attaacatgt    48060
tataaaattg tggtagccgg ccccccaagat ggcctccaat gaatccttca cctcttggta    48120 ttcataccttt tgtgtaggta ggtctgtgta acccatagaa tacagcacag tgacagtagg    48180
tcacttccga ggttaggttg tgaaagacac tgtggtttct gcctctctct cagatcacgt    48240
gctctggggg aaaagccagg tgtcattttg tgaagacact caagcagcct ttagatgact    48300
gcaaccacat aagaggctcc gaactggagc cactcagcta aaccactccc agattcctga    48360
ccatgtatca tttcatacac aatgtatgaa atgacaaatg tctgttgttt taagctgttt    48420
ggggaataat ttgttacata acaaaatata actaatacaa taatacatac tgatttaact    48480
gaagttgtaa cttcataact tatttaggta ctaaaaatca cagcaacccg atgcaaagta    48540
ctaaaaaaaa aatccattaa tacctattga gtactgttga gggcatgagg aaagctcttt    48600
```

```
catactccac ataaaacttc cttaccgtaa tattcatggc tgacctctac tcttaactcc   48660
tttctaggat aggaggggct aactgatctg acagcaagtt tgggagaaaa aattctgagg   48720
ctcggccaac ttcctctctt ctttccattt gggatttggc tgactgaaga gggtcatttg   48780
ttttggcctg ctctcttaca cagtaaatgt agtgggacaa gctctattct tgttgataga   48840
aaaactcgaa ttttaaatct gcctagttct ttgcagctcg ttgttgctcc aaatctcagc   48900
tacctttga aacaactttt ttcagtaaac ttaatttcaa tcttcatgtg atttaactgg   48960
atccaaacac aggcagataa aaaaggtggg gcattactta tcaacctcta aactaagttt   49020
aattttgtgc cctcatggag tttatagtat atttgaggtt taaactaaaa cacctggttt   49080
taaacagaaa ctataaaaaa cacgattaat aggtgaggcc gggcgcggcg gctcacgcct   49140
gtaatcccag cacttgggga ggccaaggcg ggtggatcac gaggtcagga gatcaagacc   49200
atcctggcta acacggtgtg aaaccccgtc tctactaaaa atacaaaaaa ttagcccggc   49260
gtagtggtgg gagcctgtag tcccagctac tcaggacgct gaggcaggag aatggcgtga   49320
acccggaagg cggagcttgc agtgagccat tgcgccactg cactccagcc tgggtgacag   49380
agccagactc cgtctcaaaa aaacaaacaa acaaaaaaca aataggtgaa aggccgtgat   49440
cattggtaag cgtaagaaaa tctgagggag aaaaaaatat agatgcccag gccccatgcc   49500
aaactcatgg aatcatgcat gaaacccaag cagctgcagt tttaacaagt tcccaatata   49560
tagttgaccc ctgaacaatg caggtttgaa ctgcctgggt ccacttataa aatggatttg   49620
attttttca ataaaagtta caccgagtgt gcctgcctct cctccctccc tcctacatg   49680
ctcctgctct taagcctctg ccatgaggct taagacagca agaacaaccc gtcctgttta   49740
tttcaatagt tttggggggt gcaggtggtt tttggttaca tggataagtt ctttagtggt   49800
gatttctgag atttagtgc aactgtcacc tgagcagtgt acactgtatc caacatgtag   49860
tcttttaacc cccatccaac cttcttcccc aacccgaatc cccaaagtcc actgtatgat   49920
tcttatgcct ctgtgttttt atagcttagc tcccactttt aagtgagaac ataccatttt   49980
tggtttccca ttcctgagct acttcactta gaatactggc ctccagctcc atccaaattg   50040
ctgcaaaaga tattatttcg ttcctttgta tggatgaata gtattccacg atgtacataa   50100
acatttctt tatccactca gctcctcttc agtctactca atgtgaaggt gacaaggacg   50160
aagatcttta tgatgatcca tttccactta atgattagta aatatactta cttttcctta   50220
tgattttctt agtaactttt tttctctaac ttactttatt gtaagaatac agtatataac   50280
acatatgaca tacaaaatac gttagtcaac aatatatgct atcagtaaac ttccagtcat   50340
cagtgggcta ttagcagcta cgttttttgg gcagtcaaaa gcatgggaa ggagagggtg   50400
gtccctaacc cctgtgttgc tcaagggtca attgtaataa tacccatttta gaatccatg   50460
gtatatatgg taagtgcaac aactctagaa gagagtgcta ggagttggaa aaggaaagag   50520
aaaacagaat ttaaagcaat ctgtaaagga catgcagggt ttagatgagg tggaagggtg   50580
agggaaaacc aacatctgct gtgagggcat attaactgcc agacattgtt ctatgtctta   50640
cctcatttaa gagaatttca tttcacacat ggaaaaactg aagcccagag aggttaaata   50700
atttgcctga ggccaaaatt agttaaataa cagaagtggg attagtagat gttttcattt   50760
tatcagtgaa actgagcctc agggaggtta aatattttgt atgaagtaac aaaactgaga   50820
ttaatatatg gccaagttta aatgagatct gtaaatctaa tgcctacact aaaacaaaaa   50880
aaaaaaagtg ggaagaaaag gtctatattg cttagcaaaa cagaggtagg gaagcaaaaa   50940
```

```
taaacttaca aaatcagatt agaccaccaa aaaacagtcc ccattttaac ttatgtggtg    51000
agaaccatat attaaagacc accagtggct taaaaatctt tttaaaaaat gaatctgttt    51060
tcattattca ttagttttta tctaatgaat aatgtatctt aactgataca tttactaaac    51120
aattaccagc tccaattagc actcagttac aattcaatca ttaaactgac cctcaattta    51180
gctgtcaacc tagtcaaaac agttaagtga ttttacggtc atcctcagtt gcagaagtat    51240
aatgtttatg gctggagtca ttttattttt aactaacatt ttttaaaaag attgctttgt    51300
aacaatgtgt tatgagtcct ttgtggtaaa tactgctttt tttttgagac gcagtctcgc    51360
tttattgccc aggctggagt gcagtggtgc gatcttggct ctgaggctcc tgcctcagcc    51420
tcctgagtag ctgggactac aggcatgcgc caacgtgccc agctaatttt ttgtttttt     51480 agtagagatg gggtttcacc atgctggcca ggctggtctc gaactcctga cctcgtgatc    51540
tgcccacctc ggccttccaa agtgctggga ttacagctat tttaaggact ttttaaaaag    51600
tgaagctaaa catttattca tccctattcc tcatctatag ggacttgtgc tctattttc     51660 tttgaagact gaagtaaaaa ttcacctttg tgagggtctt cctataatta aaattaatca    51720
ttttttcctc catagcttct acaaaacatt gcctgtacaa ctctatttag cacttatttc    51780
atcccgcctt gtatgaaaac tatttgttta caaacgtttc tacttctctt taggaataag    51840
gactatgcat tattcactgt tgtattctcc ctgcatttat ggcagtccct tgcacattaa    51900
atacaagctt tttggctctg tgcatctctt catctggctg ttcatctgta ccctttaaaa    51960
catcctttat taaaaaaaca gtaaatgtaa aaaaaaaaa aagccattga tgaaaaagtt     52020
aatagctttc tcaataagaa aagagtatca attatgcata cgtctgaact aacaaacatg    52080
aatgaaatag gctatttaat acattctgtt ttaaaagtag gtttggtcag ccatgtaaat    52140
tgaaaattgg gagccaccaa gataactcat caacaaatat gcactatgta ctaggcacta    52200
tatagatgat ggtgaaccaa acagatgtaa tccttgctct tacagatctc acaacctact    52260
atggggccaa aaatatatgt gtatgtgtgt gtgttataca tatatacaca cacatacatg    52320
tatatataca tatacacata cacatatata catcgcaca catacacata tatacacaca    52380
catacatatg ctatgaggaa aacaaacagg tggtgagaaa gaattagagt aggggtagag    52440
gacagagggc tcctcaaata gggtggacag cttgacacaa gacactcgag ctaagactcc    52500
aaggatgaga agacagttat gtaaagaaaa ggggactagc attgtcagca ggtagctaag    52560
gccttaaagc agacagtcat gtgctgcaat gccagcttca agcgaataca gttactaaag    52620
catatctaac cttctatgtg aatgtagtta ctaaagcata tcctccaact ttccattttt    52680
cttttgctat tgtttctacc acttctcctt ttctgttgac aattatttta aatttcctgg    52740
ctaaattaaa tgatggcatg aactctgggg aaagtaagac tacctatgtc caaataatcc    52800
taaattcctt ctagtcctta tgactgatca attcaccctg aagtgacaac tatgtcccaa    52860
ttaggaaaga gtgtttcttt atctgcactt aattttttga tttggaggct tcctgattgc    52920
taatcaacat gttgtgtgat tacttcaaca agtacttata gaacgttatt ttgtcactgg    52980
aaaaacgttc tgctgctttc tgaactttag gttgctctag agtctaggaa gagtgactgt    53040
acctaaagca gttcctaatt actggacatt ctcagatctg ctagagctac atgtccaatt    53100
acgagaatat actggaaaaa gccctggatt agaaatgaga ggatgtaggt tttagtacca    53160
ggtcagccac cttgttaatg caaatttgag taaattgtta cttcttttag gccttgtttt    53220
tgctgttttg ttttttctgac agtatggtct ctgtggtcca ggctggagtg cagaggcaca    53280
atatcaggtc cctgcagtct ctacctccca ggatcaagcc attttcatgc ctcatcctcc    53340
```

```
tgagtagctg ggattacagg catgtgccac cacaccctcg aactcctgac ctcaagtgat   53400
ctgcttgcct cagcctccca aagtgctggg attagaggtg tgagccactg tgcctagcct   53460
tacacattgt tttcttactg gtaaagtggg aatatctaga agttgcatgc tacataaatt   53520
caaccatata ttattggcaa aaaatttttaa agaaaaacat cagcttaaga gtactaattg   53580
agtacatgcc ttggaatgag catgagctgg aagaacaaa cctgttgtta catcactcat   53640
tgctgttttc atatgctgct cattgtaaat cttgctcagt ggcatgattt tagtgtttaa   53700
agatttattt gtttgtttgt ttaggacaaa gtctctacac ataatctact tgcttcatat   53760
atacatactt atgcatatta tgtatgtaca tacatgctct cagggctcac atgaaaaaac   53820
agccattcag gtgatgtgat ttatctcata tgcttacttt agagtcaaca gggtgttgac   53880
tccactatac aatactggca tggagaacac ataagtcaaa gtagacagga cccagccgta   53940
ccattggcta gggcacaaat atattccat atgtggagaa tgatgtacgt agaaaggtct   54000
tcattgcaca atgctcttta ataaagatct ggaaaaaaaa aacacctaaa tgttcaaaag   54060
gatagggtag atgaaataat ggtacattat aaaatggaag attatgcagc cataaaaata   54120
aggaaatacc ttaaataata acagaacaac ttttaaggta agtgaacaaa taaggtacat   54180
aatcactatg catagtatgt accatttaca tagaaaaagg gaagaaaaat aaaatatata   54240
tagtaattta tttgttctta catgtgtaaa attttctga aaaatatacc agaaactggt   54300
agcactggtt gcttcctagg cagaaaatga ctgagtatcc ttttgtacct tttgaatttt   54360
gaaccacgtg aatgaatgtg ttacctatga acaaaatgac aagtttagat cagcaagaca   54420
gcagtttgag atgaaatggg attacaccct tagtaggaaa aactttttaa agcaggtggt   54480
acttctaaga gcaaatacct gcacatgaa tgttgaaact ataaggaact ctccttaaga   54540
gatccatcta ttccaaactt ctcatttat agatctgtaa actgagacct taaaaattca   54600
gtgacttgca taaggtcaca cagcagaaga gatgggatta gatgctagat attccaatat   54660
caagtttaga ctattaaaaa ttcagtgact tgtgtaaggt cacacagcag aagagatggg   54720
attagatgtc agatattcca gtatcaactt tagactatta tcacaccatc ttctcatttt   54780 ctggggggcaa aacagaacca agtaagtttg ggctacatta cgagttgtca tgttttttgt   54840 tttgttttt tgagatggag tcttgctctg tcgctcaggc tggagtgcag tggtgtaatc   54900
tcagctcatt gcaatctctg acccccgggg ttcaagcaat tctccctgcc ttagcctccc   54960
gagtagctgg gttacaggc gcctcccacc gcgcccggtt aattttttgta tttttttttt   55020 tttttttag tagagacggg gtttcaccat cttggccagg ctggtcttga actcctgacc   55080
tcgtgatcca cccacctcag cctcccaaag tgctgggatt acaggtgtga gccaccacgc   55140
ccggccgagt tgtcatgttt tatctaaatt ttagagtcta atgtataaat taaccttaag   55200
ccctgaaact actaatttct tgtttggatc actatacggc tacacttaaa aatatgctgt   55260
gcatacctct atcattgcat gtatacaata tgatagatgc atgatatgac agacacacaa   55320
tatgatacac gtatttttt ctatcctaac acatctgaat ttactgaaat aactaaaatg   55380
tcttaagtta ctttttaaa tatacacatg catagcacaa gcgtgttgcc aaaaatatga   55440
atacaggttt acaattcctt aactaaaacc caagggttgg atgtgtttta gaataagaa   55500 tttcatacaa ttttttaagtg ttacagggta tataaaccat tatataacac ataccagggg   55560
ccaagggcag cacccccataa tcaaacatat taatatagtt tcagcaaaac acatgggata   55620
aagactatat acagcttctc aatagttcag gtcatatttt gctaccaaat gaattttgtt   55680
```

```
gccaagctta agaagttttt ggttttcacc gctttctgaa tgttagattg agatgtggga    55740
ttacagactg tactcataga gtgcttctag aaagcagtca gtcacttcaa ctctcatttt    55800 tttttttatga gactaaaaaa gaaatcatag caagtagctt ttatatccca ggtttgggcc   55860
aaagacttgt attgtggtta aggaatctaa cttagtagaa ggtgcacgag ctgacatcgt    55920
gagtggctaa aatgagagaa aaaagagaa aatcctaatc atacagaagc actgaactac     55980
tgcagctgtt cgttagttat taatttaata aaagcttcct ccctttaaat catgtgagtt    56040
tataactgga aataggtcaa taaaatttct gtcccacact gctgacaagc gatggacgca    56100
attagcttta atcccactgg aaggtactgc actctctctg ggaccaggat atgtagaaaa    56160
aagcatttca aatatatagg aataaccaga aatgtataca gtattctcaa cttgggaccg    56220
ttactctata atataaacga aaggggtttt ctagtcaatc tctgctgatc tcctgtacca    56280
aagttcttcc ctttataagt cttgtactac cttttacaag aggaaaaagc tctagagcga    56340
aaacacagaa cacactaaaa tcccttcctt tctctttaca actcaagccc cgcctccatt    56400
ttgtttctgt tactaatttt tcttctgaaa aaataccaaa tttacactga aagactaaaa    56460
ttcaactttg cagacaacgt tttaaaaaat acaattcagt ttggtgatgt tgttttgcag    56520
tcttacaatt ttagctacat tttaactgaa ccaattgttt tgttcaattt atgagttaat    56580
actcagcaag tttgtttttt acaaatagtg tattccattc taaaaatgga agtagcagtg    56640
gtgaacaaga aaacaaccct ctgagttttg tctatttcag gaggaagtac tactttctcc    56700
aattttaatc acaattcata aaaagaaaa acctaactag ctagatctta aatatacaaa     56760
tacattaaca atctagtaaa gcaacagaaa aaggtaaaca aactaaccag cctatttttg    56820
tctggagaaa ccccaacaaa ctgctggatt ccttggccat ttgcattcag aagtaccaaa    56880
aactaaaatc cttttttacta ataatttct tctacacgag acttgtttcc tccacaccac    56940
cctatccaaa ttgtcagcat tattccagaa tataatcatt tagtttgaga ccactaaaaa    57000
accccgcagt ccaaaatacc aattgtggtt tttctgtaaa gaaatggtca gaaactacaa    57060
attgttatcc taggacacag aaccaatcga ccaaaaggac ttctggaata tgctgccccc    57120
aagatttaga atgcacaggc agaaatagca tacgcggtca cgatgtccct taagccacat    57180
gaccttccta cgaaagcaaa ggcttaaact tatcaaatga gaactccccc tttctctgaa    57240
gttaaaacaa ggcagggcag ctggaattag agcagcaggg acagatcggc tgttgactag    57300
tcagaacggg tcgtggaatg caaagtccct gcgctttcgc tgctccccct accgtgagaa    57360
gatctgggag ggaggaaagg aggagaaaca ccccagaatc ctggtagaaa agcccctggc    57420
ctcgaagatg ggctctaggg agacaggag gggcagctcc gtgtgtgatg accctttgtg     57480
aacatgcact ctgtggcagc ttcagctcca ccgaggcttt gggagagcgg actacggatg    57540
cccggcgcgg cccagctgtg aaggccgcgc cggcggagag ggtccatggc accccgccg     57600 gcttcggaag cccttccctc tcccacctcc gcggtcacc ccaggaacca gcggctcccg     57660
accacgctcg cgcggaccac ggaacagcga cgcgcaagca ggtctctttc gtcagcgtaa    57720
tccctccgca gaaagccgcg cactagtttt aatcacgccc cacccctgg ccgctggcgc     57780 cacctccgcc actcgggcgc tttccagcag cttccagaaa cgtcgcctcc ccaaacccag    57840
ccactcacac atggcgggct cagcagccac cggcccgcc cctcctcgtc gccgcagtcg     57900
caactgcgtc tgcggccaca gggcggacag ccacgcctct gcggagggcg accggaagtg    57960
ctcacgtctt caccttcccc gccacgccac cgtccttca ggcccagcgt gcagcaggaa     58020
ggaggactct tttgccgcgg actcaagccg gaagccgcct tcctagtgga gacgcgagtg    58080
```

```
ggggaggagc agtccgaggg gaacgtgggt tgaacgttgc aactagggtg gagatcaagc   58140
tggaacagga gttccgatcg acccggtacc aagaagggga gtgcccgcgg caggtaaggg   58200
agaagaggga ggggtttctt tccgctctcg aaattgggaa aagagacaga gctgggatga   58260
cctatgggt agtcggcgcg ctgaaaggat gggctgggct gggacggggt tcaagtggga    58320
aaggttgatg attaaggtat agagttggac ttacagatcc gtttgggcgc agagaggtga   58380
acgctgaaga gaaaccagag tttgttttcg ttttccaagg agcgtggaga tgggcagggt   58440
taacggaccc tgcgcctcct tcggcttctt agtttgggtg ttgaaactca cctcctttgg   58500
tcctgttcgt ctctgattca agacagttgg gtttggtacc tgacagggct gggtgcagaa   58560
agctgaccct gttcctcggc ttccaggtcg gttgtggcct cgcttttgac agttcacgtg   58620
ccgagcctac tcgctctcgg agggcgagct caaatggtg ggtttaaggc cccctcttcg    58680
aacagctgtt tccctgggtt tctccatttt gcacacagga gtgtgaatta agtttaattg   58740
aatacttttt gcgattccca gggccacctt gacacgttca ttgtgctatc taactgggtt   58800
catgctgggc taataattca cattaaggct tctggagtat aagtggttca cagaagtatg   58860
aaaagggat gttagaagaa agatgctggg ggtgaagtag agttgaggaa gacagaactg    58920
gaaagctagg ttggtttcac agtacaatga gctttaggtc ataatactac ctttaggtta   58980
tattgggctg tttggacgga gtttgctgta atcaggctag agtaaataga gaattttaaa   59040
ctaagcattg acaggctcag acttgtagag gcatcatttt gacagtgata tggaagggaa   59100
agaggtagag atttgagacc tttccaaaga actgtccaca gaatttggtg acttactgtg   59160
cgaagaggga aataaagaat agggaacaac tcaagacttt ctagtctgtg tgtttggaag   59220
gatggagacg cccacattta agtgagatat gggaaggagg agcagattgt ttttgaaggg   59280
aggaagagca gttacttagg gtcaaattaa gttgtaaaat cccccccggg attttgtatg   59340
taagtcaaag tgaattgtat ttggaagaag aactggggag cccacctctg gtattttttt   59400
tatgtccctc atatggacaa ataaacctct ggtattaaat gaattttctt ttgggggatt   59460
ctatatattc gggatttcaa ccaccaacct atctggtttt tcccgctgaa atgttgggtg   59520
atggaatcag gagagcagat ttggagactc tttatatttt ataattgaga gagacaaaga   59580
gaaaaccgtt tgatttgaaa aagttttcta ggttccctca ggtagatgga aattttcatc   59640
aaaaacagtt tattcaaggt acatagccta ctagtttccc atttgagagt accgcagaat   59700
gatacgacgt gtactgcttc tctacgcaga atgaagtata aaattagcac caaatagtaa   59760
ctttaatttg tcaggtgcta aacttttac atgctttatc tcatttaatt cttagaagaa    59820
actaatttta caagtaagtg tctggaccaa catctgcagg tacaaagcct gaaaagcgta   59880
agtttgactc ctacatagtt ctcttttgta agtagattat aaatagaacc agccaaaggt   59940
aataagttgt ctgtgcctaa aaagaaagaa aaaagttagc atcagtagtt ctcaccagaa   60000
ggggtgattt tgcttaccag gggacatttg gcaagtcagg aaacttttgg ctgttggatc   60060
tagagggtaa aggtcagtga cgctgctaaa catcgtcagt gcatagaaca gccttcacaa   60120
acaattattt ggtcaaagat atttgtagtg ctgcagttga gaaatttctg tcttatggtt   60180
atttcttcag gaataggaaa ttaagattcg ccgatacttt cttttaaaaag cagttttatt   60240
tttgaaatta ttccttggct tgaaaggttt gtgaagttta tatagccgaa ccagaatagc   60300
gtaattagat tttaaagtga attgtgagcc atcgattccc aggagatggg tgtcatagaa   60360
tcatggattc ttggatttgg gaaagactta tgcctagaat tatttttacaa catttctgct  60420
```

```
aagtggtaat tctcctctgc cctaaaggtc tcctgtattt gattttccta tcattgtgaa  60480
cccacaatta aaatgctctt aattattttt tgcttacact gagctccggt ctcttgtaat  60540
ttttactctg ttaaatgtgg ttctgcacca taggactgca ctcaaaacaa gcttgccaca  60600
tatgtaattt gtactaggac agtgtttata tttttgttca gataacaaaa taagttaaat  60660
gtggtgtaaa ttagatcatt tacaaataat aatttgttag cagcttttaa taagtagtat  60720
ttttcccaac tggtgaagta ttaatgttgg tagttgaaaa caataggaat gtatggaata  60780
tatggttcac tggttctttt gttcctgtca aatagtggca caatggatct ggggtttttc  60840
tcagtataat gctggcatat ttgttttcaaa ttgtacatag actctaaaaa gttaggcttt  60900
caaattctgg tcaatatagt ttgctttaaa tagtagctgc ctctactaca agttttattt  60960
aatttgttga caaatgagtc tgctatgaaa accggtcctg ttgccagtca ctaccctctg  61020
ttcacaaatt tgctgggttt ataaatatag gtatcatttt cacttcaaga ttataatttt  61080
agaatatgtt tattctagga catatagccc tcaaaatctg cttactatat acgtcttata  61140
aaatagcatg gttcttttt atagtaaata gaattttat ttaattgtct attgactttt  61200
tttttccagg gttcattgaa aaaatcctta gtgatattga catgtctcaa gtgacataaa  61260
ttagccaatg actcggaatg atggattctc cgaagattgg aaatggtttg ccagtgattg  61320
gaccagggac tgatataggg atatcttcac tccacatggt ggggtatttg ggaaaagtta  61380
gtgaacttat tttttgcctg agtgcaaagt tttttttttt tctctatttt tgagacttaa  61440
attcaatttt gatgttacca gttaacttct aaaaaattgt gtcttccacg gaaatcttac  61500
agtaatggcg aaagattgtt ttaatgtgtt tacctttctg tgttttattg atacatgaaa  61560
gtggaaataa aacatagacc ttatgattta ctgttctttg aaaatatggt acataaattc  61620
tcccgggtaa ttgatgttac tttttccttt gcaaataaaa ttgatactat tcttaacaca  61680
taaaatttaa tatttaaaac tataacataa ttcttttttgg aataatagct gtatttaaag  61740
gcttatatgc atttcttttg tttgccatgt ttaaaatacc ttgtcaggat acttgtaatt  61800
gaaaattata attttttctg gttaccttttc catttaactt ttaatatttt gatatattct  61860
aggaatgtct atattttaat ttgctttatt tctcttttag aattttgatt cagctaaagt  61920
tccatcagat gagtattgcc ctgcttgtag agagaaggga aagttaaaag ccttaaagac  61980
ttaccgaatt agttttcaag aatctatctt tttgtgtgag gatctgcagg taaagtatta  62040
atcttatata gtatatataa gattttctt ttttctttg cttttttatt aattgtttta  62100
aaagtttact cattttttgt tttttagact agattttaa tatgtaatct cagtttgtaa  62160
gtctgtctgg tatacaatgt tatttttcca cctaccttta cttggttgcg taaagatgtt  62220
cgttttatt gccatttgat ttgcgagagg agaaaataca tttcaaggtt tttttcttt  62280
tttttaacct tttggaggtc cttgttagct attagcatat agtagttact ctctcatctc  62340
tttggtttat ctttgcaact gatgggaaaa gttatgaatt tctaatgtac ctggaagagt  62400
attttggaaa ttggttagtc caaaaccagt atatatactc tgaactaaag agagtataga  62460
atcttgtaaa ttctaaaaga tccttttaga agctctaaat cgcttttaga attatagtaa  62520
tttgtaccga ctggtacggc ttttatatag cagctcatta aattctgtaa tactccacat  62580
tttattgtat ttgacagttt atgagactgt ctcatacact tttaattctc agaactttgc  62640
aagatttgta ttcctatttc atgaataaga aaataaattg atttcagagg gtttgggaac  62700
ataagatcct gatacagtgg cagagctgtg gttggaatac agacttctaa tttcagatct  62760
gtttattcca gcaaaaaatt agcagttcat cagaattacc tggagtgctt ttaataaatt  62820
```

```
tctgagtatc accccccagat gctgattcaa tagagttggc ccagaattct gtggttttgt    62880
aacatttgag gatgagtctg atcatcatca gccaggtttg gaaaatacta gactaaatca    62940
catggttgtt aatagatact tatgctgggt ataatttgaa gtaaagtaat cccaggcgtg    63000
tctacaaata taaatttctt tatgtttata ttcagtaatt ttttttatga gtgtcactgt    63060
ttggcactgt tgcagataca atgttaggat acaataataa aacaaaaatt tcttgcccctt   63120 aaggaagtta tgtcatagag tgggaaagac agtgaacaag tatgtgtttt tctgtcaggt    63180
gataaaaagt gctgtggaga aaaataaggc agtagggact ggaatgccaa agtaggggga    63240
gtttgcaatt ttaaatagga tggtgagggg aacgcttcaa tgaaaagtgc aattcgagca    63300
aaagcctgaa agaggtgaag agcagtgagc tttctaggca ggggaagcaa gttccaggaa    63360
ggccctgaga gaatggaggc tgcctgtcat gtttgtgcta ctgcaatgaa agcagcagag    63420
cgatagaagg tggatcagaa aaataatggg ggagctggac caagtagggt cttataagcc    63480
attgtaagct ttctggcttt tactatgggt gaaaccagga accatggcag agatgttggc    63540
agaggagtga cataagttga cttcagtgtt aaaagcatta ctgtggctgc actgttgaaa    63600
atatatgtaa tgggcaagac ctgaagcagg gagattagtt atagtataat atgaattata   63660
tttggtcctt gtctatggtt tccgttacag agctaaaagt cttggaattt cctgaatgat    63720
aagagtgtcc tgttattcag aatgagcctg tttgctaaca ccggggttca tactattgtg    63780
gtgacttagg atggagccgt agatagcctc agatggggca agtagctgga aagaccacat    63840
gattagagaa ttaacgggtt agaacttta gccccacgta caggcctcca ggaaaggagt    63900
ggaggggctg gagatcaagc tgtataaaaa tatcaagatt tggatttaat gagtgggttg    63960
ctgggggctg gtgccgtgta ggaggtggta tgcttagagg aagtggaagc ttcatacctc    64020
ttctgtccca taccttgccc tactcatttc ttcatctata ccctttataa tatcctttag    64080
gataaaccaa taaacataag taagtgtttg tttgagttct gcgagctgtc cttgcaaact    64140
agttatgccc aagaagggg agtgggaacc tttgtagcca gtcagtcaga tgtactggtg    64200
gcctggatgt gggattggca tctgaagtgg agggagtcat gggactgagc cctcaacctg    64260
taggatctga catggtctct aggtagataa catccaaatg gaattggatt ataggatacc    64320
catttggtgt cctctggaga attgcttggt gtggggaaaa agcccccaca catctggtca    64380
caaaagtgtg ctgggaggat agaatatgtg aaaattgtca taatcaaaat ggagtcactt    64440
gtgttaaaaa agaaaaaaaa atcctgactg gccaggcaca gtggctgaca actgtaatcc    64500
caacactttg ggaggctgag gcaggaggat tgcttgatcc caggaattgg agaccagccc    64560
atgcaacata gtgtggcctt gtctctacaa aaaaaaaaat ttaaattagc tgggcatggt    64620
ggtgtgagtc tgtagcccca gctacccggg aggggggacta cgggtgcacg gcaccatgcc    64680
caggaggtcc aggctgcagt gagctgtgat tgtgccactg cattccagtc aggatgacag    64740
agtgtgagac cctgtctcta ttaaaagaaa aaaaaaagac aaatagatcc aggaaaggct    64800
atgaagagag agctttcatg cataaatacc aaaatatctc aaaagactct gcaaaaacca    64860 caccccttgca caaaggccat catgaaatac ttctgaaata cacagaaaat acatcatgaa    64920
ataaatacac agaaaatact tctgcaagga catctgccca gcaactgcct ggtccatctg    64980
tggacgggtg tcatccttgt tatttgatcct tgtagccaag ggtaattatc tcaaaacaag    65040
tatgtgatcc tccttatttt cctttaaaaa ccttttgtct tcccttacct ccctgaacac    65100
acacagttta ctatggcatg tgtattccca ttggaatact ttattcctga ataaatgtca    65160
```

```
ctttcttttt agaagcttct cttttctttt tatttagatt gataagtaga aggaaaaaa    65220
agcttttttc cctttggact agttgaaggc agttgcagta ttctggggga gagggtggtg   65280
gcagaggtgt tgaggcatgg ttggagttta tttatacttt gaaggtaaag ccaacaggat   65340
ttgctgaaag attgggatat ggggttggaa agaggaatca aggatagttc caagattttt   65400
ggcttgaaaa attagaagaa tggaatcgtg aattactgag ctgggaagac ttggaagagc   65460
aaggttttgg ggagaagatc aggactgtaa gaatagagaa gtccttgtcc ccaggagtta   65520
ggttttggc tattaaagtt agatgtacta catagatttt tagttggttt tttgtttttt    65580
gtttttttt tttttttttt tgagacggag tctcgctctg tcacgaggct ggagtgcagt    65640
ggtgcgatct cggctcaccg caacctccga ctccctggtt caagggattc tcctgcctca   65700
gcctcctcag taggtgagat tacaggcatg tgccacccag cccagctaat ttttgtattt   65760
ttagtagaga cggggtttca ctatggccag gatgggcttg atttcctgac ctcaggtgat   65820
ccacccacct cggcctccca aaatgctggg gttacaggtg tgagccacca cgcccagccc   65880
ggagttttgg ttttttgaagc attcttttc aagtgataaa gcaaaaaata tataatcaag   65940
aattttaagt atatactttg gaaatgttaa aaaggaacat gagtaattta ttattatttt   66000
tttaatttct agtcagcaat gagagcccag tgtactttat gaagtagatt ggtttacacc   66060
aggagtgagc agacattttg tatgatgcac aaacaaggaa tgatttttt gttttttaaa    66120
tggttaggaa aatatcaaaa taaaaaatgc cagaaaaaat caaagaagg gccaggtgca    66180
gtgtttcaca cctgtaatcc cagcactttg ggaggccaag gtgggtggat tctcttgagg   66240
tcaggagttc gagaccagcc tggccaacat ggtgaaaacc tgtctctact aaaaatacaa   66300
aatagccggg tgtggtggca tatgcctgta atcccagcta cttgggaggc tgaggcagga   66360
gagtcgcttg aagccagtgg cagaagttgc agtgagccaa gatttgagcc actgcactcc   66420
agcctgggcg acagaggaga ctctatctca aaataaataa ataaataaat aaataaataa   66480
ataaatcaaa agaagaatac ccttcataa tatgtgaaaa ttaaatgaaa ttcaaatttc    66540
agtgttcata aataaagttt taccggaaca tagccatgct caatcattta tgtattgttc   66600
atggcttctt ttgcatacaa caacagagtt gggtagttgt gacagactat gtagctcata   66660
aaatctaaat atttattatc tagcccttta tcagtaaact ttgctgatcc ctgtataagt   66720
cctctgaatc aaattatttc caaagagttc cgttataaaa tttggagttt actctgctgt   66780
aaattgcaaa gaaccatttg gaaacctct tttagtcagg tatttacatt aaaatgttcc    66840
ttgatttgta aacactaata ttcaagactg gtccaaaatt ataccaaatt gaaactctca   66900
agtgtttta aacagtagga agttttaact ttttttttt cgtggagtag tctatcattc     66960
agcgtttact ttgaacatt taattagtct tttttaaaaa cccatgaaat ttataataaa    67020
aatttaaat cattaatgtt gagtaatcaa agaaaacttt ttttgttttc tccatttgta    67080
aaatgagtac attattatta taatttgtct ttggccatac cttgttgata attacttata   67140
caagtataag aagacatggt atgttttcct ttttcctatt tcacaagaat aagtacagga   67200
atttacttaa gctgctccaa aactcagtga aagagacagg attaggtttt ttcagcatt    67260
ggattttaaa tgatactaga tggttgcgct gggctaaaat actaatgctt tgtgtatatt   67320
tttatgactt ttttgaagac agcttaaaag ctttattcta gttataaaaa tgatacatgt   67380
tcactgtaaa tagaaacaag tcaggtatac agagatacaa atatttagaa catgtggaaa   67440
gaggcaacaa aattttataa aaagaaaaaa gataaaaatc tgaaatcatt aatttataag   67500
ggaaaaatca gggcaaggac aaattatatt acagattggc ctatggtggg agcacagatt   67560
```

```
atatagagaa aagtcagtga agacacttgc gaagagtgtg ggtggaaatc actaagtttt   67620
gcagtcccgg ggcctcttat ggtttattac tgttttgttc ttttttttt ttaatatgc    67680
attcctttgg aaccaagggt ttattatgtt ttgaataaag tagaggtgta agtaggatgc   67740
ataccatg atcttgacta cttgagattc acaaagggtt ttcgtctcag gatttttttt    67800
tctcttaaaa aaatttgtat taattttaa attgtaaaaa aattcatcaa cttaaccatt    67860
tttatgtata gagttcagga gtattaggta tattcacttg tgcagcagat ctctagaact   67920
tttttcatct tgcaaaactg aaactctgta cccattaaac aaccacttcc cattttcctc   67980
tcccccagct tctggcaacc attctagttt ctgtttcttt tcttttttt tcttttgaga    68040
tggagtctct gtcgcccagg ctggagtgta gtggcatgat ctcggctcgc tgcaacttct   68100
gcctgcgggt tcaagcagtt ctcctccctc agcctcctga gtagctggga ctacaggggt   68160
gcaccaccat gcctggctaa tttttttttt tttttttttt tttgtatttt tagtagagac   68220
gggggtttca ccatgttggc caggctggtc tcgaactcct gacctcaggt gttctgcctg   68280
cctcagcctc ccaaagtgct gggattacag gcttgagcca ctgtaccggg cctctagttt   68340
atgtttctat gaatcagact cagtacctca tataaacgga atcatacagt atttgccttt   68400
tttgtgactg gcttatttca cttggcataa tggcctcaag attcatccat gttgtagcat   68460
ggatgaatat acagttagga gttccttttc ttttttaagt cttaatctcc agtttatttc   68520
tgtttattta tttatttat tatacttta gttctgggat acatgtgcag aacgtgcagg     68580
cttgttacat aggtatacac gtgccatggt ggtttgttgc acctgtcagc ctgtcatcta   68640
cgttaggtat ttctcctaat gctatccctc ccctagcccc ctaccgccg acaggccccg    68700
gtgtgtgatg ttcccctctc tgtgtccgtg tgttctcatt gttcagctcc cacttacgag   68760
tgagaacatg cggtgtttgg ttttctgttc ctgtgttagt ttgctgagaa tgatggtttc   68820
cagcttcatc catgtctctg caaaggacat gaggagtttc ttacttttaa ggttgagtaa   68880
tattccacat tatgtgtatg ccacattttc tttatccatt cacctatctg cagatgtttg   68940
agttgctttc acttttgggg aattgtgaat aatgctgcag tgaatgtggg tgtgcaggta   69000
ccttttcaag attctgcttt tgagtttttt ttggatacgt accttttat gatgctttaa     69060
atacatatat gctattttta aaggattctc agttttctga catatgatag gacttaggaa   69120
gtaatctcaa agcatcatgt tgacaggttg ttagttgatg gtgactgcag ctagttggaa   69180
agtcagaaga atctagaact tgtccattta tactaaagaa tttcatagta agtgcagtat   69240
tatgagtgta atgttcaatt ggtagaagag gctatctgag gggatttagt gcatttcagt   69300
tatctgtttg tgtgaaacga atcaccttga aacttagtcg ctcaaaaatt ttaatggtgg   69360
ctgggcatgg tggctcacat ctggaactcc agcactttgg gaggccgagg caggcagatt   69420
gcttgaaccc aggagtttga gagcagcctg ggcaacgtgg tgaaaccttg tctctacaga   69480
aaataccgtg gcaggcgcct ttagcaccag ctactgggga ggctaaggtt gtaggatctc   69540
ttgatcccag gaggcagagg ttgcagtgag ctgggatcgt gccactatac tccagcctgg   69600
ataacagagc cagaccctgt ctcaaaaaaa aattttaatg gctccatta ttatttcaca     69660
tgattatgtg agttgactag ggaattctta cacatcacac catgtcagct gggacagctg   69720
aaatgtccac atggctggca gttggtacta gctgctagct ggaagttgag ttcaaatagt   69780
cagccagggg tctcagttat tttccatgag gttctctcca tgaggccagc tgggctcttc   69840
acagtgtgat agctgggact aagaaggagt gttccagaag aagggcttgt cctcttgagc   69900
```

```
cagtgcttat caggcctcta tgtatatcat gtgtgctaat gttccatcaa agctagtcac   69960
agggccaagc caactctgta cagtgtaggg actggctgca ggagggcatg aattaccagg   70020
aggtgtagtt ctctagttca tagggagggc catcaagata gtagtctacc atacttgtgt   70080
aaaagaaggc attaattaac tattattatt attattatta ttattttaga gacagggtct   70140
tgctctgttg cccaggctgg agcagtagag tggggcaatc atagctcatt gcagcctcca   70200
actcctgggc ttaagcaatc ctcccatctc agcctcccaa gtagctggga tacgggagt    70260 gtactgccat gcccacctga aaagaaggc atattttaaa agcagacctt tagtgtagag    70320
ggttcttgaa tttgttattt aaaatattct ggtagttttt aaacttagga agacccact    70380 gattcttta gtgatatgtt tacattgttg ttatttggca taaattgtgt taatgcacag    70440
taagatttca tgaagtcatt aaaattcagc cacttggact ctaaacccaa taaagatgta   70500
aaacagcagt gctatgagat gcatattcag tttcaaaata taggaaacac agaaattact   70560
ctgtgcactt ttaatttgaa atacttta aaatgtgtag tataatgtag tgtctgtccc    70620
aaaagagtaa cattcattat agtgtttctt tacgttgttg aaaatttaa attcacttaa    70680 cattagattt ttattaaagc aaaaatatgt tttccttatt agcttaccct tttgtaactc   70740
agattaaacc cttgattgtt caaattaacc tgaaaaaaat tattcttttg gaggccaaac   70800
ttttgattaa gtagttgttt gtctctaatt ttttcaaatt tatgtgtata aatataaccct  70860 gtcatcaaat caatgctaac attctataca tgttttcat gatatgaaaa ctataaaaca    70920
tgaagttatt tgaatttgtg tagtttttat catttttt ttactttcca gtgcatctat     70980
cctttgggct ctaaatcact taataaccta atttctcctg atttggaaga atgtcacact   71040
ccacataagc ctcagaaaag gaagagctta gaaagcagct ataaggattc acttctttta   71100
gcaaattcca aaaagactag aaattatatt gctattgacg gtggaaaagt tttgaacagc   71160
aaacataatg gagaagtata tgacgaaacc tcgtcaaact tacctgatag tagtggtcaa   71220
cagaatccaa ttaggacagc tgattccttg gagcggaatg agatttttgga agctgatact  71280 gttgacatgg ctactacaaa agatcctgct acagttgatg tctctggaac tggcagacct   71340
tcccctcaaa atgaaggatg tacatctaaa ctggaaatgc cactggagag caaatgtaca   71400
tcattccccc aggctttatg tgtccagtgg aaaaatgctt atgctctctg ttggttagac   71460
tgtatcctgt cagctttggt gcactcggaa gagttaaaga acaccgtgac tggactgtgc   71520
tcgaaggagg aatctatatt ctggcggttg cttacaaaat ataatcaagc aaatacactt   71580
ctatatacca gtcaattgag tggtgttaaa ggttggtact aatattttat ttttatttac   71640
ttatttattc atctggagtc agggtctcat tctgtcaccc aggctggagt gcagtggcat   71700
gatcatgtct ccttgcagcc ttgacttccc tggctcaggg gggcctccca cctcagtctc   71760
ccaagtagct ggaactacag tcgtgcacca ccatagccag ctaagatagt gagatggtgg   71820
ccccactgtc ttgcccaggc tggactcgat ttcctgggtg caagcaccct tcccgcctca   71880
gcctcccaaa gtgctgggat tacaggcatg agtcaccatt ccagcctact tgtctttaat   71940
tcttaaaaat attaatgttg agttttgtct cccagcatgt gggaaagatg tcatccattg   72000
cttctgtttc ctggaggcct gggagcaagg agcccaggaa cagtatcacg aagcttgaga   72060
taataccagt tacattatcc tgactgccca aaaggcagtt ttttgtttt tttttttat     72120 actttaagtt ctggggtaca tgtgcagaac gtgcagtttt gttacatagg tatacgtgtg   72180
ccatggtggt ttgttgcacc catcaacccg tcacctatat taggtatttc tcctaatgct   72240
gtccttcccc aaccctccca ttccccatca ggccccagtg tgtgatgttc ccctccctgt   72300
```

```
gtccatgtgt tctcattgtt caactgtcac ttatgagtga aatatatgg tgtttggttt    72360 tttgttcttg tgttagtttg ctgagaatga tggtttccag ctttatccat gtccctgcaa    72420
aggacatgaa ctcatccttt tttatggctg catagtattc tatggtgtat atgtgccaca    72480
ttttctttat ccagtctatc attgatgggc atttggggttg gttccaagtc tttgctattg    72540 tgatttttt tttttttttt tttttttaa gacagagcct cactctgttg cccaggctgg    72600
agtgcgatgg catgatctca gctcactgca acctccgcct ctcaggttca gcaattctt    72660 ctgcctcagc ctcccaagta gctgggacta caggcgccca ccaccaggcc cagctaattt    72720
ttgtattttt agtagagaca gggtttcacc atgttggtca ggctggtctt gaactccaga    72780
cctcatgatc tgcctgcctt ggcctcccaa agtgctgaaa ttacaggtgt gagccaccat    72840
acctggccta ggcagtcttt ttcaaaactc taagactgtg cttgtgtctc agggtgtcag    72900
gataatagtg gttagtttta agtgtttaaa ctactgaaaa gcagaatgaa gaagtgagta    72960
aaaatcaccc ataatcacac aacctcctaa gatctcttgg cacaataagg gatatgtttt    73020
tcattttatt ctctgtaaaa taggatactt atgaacccac ctcccaacac aggaagaatt    73080
aaaacattcc caataactta catttaccta tgcgtttcct cccatcccat tctctacctc    73140 cccccatat gtaatcatta tctgaaatgt gtttcatcat tccatctttt cttagttttt    73200
cttacatgtg tttatctaaa cagtatacag tagtctcccc ttattgtagt tgtacttttc    73260
ttggtttcat ttaacccgag gtctgaaagt agatgagtat agtacagtaa tatattttga    73320
gagagaggga gaccacattc acataacttt cattacagca tattgttata attgttgtat    73380
tttattatta gttttaatct tactatgcct aattataaaa cttgatcata ggtatgtagt    73440
tataggaaaa agcataatat ataaaatgtt tagttactat ccaaggtttt aggcatccac    73500
tggggtcttg gaaggtatcc ctctcagata tgggggatg gatggtactg aaccctgtat    73560
atacaatgtt tttccctata catacataat tatgatcaag tttaattaag agtaaattaa    73620
atgtgggcca ggtgcagtgg ctcacatctg taatcccagc actttaggaa gctgaagcgg    73680
gcagatctca tgaggtcaag agttcgagac cagcctggcc aacatggtga aaccccatct    73740
ctactaaaaa atacaaaaat tggctggcta tggtggcaca cgcctgtagt cacagctact    73800
ctgggaggtt gaggcaggag aattgcttga acccaggagg tggaagttga acaatcactt    73860
gaacctggga tcacgccact gcactccaac ctgcctgggt gatagaatga gactctgtct    73920
caaaaaaaaa aaaaaaaaa aaaagtaaa gtaaatgtgg ctcaacatgt tgctgtcagt    73980
tggaacattt gtttctgatc gtgtcttcca cccacaaatt gaatgctttt tccatcttaa    74040
cacttatcag gcactgtggc cataacttga gcagttgaga tgcaacagca aaattagcac    74100
aaattctttt ttctttcttc gcagtttcat ggataagaga tttgttctta gatctcagca    74160
acctcagcat atgatttttt tctttaagtt gagaactttg acctttttac ttagagaagc    74220
attttacagc ttctctttgg catatctgaa ttgccagcat tactatgctc gtgctttggg    74280
gccattatta agtcaaataa gggttgcttg aacacaagca ctgcaatacc atggcaatag    74340
atcgcatcac caagatggct gctaagtgaa ccacaggcag gagtgtagac agcatggaca    74400
cattagacga agggaagatt cacgttgcca gtggaacaca gcaggacagc aagagagttc    74460
atgatgctac tcagaatggc atgaaattta agcttataa attgtttctg gaattttccg    74520 cttaatatt tcagaccacg gttgagttca ggtaactgaa accataggaa gcaaaacacg    74580
gatgaagagg gaccacttcg tattgcctaa tttagtttgt tttgatcttc tgggaccttt    74640
```

```
ttttcttgtt gtaaaaattt atggggctgt ttatagttgt ggctcattga tttttcattg    74700
ctacataata cttccatttt gtaaatataa cagaatattc atctacctgt cagtggacag    74760
tggggttttt ttgccattat aaatgctgct gctgtgacca tttgggggc aagtctcctg     74820 gggcacagta tgagtttccc ttctgtataa caaaggaatg gaaaattata gactttcgtg    74880
tccaaattta caagataatg acaattgttt tccaaagtgg ttgtaccaag caattctccc    74940
attaatagtg tatataagag gtcttcctga tccatatatt cttcttggtt tattttcaca    75000
cttttgagat ttttgctatt tgagtggtat aaaatggtct gtgatcttga tttgccgttt    75060
ccacattttg aagaggttgt cggctctatg tgtatatatt gctcatattt gttccctctt    75120
ctgtgaaatg ccttttgtat cttatcccta tttgttctgt tctgttgatt gtcacgtttt    75180
aattgatttg tatgagtttg ttccttgtat cattgttgct agagttacat cagatgtgtt    75240
gctgaatctg ctcccagttt gcagcttgtg tttttacttt ttaaaaactg tcttgattta    75300
tagggaagtc tttatctttt catttggagc tagtaatgtt tgtggctttt taaagaaatt    75360
attactattc ccaaggtcag aaaatcattc acctatattt taactgaaaa gttataaagt    75420
tttgcttttg acattgaaat ttctcattca gttggaattc atattgatgt gtggtatgag    75480
gtaaggatcc atttttttcc catttgcata gccagttttt gtagctccac tttatttttct   75540 cacttgatct gccatgccac ctctagcatg tatcaacata tcatgtatgt gtgcagctgt    75600
tccttaactc tcaattttat tctcttggtt actttgtcta acccagcact catacttttt    75660
aaattattat ggctaccttg tagggcaaga atcctcactt ttattcaact tcttttgaag    75720
tgtcttgatg catattttt ctgatcttac ttggccatat atattttggg gacagatgtg     75780
acatcatacc aagcttttctt tgcttgacat tgtagatatt ttcttattca ttaatgtgct   75840
aaaaattttg agtttggtca tacagtcttt tatatggatc ttatacatcg tttccctctt    75900
gttaaccatt caggctgtta ctagttttg ctgttgtgaa ttaacaccag acaaatatc      75960 catatatctt ttgaattaat tactgactag tttcctagga aagatattag aatatgaata    76020
ttaaaggtct tgctgaatac agttttcaga atggttgtac caatatataa ttccatttc     76080 attatgtaga aaaaatacct cagtgttttc taaccaccctt tggttagaac attcaagacg   76140
ttatggtttt gttaggtaag aaatattttg tttcagtgta ggttttcttt gagactgaac    76200
ttttttgtgt gtgtcagtca tttacagttt tttgcaattt ttaaaattca gtttctcaca    76260
agcattttgc ctttgacttt tcttctattt ctgctttctc taattacaga aaccccagtg    76320
ttaagtaggt gacagttcag ttgtttgctg cagaagagca gcagttcaat attggaatta    76380 acttttaattt tatgttttta atctgttact aatttttttac agaataattg tagttttttat 76440 aatctggtta attatatgtt tgagctgcat tactttgcaa tgtaagtttt ttttttggc     76500 atggtcaaat aacaaaaatt ctggttaatg cttatttcat attacaggag aatccagata    76560
tttcattagg gaaacatata agcagagtgt gatcaggctg tatgaattat ttataagaga    76620
tgtgagtgaa aagatctatt tgtagcttaa gagtaagtag agtcagatgc atgtagagtc    76680
ttttattcaa ataatttc ttattaatct tggatagttt cttgtcacag taattccatt      76740
ttgaagataa taaatattac cataaagaag tgatcaaaaa catagatatg tgtgcccaaa    76800
ggtatttatc acaatagtat ttataatagt gaaaaagaa acaactaaaa tgtctggcaa     76860
taggagaatg attaataaag cgatgtttca gctgaatata gtggcatgcg cctgtaagcc    76920
cagctactca ggaggttgag gctgcaagat ggcttgagcc caggagttaa tgaccagccc    76980
aggcaacata gcaagaccct gtctccaaac acacaaacac acacacaagt gctatgtttc    77040
```

```
agtcactgta taataactag ccagattttt tgttgttgtt gttttgtttt tgttttgttt   77100
ttttgagaga gcatctcact tgcccaggct ggagtgcagt agtacaatca cagctcactg   77160
cagcttgtag aaccctaacc ctcctgggct caaatgatcc tcccacctca gcctcctgag   77220
tagctgggac tacgggtggg taccaccata cccagctttt tttctaagag ataggggttt   77280
cactatgttg cccaggctgg tcagttttta atgaagcaca tttgtgtaga caaagcagga   77340
tgtggaaccg ataaacact  atgttgccac tgaagacccc ttcaaacccc tcaaaaatga   77400
catagaaggg aaatatgaga tattagtttg ggaataatt  gtaactttat taagactcct   77460
tataaattta tctgttccta tgacctggct aagttcaata aaagttacac agagtggaat   77520
aaatggttag acatcatttg tagtataagt aattgcacat aaggaggtaa ctttagctgt   77580
tttagagata gacatagtat ctgaaaggtt agttatttta ctagacctgt gattatttgg   77640
gtgagaaagg ctttcactga gattttaccc attcagtaag tactaatgat attgtgctga   77700
tagcatatat taagggaata tatggtatac cacagagaaa gaattaagga aattttgtgt   77760
tttgcttttt gtctgtttgc aaaacttact gactcagctt tcattcttgg gaatgtgtca   77820
gttttctgtg ggaagatata cattgatgag gaattgataa tgttctctgt attttcttag   77880
atggagattg taaaaaactt acctcagaaa tatttgcaga gatagagacc tgtctgaatg   77940
aagttagaga tgaaattttt attagccttc agccccagct tagatgcaca ttaggtaagt   78000
aattggtaaa acttacttgt attatactca tctaccatat agaaatatgt acctcataag   78060
gaaatataat actgtttgat taccttggat gatcatattc ttgggagaga gaatctgagt   78120
agtttgactt aggaatctac cactgggtaa gttattgtag ggcagagctg ttccatataa   78180
atatgtaggc tggtgttcca cctcttgaga gtgggtgcag ttctcagaac caggagaatt   78240
ttagggggca tatcattagt tgcttctcta gtacgtttcc tagtagacag atctagcatt   78300
tttaacctca attgtgcatt aaaaagcacc gagggaattt aaaagtaaat gccaatgctg   78360
gggcatttga attaggatct cagggatggg gctcaggaaa tcagtaattt ttagaaaccc   78420
cacatgattg ttatatgtac ccagggttta gaatctcatc taaaccaacc atagtaattc   78480
tacttcccta ccagtgattg gtttaggaat gtccttgtgg tagagttttg gccagtggat   78540
attaagagaa atatgctgat ggccttttgg gaaagcttcc tcgcctttag aaagggcaca   78600
aggatgggac ctctttgttc tctgtgactt ggttttttggc ctgtgggagt ggcgtgcagc   78660
aagtgagcta gagagtctgt ccaaacccttt ctaaattttt ttagtattgc gaaaaggagc   78720
tgcggggttt ttttgtttgt ttttgttttg aaagggcttt ttgttttatt tttcttgtat   78780
ccttgtatta actcttctat taatgttata gtagcagaat atgatactcc ctattagtaa   78840
taacccatat tatgtaaaat atcagtgcct tctagttttt ctctcaatga gtgacattta   78900
acttatatta aaaatgata  tttatatttt ataataaaat cagttgttgc tactgatttg   78960
tctagcatgt acaaaagaca ccatgcttcc agatcattat aaaatatgat attttataat   79020
atatttacaa tatatttata acatatttat atacttagaa tatattttat aaggctgggc   79080
ttggtggctc atgcttgtaa tcccagcact ttgggaggcc aaggcaggcg tatcacaagg   79140
tcaagagatt gagaccatcc tggccaacat ggtgaaaccc tgtctctact aaaaatacaa   79200
aaattagccg ggcgtggtag tgtgtgcctg tagttccagc tactcgggag gctgaggcag   79260
gagaatcgct tgaacttggg agacagaggt tgcagtgagc tgagatcacg ccattgcatt   79320
ccagcctggg gacagagcga gactccgtct caaaaaatgt atatatatat atatatatat   79380
```

```
atgtgtgtat gtgtgtgtat gtgcgtgtgt atatatatat atcgggaagc atggcatctt   79440
ttgtacatgc tggacagctt ttgacgtact tctttgactc atgcttctgc cccctaattt   79500 tcacttttt  tcctacattt tattaaaatt aatatataat agttgtatat ctgctttatt   79560
tttcatggac ttatacatac atatttattc tgttcttata aaagtctgat ttttcgtatg   79620
ccaaatttct gacatttcct cctctaggcc tgaagaactg ttgtaattta tgcatcagat   79680
aggccctcag atggaatgaa tattcttttt tctttatatc aaggtgtaat ttacatatag   79740
taagaccgtt tttaagtgtg tacagctctg taaccctcac tacaatcaag ataggact    79800 ctgtcactct aaaacttctc accaggttca tcaccccccag ccactgatct gttgagcgaa  79860
tactcatttc aaaggagctt tttccgtaag atccctagag tttagatgga agggctttcg   79920
tggtgcattt agcagatacc atttcccttc tagactccct acttcagttc ccagttgaat   79980
taaagaatgg tttctccccc agcctgagtc actacccttc ttatccctga taattatttt   80040
tggaacaaag ttcatctttt tgctccacct ccgccatggg cctggttttc tatgtaacag   80100
aaggaatttt taaattattg ttttgtgtaa tcataataat tgggcaagca tacagctctt   80160
ttcagtgcag gaggattcct ctcttgtttt actgcccatt caaggatagg tgctatattt   80220
tagctgaaga tcttactaat gaaatgctct gtaatcatat aacttattta aagatgtgtt   80280
ttgagctctt tcataatatt ttaattcatg gagaacttta tgtatttag  acctgaagat   80340 tttatattgt cattatgaaa tgtaaattgt ttgcttttc agttaatata tagttacaat    80400
agaatacgga tttaaaggct gataatgaat tacaaaattg tgctatatga catactgttt   80460
atgcatacag tgttgcatat tttcatttct aggatattga tttgtatttc tacttacaaa   80520 aaaactttt  aaaacttatt ttatggctgg gcccggtggc tcacacctgt aatcccagca   80580
ctttgggagg ccgaggcggg tggatcacct gaggtcagga gttcaagatc agcctggcca   80640
acatggtgaa accctgtctc tactaaaaat acaaaaaatt agccggacgt ggtgtaggtg   80700
cctgtaatcc cagctactcg ggaggctgag gcaggaaaat tgcttgaaac caggaggcag   80760
tggttgcagc gagcagagat tgcgccattg cactccaacc tgagcaacaa gtgcgaaact   80820
ccttctcaaa aagaaacaaa aaaacttttt ttaatgtttt tgttcaaaag tagcagtgag   80880
actatcccgc aaaggtgact actaaaatag cctttgtaac tactgatatt tatagaaatat  80940 gcttagggtt agggtataac tcgcttgtat tatactcatc taccatgtag aaatatgtac   81000
atcataagga aatataatac tgtttgatta ccttggatga tcatattctt gggagagaga   81060
atctgagtag tttgacttag gaatctacca ctgggtaagt tattgtaggg cagagctgtt   81120
ccatataaat atgtaggctg gtgttccacc tcttgagagt gggtgcagtt ctcagaaccg   81180
ggagaatatt taggggacat attgttagtt gcttctctag tacttttccc agtagacaga   81240
tctagcattt ttaacctcaa ttgtgcatta aaaagcaccg agggaattta aaagtaaata   81300
ccaatcatag ggacatttga attaggatct cagggaaggg gctcaggaaa tcagtaatttt  81360 ttagaaaccc cacatgattg ttattgctta ggtaataaca cctactgtct accttgtggt   81420
cctgccaagg tgactgttcc tggccatgtt ccaggcaact gtagttccag gctagggga    81480 gaactggacc atggaagtga ggctctgtcc agggtagggg aagggatgga aggtgactgt   81540
tcctggccat gttccaggca actgtagttc caggctaggg ggagaactgg accatggaag   81600
tgaggctctg tgcagggtag gggaagggat ggaaggactc agtctcttgg gccaaatcgg   81660
taaggcagca tctaagctcc tctgagaata ggaaggagag caaccaattg gaaaaagaat   81720
gggaaacatg tagattctcc tgcttaacctt actttccagt ctcaaagctg gaagccagca   81780
```

```
ttcactgttc agttattttc aatgacaaca agattcaaat cttcagttgt aaagttgtta    81840
aaggaaagga ttagactgaa aagttaagaa gaacggtaga tgaagagtcc aaagagttga    81900
ggctggtcat ttaaccattg tgtggccacg ccctctccac aggtggaaca agatgatcag    81960
aatagaaatg gccaattctg atgtgtttct acagtgtttc actgattaca ttttttaaca    82020
tctgtagcaa accatttcca taattttttt ttttttttt agagacgagg tctcgctctg    82080
tcacccaggc tggtatgcag cggcatgatc atagctcact gcagcctcaa attcctgggc    82140
tcaaatgagc ctcctgcctt agcctcctaa gtagcttgga ctacaggtgt gtagcaccac    82200
tctcagctaa tttatttcat tttattttt gtagagataa tgcctcgcta tattggccag    82260
gatggtctca aacgttcata gaaactggtt ttaggttcct agaggctggc agcaattctc    82320
agaggtaacg caagcagtct tcctgccttg gcctcccagt gtgctgggat tacaaggtgt    82380
gagccaccac acctcatcaa tttttgtttt aatatactct aaggcttatc atagttccga    82440 gatcttttt tttttcctga gaaatctaga aagatggaag acagtatggg tcttttgtgg    82500 atttttgtc ctaagaaatt ttcataaatg tctgccaagg aaaaggaaag agatcaaagt    82560
ggtaattaaa tctttaggat ggacattttt agaaaaatgc tttataaact tcccctctcc    82620
caactctgag tgacttattg tgtcatactg tattaacaca tattcatgct gtaaatatag    82680
taagaaaaga caatagttca caattttggt ttagtttttg ccattattga ttatgagcag    82740
taattcttcc ttttctttt gaaggtgata tggaaagccc tgtgtttgca tttcccctgc    82800
tcttaaaact agaaacccac attgaaaagc tcttcctata ttcttttttct tgggactttg    82860 aatgttcgca gtgtggacac caatatcaaa acaggttagt ttcttttgtt ttttaaaatg    82920
ggttcttcta gtttctccac cactaaggtt aagagaacaa tttgagcacc agacactaca    82980
gtttgcttgc ttcttttaaac tggaagggtc aaaacctcat cgtttgatag actgctagta    83040
ggatatttcc taaggagttc ttcagtggga aataggacg atgagaggaa taatacacct    83100
cccttctcca gagtccttgc tgagtagaat acctctcaga atgccatgaa actgtaggca    83160 ttttgttta ttcctctatt agaaatgagg ggttttgctt gtttacttta ggttctaac    83220 attatagaca ctagttttag gctcttggag gctagcagca attctcagag gtaatgcaag    83280
cttccccatt tcttcccgta gtcctgtgaa agaccagcca cctccagaag cctacacatg    83340
agtcttctca gccatacttt ctgcttttcc taatgcctct cagcagcgta ttagaaaggc    83400
catgatcgat gtacctgtta ccttcaggct ttgcataagg tgtatatgaa acataatgaa    83460
tttcgtgttt aggctcaggt cccatcccca ggttacctct ttatcttgga gacacttctg    83520
gtcccataca tttcagataa gagatattca acctgtaccc accacgtaag gagaggaata    83580
ggttttagaa gaggagtcag ggaggcaagg tattcccaga gggatattct cacttggtcc    83640
atacctgaga aagttgctgg ctggcagtta ggaagatgac cagactggct caattgttcg    83700
tgtattcaaa ttattacaat agaaataact ctttccaccc cccccgccc tttttttttt    83760 tttgagttgg agtctcgctc ccgtcacaca ggctggagtg cagcagcgtg atccggctc    83820 actgcagcct ccacctcctg ggttaaagcg attctccttc ctcagcttcc tgagtagctg    83880
ggattacagg tgtgtgccac cacgcccggc tgattttgt attttagta gagacagggt    83940 tttgccatgt tggccaggct ggtcttgaac tcctgacctc aggtgatcca gccacctgag    84000
cctcccacag tgctgggatt acaggtgtga gccaccatgc ctagccacac ttttctttag    84060
cttaagtgct taagttagaa aacttgaagt ctctctaagt tactcaagta aaatgtgaga    84120
```

```
taaaaatatt acttttgaag gccgggcaca gtggctcaca tctgtaatcc cagcactttg   84180
gtaggccgag gcgggtggat cacgaggtca ggagtttgag accagcctgg ccaacatggt   84240
gaaacgctgt ctctactgaa aatacaaaaa ttagccgggc atgatggcgg acacctgtag   84300
tcccagctac tcgggaggct gaggcaggag aataacttga aacccgaagg tggaggttgc   84360
agtgagctga gattgcacca ctgcactcca gcctggtcaa caagaatgac actccgtctc   84420
aaaaaaaatt aaaaaaaatt acttagatat tcattatcta aatatgaaat ccttttaggg   84480
tatttaagga gtagtcaagg agagttcagt ctgggaggat gctccaggga atgcaggcaa   84540
caaaggtttt gttttttttt taactggtta actcagatct actagaacag ggtaagggag   84600
gccacagagt agacaccatg agcaaagcta accctcctga gttgaaaaaa ttatggacga   84660
gaagttatca ttgaaattaa ctgttggcag acatatccaa agaatatcgc aaggatttgg   84720
tccctttatg catcctgaga cagatgaatg tgtggaatgg cagctggtgg gcaacagagc   84780
gatattggca tggtggtgat acagggaaat agtttcatcg tgttaaaagc catgaacaa   84840 agatacataa tggctgctct gcagaaaaat ccacgtcccc tctccaaagg gcctgtttta   84900
ctctgatgta aaaattgggt cagataaatt ttcatattaa gcttttttgtt gagtaaactt   84960 ttgtaatagt ccccaaaact cccactagaa cagggtgaga attaacgttt tattcatacc   85020
taggacttaa ataatttagt gtaagcaagt gagtatgaga acacatctgt ttccagtctt   85080
ctatcattgc tttatataaa ttctctggtt ttctcctcac agtaactcag tgaggaagat   85140
cctagtgtcc tcatttggca cgtatggata tgacagcttg aaaggggtta gattgattcc   85200
caagatgaca cactgtaagt ggcagagtca ggagacacac ttaggctctt ctggcctcta   85260
agactttctt gctcactgtg gtatactcct taatcactac ctgggtttta aataatataa   85320
ataaccttgc tgattaaaat cagcttaatt gtagcttctc tggaatccat atcttagttg   85380
tttgacagtt ttcggttgag tgtcttctgt gtgttaggaa ctcaggcact ggaaatagtg   85440
tatctttgcc aaatttacta attaggtaga gagataatac acgaacacat aatagaggtc   85500
cagtgacttc gtaattaatc tgatctttgg gctgcttaac gttagctttg aatgcaagat   85560
gttaaatgcg ttttagagat atatagcaca aactgtgaga gctcaaggga gggaagccac   85620
tagccgcttt tgtttgcttt tttgtttttt aaaaataatc ttactttgtt ctaaaaataa   85680
aagtagttat agagggaaag ctaaaatgaa gtgacgtttt cttaaatatg ttttaatatg   85740
tcataactta aaacttattt ccacttaatc tgaaggagaa ctgtccagca aattcctttg   85800
tttttgtgaa gctgttttta gtgccagcat aagggctttt tactcaactt ggaaagtgta   85860
acccagagtc agttaaaaac atagtcttca gaggcagatc tcaggtctgt tatttatcac   85920
tgtactctat gtgtcacttt ccccatctgt aaaatgggga taagaatagc acctgcctct   85980
gagagttgtt tggaagatga gtgtccagtg ccatgccctt tgcacatagt ttaagtgttc   86040
agaaatgtca gatgtcatgt ggagaattaa cacttacttg ctgagacagt ctcctttta   86100 taaactaaac agtaggagcc tttacataac aattatcttt gaaaatttaa gaatttagca   86160
gaaatcagtg catttgttga tatctttatg ttgctttgct tttaaaatgt taacctccct   86220
gactactgat gttttaaca gacagtgctt cctcacaaga tttataagta tttgctattg   86280
tttagaaagg aagcttgtat ctcttaagta gctgctcttt aaattacaaa tatttttatt   86340
aaagtggatg cagttgaggt ttagtgtaca tcttttaaagg tcatctttt agatggcgtt   86400 gctctcaagt attcagacta aagtgcaaat ttagaacttg tgtaacctgt gaaacaaaa   86460 tttgttcaca attaatgctg tgtgtgtgtg tgttttttttt ttaaggatta aaaaaagtta   86520
```

```
agttgtatgt attcctgatt ttatgtttgg aaacatcccc ttttcatttt tggttgtctg   86580
taatggctag ccagtttgag ttatttgagt aagggggtgag ctcttaataa atttgacaac   86640
cttagaacag tggttcttca ctaagggcta ttttttcccc cttgggacat ttggcaacat   86700
ctacagacaa ctggatgccg ttactggcat ctggtgagga gaggccaggg atgatgctta   86760
acatcctaca gtgcacagga cagtgcttca cagcaaagac tctctggtga aaaatgcagt   86820
gataccattg aggaaccctg tctttttttc ttgcttcatc tcatagttga aagatatggg   86880
aaattaacat ggagcatctt cacagagctt ctttactaga ggtagggagg aacattgcca   86940
tattaacatg atttggggaa ataagaaagt atgaatcacg aaaaagggga ggaatacttt   87000
tagacattgg tttaaattaa tgtaaatgca tttaacgtta atgaatttgt tatgtcattt   87060
ttttataggc atatgaagag tctggtcacc tttacaaatg tcatccctga gtggcaccca   87120
cttaatgctg cccatttttgg tccatgtaac aattgcaaca gtaaatcaca aataagaaaa   87180
atggtattag aaaagtgagt taaaattgtc ttataatttt tagtacaaaa tgaaggtgga   87240
tttacatttt tcttaatgtg taggattgaa aatggtgaca acaacttacc tttctgaaat   87300
ttgagttaac atatatttct gggttgccag ctgcctcgct ctatctggcc agtgagccca   87360
ctgtcacggt gaagccactg aaaagccaac ttaggctgac tctctggccc cactctccta   87420
gtgtctttcc ttcttttttgc cttttttctc ccttaaggga tatcaagctt cagttttttct   87480 ctcctctgcc aagtgtatgg agtttctaga attctgggat ttccttaatc agatttcaag   87540
aactaagatg attcaaagat aagccacagg ctcatctctc tgaatttcca tcttctccta   87600
gatctcagca tgctaattcc tcatcatctt gaaagctatc tagtggcctt gagcagatat   87660
attttcattg tattttgcca gcttttctgt ttgtcctcag ttggggaggt tggtcagcat   87720
taccttttcc agtattacca gagaaccatc tgtttaaact cacaggtcag ttccatctca   87780
ggccgtttcc ctctgtctca ttaatgcact cacacatgta cacaacctct ctactcttca   87840
ttttcagtct aatcgtacat taaggaaatg ttttgaggtc taatttgatg taataaagaa   87900
ccgggaacat taacctttat gcccttgaat gtgccagaaa cccttcagaa tctttcctaa   87960
aggtttattc tcattgaagt aataaatcct cagtttatca gtgcttacag gctcaaaagg   88020
gaaaaagggc agtagtcccc tgttccctcc tccaggtatc tactttaaac cttcaaatta   88080
aggtagtatt tacttttact tttcaaattg atgtgcctat tctaccgtaa tgcagtctgt   88140 tctccttttta tagtaattga gactagggtt ctcacaccaa cacctgggcc ccatctctgt   88200
ttagcctttc cctgtccttt caatgcaatt gcgtatttgg ctaactcagt actcggtgtt   88260
tgcattgtta ttaatataca tgtgttattc cctcttcagc caagcagtat atatagttag   88320
gtttcacttt tacaattctt attttttccgg gaattgttat ttgccttgtt ttcatttgtt   88380
ttattatgta ctgtgagttt ttgccaaata ctttaaagac ttattaataa attttcaata   88440
ctcagatgct tcacagtttt ttactctgtt cctctcccct tttttttcctg gaactctttc   88500 ctgccacctt tcactctttg ctgcagtctg cgctggttcc tctctgggcc tgcagcatag   88560
ggtgctcttt attatgtaca cacttccagt cactatcgta gttttttagcc caaggcctca   88620 tccccacatt ctatcacatc tgttgcccat aaatatccag tccttttaggg gttctctggg   88680 aaaaataagc tcttctttgt catcaacata tgcactccgt agtactcatg tcttcacttt   88740
gcccgttctg ctgggtaagg tgccacttct ctgtttgctt tctgtcctct aaatatttga   88800
cttcttattt gcttatttc ctttcttttgt ccttttggac tcatatctttt tttgccccctc   88860
```

```
actattattt gatagcattt gtgtaggagg gcgaagtggg aaggaagagg aggtgtctgt   88920
atctgtctga agattacaga agtctgtaat ctgtcttggc tgccaggtgt cagttttgag   88980
atgtaaatgt tgatgatgag gtgaggagaa gagcagcaga gcatggggtc tgccatcctg   89040
ccttggacca tggcctgctt taggctgctt ggtgtatatg atttcatcta gctgttcata   89100
cctgcttttt cctgtgcccc agcactgaac atagactcgt accattgttt tgtgtaatct   89160
gttaattggt tgcactgcag catatatatt ttttaactat acaaataagt tgcttccctt   89220
aaagattcat gctctgatct ggaaatggat tcattaggta aaagtctttt aatggaaaat   89280
gtgttttgag ttccagtggg ccaatttatg agcagaattt ataatgtggg catttcctgt   89340
tttcttcaaa agtaaattga actagtgtat gaagtttcac ttaaatttta aatgccaagg   89400
tctttatata agtcctttgt gttttttttaa ttttgaaatt tgtataactt gatttgtttg   89460
tgtctaatgg aatttagaaa taaatttaat atagttttta gggctaacct aaaagtaatt   89520
gggttcatca tggtgtcata tgtaattaaa acatatagaa tcctaaaaac taattaagtt   89580
ccttggacac cttatctcac ataacccaca tctctaatgt ctccccattg ggaaaagagt   89640
ccattgataa atcaggtgaa ttatgcctag cgggcccaaa tctgctactt ttctttaagt   89700
tgtttaggag ttacattcag accatggtga catggagcac caagaactta gaatcagatt   89760
tcattttact tgacaaactc ttgaaaggtc actgccacag tctctcttga gtgcaaggct   89820
atggctatgc tttgtagcac agggacgcga tatttctctg ctatctttgg gtagcagagg   89880
ttaacacagc tcccttgtgc tttctttctc tcttttctat tttcttttct tttcctaagg   89940
atagatcttt aaataggagg agtttaaccc catgttaggt gaattcaaat ggatcttagc   90000
ctgatgtctc ttgttctctt ttggttccag tttggttaat tcctttcatc caattttcca   90060
gtggttgagg gagaacctaa cttgctctcc tcgactctga gcatcatcct tcactgacag   90120
ttcaggcatt gtgggtagga agaagtctga gaacaaaacc tagggataaa gtttagtaga   90180
gatggggttt caccatgttg gccaggttgg tctcgaactc ccgacctcag gtaatccacc   90240
tgccttggcc tcccaaagtg aggctggaaa taagacatgc tggaattgta agtaggacac   90300
tagagtctag gggaatcaaa gaggaaaatg aacagaaaag ggaaggggaa ggatattatt   90360
tgattgactc caagatgcta ctgtttgtaa gttttaccat tttaaaaata tgccattaag   90420
aaagaaatgc tggccgggca tggtggctta tgcctgtagt cccagcactt tgggaggctg   90480
aagcggacag atcacctgag actaggaatt tgagaccatc ctggccaacg tggtgaaacc   90540
gcatctctac taaaaataca aaaatcagct ggatatggtg gcacatgcct attgtcccag   90600
ctactcagga ggctgagaca ttagtactgc ttgaactggg gaggcaaagg tttcagtgag   90660
cagagattgt gccactgcac tccagcctgg gcaacagagt gagactgtct caaaaaaaaa   90720 aaaaaaaga aagaaatgct gcttatttaa ctgtgttctg tcaatgttaa ggtgtatccc   90780
gacttcagag atgttaacaa atgggaaaaa atttggaatt cattaggcat ttggaactta   90840
caaagtttcg gccgggcata gtggctcatg cctgtaatca ctttgggagg ccaaggcggg   90900
tggattacct aaggtcagga gttcgagacc aatctggcca acatggtgaa accccatctc   90960
tactaaaaat acaaaaatta gctgggtgtg gtggcatgcg cctgtagtcc cagctactca   91020
ggaggctaag gcaggagaat cgcttgaacc caggggcgg aggttgcaga gagctgagat   91080
cgtgccctgc actccaactt ggacaacaga gtgagacgcc atctcaaaaa caaacaaacc   91140
aaaaaaaaaa aaaaaatttc atagttacag aaagtagtat ggaggccata ccagagatttt   91200 cgacatggta gtaaaactct gcattatggc tctgttctgc atcatctctg ttctgcatcg   91260
```

```
tttcactcca catcagaccc tggatagctt tggtgtactg gtcgatcttg tggcagtaag    91320
gctagtgtaa ttaagaggat attttaaaac ttaacatata attgctctag ttgttgtctc    91380
tttttttgctg gttaagaaaa tcaaatttct atcctatctg aatctcatag cagactttgg   91440
agatttctga caagtcattt cttactacct aggggaatgt acttgtactc agctagagtc    91500
tgagtatctt ctacatccag ggaattgggc tgagtgtgga ttttggtctt ggcagttttt    91560
acttttatta atttgcaaaa gaatagaaga cttggaatgt acaagaagca taaaaatgtg    91620
tcaggtggtt ttacatgcgt tatttatcac gttaatatgt cttaagatat tttccacgtg    91680
taaacttatg taaaggcagg aaactagtga gatttcatat tctagggatc aagagattgt    91740
tttagtaact agcctcagaa agtatcttga aaggtattat ataaggtcaa ggaactaaat    91800
attagtaaag agtcaggcca ggcgtggtgg cttatgcctg taatcccagc actttgggag    91860
gccaaggcag gcagatcact tgaagtcagc agttcgagac cagcctggcc aacatggtga    91920
aaccctgtct ttactaaaaa tagtagtgtg tggtatggtg gcgcatgcct gtaatccagc    91980
tcctcaggag gctgtggtgg gagaatcact tgagcccagg aggcggagat tgcagtaagc    92040
tgagattgca ccactgcact ccaacctggg tgacagagct agtgtctgtc tcaaaaaaag    92100
aaaaaaaaaa aggtcagata ggtgcctaaa gcctgtgtgt ctcgctatga gaatacatct    92160
caagttttac tgtggttcat tgattcagac atgtagttca cattttaacc tgtctgaaat    92220
ggtaatatgt gaaattgatg tcatgatata gtttaattgg cagcatgttt tcatagtggt    92280
acattttata attagtgaaa tcttagattt gatgaaatag atatgatttt ttaaagtggg    92340
aaagtttagt gttatagaca gtttgcagga cttttttattt tgtaggtact taaattttga    92400
ggacttaatt attctctaat aaagtgattg acaaggatta atgtataaat tataccttgt    92460
cagtctgaac aatctgcagt ttggacattg attcaaattc atttaggctg aataaatttt    92520
gataaactaa gtaagttttg acagctattt aaatattggg aaagggggata ttcaacattt   92580
ttcttacatc ctgagagctt tgttaaattt agttatttga gacccattgg gttctatttt    92640
ctggttcagc atgttgctgt aatggtaaaa tacaattttg aaattatagt tgtcttgaag    92700
ttaataataa attgaccaat atgttgtatt ttttctcta cttagttaca aattgaactt     92760
ttcctaagta gaacttttaa tttgacaggc ccccttttgct tcctgaggta actgaaatag   92820
gccaaattaa tgctttttttg aatatcttag gtttgttgct ttctttcaca tgttacctac   92880
cccacttaac aaaagcaatt aatctcagca cttgatgcca agaaaattc taaaggtct      92940
ggattttttc cttggatttt acaaagtagc tacaatggga cttttaagac aaagctgcat    93000
tgctgcttac agagcaattt ttgtttaatg gtctgtgtta gagtcatact gcatgatgac    93060
ttccaactgt ctgggatacc attctgaaaa gggtttagtg ttacatactt cttagagaga    93120
gttctccatt tctaattaag gcacacatct ggaggtgctc aagaaaaatt agtgcagtta    93180
gccttggaag tgttatgtgt gactagttca cttcagacat cttttgtata atcagacaca    93240
tggcattaaa tttatttaac ttctcttgct tttctctccc acagagtatc tcccatattc    93300
atgttgcact ttgtagaagg cttaccacag aatgacttgc agcactatgc atttcatttt    93360
gaaggctgtc tttatcagat aacttctgta attcagtatc gagcaaataa tcattttata   93420
acatggattt tagatgctga tggtaagtgt ttagaggttt tctttttaaga taattggcat   93480
agaaactaaa ttctagcatg tggggacttt tggttttttg ttttataaaa aaagacaaac    93540
tttgtcctga ctctttctct ctccattctc gcctttgcct tctgcccctc ctcgcatcta    93600
```

```
ttaaaagtga tggttttagt atcctgtctc atttttccct ttccttacat catgtattat    93660
aggtaaacac atgcgcatgt gtgtatttct cttttagaca aaggatgaga ttactactgt    93720
tagctcagtt ttttttcccc tacttaacat cttttgcttt attttttaga catatttcta    93780
agactattaa acattagact tacgtagccc ttctgtcatt gtgaaataca tagtttacta    93840
acagctacca tcaagataaa gcctttattt aaataattaa acttcttagt ggaaagctaa    93900
gtaagcacag tttatggatt tgggaatttt tgccttgca tttgtctgat atggtaaaat     93960
attgagtttg tttttctcat aatgttcact ttgtcttaga caagataact caatcccctt    94020
aaagggttgt atcaagccat tgataagggc tcactttgat ataaccattt tctgttattt    94080
agacactctt tcacacttcc tattttcctc ctggggatgg tttgaatgga tgacacaata    94140
ccatattata aaagcacttt acaaactgta acttatgtta taaatgtaat tattaccttta   94200 aggttttacc ctgtttcaga tttgagtgga agtagttctt tacaatacaa aacaacttat    94260
tttaactttt tttgcatttc aaagaatgat caatccactt caggtgcagc atggtttcca    94320
accctgacag catggaagaa tcatttattt agcttctaaa aatgtgcagg ctgtacccta    94380
gaccagcctt ggggattagg cccaaatatc aatgttgggt gttttggta ttggtttttg     94440 gcccgcctac ccgcccttcc ttccttcgtt cctctctctc attctctctc tctctctctt    94500
tctctctctc cttctttgct ccttcattcc ttctctctct ctcttttttt tttgagacag    94560
catctcacta tattgcccag gctgttctca aactcctggg ctcaagtgat cctcctgcct    94620
cagcttcctg agtagctagg actacaggca catgctatgg caatactgtt ttaaacattg    94680
ttttcaaggc tccccaggtg attccagtgt gggtcatgtg gtagagaacc actgacacag    94740
gcaaacaaag gatacataaa gttgtctatt taatgggtag gtgcaggtag tagataagag    94800
tgtagccaca taaaccacat gcttagtgaa cggttttgtt ttgtgtgtat gtgagggatt    94860
agcatctctg agtatatttt gttttcccct ttgaaactta tcagagaatt catatgtctg    94920
ttatgtgact aatgctcaca ttaaaaaaag ttatgtgact ttttttaatt catatgtctt    94980
tttaattcat ttattcattc atatgtctgt tatgtgacta atgctctcat aaaaaaagta    95040
atgctcagtt tactttttt atatcagatc atatatatat gttttttttt ttgagatgga    95100
gttttgctct tgttgcccag gctggagtgt attggcgcag tcttgtctca ccaccacgtc    95160
tgcctcccgg gttcaagtga ttctcctgcc tcatcctcct gagtagccgg aatacacgca    95220
ggcgctacca tgcccggcta atttttgtatt tttagtagag acagggtttc tccatgttgg    95280
tcaggttggt cttgaactcc caacctcagg tgacccaccc gcctcggcct cccgaagtgc    95340
tgggattaca ggcatgagcc accgcacccg gccatatctt atattttaat aaatatttta    95400
atttggtctg taaatttttc ttttttgggga atgtgtttta agtctgtgtt gagtcctaga    95460
catttgttgt tctcagatag tcactagtga taccttaaca ttaaccagcc tgttggcaac    95520
taaattggcc tgaagtgaca actaaggaaa ggtctctttc tcctttctta atctttgcat    95580
tccttaagat tagttctttg taggaaggct ttgaagtctg gtggcaagta ccctttatcc    95640
ctcacaatct taagataagg tctttctgag cattaaaaag tgactgtggg agatatgtca    95700
aatgagtttt ctgtgtgtgc tctgagaaat cttttttttca aaaaggata gatgtacttg     95760 tataaggaaa agagaaactg agcgcacttt caatatttaa gtaagtgtct ctaacatgtt    95820
ttgcaacata aaatgatgac cactgtgttg gtcattactt ctctactgct aaaacaatgt    95880
tttctaaaat aatatactcc ttagaaaaaa atatagtgct ttgggtgtgc actgttgtaa    95940
tccaaggaat aggaaatgtt ttgtagtaag tgcgatggtg tttgacatcg tgatttatta    96000
```

```
atttatcaca tttggtttca tagaaataga gtaagctacg tatttgctgt gccgcaatta    96060
ccatgacatt acacttgtat ctatttctgt ttcatagatg tgtagatatt gatatataca    96120
gtggaagtat ggattgtttt gataagtttc taatgaaagt acagatattt gttgattatt    96180
tattaagaaa ggttgttact catccaagcc cgtggttagc ttttcccaaa ttatcatgtg    96240
gtagtaagta aaatgtaaag aaatataccc tcccttaacc ccacaccacc tgttagcacc    96300
tagccacctt cctttacttc tcagccgtac tttttgtatt tttttgttgt agtggtaaaa    96360
tataaataac ataaaattta ccattttaac atttgtaagt gtacaattca ttggcattga    96420
atacattgtg tgcaaccacc atcaccatca ggactttttc atcaacccaa acagaaacta    96480
ctcattaaac ataactccg catccttcca ccccaaagcc ctggtaacca ctattctact    96540
ttctgtctct gtgaatctgt ctattctaga tacctcatag aagtggaatc gtacattatt    96600
tgtccttttg tgtctggctt attttactca gcatattttc aagattcatt tgtgttgtgg    96660
gatgtagcag aatgtcattc ctttctaagg ctgagtagca ttgtatgtat tatccattta    96720
tctgttacgg acatttgact attgtgaata atgctgttgt gaacattggt ggacaaggaa    96780
ctgaaagtcc ctgcttttca ttctttttgg cataaaccta caagaggaat tgctgggtct    96840
taacggtaat tctgtgttta attttttggac gaactgccag actgtttcca cagcagttgt    96900 actatttac atccccacca gcgttacaca aggattccaa tttctctaca tccttgccaa    96960
catttgctat tttctatttt tttttaataa tatccatcct aatgggtgtc ttttttttttt    97020 tttaaggaa tggtttaaac aggttacctt cttactcctc attcatgctt tagttgacta    97080
cataaggacc cctctcccta ttggcaccat tgaaattgtt caggcaaaaa taactgccag    97140
cgacacactg ctttaagtaa tggacttttc ccaagttttg tattaatatt tcagtatttg    97200
gtagtgcatc ctactgctag tttttaaact cttcccttgt catctatcat ctcattctct    97260
cttgacaaat gtgaaaatgg aagctcagaa ataaaacaag aattaaaacg aatagtgatc    97320
cttcaggtaa caagcttcat ttatcatgaa aacatatatg tatgaaacat tctgtttctc    97380
gatgttattg gataaattag gtgataacca aattctaagt tccaaaaatt aaatatactc    97440
tatctaagga ctttaacatg gcagacaatg gtgacaaggt caagaacatg ttttagagtc    97500 ttctccttttg gtcggtattc aatgatacaa cagttgaaaa ggccagaaga aagttaacct    97560
aggatggtgg ttttttgaata tctaactttc acttctttcc catcttccag gaagttggct    97620
ggaatgtgat gacttaaaag gcccatgttc tgaaaggcac aagaaatttg aagttcctgc    97680
ttcagagata catattgtta tttgggaaag aaaaatatcc caagtgacag ataaagaagc    97740
tgcctgcctt ccacttaaaa agactaatga ccaacacgct ctcagtaatg agaaaccagt    97800
atctttaaca tcgtgttctg tgggtgatgc tgcctcagct gaaacagcct cagtaactca    97860
ccctaaagat atatcagttg cccctcgtac tcttttcacag gacacagctg taactcatgg    97920
agatcattta ctttcaggtc caaaaggttt ggttgacaat attttacctc tgacacttga    97980
agaaactatc cagaaaacag cctcagtttc acagttaaat tctgaagctt tcctgttaga    98040
aaataaacct gtagcagaaa atacaggaat tctcaaaacc aatactttgc tatcacaaga    98100
atcactaatg gcttcttcag tatcagctcc atgtaatgaa aagcttattc aagaccaatt    98160
tgtggacata agttttccat cccaagttgt aaatacaaac atgcagtcag tacagctgaa    98220
tacagaagat actgtaaaata ctaaatctgt gaataatact gatgctactg gtcttataca    98280
gggagtgaag tcagtagaaa ttgagaagga cgctcagtta aaacaattcc ttacaccaaa    98340
```

```
aactgaacaa ttaaaaccag aacgtgtcac atctcaggta tctaatttga agaaaaaga   98400 aactacagca gattctcaaa ccacaacatc taagtcatta cagaatcagt ctctgaaga   98460 aaatcagaag aagccatttg tgggaagttg ggttaaaggc ttaataagca ggggtgcttc   98520
ttttatgcca ctctgtgttt cagctcataa tagaaacact ataactgatt tacaaccttc   98580
agttaaaggg gtaaataatt ttggtggctt taaaactaaa ggtataaacc agaaggccag   98640
ccacgtatcc aagaaagctc gtaagagtgc aagtaagcct cctcccatca gtaagccacc   98700
agcaggccct ccatcgtcta atggcacagc tgcccaccca catgctcatg ctgcttcaga   98760
agttttggaa aagtctggaa gcacctcatg tggagctcaa ctcaaccaca gttcttatgg   98820
gaatggtatt tcttcagcaa accatgaaga cttggtggaa ggtcagattc ataaacttcg   98880
tctaaaactt cgtaaaaagc taaggcaga aagaagaaa ttagctgctc ttatgtcttc   98940
cccgcaaagc agaacagttc gaagtgaaaa tctagaacag gtgccccagg atgggtctcc   99000
aaatgattgt gaatcaatag aggacttgtt aaatgagcta ccatatccaa ttgatattgc   99060
cagtgagtct gcatgcacca ctgttcctgg tgtttccctg tacagtagtc aaactcatga   99120
agaaatttta gcggaattat tgtctcctac acctgtttca acagagctgt cagaaaatgg   99180
ggaaggtgac tttaggtatt tgggaatggg agatagtcat atcccaccac cagtaccaag   99240
tgaattcaat gatgtttccc agaacacaca tctgagacag gaccataatt attgtagccc   99300
caccaagaaa aatccatgtg aagttcagcc agactctctg acaaataatg cctgcgttag   99360
aacattaaac ttggagagtc cgatgaagac tgatattttc gatgagtttt tttcctcctc   99420
agcattaaat gctttagcaa atgacacatt agacctacct catttcgatg aatatctgtt   99480
tgagaattat tgaattaatg cttgttaact tttttcatat aatatttatt attattagaa   99540
gaacttacaa tgtgttcagg tagtgtttat acactggact tgtgtaatta cttgtgtaat   99600
aaccatgaac aaaatgcaag gtttaacctt tggttctgcc catgaagcat gtaatctttc   99660
ttacacatta aaatcactga atgtgttctc cttttggtt tcattttgtt cttgtgagag   99720
tatgaggatt tcaaaatgtt aaagatgaaa agtggcgtct agtttctgac agtttgtaca   99780
gttggatgca ttacatttt agatttgaag ttttggttat gttagtgtta tgagtgatct   99840
ttgtggtggt tttcttcccc tggaaacctg ttgctcgtgg cgctttgccc acggtgcccg   99900
agttcttgtc ctgtgtccag atatgcagac aaatgaaggg tgaagaagaa gaagaggagc   99960
tttatttagt gttagaacag ctcagaagga gacccacagt gagcagctcc cctgtgtcgg  100020
cgggcaggtc gtccctcaag tgttcagctc tcagcagaga aaaggccctg gagagggtga  100080
ctcctctcag ctctcagcag agaagcagcc ctggagaagg tagcttctgt tcgcaggcag  100140
attgtccaga ggtcctgctg ctctcagacg gggccctgga gaggatagct tctatccata  100200
ggcaggttgt tctgccgtct ctacaggtct ctgaagctct tagcagagag ggtagctcct  100260
ccctgttgct ggtcgtccca ccctctgctc agttctggct gagcctgggg catttttacgg  100320 gcctcggggg aggaagtgca tacttactgg cctggaaaag gcaccagttc ccactcctac  100380
aggtgggact ggcagcctgg ccctcagcct tcaggccctc cctgttcatg gcttccaggc  100440 ttaccccct gctttgatct gagagctggt gccaatagca gggagaagcc aagctgcaga  100500
ggcaagcact tccgagcctg caaaagcagg cccccaaaag tgcagggatg cctgagtctg  100560
cacccgcacc caggagggtg gagatcttgc ctgctccaag gctgcagccg gaatgatagc  100620
aggctgactg gagcacctgc caccatcatt agttcaagag tttatgcaga tttaagttgt  100680
atacggtata tgaatgtgtg acagttttcc ttatggttgt gtggccttct gtaagagcct  100740
```

```
acgcctgttt gttacaccgg tagagtgctg tggaatgtaa actttccta tgtcacttat  100800 ctcctttatc tctccataca gaggagggca agaaaccttg ttacttgaac tttagtaatg  100860
ttaagtgatc aataaatcta taaataaatg atagcagaaa aaagttacct gttttttgtga  100920 tgatgtacaa actttacatg ttatcacaaa taccatcttt cttcccaaga catttacttc  100980
tgtaaccaaa gtgggacacc atctaacagt tctgttttgg gagagagtaa taaccagtgc  101040
ttgtgaggct tgttagatgt tggttgtgat atatgagata gatgttattt catttagacc  101100
tcaacattcc tgtgcgtgag atactttat cacatcttac agataaggag actgtactca  101160
ttcagttgtg gagctgagat tgagtagagt ggctattaca gcagttgagt gctgagctta  101220
tcaatatatg ttccactcct caggcttcat ttaaagtagg atgcccaaac agcaccactg  101280
ccgtagagat ttgagttaac agcagtactt actgaggttt aaggctggca gccagtgtcc  101340
ttgcagtaaa attatttgct agggactcag tacttcataa tctatttgtc agatttactc  101400
ctaagcttct gtgttgtttt attttttttc tgacaaaagt agtgcatatt gtcaaggaaa  101460
aactaggaaa ataccaaaaa aaagatttt tgaccatgca tttaatact tagtgactac  101520 aaacattttc ctattttatg catatagatt ttaaataaac gtgagatcct attgtatctg  101580
ttttaatgga taaacattgt ttcactgttt taagattctg aggtgattta tactgtcttg  101640
ccattgttaa ttgcagcagt tagccttgtt gataaattt tgcatggatc caagttttgt  101700
tttccaggag tggagttgct tggtcaaagg aaatgcacat ttaaggtttt ttggtgattg  101760
catgactgac ttccctgggc cctcgccaac actaggtagt agtattggga ggaaggggg  101820 aaccaatcct gggtgctcca agattactag tgagcctgaa catttttctat aactattgtc  101880 cacttgagtt gttgttttgt ttttttttg gtggaggcgg gggtgggttt aagaattgct  101940
tatcctttgc ttgtactaat tatcttttca acaaatattt ctagattact gctaaggacc  102000
aagcactgtt atcagcctga gataaggcag cacactagaa ggaaatcctt gctcctttg  102060 agtttgcctt ccaaacatgg agatcaatat ataatgttag gtagtaatag gagatacatg  102120
cagttgattc atgtcatttg tagtagttat ggtcaataaa gttgccttga acactgaatt  102180
agtataaact gaaatactgt tcctagggga aataggttcc tgctagcctg tggtcatgag  102240
atttttgtca aacaatcact atataacctt ttctgtttct gtttaaagac atgttattg  102300 atctatatgg ttgattcttt acattaacat ggccaacagc actgtaactc agcctgaacg  102360
aagcttatct gacacatggt gttctccata aggcacatca tagcttcctg tgcttaggaa  102420
cactagacgg cacttcagca ctgcacttga ggacgtttta aacagtgaaa tcaacaaaaa  102480
gcacaaaaaa atgcaacaat aggctgggca aggtggctca cgcctgtaat cccatcactt  102540
agggaggccg aggcgggcgg atcacgaggt caggagatca agaccatcct ggctaacacg  102600
gtgaaacccc gtctctacta aaaatacaaa gaattagccg ggcgaggtgg caggcgcctg  102660
tagtcccagc tactcgggag gctgaggcaa gagaatggtg tgaacctggg aggcggagct  102720
tgaagtgagc cgagattgcg ccactgcact ccagcctggg cgacagagcg agactgcgtc  102780
tcaaaaaaaa aaaaaagga acaataacaa agacactagt cccccaaaaa tacacttgtt  102840
tacagtgtga actgaaagag gaaggtggag tattgacttg tttgacctca gctggaaatg  102900
tgcacgtcct gtgactcaaa ttttttctctg ttctgtgcat gcatgtccac gaataaccac  102960
aagaagcact gaaagcattg attttttaggg ttacaaatta attttagcaa gtaaatgaat  103020
tcacaaatac ggaatctgtg agtaatgagg actgattctt ttttttttg gagatggagt  103080
```

```
ttcactcttg tagcctaggc tggagtgcaa tggcatgatc tcggctcact gcaacctccg    103140
cctcccgggt tcagcctcca cctcccgggt tcaagcgatt ctcctgcctc agcctcccga    103200
atagctggga ttacaggctt gcaccaccat gcccggctaa ttttttgtatt tttagtacag    103260 acggggtttc accatgttgg ccaggctagc ctcgaactcc tgacctcagg caatccaccc    103320
acctcagcct ctcaaagtgc tgggattaca ggcgtgagcc accgcgcccg gccgaggact    103380
gattcttatg tcagatggca ctaaatgcta tggagaagag gagtggatga gagggagaag    103440
tattttagac caggtagact tggaaggttt cttggaggtg ggtgatgttt gagaagaggc    103500
ttcaataaag ttagggagct cgccatgtga ttgcaggaag agcgttccag gagaacaaaa    103560
gtcatgaaga gtgagtgcta ggcatgtgtc tggtctgttt gggctgctat aacaaaatac    103620
cttagactgg gtaaaatgta taaataatag aagtgtattg cttatagttc tagaagctgg    103680
gaagtccaag atcaaggtat cagcacattc tggtgaaagc tgctctgctt catggctggt    103740
tctctcactg tcctcacatg gcataagagg ggcacagagc cctcaaccgt ctctccagtg    103800
gccccatctc ttagtactgt tggattgggg atttagactt cactaatttt gggggacac    103860 aaacattgag accacagcag catgactgag gataagcaag aggccagtgt ggttgagcag    103920
agtgatcagt gaaggagagt taggacatga gtaaagaggc tagcagacac cagatctcat    103980
atggctttgt aggccatagt gaggactttg tttaagctga gaataataga taacctcagg    104040
aaagtttcag gcaagagggt aacatgatct gatctgggtt ttaaaaggat cactgaagtg    104100
gggagactgt ctacagatgg tctgaatagg agtcctagtc tattacaatc tccttggagt    104160
ttagggtggt aactggaggt gttcaagagt agttggatta ctgttggatt tcaaaagtag    104220
agccaacacg atatgtgcat tggctgtgag gtagaagagg agtcaaaatg aactccaggt    104280
tttattgact gagcaattgt gccatttcct gagatgggtc agatttggga aggaaagaat    104340
ttaaagggga taagataatc ccattaggag tgtgttaagt gtgagattcc tattagactt    104400
tcgagtggag atgatttaat aggaagatag atctgcaaca ctggagctca gcggagaggg    104460
acaccctgga gatagccgtt tgggaattag gaatgtgtgg atcatgttat aggatggggt    104520
catttaggga cttaaaacag ctctgaagaa caaaaatggt gccttgatct tggacttcct    104580
ggtttataga actgtgagca atatatatat attttttttca agacagagtc ttgctccgtc    104640
atccaggctg gagtgcagtc gcaccatctc ggctcactgc aacctccact tcctggttca    104700
agcaattctg gtgcctaagc ctcccaagtg gttgggacta taggtgtatg acaccatgcc    104760
cgactaattt ttgtattttt ttgtagagac agggttttgc catgttggcc aggctggtct    104820
caaactcctg acctcaagtg atctgcctgc cttggcctcc caaagtgctt ggattatagg    104880
cgtgagccac catgcccaga ctaaatttct aacatttata aattatccag tctaagatat    104940
tttgtgatag cagcccaagc agaccaaggc aaaggccaag cacacttgct cctcctgact    105000
tttgctcttc ctggaatgtt cttcctttag tcacatggtt gcctgcctag cttcattcaa    105060
taggagtgtg gtgccctgaa aatacaagga agaatgcttt tctttttttt aaaaggaagg    105120
gatgattatc tgtcagatgc tgctgaaaaa gagtaataga gtaattggcc actggctctg    105180 gcaatagga agttagctct gctaactcca catgaacagt ttcacatgaa caagtgtgag    105240
tgggctcaag agaagggatg tgagaaagt ggagctatgg actcactctt gaaacatttt    105300
ctggtgcctc gtagggcaat gtgaggtcaa ggttttttgtt actgttctga agatgggaga    105360
ggctgacaca tggatgttgt aggtgagaga aggggcgctt gcgggggcaa acttctccag    105420
ggatgggatt ccagtgtcta agaggaggcg gtgtgaccct aagagctaga aaaattattt    105480
```

```
tattaatagg aaagacaaag tacttaggct cagatgctaa gagatttgct gataaaagaa   105540
tgagaacggt ctcttctgat tattttcttg gggaaataaa tagatcatca gctgagggtg   105600
tgaggggaga aggagttgaa catggaggaa gacaggtgtg aaatattggt ctcagaatgg   105660
agagcgaatt gaatagggac atgcagtggg cttgctaagc tgtgcggaga gcccgtggga   105720
agtttatggt catcaattta atggcgacca gccaagatgg tggtttattt ttctccagtt   105780
gtatttaact gctcaggtgc aggacagaga gactaagtgt gaagttaatt tcagccaacg   105840
tagaggaatt gtcaggcaga tgggacaagg agatagagga gaaaaggaat aaggcttcct   105900
gcaagggtaa tgattgtagg gatggataag taaggaacac aggaagtggc tgtctgctga   105960
gtggtggcag agctcagtgg gtcagagcaa ggttcaaaga atggcagaga ggcacttgtg   106020
gaggaagtaa gctggctaga aagtagtgtg cttgaaatta agcttctgga gatagcaagg   106080
ttacaggtga tgacaaagtc tgagtatgac aaggaaactg cagggccaga gttggcaaga   106140
attcatgaaa aatgaggaga agaggcacc aagaggctgg gatagcacat ggattgtctc   106200
tgtgtgaggc aaagtcatct aaatggcagc agtggcccta gcagaaagaa atatacagtg   106260
agccggagca aaaatcctca aggacaggca gaacgccatg aaaacggcag atgacagcca   106320
aaggagcagg ggcaggggct cagtccaaag tgtttcagag tcactggagg gttgagtggg   106380
aaggggaggg agtggctgaa atggcaacaa ggaagaacct ctctcatctc caggcccaaa   106440
agtatgtgga atgcgggaga taagacagcc accactggcc agggctgtaa agggacattc   106500
agcgaatatt caggttccat ttagcacgac agcaggaag ggactgttgg cagaaaaaaa   106560
ctggggcagt gggattaaag acagaccaca cattccaaaa ggcaccgtgg gagggtcagg   106620
gggcgaggtt aggtctaggc ttcagtgtcc tgggagactc agtcttcaca gggtgacagc   106680
gatcaagagt gcagcttagg ctgggtgcag tggctcatgc ctgtagtccc agcactttgg   106740
gaggccgaga cgggaggatt gcttgaagcc aggagtttga gaccagtctg accaacatgg   106800 caaaaccca tctctactaa aaatacaaaa atcaactggg catggtggcg tgtgcctgta   106860
gtcccagcta cttgagaggc tgaggcaaga gaatcacttg aacctgggaa gcagaggttg   106920
cagtgagctg agatcgtgcc actgcactcc aacctgggca acagagtgag accctgtctc   106980
aaaaacaaca caacaaaaa agaaaagagt acaacttatg aagggtctc ctggggagag   107040 ggttttggg attctcctgc ctctcaaagt gctgggatta tgggcgtgag ccaccacacc   107100
cagccgaggg aggctgagtt ctaattgttg tatctctctt gggattggcc tcctgggcag   107160
tttaaaagac aaggcaagga atcttttgga gaaagagact ggggcaagg tgtgtctgaa   107220 caagaagtgt gagaagctct gtgggctccc ttcagacttc cagtcgttga attgggatct   107280
catttatatc agctctaggt gtaacgatat taaatcttct ctgtcatttg gcaattttgg   107340
tttatgcttg atcatcattt ttaatgtttc gacatgtaga agtttaacat tattttacat   107400
tcttttcctt ctggcatcat gttttagcaa gattgtttcc accaaaagaa tatatatatc   107460
ttctaatgaa actacgtttc tttttttttt tcctttgct ttctcttttg gtatatgaat   107520
ctttgattat ttgtaatgta ttttgatgtg taacactgaa gtttctattt tgtactattt   107580
ttttccccaa acagtaaact tattgttcaa atacttattg aacaaccttc actattcttt   107640
aaccatttag aatacgccat tcacatatct ttcatactac atttaataac attttttaat   107700
taaaaaatat tctactgatt tgttattttt gagaccaggt tatgaaactg gctaattttt   107760
gtatttttgt taaataccga aattcactgt gttgccaagg ctggtctcga actcctgggc   107820
```

```
tcaagcaatc tgcccacctt ggcgtctcaa agtgctggga ttacaggtgt gagccgctac 107880
acccggccac acccggccaa cacatattat ttgttattac atttaattcc cacagtacat 107940
tgaaattatc agggaaaagt tttcagtgaa acattattga acgccacatt aaaagtgtaa 108000
attacaaaga tttaatgcca attttttcaga agaaaaaaga ccaggaggaa ggtctatgaa 108060
gttttagcca gtctctcatc cacctaccat ttcacgatca tgcactgtgt aagtcaggaa 108120
aagagtaaga aaagtgaaag atacaattga ttagagagtt ttgctggata ctatagatga 108180
aaagaacaca aaatggaaca gcctcttcaa gcttagagtc aacggctgta gtcccaaaga 108240
ctgtagtcag aggcggtagg gccaaaagac atgacttatg cattggagg aagaggatgc 108300 tttgggagtt catggtagaa gaggcggaaa aaatctggtg gattaaagaa agcatcccaa 108360
agtgacatta aactaatgac taaattctga gctgttttca ggggcaaagc ctgtttgggc 108420
acccctgcca cacttaaaga gtcacctagg tatggttcgt gggctctgaa caggcctgct 108480
cagtgaacat atttgtgact gtttctccgg ccctttagc tgtattgagt aaaatttaaa 108540
gagaccattg tttttggccta agctcctgcc ctaggcccaa agaacagacc aaacctgaat 108600
ggcttcactt gtcctaggtg ctgtgtactc aaactgaact ttgaaacagg tcggtttttc 108660
aaaaaaagca aaagattcac agcaaccaat tagaagaggc ccggtcaacc tgagccagca 108720
tgatgaggct cttctgcttt aatcctacaa ggaaagaaac tttgaaatga ccaatcgct 108780 ttcattcttg gtttctgctt tctttggtct atttctgcct gtaaaaccta tctcctctgc 108840
tcagctcatt gaagtaccct tctatttata gatgggatgc tgcccgactc atgtatcgct 108900
agtaaaagcc aattaaatta ttacactcga tttgttggaa ttttgctatt ttgacagctt 108960
ttcaaaaaca ccagtaggtt cacatcccta attccccagc cagtgttccc tcaaggaacc 109020
atggaagaag caaaggtggc tgaaaggcgc ctcaggatgc ttctaagcac ggcacatcca 109080
tgaaaaggca cttactaata tttgcaggat agcaaagcac tgcagtgacg ataaatctag 109140
tattggagaa gttcaaaata atcagtagat taacacagaa gccagagctt ataggagaa 109200 aaggaaccct atgaaatact tcaaatccga aaacgaacat gcatttcctg tttagttagt 109260
gcaggtacgt aaaagcttgg taaagtaccc ttcttgccag ctttctcttt cttacaagcc 109320
ttttcactgg gctgggaggc tgatattatc taaatatgct gaggaggttc aagtatctcc 109380
acaactcacc tcagagtgaa tgctccctc ggccttaagg caatataaac cagccctgtt 109440
tagcaggata gcaaaatgtt tgcggttgta aactggtgtc ccattggctg tggcgcttgt 109500
ggtgtaaaga atccctgtgc ttggtaatta atagagaaat tctatatttt aaacttcagt 109560
tgtatattgg ctcttatcca tggcagattt tcacgtatgt gttatttttt tatttattca 109620
gagccggagt ctcgctttgt cgcccaggct ggagtgcagt ggcgcgatct tggctcattg 109680
cagcctctgc ctcttgggct caagcaattc ttctgcctca gcctcctag tagctgggac 109740 tacaggtgca tgccaccacg cccggctaat tttttgtatt ttagtagaga tggggtttca 109800
ccgtgttgct caggctggtc ttgaatttct gagctcaggc aatccgcccg cctcggcctc 109860
ccaaagtgct gggattatag gtgtgagcca tcatgctcgg ccctatgtga tatttattac 109920
aatgaattcc aatgatcaga cctatactca agtataagtg aatatatcat tcaatgaagt 109980
ataaatgatc attatgttca tattcacaca tacaataatg tactcaagtt tattgctaag 110040
gtaattcaga atctccttat tttgaagtgt gcatttgata tacctgtttg ggaataacta 110100
gtttcttatc tttgacagaa aataatttg ttgttttgtt tttactaaaa aagcatggtg 110160
aaaaatggct ccatttctaa gagaggtaac taaaatatcg caatttgctg ggtgtcatta 110220
```

```
aagtaactca caagggaaaa aatgcaaatt ggtatctgct gatggagtaa atctccgcag 110280
aagtgatgac cctgaaagga tcaatatatt aaagcccctc ccagctggtc attccagatt 110340
gcaacaataa agcattaagt gttaaaacct caaggcagct tttttttttt tttttttgtct 110400
caagtccttt attattaatt ttatagacct acttaattac taagccaaaa aaaatcaaac 110460
ttgtttctct ttgtgacttg tcaatagtat taaactattc tggttttta ttttttgtgtt 110520
accttaaagt ctccagttta gtaattttc tgtacctaaa cacttcggat ttgacatgct 110580
ttgtggcctt tatcagtagt tagaatgtaa atccaataaa taaagtaaaa gccaggtctt 110640
caaaacctgg gggccaagaa ctctgtttta gagggcctgt gactctcttg acactggac 110700
aaaatctcat ctctaaatat ggatatttta gggagagggt ctttaggctg tcatttggat 110760
tttcacaggg ctccatgtat ccataaggta gtctcttggg aagtttgact tcaataaatg 110820
aagtttaact taaacctaaa atgaaattta actgaaaaac aaaatccaat gaaagatgct 110880
ttcttatgca aaacaaaca aacaaaaaaa aaacaaaaaa accccaaaaa acccaaagcc 110940
aaagattgtt tctgaaatta ggttctaggt tccagagcaa ctccatggtg gggaatcagc 111000
cacatgtaaa gtaagctaag agtttggaca atttgtaata tttattccta ggtttcttta 111060
agacccttc agattttgaa ttcctattag tagcatcagc caggttctaa atgtaggcat 111120
caccatagac acttccccac tgctgcagtc cccaacactt gcccaatttt cccttgaatt 111180
gcacccatgc tgccttctcc aggcctattt gaacccagaa cctcgttgtg cctcgtttga 111240
aatataattt cctcctaact agtctctgat ctactatttc ccctacattg ctgccacact 111300
aatcacctaa aatagatttc attctaccct gaaacagaaa tctctaataa gttactccct 111360
tcccttacgg ggtaaagtta gccacatcct aggtattcaa ggaccttcca ggagctaaga 111420
acatttcccc tgcaccttct tgaagtacac ttgtcctatg tactggttat gttcatttct 111480
taccctcgct ctcgtttgt ctggaattt ccttggcctt aaatgcctct cacctgcctg 111540
cccacatctc tcagggttgt ttcaaatcct caatgaaggc tcacagcccc agtctatgtt 111600
ggccacttac ttcgtggcct gggaacattt ttctttggct gacttgctga cactccatca 111660
gatgcatttt tatctggttg tccatctgtg aaccataccc tgagaaggca gagagtgcct 111720
ctgcactgaa catgtgctag gggacaggtc tgtgctagag gggcaagcac tgggaatgaa 111780
gaactggtcc ctactcccaa ggagttcata tctcagtgga ggtgacaagc aactcactgt 111840
ttccgggggt tgtggtgact gctggggagaa ggggtgtcta tattagatcg aagcagcatc 111900
agggggaggtt ccctgagaag gtgatgcctc agcggatgtc tcccagctaa gtgggtgga 111960
ggtggagaag ggcagagcag ggagaggatc taggtgggc gtgtaagtct gcatgggtaa 112020
ctcagggaac ccttggtaac tgcatgtaac tgtgtgaagc tttcatgaag gaacatggta 112080
ggagactagg gtatggacta tagaagccct tttgctaagc tcaagaattt gaggccggga 112140
gcggtggctc acgcctgaaa tcccagcact ttgggaggcc aaggcgggcg gatcacgagg 112200
tcaggagatc gagaccatcc tggctaacat ggtgaaaccc cgtctctact aaaaaaaaag 112260
tacaaaaaat tagcggggcg tggtggcggg cgcccgtagt cccagctact cagggagctg 112320
aggcaggaga atggcatgaa cccgggaggc ggagcttgca gtgggcggag actgtgccac 112380
tgcactccag cctgggcaac agtgcaagac tccatctgaa acaacaaca acaacaaaaa 112440
atttgaagtg tatcttgaag gaaatccctt ggagcctaaa aatgatcatt gataacagaa 112500
aatgatctct gctctcgcct agggtaatat attcagcttc aaagtggaag ggcatgtttt 112560
```

```
ccaagggcat gttttctaag tccctgtaat tgtagtgata gcaaatatat gccctgcatc    112620
ttgaaatgta agactaggtt tgaacagtat ataaattatc ttatgatcta atttcccctc    112680
attttgtggt ttctactata agctacccag aagtgtagac aggacgtttg gaatttgatg    112740
ggcatcggaa agattcctac ctaagaacat tttttttttt tttttttttt ctgagaagga    112800
gccttgctct gtcacccagg ctggagtgca gtggcacgat ctcagcttac tgcaacctcc    112860
acctctcagg ttcaagtgat tctcctgcct cagcctcctg agtagctggg actacaggtg    112920
tgcaccatca tgcctagtta attttttatat ttttaataaa ggcaggattt cactatgtta    112980
gccaggctgg tcttgaactc ctgacccat gatctgccca ccttggcctc ccaaagtgct    113040
gggattacag gtgtgagcca ctgcgcccgg cctctaagaa aattttgag agctacttgt    113100 tctgttgcct ggaattccac cgtaagtacg acgttgtgtc tccttctcca gggctactaa    113160
ctaaacaaca gagggtattg tgttatcgac aattatttga ttgataacta tcagcaaaca    113220
tttgccaagg cattccttta aagatagcct agtgactcta ttaactactc cttcttccag    113280
gcttctaagt tctgttggag gtaagtagat cccagagata aagcacctac cataggacct    113340
gaatcttggt agaaataaat tatatcatca tgttatcata ttatcatgtg tttttctatc    113400
tttaaagtct tatgtgaata ttctgcttga aaaatatgtg tcctctgtta gaccagagtt    113460
gaaaatatgt tattcaagaa cttgtaacag gaacccgcac aatttctgct ggagtttaat    113520
ttcagggtta attctgtcag caatctaagg taaacattaa catttttccc tagattcaag    113580
tccgttgtcc aaaagctgta acagaactta actgaataaa tagtttctta agatggtaag    113640
cttccatatg cttataatga ctcctctaca cgttttcatc tggaaggctg ctcatgcttt    113700
tggaagcaaa gaagacaatc ttaaataact acatttgctt tttggtggtg ccagattttt    113760
ctgagaaaca ccaatggaat ttataaattc accagtcaat gggcaattga gttgctgttt    113820
tgctattacc actgccgttt gtgagcattg ttgggaaggt gtcttgaagc acacgtgcaa    113880
gtttcccttg gataagtagt aggaatagaa ttgccaaacc atggcttcca gtgcagacac    113940
agtctctccc ttgggcccag ccactaggca ccacacatta agaggatatt gtctgtccat    114000
gtcctagaaa cgttgtagca tcatgctcct attcgattaa aaatctcatt attaaaatga    114060
accatcgggt aaatgttgtc tcgggaaaag aagcactgac cgtccctggg tgggctcgaa    114120
ccaccaacct ttcggttaac agccgaacgc gctaaccgat tgcgccacag agacccagtt    114180
actcaggccg cgctgcggtg tgtacagatt tccgcggcgc cggcagccgc tctagccacc    114240
ctgggcgtcg ccaccccagg cgttgccacc ccaggcacgg gctgagaagt cgcggggcgc    114300
gccgaggagg cagcggaagc ggccgaggtg cccagcggcc gccgcggggg gagaggctgt    114360
gccccggcgc gcgggagggg gcgggcgagg ccgcgtgact ccgggcttct ctgggacga    114420 agcgcgcccc tcgtggcggc agcggccagt ggtccgcagt cggcccggac tcggggtagg    114480
aaagatcctc tcagcaatgg ctgcgcgcca tgcgtgctct gcggcgggga ccgtgccggc    114540
cgggcgcgcc accagtaacc agggacccag gggagaacct gccaagggga ataggtcgca    114600
cggagagaat acgacacgct tggagggaag aaccacgtgc tgtacaggtt taaaggatgg    114660
agagtcacgt gcgcttaggt cccaaactta agggacctaa ccctttttct gggttgccgc    114720
tattgcccct tctccttaga cagttttca tctcatcacc tctcacccg taaaatgcaa    114780 cgaacataga taggctgtgt atcaatgtag actgtatgta tatctgtgct tcgtacataa    114840
aaagaatatg atttttgcca ccttctaaga accaatttgc accccatttt gaggcatatg    114900
gcctctgttg agattgcata gtttagggga catcaaaaaa gccttataga gggactggca    114960
```

```
attaagatag cctttcagtt tgaaatggcc attgaaggct tctcccttc cctgacttct    115020
gaattttttt ttttttttt ttttttttt tttgagatgg agtcttgccc tgttgctgga    115080
gtgcaatggc gcgatctcgg ctcactgcaa cctccgcctc ccgggttcaa gcgattcctg    115140
cctcagcctc ccgagtagct gggaatacag gcgcctgcca ccacgcccag ctaactttg    115200
tattttagt agaggcgggg tttcgccatg ctggccaggc tggtctggta ctcctgacct    115260
cgtgatccgc ccgcctccgc ctcccaaagt gctgggatga cattacaggc gtgagccacc    115320
gtgcccggcc aattttttta ggcgcactgt tcagtggcac taagtacatt cacattgtta    115380
tgcaactatc accgccatcc atttccagaa ccttttcatc ttccgaaaca gaagctccct    115440
acccattaca cggtaactca cgattcccct cctctagtcg gaacaatcac cattctactt    115500
tctgtccctt tgaatttgac tactcttaga gacctcatgt aaatggagtc atacggtgtt    115560
tgcctgtggc tggcttattt cacttaccat atgtcttcaa ggtccatcca cgttgtagcc    115620
tgtgtcagga tttccttcct ggataaggct gaataagctg cactgtatgc aggtatcgca    115680
ttttgctttt ccattcatct ctccgtgaac attagggttg cttccacctg cagctatgaa    115740
catgggtcta caaataactg attccctgct ttcaattctt tgggaatat acccagagat    115800
ggagtagctg gatcacatgg tttgctattg gctgtaccat tttacattcg caccaacagt    115860
gtacaagagt ccctatttct cctcatctat ttttttttta aataatgggc atcctaatgg    115920
gtatgaagta tcatctcatt gtggttttgc tctgcatttc tctaacgatt agtggtgttg    115980
ggcatctttt ccagacacca ccaatctgaa ttctatggcc cttcgtttac tcacttcctc    116040
ccagcaagag ccatttctgc ttcagcaagg aggaagctgc gactgataga gggaagggc    116100
ccaggggct tgcagagtgg ggcctgtgcc atgcaaggag aggagaagaa ggtggatctt    116160
tgagtaggac tatctggaga tcctgctttc acaaggtcct tgcttgtgtg ctgggcagct    116220
tttggagcta gttatcttta ttttagccct tgagggatat ttaggcatgt ggtgcttgtg    116280
agcagccaat ccatgaagaa ggaactgatg gtctccacct tggaaatatt ggaagagata    116340
atgccgtcca aattgcagtt ttagaagtta acttaaaatt atgctatttt aatggaattt    116400
tgggtgcatt tccatttct tcttaagaat tgctggaatt tcttaagtgt ttaggtgatg    116460
atctcttttt gtgattcctt ttttaaaaaa caacaacaaa atcttcaaa tacataagaa    116520
ataggccggg cacggtggcg taatcccacc actttgggag gccgaggagg gcggatcatg    116580
aggtcaggag atcaagacca tcccggctaa cacggtgaaa ccccgtctct actaaaaaat    116640
acaaaaaatt agccgggcgt ggtggcgggc gcctgtagtc ccagctactc gggaggctga    116700
ggcaggagaa tggcatgaac ccgggaggcg aagcttgcag tgagcctaga tcgcaccact    116760
gtactttagc ctgggcgatg gagcaagact gtctcaaaaa aaaaaaaag aaaaaaaaag    116820
aaagaaatag accttatttt ttctgtaact ccacaaaatt tctatttga ttccctatta    116880
ttttgctatt gtcaacacag tctcagtcaa ttcaagatcc tgtttgtgcc tttccctgga    116940
gtcatttcca agtgctaagg ctttggtcca tgagtcgcat gtgcacactc atggctgtag    117000
agggagtttt gctcccggtg aaggtcttgg tggctcttct ataccttgat tgagggaaag    117060
gaatcttatg tgaagttagc tttgttgtat cagatattcc ataaagccat ttctgggaca    117120
gtcccctctg tttatcggac cacaagcttc tctgtcctca tcaagcccac ctttatactt    117180
catttctcca gacttcatgt ccagactgtg ggatgaacaa gtggttataa ggttttagag    117240
gctcctgtag gactagatgg aaggcaaaaa aaggaaataa cctttaagca tgctctcgat    117300
```

```
tccttaaatc ccatctgaaa gtcttaagga tgtcttctca gtcatactta tttgacaata    117360
ttacctaatt ttctccatta gcccaagctc aggggtcttt cttcttccat attcacatgg    117420
gtgcaatggt tttctgaaag gaaaacagca ttactagggc agtaacattt aattaatcac    117480
aggtacttat caaactacaa aacaggcatt ccaggaactg ggtgtttctg tttgtaaaat    117540
tacactctcg tgtacatgct cccactaaaa tgtaagttcg ctgaggatgg aggttttggt    117600
ctctttgctc tgtgctgtaa ccccaacact gcagcagggc ctggcacata gcaggcatgc    117660
agggactatg cactgaatca atgaggaaat gaaaaccagg accatgaagt aaactggaca    117720
aaataaaatg tgatagaaaa tctaaattcc taatacataa ggagcactta tcaattgata    117780
tttacaaaat cttttttacaa ttcaattaaa gacaacataa acaaataag atgggggaca    117840 ggaacagaaa attcccccaa agaaaaaaat atatatacat ggtacagcca ttgtggaaag    117900
cagtatggag ttctcaaaaa tattaaaata gaactatcat ataatccagc aatcccatcc    117960
ctgggtatat atctaaagga aatgaaatca gtaccccaaa gaggtgtctg cactcccatg    118020
tttattgcag cattagttac aacagccaag atatggaatc aacccatcag cagatgaaag    118080
gataaaggac atgtgataca tatacacaat ggagtagtat tcagccttaa aaagaagaa    118140 aatcctgtca tttgcaacaa catggatgag cctagagaac atactaaatg aaataagcca    118200
ggcatagaaa gacaaatgct gcatagtctc acttaggtgt ggaatctaaa aaagtcaaat    118260
taaaaaaaaa tgtcaagcag agaatagaat ggtagttgcc agggactctg ggaagtagca    118320
ggggtggggg tggaggggag gggatgggca gaagttggtc aaaaggtaca aagtttcagg    118380
tagacaggtg taagttctgg ggatctattg tacagcgtgg tgactgtagt taatactgta    118440
ttgtgtactt aaaaattgct caccaaaaat gttctcacca aaaaaatgat gtttggatat    118500
gttaaacagt ttgatttaat cattttgacg tgtgtgtgtg tgtgtgtgtg tgtgtgtgtg    118560
tgtatacatc aaaacatcac attatatacc atatacaatt aatatataca attttttgtca    118620 aagaaaaaat gcacatgacc aatatgataa aagtttagtc tcactagtaa taaaaatcaa    118680
aattaaatga aataaaaatt tctttcccca aatcgcaaaa gagaaagaaa ggtaatacta    118740
aaacacagtc acggtgtagt gagagggctg ctctcacaca ggactgatga gaataaaatt    118800
ggagagcagt gtggtaatat acatattaaa caatgtatat accctctcat tttagaaatt    118860
ctatattaga aatccatcct aagaaaataa ccagggatgt gatcaaaatt ttgaatgcag    118920
cagcacagta ttatttataa tagttataaa taagaaacaa cctgaatgtc cagcaacagg    118980
caaaaatgat aaataaattg tggcatattt aagctggtgg ctcatgcctg taatcccagc    119040
actttgggag gctgaggcag gaggatctct tgaggccagg agtttgaaac ctgtctgggc    119100
aacataacga gacccagtct ctacaacata ttttttaaaa ttaggtgggg catggtaact    119160
catgcctgta atcccagcac tttgggaggc tgaggtgagc agatcacctg aggtgaggag    119220
tttgaaacta gcctggccaa catggtgtaa caccatctct acaaaaaata caaaaattag    119280
ccagggtggg gtgcgttcct gtagtcccag ctactcggca gactgaggta ggagaatcac    119340
ttgaacccgg gattcggagg ttgcattgag ctgatatcat gccactgcac tccagcctgg    119400
gtgagaccct gtctcaaaaa aaaaaaaaa agaaaaagaa aaaattagct gggcgtggtg    119460
ctgtacgcct gtagtcccag ctattccgga agctgaagcg gggggattgc ttgagcccag    119520
gaatttaagg ctgcagtgag ctatgattgt gccactccgc tccagcctga gtgagaaagc    119580
aagactctgt ctcttaaaaa aaaaaaagtg atatattttt aaaatagagt atattactta    119640
tatagacatc aaaaacaata ttttcaaggg atatttaaaa acataggatc atgacaaaat    119700
```

```
gtaaagttca aaggtaagat ggagaatgga gaactgtggg gaactgtata atctgacaat 119760
tcgtagttgc atacatcttt ctgtgtgctg gtgctgttag aacactttgt acgcatcacc 119820
tcatttaagt tcagcatccc taggtggcag atactattat tatattccag ttttgtttca 119880
cgttgtatat gcggtgtgag ccccaatatg ggatgtgtgt gtgcacatgt gcagtatttg 119940
gaaagttcta tgaaatatta ttagtggtta tctctgggag gtgattttta ttccttttcc 120000
agtatgttct caagcatttg ctgcaagcag tcttttgcgg ggccagggtt gagaggcagc 120060
agcagtttcc ctaaattaca gatagaggga ggtaggtggt tatgcttggc cagatctctg 120120
tctaggggta gaggagtgcc tgtgtgtggg tagggacacc ggcgggggc tttgccaaac 120180 acagtggaac tgtcacgctg gtctctcttc tcaactcttt cactcacctg agaaagggt 120240 gtctatggac catgcacact tctgtgggga attttacaag atgtgaatca tcagtgatga 120300
agatgctttc atttaaaaag aattggagta cctgagatta gagataactt ctacccttt 120360 aaaatatttt taaaaatttc tttgcactga ttttttttct tcgtttttat gagttgtttt 120420
catttgggtg ggataactca atctacagga gaatattaag acttttttaaa ttttaaaaaa 120480 tatactttca aatacttaat acattttgtg ttaaatgaca gccagcagat attgactgaa 120540
ttgggctaga tgcttcaggg atctcccttc catttaagac tctccgagag gccattcctg 120600
actgcaggtc actgtattat ttttaatttt aaaattttta cttacttatt ttatttaatt 120660 ttatttttg agacagagtc tcactctgtc gcccaggttg gagtgcagtg gcacaatctc 120720
agctcactgc aacctccacc tcccgggctc aagcgattct cctgcctcag cctcctgact 120780
agctggggtt acaggtgcag gccaccacac ccgttaatt tttgtatatt tagtggagtc 120840
agggattcgc catgttggcc aggctagtct caaactcctg acctcaagcg atccttccac 120900
ctcagcctcc caaatgctg ggattacagg cctgagccac cccactcggc ctactttatt 120960
aatccacttg cagaaacagg atatacacaa aaacgtttca aggctgtaag tgccactgca 121020
tggcaccaat ggtaaacgtt ttacaaattt gagtcaggaa caatcattag tgtcactagc 121080
aacaaaaatc aaaattaaat gaaataaaaa atttctttcc ccaaatggca aaggagaaag 121140
aaaggtaata ctaacacgca gtcagggtgt agtgagaggg ccgctctcac acaggactgg 121200
taagtacaga gccatggagt aagcaggtct tgagctgaca ctggagagga tccttttttt 121260
tttttatttt tattttttta gagtcagggt cttgcttttt tacccaggct ggagtacagt 121320
ggtgccatca tagctcactg cagcttcaaa ctcctgggct caagagatcc tcctgcctca 121380
gcatccccag tagcagggac cacaagtgag aggatccttt agtgttgtca aggagaagga 121440
acagaggtgt ggatgggtgg gcacagacac aggagcacag ctgaagcaga ggattacaaa 121500
gggtggagcc tgatgtaaag aaacctaata ggtgacagag catggaggct cttgaatacc 121560
aggctggaaa ctgcattagg aacggtgctc ataattgcag aaaattttac atggcctaga 121620
tagtcatcaa aggatgatgt acaaacaact atggcatatt tatacaatgt gccgacagga 121680
tgcactgaac attttgaaca acaaagagac ttgataatgg cgaggttttg aggaggtgaa 121740
tcaggatgca aaaaagcaa acaactaata aagttgattg atgacaaaca ctatcaaaag 121800
gcagccagga gaaagctac tggttacctc cagggagctg gtgagggagg ctgggtggga 121860
ggatctaccc ttctgaattc tgagggcacc tccagtgtgg ccctcagaaa gcaggagctt 121920
ccaggctaga atcagatccc gacatccctg ttaattccac ggattccaca ccgagtcaga 121980
tttatgattt actatagggt tttaaaaacc aaattgcagg gatgctagcc tatcacagct 122040
```

-continued

```
tatctcagac attgtccact aaggtataca gagtgctgcc tgttcctttg gtacccaat  122100
caggaaaccc catcagatct gctccttcct atggggtagt gagtaacacg aaggcttacc  122160
atctcacaca gataactggt cataggtcca gcagaagttt aaaacagaaa atgaggaaag  122220
ccatgtgatt aactgctgcc agactgtttg tgttacaaac agcagttcct taggcattgc  122280
ctgggacatg caataatttc tgttacacaa tctgtggtag ttaaaatgct gcacgatgaa  122340
agctatctga tttggattca ttattaggtg agccatctcg tctgcaattt ggttccacca  122400
ttttcattta acaaatgtaa aaaagtttat taagctctta caaagttatg ctgggcaaat  122460
atgcaaaagt ccagatcacc taccgcagga actaatctag cctcctctct gggcaccctg  122520
ttgtttgggg ctgggcagtt ctttcctgtg tagaaccatc tagggctgaa taggtcattc  122580
tgacacctgg gcacctctgc ctgctcgtaa atgggacaat cagaaagggc ccttatgttt  122640
ccaaactttc tttaaagtag ctgttctgaa acatggtcc agggacccct gattgtccct  122700
gagacctttg aggggatctt caaggttaaa attaatgtca taataatact aatatgttat  122760
ctgtcttttt tcactctcac tttctcacac gtgaacagtg gcattttcca ggtgacagag  122820
tgtgtgataa tgaacctaac tgaatgcaga agcaaacatg agaacctagt tttttcaatc  122880
aaaccagacg tgaaagagat ttgcaaaaat gaaaaaacaa tgctatcctc ctcacaatat  122940
ttttgtttta gaaaataaag ttattttttcc tagaaatgtt tttgagttta tcagtcatag  123000
gtttattatt ataattaaaa aatgaaatat acatacacag acatattttt taaagttctc  123060
agttttaatc tctttttttt ttttttttttt tttgagacgg agtctcgctc tgtcgcccag  123120
gttggagtgc agtggtgcga tctcagctca ctgcaagctc cgcctccctg gttcgcgcca  123180
ttctcctgcc tcagcctccc gagtagctgg gactacaggc acccgccacc gcgcccggct  123240
aatttttttgt attttttagta gagacggtgt ttcaccatgt tagccaggat ggtctcgatc  123300
tcctgacctc gtgatctgcc cacctcggcc tcccaaagtg ctgggattac aggcgtgaac  123360
caccacgccc ggtctcagtt ttaatttcta atacagtaag tattgatcag tgtgcccac  123420
attagtaaaa gctcttgggg tcctcagtac ttcttttttaa gagttgtcaa ggagtcctgt  123480
gaccaaaaat aggagagcca ctgccctaga aggacagccc cagcccgggt caggaacaac  123540
tgggacagaa cctactgctc ctagtggatt gtaatatgat aggatttaac cttcaaggtt  123600
tcaactcttg gcaagagtcc atgaggggcc atggtttgtc ctgagcattg cttactgtta  123660
acaggagcaa gttccttagg ctggtgagcc aagccagcct gacgctggcc atggacatct  123720
tagtgggctg cttgttctag tgtgggtttt catttttatgg gaaatgtcat ctgctctaag  123780
gctcttctca tttggggaaa tcacaagttc tcagaatgtt tgtctctctt ggttggggcc  123840
tctataatta aattataaaa cagaggtaat ggttaagtaa tgcaagattt gacagaaacc  123900
acagaggatt tagggtttaa tttgagtgag gcaaagggg gatgaagatg agcggtcctg  123960
gagacaagaa aaagattgga tgaagctggg cacggtggct cacgcctgta atcccagtac  124020
tttgggaggc caaggtgggc agatcacttg aggccaggag tttgagacca gcctggctaa  124080
cataatgcaa ccccgtctct actaaaaata caaaaattag ccaggcgtgt tggtgtgtgc  124140
ctgtagtcac agctacttgg gaggctgagg catgagaatc gcttgaatcc gggaggcaga  124200
ggttgcagtg agcagagatc atgccactgc actccagcct aggcaacagg gtgagactct  124260
gtcttctttt ttttttgagac ggagtctgtc gcccaggctg gagtgcagtg catgatctc  124320
tgctcactgc aagctccgcc tcccagcttc aagcgagtct cctgcctcag cctcccgagt  124380
agctgggatt acaggcatgt gccaccacac ccagctaatt tttatatttt tagtagagac  124440
```

```
ggggtttcac catgttggtc aggctggtct caaactcctg acctcgtgat ctgcccgccg 124500
cggcctccca aagtgctggg attacaggtg tgagccacca tacctggctg agactctgtc 124560
tttaaaaaaa aaagagagag agggagagaa agattggatg aaacaacaga gtggggagga 124620
cctgtgagct tggtagcttg gtgaaggcag ggctttattg ggggccttag aggggatcca 124680
ataaaggttc ccagtcatgg tagtgaccta aagaaaatag cattttaaca tctttcattt 124740
cataatagac agtcacagtt tacaagaccc tttccataca ttccttatga catccatact 124800
acagcccaga ggcaagttgt gcactctctc ctctcacaaa tacaaaaact cagcctctag 124860
aggccagcga cctgctcagg gtgatgtgca attcagggat gacagagtcg aggctcccag 124920
cccagtggtt atccctcaca ggcacgttgc ctgtcagtgt gcagtataaa actttgtaca 124980
agaaatcaag ttgcattagt cagtcggatt ccccaaatga tcacattgta gatggtgtat 125040
gctgtgggca gagcaagggc tgctgtttct tgggcaaaac aatcagtccc cctccccccc 125100
aaaataaatg aatgccaatg gtgtgacttt atttttattta ttttatttt attattattt 125160
gtgagacaga gtctcactct ttcacccagg ctggagtgca atggcatggt ctcggctcac 125220
tgcaacctct gcctcctggg ttcaagcgat tctcccgcct caccctcccg agtagctggg 125280
actacaagtg catgccactg cacccggcta atttttgtat tttttttaag tagagacagg 125340
gtttcactat gttggtcagg ctggtcttga actcctgacc tcatgatcca cctgcctcag 125400
cctcccaaag tgctgggatt acaggcatga gccaccgcgc ccagcaatgt gactttataa 125460
ttacagaatg taggactcag ctcccactat tgttatgact caatattctc ttagataatg 125520
tttggggcac tagcttacag gcagcattgc ccggtggtta atgttgtagc tttgcaggca 125580
gactgaccat attaaaattc gatcacacca tttgctaagc ctgtggactc gggcacgctt 125640
ctttctctgc gttagtttcc tcctctgtaa aacacggatg atgctataaa cacacccaag 125700
tcctagaatt gttatatgag ttagaaaaga taggcaaata caactctcac aagacagcct 125760
ggcctccagt aagtgccact gagtgtttgc tcttattgta cagtggctcc aagtgcttct 125820
gtcttggatt atttctgacc aggtggctat gtctcctagt aacttaccaa tcctgttgag 125880
tcttaataag cacgtctttg atgcctacag tgcgactgaa tttccaggcc tcattactgg 125940
agacacaatc atcctatatg ctttttttcca tttgttttta ataaagtggt acatgtgtat 126000
ggcaccagat caaacagtac agaacaagtt acaatggaag agaatggcct cccagctttc 126060
ctgaaatcct caactcagag acaacttttt tttttctgac ggtttcttta tacagccctt 126120
tttgtggtta ccttcctaac tctagaaaaa ctattcttac ctctgtttat ttacttagaa 126180
acattagacg ttacctttca actcctcagt atgaagcttt agttttcagc accccaggcc 126240
accaccctct ttccaggact tactacttat actggtggta ggtggaattt taaaattcat 126300
cagcattctt ttgtgattct ctgtgtgttc cagttttaca gcaacccgta cttgttgcat 126360
gagtacagta gaactgggag gctcataact tagcctgcag gacttttcac ttaaagcctg 126420
gccctcaggg tgatgtcacc cacctcattg tgcctggctc aggagtttag tccctcagtt 126480
gcctggttgt atagtttgga tgttcagcac ctccaaatct cacattgaaa tgtgatctcc 126540
aatgttggat gtggggcctg gtgggaggtg tctgggtcat caggtgggtc cctcttgaat 126600
ggcttggtgc cttcccccatc gtaacgagtg agttcttgct ctggcagttc acacaagagc 126660
tggcttttta aaggagcctg gcaccttccg ctctttctct tgctcttcct cttcccttcc 126720
tttgtcacta aaagcttcct gagccctcac cagaagcggt gcagatgctg gtgccatgct 126780
```

```
tggacctcct gtagaactgt gagccaaata aactctttcc tataaattac ccagtttcag 126840
gtattccttt atacaatgca aaacagactc acacatctgg taaaccccag ttgtttgctt 126900
ctaggtaaga cgggaggagt ggggagctgg tgagggtttc cactgcattg tctattttca 126960
ggcaaggtgt ctccactgag taggcttcac attcagagct ctgggtaagg tgggcaggaa 127020
gagggttgca ggctgcccaa aggagggaga gaagaaggct gaatccttca gtgacaacct 127080
gtgaaccaga gtcttagctc tctttgaata ttttgttcag tatctttggg ttttgtttta 127140
ttttgcctag gggtaaatgc tgactgcctg ttctctggac aggaatggag aagatggtgc 127200
tagcagggtt gctgttcata tgtagacatt catgcagtca ctctcttttc agcacacttc 127260
ttacttctgc cctgggttca gttgctgact ctgagcccag aaaccttcta gggttctgtt 127320
aggtagattg gcttccaccg tctttgcgac aaccacagaa aattctagac tgttttctct 127380
tcgggcttca ttagtcaact tgcttcagtc tgtcttgcat cttctaaata tttatagatc 127440
tctctctttt gttggagtgg cagaaaatgc tagttgacca cccaatattc aaattatcct 127500
gcctccttaa taacagaata tcattggatg tggtgggtaa ataatatacc ctaactttcc 127560
ttgcagagag gggtggccaa tgagatggaa atgaaagtca ttgggaaaga ctcccaagac 127620
atctctttaa acaagacaga ctgaagcaag ttgactaatg aagcccaaag ctagcagttg 127680 ttttgttta tctttgcctc tttcttcttc ttcctgtggg gacaaagggc agtgatatct 127740
ggagctgcag cagccatttt ggcataatgt tggaaaagcc aagagactct cagagaccgc 127800
agctccagca gttttttatt ttttccaaat atttgctcca ctgcaggagg atgagatatt 127860
cgtgtttgtt gccttgtgac tgtaggagga ctgcacttcc ctgccttgtt gtcaagtttc 127920
cccatgtggt ctgctttggc cagtaaaaca tgagtgggag aagcttggtg aaccattgca 127980
tgtctaccag cttttttgct ctcttccctt tggcattaga aaggcatgtc caggatggag 128040
ttgttccttc agcctagatt gggttatgag aagctagctg ggggagtcca gtaacatata 128100
aagcgagtta gaaataaaac tttgttgttg taagctatat atatatatat atatatatat 128160
atatatatat atatatatat aatatgtatg taatatataa atacatatta tactttaagt 128220
tctagggtac atttgcacaa tgtgcaggtt tattacatag gtatacatgt gccatgttgg 128280
tttgctgcac ccatcaactg ctcatttaca ttaggtattt ctcctaatgc tatccctccc 128340
cagcccccca cccctcaaca agccctagtg tgtgatgttc cccttcctgt gtccaagtgt 128400
tctcattgtt caattcccac ctatgagtga gaacatgtgg tgtttggttt tctgtccttg 128460
tgatagtttg ctgagaataa tggtttccag cttcattcgt gtccctgcaa aggacatgaa 128520
ctcatccttt tttatggctg catggtattc catggtgtat atgtgccaca ttttcttaat 128580
ctagtctatc attgatggac atttgggttg gttccaagta tttgctattg tgaatagtgc 128640
cgcaataaac atatgtgtgc atgtgtcttt atagtagcat gatttataat tctttggata 128700
tatacccagt aatgggatca ctgggttaag tggtatttca agttctagat ccttgaggag 128760
tcgccacact gtcttccaca gtggttgaac taatttacac tcccaccatc agtgtaaaag 128820
cattcctatt cctatgtctc cacatcctct ccagaatctg ttgtttcctg acttttttaat 128880 gattgccatt ctaattggcc tgagatggta cctcattatg gttttgattt gcatttctct 128940
gatgaccagt gatgatgagc atttttttcat gtgtctgttg gctgcataaa tgtcttcttt 129000
tgagtagtgt ctgttcatat tgtttgccca ttttttgatg gggttgtttg ttttttttct 129060
tgtaaatttg tttcagttct ttgtagattc tggatattag ccctttgtca gatgggtagg 129120
ttgcaaaaat tatctcccat tctgtaggtt gcctgttcac tctgatgata gtttcttttg 129180
```

```
ctgtgcagaa gctctttagt ttaattagat cccatttatc tatttttggct tttgttgcca   129240
ttgcttttgg tgttttagac atgaagtcct tgcccatacc tatgtcctga atggtatcgc   129300
ctaggttttc ttctagggtt tttatggttt ttaggtctaa catttaagtc tttaatccat   129360
cttgaattaa tttttgtata aggtgtaagg atggtttcca gtttcagctt tctacatatg   129420
gctggccagt tttcccagca ccatttatta aataggaat cgtttcccca tttcttgagc   129480
tacagatatt ttgagtttgg ttaccacagt attatctagt ggaagttgac ttatacagta   129540
tgtaatagga taaatatagg tgtgtaacag aatattaagt gttcgtgttt caaagctgag   129600
gggaaaatgt taaaagtgtt cacacactct aaaaagagat tagctaaaac tgcttcatta   129660
accacacttt ggggaaacca gttctgagat tcttctccat tactctgaca ggttggaccc   129720
tctggggagc agatctcaag atcaagttat gagtgcaaga ggtgtgttgg aagcgatgg   129780
ttgtaaaaga atcctgcagt agcaccaggc acaagtctgt ccagggagag gaggacttct   129840
actctctacc agcatctctc ctaagtcccc ttaggggacg ggggcaagga agtgctggga   129900
agggcagggc atggttcctg gctaggactc cacccccctg gggcctgtac ccacggacct   129960
aggtgaagac aggcactcct gccttctcgc ccaacggttg cgtttcccaa gatcatcctg   130020
gcctgccacg cccccatcta cctattaaac tcccccacct tccccaaacc ctagcaggca   130080
gacacacatc ggtggaagaa gacaggagcg gctggacatt gaaaggacgt cgagaggagc   130140
acacctgcac accatcgacc agcggaacga ggcagagtgt ggctggagca gtcggaggga   130200
agcctgggcc gctgactcca ggggaaaacc atctcctttc tggctccccc ctctgctggg   130260
agatactttc actgaataaa accttgcact cattctccaa gcccacctgt gatccgattc   130320
ttcctgtaca ccaaggcaag aacctgggat acagaaagcc ctctgtcctt gtgataaggt   130380
agagggtcta actgagctgg ttaacacaag ctgcctatag acagcgaaac tgaaagagca   130440
cacaatagca cacactcatt ggggcttcag gagctgtaaa tatccacccc tagacgctgc   130500
catgggcgg gagccccaca gcctgcccgt ctagaggttt gagcagcggg acactgaaga   130560
agagagccac accctcatcg cacgtcctgc gagggagaca agggaacttt tccggtttca   130620
cttctgcttg gcttgagctg gcactgaagc acccttttcc ctcctcactg agggagcaga   130680
ggggaaaagc ggtagaacta acaggctaac aatgctcctc cgaaaatata tcgtattttt   130740
ggatccctag agataggtga tcacggcagc cgcggagtgc atttgggtct cctttcaaga   130800
aagaacttgc tgctcagcgt tgaagaatgc agttggccaa cagcctccag ctgctctgtc   130860
ttcagcatct gccatggcat ctgagctgag gtcatgttct tcctgggagg tccccagcag   130920
aaggatcacg tggaagctcc acaagctcca cagatgttcc aggagaggaa taggcagcat   130980
ttggaagaca tatcctgcca taacagaggg catttgctag tagagacaac aaacagcaac   131040
agccaagtaa acaaacacac aagcacaaag cactttctcc catttcccct cattgatcct   131100
gtccgggtag aagctgggga ggaagtagaa tagggtgagg cggggtgggg ctgggggcc   131160
tacaccttct tccttccccc gcaggtcctg tccctgggcc aggcttgaac taggggaatg   131220
ggaaaagctg tgaagtgaat gagaattagg agttttatt tagactggac ttgaattttt   131280
tttttttttt tttttttttt gagacagagc ctcgctctgt cacccaggct ggagtcccgt   131340
ggcgccatct tggctcacta cagcctctgc ctcccgggtt caagcgatcc tcccaccaca   131400
gtctcctgag tagccgggat tacaggtgcc tgccaccatg cccagctatt ttttttttt   131460
tttgtatttt tagtagagac agggcgtcac cgtgttggcc aggctggtct cgaactcctg   131520
```

```
gcctcaagtg atctgtccgc ctcggcctcc ccaagtgcta ggattatagg agtgagccac 131580
cacgcctggc ctggacttga attttttaatt cctaaaaatg aactaccagt taaaatttaa 131640
aaatgaccaa aaaagctatg ggatatgctg atgttttgct ttgggggataa ggaaaagata 131700
tctggttgag cggcattgaa aacagtgtag ggagagaaaa actcattcct ggctcaccct 131760
tttgagtccc actatctcaa taatctgatg ttatatgaca cacacacaca cacacgagg 131820
aatcctggaa gactccatat caaggtggtg atgaaggtga ccagtgggtg ataggattat 131880
aggtgtgtgt ttatttattt attttaatta cctttttttta gagacagggt ctctgtcatc 131940
caggctgcag tgcagtggtg tgatcatggc tcactgcagt cttgcactcc agggctcaat 132000
cctcctgcct cagtctcctg agtagctgga gctgcagtca tgcaccaacg tgcccaacta 132060
atttactttta ttttattttt tatttttttgt taagatggaa tctcacttta ttgcctaggc 132120
tggtcttaaa ctcctggttt caagcattcc tcctacctca gcctctcaaa gtgctggaat 132180
tactgcactt ggccctatta tattttttaaa aaatttcaat agttttaggg gtaaaagtgg 132240
ctttggttac atagatgaat tgtatagtga tgaagtctgg attttttagtg tacccatcac 132300
ccaaatagtg tacattgtac ccaatgagta gttttttcatt cctcaccccc acactgtccc 132360
cacttctgag tctcctgatg tccattatag caccctgctt ttgcgcactt agagcttacc 132420
tcccacttag aagtgagaac atgtggtagt tggttttccc ttcctgagtt acttcactta 132480
ggtcagtggc ctccaatttc atctgagttg ctgcacataa catgatttca ttcttttttt 132540
gactgagtag tagtccatct ctctctctca cacacacaca tacacacaca cacacacaca 132600
cacacacaca cacatttatc cactcatcca ttgatgggca cttaggttgc ttctatatct 132660
ttgcaattgt gaattgtgct ccaataaaca tacatgtgca agtgctgttt tttctcccctt 132720
ttatccttct tttcttccct atgcttccat aggtactgag aaagagtctt ttttatataa 132780
ttatttctttt tcctttggga agataccccag tagtgggatg gcttgatcca atggtagatc 132840
tgttttttagt tctttgagaa atctccatat tatctccata ttgtttttcca tagagattgt 132900
actaatttac attcccacca acaatgtatg tgttccattt tcactgcatc ggcaccaaca 132960
acggttgttt tttgactttt taataatggc cattctggct gggggtaaggt ggtatctcac 133020
tgtggtttta acttgtatttt ccctgataat tagtgatgtt gagcatttaa gaaatatatt 133080
tgttggccat ttgtatatct tcttttaaga aatatctctt gaagttgttt gcccacttttt 133140
taatgtgatt atttgttttt ttttcttgct gatttgtttg agttccttgt agcttctgaa 133200
tattagtcct ttgtcagagg tatagtttgc aaatactttc tcccattctg taggttgtct 133260
ctttactctg ttggttattt cttttgctat gcagaagctt tttagaataa ttaggtccca 133320
tttacttatt tctgttattt tgttgcattt gttttttgggg tgttagtcac aaattctttg 133380
cctagaccaa tgtccagaag agttttttcct aggttttctt ctagaatttt tatggtttca 133440
ggtcttagat ttatgtcttt aatccatctt gaattaaattt ttgtatatgg tgagagatag 133500
gaacccggtt tcattctttt acactacatg tggctatcca attttcccag cactgtttat 133560
tgaataggat ttcctttccc cagtgtatgt ttttgtttgt ttggctgaag atcagttggt 133620
tgtaggtatt tggttttatt tctgggttct ctatgctatt ctactttttat accggttcca 133680
tgctgttttg attacaatag cctcgtagta taatttgaag ttgggtaatg tgatgcctcc 133740
agatttgctc tttttttgct taggattgct ttggctattt ggacccctct ttggtctcat 133800
ataaattttta ggattggttt ttctaattct gtgaaaaatg acattggtat tttgataagg 133860
gttgcactga atctgtggat tgctttgggt agtatagtca tttttacaat attgattctt 133920
```

```
ctaatccata agcatggtat gtttctccat ttgcttgtgt catctattat ttctttcatt   133980
agtgttttgt aattctcctt gtaggggtct ttcacctcct tggttaagta tattcctatg   134040
tattttattt ttattttttg cagctattgt aaatgggatt gagttcttga tttgattttg   134100
agcttggcca tcattggtgt atagcagtgc tagtgatttg tgtacattga ttttgtaacc   134160
taacactact aaattcactt atcaaatctg ggagatttt gaggattcct taggatttc    134220
taggtatgag atcatatcat tggtagaggt agtttgagtt tctctttttcc agtttggatg  134280
cccttttatt ctttctcttg cctgattgct ctgactaggg cttctagtac tatgttgaat   134340
agaaatggtg aaaagtgggc atccttgtct cattctaatt tttaggggga aatgctttca   134400
acttttcccc attcattttg atgttggctg tgagtttgtc atagatgatt cttactattt   134460
tgagatatat tcatttgatg cctagtttgt tgagggattt tatcataaaa ggaggctgga   134520
ttttattgaa tgcttttct gcatctatta aaatgattac gttttcatt tttaattctg     134580
tttatgtcat gaatcacatt tattgactta tgtttatttg ttgcttacat ctactttcta   134640
attttactat aataaacatg tataatttg ttatcagaaa agtaaatgta aaagtgagtt    134700
ttaattttaa aacttgggcc taagtcttcc tgcctcccaa gcccattccc ttcctgatat   134760
ctggggcttc cctcctcaag cctgctctgc aggataaggg gatacagtcc acatgcctgc   134820
tgctggtttg gcccatgata acctccatgg gcaatgtctg agcctctgct gttgagtttt   134880
gctttacaca ctcctggcaa ggaaaggat gccaacatgg cttggacatg ggttgctgat    134940
aattggtgat gtctcatgac tggttctgcc tggagggctt gctgtaagtc cctgatagga   135000
ggaacatgga cctgcacaag agcagaactt atctgacact gaagaggaca cttcaagaac   135060
agattatcaa agtctagctc agggagaaat atactttaga gcagaatgag gaatggcgag   135120
gcagctgagc ttagacacaa gcagaaggaa atccatggtg agggcacagg caaggaaagg   135180
ggctgagaga gcattagtgg gggcagtcag gggcagtggt caggatgctc ggatgccagc   135240
gtgaacaatc gcatcaagat taaacaccat gaggatcgtt agacttcctg tcatatgtct   135300
ccaggtggtc ctccaaatat cctaaaccag atgacagcac ccctccaccc tctgctgtat   135360
aagcacatct gctctcctat aatcattccc acatagcaat ttatcatttt tattgatttt   135420
tcttcattta atacacgtat aagtgtgtct tttattttta aaaatttgca ttcctttaat   135480
tgctttggag attgtgcatt tttctctctg ttgatttact ctgccaataa acatgtaatc   135540
ctaccataag catgttttac ttgtgtaatc aaccaaaata aaaaatttaa aaaggaatca   135600
ctgactatga attagacatg tggataggca ccagggttgc agacatggcc cacgttcttg   135660
cattaacttg cactgtggct ggggcattgg atgggtacat taaaaggatt aaagtaatat   135720
aaggcagtat ttattaagtg ttgagtgagc actacagaac ccaagtgctg agggagtttc   135780
atgcaggaag agatcaagag taacacagag aagaagaata gatcaattta gcgcattcat   135840
ttaaaaattc accttttgca taaggggatg tgtcttttgt ggggaggagg ggagttccga   135900
ttggcagttt gttctcaggg agcttgaaga agagatcttg gagaggagac gcagagaaaa   135960
caaatgaaga aaatgtcaaa atggaagggg ttggcccggc tatgcatacc ttagttagct   136020
taggtagagt ctaaactttt acaagtggtt tcaataggtg tgtttggtct gggttctttg   136080
ggaggtatca taggagaatg aaggcaggga ggacgcttcc agcaccaaaa ttcaagggga   136140
aatgtatttt acatgcatag cattgttta ctctctttcc atttggagca tatcttaaaa    136200
attccatttg gagcatatct taaaaaaccc atttctctga caatggttct aaaaggggga   136260
```

```
aacatccttt gcaacagaat cattcattct ctcattcatc aaccactgat tgtgtactaa   136320
gtgtcagacc tgatctccat cctgcctggt atggcactag cttctgtctt gagacaagca   136380
ttgtgataaa ccatgaccaa aaaaagggca gttttataaa cacaagtctg ccaggctttc   136440
agcaattcta aatttccttt tgcaagtcag gctggagtta atggctcttt cctgcagcgg   136500
cggagatgac agggctctcc cacagtgctg agcaggcagt ttgaaagccc cacttcctgt   136560
ctctgcatgg gcgagtgtcc actggaagcc actgagagga aggagggaaa cctcagaaac   136620
cggcccctgc ctggctgctt caccctagaa agcccaggca gaggagggaa aggtgaagtg   136680
ctgaaaaaga ataaaaaagg gggaacatga aaaagagcaa gagcaggaag gaggcaggga   136740
cgggaaagga ggggaagcac ggaaacagcc aatgtcaagg agaagaaaag atggctggtg   136800
gaaaggagct tccaggaatt gggacacagc cctgtcttat tgcaaaagat ggaaaccctg   136860
aaggagaaca ggaaggaaaa agaaaacaag tccgtctgag ctggcagggt ccactttctc   136920
attctacaga tgaggaaaca gaggcacaga gaggaagtgg cttgcccaag ggggcagatt   136980
cttgaaagga tcatctgcac tctctctccc ttaatgcatt cttacctctt ctttactcgt   137040
gagtcagtcc tgaaggacaa gctgcctgaa gtcccacaca gatgggcctg gggcaagcat   137100
caaacatcct gggggccctg ggtgaggttt gcttttaaat tccaggtcag ggaaaggaag   137160
gtctttaagt tgtctgctct aagcttagta atcccctca gagttatggg tgcggtgtct   137220
ggggtagccg ttgcgtctct gggcaaatac cctggagaat gcagtgttgg ttgtctgagc   137280
tggggacaga gtgacagcat agttgcatgc agagctggag gctcctgcag ctgtacaggt   137340
aaggtgctga aattctccac caaccctccc tctttgcccc cagcaccacg aagataaccc   137400
tctttgaata tgtggaagtc tgttctccaa actttctaac attctcatgt cagtcttaat   137460
agattcagct cagttactgc ctcctccagg aagtcctcct tgtctgcaaa tcggctgccc   137520
accatgccgg ctcactcata gttttaactc tgtatctttc taatatgcct tagcccactc   137580
tgtcaggatt ccagtcagct tccttctcct agactaggag ttgcctcagg ccaggaggac   137640
cagccttgtt catatctgta ccctgcaaac ctgtcaatgc ccaaacctgc tcagtgcttt   137700
ggagtatgga accagccgtc aatgcaggaa tgttacactc taagagttcc caaaggtaga   137760
gagatgaggg attggtgctg gaagtgggag gttattctaa ggatgggtat ggcaggaaac   137820
acaattatag ttcagggagt ggagtgtcca ggagtgggag gagaggaact gggagaaaga   137880
gcagagagtg aaagtgagag cgggcacaaa gaaaggaaa aagagtcagg gatcaaccaa   137940
agtgcatgct tcctttcag ccctgccagg atgtgcaggg cggctgctgt ggacgcgtca   138000
aggctcagcc tcaaacatgt cttcttcctt gactttgtc tatcattcta aagctaggtc   138060
atttaaaaag ttcttttgtt ttctttccac cgatactctg atttctgaca ttcgccaaaa   138120
agaggtcaag accctggcat accgccctac taagattaaa ataaatatta tccattgaaa   138180
ctgttatttt ttccttaact gttatttgta gagttaaaga ttcccatgat cgcgctggct   138240
ctaacatcat ttttggctct tttgagatca aatttgcaat ttgatgcaaa aatagctgtg   138300
acgcatatgt gtctgtatgt gtgtggttag gagattttt atcattacat cttcttttgc   138360
cctgcctttc tgcctttctg tccttttaat ttgcgggctt ttggcaacca cagcacgggt   138420
ctggtttcct aggagtttct tttgtaggat caaaccgcta gttggctctt ggccctgtga   138480
tagggccctg ggctaactta ttgggaaaat gttgctgtaa ccctgccca gaggtgcctg   138540 tgacatgggc cgccatcttc tcctcttccc ttggcttcag ccccacctag aaacctgaac   138600
aaacattttc cttgacattt cataaagtgt cagtggctcc tcatttagca aaatacatcc   138660
```

```
cagggaagtt caaaagtgaa aaaaggccgt aacttcttct tcttctcagg gacctacaga 138720
aaatatgtgg cacctcggca gcctggcctg cagcactccc ctccccatcg gtgagtcctg 138780
ctacagtggg tccaggtgtc tggacgcccg gcacgcacgg ctctctgcag acctctggac 138840
agtaccatgg gagccgcaca gtccctgcct gttctgtccg gcagttcttg tttcccagca 138900
ccctgtctca ggtgagaggt tccctcttct gctgggcttc cctccctgc tgtgaaccc 138960 aaatatctga ggcaggtcaa tttaggaacc ttattttgcc aaagttgagg atgtacccat 139020
gacacggcct caggaggtcc tgaagacaag tgcccgaggt gatcgcggca cagcttggtt 139080
ttatacattt atacagacat cagtcaatat atgtaagata aacattggtt cggtcccgaa 139140
aggccggaca actccaagtg gagagggggc ttccagttca caggtagata agagacaaaa 139200
tgttgcattc ttttgagttt ctgattagct tttccaaagg aggcaatcag atatgcattt 139260
atctcagtga gcagagggt gacttggaat ggaatggaag gcagttctca gtttaaattt 139320 tcccttagc ttagtgattt tggggtccca agatttattt tccattcact ctgcagacag 139380
gggcttctgt gcatccaggg agcccctcct cacagaagga agcaggccat taatgagacc 139440
caatccagct tcaaccacct ggtaacaatt aggacatcac ttctctgagc aagagctcct 139500
gcctgtccat gagttatcaa gacattccaa ttgttcctcc acatctttga catgaagact 139560 tgaggggtc agatttcca gggggcttga tggcatgttc tcttcactgt tccctgccct 139620
ggtcatccaa gtgacccttg gcagggaaga ggccccgagt tgcagaatct ctgttctcac 139680
aagccattgc caacccggag agtggctttg ccactattcc tagcatgttg ttggctattt 139740
caggaatggg agtatttgac tttccctt gcagtgattg ctgcaaggag aggaattgag 139800
agactcaagt ccctgagata aatatttatc aactattact gaaagggagt atgtcaaaga 139860
aaaaatgtgg agaaacttca gcttgaacac atagtttaaa tccagcttgg gtgtactcca 139920
gtgggcatgg atgtattact gtttgcagt gcattcttct atgatcaata cacagaagca 139980
aacaggccac gtgggtaaac agtaattttc atttaccagg gtgaatatgg aagtcctctt 140040
gtttccatgt catgatgaag gaaagcaagg accatctttt gccaaggaac agtggctgtg 140100
ggggaactga ggagatggaa ggacaaggca gtcaaaagct ttgaacaac tctttttg 140160 agatggagtt ttgctcttgt tgtccaggct ggagtgcaat ggcacgacct cggctcacca 140220
caaccgctgc ctcccaggtt caagtgattc tcctgcctca gcctcccgag tagctgggat 140280
tgcaggtatg ctccaccatg cctggctaat tttgtatttt taatagagac gggatttctc 140340
cacgttggtc agctggtctt gaactcccga cctcaggtga tccacctgcc tcggcctccc 140400
aaagtgctgg gattacaggc atgagccacc atacccggcc ctttttgga ataatttat 140460 aggttttcaa actattacac ttaccttttt atataagaga caggacatag tcactgaaca 140520
atcactccag attttaagta agtccaggat gggatgacaa tggaacaacc atgaaatgaa 140580
aggaagaatg tgtcactggt atgtccacac gtctccaaat ctctcacctc tgtcagctgc 140640
aaacagagcc tgaaataaat gtttcctctg tgcacagcct ccacaacttc ctccctccac 140700
gtttctcact cactcctctc cagcacttct ctccgggttc tgcttacaaa cttgaaaccg 140760
gctatgcaaa aattataact gtggaaatta tgacagtgaa agagatcaga cctaaccgac 140820
tccatcttgc ttctaacctt taagctgtcc ttgttcattt ttgggctgaa ctaactttgg 140880
gaaggaattc agttcatggt agaactctga aacaaaattg ataatagccc tttcctgaaa 140940 agacccccctt cttgcctggg gacaagtctg ccattgtagg actaacaaat taactacaag 141000
```

```
attagaaatt aaggtttagg gttcatgcag cctccagttc caagagtcta aacctcccca  141060
aattgctcct ggggataaca tcactgttgt aaaagctaag accagtgctt gagatatttt  141120
gtagaccctg ctctggatgg atcagctgac accatccaga ctggtaattt ggctcaacca  141180
gctctgccat cccacccagg aacagaaaaa tactcacttc atcaccccat gagtccatct  141240
ctaacctgac caatcagcac tccctacttc ccaggcccct actcgccaaa tctgcctttg  141300
gaggcagata acaacttatc tttaaaaact ctgatccctg aatgctcagg agactgattt  141360
gagtaataat aaaactccgg ctctgcatga attactcctt ttccattgca attctcttgt  141420
cttgataaat tggttctgtc taggcagcca gcaaggcgaa ccctttgggc ggttacaaac  141480
tcatcctctg tggaagagta ggagttcatg gagaaattgg ttgcaaatta caaaatttta  141540
ttgtaaggtc aacttgtccc agtgtccgtc tgtgcagcga agggccctg catggtttag  141600
tgattgcaag ttgagcctct agggtcaggt tgtctaggtt tccatcccag ctcattcact  141660
tattatctgt gtgttcttga gcaagctcct taatcaattg aggctttgtc cttctgtttt  141720
tataatgatg agaataataa cctccacaat aacctcatca taaggttgtt gtgaagatgg  141780
atcagataat atatatgtag agtgcttata acagtgcctg gcacataaaa aatgctcaaa  141840
aatcttaagt gttattaata ataaactgac atatatttct tgagcagggt ggtggtaaat  141900
gggtgttctt tttattaagc tttaaagtgt gcatagatca tattaattct ttttatgcat  141960
atgatatatt gcacatgcat gaaaatacat gcattaaaaa taaatgagca tttatgagat  142020
ttagtttagc agtcacatgt cccaggatta caagccagca ataatgggtt ggaaaacatt  142080
ccaacccatt ccaaccattg gaaaacattc caacccatca ctggacccat gtgccaaaca  142140
atggaaccgc ccacaggttc tcattcttgg ttaaaaaaat atgattatta cgggaataat  142200
actgattccc taagaattaa tatctgagca gtttcttttt ttttcctgtc ttcttggaag  142260
atcagcaggt tctagattca atggagtcac taggattgag ccaccagtat acgccagtcc  142320
tctccagaac ggccacctgg tggtgggcac taaggcagtc tcagatgagg actgattgac  142380
ttttgtgtga actcaaactg ccaaagtccc tccctcacct tgcaaacttc aaagcacaac  142440
tttcaaagca ctactttctt tcttggctct caattctctg cctagaaaaa gggaggtgtt  142500
ggcaaggatg tttgtttagt tctgggcatc agtcaatggt acccagatct tgctgaacag  142560
aaaagacaca gatttgtttc tctgaggcag ttggtagtgc ttattgctta ttgctctcag  142620
gggcttctgc agcagtagaa gggccctctt cccctgccat gccacactga gaggagcatc  142680
cttggagtca tggttggaat ctgttttgt tatgctagtc ctcttccgca tgctagctgt  142740
tgcattgcag ggatatgtgt acctgtttat cttctccact aggctctaag aagccaggtt  142800
tcttaaagga aggaagctga tcttgtttat cttgaagtcc tcacagtgac attgctcagt  142860
caatgttgag tgtatgaatg aataaacggg aaccatcacg aaaagccga aaatacagtg  142920
gaaagactgg atcataaaat cttctaagca aattttttt cctcttacac tccatttcca  142980
aatagataaa gtattttta aaatcctatc agaatattct aacacactga gttgacagaa  143040
tagagatttt taaatgcagt gtcatttggc cagccatttg tgagaattta taatgttttc  143100
agtaggttga aaacactata aaagcaagga ctatgttcat acccaacagc tggcacttag  143160
tatgaatgct aaatgaaaca ttctcttctc tttcaagagt cagtccaacc agtgaccctg  143220
acaagaagga aggcacattt aactcaattt aatgaactct tatagagcat ctccttctcc  143280
aagtgctttg ctaaggatgg ggtaaaaaca tgaataagtc ttggattctg tccttcagga  143340
attttcagtc tttggaggca gatacatttg cacccaacta ttatcctagg cagagtgtga  143400
```

-continued

```
taagtacgat aatagcagta aaagctctaa gttaggcagg agaggaggag ctcgttaaag 143460
cttatggggc ctgggaggct ttcggcggag taaactccag ggggacagct aggcatctgg 143520
ctgctggaat tggaggaggg atcattttaa gtggctacaa ctctgggtgc acaggactag 143580
agggtgaggg ccaagatggg aaattgtggc agccatcttc cacactgggc gcccgccgac 143640
ccttgcttcc tggtattcat attattgtgt agtgtccccc aacattgtat cagggttggc 143700
ctgtgtgacc aattgcatat ggtgggaatg atggtgtgtg acttctaaga ccagttcata 143760
gaagatgtgg ccaattccct tactgtcttt ttttttggca ggggagtgcc gagtttcacc 143820
cttgtcgccc aggctggagt gcaatggtgc gatctctgct cactgcaacc tctgcctccc 143880
aggttcaagt gattctcctg cctcagcctc ccaactagct gtgattacag gtatgcgcca 143940
ccatgcctgg ctaattttgt attttagta gagacggggt gagatcaatg aggcagtcaa 144000
ttggccagcc tggttttgaa ctcctgacct caggtgatcc acccgcctcg gcctcccaaa 144060
gtgctgggat tacaggcatg cgccaaccgc gcctggccct tactgtcctt tggatcagct 144120
gctctggggc taggtcaatc cttcatgtga ctgcagcccc agccaacatc tggactgaaa 144180
cccatgagac accctgagcc aaaaaagccc agctaagact tcctgcattt ctgacccaca 144240
gaaactgaga aaagaaatgt tttgttgttg cttttaagcca ctgacttctg gggtcatttg 144300
ttttgcagaa atagatagca gatacagaaa agcaggctgg tggaacagtg tgggaaacac 144360
cttgattttc agggagttgc actttgttta tgtgcaatgg tgcactgttt ttagaaagac 144420
acaaagatga taatactggt gatgggcata atacggttg tcaagaggag tgactgaggc 144480
ggggataatt taagaggcca cagcagtagt gtggcaagag gtaatgaggg aattgaactt 144540
ggtgggaatg ggtgagatca acgaggcagt caatatgggc agtgagtgtg aaggagctgc 144600
gaaggatgat tctttggttt tgagcttagg aacatgagag aaccaagatc tcatttatcc 144660
aaagaggaaa cacagaagtg agcccctgtt tgggggcagg gctgggtagg aggaaaagag 144720
tggagacgtc tatctcccca ggaagagagc ccctgcttc cagatcccag tggatggcag 144780
ggcactcggc tcattcacag actgggctcg ttgagaaacc tttccctgga gggcagggct 144840
gctctgtttc acagcccata tccctcatgg ccaagtgttc ctcgagtgac agtctctgcc 144900
atcaatatt ttagcatgtg gtcttttcaga gactaaagag tggcatccat ctcctgaaac 144960
tccttcccca gctgacagct ggtgacccgt ggaggaggga gcttcaggga gcctgatggg 145020
cgagagtctg ttccaatgcc aatccattgg aagagatgaa gtcagacccg agtttgatag 145080
aaagcctact tcctcccttg tatccagctg tggagaccta ccaacatcaa tgcaaaccag 145140
aagctaacac ccagttcata tatcccaagt ggaaggaagc ttctcgtgga attgtcttac 145200
atgacagtaa cataaatcct gaaggtaata cttggccagg taatgttaga aaagaaacccg 145260
aacataggca ttgctattat agatcctagg ataggcctga gcaaaaactg tctgggattc 145320
ataacatgct tcgttgcaat ctgatagagg gagtgagatc cactccaaat ggagtctgat 145380
ttggggcaaa gcaaagagta tggaaggaaa cttgagaaag ggggacagct tctcaaatgg 145440
agtctggcca cagctggggc tggaaaagag acatgactgc gcttgcagag tggtgagaat 145500
ttgctgctag aattttttaag ttgtgtgttt tcatttttat gataatgtaa actgagataa 145560
gcatattctc tgctatccca atgagcccct cctctaggag gactaccttg ccaccttatc 145620
cataaatgtg tttataaatt attttgatgc cagctggtat ttttttaaaaa gtggttttgg 145680
actcacaaaa aaaaccatga tggatttaat acataacaaa gcatttgtgt caagtgaagg 145740
```

```
ccaagtaaca tcttagcgtc ctgtgtgagc gaaggtgtcg tggcagttca aacaagaatg   145800
ccgatgaagc tgcccaggat ggccaaggcc accttggtgt gtttgagggg aattagagtt   145860
tagaaaaaaa aaaaaaggca cctgacactc tgaactaatg tggttacctg gaattttggg   145920
gttttgaagc tttgcattta atttgcagct tatggcctga aggaaaagac aggtgaaatg   145980
catatcctgg gatgagtcac ctggaggaga gggctgggaa ggggctgagc tgcacatgct   146040
cagatcttct cccaggctta tcgacccagt gagtcaagtc ttcttccaac gggatagagt   146100
gtgagagaga gcagggaaca gaagccagag tctctgttaa atttctcggt acatttctgt   146160
tagagaatgg aagtttctct atcgtaggag accttgagag cctgggatag aaattacccc   146220
tttgtcatgt attttcctcc cagaaatagc atggccactg tcactgctaa gctggagtat   146280
catgagcaca atttctctca ctttctatac ccatgccttt ctaggagatt ggtggctcca   146340
tcaaaagga gttaaaaga agcagcacta ttttgtggaa tacaatcatc accattatca   146400
ccatcagcac caccaaccag caccaccatt atcaaaagca ttcacctggt gtctgcctta   146460
caaactgcaa actgcagtag gtatttgtaa tagaatgttt cctttccccc ttgggatctg   146520
cagaaaagct ggagaatgtt ttggtatcaa cacactaggt tgcattgcta atcatgtgat   146580
ggccccatga cagtctctgt tggctggtgt agttcaggtg gacgactgca ggattttgtt   146640
cttggagcct cagttctgac tgggcttggg gtgtaaaagg tttgggagcc agatgacaag   146700
agtatttgat gggtagaata atgggttcat ccaaaagatc accagaatgg ttattaaata   146760
gtacaaagga ggaatttact ggtaatacca gtttgcaaac agagaagaga gtctccaatg   146820
tggactgaaa gtgctctctc tttgaagagg ggaaggacag attgggtttt atgcctcaca   146880
ggactggtac catacatatt cagcaggttt tgggggaaaa tctatacata tttataaggt   146940
gagctgatgc ctgcataata gataaacata tatgtaacat acttttcata ttcattttgg   147000
gactgggttt tggcactaaa atttgtggaa tttggctctt tatgttaaaa ggtgaactag   147060
aggacacaaa gacggtttgt gtgcaccctc tataaactgg ctgaaactgg cttaaggtct   147120
gcaactgctt atccaaaaag aatgtttgta aggccaggcc tctgtccagt cagagttgta   147180
gtggtccagg ttgtaaatca aagtttatag ctcttttgt tagagagttc agctgtagga   147240
atttagaaat ttgccatgcc tgccaggccc tgaacctttg acccataggt aactttattt   147300
ccttaacctt agggtcagtc ttagttgata tggggcatct attctggtat ctcagatcct   147360
atggtcaaga gaaagatcc tccacaagag ggtcctatgt ggctgcaaaa actgctctga   147420
gctaaatcca ctcaaaatca ctgcaggatg tcactactag aaaatagggc agggataggg   147480
atccccttcc catgctgcca gaaaatgcct gatagcttac ctcccccggc ccttgaggct   147540
cccttggaat aggcacatgc aatcccatct ccacccaata gagcttgtcc tagagctcag   147600
tttttttccca tagttttccc acccacttgc accagaaaat ctaataaagt catgtgatta   147660
atacaattca ttttatcacg cttctgaaga tttaagagag agcggtcaca ttggattcca   147720
cagtaccgac cttctgacga ttcttcattt cacctttatc tattttatt tttattttat   147780
ttttttttcg agacggggtc tcactctgtc acccaggctg gagtgcagtg gggcaattac   147840
ggctcactgc aacctctgcc ttctgtgctc aagcaatcct cccacctcag cctcccaagt   147900
agctgggatc ataggtgcac atcaccaagc ctggctaatt ttttgtattt ttggtagaga   147960
tggggtttca ccatgttgcc caggctggtc ttgaacttct gagctcaagt gatctgccca   148020
ccatagcctc ccaaagtgct gggattactc acgtgagcca cctcgcctgg tcccttttcac   148080
cttattatc tttgcctttaa actctagtgc ttcctccctg aatcagttaa ggattgcatt   148140
```

```
tggctgcatt aacagaaacc tgactgcaga agcttaacca aatagggtag ttttttaaaga 148200 gagattgctt acatcacgca aattgcacaa attttaagtg catagttcaa tgagttttga 148260
caaatgtaga ataacatagc tatataaaac cattccatca aaaaatttt atcaccatag 148320 gaaattgtgt cctgtccctt tcttgtcaat cccaactcct ccccacaagg caaccttcat 148380
tctcatttct ctcaccatag cttagtttta catgtttcta taatacagca tcatataaat 148440
ggaataatac agaatgcaat cttttgtatg aagcttcctt tggctcaatg taatgtttat 148500
gagattcatc catgttattg aatgtatcag tagtgttttc atttatattt cctagtgttc 148560
tattgaataa atatactaca atttgtttat ccacttattt gttgatgaac atttggaccg 148620
ttggcaattt ttgcctatta tgcataaagc tgttaaaaaa cattcttgta caagtctttc 148680
atttcatatg ttttttcttt tctgaggtaa ataactacaa gtagaattgt tgggtaataa 148740
ataggcatcc atctaatatt ataagcaact gcacaacagt ttttcaacgt ggctgtacta 148800
tttcactctc ccaatagcaa cgtatgtgtt ttccagctac tccacatgct cactggcatt 148860
tcctgttgcc agtttaaaca tttcagccat tccagtggat atgaaatctc tctggctata 148920
ataattgtat ttctctgatg actaattatg tcaagcccct tttcaaatgc ttatcagcca 148980
cttctatact gtcctctgtg acatgtccgt tcaatctttt tgctcattct ttaaaaacat 149040
tgggttgttt gtcttttttct tagtttgtct tttgcttttc atttatagga gtacatatct 149100
tcggaataca agtcctttgt cagataaatg tattgtgaat aattttctcc tagtttgtgg 149160 tttgccttttt cacattctta atatcttttg atgagtggaa actaactttc aaattatgtt 149220
cagtagatta acttgttttt gttttgtttt gtttttgtttt ttgttttttaa cactgggtct 149280 cacttgttgc ccaggctgga gtgtagtggt gccatcatgg ctcactgcaa cctctgcctc 149340
ctggactcaa gggatcctcc tgcctcagcc tcccaagtag ctgggaccac aagcacgcac 149400
cactacactt ggctactttt ttatattttt ggtagacaca ggatttcgcc atgttgctca 149460
ggctggtctg gagctcctga gctcaagcga ttcacccacc tcagcctacc aaagtgctgg 149520
gattacaggc gtgagccacc acgcccagtc gagtagatca agttttaatt ttatggccag 149580
tagagatcta tttcaaggct ctctattttg ttctgttgct ctatttatct acctttatgc 149640
caattttctt ctcttttgat tcagataggg ttataataat aattatttttt tccagggatt 149700 agatggacca gggctggtga agttgttcaa gggagtgatc aagagcctgg ctcctttcat 149760
ccttctgttc catctccttt ggctcatgga ttttgttttc caagtggcaa gatggcgcct 149820 ccaccttttgg tatcctattt tagttcctgg cagaaagaaa ggaacaggct aatggccctg 149880
atgagtctac cccttttaa caggagaaaa tttaaaaaac aaaaaccatg aaacccttc 149940 ccagaggcaa caaccagaat tccatttatc tttcattgac cagaacagac cacatggtca 150000
ctggtggtgg caatggagac tggggagatg aatattttta aggtggcata ttccagaaga 150060
acactgtgca ctgattgcat taatgaaccc attaatgtgc caaggggagg tttacctatg 150120
agcatgggca aattagaacc cactcttgga gctgcaggtg agccaatccc acctaaacag 150180
tgtggatgct acaagatggg gaagtaaatt gattctattc catacccctaa cctctctcca 150240 agatgtattc ttaaaataga agagggaaga cagaagaaaa catccagaat atattttat 150300 tgtcttttac ttcttcagtg catttttgat cagtgcttct caatctggca aggggcatgc 150360
aggaggatgt gagtttttatc aggaaaacta cacaaccccc caaccacaat gctacccca 150420 ctcctgtgga ccttctttaa gagagactca ctattataga tggagttgat acgattttaa 150480
```

```
gagaggccat atattatttg ctttctgtct tgaaaaactt gtgattttc tgtattgtgc    150540
tactgccaaa gagaatagaa acctgactga ggtgtcaatg tttatgtaac tgatttcatg    150600
tactttctgt agttctacca tttctgatgg ttaaaaattt cttgtgtgtg tgcagttggg    150660
gagtgtgtcc tcctccttct gctcttatac cacacattag cacatcaaaa tgctctaatc    150720
tttgtatgat tatgtggcat gtggtgatgc agcctcacag tggaaaaact tctcttgggc    150780
cattgcaaat gtaacatttc tttcaatcag atagtgccat taaggatttc attatggccg    150840
tcacatcctg tgacatctct aaacatgcag cattagggcc taagtgcagc cctgcaggta    150900
gagttgccag gtttaacaaa taaaaattac acgctggcca ggcggggtgg ctcatgcctg    150960
taatcccagc actttgggag gctgaggcag gtggatcatt tgaggtcagg agttcgaaac    151020
cagcctggcc aacatggtga acccccatct ctactaaaaa tacaaaaatt agctgggcat    151080
ggtggcaaat gcctgtaatc ctagctactt gcgaggctga ggcaggagaa tcacttgagc    151140
cctggaggcg ggggttgcag tgagcagaga tcacaccatt gcactccagc ctgggtggca    151200
gagcgagatt ctgtctaaaa acaacaccg tatttgggc atgctgatac taaaaaatta    151260
ttcattgttt gtctgaaatt aaaatttaaa ttgggggccc tgtattttac tgggcaaccc    151320
atttgcaata tcagcaacaa tctcttattc agaccactga ttaagtgtgc aaaatttgaa    151380
tctctgaaca gtacctatgt ccttgatatc ttaaattaat gagtgtctta gacactcaaa    151440
gcaggaggaa gcattatggc agatgtttga gccccagaga tgtccatgag cacagcatag    151500
agctcagagc cttctttatt atttgcttca cgacagagca aaggactgca gcaggttgac    151560
tgatataaaa gttttaccat gtctcacagc aggcctttgc tcaagtttcc agtaaggata    151620
ttgtatcatt tcttgcctgc agtacttgta aatccactta cactgcctgc tgttgagtca    151680
tttgtttcgt cttgagtagc atgtcatcct tgttcctaga agatagtgag tttagagaca    151740
gtagccaagc aacagcagag cagcctcaac caaaacgatt ttccattttg gtgggatgaa    151800
ttgaaacaca agcatcttct atccagggga gatttgggga tcataaagaa tcaatctgag    151860
ctggtaccac catattggct gctgcatttt ctagagttgc cgtaactagt ctcacaagct    151920
gggaggcttt acacaacaga catgtattgt ctcatagttc tggatgctag aaatctggaa    151980
tcaaggctcc aggggagaag ctgctccatg gttttctctt agcttctggt gttgccagca    152040
atccctggtg ttccttggcc cgcaggcgga tcactcccat ctctgcctcc attgtcacac    152100
ggcattttcc cagtgtgcct gactctgtgt ttcttctcat aagaacatcg gtcatattgg    152160
attacaggcc cgtgctactc cattatgacc tcatcttaac ttaaacaatt acatctgcag    152220
tgatcctgtt tgcaaataag gtcacattct gaggttccag gaattagaac atagacatat    152280
cttttgggaa caaaattcca gtgataacag tttcggagac agactagtcc tggagtttgt    152340
aaggtgagcc aggaccaagg tgccaggatt ctcattttgt aaggtccagg aacaaagtga    152400
tgttaataga aagaacatgt ttttgtttgt ttatttgttt ttgagacagt ctcactccat    152460
cacccaggct ggaatgcagt ggtacaatct cggctcactg ccgctgccat ctcccaggtt    152520
caagcgattc tcctgcctca gcctcctaag tagctggaat tacaggtgtg tcccaccatg    152580
cccagctaat ttttgtatat ttgtgtgtgt gtgtgtgtgt atatatatac acacacacat    152640
acatacatat atatacatac atatatatat acacacacac acatatatat atatataaaa    152700
tatatatttc ttttagtaga ctgggttt caccatgttg cccaggctgg tctcgaactc    152760
ctgcgctcaa gtgatccacc tgtccttggac tccctaagtg gtgggactac aggcacaaac    152820
caccacgccc agacagaagg aatatgtttc cttccagtct cacttgactg gctgcttccc    152880
```

```
tagataacaa cagaggatgt ctgttgcagt tctcattgct ggggagtcta aactggaata   152940
aaacacccac tatctccatc aggcttgcac tagagcccag ctctagctgg agagaaagaa   153000
gctaacccgc acagacacag gactgtaggc agggagcatc cggggtatt tgggtcctgg    153060 ctctgatgtg cctaaggcca acttctctct ggccatgctg gcgtgcatga gctcactaat   153120
cttccttttt gccttccatt ttctccaatc ctgacttagc aaaggttggg caaaagagac   153180
tctgtgtgag ttcgagcaaa gcctgagatg ctggattttc caagatacga aaggggctg    153240 ggggctgggt gaactggtgg tggaggaggg aaggattaat ttcccaagga ggggaagggg   153300
ccaggacatc aggccccggg gactttgaag agagggtcgt gggtaggagg tagatcaagt   153360
ggagtgacac aaaggtcagg aaagaggaag tgtccacact gtccttcgac agacttgagt   153420
ctatgggact tcctccctgc acggtacaag gaaatgagta agtgagataa tgttgtaact   153480
tctggccctc tgacattgca ctgccccgat gtcacagttg gaaactgtac ctgcccccat   153540
ccttgtctgg ggtgtgtttg gtctggggag ggctggtgaa gcaagaggta ctcagaaaaa   153600
ggacagaaat tgcttcctat tatctgggca tttggaggtg aagggtcac  agctctggca   153660 aagatggggt tgaaagggcc cggactccag ggaggggcag ctctgcatgg cctgattcct   153720 gcacccacc  tttgcccct  cacacctcct ctcatctccc gttttgaag  aggaggaccc   153780 tgtcacatct ggacaattct gcaagaactc tgtagaactg acttcactgt gaaccaggct   153840
ccagaagtca acagaaacaa aaatgctcac atttaatcac gatgctccct ggcatacaca   153900
gaagactctg aaaacttctg aatttgggaa atcctttggc accttggggc acattgggaa   153960
cataagccat cagtgctggt gtgtgtgtgt gtgcgcgcac acgcgcatgt gtgtgcatct   154020
tctaccatgc ctcctacaaa tttgacctgg gcccagggcc atgttcggtg gtttttaaga   154080
accgaggctc ccagaagcag tattgggcag ctagagtggc cccaggatct atatcaaact   154140
ctacctgttt ctgaaccaaa tttcttctag aattttattc cataaatctg aattatggtg   154200
tcagactcct agcatacact aaaggaactc tctgccttgc attaaataac aggagttacc   154260
cctggaggta actcctagcc ctggctcttt agagaacaga tgccgaatag cattagggg    154320 atgtgatgga tgtgctaact ttcaaaaaaa aaaaaaaaa aaggcctgag ctgagtgctc    154380
agagattcac aaaaagctga cagcatctct ctgttccatt ggaagctggg tgatcctttc   154440
tactctttcc tgagaaaggc agttgggcag gaaaaagctg tatctctgtc ctcactgaga   154500 ggttcccca gtctgagggt gaaggatcag gagagggaga cctgacgggt cgatgtgggg    154560
catcatccac ttgagtgaga accagaggga tcccgtcatt gcccagggca gatgctccat   154620 tttgggggc atcattcatt cttcctgtt ctccctgcat tcctctggct cctgcccagg    154680
agaggtggcc gctggcaaga gagcttggtg gaggtgggag gtgggaggtg gggggtgggg   154740
ggtggggagt tcttgagcca ggacctagcg catagtctcc agcctgctga tggctgtctt   154800
ggatgcttca aaggggagaa gatcctagat gtgggaaaca ttggtgggcg ttctgctggg   154860
gcatctgtag cctctgagaa ggctaccagt ctctcctaag cttacgccgt cacaccctgg   154920
gcacttgttg aatgacttta cttagcttac agcctctggt tcctgttggg aaacttaggg   154980
cttgccacag tgttcatttt cctttgcggg caactccgtt cctggcactt atcatattac   155040
ccactgtact ccccgcttag agctgtgtca aggttctgag aatctatccc ttggcttgga   155100
aggggtcatc tctctggcca gatcatttcc tgataggtcc tgaggcacca caacacatag   155160
gaggcttgtc ctctctctgg ggttcactgc cttgctcctt ctccaggtca atatgtgacc   155220
```

```
ttggaccggt tgcttgagtc ccctggtcat tcagaaacaa ttgggtttcc ctggctttgg    155280
agcctggcag cctggctttg agaaccgggc tttaacttgt cacatgacta tggccaagtt    155340 cctgggctc tccaagcttc acttcctctg taaaaagggc aataatataa tacctgtctt    155400
attgggtttt gtccatgtta gatgagacat tgggtacaaa gcacttggtc ccgtgcctgg    155460
cacatttact gcacttaatg tatgatagtt ttcttattat tctaataaac aatatggctt    155520
tgggagtata gttctgccac attgcagtgg ccagagtgaa ggtggtgagt gccttctggg    155580
gccctgggag tcaaggttat ccgcatgccc tttcttgctt gctcctcagt gtggctgcct    155640
ctatgtccac accatgcaga tgcaacaggt agtttgaacc tctgaggccc acagtgggat    155700
ggggaggcag ggacatcact tatggggtgg gaagtcaccc attccccagg aaatggcccc    155760
agctgccttt tccatgactc ctcttgaaac cctgtggagg ccacattcgt gttgggcga    155820 tctttcccat gaggatatgt tcagatgccg aggcattttg aaaagccctc catagagttt    155880
cctttcataa cacatgatca tccccttggg cttctggttt tttttctttc aggaccttat    155940
tttcaggcaa gtggcctttg acctctaagg ctgtcctttc ctagctaccg aatccagcat    156000
tcaaagtgat ggaaatatgt atatatagta atagtaaaat atcagcactt aatggcctga    156060
taagaatgtc actgcaatgc tgagtttgga ccaacatttg cctgctcctg ccattgagcc    156120
cgggctcccc tccagagctg agctgctgca agggatctga gtaactaggg ctgtgtcaga    156180
gtggcgatga cagccaccac atgctaagga agagatcccc aaggacaagg agaatcccac    156240
gtggagctac ttgcttcttt gtcagtcttg ttttcttat ttcacaacct tctaaaacac    156300
aatctctcaa cctctattgt tagcttgcat ttttcaatca tgagcacagc tttacctggc    156360
tccatgcttt gattgactct acctgccaac actgcaacaa cagggaaagg gacaccggcc    156420
tcataccatt agatggtgtg tagcctgggc atgaggataa ttaaaaactc caaggggat    156480 tttaacatgt aacacagttt ggaaaccatt gatgtaagat cttcttactc aacatgtgct    156540
ccaaggagct gttgtatcag cttatcagaa atgtagatca ggccgcactt ggacctgtag    156600
aatcagaatc tgcattttat cagattccga cattatttgt atgaacatta gcttttgaga    156660
agtgttgctt taagagacta agggggtcaa tctacctcac tttgcagctc tgtgttcctt    156720
agtcattggc taaatatca gccccctgc aatgagccat cctcccttgt atagtcagtg    156780
atggcctgtg aaccttagc caactggaag tgggagggga cacagtccac aaaacactat    156840
cctgactttt gacaccaact acaagtcaag gggttcccca aaccaccctg agttgtgata    156900
attcgctggg agatctgaca gaactcactg aaggttgtta tactcatggt tgtgatctct    156960
tatagggagg gaatacagat taaaatcagc caaaggaaga agcacacagc acagagtcca    157020
ggacagtgcc tgacatggag cccctacggt cctctcccgt ggagtcacgg acagcgccac    157080
tctcctggca ttgatgtgtg acaacacaca gggagtgttc cccaccaggg aagccttggt    157140
gtccagggtc tttactgtgg ctctgtcaca tgagcacagc tgactgccca tgcggccgat    157200
ctgttcccag actctccacc gctacacatc actcacagtc cctgctctaa atcacacacc    157260
atgacccaat gtccccgggc aaatgaaaac acctctagca ggcaggacgt tccaaagcct    157320
tagagatcac ctctcagaag ctgagggcag aagccagacc tcttttggg cagggttaaa    157380 ttcttatta ctgttttga aaaaactccc aaattgagtt tttcctcttc acttacagca    157440
gcataacaac aatcatcaat gcagaagact tctgcgagca aaggtgtggg ggaaaacccc    157500
aagcagtgga cactagctgg tgtcctccaa tttgattctg atgctgtcta ctgggagata    157560
gtgtcagatc ctcaagccta aaccctcctt ctcccagtca gagggctggc ctttggaact    157620
```

```
tctgaccaat ccacttcaag ttgaggttcc aaccactccg ctctttgggt ttggttgatt    157680
tgctagagtg gctcacagaa ctcagggaaa cacagctacc agtttattgc gaaggacatt    157740
ttaaaggata aaagtaggca gataaagaga tgcatagggc gaggtgtgga aaggtcccta    157800
gtgcaggagc ttctgtccat gtggagcggg ggtgcaccac cctctcagta catgaatgag    157860
ttctccttca cctgcctatc agcctctaca tgttcagctc cccaacccag tcctcttggg    157920
tttttatgga agcttcaaga cacccacatt ctttccccag agtatagggc aagaccttct    157980
ctggggaggg ttttaagacc cacagtcaga aaggtgggt ggggtcaaga ttagagtcct    158040
gccttgacgg gcaggtgaaa ggggtagggg gagtaggtga gaaaaattct gtttatttt    158100 tcttttttt tttgagacgg agtttcactc ttgttgccca gggtggagtg caatggcaca    158160
atctcagctc actgcaacct ccgcctccca ggtttaagcg attctcctgc ctcagcctcc    158220
cgagtagctg ggattacagg cgtgtgccac catgcctggc taattttgta tttttaatag    158280
agacagggtt tctccatgtt ggtcaggctg gtctcaaact cctgacctca ggtgatccac    158340
ttgcctcagc ctcccaaagt gctgggatca caggtgtgag ccactgcatc tggccaaaag    158400
attctgtttt tgaggcctgc ctctgaggtc taacacactc aacattataa caagactgta    158460
gtaagggcta tgggagttat gagccaggaa ctgtggatga aaacctatca cagatatgca    158520
tatatatata tatatatata tatgcatatc tataataact ccacaactac acactgcctt    158580
attgctcagt tcttctctcc atgtctctga cccacccttg ccccctccct ccatccttt    158640 ctccattgca tacccatcca ctgtgccctt tggaatgctc acaccatgaa ctgcaaactc    158700
tcgtgtggct tcagcctctt ctctgaaagt tcctctcacc tattactttc tctggaacct    158760
gccatccctg ccaccttctc aaaaaaggcc ttttattctc ttcattccac aaagctcagt    158820
gtcaaaacat gggggtttaca ctggaagctg aggtcacatc agtagccggg atcagggtcg    158880
ccctagctgc ccaatgcagc tcccaggcct cctgtaaaac cttgaccttt gaggtcatga    158940
cagccctctc ctgctatgct catagctgac cactgaactc ctggacactc cctcccccaa    159000
gttcacagag aatgtgggca catgccttac agtcttccct tgatccaaac tactgccttc    159060
atcttgagtg acagcagcat ctttggatg tcttggcctg tctagcttta ttttttttgtg    159120 ttctgccatc aagttgctac ttctgttgcc atcgtgcctg tcagcgcagt gcaggctgtg    159180
gtgaaatccc acgaactcag gcatcacact gaccgggtct gagtcctgtc tcagttgtca    159240
gctagttgtg caatgaaggg aaagggacct acactttcca agcctcaatt cactcatcta    159300
tggcatggtg acaataatgg aggttgattt aaagtccttt gtaagaatta agagttataa    159360
tagacataaa gtgctgtatc tggtatacct agaaaacatt ccataaaagt tagtaattgt    159420
tggtcatgta atgatgactc tctaggctag gatttcagct tcattgcatg cacatggtgc    159480
actcacaggg cgtgacctct ctctgtctca gtaacctcat ctgaggaccg ggataatcat    159540
accgcttcaa agggatgtca taaagattaa ataatatgtg taaggctgct tgcatttagc    159600
tgcattcaac aaatatttct gtatctttct cctcatttct ccttactttc ttgcttatta    159660
tctgctctag gtatagattt cagagaacta agcttgttac aatccttcat aaaataacca    159720
ggttggttag ggcatttcca agagtcaata ctgtttagtg actattctct gtttaatcta    159780
ttttgattgt ccagggtcat cttttgctat gtcataggtt gttggcttct tctagagaag    159840
tgagacgatg gacaagttcc aagtgagtga ggcgactggt caggatattc cgctgaaaaa    159900
ctcatgtcag ttctaattcg tgattgtaat tcaatcacag cctgagaaca gtaggactgt    159960
```

```
agttcaaatg ctctgttccc tttttttttt cccagaggat aattttttt tttctttgag    160020
atggagtctt gctctgtcac taggctggag tgcagtggcg tgatctcggc tcactgcaac    160080
ctccgcctcc tgggttcaag caattctcct gcctcagcct cccaagtagc tgggactaca    160140
ggcacatgcc accacgccca gataattttc gtattttag tagagacggg gtttccccttt    160200
gttggccagg gtggtcttga tctcttgacc tcatgatccg cccacctcgg cctcccaaag    160260
tgctgggatt acaggcgtga gccaccgcgc ccggcctcta gaggataatt tttaaatgtg    160320
cttttgcatt tggaaaatgt gattggcatt ttttctaat tttctaatat gatacgctgt    160380
cggatgctat ggattactta aaccctctgg ctacctagaa agatctttaa gtggttctca    160440
acaagcttca tacgcaatgt aaattgtatt atctctcagg atgtgtgaga acatctgttt    160500
ttcttctaat gcagtaaaca tataagggtc tcttgggata tcttttaaat agacttaata    160560
caacattcag gaatgataac aaaatataat cacagttgta agggaatgtg agcatttcat    160620
attaataaca ttggaacctt atgtttaata cagtgttaaa agttgacaaa catgtaggag    160680
tcagaaaatt caattaaaat tatcacagta atatgaattt agccacatcc tgtgttagtt    160740
atgaaatcca tttaacacca caaacagtaa tattttagc cagtttattc aaaaggaaaa    160800
caggaactaa accactttca tgcaatatat actctgttaa tgtggtcagg ctaattttgc    160860
tgggggaagg aacttaactt ttgaatattt gaatgcccag tcatttaatc tgaatatcct    160920
atttccttgc atgttgcaaa attttgtca ataaaaggca gaaaagaaa tctcttctcc    160980
atgctcatcc ctaagagaat gggttgtctg taccctgaga gcattttatg gagggacaa    161040
ccactttct aattttcctt cccacttctc tgtgggcaca aatgctcttt ggttgaaaga    161100
gttgtaattc agtcccaaga tgaggtgtgg ttactgcatc cctaacctat atctggggac    161160
cccacagcca cacacatggg ggaaatggag cttgtcattc agttctccag ccattgcaca    161220
gggttcatgg actcttcgtt gatcccaccc cacgcttctt ctctctgcta gccgaacaca    161280
cttctctctt ctttatcagg aggccatagg agaagggcat tcatttttaa tacacataca    161340
tctgcatcaa gtctaatttt gccatgtctc aatccaactg tcaaatgggt tgtttggggg    161400
ctatggtgct tatcaaacat ttactcaaga atagccaaaa ttagccaagc aaggagaact    161460
tcagcaacgt tcccaaatgg ccccaaccaa gtactgtaag actgaggata gctaaagggt    161520
cttgagaggg acttctcagg cagtggcccc gacatttatc tgttttttta agtgagaaat    161580
ctgagtacca ttcttgactc ctcttcctta ccccaaccc ctcactaagc cttgtgctac    161640
tatttagtaa acagaccctc aatgcacaaa cttctgtcta aggccatggc caccaccta    161700
gtctaatcca ccatctcttc tctggaacag accccagctg ctctccctgt ctctgtgctg    161760
gtctctcaat ccatgctcca cactgcagcc agagtgctct acaatgcaaa tccatttgtg    161820
agactcctcc tcttaaaatc ctcaagtggc ttctctttgc ccccaggatc attttgaaac    161880
tccttaatgg aagaggcatg gccctttggg atgtggttcc caacccctc ccacatcatc    161940
ttttcaatca gatttcccac taaatggaaa tttttttcagg tcctcaactt tatggtgact    162000
ttctcttgct caggatcttt gaacatactg tttcttcttt cctttgtat ttgccaagac    162060
aacacttcct ctggtaagat tttcctgaca tcctctataa aaaagattg agatagttga    162120
ctacccaaaa tgtttcccat tcattccaag ctctattcaa ggcagtaaag tgcccggctg    162180
acagattgca ttcctcatct tttctgaagc tagcaatggc catgcaacag cattctggcc    162240
aataagatag aagtcgaagt tgaagggtgg gatttcaag aaagctcgtt gaagacataa    162300
ttcctcattt cacttcttac tctttctctt tcctgcttcc taaaatgcgg tgcagatggc    162360
```

```
agacacttca aagctgtctc aggcaatcag gtgatgttaa ggcagaaacc agctttatga    162420
tgggtagaac aggaagaaag aaggcaccta tgttcttgtt caccttgaac cacaccagca    162480
ctgccttgcc taccCctgga attccTttaa tgagaggcaa atgagagctt acgtgtttaa    162540
gccattgcta ttttatttTt ttTtgtttat atgcaaaaga acttaatcct aactgatatt    162600
aacactaact gggtctattg cttggtacca agccaatgca tgacacatgg tatatatgct    162660
cagtaagtat ttgttgaatg agtgaggcaa tgaaagaaca tagaggatat atataacagt    162720
cctcctgccc agatgtcatc tgatcctctt taggatctgg gcccataaaa ctgtatctga    162780
tatagtttga atatttgttc cctacaaatc tcatgttgac attttatccc taatattgga    162840
ggcagggcct agtaggaggt gttttggtca tagtgataaa tggcttggtg ccgttctcac    162900
agtaacgagt gagtttttat tctagtggtt cctgcaagaa ctgattgtta aaagagcttg    162960
gatccttcca cccctctctc actcttgctt cctctctctc accttgtaat ctctacaagc    163020
tcttcacctc cccttctcct tttgccataa gtggaagatt tctgaggcct caccagaagc    163080
agatgttggt tccatgcttc ttgtacagcc tgcagaacca tgagccaaat caacttcttt    163140
tctttataat tatccagtct caggtattcc tttatagcaa cacaaatgga ctaagacagt    163200
ttctaatgct atggttcctt tagtaggtca gtgtaaaacc ctggatcact cctgtaacaa    163260
attacttgga actcttctca ccatacatat ttaaaaatag ttgccatgtt gaaaatccta    163320
taagatcata tttTatttca aatccaacaa ctcattgcta aggagataca agaagcagaa    163380
aatacagaga gactaatgtg ttgatgattt ttgtgaggga cataaggtct gtgtctagat    163440
tcattttttt gcatgtggat gtccagttgt tccagcacca tttgttgaaa agactatctt    163500
tgctccactg tattgctttt tctcctttgt catagatatc tggtcacctt accttagagt    163560
cacagatgaa tggtcctatt acttaactac tgaaaataca ggccaaagca aacagaggaa    163620
taagggatat ataataaagt atttgtgtac ttgacttggc tctaaaggaa gcattgcgtg    163680
tctgtgtaaa aagaatgggt gagagttttc caccattcaa tatttctaat ctttctgaaa    163740
tacaaagcca ggacatcctc taatccatac attccatagt ttggttaata taaattcctt    163800
tattaaatcc ttattaaata aagttattta tgtttctatg aaactcattt taactcctaa    163860
gtgaaaaata ctactgagct aactaaacat caaacatttt taatttttta aattttttta    163920
gagacagggt cttgctatgt tgcccaggct ggctttgaac tcctgtgctc aagcgatcct    163980
ccaaactcag cctcccgagt agctgggact acaggtgcat gccactgtgc tcagctaaac    164040 attttttga aatgctcttt taaaatcaat tttattgaag tataagttac ataccataaa    164100
agtactcatt ttgagtgtac agattgacaa gttctgacaa atgtgaacaa ccatgtaacc    164160
atcaccaaaa ataaagatat gagacatttc cattacccca aaagttccc gtgtccctct    164220 ccagtcaata tccagcccta gccccagctc caggcaacca ccaatctgct ttctgttgct    164280
ataaattgta cttatctttt ctagtgtttc atacaaatgg aatcatacag catttactct    164340
tttgtgtctg tcttcttctg ctcagtgtaa tgttttgag attcatctat gttcctgcc    164400 tcagtagttt gttcttttta ttactggata attccattat aagaatatac cacaatttgt    164460
ttatccattt actgcctgat gggcatttgg ttgtttccag cttTgaacta ttttgaatcc    164520
taaaagactg ccagttttga atgagacccc agaacaatga atgtaggctc tgtatacaag    164580
ttcaggctgc tgggcaactt aggccttaag acacaactct gccacttagg ccttaagaca    164640
caactgacat gatggtgctt aaagtggctg tgatggaaaa ggaggctgtt tggagccttt    164700
```

```
ggagtgcctt tataggtgaa ccccagcata gcacctaatg atttggagca aagctgtgtc 164760
attccccaaa gataactatt cgccttttga gaaacatctt ctagctacta tcaataataa 164820
acacagaatg catcaccatg ggccaccgtg ttgtcttttg acctgagttt ccattgtgaa 164880
caagagtcat ttgatccaag gcagaaagtt gggtgcacac agcagtgttc catcatcaaa 164940
tggaatatga gattgggccc aagtaggtcc tgcagacaca aataagttgc aagagcaagt 165000
agtacaggcg cttggcctgg ccagtactgt tgccaagttg actgcttccc ctcagtctgc 165060
atctgtggct tcatggggag tttcctatga ccacttgatg gaggaaaaaa caaattggag 165120
catagtttat agtgctggta ctacccaaag tggctagctg aggcactaca tctccactct 165180
ggggtgcccg tgaaggacag tgccaaagga aaacccctc agtgagcaga acttggagca 165240
atacaagtgg gtgttcattt tacctagaag agaagatgtc cgtgagttac agatctacac 165300
aaaatcacag agagtggtta atcgtttagt ctgatggtca gggacttcca agagacatga 165360
ttagaaaact ggtgacaagg agtcctgggg aagaggcata tggatacctc tgaacacaca 165420
caaaacatga gaatatgtat cccatatgaa tgttaaccaa agagcagcca aacagaaga 165480
ggattttaaa atcagctgaa taagatgatt cattctgaca gcatcagcta gtctctttcc 165540
ccagccactg ttgcccagtg ggcttacata tatcatggcc atgggggcag ggctatgtat 165600
ggacacagca acatgaattt ccactcatca aggccaattt ggctccagcc attgctgagt 165660
gctcagcctg ccaagataga aatctacgcc aatatggcac cattccctgg gctagaaaac 165720
caactggtgg aaggttgatt acattggacc atttccatca tggaagggc agtgctttgt 165780
cttccctgga atagacattt actctggata tggatgtgcc ttccctgact actacaatgc 165840
tctgccaaac ctaccatcca tgggcttaat tttatttgtt ataaaatttc aaccaccatt 165900
gcttctgacc aaggaagtaa tcttacagca aaggaagtac agatatgagc ttctgatcat 165960
gggcttcact ggcctcacag tgaagcaggt ggccagatta gaacagtgga atggatttta 166020
aaggctcagt tacagcacca gctgggtagc aacaccctgc tggcctgggg ttatgtcctg 166080
caggatgctt taagtcagtg accaatatat gatgctattt ctcccattgt caggattcat 166140
gggtccaaga atcatggggt caaaatggga gtggcttttc tcactatcac cctggtgttc 166200
gggtagtaat ttttccttcc cattcctgta actttgggct ctgctattgc agaaatctta 166260
gctcctgtgg ggggaatgct tccatcaggg aatacaatgg tggttccact aaactgacag 166320
ctgagtttgc catctcctcg tgccagtgaa tacacaagca aggaagggg ttcctttctc 166380
acctagggtg actgatccta attaccaagg agaaattgga ctgccacttc acaatgaggg 166440
tgaggagtat gtactctatg tgtctgtgat taatgtcaat agaaagtgac accaacctag 166500
tacacagagg actgatcatg gtccaggccc ttcaggaatg aagatttgag tcaccaggca 166560
aggaacttgg actcactgag gagggcatat tccaaggaga atattttatc tatgtccatc 166620
tatgtccatc tatattccat ctgtgttccc cttggaattc ctattcatga acatggggaa 166680
ttccaagggg aatatagaat gagtagtgga aggtagttat aaatgtaagt caaaaaccac 166740
acaaccaatt tgagaaatga ggaaggtaat agtgttgaat atgtcttctt tatcttgata 166800
taaatgtatt tgtgcatata ttaaccagtt tatttattta ttattatttt ttgagatgag 166860
ctctcgccat gttgcccagg ctggtcttga actcctgggc tcaactgatt ctaccattta 166920
gtcctccgag tagctgggac tacaggcatg caccaccata cccagctgac cagtttttc 166980
ctattcctct acttaatttc tctactatac aacataataa gtgttaatgg tagttaactt 167040
tatatctcag tattaagtca caagatatca aaaagggaat gcgacttagt tacaagcaga 167100
```

```
atgaatatca ctcaaagatg aataaagaga agagggttag tgcattttct gttggatgag  167160
agaaagtttc attgttaggc agaagcatga ttttgccttt ttttttttt  tccaaggtct  167220
cactctgtgg cccaggctgc agtgcagtgg tgcgatcttg gctcactaca acctctgcct  167280
cccgggttca agtgattctc cagcctcagc ctccagagta gctgggatta taggtgcgcc  167340
aggttaattt ttgtattttt agtagagaag gtgtttctcc atgttggcca ggctggtctt  167400
gaactcctgg cctcaagtga cccacctgct ttgacctccc aaagtgctag gattacaggt  167460
gtgagccact gtgcacagtc accacggtct ttttgggagg caactttagc atggttaaga  167520
ggtgcgaatg gatgttaagc taacaccagg taagccctgg tagatgtgta ttgtgtcagt  167580
gggcctacgc tggagccatg tttccccaaa ttcacttttc ctatgtacct ctggattagt  167640
gtgggccact ggagacattt cacatgagat gaggaaggtg ggagtgaagg agcagcatct  167700
ttttacacta agcaggtcgg ggagggcatg tggctctgtc tcacattgtt gggaatctgt  167760
ccatcatctg gttggcttag gtcagtgggt gagttcacag ctgttccagc ttctgctgga  167820
aactccttcg gtttctctga ctgctccgta atgagggcat cagattctcc tgcagaaagc  167880
cccagtgttg aagttggggc ttcatgttgg tgagtgatag ttacgggttc tagcccaacc  167940
tgtggtttct tgcaaatttc agtgtcagct cagtcttgcg ggttttgggt tgtccttgct  168000
tcccacactt catgcctttc tttccctcct gacagtctgc cctttagatt ttaggattca  168060
gcaccagcca cagaaacagc aacctcactg ttaagggttg aattgtatct ccccaaaagg  168120
taggttgagg ccctacctgc caggacttca gaatgtaacc tcatctggga atagcatcat  168180
tgcaaatata attaattaag atgagggcat actggctcag gatgggctcc taattcaata  168240
caactaatgt ccttctatga cagccacagg aagacagaaa cgccaaggga gaacaccata  168300
tgctgatgga ggcagtggca gctgccagcc aaggattata accagaagtc aggaaaaagc  168360
aagaaggaat cctcccttag tgattttaca gggagcatag ccctgctgac accttgattt  168420
tggactttta ttccccaaaa ctgtaaaaca atacacttct gttgttttaa gccactcagt  168480
ttgtgctact ttgttatggc aactccagaa aacaaaaata cactcagact gtttaatcaa  168540
cctccataat tgcataaggt ctaatcccta taataaatcc cttaaaaatg tctgtgtata  168600
tatatttaaa aatataaaat atcttctagt ggttctgcat ctctggtcaa tccctgactg  168660
atacagaata tgtattttca tttctaatga tgaaatacct gaatgaaatt tctaggacat  168720
atggtaagtg tatgtttagc ttttaagaaa ctgccaactt gggggaattg cttgaggcca  168780
ggagttcaaa cagcctgggt aacagtgata ccctgtctgt acaaaataaa aaatattagc  168840
agcgtgtggt ggtgtgtgtc tgtagtccca gctactcagg aggctgaggt gggagattca  168900
cctgagccca gatctttgaa gttatagtga gctatgatca cgccactgca ctctagcctg  168960
ggtgacagag tgagaaagct ggtctctaaa aaacaaacaa acaaaaaaga aactgtcaaa  169020
ctcttcccaa catgttgcca tttttacatt taccattta  cattcttacc agcaatgatt  169080
gatagttcca gttgctccat acccttgctg accattccaa tagatgtatt gtgttatctc  169140
attgtagttc taatttgtat ttccctagtg attaatgatg tttaacatct tttcatgcac  169200
ctattggcta tatgtatatc ttcttttagca aaatatatgt tgttatttga agagcggaag  169260
ttttacattt tgatgaagtc taatttattg atttttttt  tcttagatgg ctcatgcttt  169320
ttgtgttatc taaaaaaaat ttgccttctt catggtcaca aagactttct cctatgtttt  169380
cttttggaag ctttatattt ttagttttta tgtttatgtt taagacccat ttctagttac  169440
```

```
aatttgtgtg attttttgga agggtcaagg ttcattttct tttccataag aatgtacagt 169500
tgttctagca cccttgttaa aaagactttc ctttccccat tgaactactt tgtcaaaaat 169560
caactgagca tatatgggca tcatgaattt taatcctgtt agaactgaat gttcccaagg 169620
caggccatgc ccatgactga cctcctttcc ttggattgcc tacaaaacag ataaagctaa 169680
gtctggagca aagaaatcca tgtctaacct gtatttttt ttttttttt ttagatgggg 169740 tctcgctctg tcacccaggc tggagtgcag tggcgtgatc ccagctcact gcaatctctg 169800
cctcctgggt tcaagtgatt ctcctgcctc agcctcccga ggggctggga ttgtaggcgt 169860
gcaccactat gcccatctaa ttttttgtatt tttagtagag atagggtttt gccattttgg 169920
ccagactgtc ttgaactcct gacctcaggt gatctgcctg cctcggcctc ccacagtttt 169980
gtgattatag gcatgagcca ccgtgcccgg ccttaacctt tgttttctta cacaacacac 170040
tacgtgatgt tttccacatg catgggtcat ttgcttcatt tacgtacaaa tgcataagca 170100
atatactgtg tggtgtgagt ttgtgatggg aaaaggaaga agttttgcgg atactacact 170160
ggcttcctgc tatctgtctg tgtgaatggc tatggacttt gtcttctatt tgttcgctta 170220
gcgcagatat gatcagctta caacttaaga ttctagagaa agagggtcat atctgtaaag 170280
cactctgagc atgtgtgaag tttaatcaat agcatatgag gttacagcaa attcactatc 170340
tttgtttctt cagctataga atggcatgag gattcatctc aatttagttc aattctgttc 170400
agaaccatga gctagctgtt catggaagga aagcccacct gattgtggcc agggaaggag 170460
aaacaacact ttaaccaggt tgatttggtt ctcacagaca ccattggcat gtgacatctg 170520
gaacagacca tgcctggtct ctgttcgtat cacttactat tcagctcaat attggtctga 170580
atattcttta gactgactga aatgaaaagg aactgttgtg taaccatcca taattccagc 170640
ctgtagacct gggctgtatc tctatgccct gcctggcaca gaccccacct cctgctcctt 170700
ctccctcacc accagtcaat ccttgtccta atgaacaggg agggcaaccc tgaatgggga 170760
gtggagggaa gagatgtcat gagatggcaa cgtgcaccct gaagtgagga tgaaggctat 170820
gtgaatgttg taggctgaca gccgggcata gtggccccgt tgccatggcg atggaggcat 170880
gttgatgcga agtgtctgca cagctcctag gattttaac agcagctggg cagagcctcg 170940
gcgtccctga attgttgccc ccctgagtca ctgcttggcc ccagctgtcc tgatctctgt 171000
tgacaaatgg ttgtccttca cagtcaaact actaacagta ctctaattaa tgaatgtgct 171060
aattattctt gcctactccc agcatatttg tctaactaac ctgtcacaca cagatcagtg 171120
cagcatatgc ataattacgg agagcgctgg gagcagggga tgggtgggag aggggtgggc 171180
tcgcagccct gtcgctgtgg gatatttctt gtaaagttac ctttgctaac ggtcagatgt 171240
cgtggggata tgttatttcc cgtgaagtgt atatgtcttc ctttctttcc tttctaagaa 171300
tctctcttca gggctgaggg gccattgctc agtgctttag cctgtgaggg gattgccagg 171360
tacaaatgca gaaggaccag ggagcccagg ttctgaagac gattccggta gcagcacgta 171420
gggtgattaa aactccagac tttaaagcca gaccggcctg ggcttgaacc cttgttctgc 171480
tccttgctat gtgggtcttt gccttgacca cattttttt ttttttttaa gacaggatct 171540
ccctctcttg cccaggctgt aatgcagtgt tgcgatcaca gctcactgaa gcctccatct 171600
ctacagcctc aagcgatcct cctgcctcag ccccgagtag ctgggactac aggtctgtgc 171660
caccacgtcc agctaattta cttttgtaga gttgggggtc ttgctatgtt gcccaggctg 171720
ttctccaact cctggactca agccatcctc tagcctcggc cttccaaagt gctgggacta 171780
taggcgtgag ccacggtgcc aggcccttga ccacattttt aacccctctg aacctcagtt 171840
```

```
tcactttctg ggcaatggga gggggtaat ttgtccctca gagggttgca ctgaggggca    171900
aatgtgaggc tctgggtaca atgcccagta cagactaggt ccccacgaca cagccgctca    171960
gcggctccgg attctgggct gctctggact gcggccaggc ggtcttctgc gggaatccgg    172020
gcaggcaggg cgggctgcgc tccctcccc ggctctcccg gtgccccttg tcttttgtt      172080
ctgtctcagc agctctctat taagatgaat ggcatttcca aaggcttcac ctctgataag    172140
tgttcctctg cagctgcagc cagaatctta atgtgcgcgc tgtaatttaa tggccgtctc    172200
ggctattaac acgctcttct cgggtgaagt ggactccctc catccccggg cctctgcacg    172260
tgctctgcgc gctggctggg ggtgactcca aggagctcag agcggggtgc ccggcacctc    172320
tcgccaggcg cctttcgacc ttctaaagcg cgaatggctg gacttttctc ccatgtgtgg    172380
ggccccagaa ggtgtggggc cccagaaggt gtggggtccc tgcgttccac ggagcccgga    172440
aggtttccag tgatggtggg ggctgaccac gttggtcccc gtgggtgctg ttttcatgtg    172500
ccggcagatt gggatgagtt taaaagacag aagcgtgtag gatagagaaa cttctttaaa    172560
aactggaaat tttaatctgg ggattataac tattggacag tcaagtgcaa gagtgaatac    172620
acttctcact ccctcctccc aattttatt tgcgggatta gtcagtcccc ctctgccaca    172680
tgataattgt gagaactacc agggtcttca ttctcctgcc atctggttga cctctccaag    172740
aatggacacc cgggcagcct gggccaatga ggctgtccta agagtttaga tgagagaagt    172800
cagtctttga caggtgatgg aagctgtaaa atgtaaaact ccacagttgg tgaagatgtc    172860
tccaggaaac aggtctgcag agagaatacg tttgacatgc taagagaagc tgagagagag    172920
cgagaggaga gattggaaga aagacagaga cagaggtaga gagaagggaa agagagagag    172980
aaagggacag aagagagaga aaagagaggg ggccgggcgc ggtggctcac gcctgtaatc    173040
tcagcacttt gggaggccga ggcgggcaga tcacgaggtc aggagatcga gaccatcccg    173100
gctaacacgg tgaaaccccc gtctctacta aaaatataaa aaaaattag ccaggcgtgg     173160
tggtgggtgc ctgtagtccc agctactgag gaggctgaga caggagaatg gcgtgaaccc    173220
gggaggcaga gcttgcagtg agctgagatc gcgccactgc actccagcct gggcaacaga    173280
gcaagactcc gtctcaaaaa aaaaaaaaa aaagagagga agggcgggag agagagagag     173340
agaaagctct ctagctccaa ggcctaacca catctctgtt cttttcaact tcagctgtca    173400
gattttaga ctcttttgagt gaataaattc tccttttgc ttaaactagt ttgagctaag     173460
tttctattgc ttgcaactgg aatactttgt aagaggactg gccttcattt ctgatgcatt    173520
gtcactaaga tgtaagtgtt agaagagcta acgctttatg gggttcaaac tccttggcta    173580
ccaaaaccta aacatcccct gaaacttacc aaactgcagg tatgaattgg atctcactaa    173640
ggtgaatata caaatcttgc aagtgctgag ccctaaccaa tcttgtaata actctgtggt    173700
agttaatttt atgtcaaatt gattgagcta aaaaatgccc aggtagctgg taaaatgttt    173760
ttttctgggt gtgttaggga gggtgtttct gaaagagatc agcactggaa tcagcggact    173820
aagtaaagaa ttcccaccct caccaatatg gtgggtgtca tcaatccact gagggcctga    173880
atagaacaaa aagcgggcag aagggcaaat tccctcttct tcttgagctg gccatccat     173940
cttctcctgc ccttggacac tggagcccct tgttctccag cttttggatt cagactgggt    174000
cttgcaccat tgccctccat cttctcctgc ccttggacac tggagcccct tgttctccag    174060
cttttggatt cagactgggt cttgcaccat tgccctcctt gatgctcagg cctttgaatg    174120
cagactggtc tccaccagca gcttttctga gtctccagct tgcagatggc aaaccatgaa    174180
```

```
acttcatggt gtccatgagc atgtgaacca atttctatta taaatctgca atatatatat   174240
atgaggagac ttatttatat attggttcag tttctctgga gagccttggc taatataaag   174300
tctatactct acaaagtgcc ctaggtactc agggagtacc caagtgtgtc atgaccagcc   174360
cgacagccct ggctgctggc ttccccgcac acaactctgc acgctgcctt catcagcctt   174420
tctctctcag ctgaaccgag ggcattgaag cgggcctctg gcactgtacc tatgagggag   174480
caatatcttc ccctacactg acctcttccg tgccgagatg cagccctccc tgctgccact   174540
agttacagtg gtccatgttc cctttcaaag tgaagttttg ataaaagcac ctcttaacca   174600
atgccaaata gctaagtctg ggacaaagat tgcaggtatt ttgcattttc catgtaacct   174660
cagagggatt gccattcaca ctgatctgag ctgcagaata ccaggcagcc acctcaccca   174720
cccagcaggt ccactcttat actttctcag aaagcacagc cactctactc ttattcagtt   174780
gaaaagaatt tccaggaagg tgtttctgcg attgcctcag aaaagtcagt tccctttggg   174840 aatttcccctt agggatcatc tgtaactcca tttctgcctt ttacctgaat tctttggttt   174900
ggtttgaatt ctttggttta atttatgaat tccctttatt acttttctct gaagaaatgg   174960
agatatcagc tgtccctccc cactgccatt tattccttcc ttcattcaaa ccttatgtgg   175020
ctgctactta ccgtgtgtta agtgttcact tttttcttg gaattcaaaa aagaaggac    175080 agtatttggg gcacagatct tttggtgttc tatacatttt tttaaagttt cattttacat   175140
ttgtgtgtgc gtgtgtgtgt gtgtgtgaga cagtcttgct ctgttgccca ggctggagtg   175200
cagtggcata atcattggct cactgtagcc tcaaagtcct gggcccaagc aatcttccca   175260
cctcagccac ccaaaatgct ggggttacag gtttatgcca ctctgtctga cctgaaagtt   175320
ttgggtttac tttcccttct ttctctttgc tgaagtcaga gatgatggca gcttccagat   175380
tctctggtgc ctgtgctggg ctcgtgctgg tcatggtctt gggtccagga ttcattctgg   175440
agactctcag ggaagtttcc catgacaagg aaatgtagga gagtgtgctg gctttgcgtg   175500
ctcctctgcc aagccctgct tctcctggtg ggacacactg aaccacagcc agggcatttt   175560
ggtggttagt taaaaaaaaa aaaaaaaaa aaaaaggaa gaagaaggca ctgtgtaatt    175620
gtgccgggga tcttcagaaa ttgtaatgat gaaagagtgc aagctctcac ttccccttcc   175680
tgtacagggc aggttgtgca gctggaggca gagcagtcct ctctggggag cctgaagcaa   175740
acatggatca agaaactgta ggcaatgttg tcctgttggc catcgtcacc ctcatcagcg   175800
tggtccagaa tggtaaggaa agcccttcac tcagggaaga acagaagggg agattttctt   175860
tgatggttgt ttgaagtca ggcttaaaca attgtgtctg tgtgtgcgca tgcacaaaca    175920
cttttacctt atctttattt tcttcttttt atttgaatgt atagggttgt gtgtatttct   175980
gtgtaaattt ggggttttcc tcctcttagt cttcactttt tgtggtgatt accagtccca   176040
tttttagagc cagggctgca acttgaaggt tttgctaaaa ccctcaccga agtgtctatg   176100
atcagcattt taactattaa ttaatgtggc caggcaaggg gtggaaggtg agaagactag   176160
aaagggaaca tgatatacac atttactcag atactgggct tttctaacat ctgcagtgca   176220
attgaagtta ccagtcatct gcagtctaaa agaaagtga ttttgggagg tgcgtagaaa    176280
aaatcatctt attatttttc ctctatatta cttttttctt tttttctcct gaagaaactt   176340
ttttttttgg tgataccttc ttttttctcta gcacgtataa ttttgaagc attttttcata   176400 tgcagtgtat acttcagaaa gagagagaga gagaggaaaa ttgtcctgtt cagcgtttgc   176460
atttccatta ttcctgctat tagttaaaaa caacaacaac aacaaaaaac aagcaggata   176520
cctagatctg gaaagggag aattgtgtag agctgtcttc ctaaagttct gagttagggc    176580
```

```
tgcctcagac cactttcata actatctcca gtggctttgt gttttatatt tattaagata   176640
gagaaaaaaa gagtaattac taagggcagc tgctgtagct ttatggtgat tactgaacat   176700
tgacatgctg tcacgttttt ggaactttga gtatttaatc actttgggat attctatttt   176760
cccccatctt gagtgtggac agatgctggt gatgtagcct tctgggcaca gagcaagcct   176820 cccccctcagc ctctgcacca gaaaggctca gcttcacaca ctccaagtat gttttctaca   176880
agaactacac tttgtggctt tctgacccaa acatttttat actaaattac acacaacaaa   176940
gttgtagctc agagagggaa caaatggctt atttaggcca ccattttctt gagccattat   177000
gatttcacac agggctccct tggccctgta aattggcaag gattccatta ttcaacccgc   177060
atacatgtac agagaccctg ctctggccca gatagtattc tgggtacagg cggatagagc   177120
aggaaacaaa acagctacag tgatggacag gtcagcctgc agcaatgcct gcagtctctg   177180
caaaggtagc tgtatgggtg ggcaggtggc tagcacttat tcagctctgg aaggatctcc   177240
cctctggcct ctcccctgac acccatcaat aaaactgagg agcatcggtg gacaggggac   177300
cttgtgcccc ctccctgcct gtgcagttgg ggctgaaccc agctacgaag tttgagctca   177360
ctctctccag ctccctctca attcagagct gaactgtggg aagcttcaga gctctctgtt   177420
tcaaggacag gttctcctca cctctcctaa tggaggtgca ccaggaaact ggccctgctc   177480
tgcccagggc tttctcctgg actttgccat catggtctag caaaccctgt tcagattgag   177540
gtgagtggtg agatttcgaa ttcttttga cagataggat taagtcttct tctgtgggac   177600
aagtgggagg tagaggtaag attaaagatg gccaaatgtc tgagtcctga cagccacaat   177660
atggagatct agacttttta cagaccacag ggcacagggg cctcactaac agagttcccg   177720
gaagtgatga gtgtgctggg ggcttcctgg ttgaagagac actagaatgg accagctggg   177780
agctaatttt ttgggctgga gtgtgatggc ctgcacatca ctgcctctgt ccctccattg   177840
tcacagctgc cccttaggag ccagctgagg caatttgtgg tcagagtgac tttgcacagt   177900
tgtcctgcct gtgttcagga agggagtttc tgtggtccct ttgaaaccac agaagagccc   177960
ctcgtatagc tctcaatgga gggggcaaaa cattcaaata actcaggaga taacacaact   178020
atttgttttt aactgtgagt ttttaggcaa tcacaaagat ccagatgtat gtccaagcct   178080
ctctttgcaa ttctaattaa cctcaatgtt gcaaccatag acctaccta cagagttcaa   178140 aaaaatatgc aaaaaccctg cctttcttct tcctcatacc ccaaaatgcc attctgaaca   178200
tttcctgtta gttaaaaaaa gatttccatg gtgttaccag gcactgtaca cagtctgtgt   178260
cccaagacaa ggaggtacag ttccacatgc gcccatgact gggttgggct ctgcactctc   178320
tctatacttt gagagcctga ttttctgtga ttgggcagag ctgcccacc tggtgcaatg   178380 tcctcctctg cctttcaaac atgttttagt catcaagatc ttcaaatttg taaccctttc   178440
cagcttgatc cagcagaatg cagatttgga aaaacagaac gagtttaaaa tacatgattc   178500
taagaaacct ggaccagaac tatcaaaact tggtttccca gagaatatag caaatgggct   178560
cattggccaa tactatgaca ttggcttttg agaaaagaaa ggctttattg caaggctggc   178620
cagcaaggag acaggagttg ggctcaaatc tgtctcccca gtttgggget tagggcaagt   178680 tttaattaca cagacgcatt tcttatgagt agcaggcaga gagcctccaa cttcttctgc   178740
ctaggtacca gcagcttaga catgatgcaa acctgggaag cacatactgt atttggagaa   178800
agtgattggg aagaaatgtg agctgagggg aggggctcag tgcccctgag ctacacttag   178860
tgatggcaga ggaaggatgt cctcccgcag gaggctgttc cacatctgct ctggttgtag   178920
```

-continued

```
ggggagctgg caggcattag cagcggcctc tttcccccaa gagaggcagc ctcctccaag  178980
ttttggcgac attatggccc tgcaatcata agggtttgtg agcatagtgc taaggaggga  179040
aatggagctg ctgttactag ttccacccca acacacacac acacactcac aagaaacctc  179100
acaagcaccg tattggaaga cttttgccatc caacctggga tttgacaggc tctagaagca  179160
gaatcataga ctcatgaagt tcccccaaag caggaatctt ccttacagta acccccaacc  179220 accccctcc accgcctcca ccggctgctt cttcctgaac actgcagtgt ttggaaaact  179280
cacaaacttc caagcttgcc tttcctattg ttgcatggat tgaaagcttg cgttgtgtga  179340
agaatggcgc ttcctgctgt gcttagtttt atctcatata atctttgcac catttaatcc  179400
ttgcactcac ccactcatgc aactgccttt gcagagactg gagggccgc tgtaggctga  179460 cctttccttc actgtaccta ttttgttccc tgctttattc ccctgcaccc aggacactgc  179520
ctggcacaaa gacaggtctt tataagtgta tgcaagtgaa taaagatata tatattatta  179580
ttgttatttt tgagacagtt tcactctgtc acccaggctg gagtgcagta gcgcaatctc  179640
agctgactgc aacctctgcc tcccaggctc aagtgattct catgtctcag cctcctgagt  179700
agctaggact acaagcatgt gccaccacgc ccagctaatt tttgtatttt tagtaaggac  179760
agggtttcac catgttggcc aggttggcct ccaactcctg acctcaagtc atcctcctgc  179820
ctcgacctcc caaagtgctg ggattacagg catgaaacca gcctagaaat acatactatt  179880
atttattctt gttttacaga taagcaaagt gagtcatgga gaatttggtt gaaagtccca  179940
aggtcaggag tcgtgaagct gggattaaaa cctaatcatc tgactttaga gagtagacac  180000
ttgctccatg catattgcct ccaattcatt cattcaagca ctccctgctc aagaagttct  180060
ttcttatgtt gagctgaaat ctgcagccct atgcgtttta cccagcagtc ctggtgctgt  180120
tccctaaaat cacttagact gtgcctgctc tttctgtgtt tacagtgtca gctgtaatat  180180
ccccctcttc ggcctaacgt ttctgaagtc ccttgccact gggtctcctc tcctcttcct  180240
gtgttctttc taagaacacc tatgcagata ggtgtcttct gtacagggaa gctgttcctg  180300
agatccgggc atcgactctg ttagaataat ctacgtatga gttatttttt tgagaactat  180360
gtgtcattgc tgactcatat taactctgtg gttaactaaa atctcaagat ctctttatgt  180420
ttgttgagaa acttatttaa cttctctggc cctccgtttc cttcactgag cagtggagtg  180480
attgataacc tccacctgtg gttgctgaag gtcttgcaca agatgatata gttaaagtag  180540
ctagcagtgc ccacgtacgg cggatgcctc acaacggttt gcagccatct ctctatctgt  180600
gtctttgtct ctctctcaca ctggttttgg cttactgtta gcagctagcc gagataagtg  180660
tgtttatggt ctttgcatgt attgtttctg tagcatactg gaggattaca agaggttggg  180720
gagtgagggg gcggtgagga gtagacaaag gcagccaact cttccaagtt tagcttagaa  180780
ggaaggagcg gtaaaccta gttgaatgtt ggactgaagc aggtttgttt ttgttttgtt  180840 taaggatag ggaagatctg tgcgtgtttc caggataaag aaaaggagag aatatgatat  180900
taaagattct ggaagtggga gaaggagcaa tgaaatacag acttgaagtc agtggcatgg  180960
acagggtcaa gatcacagtt agaggatgca gccttagaga aaaggaaggg gctcggttct  181020
ctgagcaagg agggaaagaa gagaggcaga tgcagagaag tacggcacat cgtgctgctg  181080
gttgtagaaa taacctctga cttttaataa agtcatccct cggtatccct gggggattag  181140
ttctatgacc tccctcggat gccaaaattc gtggatgctc aagtccctga tataaaatgg  181200
catagtattt gcatttaacc tacacacatc ctccatatcc tttttttttt ttttttttt  181260 ttttttttt tttttgtgag atggagtctt gctctgtcgc cctggctgga gtacagtggc  181320
```

```
tcgatcttgg ctcactgcaa gctccgcctc ccgggttcat gccattctcc tgcctcagcc   181380
tacaggtgcc tgccaccacg cccagctaat ttttttttg tattttttag tagagacagg    181440
gtttcaccat gttagccagg atggtctcga cacatcctcc atatacttta agtaacctct   181500
agataatctc tagattactt gttttgtctt ttttttttt ttttcttttt gagatggagt    181560
ttcactcttg tcacccaggc tggagtgcaa tggtgcaatc tcagttcact gcaacctccg   181620
cctcctgggt tcaagcaatt ctcctgtctc agcctcctgt gtagctagga ttacaggccc   181680
ctccccaccc ccaccccca acaactggct aattttgta tttttagtag atgggggtg      181740 tcaccacgtt ggcctggctg tcttgaact cctgacctca ggtgatctac ccgcttcagc    181800
ctcccaaagt gatgggatta taggcatgag ccactgtgtg tggcctagat tacttataat   181860
acctgataga atgtaaatgc tatgtaaaca gttgttatac tgtattgtta aagacagta    181920 acaagaaaaa aaatctgtac atgttcagtc cagacaaatg gttttctgtt ttttttttt    181980 ttttttaata ttttttggtca gtggttggtt gactccagga atgcagaacc cgcagatata  182040
gaaggttgat tatgcgttca gaggcaggga ataccatctt gggttccaga agaaaatga    182100 tcagcatttt ctgtcatact ctggtaaaaa cagatctttt gaatggacag gtgtattaaa   182160
ccctgtggag ctggctgggc ctggcggctc acgcctgtaa tcccagcact ttgggaggct   182220
gaggcaggtg gatcacgagg tcaggagttc gagaccagcc tggccaatat ggtgaaaccc   182280
caactctact aaaaatacaa aaattagccg ggcgtgatga cgcatgcctg tagtcccagc   182340
tactcgggag gctgaggcag aagaatcgct tgaaccctgg aggtggaggt tgcagtgagc   182400
cgagatcacg ccactgcact ccagcctggg caacagagtg agactccgta tctaaaaaaa   182460
aaaaacaaaa acctgtggag ctgatgaaat cctgcaggga gcttcacggt gacagcaaga   182520
ggagaaacac atccccatat gccccgcaga gtttgaagtc ccggctgcac ctctccccag   182580
cagcaggttg actctggaaa gttgcagcgt tcttacctac agagtgggaa cagtactacc   182640
cattgcacag agtgggtgca aagctctgtg acggaataca tggcaagtgc ccaccacatt   182700
gcctgggatg aggtgggccc ttcctttacg taagagagcc ctacagatac actcaaagtg   182760
ggcacattcc tacagaagga gtgttatttg tgtagaaaag aaaaacatga aaggctttta   182820
ttcctataca caataaagca cccctttaat gtctttttga ggaggataat atgaaattga   182880
tgaaaaggaa ccctgtggtt ggatccctga caatcacatg tatcccttt ttcactcttg    182940 aaaaaggagt aaaggaataa aatagaaggg gagaggggc agagagacct tcaccgcccc    183000
ccccccaccc cccatcatcc aatctatagt caaaccctcc agactgtgtc tccttggcat   183060
ctctgacacc cccaccgcca ccacccccagt caattcctat cttatccccc tatcctggat  183120
ctgattctgc taagttcctg ccacactaaa gacagggtgg ctttctgatg acaacattcc   183180
tctgcttaaa cctgtcagta attccttgtt gctctcagac ggaactaagt tctgaatttc   183240
ttcacacggc tctcagcaag gtcacagtca ccctgctagg ccccaggggc aaatctcaat   183300
ggtcatcttc ttgaagacct ggctcagtta tttctttctc attgaggctc acgacccac    183360 cttcttgcat gcctcaaacg gccccttacc atgtctcttct ttcgcccata gctcagcaca   183420
ccatatcatt ttaatttatg tattttgctt aatgtggatg atctgtctcc tcctctgctg   183480
tcctcaccag agcatcagtt cctcaaacca aggctctttg ttttgttctt ggatgcaagc   183540
taaatgtctg gcatgtggca aatggtcata gatacatgtc attgaaagaa tgattcatca   183600
cctccctctt tggccttgtc tgtggttcta ccaaatccca ttccctcccc agtgccctcc   183660
```

```
attcccctc cttggctgaa cattctgaac cacagacagt tctttaccct gaacctttgc    183720
atattttgtt ctcttagctt agagcggccc ctctccctcc gtctgcttgg ctaatttcta    183780
cttgttcttc agattttatc ttagatgtca ttccctcaag gaatccttct gtgactcaac    183840
atggaattaa gttgcctcct ttgaccctga aagcaccatg tactcaatct catcttggca    183900
tgactcactt tgctgtgtgg aatgtctgct ttccttgttt gtctattcct ttagactgta    183960
agatcctaga aagtggggc cgtgccttgc tcatgactgt gtttctaaca ccaaacacag    184020
tgttcagtag agagcagctg ctgagtacgt ttctgctaaa tgacagttga tggaggacat    184080 ttaggggttgc ttggaggtca agtcaaggag gcatttaaca ttctagtaaa acaaggaagt    184140
aacaggctcc tgaacatgcc cacaatgaac cagatgcaaa cctttcccct tggcaggatt    184200 cttttgcccat aaagtggagc acgaaagcag gacccagaat gggaggagct tccagaggac    184260
cggaacactt gcctttgagc gggtctacac tgccaagtga gtcctaaccc tgatgttgct    184320
aataagtggg ggcatgggca gggggcctc cttctaggag tgatgaccac ccttaatacc    184380
acatgtctgt ctgagccaag tttctgagcg ccagggaggt gaggaaggtt ggacttcacc    184440
agagaggctt tgtggacacc ctttatcatc ttagtgagtg ctagtgtcaa acaaaaggga    184500
gtggggatat ggggcacatt ggtggaggga ggtgtgatct ctgcagcttc agaaagatct    184560
gaaagagtca tttggttaga gaagttgacc tatttcctgt ggggttagac cagggttgct    184620
actgtgaaca ccagccatga ctcaccagtc accttcagaa gccacaggca ggacatgctg    184680
acgacagcct tcaactcacc cacccccttgc tcccctgcgg gtggaagtct ggaggtgaca    184740
ccactgcatt ttctaacacg ggggctcctt gagcaactag aacaagaaca gaaagaatgg    184800
ggacattagc aggtgctttc cccctctctc attcttttct ttgaataaaa aggttgtttg    184860
aaaacacctg agcggctcct aaagatgggt gcaatctatt cgggatgcaa atccgaatga    184920
atgttattca aatgctcctc tcttcttat gcagagtgta tttcaaggct cagccagtgg    184980
caggcatgct ggggactatg gactacggac tagggcctg tcacagagga aggcctcatg    185040
ctagagagct aagggaggag ctggccttca gttccatccc aggagcaact ttgatgttcc    185100
cagagatcct tccaaagggg gagtcatggt cacccaagaa aaatgtattc agaatgccaa    185160
gaatggtgca aactcaggac aaagattcac actgcagggt tggagtccct gggcttgctg    185220
ctggcaccat gggagggagg gtccccttca ggggtaccgt tggtttcctg tgaattaaac    185280
tggcttcaag ggatctcgac tgaacaggcc tatatcacac tcactgatat actctctctt    185340
cagtccttct cctcatctag gtattttttaa ttgtttcagt gaggtgtagg catgagggga    185400
ttggaggggg catctcctcc attgcagttt ttcattggct gctttgctcc ctcagctccg    185460 aaaatcgctgg gccactctcg aacgcattag tacggtagtc acaggttgat tgcctggccc    185520
cttgccctct gtgggcattt tccctttcag acagcccctg agtactcaca gtgctgctac    185580
agtgggccac ctagatctcc ctctttctcc atgctcccac gtgctctggg ctccactccc    185640
ttctcccaag cacttctgtc cagggctatt ccagcagtct gacctcaagg aaatcctttg    185700
ctaaactgat tatagagagg tttctatttt aacatttagg tcttccatgt attaattctc    185760
agaatcaatt taagatgttt aaaggtgtga tttaagacat tttaaaacca tttggaggag    185820
agtacagaaa ttatgtcact tgctgtcagc ctctttgcac catctgcaga gaaagatact    185880
agagtcccgc cttggacaca tccacatgca agaggtgcaa agaaggtgtc tttgatgagg    185940
caaggtcaaa acttctcccc agacgaaatc caaagaaagc attcctacta tgctatatca    186000
gtttggaaag aaaaacttct gccaggtgac tgcattctca ctggtcacat tgtgttccta    186060
```

```
tggactcctc agctcaacca atttggagaa gttatggtgc aatttcacca tatctggtta  186120
gaagttaagt ttccaatttg ctggcaatga agaagaaatg gagcaggcca ggctgtgtag  186180
tttctgccac gtgcccccgg gagtgaacag ctctgtttgt aagaagccat ggtgcttaga  186240
cctgggctcg ctagttgcca gcctccaaat tgcagaagtg ccctttggtt ggtggctatg  186300
ctgtgtcact tgggaaggtc gtttggaagt tccacagtcg ttgtggggtg ccagagatta  186360
aaaagcgtaa gaggagagtg gaaagtgatt gttgctgctt gggcatcccc accgtgtggg  186420
tgctgcagcc cagctctcaa aacccatggg tctgtacact caacctccat gagagggaag  186480
gagaaggatg agggagggga gagatagcca tggaaaggta ggaactaagc aggcagggtg  186540
gagagttttc tgtaagacaa aaactgtctg gacactgctg cggttctgtt acaaagacca  186600
cttcctccct gggccagcaa catatctgtg tgcctgtctg ggttgtaaaa agggtcaaag  186660
atcaatgcag caggcagcta catgctgcaa aaagccagag gcagctggtc tgtttgcctg  186720
tgccaggaaa ccactgggaa tggggttgtg tgttattcta ggagaaagtc gtcccagcag  186780
cagcttctcc aggggcatcc aagagcactg aaaaggggttg caagatgacc catgaggctg  186840
caggaagaaa agaacatgca tttaatcttg ctatctgaaa agtaagacat gaagctttcc  186900
tcattttttaa tatacacatg gacagtagta tgtgtatata gtttatatgc aaatatactt  186960
gttataaggt tgcatgctca aaattttttgg ttcatggggt gtgggatcat aaatgtttag  187020
ggaccatggc tatcaaggaa aaacagcatg aaggataaat gatactggtg gattaaaaag  187080
acagatgcat gtatttttag cataaaacac aactgctgac tgatacagat agctcaagat  187140
tctggggcag ctgctgaaca gatacactag ccagtgtggc tcatcggctc agacttggcc  187200
ttaattaatg ggctgtccct ccacccatct cccatgaggg cagagctgag ccagggtttg  187260
agagctaaaa ggaattggac ctggactctg ttcacgtgta tatttttaatt ctaattaatt  187320
cattcttttg aaagacagag tcacactctg ttgcctaggc tggagtgcag tggcacgatc  187380
ttggctcact gcaacctcgg cctcccaggt tcaagttatt ctcctgcttc agcctcctga  187440
gtagctggga ttataggcac atgcccccat gcctgactaa ttttttgtatt tttagtagag  187500
acggggtttc accatgtcag gctggtcttg aactcctgac ctcaggttat ccacccgcct  187560
tggcccctca aagtgttgga attacaggtg tgagccaccg tgcctggcct gttcacatgt  187620
ataaaacaca gtttaatgtc ctattcccag ccaatgagca tggctagagc agccttggtc  187680
aaagtttggt ttttgagaaa aaatccttgt tagctgacct aagattcctc tttgtgagtg  187740
taagtaagca caggttgcag agaggagaag ggtctctgga gaggtgtaat tttctaaatg  187800
gattacaagt tcatggactt ttaacaggtg ttacagggga taacaagttc tttatagaca  187860
gactttttgag gacgtttaag ggtattctga ttcttggttt tctaagaggg gaatgtatta  187920
tttaactaca gacacccta ccgcccactt tttgcagagt gtatcaaaac atgttttttgg  187980
aataccaccc tcatgtcgct tctccctgca tctcttatct cttggtgtcc attctagact  188040
cactttcttt ctgttttttta tttttatttt tttttgagat ggagcttcac tctgtcacca  188100
ggctggagtg cagtggtgca atcttggctg actgcaacct ctgccttccg ggcttaagca  188160
attttttgtgc ctcagcctcc tgagtagctg ggattacagc atgcaccacc atgtccggct  188220
aattttttgta tctttagtag agacagggtt tcactatgct ggccagcctg gtctcaaact  188280
ccttacctca ggtgatctgc ccgcctcggc ctcccagagt gctcagatta cagacgtgag  188340
ccactggtgc ctggcctaga ctcactttca agtggcatag acttgtaaaa ttatttaaag  188400
```

```
gtgataggtc tacaatgatc ctgtcaatta gtattgacac tattattaat aaactgttat  188460
taattatatt tacttacttt aaattaatcc aaactaatta acggaacact aaagagtttc  188520
tatgttttat tcccagaggt gggagaaaaat gaaagggaat atagcaacga attcttttct  188580
ccataaaaac atgaatagtg cagcacatca agttgaacat accacagcaa attgttgcaa  188640
gatctgctga gtagctccta tttagacctc aaggaatgag actcaaaatg ggttcatcag  188700
ttctgttttg cagaaaaaat agcgcaaaat ttctcaaaag aaaatccaga ataataataa  188760
tttgtcaata ggaaagacat ttccactggg ggttaagaag gaagacattg gaacaatgat  188820
agccaccact tattgaatgc ttactgtgag ccaggtggca cttcacctcg tttcattctc  188880
acaacagtct agggaagtaa ttactaatgt ctccatccac ctcttgtaga tgagcaaact  188940
gaggctcatt gaggctagga aatgcaccca cactcacata gcccataaga ggcagccatg  189000
gcattgggcc cagaccatgt gaacttcaaa gactacacga gcagccactg gcagctgtc   189060 atggctaaag ccacttgaat tcagcccagc agcaaccccc tctccaggag gggcacataa  189120
gcttgcagct ttgggtagaa gctgcacttg aagtcctgga tggcgagagg gactggcttg  189180
agccagagcc aggaacaagg ctctgagaat attctggaaa tccacaggag gaacccattt  189240
tcttacagct gggagaattt cattcaactc caggctgacc atgttttatt aggaacgaag  189300
gtgacttgaa ctaatagtca ggaatggttg aatacggacc caatgtcaaa tcactaggca  189360
gttcacattt ctaatgagca aatcccttag acaattaaga attttttttcc ttttgcataa  189420 cccagacaaa atcgctactt aaaaacaaac caaagacccg aaacatgaga aagagaagga  189480 agcagggggaa atctttggta ctaataagtt tttaaacaat aagagcacca gatattttac  189540
cccatcagac acagaatgtt attcgaataa ccaaaaaagg aatttttttct ctaagtttct  189600 tgaactggaa aatgaatcat attttctcag tcctgaggct gcaattttgt gcctctagta  189660
acatataaga atagatgtga tgccagtgcc cagtagctgc tgcaattgtt acttggggac  189720
ctgtttattc actaagcact tcaccccagt gataaatttg taggggcctc ctgcccttgt  189780
gagctcctac cgtgtccatt agatcagtgg aaattctggg attcagagca ctttgcaagg  189840
tcagcagggg tctgctcttt ctgtcctgtt cctggttttt ggttgtgcct ggattccagg  189900
gtaggtttct catctgttac cttcatagac ttctccagaa aaggatcttt tgaccatcag  189960
aggaccacga agattccatt ggtgaggcgc agataacctg atctctctgg gttctctgca  190020
gggcacagat gaagggctgg ccattcccaa gttctcagtg gtaccactga ggcatgagac  190080
cctaatggtt tgcatgagca gtttgaaaat tgcatctttg ttttaccta tataatcaca   190140 tgaaacccgt ggttctcaaa cgtcagcagg catcagcatc acatggaggg cttgttaaaa  190200
cagatttctg ggccccaaca cagagtttta aattctgaag gcctgaggtg ggtgtgaaca  190260
tttgcatttc taacatgttc tcgatgctgc tgccgcctct ggtcccgaga gcatgcctgg  190320
agaactgcca ccttcgacca tggactgtga gaattcacat ggacctcaga attataatca  190380
gtctctcagt tttacagata aggaaactaa atccagagag attgttttgc caatggtgaa  190440
cagctggtta aagtcaggat ggagacttta atcctagtca agtgaccttt cctctgtatt  190500
tatttccctc ccttttttatg cctctcaagt ctagttacac tgttttcat ggatgggcat   190560 atttattgtc ctgatctgga ctgcagactt ctcaggagga cacctatgat ttaatttagt  190620
atagttgaag agttaacaga catggctttg gagacagact gattatggtg tgaatcccgg  190680
ctttgccact ccctagctgg atgacccctga gcaagttatt cagcttctcc aagcctgagt  190740
tccttattgg aaacatgaga gcaattgtga taggcagaat aatggcccccc tcaccaatca  190800
```

```
tgcccacatc ctaatcctag gaacctgtga atatgttatg ttacatggca aggggaaatt   190860
caggcagcta gccagttggc cttaaaataa agagattatc ctggatgatc tgggtaggac   190920
ctgatgtaac cacaagggtc tttttaatgt ggaagaagga ggcataagag tagatgtcag   190980
agtcattcaa ataagaaag  atttgatggg ccatccctga ctttcaggtt ggaaggaggt   191040
tctgagtcaa ggaatacagg tgacctctag aagctggaga aggcaaggaa atggtttctc   191100
ccctagaagt tccagaagga ttgcagccct gctaatatct tgactttata gccctttgag   191160
atttattttg gatttctgac atcctgaacc atagtaaaag ggtgtttttt gttttttga    191220 gacagagtct tgctctgttg cctgggctgg agtgcagtgg tgtgatcttg gctcgctgca   191280
acctccgcct cccaggttca agtgattctc ctgcctcagc ctcctgagta gctgggatta   191340
caggtgcttg ccaccacacc tggctatttt ttgtgttttt agtagagaca gggtttcacc   191400
atgttggcca ggctggtctt gaactcctga ccttgtgatc tgcctgcctc agcctcccaa   191460
attgctggga ttacaaggcg tgttgtttta agccactcag tttgtggcca cttgttacag   191520
cagcaagagg aaactcatac agttatcatg tgaactcaca ggaatatggt gagttaaaaa   191580
gagaggaagg gtgcaaaaca tccacggtag agtgagaact ctccagggag tgaggactgt   191640
gcccagcata cagtgatcac cctcttagta agctaagttt ctgagcacca gcttttttga   191700
gttgactttg ttgtctttaa catttgaaga tcacccttct ttgctcagcc tggcttgcag   191760
acctgggctg atttgtggat ctgatagaaa agtttcctta gttgggctct tctccccgac   191820 caccccatg ccagtgtggc cacatcctct gtctgcattg ctcactcttc aattccaaga    191880
agcgcagggg caccgccagg aacaggaacc ctgccagagg aatacatcaa gaaaccaagt   191940
ctcccttacg catcaccgta ggaacagagt taatggatta tgaacatgtg tttgctttat   192000
accattgttt gtttcccagg tggcagctgg ctgccccatc ttattgggta gatgtaagtg   192060
gaattacgaa tgggatttat gtttcatgca cgatggtgat tattaacttc aactttcagg   192120
taattttcag accacattgc actaacttgg tctctgattg ttttctcct tgtttgttta    192180 ttctgcagcc agaactgtgt agatgcgtac cccactttcc tcgctgtgct ctggtctgcg   192240
gggctacttt gcagccaagg taactcagac ttcccttgt tcattctcct tctataaagt    192300
gcatctcaag gaggttcaaa gggcaggctt tttgttgaaa ggactttgcc tgacctctgg   192360
ctcccatctg tgaagccctg gagaggtgag agccctcggg aggccgtgtt tcaggcatgc   192420
tctgcacccg tgcagagcgc gtgtgataat gcattgctaa tgcttgctcc ctggtggctg   192480
gctgagagct gctgtgctga caagggtggt ttaaggctaa atgtgactca gaatccttaa   192540
gcagtgttag ttcagataca agggcattat aaatgagagt gcctgaggga tctattttgg   192600
gaccgctgtc acttggctct tctgctaata agcttccagt gtggtggccc tccttcaggc   192660
atgtttccac tgagccacgg gctggatgcc acatccccgg ccttcccaca gttatcagca   192720
gcccacaggc ttgacttgag caagttggaa agacaaatca acttccagag ttgatttaac   192780
attgagtgga aatcagtcat acttttggtc ccctttcggg gccacgcctg gcactgtgcc   192840
tggtggcaga tcggcatgaa ctggccagct tctgtggccc tggagggcac aggcagaaag   192900
gccacactca gtcccatgat gaactgttta agacttattg ttgtctcccc gctctgtaaa   192960
gtagatagag tggattttat gtcccttatt acctttcagg atactttgac tcaggggagat   193020 aaagtaactt gggtacagct actcagctgg tgaagaacac aggcagaatg agtgcctggg   193080
tcttttgact taaaattctg gattttttcac aaagatcctc ttactttatt catttacata   193140
```

```
ataaatatat attgaagagc tactctgtgc caagccctgt gcctagatat acagtgataa    193200
ataaagagta gcttctagag gtcacctggc ggtgaggcac aggccagctg gcaagatgga    193260
ccacagaagt cagtgaatga agacaatgac aagggtggga agcgccatat gggaagagaa    193320
ccaagttcag tgatagagag cagaggtgag gcggcagcag aaaccactta agggacacca    193380
cgtggcactc cttctgtgct gagaaggctg tcagtaagct caccatttat ttcctatttt    193440
ctctcctgag ttaaatagga aacatgtctc gcattacttg aaaaatcaag tcaaactatg    193500
ctcttactag gagttatggt tcttttatg tcttagatga tgcttgatct agatgaatgc     193560
ggacttgctg tagctagata aatacaatgg gagtttgaag gtgtttcgta gccctggaaa    193620
taggtatttc ctgtcaaaac aagctttgtc attgccagca gacaaaagca tcagtaacct    193680
tggttgataa tcgtcatttc ttaggaataa agtagactgt agaatttttt ttagcagaaa    193740
ggaaacccaa agataattct agtgcaaatc cctcacttta tagagcagaa gctcaagtcc    193800
cagaggaaca agtggcttga acgaacatca gaattttagg ggctggattt gtaccctcct    193860
ggtgccagca gcccacttcc ctgcaggagg cactcacctt ccttgcacag gggtatgagt    193920
gtggccattt tccacccata atctctgtta gctcatgttc aattgggttc ccattgaaag    193980
aaaaatggac cagtaagttg gagcagaatc attcagatgg tataacataa ggaaaaactt    194040
tgcccaaggc aaatcgtgat tgtgacagct ttgtgatttt tagagaatag catgggccag    194100
gcacagtggc tcatgcctgt aatcccagca cttgggagg ccgaggcagg caggtcactt     194160
gaggttggga gttcgacaac agcctgacca acatggagaa accctgtctc tactaaaaat    194220
acaaaattag ctgggcgtgg tggtgcatgc ctgtaatgcc agctactcgg gaggctgagg    194280
caggagaatc acttaaacct gggaggcgga ggttgcggtg aaccaagata gcaccattgc    194340
actccagcct gggcaacaag agtgaaactc cgtctcaaaa agagttcaca gtttctcttt    194400
tgctttgatt ttcttatctg ccggataaca atagtatttt ggaaggcagg aggaattgtg    194460
gaaagaaatg ggttttgggg agtggctgat tggaggcaaa tccaaggaca ctcattgctg    194520
gtgtgtgact ccaggcagtt actcagcttt tccaagcctc agtttcctta ttgtaaaaca    194580
ggaccatggt ctagctagta gcattcctat ggtgagtgaa ataatatgta taaagctcct    194640
gacacagtgc ttggcatata tcagattgag ccatgtaaaa ctgccaatat ctggctattt    194700
atgacctaca aaaatagcat ttcatatgat tccacctaac atctgaagcg caataaatgt    194760
tattattgat aatgcaggtg gtggtgataa agttttgaaa tcagaaagac ctggcttcaa    194820
attccacgcc ttcactggcc tgacttattt tcattcattt gacaaatatt attttgaaca    194880 ccctatgtg ccaggcacta tgccaggctc agagatgatc taggaaaaag acagatgtcc     194940
tcatctgtct taggctcttg tggcctaagc ctaaattcc tcgtctgtca aatggtgaca     195000
gtaacacact ccttaccaga gagctgggag gattggagac tcaagttccc aaaacgccag    195060
gagcactgcg gcaggtgaaa agtattccct caatggcgga agtgtttaaa ttgcttttat    195120
atctgtagct ctagataaca ctagttccag cttagttaac tcccagctcc aagccttcag    195180
gacttcatag agttattggg gtgctgctct tggcagtttc ccaaaaagct agaatgcaga    195240
gggaatctcc ttcccaaaaa gctagaatgc agagggaatc tccttcccaa aaggctagaa    195300
cgcagaggga atctccttcc caaaaggcta gaacgcagag gaatctcct tcccaaaagg     195360 ctagaatgca gagggaatgt ccttctcttc taaatggtag ctgttagttc aagaaaggtt    195420
aaacattgtg ctgtggggag gctcagggga gaagggtgta cttttaagag aaccagtttc    195480
agagctgggt ttggggttta agccctaccc tctgccccct tttacgagct gacagcctta    195540
```

```
tgcaagcctg gttgaccacc tgaacccacg tttccacatc tggaaataga aatgtgggta 195600
ctagttatgt tgaaaggact caggttagat gatagatatg caaataccct ggaaaccagg 195660
agtgtccagt cttttgggtt ccctgagcca cactggaaga agagttgtct tgggccacac 195720
atagaataca ctaaccctat caatagctga tgagctaaag aaaaaacgtt gcaaaaaaaa 195780
tctcatattt ttaagaaagt ttatgaattt gtgttgggct gtattcaaag ccatcctggg 195840
ccacgtgcga cccgcaggct ccgggttgga caagtttgtt gtaaacaatg ccatgatgcc 195900
ggcataaggt cgttaccagt attaggaagg ttctcaggtt tcctctagcc cttgggctct 195960
tttcctgaag tgcgtgtgtc ttctgctaga ttttgtgacc aatgttgatt gcctaattgg 196020
gctaacagca tgttttggtg gctacgaaac tgacacaggt gttttcattt ctccacttag 196080
ttcctgctgc gtttgctgga ctgatgtact tgtttgtgag gcaaaagtac tttgtcggtt 196140
acctaggaga gagaacgcag aggtaggtaa ctgggactac taaagaactg tggagcgatt 196200
cctgattttt gagcaggaag agtgacaatt caaaacagta tttgactaga ttcacggctc 196260
cgtagcatcc ccttgggtgg gaggggaag gctgactagg acctctgatt cttctttccc 196320
tgagctttga aggctctgaa aatacagctg ggggacttg cccagttttc ttattaagca 196380
attcctccgc atggtgctgg cttttcaaagg gtgcttcagt gctgtttgct gcacgtgcct 196440
tgcagcccca caccctgcac tcccgccctg cagagtctgg cgctggaatg acattttagg 196500
tctgggttcc caggcctcct gagagtgaaa tgtttcattg tttgtctaga gaatgagaa 196560 ctaaagcttg caccttgtga taagttgtcc tgaggaacat atctttcagg accagaaga 196620 aagaatgttg ggaaaataag atgcagtaag atgcagacat gacagcaggg tgcagcggct 196680
cacgcctata atcccagcac tttgggaggc tgaggtgggt ggatcacctg aggtcaggag 196740
tttgagacca gcctggccaa catggtgaaa ccccgtctct actaaaaaat atacaaaaca 196800
ttagccaggc atggtggtgg gcgcctgtaa tcccagctac tccataggct gaggctggag 196860
aatcgcttga acccaggagg cagaggttgc agtgagccga gattgcgcca ctgcactcca 196920
gcctgggcaa caaaagcaaa actccatctc aaaaaaaaaa aaaaaaaaa aaaaaagat 196980 gcagacacga gactgtgaaa ctgactagca tcaccattgc attgtttata gatgttgcca 197040
gacagaaagc cccaaagcag cacagtacct tcctgacatc tggactagga aatctagatt 197100
ttagtaaaat acatgctaat acttacagaa gaaatgtcgg cgttagagta tgccgtcagt 197160
tccttagaga ttgcaattcc taatgcacta gtatggtttc aggtgccagg aacacgttct 197220
gtgaggctgc tgccccaggt gctgaccca gccttccaca ccatttttcct tccttgtgtt 197280 cacagccgct ctgtctttta caatagcacc cctctctagt ggctaatggg ctctatgatt 197340
agatagcatc cttcagtagt gataaaggca gtgacatcct agggaggtca gcgggtgaaa 197400
gcgctatatc tggaaaacct gagagcctgt gaagctcaag gacttgacgg ggttagaccg 197460
tgagccgggc tgcagctgga aaagaatga ctgttctttc agcagatcct tccctgtgcc 197520
atctctttct tcattcctct ctagtggcat tcttatttat cctctaaaac cacaattcca 197580
ttatctctcc tattcttatc aacactgccc taaatgatat tctttattct cttttgccct 197640
ggaaaacctc tatcatgcct tttcccatgt gattacctcg ttaagagtgg gggtggaatg 197700
tctagcaatg aaataagagg gtcttctctt ttgcctggct ccctatgcag ccctatctta 197760
ccccctgcaa agtcccaggg atgtggctca gtcactgctc ctctcttcat ctgtcaccac 197820
ttgcttgaga tcctacagct gctttaattc cgagaccatc tgcagaacat gacaaaattt 197880
```

```
gtccacctac ccacatgtcc tttttaacttt aaaggctttta ctaactgatt cctattaggg  197940
aatgaacaga ggtggcaaaa ataaacaata ggagattgat ttacaagaaa tctttaaaat  198000
agtagatttc ttcggacctc attgaaatat aaatggcctg ccttcttgtg tccctccctg  198060
gtctccctct ttaggtgata agaagaagat cctgccagcc ccataacccg ccatctgcgc  198120
gggttctaga ccccccttctc ctcccctctg gccgtggtag gcattactga tgaatcatgg  198180
tgctctttct tccagagacc aaacctggcc tcggaatcct tcttaacaca gatactgctt  198240
aacacaacca ctctgagcag ctgtcataag tagaagtaat agatactaga agaaatgtct  198300
aagcctaatc tagaccaaaa tacggcctga tatagatgca agccagaggg gctttatggt  198360
taaatgcaag gagattttca accctgccgt ctagaagcta cttgctgaga tcttcttcag  198420
ttgggcccat ctcctcccca ggcctctctt ctgttcctgg gctatgtcac acttggactc  198480
tgcagacacc taatgctctt gggacctgct ttagttcttg acctcaccaa ccgaggagga  198540
attgctagat gagatccttc ccccggaatt tctctcttga accccagatg gtccgttgcc  198600
cctttccaga agttgctcca gccctgtccg cttaggaagt tcagtgtcat ccttgatcca  198660
gtgggtaggg aagacattcc ataatgaatg ccccagtctg agcttcttcc ttcaggcttc  198720
aggctgccct gcgaggattt tgcagctccc ttttttaatgc cctctagaag tttctggctc  198780
ttattttcag ccccttcatcc tactctctct gacccccttcc tctatcctgt ttagttcacc  198840
tgtagcagtt actacccagc agtgaaggat gaatcttggt ttcgtttctt ttctcttctt  198900 ttctttttttc tcttctctttt tcccctttccc ttcccttccc tcccttcaca tcacctcatc  198960
tcacctcacc ttacatagtc ttgctctgtc acccaaactg gagtgcagtg gcctgatctt  199020
ggctcactgc aacctccacc tcttcccagg ttcaagtgat tcttatacct cagcctcttg  199080
agtagctgag actacaggtg tgcactacca cacccagcta attttttgta tttttagtag  199140
agatagggtt tagctatgtt ggccaggctg gtctcgaact gctgaactca agcaatctgc  199200
catccccggc ctcccaaagt actgggagta taggcataag ccaccatga tgcccagcct  199260 gaatcttggt ttcttcccca ttcatttaag ctattacctg ggcctgaact caatggcacc  199320
tggcaccaac tggcaactga ctcttggtct tttattacct accttcccta gcaggcactg  199380
ggttgctccc tcttcctatc ccatggagtc ctgtcctctg ttggggctcc tactgatcct  199440
cttggcaata tgaagttctc agctcaatgg tgggtgggca atgactgcca actcttgagg  199500
ccaatgaact caggttaccc cactcctcct cctcctgagt tgctcactca ctcctcattc  199560
actcaacatt gattcagtag atatttgcta cctgctctgt gccaggtacc aggtcagttg  199620
ctgaaggagt aacagtgaac atgacggagt ctttgtcccc aaggagaccc aaggtgtctc  199680
ctagagccag gggcacattg caagaccaaa tatattcaac ttaccaaaat aatcatagac  199740
ctagttctca aaaagcaaga agactgattc ctcgttgtca tttctcctcc tcagcatcaa  199800
tgttttagag tctgtgggcc cctccaagtg tggagtatgg tgttacttca ccagagtttg  199860
aggagaaaca ttcttctttt ggaaggccgg ggagcataga tggatatcaa ggctgctgtt  199920
tctaaaagcg aaacccacca aacaacagta ttagaatcat ctgtggtgct tattaaagat  199980
acagattcct gggccccatc ccagacttat gaatcagaat ctctgccaga ggaagcctga  200040
gaatttgcat tctcagatga ttctgcattc tcagataaca cattcttag gtgattctta  200100 cacacactgg agtttgggaa tcgctgaagg ctgttcactt ctctttctg agaaatgatt  200160 cattcatttc agaaatattt gcagaggtcc ttatttattg gagatttgtg ggtgggcaga  200220
ggagaaatat cttgtcctca cagagcttac aattttttatt ttctttagag gtcaccaggc  200280
```

```
ttaaaatgac acttccctaa attctgaaaa gaacagattt ttaaaacaag aagggactgt 200340
aatgttttct gttcctacct cgtatttgt tcacattaag aacctggggt gggaagtgga 200400
ggagggggg tgactggcgg ggggccacag agagctgagc tggggtggtc tcgaactcct 200460
gaactcaagc aatctgccag cctcagtctc ccaaagtgct gggattatag gcatgagcca 200520
cccacgatgc ctgggtggaa ctcagggctc tggatgcctg ggcgccccca tctcccacac 200580
tacggcgcct catcctagaa gtggttagca cctttgagat gggaattatt tagcaggatg 200640
cttttgtgtt ttcatgtaag ttttatgctg cctgtggagg gcacagctgt ttcaaaacta 200700
ataaccaaat cctggtctcc gaagtctgaa ggcatccttt gccctgcagt gcaaagcacg 200760
ggattctggc ctcacacagg caggtctgaa ctcctgtgtt gcctcttgct ggctgtggga 200820
cctgaggcaa atcatgcaac ctctcttttc tgtttgccta gatggaaaat aggtttacaa 200880
tacgccccca taggatggct gtgagaatta aaggaagtca tgggtgtaca ataacctggcc 200940
ccgaaagatg cttaataatt taattctgac cttcctcact catttaggat tatgtaccaa 201000
cttttagaaa caatgaaaga ttagtgagtc ttctgtggtt ggtataaaaa aaaaatagaa 201060
acatgaaaga gatgtcctcc ttgttcaagg gctaatgacc ctggtgtgcg ctgtctaggc 201120
ccccaaggtc ttccttccct gctcacagca tttcaggttc tccgcagctt tgctgagcct 201180
gggtcaggtt cggtatctgc ccaccatgct cacttgccac agctgtggcc ccatttccaa 201240
acttcagaga cttaaaggtg cagctaatga tgtgcccggc ctggggtcac attccctgag 201300
ccctgcagac aagggagcag gaggctgagc tcttatcttc cacaccctgt gcacagcctg 201360
ggaagagtta aagcacccta gtcctatgct gcgagggcca catgccctga gaccttggaa 201420
aaaatcctac ctgaattgaa gagcatcact atttcatcag gaggcgctgc catttcattt 201480
ttcacttcgg ttttatcttg agtgtaaaac agcttcgcaa atcactttt cttgtttctg 201540
taatgagcat atggtggcct cattcgtgtg ataaatctga gccaccacga tatttgactt 201600
ttcacaattt aatttatctg aaccctctat tctctggcta aaaaatatcc cttacttgga 201660
cttctttatt ttattttcaa ttcccttacc agcactagca ggggactctg tactcatctg 201720
ctggcgctgc cataacaaag cactgcagcc tgggggctc aaaccacaga atttattctc 201780
tcacagtcct agaggctaga agtccaagat caaagtgtgg gcagggtcgg tttctcctgc 201840
agcctctctc cttggcttat agagtgccac cttctacctg tgtcttcaca tcatcacctc 201900
actgagcatg tctgtgtcca aatctcccct tcttataaga ccccagtcat actggatgag 201960
gatccaccca tatgagttca ttttaccttaa attatctctt taaacaccct gtctccaaat 202020
acagtcccat tctgaggaac tgagagtaaa gattcaacat atgaattttg aagggacct 202080
aattcagccc acaacaccct cttttgggat gtttattttc ccccttaagg agctagttag 202140
gatgtcttat ctcatgaaca tgactgtgaa caggaaaaca gggagagaat gaagctggcc 202200
aaggaacagg gctggtgtca gctagcagtg cttttctgat gtgagtgggt cccacaggga 202260
gcttgttaaa atgcagattc tgattcatta ggttccagag ggacctgaga tttcccattt 202320
ctgacaagtt tccagtgtgg gggctgatgc tgctggtcca cggaccatac tttgagtagc 202380
aaggagcttg atacataatg gctgagtgac tttcagactc ctgctgtaga aaaattatga 202440
gttggctggg cgtggtggct cacgcctgta atcccagcac tttgggaggc cgaggtgggc 202500
agatcacctg aggtcaggag ttcgagacca gcctggccaa catggtgaaa caccatctct 202560
accaaaaata caaaaattag ccaggtgtgg tggcaggtgc ctgtaatccc agctactcag 202620
```

```
gaggctgagg caggagaatc gcttgaaccc gggaggcaga ggttgcagtg atctgagatc  202680
gtgccactgc actccagctg ggcaatagag cttgactcag tctcaaaaaa aaaaaaagaa  202740
aagaaaaaga aaaattatga gttatattat cagcatatgg ggtgcctttc aaattgataa  202800
aatttctaat attaaacctg tggatgccaa atgctgctct ctgattatgg caggaaacgg  202860
cacttggcag tacgaagtta gctgttgggc tgagctggct catcttgttg tgcggtcctg  202920
attgcctaaa gatgccttcc caggatcttt actaacaatc ctcctgagtc atttggactt  202980
tcccaacctg ttatcacctc tcagatgggc cagccatgga ggcagtcaga ggagggctct  203040
gcagagggag ggcagaaaca gggtggcctc tgcatgccat taggaggtca catctcactg  203100
ggggatgcag tttaggattt agtgccttgg agagaaggat agagtatatt aaaacatgtc  203160
tccgctaggc atggtggttt acgcctataa tcccagcact tgggaggcc gaggtgagtg  203220
gattgcctga gctcaggagt tcaagaccag cctggctaac atgacgaaac ctcatctcta  203280
ctaaaataca aaaagttagc tgggagtggt ggcgtgcgcc tgtagttgca gctacttggg  203340
aggctgaggc atgagaatca cttaagccca gaagactgag gttgcagtga gccgagattg  203400
caccactgca ctccagcttg ggctacagag tgagactcta tctcaaaaac aaagaaacaa  203460
acaacaacaa taacaacaaa aaccaagtct ctccctccac tcaaaaatgc aagggcctgt  203520
ctcccattgc tgggtgccca ggtctcatga atgtagatat gaattattcc agtcagcctc  203580
aggagaatag aatgagccct cagatgccga agcacctttc agattccacc ggttttatcg  203640
gctcatttaa acttcacttc taacacagtc ctgcattaca cacgtgtctg tcgttatggg  203700
cagctgcaga gagggtctta atggtcctaa tgctcagtga ggatgccaa tggtcaacag  203760
aacctgccat cttcaggcca tcaaggagct ctggagttaa ggaaatcatg agagcacaga  203820
ggggcgggta cagcagagcc ctcgtggtaa tgggttttga ggtctaggct ctcttcactt  203880
gggtttgaaa taagttcaat gactagtaat agctgagaca cttctaccct tcaaatgaag  203940
taaatgggaa aatggagcat tgttgagtcc agggagctat aatttaaacc ccatatatct  204000
aaaagggta acattttgt gtgtgtgaaa ttggtgtcat tcgcactgca tctacagttt  204060
tcttttttcct tctcttccag caccctggc tacatatttg ggaaacgcat catactcttc  204120
ctgttcctca tgtccgttgc tggcatattc aactattacc tcatcttctt tttcggaagt  204180
gactttgaaa actacataaa gacgatctcc accaccatct cccctctact tctcattccc  204240
taactctctg ctgaatatgg ggttggtgtt ctcatctaat caatacctac aagtcatcat  204300
aattcagctc ttgagagcat tctgctcttc tttagatggc tgtaaatcta ttggccatct  204360
gggcttcaca gcttgagtta accttgcttt tccgggaaca aaatgatgtc atgtcagctc  204420
cgccccttga acatgaccgt ggccccaaat ttgctattcc catgcatttt gtttgtttct  204480
tcacttatcc tgttctctga agatgttttg tgaccaggtt tgtgttttct taaaataaaa  204540
tgcagagaca tgttttaagc tgatagttga ggggttttgt taatggcttt tgggggattt  204600
atctctatac ccacaaacga ctagtttgtt ttcctcaaac taaatgataa tattaaaaat  204660
acacatcctg gccaggtgtg gtggctcata cctgtaatcc cagcactttg ggaggccgag  204720
gcaggtggat cacttgaggt caggaattaa gaccagcctg gccaatatgg tgaaagcctg  204780
tctgtactaa aaatacaaaa attagccagg tatgctggtg gatgcttata atcccagcta  204840
cttgggaggt tgaggcagga gaattgcttg aacccgggag gtagaggttg cagtgagcca  204900
agatcatgcc actgcactcc agcttgggca acagagtgag actccatctc aaattaaaaa  204960
aaatacacat ctggcttctg gaaaaattac ttgaagatct tttatgacat ccatccctct  205020
```

```
tcacacagcc atgtgaatta ggttggtatc ttcatatact agcatcgtgc ccagcacttc    205080
catgttatac agtttaaaat gttctgtaat tccctgtggg aacctaagat aatgcgagga    205140
ccgtcatacg tgcccccaaa tattggcaaa ccaatgaata aatgaatgaa tgagtttatg    205200
aatcgctaac tggctgtatt taatgaagta tgtgtgttga gccatttccc acagtgtgga    205260
cagatttgtc ccacaatatg ggcctcttcc caaaggccct accacctaat gccatcacac    205320
tggggatttg atttcaacat gtgaatttgg ggagagtgca aacactcaga ccatagcacc    205380
atctcagtaa atgtcccact ggtcactcag ttcatagtga cagtgatcca gccactgtca    205440
tgacaggtgc cacttggcag aaacagcaca gcttggaaga tggcggggtg tagtcaagat    205500
tccaggatcc ccaacagaga agccagctct tatagggggag ccattcatca ggattgaact    205560
ctcaatcgag ctggacagta ataggtgggt ctgtgttatt ccccagatga gtatcatgac    205620
agtcacaatc ctaggaagga tgtgaagcct cccccagctc tcctccagtt gcctgcttgg    205680
gcagcagaga tgatggaatg tggagtctgg cgtggtctga ggcctgaatc catgtgcctc    205740
atgtatgatg ctcaggcaag aggatctctc aattcaaggg agagggcctg aatgagcctt    205800 gcttccagg cctgtctgat ggtccaggct gaagcccctc ctggcttgca ctgccagacc    205860
tcatccagca ggagctcctt ggcattgact gcttcaggat agttgcttct gctctgagtg    205920
ctctctaaag agcagtgctc taccatccaa gctgggcttt tcttttcttc ttgctgatag    205980
ggaaggcatg ggacattgca ggatggaagt ggcccccagg ccttctcatg cctgggcttg    206040
gtttggaagg tggtcaggtg atcaataatc ctgattggcc tggcattgag gagttttcct    206100
gggatgtggt cctttcggtt ttttaaaaat tatttttatt gatacacata tttgtaggta    206160 tttgtgggt gcatgtgata cttattatg tgtgtggatt gtgtaatgat gaagtcaggg    206220
catttagggt cttcatcacc ttgattatca tttctatgtg ttgagaacat ttcaagttct    206280
cagttccagc tattttgaaa tagacagtcc atttttgttag ctacagtcac ccaacccggc    206340
tgtcagacat tggaacttac tcctattgaa ctgtgtattt gtacccattc accaaactct    206400
ctttgggctt tcagttttac aactgggatg atcctgggaa aactaaagta aatcagacac    206460
ccgacgtgtg agctaggtta taatatgccc agtggaccct ggggacatct tagctttcag    206520
aggtcatgct gtccaagctg actgtggggc ttccagaagg tggggagagg aaatgatgca    206580
atggcccatc agaggcacta cttggggcct ggggccagag tgcatgtcta aggcattaag    206640
gggaggggag agcagccttc ataattatga agaggagtct caggtgcaca gcttctgatg    206700
agggacagct tctaattgaa gacagcattg tgtaatgctc aaactccctg tcttcagagt    206760
gcctgctgta tcccaccatc agttctgtga cttctcccta agcctcaatt ttgcatgtgt    206820
tacattggga taataatagt gccaaactca tggggttgtg aggaataatg aggtaaagca    206880
attgaaaagg tttagcacaa tataagtgct caataaaagc cattattatt attttattac    206940
actagttttc aattcctgca tagcaaattc ttgcaaatgt agggactcaa aacaatataa    207000
atttattatc tgacagtttt tctgggtcag aggtcttact aggctgtaat cagagggcaa    207060
ccaaagctgt gatctcagct gaagctcagg attctcttcc aagctcactg gttgttggca    207120
gaattcagtt ctttccagtt ggaagactaa agcctacagt cttcagtctc tagaagcctt    207180
ttctctggca caggtttctc tacaacatgg ccatttatgt cttaaggcc aataggagaa    207240 catgattagc atattttttt taagtgaact ttagacccct tttaaaggc ctatctgatt    207300 aggccaggcc caagtgagct ttaagtcaac tgattagaga tcttaattac atctgcaaag    207360
```

```
tcccttcatg tttaccgtat aacataactt agtgaaagga gtgaaattgc aaccaggttc 207420
tgcctgcact ccacggaagg ggattctgca gaagtgtggg tcacgggggg gttattttgg 207480
gattctgcct acgtcactga gtcaaaagaa gctgaatggt tgtgatgctg aggttttgg  207540 gcagcagcag tgtgtgtgtg tgagtgaatt catacgtatg accacctggg aagaaaggag 207600
gctgtggttt cctccacctc ctggcagaca gagaaatttc tttttttttt tgagacaggg 207660
tctggctctg ttacccaggc tggagtgcag tggcttgatc tctgctcact ggctcactgc 207720
agcctctgcc tcccaggttc aagtaattct tgtgcctcaa ctccaagtag ctgggattac 207780
agacacacac tgccacgcct ggctaatttt tgtatttta gtagagacga ggttttgcca  207840
tgttggccag gctggtcttg aactcctgac ctcaagtgat ccgcccacct cagcctccca 207900
aagtgctggg attacagacg tgagccacca ttaaccattt ttctatctcc tgtgggaaag 207960
ggcacagtga agaacagat gaagctgaga catacaagtg aactcctccc tcctctccat  208020
ttagactaaa ataggattat tcatactgag attctccctg gttgcaaaga gataatctgt 208080
gcaactgggt ttttacaatt atccctaccc tatgctttcc tcatctgtct tcctcgtagt 208140
cagctcaggc tgctataaca aaacaccata actgggggct tttgaacaac aaaactttac 208200
ttctcacagt tctagaggct ggaaatccaa gatcaagttt ctggcagatt cggtgtctaa 208260
tgaggtcctg ctttccagtt tatagacagt gccttatcgc taccgcctta cacagtggaa 208320
ggagaggacg agaagctcct tgggcttttt tttgtttctt tctttctctc tctctctctt 208380
tttttttttt ttaataaggt cactatctta gtccattttg tgttgctaaa aggaacatct 208440
gaggttgagt aatttatttt attttaaaaa gtggccaggc atggaggctt atcctgtaac 208500
cctaatcctt taggaggcca aaacagcagg attgtttgag gccaggagtt caagaccagc 208560
ctaggcaaga tagtgagacc ccatctaccc catctctact aaaattttaa aaaattagct 208620
gtgtgttgta aagtgtgctt gtagtcccgg ccacttgaga ggctgaggtg ggtggagttc 208680
aaggctgcag tgagttatga ttgagccact gcactccaac ccgggtaacg gggcaagacc 208740
ttgtctctat ttaaaaaaaa aaaatcttta tgtggctcac tattctgggt ggctggaaag 208800
ttcaagattg ggcatctgca tctggtgaca gcctcatgtc gcttccagtc atggggaag  208860 acgaaggaga gctggcacgt gcagatatca cgtgttgagg gcagaagcga gagagagagg 208920
ggagagatgc caggctcttt ttaacaacca gcactgggga aactaataga gtgagagctc 208980
actgactcct gagggaggac attaatctat tgatgagcga cctgcctcca tgacccaaac 209040
acctccaacg ataccccacc tccaacactg ccacactagg gattaacttt caacttgaga 209100
tttagagggg ggaaacttac aaactatcgc aggcactaat accactcatg agggctccac 209160
cttcatgacc taatcacttc ctaaaggcct tacctcttaa tctcatcaca ttgaggattc 209220
gatttcaact tgaatttgg ggggacacaca acattcaggc catagcatca tctcaataac 209280
tgtcccattg gtggtcactc aggccccaaa caaaggaacc ttcctccatt cctttccgcc  209340
ctcccaccca cagtcaatca tccccaagct ccatcagctc cacctttaac ggccaaccca 209400
cctctgccac atctcaccat ctccactgct atccctgtca cctgggccca ccattctctc 209460
tcctggacag tctccatagc cacctctgtc agatttattt tatttttta ttttttttt   209520 tgagacaggt tcctgctctg ttgcccagac tggagtgcca tggcatgatc acatctcact 209580
gcggcctcca tcacctgggc tcaagcaatc ctcccatctc agcctcccaa gtagctggga 209640
ctactggcac caccatacct ggctaatttt tgttgttgt tgtttaattt ttaatacaga  209700
tgaagcctca ctatgttgcc caggctgctc ttgaactcct gggctcaagt gatcctccgg 209760
```

```
ccttggcctc ccaaagtgct gggattacag gcatgagcca ccgtgcccag cccatcagat   209820
gttaatgcta cacgcacttg cttaaaatcc cccagataat tctcgctgct cttggaataa   209880
ttcccacaca ccttggcgtg gccatgcagg ctctgtgcca tcggatatgt ccctgccccc   209940
tctcccaact cctcctttcg cttgctcgtt cactcagttc cagccacatt gccctgggag   210000
ctgctcccac catggggctt cctaatgcac tggtctctct catgcagtgg ggcctctccc   210060
tcctttact cagtgtctcc cagcacccac ctcctccaga gccttccctg accaccacac   210120
ctacacctag gcccttcctc ctccacgctc cctcctccac cccggcctcc tacccacgtg   210180
tcacttcttt atactcgctg ccacctgaaa ttagatcatt tatttacccc tttatttgtt   210240
cagtttgcct tgtccgttag aatataagct tccaaagggc aggagctttg cctatattgt   210300
taggccgggc atacaatgag cactcaaaaa aatatttgat gagtgtatga agaacagac   210360
tgggttatgt aattgtgcct acttacctat atgaccgtgt ggtggggttt atggtgggtg   210420
tggtggtgat ggctataggg ctataagcaa atttgggaca gggagtctaa gaaatgttct   210480
taaatttag taagcaaagc atcctctaca gaacctgtct taaaacatga aagttcctta   210540
gtgctacccc cagaggtatg atttggtagg tcaaggatag ggcctggaaa ttcacattct   210600
tgttaagatg ttcttcatcc gggtttgtt gaccaccttt tcagaagatt tttgctctgt   210660
agctgtacta cccaatgcag tagttcgtag tcagtgtggc tcctgagccc ttgaagtgta   210720
gctcctctga actgagacgt gctgtaaatg taaattgcac accggagttt gaagagttaa   210780
tacaaagaaa aaggaatgca aaacatctca ttaataatgc tttacactga ttacatattg   210840
aaatggtaat cttgtagata tagtgcgtta aataaaatat actgttaggc ttaattcac    210900
gtctttatac ttttaatgtg gctactagaa aaatttaaat aacatattca gctcacatta   210960
tactcctatt gaacagagct gatctataag ttccatggaa gatggcaagt cttcgcagct   211020
gaaataaagg ctggatccca ttctacgggc tcatctttag caatgatttc ttgcagacga   211080
tattgaaaaa tgtggcaatg aaagttacca caagcatcaa accagtcctg cctaaatctg   211140
gaaaatagtt atctgaggct gttagcatat gatcatgaga gcgtttcacc atggatttct   211200
gatcacagat gtggcacatt attaaaatat cacttttaca gtcaccctag aggctagggt   211260
tatctgaata tggagaaaga aacagcttgt ggagctgttg tataaatgaa attactagaa   211320
agtaatgcac tcaattgcat attggctcgg ggggttattc ttattaaaat gtttagagag   211380
gactttctgt tcatttctgc agaattgctc ttcaaattaa gaatttgctt gacacgctaa   211440
tagaccacag tcccaagaga agtttatcct ttttttcttct tatccttgct aagcacttag   211500
atgctctgct gataggtagc atatattgtc tatatgaagc ttttgtgtta acattgacta   211560
gtcctgcaag ttggcacact cttacttggc ctaaaagaaa tcagcaccag gctttaagaa   211620
aatcagatga tctacctaaa ggaacacaac tctgtctctc ttttgacaat gttgtaaac    211680
aaatttaat ggaaatttgc cttaattgtg aagaagttgc tgctaaaatg gacttgccat    211740
taatggactg gaacccattg cataagcaga atgaaatata agccttctca ggattcacac   211800
ttataaaaaa ccattcagcc aatcaacaag agggcaaaag aacaaacatt tgatgtgtaa   211860
ttacttaatt tagtgcatat gcatttgggt cctcaatgtc agcactatgg caaccagaac   211920
atggccacaa taactgtctg gaaatgtcta ttccttacctg gacccagcag gccatgcccc   211980
actgattata taatctcccct ctctccttgt tacggtctga atgcttgcat ccctcaaaaa   212040
ttcatgtgtt gaaatcctaa cccccaaggt gatgatatta ggaggtcggc cttttgagag   212100
```

```
gtaattaggt catgaagaca gcatcctcat gaatgggatt agtgtcctta taaaataggc  212160
ccaagggagc tcattcactt tgtccaccat gtgagaacac agcgagaggg caccatttat  212220
gcaccaggaa atgggccttt tccagacaat ctgtcggtgc ctggatcttg gacttcacag  212280
cctctagaac tgtgagaaat taatttgttt tttataagcc accaaatcta tggttttttt  212340
tatagaaacc gtaatggact aaaacactcc ctaattatat ttaaacttat cagtgcactg  212400
ggcagtgaca tattaaaaga atgctggcca acgtaattga caccataagg ctggatgatt  212460
cttgtaattt tcagcctcag aaaaaggctg gggagaggag tcaggggaaa ggaggtggtg  212520
tgtgtgtgtg tgtgtgtgtg tgtgtgtgtg tgtgtggtac ggtggatgcc tgctgagaga  212580
gaaagagcta taataacatt ctgtggttca gctgacacat cctttctgca tcccctccaa  212640
tcacctgggt taatggggac ctcgctaatg tctgaacctc atctcatttt aacctttgt   212700
ttcaaagcct ctcttttcat gacttccccg ccttcatttt tcccatatgg tggggttatt  212760
attaagacat taaatgagag tggacaggta ggcaaaggag gtgggttgca ggggagttga  212820
gggttgcctg tgtacttttc tagactgttc cacttcacat cagtgaaata ttcccaattg  212880
atactatcat gaaacaaagc aaatgaaatg ctgagcacgg agcttcgtct tgatgaaatg  212940
ctgaaagaaa agaaaggaaa aataaagtag ccattatttt tgcccttcct cccaccccca  213000
tgtttactac tcttatttct cttttgtatt gttgtgttgg aagcacagca tcagaaaaac  213060
tcccagtttt gagagataac tcagtgttta gttcacttaa acctgagaaa ggagaagagg  213120
atgccaccgt gaggtccagg acgtaaagag gaaaaaaaca gacaaaaaaa tccatatgaa  213180
atgaaaatgt gaaagaggcg ctttcgagca gatgagtgtt gtagattaca gtgttgagag  213240
ctgtttgtgt ccagagctgc ttgctgcacc tggcgggata aacactggtc taacagagga  213300
tccttgtttc aaggaggctg cctttttattt gggggggacaa aattgttctt gaaagctgct  213360
cagtggttca agctacagca tggtggacta gcagaatgga ctccagggcc tccgaggaga  213420
cagtgactgc tgccagaaat agtcaaggat agaaaggaag gacttcactg aggcctggga  213480
gaagattatg gaatgggact gacagcagtg acggggagta aaaggggggtg tctgggggaa  213540
ttgtgcccca tggtgagagc tagagggttc acaaagactt aacccgacgc atctctctca  213600
ccctggagat tgggcccgtt caatctaact ggatggctat aatttaaaag gtttaggtat  213660
tatgacaaac atggatatat taggtgatag caatgcaaaa tgcatatggc ttcttgatat  213720
aaaacacaag acttgaaagc agcatctttg gctgggtact acagccaccc tcctctgtca  213780
ctaagggagg ctttggtgga aagggctgag agcctctaga ctgtgaacaa agtaggcac   213840
agaagaacag ttggagataa taagtaaacc atcttgacag gaatgaagaa tttcctgaaa  213900
ggaaggtccc tgagttaggt tgttggatgc tttcagtagt gagttattga aagtgtttgg  213960
ggggtgtgtg tgtgtgtgtg tatgtgcagt atgtgtgtgt                        214000
```

<210> SEQ ID NO 2
<211> LENGTH: 161
<212> TYPE: PRT
<213> ORGANISM: Homo sapiens

<400> SEQUENCE: 2

Met Asp Gln Glu Thr Val Gly Asn Val Val Leu Leu Ala Ile Val Thr
 1               5                  10                  15

Leu Ile Ser Val Val Gln Asn Gly Phe Phe Ala His Lys Val Glu His
                20                  25                  30

Glu Ser Arg Thr Gln Asn Gly Arg Ser Phe Gln Arg Thr Gly Thr Leu

```
                35                  40                  45
Ala Phe Glu Arg Val Tyr Thr Ala Asn Gln Asn Cys Val Asp Ala Tyr
 50                  55                  60

Pro Thr Phe Leu Ala Val Leu Trp Ser Ala Gly Leu Leu Cys Ser Gln
 65                  70                  75                  80

Val Pro Ala Ala Phe Ala Gly Leu Met Tyr Leu Phe Val Arg Gln Lys
                 85                  90                  95

Tyr Phe Val Gly Tyr Leu Gly Glu Arg Thr Gln Ser Thr Pro Gly Tyr
                100                 105                 110

Ile Phe Gly Lys Arg Ile Ile Leu Phe Leu Phe Leu Met Ser Val Ala
                115                 120                 125

Gly Ile Phe Asn Tyr Tyr Leu Ile Phe Phe Phe Gly Ser Asp Phe Glu
            130                 135                 140

Asn Tyr Ile Lys Thr Ile Ser Thr Thr Ile Ser Pro Leu Leu Leu Ile
145                 150                 155                 160

Pro

<210> SEQ ID NO 3
<211> LENGTH: 873
<212> TYPE: DNA/RNA
<213> ORGANISM: Homo sapiens

<400> SEQUENCE: 3
acttcccctt cctgtacagg gcaggttgtg cagctggagg cagagcagtc ctctctgggg      60
agcctgaagc aaacatggat caagaaactg taggcaatgt tgtcctgttg gccatcgtca     120
ccctcatcag cgtggtccag aatggattct tgcccataaa gtggagcac gaaagcagga      180 cccagaatgg gaggagcttc agaggaccg aacacttgc cttttgagcgg gtctacactg      240 ccaaccagaa ctgtgtagat gcgtaccca cttttcctcgc tgtgctctgg tctgcggggc     300
tactttgcag ccaagttcct gctgcgtttg ctggactgat gtacttgttt gtgaggcaaa     360
agtactttgt cggttaccta ggagagagaa cgcagagcac ccctggctac atatttggga     420
aacgcatcat actcttcctg ttcctcatgt ccgttgctgg catattcaac tattacctca     480
tcttcttttt cggaagtgac tttgaaaact acataaagac gatctccacc accatctccc     540
ctctacttct cattccctaa ctctctgctg aatatgggt tggtgttctc atctaatcaa      600
tacctacaag tcatcataat tcagctcttg agagcattct gctcttcttt agatggctgt     660
aaatctattg gccatctggg cttcacagct tgagttaacc ttgcttttcc gggaacaaaa     720
tgatgtcatg tcagctccgc cccttgaaca tgaccgtggc cccaaatttg ctattcccat     780 gcatttgtt tgtttcttca cttatcctgt tctctgaaga tgttttgtga ccaggtttgt      840
gttttcttaa aataaaatgc agagacatgt ttt                                  873

<210> SEQ ID NO 4
<211> LENGTH: 24
<212> TYPE: DNA
<213> ORGANISM: Homo sapiens

<400> SEQUENCE: 4
cctttgcttt gttcctattt cttt                                            24

<210> SEQ ID NO 5
<211> LENGTH: 20
<212> TYPE: DNA
<213> ORGANISM: Homo sapiens
```

-continued

```
<400> SEQUENCE: 5
tcccattgcc cagagttaat                                              20

<210> SEQ ID NO 6
<211> LENGTH: 23
<212> TYPE: DNA
<213> ORGANISM: Homo sapiens

<400> SEQUENCE: 6
tcctcatgtc ttcacctaga agc                                          23

<210> SEQ ID NO 7
<211> LENGTH: 20
<212> TYPE: DNA
<213> ORGANISM: Homo sapiens

<400> SEQUENCE: 7
ccactcatga gggagctgtt                                              20

<210> SEQ ID NO 8
<211> LENGTH: 21
<212> TYPE: DNA
<213> ORGANISM: Homo sapiens

<400> SEQUENCE: 8
tgtcacaggc acacactctc t                                            21

<210> SEQ ID NO 9
<211> LENGTH: 20
<212> TYPE: DNA
<213> ORGANISM: Homo sapiens

<400> SEQUENCE: 9
gagtatggct gctgctcctc                                              20

<210> SEQ ID NO 10
<211> LENGTH: 20
<212> TYPE: DNA
<213> ORGANISM: Homo sapiens

<400> SEQUENCE: 10
atggctcaca ctggcctaaa                                              20

<210> SEQ ID NO 11
<211> LENGTH: 23
<212> TYPE: DNA
<213> ORGANISM: Homo sapiens

<400> SEQUENCE: 11
tgaacagacc aataatagtg cag                                          23

<210> SEQ ID NO 12
<211> LENGTH: 20
<212> TYPE: DNA
<213> ORGANISM: Homo sapiens

<400> SEQUENCE: 12
aagccaccct ttaaacagca                                              20

<210> SEQ ID NO 13
<211> LENGTH: 20
<212> TYPE: DNA
<213> ORGANISM: Homo sapiens
```

```
<400> SEQUENCE: 13
gctgaggaag caactccact                                               20

<210> SEQ ID NO 14
<211> LENGTH: 20
<212> TYPE: DNA
<213> ORGANISM: Homo sapiens

<400> SEQUENCE: 14
gctctgaatt ccctggcata                                               20

<210> SEQ ID NO 15
<211> LENGTH: 21
<212> TYPE: DNA
<213> ORGANISM: Homo sapiens

<400> SEQUENCE: 15
ttagccctag tcccactctc c                                             21

<210> SEQ ID NO 16
<211> LENGTH: 20
<212> TYPE: DNA
<213> ORGANISM: Homo sapiens

<400> SEQUENCE: 16
caagaggcct gcataaggaa                                               20

<210> SEQ ID NO 17
<211> LENGTH: 20
<212> TYPE: DNA
<213> ORGANISM: Homo sapiens

<400> SEQUENCE: 17
agattgccgg tggcttaaat                                               20

<210> SEQ ID NO 18
<211> LENGTH: 20
<212> TYPE: DNA
<213> ORGANISM: Homo sapiens

<400> SEQUENCE: 18
tgtctgttcc cgtctgtctg                                               20

<210> SEQ ID NO 19
<211> LENGTH: 20
<212> TYPE: DNA
<213> ORGANISM: Homo sapiens

<400> SEQUENCE: 19
ttcatcctct gccaaattcc                                               20

<210> SEQ ID NO 20
<211> LENGTH: 20
<212> TYPE: DNA
<213> ORGANISM: Homo sapiens

<400> SEQUENCE: 20
ggcatgtatt cactgcctga                                               20

<210> SEQ ID NO 21
<211> LENGTH: 23
<212> TYPE: DNA
```

```
<213> ORGANISM: Homo sapiens

<400> SEQUENCE: 21
aaacccattc ttcttcctct tac                                        23

<210> SEQ ID NO 22
<211> LENGTH: 21
<212> TYPE: DNA
<213> ORGANISM: Homo sapiens

<400> SEQUENCE: 22
tatgtgttca gcccagacct c                                          21

<210> SEQ ID NO 23
<211> LENGTH: 19
<212> TYPE: DNA
<213> ORGANISM: Homo sapiens

<400> SEQUENCE: 23
ccctgccatg tgcatttac                                             19

<210> SEQ ID NO 24
<211> LENGTH: 20
<212> TYPE: DNA
<213> ORGANISM: Homo sapiens

<400> SEQUENCE: 24
catttcggaa ggcaaagaaa                                            20

<210> SEQ ID NO 25
<211> LENGTH: 20
<212> TYPE: DNA
<213> ORGANISM: Homo sapiens

<400> SEQUENCE: 25
ttgcaatgag gaatgaagca                                            20

<210> SEQ ID NO 26
<211> LENGTH: 23
<212> TYPE: DNA
<213> ORGANISM: Homo sapiens

<400> SEQUENCE: 26
tccattatcc atctgttcat tca                                        23

<210> SEQ ID NO 27
<211> LENGTH: 25
<212> TYPE: DNA
<213> ORGANISM: Homo sapiens

<400> SEQUENCE: 27
gaagaattaa ttgtaggagg caaga                                      25

<210> SEQ ID NO 28
<211> LENGTH: 21
<212> TYPE: DNA
<213> ORGANISM: Homo sapiens

<400> SEQUENCE: 28
ctgacatcac cacattgatc g                                          21

<210> SEQ ID NO 29
<211> LENGTH: 22
```

```
<212> TYPE: DNA
<213> ORGANISM: Homo sapiens

<400> SEQUENCE: 29
catacacagc catgtggaat ta                                              22

<210> SEQ ID NO 30
<211> LENGTH: 20
<212> TYPE: DNA
<213> ORGANISM: Homo sapiens

<400> SEQUENCE: 30
acggtgatga cgcctacatt                                                 20

<210> SEQ ID NO 31
<211> LENGTH: 23
<212> TYPE: DNA
<213> ORGANISM: Homo sapiens

<400> SEQUENCE: 31
tcacatggac caattaccta gaa                                             23

<210> SEQ ID NO 32
<211> LENGTH: 25
<212> TYPE: DNA
<213> ORGANISM: Homo sapiens

<400> SEQUENCE: 32
aaattacttc atcttgacga taaca                                           25

<210> SEQ ID NO 33
<211> LENGTH: 20
<212> TYPE: DNA
<213> ORGANISM: Homo sapiens

<400> SEQUENCE: 33
ctattgggga ctgcagagag                                                 20

<210> SEQ ID NO 34
<211> LENGTH: 20
<212> TYPE: DNA
<213> ORGANISM: Homo sapiens

<400> SEQUENCE: 34
agccagtgtc cacaaggaag                                                 20

<210> SEQ ID NO 35
<211> LENGTH: 21
<212> TYPE: DNA
<213> ORGANISM: Homo sapiens

<400> SEQUENCE: 35
gagggtgaga cacatctctg g                                               21

<210> SEQ ID NO 36
<211> LENGTH: 20
<212> TYPE: DNA
<213> ORGANISM: Homo sapiens

<400> SEQUENCE: 36
aatcgtgcct cagttccatc                                                 20

<210> SEQ ID NO 37
```

```
<211> LENGTH: 20
<212> TYPE: DNA
<213> ORGANISM: Homo sapiens

<400> SEQUENCE: 37
ccaccaggaa caacacacac                                              20

<210> SEQ ID NO 38
<211> LENGTH: 18
<212> TYPE: DNA
<213> ORGANISM: Homo sapiens

<400> SEQUENCE: 38
ttgctctcca gcctgggc                                                18

<210> SEQ ID NO 39
<211> LENGTH: 18
<212> TYPE: DNA
<213> ORGANISM: Homo sapiens

<400> SEQUENCE: 39
ttcctctggc tgcctgcg                                                18

<210> SEQ ID NO 40
<211> LENGTH: 20
<212> TYPE: DNA
<213> ORGANISM: Homo sapiens

<400> SEQUENCE: 40
tcctgcatga gaaggaactg                                              20

<210> SEQ ID NO 41
<211> LENGTH: 20
<212> TYPE: DNA
<213> ORGANISM: Homo sapiens

<400> SEQUENCE: 41
cgacattcac tgtggctctt                                              20

<210> SEQ ID NO 42
<211> LENGTH: 20
<212> TYPE: DNA
<213> ORGANISM: Homo sapiens

<400> SEQUENCE: 42
tttgattccg tggtccatta                                              20

<210> SEQ ID NO 43
<211> LENGTH: 21
<212> TYPE: DNA
<213> ORGANISM: Homo sapiens

<400> SEQUENCE: 43
ttatttggtc ggtgcacctt t                                            21

<210> SEQ ID NO 44
<211> LENGTH: 20
<212> TYPE: DNA
<213> ORGANISM: Homo sapiens

<400> SEQUENCE: 44
ggtgcaccga ccaaataagt                                              20
```

```
<210> SEQ ID NO 45
<211> LENGTH: 22
<212> TYPE: DNA
<213> ORGANISM: Homo sapiens

<400> SEQUENCE: 45
ccagcttatt ctctctgcct tc                                          22

<210> SEQ ID NO 46
<211> LENGTH: 22
<212> TYPE: DNA
<213> ORGANISM: Homo sapiens

<400> SEQUENCE: 46
ggtaggttga aatgggctaa ca                                          22

<210> SEQ ID NO 47
<211> LENGTH: 21
<212> TYPE: DNA
<213> ORGANISM: Homo sapiens

<400> SEQUENCE: 47
tcatgacaag gtgttggatt t                                           21

<210> SEQ ID NO 48
<211> LENGTH: 20
<212> TYPE: DNA
<213> ORGANISM: Homo sapiens

<400> SEQUENCE: 48
cctcctctgc catgaagcta                                             20

<210> SEQ ID NO 49
<211> LENGTH: 20
<212> TYPE: DNA
<213> ORGANISM: Homo sapiens

<400> SEQUENCE: 49
ctatttggtc tgcgggttgt                                             20

<210> SEQ ID NO 50
<211> LENGTH: 20
<212> TYPE: DNA
<213> ORGANISM: Homo sapiens

<400> SEQUENCE: 50
tactgggtta tcgcctgacc                                             20

<210> SEQ ID NO 51
<211> LENGTH: 20
<212> TYPE: DNA
<213> ORGANISM: Homo sapiens

<400> SEQUENCE: 51
ccaatggacc tcttggacat                                             20

<210> SEQ ID NO 52
<211> LENGTH: 20
<212> TYPE: DNA
<213> ORGANISM: Homo sapiens

<400> SEQUENCE: 52
tttcggcaca gtcctcaata                                             20
```

```
<210> SEQ ID NO 53
<211> LENGTH: 19
<212> TYPE: DNA
<213> ORGANISM: Homo sapiens

<400> SEQUENCE: 53
cagctgggtg tggtgacat                                                  19

<210> SEQ ID NO 54
<211> LENGTH: 20
<212> TYPE: DNA
<213> ORGANISM: Homo sapiens

<400> SEQUENCE: 54
cagagaggaa caggcagagg                                                 20

<210> SEQ ID NO 55
<211> LENGTH: 20
<212> TYPE: DNA
<213> ORGANISM: Homo sapiens

<400> SEQUENCE: 55
agtggctggg aagccttatt                                                 20

<210> SEQ ID NO 56
<211> LENGTH: 23
<212> TYPE: DNA
<213> ORGANISM: Homo sapiens

<400> SEQUENCE: 56
aggtgagaga acaaacctgt ctt                                             23

<210> SEQ ID NO 57
<211> LENGTH: 20
<212> TYPE: DNA
<213> ORGANISM: Homo sapiens

<400> SEQUENCE: 57
gccttccttc taaggccaac                                                 20

<210> SEQ ID NO 58
<211> LENGTH: 26
<212> TYPE: DNA
<213> ORGANISM: Homo sapiens

<400> SEQUENCE: 58
ctgtagactt tatccctgac ttactg                                          26

<210> SEQ ID NO 59
<211> LENGTH: 24
<212> TYPE: DNA
<213> ORGANISM: Homo sapiens

<400> SEQUENCE: 59
caatgaatga tgaagattcc actc                                            24

<210> SEQ ID NO 60
<211> LENGTH: 23
<212> TYPE: DNA
<213> ORGANISM: Homo sapiens

<400> SEQUENCE: 60
tgacaccatg tcttactgtt tgc                                             23
```

```
<210> SEQ ID NO 61
<211> LENGTH: 25
<212> TYPE: DNA
<213> ORGANISM: Homo sapiens

<400> SEQUENCE: 61
gaggatacaa tgagaaccaa atctc                                          25

<210> SEQ ID NO 62
<211> LENGTH: 20
<212> TYPE: DNA
<213> ORGANISM: Homo sapiens

<400> SEQUENCE: 62
caggatcatc agccaggttt                                                20

<210> SEQ ID NO 63
<211> LENGTH: 20
<212> TYPE: DNA
<213> ORGANISM: Homo sapiens

<400> SEQUENCE: 63
gctgcatgtc actaggcatt                                                20

<210> SEQ ID NO 64
<211> LENGTH: 20
<212> TYPE: DNA
<213> ORGANISM: Homo sapiens

<400> SEQUENCE: 64
ccacagaatg ctccaaaggt                                                20

<210> SEQ ID NO 65
<211> LENGTH: 22
<212> TYPE: DNA
<213> ORGANISM: Homo sapiens

<400> SEQUENCE: 65
gagttcaagt gatggatgac ga                                             22

<210> SEQ ID NO 66
<211> LENGTH: 24
<212> TYPE: DNA
<213> ORGANISM: Homo sapiens

<400> SEQUENCE: 66
cagatagatg aataggtgga tgga                                           24

<210> SEQ ID NO 67
<211> LENGTH: 20
<212> TYPE: DNA
<213> ORGANISM: Homo sapiens

<400> SEQUENCE: 67
cactgttcca agtgctttgc                                                20

<210> SEQ ID NO 68
<211> LENGTH: 20
<212> TYPE: DNA
<213> ORGANISM: Homo sapiens

<400> SEQUENCE: 68
```

-continued tatgcgttgt gtgtgctgtg                      20

<210> SEQ ID NO 69
<211> LENGTH: 22
<212> TYPE: DNA
<213> ORGANISM: Homo sapiens

<400> SEQUENCE: 69 gggcccttaga ttcttgtagt gg                  22

<210> SEQ ID NO 70
<211> LENGTH: 20
<212> TYPE: DNA
<213> ORGANISM: Homo sapiens

<400> SEQUENCE: 70
tgtccagact gcctcctaca                      20

<210> SEQ ID NO 71
<211> LENGTH: 20
<212> TYPE: DNA
<213> ORGANISM: Homo sapiens

<400> SEQUENCE: 71
tgcaacacct ggttcacaat                      20

<210> SEQ ID NO 72
<211> LENGTH: 20
<212> TYPE: DNA
<213> ORGANISM: Homo sapiens

<400> SEQUENCE: 72
tttgcgagtc cttgtggagt                      20

<210> SEQ ID NO 73
<211> LENGTH: 20
<212> TYPE: DNA
<213> ORGANISM: Homo sapiens

<400> SEQUENCE: 73
acagtccgct ccctcctaat                      20

<210> SEQ ID NO 74
<211> LENGTH: 18
<212> TYPE: DNA
<213> ORGANISM: Homo sapiens

<400> SEQUENCE: 74
atgcttggcc ctcagttt                        18

<210> SEQ ID NO 75
<211> LENGTH: 21
<212> TYPE: DNA
<213> ORGANISM: Homo sapiens

<400> SEQUENCE: 75
ttggcaaccc aagctaatat g                    21

<210> SEQ ID NO 76
<211> LENGTH: 19
<212> TYPE: DNA
<213> ORGANISM: Homo sapiens

<400> SEQUENCE: 76

```
ctccacagtg acagtgagg                                             19

<210> SEQ ID NO 77
<211> LENGTH: 17
<212> TYPE: DNA
<213> ORGANISM: Homo sapiens

<400> SEQUENCE: 77
gagaggttcc caatccc                                               17

<210> SEQ ID NO 78
<211> LENGTH: 20
<212> TYPE: DNA
<213> ORGANISM: Homo sapiens

<400> SEQUENCE: 78
cagctcctgg ccatatttct                                            20

<210> SEQ ID NO 79
<211> LENGTH: 20
<212> TYPE: DNA
<213> ORGANISM: Homo sapiens

<400> SEQUENCE: 79
gagccatttc tctgggtctg                                            20

<210> SEQ ID NO 80
<211> LENGTH: 20
<212> TYPE: DNA
<213> ORGANISM: Homo sapiens

<400> SEQUENCE: 80
ggtccgtgtc aacccttaga                                            20

<210> SEQ ID NO 81
<211> LENGTH: 19
<212> TYPE: DNA
<213> ORGANISM: Homo sapiens

<400> SEQUENCE: 81
caggttgatg ggagggaaa                                             19

<210> SEQ ID NO 82
<211> LENGTH: 20
<212> TYPE: DNA
<213> ORGANISM: Homo sapiens

<400> SEQUENCE: 82
cgggaaatga cagtgagacc                                            20

<210> SEQ ID NO 83
<211> LENGTH: 20
<212> TYPE: DNA
<213> ORGANISM: Homo sapiens

<400> SEQUENCE: 83
tgcctagatt ctcccgtaag                                            20

<210> SEQ ID NO 84
<211> LENGTH: 16
<212> TYPE: DNA
<213> ORGANISM: Homo sapiens
```

```
<400> SEQUENCE: 84
gtgcccagcc agattc                                                    16

<210> SEQ ID NO 85
<211> LENGTH: 16
<212> TYPE: DNA
<213> ORGANISM: Homo sapiens

<400> SEQUENCE: 85
gcccccagtc aggttt                                                    16

<210> SEQ ID NO 86
<211> LENGTH: 21
<212> TYPE: DNA
<213> ORGANISM: Homo sapiens

<400> SEQUENCE: 86
tttctctctc cacggaatga a                                              21

<210> SEQ ID NO 87
<211> LENGTH: 21
<212> TYPE: DNA
<213> ORGANISM: Homo sapiens

<400> SEQUENCE: 87
aacccattct cacagggtgt a                                              21

<210> SEQ ID NO 88
<211> LENGTH: 20
<212> TYPE: DNA
<213> ORGANISM: Homo sapiens

<400> SEQUENCE: 88
aggagtgtgg cagctttgag                                                20

<210> SEQ ID NO 89
<211> LENGTH: 20
<212> TYPE: DNA
<213> ORGANISM: Homo sapiens

<400> SEQUENCE: 89
tggattcccg tgagtaccag                                                20

<210> SEQ ID NO 90
<211> LENGTH: 17
<212> TYPE: DNA
<213> ORGANISM: Homo sapiens

<400> SEQUENCE: 90
atgctgggat cacaggc                                                   17

<210> SEQ ID NO 91
<211> LENGTH: 19
<212> TYPE: DNA
<213> ORGANISM: Homo sapiens

<400> SEQUENCE: 91
aacctggtgg acttttgct                                                 19

<210> SEQ ID NO 92
<211> LENGTH: 20
<212> TYPE: DNA
<213> ORGANISM: Homo sapiens
```

```
<400> SEQUENCE: 92
agcatttcca atggtgcttt                                          20

<210> SEQ ID NO 93
<211> LENGTH: 21
<212> TYPE: DNA
<213> ORGANISM: Homo sapiens

<400> SEQUENCE: 93
catgttgata tgcctgaagg a                                        21

<210> SEQ ID NO 94
<211> LENGTH: 20
<212> TYPE: DNA
<213> ORGANISM: Homo sapiens

<400> SEQUENCE: 94
cactgtctgc tgccactcat                                          20

<210> SEQ ID NO 95
<211> LENGTH: 27
<212> TYPE: DNA
<213> ORGANISM: Homo sapiens

<400> SEQUENCE: 95
agagattatg tgatgtaccc tctctat                                  27

<210> SEQ ID NO 96
<211> LENGTH: 20
<212> TYPE: DNA
<213> ORGANISM: Homo sapiens

<400> SEQUENCE: 96
tgatgaagat ctgggcgtta                                          20

<210> SEQ ID NO 97
<211> LENGTH: 20
<212> TYPE: DNA
<213> ORGANISM: Homo sapiens

<400> SEQUENCE: 97
tgcctgtgct cactcactct                                          20

<210> SEQ ID NO 98
<211> LENGTH: 22
<212> TYPE: DNA
<213> ORGANISM: Homo sapiens

<400> SEQUENCE: 98
atgacctaga aatgatactg gc                                       22

<210> SEQ ID NO 99
<211> LENGTH: 20
<212> TYPE: DNA
<213> ORGANISM: Homo sapiens

<400> SEQUENCE: 99
cagacaccac aacacacatt                                          20

<210> SEQ ID NO 100
<211> LENGTH: 20
<212> TYPE: DNA
```

```
<213> ORGANISM: Homo sapiens

<400> SEQUENCE: 100
tggtttaaaa acctcatgcc                                          20

<210> SEQ ID NO 101
<211> LENGTH: 25
<212> TYPE: DNA
<213> ORGANISM: Homo sapiens

<400> SEQUENCE: 101
atcccaaact ctgtacttat gtagg                                    25

<210> SEQ ID NO 102
<211> LENGTH: 20
<212> TYPE: DNA
<213> ORGANISM: Homo sapiens

<400> SEQUENCE: 102
ccttggctgt tgtgactggt                                          20

<210> SEQ ID NO 103
<211> LENGTH: 20
<212> TYPE: DNA
<213> ORGANISM: Homo sapiens

<400> SEQUENCE: 103
cactcaggtg ggaggatcac                                          20

<210> SEQ ID NO 104
<211> LENGTH: 20
<212> TYPE: DNA
<213> ORGANISM: Homo sapiens

<400> SEQUENCE: 104
cactttgcca gtagccttga                                          20

<210> SEQ ID NO 105
<211> LENGTH: 21
<212> TYPE: DNA
<213> ORGANISM: Homo sapiens

<400> SEQUENCE: 105
ttgggaaagt taacccagag a                                        21

<210> SEQ ID NO 106
<211> LENGTH: 20
<212> TYPE: DNA
<213> ORGANISM: Homo sapiens

<400> SEQUENCE: 106
tttgggaaga gccatgagac                                          20

<210> SEQ ID NO 107
<211> LENGTH: 20
<212> TYPE: DNA
<213> ORGANISM: Homo sapiens

<400> SEQUENCE: 107
ctctgggcat tggaggatta                                          20

<210> SEQ ID NO 108
<211> LENGTH: 20
```

```
<212> TYPE: DNA
<213> ORGANISM: Homo sapiens

<400> SEQUENCE: 108
gggagacaag tcaggtgagg                                            20

<210> SEQ ID NO 109
<211> LENGTH: 26
<212> TYPE: DNA
<213> ORGANISM: Homo sapiens

<400> SEQUENCE: 109
ctgagtatgg agtcttcatc attatc                                     26

<210> SEQ ID NO 110
<211> LENGTH: 22
<212> TYPE: DNA
<213> ORGANISM: Homo sapiens

<400> SEQUENCE: 110
tgctactaga tttgaccaac ca                                         22

<210> SEQ ID NO 111
<211> LENGTH: 26
<212> TYPE: DNA
<213> ORGANISM: Homo sapiens

<400> SEQUENCE: 111
gacttgtaaa ggatttagtg atttcg                                     26

<210> SEQ ID NO 112
<211> LENGTH: 20
<212> TYPE: DNA
<213> ORGANISM: Homo sapiens

<400> SEQUENCE: 112
gtggaaggcc tctctctgtg                                            20

<210> SEQ ID NO 113
<211> LENGTH: 20
<212> TYPE: DNA
<213> ORGANISM: Homo sapiens

<400> SEQUENCE: 113
tgcttcttga gggaaagcat                                            20

<210> SEQ ID NO 114
<211> LENGTH: 21
<212> TYPE: DNA
<213> ORGANISM: Homo sapiens

<400> SEQUENCE: 114
ccttcagagg atttcccttt c                                          21

<210> SEQ ID NO 115
<211> LENGTH: 20
<212> TYPE: DNA
<213> ORGANISM: Homo sapiens

<400> SEQUENCE: 115
ctggtttgac tccagcttca                                            20

<210> SEQ ID NO 116
```

```
<211> LENGTH: 20
<212> TYPE: DNA
<213> ORGANISM: Homo sapiens

<400> SEQUENCE: 116
cctggcacgg aatagacact                                               20

<210> SEQ ID NO 117
<211> LENGTH: 19
<212> TYPE: DNA
<213> ORGANISM: Homo sapiens

<400> SEQUENCE: 117
ggcctccttt gctctgaag                                                19

<210> SEQ ID NO 118
<211> LENGTH: 21
<212> TYPE: DNA
<213> ORGANISM: Homo sapiens

<400> SEQUENCE: 118
catccctgtg gctgattaag a                                             21

<210> SEQ ID NO 119
<211> LENGTH: 20
<212> TYPE: DNA
<213> ORGANISM: Homo sapiens

<400> SEQUENCE: 119
aacagttcca gcccgttcta                                               20

<210> SEQ ID NO 120
<211> LENGTH: 22
<212> TYPE: DNA
<213> ORGANISM: Homo sapiens

<400> SEQUENCE: 120
tttcaaagga atatccaagt gc                                            22

<210> SEQ ID NO 121
<211> LENGTH: 24
<212> TYPE: DNA
<213> ORGANISM: Homo sapiens

<400> SEQUENCE: 121
tggcgtacca tataaacagt tctc                                          24

<210> SEQ ID NO 122
<211> LENGTH: 20
<212> TYPE: DNA
<213> ORGANISM: Homo sapiens

<400> SEQUENCE: 122
ttcaatgaag gtgccgaagt                                               20

<210> SEQ ID NO 123
<211> LENGTH: 20
<212> TYPE: DNA
<213> ORGANISM: Homo sapiens

<400> SEQUENCE: 123
tgtctatccc aaagctgcaa                                               20
```

```
<210> SEQ ID NO 124
<211> LENGTH: 21
<212> TYPE: DNA
<213> ORGANISM: Homo sapiens

<400> SEQUENCE: 124
gctcagtcca agttcatgct c                                      21

<210> SEQ ID NO 125
<211> LENGTH: 20
<212> TYPE: DNA
<213> ORGANISM: Homo sapiens

<400> SEQUENCE: 125
tgggattggg ttctggatac                                        20

<210> SEQ ID NO 126
<211> LENGTH: 22
<212> TYPE: DNA
<213> ORGANISM: Homo sapiens

<400> SEQUENCE: 126
cctactttcc atctcctcct tg                                     22

<210> SEQ ID NO 127
<211> LENGTH: 24
<212> TYPE: DNA
<213> ORGANISM: Homo sapiens

<400> SEQUENCE: 127
tggagtaagt tggagaattg ttga                                   24

<210> SEQ ID NO 128
<211> LENGTH: 24
<212> TYPE: DNA
<213> ORGANISM: Homo sapiens

<400> SEQUENCE: 128
gcaagactct gttgaagaag aaga                                   24

<210> SEQ ID NO 129
<211> LENGTH: 21
<212> TYPE: DNA
<213> ORGANISM: Homo sapiens

<400> SEQUENCE: 129
tccctctgtt tgagtttctc g                                      21

<210> SEQ ID NO 130
<211> LENGTH: 20
<212> TYPE: DNA
<213> ORGANISM: Homo sapiens

<400> SEQUENCE: 130
ccttgggcag tcagagaaac                                        20

<210> SEQ ID NO 131
<211> LENGTH: 20
<212> TYPE: DNA
<213> ORGANISM: Homo sapiens

<400> SEQUENCE: 131
cccgtgaagt ctgagaggtg                                        20
```

```
<210> SEQ ID NO 132
<211> LENGTH: 19
<212> TYPE: DNA
<213> ORGANISM: Homo sapiens

<400> SEQUENCE: 132
aggcacagtc gctcatgtc                                           19

<210> SEQ ID NO 133
<211> LENGTH: 24
<212> TYPE: DNA
<213> ORGANISM: Homo sapiens

<400> SEQUENCE: 133
aaactttagc taatggtggt caaa                                     24

<210> SEQ ID NO 134
<211> LENGTH: 25
<212> TYPE: DNA
<213> ORGANISM: Homo sapiens

<400> SEQUENCE: 134
gagcatgtgt gactttcata ttcag                                    25

<210> SEQ ID NO 135
<211> LENGTH: 22
<212> TYPE: DNA
<213> ORGANISM: Homo sapiens

<400> SEQUENCE: 135
agtggctatt cattgctaca gg                                       22

<210> SEQ ID NO 136
<211> LENGTH: 20
<212> TYPE: DNA
<213> ORGANISM: Homo sapiens

<400> SEQUENCE: 136
ttgctggatg ctggtttcta                                          20

<210> SEQ ID NO 137
<211> LENGTH: 27
<212> TYPE: DNA
<213> ORGANISM: Homo sapiens

<400> SEQUENCE: 137
aaagagagag agaaagagaa agaaaga                                  27

<210> SEQ ID NO 138
<211> LENGTH: 22
<212> TYPE: DNA
<213> ORGANISM: Homo sapiens

<400> SEQUENCE: 138
aaagtggatg cagttgaggt tt                                       22

<210> SEQ ID NO 139
<211> LENGTH: 22
<212> TYPE: DNA
<213> ORGANISM: Homo sapiens

<400> SEQUENCE: 139
gctagccatt acagacaacc aa                                       22
```

<210> SEQ ID NO 140
<211> LENGTH: 21
<212> TYPE: DNA
<213> ORGANISM: Homo sapiens

<400> SEQUENCE: 140
cagggctcca tgtatccata a                                              21

<210> SEQ ID NO 141
<211> LENGTH: 20
<212> TYPE: DNA
<213> ORGANISM: Homo sapiens

<400> SEQUENCE: 141
caatctttgg ctttgggttt                                                20

<210> SEQ ID NO 142
<211> LENGTH: 16
<212> TYPE: DNA
<213> ORGANISM: Homo sapiens

<400> SEQUENCE: 142
ctggttgagc ggcatt                                                    16

<210> SEQ ID NO 143
<211> LENGTH: 16
<212> TYPE: DNA
<213> ORGANISM: Homo sapiens

<400> SEQUENCE: 143
tgcagcctgg atgaca                                                    16

<210> SEQ ID NO 144
<211> LENGTH: 22
<212> TYPE: DNA
<213> ORGANISM: Homo sapiens

<400> SEQUENCE: 144
cctatggaag catagggaag aa                                             22

<210> SEQ ID NO 145
<211> LENGTH: 21
<212> TYPE: DNA
<213> ORGANISM: Homo sapiens

<400> SEQUENCE: 145
cccacttctg agtctcctga t                                              21

<210> SEQ ID NO 146
<211> LENGTH: 20
<212> TYPE: DNA
<213> ORGANISM: Homo sapiens

<400> SEQUENCE: 146
gggaaatgga gctgctgtta                                                20

<210> SEQ ID NO 147
<211> LENGTH: 20
<212> TYPE: DNA
<213> ORGANISM: Homo sapiens

<400> SEQUENCE: 147
gagtgggtga gtgcaaggat 20

<210> SEQ ID NO 148
<211> LENGTH: 17
<212> TYPE: DNA
<213> ORGANISM: Homo sapiens

<400> SEQUENCE: 148
ctctcagcag gcatcca 17

<210> SEQ ID NO 149
<211> LENGTH: 19
<212> TYPE: DNA
<213> ORGANISM: Homo sapiens

<400> SEQUENCE: 149
gccaacgtaa ttgacacca 19

<210> SEQ ID NO 150
<211> LENGTH: 21
<212> TYPE: DNA
<213> ORGANISM: Homo sapiens

<400> SEQUENCE: 150
tgaaaggaag gtccctgagt t 21

<210> SEQ ID NO 151
<211> LENGTH: 21
<212> TYPE: DNA
<213> ORGANISM: Homo sapiens

<400> SEQUENCE: 151
ccctgctttg cacaagttat c 21

<210> SEQ ID NO 152
<211> LENGTH: 20
<212> TYPE: DNA
<213> ORGANISM: Homo sapiens

<400> SEQUENCE: 152
cacatgaggc tgtatgtgga 20

<210> SEQ ID NO 153
<211> LENGTH: 20
<212> TYPE: DNA
<213> ORGANISM: Homo sapiens

<400> SEQUENCE: 153
tgtgcaggaa tgagaagtcg 20

<210> SEQ ID NO 154
<211> LENGTH: 18
<212> TYPE: DNA
<213> ORGANISM: Homo sapiens

<400> SEQUENCE: 154
ccttaggccc cataatct 18

<210> SEQ ID NO 155
<211> LENGTH: 21
<212> TYPE: DNA
<213> ORGANISM: Homo sapiens

<400> SEQUENCE: 155

-continued caaattcctc aattgcaaaa t    21

<210> SEQ ID NO 156
<211> LENGTH: 20
<212> TYPE: DNA
<213> ORGANISM: Homo sapiens

<400> SEQUENCE: 156
ggtcattcag ggagccattc    20

<210> SEQ ID NO 157
<211> LENGTH: 25
<212> TYPE: DNA
<213> ORGANISM: Homo sapiens

<400> SEQUENCE: 157
ccattatatt tcaccaagag gctgc    25

<210> SEQ ID NO 158
<211> LENGTH: 20
<212> TYPE: DNA
<213> ORGANISM: Homo sapiens

<400> SEQUENCE: 158
agtcaaggct gacagggaag    20

<210> SEQ ID NO 159
<211> LENGTH: 20
<212> TYPE: DNA
<213> ORGANISM: Homo sapiens

<400> SEQUENCE: 159
gctctcagcc ctcaatgtgt    20

<210> SEQ ID NO 160
<211> LENGTH: 20
<212> TYPE: DNA
<213> ORGANISM: Homo sapiens

<400> SEQUENCE: 160
atttgggttc ctctcccaat    20

<210> SEQ ID NO 161
<211> LENGTH: 20
<212> TYPE: DNA
<213> ORGANISM: Homo sapiens

<400> SEQUENCE: 161
acaaactctt gctgctggtg    20

<210> SEQ ID NO 162
<211> LENGTH: 20
<212> TYPE: DNA
<213> ORGANISM: Homo sapiens

<400> SEQUENCE: 162
tgcctggtca tctacccatt    20

<210> SEQ ID NO 163
<211> LENGTH: 20
<212> TYPE: DNA
<213> ORGANISM: Homo sapiens

<400> SEQUENCE: 163
tctactgcag cgctgatctt 20

<210> SEQ ID NO 164
<211> LENGTH: 20
<212> TYPE: DNA
<213> ORGANISM: Homo sapiens

<400> SEQUENCE: 164
tccttccaga aggtttgcat 20

<210> SEQ ID NO 165
<211> LENGTH: 23
<212> TYPE: DNA
<213> ORGANISM: Homo sapiens

<400> SEQUENCE: 165
tgcaaagttg ttcaagagag aca 23

<210> SEQ ID NO 166
<211> LENGTH: 20
<212> TYPE: DNA
<213> ORGANISM: Homo sapiens

<400> SEQUENCE: 166
cagcaggaag atggacaggt 20

<210> SEQ ID NO 167
<211> LENGTH: 21
<212> TYPE: DNA
<213> ORGANISM: Homo sapiens

<400> SEQUENCE: 167
cacactgcat cacacatacc c 21

<210> SEQ ID NO 168
<211> LENGTH: 18
<212> TYPE: DNA
<213> ORGANISM: Homo sapiens

<400> SEQUENCE: 168
tatgccagta tgcctgct 18

<210> SEQ ID NO 169
<211> LENGTH: 19
<212> TYPE: DNA
<213> ORGANISM: Homo sapiens

<400> SEQUENCE: 169
gtcacatcag tccatttgc 19

<210> SEQ ID NO 170
<211> LENGTH: 23
<212> TYPE: DNA
<213> ORGANISM: Homo sapiens

<400> SEQUENCE: 170
ggtttatgtc tgtgtgtgtg tgc 23

<210> SEQ ID NO 171
<211> LENGTH: 23
<212> TYPE: DNA
<213> ORGANISM: Homo sapiens

```
<400> SEQUENCE: 171
tgagggatgt cagagaaata tgc                                        23

<210> SEQ ID NO 172
<211> LENGTH: 22
<212> TYPE: DNA
<213> ORGANISM: Homo sapiens

<400> SEQUENCE: 172
tgatgaaatt gcctagtgat gc                                         22

<210> SEQ ID NO 173
<211> LENGTH: 20
<212> TYPE: DNA
<213> ORGANISM: Homo sapiens

<400> SEQUENCE: 173
ggatccaatc gtacgctacc                                            20

<210> SEQ ID NO 174
<211> LENGTH: 20
<212> TYPE: DNA
<213> ORGANISM: Homo sapiens

<400> SEQUENCE: 174
acctaaacac cacggactgg                                            20

<210> SEQ ID NO 175
<211> LENGTH: 22
<212> TYPE: DNA
<213> ORGANISM: Homo sapiens

<400> SEQUENCE: 175
caggtatcga cattcttcca aa                                         22

<210> SEQ ID NO 176
<211> LENGTH: 26
<212> TYPE: DNA
<213> ORGANISM: Homo sapiens

<400> SEQUENCE: 176
ggtgatctag ggaattattt gtcttc                                     26

<210> SEQ ID NO 177
<211> LENGTH: 20
<212> TYPE: DNA
<213> ORGANISM: Homo sapiens

<400> SEQUENCE: 177
ttggccacta aggtccagat                                            20

<210> SEQ ID NO 178
<211> LENGTH: 20
<212> TYPE: DNA
<213> ORGANISM: Homo sapiens

<400> SEQUENCE: 178
cctttgaggc tggatctgtt                                            20

<210> SEQ ID NO 179
<211> LENGTH: 23
<212> TYPE: DNA
```

```
<213> ORGANISM: Homo sapiens

<400> SEQUENCE: 179
tttccttatc attcattccc tca                                          23

<210> SEQ ID NO 180
<211> LENGTH: 22
<212> TYPE: DNA
<213> ORGANISM: Homo sapiens

<400> SEQUENCE: 180
agatattgtc tccgttccat ga                                           22

<210> SEQ ID NO 181
<211> LENGTH: 22
<212> TYPE: DNA
<213> ORGANISM: Homo sapiens

<400> SEQUENCE: 181
cccagatata aggacctggc ta                                           22

<210> SEQ ID NO 182
<211> LENGTH: 23
<212> TYPE: DNA
<213> ORGANISM: Homo sapiens

<400> SEQUENCE: 182
tttaagccct gtggaatgta ttt                                          23

<210> SEQ ID NO 183
<211> LENGTH: 21
<212> TYPE: DNA
<213> ORGANISM: Homo sapiens

<400> SEQUENCE: 183
gacattgcag gtcaagtagg g                                            21

<210> SEQ ID NO 184
<211> LENGTH: 20
<212> TYPE: DNA
<213> ORGANISM: Homo sapiens

<400> SEQUENCE: 184
tgcataaggc tggagacaga                                              20

<210> SEQ ID NO 185
<211> LENGTH: 19
<212> TYPE: DNA
<213> ORGANISM: Homo sapiens

<400> SEQUENCE: 185
cacagcagat gggagcaaa                                               19

<210> SEQ ID NO 186
<211> LENGTH: 21
<212> TYPE: DNA
<213> ORGANISM: Homo sapiens

<400> SEQUENCE: 186
agccagttgt ctttcatcct g                                            21

<210> SEQ ID NO 187
<211> LENGTH: 23
```

```
<212> TYPE: DNA
<213> ORGANISM: Homo sapiens

<400> SEQUENCE: 187
tgcctgtgct tgtatattct gtg                                          23

<210> SEQ ID NO 188
<211> LENGTH: 20
<212> TYPE: DNA
<213> ORGANISM: Homo sapiens

<400> SEQUENCE: 188
gtgcatgtgc ataccagacc                                              20

<210> SEQ ID NO 189
<211> LENGTH: 20
<212> TYPE: DNA
<213> ORGANISM: Homo sapiens

<400> SEQUENCE: 189
ggcaagatga cctctggaaa                                              20

<210> SEQ ID NO 190
<211> LENGTH: 22
<212> TYPE: DNA
<213> ORGANISM: Homo sapiens

<400> SEQUENCE: 190
tttgtgttcc aggtgagaat tg                                           22

<210> SEQ ID NO 191
<211> LENGTH: 20
<212> TYPE: DNA
<213> ORGANISM: Homo sapiens

<400> SEQUENCE: 191
gaaccatatc ccaaggcact                                              20

<210> SEQ ID NO 192
<211> LENGTH: 22
<212> TYPE: DNA
<213> ORGANISM: Homo sapiens

<400> SEQUENCE: 192
ttgttcccac attcattcta ca                                           22

<210> SEQ ID NO 193
<211> LENGTH: 20
<212> TYPE: DNA
<213> ORGANISM: Homo sapiens

<400> SEQUENCE: 193
ttaaactcgt ggcaaagacg                                              20

<210> SEQ ID NO 194
<211> LENGTH: 18
<212> TYPE: DNA
<213> ORGANISM: Homo sapiens

<400> SEQUENCE: 194
caccatgcct ggctctttt                                               18

<210> SEQ ID NO 195
```

```
<211> LENGTH: 22
<212> TYPE: DNA
<213> ORGANISM: Homo sapiens

<400> SEQUENCE: 195
aacttctcca gttgtgtggt tg                                              22

<210> SEQ ID NO 196
<211> LENGTH: 20
<212> TYPE: DNA
<213> ORGANISM: Homo sapiens

<400> SEQUENCE: 196
cctaccattg acactctcag                                                 20

<210> SEQ ID NO 197
<211> LENGTH: 16
<212> TYPE: DNA
<213> ORGANISM: Homo sapiens

<400> SEQUENCE: 197
tagggccatc cattct                                                     16

<210> SEQ ID NO 198
<211> LENGTH: 25
<212> TYPE: DNA
<213> ORGANISM: Homo sapiens

<400> SEQUENCE: 198
tctgtgtgta ttgtgtactc ctctg                                           25

<210> SEQ ID NO 199
<211> LENGTH: 22
<212> TYPE: DNA
<213> ORGANISM: Homo sapiens

<400> SEQUENCE: 199
tcacacaatt tgaaccaatc ct                                              22

<210> SEQ ID NO 200
<211> LENGTH: 20
<212> TYPE: DNA
<213> ORGANISM: Homo sapiens

<400> SEQUENCE: 200
accaagatat gaaggccaaa                                                 20

<210> SEQ ID NO 201
<211> LENGTH: 22
<212> TYPE: DNA
<213> ORGANISM: Homo sapiens

<400> SEQUENCE: 201
cctccagcta gaacaatgtg aa                                              22

<210> SEQ ID NO 202
<211> LENGTH: 21
<212> TYPE: DNA
<213> ORGANISM: Homo sapiens

<400> SEQUENCE: 202
tgatcatgtc agcagcagaa g                                               21
```

<210> SEQ ID NO 203
<211> LENGTH: 20
<212> TYPE: DNA
<213> ORGANISM: Homo sapiens

<400> SEQUENCE: 203
agtaacaggt gagggcatgg                                               20

<210> SEQ ID NO 204
<211> LENGTH: 21
<212> TYPE: DNA
<213> ORGANISM: Homo sapiens

<400> SEQUENCE: 204
tgtccatagc tgtagccctg t                                             21

<210> SEQ ID NO 205
<211> LENGTH: 20
<212> TYPE: DNA
<213> ORGANISM: Homo sapiens

<400> SEQUENCE: 205
ctcaatgggc atctttaggc                                               20

<210> SEQ ID NO 206
<211> LENGTH: 22
<212> TYPE: DNA
<213> ORGANISM: Homo sapiens

<400> SEQUENCE: 206
caaacaaaca aacaagcaaa cc                                            22

<210> SEQ ID NO 207
<211> LENGTH: 21
<212> TYPE: DNA
<213> ORGANISM: Homo sapiens

<400> SEQUENCE: 207
tggacgtttc tttcagtgag g                                             21

<210> SEQ ID NO 208
<211> LENGTH: 23
<212> TYPE: DNA
<213> ORGANISM: Homo sapiens

<400> SEQUENCE: 208
tgataactta ccagcatgtg agc                                           23

<210> SEQ ID NO 209
<211> LENGTH: 21
<212> TYPE: DNA
<213> ORGANISM: Homo sapiens

<400> SEQUENCE: 209
tcacctcacc taaggatctg c                                             21

<210> SEQ ID NO 210
<211> LENGTH: 23
<212> TYPE: DNA
<213> ORGANISM: Homo sapiens

<400> SEQUENCE: 210
gctagcaaat ctctcaactt cca                                           23

```
<210> SEQ ID NO 211
<211> LENGTH: 20
<212> TYPE: DNA
<213> ORGANISM: Homo sapiens

<400> SEQUENCE: 211
tcttctccat gctgcttcct                                               20

<210> SEQ ID NO 212
<211> LENGTH: 20
<212> TYPE: DNA
<213> ORGANISM: Homo sapiens

<400> SEQUENCE: 212
catgcaattg cccaatagag                                               20

<210> SEQ ID NO 213
<211> LENGTH: 22
<212> TYPE: DNA
<213> ORGANISM: Homo sapiens

<400> SEQUENCE: 213
ttgggcttgt ctacctagtt ca                                            22

<210> SEQ ID NO 214
<211> LENGTH: 20
<212> TYPE: DNA
<213> ORGANISM: Homo sapiens

<400> SEQUENCE: 214
gctgcacgta tttgttggtg                                               20

<210> SEQ ID NO 215
<211> LENGTH: 20
<212> TYPE: DNA
<213> ORGANISM: Homo sapiens

<400> SEQUENCE: 215
aaacagcaga aatgggaacc                                               20

<210> SEQ ID NO 216
<211> LENGTH: 20
<212> TYPE: DNA
<213> ORGANISM: Homo sapiens

<400> SEQUENCE: 216
ccgtgggcta tcaatttctg                                               20

<210> SEQ ID NO 217
<211> LENGTH: 21
<212> TYPE: DNA
<213> ORGANISM: Homo sapiens

<400> SEQUENCE: 217
aagatgcaat ctggtttcca a                                             21

<210> SEQ ID NO 218
<211> LENGTH: 20
<212> TYPE: DNA
<213> ORGANISM: Homo sapiens

<400> SEQUENCE: 218
cccaagactg aggaggtcaa                                               20
```

```
<210> SEQ ID NO 219
<211> LENGTH: 20
<212> TYPE: DNA
<213> ORGANISM: Homo sapiens

<400> SEQUENCE: 219
gctgacggag aggaaagaga                                               20

<210> SEQ ID NO 220
<211> LENGTH: 20
<212> TYPE: DNA
<213> ORGANISM: Homo sapiens

<400> SEQUENCE: 220
tcacaaagca agcaatcaca                                               20

<210> SEQ ID NO 221
<211> LENGTH: 20
<212> TYPE: DNA
<213> ORGANISM: Homo sapiens

<400> SEQUENCE: 221
tgatggatgc accatgttta                                               20

<210> SEQ ID NO 222
<211> LENGTH: 20
<212> TYPE: DNA
<213> ORGANISM: Homo sapiens

<400> SEQUENCE: 222
tgagaagcct gggcattaag                                               20

<210> SEQ ID NO 223
<211> LENGTH: 20
<212> TYPE: DNA
<213> ORGANISM: Homo sapiens

<400> SEQUENCE: 223
acaagctcat ccagggaaag                                               20

<210> SEQ ID NO 224
<211> LENGTH: 19
<212> TYPE: DNA
<213> ORGANISM: Homo sapiens

<400> SEQUENCE: 224
agagctgatc tggccgaag                                                19

<210> SEQ ID NO 225
<211> LENGTH: 21
<212> TYPE: DNA
<213> ORGANISM: Homo sapiens

<400> SEQUENCE: 225
ggtggacaca gaatccacac t                                             21

<210> SEQ ID NO 226
<211> LENGTH: 18
<212> TYPE: DNA
<213> ORGANISM: Homo sapiens

<400> SEQUENCE: 226
```

```
ggcctgaaag gtatcctc                                                    18

<210> SEQ ID NO 227
<211> LENGTH: 18
<212> TYPE: DNA
<213> ORGANISM: Homo sapiens

<400> SEQUENCE: 227
tcccaccata agcacaag                                                    18

<210> SEQ ID NO 228
<211> LENGTH: 22
<212> TYPE: DNA
<213> ORGANISM: Homo sapiens

<400> SEQUENCE: 228
tcaacctagg attggcatta ca                                               22

<210> SEQ ID NO 229
<211> LENGTH: 21
<212> TYPE: DNA
<213> ORGANISM: Homo sapiens

<400> SEQUENCE: 229
tctaggattt gtgcctttcc a                                                21

<210> SEQ ID NO 230
<211> LENGTH: 20
<212> TYPE: DNA
<213> ORGANISM: Homo sapiens

<400> SEQUENCE: 230
attcgtgcag ctgtttctgc                                                  20

<210> SEQ ID NO 231
<211> LENGTH: 22
<212> TYPE: DNA
<213> ORGANISM: Homo sapiens

<400> SEQUENCE: 231
gcatgacatt gtaaatggag ga                                               22

<210> SEQ ID NO 232
<211> LENGTH: 20
<212> TYPE: DNA
<213> ORGANISM: Homo sapiens

<400> SEQUENCE: 232
ggtgggaatg tgtgactgaa                                                  20

<210> SEQ ID NO 233
<211> LENGTH: 22
<212> TYPE: DNA
<213> ORGANISM: Homo sapiens

<400> SEQUENCE: 233
ccaggtacaa cattctcctg at                                               22

<210> SEQ ID NO 234
<211> LENGTH: 16
<212> TYPE: DNA
<213> ORGANISM: Homo sapiens

<400> SEQUENCE: 234
```
tgcaggtggg agtcaa                                             16

<210> SEQ ID NO 235
<211> LENGTH: 24
<212> TYPE: DNA
<213> ORGANISM: Homo sapiens

<400> SEQUENCE: 235
aaataacaag aagtgacctt ccta                                    24

<210> SEQ ID NO 236
<211> LENGTH: 21
<212> TYPE: DNA
<213> ORGANISM: Homo sapiens

<400> SEQUENCE: 236
aaaggatgca ttcggttaga g                                       21

<210> SEQ ID NO 237
<211> LENGTH: 20
<212> TYPE: DNA
<213> ORGANISM: Homo sapiens

<400> SEQUENCE: 237
actgtcctgt gcctgtgctt                                         20

<210> SEQ ID NO 238
<211> LENGTH: 20
<212> TYPE: DNA
<213> ORGANISM: Homo sapiens

<400> SEQUENCE: 238
gtccacctaa tggctcattc                                         20

<210> SEQ ID NO 239
<211> LENGTH: 21
<212> TYPE: DNA
<213> ORGANISM: Homo sapiens

<400> SEQUENCE: 239
caagaagcac tcatgtttgt g                                       21

<210> SEQ ID NO 240
<211> LENGTH: 19
<212> TYPE: DNA
<213> ORGANISM: Homo sapiens

<400> SEQUENCE: 240
agcctgtgat tggctgaga                                          19

<210> SEQ ID NO 241
<211> LENGTH: 20
<212> TYPE: DNA
<213> ORGANISM: Homo sapiens

<400> SEQUENCE: 241
ggcttacagc tgcctccttt                                         20

<210> SEQ ID NO 242
<211> LENGTH: 21
<212> TYPE: DNA
<213> ORGANISM: Homo sapiens -continued

```
<400> SEQUENCE: 242
cccacagagc actttgttag a                                              21

<210> SEQ ID NO 243
<211> LENGTH: 21
<212> TYPE: DNA
<213> ORGANISM: Homo sapiens

<400> SEQUENCE: 243 gcctcccctta agctgttatg c                                             21

<210> SEQ ID NO 244
<211> LENGTH: 23
<212> TYPE: DNA
<213> ORGANISM: Homo sapiens

<400> SEQUENCE: 244
cactctttac tgccaatcac tcc                                            23

<210> SEQ ID NO 245
<211> LENGTH: 19
<212> TYPE: DNA
<213> ORGANISM: Homo sapiens

<400> SEQUENCE: 245
gccgtgtggg tgtatgaat                                                 19

<210> SEQ ID NO 246
<211> LENGTH: 22
<212> TYPE: DNA
<213> ORGANISM: Homo sapiens

<400> SEQUENCE: 246
ttgtaccagg aaccaaagac aa                                             22

<210> SEQ ID NO 247
<211> LENGTH: 20
<212> TYPE: DNA
<213> ORGANISM: Homo sapiens

<400> SEQUENCE: 247
cacagacaga ggcacattga                                                20

<210> SEQ ID NO 248
<211> LENGTH: 20
<212> TYPE: DNA
<213> ORGANISM: Homo sapiens

<400> SEQUENCE: 248
gctctggtca ctcctgctgt                                                20

<210> SEQ ID NO 249
<211> LENGTH: 19
<212> TYPE: DNA
<213> ORGANISM: Homo sapiens

<400> SEQUENCE: 249
catgcctggc tgattgttt                                                 19

<210> SEQ ID NO 250
<211> LENGTH: 16
<212> TYPE: DNA
<213> ORGANISM: Homo sapiens
```

<400> SEQUENCE: 250
ccaacatcgg gaactg                                            16

<210> SEQ ID NO 251
<211> LENGTH: 21
<212> TYPE: DNA
<213> ORGANISM: Homo sapiens

<400> SEQUENCE: 251
tgcattcttt aagtccatgt c                                      21

<210> SEQ ID NO 252
<211> LENGTH: 21
<212> TYPE: DNA
<213> ORGANISM: Homo sapiens

<400> SEQUENCE: 252
cagcaactga caactcatcc a                                      21

<210> SEQ ID NO 253
<211> LENGTH: 20
<212> TYPE: DNA
<213> ORGANISM: Homo sapiens

<400> SEQUENCE: 253
cctcaatcct cagctccaac                                        20

<210> SEQ ID NO 254
<211> LENGTH: 21
<212> TYPE: DNA
<213> ORGANISM: Homo sapiens

<400> SEQUENCE: 254
tgattggttc tgttgttgct g                                      21

<210> SEQ ID NO 255
<211> LENGTH: 19
<212> TYPE: DNA
<213> ORGANISM: Homo sapiens

<400> SEQUENCE: 255
agcccaaggc tcttgtgag                                         19

<210> SEQ ID NO 256
<211> LENGTH: 21
<212> TYPE: DNA
<213> ORGANISM: Homo sapiens

<400> SEQUENCE: 256
tccttcacag cttcaaactc a                                      21

<210> SEQ ID NO 257
<211> LENGTH: 22
<212> TYPE: DNA
<213> ORGANISM: Homo sapiens

<400> SEQUENCE: 257
agtgagaagc ttccatactg gt                                     22

<210> SEQ ID NO 258
<211> LENGTH: 20
<212> TYPE: DNA

<213> ORGANISM: Homo sapiens

<400> SEQUENCE: 258
gccaaccgtt agacaaatga                    20

<210> SEQ ID NO 259
<211> LENGTH: 21
<212> TYPE: DNA
<213> ORGANISM: Homo sapiens

<400> SEQUENCE: 259
ctacatgtgc accacaacac c                  21

<210> SEQ ID NO 260
<211> LENGTH: 19
<212> TYPE: DNA
<213> ORGANISM: Homo sapiens

<400> SEQUENCE: 260
agtttattgc cgccgagag                     19

<210> SEQ ID NO 261
<211> LENGTH: 19
<212> TYPE: DNA
<213> ORGANISM: Homo sapiens

<400> SEQUENCE: 261
acccaccaca ttcacaagc                     19

<210> SEQ ID NO 262
<211> LENGTH: 20
<212> TYPE: DNA
<213> ORGANISM: Homo sapiens

<400> SEQUENCE: 262
cgattgccat gtctctttga                    20

<210> SEQ ID NO 263
<211> LENGTH: 20
<212> TYPE: DNA
<213> ORGANISM: Homo sapiens

<400> SEQUENCE: 263
gagatctggc ctggatttgt                    20

<210> SEQ ID NO 264
<211> LENGTH: 23
<212> TYPE: DNA
<213> ORGANISM: Homo sapiens

<400> SEQUENCE: 264
tcattgtcag cacagaatga act                23

<210> SEQ ID NO 265
<211> LENGTH: 20
<212> TYPE: DNA
<213> ORGANISM: Homo sapiens

<400> SEQUENCE: 265
ggagggaggg aagaaaagaga                   20

<210> SEQ ID NO 266
<211> LENGTH: 22

```
<212> TYPE: DNA
<213> ORGANISM: Homo sapiens

<400> SEQUENCE: 266
gggaagagga gattgacttg tt                                           22

<210> SEQ ID NO 267
<211> LENGTH: 20
<212> TYPE: DNA
<213> ORGANISM: Homo sapiens

<400> SEQUENCE: 267
ggaacaccat cattccaacc                                              20

<210> SEQ ID NO 268
<211> LENGTH: 20
<212> TYPE: DNA
<213> ORGANISM: Homo sapiens

<400> SEQUENCE: 268
tacaagctcc accgtccttc                                              20

<210> SEQ ID NO 269
<211> LENGTH: 20
<212> TYPE: DNA
<213> ORGANISM: Homo sapiens

<400> SEQUENCE: 269
tgagttgctg cctcttcaaa                                              20

<210> SEQ ID NO 270
<211> LENGTH: 20
<212> TYPE: DNA
<213> ORGANISM: Homo sapiens

<400> SEQUENCE: 270
tgctaatggg ccaaggaata                                              20

<210> SEQ ID NO 271
<211> LENGTH: 23
<212> TYPE: DNA
<213> ORGANISM: Homo sapiens

<400> SEQUENCE: 271
gctaaatgtc ctcatgaata gcc                                          23

<210> SEQ ID NO 272
<211> LENGTH: 20
<212> TYPE: DNA
<213> ORGANISM: Homo sapiens

<400> SEQUENCE: 272
tgtcctgcag acagatggtc                                              20

<210> SEQ ID NO 273
<211> LENGTH: 20
<212> TYPE: DNA
<213> ORGANISM: Homo sapiens

<400> SEQUENCE: 273
cctccggagt agctggatta                                              20

<210> SEQ ID NO 274
```

```
<211> LENGTH: 20
<212> TYPE: DNA
<213> ORGANISM: Homo sapiens

<400> SEQUENCE: 274
gagactggcc ctcattcttg                                               20

<210> SEQ ID NO 275
<211> LENGTH: 25
<212> TYPE: DNA
<213> ORGANISM: Homo sapiens

<400> SEQUENCE: 275
aagaagccag agacaaagaa ataca                                         25

<210> SEQ ID NO 276
<211> LENGTH: 24
<212> TYPE: DNA
<213> ORGANISM: Homo sapiens

<400> SEQUENCE: 276
catctatctt tggattcagt ggtg                                          24

<210> SEQ ID NO 277
<211> LENGTH: 20
<212> TYPE: DNA
<213> ORGANISM: Homo sapiens

<400> SEQUENCE: 277
tgctcccaac atcttaccag                                               20

<210> SEQ ID NO 278
<211> LENGTH: 23
<212> TYPE: DNA
<213> ORGANISM: Homo sapiens

<400> SEQUENCE: 278
tgtcctctgg tcatttctat ggt                                           23

<210> SEQ ID NO 279
<211> LENGTH: 23
<212> TYPE: DNA
<213> ORGANISM: Homo sapiens

<400> SEQUENCE: 279
catgaatgag aagtgatgaa tgg                                           23

<210> SEQ ID NO 280
<211> LENGTH: 22
<212> TYPE: DNA
<213> ORGANISM: Homo sapiens

<400> SEQUENCE: 280
cagacactgt aaactggctt cg                                            22

<210> SEQ ID NO 281
<211> LENGTH: 20
<212> TYPE: DNA
<213> ORGANISM: Homo sapiens

<400> SEQUENCE: 281
gccacattgc tatcagcgta                                               20
```

```
<210> SEQ ID NO 282
<211> LENGTH: 20
<212> TYPE: DNA
<213> ORGANISM: Homo sapiens

<400> SEQUENCE: 282
atgtgctgtg gtccagattt                                              20

<210> SEQ ID NO 283
<211> LENGTH: 25
<212> TYPE: DNA
<213> ORGANISM: Homo sapiens

<400> SEQUENCE: 283
cctactactg caattactcc ctacc                                        25

<210> SEQ ID NO 284
<211> LENGTH: 21
<212> TYPE: DNA
<213> ORGANISM: Homo sapiens

<400> SEQUENCE: 284
tgtcataggc ttgcggtatt t                                            21

<210> SEQ ID NO 285
<211> LENGTH: 20
<212> TYPE: DNA
<213> ORGANISM: Homo sapiens

<400> SEQUENCE: 285
ttggtagggt cctttccttt                                              20

<210> SEQ ID NO 286
<211> LENGTH: 20
<212> TYPE: DNA
<213> ORGANISM: Homo sapiens

<400> SEQUENCE: 286
gcctgctcac tgttgtttga                                              20

<210> SEQ ID NO 287
<211> LENGTH: 21
<212> TYPE: DNA
<213> ORGANISM: Homo sapiens

<400> SEQUENCE: 287
cggttatcag agactggtgg t                                            21

<210> SEQ ID NO 288
<211> LENGTH: 21
<212> TYPE: DNA
<213> ORGANISM: Homo sapiens

<400> SEQUENCE: 288
ggcttatttc atgtacggct a                                            21

<210> SEQ ID NO 289
<211> LENGTH: 26
<212> TYPE: DNA
<213> ORGANISM: Homo sapiens

<400> SEQUENCE: 289
ggttaaactc tacttagtcc tgatgc                                       26
```

```
<210> SEQ ID NO 290
<211> LENGTH: 20
<212> TYPE: DNA
<213> ORGANISM: Homo sapiens

<400> SEQUENCE: 290
gaactctgca ggcacctctt                                               20

<210> SEQ ID NO 291
<211> LENGTH: 20
<212> TYPE: DNA
<213> ORGANISM: Homo sapiens

<400> SEQUENCE: 291
cctgaagcgc ttgtactgaa                                               20

<210> SEQ ID NO 292
<211> LENGTH: 20
<212> TYPE: DNA
<213> ORGANISM: Homo sapiens

<400> SEQUENCE: 292
ttggcttctc gctctttctt                                               20

<210> SEQ ID NO 293
<211> LENGTH: 20
<212> TYPE: DNA
<213> ORGANISM: Homo sapiens

<400> SEQUENCE: 293
agccatcagt cacatgcaaa                                               20

<210> SEQ ID NO 294
<211> LENGTH: 20
<212> TYPE: DNA
<213> ORGANISM: Homo sapiens

<400> SEQUENCE: 294
agatctccag ggcagaggac                                               20

<210> SEQ ID NO 295
<211> LENGTH: 20
<212> TYPE: DNA
<213> ORGANISM: Homo sapiens

<400> SEQUENCE: 295
ccttcctccc tccttctctc                                               20

<210> SEQ ID NO 296
<211> LENGTH: 22
<212> TYPE: DNA
<213> ORGANISM: Homo sapiens

<400> SEQUENCE: 296
cagtcaaatg tctcaacctt cc                                            22

<210> SEQ ID NO 297
<211> LENGTH: 20
<212> TYPE: DNA
<213> ORGANISM: Homo sapiens

<400> SEQUENCE: 297
ctagcaacat ggccaagaaa                                               20
```

```
<210> SEQ ID NO 298
<211> LENGTH: 21
<212> TYPE: DNA
<213> ORGANISM: Homo sapiens

<400> SEQUENCE: 298
cgtcattgat cccaatcatc t                                           21

<210> SEQ ID NO 299
<211> LENGTH: 20
<212> TYPE: DNA
<213> ORGANISM: Homo sapiens

<400> SEQUENCE: 299
ggctgatagc ctcccttgta                                             20

<210> SEQ ID NO 300
<211> LENGTH: 20
<212> TYPE: DNA
<213> ORGANISM: Homo sapiens

<400> SEQUENCE: 300
acctttcaag cttccggttt                                             20

<210> SEQ ID NO 301
<211> LENGTH: 20
<212> TYPE: DNA
<213> ORGANISM: Homo sapiens

<400> SEQUENCE: 301
ttccatccgt ccatctatcc                                             20

<210> SEQ ID NO 302
<211> LENGTH: 23
<212> TYPE: DNA
<213> ORGANISM: Homo sapiens

<400> SEQUENCE: 302
ttaaagtcac ttgtctgtgg tca                                         23

<210> SEQ ID NO 303
<211> LENGTH: 27
<212> TYPE: DNA
<213> ORGANISM: Homo sapiens

<400> SEQUENCE: 303
tttgtaggaa tcaagtcaaa taatgta                                     27

<210> SEQ ID NO 304
<211> LENGTH: 20
<212> TYPE: DNA
<213> ORGANISM: Homo sapiens

<400> SEQUENCE: 304
ctttcggaag cttgagccta                                             20

<210> SEQ ID NO 305
<211> LENGTH: 20
<212> TYPE: DNA
<213> ORGANISM: Homo sapiens

<400> SEQUENCE: 305
```

-continued cccaagacca ctgccatatt                                    20

<210> SEQ ID NO 306
<211> LENGTH: 22
<212> TYPE: DNA
<213> ORGANISM: Homo sapiens

<400> SEQUENCE: 306
tgacaggttt gggtatattg ga                                 22

<210> SEQ ID NO 307
<211> LENGTH: 20
<212> TYPE: DNA
<213> ORGANISM: Homo sapiens

<400> SEQUENCE: 307
tgcttaatgt agtggcagca                                    20

<210> SEQ ID NO 308
<211> LENGTH: 20
<212> TYPE: DNA
<213> ORGANISM: Homo sapiens

<400> SEQUENCE: 308
tcctgccttt gtgaattcct                                    20

<210> SEQ ID NO 309
<211> LENGTH: 20
<212> TYPE: DNA
<213> ORGANISM: Homo sapiens

<400> SEQUENCE: 309
gttgaatgag gtgggcatta                                    20

<210> SEQ ID NO 310
<211> LENGTH: 22
<212> TYPE: DNA
<213> ORGANISM: Homo sapiens

<400> SEQUENCE: 310
ttgggaataa atcaggtgtt ga                                 22

<210> SEQ ID NO 311
<211> LENGTH: 20
<212> TYPE: DNA
<213> ORGANISM: Homo sapiens

<400> SEQUENCE: 311
gcagcagctc agcatttctc                                    20

<210> SEQ ID NO 312
<211> LENGTH: 21
<212> TYPE: DNA
<213> ORGANISM: Homo sapiens

<400> SEQUENCE: 312
ccatttaatc ctccagccat t                                  21

<210> SEQ ID NO 313
<211> LENGTH: 20
<212> TYPE: DNA
<213> ORGANISM: Homo sapiens

<400> SEQUENCE: 313

```
gctccacctt gttaccctga                                              20

<210> SEQ ID NO 314
<211> LENGTH: 20
<212> TYPE: DNA
<213> ORGANISM: Homo sapiens

<400> SEQUENCE: 314
acaaccctgg aatctggact                                              20

<210> SEQ ID NO 315
<211> LENGTH: 22
<212> TYPE: DNA
<213> ORGANISM: Homo sapiens

<400> SEQUENCE: 315
gaaggaaagg aaaggaaaga aa                                           22

<210> SEQ ID NO 316
<211> LENGTH: 23
<212> TYPE: DNA
<213> ORGANISM: Homo sapiens

<400> SEQUENCE: 316
tgacaagact gaaacttcat cag                                          23

<210> SEQ ID NO 317
<211> LENGTH: 20
<212> TYPE: DNA
<213> ORGANISM: Homo sapiens

<400> SEQUENCE: 317
gatgcttgct ttgggaggta                                              20

<210> SEQ ID NO 318
<211> LENGTH: 20
<212> TYPE: DNA
<213> ORGANISM: Homo sapiens

<400> SEQUENCE: 318
caggttagag cccatccaag                                              20

<210> SEQ ID NO 319
<211> LENGTH: 20
<212> TYPE: DNA
<213> ORGANISM: Homo sapiens

<400> SEQUENCE: 319
aggctcagct tcatccacat                                              20

<210> SEQ ID NO 320
<211> LENGTH: 20
<212> TYPE: DNA
<213> ORGANISM: Homo sapiens

<400> SEQUENCE: 320
aagcaaatat gcaaaattgc                                              20

<210> SEQ ID NO 321
<211> LENGTH: 23
<212> TYPE: DNA
<213> ORGANISM: Homo sapiens
```

```
<400> SEQUENCE: 321
tccttctgtt tcttgactta aca                                    23

<210> SEQ ID NO 322
<211> LENGTH: 20
<212> TYPE: DNA
<213> ORGANISM: Homo sapiens

<400> SEQUENCE: 322
gggaacaggt cacaggtcat                                        20

<210> SEQ ID NO 323
<211> LENGTH: 20
<212> TYPE: DNA
<213> ORGANISM: Homo sapiens

<400> SEQUENCE: 323
ggaagactgg gtggtcacag                                        20

<210> SEQ ID NO 324
<211> LENGTH: 20
<212> TYPE: DNA
<213> ORGANISM: Homo sapiens

<400> SEQUENCE: 324
ttccttctgc ttgtgagctg                                        20

<210> SEQ ID NO 325
<211> LENGTH: 20
<212> TYPE: DNA
<213> ORGANISM: Homo sapiens

<400> SEQUENCE: 325
taccctcacc ttcctcatgc                                        20

<210> SEQ ID NO 326
<211> LENGTH: 20
<212> TYPE: DNA
<213> ORGANISM: Homo sapiens

<400> SEQUENCE: 326
gaagacattg gcaggtctgg                                        20

<210> SEQ ID NO 327
<211> LENGTH: 20
<212> TYPE: DNA
<213> ORGANISM: Homo sapiens

<400> SEQUENCE: 327
gagccctcat gttgggataa                                        20

<210> SEQ ID NO 328
<211> LENGTH: 22
<212> TYPE: DNA
<213> ORGANISM: Homo sapiens

<400> SEQUENCE: 328
ttgttgattc tcccattctg tg                                     22

<210> SEQ ID NO 329
<211> LENGTH: 25
<212> TYPE: DNA
<213> ORGANISM: Homo sapiens
```

```
<400> SEQUENCE: 329
tcacctacct catctcatac tcaaa                                         25

<210> SEQ ID NO 330
<211> LENGTH: 20
<212> TYPE: DNA
<213> ORGANISM: Homo sapiens

<400> SEQUENCE: 330
tcttccggac aagtttccaa                                               20

<210> SEQ ID NO 331
<211> LENGTH: 20
<212> TYPE: DNA
<213> ORGANISM: Homo sapiens

<400> SEQUENCE: 331
tgggtcattc tggacattca                                               20

<210> SEQ ID NO 332
<211> LENGTH: 20
<212> TYPE: DNA
<213> ORGANISM: Homo sapiens

<400> SEQUENCE: 332
gcaaatgagg ctggtaaggt                                               20

<210> SEQ ID NO 333
<211> LENGTH: 20
<212> TYPE: DNA
<213> ORGANISM: Homo sapiens

<400> SEQUENCE: 333
tgcactgtgg tagagggaaa                                               20

<210> SEQ ID NO 334
<211> LENGTH: 27
<212> TYPE: DNA
<213> ORGANISM: Homo sapiens

<400> SEQUENCE: 334
caacatactc ctatgcctag aaagaaa                                       27

<210> SEQ ID NO 335
<211> LENGTH: 20
<212> TYPE: DNA
<213> ORGANISM: Homo sapiens

<400> SEQUENCE: 335
ctcaccaggc agaaacaggt                                               20

<210> SEQ ID NO 336
<211> LENGTH: 19
<212> TYPE: DNA
<213> ORGANISM: Homo sapiens

<400> SEQUENCE: 336
cccaatggca tgcttcact                                                19

<210> SEQ ID NO 337
<211> LENGTH: 19
<212> TYPE: DNA
```

```
<213> ORGANISM: Homo sapiens

<400> SEQUENCE: 337
ggttctccca gcattggtt                                               19

<210> SEQ ID NO 338
<211> LENGTH: 20
<212> TYPE: DNA
<213> ORGANISM: Homo sapiens

<400> SEQUENCE: 338
aaggcctctg ggtaggtagg                                              20

<210> SEQ ID NO 339
<211> LENGTH: 20
<212> TYPE: DNA
<213> ORGANISM: Homo sapiens

<400> SEQUENCE: 339
aagcaatcct tatgggctct                                              20

<210> SEQ ID NO 340
<211> LENGTH: 20
<212> TYPE: DNA
<213> ORGANISM: Homo sapiens

<400> SEQUENCE: 340
ccaggtaatc agaagcctca                                              20

<210> SEQ ID NO 341
<211> LENGTH: 20
<212> TYPE: DNA
<213> ORGANISM: Homo sapiens

<400> SEQUENCE: 341
ttccgttaaa tccagccatc                                              20

<210> SEQ ID NO 342
<211> LENGTH: 20
<212> TYPE: DNA
<213> ORGANISM: Homo sapiens

<400> SEQUENCE: 342
cagggactgc agtgtctcaa                                              20

<210> SEQ ID NO 343
<211> LENGTH: 20
<212> TYPE: DNA
<213> ORGANISM: Homo sapiens

<400> SEQUENCE: 343
atgccacatt tgcctctctc                                              20

<210> SEQ ID NO 344
<211> LENGTH: 25
<212> TYPE: DNA
<213> ORGANISM: Homo sapiens

<400> SEQUENCE: 344
ccaccttcca cttaatacaa acttc                                        25

<210> SEQ ID NO 345
<211> LENGTH: 21
```

```
<212> TYPE: DNA
<213> ORGANISM: Homo sapiens

<400> SEQUENCE: 345
gaagcaatcc attccaagaa a                                            21

<210> SEQ ID NO 346
<211> LENGTH: 20
<212> TYPE: DNA
<213> ORGANISM: Homo sapiens

<400> SEQUENCE: 346
gtcctgaggg tgtccaggta                                              20

<210> SEQ ID NO 347
<211> LENGTH: 22
<212> TYPE: DNA
<213> ORGANISM: Homo sapiens

<400> SEQUENCE: 347
gctggagaac tcctattctg ct                                           22

<210> SEQ ID NO 348
<211> LENGTH: 20
<212> TYPE: DNA
<213> ORGANISM: Homo sapiens

<400> SEQUENCE: 348
tggagctatt gcggttctct                                              20

<210> SEQ ID NO 349
<211> LENGTH: 23
<212> TYPE: DNA
<213> ORGANISM: Homo sapiens

<400> SEQUENCE: 349
tcaaatctct ctttcctcct cct                                          23

<210> SEQ ID NO 350
<211> LENGTH: 20
<212> TYPE: DNA
<213> ORGANISM: Homo sapiens

<400> SEQUENCE: 350
cagttccagc tacgggagaa                                              20

<210> SEQ ID NO 351
<211> LENGTH: 20
<212> TYPE: DNA
<213> ORGANISM: Homo sapiens

<400> SEQUENCE: 351
ccgcatttag gcaagtctca                                              20

<210> SEQ ID NO 352
<211> LENGTH: 20
<212> TYPE: DNA
<213> ORGANISM: Homo sapiens

<400> SEQUENCE: 352
aagcacacac agatgctagg                                              20

<210> SEQ ID NO 353
```

-continued

```
<211> LENGTH: 20
<212> TYPE: DNA
<213> ORGANISM: Homo sapiens

<400> SEQUENCE: 353
cctcagcctc cataatctca                                                 20

<210> SEQ ID NO 354
<211> LENGTH: 20
<212> TYPE: DNA
<213> ORGANISM: Homo sapiens

<400> SEQUENCE: 354
gtacagagcc caccttctgg                                                 20

<210> SEQ ID NO 355
<211> LENGTH: 20
<212> TYPE: DNA
<213> ORGANISM: Homo sapiens

<400> SEQUENCE: 355
tcactatgct gcaaggcaag                                                 20

<210> SEQ ID NO 356
<211> LENGTH: 23
<212> TYPE: DNA
<213> ORGANISM: Homo sapiens

<400> SEQUENCE: 356
ggtgcttgct gtaaatataa ttg                                             23

<210> SEQ ID NO 357
<211> LENGTH: 20
<212> TYPE: DNA
<213> ORGANISM: Homo sapiens

<400> SEQUENCE: 357
cactacagca gattgcacca                                                 20

<210> SEQ ID NO 358
<211> LENGTH: 20
<212> TYPE: DNA
<213> ORGANISM: Homo sapiens

<400> SEQUENCE: 358
gatttgaaaa tgagcagtcc                                                 20

<210> SEQ ID NO 359
<211> LENGTH: 20
<212> TYPE: DNA
<213> ORGANISM: Homo sapiens

<400> SEQUENCE: 359
gtcgggcact acgtttatct                                                 20

<210> SEQ ID NO 360
<211> LENGTH: 20
<212> TYPE: DNA
<213> ORGANISM: Homo sapiens

<400> SEQUENCE: 360
tgggtgaaga tgctacctga                                                 20
```

```
<210> SEQ ID NO 361
<211> LENGTH: 20
<212> TYPE: DNA
<213> ORGANISM: Homo sapiens

<400> SEQUENCE: 361
cccttcttcc tttccctctc                                              20

<210> SEQ ID NO 362
<211> LENGTH: 21
<212> TYPE: DNA
<213> ORGANISM: Homo sapiens

<400> SEQUENCE: 362
tgccaggtct gagttgtaag c                                            21

<210> SEQ ID NO 363
<211> LENGTH: 20
<212> TYPE: DNA
<213> ORGANISM: Homo sapiens

<400> SEQUENCE: 363
cagcatgaga ccctgtcaaa                                              20

<210> SEQ ID NO 364
<211> LENGTH: 27
<212> TYPE: DNA
<213> ORGANISM: Homo sapiens

<400> SEQUENCE: 364
gaaagaaaga aagaaagaag aaagaaa                                      27

<210> SEQ ID NO 365
<211> LENGTH: 20
<212> TYPE: DNA
<213> ORGANISM: Homo sapiens

<400> SEQUENCE: 365
aatcaccaaa cctggaagca                                              20

<210> SEQ ID NO 366
<211> LENGTH: 27
<212> TYPE: DNA
<213> ORGANISM: Homo sapiens

<400> SEQUENCE: 366
gaaagaaaga aagaaagaag aaagaaa                                      27

<210> SEQ ID NO 367
<211> LENGTH: 20
<212> TYPE: DNA
<213> ORGANISM: Homo sapiens

<400> SEQUENCE: 367
aatcaccaaa cctggaagca                                              20

<210> SEQ ID NO 368
<211> LENGTH: 25
<212> TYPE: DNA
<213> ORGANISM: Homo sapiens

<400> SEQUENCE: 368
tctgagttaa acacttgagt tgctg                                        25
```

```
<210> SEQ ID NO 369
<211> LENGTH: 21
<212> TYPE: DNA
<213> ORGANISM: Homo sapiens

<400> SEQUENCE: 369
ccagtaaatg gcagtgtggt t                                        21

<210> SEQ ID NO 370
<211> LENGTH: 27
<212> TYPE: DNA
<213> ORGANISM: Homo sapiens

<400> SEQUENCE: 370
tgtcatggat atttctacat aaaccaa                                  27

<210> SEQ ID NO 371
<211> LENGTH: 23
<212> TYPE: DNA
<213> ORGANISM: Homo sapiens

<400> SEQUENCE: 371
tgaagatggt tattgcttcc ttc                                      23

<210> SEQ ID NO 372
<211> LENGTH: 20
<212> TYPE: DNA
<213> ORGANISM: Homo sapiens

<400> SEQUENCE: 372
cgctttgttt ggtttggttt                                          20

<210> SEQ ID NO 373
<211> LENGTH: 20
<212> TYPE: DNA
<213> ORGANISM: Homo sapiens

<400> SEQUENCE: 373
atgcagttgt cccacatgct                                          20

<210> SEQ ID NO 374
<211> LENGTH: 20
<212> TYPE: DNA
<213> ORGANISM: Homo sapiens

<400> SEQUENCE: 374
tcctgcactc caaaggaaac                                          20

<210> SEQ ID NO 375
<211> LENGTH: 25
<212> TYPE: DNA
<213> ORGANISM: Homo sapiens

<400> SEQUENCE: 375
aactctggtt taattcagct ttgtc                                    25

<210> SEQ ID NO 376
<211> LENGTH: 21
<212> TYPE: DNA
<213> ORGANISM: Homo sapiens

<400> SEQUENCE: 376
ttcttgaggg cataaagctg a                                        21
```

<210> SEQ ID NO 377
<211> LENGTH: 20
<212> TYPE: DNA
<213> ORGANISM: Homo sapiens

<400> SEQUENCE: 377
cacactcacc aggcactctg                                          20

<210> SEQ ID NO 378
<211> LENGTH: 23
<212> TYPE: DNA
<213> ORGANISM: Homo sapiens

<400> SEQUENCE: 378
caggtttgat gaaggaaata tgc                                      23

<210> SEQ ID NO 379
<211> LENGTH: 22
<212> TYPE: DNA
<213> ORGANISM: Homo sapiens

<400> SEQUENCE: 379
gggatcctct gcatttctct aa                                       22

<210> SEQ ID NO 380
<211> LENGTH: 20
<212> TYPE: DNA
<213> ORGANISM: Homo sapiens

<400> SEQUENCE: 380
tttgccaaat caaccttcag                                          20

<210> SEQ ID NO 381
<211> LENGTH: 20
<212> TYPE: DNA
<213> ORGANISM: Homo sapiens

<400> SEQUENCE: 381
cctgcttcac acctctgacc                                          20

<210> SEQ ID NO 382
<211> LENGTH: 20
<212> TYPE: DNA
<213> ORGANISM: Homo sapiens

<400> SEQUENCE: 382
actcacacac aaccaccaca                                          20

<210> SEQ ID NO 383
<211> LENGTH: 20
<212> TYPE: DNA
<213> ORGANISM: Homo sapiens

<400> SEQUENCE: 383
gctactggtg ggtcgtaagc                                          20

<210> SEQ ID NO 384
<211> LENGTH: 18
<212> TYPE: DNA
<213> ORGANISM: Homo sapiens

<400> SEQUENCE: 384

```
ttcagagacc atcacggc                                          18

<210> SEQ ID NO 385
<211> LENGTH: 25
<212> TYPE: DNA
<213> ORGANISM: Homo sapiens

<400> SEQUENCE: 385
ctggaaaaat cagttgaatc ctagc                                  25

<210> SEQ ID NO 386
<211> LENGTH: 20
<212> TYPE: DNA
<213> ORGANISM: Homo sapiens

<400> SEQUENCE: 386
aggaaagccg agaaagcata                                        20

<210> SEQ ID NO 387
<211> LENGTH: 20
<212> TYPE: DNA
<213> ORGANISM: Homo sapiens

<400> SEQUENCE: 387
catgtatcca catgcccaga                                        20

<210> SEQ ID NO 388
<211> LENGTH: 20
<212> TYPE: DNA
<213> ORGANISM: Homo sapiens

<400> SEQUENCE: 388
ccttcagcgc agctacatct                                        20

<210> SEQ ID NO 389
<211> LENGTH: 20
<212> TYPE: DNA
<213> ORGANISM: Homo sapiens

<400> SEQUENCE: 389
agaactgcga ggtccaagtg                                        20

<210> SEQ ID NO 390
<211> LENGTH: 22
<212> TYPE: DNA
<213> ORGANISM: Homo sapiens

<400> SEQUENCE: 390
gggagaaaga gaggtaggaa gg                                     22

<210> SEQ ID NO 391
<211> LENGTH: 20
<212> TYPE: DNA
<213> ORGANISM: Homo sapiens

<400> SEQUENCE: 391
ttcccaagtt agcagcatcc                                        20

<210> SEQ ID NO 392
<211> LENGTH: 27
<212> TYPE: DNA
<213> ORGANISM: Homo sapiens

<400> SEQUENCE: 392
```

-continued ttctagagga gtctatttct ttactgg 27

<210> SEQ ID NO 393
<211> LENGTH: 21
<212> TYPE: DNA
<213> ORGANISM: Homo sapiens

<400> SEQUENCE: 393
ggagctgtca cttgagcttt g 21

<210> SEQ ID NO 394
<211> LENGTH: 20
<212> TYPE: DNA
<213> ORGANISM: Homo sapiens

<400> SEQUENCE: 394
ccgtgaccta cagggaacat 20

<210> SEQ ID NO 395
<211> LENGTH: 20
<212> TYPE: DNA
<213> ORGANISM: Homo sapiens

<400> SEQUENCE: 395
ggcatcgggt gtttctattc 20

<210> SEQ ID NO 396
<211> LENGTH: 20
<212> TYPE: DNA
<213> ORGANISM: Homo sapiens

<400> SEQUENCE: 396
agacctgcct gtgttctggt 20

<210> SEQ ID NO 397
<211> LENGTH: 23
<212> TYPE: DNA
<213> ORGANISM: Homo sapiens

<400> SEQUENCE: 397
ggagtgaaat aagtggaact gga 23

<210> SEQ ID NO 398
<211> LENGTH: 26
<212> TYPE: DNA
<213> ORGANISM: Homo sapiens

<400> SEQUENCE: 398
cattaaatga gtcataaagg tcatgg 26

<210> SEQ ID NO 399
<211> LENGTH: 20
<212> TYPE: DNA
<213> ORGANISM: Homo sapiens

<400> SEQUENCE: 399
aacattgttg ctttgctgga 20

<210> SEQ ID NO 400
<211> LENGTH: 20
<212> TYPE: DNA
<213> ORGANISM: Homo sapiens

```
<400> SEQUENCE: 400
ggccttagct cagtttctgg                                              20

<210> SEQ ID NO 401
<211> LENGTH: 20
<212> TYPE: DNA
<213> ORGANISM: Homo sapiens

<400> SEQUENCE: 401
tgcaaagaca tttgcggata                                              20

<210> SEQ ID NO 402
<211> LENGTH: 19
<212> TYPE: DNA
<213> ORGANISM: Homo sapiens

<400> SEQUENCE: 402
cctgcatttg tgtacgtgt                                               19

<210> SEQ ID NO 403
<211> LENGTH: 23
<212> TYPE: DNA
<213> ORGANISM: Homo sapiens

<400> SEQUENCE: 403
cagagccgtg gtagtatatt ttt                                          23

<210> SEQ ID NO 404
<211> LENGTH: 20
<212> TYPE: DNA
<213> ORGANISM: Homo sapiens

<400> SEQUENCE: 404
ggaaccagtc atttgggtgt                                              20

<210> SEQ ID NO 405
<211> LENGTH: 20
<212> TYPE: DNA
<213> ORGANISM: Homo sapiens

<400> SEQUENCE: 405
ttattgctcc ctcgtccaag                                              20

<210> SEQ ID NO 406
<211> LENGTH: 26
<212> TYPE: DNA
<213> ORGANISM: Homo sapiens

<400> SEQUENCE: 406
tgccttaagg tctattattt cctttc                                       26

<210> SEQ ID NO 407
<211> LENGTH: 20
<212> TYPE: DNA
<213> ORGANISM: Homo sapiens

<400> SEQUENCE: 407
accaatgcag gaagactcaa                                              20

<210> SEQ ID NO 408
<211> LENGTH: 21
<212> TYPE: DNA
<213> ORGANISM: Homo sapiens
```

<400> SEQUENCE: 408
ctgatgaaag gacacacatg c                                            21

<210> SEQ ID NO 409
<211> LENGTH: 23
<212> TYPE: DNA
<213> ORGANISM: Homo sapiens

<400> SEQUENCE: 409
tgcattaact atgcagcttg aaa                                          23

<210> SEQ ID NO 410
<211> LENGTH: 18
<212> TYPE: DNA
<213> ORGANISM: Homo sapiens

<400> SEQUENCE: 410
gtcgtgcaat cccgagag                                                18

<210> SEQ ID NO 411
<211> LENGTH: 20
<212> TYPE: DNA
<213> ORGANISM: Homo sapiens

<400> SEQUENCE: 411
ggattcctgc tggctcttct                                              20

<210> SEQ ID NO 412
<211> LENGTH: 20
<212> TYPE: DNA
<213> ORGANISM: Homo sapiens

<400> SEQUENCE: 412
ctggtgtggt caggaaatga                                              20

<210> SEQ ID NO 413
<211> LENGTH: 24
<212> TYPE: DNA
<213> ORGANISM: Homo sapiens

<400> SEQUENCE: 413
gtgctaaaca catgtgagtg agag                                         24

<210> SEQ ID NO 414
<211> LENGTH: 22
<212> TYPE: DNA
<213> ORGANISM: Homo sapiens

<400> SEQUENCE: 414
tttgaccatg ctttctcttt ga                                           22

<210> SEQ ID NO 415
<211> LENGTH: 20
<212> TYPE: DNA
<213> ORGANISM: Homo sapiens

<400> SEQUENCE: 415
gcttgatgac tccctgctgt                                              20

<210> SEQ ID NO 416
<211> LENGTH: 20
<212> TYPE: DNA

<210> SEQ ID NO 416
<211> LENGTH: 20
<212> TYPE: DNA
<213> ORGANISM: Homo sapiens

<400> SEQUENCE: 416
aagccattga aaggcaggta                                          20

<210> SEQ ID NO 417
<211> LENGTH: 20
<212> TYPE: DNA
<213> ORGANISM: Homo sapiens

<400> SEQUENCE: 417
gggactttcc ggcttctatt                                          20

<210> SEQ ID NO 418
<211> LENGTH: 20
<212> TYPE: DNA
<213> ORGANISM: Homo sapiens

<400> SEQUENCE: 418
ggtttgggaa ccattctcct                                          20

<210> SEQ ID NO 419
<211> LENGTH: 22
<212> TYPE: DNA
<213> ORGANISM: Homo sapiens

<400> SEQUENCE: 419
gcagagaagg gatttactcc ag                                       22

<210> SEQ ID NO 420
<211> LENGTH: 20
<212> TYPE: DNA
<213> ORGANISM: Homo sapiens

<400> SEQUENCE: 420
acttgacatg gagcaagctg                                          20

<210> SEQ ID NO 421
<211> LENGTH: 21
<212> TYPE: DNA
<213> ORGANISM: Homo sapiens

<400> SEQUENCE: 421
agctcatcat gctgtaagga g                                        21

<210> SEQ ID NO 422
<211> LENGTH: 20
<212> TYPE: DNA
<213> ORGANISM: Homo sapiens

<400> SEQUENCE: 422
cacaggctct cacattctcg                                          20

<210> SEQ ID NO 423
<211> LENGTH: 20
<212> TYPE: DNA
<213> ORGANISM: Homo sapiens

<400> SEQUENCE: 423
tgacactcat ccctctgctg                                          20

<210> SEQ ID NO 424
<211> LENGTH: 27

```
<212> TYPE: DNA
<213> ORGANISM: Homo sapiens

<400> SEQUENCE: 424
tgagtttcat aagtttacta cctgctg                                          27

<210> SEQ ID NO 425
<211> LENGTH: 20
<212> TYPE: DNA
<213> ORGANISM: Homo sapiens

<400> SEQUENCE: 425
ggcagggaga aaggacaaat                                                  20

<210> SEQ ID NO 426
<211> LENGTH: 22
<212> TYPE: DNA
<213> ORGANISM: Homo sapiens

<400> SEQUENCE: 426
tcccttatgt gggattagtt ga                                               22

<210> SEQ ID NO 427
<211> LENGTH: 23
<212> TYPE: DNA
<213> ORGANISM: Homo sapiens

<400> SEQUENCE: 427
cagacatgga actgagattt ttt                                              23

<210> SEQ ID NO 428
<211> LENGTH: 22
<212> TYPE: DNA
<213> ORGANISM: Homo sapiens

<400> SEQUENCE: 428
tgttccatct ctctacccat gt                                               22

<210> SEQ ID NO 429
<211> LENGTH: 24
<212> TYPE: DNA
<213> ORGANISM: Homo sapiens

<400> SEQUENCE: 429
tcaatgttct tattgagtgg gaaa                                             24

<210> SEQ ID NO 430
<211> LENGTH: 20
<212> TYPE: DNA
<213> ORGANISM: Homo sapiens

<400> SEQUENCE: 430
atatccaccc acccacacat                                                  20

<210> SEQ ID NO 431
<211> LENGTH: 20
<212> TYPE: DNA
<213> ORGANISM: Homo sapiens

<400> SEQUENCE: 431
tagctctgag ggcagagacc                                                  20

<210> SEQ ID NO 432
```

```
<211> LENGTH: 19
<212> TYPE: DNA
<213> ORGANISM: Homo sapiens

<400> SEQUENCE: 432
ccgtccttcc tccactgat                                                19

<210> SEQ ID NO 433
<211> LENGTH: 20
<212> TYPE: DNA
<213> ORGANISM: Homo sapiens

<400> SEQUENCE: 433
agagcactga gggagcaaat                                               20

<210> SEQ ID NO 434
<211> LENGTH: 20
<212> TYPE: DNA
<213> ORGANISM: Homo sapiens

<400> SEQUENCE: 434
agctacagca cgaggcagtt                                               20

<210> SEQ ID NO 435
<211> LENGTH: 21
<212> TYPE: DNA
<213> ORGANISM: Homo sapiens

<400> SEQUENCE: 435
tttgaattga gttgctgttc g                                             21

<210> SEQ ID NO 436
<211> LENGTH: 21
<212> TYPE: DNA
<213> ORGANISM: Homo sapiens

<400> SEQUENCE: 436
tgtacaccac caaccattct g                                             21

<210> SEQ ID NO 437
<211> LENGTH: 20
<212> TYPE: DNA
<213> ORGANISM: Homo sapiens

<400> SEQUENCE: 437
gggaagaaag gcaaatagca                                               20

<210> SEQ ID NO 438
<211> LENGTH: 20
<212> TYPE: DNA
<213> ORGANISM: Homo sapiens

<400> SEQUENCE: 438
ggattggcaa ttagcaggtc                                               20

<210> SEQ ID NO 439
<211> LENGTH: 22
<212> TYPE: DNA
<213> ORGANISM: Homo sapiens

<400> SEQUENCE: 439
gcctggtcaa agataacaga cg                                            22
```

-continued

<210> SEQ ID NO 440
<211> LENGTH: 20
<212> TYPE: DNA
<213> ORGANISM: Homo sapiens

<400> SEQUENCE: 440
cctgattaag ctggcctttg                                        20

<210> SEQ ID NO 441
<211> LENGTH: 20
<212> TYPE: DNA
<213> ORGANISM: Homo sapiens

<400> SEQUENCE: 441
atccttctgg gaccctcatc                                        20

<210> SEQ ID NO 442
<211> LENGTH: 20
<212> TYPE: DNA
<213> ORGANISM: Homo sapiens

<400> SEQUENCE: 442
gctttgcttc cttcttggtg                                        20

<210> SEQ ID NO 443
<211> LENGTH: 20
<212> TYPE: DNA
<213> ORGANISM: Homo sapiens

<400> SEQUENCE: 443
caacattacg gccagtctca                                        20

<210> SEQ ID NO 444
<211> LENGTH: 20
<212> TYPE: DNA
<213> ORGANISM: Homo sapiens

<400> SEQUENCE: 444
ggtgcatctg ataagccaaa                                        20

<210> SEQ ID NO 445
<211> LENGTH: 20
<212> TYPE: DNA
<213> ORGANISM: Homo sapiens

<400> SEQUENCE: 445
gctgtcttgg acacagtgga                                        20

<210> SEQ ID NO 446
<211> LENGTH: 20
<212> TYPE: DNA
<213> ORGANISM: Homo sapiens

<400> SEQUENCE: 446
caccatcatc atctggttgg                                        20

<210> SEQ ID NO 447
<211> LENGTH: 20
<212> TYPE: DNA
<213> ORGANISM: Homo sapiens

<400> SEQUENCE: 447
gagctcattg aaaggcagga                                        20

```
<210> SEQ ID NO 448
<211> LENGTH: 25
<212> TYPE: DNA
<213> ORGANISM: Homo sapiens

<400> SEQUENCE: 448
ccatccatct atccatttat ctctg                                              25

<210> SEQ ID NO 449
<211> LENGTH: 20
<212> TYPE: DNA
<213> ORGANISM: Homo sapiens

<400> SEQUENCE: 449
ggatttatcc ttgccctgct                                                    20

<210> SEQ ID NO 450
<211> LENGTH: 23
<212> TYPE: DNA
<213> ORGANISM: Homo sapiens

<400> SEQUENCE: 450
ctatcatcca tccatcctat ttg                                                23

<210> SEQ ID NO 451
<211> LENGTH: 20
<212> TYPE: DNA
<213> ORGANISM: Homo sapiens

<400> SEQUENCE: 451
ttagggcagc tacctggaaa                                                    20

<210> SEQ ID NO 452
<211> LENGTH: 20
<212> TYPE: DNA
<213> ORGANISM: Homo sapiens
<220> FEATURE:
<221> NAME/KEY: misc_feature
<222> LOCATION: 8
<223> OTHER INFORMATION: n = A,T,C or G

<400> SEQUENCE: 452
aggactanag atgaatgctc                                                    20

<210> SEQ ID NO 453
<211> LENGTH: 20
<212> TYPE: DNA
<213> ORGANISM: Homo sapiens

<400> SEQUENCE: 453
gacatgactc catgtttggt                                                    20

<210> SEQ ID NO 454
<211> LENGTH: 20
<212> TYPE: DNA
<213> ORGANISM: Homo sapiens

<400> SEQUENCE: 454
cctcaccttg caatttcctg                                                    20

<210> SEQ ID NO 455
<211> LENGTH: 20
<212> TYPE: DNA
<213> ORGANISM: Homo sapiens
```

```
<400> SEQUENCE: 455
ctgacttgcc tgttggcata                                          20

<210> SEQ ID NO 456
<211> LENGTH: 21
<212> TYPE: DNA
<213> ORGANISM: Homo sapiens

<400> SEQUENCE: 456
tttgggatct tgaagacctt t                                        21

<210> SEQ ID NO 457
<211> LENGTH: 19
<212> TYPE: DNA
<213> ORGANISM: Homo sapiens

<400> SEQUENCE: 457
ttgtggcatg tccttggtt                                           19

<210> SEQ ID NO 458
<211> LENGTH: 23
<212> TYPE: DNA
<213> ORGANISM: Homo sapiens

<400> SEQUENCE: 458
tgtacactgc aaacattgct aaa                                      23

<210> SEQ ID NO 459
<211> LENGTH: 24
<212> TYPE: DNA
<213> ORGANISM: Homo sapiens

<400> SEQUENCE: 459
ttgtcctttc attatgacgt gtct                                     24

<210> SEQ ID NO 460
<211> LENGTH: 23
<212> TYPE: DNA
<213> ORGANISM: Homo sapiens

<400> SEQUENCE: 460
aagcctgaaa ggatacacac aaa                                      23

<210> SEQ ID NO 461
<211> LENGTH: 20
<212> TYPE: DNA
<213> ORGANISM: Homo sapiens

<400> SEQUENCE: 461
caggatccca gactttccag                                          20

<210> SEQ ID NO 462
<211> LENGTH: 20
<212> TYPE: DNA
<213> ORGANISM: Homo sapiens

<400> SEQUENCE: 462
ggtgaatccc accctcatac                                          20

<210> SEQ ID NO 463
<211> LENGTH: 24
<212> TYPE: DNA
```

-continued

<213> ORGANISM: Homo sapiens

<400> SEQUENCE: 463
ttggtatgtt tcctattgtt gcat                                    24

<210> SEQ ID NO 464
<211> LENGTH: 21
<212> TYPE: DNA
<213> ORGANISM: Homo sapiens

<400> SEQUENCE: 464
gaaccagtga gttttatta c                                        21

<210> SEQ ID NO 465
<211> LENGTH: 21
<212> TYPE: DNA
<213> ORGANISM: Homo sapiens

<400> SEQUENCE: 465
agacacagca tataatacat g                                       21

<210> SEQ ID NO 466
<211> LENGTH: 20
<212> TYPE: DNA
<213> ORGANISM: Homo sapiens

<400> SEQUENCE: 466
tgaagctttg tggcttgttg                                         20

<210> SEQ ID NO 467
<211> LENGTH: 20
<212> TYPE: DNA
<213> ORGANISM: Homo sapiens

<400> SEQUENCE: 467
gactgagtcc acagcccatt                                         20

<210> SEQ ID NO 468
<211> LENGTH: 25
<212> TYPE: DNA
<213> ORGANISM: Homo sapiens

<400> SEQUENCE: 468
cctggcctgt tagtttttat tgtta                                   25

<210> SEQ ID NO 469
<211> LENGTH: 22
<212> TYPE: DNA
<213> ORGANISM: Homo sapiens

<400> SEQUENCE: 469
cccagtcttg ggtatgtttt ta                                      22

<210> SEQ ID NO 470
<211> LENGTH: 20
<212> TYPE: DNA
<213> ORGANISM: Homo sapiens

<400> SEQUENCE: 470
ccaccatgca agaacagatg                                         20

<210> SEQ ID NO 471
<211> LENGTH: 20

```
<212> TYPE: DNA
<213> ORGANISM: Homo sapiens

<400> SEQUENCE: 471
gctttgcact tggctgtctt                                              20

<210> SEQ ID NO 472
<211> LENGTH: 24
<212> TYPE: DNA
<213> ORGANISM: Homo sapiens

<400> SEQUENCE: 472
ttgcatgaag taaagtatcc ctgt                                         24

<210> SEQ ID NO 473
<211> LENGTH: 21
<212> TYPE: DNA
<213> ORGANISM: Homo sapiens

<400> SEQUENCE: 473
cacaaaccac aagatgattg g                                            21

<210> SEQ ID NO 474
<211> LENGTH: 21
<212> TYPE: DNA
<213> ORGANISM: Homo sapiens

<400> SEQUENCE: 474
gggcatcatg tctacaactc a                                            21

<210> SEQ ID NO 475
<211> LENGTH: 20
<212> TYPE: DNA
<213> ORGANISM: Homo sapiens

<400> SEQUENCE: 475
accaagggca cttgctgata                                              20

<210> SEQ ID NO 476
<211> LENGTH: 20
<212> TYPE: DNA
<213> ORGANISM: Homo sapiens

<400> SEQUENCE: 476
aggatgaaga gggaggaagg                                              20

<210> SEQ ID NO 477
<211> LENGTH: 26
<212> TYPE: DNA
<213> ORGANISM: Homo sapiens

<400> SEQUENCE: 477
ccagactgat cttccttaat tagttg                                       26

<210> SEQ ID NO 478
<211> LENGTH: 20
<212> TYPE: DNA
<213> ORGANISM: Homo sapiens

<400> SEQUENCE: 478
cctcctcttt ctgctgctgt                                              20

<210> SEQ ID NO 479
```

```
<211> LENGTH: 21
<212> TYPE: DNA
<213> ORGANISM: Homo sapiens

<400> SEQUENCE: 479
agccaaagaa cccaaagaaa c                                          21

<210> SEQ ID NO 480
<211> LENGTH: 20
<212> TYPE: DNA
<213> ORGANISM: Homo sapiens

<400> SEQUENCE: 480
gccctacttt gcctcagaaa                                            20

<210> SEQ ID NO 481
<211> LENGTH: 20
<212> TYPE: DNA
<213> ORGANISM: Homo sapiens

<400> SEQUENCE: 481
gcaactcatg ccagcctcta                                            20

<210> SEQ ID NO 482
<211> LENGTH: 22
<212> TYPE: DNA
<213> ORGANISM: Homo sapiens

<400> SEQUENCE: 482
aactgtgtta atgatgggca aa                                         22

<210> SEQ ID NO 483
<211> LENGTH: 20
<212> TYPE: DNA
<213> ORGANISM: Homo sapiens

<400> SEQUENCE: 483
aacgagcgca tgaaacctat                                            20

<210> SEQ ID NO 484
<211> LENGTH: 20
<212> TYPE: DNA
<213> ORGANISM: Homo sapiens

<400> SEQUENCE: 484
cctggtcaat tgaacccaaa                                            20

<210> SEQ ID NO 485
<211> LENGTH: 23
<212> TYPE: DNA
<213> ORGANISM: Homo sapiens

<400> SEQUENCE: 485
tgaaggaaga taaagcaggg taa                                        23

<210> SEQ ID NO 486
<211> LENGTH: 20
<212> TYPE: DNA
<213> ORGANISM: Homo sapiens

<400> SEQUENCE: 486
ctctctctgg ccctctcttg                                            20
```

```
<210> SEQ ID NO 487
<211> LENGTH: 23
<212> TYPE: DNA
<213> ORGANISM: Homo sapiens

<400> SEQUENCE: 487
ggtaacttgc cattcttcta cca                                           23

<210> SEQ ID NO 488
<211> LENGTH: 20
<212> TYPE: DNA
<213> ORGANISM: Homo sapiens

<400> SEQUENCE: 488
actccacctg aagggagaaa                                               20

<210> SEQ ID NO 489
<211> LENGTH: 21
<212> TYPE: DNA
<213> ORGANISM: Homo sapiens

<400> SEQUENCE: 489
tggaagccac taattggaga a                                             21

<210> SEQ ID NO 490
<211> LENGTH: 23
<212> TYPE: DNA
<213> ORGANISM: Homo sapiens

<400> SEQUENCE: 490
aatggatgga tacctcctta tca                                           23

<210> SEQ ID NO 491
<211> LENGTH: 20
<212> TYPE: DNA
<213> ORGANISM: Homo sapiens

<400> SEQUENCE: 491
ctcattgtgg ctttctgtgc                                               20

<210> SEQ ID NO 492
<211> LENGTH: 20
<212> TYPE: DNA
<213> ORGANISM: Homo sapiens

<400> SEQUENCE: 492
gtacccacac ctcaccaagc                                               20

<210> SEQ ID NO 493
<211> LENGTH: 20
<212> TYPE: DNA
<213> ORGANISM: Homo sapiens

<400> SEQUENCE: 493
cgtagctcac attcccaaca                                               20

<210> SEQ ID NO 494
<211> LENGTH: 20
<212> TYPE: DNA
<213> ORGANISM: Homo sapiens

<400> SEQUENCE: 494
ggcgagtgaa agagaggaca                                               20
```

```
<210> SEQ ID NO 495
<211> LENGTH: 20
<212> TYPE: DNA
<213> ORGANISM: Homo sapiens

<400> SEQUENCE: 495
gggtggtaat tcccagatga                                              20

<210> SEQ ID NO 496
<211> LENGTH: 20
<212> TYPE: DNA
<213> ORGANISM: Homo sapiens

<400> SEQUENCE: 496
tctgcaacag ccagaatcaa                                              20

<210> SEQ ID NO 497
<211> LENGTH: 22
<212> TYPE: DNA
<213> ORGANISM: Homo sapiens

<400> SEQUENCE: 497
tgtctgttgg caactttctg tc                                           22

<210> SEQ ID NO 498
<211> LENGTH: 20
<212> TYPE: DNA
<213> ORGANISM: Homo sapiens

<400> SEQUENCE: 498
aggtgaaccc agtccagcta                                              20

<210> SEQ ID NO 499
<211> LENGTH: 20
<212> TYPE: DNA
<213> ORGANISM: Homo sapiens

<400> SEQUENCE: 499
tcttaggcaa aggagccagt                                              20

<210> SEQ ID NO 500
<211> LENGTH: 19
<212> TYPE: DNA
<213> ORGANISM: Homo sapiens

<400> SEQUENCE: 500
acatgagcac tggtgactg                                               19

<210> SEQ ID NO 501
<211> LENGTH: 20
<212> TYPE: DNA
<213> ORGANISM: Homo sapiens

<400> SEQUENCE: 501
ggcctcaaat gttttaagca                                              20

<210> SEQ ID NO 502
<211> LENGTH: 20
<212> TYPE: DNA
<213> ORGANISM: Homo sapiens

<400> SEQUENCE: 502
ttctgggtgt tcgctattcc                                              20
```

```
<210> SEQ ID NO 503
<211> LENGTH: 20
<212> TYPE: DNA
<213> ORGANISM: Homo sapiens

<400> SEQUENCE: 503
tttcctgtcc agtcctgacc                                                   20

<210> SEQ ID NO 504
<211> LENGTH: 22
<212> TYPE: DNA
<213> ORGANISM: Homo sapiens

<400> SEQUENCE: 504
gttttgcagg tctaggtcac ac                                                22

<210> SEQ ID NO 505
<211> LENGTH: 17
<212> TYPE: DNA
<213> ORGANISM: Homo sapiens

<400> SEQUENCE: 505
aggatagctt gagcccg                                                      17

<210> SEQ ID NO 506
<211> LENGTH: 396
<212> TYPE: DNA
<213> ORGANISM: Homo sapiens

<400> SEQUENCE: 506
gattatatcc cacctaccac tgcagctcca ggatccagct tcacaaacat ttgttgaatg       60
aatgaataag aaaagaggac accccaaag aggctgcaag ggaaaaagct acaaagacag       120
aagcaccagg aaaagtagg gtcatgtaag tcaaagcagg aaaaaagttc catggtgggg      180
tggtcagcag tgtctaatrc cacgaaggca caaagtagga taaaggttaa aaatcagcct     240
ttggttttgg caaatatgaa gcttatcggt agccttagcg agaacaattc catcaggag      300 cagaagctaa ctgcagtggg ttgagtcatc aagcaggcat aaggaagtag ggatacccca    360
ttataagcta ctctttcaag aagctcaaat ctgaag                               396

<210> SEQ ID NO 507
<211> LENGTH: 396
<212> TYPE: DNA
<213> ORGANISM: Homo sapiens

<400> SEQUENCE: 507
acaaaaatta ccatcatatg ctgtcatgca tgtctgccag tctatttatc atattattta      60
agaaacaaac atttattgaa gatttatcat gtgctcagca ctgccaaaga ggaaataaag    120
agcataatat ctattcttag aaaataacat taacacaaat agaaacaag aaaccataat      180 gttaaaaata ttacatagya acacagaaag acaatgtata attatacata cgcactaaag    240
caaagataac ataatttata aattatgagg tacagaatag ttagattctg aaaattaaaa    300
taatcaggaa aaacttcatg aagatgagat ctgggctgga tcccaaagga taggcaggtg    360
gatcatgtag aacaggggaa aggagttcct gatcgg                              396

<210> SEQ ID NO 508
<211> LENGTH: 396
<212> TYPE: DNA
```

<213> ORGANISM: Homo sapiens

<400> SEQUENCE: 508

```
aactaaagaa agccacaaaa gttcacctca atgccaagac atttcttgat ttttgaaaac    60
ccagttgtcg aaccacccat ctatagaaac ttgaaagact aaaaactatc ttactctaaa   120
cattttctag gaagttgatt ctacaacaca ttttggtttt ccaatttggc ttctaataat   180
tatttcaaag tttctgtgrc ctaaattttg ttttacattg atcctttgaa tggactactg   240
tttccacatt ttagaacatt taaaagata tctacaaccc gagtctaatc ataaaaaaaa   300
tcagacagat ccaaaatgtg aacattcca ctaaaaaagg agtggggaga ggtctttatt   360
cttccaaaaa tatcaatgcc ataaaagaca aagacg                             396
```

<210> SEQ ID NO 509
<211> LENGTH: 396
<212> TYPE: DNA
<213> ORGANISM: Homo sapiens

<400> SEQUENCE: 509

```
acccttcaac cccagcccag ctgctaactg actacagcca catgaacaga accaggtgag    60
accagaggaa acttccagtc acctaccaga tcatgacaaa taataaacga tgttttttaa   120
accacaaaga tttggagcag catttgttac acaaaattag acaactatta cagttcgact   180
aaaaacatgt tcatttacra tactaaatta gaagtgtaag aatgggagaa aaacttcata   240
ctttaaaagt cattttttcc tccaaaaact tccaactttg aaaaactgat ttttataatg   300
cataaaaatt aaaataacct tagaatttat atgagtagca tagccagctg gctttattat   360
ctgttgtact caacacttca ataatcactg atgttt                             396
```

<210> SEQ ID NO 510
<211> LENGTH: 396
<212> TYPE: DNA
<213> ORGANISM: Homo sapiens

<400> SEQUENCE: 510

```
atgaccttac ctcgttttgt tttccttgtc tgagagaaac acattagcag tctcccatct    60
tgttttttcct tttcctgtca cccaggacag agggcagtgg tgtgatcaca gctctgcagc   120
acgacttccc caggttcagg tgatcctccc acctcagcct cccaaggagc tgggaccaca   180
ggcacatgcc accacgtcsa gcttaatttt gtattttttt ggtagagatc aggttttgcc   240
ttattgcccc aagctgatct tgaattcctg ggctgaagca atctgcctgc cctgcctct   300
ccaagtgtta ggattacagg tataagccac cgtgcagcct tatatttgt tttaaatttt   360
cctctgtatt tttctctctg gcaaattgtt taggga                             396
```

<210> SEQ ID NO 511
<211> LENGTH: 396
<212> TYPE: DNA
<213> ORGANISM: Homo sapiens

<400> SEQUENCE: 511

```
tttttttggta gagatcaggt tttgccttat tgccccaagc tgatcttgaa ttcctgggct    60
gaagcaatct gcctgccctg gcctctccaa gtgttaggat tacaggtata agccaccgtg   120
cagccttata ttttgtttta aatttcctc tgtatttttc tctctggcaa attgtttagg   180
gagtttcttt agtttatcrg actaaatttc aaggctttcc ttccaatttt gacatgtaaa   240
cagtccctca tttctgctta tctagtgatt attcccaaat ctgtgtttac agtctagctg   300
```

```
tctctcctga gattaagact tgtttctcta actacctgac ggcagaatct cctcttggaa      360
gtatcaagga ggcagttcaa aactgaactg ggcatt                                396
```

<210> SEQ ID NO 512
<211> LENGTH: 396
<212> TYPE: DNA
<213> ORGANISM: Homo sapiens

<400> SEQUENCE: 512

```
gctgatcttg aattcctggg ctgaagcaat ctgcctgccc tggcctctcc aagtgttagg       60
attacaggta taagccaccg tgcagcctta tattttgttt taaattttcc tctgtatttt      120
tctctctggc aaattgttta gggagtttct ttagtttatc agactaaatt tcaaggcttt      180
ccttccaatt ttgacatgya aacagtccct catttctgct tatctagtga ttattcccaa      240
atctgtgttt acagtctagc tgtctctcct gagattaaga cttgtttctc taactacctg      300
acggcagaat ctcctcttgg aagtatcaag gaggcagttc aaaactgaac tgggcattgg      360
ctccactcct tctccttctc tttactatta ataccc                                396
```

<210> SEQ ID NO 513
<211> LENGTH: 396
<212> TYPE: DNA
<213> ORGANISM: Homo sapiens

<400> SEQUENCE: 513

```
taagtcttat ttaggcatcg tttcttctgg gagacctttg tagaatctct gaggttatgt       60
taacatgcta aggttttctt gacattctca gattgggtta ggtgaacttt tagcaactta      120 tcttttact aaaaagtcat ccctcagtat ctgtggggaa ttggttctag gactccctaa       180
ggatatcaaa atctgcatra gcagcccagg tgagaccagc agaagcactt tacagtcacc      240
tacaggatca tgacaaataa taatcatgt ttaagccaca aagtccttta cataaaatgg       300
tatagtattt gcatataacc tacacatctt cctgtatcct ttaaatcatc tctagtttat      360
aatacctcat acgatgaaaa tactacgtaa atagtt                                396
```

<210> SEQ ID NO 514
<211> LENGTH: 396
<212> TYPE: DNA
<213> ORGANISM: Homo sapiens

<400> SEQUENCE: 514

```
aagcagttcc taattactgg acattctcag atctgctaga gctacatgtc caattacgag       60
aatatactgg aaaagcccct ggattagaaa tgagaggatg taggttttag taccaggtca      120
gccaccttgt taatgcaaat ttgagtaaat tgttacttct tttaggcctt gttttttgctg     180 ttttgttttt ctgacagtmt ggtctctgtg gtccaggctg gagtgcagag cacaatatc       240 aggtccctgc agtctctacc tcccaggatc aagccatttt catgcctcat cctcctgagt      300
agctgggatt acaggcatgt gccaccacac cctcgaactc ctgacctcaa gtgatctgct      360
tgcctcagcc tcccaaagtg ctgggattag aggtgt                                396
```

<210> SEQ ID NO 515
<211> LENGTH: 396
<212> TYPE: DNA
<213> ORGANISM: Homo sapiens

<400> SEQUENCE: 515

```
gaatatactg gaaaaagccc tggattagaa atgagaggat gtaggtttta gtaccaggtc    60
agccaccttg ttaatgcaaa tttgagtaaa ttgttacttc ttttaggcct tgttttttgct  120 gttttgtttt tctgacagta tggtctctgt ggtccaggct ggagtgcaga ggcacaatat   180
caggtccctg cagtctctrc ctcccaggat caagccattt tcatgcctca tcctcctgag   240
tagctgggat tacaggcatg tgccaccaca ccctcgaact cctgacctca agtgatctgc   300
ttgcctcagc ctcccaaagt gctgggatta gaggtgtgag ccactgtgcc tagccttaca   360
cattgttttc ttactggtaa agtgggaata tctaga                             396
```

<210> SEQ ID NO 516
<211> LENGTH: 396
<212> TYPE: DNA
<213> ORGANISM: Homo sapiens

<400> SEQUENCE: 516

```
gttttgtttt tctgacagta tggtctctgt ggtccaggct ggagtgcaga ggcacaatat    60
caggtccctg cagtctctac ctcccaggat caagccattt tcatgcctca tcctcctgag   120
tagctgggat tacaggcatg tgccaccaca ccctcgaact cctgacctca agtgatctgc   180
ttgcctcagc ctcccaaakt gctgggatta gaggtgtgag ccactgtgcc tagccttaca   240
cattgttttc ttactggtaa agtgggaata tctagaagtt gcatgctaca taaattcaac   300
catatattat tggcaaaaaa ttttaaagaa aaacatcagc ttaagagtac taattgagta   360
catgccttgg aatgagcatg agctggaaag aacaaa                             396
```

<210> SEQ ID NO 517
<211> LENGTH: 396
<212> TYPE: DNA
<213> ORGANISM: Homo sapiens

<400> SEQUENCE: 517

```
ggcaaaaaat tttaaagaaa aacatcagct taagagtact aattgagtac atgccttgga    60
atgagcatga gctggaaaga acaaacctgt tgttacatca ctcattgctg ttttcatatg   120
ctgctcattg taaatcttgc tcagtggcat gattttagtg tttaaagatt tatttgtttg   180
tttgtttagg acaaagtcyc tacacataat ctacttgctt catatataca tacttatgca   240
tattatgtat gtacatacat gctctcaggg ctcacatgaa aaaacagcca ttcaggtgat   300
gtgatttatc tcatatgctt actttagagt caacagggtg ttgactccac tatacaatac   360
tggcatggag aacacataag tcaaagtaga caggac                             396
```

<210> SEQ ID NO 518
<211> LENGTH: 396
<212> TYPE: DNA
<213> ORGANISM: Homo sapiens

<400> SEQUENCE: 518

```
tttatttgtt tgtttgttta ggacaaagtc tctacacata atctacttgc ttcatatata    60
catacttatg catattatgt atgtacatac atgctctcag ggctcacatg aaaaaacagc   120
cattcaggtg atgtgattta tctcatatgc ttactttaga gtcaacaggg tgttgactcc   180
actatacaat actggcatrg agaacacata agtcaaagta gacaggaccc agccgtacca   240
ttggctaggg cacaaatata ttcacatatg tggagaatga tgtacgtaga aaggtcttca   300
ttgcacaatg ctctttaata aagatctgga aaaaaaaaac acctaaatgt tcaaaggat    360 agggtagatg aaataatggt acattataaa atggaa                             396
```

<210> SEQ ID NO 519
<211> LENGTH: 396
<212> TYPE: DNA
<213> ORGANISM: Homo sapiens

<400> SEQUENCE: 519

| | | | | | |
|---|---|---|---|---|---|
| tctgtcaccc | aggctggagt | gcagtggcat | gatcatgtct | ccttgcagcc | ttgacttccc | 60 |
| tggctcaggt | gggcctccca | cctcagtctc | ccaagtagct | ggaactacag | tcgtgcacca | 120 |
| ccatagccag | ctaagatagt | gagatggtgg | ccccactgtc | ttgcccaggc | tggactcgat | 180 |
| ttcctgggtg | caagcaccst | tcccgcctca | gcctcccaaa | gtgctgggat | tacaggcatg | 240 |
| agtcaccatt | ccagcctact | tgtctttaat | tcttaaaaat | attaatgttg | agttttgtct | 300 |
| cccagcatgt | gggaaagatg | tcatccattg | cttctgtttc | ctggaggcct | gggagcaagg | 360 |
| agcccaggaa | cagtatcacg | aagcttgaga | taatac | | | 396 |

<210> SEQ ID NO 520
<211> LENGTH: 396
<212> TYPE: DNA
<213> ORGANISM: Homo sapiens

<400> SEQUENCE: 520

| | | | | | |
|---|---|---|---|---|---|
| atcattgatg | ggcatttggg | ttggttccaa | gtctttgcta | ttgtgatttt | tttttttttt | 60 |
| tttttttttt | taagacagag | cctcactctg | ttgcccaggc | tggagtgcga | tggcatgatc | 120 |
| tcagctcact | gcaacctccg | cctctcaggt | tcaagcaatt | cttctgcctc | agcctcccaa | 180 |
| gtagctggga | ctacaggcrc | ccaccaccag | gcccagctaa | ttttttgtatt | tttagtagag | 240 |
| acagggtttc | accatgttgg | tcaggctggt | cttgaactcc | agacctcatg | atctgcctgc | 300 |
| cttggcctcc | caaagtgctg | aaattacagg | tgtgagccac | catacctggc | ctaggcagtc | 360 |
| tttttcaaaa | ctctaagact | gtgcttgtgt | ctcagg | | | 396 |

<210> SEQ ID NO 521
<211> LENGTH: 395
<212> TYPE: DNA
<213> ORGANISM: Homo sapiens

<400> SEQUENCE: 521

| | | | | | |
|---|---|---|---|---|---|
| ggtatgaggt | aaggatccat | ttttttccca | tttgcatagc | cagttttttgt | agctccactt | 60 |
| tattttctca | cttgatctgc | catgccacct | ctagcatgta | tcaacatatc | atgtatgtgt | 120 |
| gcagctgttc | cttaactctc | aatttttattc | tcttggttac | tttgtctaac | ccagcactca | 180 |
| tacttttttaa | attattaygg | ctaccttgta | gggcaagaat | cctcacttttt | attcaacttc | 240 |
| ttttgaagtg | tcttgatgca | tatttttttct | gatcttactt | ggccatatat | attttgggga | 300 |
| cagatgtgac | atcataccaa | gctttctttg | cttgacattg | tagatatttt | cttattcatt | 360 |
| aatgtgctaa | aaattttgag | tttggtcata | cagtc | | | 395 |

<210> SEQ ID NO 522
<211> LENGTH: 396
<212> TYPE: DNA
<213> ORGANISM: Homo sapiens

<400> SEQUENCE: 522

| | | | | | |
|---|---|---|---|---|---|
| gtttctaaca | ttatagacac | tagttttagg | ctcttggagg | ctagcagcaa | ttctcagagg | 60 |
| taatgcaagc | ttccccattt | cttcccgtag | tcctgtgaaa | gaccagccac | ctccagaagc | 120 |

```
ctacacatga gtcttctcag ccatactttc tgcttttcct aatgcctctc agcagcgtat    180
tagaaaggcc atgatcgayg tacctgttac cttcaggctt tgcataaggt gtatatgaaa    240
cataatgaat ttcgtgttta ggctcaggtc ccatccccag gttacctctt tatcttggag    300
acacttctgg tcccatacat ttcagataag agatattcaa cctgtaccca ccacgtaagg    360
agaggaatag gttttagaag aggagtcagg gaggca                              396
```

<210> SEQ ID NO 523
<211> LENGTH: 396
<212> TYPE: DNA
<213> ORGANISM: Homo sapiens

<400> SEQUENCE: 523

```
gcatctatta aaagtgatgg ttttagtatc ctgtctcatt ttttcctttc cttacatcat     60
gtattatagg taaacacatg cgcatgtgtg tatttctctt ttagacaaag gatgagatta    120
ctactgttag ctcagttttt ttttccctac ttaacatctt tgcttttatt ttttagacat    180
atttctaaga ctattaaaya ttagacttac gtagcccttc tgtcattgtg aaatacatag    240
tttactaaca gctaccatca agataaagcc tttatttaaa taattaaact tcttagtgga    300
aagctaagta agcacagttt atggattttg gaattttttg ccttgcattt gtctgatatg    360
gtaaaatatt gagtttgttt ttctcataat gttcac                              396
```

<210> SEQ ID NO 524
<211> LENGTH: 396
<212> TYPE: DNA
<213> ORGANISM: Homo sapiens

<400> SEQUENCE: 524

```
gataactcaa tccccttaaa gggttgtatc aagccattga taagggctca ctttgatata     60 accatttttct gttatttaga cactcttttca cacttcctat tttcctcctg gggatggttt    120
gaatggatga cacaatacca tattataaaa gcactttaca aactgtaact tatgttataa    180
atgtaattat taccttaarg ttttaccctg tttcagattt gagtggaagt agttcttttac    240 aatacaaaac aacttatttt aacttttttt gcatttcaaa gaatgatcaa tccacttcag    300
gtgcagcatg gtttccaacc ctgacagcat ggaagaatca tttatttagc ttctaaaaat    360
gtgcaggctg taccctagac cagccttggg gattag                              396
```

<210> SEQ ID NO 525
<211> LENGTH: 396
<212> TYPE: DNA
<213> ORGANISM: Homo sapiens

<400> SEQUENCE: 525

```
tcctctctct cattctctct ctctctctct ttctctctct ccttctttgc tccttcattc     60
cttctctctc tctctttttt ttttgagaca gcatctcact atattgccca ggctgttctc    120
aaactcctgg gctcaagtga tcctcctgcc tcagcttcct gagtagctag gactacaggc    180
acatgctatg gcaatactrt tttaaacatt gttttcaagg ctccccaggt gattccagtg    240
tgggtcatgt ggtagagaac cactgacaca ggcaaacaaa ggatacataa agttgtctat    300
ttaatgggta ggtgcaggta gtagataaga gtgtagccac ataaaccaca tgcttagtga    360
acggttttgt tttgtgtgta tgtgagggat tagcat                              396
```

<210> SEQ ID NO 526
<211> LENGTH: 396

```
<212> TYPE: DNA
<213> ORGANISM: Homo sapiens

<400> SEQUENCE: 526
ttcaggttcc atttagcacg acagcaggga agggactgtt ggcagaaaaa aactggggca      60
gtgggattaa agacagacca cacattccaa aaggcaccgt gggagggtca ggggggcgagg    120
ttaggtctag gcttcagtgt cctgggagac tcagtcttca cagggtgaca gcgatcaaga    180
gtgcagctta ggctgggtrc agtggctcat gcctgtagtc ccagcacttt gggaggccga    240
gacgggagga ttgcttgaag ccaggagttt gagaccagtc tgaccaacat ggcaaaaccc    300
catctctact aaaaatacaa aaatcaactg gcatggtgg cgtgtgcctg tagtcccagc     360
tacttgagag gctgaggcaa gagaatcact tgaacc                              396

<210> SEQ ID NO 527
<211> LENGTH: 396
<212> TYPE: DNA
<213> ORGANISM: Homo sapiens

<400> SEQUENCE: 527
taaatgatca ttatgttcat attcacacat acaataatgt actcaagttt attgctaagg     60
taattcagaa tctccttatt ttgaagtgtg catttgatat acctgtttgg gaataactag    120
tttcttatct ttgacagaaa ataattttgt tgttttgttt ttactaaaaa agcatggtga    180
aaaatggctc catttctawg agaggtaact aaaaatatcgc aatttgctgg gtgtcattaa    240
agtaactcac aagggaaaaa atgcaaattg gtatctgctg atggagtaaa tctccgcaga    300
agtgatgacc ctgaaaggat caatatatta agcccctcc cagctggtca ttccagattg     360
caacaataaa gcattaagtg ttaaaacctc aaggca                              396

<210> SEQ ID NO 528
<211> LENGTH: 396
<212> TYPE: DNA
<213> ORGANISM: Homo sapiens

<400> SEQUENCE: 528
ctcatcaagc ccacctttat acttcatttc tccagacttc atgtccagac tgtgggatga     60
acaagtggtt ataaggtttt agaggctcct gtaggactag atggaaggca aaaaaggaa    120
ataaccttta agcatgctct cgattcctta aatcccatct gaaagtctta aggatgtctt    180
ctcagtcata cttatttgrc aatattacct aattttctcc attagcccaa gctcaggggt    240
cttctcttctt ccatattcac atgggtgcaa tggttttctg aaaggaaaac agcattacta    300
gggcagtaac atttaattaa tcacaggtac ttatcaaact acaaaacagg cattccagga    360
actgggtgtt tctgtttgta aaattacact ctcgtg                              396

<210> SEQ ID NO 529
<211> LENGTH: 396
<212> TYPE: DNA
<213> ORGANISM: Homo sapiens

<400> SEQUENCE: 529
taggactaga tggaaggcaa aaaaaggaaa taacctttaa gcatgctctc gattccttaa     60
atcccatctg aaagtcttaa ggatgtcttc tcagtcatac ttatttgaca atattaccta    120
attttctcca ttagcccaag ctcagggtc tttcttcttc catattcaca tgggtgcaat     180
ggttttctga aaggaaaaya gcattactag ggcagtaaca tttaattaat cacaggtact    240
```

```
tatcaaacta caaaacaggc attccaggaa ctgggtgttt ctgtttgtaa aattacactc    300
tcgtgtacat gctcccacta aaatgtaagt tcgctgagga tggaggtttt ggtctctttg    360
ctctgtgctg taaccccaac actgcagcag ggcctg                              396
```

<210> SEQ ID NO 530
<211> LENGTH: 396
<212> TYPE: DNA
<213> ORGANISM: Homo sapiens

<400> SEQUENCE: 530

```
gctgcatagt ctcacttagg tgtggaatct aaaaaagtca aattaaaaaa aaatgtcaag     60
cagagaatag aatggtagtt gccagggact ctgggaagta gcaggggtgg gggtggaggg    120
gaggggatgg gcagaagttg gtcaaaaggt acaaagtttc aggtagacag gtgtaagttc    180
tggggatcta ttgtacagmg tggtgactgt agttaatact gtattgtgta cttaaaaatt    240
gctcaccaaa aatgttctca ccaaaaaaat gatgtttgga tatgttaaac agtttgattt    300
aatcattttg acgtgtgtgt gtgtgtgtgt gtgtgtgtgt gtgtgtatac atcaaaacat    360
cacattatat accatataca attaatatat acaatt                              396
```

<210> SEQ ID NO 531
<211> LENGTH: 396
<212> TYPE: DNA
<213> ORGANISM: Homo sapiens

<400> SEQUENCE: 531

```
ggggtaaatg ctgactgcct gttctctgga caggaatgga gaagatggtg ctagcagggt     60
tgctgttcat atgtagacat tcatgcagtc actctctttt cagcacactt cttacttctg    120
ccctgggttc agttgctgac tctgagccca gaaaccttct agggttctgt taggtagatt    180
ggcttccacc gtctttgcra caaccacaga aaattctaga ctgttttctc ttcgggcttc    240
attagtcaac ttgcttcagt ctgtcttgca tcttctaaat atttatagat ctctctcttt    300
tgttggagtg gcagaaaatg ctagttgacc acccaatatt caaattatcc tgcctcctta    360
ataacagaat atcattggat gtggtgggta aataat                              396
```

<210> SEQ ID NO 532
<211> LENGTH: 396
<212> TYPE: DNA
<213> ORGANISM: Homo sapiens

<400> SEQUENCE: 532

```
atggagaaga tggtgctagc agggttgctg ttcatatgta gacattcatg cagtcactct     60
cttttcagca cacttcttac ttctgccctg ggttcagttg ctgactctga gcccagaaac    120
cttctagggt tctgttaggt agattggctt ccaccgtctt tgcgacaacc acagaaaatt    180
ctagactgtt ttctcttcrg gcttcattag tcaacttgct tcagtctgtc ttgcatcttc    240
taaatattta tagatctctc tcttttgttg gagtggcaga aaatgctagt tgaccaccca    300
atattcaaat tatcctgcct ccttaataac agaatatcat tggatgtggt gggtaaataa    360
tataccctaa ctttccttgc agagaggggt ggccaa                              396
```

<210> SEQ ID NO 533
<211> LENGTH: 396
<212> TYPE: DNA
<213> ORGANISM: Homo sapiens

<400> SEQUENCE: 533

```
cagggttgct gttcatatgt agacattcat gcagtcactc tcttttcagc acacttctta      60
cttctgccct gggttcagtt gctgactctg agcccagaaa ccttctaggg ttctgttagg     120
tagattggct tccaccgtct ttgcgacaac cacagaaaat tctagactgt tttctcttcg     180
ggcttcatta gtcaacttkc ttcagtctgt cttgcatctt ctaaatattt atagatctct     240
ctcttttgtt ggagtggcag aaaatgctag ttgaccaccc aatattcaaa ttatcctgcc     300
tccttaataa cagaatatca ttggatgtgg tgggtaaata atataccta actttccttg      360 cagagagggg tggccaatga gatggaaatg aaagtc                               396
```

<210> SEQ ID NO 534
<211> LENGTH: 396
<212> TYPE: DNA
<213> ORGANISM: Homo sapiens

<400> SEQUENCE: 534

```
tgggattgag ttcttgattt gattttgagc ttggccatca ttggtgtata gcagtgctag      60
tgatttgtgt acattgattt tgtaacctaa cactactaaa ttcacttatc aaatctggga     120 gattttgag gattccttag gattttctag gtatgagatc atatcattgg tagaggtagt     180
ttgagtttct cttttccart ttggatgccc tttattcttt tctcttgcct gattgctctg     240
actagggctt ctagtactat gttgaataga aatggtgaaa agtgggcatc cttgtctcat     300
tctaattttt aggggaaat gctttcaact tttccccatt cattttgatg ttggctgtga      360
gtttgtcata gatgattctt actattttga gatata                               396
```

<210> SEQ ID NO 535
<211> LENGTH: 396
<212> TYPE: DNA
<213> ORGANISM: Homo sapiens

<400> SEQUENCE: 535

```
tcttttgccc tgcctttctg cctttctgtc cttttaattt gcgggctttt ggcaaccaca      60
gcacgggtct ggtttcctag gagtttcttt tgtaggatca aaccgctagt tggctcttgg     120
ccctgtgata gggccctggg ctaacttatt gggaaatgt tgctgtaacc cctgcccaga      180
ggtgcctgtg acatgggcyg ccatcttctc ctcttcctt ggcttcagcc ccacctagaa      240
acctgaacaa acatttcct tgacatttca taaagtgtca gtggctcctc atttagcaaa      300
atacatccca gggaagttca aaagtgaaaa aaggccgtaa cttcttcttc ttctcaggga     360
cctacagaaa atatgtggca cctcggcagc ctggcc                               396
```

<210> SEQ ID NO 536
<211> LENGTH: 396
<212> TYPE: DNA
<213> ORGANISM: Homo sapiens

<400> SEQUENCE: 536

```
catggatttt gttttccaag tggcaagatg gcgcctccac ctttggtatc ctattttagt      60
tcctggcaga aagaaaggaa caggctaatg gccctgatga gtctaccccc ttttaacagg     120
agaaaattta aaaacaaaa accatgaaac cctttcccag aggcaacaac cagaattcca      180
tttatctttc attgaccara acagaccaca tggtcactgg tggtgcaat ggagactggg      240 gagatgaata tttttaaggt ggcatattcc agaagaacac tgtgcactga ttgcattaat     300
gaacccatta atgtgccaag gggaggttta cctatgagca tgggcaaatt agaacccact     360
```

```
<210> SEQ ID NO 537
<211> LENGTH: 396
<212> TYPE: DNA
<213> ORGANISM: Homo sapiens

<400> SEQUENCE: 537
tggtggtggc aatggagact ggggagatga atattttaa  gtggcatat  tccagaagaa   60
cactgtgcac tgattgcatt aatgaaccca ttaatgtgcc aaggggaggt ttacctatga  120
gcatgggcaa attagaaccc actcttggag ctgcaggtga gccaatccca cctaaacagt  180
gtggatgcta caagatggrg aagtaaattg attctattcc atacccctaac ctctctccaa  240
gatgtattct taaaatagaa gagggaagac agaagaaaac atccagaata tatttttatt  300
gtcttttact tcttcagtgc attttagatc agtgcttctc aatctggcaa ggggcatgca  360
ggaggatgtg agttttatca ggaaaactac acaacc                            396

<210> SEQ ID NO 538
<211> LENGTH: 396
<212> TYPE: DNA
<213> ORGANISM: Homo sapiens

<400> SEQUENCE: 538
tgagccaatc ccacctaaac agtgtggatg ctacaagatg gggaagtaaa ttgattctat   60
tccataccct aacctctctc caagatgtat tcttaaaata gaagagggaa gacagaagaa  120
aacatccaga atatatttt attgtctttt acttcttcag tgcattttag atcagtgctt  180
ctcaatctgg caaggggcrt gcaggaggat gtgagtttta tcaggaaaac tacacaaccc  240
cccaaccaca atgctacccc cactcctgtg gaccttcttt aagagagact cactattata  300
gatggagttg atacgatttt aagagaggcc atatattatt tgctttctgt cttgaaaaac  360
ttgtgatttt tctgtattgt gctactgcca aagaga                            396

<210> SEQ ID NO 539
<211> LENGTH: 396
<212> TYPE: DNA
<213> ORGANISM: Homo sapiens

<400> SEQUENCE: 539
gggttgcagt gagcagagat cacaccattg cactccagcc tgggtggcag agcgagattc   60
tgtctaaaaa acaacaccgt atttggggca tgctgatact aaaaaattat tcattgtttg  120
tctgaaatta aaatttaaat tggggcccct gtattttact gggcaaccca tttgcaatat  180
cagcaacaat ctcttattsa gaccactgat taagtgtgca aaatttgaat ctctgaacag  240
tacctatgtc cttgatatct taaattaatg agtgtcttag acactcaaag caggaggaag  300
cattatggca gatgtttgag ccccagagat gtccatgagc acagcataga gctcagagcc  360
ttctttatta tttgcttcac gacagagcaa aggact                            396

<210> SEQ ID NO 540
<211> LENGTH: 396
<212> TYPE: DNA
<213> ORGANISM: Homo sapiens

<400> SEQUENCE: 540
catttgcaat atcagcaaca atctcttatt cagaccactg attaagtgtg caaaatttga   60
atctctgaac agtacctatg tccttgatat cttaaattaa tgagtgtctt agacactcaa  120
```

```
agcaggagga agcattatgg cagatgtttg agcccagag atgtccatga gcacagcata    180
gagctcagag ccttctttrt tatttgcttc acgacagagc aaaggactgc agcaggttga    240
ctgatataaa agttttacca tgtctcacag caggcctttg ctcaagtttc agtaaggat     300 attgtatcat ttcttgcctg cagtacttgt aaatccactt acactgcctg ctgttgagtc    360
atttgtttcg tcttgagtag catgtcatcc ttgttc                              396

<210> SEQ ID NO 541
<211> LENGTH: 396
<212> TYPE: DNA
<213> ORGANISM: Homo sapiens

<400> SEQUENCE: 541
ttgcagttct cattgctggg gagtctaaac tggaataaaa cacccactat ctccatcagg    60
cttgcactag agcccagctc tagctggaga gaaagaagct aacccgcaca gacacaggac    120
tgtaggcagg gagcatccgg gggtatttgg gtcctggctc tgatgtgcct aaggccaact    180
tctctctggc catgctggyg tgcatgagct cactaatctt ccttttttgcc ttccattttc    240 tccaatcctg acttagcaaa ggttgggcaa aagagactct gtgtgagttc gagcaaagcc    300
tgagatgctg gattttccaa gatacgagaa ggggctgggg gctgggtgaa ctggtggtgg    360
aggagggaag gattaatttc ccaaggaggg gaaggg                              396

<210> SEQ ID NO 542
<211> LENGTH: 396
<212> TYPE: DNA
<213> ORGANISM: Homo sapiens

<400> SEQUENCE: 542
gagaaagaag ctaacccgca cagacacagg actgtaggca gggagcatcc gggggtattt    60
gggtcctggc tctgatgtgc ctaaggccaa cttctctctg gccatgctgg cgtgcatgag    120
ctcactaatc ttccttttg ccttccattt tctccaatcc tgacttagca aaggttgggc     180
aaaagagact ctgtgtgart tcgagcaaag cctgagatgc tggattttcc aagatacgag    240
aaggggctgg ggctgggtg aactggtggt ggaggaggga aggattaatt tcccaaggag     300
gggaaggggc caggacatca ggccccgggg acttgaaga gagggtcgtg ggtaggaggt     360
agatcaagtg gagtgacaca aaggtcagga aagagg                              396

<210> SEQ ID NO 543
<211> LENGTH: 396
<212> TYPE: DNA
<213> ORGANISM: Homo sapiens

<400> SEQUENCE: 543
catgcctcct acaaatttga cctgggccca gggccatgtt cggtggtttt taagaaccga    60
ggctcccaga agcagtattg ggcagctaga gtggcccag gatctatatc aaactctacc     120
tgtttctgaa ccaaatttct tctagaattt tattccataa atctgaatta tggtgtcaga    180
ctcctagcat acactaaakg aactctctgc cttgcattaa ataacaggag ttaccctgg     240 aggtaactcc tagcccctggc tctttagaga acagatgccg aataggcatt aggggatgtg    300
atggatgtgc taactttcaa aaaaaaaaaa aaaaaaggc ctgagctgag tgctcagaga     360
ttcacaaaaa gctgacagca tctctctgtt ccattg                              396

<210> SEQ ID NO 544
```

<211> LENGTH: 396
<212> TYPE: DNA
<213> ORGANISM: Homo sapiens

<400> SEQUENCE: 544

```
ctttggagcc tggcagcctg gctttgagaa ccgggcttta acttgtcaca tgactatggc    60
caagttcctg gggctctcca agcttcactt cctctgtaaa aagggcaata atataatacc   120
tgtcttattg ggttttgtcc atgttagatg agacattggg tacaaagcac ttggtcccgt   180
gcctggcaca tttactgcrc ttaatgtatg atagttttct tattattcta ataaacaata   240
tggctttggg agtatagttc tgccacattg cagtggccag agtgaaggtg gtgagtgcct   300
tctggggccc tgggagtcaa ggttatccgc atgccctttc ttgcttgctc ctcagtgtgg   360
ctgcctctat gtccacacca tgcagatgca acaggt                             396
```

<210> SEQ ID NO 545
<211> LENGTH: 396
<212> TYPE: DNA
<213> ORGANISM: Homo sapiens

<400> SEQUENCE: 545

```
acatgatcat cccttgggc ttctggtttt ttttctttca ggaccttatt ttcaggcaag     60
tggcctttga cctctaaggc tgtccttcc tagctaccga atccagcatt caaagtgatg    120
gaaatatgta tatatagtaa tagtaaaata tcagcactta atggcctgat aagaatgtca   180
ctgcaatgct gagtttggrc caacatttgc ctgctcctgc cattgagccc gggctcccct   240
ccagagctga gctgctgcaa gggatctgag taactagggc tgtgtcagag tggcgatgac   300
agccaccaca tgctaaggaa gagatcccca aggacaagga gaatcccacg tggagctact   360
tgcttctttg tcagtcttgt ttttcttatt tcacaa                             396
```

<210> SEQ ID NO 546
<211> LENGTH: 396
<212> TYPE: DNA
<213> ORGANISM: Homo sapiens

<400> SEQUENCE: 546

```
ccgaatccag cattcaaagt gatggaaata tgtatatata gtaatagtaa aatatcagca    60
cttaatggcc tgataagaat gtcactgcaa tgctgagttt ggaccaacat ttgcctgctc   120
ctgccattga gcccgggctc ccctccagag ctgagctgct gcaagggatc tgagtaacta   180
gggctgtgtc agagtggcra tgacagccac cacatgctaa ggaagagatc cccaaggaca   240
aggagaatcc cacgtggagc tacttgcttc tttgtcagtc ttgttttct tatttcacaa    300 ccttctaaaa cacaatctct caacctctat tgttagcttg cattttcaa tcatgagcac   360 agctttacct ggctccatgc tttgattgac tctacc                             396
```

<210> SEQ ID NO 547
<211> LENGTH: 396
<212> TYPE: DNA
<213> ORGANISM: Homo sapiens

<400> SEQUENCE: 547

```
tcttatttca aaccttcta aaacacaatc tctcaacctc tattgttagc ttgcattttt    60
caatcatgag cacagcttta cctggctcca tgctttgatt gactctacct gccaacactg   120
caacaacagg gaaagggaca ccggcctcat accattagat ggtgtgtagc ctgggcatga   180
ggataattaa aaactcccwa ggggatttta acatgtaaca cagtttggaa accattgatg   240
```

```
taagatcttc ttactcaaca tgtgctccaa ggagctgttg tatcagctta tcagaaatgt    300
agatcaggcc gcacttggac ctgtagaatc agaatctgca ttttatcaga ttccgacatt    360
atttgtatga acattagctt ttgagaagtg ttgctt                              396
```

<210> SEQ ID NO 548
<211> LENGTH: 396
<212> TYPE: DNA
<213> ORGANISM: Homo sapiens

<400> SEQUENCE: 548

```
cttttgacac caactacaag tcaaggggtt ccccaaacca ccctgagttg tgataattcg     60 ctggagatc tgacagaact cactgaaggt tgttatactc atggttgtga tctcttatag    120
ggagggaata cagattaaaa tcagccaaag gaagaagcac acagcacaga gtccaggaca   180
gtgcctgaca tggagcccyt acggtcctct cccgtggagt cacggacagc gccactctcc   240
tggcattgat gtgtgacaac acacagggag tgttccccac cagggaagcc ttggtgtcca   300
gggtctttac tgtggctctg tcacatgagc acagctgact gcccatgcgg ccgatctgtt   360
cccagactct ccaccgctac acatcactca cagtcc                            396
```

<210> SEQ ID NO 549
<211> LENGTH: 396
<212> TYPE: DNA
<213> ORGANISM: Homo sapiens

<400> SEQUENCE: 549

```
gtggctcaca gaactcaggg aaacacagct accagtttat tgcgaaggac attttaaagg     60
ataaaagtag gcagataaag agatgcatag ggcgaggtgt ggaaaggtcc ctagtgcagg    120
agcttctgtc catgtggagc gggggtgcac caccctctca gtacatgaat gagttctcct   180
tcacctgcct atcagccyt acatgttcag ctccccaacc cagtcctctt gggttttat   240 ggaagcttca agacacccac attctttccc cagagtatag ggcaagacct tctctgggga   300
gggttttaag acccacagtc agaaaggtgg ggtggggtca agattagagt cctgccttga   360
cgggcaggtg aaaggggtag ggggagtagg tgagaa                            396
```

<210> SEQ ID NO 550
<211> LENGTH: 396
<212> TYPE: DNA
<213> ORGANISM: Homo sapiens

<400> SEQUENCE: 550

```
cgggggtgca ccaccctctc agtacatgaa tgagttctcc ttcacctgcc tatcagcctc     60
tacatgttca gctccccaac ccagtcctct tgggttttta tggaagcttc aagacaccca    120
cattctttcc ccagagtata gggcaagacc ttctctgggg agggttttaa gacccacagt   180
cagaaaggtg gggtggggkc aagattagag tcctgccttg acgggcaggt gaaaggggta   240
gggggagtag gtgagaaaaa ttctgtttat tttttctttt tttttttgag acggagtttc   300
actcttgttg cccagggtgg agtgcaatgg cacaatctca gctcactgca acctccgcct   360
cccaggttta gcgattctc ctgcctcagc ctcccg                             396
```

<210> SEQ ID NO 551
<211> LENGTH: 396
<212> TYPE: DNA
<213> ORGANISM: Homo sapiens

```
<400> SEQUENCE: 551
atgagttctc cttcacctgc ctatcagcct ctacatgttc agctccccaa cccagtcctc      60
ttgggttttt atggaagctt caagacaccc acattctttc cccagagtat agggcaagac     120
cttctctggg gagggtttta agacccacag tcagaaaggt ggggtggggt caagattaga     180
gtcctgcctt gacgggcarg tgaaaggggt agggggagta ggtgagaaaa attctgttta     240
ttttttcttt ttttttttga gacgagtttt cactcttgtt gcccagggtg gagtgcaatg     300
gcacaatctc agctcactgc aacctccgcc tcccaggttt aagcgattct cctgcctcag     360
cctcccgagt agctgggatt acaggcgtgt gccacc                               396

<210> SEQ ID NO 552
<211> LENGTH: 396
<212> TYPE: DNA
<213> ORGANISM: Homo sapiens

<400> SEQUENCE: 552
tcttcattcc acaaagctca gtgtcaaaac atggggttta cactggaagc tgaggtcaca      60
tcagtagccg ggatcagggt cgccctagct gcccaatgca gctcccaggc ctcctgtaaa     120
accttgacct ttgaggtcat gacagccctc tcctgctatg ctcatagctg accactgaac     180
tcctggacac tccctcccsc aagttcacag agaatgtggg cacatgcctt acagtcttcc     240
cttgatccaa actactgcct tcatcttgag tgacagcagc atcttttgga tgtcttggcc     300
tgtctagctt tatttttttg tgttctgcca tcaagttgct acttctgttg ccatcgtgcc     360
tgtcagcgca gtgcaggctg tggtgaaatc ccacga                               396

<210> SEQ ID NO 553
<211> LENGTH: 396
<212> TYPE: DNA
<213> ORGANISM: Homo sapiens

<400> SEQUENCE: 553 tattttttg tgttctgcca tcaagttgct acttctgttg ccatcgtgcc tgtcagcgca       60
gtgcaggctg tggtgaaatc ccacgaactc aggcatcaca ctgaccgggt ctgagtcctg     120
tctcagttgt cagctagttg tgcaatgaag ggaaagggac ctacactttc caagcctcaa     180
ttcactcatc tatggcatkg tgacaataat ggaggttgat ttaaagtcct ttgtaagaat     240
taagagttat aatagacata agtgctgta tctggtatac ctagaaaaca ttccataaaa      300
gttagtaatt gttggtcatg taatgatgac tctctaggct aggatttcag cttcattgca     360
tgcacatggt gcactcacag ggcgtgacct ctctct                               396

<210> SEQ ID NO 554
<211> LENGTH: 396
<212> TYPE: DNA
<213> ORGANISM: Homo sapiens

<400> SEQUENCE: 554
ggtataccta gaaaacattc cataaaagtt agtaattgtt ggtcatgtaa tgatgactct      60
ctaggctagg atttcagctt cattgcatgc acatggtgca ctcacagggc gtgacctctc     120
tctgtctcag taacctcatc tgaggaccgg gataatcata ccgcttcaaa gggatgtcat     180
aaagattaaa taatatgtrt aaggctgctt gcatttagct gcattcaaca aatatttctg     240
tatctttctc ctcatttctc cttactttct tgcttattat ctgctctagg tatagatttc     300
agagaactaa gcttgttaca atccttcata aaataaccag gttggttagg gcatttccaa     360
```

-continued gagtcaatac tgtttagtga ctattctctg tttaat                                    396

<210> SEQ ID NO 555
<211> LENGTH: 396
<212> TYPE: DNA
<213> ORGANISM: Homo sapiens

<400> SEQUENCE: 555
aaggctgctt gcatttagct gcattcaaca aatatttctg tatctttctc ctcatttctc        60
cttactttct tgcttattat ctgctctagg tatagatttc agagaactaa gcttgttaca       120
atccttcata aaataaccag gttggttagg gcatttccaa gagtcaatac tgtttagtga       180
ctattctctg tttaatctmt tttgattgtc cagggtcatc ttttgctatg tcataggttg       240
ttggcttctt ctagagaagt gagacgatgg acaagttcca agtgagtgag gcgactggtc       300
aggatattcc gctgaaaaac tcatgtcagt tctaattcgt gattgtaatt caatcacagc       360
ctgagaacag taggactgta gttcaaatgc tctgtt                                  396

<210> SEQ ID NO 556
<211> LENGTH: 396
<212> TYPE: DNA
<213> ORGANISM: Homo sapiens

<400> SEQUENCE: 556
cctgggttca agcaattctc ctgcctcagc ctcccaagta gctgggacta caggcacatg        60
ccaccacgcc cagataattt tcgtattttt agtagagacg gggtttcccc ttgttggcca       120
gggtggtctt gatctcttga cctcatgatc cgcccacctc ggcctcccaa agtgctggga       180
ttacaggcgt gagccaccrc gcccggcctc tagaggataa ttttttaaatg tgcttttgca      240 tttggaaaat gtgattggca ttttttttcta attttctaat atgatacgct gtcggatgct      300
atggattact taaaccctct ggctacctag aaagatcttt aagtggttct caacaagctt       360
catacgcaat gtaaattgta ttatctctca ggatgt                                  396

<210> SEQ ID NO 557
<211> LENGTH: 396
<212> TYPE: DNA
<213> ORGANISM: Homo sapiens

<400> SEQUENCE: 557
tgtgattggc attttttttct aattttctaa tatgatacgc tgtcggatgc tatggattac       60
ttaaaccctc tggctaccta gaaagatctt taagtggttc tcaacaagct tcatacgcaa      120
tgtaaattgt attatctctc aggatgtgtg agaacatctg ttttttcttct aatgcagtaa     180 acatataagg gtctcttgrg atatctttta aatagactta atacaacatt caggaatgat      240
aacaaaatat aatcacagtt gtaagggaat gtgagcattt catattaata acattggaac     300
cttatgttta atacagtgtt aaaagttgac aaacatgtag gagtcagaaa attcaattaa     360
aattatcaca gtaatatgaa tttagccaca tcctgt                                 396

<210> SEQ ID NO 558
<211> LENGTH: 396
<212> TYPE: DNA
<213> ORGANISM: Homo sapiens

<400> SEQUENCE: 558
acttaaaccc tctggctacc tagaaagatc tttaagtggt tctcaacaag cttcatacgc        60

-continued

```
aatgtaaatt gtattatctc tcaggatgtg tgagaacatc tgttttctt ctaatgcagt      120 aaacatataa gggtctcttg ggatatcttt taaatagact taatcaaca ttcaggaatg      180 ataacaaaat ataatcacrg ttgtaaggga atgtgagcat ttcatattaa taacattgga    240
accttatgtt taatacagtg ttaaaagttg acaaacatgt aggagtcaga aaattcaatt    300
aaaattatca cagtaatatg aatttagcca catcctgtgt tagttatgaa atccatttaa    360
caccacaaac agtaatattt ttagccagtt tattca                              396
```

<210> SEQ ID NO 559
<211> LENGTH: 396
<212> TYPE: DNA
<213> ORGANISM: Homo sapiens

<400> SEQUENCE: 559

```
catttaacac cacaaacagt aatattttta gccagtttat tcaaaaggaa aacaggaact     60
aaaccacttt catgcaatat atactctgtt aatgtggtca ggctaatttt gctgggggaa   120
ggaacttaac ttttgaatat ttgaatgccc agtcatttaa tctgaatatc ctatttcctt    180
gcatgttgca aaattttttkt caataaaagg cagaaaaaga atctcttct ccatgctcat    240 ccctaagaga atgggttgtc tgtaccctga gagcatttta tggaggggac aaccacttt    300 ctaattttcc ttcccacttc tctgtgggca caaatgctct ttggttgaaa gagttgtaat   360
tcagtcccaa gatgaggtgt ggttactgca tccta                               396
```

<210> SEQ ID NO 560
<211> LENGTH: 396
<212> TYPE: DNA
<213> ORGANISM: Homo sapiens

<400> SEQUENCE: 560

```
tcaatccatg ctccacactg cagccagagt gctctacaat gcaaatccat ttgtgagact      60
cctcctctta aaatcctcaa gtggcttctc tttgccccca ggatcatttt gaaactcctt    120
aatggaagag gcatggccct tgggatgtg gttccccaac ccctcccaca tcatcttttc      180
aatcagattt cccactaart ggaaattttt tcaggtcctc aacttatgg tgactttctc     240 ttgctcagga tctttgaaca tactgtttct tctttccttt tgtatttgcc aagacaacac    300
ttcctctggt aagattttcc tgacatcctc tataaaaaaa gattgagata gttgactacc   360
caaaatgttt cccattcatt ccaagctcta ttcaag                              396
```

<210> SEQ ID NO 561
<211> LENGTH: 396
<212> TYPE: DNA
<213> ORGANISM: Homo sapiens

<400> SEQUENCE: 561

```
aacacttcct ctggtaagat tttcctgaca tcctctataa aaaagattg agatagttga     60 ctacccaaaa tgtttcccat tcattccaag ctctattcaa ggcagtaaag tgcccggctg    120
acagattgca ttcctcatct tttctgaagc tagcaatggc catgcaacag cattctggcc   180
aataagatag aagtcgaart tgaagggtgg gatttccaag aaagctcgtt gaagacataa    240
ttcctcattt cacttcttac tcttttctctt tcctgcttcc taaaatgcgg tgcagatggc   300
agacacttca agctgtctc aggcaatcag gtgatgttaa ggcagaaacc agctttatga    360
tgggtagaac aggaagaaag aaggcaccta tgttct                              396
```

<210> SEQ ID NO 562
<211> LENGTH: 396
<212> TYPE: DNA
<213> ORGANISM: Homo sapiens

<400> SEQUENCE: 562

| | | | | | |
|---|---|---|---|---|---|
| cctacaaatc | tcatgttgac | attttatccc | taatattgga | ggcagggcct | agtaggaggt | 60 |
| gttttggtca | tagtgataaa | tggcttggtg | ccgttctcac | agtaacgagt | gagtttttat | 120 |
| tctagtggtt | cctgcaagaa | ctgattgtta | aaagagcttg | gatccttcca | ccctctctc | 180 |
| actcttgctt | cctctctcwc | accttgtaat | ctctacaagc | tcttcacctc | cccttctcct | 240 |
| tttgccataa | gtggaagatt | tctgaggcct | caccagaagc | agatgttggt | tccatgcttc | 300 |
| ttgtacagcc | tgcagaacca | tgagccaaat | caacttcttt | tctttataat | tatccagtct | 360 |
| caggtattcc | tttatagcaa | cacaaatgga | ctaaga | | | 396 |

<210> SEQ ID NO 563
<211> LENGTH: 396
<212> TYPE: DNA
<213> ORGANISM: Homo sapiens

<400> SEQUENCE: 563

| | | | | | |
|---|---|---|---|---|---|
| gttgtttcca | gctttgaact | attttgaatc | ctaaaagact | gccagttttg | aatgagaccc | 60 |
| cagaacaatg | aatgtaggct | ctgtatacaa | gttcaggctg | ctgggcaact | taggccttaa | 120 |
| gacacaactc | tgccacttag | gccttaagac | acaactgaca | tgatggtgct | taaagtggct | 180 |
| gtgatggaaa | aggaggctrt | ttggagccct | tggagtgcct | ttataggtga | accccagcat | 240 |
| agcacctaat | gatttggagc | aaagctgtgt | cattccccaa | agataactat | tcgcctttg | 300 |
| agaaacatct | tctagctact | atcaataata | aacacagaat | gcatcaccat | gggccaccgt | 360 |
| gttgtctttt | gacctgagtt | tccattgtga | acaaga | | | 396 |

<210> SEQ ID NO 564
<211> LENGTH: 396
<212> TYPE: DNA
<213> ORGANISM: Homo sapiens

<400> SEQUENCE: 564

| | | | | | |
|---|---|---|---|---|---|
| aactctgcca | cttaggcctt | aagacacaac | tgacatgatg | gtgcttaaag | tggctgtgat | 60 |
| ggaaaaggag | gctgtttgga | gcctttggag | tgcctttata | ggtgaacccc | agcatagcac | 120 |
| ctaatgattt | ggagcaaagc | tgtgtcattc | cccaaagata | actattcgcc | ttttgagaaa | 180 |
| catcttctag | ctactatcra | aataaacac | agaatgcatc | accatgggcc | accgtgttgt | 240 |
| cttttgacct | gagtttccat | tgtgaacaag | agtcatttga | tccaaggcag | aaagttgggt | 300 |
| gcacacagca | gtgttccatc | atcaaatgga | atatgagatt | gggcccaagt | aggtcctgca | 360 |
| gacacaaata | agttgcaaga | gcaagtagta | caggcg | | | 396 |

<210> SEQ ID NO 565
<211> LENGTH: 396
<212> TYPE: DNA
<213> ORGANISM: Homo sapiens

<400> SEQUENCE: 565

| | | | | | |
|---|---|---|---|---|---|
| gaaaaggagg | ctgtttggag | cctttggagt | gcctttatag | gtgaacccca | gcatagcacc | 60 |
| taatgatttg | gagcaaagct | gtgtcattcc | ccaaagataa | ctattcgcct | tttgagaaac | 120 |
| atcttctagc | tactatcaat | aataaacaca | gaatgcatca | ccatgggcca | ccgtgttgtc | 180 |

```
ttttgacctg agtttccayt gtgaacaaga gtcatttgat ccaaggcaga aagttgggtg      240
cacacagcag tgttccatca tcaaatggaa tatgagattg ggcccaagta ggtcctgcag      300
acacaaataa gttgcaagag caagtagtac aggcgcttgg cctggccagt actgttgcca      360
agttgactgc ttcccctcag tctgcatctg tggctt                               396
```

<210> SEQ ID NO 566
<211> LENGTH: 396
<212> TYPE: DNA
<213> ORGANISM: Homo sapiens

<400> SEQUENCE: 566

```
ccccaaagat aactattcgc cttttgagaa acatcttcta gctactatca ataataaaca      60
cagaatgcat caccatgggc caccgtgttg tcttttgacc tgagtttcca ttgtgaacaa     120
gagtcatttg atccaaggca gaaagttggg tgcacacagc agtgttccat catcaaatgg     180
aatatgagat tgggcccarg taggtcctgc agacacaaat aagttgcaag agcaagtagt     240
acaggcgctt ggcctggcca gtactgttgc caagttgact gcttcccctc agtctgcatc     300
tgtggcttca tggggagttt cctatgacca cttgatggag gaaaaaacaa attggagcat     360
agtttatagt gctggtacta cccaaagtgg ctagct                              396
```

<210> SEQ ID NO 567
<211> LENGTH: 396
<212> TYPE: DNA
<213> ORGANISM: Homo sapiens

<400> SEQUENCE: 567

```
gtccgtgagt tacagatcta cacaaaatca cagagagtgg ttaatcgttt agtctgatgg      60
tcagggactt ccaagagaca tgattagaaa actggtgaca aggagtcctg gggaagaggc     120
atatggatac ctctgaacac acacaaaaca tgagaatatg tatcccatat gaatgttaac     180
caaagagcag ccacaacasa agaggatttt aaaatcagct gaataagatg attcattctg     240
acagcatcag ctagtctctt tccccagcca ctgttgccca gtgggcttac atatatcatg     300
gccatggggg cagggctatg tatggacaca gcaacatgaa tttccactca tcaaggccaa     360
tttggctcca gccattgctg agtgctcagc ctgcca                              396
```

<210> SEQ ID NO 568
<211> LENGTH: 396
<212> TYPE: DNA
<213> ORGANISM: Homo sapiens

<400> SEQUENCE: 568

```
acatgattag aaaactggtg acaaggagtc ctggggaaga ggcatatgga tacctctgaa      60
cacacacaaa acatgagaat atgtatccca tatgaatgtt aaccaaagag cagccacaac     120
agaagaggat tttaaaatca gctgaataag atgattcatt ctgacagcat cagctagtct     180 cttccccag ccactgttrc ccagtgggct tacatatatc atggccatgg gggcagggct     240
atgtatggac acagcaacat gaatttccac tcatcaaggc caatttggct ccagccattg     300
ctgagtgctc agcctgccaa gatagaaatc tacgccaata tggcaccatt ccctgggcta     360
gaaaaccaac tggtggaagg ttgattacat tggacc                              396
```

<210> SEQ ID NO 569
<211> LENGTH: 396
<212> TYPE: DNA
<213> ORGANISM: Homo sapiens

<400> SEQUENCE: 569

```
gggaatacaa tggtggttcc actaaactga cagctgagtt tgccatctcc tcgtgccagt      60
gaatacacaa gcaaggaagg gggttccttt ctcacctagg gtgactgatc ctaattacca    120
aggagaaatt ggactgccac ttcacaatga gggtgaggag tatgtactct atgtgtctgt    180
gattaatgtc aatagaaart gacaccaacc tagtacacag aggactgatc atggtccagg    240
cccttcagga atgaagattt gagtcaccag gcaaggaact tggactcact gaggagggca    300
tattccaagg agaatatttt atctatgtcc atctatgtcc atctatattc catctgtgtt    360
cccccttggaa ttcctattca tgaacatggg gaattc                             396
```

<210> SEQ ID NO 570
<211> LENGTH: 396
<212> TYPE: DNA
<213> ORGANISM: Homo sapiens

<400> SEQUENCE: 570

```
tatagaatga gtagtggaag gtagttataa atgtaagtca aaaccacac aaccaatttg       60
agaaatgagg aaggtaatag tgttgaatat gtcttcttta tcttgatata aatgtatttg    120
tgcatatatt aaccagttta tttatttatt attatttttt gagatgagct ctcgccatgt    180
tgcccaggct ggtcttgamc tcctgggctc aactgattct accatttagt cctccgagta    240
gctgggacta caggcatgca ccaccatacc cagctgacca gtttttttcct attcctctac    300
ttaatttctc tactatacaa cataatatgt gttaatggta gttaacttta tatctcagta    360
ttaagtcaca agatatcaaa aagggaatgc gactta                              396
```

<210> SEQ ID NO 571
<211> LENGTH: 396
<212> TYPE: DNA
<213> ORGANISM: Homo sapiens

<400> SEQUENCE: 571

```
atgtcttctt tatcttgata taaatgtatt tgtgcatata ttaaccagtt tatttattta     60
ttattatttt ttgagatgag ctctcgccat gttgcccagg ctggtcttga actcctgggc    120
tcaactgatt ctaccattta gtcctccgag tagctgggac tacaggcatg caccaccata    180
cccagctgac cagttttttyc ctattcctct acttaatttc tctactatac aacataatat    240
gtgttaatgg tagttaactt tatatctcag tattaagtca agatatca aaaagggaat      300
gcgacttagt tacaagcaga atgaatatca ctcaaagatg aataaagaga agagggttag    360
tgcattttct gttggatgag agaaagtttc attgtt                              396
```

<210> SEQ ID NO 572
<211> LENGTH: 396
<212> TYPE: DNA
<213> ORGANISM: Homo sapiens

<400> SEQUENCE: 572

```
gcagtggcgt gatcccagct cactgcaatc tctgcctcct gggttcaagt gattctcctg      60
cctcagcctc ccgaggggct gggattgtag gcgtgcacca ctatgcccat ctaattttg    120
tatttttagt agagataggg ttttgccatt ttggccagac tgtcttgaac tcctgacctc    180
aggtgatctg cctgcctcrg cctcccacag ttttgtgatt ataggcatga gccaccgtgc    240
ccggccttaa cctttgtttt cttacacaac acactacgtg atgttttcca catgcatggg    300
```

```
tcatttgctt catttacgta caaatgcata agcaatatac tgtgtggtgt gagtttgtga    360
tgggaaaagg aagaagtttt gcggatacta cactgg                              396

<210> SEQ ID NO 573
<211> LENGTH: 396
<212> TYPE: DNA
<213> ORGANISM: Homo sapiens

<400> SEQUENCE: 573
gcccaggctg ttctccaact cctggactca agccatcctc tagcctcggc cttccaaagt     60
gctgggacta taggcgtgag ccacggtgcc aggcccttga ccacatttt aaccccctctg   120
aacctcagtt tcactttctg ggcaatggga gggggtaat ttgtccctca gagggttgca    180
ctgaggggca aatgtgagsc tctgggtaca atgcccagta cagactaggt ccccacgaca   240
cagccgctca gcggctccgg attctgggct gctctggact gcggccaggc ggtcttctgc   300
gggaatccgg gcaggcaggg cgggctgcgc tcccctcccc ggctctcccg gtgccccttg   360
tcttttgtt ctgtctcagc agctctctat taagat                              396

<210> SEQ ID NO 574
<211> LENGTH: 396
<212> TYPE: DNA
<213> ORGANISM: Homo sapiens

<400> SEQUENCE: 574
tttttgttct gtctcagcag ctctctatta agatgaatgg catttccaaa ggcttcacct     60
ctgataagtg ttcctctgca gctgcagcca gaatcttaat gtgcgcgctg taatttaatg   120
gccgtctcgg ctattaacac gctcttctcg ggtgaagtgg actccctcca tccccgggcc   180
tctgcacgtg ctctgcgcrc tggctggggg tgactccaag gagctcagag cggggtgccc   240
ggcacctctc gccaggcgcc tttcgacctt ctaaagcgcg aatggctgga cttttctccc   300
atgtgtgggg ccccagaagg tgtggggccc cagaaggtgt ggggtccctg cgttccacgg   360
agcccggaag gtttccagtg atggtggggg ctgacc                              396

<210> SEQ ID NO 575
<211> LENGTH: 396
<212> TYPE: DNA
<213> ORGANISM: Homo sapiens

<400> SEQUENCE: 575
ggagcccgga aggtttccag tgatggtggg ggctgaccac gttggtcccc gtgggtgctg     60
ttttcatgtg ccggcagatt gggatgagtt taaaagacag aagcgtgtag gatagagaaa   120
cttctttaaa aactgaaaat tttaatctgg ggattataac tattggacag tcaagtgcaa   180
gagtgaatac acttctcast ccctcctccc aattttatt tgcgggatta gtcagtcccc    240
ctctgccaca tgataattgt gagaactacc agggtcttca ttctcctgcc atctggttga   300
cctctccaag aatggacacc cgggcagcct gggccaatga ggctgtccta agagtttaga   360
tgagagaagt cagtctttga caggtgatgg aagctg                              396

<210> SEQ ID NO 576
<211> LENGTH: 396
<212> TYPE: DNA
<213> ORGANISM: Homo sapiens

<400> SEQUENCE: 576
cagtgatggt gggggctgac cacgttggtc cccgtgggtg ctgttttcat gtgccggcag     60
```

```
attgggatga gtttaaaaga cagaagcgtg taggatagag aaacttcttt aaaaactgga      120
aattttaatc tggggattat aactattgga cagtcaagtg caagagtgaa tacacttctc      180
actccctcct cccaatttyt atttgcggga ttagtcagtc ccctctgcc acatgataat       240 tgtgagaact accagggtct tcattctcct gccatctggt tgacctctcc aagaatggac      300
acccgggcag cctgggccaa tgaggctgtc ctaagagttt agatgagaga agtcagtctt      360
tgacaggtga tggaagctgt aaaatgtaaa actcca                                396

<210> SEQ ID NO 577
<211> LENGTH: 396
<212> TYPE: DNA
<213> ORGANISM: Homo sapiens

<400> SEQUENCE: 577
taagagaagc tgagagagag cgagaggaga gattggaaga aagacagaga cagaggtaga       60
gagaagggaa agagagagag aaagggacag aagagagaga aaaagaggg ggccgggcgc      120 ggtggctcac gcctgtaatc tcagcacttt gggaggccga ggcgggcaga tcacgaggtc      180
aggagatcga gaccatccyg gctaacacgg tgaaacccc gtctctacta aaaatataa       240 aaaaaattag ccaggcgtgg tggtgggtgc ctgtagtccc agctactgag gaggctgaga      300
caggagaatg gcgtgaaccc gggaggcaga gcttgcagtg agctgagatc gcgccactgc      360
actccagcct gggcaacaga gcaagactcc gtctca                                396

<210> SEQ ID NO 578
<211> LENGTH: 396
<212> TYPE: DNA
<213> ORGANISM: Homo sapiens

<400> SEQUENCE: 578
tccaccagca gcttttctga gtctccagct tgcagatggc aaaccatgaa acttcatggt       60
gtccatgagc atgtgaacca atttctatta taaatctgca atatatatat atgaggagac      120
ttatttatat attggttcag tttctctgga gagccttggc taatataaag tctatactct      180
acaaagtgcc ctaggtackc agggagtacc caagtgtgtc atgaccagcc cgacagccct      240
ggctgctggg ttcccccgcac acaactctgc acgctgcctt catcagcctt tctctctcag      300
ctgaaccgag ggcattgaag cgggcctctg gcactgtacc tatgagggag caatatcttc      360
ccctacactg acctcttccg tgccgagatg cagccc                                396

<210> SEQ ID NO 579
<211> LENGTH: 396
<212> TYPE: DNA
<213> ORGANISM: Homo sapiens

<400> SEQUENCE: 579
gcctctggca ctgtacctat gagggagcaa tatcttcccc tacactgacc tcttccgtgc       60
cgagatgcag ccctccctgc tgccactagt tacagtggtc catgttccct ttcaaagtga      120
agttttgata aaagcacctc ttaaccaatg ccaaatagct aagtctggga caaagattgc      180
aggtattttg cattttccwt gtaacctcag agggattgcc attcacactg atctgagctg      240
cagaatacca ggcagccacc tcacccaccc agcaggtcca ctcttatact ttctcagaaa      300
gcacagccac tctactctta ttcagttgaa aagaatttcc aggaaggtgt ttctgcgatt      360
gcctcagaaa agtcagttcc ctttgggaat ttccct                                396
```

<210> SEQ ID NO 580
<211> LENGTH: 396
<212> TYPE: DNA
<213> ORGANISM: Homo sapiens

<400> SEQUENCE: 580

```
tactttctc tgaagaaatg gagatatcag ctgtccctcc ccactgccat ttattccttc      60
cttcattcaa accttatgtg gctgctactt accgtgtgtt aagtgttcac tttttttctt    120
ggaattcaaa aaaagaagga cagtatttgg ggcacagatc ttttggtgtt ctatacattt    180
ttttaaagtt tcattttaya tttgtgtgtg cgtgtgtgtg tgtgtgtgag acagtcttgc    240
tctgttgccc aggctggagt gcagtggcat aatcattggc tcactgtagc ctcaaagtcc    300
tgggcccaag caatcttccc acctcagcca cccaaaatgc tggggttaca ggtttatgcc    360
actctgtctg acctgaaagt tttgggttta ctttcc                              396
```

<210> SEQ ID NO 581
<211> LENGTH: 396
<212> TYPE: DNA
<213> ORGANISM: Homo sapiens

<400> SEQUENCE: 581

```
gcataatcat tggctcactg tagcctcaaa gtcctgggcc caagcaatct tcccacctca     60
gccacccaaa atgctggggt tacaggttta tgccactctg tctgacctga aagttttggg    120
tttactttcc cttctttctc tttgctgaag tcagagatga tggcagcttc cagattctct    180
ggtgcctgtg ctgggctcrt gctggtcatg gtcttgggtc caggattcat tctggagact    240
ctcagggaag tttcccatga caaggaaatg taggagagtg tgctggcttt gcgtgctcct    300
ctgccaagcc ctgcttctcc tggtgggaca cactgaacca cagccagggc attttggtgg    360
ttagttaaaa aaaaaaaaaa aaaaaaaaaa aggaag                              396
```

<210> SEQ ID NO 582
<211> LENGTH: 396
<212> TYPE: DNA
<213> ORGANISM: Homo sapiens

<400> SEQUENCE: 582

```
cttcagaaat tgtaatgatg aaagagtgca agctctcact tccccttcct gtacagggca     60
ggttgtgcag ctggaggcag agcagtcctc tctggggagc ctgaagcaaa catggatcaa    120
gaaactgtag gcaatgttgt cctgttggcc atcgtcaccc tcatcagcgt ggtccagaat    180
ggtaaggaaa gcccttcamt cagggaagaa cagaagggga gattttcttt gatggttgtt    240
tggaagtcag gcttaaacaa ttgtgtctgt gtgtgcgcat gcacaaacac ttttaccttq    300
tcttattt cttctttta tttgaatgta tagggttgtg tgtatttctg tgtaaatttg       360
gggttttcct cctcttagtc tttcactttt gtggtg                              396
```

<210> SEQ ID NO 583
<211> LENGTH: 396
<212> TYPE: DNA
<213> ORGANISM: Homo sapiens

<400> SEQUENCE: 583

```
ttttctaaca tctgcagtgc aattgaagtt accagtcatc tgcagtctaa aaagaaagtg     60
attttgggag gtgcgtagaa aaaatcatct tattattttt cctctatatt acttttttct    120
ttttttctcc tgaagaaact ttttttttg gtgataccct cttttttctct agcacgtata    180
```

```
attttggaag catttttcrt atgcagtgta tacttcagaa agagagagag agagaggaaa        240
attgtcctgt tcagcgtttg catttccatt attcctgcta ttagttaaaa acaacaacaa        300
caacaaaaaa caagcaggat acctagatct ggaaaaggga gaattgtgta gagctgtctt        360
cctaaagttc tgagttaggg ctgcctcaga ccactt                                  396

<210> SEQ ID NO 584
<211> LENGTH: 396
<212> TYPE: DNA
<213> ORGANISM: Homo sapiens

<400> SEQUENCE: 584
ttttggaagc attttcata tgcagtgtat acttcagaaa gagagagaga gagaggaaaa         60
ttgtcctgtt cagcgtttgc atttccatta ttcctgctat tagttaaaaa caacaacaac       120
aacaaaaaac aagcaggata cctagatctg gaaaagggag aattgtgtag agctgtcttc       180
ctaaagttct gagttaggrc tgcctcagac cactttcata actatctcca gtggctttgt       240
gttttatatt tattaagata gagaaaaaaa gagtaattac taagggcagc tgctgtagct       300
ttatggtgat tactgaacat tgacatgctg tcacgttttt ggaactttga gtatttaatc       360
actttgggat attctatttt ccccatcttt gagtgt                                 396

<210> SEQ ID NO 585
<211> LENGTH: 396
<212> TYPE: DNA
<213> ORGANISM: Homo sapiens

<400> SEQUENCE: 585
ggaactttga gtatttaatc actttgggat attctatttt ccccatcttt gagtgtggac        60
agatgctggt gatgtagcct tctgggcaca gagcaagcct cccctcagc ctctgcacca       120 gaaaggctca gcttcacaca ctccaagtat gttttctaca agaactacac tttgtggctt       180
tctgacccaa acatttttrt actaaattac acaacaaa gttgtagctc agagagggaa        240
caaatggctt atttaggcca ccatttttctt gagccattat gatttcacac agggctccct      300
tggccctgta aattggcaag gattccatta ttcaacccgc atacatgtac agagaccctg      360
ctctggccca gatagtattc tgggtacagg cggata                                 396

<210> SEQ ID NO 586
<211> LENGTH: 396
<212> TYPE: DNA
<213> ORGANISM: Homo sapiens

<400> SEQUENCE: 586
tgtggacaga tgctggtgat gtagccttct gggcacagag caagcctccc cctcagcctc        60
tgcaccagaa aggctcagct tcacacactc caagtatgtt ttctacaaga actcactttt       120
gtggctttct gacccaaaca ttttatact aaattacaca caacaaagtt gtagctcaga       180
gagggaacaa atggcttayt taggccacca ttttcttgag ccattatgat ttcacacagg      240
gctcccttgg ccctgtaaat tggcaaggat tccattattc aacccgcata catgtacaga      300
gaccctgctc tggcccagat agtattctgg gtacaggcgg atagagcagg aaacaaaaca      360
gctacagtga tggacaggtc agcctgcagc aatgcc                                 396

<210> SEQ ID NO 587
<211> LENGTH: 396
<212> TYPE: DNA
```

<213> ORGANISM: Homo sapiens

<400> SEQUENCE: 587

| | | | | | |
|---|---|---|---|---|---|
| tttttatact | aaattacaca | caacaaagtt | gtagctcaga | gagggaacaa | atggcttatt | 60 |
| taggccacca | ttttcttgag | ccattatgat | ttcacacagg | gctcccttgg | ccctgtaaat | 120 |
| tggcaaggat | tccattattc | aacccgcata | catgtacaga | gaccctgctc | tggcccagat | 180 |
| agtattctgg | gtacaggcrg | atagagcagg | aaacaaaaca | gctacagtga | tggacaggtc | 240 |
| agcctgcagc | aatgcctgca | gtctctgcaa | aggtagctgt | atgggtgggc | aggtggctag | 300 |
| cacttattca | gctctggaag | gatctcccct | ctggcctctc | ccctgacacc | catcaataaa | 360 |
| actgaggagc | atcggtggac | aggggacctt | gtgccc | | | 396 |

<210> SEQ ID NO 588
<211> LENGTH: 396
<212> TYPE: DNA
<213> ORGANISM: Homo sapiens

<400> SEQUENCE: 588

| | | | | | |
|---|---|---|---|---|---|
| ttttcttgag | ccattatgat | ttcacacagg | gctcccttgg | ccctgtaaat | tggcaaggat | 60 |
| tccattattc | aacccgcata | catgtacaga | gaccctgctc | tggcccagat | agtattctgg | 120 |
| gtacaggcgg | atagagcagg | aaacaaaaca | gctacagtga | tggacaggtc | agcctgcagc | 180 |
| aatgcctgca | gtctctgcra | aggtagctgt | atgggtgggc | aggtggctag | cacttattca | 240 |
| gctctggaag | gatctcccct | ctggcctctc | ccctgacacc | catcaataaa | actgaggagc | 300 |
| atcggtggac | aggggacctt | gtgccccctc | cctgcctgtg | cagttggggc | tgaacccagc | 360 |
| tacgaagttt | gagctcactc | tctccagctc | cctctc | | | 396 |

<210> SEQ ID NO 589
<211> LENGTH: 396
<212> TYPE: DNA
<213> ORGANISM: Homo sapiens

<400> SEQUENCE: 589

| | | | | | |
|---|---|---|---|---|---|
| gacaggtcag | cctgcagcaa | tgcctgcagt | ctctgcaaag | gtagctgtat | gggtgggcag | 60 |
| gtggctagca | cttattcagc | tctggaagga | tctcccctct | ggcctctccc | ctgacaccca | 120 |
| tcaataaaac | tgaggagcat | cggtggacag | gggaccttgt | gccccctccc | tgcctgtgca | 180 |
| gttgggctg | aacccagcya | cgaagtttga | gctcactctc | tccagctccc | tctcaattca | 240 |
| gagctgaact | gtgggaagct | tcagagctct | ctgtttcaag | gacaggttct | cctcacctct | 300 |
| cctaatggag | gtgcaccagg | gaactggccc | tgctctgccc | agggctttct | cctggacttt | 360 |
| gccatcatgg | tctagcaaac | cctgttcaga | ttgagg | | | 396 |

<210> SEQ ID NO 590
<211> LENGTH: 396
<212> TYPE: DNA
<213> ORGANISM: Homo sapiens

<400> SEQUENCE: 590

| | | | | | |
|---|---|---|---|---|---|
| cactctctcc | agctccctct | caattcagag | ctgaactgtg | ggaagcttca | gagctctctg | 60 |
| tttcaaggac | aggttctcct | cacctctcct | aatggaggtg | caccagggaa | ctggccctgc | 120 |
| tctgcccagg | gctttctcct | ggactttgcc | atcatggtct | agcaaaccct | gttcagattg | 180 |
| aggtgagtgg | tgagatttyg | aattcttttt | gacagatagg | attaagtctt | cttctgtggg | 240 |
| acaagtggga | ggtagaggta | agattaaaga | tggccaaatg | tctgagtcct | gacagccaca | 300 |

```
atatggagat ctagactttt tacagaccac agggcacagg ggcctcacta acagagttcc      360
cggaagtgat gagtgtgctg ggggcttcct ggttga                                396

<210> SEQ ID NO 591
<211> LENGTH: 396
<212> TYPE: DNA
<213> ORGANISM: Homo sapiens

<400> SEQUENCE: 591
taggattaag tcttcttctg tgggacaagt gggaggtaga ggtaagatta aagatggcca      60
aatgtctgag tcctgacagc cacaatatgg agatctagac ttttttacaga ccacagggca    120 caggggcctc actaacagag ttcccggaag tgatgagtgt gctgggggct tcctggttga    180
agagacacta gaatggacsa gctgggagct aatttttttgg gctggagtgt gatggcctgc    240
acatcactgc ctctgtccct ccattgtcac agctgcccct taggagccag ctgaggcaat    300
ttgtggtcag agtgactttg cacagttgtc ctgcctgtgt tcaggaaggg agtttctgtg    360
gtccctttga aaccacagaa gagcccctcg tatagc                              396

<210> SEQ ID NO 592
<211> LENGTH: 396
<212> TYPE: DNA
<213> ORGANISM: Homo sapiens

<400> SEQUENCE: 592
agttgtcctg cctgtgttca ggaagggagt ttctgtggtc cctttgaaac cacagaagag      60
cccctcgtat agctctcaat ggaggggca aaacattcaa ataactcagg agataacaca    120
actatttgtt tttaactgtg agtttttagg caatcacaaa gatccagatg tatgtccaag    180
cctctctttg caattctawt taacctcaat gttgcaacca tagacctacc ttacagagtt    240
caaaaaaata tgcaaaaacc ctgcctttct tcttcctcat accccaaaat gccattctga    300
acatttcctg ttagttaaaa aaagatttcc atggtgttac caggcactgt acacagtctg    360
tgtcccaaga caaggaggta cagttccaca tgcgcc                              396

<210> SEQ ID NO 593
<211> LENGTH: 396
<212> TYPE: DNA
<213> ORGANISM: Homo sapiens

<400> SEQUENCE: 593 aggggggcaaa acattcaaat aactcaggag ataacacaac tatttgtttt taactgtgag      60 ttttttaggca atcacaaaga tccagatgta tgtccaagcc tctctttgca attctaatta    120
acctcaatgt tgcaaccata gacctacctt acagagttca aaaaaatatg caaaaaccct    180
gcctttcttc ttcctcatwc cccaaaatgc cattctgaac atttcctgtt agttaaaaaa    240
agatttccat ggtgttacca ggcactgtac acagtctgtg tcccaagaca aggaggtaca    300
gttccacatg cgcccatgac tgggttgggc tctgcactct ctctatactt tgagagcctg    360
attttctgtg attgggcaga gctggcccac ctggtg                              396

<210> SEQ ID NO 594
<211> LENGTH: 396
<212> TYPE: DNA
<213> ORGANISM: Homo sapiens

<400> SEQUENCE: 594
```

```
tctgcactct ctctatactt tgagagcctg attttctgtg attgggcaga gctggcccac      60
ctggtgcaat gtcctcctct gcctttcaaa catgttttag tcatcaagat cttcaaattt     120
gtaacccttt ccagcttgat ccagcagaat gcagatttgg aaaaacagaa cgagtttaaa     180
atacatgatt ctaagaaayc tggaccagaa ctatcaaaac ttggtttccc agagaatata     240
gcaaatgggc tcattggcca atactatgac attggctttt gagaaagaa aggctttatt      300 gcaaggctgg ccagcaagga acaggagtt gggctcaaat ctgtctcccc agtttggggc      360
ttagggcaag ttttaattac acagacgcat ttctta                               396
```

<210> SEQ ID NO 595
<211> LENGTH: 396
<212> TYPE: DNA
<213> ORGANISM: Homo sapiens

<400> SEQUENCE: 595

```
aacccttttcc agcttgatcc agcagaatgc agatttggaa aaacagaacg agtttaaaat     60
acatgattct aagaaacctg accagaact atcaaaactt ggtttccag agaatatagc       120 aaatgggctc attggccaat actatgacat tggcttttga gaaagaaag ctttattgc       180 aaggctggcc agcaaggara caggagttgg gctcaaatct gtctcccag tttggggctt      240 agggcaagtt ttaattacac agacgcattt cttatgagta gcaggcagag agcctccaac    300
ttcttctgcc taggtaccag cagcttagac atgatgcaaa cctgggaagc acatactgta    360
tttggagaaa gtgattggga agaaatgtga gctgag                               396
```

<210> SEQ ID NO 596
<211> LENGTH: 396
<212> TYPE: DNA
<213> ORGANISM: Homo sapiens

<400> SEQUENCE: 596

```
tacatgattc taagaaacct ggaccagaac tatcaaaact tggtttccca gagaatatag      60
caaatgggct cattggccaa tactatgaca ttggcttttg agaaaagaaa ggctttattg     120
caaggctggc cagcaaggag acaggagttg ggctcaaatc tgtctcccca gtttggggct    180
tagggcaagt tttaattaya cagacgcatt tcttatgagt agcaggcaga gagcctccaa    240
cttcttctgc ctaggtacca gcagcttaga catgatgcaa acctgggaag cacatactgt    300
atttggagaa agtgattggg aagaaatgtg agctgagggg agggctcag tgcccctgag    360 ctacacttag tgatggcaga ggaaggatgt cctccc                               396
```

<210> SEQ ID NO 597
<211> LENGTH: 396
<212> TYPE: DNA
<213> ORGANISM: Homo sapiens

<400> SEQUENCE: 597

```
tggggcttag ggcaagtttt aattacacag acgcatttct tatgagtagc aggcagagag      60
cctccaactt cttctgccta ggtaccagca gcttagacat gatgcaaacc tgggaagcac    120
atactgtatt tggagaaagt gattgggaag aaatgtgagc tgaggggagg ggctcagtgc    180
ccctgagcta cacttagtra tggcagagga aggatgtcct cccgcaggag ctgttccac     240 atctgctctg gttgtagggg gagctggcag gcattagcag cggcctcttt cccccaagag    300
aggcagcctc ctccaagttt tggcgacatt atggccctgc aatcataagg gtttgtgagc    360
atagtgctaa ggagggaaat ggagctgctg ttacta                               396
```

<210> SEQ ID NO 598
<211> LENGTH: 396
<212> TYPE: DNA
<213> ORGANISM: Homo sapiens

<400> SEQUENCE: 598

```
cctcctgagt agctaggact acaagcatgt gccaccacgc ccagctaatt tttgtatttt      60
tagtaaggac agggtttcac catgttggcc aggttggcct ccaactcctg acctcaagtc     120
atcctcctgc ctcgacctcc caaagtgctg gattacagg catgaaacca gcctagaaat      180
acatactatt atttattcyt gttttacaga taagcaaagt gagtcatgga gaatttggtt     240
gaaagtccca aggtcaggag tcgtgaagct gggattaaaa cctaatcatc tgactttaga     300
gagtagacac ttgctccatg catattgcct ccaattcatt cattcaagca ctccctgctc     360
aagaagttct ttcttatgtt gagctgaaat ctgcag                               396
```

<210> SEQ ID NO 599
<211> LENGTH: 396
<212> TYPE: DNA
<213> ORGANISM: Homo sapiens

<400> SEQUENCE: 599

```
tcatctgact ttagagagta gacacttgct ccatgcatat tgcctccaat tcattcattc      60
aagcactccc tgctcaagaa gttctttctt atgttgagct gaaatctgca gccctatgcg     120
ttttacccag cagtcctggt gctgttccct aaaatcactt agactgtgcc tgctctttct     180
gtgtttacag tgtcagctrt aatatcccc  tcttcggcct aacgtttctg aagtcccttg     240
ccactgggtc tcctctcctc ttcctgtgtt cttttctaaga acacctatgc agataggtgt    300
cttctgtaca gggaagctgt tcctgagatc cgggcatcga ctctgttaga ataatctacg     360
tatgagttat ttttttgaga actatgtgtc attgct                                396
```

<210> SEQ ID NO 600
<211> LENGTH: 396
<212> TYPE: DNA
<213> ORGANISM: Homo sapiens

<400> SEQUENCE: 600

```
atgttgagct gaaatctgca gccctatgcg ttttacccag cagtcctggt gctgttccct      60
aaaatcactt agactgtgcc tgctctttct gtgtttacag tgtcagctgt aatatcccc      120
tcttcggcct aacgtttctg aagtcccttg ccactgggtc tcctctcctc ttcctgtgtt    180
cttttctaaga acacctatrc agataggtgt cttctgtaca gggaagctgt tcctgagatc   240
cgggcatcga ctctgttaga ataatctacg tatgagttat ttttttgaga actatgtgtc    300
attgctgact catattaact ctgtggttaa ctaaaatctc aagatctctt tatgtttgtt    360
gagaaactta tttaacttct ctggccctcc gtttcc                               396
```

<210> SEQ ID NO 601
<211> LENGTH: 396
<212> TYPE: DNA
<213> ORGANISM: Homo sapiens

<400> SEQUENCE: 601

```
gtcctggtgc tgttccctaa aatcacttag actgtgcctg ctctttctgt gtttacagtg     60
tcagctgtaa tatcccctc  ttcggcctaa cgtttctgaa gtcccttgcc actgggtctc    120
```

```
ctctcctctt cctgtgttct ttctaagaac acctatgcag ataggtgtct tctgtacagg    180
gaagctgttc ctgagatcyg ggcatcgact ctgttagaat aatctacgta tgagttattt    240
ttttgagaac tatgtgtcat tgctgactca tattaactct gtggttaact aaaatctcaa    300
gatctcttta tgtttgttga gaaacttatt taacttctct ggccctccgt ttccttcact    360
gagcagtgga gtgattgata acctccacct gtggtt                             396

<210> SEQ ID NO 602
<211> LENGTH: 396
<212> TYPE: DNA
<213> ORGANISM: Homo sapiens

<400> SEQUENCE: 602
cacctatgca gataggtgtc ttctgtacag ggaagctgtt cctgagatcc gggcatcgac     60
tctgttagaa taatctacgt atgagttatt ttttgagaa ctatgtgtca ttgctgactc    120
atattaactc tgtggttaac taaaatctca agatctcttt atgtttgttg agaaacttat    180
ttaacttctc tggccctcmg tttccttcac tgagcagtgg agtgattgat aacctccacc    240
tgtggttgct gaaggtcttg cacaagatga tatagttaaa gtagctagca gtgcccacgt    300
acggcggatg cctcacaacg gtttgcagcc atctctctat ctgtgtcttt gtctctctct    360
cacactggtt ttggcttact gttagcagct agccga                             396

<210> SEQ ID NO 603
<211> LENGTH: 396
<212> TYPE: DNA
<213> ORGANISM: Homo sapiens

<400> SEQUENCE: 603
tctgtggtta actaaaatct caagatctct ttatgtttgt tgagaaactt atttaacttc     60
tctggccctc cgtttccttc actgagcagt ggagtgattg ataacctcca cctgtggttg    120
ctgaaggtct tgcacaagat gatatagtta agtagctag cagtgcccac gtacggcgga    180
tgcctcacaa cggtttgcmg ccatctctct atctgtgtct ttgtctctct ctcacactgg    240
ttttggctta ctgttagcag ctagccgaga taagtgtgtt tatggtctttt gcatgtattg    300 tttctgtagc atactggagg attacaagag gttggggagt gaggggcgg tgaggagtag    360 acaaaggcag ccaactcttc caagtttagc ttagaa                             396

<210> SEQ ID NO 604
<211> LENGTH: 396
<212> TYPE: DNA
<213> ORGANISM: Homo sapiens

<400> SEQUENCE: 604
ttgataacct ccacctgtgg ttgctgaagg tcttgcacaa gatgatatag ttaaagtagc     60
tagcagtgcc cacgtacggc ggatgcctca caacggtttg cagccatctc tctatctgtg    120
tctttgtctc tctctcacac tggttttggc ttactgttag cagctagccg agataagtgt    180
gtttatggtc tttgcatgya ttgtttctgt agcatactgg aggattacaa gaggttgggg    240
agtgaggggg cggtgaggag tagacaaagg cagccaactc ttccaagttt agcttagaag    300 gaaggagcg taaaccctag ttgaatgttg gactgaagca ggtttgtttt tgttttgttt    360
aaaggatagg gaagatctgt gcgtgtttcc aggata                             396

<210> SEQ ID NO 605
<211> LENGTH: 396
```

<212> TYPE: DNA
<213> ORGANISM: Homo sapiens

<400> SEQUENCE: 605

```
acttgaagtc agtggcatgg acagggtcaa gatcacagtt agaggatgca gccttagaga      60
aaaggaaggg gctcggttct ctgagcaagg agggaaagaa gagaggcaga tgcagagaag     120
tacggcacat cgtgctgctg gttgtagaaa taacctctga cttttaataa agtcatccct     180
cggtatccct gggggattrg ttctatgacc tccctcggat gccaaaattc gtggatgctc     240
aagtccctga tataaaatgg catagtattt gcatttaacc tacacacatc ctccatatcc     300
tttttttttt tttttttttt tttttttttt tttttgtgag atggagtctt gctctgtcgc     360
cctggctgga gtacagtggc tcgatcttgg ctcact                               396
```

<210> SEQ ID NO 606
<211> LENGTH: 396
<212> TYPE: DNA
<213> ORGANISM: Homo sapiens

<400> SEQUENCE: 606

```
aatacctgat agaatgtaaa tgctatgtaa acagttgtta tactgtattg ttaaaagaca      60
gtaacaagaa aaaaaatctg tacatgttca gtccagacaa atggttttct gttttttttt     120
tttttttta atattttttgg tcagtggttg gttgactcca ggaatgcaga acccgcagat     180
atagaaggtt gattatgcrt tcagaggcag ggaataccat cttgggttcc agaaagaaaa     240
tgatcagcat tttctgtcat actctggtaa aaacagatct tttgaatgga caggtgtatt     300
aaaccctgtg gagctggctg ggcctggcgg ctcacgcctg taatcccagc actttgggag     360
gctgaggcag gtggatcacg aggtcaggag ttcgag                               396
```

<210> SEQ ID NO 607
<211> LENGTH: 396
<212> TYPE: DNA
<213> ORGANISM: Homo sapiens

<400> SEQUENCE: 607

```
tgccccgcag agtttgaagt cccggctgca cctctcccca gcagcaggtt gactctggaa      60
agttgcagcg ttcttaccta cagagtggga acagtactac ccattgcaca gagtgggtgc     120
aaagctctgt gacggaatac atggcaagtg cccaccacat tgcctgggat gaggtgggcc     180
cttcctttac gtaagagarc cctacagata cactcaaagt gggcacattc ctacagaagg     240
agtgttattt gtgtagaaaa gaaaaacatg aaaggctttt attcctatac acaataaagc     300
accccttttaa tgtctttttg aggagggtaaa tatgaaattg atgaaaagga accctgtggt     360
tggatccctg acaatcacat gtatcccttt tttcac                               396
```

<210> SEQ ID NO 608
<211> LENGTH: 396
<212> TYPE: DNA
<213> ORGANISM: Homo sapiens
<220> FEATURE:
<221> NAME/KEY: misc_feature
<222> LOCATION: (227)..(326)
<223> OTHER INFORMATION: n = A,T,C or G

<400> SEQUENCE: 608

```
tacagataca ctcaaagtgg gcacattcct acagaaggag tgttatttgt gtagaaaga       60
aaaacatgaa aggctttat tcctatacac aataaagcac cccttaatg tcttttgag       120
```

```
gaggataata tgaaattgat gaaaaggaac cctgtggttg gatccctgac aatcacatgt        180 atccctttt tcactcttra aaaggagta aaggaataaa atagaannnn nnnnnnnnnn          240
nnnnnnnnnn nnnnnnnnnn nnnnnnnnnn nnnnnnnnnn nnnnnnnnnn nnnnnnnnnn        300
nnnnnnnnnn nnnnnnnnnn nnnnnnatgt ttcagtcact gtataataac tagccagatt        360
ttttgttgtt gttgttttgt ttttgttttt gttttt                                  396
```

<210> SEQ ID NO 609
<211> LENGTH: 396
<212> TYPE: DNA
<213> ORGANISM: Homo sapiens

<400> SEQUENCE: 609

```
acattctgaa ccacagacag ttctttaccc tgaacctttg catattttgt tctcttagct         60
tagagcggcc cctctccctc cgtctgcttg gctaatttct acttgttctt cagattttat        120
cttagatgtc attccctcaa ggaatccttc tgtgactcaa catggaatta agttgcctcc        180
tttgaccctg aaagcaccrt gtactcaatc tcatcttggc atgactcact ttgctgtgtg        240
gaatgtctgc tttccttgtt tgtctattcc tttagactgt aagatcctag aaagtggggg        300
ccgtgccttg ctcatgactg tgtttctaac accaaacaca gtgttcagta gagagcagct        360
gctgagtacg tttctgctaa atgacagttg atggag                                  396
```

<210> SEQ ID NO 610
<211> LENGTH: 396
<212> TYPE: DNA
<213> ORGANISM: Homo sapiens

<400> SEQUENCE: 610

```
aatccttctg tgactcaaca tggaattaag ttgcctcctt tgaccctgaa agcaccatgt         60
actcaatctc atcttggcat gactcacttt gctgtgtgga atgtctgctt tccttgtttg        120
tctattcctt tagactgtaa gatcctagaa agtggggcc gtgccttgct catgactgtg         180
tttctaacac caaacacart gttcagtaga gagcagctgc tgagtacgtt tctgctaaat        240
gacagttgat ggaggacatt tagggttgct tggaggtcaa gtcaaggagg catttaacat        300
tctagtaaaa caaggaagta acaggctcct gaacatgccc acaatgaacc agatgcaaac        360 cttttcccctt ggcaggattc tttgcccata aagtgg                                 396
```

<210> SEQ ID NO 611
<211> LENGTH: 396
<212> TYPE: DNA
<213> ORGANISM: Homo sapiens

<400> SEQUENCE: 611

```
aaagcaccat gtactcaatc tcatcttggc atgactcact ttgctgtgtg gaatgtctgc         60
tttccttgtt tgtctattcc tttagactgt aagatcctag aaagtggggg ccgtgccttg        120
ctcatgactg tgtttctaac accaaacaca gtgttcagta gagagcagct gctgagtacg        180
tttctgctaa atgacagtkg atggaggaca tttaggttg cttggaggtc aagtcaagga         240
ggcatttaac attctagtaa aacaaggaag taacaggctc ctgaacatgc ccacaatgaa        300
ccagatgcaa accttttccc ttggcaggat tctttgccca taaagtggag cacgaaagca        360
ggacccagaa tgggaggagc ttccagagga ccggaa                                  396
```

<210> SEQ ID NO 612
<211> LENGTH: 396

```
<212> TYPE: DNA
<213> ORGANISM: Homo sapiens

<400> SEQUENCE: 612
ttctgctaaa tgacagttga tggaggacat ttagggttgc ttggaggtca agtcaaggag      60
gcatttaaca ttctagtaaa acaaggaagt aacaggctcc tgaacatgcc cacaatgaac     120
cagatgcaaa ccttttccct tggcaggatt ctttgcccat aaagtggagc acgaaagcag     180
gacccagaat gggaggagyt tccagaggac cggaacactt gcctttgagc gggtctacac     240
tgccaagtga gtcctaaccc tgatgttgct aataagtggg gcatgggca gggggcctc      300 cttctaggag tgatgaccac ccttaatacc acatgtctgt ctgagccaag tttctgagcg     360
ccagggaggt gaggaaggtt ggacttcacc agagag                               396

<210> SEQ ID NO 613
<211> LENGTH: 396
<212> TYPE: DNA
<213> ORGANISM: Homo sapiens

<400> SEQUENCE: 613
ggcatttaac attctagtaa aacaaggaag taacaggctc ctgaacatgc ccacaatgaa      60
ccagatgcaa accttttccc ttggcaggat tctttgccca taaagtggag cacgaaagca     120
ggacccagaa tgggaggagc ttccagagga ccggaacact tgcctttgag cgggtctaca     180
ctgccaagtg agtcctaamc tgatgttgc taataagtgg gggcatgggc agggggggcct   240 ccttctagga gtgatgacca ccttaatac cacatgtctg tctgagccaa gtttctgagc     300
gccagggagg tgaggaaggt tggacttcac cagagaggct tgtggacac ctttatcat    360 cttagtgagt gctagtgtca aaacaaaggg agtggg                               396

<210> SEQ ID NO 614
<211> LENGTH: 396
<212> TYPE: DNA
<213> ORGANISM: Homo sapiens

<400> SEQUENCE: 614
gctcctgaac atgcccacaa tgaaccagat gcaaaccttt tcccttggca ggattctttg      60
cccataaagt ggagcacgaa agcaggaccc agaatgggag gagcttccag aggaccggaa     120
cacttgcctt tgagcgggtc tacactgcca agtgagtcct aaccctgatg ttgctaataa     180 gtggggcat gggcagggrg gcctccttct aggagtgatg accacccta ataccacatg    240 tctgtctgag ccaagtttct gagcgccagg gaggtgagga aggttggact tcaccagaga     300
ggctttgtgg acacccttta tcatcttagt gagtgctagt gtcaaaacaa agggagtggg     360
gatatggggc acattggtgg agggaggtgt gatctc                               396

<210> SEQ ID NO 615
<211> LENGTH: 396
<212> TYPE: DNA
<213> ORGANISM: Homo sapiens

<400> SEQUENCE: 615
ttgcccataa agtggagcac gaaagcagga cccagaatgg gaggagcttc cagaggaccg      60
gaacacttgc ctttgagcgg gtctacactg ccaagtgagt cctaaccctg atgttgctaa     120 taagtgggg catgggcagg ggggcctcct tctaggagtg atgaccaccc ttaataccac     180
atgtctgtct gagccaagyt tctgagcgcc agggaggtga ggaaggttgg acttcaccag     240
```

```
agaggctttg tggacaccct ttatcatctt agtgagtgct agtgtcaaaa caaagggagt    300
ggggatatgg ggcacattgg tggagggagg tgtgatctct gcagcttcag aaagatctga    360
aagagtcatt tggttagaga agttgaccta tttcct                              396
```

<210> SEQ ID NO 616
<211> LENGTH: 396
<212> TYPE: DNA
<213> ORGANISM: Homo sapiens

<400> SEQUENCE: 616

```
aaacaaaggg agtggggata tggggcacat tggtggaggg aggtgtgatc tctgcagctt     60
cagaaagatc tgaaagagtc atttggttag agaagttgac ctatttcctg tggggttaga   120
ccagggttgc tactgtgaac accagccatg actcaccagt caccttcaga agccacaggc   180
aggacatgct gacgacagyc ttcaactcac ccaccccttg ctccctgcg ggtggaagtc    240 tggaggtgac accactgcat ttctaacac gggggctcct tgagcaacta gaacaagaac    300
agaaagaatg gggacattag caggtgcttt ccccctctct cattcttttc tttgaataaa   360
aaggttgttt gaaaacacct gagcggctcc taaaga                              396
```

<210> SEQ ID NO 617
<211> LENGTH: 396
<212> TYPE: DNA
<213> ORGANISM: Homo sapiens

<400> SEQUENCE: 617

```
ctcctctctt ctttatgcag agtgtatttc aaggctcagc cagtggcagg catgctgggg     60
actatggact acggactagg ggcctgtcac agaggaaggc ctcatgctag agagctaagg   120
gaggagctgg ccttcagttc catcccagga gcaactttga tgttcccaga gatccttcca   180 aaggggagt catggtcamc caagaaaaat gtattcagaa tgccaagaat ggtgcaaact    240
caggacaaag attcacactg cagggttgga gtccctgggc ttgctgctgg caccatggga   300
gggagggtcc ccttcagggg taccgttggt ttcctgtgaa ttaaactggc ttcaagggat   360
ctcgactgaa caggcctata tcacactcac tgatat                              396
```

<210> SEQ ID NO 618
<211> LENGTH: 396
<212> TYPE: DNA
<213> ORGANISM: Homo sapiens

<400> SEQUENCE: 618

```
tctcctcatc taggtatttt taattgtttc agtgaggtgt aggcatgagg ggattggagg     60
gggcatctcc tccattgcag ttttcattg gctgctttgc tccctcagct ccgaaatcgc    120
tgggccactc tcgaacgcat tagtacggta gtcacaggtt gattgcctgg cccttgccc    180 tctgtgggca ttttccctyt cagacagccc ctgagtactc acagtgctgc tacagtgggc   240
cacctagatc tccctctttc tccatgctcc cacgtgctct gggctccact cccttctccc   300
aagcacttct gtccagggct attccagcag tctgacctca aggaaatcct ttgctaaact   360
gattatagag aggtttctat tttaacattt aggtct                              396
```

<210> SEQ ID NO 619
<211> LENGTH: 396
<212> TYPE: DNA
<213> ORGANISM: Homo sapiens

<400> SEQUENCE: 619

```
atctaggtat ttttaattgt tcagtgagg tgtaggcatg aggggattgg aggggggcatc      60 tcctccattg cagtttttca ttggctgctt tgctccctca gctccgaaat cgctgggcca     120
ctctcgaacg cattagtacg gtagtcacag gttgattgcc tggcccttg ccctctgtgg      180 gcatttcccc tttcagacwg cccctgagta ctcacagtgc tgctacagtg ggccacctag     240
atctccctct ttctccatgc tcccacgtgc tctgggctcc actcccttct cccaagcact     300
tctgtccagg gctattccag cagtctgacc tcaaggaaat cctttgctaa actgattata     360
gagaggtttc tattttaaca tttaggtctt ccatgt                              396

<210> SEQ ID NO 620
<211> LENGTH: 396
<212> TYPE: DNA
<213> ORGANISM: Homo sapiens

<400> SEQUENCE: 620
aggtgtaggc atgaggggat tggagggggc atctcctcca ttgcagtttt tcattggctg      60
ctttgctccc tcagctccga aatcgctggg ccactctcga acgcattagt acggtagtca     120
caggttgatt gcctggcccc ttgccctctg tgggcatttt cccttcaga cagcccctga      180 gtactcacag tgctgctaya gtgggccacc tagatctccc tctttctcca tgctcccacg     240
tgctctgggc tccactccct tctcccaagc acttctgtcc agggctattc cagcagtctg     300
acctcaagga aatcctttgc taaactgatt atagagaggt ttctatttta acatttaggt     360
cttccatgta ttaattctca gaatcaattt aagatg                              396

<210> SEQ ID NO 621
<211> LENGTH: 396
<212> TYPE: DNA
<213> ORGANISM: Homo sapiens

<400> SEQUENCE: 621
cctttcagac agcccctgag tactcacagt gctgctacag tgggccacct agatctccct      60 cttttctccat gctcccacgt gctctgggct ccactccctt ctcccaagca cttctgtcca    120
gggctattcc agcagtctga cctcaaggaa atcctttgct aaactgatta tagagaggtt     180
tctattttaa catttaggyc ttccatgtat taattctcag aatcaattta agatgtttaa     240
aggtgtgatt taagacattt taaaaccatt tggaggagag tacagaaatt atgtcacttg     300
ctgtcagcct ctttgcacca tctgcagaga aagatactag agtcccgcct tggacacatc     360
cacatgcaag aggtgcaaag aaggtgtctt tgatga                              396

<210> SEQ ID NO 622
<211> LENGTH: 396
<212> TYPE: DNA
<213> ORGANISM: Homo sapiens

<400> SEQUENCE: 622
ttctcagaat caatttaaga tgtttaaagg tgtgatttaa gacattttaa aaccatttgg      60
aggagagtac agaaattatg tcacttgctg tcagcctctt tgcaccatct gcagagaaag     120
atactagagt cccgccttgg acacatccac atgcaagagg tgcaaagaag gtgtctttga     180
tgaggcaagg tcaaaactyc tccccagacg aaatccaaag aaagcattcc tactatgcta     240
tatcagtttg gaaagaaaaa cttctgccag gtgactgcat tctcactggt cacattgtgt     300
tcctatggac tcctcagctc aaccaatttg gagaagttat ggtgcaattt caccatatct     360
```

```
ggttagaagt taagtttcca atttgctggc aatgaa                                396
```

<210> SEQ ID NO 623
<211> LENGTH: 396
<212> TYPE: DNA
<213> ORGANISM: Homo sapiens

<400> SEQUENCE: 623

```
aagaaggtgt ctttgatgag gcaaggtcaa aacttctccc cagacgaaat ccaaagaaag     60
cattcctact atgctatatc agtttggaaa gaaaaacttc tgccaggtga ctgcattctc    120
actggtcaca ttgtgttcct atggactcct cagctcaacc aatttggaga agttatggtg    180
caatttcacc atatctggyt agaagttaag tttccaattt gctggcaatg aagaagaaat    240
ggagcaggcc aggctgtgta gtttctgcca cgtgcccccg ggagtgaaca gctctgtttg    300
taagaagcca tggtgcttag acctgggctc gctagttgcc agcctccaaa ttgcagaagt    360
gcccttggt tggtggctat gctgtgtcac ttggga                                396
```

<210> SEQ ID NO 624
<211> LENGTH: 396
<212> TYPE: DNA
<213> ORGANISM: Homo sapiens

<400> SEQUENCE: 624

```
gcaacatatc tgtgtgcctg tctgggttgt aaaaagggtc aaagatcaat gcagcaggca     60
gctacatgct ggcaaaagcc agaggcagct ggtctgtttg cctgtgccag gaaaccactg    120
ggaatggggt tgtgtgttat tctaggagaa agtcgtccca gcagcagctt ctccaggggc    180
atccaagagc actgaaaarg gttgcaagat gacccatgag gctgcaggaa gaaaagaaca    240
tgcatttaat cttgctatct gaaaagtaag acatgaagct ttcctcattt ttaatataca    300
catggacagt agtatgtgta tatagtttat atgcaaatat acttgttata aggttgcatg    360
ctcaaaattt ttggttcatg gggtgtggga tcataa                               396
```

<210> SEQ ID NO 625
<211> LENGTH: 396
<212> TYPE: DNA
<213> ORGANISM: Homo sapiens

<400> SEQUENCE: 625

```
cagctacatg ctggcaaaag ccagaggcag ctggtctgtt tgcctgtgcc aggaaaccac     60
tgggaatggg gttgtgtgtt attctaggag aaagtcgtcc cagcagcagc ttctccaggg    120
gcatccaaga gcactgaaaa gggttgcaag atgacccatg aggctgcagg aagaaaagaa    180
catgcattta atcttgctrt ctgaaaagta agacatgaag ctttcctcat ttttaatata    240
cacatggaca gtagtatgtg tatatagttt atatgcaaat atacttgtta taaggttgca    300
tgctcaaaat ttttggttca tggggtgtgg gatcataaat gtttagggac catggctatc    360
aaggaaaaac agcatgaagg ataaatgata ctggtg                               396
```

<210> SEQ ID NO 626
<211> LENGTH: 396
<212> TYPE: DNA
<213> ORGANISM: Homo sapiens

<400> SEQUENCE: 626

```
ctatctgaaa agtaagacat gaagctttcc tcatttttaa tatacacatg gacagtagta     60
tgtgtatata gtttatatgc aaatatactt gttataaggt tgcatgctca aaattttgg    120
```

```
ttcatgggt gtgggatcat aaatgtttag ggaccatggc tatcaaggaa aaacagcatg    180
aaggataaat gatactggyg gattaaaaag acagatgcat gtattttag cataaaacac    240 aactgctgac tgatacagat agctcaagat tctggggcag ctgctgaaca gatacactag    300
ccagtgtggc tcatcggctc agacttggcc ttaattaatg ggctgtccct ccacccatct    360
cccatgaggg cagagctgag ccagggtttg agagct                              396
```

<210> SEQ ID NO 627
<211> LENGTH: 396
<212> TYPE: DNA
<213> ORGANISM: Homo sapiens

<400> SEQUENCE: 627

```
agtttatatg caaatatact tgttataagg ttgcatgctc aaaattttg gttcatgggg     60 tgtgggatca taaatgttta gggaccatgg ctatcaagga aaaacagcat gaaggataaa    120
tgatactggt ggattaaaaa gacagatgca tgtatttta gcataaaaca caactgctga    180
ctgatacaga tagctcaasa ttctggggca gctgctgaac agatacacta gccagtgtgg    240
ctcatcggct cagacttggc cttaattaat gggctgtccc tccacccatc tcccatgagg    300
gcagagctga gccagggttt gagagctaaa aggaattgga cctggactct gttcacgtgt    360
atattttaat tctaattaat tcattctttt gaaaga                              396
```

<210> SEQ ID NO 628
<211> LENGTH: 394
<212> TYPE: DNA
<213> ORGANISM: Homo sapiens

<400> SEQUENCE: 628

```
gtattttag cataaaacac aactgctgac tgatacagat agctcaagat tctggggcag     60
ctgctgaaca gatacactag ccagtgtggc tcatcggctc agacttggcc ttaattaatg    120
ggctgtccct ccacccatct cccatgaggg cagagctgag ccagggtttg agagctaaaa    180
ggaattggac ctggactcdg ttcacgtgta tattttaatt ctaattaatt cattcttttg    240
aaagacagag tcacactctg ttgcctaggc tggagtgcag tggcacgatc ttggctcact    300
gcaacctcgg cctcccaggt tcaagttatt ctcctgcttc agcctcctga gtagctggga    360
ttataggcac atgcccccat gcctgactaa tttt                                394
```

<210> SEQ ID NO 629
<211> LENGTH: 396
<212> TYPE: DNA
<213> ORGANISM: Homo sapiens

<400> SEQUENCE: 629

```
gctaaaagga attggacctg gactctgttc acgtgtatat tttaattcta attaattcat     60
tcttttgaaa gacagagtca cactctgttg cctaggctgg agtgcagtgg cacgatcttg    120
gctcactgca acctcggcct cccaggttca agttattctc ctgcttcagc ctcctgagta    180
gctgggatta taggcacayg cccccatgcc tgactaattt ttgtatttt agtagagacg    240 gggtttcacc atgtcaggct ggtcttgaac tcctgacctc aggttatcca cccgccttgg    300
cccctcaaag tgttggaatt acaggtgtga gccaccgtgc ctggcctgtt cacatgtata    360
aaacacagtt taatgtccta ttcccagcca atgagc                              396
```

<210> SEQ ID NO 630

```
<211> LENGTH: 396
<212> TYPE: DNA
<213> ORGANISM: Homo sapiens

<400> SEQUENCE: 630
tcaggttatc acccgccctt ggcccctcaa agtgttggaa ttacaggtgt gagccaccgt        60
gcctggcctg ttcacatgta taaaacacag tttaatgtcc tattcccagc caatgagcat       120
ggctagagca gccttggtca aagtttggtt tttggagaaa atccttgtt agctgaccta        180 agattcctct ttgtgagtkt aagtaagcac aggttgcaga gaggagaagg gtctctggag       240
aggtgtaatt ttctaaatgg attacaagtt catggacttt taacaggtgt tacaggggat       300
aacaagttct ttatagacag acttttgagg acgtttaagg gtattctgat tcttggtttt       360
ctaagagggg aatgtattat ttaactacag acaccc                                 396

<210> SEQ ID NO 631
<211> LENGTH: 396
<212> TYPE: DNA
<213> ORGANISM: Homo sapiens

<400> SEQUENCE: 631
aaaatccaga ataataataa tttgtcaata ggaaagacat ttccactggg ggttaagaag        60
gaagacattg gaacaatgat agccaccact tattgaatgc ttactgtgag ccaggtggca       120
cttcaccttg tttcattctc acaacagtct agggaagtaa ttactaatgt ctccatccac       180
ctcttgtaga tgagcaaayt gaggctcatt gaggctagga aatgcaccca cactcacata       240
gcccataaga ggcagccatg gcattgggcc cagaccatgt gaacttcaaa gactacacga       300
gcagccactg ggcagctgtc atggctaaag ccacttgaat tcagcccagc agcaaccccc       360
tctccaggag gggcacataa gcttgcagct ttgggt                                 396

<210> SEQ ID NO 632
<211> LENGTH: 396
<212> TYPE: DNA
<213> ORGANISM: Homo sapiens

<400> SEQUENCE: 632
ataataataa tttgtcaata ggaaagacat ttccactggg ggttaagaag gaagacattg        60
gaacaatgat agccaccact tattgaatgc ttactgtgag ccaggtggca cttcaccttg       120
tttcattctc acaacagtct agggaagtaa ttactaatgt ctccatccac ctcttgtaga       180
tgagcaaact gaggctcayt gaggctagga aatgcaccca cactcacata gcccataaga       240
ggcagccatg gcattgggcc cagaccatgt gaacttcaaa gactacacga gcagccactg       300
ggcagctgtc atggctaaag ccacttgaat tcagcccagc agcaaccccc tctccaggag       360
gggcacataa gcttgcagct ttgggtagaa gctgca                                 396

<210> SEQ ID NO 633
<211> LENGTH: 396
<212> TYPE: DNA
<213> ORGANISM: Homo sapiens

<400> SEQUENCE: 633
gcacttgaag tcctggatgg cgagagggac tggcttgagc cagagccagg aacaaggctc        60
tgagaatatt ctggaaatcc acaggaggaa cccatttct tacagctggg agaatttcat         120
tcaactccag gctgaccatg ttttattagg aacgaaggtg acttgaacta atagtcagga       180
atggttgaat acggacccra tgtcaaatca ctaggcagtt cacatttcta atgagcaaat       240
```

```
ccettagaca attaagaatt ttttteettt tgcataacce agacaaaatc gctacttaaa    300
aacaaaccaa agacccgaaa catgagaaag agaaggaagc aggggaaatc tttggtacta    360
ataagttttt aaacaataag agcaccagat atttta                              396
```

<210> SEQ ID NO 634
<211> LENGTH: 396
<212> TYPE: DNA
<213> ORGANISM: Homo sapiens

<400> SEQUENCE: 634

```
atgagcaaat cccttagaca attaagaatt ttttteettt tgcataacce agacaaaatc     60 gctacttaaa aacaaaccaa agacccgaaa catgagaaag agaaggaagc aggggaaatc    120
tttggtacta ataagttttt aaacaataag agcaccagat attttaccce atcagacaca    180 gaatgttatt cgaataacsa aaaaggaat ttttctcta agtttcttga actggaaaat     240
gaatcatatt ttctcagtcc tgaggctgca attttgtgcc tctagtaaca tataagaata    300
gatgtgatgc cagtgcccag tagctgctgc aattgttact tggggacctg tttattcact    360
aagcacttca ccccagtgat aaatttgtag gggcct                              396
```

<210> SEQ ID NO 635
<211> LENGTH: 396
<212> TYPE: DNA
<213> ORGANISM: Homo sapiens

<400> SEQUENCE: 635

```
ccgtgtccat tagatcagtg gaaattctgg gattcagagc actttgcaag gtcagcaggg     60
gtctgctctt tctgtcctgt tcctggtttt tggttgtgcc tggattccag ggtaggtttc    120
tcatctgtta ccttcataga cttctccaga aaaggatctt ttgaccatca gaggaccacg    180
aagattccat tggtgaggyg cagataacct gatctctctg ggttctctgc agggcacaga    240
tgaagggctg gccattccca agttctcagt ggtaccactg aggcatgaga ccctaatggt    300
ttgcatgagc agtttgaaaa ttgcatcttt gttttacct atataatcac atgaaacccg    360
tggttctcaa acgtcagcag gcatcagcat cacatg                              396
```

<210> SEQ ID NO 636
<211> LENGTH: 396
<212> TYPE: DNA
<213> ORGANISM: Homo sapiens

<400> SEQUENCE: 636

```
tcagtggtac cactgaggca tgagacccta atggtttgca tgagcagttt gaaaattgca     60
tctttgtttt tacctatata atcacatgaa acccgtggtt ctcaaacgtc agcaggcatc    120
agcatcacat ggagggcttg ttaaaacaga tttctgggcc ccaacacaga gttttaaatt    180
ctgaaggcct gaggtgggyg tgaacatttg catttctaac atgttctcga tgctgctgcc    240
gcctctggtc ccgagagcat gcctggagaa ctgccacctt cgaccatgga ctgtgagaat    300
tcacatggac ctcagaatta taatcagtct ctcagtttta cagataagga aactaaatcc    360
agagagattg ttttgccaat ggtgaacagc tggtta                              396
```

<210> SEQ ID NO 637
<211> LENGTH: 396
<212> TYPE: DNA
<213> ORGANISM: Homo sapiens

```
<400> SEQUENCE: 637
atggtttgca tgagcagttt gaaaattgca tctttgtttt tacctatata atcacatgaa    60
acccgtggtt ctcaaacgtc agcaggcatc agcatcacat ggagggcttg ttaaaacaga   120
tttctgggcc ccaacacaga gttttaaatt ctgaaggcct gaggtgggtg tgaacatttg   180
catttctaac atgttctcra tgctgctgcc gcctctggtc ccgagagcat gcctggagaa   240
ctgccacctt cgaccatgga ctgtgagaat tcacatggac tcagaattta taatcagtct   300
ctcagtttta cagataagga aactaaatcc agagagattg ttttgccaat ggtgaacagc   360
tggttaaagt caggatggag actttaatcc tagtca                             396

<210> SEQ ID NO 638
<211> LENGTH: 396
<212> TYPE: DNA
<213> ORGANISM: Homo sapiens

<400> SEQUENCE: 638
gagcagtttg aaaattgcat ctttgttttt acctatataa tcacatgaaa cccgtggttc    60
tcaaacgtca gcaggcatca gcatcacatg gagggcttgt taaaacagat ttctgggccc   120
caacacagag ttttaaattc tgaaggcctg aggtgggtgt gaacatttgc atttctaaca   180
tgttctcgat gctgctgcyg cctctggtcc gagagcatg cctggagaac tgccaccttc    240
gaccatggac tgtgagaatt cacatggacc tcagaattat aatcagtctc tcagttttac   300
agataaggaa actaaatcca gagagattgt tttgccaatg gtgaacagct ggttaaagtc   360
aggatggaga ctttaatcct agtcaagtga cctttc                             396

<210> SEQ ID NO 639
<211> LENGTH: 396
<212> TYPE: DNA
<213> ORGANISM: Homo sapiens

<400> SEQUENCE: 639
agtttgaaaa ttgcatcttt gttttacct atataatcac atgaaacccg tggttctcaa     60
acgtcagcag gcatcagcat cacatggagg gcttgttaaa acagatttct ggaccccaac   120
acagagtttt aaattctgaa ggcctgaggt gggtgtgaac atttgcattt ctaacatgtt   180
ctcgatgctg ctgccgcckc tggtcccgag agcatgcctg gagaactgcc accttcgacc   240
atggactgtg agaattcaca tggacctcag aattataatc agtctctcag ttttacagat   300
aaggaaacta atccagaga gattgttttg ccaatggtga acagctggtt aaagtcagga    360
tggagacttt aatcctagtc aagtgacctt tcctct                             396

<210> SEQ ID NO 640
<211> LENGTH: 396
<212> TYPE: DNA
<213> ORGANISM: Homo sapiens

<400> SEQUENCE: 640
catctttgtt tttacctata taatcacatg aaacccgtgg ttctcaaacg tcagcaggca    60
tcagcatcac atggagggct tgttaaaaca gatttctggg ccccaacaca gagttttaaa   120
ttctgaaggc ctgaggtggg tgtgaacatt tgcatttcta acatgttctc gatgctgctg   180
ccgcctctgg tcccgagakc atgcctggag aactgccacc ttcgaccatg gactgtgaga   240
attcacatgg acctcagaat tataatcagt ctctcagttt tacagataag gaaactaaat   300
ccagagagat tgttttgcca atggtgaaca gctggttaaa gtcaggatgg agactttaat   360
```

```
cctagtcaag tgacctttcc tctgtattta tttccc                               396
```

<210> SEQ ID NO 641
<211> LENGTH: 396
<212> TYPE: DNA
<213> ORGANISM: Homo sapiens

<400> SEQUENCE: 641

```
atttctgaca tcctgaacca tagtaaaagg gtgttttttg ttttttttgag acagagtctt    60
gctctgttgc ctgggctgga gtgcagtggt gtgatcttgg ctcgctgcaa cctccgcctc   120
ccaggttcaa gtgattctcc tgcctcagcc tcctgagtag ctgggattac aggtgcttgc   180
caccacacct ggctatttkt tgtgttttta gtagagacag ggtttcacca tgttggccag   240
gctggtcttg aactcctgac cttgtgatct gcctgcctca gcctcccaaa ttgctgggat   300
tacaaggcgt gttgttttaa gccactcagt tgtggccac ttgttacagc agcaagagga    360
aactcataca gttatcatgt gaactcacag gaatat                             396
```

<210> SEQ ID NO 642
<211> LENGTH: 396
<212> TYPE: DNA
<213> ORGANISM: Homo sapiens

<400> SEQUENCE: 642

```
gatctgcctg cctcagcctc ccaaattgct gggattacaa ggcgtgttgt tttaagccac    60
tcagtttgtg gccacttgtt acagcagcaa gaggaaactc atacagttat catgtgaact   120
cacaggaata tggtgagtta aaagagagg aagggtgcaa acatccacg gtagagtgag     180
aactctccag ggagtgagra ctgtgcccag catacagtga tcaccctctt agtaagctaa   240
gtttctgagc accagctttt ttgagttgac tttgttgtct ttaacatttg aagatcaccc   300
ttctttgctc agcctggctt gcagacctgg gctgatttgt ggatctgata gaaaagtttc   360
cttagttggg ctcttctccc cgaccacccc catgcc                             396
```

<210> SEQ ID NO 643
<211> LENGTH: 396
<212> TYPE: DNA
<213> ORGANISM: Homo sapiens

<400> SEQUENCE: 643

```
tgcctcagcc tcccaaattg ctgggattac aaggcgtgtt gttttaagcc actcagtttg    60
tggccacttg ttacagcagc aagaggaaac tcatacagtt atcatgtgaa ctcacaggaa   120
tatggtgagt taaaaagaga ggaagggtgc aaaacatcca cggtagagtg agaactctcc   180
agggagtgag gactgtgcmc agcatacagt gatcaccctc ttagtaagct aagtttctga   240
gcaccagctt ttttgagttg actttgttgt ctttaacatt tgaagatcac ccttctttgc   300
tcagcctggc ttgcagacct gggctgattt gtggatctga tagaaaagtt tccttagttg   360
ggctcttctc cccgaccacc cccatgccag tgtggc                             396
```

<210> SEQ ID NO 644
<211> LENGTH: 396
<212> TYPE: DNA
<213> ORGANISM: Homo sapiens

<400> SEQUENCE: 644

```
gctactttgc agccaaggta actcagactt cccttttgttc attctccttc tataaagtgc   60
```

| | |
|---|---|
| atctcaagga ggttcaaagg gcaggcttt tgttgaaagg actttgcctg acctctggct | 120 |
| cccatctgtg aagccctgga gaggtgagag ccctcgggag gccgtgttc aggcatgctc | 180 |
| tgcacccgtg cagagcgcrt gtgataatgc attgctaatg cttgctccct ggtggctggc | 240 |
| tgagagctgc tgtgctgaca agggtggtt aaggctaaat gtgactcaga atccttaagc | 300 |
| agtgttagtt cagatacaag ggcattataa atgagagtgc ctgagggatc tattttggga | 360 |
| ccgctgtcac ttggctcttc tgctaataag cttcca | 396 |

<210> SEQ ID NO 645
<211> LENGTH: 396
<212> TYPE: DNA
<213> ORGANISM: Homo sapiens

<400> SEQUENCE: 645

| | |
|---|---|
| acagttatca gcagcccaca ggcttgactt gagcaagttg gaaagacaaa tcaacttcca | 60 |
| gagttgattt aacattgagt ggaaatcagt catactttg gtccccttc ggggccacgc | 120 |
| ctggcactgt gcctggtggc agatcggcat gaactggcca gcttctgtgg ccctggaggg | 180 |
| cacaggcaga aaggccacrc tcagtcccat gatgaactgt ttaagactta ttgttgtctc | 240 |
| cccgctctgt aaagtagata gagtggattt tatgtcccct attacctttc aggatacttt | 300 |
| gactcaggga gataaagtaa cttgggtaca gctactcagc tggtgaagaa cacaggcaga | 360 |
| atgagtgcct gggtcttttg acttaaaatt ctggat | 396 |

<210> SEQ ID NO 646
<211> LENGTH: 396
<212> TYPE: DNA
<213> ORGANISM: Homo sapiens

<400> SEQUENCE: 646

| | |
|---|---|
| ctgtgcctgg tggcagatcg gcatgaactg gccagcttct gtggccctgg agggcacagg | 60 |
| cagaaaggcc acactcagtc ccatgatgaa ctgtttaaga cttattgttg tctccccgct | 120 |
| ctgtaaagta gatagagtgg atttatgtc ccttattacc tttcaggata ctttgactca | 180 |
| gggagataaa gtaacttgsg tacagctact cagctggtga agaacacagg cagaatgagt | 240 |
| gcctgggtct tttgacttaa aattctggat ttttcacaaa gatcctctta ctttattcat | 300 |
| ttacataata aatatatatt gaagagctac tctgtgccaa gccctgtgcc tagatataca | 360 |
| gtgataaata aagagtagct tctagaggtc acctgg | 396 |

<210> SEQ ID NO 647
<211> LENGTH: 396
<212> TYPE: DNA
<213> ORGANISM: Homo sapiens

<400> SEQUENCE: 647

| | |
|---|---|
| aagttcagtg atagagagca gaggtgaggc ggcagcagaa accacttaag ggacaccacg | 60 |
| tggcactcct tctgtgctga gaaggctgtc agtaagctca ccatttattt cctattttct | 120 |
| ctcctgagtt aaataggaaa catgtctcgc attacttgaa aaatcaagtc aaactatgct | 180 |
| cttactagga gttatggtyc tttttatgtc ttagatgatg cttgatctag atgaatgcgg | 240 |
| acttgctgta gctagataaa tacaatggga gtttgaaggt gtttcgtagc cctggaaata | 300 |
| ggtatttcct gtcaaaacaa gctttgtcat tgccagcaga caaaagcatc agtaaccttg | 360 |
| gttgataatc gtcatttctt aggaataaag tagact | 396 |

<210> SEQ ID NO 648
<211> LENGTH: 396
<212> TYPE: DNA
<213> ORGANISM: Homo sapiens

<400> SEQUENCE: 648

```
gtatttcctg tcaaaacaag ctttgtcatt gccagcagac aaaagcatca gtaaccttgg      60
ttgataatcg tcatttctta ggaataaagt agactgtaga attttttta gcagaaagga     120 aacccaaaga taattctagt gcaaatccct cactttatag agcagaagct caagtcccag    180
aggaacaagt ggcttgaayg aacatcagaa ttttaggggc tggatttgta ccctcctggt    240
gccagcagcc cacttccctg caggaggcac tcaccttcct tgcacagggg tatgagtgtg    300
gccattttcc acccataatc tctgttagct catgttcaat tgggttccca ttgaaagaaa    360
aatggaccag taagttggag cagaatcatt cagatg                              396
```

<210> SEQ ID NO 649
<211> LENGTH: 396
<212> TYPE: DNA
<213> ORGANISM: Homo sapiens

<400> SEQUENCE: 649

```
agctttgtca ttgccagcag acaaaagcat cagtaacctt ggttgataat cgtcatttct     60
taggaataaa gtagactgta gaattttttt tagcagaaag gaaacccaaa gataattcta    120
gtgcaaatcc ctcactttat agagcagaag ctcaagtccc agaggaacaa gtggcttgaa    180
cgaacatcag aattttagkg ctggatttg taccctcctg gtgccagcag cccacttccc    240
tgcaggaggc actcaccttc cttgcacagg ggtatgagtg tggccatttt ccacccataa    300
tctctgttag ctcatgttca attgggttcc cattgaaaga aaaatggacc agtaagttgg    360
agcagaatca ttcagatggt ataacataag gaaaaa                              396
```

<210> SEQ ID NO 650
<211> LENGTH: 396
<212> TYPE: DNA
<213> ORGANISM: Homo sapiens

<400> SEQUENCE: 650

```
tgtttaaatt gcttttatat ctgtagctct agataacact agttccagct tagttaactc     60
ccagctccaa gccttcagga cttcatagag ttattggggt gctgctcttg cagtttccc    120 aaaaagctag aatgcagagg gaatctcctt cccaaaaagc tagaatgcag agggaatctc    180
cttcccaaaa ggctagaayg cagagggaat ctccttccca aaaagctaga atgcagaggg    240
aatctccttc ccaaaaggct agaacgcaga gggaatctcc ttcccaaaag ctagaacgc    300 agagggaatc tccttcccaa aggctagaa tgcagaggga atgtccttct cttctaaatg    360
gtagctgtta gttcaagaaa ggttaaacat tgtgct                              396
```

<210> SEQ ID NO 651
<211> LENGTH: 396
<212> TYPE: DNA
<213> ORGANISM: Homo sapiens

<400> SEQUENCE: 651

```
gctgcgtttg ctggactgat gtacttgttt gtgaggcaaa agtactttgt cggttaccta     60
ggagagagaa cgcagaggta ggtaactggg actactaaag aactgtggag cgattcctga    120
tttttgagca ggaagagtga caattcaaaa cagtatttga ctagattcac ggctccgtag    180
```

```
catcccttg ggtgggagsg ggaaggctga ctaggacctc tgattcttct ttccctgagc    240
tttgaaggct ctgaaaatac agctgggggg acttgcccag ttttcttatt aagcaattcc    300
tccgcatggt gctggctttc aaagggtgct tcagtgctgt ttgctgcacg tgccttgcag    360
ccccacaccc tgcactcccg ccctgcagag tctggc                              396

<210> SEQ ID NO 652
<211> LENGTH: 396
<212> TYPE: DNA
<213> ORGANISM: Homo sapiens

<400> SEQUENCE: 652
gaggcaaaag tactttgtcg gttacctagg agagagaacg cagaggtagg taactgggac    60
tactaaagaa ctgtggagcg attcctgatt tttgagcagg aagagtgaca attcaaaaca    120
gtatttgact agattcacgg ctccgtagca tcccttgggt gggaggggg aaggctgact     180 aggacctctg attcttctyt ccctgagctt tgaaggctct gaaaatacag ctgggggac    240 ttgcccagtt ttcttattaa gcaattcctc cgcatggtgc tggctttcaa agggtgcttc    300
agtgctgttt gctgcacgtg ccttgcagcc ccacacctg cactcccgcc ctgcagagtc    360
tggcgctgga atgacatttt aggtctgggt tcccag                              396

<210> SEQ ID NO 653
<211> LENGTH: 396
<212> TYPE: DNA
<213> ORGANISM: Homo sapiens

<400> SEQUENCE: 653
tatctttcag ggaccagaag aaagaatgtt gggaaaataa gatgcagtaa gatgcagaca    60
tgacagcagg gtgcagcggc tcacgcctat aatcccagca ctttgggagg ctgaggtggg    120
tggatcacct gaggtcagga gtttgagacc agcctggcca acatggtgaa accccgtctc    180
tactaaaaaa tatacaaarc attagccagg catggtggtg ggcgcctgta atcccagcta    240
ctccataggc tgaggctgga gaatcgcttg aacccaggag gcagaggttg cagtgagccg    300
agattgcgcc actgcactcc agcctgggca acaaaagcaa aactccatct caaaaaaaaa    360
aaaaaaaaaa aaaaaaagga tgcagacacg agactg                              396

<210> SEQ ID NO 654
<211> LENGTH: 396
<212> TYPE: DNA
<213> ORGANISM: Homo sapiens

<400> SEQUENCE: 654
tgggcgcctg taatcccagc tactccatag gctgaggctg gagaatcgct tgaacccagg    60
aggcagaggt tgcagtgagc cgagattgcg ccactgcact ccagcctggg caacaaaagc    120
aaaactccat ctcaaaaaaa aaaaaaaaaa aaaaaaaaaa gatgcagaca cgagactgtg    180
aaactgacta gcatcaccwt tgcattgttt atagatgttg ccagacagaa agccccaaag    240
cagcacagta ccttcctgac atctggacta ggaaatctag attttagtaa aatacatgct    300
aatacttaca gaagaaatgt cggcgttaga gtatgccgtc agttccttag agattgcaat    360
tcctaatgca ctagtatggt ttcaggtgcc aggaac                              396

<210> SEQ ID NO 655
<211> LENGTH: 396
<212> TYPE: DNA
<213> ORGANISM: Homo sapiens
```

```
<400> SEQUENCE: 655
actccatctc aaaaaaaaaa aaaaaaaaaa aaaaaaagat gcagacacga gactgtgaaa      60
ctgactagca tcaccattgc attgtttata gatgttgcca gacagaaagc cccaaagcag     120
cacagtacct tcctgacatc tggactagga aatctagatt ttagtaaaat acatgctaat     180
acttacagaa gaaatgtcrg cgttagagta tgccgtcagt tccttagaga ttgcaattcc     240
taatgcacta gtatggtttc aggtgccagg aacacgttct gtgaggctgc tgccccaggt     300
gctgacccca gccttccaca ccatttttcct tccttgtgtt cacagccgct ctgtctttta    360
caatagcacc cctctctagt ggctaatggg ctctat                               396

<210> SEQ ID NO 656
<211> LENGTH: 396
<212> TYPE: DNA
<213> ORGANISM: Homo sapiens

<400> SEQUENCE: 656
aaaaaaaaaa aaaaaaaaaa aagatgcaga cacgagactg tgaaactgac tagcatcacc      60
attgcattgt ttatagatgt tgccagacag aaagccccaa agcagcacag taccttcctg     120
acatctggac taggaaatct agattttagt aaaatacatg ctaatactta cagaagaaat     180
gtcggcgtta gagtatgcyg tcagttcctt agagattgca attcctaatg cactagtatg     240
gtttcaggtg ccaggaacac gttctgtgag gctgctgccc caggtgctga ccccagcctt     300
ccacaccatt ttccttcctt gtgttcacag ccgctctgtc ttttacaata gcacccctct     360
ctagtggcta atgggctcta tgattagata gcatcc                               396

<210> SEQ ID NO 657
<211> LENGTH: 396
<212> TYPE: DNA
<213> ORGANISM: Homo sapiens

<400> SEQUENCE: 657
tttcaggtgc caggaacacg ttctgtgagg ctgctgcccc aggtgctgac cccagccttc      60
cacaccattt tccttccttg tgttcacagc cgctctgtct tttacaatag cacccctctc     120
tagtggctaa tgggctctat gattagatag catccttcag tagtgataaa ggcagtgaca     180
tcctagggag gtcagcggkt gaaagcgcta tatctggaaa acctgagagc ctgtgaagct     240
caaggacttg acggggttag accgtgagcc gggctgcagc tggaaaaaga atgactgttc     300
tttcagcaga tccttccctg tgccatctct ttcttcattc ctctctagtg gcattcttat     360
ttatcctcta aaaccacaat tccattatct ctccta                               396

<210> SEQ ID NO 658
<211> LENGTH: 396
<212> TYPE: DNA
<213> ORGANISM: Homo sapiens

<400> SEQUENCE: 658
gagggtcttc tcttttgcct ggctccctat gcagccctat cttaccccct gcaaagtccc      60
agggatgtgg ctcagtcact gctcctctct tcatctgtca ccacttgctt gagatcctac     120
agctgcttta attccgagac catctgcaga acatgacaaa atttgtccac ctacccacat     180 gtcctttttaa ctttaaagrc tttactaact gattcctatt agggaatgaa cagaggtggc     240
aaaaataaac aataggagat tgatttacaa gaaatcttta aaatagtaga tttcttcgga     300
```

```
cctcattgaa atataaatgg cctgccttct tgtgtccctc cctggtctcc ctctttaggt    360
gataagaaga agatcctgcc agccccataa cccgcc                             396
```

<210> SEQ ID NO 659
<211> LENGTH: 396
<212> TYPE: DNA
<213> ORGANISM: Homo sapiens

<400> SEQUENCE: 659

```
ttaaaatagt agatttcttc ggacctcatt gaaatataaa tggcctgcct tcttgtgtcc    60
ctccctggtc tccctcttta ggtgataaga agaagatcct gccagcccca taacccgcca   120
tctgcgcggg ttctagaccc ccttctcctc ccctctggcc gtggtaggca ttactgatga   180
atcatggtgc tctttcttmc agagaccaaa cctggcctcg gaatccttct aacacagat   240 actgcttaac acaaccactc tgagcagctg tcataagtag aagtaataga tactagaaga   300
aatgtctaag cctaatctag accaaaatac ggcctgatat agatgcaagc cagaggggct   360
ttatggttaa atgcaaggag attttcaacc ctgccg                             396
```

<210> SEQ ID NO 660
<211> LENGTH: 396
<212> TYPE: DNA
<213> ORGANISM: Homo sapiens

<400> SEQUENCE: 660

```
ctggtctccc tctttaggtg ataagaagaa gatcctgcca gccccataac cgccatctg    60 cgcgggttct agaccccctt ctcctcccct ctggccgtgg taggcattac tgatgaatca   120
tggtgctctt tcttccagag accaaacctg gcctcggaat ccttcttaac acagatactg   180
cttaacacaa ccactctgrg cagctgtcat aagtagaagt aatagatact agaagaaatg   240
tctaagccta atctagacca aaatacggcc tgatatagat gcaagccaga ggggctttat   300
ggttaaatgc aaggagattt caaccctgc cgtctagaag ctacttgctg agatcttctt    360
cagttgggcc catctcctcc ccaggcctct cttctg                             396
```

<210> SEQ ID NO 661
<211> LENGTH: 396
<212> TYPE: DNA
<213> ORGANISM: Homo sapiens

<400> SEQUENCE: 661

```
ccataacccg ccatctgcgc gggttctaga ccccttctc ctcccctctg gccgtggtag    60
gcattactga tgaatcatgg tgctctttct tccagagacc aaacctggcc tcggaatcct   120
tcttaacaca gatactgctt aacacaacca ctctgagcag ctgtcataag tagaagtaat   180
agatactaga agaaatgtmt aagcctaatc tagaccaaaa tacggcctga tatagatgca   240
agccagaggg gctttatggt taaatgcaag gagattttca accctgccgt ctagaagcta   300
cttgctgaga tcttcttcag ttgggcccat ctcctcccca ggcctctctt ctgttcctgg   360
gctatgtcac acttggactc tgcagacacc taatgc                             396
```

<210> SEQ ID NO 662
<211> LENGTH: 396
<212> TYPE: DNA
<213> ORGANISM: Homo sapiens

<400> SEQUENCE: 662

```
tggtaggcat tactgatgaa tcatggtgct ctttcttcca gagaccaaac ctggcctcgg    60
```

```
aatccttctt aacacagata ctgcttaaca caaccactct gagcagctgt cataagtaga    120
agtaatagat actagaagaa atgtctaagc ctaatctaga ccaaaatacg gcctgatata    180
gatgcaagcc agagggckt tatggttaaa tgcaaggaga ttttcaaccc tgccgtctag    240
aagctacttg ctgagatctt cttcagttgg gcccatctcc tccccaggcc tctcttctgt    300
tcctgggcta tgtcacactt ggactctgca gacacctaat gctcttggga cctgctttag    360
ttcttgacct caccaaccga ggaggaattg ctagat                              396
```

<210> SEQ ID NO 663
<211> LENGTH: 396
<212> TYPE: DNA
<213> ORGANISM: Homo sapiens

<400> SEQUENCE: 663

```
cagagaccaa acctggcctc ggaatccttc ttaacacaga tactgcttaa cacaaccact     60
ctgagcagct gtcataagta gaagtaatag atactagaag aaatgtctaa gcctaatcta    120
gaccaaaata cggcctgata tagatgcaag ccagaggggc tttatggtta atgcaagga    180 gattttcaac cctgccgtyt agaagctact tgctgagatc ttcttcagtt gggcccatct    240
cctccccagg cctctcttct gttcctgggc tatgtcacac ttggactctg cagacaccta    300
atgctcttgg gacctgcttt agttcttgac ctcaccaacc gaggaggaat tgctagatga    360
gatccttccc ccggaatttc tctcttgaac cccaga                              396
```

<210> SEQ ID NO 664
<211> LENGTH: 396
<212> TYPE: DNA
<213> ORGANISM: Homo sapiens

<400> SEQUENCE: 664

```
gggctttatg gttaaatgca aggagatttt caaccctgcc gtctagaagc tacttgctga     60
gatcttcttc agttgggccc atctcctccc caggcctctc ttctgttcct gggctatgtc    120
acacttggac tctgcagaca cctaatgctc ttgggacctg ctttagttct tgacctcacc    180
aaccgaggag gaattgctmg atgagatcct tcccccggaa tttctctctt gaaccccaga    240
tggtccgttg ccccttttcca gaagttgctc cagcccgtc cgcttaggaa gttcagtgtc    300
atccttgatc cagtgggtag ggaagacatt ccataatgaa tgccccagtc tgagcttctt    360
ccttcaggct tcaggctgcc ctgcgaggat tttgca                              396
```

<210> SEQ ID NO 665
<211> LENGTH: 396
<212> TYPE: DNA
<213> ORGANISM: Homo sapiens

<400> SEQUENCE: 665

```
gtagctgaga ctacaggtgt gcactaccac acccagctaa tttttgtat ttttagtaga      60 gatagggttt agctatgttg gccaggctgg tctcgaactg ctgaactcaa gcaatctgcc    120
atccccggcc tcccaaagta ctgggagtat aggcataagc cacccatgat gcccagcctg    180
aatcttggtt tcttcccrt tcatttaagc tattacctgg gcctgaactc aatggcacct    240
ggcaccaact ggcaactgac tcttggtctt ttattaccta ccttccctag caggcactgg    300
gttgctccct cttcctatcc catggagtcc tgtcctctgt tggggctcct actgatcctc    360
ttggcaatat gaagttctca gctcaatggt gggtgg                              396
```

<210> SEQ ID NO 666
<211> LENGTH: 396
<212> TYPE: DNA
<213> ORGANISM: Homo sapiens

<400> SEQUENCE: 666

```
cccggcctcc caaagtactg ggagtatagg cataagccac ccatgatgcc cagcctgaat      60
cttggtttct tccccattca tttaagctat tacctgggcc tgaactcaat ggcacctggc     120
accaactggc aactgactct tggtctttta ttacctacct tccctagcag gcactgggtt     180
gctccctctt cctatcccrt ggagtcctgt cctctgttgg ggctcctact gatcctcttg     240
gcaatatgaa gttctcagct caatggtggg tgggcaatga ctgccaactc ttgaggccaa     300
tgaactcagg ttaccccact cctcctcctc ctgagttgct cactcactcc tcattcactc     360
aacattgatt cagtagatat ttgctacctg ctctgt                               396
```

<210> SEQ ID NO 667
<211> LENGTH: 396
<212> TYPE: DNA
<213> ORGANISM: Homo sapiens

<400> SEQUENCE: 667

```
ccggcctccc aaagtactgg gagtataggc ataagccacc catgatgccc agcctgaatc      60
ttggtttctt ccccattcat ttaagctatt acctgggcct gaactcaatg cacctggca     120
ccaactggca actgactctt ggtcttttat tacctacctt ccctagcagg cactgggttg     180
ctccctcttc ctatcccayg gagtcctgtc ctctgttggg gctcctactg atcctcttgg     240
caatatgaag ttctcagctc aatggtgggt gggcaatgac tgccaactct tgaggccaat     300
gaactcaggt taccccactc ctcctcctcc tgagttgctc actcactcct cattcactca     360
acattgattc agtagatatt tgctacctgc tctgtg                               396
```

<210> SEQ ID NO 668
<211> LENGTH: 396
<212> TYPE: DNA
<213> ORGANISM: Homo sapiens

<400> SEQUENCE: 668

```
ggcataagcc acccatgatg cccagcctga atcttggttt cttccccatt catttaagct      60
attacctggg cctgaactca atggcacctg gcaccaactg gcaactgact cttggtctt     120
tattacctac cttccctagc aggcactggg ttgctccctc ttcctatccc atggagtcct     180
gtcctctgtt ggggctccya ctgatcctct tggcaatatg aagttctcag ctcaatggtg     240
ggtgggcaat gactgccaac tcttgaggcc aatgaactca ggttacccca ctcctcctcc     300
tcctgagttg ctcactcact cctcattcac tcaacattga ttcagtagat atttgctacc     360
tgctctgtgc caggtaccag gtcagttgct gaagga                               396
```

<210> SEQ ID NO 669
<211> LENGTH: 396
<212> TYPE: DNA
<213> ORGANISM: Homo sapiens

<400> SEQUENCE: 669

```
cctggcacca actggcaact gactcttggt cttttattac ctaccttccc tagcaggcac      60
tgggttgctc cctcttccta tcccatggag tcctgtcctc tgttggggct cctactgatc     120
ctcttggcaa tatgaagttc tcagctcaat ggtgggtggg caatgactgc caactcttga     180
```

```
ggccaatgaa ctcaggttwc cccactcctc ctcctcctga gttgctcact cactcctcat    240
tcactcaaca ttgattcagt agatatttgc tacctgctct gtgccaggta ccaggtcagt    300
tgctgaagga gtaacagtga acatgacgga gtctttgtcc ccaaggagac caaggtgtc     360 tcctagagcc agggcacat tgcaagacca aatata                               396

<210> SEQ ID NO 670
<211> LENGTH: 396
<212> TYPE: DNA
<213> ORGANISM: Homo sapiens

<400> SEQUENCE: 670
ctggcaactg actcttggtc ttttattacc taccttccct agcaggcact gggttgctcc    60
ctcttcctat cccatggagt cctgtcctct gttggggctc ctactgatcc tcttggcaat    120
atgaagttct cagctcaatg gtgggtgggc aatgactgcc aactcttgag gccaatgaac    180
tcaggttacc ccactcctyc tcctcctgag ttgctcactc actcctcatt cactcaacat    240
tgattcagta gatatttgct acctgctctg tgccaggtac caggtcagtt gctgaaggag    300
taacagtgaa catgacggag tctttgtccc caaggagacc caaggtgtct cctagagcca    360
ggggcacatt gcaagaccaa atatattcaa cttacc                              396

<210> SEQ ID NO 671
<211> LENGTH: 396
<212> TYPE: DNA
<213> ORGANISM: Homo sapiens

<400> SEQUENCE: 671
ccatggagtc ctgtcctctg ttggggctcc tactgatcct cttggcaata tgaagttctc    60
agctcaatgg tgggtgggca atgactgcca actcttgagg ccaatgaact caggttaccc    120
cactcctcct cctcctgagt tgctcactca ctcctcattc actcaacatt gattcagtag    180
atatttgcta cctgctctrt gccaggtacc aggtcagttg ctgaaggagt aacagtgaac    240
atgacggagt ctttgtcccc aaggagaccc aaggtgtctc ctagagccag ggcacattg    300 caagaccaaa tatattcaac ttaccaaaat aatcatagac ctagttctca aaaagcaaga    360
agactgattc ctcgttgtca tttctcctcc tcagca                              396

<210> SEQ ID NO 672
<211> LENGTH: 396
<212> TYPE: DNA
<213> ORGANISM: Homo sapiens

<400> SEQUENCE: 672
ttagagtctg tgggcccctc caagtgtgga gtatggtgtt acttcaccag agtttgagga    60
gaaacattct tcttttggaa ggccggggag catagatgga tatcaaggct gctgtttcta    120
aaagcgaaac ccaccaaaca acagtattag aatcatctgt ggtgcttatt aaagatacag    180
attcctgggc cccatcccmg acttatgaat cagaatctct gccagaggaa gcctgagaat    240
ttgcattctc agatgattct gcattctcag ataacacatt ctttaggtga ttcttacaca    300
cactggagtt tgggaatcgc tgaaggctgt tcacttctct tttctgagaa atgattcatt    360
catttcagaa atatttgcag aggtccttat ttattg                              396

<210> SEQ ID NO 673
<211> LENGTH: 396
<212> TYPE: DNA
```

<213> ORGANISM: Homo sapiens

<400> SEQUENCE: 673

| | |
|---|---|
| tggcctcatt cgtgtgataa atctgagcca ccacgatatt tgacttttca caatttaatt | 60 |
| tatctgaacc ctctattctc tggctaaaaa atatcccttta cttggacttc tttattttat | 120 |
| tttcaattcc cttaccagca ctagcagggg actctgtact catctgctgg cgctgccata | 180 |
| acaaagcact gcagcctgkg gggctcaaac cacagaattt attctctcac agtcctagag | 240 |
| gctagaagtc caagatcaaa gtgtgggcag ggtcggtttc cctgcagcc tctctccttg | 300 |
| gcttatagag tgccaccttc tacctgtgtc ttcacatcat cacctcactg agcatgtctg | 360 |
| tgtccaaatc tccccttctt ataagacccc agtcat | 396 |

<210> SEQ ID NO 674
<211> LENGTH: 396
<212> TYPE: DNA
<213> ORGANISM: Homo sapiens

<400> SEQUENCE: 674

| | |
|---|---|
| tctccttggc ttatagagtg ccaccttcta cctgtgtctt cacatcatca cctcactgag | 60 |
| catgtctgtg tccaaatctc cccttcttat aagacccag tcatactgga tgaggatcca | 120 |
| cccatatgag ttcattttac cttaattatc tcttttaaaca ccctgtctcc aaatacagtc | 180 |
| ccattctgag gaactgagrg taaagattca acatatgaat tttggaaggg acctaattca | 240 |
| gcccacaaca ccctcttttg ggatgtttat ttccccctt aaggagctag ttaggatgtc | 300 |
| ttatctcatg aacatgactg tgaacaggaa acagggaga gaatgaagct ggccaaggaa | 360 |
| cagggctggt gtcagctagc agtgcttttc tgatgt | 396 |

<210> SEQ ID NO 675
<211> LENGTH: 396
<212> TYPE: DNA
<213> ORGANISM: Homo sapiens

<400> SEQUENCE: 675

| | |
|---|---|
| cattttacct taattatctc tttaaacacc ctgtctccaa atacagtccc attctgagga | 60 |
| actgagagta aagattcaac atatgaattt tggaagggac ctaattcagc ccacaacacc | 120 |
| ctcttttggg atgtttattt tccccttaa ggagctagtt aggatgtctt atctcatgaa | 180 |
| catgactgtg aacaggaara cagggagaga atgaagctgg ccaaggaaca gggctggtgt | 240 |
| cagctagcag tgcttttctg atgtgagtgg gtcccacagg gagcttgtta aaatgcagat | 300 |
| tctgattcat taggttccag agggacctga gatttcccat ttctgacaag tttccagtgt | 360 |
| ggggggctgat gctgctggtc cacggaccat actttg | 396 |

<210> SEQ ID NO 676
<211> LENGTH: 396
<212> TYPE: DNA
<213> ORGANISM: Homo sapiens

<400> SEQUENCE: 676

| | |
|---|---|
| gggagagaat gaagctggcc aaggaacagg gctggtgtca gctagcagtg cttttctgat | 60 |
| gtgagtgggt cccacaggga gcttgttaaa atgcagattc tgattcatta ggttccagag | 120 |
| ggacctgaga tttcccattt ctgacaagtt ccagtgtgg gggctgatgc tgctggtcca | 180 |
| cggaccatac tttgagtakc aaggagcttg atacataatg gctgagtgac ttcagactc | 240 |
| ctgctgtaga aaaattatga gttggctggg cgtggtggct cacgcctgta atcccagcac | 300 |

```
tttgggaggc cgaggtgggc agatcacctg aggtcaggag ttcgagacca gcctggccaa    360
catggtgaaa caccatctct accaaaaata caaaaa                              396
```

<210> SEQ ID NO 677
<211> LENGTH: 396
<212> TYPE: DNA
<213> ORGANISM: Homo sapiens

<400> SEQUENCE: 677

```
acttaagccc agaagactga ggttgcagtg agccgagatt gcaccactgc actccagctt     60
gggctacaga gtgagactct atctcaaaaa caaagaaaca acaacaaca ataacaacaa    120 aaaccaagtc tctccctcca ctcaaaaatg caagggcctg tctcccattg ctgggtgccc    180
aggtctcatg aatgtagaya tgaattattc cagtcagcct caggagaata gaatgagccc    240
tcagatgccg aagcaccttt cagattccac cggtttatc ggctcattta aacttcactt    300
ctaacacagt cctgcattac acacgtgtct gtcgttatgg gcagctgcag agagggtctt    360
aatggtccta atgctcagtg aggatgccca atggtc                              396
```

<210> SEQ ID NO 678
<211> LENGTH: 396
<212> TYPE: DNA
<213> ORGANISM: Homo sapiens

<400> SEQUENCE: 678

```
ctcaaaaaca aagaaacaaa caacaacaat aacaacaaaa accaagtctc tccctccact     60
caaaaatgca agggcctgtc tcccattgct gggtgcccag gtctcatgaa tgtagatatg    120
aattattcca gtcagcctca ggagaataga atgagccctc agatgccgaa gcacctttca    180
gattccaccg gttttatcrg ctcatttaaa cttcacttct aacacagtcc tgcattacac    240
acgtgtctgt cgttatgggc agctgcagag agggtcttaa tggtcctaat gctcagtgag    300
gatgcccaat ggtcaacaga acctgccatc ttcaggccat caaggagctc tggagttaag    360
gaaatcatga gagcacagag gggcgggtac agcaga                              396
```

<210> SEQ ID NO 679
<211> LENGTH: 396
<212> TYPE: DNA
<213> ORGANISM: Homo sapiens

<400> SEQUENCE: 679

```
tgtagatatg aattattcca gtcagcctca ggagaataga atgagccctc agatgccgaa     60
gcacctttca gattccaccg gttttatcgg ctcatttaaa cttcacttct aacacagtcc    120
tgcattacac acgtgtctgt cgttatgggc agctgcagag agggtcttaa tggtcctaat    180
gctcagtgag gatgcccart ggtcaacaga acctgccatc ttcaggccat caaggagctc    240
tggagttaag gaaatcatga gagcacagag gggcgggtac agcagagccc tcgtggtaat    300
gggttttgag gtctaggctc tcttcacttg ggtttgaaat aagttcaatg actagtaata    360
gctgagacac ttctaccctt caaatgaagt aaatgg                              396
```

<210> SEQ ID NO 680
<211> LENGTH: 396
<212> TYPE: DNA
<213> ORGANISM: Homo sapiens

<400> SEQUENCE: 680

```
agcaccttc agattccacc ggttttatcg gctcatttaa acttcacttc taacacagtc    60
ctgcattaca cacgtgtctg tcgttatggg cagctgcaga gagggtctta atggtcctaa   120
tgctcagtga ggatgcccaa tggtcaacag aacctgccat cttcaggcca tcaaggagct   180
ctggagttaa ggaaatcawg agagcacaga ggggcgggta cagcagagcc ctcgtggtaa   240
tgggttttga ggtctaggct ctcttcactt gggtttgaaa taagttcaat gactagtaat   300
agctgagaca cttctaccct tcaaatgaag taaatgggaa aatggagcat tgttgagtcc   360
agggagctat aatttaaacc ccatatatct aaaagg                             396
```

<210> SEQ ID NO 681
<211> LENGTH: 396
<212> TYPE: DNA
<213> ORGANISM: Homo sapiens

<400> SEQUENCE: 681

```
cacacgtgtc tgtcgttatg ggcagctgca gagagggtct taatggtcct aatgctcagt    60
gaggatgccc aatggtcaac agaacctgcc atcttcaggc atcaaggag ctctggagtt   120 aaggaaatca tgagagcaca gaggggcggg tacagcagag ccctcgtggt aatgggtttt   180
gaggtctagg ctctcttcrc ttgggtttga ataagttca atgactagta atagctgaga   240
cacttctacc cttcaaatga agtaaatggg aaaatggagc attgttgagt ccagggagct   300
ataatttaaa ccccatatat ctaaaagggg taacattttt gtgtgtgtga aattggtgtc   360
attcgcactg catctacagt tttcttttc cttctc                              396
```

<210> SEQ ID NO 682
<211> LENGTH: 396
<212> TYPE: DNA
<213> ORGANISM: Homo sapiens

<400> SEQUENCE: 682

```
acatatttgg gaaacgcatc atactcttcc tgttcctcat gtccgttgct ggcatattca    60 actattaccct catcttcttt ttcggaagtg actttgaaaa ctacataaag acgatctcca   120
ccaccatctc ccctctactt ctcattccct aactctctgc tgaatatggg gttggtgttc   180
tcatctaatc aatacctaya agtcatcata attcagctct tgagagcatt ctgctcttct   240
ttagatggct gtaaatctat tggccatctg ggcttcacag cttgagttaa ccttgctttt   300
ccgggaacaa aatgatgtca tgtcagctcc gccccttgaa catgaccgtg gccccaaatt   360
tgctattccc atgcattttg tttgtttctt cactta                             396
```

<210> SEQ ID NO 683
<211> LENGTH: 396
<212> TYPE: DNA
<213> ORGANISM: Homo sapiens

<400> SEQUENCE: 683

```
tggtgttctc atctaatcaa tacctacaag tcatcataat tcagctcttg agagcattct    60
gctcttcttt agatggctgt aaatctattg gccatctggg cttcacagct tgagttaacc   120
ttgcttttcc gggaacaaaa tgatgtcatg tcagctccgc ccttgaaca tgaccgtggc   180 ccaaatttg ctattcccrt gcattttgtt tgtttcttca cttatcctgt tctctgaaga   240
tgttttgtga ccaggtttgt gttttcttaa aataaaatgc agagacatgt tttaagctga   300
tagttgaggg gttttgttaa tggcttttgg gggattatc tctataccca caaacgacta   360
gtttgttttc ctcaaactaa atgataatat taaaaa                             396
```

<210> SEQ ID NO 684
<211> LENGTH: 396
<212> TYPE: DNA
<213> ORGANISM: Homo sapiens

<400> SEQUENCE: 684

```
ttatctctat acccacaaac gactagtttg ttttcctcaa actaaatgat aatattaaaa      60
atacacatcc tggccaggtg tggtggctca tacctgtaat cccagcactt tgggaggccg     120
aggcaggtgg atcacttgag gtcaggaatt aagaccagcc tggccaatat ggtgaaagcc     180
tgtctgtact aaaaatacra aaattagcca ggtatgctgg tggatgctta taatcccagc     240
tacttgggag gttgaggcag gagaattgct tgaacccggg aggtagaggt tgcagtgagc     300
caagatcatg ccactgcact ccagcttggg caacagagtg agactccatc tcaaattaaa     360
aaaaatacac atctggcttc tggaaaaatt acttga                               396
```

<210> SEQ ID NO 685
<211> LENGTH: 396
<212> TYPE: DNA
<213> ORGANISM: Homo sapiens

<400> SEQUENCE: 685

```
gatcatgcca ctgcactcca gcttgggcaa cagagtgaga ctccatctca aattaaaaaa      60
aatacacatc tggcttctgg aaaaattact tgaagatctt ttatgacatc catccctctt     120
cacacagcca tgtgaattag gttggtatct tcatatacta gcatcgtgcc cagcacttcc     180
atgttataca gtttaaaakg ttctgtaatt ccctgtggga acctaagata atgcgaggac     240
cgtcatacgt gcccccaaat attggcaaac caatgaataa atgaatgaat gagtttatga     300
atcgctaact ggctgtattt aatgaagtat gtgtgttgag ccatttccca cagtgtggac     360
agatttgtcc cacaatatgg gcctcttccc aaaggc                                396
```

<210> SEQ ID NO 686
<211> LENGTH: 396
<212> TYPE: DNA
<213> ORGANISM: Homo sapiens

<400> SEQUENCE: 686

```
aattaaaaaa aatacacatc tggcttctgg aaaaattact tgaagatctt ttatgacatc      60
catccctctt cacacagcca tgtgaattag gttggtatct tcatatacta gcatcgtgcc     120
cagcacttcc atgttataca gtttaaaatg ttctgtaatt ccctgtggga acctaagata     180
atgcgaggac cgtcatacrt gcccccaaat attggcaaac caatgaataa atgaatgaat     240
gagtttatga atcgctaact ggctgtattt aatgaagtat gtgtgttgag ccatttccca     300
cagtgtggac agatttgtcc cacaatatgg gcctcttccc aaaggcccta ccacctaatg     360
ccatcacact ggggatttga tttcaacatg tgaatt                                396
```

<210> SEQ ID NO 687
<211> LENGTH: 396
<212> TYPE: DNA
<213> ORGANISM: Homo sapiens

<400> SEQUENCE: 687

```
agttcatagt gacagtgatc cagccactgt catgacaggt gccacttggc agaaacagca      60
cagcttggaa gatggcgggg tgtagtcaag attccaggat ccccaacaga gaagccagct     120
```

```
cttataggggg agccattcat caggattgaa ctctcaatcg agctggacag taataggtgg      180
gtctgtgtta ttccccagrt gagtatcatg acagtcacaa tcctaggaag gatgtgaagc      240
ctcccccagc tctcctccag ttgcctgctt gggcagcaga gatgatggaa tgtggagtct      300
ggcgtggtct gaggcctgaa tccatgtgcc tcatgtatga tgctcaggca agaggatctc      360
tcaattcaag ggagagggcc tgaatgagcc ttgctt                                396
```

<210> SEQ ID NO 688
<211> LENGTH: 396
<212> TYPE: DNA
<213> ORGANISM: Homo sapiens

<400> SEQUENCE: 688

```
cttggcagaa acagcacagc ttggaagatg gcggggtgta gtcaagattc caggatcccc      60
aacagagaag ccagctctta taggggagcc attcatcagg attgaactct caatcgagct      120
ggacagtaat aggtgggtct gtgttattcc ccagatgagt atcatgacag tcacaatcct      180
aggaaggatg tgaagcctyc cccagctctc ctccagttgc ctgcttgggc agcagagatg      240
atggaatgtg gagtctggcg tggtctgagg cctgaatcca tgtgcctcat gtatgatgct      300
caggcaagag gatctctcaa ttcaagggag agggcctgaa tgagccttgc tttccaggcc      360
tgtctgatgg tccaggctga agcccctcct ggcttg                                396
```

<210> SEQ ID NO 689
<211> LENGTH: 396
<212> TYPE: DNA
<213> ORGANISM: Homo sapiens

<400> SEQUENCE: 689

```
ctggcgtggt ctgaggcctg aatccatgtg cctcatgtat gatgctcagg caagaggatc      60
tctcaattca agggagaggg cctgaatgag ccttgctttc aggcctgtc tgatggtcca      120 ggctgaagcc cctcctggct tgcactgcca gacctcatcc agcaggagct ccttggcatt      180
gactgcttca ggatagttsc ttctgctctg agtgctctct aaagagcagt gctctaccat      240
ccaagctggg ctttctttt cttcttgctg atagggaagg catgggacat tgcaggatgg      300
aagtggcccc caggccttct catgcctggg cttggtttgg aaggtggtca ggtgatcaat      360
aatcctgatt ggcctggcat tgaggagttt tcctgg                                396
```

<210> SEQ ID NO 690
<211> LENGTH: 396
<212> TYPE: DNA
<213> ORGANISM: Homo sapiens

<400> SEQUENCE: 690

```
tgctctctaa agagcagtgc tctaccatcc aagctgggct tttcttttct tcttgctgat      60
agggaaggca tgggacattg caggatggaa gtggccccca ggccttctca tgcctggct      120 tggtttggaa ggtggtcagg tgatcaataa tcctgattgg cctggcattg aggagttttc      180
ctgggatgtg gtccttttcrg ttttttaaaa attattttta ttgatacaca tatttgtagg      240
tatttgtggg gtgcatgtga tactttatta tgtgtgtgga ttgtgtaatg atgaagtcag      300
ggcatttagg gtcttcatca ccttgattat catttctatg tgttgagaac atttcaagtt      360
ctcagttcca gctattttga aatagacagt ccattt                                396
```

<210> SEQ ID NO 691
<211> LENGTH: 396

```
<212> TYPE: DNA
<213> ORGANISM: Homo sapiens

<400> SEQUENCE: 691
gatactttat tatgtgtgtg gattgtgtaa tgatgaagtc agggcattta gggtcttcat    60
caccttgatt atcatttcta tgtgttgaga acatttcaag ttctcagttc cagctatttt   120
gaaatagaca gtccattttg ttagctacag tcacccaacc cggctgtcag acattggaac   180
ttactcctat tgaactgtrt atttgtaccc attcaccaaa ctctctttgg ctttcagtt    240
ttacaactgg gatgatcctg ggaaaactaa agtaaatcag acacccgacg tgtgagctag   300
gttataatat gcccagtgga ccctggggac atcttagctt tcagaggtca tgctgtccaa   360
gctgactgtg gggcttccag aaggtgggga gaggaa                             396

<210> SEQ ID NO 692
<211> LENGTH: 396
<212> TYPE: DNA
<213> ORGANISM: Homo sapiens

<400> SEQUENCE: 692
tatgtgtgtg gattgtgtaa tgatgaagtc agggcattta gggtcttcat caccttgatt    60
atcatttcta tgtgttgaga acatttcaag ttctcagttc cagctatttt gaaatagaca   120
gtccattttg ttagctacag tcacccaacc cggctgtcag acattggaac ttactcctat   180
tgaactgtgt atttgtacyc attcaccaaa ctctctttgg ctttcagtt ttacaactgg    240
gatgatcctg ggaaaactaa agtaaatcag acacccgacg tgtgagctag gttataatat   300
gcccagtgga ccctggggac atcttagctt tcagaggtca tgctgtccaa gctgactgtg   360
gggcttccag aaggtgggga gaggaaatga tgcaat                             396

<210> SEQ ID NO 693
<211> LENGTH: 396
<212> TYPE: DNA
<213> ORGANISM: Homo sapiens

<400> SEQUENCE: 693
tgggaaaact aaagtaaatc agacacccga cgtgtgagct aggttataat atgcccagtg    60
gaccctgggg acatcttagc tttcagaggt catgctgtcc aagctgactg tggggcttcc   120
agaaggtggg gagaggaaat gatgcaatgg cccatcagag gcactacttg gggcctgggg   180
ccagagtgca tgtctaagsc attaagggga ggggagagca gccttcataa ttatgaagag   240
gagtctcagg tgcacagctt ctgatgaggg acagcttcta attgaagaca gcattgtgta   300
atgctcaaac tccctgtctt cagagtgcct gctgtatccc accatcagtt ctgtgacttc   360
tccctaagcc tcaattttgc atgtgttaca ttggga                             396

<210> SEQ ID NO 694
<211> LENGTH: 396
<212> TYPE: DNA
<213> ORGANISM: Homo sapiens

<400> SEQUENCE: 694
cctgcatagc aaattcttgc aaatgtaggg actcaaaaca atataaattt attatctgac    60
agttttctg ggtcagaggt cttactaggc tgtaatcaga gggcaaccaa agctgtgatc    120
tcagctgaag ctcaggattc tcttccaagc tcactggttg ttggcagaat tcagttcttt   180
ccagttggaa gactaaagyc tacagtcttc agtctctaga agccttttct ctggcacagg   240
```

```
tttctctaca acatggccat ttatgtcttt aaggccaata ggagaacatg attagcatat    300
tttttttaag tgaactttag accctttttt aaaggcctat ctgattaggc caggcccaag    360
tgagctttaa gtcaactgat tagagatctt aattac                              396
```

<210> SEQ ID NO 695
<211> LENGTH: 396
<212> TYPE: DNA
<213> ORGANISM: Homo sapiens

<400> SEQUENCE: 695

```
ctgaagctca ggattctctt ccaagctcac tggttgttgg cagaattcag ttctttccag     60
ttggaagact aaagcctaca gtcttcagtc tctagaagcc ttttctctgg cacaggtttc    120
tctacaacat ggccatttat gtctttaagg ccaataggag aacatgatta gcatattttt    180
tttaagtgaa ctttagacyc ttttttaaag gcctatctga ttaggccagg cccaagtgag    240
ctttaagtca actgattaga gatcttaatt acatctgcaa agtcccttca tgtttaccgt    300
ataacataac ttagtgaaag gagtgaaatt gcaaccaggt tctgcctgca ctccacggaa    360
ggggattctg cagaagtgtg ggtcacgggg gggtta                              396
```

<210> SEQ ID NO 696
<211> LENGTH: 396
<212> TYPE: DNA
<213> ORGANISM: Homo sapiens

<400> SEQUENCE: 696

```
agaacatgat tagcatattt ttttaagtg aactttagac ccttttttaa aggcctatct     60
gattaggcca ggcccaagtg agctttaagt caactgatta gagatcttaa ttacatctgc    120
aaagtccctt catgtttacc gtataacata acttagtgaa aggagtgaaa ttgcaaccag    180
gttctgcctg cactccacrg aaggggattc tgcagaagtg tgggtcacgg ggggttatt    240 ttgggattct gcctacgtca ctgagtcaaa agaagctgaa tggttgtgat gctgaggttt    300
ttgggcagca gcagtgtgtg tgtgtgagtg aattcatacg tatgaccacc tgggaagaaa    360
ggaggctgtg gtttcctcca cctcctggca gacaga                              396
```

<210> SEQ ID NO 697
<211> LENGTH: 396
<212> TYPE: DNA
<213> ORGANISM: Homo sapiens

<400> SEQUENCE: 697

```
gggattacag acacacactg ccacgcctgg ctaattttg tattttagt agagacgagg       60 ttttgccatg ttggccaggc tggtcttgaa ctcctgacct caagtgatcc gcccacctca    120
gcctcccaaa gtgctgggat tacagacgtg agccaccatt aaccatttt ctatctcctg    180 tgggaaggg cacagtgara gaacagatga agctgagaca tacaagtgaa ctcctccctc    240
ctctccattt agactaaaat aggattattc atactgagat tctccctggt tgcaaagaga    300
taatctgtgc aactgggttt ttacaattat ccctacccta tgctttcctc atctgtcttc    360
ctcgtagtca gctcaggctg ctataacaaa acacca                              396
```

<210> SEQ ID NO 698
<211> LENGTH: 396
<212> TYPE: DNA
<213> ORGANISM: Homo sapiens

<400> SEQUENCE: 698

```
ggcagattcg gtgtctaatg aggtcctgct ttccagttta tagacagtgc cttatcgcta    60
ccgccttaca cagtggaagg agaggacgag aagctccttg ggcttttttt tgtttctttc   120
tttctctctc tctctctttt tttttttttt aataaggtca ctatcttagt ccattttgtg   180
ttgctaaaag gaacatctra ggttgagtaa tttattttat tttaaaagt ggccaggcat   240 ggaggcttat cctgtaaccc taatccttta ggaggccaaa acagcaggat tgtttgaggc   300
caggagttca agaccagcct aggcaagata gtgagacccc atctacccca tctctactaa   360
aattttaaaa aattagctgt gtgttgtaaa gtgtgc                             396

<210> SEQ ID NO 699
<211> LENGTH: 396
<212> TYPE: DNA
<213> ORGANISM: Homo sapiens

<400> SEQUENCE: 699
aatttatttt attttaaaaa gtggccaggc atggaggctt atcctgtaac cctaatcctt    60
taggaggcca aaacagcagg attgtttgag gccaggagtt caagaccagc ctaggcaaga   120
tagtgagacc ccatctaccc catctctact aaaattttaa aaaattagct gtgtgttgta   180
aagtgtgctt gtagtcccrg ccacttgaga ggctgaggtg ggtggagttc aaggctgcag   240
tgagttatga ttgagccact gcactccaac ccgggtaacg gggcaagacc ttgtctctat   300
ttaaaaaaaa aaaatcttta tgtggctcac tattctgggt ggctggaaag ttcaagattg   360
ggcatctgca tctggtgaca gcctcatgtc gcttcc                             396

<210> SEQ ID NO 700
<211> LENGTH: 396
<212> TYPE: DNA
<213> ORGANISM: Homo sapiens

<400> SEQUENCE: 700
taaccctaat cctttaggag gccaaaacag caggattgtt tgaggccagg agttcaagac    60
cagcctaggc aagatagtga gaccccatct accccatctc tactaaaatt ttaaaaaatt   120
agctgtgtgt tgtaaagtgt gcttgtagtc ccggccactt gagaggctga ggtgggtgga   180
gttcaaggct gcagtgagwt atgattgagc cactgcactc caacccgggt aacggggcaa   240
gaccttgtct ctatttaaaa aaaaaaaatc tttatgtggc tcactattct gggtggctgg   300
aaagttcaag attgggcatc tgcatctggt gacagcctca tgtcgcttcc agtcatgggg   360
gaagacgaag gagagctggc acgtgcagat atcacg                             396

<210> SEQ ID NO 701
<211> LENGTH: 396
<212> TYPE: DNA
<213> ORGANISM: Homo sapiens

<400> SEQUENCE: 701
atcctttagg aggccaaaac agcaggattg tttgaggcca ggagttcaag accagcctag    60
gcaagatagt gagaccccat ctaccccatc tctactaaaa ttttaaaaaa ttagctgtgt   120
gttgtaaagt gtgcttgtag tcccggccac ttgagaggct gaggtgggtg gagttcaagg   180
ctgcagtgag ttatgattra gccactgcac tccaacccgg gtaacggggc aagaccttgt   240
ctctatttaa aaaaaaaaaa tctttatgtg gctcactatt ctgggtggct ggaaagttca   300
agattgggca tctgcatctg gtgacagcct catgtcgctt ccagtcatgg gggaagacga   360
```

```
aggagagctg gcacgtgcag atatcacgtg ttgagg                               396
```

<210> SEQ ID NO 702
<211> LENGTH: 396
<212> TYPE: DNA
<213> ORGANISM: Homo sapiens

<400> SEQUENCE: 702

```
ttaaaaaatt agctgtgtgt tgtaaagtgt gcttgtagtc ccggccactt gagaggctga    60
ggtgggtgga gttcaaggct gcagtgagtt atgattgagc cactgcactc caacccgggt   120
aacgggcaa gaccttgtct ctatttaaaa aaaaaaatc tttatgtggc tcactattct    180
gggtggctgg aaagttcarg attgggcatc tgcatctggt gacagcctca tgtcgcttcc   240
agtcatgggg gaagacgaag gagagctggc acgtgcagat atcacgtgtt gagggcagaa   300
gcgagagaga gaggggagag atgccaggct cttttttaaca accagcactg gggaaactaa   360
tagagtgaga gctcactgac tcctgaggga ggacat                              396
```

<210> SEQ ID NO 703
<211> LENGTH: 396
<212> TYPE: DNA
<213> ORGANISM: Homo sapiens

<400> SEQUENCE: 703

```
atgggggaag acgaaggaga gctggcacgt gcagatatca cgtgttgagg gcagaagcga    60
gagagagagg ggagagatgc caggctcttt ttaacaacca gcactgggga aactaataga   120
gtgagagctc actgactcct gagggaggac attaatctat tgatgagcga cctgcctcca   180
tgacccaaac acctccaayg ataccccacc tccaacactg ccacactagg gattaacttt   240
caacttgaga tttagagggg ggaaacttac aaactatcgc aggcactaat accactcatg   300
agggctccac cttcatgacc taatcacttc ctaaaggcct tacctcttaa tctcatcaca   360
ttgaggattc gatttcaact tgaattttgg ggggac                              396
```

<210> SEQ ID NO 704
<211> LENGTH: 396
<212> TYPE: DNA
<213> ORGANISM: Homo sapiens

<400> SEQUENCE: 704

```
ctcgctgcca cctgaaatta gatcatttat ttaccccttt atttgttcag tttgccttgt    60
ccgttagaat ataagcttcc aaagggcagg agctttgcct atattgttag gccgggcata   120
caatgagcac tcaaaaaaat atttgatgag tgtatgaaag aacagactgg gttatgtaat   180
tgtgcctact tacctatayg accgtgtggt ggggtttatg gtgggtgtgg tggtgatggc   240
tatagggcta taagcaaatt tgggacaggg agtctaagaa atgttcttaa attttagtaa   300
gcaaagcatc ctctacagaa cctgtcttaa aacatgaaag ttccttagtg ctaccccag    360
aggtatgatt tggtaggtca aggatagggc ctggaa                              396
```

<210> SEQ ID NO 705
<211> LENGTH: 396
<212> TYPE: DNA
<213> ORGANISM: Homo sapiens

<400> SEQUENCE: 705

```
tgccacctga aattagatca tttatttacc cctttatttg ttcagtttgc cttgtccgtt    60
agaatataag cttccaaagg gcaggagctt tgcctatatt gttaggccgg gcatacaatg   120
```

```
agcactcaaa aaaatatttg atgagtgtat gaaagaacag actgggttat gtaattgtgc      180
ctacttacct atatgaccrt gtggtggggt ttatggtggg tgtggtggtg atggctatag      240
ggctataagc aaatttggga cagggagtct aagaaatgtt cttaaatttt agtaagcaaa      300
gcatcctcta cagaacctgt cttaaaacat gaaagttcct tagtgctacc cccagaggta      360
tgatttggta ggtcaaggat agggcctgga aattca                                396

<210> SEQ ID NO 706
<211> LENGTH: 396
<212> TYPE: DNA
<213> ORGANISM: Homo sapiens

<400> SEQUENCE: 706
cctgtcttaa aacatgaaag ttccttagtg ctaccccccag aggtatgatt tggtaggtca     60
```

```
agcactcaaa aaaatatttg atgagtgtat gaaagaacag actgggttat gtaattgtgc      180
ctacttacct atatgaccrt gtggtggggt ttatggtggg tgtggtggtg atggctatag      240
ggctataagc aaatttggga cagggagtct aagaaatgtt cttaaatttt agtaagcaaa      300
gcatcctcta cagaacctgt cttaaaacat gaaagttcct tagtgctacc cccagaggta      360
tgatttggta ggtcaaggat agggcctgga aattca                                396

<210> SEQ ID NO 706
<211> LENGTH: 396
<212> TYPE: DNA
<213> ORGANISM: Homo sapiens

<400> SEQUENCE: 706
cctgtcttaa aacatgaaag ttccttagtg ctaccccccag aggtatgatt tggtaggtca      60
aggatagggc ctggaaattc acattcttgt taagatgttc ttcatccggg gtttgttgac     120
caccttttca gaagattttt gctctgtagc tgtactaccc aatgcagtag ttcgtagtca     180
gtgtggctcc tgagccctyg aagtgtagct cctctgaact gagacgtgct gtaaatgtaa     240
attgcacacc ggagtttgaa gagttaatac aaagaaaaag gaatgcaaaa catctcatta     300
ataatgcttt acactgatta catattgaaa tggtaatctt gtagatatag tgcgttaaat     360
aaaatatact gttaggctta atttcacgtc tttata                                396

<210> SEQ ID NO 707
<211> LENGTH: 396
<212> TYPE: DNA
<213> ORGANISM: Homo sapiens

<400> SEQUENCE: 707
tcagccaatc aacaagaggg caaaagaaca acatttgat gtgtaattac ttaatttagt       60
gcatatgcat ttgggtcctc aatgtcagca ctatggcaac cagaacatgg ccacaataac     120
tgtctggaaa tgtctattct tacctggacc cagcaggcca tgccccactg attatataat     180
ctccctctct ccttgttayg gtctgaatgc ttgcatccct caaaaattca tgtgttgaaa     240
tcctaacccc caaggtgatg atattaggag gtcggccttt tgagaggtaa ttaggtcatg     300
aagacagcat cctcatgaat gggattagtg tccttataaa ataggcccaa gggagctcat     360
tcactttgtc caccatgtga gaacacagcg agaggg                                396

<210> SEQ ID NO 708
<211> LENGTH: 396
<212> TYPE: DNA
<213> ORGANISM: Homo sapiens

<400> SEQUENCE: 708
ccttgttacg gtctgaatgc ttgcatccct caaaaattca tgtgttgaaa tcctaacccc      60
caaggtgatg atattaggag gtcggccttt tgagaggtaa ttaggtcatg aagacagcat     120
cctcatgaat gggattagtg tccttataaa ataggcccaa gggagctcat tcactttgtc     180
caccatgtga gaacacagyg agagggcacc atttatgcac caggaaatgg ccttttcca     240 gacaatctgt cggtgcctgg atcttggact tcacagcctc tagaactgtg agaaattaat     300
ttgtttttta taagccacca aatctatggt tttttttata gaaaccgtaa tggactaaaa     360
cactccctaa ttatatttaa acttatcagt gcactg                                396

<210> SEQ ID NO 709
```

<210> SEQ ID NO 709
<211> LENGTH: 396
<212> TYPE: DNA
<213> ORGANISM: Homo sapiens

<400> SEQUENCE: 709

```
ctaaccccca aggtgatgat attaggaggt cggccttttg agaggtaatt aggtcatgaa      60
gacagcatcc tcatgaatgg gattagtgtc cttataaaat aggcccaagg gagctcattc     120
actttgtcca ccatgtgaga acacagcgag agggcaccat ttatgcacca ggaaatgggc     180
cttttccaga caatctgtyg gtgcctggat cttggacttc acagcctcta gaactgtgag     240
aaattaattt gttttttata agccaccaaa tctatggttt tttttataga aaccgtaatg     300
gactaaaaca ctccctaatt atatttaaac ttatcagtgc actgggcagt gacatattaa     360
aagaatgctg gccaacgtaa ttgacaccat aaggct                               396
```

<210> SEQ ID NO 710
<211> LENGTH: 396
<212> TYPE: DNA
<213> ORGANISM: Homo sapiens

<400> SEQUENCE: 710

```
tcatctcatt ttaaccttttt gtttcaaagc ctctcttttc atgacttccc cgccttcatt     60
tttcccatat ggtggggtta ttattaagac attaaatgag agtggacagg taggcaaagg    120
aggtgggttg caggggagtt gagggttgcc tgtgtacttt tctagactgt tccacttcac    180
atcagtgaaa tattcccart tgatactatc atgaaacaaa gcaaatgaaa tgctgagcac    240
ggagcttcgt cttgatgaaa tgctgaaaga aagaaagga aaaataaagt agccattatt     300
tttgcccttc ctcccacccc catgtttact actcttattt ctcttttgta ttgttgtgtt    360
ggaagcacag catcagaaaa actcccagtt ttgaga                              396
```

<210> SEQ ID NO 711
<211> LENGTH: 396
<212> TYPE: DNA
<213> ORGANISM: Homo sapiens

<400> SEQUENCE: 711

```
acaggtaggc aaaggaggtg ggttgcaggg gagttgaggg ttgcctgtgt acttttctag     60
actgttccac ttcacatcag tgaaatattc ccaattgata ctatcatgaa acaaagcaaa    120
tgaaatgctg agcacggagc ttcgtcttga tgaaatgctg aaagaaaaga aggaaaaat    180
aaagtagcca ttattttttrc cttcctcccc accccatgtt tactactct tatttctctt    240
ttgtattgtt gtgttggaag cacagcatca gaaaaactcc cagttttgag agataactca    300
gtgtttagtt cacttaaacc tgagaaagga gaagaggat ccaccgtgag gtccaggacg    360
taaagaggaa aaaacagac aaaaaaatcc atatga                               396
```

<210> SEQ ID NO 712
<211> LENGTH: 396
<212> TYPE: DNA
<213> ORGANISM: Homo sapiens

<400> SEQUENCE: 712

```
caggtaggca aaggaggtgg gttgcagggg agttgagggt tgcctgtgta cttttctaga     60
ctgttccact tcacatcagt gaaatattcc caattgatac tatcatgaaa caaagcaaat    120
gaaatgctga gcacggagct tcgtcttgat gaaatgctga aagaaagaa aggaaaata    180
aagtagccat tattttttgmc cttcctccca ccccatgtt tactactctt atttctcttt    240
```

| tgtattgttg tgttggaagc acagcatcag aaaaactccc agttttgaga gataactcag | 300 |
| tgtttagttc acttaaacct gagaaaggag aagaggatgc caccgtgagg tccaggacgt | 360 |
| aaagaggaaa aaaacagaca aaaaaatcca tatgaa | 396 |

<210> SEQ ID NO 713
<211> LENGTH: 396
<212> TYPE: DNA
<213> ORGANISM: Homo sapiens

<400> SEQUENCE: 713

| ttcgtcttga tgaaatgctg aaagaaaaga aggaaaaat aaagtagcca ttattttttgc | 60 |
| ccttcctccc accccatgt ttactactct tatttctctt ttgtattgtt gtgttggaag | 120 |
| cacagcatca gaaaaactcc cagttttgag agataactca gtgtttagtt cacttaaacc | 180 |
| tgagaaagga gaagaggayg ccaccgtgag gtccaggacg taaagaggaa aaaaacagac | 240 |
| aaaaaaatcc atatgaaatg aaaatgtgaa agaggcgctt tcgagcagat gagtgttgta | 300 |
| gattacagtg ttgagagctg tttgtgtcca gagctgcttg ctgcacctgg cgggataaac | 360 |
| actggtctaa cagaggatcc ttgtttcaag gaggct | 396 |

<210> SEQ ID NO 714
<211> LENGTH: 396
<212> TYPE: DNA
<213> ORGANISM: Homo sapiens

<400> SEQUENCE: 714

| aagaaaagaa aggaaaaata aagtagccat tattttttgcc cttcctccca ccccatgtt | 60 |
| tactactctt atttctcttt tgtattgttg tgttggaagc acagcatcag aaaaactccc | 120 |
| agttttgaga gataactcag tgtttagttc acttaaacct gagaaaggag aagaggatgc | 180 |
| caccgtgagg tccaggacrt aaagaggaaa aaaacagaca aaaaaatcca tatgaaatga | 240 |
| aaatgtgaaa gaggcgcttt cgagcagatg agtgttgtag attacagtgt tgagagctgt | 300 |
| ttgtgtccag agctgcttgc tgcacctggc gggataaaca ctggtctaac agaggatcct | 360 |
| tgtttcaagg aggctgcctt ttatttgggg ggacaa | 396 |

<210> SEQ ID NO 715
<211> LENGTH: 396
<212> TYPE: DNA
<213> ORGANISM: Homo sapiens

<400> SEQUENCE: 715

| attattttttg cccttcctcc caccccatg tttactactc ttatttctct tttgtattgt | 60 |
| tgtgttggaa gcacagcatc agaaaaactc ccagttttga gagataactc agtgtttagt | 120 |
| tcacttaaac ctgagaaagg agaagaggat gccaccgtga ggtccaggac gtaaagagga | 180 |
| aaaaaacaga caaaaaaayc catatgaaat gaaaatgtga agaggcgct tcgagcaga | 240 |
| tgagtgttgt agattacagt gttgagagct gtttgtgtcc agagctgctt gctgcacctg | 300 |
| gcgggataaa cactggtcta acagaggatc cttgtttcaa ggaggctgcc ttttatttgg | 360 |
| ggggacaaaa ttgttcttga aagctgctca gtggtt | 396 |

<210> SEQ ID NO 716
<211> LENGTH: 396
<212> TYPE: DNA
<213> ORGANISM: Homo sapiens

```
<400> SEQUENCE: 716
tttgtattgt tgtgttggaa gcacagcatc agaaaaactc ccagttttga gagataactc      60
agtgtttagt tcacttaaac ctgagaaagg agaagaggat gccaccgtga ggtccaggac     120
gtaaagagga aaaaaacaga caaaaaaatc catatgaaat gaaaatgtga aagaggcgct     180
ttcgagcaga tgagtgttrt agattacagt gttgagagct gtttgtgtcc agagctgctt     240
gctgcacctg gcgggataaa cactggtcta acagaggatc cttgtttcaa ggaggctgcc     300
ttttatttgg ggggacaaaa ttgttcttga aagctgctca gtggttcaag ctacagcatg     360
gtggactagc agaatggact ccagggcctc cgagga                               396

<210> SEQ ID NO 717
<211> LENGTH: 396
<212> TYPE: DNA
<213> ORGANISM: Homo sapiens

<400> SEQUENCE: 717
ttttgagaga taactcagtg tttagttcac ttaaacctga gaaggagaa gaggatgcca       60 ccgtgaggtc caggacgtaa agaggaaaaa aacagacaaa aaatccata tgaaatgaaa      120 atgtgaaaga ggcgctttcg agcagatgag tgttgtagat tacagtgttg agagctgttt     180
gtgtccagag ctgcttgcyg cacctggcgg gataaacact ggtctaacag aggatccttg     240
tttcaaggag gctgcctttt atttgggggg acaaaattgt tcttgaaagc tgctcagtgg     300
ttcaagctac agcatggtgg actagcagaa tggactccag gcctccgag gagacagtga     360 ctgctgccag aaatagtcaa ggatagaaag gaagga                               396
```